US010077433B2

(12) United States Patent
Binkowski et al.

(10) Patent No.: US 10,077,433 B2
(45) Date of Patent: Sep. 18, 2018

(54) PERMUTED AND NONPERMUTED LUCIFERASE BIOSENSORS

(71) Applicant: PROMEGA CORPORATION, Madison, WI (US)

(72) Inventors: Brock Binkowski, Sauk City, WI (US); Frank Fan, Verona, WI (US); Susan Wigdal, Belleville, WI (US); Keith V. Wood, Mount Horeb, WI (US); Monika G. Wood, Mount Horeb, WI (US)

(73) Assignee: PROMEGA CORPORATION, Madison, WI (US)

( * ) Notice: Subject to any disclaimer, the term of this patent is extended or adjusted under 35 U.S.C. 154(b) by 0 days.

(21) Appl. No.: 15/168,631

(22) Filed: May 31, 2016

(65) Prior Publication Data

US 2016/0340654 A1 Nov. 24, 2016

Related U.S. Application Data

(62) Division of application No. 11/732,105, filed on Apr. 2, 2007, now Pat. No. 9,359,635.

(60) Provisional application No. 60/901,133, filed on Feb. 14, 2007, provisional application No. 60/879,771, filed on Jan. 10, 2007, provisional application No. 60/788,608, filed on Apr. 3, 2006.

(51) Int. Cl.
*C12N 9/02* (2006.01)
*G01N 33/84* (2006.01)
*C12Q 1/66* (2006.01)

(52) U.S. Cl.
CPC ......... *C12N 9/0069* (2013.01); *C12N 9/0004* (2013.01); *C12Q 1/66* (2013.01); *C12Y 113/12007* (2013.01); *G01N 33/84* (2013.01)

(58) Field of Classification Search
None
See application file for complete search history.

(56) References Cited

U.S. PATENT DOCUMENTS

| | | | |
|---|---|---|---|
| 5,097,026 | A | 3/1992 | Jahnsen |
| 6,251,667 | B1 | 6/2001 | Habener et al. |
| 6,270,964 | B1 | 8/2001 | Michnick et al. |
| 6,294,330 | B1 | 9/2001 | Michnick et al. |
| 6,406,856 | B1 | 6/2002 | Glover et al. |
| 6,428,951 | B1 | 8/2002 | Michnick et al. |
| 6,573,059 | B1 | 6/2003 | Reymond |
| 6,602,677 | B1 | 8/2003 | Wood et al. |
| 6,762,026 | B1 | 7/2004 | Sugiyama |
| 6,808,874 | B2 | 10/2004 | Griffiths |
| 6,855,515 | B1 | 2/2005 | Rosen et al. |
| 6,890,745 | B1 | 5/2005 | Leng |
| 6,936,687 | B1 | 8/2005 | Komoriya et al. |
| 7,083,911 | B2 | 8/2006 | Wood et al. |
| 7,241,584 | B2 | 7/2007 | Wood et al. |
| 7,452,663 | B2 | 11/2008 | Wood et al. |
| 7,700,310 | B2 | 4/2010 | Somberg et al. |
| 7,732,128 | B2 | 6/2010 | Wood et al. |
| 7,741,067 | B2 | 6/2010 | Hawkins et al. |
| 7,927,816 | B2 | 4/2011 | Reed et al. |
| 7,927,871 | B2 | 4/2011 | Packard et al. |
| 8,030,017 | B2 | 10/2011 | Wood et al. |
| 8,183,036 | B2 | 5/2012 | Fan et al. |
| 8,227,572 | B2 | 7/2012 | Leitch et al. |
| 8,673,558 | B2 | 3/2014 | Fan et al. |
| 8,735,559 | B2 | 5/2014 | Binkowski et al. |
| 9,290,794 | B2 | 3/2016 | Binkowski et al. |
| 2002/0022220 | A1 | 2/2002 | Izevbigie |
| 2002/0132327 | A1 | 9/2002 | Hay et al. |
| 2002/0150885 | A1 | 10/2002 | Weber et al. |
| 2002/0151014 | A1 | 10/2002 | Campbell |
| 2003/0003506 | A1 | 1/2003 | Umezawa et al. |
| 2003/0053995 | A1 | 3/2003 | Hung et al. |
| 2003/0068801 | A1 | 4/2003 | Wood et al. |
| 2003/0092098 | A1 | 5/2003 | Bryan et al. |
| 2003/0104507 | A1 | 6/2003 | Wood et al. |
| 2003/0170850 | A1 | 9/2003 | Cardone et al. |
| 2003/0203407 | A1 | 10/2003 | Craig et al. |
| 2003/0232404 | A1 | 12/2003 | Wood et al. |

(Continued)

FOREIGN PATENT DOCUMENTS

| | | |
|---|---|---|
| EP | 1097992 | 5/2001 |
| EP | 1229330 | 8/2002 |

(Continued)

OTHER PUBLICATIONS

Packard et al., "Granzyme B activity in Target Cells Detects Attack by Cytotoxic Lymphocytes," The Journal of Immonology, 2007, vol. 179, No. 6, pp. 3812-3820.
European Patent Office Action for Application No. 12791055.2 dated May 30, 2017 (7 pages).
Wikipedia G Protein Coupled Receptor entry <https://en.wikipedia.org/wiki/G_protein%E2%80%93coupled_receptor>, retrieved Sep. 27, 2016.

(Continued)

*Primary Examiner* — Channing S Mahatan
(74) *Attorney, Agent, or Firm* — Michael Best & Friedrich LLP

(57) ABSTRACT

A modified luciferase protein which is a sensor for molecules including cAMP, cGMP, calcium, chelators thereof, kinases, or phosphatases is provided. Also provided is a circularly permuted anthozoan luciferase protein and a decapod crustacean luciferase protein, optionally containing one or more heterologous amino acid sequences, at least one of which directly or indirectly interacts with a molecule of interest. Further provided is a modified anthozoan luciferase protein and a decapod crustacean luciferase protein containing an insertion of one or more heterologous amino acid sequences, at least one of which directly or indirectly interacts with a molecule of interest.

18 Claims, 203 Drawing Sheets

Specification includes a Sequence Listing.

(56) References Cited

U.S. PATENT DOCUMENTS

| | | | |
|---|---|---|---|
| 2004/0096926 | A1 | 5/2004 | Packard et al. |
| 2004/0101922 | A1 | 5/2004 | Somberg et al. |
| 2004/0157272 | A1 | 8/2004 | Cardone et al. |
| 2005/0026171 | A1 | 2/2005 | Hawkins et al. |
| 2005/0054573 | A1 | 3/2005 | Werner et al. |
| 2005/0170442 | A1 | 8/2005 | Kupcho et al. |
| 2005/0176071 | A1 | 8/2005 | Nikiforov et al. |
| 2005/0181452 | A1 | 8/2005 | Westwick et al. |
| 2006/0048592 | A1 | 3/2006 | Wood et al. |
| 2006/0110364 | A1 | 5/2006 | Harding |
| 2006/0183212 | A1 | 8/2006 | Wood et al. |
| 2007/0184493 | A1 | 8/2007 | Packard et al. |
| 2008/0199898 | A1 | 8/2008 | Packard et al. |
| 2008/0206798 | A1 | 8/2008 | Wood et al. |
| 2009/0075292 | A1 | 3/2009 | Reed et al. |
| 2009/0137019 | A1 | 5/2009 | Wood et al. |
| 2009/0215864 | A1 | 8/2009 | Feinstein |
| 2009/0253131 | A1 | 10/2009 | Wigdal et al. |
| 2009/0286299 | A1 | 11/2009 | Ronaghi et al. |
| 2009/0305280 | A1 | 12/2009 | Binkowski et al. |
| 2009/0311769 | A1 | 12/2009 | Wood et al. |
| 2010/0021949 | A1 | 1/2010 | Somberg et al. |
| 2010/0297620 | A1 | 11/2010 | Umezawa et al. |
| 2011/0039257 | A1 | 2/2011 | Binkowski et al. |
| 2012/0009647 | A1 | 1/2012 | Wood et al. |
| 2012/0117667 | A1 | 5/2012 | Klaubert et al. |
| 2012/0174242 | A1 | 7/2012 | Binkowski et al. |
| 2014/0273156 | A1 | 9/2014 | Fan et al. |
| 2014/0298500 | A1 | 10/2014 | Binkowski et al. |
| 2014/0308211 | A1 | 10/2014 | Binkowski et al. |
| 2016/0115522 | A1 | 4/2016 | Binkowski et al. |

FOREIGN PATENT DOCUMENTS

| | | |
|---|---|---|
| JP | 5501862 | 4/1993 |
| JP | 2002315589 | 10/2002 |
| JP | 2012/090635 | 5/2012 |
| WO | WO 95/18853 | 7/1995 |
| WO | WO 00/14267 | 3/2000 |
| WO | WO 00/24768 | 5/2000 |
| WO | WO 00/24878 | 5/2000 |
| WO | WO 00/75332 | 12/2000 |
| WO | WO 01/20002 | 3/2001 |
| WO | WO 02/06458 | 1/2002 |
| WO | WO 02/08766 | 1/2002 |
| WO | WO 02/16944 | 2/2002 |
| WO | WO 02/059262 | 8/2002 |
| WO | WO 03/066883 | 8/2003 |
| WO | WO 2004/027094 | 4/2004 |
| WO | WO 2004/038039 | 5/2004 |
| WO | WO 2004/043992 | 5/2004 |
| WO | WO 2004/059294 | 7/2004 |
| WO | WO 2004/081189 | 9/2004 |
| WO | WO 2005/015161 | 2/2005 |
| WO | WO 2005/038029 | 4/2005 |
| WO | WO 2005/052186 | 6/2005 |
| WO | WO 2006/023972 | 3/2006 |
| WO | WO 2007/120522 | 10/2007 |
| WO | WO 2008/030968 | 3/2008 |
| WO | WO 2009/049892 | 4/2009 |
| WO | WO 2009/142735 | 11/2009 |
| WO | WO 2011/143339 | 11/2011 |
| WO | WO 2013/071237 | 5/2013 |

OTHER PUBLICATIONS

United States Patent Office Action for U.S. Appl. No. 14/695,944 dated Oct. 5, 2016 (8 pages).

United States Patent Office Action for U.S. Appl. No. 14/990,279 dated Dec. 28, 2016 (13 pages).

Japanese Patent Office Action for Application No. 2014-266438 dated Jun. 5, 2017 (10 pages, English translation included).

United States Patent Office Notice of Allowance for U.S. Appl. No. 14/990,279 dated May 8, 2017 (8 pages).

United States Patent Office Action for U.S. Appl. No. 14/990,279 dated Jul. 12, 2016 (12 pages).

Goodsell, "PDB Molecule of the Month: Estrogen Receptor," http://www.resb.org/pdb/molecules/pdb45_1.html, (observed Dec. 8, 2003) 2 pages.

Baird, G.S. et al., "Circular permutation and receptor insertion within green fluorescent proteins," Proc. Natl. Acad. Sci. USA (1999) 96:11241-11246.

Berman, H.M.et al., "The cAMP binding domain an ancient signaling module," Proc. Natl. Acad. Sci. USA (2000) 102(1):45-50.

Binkowski et al., Engineered luciferases for molecular sensing in living cells, Current Opinion in Biotechnology, vol. 20, Iss. 1, Feb. 2009, pp. 14-18.

Bos, J.L., "Epac: a new cAMP target and new avenues in cAMP research," Nat. Rev. Mol. Cell. Biol. (2003) 4:733-738.

Burbelo, P.D. et al., "Detecting protein-protein interactions using renilla luciferase fusion proteins," Biotech. (2002) 33(5):1044-1049.

Chong, S. et al., "Single-column purification of free recombinant proteins using a self-cleavable affinity tag derived from a protein splicing element," Gene (1997) 192:271-281.

Daugherty et al., "Quantitative analysis of the effect of the mutation frequency on the affinity maturation of single chain Fv antibodies," PNAS USA 97(5):2029-2034 (2000).

Dremier, S. et al., "Search for new cyclic AMP-binding proteins," FEBS Lett. (2003) 546:103-107.

Fan, F. et al., "Novel genetically encoded biosensors using firefly luciferase," ACS Chemical Biology (2008) 3(6):346-351.

Genbank Accession No. AF115480, Sequence ID No. 123, "Mus musculus cAMP-dependent Rap1 guanine-nucleotide exchange factor mRNA, complete cds" (1999) 2 pages.

Genbank Accession No. AF192755, Seq. ID No. 125, "Trypanosoma brucei cyclic nucleotide phophodiesterase (PDE) gene, complete cds" (2002) 2 pages.

Genbank Accession No. M124921, "Rat type II cAMP-dependent protein kinase regulatory subunit mRNA, 3' end" (2002) 2 pages.

Genbank Accession No. NM_002734, "*Homo sapiens* protein kinase, cAMP-dependent, regulatory, type I, alpha (tissue specific extinguisher1), (PRKAR1A), transcript variant 1, mRNA," (2010) 5 pages.

Graf, R. et al., "Random circular permutation of genes and expressed polypeptide chains: application of the method to the catalytic chains of aspartate transcarbamoylase," Proc. Natl. Acad. Sci. USA (1996) 93:11591-11596.

Greer, L.F. et al., "Imaging of light emission from the expression of luciferases in living cells and organisms: a review," Luminescence (2002) 17(1):43-74.

Hanks, S.K. et al., "The eukaryotic protein kinase super family: kinase (catalytic) domain structure and classification," FASEB J. (1995) 9:576-596.

Heinemann, U. et al., "Circular permutation of polypeptide chains: implications for protein folding and stability," Prog. Biophys. Mol. Biol. (1995) 64(2-3):121-143.

Kaihara, A. et al., "Locating a protein-protein interaction in living cells via split renilla luciferase complementation," Anal. Chem. (2003) 75(16):4176-4181.

Kim et al., Circularly permutated bioluminescent probes for illuminating ligand-activated protein dynamics, Bioconjugate Chem, 2008, 19, pp. 2480-2486.

Kunkel, "Rapid and efficient site-specific mutagenesis without phenotypic selection," PNAS USA 82(2):488-492 (1985).

Laxman, B. et al., "Noninvasive real-time imaging of apoptosis," Proc. Natl. Acad. Sci. USA (2002) 99(26):16551-16555.

Leclerc, G.M. et al., "Development of a destabilized firefly luciferase enzyme for measurement of gene expression," BioTech. (2000) 29(3):590-601.

Lee, J-C., "Development of a cell-based assay for monitoring specific hepatitis C virus NS3/4A protease activity in mammalian cells," Anal. Biochem. (2003) 316(2):162-170.

Li, I.T. et al., "Protein biosensors based on the principle of fluorescene resonance energy transfer for monitoring cellular dynamics," Biotech. Lett. (2006) 28(24):1971-1982.

(56) References Cited

OTHER PUBLICATIONS

Littlewood, T.D. et al., "A modified oestrogen receptor ligand-binding domain as an improved switch for the regulation of heterologous proteins," Nucl. Acids Res. (1995) 23(10):1686-1690.
Lorenz, W. et al., "Isolation and expression of a cDNA encoding renilla reniformis luciferase," Proc. Natl. Academ. Sci. USA, May 1991, vol. 88, pp. 4438-4442.
Luker, K.E. et al., "Kinetics of regulated protein-protein interactions revealed with firefly luciferase complementation imaging in cells and living animals," Proc. Natl. Acad. Sci. USA (2004) 101(33):12288-12293.
Lykens et at, "Perforin is a critical physiologic regulator of T-cell activation," Blood, 118:618-626 (2011).
Maldonado, F. et al., "A cDNA clone encoding human cAMP-dependent protein kinase catalytic subunit calpha," Nucl. Acids Res. (1988) 16(16):8189-8190.
Massoud, T.F. et al., "Molecular imaging of homodimeric protein-protein interactions in living subjects," The FASEB Journal (2004) 18:1105-1107.
Mayer, B.J. et al., "Signaling through SH2 and SH3 domains," Trends Cell Biol. (1993) 3:8-13.
Michel, P. et al, "Expression and purification of polyhistidine-tagged firefly luciferase in insect cells—a potential alternative for process scale-up," J. Biotech., Short Technical Reports (2001) 85(1):49-56.
Murray et al., "Codon usage in plant genes" NAR 17: 477-498 (1989).
Nagai, T. et al., "Development of a GFP variant with fast and efficient maturation properties," Seibutsu Butsuri, The Biophysical Society of Japan, (2002) 42(6):305-308.
Nagai, T. et al., Circularly permuted green fluorescent proteins engineered to sense Ca2+, Proc. Natl. Acad. Sci. USA, 2001, 98, pp. 3197-3202.
Nikolaev, V.O. et al., "Novel single chain cAMP sensors for receptor-induced signal propagation," J. Biol. Chem. (2004) 279(36):37215-37218.
Niles, A.L. et al., "Caspase activity assays," Meth. Mol. Biol. (2008) 414:137-150.
Øyen, O. et al., "Human testis cDNA for the regulatory subunit R11α of cAMP-dependent protein kinase encodes an alternative amino-terminal region," FEBS Lett. (1989) 246(1-2):57-64.
Ozawa, T. et al., "Split luciferase as an optical probe for detecting protein-protein interactions in mammalian cells based on protein splicing," Anal. Chem. (2001) 73(11):2516-2521.
Paulmurugan, R. et al., "An intramolecular folding sensor for imaging estrogen receptor-ligand interactions," Proc. Natl. Acad. Sci. USA (2006) 103(43):15883-15888.
Paulmurugan, R. et al., "Molecular imaging of drug-modulated protein-protein interactions in living subjects," Cancer Res. (2004) 64:2113-2119.
Paulmurugan, R. et al., "Monitoring protein-protein interactions using split synthetic renilla luciferase protein-fragment-assisted complementation," Anal. Chem. (2003) 75(7):1584-1589.
Paulmurugan, R. et al., "Novel fusion protein approach for efficient high-throughput screening of small molecule-mediating protein-protein interactions in cells in living animals," Cancer Res. (2005) 65(16):7413-7420.
Paulmurugan, R. eta l., "Noninvasive imaging of protein-protein interactions in living subjects by using reporter protein complementation and reconstitution strategies," Proc. Natl. Acad. Sci. USA (2002) 99(24):15608-15613.
Plainkum, P. et al., "Creation of a zymogen," Nature Structural Biology (2003) 10(2):115-119.
Qian, Z. et al., "Improving the catalytic activity of candida antarctica lipase B by circular permutation," J. Am. Chem. Soc. (2005) 127:13466-13467.
Sadowski, I. et al., "A noncatalytic domain conserved among cytoplasmic protein-tyrosine kinases modifies the kinase function and transforming activity of fujinami sarcoma virus P130 gaag-fps," Mol. Cell. Biol. (1986) 6:4396-4408.
Sala-Newby, G., "Engineering a bioluminescent indicator for cyclic AMP-dependent protein kinase," Biochem. J. (1991) 279(Part 3):727-732.
Sala-Newby, G., "Engineering firefly luciferase as an indicator of cyclic AMP-dependent protein kinase in living cells," FEBS Letters (1992) 307(2):241-244.
Siehler, S., "Cell-based assays in GPCR drug discovery," Biotechnol. J. (2008) 3:471-483.
Spotts, J.M. et al., "Time-lapse imaging of a dynamic phosphorylation-dependent protein-protein interaction in mammalian cells," Proc. Natl Acad. Sci. USA (2002) 99(23):15142-15147.
Tanenbaum, D.M. et al., "Crystallographic comparison of the estrogen and progesterone receptor's ligand binding domains," Proc. Natl. Acad. Sci. USA (1998) 95:5998-6003.
Umezawa, Y., "Assay and screening methods for bioactive substances based on cellular signaling pathways," Reviews in Mol. Biotech. (2001) 82:357-370.
Wada et al., "Codon usage tabulated from the GenBank genetic sequence data" NAR 18: 2367-2411 (1990).
Wang, X. et al., "Effect of removal of the N-terminal amino acid residues on the activity and conformation of firefly luciferase," Intl. J. Biochem. Cell Biol. (2002) 34(8):983-991.
Waud, J.P. et al., "Engineering the C-terminus of firefly luciferase as an indicator of covalent modification of proteins," Biochim. Biophys. Acta (1996) 1292(1):89-98.
Wigdal, S.S. et al., "A novel bioluminescent protease assay using engineered firefly luciferase," Curr. Chem. Genomics (2008) 2(1):16-28.
Wiley, S.R. et al., "Identification and characterization of a new member of the TNF family that induces apoptosis," Immunity (1995) 3(6):673-682.
Ye, L. et al., "Cloning and sequencing of a cDNA for firefly luciferase from photuris pennsylvanica," Biochimica et Biophysica Acta (1997) 1339:39-52.
Zagotta, W.N. et al., "Structural basis for modulation and agonist specificity of HCN pacemaker channels," Nature (2003) 425:200-205.
Zako, T. et al., "Luminescent and substrate binding activities of firefly luciferase N-terminal domain," Biochim. Biophys. Acta—Proteins & Proteomics (2003) 1649(2):183-189.
Zhang et al., "A Simple Statistical Parameter for Use in Evaluation and Validation of High Throughput Screening Assays," Biomol Screen. 4:67-73 (1999).
Zhang, J. et al., "Creating new fluorescent probes for cell biology," Mol. Cell Biol. (2002) 3:906-918.
Zhao, H. et al., "Emission spectra of bioluminescent reporters and interaction with mammalian tissue determine the sensitivity of detection in vivo," J. Biomed. Optics (2005) 10(4):041230-1-041230-9.
De Wet, J.R., et al., 1987, "Firefly luciferase gene: structure and expression in mammalian cells", Molecular and Cellular Biology, vol. 7, No. 2, pp. 725-737.
Tatsumi, H., et al., 1992, "Molecular cloning and expression in *Escherichia coli* of a eDNA clone encoding luciferase of a firefly, *Luciola lateralis*", Biochimica et Biophysica Acta, vol. 1131, pp. 161-165.
Devine, J.H., et al., 1993, "Luciferase from the East European firefly *Luciola mingrelica*: cloning and nucleotide sequence of the eDNA, overexpression in *Escherichia coli* and purification of the enzyme", Biochimica et Biophysica Acta, vol. 1173, pp. 121-132.
Sala-Newby, G.B., et al., 1996, "Sequence and biochemical similarities between the luciferases of the glow-worm *Lampyris noctiluca* and the firefly *Photinus pyralis*", Biochemical Journal, vol. 313, pp. 761-767.
Alipour B.S., et al., 2004, "Molecular cloning, sequence analysis, and expression of a eDNA encoding the luciferase from the glow-worm, *Lampyris turkestanicus*", Biochemical and Biophysical Research Communications, vol. 325, pp. 215-222.
Viviani, V. R., et al., 2004, "Cloning and characterization of the eDNA for the Brazilian Cratomorphus distinctus larval firefly luciferase: similarities with European Lampyris noctiluca and Asiatic Pyrocoelia luciferases", Comparative Biochemistry and Physiology, Part B, vol. 139, pp. 151-156.

(56) References Cited

OTHER PUBLICATIONS

Li, X., et al., 2006, "Phylogenetic relationship of the firefly, Diaphanes pectineal is based on the DNA sequence and gene structure of luciferase", Dong Wu Xue Za Zhi [Zoological Research], vol. 27, No. 4, pp. 367-374.
Oba, Y., et al., 2010, "Identification and characterization of a luciferase isotype in the Japanese firefly, *Luciola cruciata*, involving in the dim glow of firefly eggs", Biochemistry, vol. 49, pp. 10788-10795.
GenBank Accession AAT93028 (2004).
GenBank Accession AF025843 (2000).
GenBank Accession AF115480 (1999).
GenBank Accession BC036285 (2005).
GenBank Accession BC075800 (2005).
GenBank Accession NM_002599 (2006).
GenBank Accession NM_005417 (2006).
GenBank Accession NM_006258 (2006).
Wilson et al., Annu. Rev. Cell Dev. Biol., 1998, vol. 14, pp. 197-230.
Thornberry, N. A., 1997, "A combinatorial approach defines specificities of members of the caspase family and granzyme B. Functional relationships established for key mediators of apoptosis", The Journal of Biological Chemistry, vol. 272, No. 29, pp. 17907-17911.
Li, H., et al., 1998, "Cleavage of BID by caspase 8 mediates the mitochondrial damage in the Fas pathway of apoptosis", Cell, vol. 94, pp. 491-501.
Gross, A., et al., 1999, "Caspase cleaved BID targets mitochondria and is required for cytochrome c release, while BCL-XL prevents this release but not tumor necrosis factor-R1/Fas death", The Journal of Biological Chemistry, vol. 274, No. 2, pp. 1156-1163.
Kanno Akira et al., "Detection of apoptosis using cyclic luciferase in living mammals," Methods in Molecular Biology, 2009, vol. 574, pp. 105-114.
Canadian Patent Office Action for Application No. 2648263 dated Feb. 8, 2011 (4 pages).
Chinese Patent Office Action for Application No. 200780020577.7 dated Jun. 4, 2010 (9 pages) with translation.
European Patent Office Action for Application No. 07754666.1 dated Jan. 11, 2010 (3 pages).
European Patent Office Action for Application No. 07754666.1 dated Feb. 13, 2009 (6 pages).
European Patent Office Action for Application No. 07754666.1 dated Aug. 19, 2011 (4 pages).
European Patent Office Partial Search Report for Application No. 11155576.9 dated May 3, 2011 (7 pages).
European Patent Office Action for Application No. 11155576.9 dated Sep. 9, 2011 (12 pages).
European Patent Office Action for Application No. 07754666.1 dated Jun. 11, 2012 (4 pages).
European Patent Office Action for Application No. 07754666.1 dated Mar. 25, 2013 (4 pages).
European Patent Office Action for Application No. 11155576.9 dated Jul. 13, 2012 (4 pages).
European Patent Office Action for Application No. 11155576.9 dated Nov. 20, 2013 (4 pages).
European Patent Office Action for Application No. 07754666.1 dated Feb. 11, 2014 (5 pages).
European Patent Office Action for Application No. 04809862.8 dated Mar. 19, 2007 (3 pages).
European Patent Office Examination Report for Application No. 04809862.8 dated Dec. 28, 2007 (3 pages).
European Patent Office Action for Application No. 04809862.8 dated Apr. 8, 2009 (4 pages).
European Patent Office Examination Report for Application No. 04809862.8 dated Dec. 23, 2009 (4 pages).
European Patent Office Action for Application No. 04809862.8 dated Dec. 1, 2010 (4 pages).
European Patent Office Action for Application No. 10182746.7 dated Feb. 10, 2011 (7 pages).
European Patent Office Action for Application No. 10182746.7 dated Jan. 17, 2013 (4 pages).
European Patent Office Action for Application No. 10182746.7 dated Nov. 21, 2013 (3 pages).
European Patent Office Action for Application No. 10182742.6 dated Jan. 10, 2013 (5 pages).
European Patent Office Action for Application No. 10182742.6 dated Oct. 15, 2013 (4 pages).
European Patent Office Action for Application No. 10182742.6 dated Apr. 2, 2014 (5 pages).
European Patent Office Action for Application No. 09750966.5 dated Apr. 19, 2011 (3 pages).
European Patent Office Action for Application No. 11720279.6 dated Sep. 24, 2013 (7 pages).
European Patent Office Action for Application No. 11720279.6 dated May 2, 2014 (5 pages).
European Patent Office Action for Application No. 12791055.2 dated Feb. 12, 2016 (17 pages).
International Search Report and Written Opinion for Application No. PCT/US2007/008176 dated Dec. 27, 2007 (18 pages).
Invitation to Pay Additional Fees and Partial Search Report for Application No. PCT/US2007/008176 dated Feb. 10, 2007 (7 pages).
International Search Report and Written Opinion for Application No. PCT/US2004/032705 dated Dec. 9, 2005 (20 pages).
Invitation to Pay Additional Fees and Partial Search Report for Application No. PCT/US2004/032705 dated May 19, 2005 (9 pages).
International Search Report and Written Opinion for Application No. PCT/US2009/003132 dated Nov. 12, 2009 (10 pages).
International Search Report and Written Opinion for Application No. PCT/US2011/036110 dated Jul. 28, 2011 (15 pages).
PCT/US2012/064675 Invitation to Pay Additional Fees and International Search Report dated Jan. 31, 2013 (9 pages).
PCT/US2012/064675 International Search Report and Written Opinion dated Apr. 3, 2013 (19 pages).
Japanese Patent Office Action for Application No. 2006-534242 dated Sep. 1, 2010 (9 pages).
Japanese Patent Office Action for Application No. 2006-534242 dated Dec. 15, 2011 (6 pages) with English translation.
Japanese Patent Office Action for Application No. 2011-43966 dated May 1, 2013 (6 pages) English translation.
Japanese Patent Office Action for Application No. 2006-534242 dated Feb. 4, 2014 (8 pages, English translation included).
Japanese Patent Office Action for Application No. 2011-43966 dated Jul. 2, 2014 (7 pages, English translation included).
Japanese Patent Office Action for Application No. 2011-043966 dated Feb. 25, 2015 (6 pages—English summary included).
Japanese Patent Office Action for Application No. 2009-504249 dated Jun. 9, 2011 (10 pages).
Japanese Patent Office Action for Application No. 2011-269846 dated May 14, 2012 (Original and English Translation, 8 pages).
Japanese Patent Office Action for Application No. 2009-504249 dated May 10, 2012 (English Translation Only, 4 pages).
Japanese Patent Office Action for Application No. 2009-504249 dated Feb. 7, 2013 (Original and English Translation, 7 pages).
Japanese Patent Office Action for Application No. 2012-248580 dated May 1, 2014 (5 pages, English translation included).
Japanese Patent Office Action for Application No. 2009-504249 dated May 26, 2014 (5 pages, English translation.
Japanese Patent Office Action for Application No. 2009-504249 dated Dec. 8, 2014 (2 pages).
Japanese Patent Office Action for Application No. 2011-510512 dated Nov. 25, 2013 (Original, 5 pages).
Japanese Patent Office Action for Application No. 2013-510280 dated Jun. 29, 2015 (Original and English Translation 11 pages).
Japanese Patent Office Action for Application No. 2014-224633 dated Oct. 5, 2015 (12 pages—including translation).
Japanese Patent Office Action for Application No. 2014-266438 dated Oct. 28, 2015 (5 pages—including translation).
Japanese Patent Office Action for Application No. 2013-510280 dated Jan. 25, 2016 (Original and English Translation 3 pages).

(56) References Cited

OTHER PUBLICATIONS

Japanese Patent Office Action for Application No. 2011-510512 dated Mar. 9, 2016 (12 pages including translation).
Japanese Patent Office Action for Application No. 2014-266438 dated Jun. 20, 2016 (8 pages including translation).
Singapore Patent Office Search Report and Written Opinion for Application No. 200807470-0 dated Jan. 29, 2010 (17 pages).
United States Patent Office Action for U.S. Appl. No. 10/957,433 dated Jan. 7, 2010 (6 pages).
United States Patent Office Action for U.S. Appl. No. 10/957,433 dated Jul. 21, 2009 (8 pages).
United States Patent Office Action for U.S. Appl. No. 10/957,433 dated Feb. 12, 2009 (5 pages).
United States Patent Office Action for U.S. Appl. No. 10/957,433 dated Sep. 4, 2008 (7 pages).
United States Patent Office Action for U.S. Appl. No. 10/957,433 dated Mar. 21, 2008 (10 pages).
United States Patent Office Action for U.S. Appl. No. 10/957,433 dated Oct. 12, 2007 (9 pages).
United States Patent Office Action for U.S. Appl. No. 10/957,433 dated Mar. 11, 2011 (6 pages).
United States Patent Office Action for U.S. Appl. No. 10/957,433 dated Jan. 31, 2012 (3 pages).
United States Patent Office Action for U.S. Appl. No. 13/454,464 dated Apr. 30, 2013 (8 pages).
United States Patent Office Action for U.S. Appl. No. 11/732,105 dated Jun. 7, 2011 (22 pages).
United States Patent Office Action for U.S. Appl. No. 11/732,105 dated Nov. 23, 2011 (19 pages).
United States Patent Office Action for U.S. Appl. No. 11/732,105 dated Sep. 4, 2013 (10 pages).
United States Patent Office Action for U.S. Appl. No. 11/732,105 dated May 23, 2014 (10 pages).
United States Patent Office Action for U.S. Appl. No. 12/454,643 dated Jan. 31, 2012 (13 pages).
United States Patent Office Final Rejection for U.S. Appl. No. 12/454,643 dated Jun. 15, 2012 (9 pages).
United States Patent Office Action for U.S. Appl. No. 12/454,643 dated Jun. 24, 2014 (14 pages).
United States Patent Office Action for U.S. Appl. No. 13/105,648 dated Jun. 20, 2013 (14 pages).
United States Patent Office Notice of Allowance for U.S. Appl. No. 13/105,648 dated Jan. 10, 2014 (12 pages).
United States Patent Office Action for U.S. Appl. No. 11/732,105 dated Oct. 9, 2014 (11 pages).
United States Patent Office Action for U.S. Appl. No. 13/674,655 dated Oct. 27, 2014 (21 pages).
United States Patent Office Notice of Allowance for U.S. Appl. No. 12/454,643 dated Jan. 26, 2015 (19 pages).
United States Patent Office Action for U.S. Appl. No. 14/180,451 dated Feb. 11, 2015 (9 pages).
United States Patent Office Action for U.S. Appl. No. 14/269,669 dated Feb. 2, 2015 (11 pages).
United States Patent Office Action for U.S. Appl. No. 14/269,689 dated Feb. 4, 2015 (16 pages).
United States Patent Office Action for U.S. Appl. No. 13/674,655 dated Apr. 1, 2015 (10 pages).
United States Patent Office Final Action for U.S. Appl. No. 14/269,669 dated Jul. 20, 2015 (11 pages).
United States Patent Office Notice of Allowance for U.S. Appl. No. 14/269,689 dated Sep. 25, 2015 (9 pages).
United States Patent Office Final Action for U.S. Appl. No. 14/180,451 dated Jul. 29, 2015 (5 pages).
United States Patent Office Final Action for U.S. Appl. No. 11/732,105 dated Oct. 9, 2015 (11 pages).
United States Patent Office Notice of Allowance for U.S. Appl. No. 13/674,655 dated Nov. 5, 2015 (10 pages).
United States Patent Office Notice of Allowance for U.S. Appl. No. 14/269,669 dated Nov. 10, 2015 (4 pages).
United States Patent Office Notice of Allowance for U.S. Appl. No. 14/269,669 dated Jan. 13, 2016 (9 pages).
United States Patent Office Notice of Allowance for U.S. Appl. No. 11/732,105 dated Feb. 8, 2016 (15 pages).
Wigdal et al., "Sensitive and Flexible Protease Assay without the Need for Chemical Synthesis," Promega Corporation, 2009, pp. 1-9.
European Patent Office Action for Application No. 15189725.3 dated Sep. 4, 2017 (8 pages).
United States Patent Office Notice of Allowance for U.S. Appl. No. 14/695,944 dated Sep. 25, 2017 (8 pages).
Backes et al., "GraBCas: a bioinformatics tool for score-based prediction of Caspase- and Granzyme B-cleavage sites in protein sequences," Nucleic Acids Research, 2005, vol. 33, W208-W213.

| | |
|---|---|
| 1 | MVKREKNVIYGPEPLHPLEDLTAGEMLFRALRKHSHLPQALVDVVGDESL |
| 51 | SYKEFFEATVLLAQSLHNCGYKMNDVVSICAENNTRFFIPVIAAWYIGMI |
| 101 | VAPVNESYIPDELCKVMGISKPQIVFTTKNILNKVLEVQSRTNFIKRIII |
| 151 | LDTVENIGHCESLPNFISRYSDGNIANFKPLHFDPVEQVAAILCSSGTTG |
| 201 | LPKGVMQTHQNICVRLIHALDPRVGTQLIPGVTVLVYLPFFHAFGFSITL |
| 251 | GYFMVGLRVIMFRRFDQEAFLKAIQDYEVRSVINVPSVILFLSKSPLVDK |
| 301 | YDLSSLRELCCGAAPLAKEVAEVAAKRLNLPGIRCGFGLTESTSANIHSL |
| 351 | RDEFKSG**S**LGRVTPLMAAKIADRE**T**GKA**L**GPNQVGELCIKGPMVSKG**YVN** |
| 401 | **NVEATKEAI**DDDGWLHSGDFGYYDEDEHFYVVDRYKELIKYKGSQVAPAE |
| 451 | LEEILLKNPCIRDVAVVGIPDLEAGELPSAFVVKQPGKEITAKEVYDYLA |
| 501 | ERVSHTKYLRGGVRFVDSIPRNVTGKITRKELLKQLLEKAGG |

*FIG. 1*

| | | | | | |
|---|---|---|---|---|---|
| 1 | MEDAKNIKKG | PAPFYPLEDG | TAGEQLHKAM | KRYALVPGTI | AFTDAHIEVD |
| 51 | ITYAEYFEMS | VRLAEAMKRY | GLNTNHRIVV | CSENSLQFFM | PVLGALFIGV |
| 101 | AVAPANDIYN | ERELLNSMGI | SQPTVVFVSK | KGLQKILNVQ | KKLPIIQKII |
| 151 | IMDSKTDYQG | FQSMYTFVTS | HLPPGFNEYD | FVPESFDRDK | TIALIMNSSG |
| 201 | STGLPKGVAL | PHRTACVRFS | HARDPIFGNQ | IIPDTAILSV | VPFHHGFGMF |
| 251 | TTLGYLICGF | RVVLMYRFEE | ELFLRSLQDY | KIQSALLVPT | LFSFFAKSTL |
| 301 | IDKYDLSNLH | EIASGGAPLS | KEVGEAVAKR | FHLPGIRQGY | GLTETTSAIL |
| 351 | ITPEGDDKPG | AVGKVVPFFE | AKVVDLDTGK | TLGVNQRGEL | CVRGPMIMSG |
| 401 | YVNNPEATNA | LIDKDGWLHS | GDIAYWDEDE | HFFIVDRLKS | LIKYKGYQVA |
| 451 | PAELESILLQ | HPNIFDAGVA | GLPDDDAGEL | PAAVVVLEHG | KTMTEKEIVD |
| 501 | YVASQVTTAK | KLRGGVVFVD | EVPKGLTGKL | DARKIREILI | KAKKGGKIAV |

(SEQID NO.: 210)

*FIG. 2*

42 amino acid Gly/Ser rich peptide:

GSSGGSGGSGGGSGGGSGGSRGGGTGGSGGGSGGGTSGGGSSG

PVGTHEMEEELAEAVALLSQRGPDALLTVALRKPPGQRTDEELDLIFEELLHIKA
VAHLSNSVKRELAAVLLFEPHSKAGTVLFSQGDKGTSWYIIWKGSVNVVTHGKG
LVTTLHEGDDFGQLALVNDAPRAATIILREDNCHFLRVDKQDFNRIIKDVEAKTM
RLEEHG (residues 10-519) (SEQ ID NO: 13)

AIAPVGTHEMEEELAEAVALLSQRGPDALLTVALRKPPGQRTDEELDLIFEELLHI
KAVAHLSNSVKRELAAVLLFEPHSKAGTVLFSQGDKGTSWYIIWKGSVNVVTHG
KGLVTTLHEGDDFGQLALVNDAPRAATIILREDNCHFLRVDKQDFNRIIKDVEAK
TMRLEEHGV (residues 1-520) (SEQ ID NO: 14)

GCGATCGCCCCCGTAGGTACCCACGAAATGGAAGAAGAACTTGCTGAAGCTG
TAGCCTTACTTAGTCAACGCGGACCTGATGCCTTATTAACCGTAGCCCTTCGT
AAACCTCCCGGCCAACGCACAGACGAAGAACTGGACCTCATTTTTGAAGAAC
TTTTGCATATTAAAGCCGTTGCGCATCTCTCTAACTCTGTTAAACGTGAACTT
GCTGCCGTACTTCTCTTCGAACCCCATTCAAAAGCCGGCACTGTTTTATTCTC
CCAAGGTGATAAAGGTACTTCTTGGTATATTATTTGGAAAGGATCAGTTAAC
GTTGTAACCCACGGAAAAGGTCTCGTAACTACATTACATGAAGGAGATGATT
TTGGACAACTCGCCTTAGTAAATGACGCCCCACGTGCTGCCACAATTATTCTG
CGCGAAGACAATTGCCATTTTTTACGTGTCGATAAACAGGATTTCAATCGTAT
TATTAAAGATGTCGAAGCGAAAACAATGCGTTTAGAAGAACATGGAGTTTAA
AC (SEQ ID NO: 15)

*FIG. 5C*

(X=4,Y=20): GSTG-R2βB-GSGGSGGSGGTSGGSGGSSG (X=10,Y=4): GSSGGSGGSG-R2βB-GSSG (X=10,Y=20): GSSGGSGGSG-R2βB-GSGGSGGSGGTSGGSGGSSG

<u>42 amino acid Gly/Ser rich peptide:</u>

GSSGGSGGSGGGSGGSGGSRGGGTGGSGGSGGTSGGSGGSSG

| | | AVG | | | Stdev | |
|---|---|---|---|---|---|---|
| CLONE | DESCRIPTION | NO cAMP | + cAMP | FOLD | NO cAMP | + cAMP |
| 201325.50.A7 | FL RENILLA | 67043672 | 76377096 | 1.1 | 1351663 | 478060.9 |
| 201325.15.A1 | CPM hRL91-42AA | 589089 | 695895 | 1.2 | 27630.88 | 16837.62 |
| 201325.44.H6 | CPM hRL91-4/20 | 607 | 69994 | 115.2 | 54.51911 | 1491.39 |
| 201325.15.B6 | CPM hRL223-42AA | 731 | 791 | 1.1 | 41.95633 | 29.50141 |
| 201325.33.C9 | CPM hRL223-4/20 | 79 | 158 | 2.0 | 6.027714 | 13.74773 |
| 201325.54.E2 | CPM hRL223-10/4 | 72 | 130 | 1.8 | 11.37248 | 17.34935 |
| 201325.54.E12 | CPM hRL223-10/20 | 128 | 250 | 1.9 | 3.511885 | 28.79236 |
| | NO DNA | 65 | 70 | 1.1 | 3.21455 | 2.081666 |
| | | | | | | |
| pBFB41 | Luc-10/4 | 102 | 8754 | 85.8 | 2.645751 | 1445.777 |

RENILLA ASSAY +/- 100 uM cAMP

| CLONE | DESCRIPTION | NO cAMP | + cAMP | FOLD |
|---|---|---|---|---|
| 201325.50.A7 | FL REN | 83996195 | 1.02E+08 | 1.2 |
| 201325.15.A1 | 91-42AA | 792579.7 | 1052418 | 1.3 |
| 201325.44.H6 | 91-4/20 | 993 | 145194.3 | 146.2 |
| 201325.58.E11 | 91-10/20 | 2431.667 | 245862.7 | 101.1 |
| 201325.15.B6 | 223-42AA | 653.6667 | 768.3333 | 1.2 |
| 201325.54.E12 | 223-10/20 | 152.3333 | 323.3333 | 2.1 |
| | NO DNA | 60.66667 | 60.66667 | 1.0 |
| | | | | |
| pBFB41 | Luc-10/4 | 155.3333 | 13812.33 | 88.9 |

| Stdev | Stdev |
|---|---|
| 1609109.21 | 2292161.12 |
| 22421.24 | 19469.28 |
| 67.82 | 2467.73 |
| 310.55 | 7741.53 |
| 3.21 | 41.79 |
| 8.50 | 18.82 |
| 1.15 | 11.93 |
| 5.13 | 5.13 |
| 16.62 | 215.22 |

Z' in 384 wells is .59 for 10R2betaB10 and .65 for 10R2betab4

For 96 well plates Z' is .87 for both

GCTTAAAAGCTTTAATACGACTCACTATAGGGCTAGCGATCGCCATGGACAC
CGCTATCCTCAGCGTGGTGCCATTTCACCACGGCTTCGGCATGTTCACCACGC
TGGGCTACTTGATCTGCGGCTTTCGGGTCGTGCTCATGTACCGCTTCGAGGAG
GAGCTATTCTTGCGCAGCTTGCAAGACTATAAGATTCAATCTGCCCTGCTGGT
GCCCACACTATTTAGCTTCTTCGCTAAGAGCACTCTCATCGACAAGTACGACC
TAAGCAACTTGCACGAGATCGCCAGCGGCGGGGCGCCGCTCAGCAAGGAGG
TAGGTGAGGCCGTGGCCAAACGCTTCCACCTACCAGGCATCCGCCAGGGCTA
CGGCCTGACAGAAACAACCAGCGCCATTCTGATCACCCCCGAAGGGGACGAC
AAGCCTGGCGCAGTAGGCAAGGTGGTGCCCTTCTTCGAGGCTAAGGTGGTGG
ACTTGGACACTGGTAAGACACTGGGTGTGAACCAGCGCGGCGAGCTGTGCGT
CCGTGGCCCCATGATCATGAGCGGCTACGTTAACAACCCCGAGGCTACAAAC
GCTCTCATCGACAAGGACGGCTGGCTGCACAGCGGCGACATCGCCTACTGGG
ACGAGGACGAGCACTTCTTCATCGTGGACCGGCTGAAGAGCCTGATCAAATA
CAAGGGCTACCAGGTAGCCCCAGCCGAACTGGAGAGCATCCTGCTGCAACAC
CCCAACATCTTCGACGCCGGGGTCGCCGGCCTGCCCGACGACGATGCCGGCG
AGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGC
GGTGGTGTTGTGTTCGTGGACGAGGTGCCTAAAGGACTGACCGGCAAGTTGG
ACGCCCGCAAGATCCGCGAGATTCTCATTAAGGCCAAGAAGGGCTCGAGCGG
AGGTTCAGGCGGTTCCGGAGGAGGTTCTGGCGGATCAGGCGGTTCGCGAGGA
GGTGGCACCGGTGGATCCGGTGGCAGCGGAGGGACGTCAGGTGGATCTGGA
GGGAGCTCCGGTGCCAAAAACATTAAGAAGGGCCCAGCGCCATTCTACCCAC
TCGAAGACGGGACCGCCGGCGAGCAGCTGCACAAAGCCATGAAGCGCTACG
CCCTGGTGCCCGGCACCATCGCCTTTACCGACGCACATATCGAGGTGGACAT
TACCTACGCCGAGTACTTCGAGATGAGCGTTCGGCTGGCAGAAGCTATGAAG
CGCTATGGGCTGAATACAAACCATCGGATCGTGGTGTGCAGCGAGAATAGCT
TGCAGTTCTTCATGCCCGTGTTGGGTGCCCTGTTCATCGGTGTGGCTGTGGCC
CCAGCTAACGACATCTACAACGAGCGCGAGCTGCTGAACAGCATGGGCATCA
GCCAGCCCACCGTCGTATTCGTGAGCAAGAAAGGGCTGCAAAAGATCCTCAA
CGTGCAAAAGAAGCTACCGATCATACAAAAGATCATCATCATGGATAGCAAG
ACCGACTACCAGGGCTTCCAAAGCATGTACACCTTCGTGACTTCCCATTTGCC
ACCCGGCTTCAACGAGTACGACTTCGTGCCCGAGAGCTTCGACCGGGACAAA
ACCATCGCCCTGATCATGAACAGTAGTGGCAGTACCGGATTGCCCAAGGGCG
TAGCCCTACCGCACCGCACCGCTTGTGTCCGATTCAGTCATGCCCGCGACCCC
ATCTTCGGCAACCAGATCATCCCCGTTTAAACTCTAGAGTCGGG (SEQ ID NO: 16)

*FIG.20*

| | |
|---|---|
| (X=4, Y=4) | GSTG-GAF-GSSG |
| (X=10,Y=10) | GSSGGSGGSG-GAF-GSGGSGGSSG |
| (X=20, Y=20) | GSSGGSGGSGGGSGGSGGSG-GAF-GSGGSGGSGGTSGGSGGSSG |
| 42 RT control | GSSGGSGGSGGGSGGSGGSRGGGTGGSGGSGGTSGGSGGSSG |

Troponin C sensors (TnC)

(X=4, Y=4) GSTG-TnC-GSSG
(X=10,Y=10) GSSGGSGGSG-TnC-GSGGSGGSSG
(X=20, Y=20) GSSGGSGGSGGGSGGSGGSG-TnC-GSGGSGGSGGTSGGSGGSSG
42 RT control GSSGGSGGSGGGSGGSGGSRGGGTGGSGGSGGTSGGSGGSSG Calmodulin sensors (CaM)

(X=8, Y=8) LEGSGGGG-CaM-GGGGSGPW

| CP site | X value | Y value | Clone ID |
|---|---|---|---|
| 37 | 38 | 35 | pBFB252 |
| 47 | 48 | 45 | pBFB253 |
| 75 | 76 | 73 | pBFB264 |
| 83 | 84 | 81 | pBFB265 |
| 107 | 108 | 105 | pBFB266 |
| 144 | 145 | 142 | pBFB267 |
| 160 | 161 | 158 | pBFB268 |
| 174 | 175 | 172 | pBFB269 |
| 188 | 189 | 186 | pBFB254 |
| 198 | 199 | 198 | pBFB251 |
| 205 | 206 | 198 | pBFB247 |
| 225 | 226 | 223 | pBFB255 |
| 233 | 234 | 233 | pBFB151 |
| 242 | 243 | 240 | pBFB257 |
| 255 | 256 | 253 | pBFB271 |
| 268 | 269 | 266 | pBFB248 |
| 308 | 309 | 306 | pBFB259 |
| 316 | 317 | 314 | pBFB260 |
| 358 | 359 | 355 | pBFB249 |
| 377 | 378 | 375 | pBFB261 |
| 403 | 404 | 401 | pBFB262 |
| 435 | 436 | 433 | pBFB270 |
| 490 | 491 | 488 | pBFB272 |

*FIG. 26*

Renilla Insertion RIIBetaB constructs

| Clone | split site | construct | description |
|---|---|---|---|
| 201325.165.A2 | 91 | 42AA | Renilla 1 - 91 / 42 amino acid linker / Renilla 92 - 311 |
| 201325.165.C5 | 229 | 42AA | Renilla 1 - 229 / 42 amino acid linker / Renilla 230 - 311 |
| 201325.177.B7 | 223 | 42AA | Renilla 1 - 223 / 42 amino acid linker / Renilla 224 - 311 |
| 201360.17.A3 | 91 | 4/4 RIIBetaB | Renilla 1 - 91 / 4 amino acid linker / RIIBetaB / 4 amino acid linker / Renilla 92 - 311 |
| 201360.17.A12 | 91 | 4/20 RIIBetaB | Renilla 1 - 91 / 4 amino acid linker / RIIBetaB / 20 amino acid linker / Renilla 92 - 311 |
| 201360.17.D7 | 91 | 10/4 RIIBetaB | Renilla 1 - 91 / 10 amino acid linker / RIIBetaB / 4 amino acid linker / Renilla 92 - 311 |
| 201360.24.A1 | 223 | 4/4 RIIBetaB | Renilla 1 - 223 / 4 amino acid linker / RIIBetaB / 4 amino acid linker / Renilla 224 - 311 |
| 201360.24.A10 | 223 | 4/20 RIIBetaB | Renilla 1 - 223 / 4 amino acid linker / RIIBetaB / 20 amino acid linker / Renilla 224 - 311 |
| 201360.24.C5 | 223 | 10/4 RIIBetaB | Renilla 1 - 223 / 10 amino acid linker / RIIBetaB / 4 amino acid linker / Renilla 224 - 311 |
| 201360.24.E11 | 223 | 10/20 RIIBetaB | Renilla 1 - 223 / 10 amino acid linker / RIIBetaB / 20 amino acid linker / Renilla 224 - 311 |
| 201360.19.E9 | 229 | 4/4 RIIBetaB | Renilla 1 - 229 / 4 amino acid linker / RIIBetaB / 4 amino acid linker / Renilla 230 - 311 |
| 201360.65.A1 | 229 | 4/20 RIIBetaB | Renilla 1 - 229 / 4 amino acid linker / RIIBetaB / 20 amino acid linker / Renilla 230 - 311 |

Nomenclature for Renilla Insertion RIIBetaB:
hRL91 = split at 91 / 92
hRL223 = split at 223 / 224
hRL229 = split at 229 / 230

*FIG. 29*

CP Renilla RIIBetaB Linker length study constructs

| Name | Vector | Description |
|---|---|---|
| 201325.50.A7 | pBFB-FL Renilla | Full length |
| 201325.15.A1 | pBFB-CPM hRL91 | 42AA |
| 201325.44.H6 | pBFB-CPM hRL91 | 4/20 RIIBetaB |
| 201325.58.E11 | pBFB-CPM hRL91 | 10/20 RIIBetaB |
| pBFB# | Sub-clone # | Description |
| pBFB197 | -1 | pCPM91Ren/human R2betaB [4,4] |
| pBFB198 | -1 | pCPM91Ren/human R2betaB [4,6] |
| pBFB199 | -1 | pCPM91Ren/human R2betaB [4,8] |
| pBFB201 | -2 | pCPM91Ren/human R2betaB [4,12] |
| pBFB202 | -3 | pCPM91Ren/human R2betaB [4,14] |
| pBFB203 | -12 | pCPM91Ren/human R2betaB [4,16] |
| pBFB205 | -1 | pCPM91Ren/human R2betaB [4,20] |
| pBFB206 | -4 | pCPM91Ren/human R2betaB [10,10] |
| pBFB207 | -1 | pCPM91Ren/human R2betaB [20,20] |
| pBFB208 | -4 | pCPM91Ren/human R2betaB [20,4] |
| pBFB209 | -1 | pCPM91Ren/human R2betaB [20,10] |

*FIG. 31*

CP Renilla RIAlphaB Linker length study constructs

| Name | Vector | Description |
|---|---|---|
| 201325.50.A7 | pBFB-FL Renilla | Full length |
| 201325.15.A1 | pBFB-CPM hRL91 | 42AA |
| pBFB210 | -1 | pCPM91Ren/human RIalphaB (245-381) [4,20] |
| pBFB211 | -1 | pCPM91Ren/human RIalphaB (245-381) [4,4] |
| pBFB212 | -1 | pCPM91Ren/human RIalphaB (245-381) [10,10] |
| pBFB213 | -5 | pCPM91Ren/human RIalphaB (245-381) [20,20] |

*FIG. 33*

```
1    mgvkvlfali ciavaeakpt ennedfniva vasnfattdl dadrgklpgk klplevlkem
61   eanarkagct rgcliclshi kctpkmkkfi pgrchtyegd kesaqggige aivdipeipg
121  fkdlepmeqf iaqvdlcvdc ttgclkglan vqcsdllkkw lpqrcatfas kiqgqvdkik
181  gaggd (SEQ ID NO: 204)
```

| | 5min | 10min | 15min | 20min | 30min | 45min | 60min | 90min | |
|---|---|---|---|---|---|---|---|---|---|
| EC50 | 4.0e-008 | 5.5e-008 | 7.1e-008 | 8.4e-008 | 9.6e-008 | 9.7e-008 | 1.2e-007 | 1.7e-007 | M |

| | Isoproterenol | Metaproterenol | Formoterol | Salbutamol |
|---|---|---|---|---|
| EC50 | 4.85e-009 | 1.02e-007 | 6.42e-010 | 2.37e-008 |

| | Alprenolol | Atenolol | Butoxamine | ICI 118551 | Propranolol |
|---|---|---|---|---|---|
| EC50 | 1.77e-011 | 1.05e-006 | 3.55e-007 | 4.16e-010 | 9.18e-012 |

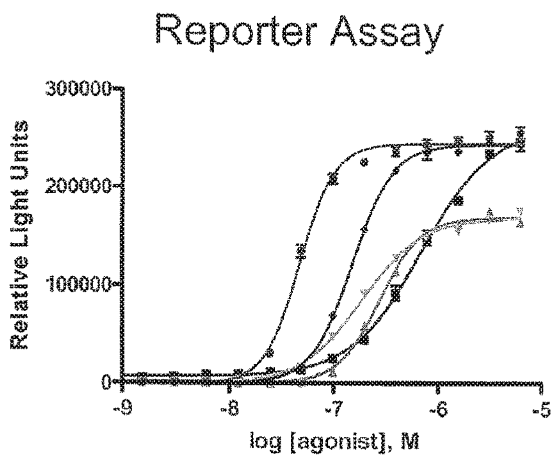
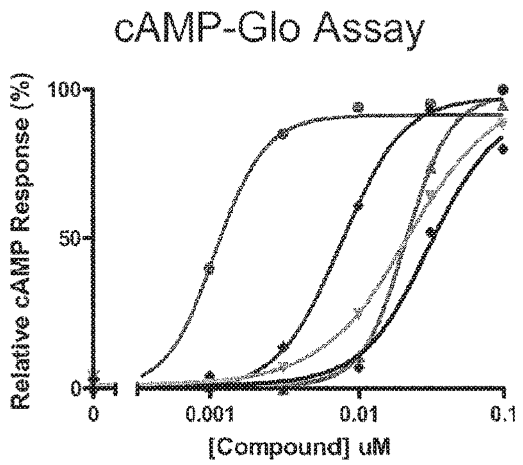
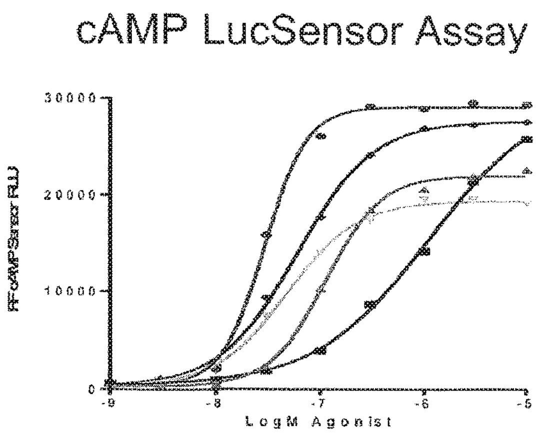
EC50 ranking
| | Reporter | cAMP-Glo | LucSensor |
|---|---|---|---|
| Dihydrexidine | 1 | 1 | 1 |
| Dopamine | 2 | 2 | 2,3 |
| SKF38393 | 3 | 3,4 | 2,3 |
| Apomorphine | 4 | 3,4 | 4 |
| Pergolide | 5 | 5 | 5 |
*FIG. 50*

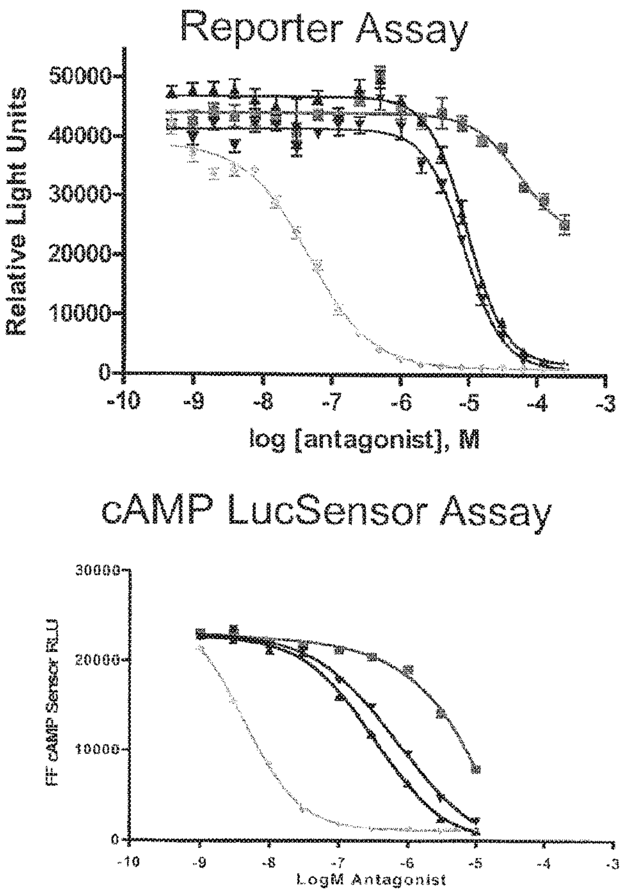
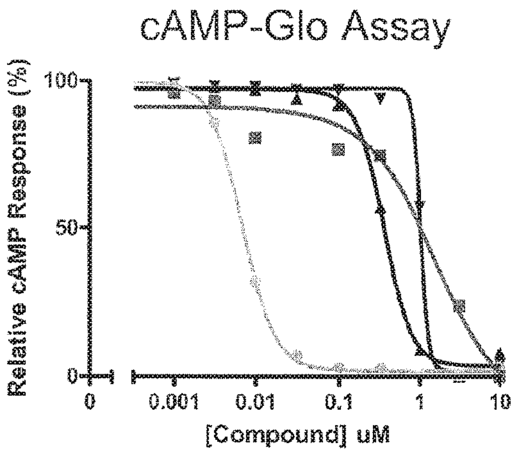
IC50 ranking
| | Reporter | cAMP-Glo | LucSensor |
|---|---|---|---|
| SCH23390 | 1 | 1,2 | 1 |
| Haloperidol | 2 | 1,2 | 2 |
| Clozapine | 3 | 3 | 3 |
| Spiperone | 4 | 4 | 4 |
*FIG. 51*

FORSKOLIN TITRATION
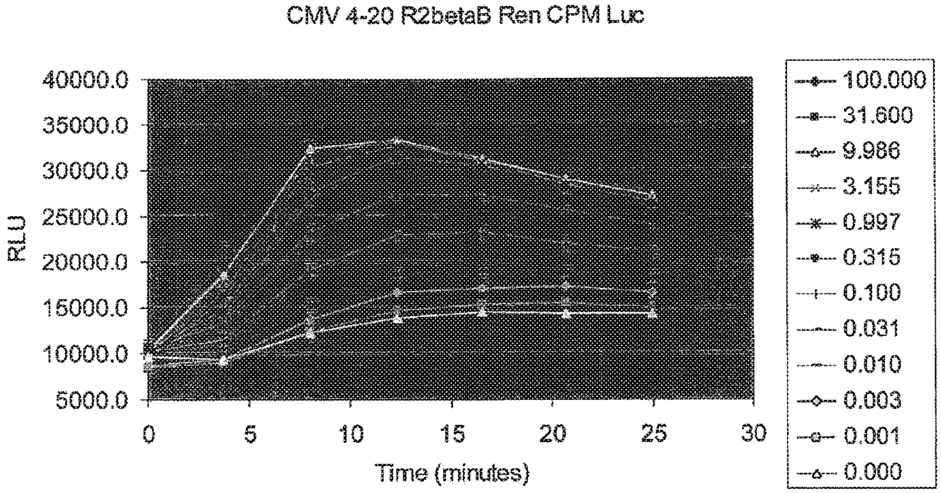
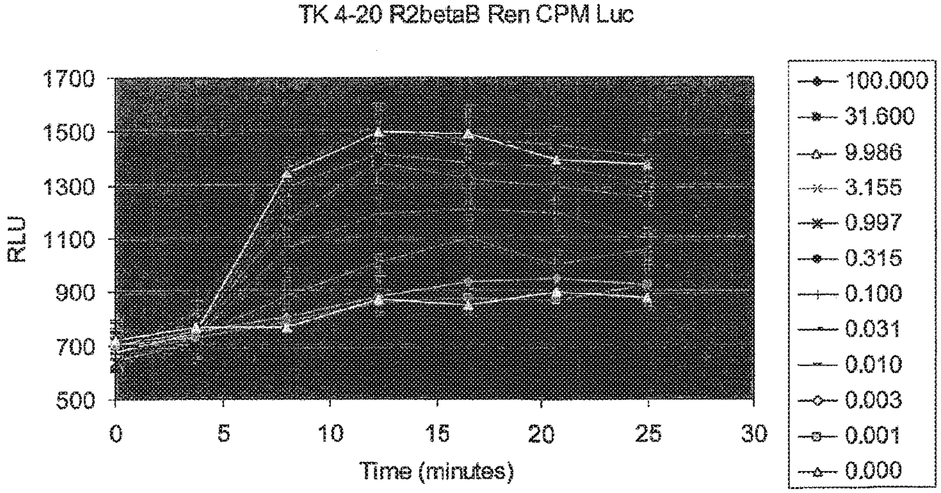
FIG. 52B

DOPAMINE TITRATION

OpLuc ORF sequences

FL OpLuc
atggtgtttacgttggcagatttcgttggagactggcaacagacagctggatacaaccaagatcaagtgttagaacaaggaggat
tgtctagtctgttccaagccctgggagtgtcagtcacCccAatCcagaaagttgtGctgtctggggagaatgggttaaaagctg
atattcatgtcatCatCccttacgagggactcagtggttttcaaatgggtctGattgaaatgatcttcaaagttgtttacccAgtgg
atgatcatcatttcaagattattctccattatggtacactcgttattgacggtgtGacaccAaacatgattgactactttggaCgCc
cttaccctggaattgctgtGtttgacggcaagcagatcacagttactggaactctgtggaacggcaacaagatctatgatgagCg
CctGatcaacccAgatggttcactcctcttcCgCgttactatcaatggagtcacCggatggCgCctttgcgagaacattcttg
cctaat (SEQ ID NO: 205)

OpLuc (1-50) – FRB
atgtttacgttggcagatttcgttggagactggcaacagacagctggatacaaccaagatcaagtgttagaacaaggaggattgt
ctagtctgttccaagccctgggAgtgtcagtcacCccAatCcagaaagttgtactgtctggggagaatGGCGGGAGC
TCTGGTGGAGGGTCTGGGGGTGTGGCCATCCTCTGGCATGAGATGTGGCATG
AAGGCCTGGAAGAGGCATCTCGTTTGTACTTTGGGGAAAGGAACGTGAAAGG
CATGTTTGAGGTGCTGGAGCCCTTGCATGCTATGATGGAACGGGGCCCCCAG
ACTCTGAAGGAAACATCCTTTAATCAGGCCTATGGTCGAGATTTAATGGAGG
CCCAAGAGTGGTGCAGGAAGTACATGAAATCAGGGAATGTCAAGGACCTCA
CCCAAGCCTGGGACCTCTATTATCATGTGTTCCGACGAATCTCA (SEQ ID NO: 206)

OpLuc (1-84) – FRB
atgtttacgttggcagatttcgttggagactggcaacagacagctggatacaaccaagatcaagtgttagaacaaggaggattgt
ctagtctgttccaagccctgggAgtgtcagtcacCccAatCcagaaagttgtGctgtctggggagaatgggttaaaagctgat
attcatgtcatCatCccttacgagggactcagtggttttcaaatgggtctGattgaaatgatcttcaaagttgtttaccccgtggat
GGCGGGAGCTCTGGTGGAGGGTCTGGGGGTGTGGCCATCCTCTGGCATGAGA
TGTGGCATGAAGGCCTGGAAGAGGCATCTCGTTTGTACTTTGGGGAAAGGAA
CGTGAAAGGCATGTTTGAGGTGCTGGAGCCCTTGCATGCTATGATGGAACGG
GGCCCCCAGACTCTGAAGGAAACATCCTTTAATCAGGCCTATGGTCGAGATT
TAATGGAGGCCCAAGAGTGGTGCAGGAAGTACATGAAATCAGGGAATGTCA
AGGACCTCACCCAAGCCTGGGACCTCTATTATCATGTGTTCCGACGAATCTCA
(SEQ ID NO: 207)

FKBP – OpLuc (51-170)
ATGGGAGTGCAGGTGGAAACCATCTCCCCAGGAGACGGGCGCACCTTCCCCA
AGCGCGGCCAGACCTGCGTGGTGCACTACACCGGGATGCTTGAAGATGGAAA
GAAATTTGATTCCTCCCGGGACAGAAACAAGCCCTTTAAGTTTATGCTAGGC
AAGCAGGAGGTGATCCGAGGCTGGGAAGAAGGGGTTGCCCAGATGAGTGTG
GGTCAGAGAGCCAAACTGACTATATCTCCAGATTATGCCTATGGTGCCACTG
GGCACCCAGGCATCATCCCACCACATGCCACTCTCGTCTTCGATGTGGAGCTT
CTAAAACTGGAAGGGCGCGCCGGAGGTGGCGGATCAGGTGGCGGAGGCTCC
gcgatcgccgggttaaaagctgatattcatgtcatCatCccttacgagggactcagtggttttcaaatgggtctGattgaaatgat
cttcaaagttgtttacccAgtggatgatcatcatttcaagattattctccattatggtacactcgttattgacggtgtGacaccAaac
atgattgactactttggaagaccttaccctggaattgctgtatttgacggcaagcagatcacagttactggaactctgtggaacggc
aacaagatctatgatgagCgCctGatcaacccAgatggttcactcctcttcCgCgttactatcaatggagtcacCggatggC
gCctttgcgagaacattcttgcc (SEQ ID NO: 208)

*FIG. 55A*

FKBP – OpLuc (85-170)
ATGGGAGTGCAGGTGGAAACCATCTCCCCAGGAGACGGGCGCACCTTCCCCA
AGCGCGGCCAGACCTGCGTGGTGCACTACACCGGGATGCTTGAAGATGGAAA
GAAATTTGATTCCTCCCGGGACAGAAACAAGCCCTTTAAGTTTATGCTAGGC
AAGCAGGAGGTGATCCGAGGCTGGGAAGAAGGGGTTGCCCAGATGAGTGTG
GGTCAGAGAGCCAAACTGACTATATCTCCAGATTATGCCTATGGTGCCACTG
GGCACCCAGGCATCATCCCACCACATGCCACTCTCGTCTTCGATGTGGAGCTT
CTAAAACTGGAAGGGCGCGCCGGAGGTGGCGGATCAGGTGGCGGAGGCTCC
gcgatcgccgatcatcatttcaagattattctccattatggtacactcgttattgacggtgtGacaccAaacatgattgactacttg
gaCgCccttaccctggaattgctgtGtttgacggcaagcagatcacagttactggaactctgtggaacggcaacaagatctatg
atgagCgCctGatcaacccAgatggttcactcctcttcCgCgttactatcaatggagtcacCggatggCgCctttgcgaga
acattcttgcc (SEQ ID NO: 209)

*FIG. 55B*

SPLIT SITE 50/51 IN VITRO SDS-PAGE 1) 201518.45.08
2) 201518.110.4-1 + 201518.57.D9
3) 201518.110.4-1
4) 201518.57.D9
5) NO DNA

SPLIT SITE 84/85 IN VITRO SDS-PAGE 1) 201518.45.08
2) 201518.104.04 + 201518.61.H3
3) 201518.104.04
4) 201518.61.H3
5) NO DNA

*fold activation using background subtracted values

OPLOPHORUS LUCIFERASE-BASED BIOSENSOR

CIRCULARY PERMUTED MUTANTS OF OPLOPHORUS LUCIFERASE WITH INSERTED RIIβB DOMAIN WERE CLONED INTO pF4K-CMV PLASMID TO ENABLE EXPRESSION UNDER T7 AND CMV PROMOTERS. RIIβB DOMAIN WAS FUSED TO THE LUCIFERASE FRAGMENTS WITH LINKERS. LENGTH OF THE LINKERS VARIED (4, 10 AND 20 AA RESIDUES) TO ADAPT TO THE BEST REFOLDING THE LUCIFERASE.

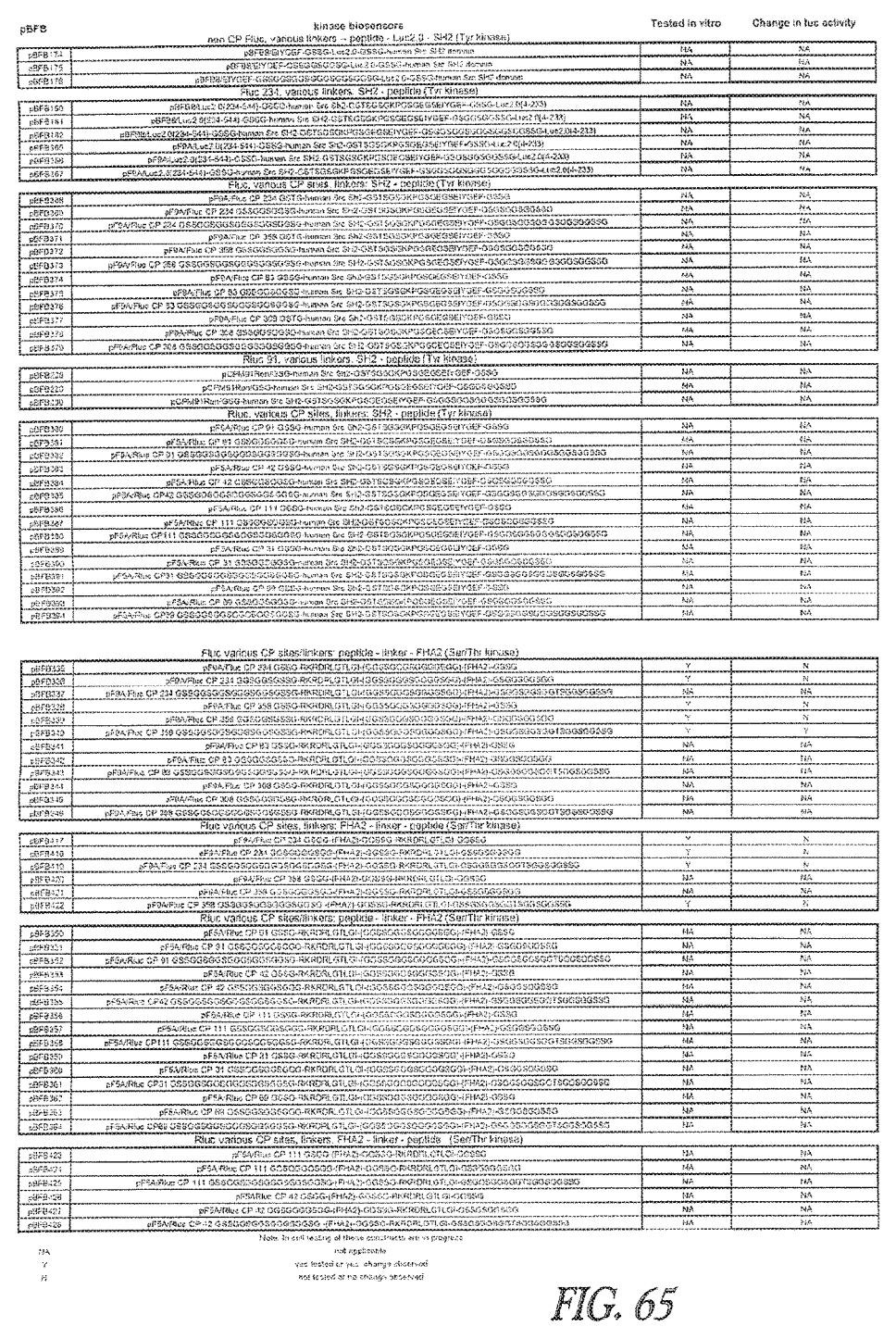

| pBFB | kinase biosensors | Tested in vitro | Change in luc activity |
|---|---|---|---|
| | non CP Fluc, various linkers -- peptide - Luc2.0 - SH2 (Tyr kinase) | | |
| pBFB174 | pBFB8/EIYGEF-GSSG-Luc2.0-GSSG-human Src SH2 domain | NA | NA |
| pBFB175 | pBFB8/EIYGEF-GSSGGSGGSG-Luc2.0-GSSG-human Src SH2 domain | NA | NA |
| pBFB176 | pBFB8/EIYGEF-GSSGGSGGSGGSGGSGGSG-Luc2.0-GSSG-human Src SH2 domain | NA | NA |
| | Fluc 234, various linkers: SH2 - peptide (Tyr kinase) | | |
| pBFB180 | pBFB8/Luc2.0(234-544)-GSSG-human Src SH2-GSTSGSGKPGSGEGSEIYGEF-GSSG-Luc2.0(4-233) | NA | NA |
| pBFB181 | pBFB8/Luc2.0(234-544)-GSSG-human Src SH2-GSTSGSGKPGSGEGSEIYGEF-GSGGSGGSSG-Luc2.0(4-233) | NA | NA |
| pBFB182 | pBFB8/Luc2.0(234-544)-GSSG-human Src SH2-GSTSGSGKPGSGEGSEIYGEF-GSGGSGGSGGSGGSGGSSG-Luc2.0(4-233) | NA | NA |
| pBFB365 | pF9A/Luc2.0(234-544)-GSSG-human Src SH2-GSTSGSGKPGSGEGSEIYGEF-GSSG-Luc2.0(4-233) | NA | NA |
| pBFB366 | pF9A/Luc2.0(234-544)-GSSG-human Src SH2-GSTSGSGKPGSGEGSEIYGEF-GSGGSGGSGGSG-Luc2.0(4-233) | NA | NA |
| pBFB367 | pF9A/Luc2.0(234-544)-GSSG-human Src SH2-GSTSGSGKPGSGEGSEIYGEF-GSGGSGGSGGSGGSGGSSG-Luc2.0(4-233) | NA | NA |
| | Fluc, various CP sites, linkers: SH2 - peptide (Tyr kinase) | | |
| pBFB368 | pF9A/Fluc CP 234 GSTG-human Src SH2-GSTSGSGKPGSGEGSEIYGEF-GSSG | NA | NA |
| pBFB369 | pF9A/Fluc CP 234 GSSGGSGGSG-human Src SH2-GSTSGSGKPGSGEGSEIYGEF-GSGGSGGSGGSG | NA | NA |
| pBFB370 | pF9A/Fluc CP 234 GSSGGSGGSGGSGGSGGSSG-human Src SH2-GSTSGSGKPGSGEGSEIYGEF-GSGGSGGSGGSGGSGGSSG | NA | NA |
| pBFB371 | pF9A/Fluc CP 358 GSTG-human Src SH2-GSTSGSGKPGSGEGSEIYGEF-GSSG | NA | NA |
| pBFB372 | pF9A/Fluc CP 358 GSSGGSGGSG-human Src SH2-GSTSGSGKPGSGEGSEIYGEF-GSGSGGSGGSG | NA | NA |
| pBFB373 | pF9A/Fluc CP 358 GSSGGSGGSGGSGGSGGSSG-human Src SH2-GSTSGSGKPGSGEGSEIYGEF-GSGGSGGSGGSGGSGGSSG | NA | NA |
| pBFB374 | pF9A/Fluc CP 83 GSSG-human Src SH2-GSTSGSGKPGSGEGSEIYGEF-GSSG | NA | NA |
| pBFB375 | pF9A/Fluc CP 83 GSSGGSGGSG-human Src SH2-GSTSGSGKPGSGEGSEIYGEF-GSGGSGGSSG | NA | NA |
| pBFB376 | pF9A/Fluc CP 83 GSSGGSGGSGGSGGSGGSSG-human Src SH2-GSTSGSGKPGSGEGSEIYGEF-GSGGSGGSGGSGGSGGSSG | NA | NA |
| pBFB377 | pF9A/Fluc CP 308 GSTG-human Src SH2-GSTSGSGKPGSGEGSEIYGEF-GSSG | NA | NA |
| pBFB378 | pF9A/Fluc CP 308 GSSGGSGGSG-human Src SH2-GSTSGSGKPGSGEGSEIYGEF-GSGSGGSGGSG | NA | NA |
| pBFB379 | pF9A/Fluc CP 308 GSSGGSGGSGGSGGSGGSSG-human Src SH2-GSTSGSGKPGSGEGSEIYGEF-GSGGSGGSGGSGGSGGSSG | NA | NA |
| | Rluc 91, various linkers: SH2 - peptide (Tyr kinase) | | |
| pBFB328 | pCPM91Ren/GSG-human Src SH2-GSTSGSGKPGSGEGSEIYGEF-GSSG | NA | NA |
| pBFB329 | pCPM91Ren/GSG-human Src SH2-GSTSGSGKPGSGEGSEIYGEF-GSGGSGGSSG | NA | NA |
| pBFB330 | pCPM91Ren/GSG-human Src SH2-GSTSGSGKPGSGEGSEIYGEF-GSGGSGGSGGSGGSGGSSG | NA | NA |
| | Rluc, various CP sites, linkers: SH2 - peptide (Tyr kinase) | | |
| pBFB380 | pF5A/Rluc CP 91 GSSG-human Src SH2-GSTSGSGKPGSGEGSEIYGEF-GSSG | NA | NA |
| pBFB381 | pF5A/Rluc CP 91 GSSGGSGGSG-human Src SH2-GSTSGSGKPGSGEGSEIYGEF-GSGSGGSGGSG | NA | NA |
| pBFB382 | pF5A/Rluc CP 91 GSSGGSGGSGGSGGSGGSSG-human Src SH2-GSTSGSGKPGSGEGSEIYGEF-GSGGSGGSGGSGGSGGSSG | NA | NA |
| pBFB383 | pF5A/Rluc CP 42 GSSG-human Src SH2-GSTSGSGKPGSGEGSEIYGEF-GSSG | NA | NA |
| pBFB384 | pF5A/Rluc CP 42 GSSGGSGGSG-human Src SH2-GSTSGSGKPGSGEGSEIYGEF-GSGSGGSGGSG | NA | NA |
| pBFB385 | pF5A/Rluc CP42 GSSGGSGGSGGSGGSGGSSG-human Src SH2-GSTSGSGKPGSGEGSEIYGEF-GSGGSGGSGGSGGSGGSSG | NA | NA |
| pBFB386 | pF5A/Rluc CP 111 GSSG-human Src SH2-GSTSGSGKPGSGEGSEIYGEF-GSSG | NA | NA |
| pBFB387 | pF5A/Rluc CP 111 GSSGGSGGSG-human Src SH2-GSTSGSGKPGSGEGSEIYGEF-GSGSGGSGGSG | NA | NA |
| pBFB388 | pF5A/Rluc CP111 GSSGGSGGSGGSGGSGGSSG-human Src SH2-GSTSGSGKPGSGEGSEIYGEF-GSGGSGGSGGSGGSGGSSG | NA | NA |
| pBFB389 | pF5A/Rluc CP 31 GSSG-human Src SH2-GSTSGSGKPGSGEGSEIYGEF-GSSG | NA | NA |
| pBFB390 | pF5A/Rluc CP 31 GSSGGSGGSG-human Src SH2-GSTSGSGKPGSGEGSEIYGEF-GSGSGGSGGSG | NA | NA |
| pBFB391 | pF5A/Rluc CP31 GSSGGSGGSGGSGGSGGSSG-human Src SH2-GSTSGSGKPGSGEGSEIYGEF-GSGGSGGSGGSGGSGGSSG | NA | NA |
| pBFB392 | pF5A/Rluc CP 69 GSSG-human Src SH2-GSTSGSGKPGSGEGSEIYGEF-GSSG | NA | NA |
| pBFB393 | pF5A/Rluc CP 69 GSSGGSGGSG-human Src SH2-GSTSGSGKPGSGEGSEIYGEF-GSGSGGSGGSG | NA | NA |
| pBFB394 | pF5A/Rluc CP69 GSSGGSGGSGGSGGSGGSSG-human Src SH2-GSTSGSGKPGSGEGSEIYGEF-GSGGSGGSGGSGGSGGSSG | NA | NA |
| | Fluc various CP sites/linkers: peptide - linker - FHA2 (Ser/Thr kinase) | | |
| pBFB335 | pF9A/Fluc CP 234 GSSG-RKRDRLGTLGI-(GGSSGGGSGGGGSGG)-(FHA2)-GSSG | Y | N |
| pBFB336 | pF9A/Fluc CP 234 GSSGGSGGSG-RKRDRLGTLGI-(GGSSGGGSGGGGSGG)-(FHA2)-GSGGSGGSGG | Y | N |
| pBFB337 | pF9A/Fluc CP 234 GSSGGSGGSGGSGGSGGSSG-RKRDRLGTLGI-(GGSSGGGSGGGGSGG)-(FHA2)-GSGGSGGSGGTSGGSGGSSG | NA | NA |
| pBFB338 | pF9A/Fluc CP 358 GSSG-RKRDRLGTLGI-(GGSSGGGSGGGGSGG)-(FHA2)-GSSG | Y | N |
| pBFB339 | pF9A/Fluc CP 358 GSSGGSGGSG-RKRDRLGTLGI-(GGSSGGGSGGGGSGG)-(FHA2)-GSGGSGGSGG | Y | N |
| pBFB340 | pF9A/Fluc CP 358 GSSGGSGGSGGSGGSGGSSG-RKRDRLGTLGI-(GGSSGGGSGGGGSGG)-(FHA2)-GSGGSGGSGGTSGGSGGSSG | Y | Y |
| pBFB341 | pF9A/Fluc CP 83 GSSG-RKRDRLGTLGI-(GGSSGGGSGGGGSGG)-(FHA2)-GSSG | NA | NA |
| pBFB342 | pF9A/Fluc CP 83 GSSGGSGGSG-RKRDRLGTLGI-(GGSSGGGSGGGGSGG)-(FHA2)-GSGGSGGSGG | NA | NA |
| pBFB343 | pF9A/Fluc CP 83 GSSGGSGGSGGSGGSGGSSG-RKRDRLGTLGI-(GGSSGGGSGGGGSGG)-(FHA2)-GSGGSGGSGGTSGGSGGSSG | NA | NA |
| pBFB344 | pF9A/Fluc CP 308 GSSG-RKRDRLGTLGI-(GGSSGGGSGGGGSGG)-(FHA2)-GSSG | NA | NA |
| pBFB345 | pF9A/Fluc CP 308 GSSGGSGGSG-RKRDRLGTLGI-(GGSSGGGSGGGGSGG)-(FHA2)-GSGGSGGSGG | NA | NA |
| pBFB346 | pF9A/Fluc CP 308 GSSGGSGGSGGSGGSGGSSG-RKRDRLGTLGI-(GGSSGGGSGGGGSGG)-(FHA2)-GSGGSGGSGGTSGGSGGSSG | NA | NA |
| | Fluc various CP sites, linkers: FHA2 - linker - peptide (Ser/Thr kinase) | | |
| pBFB417 | pF9A/Fluc CP 234 GSSG-(FHA2)-GGSSG-RKRDRLGTLGI-GGSSG | Y | N |
| pBFB418 | pF9A/Fluc CP 234 GGSGGSGGSG-(FHA2)-GGSSG-RKRDRLGTLGI-GSSGGSGGSG | Y | N |
| pBFB419 | pF9A/Fluc CP 234 GSSGGSGGSGGSGGSGGSSG-(FHA2)-GGSSG-RKRDRLGTLGI-GSGGSGGSGGTSGGSGGSSG | Y | N |
| pBFB420 | pF9A/Fluc CP 358 GSSG-(FHA2)-GGSSG-RKRDRLGTLGI-GGSSG | NA | NA |
| pBFB421 | pF9A/Fluc CP 358 GGSGGSGGSG-(FHA2)-GGSSG-RKRDRLGTLGI-GSSGGSGGSG | NA | NA |
| pBFB422 | pF9A/Fluc CP 358 GSSGGSGGSGGSGGSGGSSG-(FHA2)-GGSSG-RKRDRLGTLGI-GSSGGSGGSGGTSGGSGGSSG | Y | N |
| | Rluc various CP sites/linkers: peptide - linker - FHA2 (Ser/Thr kinase) | | |
| pBFB350 | pF5A/Rluc CP 91 GSSG-RKRDRLGTLGI-(GGSSGGGSGGGGSGG)-(FHA2)-GSSG | NA | NA |
| pBFB351 | pF5A/Rluc CP 91 GSSGGSGGSGGG-RKRDRLGTLGI-(GGSSGGGSGGGGSGG)-(FHA2)-GSGGSGGSSG | NA | NA |
| pBFB352 | pF5A/Rluc CP 91 GSSGGSGGSGGSGGSGGSSG-RKRDRLGTLGI-(GGSSGGGSGGGGSGG)-(FHA2)-GSGGSGGSGGTSGGSGGSSG | NA | NA |
| pBFB353 | pF5A/Rluc CP 42 GSSG-RKRDRLGTLGI-(GGSSGGGSGGGGSGG)-(FHA2)-GSSG | NA | NA |
| pBFB354 | pF5A/Rluc CP 42 GSSGGSGGSGGG-RKRDRLGTLGI-(GGSSGGGSGGGGSGG)-(FHA2)-GSGGSGGSSG | NA | NA |
| pBFB355 | pF5A/Rluc CP42 GSSGGSGGSGGSGGSGGSSG-RKRDRLGTLGI-(GGSSGGGSGGGGSGG)-(FHA2)-GSGGSGGSGGTSGGSGGSSG | NA | NA |
| pBFB356 | pF5A/Rluc CP 111 GSSG-RKRDRLGTLGI-(GGSSGGGSGGGGSGG)-(FHA2)-GSSG | NA | NA |
| pBFB357 | pF5A/Rluc CP 111 GSSGGSGGSGGG-RKRDRLGTLGI-(GGSSGGGSGGGGSGG)-(FHA2)-GSGGSGGSSG | NA | NA |
| pBFB358 | pF5A/Rluc CP111 GSSGGSGGSGGSGGSGGSSG-RKRDRLGTLGI-(GGSSGGGSGGGGSGG)-(FHA2)-GSGGSGGSGGTSGGSGGSSG | NA | NA |
| pBFB359 | pF5A/Rluc CP 31 GSSG-RKRDRLGTLGI-(GGSSGGGSGGGGSGG)-(FHA2)-GSSG | NA | NA |
| pBFB360 | pF5A/Rluc CP 31 GSSGGSGGSGGG-RKRDRLGTLGI-(GGSSGGGSGGGGSGG)-(FHA2)-GSGGSGGSSG | NA | NA |
| pBFB361 | pF5A/Rluc CP31 GSSGGSGGSGGSGGSGGSSG-RKRDRLGTLGI-(GGSSGGGSGGGGSGG)-(FHA2)-GSGGSGGSGGTSGGSGGSSG | NA | NA |
| pBFB362 | pF5A/Rluc CP 69 GSSG-RKRDRLGTLGI-(GGSSGGGSGGGGSGG)-(FHA2)-GSSG | NA | NA |
| pBFB363 | pF5A/Rluc CP 69 GSSGGSGGSGGG-RKRDRLGTLGI-(GGSSGGGSGGGGSGG)-(FHA2)-GSGGSGGSSG | NA | NA |
| pBFB364 | pF5A/Rluc CP69 GSSGGSGGSGGSGGSGGSSG-RKRDRLGTLGI-(GGSSGGGSGGGGSGG)-(FHA2)-GSGGSGGSGGTSGGSGGSSG | NA | NA |
| | Rluc various CP sites, linkers, FHA2 - linker - peptide (Ser/Thr kinase) | | |
| pBFB423 | pF5A/Rluc CP 111 GSSG-(FHA2)-GGSSG-RKRDRLGTLGI-GGSSG | NA | NA |
| pBFB424 | pF5A/Rluc CP 111 GGSGGSGGSG-(FHA2)-GGSSG-RKRDRLGTLGI-GSSGGSGGSG | NA | NA |
| pBFB425 | pF5A/Rluc CP 111 GSSGGSGGSGGSGGSGGSSG-(FHA2)-GGSSG-RKRDRLGTLGI-GSSGGSGGSGGTSGGSGGSSG | NA | NA |
| pBFB426 | pF5A/Rluc CP 42 GSSG-(FHA2)-GGSSG-RKRDRLGTLGI-GGSSG | NA | NA |
| pBFB427 | pF5A/Rluc CP 42 GGSGGSGGSG-(FHA2)-GGSSG-RKRDRLGTLGI-GSSGGSGGSG | NA | NA |
| pBFB428 | pF5A/Rluc CP 42 GSSGGSGGSGGSGGSGGSSG-(FHA2)-GGSSG-RKRDRLGTLGI-GSSGGSGGSGGTSGGSGGSSG | NA | NA |

Note: In cell testing of these constructs are in progress

NA not applicable

Y yes tested or yes change observed

N not tested or no change observed

FIG. 65

A) Sgf I + 1 nt preceding ORF: GCGATCGCC (SEQ ID NO:308)

B) Pme I following ORF: GTTTAAAC (SEQ ID NO:309)

C) pBFB10 Sgf to Pme (SEQ ID NO:310)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAATGTATGAAAGCTTTATTGAGTCACTGCCATTCCTTAAATCTTTGGAGTTTTCTGAACGCCTGAA
AGTAGTAGATGTGATAGGCACCAAAGTATACAACGATGGAGAACAAATCATTGCTCAGGGAGATTCGGCTGATTCTTTTT
TCATTGTAGAATCTGGAGAAGTGAAAATTACTATGAAAAGAAAGGGTAAATCAGAAGTGGAAGAGAATGGTGCAGTAGAA
ATCGCTCGATGCTCGCGGGGACAGTACTTTGGAGAGCTTGCCCTGGTAACTAACAAACCTCGAGCAGCTTCTGCCCACGC
CATTGGGACTGTCAAATGTTTAGCAATGGATGTGCAAGCATTTGAAAGGCTTCTGGGACCTTGCATGGAAATTATGAAAA
GGAACATCGCTACCTATGAAGAACAGTTAGTTGCCCTGTTTGGAACGAACATGGATATTGTAGGGTCAGGTGGATCTGGA
GGGAGCTCCGGTGCCAAAAACATTAAGAAGGGCCCAGCGCCATTCTACCCACTCGAAGACGGGACCGCCGGCGAGCAGCT
GCACAAAGCCATGAAGCGCTACGCCCTGGTGCCCGGCACCATCGCCTTTACCGACGCACATATCGAGGTGGACATTACCT
ACGCCGAGTACTTCGAGATGAGCGTTCGGCTGGCAGAAGCTATGAAGCGCTATGGGCTGAATACAAACCATCGGATCGTG
GTGTGCAGCGAGAATAGCTTGCAGTTCTTCATGCCCGTGTTGGGTGCCCTGTTCATCGGTGTGGCTGTGGCCCCAGCTAA
CGACATCTACAACGAGCGCGAGCTGCTGAACAGCATGGGCATCAGCCAGCCCACCGTCGTATTCGTGAGCAAGAAAGGGC
TGCAAAAGATCCTCAACGTGCAAAAGAAGCTACCGATCATACAAAAGATCATCATCATGGATAGCAAGACCGACTACCAG
GGCTTCCAAAGCATGTACACCTTCGTGACTTCCCATTTGCCACCCGGCTTCAACGAGTACGACTTCGTGCCCGAGAGCTT
CGACCGGGACAAAACCATCGCCCTGATCATGAACAGTAGTGGCAGTACCGGATTGCCCAAGGGCGTAGCCCTACCGCACC
GCACCGCTTGTGTCCGATTCAGTCATGCCCGCGACCCCATCTTCGGCAACCAGATCATCCCCGTTTAAAC

D) pBFB100 Sgf to Pme (SEQ ID NO:311)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGATGTATGAA
AGCTTTATTGAGTCACTGCCATTCCTTAAATCTTTGGAGTTTTCTGAACGCCTGAAAGTAGTAGATGTGATAGGCACCAA
AGTATACAACGATGGAGAACAAATCATTGCTCAGGGAGATTCGGCTGATTCTTTTTTCATTGTAGAATCTGGAGAAGTGA
AAATTACTATGAAAAGAAAGGGTAAATCAGAAGTGGAAGAGAATGGTGCAGTAGAAATCGCTCGATGCTCGCGGGGACAG
TACTTTGGAGAGCTTGCCCTGGTAACTAACAAACCTCGAGCAGCTTCTGCCCACGCCATTGGGACTGTCAAATGTTTAGC
AATGGATGTGCAAGCATTTGAAAGGCTTCTGGGACCTTGCATGGAAATTATGAAAAGGAACATCGCTACCTATGAAGAAC
AGTTAGTTGCCCTGTTTGGAACGAACATGGATATTGTAGGGTCAGGTGGATCTGGAGGGAGCTCCGGTGCCAAAAACATT
AAGAAGGGCCCAGCGCCATTCTACCCACTCGAAGACGGGACCGCCGGCGAGCAGCTGCACAAAGCCATGAAGCGCTACGC
CCTGGTGCCCGGCACCATCGCCTTTACCGACGCACATATCGAGGTGGACATTACCTACGCCGAGTACTTCGAGATGAGCG
TTCGGCTGGCAGAAGCTATGAAGCGCTATGGGCTGAATACAAACCATCGGATCGTGGTGTGCAGCGAGAATAGCTTGCAG
TTCTTCATGCCCGTGTTGGGTGCCCTGTTCATCGGTGTGGCTGTGGCCCCAGCTAACGACATCTACAACGAGCGCGAGCT
GCTGAACAGCATGGGCATCAGCCAGCCCACCGTCGTATTCGTGAGCAAGAAAGGGCTGCAAAAGATCCTCAACGTGCAAA

FIG. 67A

AGAAGCTACCGATCATACAAAAGATCATCATCATGGATAGCAAGACCGACTACCAGGGCTTCCAAAGCATGTACACCTTC
GTGACTTCCCATTTGCCACCCGGCTTCAACGAGTACGACTTCGTGCCCGAGAGCTTCGACCGGGACAAAACCATCGCCCT
GATCATGAACAGTAGTGGCAGTACCGGATTGCCCAAGGGCGTAGCCCTACCGCACCGCACCGCTTGTGTCCGATTCAGTC
ATGCCCGCGACCCCATCTTCGGCAACCAGATCATCCCCGTTTAAAC

E) pBFB101 Sgf to Pme (SEQ ID NO:312)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAATG
TATGAAAGCTTTATTGAGTCACTGCCATTCCTTAAATCTTTGGAGTTTTCTGAACGCCTGAAAGTAGTAGATGTGATAGG
CACCAAAGTATACAACGATGGAGAACAAATCATTGCTCAGGGAGATTCGGCTGATTCTTTTTTCATTGTAGAATCTGGAG
AAGTGAAAATTACTATGAAAAGAAAGGGTAAATCAGAAGTGGAAGAGAATGGTGCAGTAGAAATCGCTCGATGCTCGCGG
GGACAGTACTTTGGAGAGCTTGCCCTGGTAACTAACAAACCTCGAGCAGCTTCTGCCCACGCCATTGGGACTGTCAAATG
TTTAGCAATGGATGTGCAAGCATTTGAAAGGCTTCTGGGACCTTGCATGGAAATTATGAAAAGGAACATCGCTACCTATG
AAGAACAGTTAGTTGCCCTGTTTGGAACGAACATGGATATTGTAGCCAAAAACATTAAGAAGGGCCCAGCGCCATTCTAC
CCACTCGAAGACGGGACCGCCGGCGAGCAGCTGCACAAAGCCATGAAGCGCTACGCCCTGGTGCCCGGCACCATCGCCTT
TACCGACGCACATATCGAGGTGGACATTACCTACGCCGAGTACTTCGAGATGAGCGTTCGGCTGGCAGAAGCTATGAAGC
GCTATGGGCTGAATACAAACCATCGGATCGTGGTGTGCAGCGAGAATAGCTTGCAGTTCTTCATGCCCGTGTTGGGTGCC
CTGTTCATCGGTGTGGCTGTGGCCCCAGCTAACGACATCTACAACGAGCGCGAGCTGCTGAACAGCATGGGCATCAGCCA
GCCCACCGTCGTATTCGTGAGCAAGAAAGGGCTGCAAAAGATCCTCAACGTGCAAAAGAAGCTACCGATCATACAAAAGA
TCATCATCATGGATAGCAAGACCGACTACCAGGGCTTCCAAAGCATGTACACCTTCGTGACTTCCCATTTGCCACCCGGC
TTCAACGAGTACGACTTCGTGCCCGAGAGCTTCGACCGGGACAAAACCATCGCCCTGATCATGAACAGTAGTGGCAGTAC
CGGATTGCCCAAGGGCGTAGCCCTACCGCACCGCACCGCTTGTGTCCGATTCAGTCATGCCCGCGACCCCATCTTCGGCA
ACCAGATCATCCCCGTTTAAAC

F) pBFB102 Sgf to Pme (SEQ ID NO:313)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAATG
TATGAAAGCTTTATTGAGTCACTGCCATTCCTTAAATCTTTGGAGTTTTCTGAACGCCTGAAAGTAGTAGATGTGATAGG
CACCAAAGTATACAACGATGGAGAACAAATCATTGCTCAGGGAGATTCGGCTGATTCTTTTTTCATTGTAGAATCTGGAG
AAGTGAAAATTACTATGAAAAGAAAGGGTAAATCAGAAGTGGAAGAGAATGGTGCAGTAGAAATCGCTCGATGCTCGCGG
GGACAGTACTTTGGAGAGCTTGCCCTGGTAACTAACAAACCTCGAGCAGCTTCTGCCCACGCCATTGGGACTGTCAAATG
TTTAGCAATGGATGTGCAAGCATTTGAAAGGCTTCTGGGACCTTGCATGGAAATTATGAAAAGGAACATCGCTACCTATG
AAGAACAGTTAGTTGCCCTGTTTGGAACGAACATGGATATTGTATCCGGTGCCAAAAACATTAAGAAGGGCCCAGCGCCA
TTCTACCCACTCGAAGACGGGACCGCCGGCGAGCAGCTGCACAAAGCCATGAAGCGCTACGCCCTGGTGCCCGGCACCAT
CGCCTTTACCGACGCACATATCGAGGTGGACATTACCTACGCCGAGTACTTCGAGATGAGCGTTCGGCTGGCAGAAGCTA
TGAAGCGCTATGGGCTGAATACAAACCATCGGATCGTGGTGTGCAGCGAGAATAGCTTGCAGTTCTTCATGCCCGTGTTG
GGTGCCCTGTTCATCGGTGTGGCTGTGGCCCCAGCTAACGACATCTACAACGAGCGCGAGCTGCTGAACAGCATGGGCAT

*FIG. 67B*

CAGCCAGCCCACCGTCGTATTCGTGAGCAAGAAAGGGCTGCAAAAGATCCTCAACGTGCAAAAGAAGCTACCGATCATAC
AAAAGATCATCATCATGGATAGCAAGACCGACTACCAGGGCTTCCAAAGCATGTACACCTTCGTGACTTCCCATTTGCCA
CCCGGCTTCAACGAGTACGACTTCGTGCCCGAGAGCTTCGACCGGGACAAAACCATCGCCCTGATCATGAACAGTAGTGG
CAGTACCGGATTGCCCAAGGGCGTAGCCCTACCGCACCGCACCGCTTGTGTCCGATTCAGTCATGCCCGCGACCCCATCT
TCGGCAACCAGATCATCCCCGTTTAAAC

G) pBFB103 Sgf to Pme (SEQ ID NO:314)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAATG
TATGAAAGCTTTATTGAGTCACTGCCATTCCTTAAATCTTTGGAGTTTTCTGAACGCCTGAAAGTAGTAGATGTGATAGG
CACCAAAGTATACAACGATGGAGAACAAATCATTGCTCAGGGAGATTCGGCTGATTCTTTTTTCATTGTAGAATCTGGAG
AAGTGAAAATTACTATGAAAAGAAAGGGTAAATCAGAAGTGGAAGAGAATGGTGCAGTAGAAATCGCTCGATGCTCGCGG
GGACAGTACTTTGGAGAGCTTGCCCTGGTAACTAACAAACCTCGAGCAGCTTCTGCCCACGCCATTGGGACTGTCAAATG
TTTAGCAATGGATGTGCAAGCATTTGAAAGGCTTCTGGGACCTTGCATGGAAATTATGAAAAGGAACATCGCTACCTATG
AAGAACAGTTAGTTGCCCTGTTTGGAACGAACATGGATATTGTATCTGGAGGGAGCTCCGGTGCCAAAAACATTAAGAAG
GGCCCAGCGCCATTCTACCCACTCGAAGACGGGACCGCCGGCGAGCAGCTGCACAAAGCCATGAAGCGCTACGCCCTGGT
GCCCGGCACCATCGCCTTTACCGACGCACATATCGAGGTGGACATTACCTACGCCGAGTACTTCGAGATGAGCGTTCGGC
TGGCAGAAGCTATGAAGCGCTATGGGCTGAATACAAACCATCGGATCGTGGTGTGCAGCGAGAATAGCTTGCAGTTCTTC
ATGCCCGTGTTGGGTGCCCTGTTCATCGGTGTGGCTGTGGCCCCAGCTAACGACATCTACAACGAGCGCGAGCTGCTGAA
CAGCATGGGCATCAGCCAGCCCACCGTCGTATTCGTGAGCAAGAAAGGGCTGCAAAAGATCCTCAACGTGCAAAAGAAGC
TACCGATCATACAAAAGATCATCATCATGGATAGCAAGACCGACTACCAGGGCTTCCAAAGCATGTACACCTTCGTGACT
TCCCATTTGCCACCCGGCTTCAACGAGTACGACTTCGTGCCCGAGAGCTTCGACCGGGACAAAACCATCGCCCTGATCAT
GAACAGTAGTGGCAGTACCGGATTGCCCAAGGGCGTAGCCCTACCGCACCGCACCGCTTGTGTCCGATTCAGTCATGCCC
GCGACCCCATCTTCGGCAACCAGATCATCCCCGTTTAAAC

H) pBFB104 Sgf to Pme (SEQ ID NO:315)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAATG
TATGAAAGCTTTATTGAGTCACTGCCATTCCTTAAATCTTTGGAGTTTTCTGAACGCCTGAAAGTAGTAGATGTGATAGG
CACCAAAGTATACAACGATGGAGAACAAATCATTGCTCAGGGAGATTCGGCTGATTCTTTTTTCATTGTAGAATCTGGAG
AAGTGAAAATTACTATGAAAAGAAAGGGTAAATCAGAAGTGGAAGAGAATGGTGCAGTAGAAATCGCTCGATGCTCGCGG
GGACAGTACTTTGGAGAGCTTGCCCTGGTAACTAACAAACCTCGAGCAGCTTCTGCCCACGCCATTGGGACTGTCAAATG
TTTAGCAATGGATGTGCAAGCATTTGAAAGGCTTCTGGGACCTTGCATGGAAATTATGAAAAGGAACATCGCTACCTATG
AAGAACAGTTAGTTGCCCTGTTTGGAACGAACATGGATATTGTAGGTGGATCTGGAGGGAGCTCCGGTGCCAAAAACATT
AAGAAGGGCCCAGCGCCATTCTACCCACTCGAAGACGGGACCGCCGGCGAGCAGCTGCACAAAGCCATGAAGCGCTACGC
CCTGGTGCCCGGCACCATCGCCTTTACCGACGCACATATCGAGGTGGACATTACCTACGCCGAGTACTTCGAGATGAGCG
TTCGGCTGGCAGAAGCTATGAAGCGCTATGGGCTGAATACAAACCATCGGATCGTGGTGTGCAGCGAGAATAGCTTGCAG

FIG. 67C

TTCTTCATGCCCGTGTTGGGTGCCCTGTTCATCGGTGTGGCTGTGGCCCCAGCTAACGACATCTACAACGAGCGCGAGCT
GCTGAACAGCATGGGCATCAGCCAGCCCACCGTCGTATTCGTGAGCAAGAAAGGGCTGCAAAAGATCCTCAACGTGCAAA
AGAAGCTACCGATCATACAAAAGATCATCATCATGGATAGCAAGACCGACTACCAGGGCTTCCAAAGCATGTACACCTTC
GTGACTTCCCATTTGCCACCCGGCTTCAACGAGTACGACTTCGTGCCCGAGAGCTTCGACCGGGACAAAACCATCGCCCT
GATCATGAACAGTAGTGGCAGTACCGGATTGCCCAAGGGCGTAGCCCTACCGCACCGCACCGCTTGTGTCCGATTCAGTC
ATGCCCGCGACCCCATCTTCGGCAACCAGATCATCCCCGTTTAAAC

I) pBFB106 Sgf to Pme (SEQ ID NO:316)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAGGT
TCAATGTATGAAAGCTTTATTGAGTCACTGCCATTCCTTAAATCTTTGGAGTTTTCTGAACGCCTGAAAGTAGTAGATGT
GATAGGCACCAAAGTATACAACGATGGAGAACAAATCATTGCTCAGGGAGATTCGGCTGATTCTTTTTTCATTGTAGAAT
CTGGAGAAGTGAAAATTACTATGAAAAGAAAGGGTAAATCAGAAGTGGAAGAGAATGGTGCAGTAGAAATCGCTCGATGC
TCGCGGGGACAGTACTTTGGAGAGCTTGCCCTGGTAACTAACAAACCTCGAGCAGCTTCTGCCCACGCCATTGGGACTGT
CAAATGTTTAGCAATGGATGTGCAAGCATTTGAAAGGCTTCTGGGACCTTGCATGGAAATTATGAAAAGGAACATCGCTA
CCTATGAAGAACAGTTAGTTGCCCTGTTTGGAACGAACATGGATATTGTATCCGGTGCCAAAAACATTAAGAAGGGCCCA
GCGCCATTCTACCCACTCGAAGACGGGACCGCCGGCGAGCAGCTGCACAAAGCCATGAAGCGCTACGCCCTGGTGCCCGG
CACCATCGCCTTTACCGACGCACATATCGAGGTGGACATTACCTACGCCGAGTACTTCGAGATGAGCGTTCGGCTGGCAG
AAGCTATGAAGCGCTATGGGCTGAATACAAACCATCGGATCGTGGTGTGCAGCGAGAATAGCTTGCAGTTCTTCATGCCC
GTGTTGGGTGCCCTGTTCATCGGTGTGGCTGTGGCCCCAGCTAACGACATCTACAACGAGCGCGAGCTGCTGAACAGCAT
GGGCATCAGCCAGCCCACCGTCGTATTCGTGAGCAAGAAAGGGCTGCAAAAGATCCTCAACGTGCAAAAGAAGCTACCGA
TCATACAAAAGATCATCATCATGGATAGCAAGACCGACTACCAGGGCTTCCAAAGCATGTACACCTTCGTGACTTCCCAT
TTGCCACCCGGCTTCAACGAGTACGACTTCGTGCCCGAGAGCTTCGACCGGGACAAAACCATCGCCCTGATCATGAACAG
TAGTGGCAGTACCGGATTGCCCAAGGGCGTAGCCCTACCGCACCGCACCGCTTGTGTCCGATTCAGTCATGCCCGCGACC
CCATCTTCGGCAACCAGATCATCCCCGTTTAAAC

J) pBFB107 Sgf to Pme (SEQ ID NO:317)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAGGT
TCAATGTATGAAAGCTTTATTGAGTCACTGCCATTCCTTAAATCTTTGGAGTTTTCTGAACGCCTGAAAGTAGTAGATGT
GATAGGCACCAAAGTATACAACGATGGAGAACAAATCATTGCTCAGGGAGATTCGGCTGATTCTTTTTTCATTGTAGAAT
CTGGAGAAGTGAAAATTACTATGAAAAGAAAGGGTAAATCAGAAGTGGAAGAGAATGGTGCAGTAGAAATCGCTCGATGC
TCGCGGGGACAGTACTTTGGAGAGCTTGCCCTGGTAACTAACAAACCTCGAGCAGCTTCTGCCCACGCCATTGGGACTGT
CAAATGTTTAGCAATGGATGTGCAAGCATTTGAAAGGCTTCTGGGACCTTGCATGGAAATTATGAAAAGGAACATCGCTA
CCTATGAAGAACAGTTAGTTGCCCTGTTTGGAACGAACATGGATATTGTTGGGAGCTCCGGTGCCAAAAACATTAAGAAG
GGCCCAGCGCCATTCTACCCACTCGAAGACGGGACCGCCGGCGAGCAGCTGCACAAAGCCATGAAGCGCTACGCCCTGGT
GCCCGGCACCATCGCCTTTACCGACGCACATATCGAGGTGGACATTACCTACGCCGAGTACTTCGAGATGAGCGTTCGGC

FIG. 67D

TGGCAGAAGCTATGAAGCGCTATGGGCTGAATACAAACCATCGGATCGTGGTGTGCAGCGAGAATAGCTTGCAGTTCTTC
ATGCCCGTGTTGGGTGCCCTGTTCATCGGTGTGGCTGTGGCCCCAGCTAACGACATCTACAACGAGCGCGAGCTGCTGAA
CAGCATGGGCATCAGCCAGCCCACCGTCGTATTCGTGAGCAAGAAAGGGCTGCAAAAGATCCTCAACGTGCAAAAGAAGC
TACCGATCATACAAAAGATCATCATCATGGATAGCAAGACCGACTACCAGGGCTTCCAAAGCATGTACACCTTCGTGACT
TCCCATTTGCCACCCGGCTTCAACGAGTACGACTTCGTGCCCGAGAGCTTCGACCGGGACAAAACCATCGCCCTGATCAT
GAACAGTAGTGGCAGTACCGGATTGCCCAAGGGCGTAGCCCTACCGCACCGCACCGCTTGTGTCCGATTCAGTCATGCCC
GCGACCCCATCTTCGGCAACCAGATCATCCCCGTTTAAAC

K) pBFB108 Sgf to Pme (SEQ ID NO:318)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAGGT
TCAATGTATGAAAGCTTTATTGAGTCACTGCCATTCCTTAAATCTTTGGAGTTTTCTGAACGCCTGAAAGTAGTAGATGT
GATAGGCACCAAAGTATACAACGATGGAGAACAAATCATTGCTCAGGGAGATTCGGCTGATTCTTTTTTCATTGTAGAAT
CTGGAGAAGTGAAAATTACTATGAAAAGAAAGGGTAAATCAGAAGTGGAAGAGAATGGTGCAGTAGAAATCGCTCGATGC
TCGCGGGGACAGTACTTTGGAGAGCTTGCCCTGGTAACTAACAAACCTCGAGCAGCTTCTGCCCACGCCATTGGGACTGT
CAAATGTTTAGCAATGGATGTGCAAGCATTTGAAAGGCTTCTGGGACCTTGCATGGAAATTATGAAAAGGAACATCGCTA
CCTATGAAGAACAGTTAGTTGCCCTGTTTGGAACGAACATGGATATTGTATCTGGAGGGAGCTCCGGTGCCAAAAACATT
AAGAAGGGCCCAGCGCCATTCTACCCACTCGAAGACGGGACCGCCGGCGAGCAGCTGCACAAAGCCATGAAGCGCTACGC
CCTGGTGCCCGGCACCATCGCCTTTACCGACGCACATATCGAGGTGGACATTACCTACGCCGAGTACTTCGAGATGAGCG
TTCGGCTGGCAGAAGCTATGAAGCGCTATGGGCTGAATACAAACCATCGGATCGTGGTGTGCAGCGAGAATAGCTTGCAG
TTCTTCATGCCCGTGTTGGGTGCCCTGTTCATCGGTGTGGCTGTGGCCCCAGCTAACGACATCTACAACGAGCGCGAGCT
GCTGAACAGCATGGGCATCAGCCAGCCCACCGTCGTATTCGTGAGCAAGAAAGGGCTGCAAAAGATCCTCAACGTGCAAA
AGAAGCTACCGATCATACAAAAGATCATCATCATGGATAGCAAGACCGACTACCAGGGCTTCCAAAGCATGTACACCTTC
GTGACTTCCCATTTGCCACCCGGCTTCAACGAGTACGACTTCGTGCCCGAGAGCTTCGACCGGGACAAAACCATCGCCCT
GATCATGAACAGTAGTGGCAGTACCGGATTGCCCAAGGGCGTAGCCCTACCGCACCGCACCGCTTGTGTCCGATTCAGTC
ATGCCCGCGACCCCATCTTCGGCAACCAGATCATCCCCGTTTAAAC

L) pBFB109 Sgf to Pme (SEQ ID NO:319)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAGGT
TCAATGTATGAAAGCTTTATTGAGTCACTGCCATTCCTTAAATCTTTGGAGTTTTCTGAACGCCTGAAAGTAGTAGATGT
GATAGGCACCAAAGTATACAACGATGGAGAACAAATCATTGCTCAGGGAGATTCGGCTGATTCTTTTTTCATTGTAGAAT
CTGGAGAAGTGAAAATTACTATGAAAAGAAAGGGTAAATCAGAAGTGGAAGAGAATGGTGCAGTAGAAATCGCTCGATGC
TCGCGGGGACAGTACTTTGGAGAGCTTGCCCTGGTAACTAACAAACCTCGAGCAGCTTCTGCCCACGCCATTGGGACTGT
CAAATGTTTAGCAATGGATGTGCAAGCATTTGAAAGGCTTCTGGGACCTTGCATGGAAATTATGAAAAGGAACATCGCTA
CCTATGAAGAACAGTTAGTTGCCCTGTTTGGAACGAACATGGATATTGTAGGTGGATCTGGAGGGAGCTCCGGTGCCAAA
AACATTAAGAAGGGCCCAGCGCCATTCTACCCACTCGAAGACGGGACCGCCGGCGAGCAGCTGCACAAAGCCATGAAGCG

*FIG. 67E*

CTACGCCCTGGTGCCCGGCACCATCGCCTTTACCGACGCACATATCGAGGTGGACATTACCTACGCCGAGTACTTCGAGA
TGAGCGTTCGGCTGGCAGAAGCTATGAAGCGCTATGGGCTGAATACAAACCATCGGATCGTGGTGTGCAGCGAGAATAGC
TTGCAGTTCTTCATGCCCGTGTTGGGTGCCCTGTTCATCGGTGTGGCTGTGGCCCCAGCTAACGACATCTACAACGAGCG
CGAGCTGCTGAACAGCATGGGCATCAGCCAGCCCACCGTCGTATTCGTGAGCAAGAAAGGGCTGCAAAAGATCCTCAACG
TGCAAAAGAAGCTACCGATCATACAAAAGATCATCATCATGGATAGCAAGACCGACTACCAGGGCTTCCAAAGCATGTAC
ACCTTCGTGACTTCCCATTTGCCACCCGGCTTCAACGAGTACGACTTCGTGCCCGAGAGCTTCGACCGGGACAAAACCAT
CGCCCTGATCATGAACAGTAGTGGCAGTACCGGATTGCCCAAGGGCGTAGCCCTACCGCACCGCACCGCTTGTGTCCGAT
TCAGTCATGCCCGCGACCCCATCTTCGGCAACCAGATCATCCCCGTTTAAAC

M) pBFB11 Sgf to Pme (SEQ ID NO:320)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAGGAGGTTCTGGCGGATCAGGCGGTTCGGGGATGTATGAAAGCTTTATTGAGTCACTGCCATTCCT
TAAATCTTTGGAGTTTTCTGAACGCCTGAAAGTAGTAGATGTGATAGGCACCAAAGTATACAACGATGGAGAACAAATCA
TTGCTCAGGGAGATTCGGCTGATTCTTTTTTCATTGTAGAATCTGGAGAAGTGAAAATTACTATGAAAAGAAAGGGTAAA
TCAGAAGTGGAAGAGAATGGTGCAGTAGAAATCGCTCGATGCTCGCGGGGACAGTACTTTGGAGAGCTTGCCCTGGTAAC
TAACAAACCTCGAGCAGCTTCTGCCCACGCCATTGGGACTGTCAAATGTTTAGCAATGGATGTGCAAGCATTTGAAAGGC
TTCTGGGACCTTGCATGGAAATTATGAAAAGGAACATCGCTACCTATGAAGAACAGTTAGTTGCCCTGTTTGGAACGAAC
ATGGATATTGTTGGGTCCGGTGGATCCGGTGGCAGCGGAGGGACGTCAGGTGGATCTGGAGGGAGCTCCGGTGCCAAAAA
CATTAAGAAGGGCCCAGCGCCATTCTACCCACTCGAAGACGGGACCGCCGGCGAGCAGCTGCACAAAGCCATGAAGCGCT
ACGCCCTGGTGCCCGGCACCATCGCCTTTACCGACGCACATATCGAGGTGGACATTACCTACGCCGAGTACTTCGAGATG
AGCGTTCGGCTGGCAGAAGCTATGAAGCGCTATGGGCTGAATACAAACCATCGGATCGTGGTGTGCAGCGAGAATAGCTT
GCAGTTCTTCATGCCCGTGTTGGGTGCCCTGTTCATCGGTGTGGCTGTGGCCCCAGCTAACGACATCTACAACGAGCGCG
AGCTGCTGAACAGCATGGGCATCAGCCAGCCCACCGTCGTATTCGTGAGCAAGAAAGGGCTGCAAAAGATCCTCAACGTG
CAAAAGAAGCTACCGATCATACAAAAGATCATCATCATGGATAGCAAGACCGACTACCAGGGCTTCCAAAGCATGTACAC
CTTCGTGACTTCCCATTTGCCACCCGGCTTCAACGAGTACGACTTCGTGCCCGAGAGCTTCGACCGGGACAAAACCATCG
CCCTGATCATGAACAGTAGTGGCAGTACCGGATTGCCCAAGGGCGTAGCCCTACCGCACCGCACCGCTTGTGTCCGATTC
AGTCATGCCCGCGACCCCATCTTCGGCAACCAGATCATCCCCGTTTAAAC

N) pBFB110 Sgf to Pme (SEQ ID NO:321)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAGGT
TCAATGTATGAAAGCTTTATTGAGTCACTGCCATTCCTTAAATCTTTGGAGTTTTCTGAACGCCTGAAAGTAGTAGATGT
GATAGGCACCAAAGTATACAACGATGGAGAACAAATCATTGCTCAGGGAGATTCGGCTGATTCTTTTTTCATTGTAGAAT
CTGGAGAAGTGAAAATTACTATGAAAAGAAAGGGTAAATCAGAAGTGGAAGAGAATGGTGCAGTAGAAATCGCTCGATGC
TCGCGGGGACAGTACTTTGGAGAGCTTGCCCTGGTAACTAACAAACCTCGAGCAGCTTCTGCCCACGCCATTGGGACTGT
CAAATGTTTAGCAATGGATGTGCAAGCATTTGAAAGGCTTCTGGGACCTTGCATGGAAATTATGAAAAGGAACATCGCTA

FIG. 67F

CCTATGAAGAACAGTTAGTTGCCCTGTTTGGAACGAACATGGATATTGTAGGGTCAGGTGGATCTGGAGGGAGCTCCGGT
GCCAAAAACATTAAGAAGGGCCCAGCGCCATTCTACCCACTCGAAGACGGGACCGCCGGCGAGCAGCTGCACAAAGCCAT
GAAGCGCTACGCCCTGGTGCCCGGCACCATCGCCTTTACCGACGCACATATCGAGGTGGACATTACCTACGCCGAGTACT
TCGAGATGAGCGTTCGGCTGGCAGAAGCTATGAAGCGCTATGGGCTGAATACAAACCATCGGATCGTGGTGTGCAGCGAG
AATAGCTTGCAGTTCTTCATGCCCGTGTTGGGTGCCCTGTTCATCGGTGTGGCTGTGGCCCCAGCTAACGACATCTACAA
CGAGCGCGAGCTGCTGAACAGCATGGGCATCAGCCAGCCCACCGTCGTATTCGTGAGCAAGAAAGGGCTGCAAAAGATCC
TCAACGTGCAAAAGAAGCTACCGATCATACAAAAGATCATCATCATGGATAGCAAGACCGACTACCAGGGCTTCCAAAGC
ATGTACACCTTCGTGACTTCCCATTTGCCACCCGGCTTCAACGAGTACGACTTCGTGCCCGAGAGCTTCGACCGGGACAA
AACCATCGCCCTGATCATGAACAGTAGTGGCAGTACCGGATTGCCCAAGGGCGTAGCCCTACCGCACCGCACCGCTTGTG
TCCGATTCAGTCATGCCCGCGACCCCATCTTCGGCAACCAGATCATCCCCGTTTAAAC

O) pBFB111 Sgf to Pme (SEQ ID NO:322)

GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAGGT
TCAGGCGGTATGTATGAAAGCTTTATTGAGTCACTGCCATTCCTTAAATCTTTGGAGTTTTCTGAACGCCTGAAAGTAGT
AGATGTGATAGGCACCAAAGTATACAACGATGGAGAACAAATCATTGCTCAGGGAGATTCGGCTGATTCTTTTTTCATTG
TAGAATCTGGAGAAGTGAAAATTACTATGAAAAGAAAGGGTAAATCAGAAGTGGAAGAGAATGGTGCAGTAGAAATCGCT
CGATGCTCGCGGGGACAGTACTTTGGAGAGCTTGCCCTGGTAACTAACAAACCTCGAGCAGCTTCTGCCCACGCCATTGG
GACTGTCAAATGTTTAGCAATGGATGTGCAAGCATTTGAAAGGCTTCTGGGACCTTGCATGGAAATTATGAAAAGGAACA
TCGCTACCTATGAAGAACAGTTAGTTGCCCTGTTTGGAACGAACATGGATATTGTAGCCAAAAACATTAAGAAGGGCCCA
GCGCCATTCTACCCACTCGAAGACGGGACCGCCGGCGAGCAGCTGCACAAAGCCATGAAGCGCTACGCCCTGGTGCCCGG
CACCATCGCCTTTACCGACGCACATATCGAGGTGGACATTACCTACGCCGAGTACTTCGAGATGAGCGTTCGGCTGGCAG
AAGCTATGAAGCGCTATGGGCTGAATACAAACCATCGGATCGTGGTGTGCAGCGAGAATAGCTTGCAGTTCTTCATGCCC
GTGTTGGGTGCCCTGTTCATCGGTGTGGCTGTGGCCCCAGCTAACGACATCTACAACGAGCGCGAGCTGCTGAACAGCAT
GGGCATCAGCCAGCCCACCGTCGTATTCGTGAGCAAGAAAGGGCTGCAAAAGATCCTCAACGTGCAAAAGAAGCTACCGA
TCATACAAAAGATCATCATCATGGATAGCAAGACCGACTACCAGGGCTTCCAAAGCATGTACACCTTCGTGACTTCCCAT
TTGCCACCCGGCTTCAACGAGTACGACTTCGTGCCCGAGAGCTTCGACCGGGACAAAACCATCGCCCTGATCATGAACAG
TAGTGGCAGTACCGGATTGCCCAAGGGCGTAGCCCTACCGCACCGCACCGCTTGTGTCCGATTCAGTCATGCCCGCGACC
CCATCTTCGGCAACCAGATCATCCCCGTTTAAAC

P) pBFB112 Sgf to Pme (SEQ ID NO:323)

GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAGGT
TCAGGCGGTATGTATGAAAGCTTTATTGAGTCACTGCCATTCCTTAAATCTTTGGAGTTTTCTGAACGCCTGAAAGTAGT
AGATGTGATAGGCACCAAAGTATACAACGATGGAGAACAAATCATTGCTCAGGGAGATTCGGCTGATTCTTTTTTCATTG
TAGAATCTGGAGAAGTGAAAATTACTATGAAAAGAAAGGGTAAATCAGAAGTGGAAGAGAATGGTGCAGTAGAAATCGCT
CGATGCTCGCGGGGACAGTACTTTGGAGAGCTTGCCCTGGTAACTAACAAACCTCGAGCAGCTTCTGCCCACGCCATTGG

FIG. 67G

GACTGTCAAATGTTTAGCAATGGATGTGCAAGCATTTGAAAGGCTTCTGGGACCTTGCATGGAAATTATGAAAAGGAACA
TCGCTACCTATGAAGAACAGTTAGTTGCCCTGTTTGGAACGAACATGGATATTGTATCCGGTGCCAAAAACATTAAGAAG
GGCCCAGCGCCATTCTACCCACTCGAAGACGGGACCGCCGGCGAGCAGCTGCACAAAGCCATGAAGCGCTACGCCCTGGT
GCCCGGCACCATCGCCTTTACCGACGCACATATCGAGGTGGACATTACCTACGCCGAGTACTTCGAGATGAGCGTTCGGC
TGGCAGAAGCTATGAAGCGCTATGGGCTGAATACAAACCATCGGATCGTGGTGTGCAGCGAGAATAGCTTGCAGTTCTTC
ATGCCCGTGTTGGGTGCCCTGTTCATCGGTGTGGCTGTGGCCCCAGCTAACGACATCTACAACGAGCGCGAGCTGCTGAA
CAGCATGGGCATCAGCCAGCCCACCGTCGTATTCGTGAGCAAGAAAGGGCTGCAAAAGATCCTCAACGTGCAAAAGAAGC
TACCGATCATACAAAAGATCATCATCATGGATAGCAAGACCGACTACCAGGGCTTCCAAAGCATGTACACCTTCGTGACT
TCCCATTTGCCACCCGGCTTCAACGAGTACGACTTCGTGCCCGAGAGCTTCGACCGGGACAAAACCATCGCCCTGATCAT
GAACAGTAGTGGCAGTACCGGATTGCCCAAGGGCGTAGCCCTACCGCACCGCACCGCTTGTGTCCGATTCAGTCATGCCC
GCGACCCCATCTTCGGCAACCAGATCATCCCCGTTTAAAC

Q) pBFB113 Sgf to Pme (SEQ ID NO:324)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAGGT
TCAGGCGGTATGTATGAAAGCTTTATTGAGTCACTGCCATTCCTTAAATCTTTGGAGTTTTCTGAACGCCTGAAAGTAGT
AGATGTGATAGGCACCAAAGTATACAACGATGGAGAACAAATCATTGCTCAGGGAGATTCGGCTGATTCTTTTTTCATTG
TAGAATCTGGAGAAGTGAAAATTACTATGAAAAGAAAGGGTAAATCAGAAGTGGAAGAGAATGGTGCAGTAGAAATCGCT
CGATGCTCGCGGGGACAGTACTTTGGAGAGCTTGCCCTGGTAACTAACAAACCTCGAGCAGCTTCTGCCCACGCCATTGG
GACTGTCAAATGTTTAGCAATGGATGTGCAAGCATTTGAAAGGCTTCTGGGACCTTGCATGGAAATTATGAAAAGGAACA
TCGCTACCTATGAAGAACAGTTAGTTGCCCTGTTTGGAACGAACATGGATATTGTTGGGAGCTCCGGTGCCAAAAACATT
AAGAAGGGCCCAGCGCCATTCTACCCACTCGAAGACGGGACCGCCGGCGAGCAGCTGCACAAAGCCATGAAGCGCTACGC
CCTGGTGCCCGGCACCATCGCCTTTACCGACGCACATATCGAGGTGGACATTACCTACGCCGAGTACTTCGAGATGAGCG
TTCGGCTGGCAGAAGCTATGAAGCGCTATGGGCTGAATACAAACCATCGGATCGTGGTGTGCAGCGAGAATAGCTTGCAG
TTCTTCATGCCCGTGTTGGGTGCCCTGTTCATCGGTGTGGCTGTGGCCCCAGCTAACGACATCTACAACGAGCGCGAGCT
GCTGAACAGCATGGGCATCAGCCAGCCCACCGTCGTATTCGTGAGCAAGAAAGGGCTGCAAAAGATCCTCAACGTGCAAA
AGAAGCTACCGATCATACAAAAGATCATCATCATGGATAGCAAGACCGACTACCAGGGCTTCCAAAGCATGTACACCTTC
GTGACTTCCCATTTGCCACCCGGCTTCAACGAGTACGACTTCGTGCCCGAGAGCTTCGACCGGGACAAAACCATCGCCCT
GATCATGAACAGTAGTGGCAGTACCGGATTGCCCAAGGGCGTAGCCCTACCGCACCGCACCGCTTGTGTCCGATTCAGTC
ATGCCCGCGACCCCATCTTCGGCAACCAGATCATCCCCGTTTAAAC

R) pBFB114 Sgf to Pme (SEQ ID NO:325)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAGGT
TCAGGCGGTATGTATGAAAGCTTTATTGAGTCACTGCCATTCCTTAAATCTTTGGAGTTTTCTGAACGCCTGAAAGTAGT
AGATGTGATAGGCACCAAAGTATACAACGATGGAGAACAAATCATTGCTCAGGGAGATTCGGCTGATTCTTTTTTCATTG
TAGAATCTGGAGAAGTGAAAATTACTATGAAAAGAAAGGGTAAATCAGAAGTGGAAGAGAATGGTGCAGTAGAAATCGCT

*FIG. 67H*

CGATGCTCGCGGGGACAGTACTTTGGAGAGCTTGCCCTGGTAACTAACAAACCTCGAGCAGCTTCTGCCCACGCCATTGG
GACTGTCAAATGTTTAGCAATGGATGTGCAAGCATTTGAAAGGCTTCTGGGACCTTGCATGGAAATTATGAAAAGGAACA
TCGCTACCTATGAAGAACAGTTAGTTGCCCTGTTTGGAACGAACATGGATATTGTATCTGGAGGGAGCTCCGGTGCCAAA
AACATTAAGAAGGGCCCAGCGCCATTCTACCCACTCGAAGACGGGACCGCCGGCGAGCAGCTGCACAAAGCCATGAAGCG
CTACGCCCTGGTGCCCGGCACCATCGCCTTTACCGACGCACATATCGAGGTGGACATTACCTACGCCGAGTACTTCGAGA
TGAGCGTTCGGCTGGCAGAAGCTATGAAGCGCTATGGGCTGAATACAAACCATCGGATCGTGGTGTGCAGCGAGAATAGC
TTGCAGTTCTTCATGCCCGTGTTGGGTGCCCTGTTCATCGGTGTGGCTGTGGCCCCAGCTAACGACATCTACAACGAGCG
CGAGCTGCTGAACAGCATGGGCATCAGCCAGCCCACCGTCGTATTCGTGAGCAAGAAAGGGCTGCAAAAGATCCTCAACG
TGCAAAAGAAGCTACCGATCATACAAAAGATCATCATCATGGATAGCAAGACCGACTACCAGGGCTTCCAAAGCATGTAC
ACCTTCGTGACTTCCCATTTGCCACCCGGCTTCAACGAGTACGACTTCGTGCCCGAGAGCTTCGACCGGGACAAAACCAT
CGCCCTGATCATGAACAGTAGTGGCAGTACCGGATTGCCCAAGGGCGTAGCCCTACCGCACCGCACCGCTTGTGTCCGAT
TCAGTCATGCCCGCGACCCCATCTTCGGCAACCAGATCATCCCCGTTTAAAC

S) pBFB115 Sgf to Pme (SEQ ID NO:326)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAGGT
TCAGGCGGTATGTATGAAAGCTTTATTGAGTCACTGCCATTCCTTAAATCTTTGGAGTTTTCTGAACGCCTGAAAGTAGT
AGATGTGATAGGCACCAAAGTATACAACGATGGAGAACAAATCATTGCTCAGGGAGATTCGGCTGATTCTTTTTTCATTG
TAGAATCTGGAGAAGTGAAAATTACTATGAAAAGAAAGGGTAAATCAGAAGTGGAAGAGAATGGTGCAGTAGAAATCGCT
CGATGCTCGCGGGGACAGTACTTTGGAGAGCTTGCCCTGGTAACTAACAAACCTCGAGCAGCTTCTGCCCACGCCATTGG
GACTGTCAAATGTTTAGCAATGGATGTGCAAGCATTTGAAAGGCTTCTGGGACCTTGCATGGAAATTATGAAAAGGAACA
TCGCTACCTATGAAGAACAGTTAGTTGCCCTGTTTGGAACGAACATGGATATTGTAGGTGGATCTGGAGGGAGCTCCGGT
GCCAAAAACATTAAGAAGGGCCCAGCGCCATTCTACCCACTCGAAGACGGGACCGCCGGCGAGCAGCTGCACAAAGCCAT
GAAGCGCTACGCCCTGGTGCCCGGCACCATCGCCTTTACCGACGCACATATCGAGGTGGACATTACCTACGCCGAGTACT
TCGAGATGAGCGTTCGGCTGGCAGAAGCTATGAAGCGCTATGGGCTGAATACAAACCATCGGATCGTGGTGTGCAGCGAG
AATAGCTTGCAGTTCTTCATGCCCGTGTTGGGTGCCCTGTTCATCGGTGTGGCTGTGGCCCCAGCTAACGACATCTACAA
CGAGCGCGAGCTGCTGAACAGCATGGGCATCAGCCAGCCCACCGTCGTATTCGTGAGCAAGAAAGGGCTGCAAAAGATCC
TCAACGTGCAAAAGAAGCTACCGATCATACAAAAGATCATCATCATGGATAGCAAGACCGACTACCAGGGCTTCCAAAGC
ATGTACACCTTCGTGACTTCCCATTTGCCACCCGGCTTCAACGAGTACGACTTCGTGCCCGAGAGCTTCGACCGGGACAA
AACCATCGCCCTGATCATGAACAGTAGTGGCAGTACCGGATTGCCCAAGGGCGTAGCCCTACCGCACCGCACCGCTTGTG
TCCGATTCAGTCATGCCCGCGACCCCATCTTCGGCAACCAGATCATCCCCGTTTAAAC

T) pBFB116 Sgf to Pme (SEQ ID NO:327)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAGGT
TCAGGCGGTATGTATGAAAGCTTTATTGAGTCACTGCCATTCCTTAAATCTTTGGAGTTTTCTGAACGCCTGAAAGTAGT
AGATGTGATAGGCACCAAAGTATACAACGATGGAGAACAAATCATTGCTCAGGGAGATTCGGCTGATTCTTTTTTCATTG

*FIG. 67I*

TAGAATCTGGAGAAGTGAAAATTACTATGAAAAGAAAGGGTAAATCAGAAGTGGAAGAGAATGGTGCAGTAGAAATCGCT
CGATGCTCGCGGGGACAGTACTTTGGAGAGCTTGCCCTGGTAACTAACAAACCTCGAGCAGCTTCTGCCCACGCCATTGG
GACTGTCAAATGTTTAGCAATGGATGTGCAAGCATTTGAAAGGCTTCTGGGACCTTGCATGGAAATTATGAAAAGGAACA
TCGCTACCTATGAAGAACAGTTAGTTGCCCTGTTTGGAACGAACATGGATATTGTAGGGTCAGGTGGATCTGGAGGGAGC
TCCGGTGCCAAAAACATTAAGAAGGGCCCAGCGCCATTCTACCCACTCGAAGACGGGACCGCCGGCGAGCAGCTGCACAA
AGCCATGAAGCGCTACGCCCTGGTGCCCGGCACCATCGCCTTTACCGACGCACATATCGAGGTGGACATTACCTACGCCG
AGTACTTCGAGATGAGCGTTCGGCTGGCAGAAGCTATGAAGCGCTATGGGCTGAATACAAACCATCGGATCGTGGTGTGC
AGCGAGAATAGCTTGCAGTTCTTCATGCCCGTGTTGGGTGCCCTGTTCATCGGTGTGGCTGTGGCCCCAGCTAACGACAT
CTACAACGAGCGCGAGCTGCTGAACAGCATGGGCATCAGCCAGCCCACCGTCGTATTCGTGAGCAAGAAAGGGCTGCAAA
AGATCCTCAACGTGCAAAAGAAGCTACCGATCATACAAAAGATCATCATCATGGATAGCAAGACCGACTACCAGGGCTTC
CAAAGCATGTACACCTTCGTGACTTCCCATTTGCCACCCGGCTTCAACGAGTACGACTTCGTGCCCGAGAGCTTCGACCG
GGACAAAACCATCGCCCTGATCATGAACAGTAGTGGCAGTACCGGATTGCCCAAGGGCGTAGCCCTACCGCACCGCACCG
CTTGTGTCCGATTCAGTCATGCCCGCGACCCCATCTTCGGCAACCAGATCATCCCCGTTTAAAC

U) pBFB117 Sgf to Pme (SEQ ID NO:328)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAATGTATGAAAGCTTTATTGAGTCACTGCCATTCCTTAAATCTTTGGAGTTTTCTGAACGCCTGAA
AGTAGTAGATGTGATAGGCACCAAAGTATACAACGATGGAGAACAAATCATTGCTCAGGGAGATTCGGCTGATTCTTTTT
TCATTGTAGAATCTGGAGAAGTGAAAATTACTATGAAAAGAAAGGGTAAATCAGAAGTGGAAGAGAATGGTGCAGTAGAA
ATCGCTCGATGCTCGCGGGGACAGTACTTTGGAGAGCTTGCCCTGGTAACTAACAAACCTCGAGCAGCTTCTGCCCACGC
CATTGGGACTGTCAAATGTTTAGCAATGGATGTGCAAGCATTTGAAAGGCTTCTGGGACCTTGCATGGAAATTATGAAAA
GGAACATCGCTACCTATGAAGAACAGTTAGTTGCCCTGTTTGGAACGAACATGGATATTGTAGCCAAAAACATTAAGAAG
GGCCCAGCGCCATTCTACCCACTCGAAGACGGGACCGCCGGCGAGCAGCTGCACAAAGCCATGAAGCGCTACGCCCTGGT
GCCCGGCACCATCGCCTTTACCGACGCACATATCGAGGTGGACATTACCTACGCCGAGTACTTCGAGATGAGCGTTCGGC
TGGCAGAAGCTATGAAGCGCTATGGGCTGAATACAAACCATCGGATCGTGGTGTGCAGCGAGAATAGCTTGCAGTTCTTC
ATGCCCGTGTTGGGTGCCCTGTTCATCGGTGTGGCTGTGGCCCCAGCTAACGACATCTACAACGAGCGCGAGCTGCTGAA
CAGCATGGGCATCAGCCAGCCCACCGTCGTATTCGTGAGCAAGAAAGGGCTGCAAAAGATCCTCAACGTGCAAAAGAAGC
TACCGATCATACAAAAGATCATCATCATGGATAGCAAGACCGACTACCAGGGCTTCCAAAGCATGTACACCTTCGTGACT
TCCCATTTGCCACCCGGCTTCAACGAGTACGACTTCGTGCCCGAGAGCTTCGACCGGGACAAAACCATCGCCCTGATCAT
GAACAGTAGTGGCAGTACCGGATTGCCCAAGGGCGTAGCCCTACCGCACCGCACCGCTTGTGTCCGATTCAGTCATGCCC
GCGACCCCATCTTCGGCAACCAGATCATCCCCGTTTAAAC

V) pBFB118 Sgf to Pme (SEQ ID NO:329)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAATGTATGAAAGCTTTATTGAGTCACTGCCATTCCTTAAATCTTTGGAGTTTTCTGAACGCCTGAA

FIG. 67J

AGTAGTAGATGTGATAGGCACCAAAGTATACAACGATGGAGAACAAATCATTGCTCAGGGAGATTCGGCTGATTCTTTTT
TCATTGTAGAATCTGGAGAAGTGAAAATTACTATGAAAAGAAAGGGTAAATCAGAAGTGGAAGAGAATGGTGCAGTAGAA
ATCGCTCGATGCTCGCGGGGACAGTACTTTGGAGAGCTTGCCCTGGTAACTAACAAACCTCGAGCAGCTTCTGCCCACGC
CATTGGGACTGTCAAATGTTTAGCAATGGATGTGCAAGCATTTGAAAGGCTTCTGGGACCTTGCATGGAAATTATGAAAA
GGAACATCGCTACCTATGAAGAACAGTTAGTTGCCCTGTTTGGAACGAACATGGATATTGTATCCGGTGCCAAAAACATT
AAGAAGGGCCCAGCGCCATTCTACCCACTCGAAGACGGGACCGCCGGCGAGCAGCTGCACAAAGCCATGAAGCGCTACGC
CCTGGTGCCCGGCACCATCGCCTTTACCGACGCACATATCGAGGTGGACATTACCTACGCCGAGTACTTCGAGATGAGCG
TTCGGCTGGCAGAAGCTATGAAGCGCTATGGGCTGAATACAAACCATCGGATCGTGGTGTGCAGCGAGAATAGCTTGCAG
TTCTTCATGCCCGTGTTGGGTGCCCTGTTCATCGGTGTGGCTGTGGCCCCAGCTAACGACATCTACAACGAGCGCGAGCT
GCTGAACAGCATGGGCATCAGCCAGCCCACCGTCGTATTCGTGAGCAAGAAAGGGCTGCAAAAGATCCTCAACGTGCAAA
AGAAGCTACCGATCATACAAAAGATCATCATCATGGATAGCAAGACCGACTACCAGGGCTTCCAAAGCATGTACACCTTC
GTGACTTCCCATTTGCCACCCGGCTTCAACGAGTACGACTTCGTGCCCGAGAGCTTCGACCGGGACAAAACCATCGCCCT
GATCATGAACAGTAGTGGCAGTACCGGATTGCCCAAGGGCGTAGCCCTACCGCACCGCACCGCTTGTGTCCGATTCAGTC
ATGCCCGCGACCCCATCTTCGGCAACCAGATCATCCCCGTTTAAAC

W) pBFB119 Sgf to Pme (SEQ ID NO:330)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAATGTATGAAAGCTTTATTGAGTCACTGCCATTCCTTAAATCTTTGGAGTTTTCTGAACGCCTGAA
AGTAGTAGATGTGATAGGCACCAAAGTATACAACGATGGAGAACAAATCATTGCTCAGGGAGATTCGGCTGATTCTTTTT
TCATTGTAGAATCTGGAGAAGTGAAAATTACTATGAAAAGAAAGGGTAAATCAGAAGTGGAAGAGAATGGTGCAGTAGAA
ATCGCTCGATGCTCGCGGGGACAGTACTTTGGAGAGCTTGCCCTGGTAACTAACAAACCTCGAGCAGCTTCTGCCCACGC
CATTGGGACTGTCAAATGTTTAGCAATGGATGTGCAAGCATTTGAAAGGCTTCTGGGACCTTGCATGGAAATTATGAAAA
GGAACATCGCTACCTATGAAGAACAGTTAGTTGCCCTGTTTGGAACGAACATGGATATTGTATCTGGAGGGAGCTCCGGT
GCCAAAAACATTAAGAAGGGCCCAGCGCCATTCTACCCACTCGAAGACGGGACCGCCGGCGAGCAGCTGCACAAAGCCAT
GAAGCGCTACGCCCTGGTGCCCGGCACCATCGCCTTTACCGACGCACATATCGAGGTGGACATTACCTACGCCGAGTACT
TCGAGATGAGCGTTCGGCTGGCAGAAGCTATGAAGCGCTATGGGCTGAATACAAACCATCGGATCGTGGTGTGCAGCGAG
AATAGCTTGCAGTTCTTCATGCCCGTGTTGGGTGCCCTGTTCATCGGTGTGGCTGTGGCCCCAGCTAACGACATCTACAA
CGAGCGCGAGCTGCTGAACAGCATGGGCATCAGCCAGCCCACCGTCGTATTCGTGAGCAAGAAAGGGCTGCAAAAGATCC
TCAACGTGCAAAAGAAGCTACCGATCATACAAAAGATCATCATCATGGATAGCAAGACCGACTACCAGGGCTTCCAAAGC
ATGTACACCTTCGTGACTTCCCATTTGCCACCCGGCTTCAACGAGTACGACTTCGTGCCCGAGAGCTTCGACCGGGACAA
AACCATCGCCCTGATCATGAACAGTAGTGGCAGTACCGGATTGCCCAAGGGCGTAGCCCTACCGCACCGCACCGCTTGTG
TCCGATTCAGTCATGCCCGCGACCCCATCTTCGGCAACCAGATCATCCCCGTTTAAAC

X) pBFB120 Sgf to Pme (SEQ ID NO:331)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT

FIG. 67K

TCAGGCGGTTCCGGAATGTATGAAAGCTTTATTGAGTCACTGCCATTCCTTAAATCTTTGGAGTTTTCTGAACGCCTGAA
AGTAGTAGATGTGATAGGCACCAAAGTATACAACGATGGAGAACAAATCATTGCTCAGGGAGATTCGGCTGATTCTTTTT
TCATTGTAGAATCTGGAGAAGTGAAAATTACTATGAAAAGAAAGGGTAAATCAGAAGTGGAAGAGAATGGTGCAGTAGAA
ATCGCTCGATGCTCGCGGGGACAGTACTTTGGAGAGCTTGCCCTGGTAACTAACAAACCTCGAGCAGCTTCTGCCCACGC
CATTGGGACTGTCAAATGTTTAGCAATGGATGTGCAAGCATTTGAAAGGCTTCTGGGACCTTGCATGGAAATTATGAAAA
GGAACATCGCTACCTATGAAGAACAGTTAGTTGCCCTGTTTGGAACGAACATGGATATTGTAGGTGGATCTGGAGGGAGC
TCCGGTGCCAAAAACATTAAGAAGGGCCCAGCGCCATTCTACCCACTCGAAGACGGGACCGCCGGCGAGCAGCTGCACAA
AGCCATGAAGCGCTACGCCCTGGTGCCCGGCACCATCGCCTTTACCGACGCACATATCGAGGTGGACATTACCTACGCCG
AGTACTTCGAGATGAGCGTTCGGCTGGCAGAAGCTATGAAGCGCTATGGGCTGAATACAAACCATCGGATCGTGGTGTGC
AGCGAGAATAGCTTGCAGTTCTTCATGCCCGTGTTGGGTGCCCTGTTCATCGGTGTGGCTGTGGCCCCAGCTAACGACAT
CTACAACGAGCGCGAGCTGCTGAACAGCATGGGCATCAGCCAGCCCACCGTCGTATTCGTGAGCAAGAAAGGGCTGCAAA
AGATCCTCAACGTGCAAAAGAAGCTACCGATCATACAAAAGATCATCATCATGGATAGCAAGACCGACTACCAGGGCTTC
CAAAGCATGTACACCTTCGTGACTTCCCATTTGCCACCCGGCTTCAACGAGTACGACTTCGTGCCCGAGAGCTTCGACCG
GGACAAAACCATCGCCCTGATCATGAACAGTAGTGGCAGTACCGGATTGCCCAAGGGCGTAGCCCTACCGCACCGCACCG
CTTGTGTCCGATTCAGTCATGCCCGCGACCCCATCTTCGGCAACCAGATCATCCCCGTTTAAAC

Y) pBFB128 Sgf to Pme (SEQ ID NO:332)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAGGT
TCAGGCGGTTCCGGAATGTATGAAAGCTTTATTGAGTCACTGCCATTCCTTAAATCTTTGGAGTTTTCTGAACGCCTGAA
AGTAGTAGATGTGATAGGCACCAAAGTATACAACGATGGAGAACAAATCATTGCTCAGGGAGATTCGGCTGATTCTTTTT
TCATTGTAGAATCTGGAGAAGTGAAAATTACTATGAAAAGAAAGGGTAAATCAGAAGTGGAAGAGAATGGTGCAGTAGAA
ATCGCTCGATGCTCGCGGGGACAGTACTTTGGAGAGCTTGCCCTGGTAACTAACAAACCTCGAGCAGCTTCTGCCCACGC
CATTGGGACTGTCAAATGTTTAGCAATGGATGTGCAAGCATTTGAAAGGCTTCTGGGACCTTGCATGGAAATTATGAAAA
GGAACATCGCTACCTATGAAGAACAGTTAGTTGCCCTGTTTGGAACGAACATGGATGCCAAAAACATTAAGAAGGGCCCA
GCGCCATTCTACCCACTCGAAGACGGGACCGCCGGCGAGCAGCTGCACAAAGCCATGAAGCGCTACGCCCTGGTGCCCGG
CACCATCGCCTTTACCGACGCACATATCGAGGTGGACATTACCTACGCCGAGTACTTCGAGATGAGCGTTCGGCTGGCAG
AAGCTATGAAGCGCTATGGGCTGAATACAAACCATCGGATCGTGGTGTGCAGCGAGAATAGCTTGCAGTTCTTCATGCCC
GTGTTGGGTGCCCTGTTCATCGGTGTGGCTGTGGCCCCAGCTAACGACATCTACAACGAGCGCGAGCTGCTGAACAGCAT
GGGCATCAGCCAGCCCACCGTCGTATTCGTGAGCAAGAAAGGGCTGCAAAAGATCCTCAACGTGCAAAAGAAGCTACCGA
TCATACAAAAGATCATCATCATGGATAGCAAGACCGACTACCAGGGCTTCCAAAGCATGTACACCTTCGTGACTTCCCAT
TTGCCACCCGGCTTCAACGAGTACGACTTCGTGCCCGAGAGCTTCGACCGGGACAAAACCATCGCCCTGATCATGAACAG
TAGTGGCAGTACCGGATTGCCCAAGGGCGTAGCCCTACCGCACCGCACCGCTTGTGTCCGATTCAGTCATGCCCGCGACC
CCATCTTCGGCAACCAGATCATCCCCGTTTAAAC

Z) pBFB129 Sgf to Pme (SEQ ID NO:333)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC

*FIG. 67L*

CTAAAGGACTGACCGGCAAGTTGGACGCCCGCAAGATCCGCGAGATTCTCATTAAGGCCAAGAAGGGCTCGACCGGAGGT
TCAGGCGGTTCCGGAATGTATGAAAGCTTTATTGAGTCACTGCCATTCCTTAAATCTTTGGAGTTTTCTGAACGCCTGAA
AGTAGTAGATGTGATAGGCACCAAAGTATACAACGATGGAGAACAAATCATTGCTCAGGGAGATTCGGCTGATTCTTTTT
TCATTGTAGAATCTGGAGAAGTGAAAATTACTATGAAAAGAAAGGGTAAATCAGAAGTGGAAGAGAATGGTGCAGTAGAA
ATCGCTCGATGCTCGCGGGGACAGTACTTTGGAGAGCTTGCCCTGGTAACTAACAAACCTCGAGCAGCTTCTGCCCACGC
CATTGGGACTGTCAAATGTTTAGCAATGGATGTGCAAGCATTTGAAAGGCTTCTGGGACCTTGCATGGAAATTATGAAAA
GGAACATCGCTACCTATGAAGAACAGTTAGTTGCCCTGTTTGGAACGAACGCCAAAAACATTAAGAAGGGCCCAGCGCCA
TTCTACCCACTCGAAGACGGGACCGCCGGCGAGCAGCTGCACAAAGCCATGAAGCGCTACGCCCTGGTGCCCGGCACCAT
CGCCTTTACCGACGCACATATCGAGGTGGACATTACCTACGCCGAGTACTTCGAGATGAGCGTTCGGCTGGCAGAAGCTA
TGAAGCGCTATGGGCTGAATACAAACCATCGGATCGTGGTGTGCAGCGAGAATAGCTTGCAGTTCTTCATGCCCGTGTTG
GGTGCCCTGTTCATCGGTGTGGCTGTGGCCCCAGCTAACGACATCTACAACGAGCGCGAGCTGCTGAACAGCATGGGCAT
CAGCCAGCCCACCGTCGTATTCGTGAGCAAGAAAGGGCTGCAAAAGATCCTCAACGTGCAAAAGAAGCTACCGATCATAC
AAAAGATCATCATCATGGATAGCAAGACCGACTACCAGGGCTTCCAAAGCATGTACACCTTCGTGACTTCCCATTTGCCA
CCCGGCTTCAACGAGTACGACTTCGTGCCCGAGAGCTTCGACCGGGACAAAACCATCGCCCTGATCATGAACAGTAGTGG
CAGTACCGGATTGCCCAAGGGCGTAGCCCTACCGCACCGCACCGCTTGTGTCCGATTCAGTCATGCCCGCGACCCCATCT
TCGGCAACCAGATCATCCCCGTTTAAAC

AA) pBFB130 Sgf to Pme (SEQ ID NO:334)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAGGT
TCAGGCGGTTCCGGAATGTATGAAAGCTTTATTGAGTCACTGCCATTCCTTAAATCTTTGGAGTTTTCTGAACGCCTGAA
AGTAGTAGATGTGATAGGCACCAAAGTATACAACGATGGAGAACAAATCATTGCTCAGGGAGATTCGGCTGATTCTTTTT
TCATTGTAGAATCTGGAGAAGTGAAAATTACTATGAAAAGAAAGGGTAAATCAGAAGTGGAAGAGAATGGTGCAGTAGAA
ATCGCTCGATGCTCGCGGGGACAGTACTTTGGAGAGCTTGCCCTGGTAACTAACAAACCTCGAGCAGCTTCTGCCCACGC
CATTGGGACTGTCAAATGTTTAGCAATGGATGTGCAAGCATTTGAAAGGCTTCTGGGACCTTGCATGGAAATTATGAAAA
GGAACATCGCTACCTATGAAGAACAGTTAGTTGCCCTGTTTGGAGCCAAAAACATTAAGAAGGGCCCAGCGCCATTCTAC
CCACTCGAAGACGGGACCGCCGGCGAGCAGCTGCACAAAGCCATGAAGCGCTACGCCCTGGTGCCCGGCACCATCGCCTT
TACCGACGCACATATCGAGGTGGACATTACCTACGCCGAGTACTTCGAGATGAGCGTTCGGCTGGCAGAAGCTATGAAGC
GCTATGGGCTGAATACAAACCATCGGATCGTGGTGTGCAGCGAGAATAGCTTGCAGTTCTTCATGCCCGTGTTGGGTGCC
CTGTTCATCGGTGTGGCTGTGGCCCCAGCTAACGACATCTACAACGAGCGCGAGCTGCTGAACAGCATGGGCATCAGCCA
GCCCACCGTCGTATTCGTGAGCAAGAAAGGGCTGCAAAAGATCCTCAACGTGCAAAAGAAGCTACCGATCATACAAAAGA
TCATCATCATGGATAGCAAGACCGACTACCAGGGCTTCCAAAGCATGTACACCTTCGTGACTTCCCATTTGCCACCCGGC
TTCAACGAGTACGACTTCGTGCCCGAGAGCTTCGACCGGGACAAAACCATCGCCCTGATCATGAACAGTAGTGGCAGTAC
CGGATTGCCCAAGGGCGTAGCCCTACCGCACCGCACCGCTTGTGTCCGATTCAGTCATGCCCGCGACCCCATCTTCGGCA
ACCAGATCATCCCCGTTTAAAC

BB) pBFB131 Sgf to Pme (SEQ ID NO:335)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC

*FIG. 67M*

CTAAAGGACTGACCGGCAAGTTGGACGCCCGCAAGATCCGCGAGATTCTCATTAAGGCCAAGAAGGGCTCGACCGGAGGT
TCAGGCGGTTCCGGAATGTATGAAAGCTTTATTGAGTCACTGCCATTCCTTAAATCTTTGGAGTTTTCTGAACGCCTGAA
AGTAGTAGATGTGATAGGCACCAAAGTATACAACGATGGAGAACAAATCATTGCTCAGGGAGATTCGGCTGATTCTTTTT
TCATTGTAGAATCTGGAGAAGTGAAAATTACTATGAAAAGAAAGGGTAAATCAGAAGTGGAAGAGAATGGTGCAGTAGAA
ATCGCTCGATGCTCGCGGGGACAGTACTTTGGAGAGCTTGCCCTGGTAACTAACAAACCTCGAGCAGCTTCTGCCCACGC
CATTGGGACTGTCAAATGTTTAGCAATGGATGTGCAAGCATTTGAAAGGCTTCTGGGACCTTGCATGGAAATTATGAAAA
GGAACATCGCTACCTATGAAGAACAGTTAGTTGCCCTGGCCAAAAACATTAAGAAGGGCCCAGCGCCATTCTACCCACTC
GAAGACGGGACCGCCGGCGAGCAGCTGCACAAAGCCATGAAGCGCTACGCCCTGGTGCCCGGCACCATCGCCTTTACCGA
CGCACATATCGAGGTGGACATTACCTACGCCGAGTACTTCGAGATGAGCGTTCGGCTGGCAGAAGCTATGAAGCGCTATG
GGCTGAATACAAACCATCGGATCGTGGTGTGCAGCGAGAATAGCTTGCAGTTCTTCATGCCCGTGTTGGGTGCCCTGTTC
ATCGGTGTGGCTGTGGCCCCAGCTAACGACATCTACAACGAGCGCGAGCTGCTGAACAGCATGGGCATCAGCCAGCCCAC
CGTCGTATTCGTGAGCAAGAAAGGGCTGCAAAAGATCCTCAACGTGCAAAAGAAGCTACCGATCATACAAAAGATCATCA
TCATGGATAGCAAGACCGACTACCAGGGCTTCCAAAGCATGTACACCTTCGTGACTTCCCATTTGCCACCCGGCTTCAAC
GAGTACGACTTCGTGCCCGAGAGCTTCGACCGGGACAAAACCATCGCCCTGATCATGAACAGTAGTGGCAGTACCGGATT
GCCCAAGGGCGTAGCCCTACCGCACCGCACCGCTTGTGTCCGATTCAGTCATGCCCGCGACCCCATCTTCGGCAACCAGA
TCATCCCCGTTTAAAC

CC) pBFB132 Sgf to Pme (SEQ ID NO:336)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAGGT
TCAGGCGGTTCCGGAATGTATGAAAGCTTTATTGAGTCACTGCCATTCCTTAAATCTTTGGAGTTTTCTGAACGCCTGAA
AGTAGTAGATGTGATAGGCACCAAAGTATACAACGATGGAGAACAAATCATTGCTCAGGGAGATTCGGCTGATTCTTTTT
TCATTGTAGAATCTGGAGAAGTGAAAATTACTATGAAAAGAAAGGGTAAATCAGAAGTGGAAGAGAATGGTGCAGTAGAA
ATCGCTCGATGCTCGCGGGGACAGTACTTTGGAGAGCTTGCCCTGGTAACTAACAAACCTCGAGCAGCTTCTGCCCACGC
CATTGGGACTGTCAAATGTTTAGCAATGGATGTGCAAGCATTTGAAAGGCTTCTGGGACCTTGCATGGAAATTATGAAAA
GGAACATCGCTACCTATGAAGAACAGTTAGTTGCCAAAAACATTAAGAAGGGCCCAGCGCCATTCTACCCACTCGAAGAC
GGGACCGCCGGCGAGCAGCTGCACAAAGCCATGAAGCGCTACGCCCTGGTGCCCGGCACCATCGCCTTTACCGACGCACA
TATCGAGGTGGACATTACCTACGCCGAGTACTTCGAGATGAGCGTTCGGCTGGCAGAAGCTATGAAGCGCTATGGGCTGA
ATACAAACCATCGGATCGTGGTGTGCAGCGAGAATAGCTTGCAGTTCTTCATGCCCGTGTTGGGTGCCCTGTTCATCGGT
GTGGCTGTGGCCCCAGCTAACGACATCTACAACGAGCGCGAGCTGCTGAACAGCATGGGCATCAGCCAGCCCACCGTCGT
ATTCGTGAGCAAGAAAGGGCTGCAAAAGATCCTCAACGTGCAAAAGAAGCTACCGATCATACAAAAGATCATCATCATGG
ATAGCAAGACCGACTACCAGGGCTTCCAAAGCATGTACACCTTCGTGACTTCCCATTTGCCACCCGGCTTCAACGAGTAC
GACTTCGTGCCCGAGAGCTTCGACCGGGACAAAACCATCGCCCTGATCATGAACAGTAGTGGCAGTACCGGATTGCCCAA
GGGCGTAGCCCTACCGCACCGCACCGCTTGTGTCCGATTCAGTCATGCCCGCGACCCCATCTTCGGCAACCAGATCATCC
CCGTTTAAAC

DD) pBFB133 Sgf to Pme (SEQ ID NO:337)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA

FIG. 67N

GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAGGT
TCAGGCGGTTCCGGAATGTATGAAAGCTTTATTGAGTCACTGCCATTCCTTAAATCTTTGGAGTTTTCTGAACGCCTGAA
AGTAGTAGATGTGATAGGCACCAAAGTATACAACGATGGAGAACAAATCATTGCTCAGGGAGATTCGGCTGATTCTTTTT
TCATTGTAGAATCTGGAGAAGTGAAAATTACTATGAAAAGAAAGGGTAAATCAGAAGTGGAAGAGAATGGTGCAGTAGAA
ATCGCTCGATGCTCGCGGGGACAGTACTTTGGAGAGCTTGCCCTGGTAACTAACAAACCTCGAGCAGCTTCTGCCCACGC
CATTGGGACTGTCAAATGTTTAGCAATGGATGTGCAAGCATTTGAAAGGCTTCTGGGACCTTGCATGGAAATTATGAAAA
GGAACATCGCTACCTATGAAGAACAGGCCAAAAACATTAAGAAGGGCCCAGCGCCATTCTACCCACTCGAAGACGGGACC
GCCGGCGAGCAGCTGCACAAAGCCATGAAGCGCTACGCCCTGGTGCCCGGCACCATCGCCTTTACCGACGCACATATCGA
GGTGGACATTACCTACGCCGAGTACTTCGAGATGAGCGTTCGGCTGGCAGAAGCTATGAAGCGCTATGGGCTGAATACAA
ACCATCGGATCGTGGTGTGCAGCGAGAATAGCTTGCAGTTCTTCATGCCCGTGTTGGGTGCCCTGTTCATCGGTGTGGCT
GTGGCCCCAGCTAACGACATCTACAACGAGCGCGAGCTGCTGAACAGCATGGGCATCAGCCAGCCCACCGTCGTATTCGT
GAGCAAGAAAGGGCTGCAAAAGATCCTCAACGTGCAAAAGAAGCTACCGATCATACAAAAGATCATCATCATGGATAGCA
AGACCGACTACCAGGGCTTCCAAAGCATGTACACCTTCGTGACTTCCCATTTGCCACCCGGCTTCAACGAGTACGACTTC
GTGCCCGAGAGCTTCGACCGGGACAAAACCATCGCCCTGATCATGAACAGTAGTGGCAGTACCGGATTGCCCAAGGGCGT
AGCCCTACCGCACCGCACCGCTTGTGTCCGATTCAGTCATGCCCGCGACCCCATCTTCGGCAACCAGATCATCCCCGTTT
AAAC

EE) pBFB134 Sgf to Pme (SEQ ID NO:338)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAGGT
TCAGGCGGTTCCGGAATGTATGAAAGCTTTATTGAGTCACTGCCATTCCTTAAATCTTTGGAGTTTTCTGAACGCCTGAA
AGTAGTAGATGTGATAGGCACCAAAGTATACAACGATGGAGAACAAATCATTGCTCAGGGAGATTCGGCTGATTCTTTTT
TCATTGTAGAATCTGGAGAAGTGAAAATTACTATGAAAAGAAAGGGTAAATCAGAAGTGGAAGAGAATGGTGCAGTAGAA
ATCGCTCGATGCTCGCGGGGACAGTACTTTGGAGAGCTTGCCCTGGTAACTAACAAACCTCGAGCAGCTTCTGCCCACGC
CATTGGGACTGTCAAATGTTTAGCAATGGATGTGCAAGCATTTGAAAGGCTTCTGGGACCTTGCATGGAAATTATGAAAA
GGAACATCGCTACCTATGAAGCCAAAAACATTAAGAAGGGCCCAGCGCCATTCTACCCACTCGAAGACGGGACCGCCGGC
GAGCAGCTGCACAAAGCCATGAAGCGCTACGCCCTGGTGCCCGGCACCATCGCCTTTACCGACGCACATATCGAGGTGGA
CATTACCTACGCCGAGTACTTCGAGATGAGCGTTCGGCTGGCAGAAGCTATGAAGCGCTATGGGCTGAATACAAACCATC
GGATCGTGGTGTGCAGCGAGAATAGCTTGCAGTTCTTCATGCCCGTGTTGGGTGCCCTGTTCATCGGTGTGGCTGTGGCC
CCAGCTAACGACATCTACAACGAGCGCGAGCTGCTGAACAGCATGGGCATCAGCCAGCCCACCGTCGTATTCGTGAGCAA
GAAAGGGCTGCAAAAGATCCTCAACGTGCAAAAGAAGCTACCGATCATACAAAAGATCATCATCATGGATAGCAAGACCG
ACTACCAGGGCTTCCAAAGCATGTACACCTTCGTGACTTCCCATTTGCCACCCGGCTTCAACGAGTACGACTTCGTGCCC
GAGAGCTTCGACCGGGACAAAACCATCGCCCTGATCATGAACAGTAGTGGCAGTACCGGATTGCCCAAGGGCGTAGCCCT
ACCGCACCGCACCGCTTGTGTCCGATTCAGTCATGCCCGCGACCCCATCTTCGGCAACCAGATCATCCCCGTTTAAAC

FF) pBFB135 Sgf to Pme (SEQ ID NO:339)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA

FIG. 67O

GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAGGAGGTATGTATGAAAGCTTTATTGAGTCACTGCCATTCCTTAAATCTTTGGAGTTTTCTGAACG
CCTGAAAGTAGTAGATGTGATAGGCACCAAAGTATACAACGATGGAGAACAAATCATTGCTCAGGGAGATTCGGCTGATT
CTTTTTTCATTGTAGAATCTGGAGAAGTGAAAATTACTATGAAAAGAAAGGGTAAATCAGAAGTGGAAGAGAATGGTGCA
GTAGAAATCGCTCGATGCTCGCGGGGACAGTACTTTGGAGAGCTTGCCCTGGTAACTAACAAACCTCGAGCAGCTTCTGC
CCACGCCATTGGGACTGTCAAATGTTTAGCAATGGATGTGCAAGCATTTGAAAGGCTTCTGGGACCTTGCATGGAAATTA
TGAAAAGGAACATCGCTACCTATGAAGAACAGTTAGTTGCCCTGTTTGGAACGAACATGGATATTGTAGCCAAAAACATT
AAGAAGGGCCCAGCGCCATTCTACCCACTCGAAGACGGGACCGCCGGCGAGCAGCTGCACAAAGCCATGAAGCGCTACGC
CCTGGTGCCCGGCACCATCGCCTTTACCGACGCACATATCGAGGTGGACATTACCTACGCCGAGTACTTCGAGATGAGCG
TTCGGCTGGCAGAAGCTATGAAGCGCTATGGGCTGAATACAAACCATCGGATCGTGGTGTGCAGCGAGAATAGCTTGCAG
TTCTTCATGCCCGTGTTGGGTGCCCTGTTCATCGGTGTGGCTGTGGCCCCAGCTAACGACATCTACAACGAGCGCGAGCT
GCTGAACAGCATGGGCATCAGCCAGCCCACCGTCGTATTCGTGAGCAAGAAAGGGCTGCAAAAGATCCTCAACGTGCAAA
AGAAGCTACCGATCATACAAAAGATCATCATCATGGATAGCAAGACCGACTACCAGGGCTTCCAAAGCATGTACACCTTC
GTGACTTCCCATTTGCCACCCGGCTTCAACGAGTACGACTTCGTGCCCGAGAGCTTCGACCGGGACAAAACCATCGCCCT
GATCATGAACAGTAGTGGCAGTACCGGATTGCCCAAGGGCGTAGCCCTACCGCACCGCACCGCTTGTGTCCGATTCAGTC
ATGCCCGCGACCCCATCTTCGGCAACCAGATCATCCCCGTTTAAAC

GG) pBFB136 Sgf to Pme (SEQ ID NO:340)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAGGAGGTTCTGGCATGTATGAAAGCTTTATTGAGTCACTGCCATTCCTTAAATCTTTGGAGTTTTC
TGAACGCCTGAAAGTAGTAGATGTGATAGGCACCAAAGTATACAACGATGGAGAACAAATCATTGCTCAGGGAGATTCGG
CTGATTCTTTTTTCATTGTAGAATCTGGAGAAGTGAAAATTACTATGAAAAGAAAGGGTAAATCAGAAGTGGAAGAGAAT
GGTGCAGTAGAAATCGCTCGATGCTCGCGGGGACAGTACTTTGGAGAGCTTGCCCTGGTAACTAACAAACCTCGAGCAGC
TTCTGCCCACGCCATTGGGACTGTCAAATGTTTAGCAATGGATGTGCAAGCATTTGAAAGGCTTCTGGGACCTTGCATGG
AAATTATGAAAAGGAACATCGCTACCTATGAAGAACAGTTAGTTGCCCTGTTTGGAACGAACATGGATATTGTAGCCAAA
AACATTAAGAAGGGCCCAGCGCCATTCTACCCACTCGAAGACGGGACCGCCGGCGAGCAGCTGCACAAAGCCATGAAGCG
CTACGCCCTGGTGCCCGGCACCATCGCCTTTACCGACGCACATATCGAGGTGGACATTACCTACGCCGAGTACTTCGAGA
TGAGCGTTCGGCTGGCAGAAGCTATGAAGCGCTATGGGCTGAATACAAACCATCGGATCGTGGTGTGCAGCGAGAATAGC
TTGCAGTTCTTCATGCCCGTGTTGGGTGCCCTGTTCATCGGTGTGGCTGTGGCCCCAGCTAACGACATCTACAACGAGCG
CGAGCTGCTGAACAGCATGGGCATCAGCCAGCCCACCGTCGTATTCGTGAGCAAGAAAGGGCTGCAAAAGATCCTCAACG
TGCAAAAGAAGCTACCGATCATACAAAAGATCATCATCATGGATAGCAAGACCGACTACCAGGGCTTCCAAAGCATGTAC
ACCTTCGTGACTTCCCATTTGCCACCCGGCTTCAACGAGTACGACTTCGTGCCCGAGAGCTTCGACCGGGACAAAACCAT
CGCCCTGATCATGAACAGTAGTGGCAGTACCGGATTGCCCAAGGGCGTAGCCCTACCGCACCGCACCGCTTGTGTCCGAT
TCAGTCATGCCCGCGACCCCATCTTCGGCAACCAGATCATCCCCGTTTAAAC

HH) pBFB137 Sgf to Pme (SEQ ID NO:341)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC

FIG. 67P

GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAGGAGGTTCTGGCGGATCAATGTATGAAAGCTTTATTGAGTCACTGCCATTCCTTAAATCTTTGGA
GTTTTCTGAACGCCTGAAAGTAGTAGATGTGATAGGCACCAAAGTATACAACGATGGAGAACAAATCATTGCTCAGGGAG
ATTCGGCTGATTCTTTTTTCATTGTAGAATCTGGAGAAGTGAAAATTACTATGAAAAGAAAGGGTAAATCAGAAGTGGAA
GAGAATGGTGCAGTAGAAATCGCTCGATGCTCGCGGGGACAGTACTTTGGAGAGCTTGCCCTGGTAACTAACAAACCTCG
AGCAGCTTCTGCCCACGCCATTGGGACTGTCAAATGTTTAGCAATGGATGTGCAAGCATTTGAAAGGCTTCTGGGACCTT
GCATGGAAATTATGAAAAGGAACATCGCTACCTATGAAGAACAGTTAGTTGCCCTGTTTGGAACGAACATGGATATTGTA
GCCAAAAACATTAAGAAGGGCCCAGCGCCATTCTACCCACTCGAAGACGGGACCGCCGGCGAGCAGCTGCACAAAGCCAT
GAAGCGCTACGCCCTGGTGCCCGGCACCATCGCCTTTACCGACGCACATATCGAGGTGGACATTACCTACGCCGAGTACT
TCGAGATGAGCGTTCGGCTGGCAGAAGCTATGAAGCGCTATGGGCTGAATACAAACCATCGGATCGTGGTGTGCAGCGAG
AATAGCTTGCAGTTCTTCATGCCCGTGTTGGGTGCCCTGTTCATCGGTGTGGCTGTGGCCCCAGCTAACGACATCTACAA
CGAGCGCGAGCTGCTGAACAGCATGGGCATCAGCCAGCCCACCGTCGTATTCGTGAGCAAGAAAGGGCTGCAAAAGATCC
TCAACGTGCAAAAGAAGCTACCGATCATACAAAAGATCATCATCATGGATAGCAAGACCGACTACCAGGGCTTCCAAAGC
ATGTACACCTTCGTGACTTCCCATTTGCCACCCGGCTTCAACGAGTACGACTTCGTGCCCGAGAGCTTCGACCGGGACAA
AACCATCGCCCTGATCATGAACAGTAGTGGCAGTACCGGATTGCCCAAGGGCGTAGCCCTACCGCACCGCACCGCTTGTG
TCCGATTCAGTCATGCCCGCGACCCCATCTTCGGCAACCAGATCATCCCCGTTTAAAC

II) pBFB138 Sgf to Pme (SEQ ID NO:342)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAGGAGGTTCTGGCGGATCAGGCGGTATGTATGAAAGCTTTATTGAGTCACTGCCATTCCTTAAATC
TTTGGAGTTTTCTGAACGCCTGAAAGTAGTAGATGTGATAGGCACCAAAGTATACAACGATGGAGAACAAATCATTGCTC
AGGGAGATTCGGCTGATTCTTTTTTCATTGTAGAATCTGGAGAAGTGAAAATTACTATGAAAAGAAAGGGTAAATCAGAA
GTGGAAGAGAATGGTGCAGTAGAAATCGCTCGATGCTCGCGGGGACAGTACTTTGGAGAGCTTGCCCTGGTAACTAACAA
ACCTCGAGCAGCTTCTGCCCACGCCATTGGGACTGTCAAATGTTTAGCAATGGATGTGCAAGCATTTGAAAGGCTTCTGG
GACCTTGCATGGAAATTATGAAAAGGAACATCGCTACCTATGAAGAACAGTTAGTTGCCCTGTTTGGAACGAACATGGAT
ATTGTAGCCAAAAACATTAAGAAGGGCCCAGCGCCATTCTACCCACTCGAAGACGGGACCGCCGGCGAGCAGCTGCACAA
AGCCATGAAGCGCTACGCCCTGGTGCCCGGCACCATCGCCTTTACCGACGCACATATCGAGGTGGACATTACCTACGCCG
AGTACTTCGAGATGAGCGTTCGGCTGGCAGAAGCTATGAAGCGCTATGGGCTGAATACAAACCATCGGATCGTGGTGTGC
AGCGAGAATAGCTTGCAGTTCTTCATGCCCGTGTTGGGTGCCCTGTTCATCGGTGTGGCTGTGGCCCCAGCTAACGACAT
CTACAACGAGCGCGAGCTGCTGAACAGCATGGGCATCAGCCAGCCCACCGTCGTATTCGTGAGCAAGAAAGGGCTGCAAA
AGATCCTCAACGTGCAAAAGAAGCTACCGATCATACAAAAGATCATCATCATGGATAGCAAGACCGACTACCAGGGCTTC
CAAAGCATGTACACCTTCGTGACTTCCCATTTGCCACCCGGCTTCAACGAGTACGACTTCGTGCCCGAGAGCTTCGACCG
GGACAAAACCATCGCCCTGATCATGAACAGTAGTGGCAGTACCGGATTGCCCAAGGGCGTAGCCCTACCGCACCGCACCG
CTTGTGTCCGATTCAGTCATGCCCGCGACCCCATCTTCGGCAACCAGATCATCCCCGTTTAAAC

JJ) pBFB139 Sgf to Pme (SEQ ID NO:343)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA

FIG. 67Q

AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAGGAGGTTCTGGCGGATCAGGCGGTTCGGGGATGTATGAAAGCTTTATTGAGTCACTGCCATTCCT
TAAATCTTTGGAGTTTTCTGAACGCCTGAAAGTAGTAGATGTGATAGGCACCAAAGTATACAACGATGGAGAACAAATCA
TTGCTCAGGGAGATTCGGCTGATTCTTTTTTCATTGTAGAATCTGGAGAAGTGAAAATTACTATGAAAAGAAAGGGTAAA
TCAGAAGTGGAAGAGAATGGTGCAGTAGAAATCGCTCGATGCTCGCGGGGACAGTACTTTGGAGAGCTTGCCCTGGTAAC
TAACAAACCTCGAGCAGCTTCTGCCCACGCCATTGGGACTGTCAAATGTTTAGCAATGGATGTGCAAGCATTTGAAAGGC
TTCTGGGACCTTGCATGGAAATTATGAAAAGGAACATCGCTACCTATGAAGAACAGTTAGTTGCCCTGTTTGGAACGAAC
ATGGATATTGTAGCCAAAAACATTAAGAAGGGCCCAGCGCCATTCTACCCACTCGAAGACGGGACCGCCGGCGAGCAGCT
GCACAAAGCCATGAAGCGCTACGCCCTGGTGCCCGGCACCATCGCCTTTACCGACGCACATATCGAGGTGGACATTACCT
ACGCCGAGTACTTCGAGATGAGCGTTCGGCTGGCAGAAGCTATGAAGCGCTATGGGCTGAATACAAACCATCGGATCGTG
GTGTGCAGCGAGAATAGCTTGCAGTTCTTCATGCCCGTGTTGGGTGCCCTGTTCATCGGTGTGGCTGTGGCCCCAGCTAA
CGACATCTACAACGAGCGCGAGCTGCTGAACAGCATGGGCATCAGCCAGCCCACCGTCGTATTCGTGAGCAAGAAAGGGC
TGCAAAAGATCCTCAACGTGCAAAAGAAGCTACCGATCATACAAAAGATCATCATCATGGATAGCAAGACCGACTACCAG
GGCTTCCAAAGCATGTACACCTTCGTGACTTCCCATTTGCCACCCGGCTTCAACGAGTACGACTTCGTGCCCGAGAGCTT
CGACCGGGACAAAACCATCGCCCTGATCATGAACAGTAGTGGCAGTACCGGATTGCCCAAGGGCGTAGCCCTACCGCACC
GCACCGCTTGTGTCCGATTCAGTCATGCCCGCGACCCCATCTTCGGCAACCAGATCATCCCCGTTTAAAC

KK) pBFB147 Sgf to Pme (SEQ ID NO:344)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAGGAGGTATGTATGAAAGCTTTATTGAGTCACTGCCATTCCTTAAATCTTTGGAGTTTTCTGAACG
CCTGAAAGTAGTAGATGTGATAGGCACCAAAGTATACAACGATGGAGAACAAATCATTGCTCAGGGAGATTCGGCTGATT
CTTTTTTCATTGTAGAATCTGGAGAAGTGAAAATTACTATGAAAAGAAAGGGTAAATCAGAAGTGGAAGAGAATGGTGCA
GTAGAAATCGCTCGATGCTCGCGGGGACAGTACTTTGGAGAGCTTGCCCTGGTAACTAACAAACCTAAAGCAGCTTCTGC
CCACGCCATTGGGACTGTCAAATGTTTAGCAATGGATGTGCAAGCATTTGAAAGGCTTCTGGGACCTTGCATGGAAATTA
TGAAAAGGAACATCGCTACCTATGAAGAACAGTTAGTTGCCCTGTTTGGAACGAACATGGATATTGTAGCCAAAAACATT
AAGAAGGGCCCAGCGCCATTCTACCCACTCGAAGACGGGACCGCCGGCGAGCAGCTGCACAAAGCCATGAAGCGCTACGC
CCTGGTGCCCGGCACCATCGCCTTTACCGACGCACATATCGAGGTGGACATTACCTACGCCGAGTACTTCGAGATGAGCG
TTCGGCTGGCAGAAGCTATGAAGCGCTATGGGCTGAATACAAACCATCGGATCGTGGTGTGCAGCGAGAATAGCTTGCAG
TTCTTCATGCCCGTGTTGGGTGCCCTGTTCATCGGTGTGGCTGTGGCCCCAGCTAACGACATCTACAACGAGCGCGAGCT
GCTGAACAGCATGGGCATCAGCCAGCCCACCGTCGTATTCGTGAGCAAGAAAGGGCTGCAAAAGATCCTCAACGTGCAAA
AGAAGCTACCGATCATACAAAAGATCATCATCATGGATAGCAAGACCGACTACCAGGGCTTCCAAAGCATGTACACCTTC
GTGACTTCCCATTTGCCACCCGGCTTCAACGAGTACGACTTCGTGCCCGAGAGCTTCGACCGGGACAAAACCATCGCCCT
GATCATGAACAGTAGTGGCAGTACCGGATTGCCCAAGGGCGTAGCCCTACCGCACCGCACCGCTTGTGTCCGATTCAGTC
ATGCCCGCGACCCCATCTTCGGCAACCAGATCATCCCCGTTTAAAC

LL) pBFB151 Sgf to Pme (SEQ ID NO:345)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG

FIG. 67R

CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAGGAGGTATGTATGAAAGCTTTATTGAGTCACTGCCATTCCTTAAATCTTTGGAGTTTTCTGAACG
CCTGAAAGTAGTAGATGTGATAGGCACCAAAGTATACAACGATGGAGAACAAATCATTGCTCAGGGAGATTCGGCTGATT
CTTTTTTCATTGTAGAATCTGGAGAAGTGAAAATTACTATGAAAAGAAAGGGTAAATCAGAAGTGGAAGAGAATGGTGCA
GTAGAAATCGCTCGATGCTCGCGGGGACAGTACTTTGGAGAGCTTGCCCTGGTAACTAACAAACCTCGAGCAGCTTCTGC
CCACGCCATTGGGACTGTCAAATGTTTAGCAATGGATGTGCAAGCATTTGAAAGGCTTCTGGGACCTTGCATGGAAATTA
TGAAAAGGAACATCGCTACCTATGAAGAACAGTTAGTTGCCCTGTTTGGAACGAACATGGATATTGTAGCCAAAAACATT
AAGAAGGGCCCAGCGCCATTCTACCCACTCGAAGACGGGACCGCCGGCGAGCAGCTGCACAAAGCCATGAAGCGCTACGC
CCTGGTGCCCGGCACCATCGCCTTTACCGACGCACATATCGAGGTGGACATTACCTACGCCGAGTACTTCGAGATGAGCG
TTCGGCTGGCAGAAGCTATGAAGCGCTATGGGCTGAATACAAACCATCGGATCGTGGTGTGCAGCGAGAATAGCTTGCAG
TTCTTCATGCCCGTGTTGGGTGCCCTGTTCATCGGTGTGGCTGTGGCCCCAGCTAACGACATCTACAACGAGCGCGAGCT
GCTGAACAGCATGGGCATCAGCCAGCCCACCGTCGTATTCGTGAGCAAGAAAGGGCTGCAAAAGATCCTCAACGTGCAAA
AGAAGCTACCGATCATACAAAAGATCATCATCATGGATAGCAAGACCGACTACCAGGGCTTCCAAAGCATGTACACCTTC
GTGACTTCCCATTTGCCACCCGGCTTCAACGAGTACGACTTCGTGCCCGAGAGCTTCGACCGGGACAAAACCATCGCCCT
GATCATGAACAGTAGTGGCAGTACCGGATTGCCCAAGGGCGTAGCCCTACCGCACCGCACCGCTTGTGTCCGATTCAGTC
ATGCCCGCGACCCCATCTTCGGCAACCAGATCATCCCCGTTTAAAC

MM) pBFB164 Sgf to Pme (SEQ ID NO:346)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGATTA
AAAAGCGTTCCAACATTCCAGAGCCTTCCTGAAGAGATCCTCAGCAAGCTTGCTGATGTCCTTGAAGAGACCCACTATGA
AAATGGAGAATATATTATCAGGCAAGGTGCAAGAGGGGACACCTTCTTTATCATCAGCAAAGGAACGGTAAATGTCACTC
GTGAAGACTCACCGAGTGAAGACCCAGTCTTTCTTAGAACTTTAGGAAAAGGAGACTGGTTTGGAGAGAAAGCCTTGCAG
GGGGAAGATGTGAGAACAGCAAACGTAATTGCTGCAGAAGCTGTAACCTGCCTTGTGATTGACAGAGACTCTTTTAAACA
TTTGATTGGAGGGCTGGATGATGTTTCTAATAAAGCAGGGAGCTCCGGTGCCAAAAACATTAAGAAGGGCCCAGCGCCAT
TCTACCCACTCGAAGACGGGACCGCCGGCGAGCAGCTGCACAAAGCCATGAAGCGCTACGCCCTGGTGCCCGGCACCATC
GCCTTTACCGACGCACATATCGAGGTGGACATTACCTACGCCGAGTACTTCGAGATGAGCGTTCGGCTGGCAGAAGCTAT
GAAGCGCTATGGGCTGAATACAAACCATCGGATCGTGGTGTGCAGCGAGAATAGCTTGCAGTTCTTCATGCCCGTGTTGG
GTGCCCTGTTCATCGGTGTGGCTGTGGCCCCAGCTAACGACATCTACAACGAGCGCGAGCTGCTGAACAGCATGGGCATC
AGCCAGCCCACCGTCGTATTCGTGAGCAAGAAAGGGCTGCAAAAGATCCTCAACGTGCAAAAGAAGCTACCGATCATACA
AAAGATCATCATCATGGATAGCAAGACCGACTACCAGGGCTTCCAAAGCATGTACACCTTCGTGACTTCCCATTTGCCAC
CCGGCTTCAACGAGTACGACTTCGTGCCCGAGAGCTTCGACCGGGACAAAACCATCGCCCTGATCATGAACAGTAGTGGC
AGTACCGGATTGCCCAAGGGCGTAGCCCTACCGCACCGCACCGCTTGTGTCCGATTCAGTCATGCCCGCGACCCCATCTT
CGGCAACCAGATCATCCCCGTTTAAAC

NN) pBFB165 Sgf to Pme (SEQ ID NO:347)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG

*FIG. 67S*

CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGATTAAAAAGCGTTCCAACATTCCAGAGCCTTCCTGAAGAGATCCTCAGCAAGCTTGCTGATGTCCT
TGAAGAGACCCACTATGAAAATGGAGAATATATTATCAGGCAAGGTGCAAGAGGGGACACCTTCTTTATCATCAGCAAAG
GAACGGTAAATGTCACTCGTGAAGACTCACCGAGTGAAGACCCAGTCTTTCTTAGAACTTTAGGAAAAGGAGACTGGTTT
GGAGAGAAAGCCTTGCAGGGGGAAGATGTGAGAACAGCAAACGTAATTGCTGCAGAAGCTGTAACCTGCCTTGTGATTGA
CAGAGACTCTTTTAAACATTTGATTGGAGGGCTGGATGATGTTTCTAATAAAGCAGGGTCAGGTGGATCTGGAGGGAGCT
CCGGTGCCAAAAACATTAAGAAGGGCCCAGCGCCATTCTACCCACTCGAAGACGGGACCGCCGGCGAGCAGCTGCACAAA
GCCATGAAGCGCTACGCCCTGGTGCCCGGCACCATCGCCTTTACCGACGCACATATCGAGGTGGACATTACCTACGCCGA
GTACTTCGAGATGAGCGTTCGGCTGGCAGAAGCTATGAAGCGCTATGGGCTGAATACAAACCATCGGATCGTGGTGTGCA
GCGAGAATAGCTTGCAGTTCTTCATGCCCGTGTTGGGTGCCCTGTTCATCGGTGTGGCTGTGGCCCCAGCTAACGACATC
TACAACGAGCGCGAGCTGCTGAACAGCATGGGCATCAGCCAGCCCACCGTCGTATTCGTGAGCAAGAAAGGGCTGCAAAA
GATCCTCAACGTGCAAAAGAAGCTACCGATCATACAAAAGATCATCATCATGGATAGCAAGACCGACTACCAGGGCTTCC
AAAGCATGTACACCTTCGTGACTTCCCATTTGCCACCCGGCTTCAACGAGTACGACTTCGTGCCCGAGAGCTTCGACCGG
GACAAAACCATCGCCCTGATCATGAACAGTAGTGGCAGTACCGGATTGCCCAAGGGCGTAGCCCTACCGCACCGCACCGC
TTGTGTCCGATTCAGTCATGCCCGCGACCCCATCTTCGGCAACCAGATCATCCCCGTTTAAAC

OO) pBFB167 Sgf to Pme (SEQ ID NO:348)

GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGAG
ATCATCACGGAGGCCAGAAACCTCAGCAACGCAGAGATCTGCTCTGTGTTCCTGCTGGATCAGAATGAGCTGGTGGCCAA
GGTGTTCGACGGGGGCGTGGTGGATGATGAGAGCTATGAGATCCGCATCCCGGCCGATCAGGGCATCGCGGGACACGTGG
CGACCACGGGCCAGATCCTGAACATCCCTGACGCATATGCCCATCCGCTTTTCTACCGCGGCGTGGACGACAGCACCGGC
TTCCGCACGCGCAACATCCTCTGCTTCCCCATCAAGAACGAGAACCAGGAGGTCATCGGTGTGGCCGAGCTGGTGAACAA
GATCAATGGGCCATGGTTCAGCAAGTTCGACGAGGACCTGGCGACGGCCTTCTCCATCTACTGCGGCATCAGCATCGCCG
GGAGCTCCGGTGCCAAAAACATTAAGAAGGGCCCAGCGCCATTCTACCCACTCGAAGACGGGACCGCCGGCGAGCAGCTG
CACAAAGCCATGAAGCGCTACGCCCTGGTGCCCGGCACCATCGCCTTTACCGACGCACATATCGAGGTGGACATTACCTA
CGCCGAGTACTTCGAGATGAGCGTTCGGCTGGCAGAAGCTATGAAGCGCTATGGGCTGAATACAAACCATCGGATCGTGG
TGTGCAGCGAGAATAGCTTGCAGTTCTTCATGCCCGTGTTGGGTGCCCTGTTCATCGGTGTGGCTGTGGCCCCAGCTAAC
GACATCTACAACGAGCGCGAGCTGCTGAACAGCATGGGCATCAGCCAGCCCACCGTCGTATTCGTGAGCAAGAAAGGGCT
GCAAAAGATCCTCAACGTGCAAAAGAAGCTACCGATCATACAAAAGATCATCATCATGGATAGCAAGACCGACTACCAGG
GCTTCCAAAGCATGTACACCTTCGTGACTTCCCATTTGCCACCCGGCTTCAACGAGTACGACTTCGTGCCCGAGAGCTTC
GACCGGGACAAAACCATCGCCCTGATCATGAACAGTAGTGGCAGTACCGGATTGCCCAAGGGCGTAGCCCTACCGCACCG
CACCGCTTGTGTCCGATTCAGTCATGCCCGCGACCCCATCTTCGGCAACCAGATCATCCCCGTTTAAAC

PP) pBFB168 Sgf to Pme (SEQ ID NO:349)

GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC

FIG. 67T

GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAGAGATCATCACGGAGGCCAGAAACCTCAGCAACGCAGAGATCTGCTCTGTGTTCCTGCTGGATCA
GAATGAGCTGGTGGCCAAGGTGTTCGACGGGGGCGTGGTGGATGATGAGAGCTATGAGATCCGCATCCCGGCCGATCAGG
GCATCGCGGGACACGTGGCGACCACGGGCCAGATCCTGAACATCCCTGACGCATATGCCCATCCGCTTTTCTACCGCGGC
GTGGACGACAGCACCGGCTTCCGCACGCGCAACATCCTCTGCTTCCCCATCAAGAACGAGAACCAGGAGGTCATCGGTGT
GGCCGAGCTGGTGAACAAGATCAATGGGCCATGGTTCAGCAAGTTCGACGAGGACCTGGCGACGGCCTTCTCCATCTACT
GCGGCATCAGCATCGCAGGGTCAGGTGGATCTGGAGGGAGCTCCGGTGCCAAAAACATTAAGAAGGGCCCAGCGCCATTC
TACCCACTCGAAGACGGGACCGCCGGCGAGCAGCTGCACAAAGCCATGAAGCGCTACGCCCTGGTGCCCGGCACCATCGC
CTTTACCGACGCACATATCGAGGTGGACATTACCTACGCCGAGTACTTCGAGATGAGCGTTCGGCTGGCAGAAGCTATGA
AGCGCTATGGGCTGAATACAAACCATCGGATCGTGGTGTGCAGCGAGAATAGCTTGCAGTTCTTCATGCCCGTGTTGGGT
GCCCTGTTCATCGGTGTGGCTGTGGCCCCAGCTAACGACATCTACAACGAGCGCGAGCTGCTGAACAGCATGGGCATCAG
CCAGCCCACCGTCGTATTCGTGAGCAAGAAAGGGCTGCAAAAGATCCTCAACGTGCAAAAGAAGCTACCGATCATACAAA
AGATCATCATCATGGATAGCAAGACCGACTACCAGGGCTTCCAAAGCATGTACACCTTCGTGACTTCCCATTTGCCACCC
GGCTTCAACGAGTACGACTTCGTGCCCGAGAGCTTCGACCGGGACAAAACCATCGCCCTGATCATGAACAGTAGTGGCAG
TACCGGATTGCCCAAGGGCGTAGCCCTACCGCACCGCACCGCTTGTGTCCGATTCAGTCATGCCCGCGACCCCATCTTCG
GCAACCAGATCATCCCCGTTTAAAC

QQ) pBFB169 Sgf to Pme (SEQ ID NO:350)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAGGAGGTTCTGGCGGATCAGGCGGTTCGGGGGAGATCATCACGGAGGCCAGAAACCTCAGCAACGC
AGAGATCTGCTCTGTGTTCCTGCTGGATCAGAATGAGCTGGTGGCCAAGGTGTTCGACGGGGGCGTGGTGGATGATGAGA
GCTATGAGATCCGCATCCCGGCCGATCAGGGCATCGCGGGACACGTGGCGACCACGGGCCAGATCCTGAACATCCCTGAC
GCATATGCCCATCCGCTTTTCTACCGCGGCGTGGACGACAGCACCGGCTTCCGCACGCGCAACATCCTCTGCTTCCCCAT
CAAGAACGAGAACCAGGAGGTCATCGGTGTGGCCGAGCTGGTGAACAAGATCAATGGGCCATGGTTCAGCAAGTTCGACG
AGGACCTGGCGACGGCCTTCTCCATCTACTGCGGCATCAGCATCGCCGGGTCCGGTGGATCCGGTGGCAGCGGAGGGACG
TCAGGTGGATCTGGAGGGAGCTCCGGTGCCAAAAACATTAAGAAGGGCCCAGCGCCATTCTACCCACTCGAAGACGGGAC
CGCCGGCGAGCAGCTGCACAAAGCCATGAAGCGCTACGCCCTGGTGCCCGGCACCATCGCCTTTACCGACGCACATATCG
AGGTGGACATTACCTACGCCGAGTACTTCGAGATGAGCGTTCGGCTGGCAGAAGCTATGAAGCGCTATGGGCTGAATACA
AACCATCGGATCGTGGTGTGCAGCGAGAATAGCTTGCAGTTCTTCATGCCCGTGTTGGGTGCCCTGTTCATCGGTGTGGC
TGTGGCCCCAGCTAACGACATCTACAACGAGCGCGAGCTGCTGAACAGCATGGGCATCAGCCAGCCCACCGTCGTATTCG
TGAGCAAGAAAGGGCTGCAAAAGATCCTCAACGTGCAAAAGAAGCTACCGATCATACAAAAGATCATCATCATGGATAGC
AAGACCGACTACCAGGGCTTCCAAAGCATGTACACCTTCGTGACTTCCCATTTGCCACCCGGCTTCAACGAGTACGACTT
CGTGCCCGAGAGCTTCGACCGGGACAAAACCATCGCCCTGATCATGAACAGTAGTGGCAGTACCGGATTGCCCAAGGGCG
TAGCCCTACCGCACCGCACCGCTTGTGTCCGATTCAGTCATGCCCGCGACCCCATCTTCGGCAACCAGATCATCCCCGTT
TAAAC

RR) pBFB171 Sgf to Pme (SEQ ID NO:351)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG

FIG. 67U

CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGATTA
AAAAGCGTTCCAACATTCCAGAGCCTTCCTGAAGAGATCCTCAGCAAGCTTGCTGATGTCCTTGAAGAGACCCACTATGA
AAATGGAGAATATATTATCAGGCAAGGTGCAAGAGGGGACACCTTCTTTATCATCAGCAAAGGAACGGTAAATGTCACTC
GTGAAGACTCACCGAGTGAAGACCCAGTCTTTCTTAGAACTTTAGGAAAAGGAGACTGGTTTGGAGAGAAAGCCTTGCAG
GGGGAAGATGTGAGAACAGCAAACGTAATTGCTGCAGAAGCTGTAACCTGCCTTGTGATTGACAGAGACTCTTTTAAACA
TTTGATTGGAGGGCTGGATGATGTTTCTAATAAAGCATATGAAGATGCAGAAGCTAAAGCAAAATATGAAGCTGAAGCGG
CTTTCTTCGCCAACCTGAAGCTGTCTGGGAGCTCCGGTGCCAAAAACATTAAGAAGGGCCCAGCGCCATTCTACCCACTC
GAAGACGGGACCGCCGGCGAGCAGCTGCACAAAGCCATGAAGCGCTACGCCCTGGTGCCCGGCACCATCGCCTTTACCGA
CGCACATATCGAGGTGGACATTACCTACGCCGAGTACTTCGAGATGAGCGTTCGGCTGGCAGAAGCTATGAAGCGCTATG
GGCTGAATACAAACCATCGGATCGTGGTGTGCAGCGAGAATAGCTTGCAGTTCTTCATGCCCGTGTTGGGTGCCCTGTTC
ATCGGTGTGGCTGTGGCCCCAGCTAACGACATCTACAACGAGCGCGAGCTGCTGAACAGCATGGGCATCAGCCAGCCCAC
CGTCGTATTCGTGAGCAAGAAAGGGCTGCAAAAGATCCTCAACGTGCAAAAGAAGCTACCGATCATACAAAAGATCATCA
TCATGGATAGCAAGACCGACTACCAGGGCTTCCAAAGCATGTACACCTTCGTGACTTCCCATTTGCCACCCGGCTTCAAC
GAGTACGACTTCGTGCCCGAGAGCTTCGACCGGGACAAAACCATCGCCCTGATCATGAACAGTAGTGGCAGTACCGGATT
GCCCAAGGGCGTAGCCCTACCGCACCGCACCGCTTGTGTCCGATTCAGTCATGCCCGCGACCCCATCTTCGGCAACCAGA
TCATCCCCGTTTAAAC

SS) pBFB172 Sgf to Pme (SEQ ID NO:352)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGATTAAAAAGCGTTCCAACATTCCAGAGCCTTCCTGAAGAGATCCTCAGCAAGCTTGCTGATGTCCT
TGAAGAGACCCACTATGAAAATGGAGAATATATTATCAGGCAAGGTGCAAGAGGGGACACCTTCTTTATCATCAGCAAAG
GAACGGTAAATGTCACTCGTGAAGACTCACCGAGTGAAGACCCAGTCTTTCTTAGAACTTTAGGAAAAGGAGACTGGTTT
GGAGAGAAAGCCTTGCAGGGGGAAGATGTGAGAACAGCAAACGTAATTGCTGCAGAAGCTGTAACCTGCCTTGTGATTGA
CAGAGACTCTTTTAAACATTTGATTGGAGGGCTGGATGATGTTTCTAATAAAGCATATGAAGATGCAGAAGCTAAAGCAA
AATATGAAGCTGAAGCGGCTTTCTTCGCCAACCTGAAGCTGTCAGGGTCAGGTGGATCTGGAGGGAGCTCCGGTGCCAAA
AACATTAAGAAGGGCCCAGCGCCATTCTACCCACTCGAAGACGGGACCGCCGGCGAGCAGCTGCACAAAGCCATGAAGCG
CTACGCCCTGGTGCCCGGCACCATCGCCTTTACCGACGCACATATCGAGGTGGACATTACCTACGCCGAGTACTTCGAGA
TGAGCGTTCGGCTGGCAGAAGCTATGAAGCGCTATGGGCTGAATACAAACCATCGGATCGTGGTGTGCAGCGAGAATAGC
TTGCAGTTCTTCATGCCCGTGTTGGGTGCCCTGTTCATCGGTGTGGCTGTGGCCCCAGCTAACGACATCTACAACGAGCG
CGAGCTGCTGAACAGCATGGGCATCAGCCAGCCCACCGTCGTATTCGTGAGCAAGAAAGGGCTGCAAAAGATCCTCAACG
TGCAAAAGAAGCTACCGATCATACAAAAGATCATCATCATGGATAGCAAGACCGACTACCAGGGCTTCCAAAGCATGTAC
ACCTTCGTGACTTCCCATTTGCCACCCGGCTTCAACGAGTACGACTTCGTGCCCGAGAGCTTCGACCGGGACAAAACCAT
CGCCCTGATCATGAACAGTAGTGGCAGTACCGGATTGCCCAAGGGCGTAGCCCTACCGCACCGCACCGCTTGTGTCCGAT
TCAGTCATGCCCGCGACCCCATCTTCGGCAACCAGATCATCCCCGTTTAAAC

TT) pBFB174 Sgf to Pme (SEQ ID NO:353)
GCGATCGCCATGGAAATTTATGGTGAATTCGGCTCGAGCGGAGCCAAAAACATTAAGAAGGGCCCAGCGCCATTCTACCC
ACTCGAAGACGGGACCGCCGGCGAGCAGCTGCACAAAGCCATGAAGCGCTACGCCCTGGTGCCCGGCACCATCGCCTTTA
CCGACGCACATATCGAGGTGGACATTACCTACGCCGAGTACTTCGAGATGAGCGTTCGGCTGGCAGAAGCTATGAAGCGC
TATGGGCTGAATACAAACCATCGGATCGTGGTGTGCAGCGAGAATAGCTTGCAGTTCTTCATGCCCGTGTTGGGTGCCCT
GTTCATCGGTGTGGCTGTGGCCCCAGCTAACGACATCTACAACGAGCGCGAGCTGCTGAACAGCATGGGCATCAGCCAGC
CCACCGTCGTATTCGTGAGCAAGAAAGGGCTGCAAAAGATCCTCAACGTGCAAAAGAAGCTACCGATCATACAAAAGATC

FIG. 67V

ATCATCATGGATAGCAAGACCGACTACCAGGGCTTCCAAAGCATGTACACCTTCGTGACTTCCCATTTGCCACCCGGCTT
CAACGAGTACGACTTCGTGCCCGAGAGCTTCGACCGGGACAAAACCATCGCCCTGATCATGAACAGTAGTGGCAGTACCG
GATTGCCCAAGGGCGTAGCCCTACCGCACCGCACCGCTTGTGTCCGATTCAGTCATGCCCGCGACCCCATCTTCGGCAAC
CAGATCATCCCCGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACCGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGGAGCTCCGGTTGG
TATTTTGGCAAGATCACCAGACGGGAGTCAGAGCGGTTACTGCTCAATGCAGAGAACCCGAGAGGGACCTTCCTCGTGCG
AGAAAGTGAGACCACGAAAGGTGCCTACTGCCTCTCAGTGTCTGACTTCGACAACGCCAAGGGCCTCAACGTGAAGCACT
ACAAGATCCGCAAGCTGGACAGCGGCGGCTTCTACATCACCTCCCGCACCCAGTTCAACAGCCTGCAGCAGCTGGTGGCC
TACTACTCCAAACACGCCGATGGCCTGTGCCACCGCCTCACCACCGTGTGCGTTTAAAC

UU) pBFB175 Sgf to Pme (SEQ ID NO:354)
GCGATCGCCATGGAAATTTATGGTGAATTCGGCTCGAGCGGAGGTTCAGGCGGTTCCGGAGCCAAAAACATTAAGAAGGG
CCCAGCGCCATTCTACCCACTCGAAGACGGGACCGCCGGCGAGCAGCTGCACAAAGCCATGAAGCGCTACGCCCTGGTGC
CCGGCACCATCGCCTTTACCGACGCACATATCGAGGTGGACATTACCTACGCCGAGTACTTCGAGATGAGCGTTCGGCTG
GCAGAAGCTATGAAGCGCTATGGGCTGAATACAAACCATCGGATCGTGGTGTGCAGCGAGAATAGCTTGCAGTTCTTCAT
GCCCGTGTTGGGTGCCCTGTTCATCGGTGTGGCTGTGGCCCCAGCTAACGACATCTACAACGAGCGCGAGCTGCTGAACA
GCATGGGCATCAGCCAGCCCACCGTCGTATTCGTGAGCAAGAAAGGGCTGCAAAAGATCCTCAACGTGCAAAAGAAGCTA
CCGATCATACAAAAGATCATCATCATGGATAGCAAGACCGACTACCAGGGCTTCCAAAGCATGTACACCTTCGTGACTTC
CCATTTGCCACCCGGCTTCAACGAGTACGACTTCGTGCCCGAGAGCTTCGACCGGGACAAAACCATCGCCCTGATCATGA
ACAGTAGTGGCAGTACCGGATTGCCCAAGGGCGTAGCCCTACCGCACCGCACCGCTTGTGTCCGATTCAGTCATGCCCGC
GACCCCATCTTCGGCAACCAGATCATCCCCGACACCGCTATCCTCAGCGTGGTGCCATTTCACCACGGCTTCGGCATGTT
CACCACGCTGGGCTACTTGATCTGCGGCTTTCGGGTCGTGCTCATGTACCGCTTCGAGGAGGAGCTATTCTTGCGCAGCT
TGCAAGACTATAAGATTCAATCTGCCCTGCTGGTGCCCACACTATTTAGCTTCTTCGCTAAGAGCACTCTCATCGACAAG
TACGACCTAAGCAACTTGCACGAGATCGCCAGCGGCGGGGCGCCGCTCAGCAAGGAGGTAGGTGAGGCCGTGGCCAAACG
CTTCCACCTACCAGGCATCCGCCAGGGCTACGGCCTGACAGAAACAACCAGCGCCATTCTGATCACCCCCGAAGGGGACG
ACAAGCCTGGCGCAGTAGGCAAGGTGGTGCCCTTCTTCGAGGCTAAGGTGGTGGACTTGGACACCGGTAAGACACTGGGT
GTGAACCAGCGCGGCGAGCTGTGCGTCCGTGGCCCCATGATCATGAGCGGCTACGTTAACAACCCCGAGGCTACAAACGC
TCTCATCGACAAGGACGGCTGGCTGCACAGCGGCGACATCGCCTACTGGGACGAGGACGAGCACTTCTTCATCGTGGACC
GGCTGAAGAGCCTGATCAAATACAAGGGCTACCAGGTAGCCCCAGCCGAACTGGAGAGCATCCTGCTGCAACACCCCAAC
ATCTTCGACGCCGGGGTCGCCGGCCTGCCCGACGACGATGCCGGCGAGCTGCCCGCCGCAGTCGTCGTGCTGGAACACGG
TAAAACCATGACCGAGAAGGAGATCGTGGACTATGTGGCCAGCCAGGTTACAACCGCCAAGAAGCTGCGCGGTGGTGTTG
TGTTCGTGGACGAGGTGCCTAAAGGACTGACCGGCAAGTTGGACGCCCGCAAGATCCGCGAGATTCTCATTAAGGCCAAG
AAGGGGAGCTCCGGTTGGTATTTTGGCAAGATCACCAGACGGGAGTCAGAGCGGTTACTGCTCAATGCAGAGAACCCGAG
AGGGACCTTCCTCGTGCGAGAAAGTGAGACCACGAAAGGTGCCTACTGCCTCTCAGTGTCTGACTTCGACAACGCCAAGG
GCCTCAACGTGAAGCACTACAAGATCCGCAAGCTGGACAGCGGCGGCTTCTACATCACCTCCCGCACCCAGTTCAACAGC
CTGCAGCAGCTGGTGGCCTACTACTCCAAACACGCCGATGGCCTGTGCCACCGCCTAACCACCGTGTGCGTTTAAAC

VV) pBFB176 Sgf to Pme (SEQ ID NO:355)
GCGATCGCCATGGAAATTTATGGTGAATTCGGCTCGAGCGGAGGTTCAGGCGGTTCCGGAGGAGGTTCTGGCGGATCAGG
CGGTTCGGGAGCCAAAAACATTAAGAAGGGCCCAGCGCCATTCTACCCACTCGAAGACGGGACCGCCGGCGAGCAGCTGC
ACAAAGCCATGAAGCGCTACGCCCTGGTGCCCGGCACCATCGCCTTTACCGACGCACATATCGAGGTGGACATTACCTAC
GCCGAGTACTTCGAGATGAGCGTTCGGCTGGCAGAAGCTATGAAGCGCTATGGGCTGAATACAAACCATCGGATCGTGGT
GTGCAGCGAGAATAGCTTGCAGTTCTTCATGCCCGTGTTGGGTGCCCTGTTCATCGGTGTGGCTGTGGCCCCAGCTAACG
ACATCTACAACGAGCGCGAGCTGCTGAACAGCATGGGCATCAGCCAGCCCACCGTCGTATTCGTGAGCAAGAAAGGGCTG
CAAAAGATCCTCAACGTGCAAAAGAAGCTACCGATCATACAAAAGATCATCATCATGGATAGCAAGACCGACTACCAGGG
CTTCCAAAGCATGTACACCTTCGTGACTTCCCATTTGCCACCCGGCTTCAACGAGTACGACTTCGTGCCCGAGAGCTTCG
ACCGGGACAAAACCATCGCCCTGATCATGAACAGTAGTGGCAGTACCGGATTGCCCAAGGGCGTAGCCCTACCGCACCGC

FIG. 67W

ACCGCTTGTGTCCGATTCAGTCATGCCCGCGACCCCATCTTCGGCAACCAGATCATCCCCGACACCGCTATCCTCAGCGT
GGTGCCATTTCACCACGGCTTCGGCATGTTCACCACGCTGGGCTACTTGATCTGCGGCTTTCGGGTCGTGCTCATGTACC
GCTTCGAGGAGGAGCTATTCTTGCGCAGCTTGCAAGACTATAAGATTCAATCTGCCCTGCTGGTGCCCACACTATTTAGC
TTCTTCGCTAAGAGCACTCTCATCGACAAGTACGACCTAAGCAACTTGCACGAGATCGCCAGCGGCGGGGCGCCGCTCAG
CAAGGAGGTAGGTGAGGCCGTGGCCAAACGCTTCCACCTACCAGGCATCCGCCAGGGCTACGGCCTGACAGAAACAACCA
GCGCCATTCTGATCACCCCCGAAGGGGACGACAAGCCTGGCGCAGTAGGCAAGGTGGTGCCCTTCTTCGAGGCTAAGGTG
GTGGACTTGGACACCGGTAAGACACTGGGTGTGAACCAGCGCGGCGAGCTGTGCGTCCGTGGCCCCATGATCATGAGCGG
CTACGTTAACAACCCCGAGGCTACAAACGCTCTCATCGACAAGGACGGCTGGCTGCACAGCGGCGACATCGCCTACTGGG
ACGAGGACGAGCACTTCTTCATCGTGGACCGGCTGAAGAGCCTGATCAAATACAAGGGCTACCAGGTAGCCCCAGCCGAA
CTGGAGAGCATCCTGCTGCAACACCCCAACATCTTCGACGCCGGGGTCGCCGGCCTGCCCGACGACGATGCCGGCGAGCT
GCCCGCCGCAGTCGTCGTGCTGGAACACGGTAAAACCATGACCGAGAAGGAGATCGTGGACTATGTGGCCAGCCAGGTTA
CAACCGCCAAGAAGCTGCGCGGTGGTGTTGTGTTCGTGGACGAGGTGCCTAAAGGACTGACCGGCAAGTTGGACGCCCGC
AAGATCCGCGAGATTCTCATTAAGGCCAAGAAGGGGAGCTCCGGTTGGTATTTTGGCAAGATCACCAGACGGGAGTCAGA
GCGGTTACTGCTCAATGCAGAGAACCCGAGAGGGACCTTCCTCGTGCGAGAAAGTGAGACCACGAAAGGTGCCTACTGCC
TCTCAGTGTCTGACTTCGACAACGCCAAGGGCCTCAACGTGAAGCACTACAAGATCCGCAAGCTGGACAGCGGCGGCTTC
TACATCACCTCCCGCACCCAGTTCAACAGCCTGCAGCAGCTGGTGGCCTACTACTCCAAACACGCCGATGGCCTGTGCCA
CCGCCTAACCACCGTGTGCGTTTAAAC

WW) pBFB180 Sgf to Pme (SEQ ID NO:356)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGATGG
TATTTTGGCAAGATCACCAGACGGGAGTCAGAGCGGTTACTGCTCAATGCAGAGAACCCGAGAGGGACCTTCCTCGTGCG
AGAAAGTGAGACCACGAAAGGTGCCTACTGCCTCTCAGTGTCTGACTTCGACAACGCCAAGGGCCTCAACGTGAAGCACT
ACAAGATCCGCAAGCTGGACAGCGGCGGCTTCTACATCACCTCCCGCACCCAGTTCAACAGCCTGCAGCAGCTGGTGGCC
TACTACTCCAAACACGCCGATGGCCTGTGCCACCGCCTCACCACCGTGTGCGGTTCCGGAGGATCTACTTCGGGGTCAGG
TAAACCTGGCTCGGGTGAGGGATCGGAAATTTATGGTGAATTCGGGAGCTCCGGTGCCAAAAACATTAAGAAGGGCCCAG
CGCCATTCTACCCACTCGAAGACGGGACCGCCGGCGAGCAGCTGCACAAAGCCATGAAGCGCTACGCCCTGGTGCCCGGC
ACCATCGCCTTTACCGACGCACATATCGAGGTGGACATTACCTACGCCGAGTACTTCGAGATGAGCGTTCGGCTGGCAGA
AGCTATGAAGCGCTATGGGCTGAATACAAACCATCGGATCGTGGTGTGCAGCGAGAATAGCTTGCAGTTCTTCATGCCCG
TGTTGGGTGCCCTGTTCATCGGTGTGGCTGTGGCCCCAGCTAACGACATCTACAACGAGCGCGAGCTGCTGAACAGCATG
GGCATCAGCCAGCCCACCGTCGTATTCGTGAGCAAGAAAGGGCTGCAAAAGATCCTCAACGTGCAAAAGAAGCTACCGAT
CATACAAAAGATCATCATCATGGATAGCAAGACCGACTACCAGGGCTTCCAAAGCATGTACACCTTCGTGACTTCCCATT
TGCCACCCGGCTTCAACGAGTACGACTTCGTGCCCGAGAGCTTCGACCGGGACAAAACCATCGCCCTGATCATGAACAGT
AGTGGCAGTACCGGATTGCCCAAGGGCGTAGCCCTACCGCACCGCACCGCTTGTGTCCGATTCAGTCATGCCCGCGACCC
CATCTTCGGCAACCAGATCATCCCCGTTTAAAC

XX) pBFB181 Sgf to Pme (SEQ ID NO:357)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA

FIG. 67X

GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGATGG
TATTTTGGCAAGATCACCAGACGGGAGTCAGAGCGGTTACTGCTCAATGCAGAGAACCCGAGAGGGACCTTCCTCGTGCG
AGAAAGTGAGACCACGAAAGGTGCCTACTGCCTCTCAGTGTCTGACTTCGACAACGCCAAGGGCCTCAACGTGAAGCACT
ACAAGATCCGCAAGCTGGACAGCGGCGGCTTCTACATCACCTCCCGCACCCAGTTCAACAGCCTGCAGCAGCTGGTGGCC
TACTACTCCAAACACGCCGATGGCCTGTGCCACCGCCTCACCACCGTGTGCGGTTCCGGAGGATCTACTTCGGGGTCAGG
TAAACCTGGCTCGGGTGAGGGATCGGAAATTTATGGTGAATTCGGATCCGGGTCAGGTGGATCTGGAGGGAGCTCCGGTG
CCAAAAACATTAAGAAGGGCCCAGCGCCATTCTACCCACTCGAAGACGGGACCGCCGGCGAGCAGCTGCACAAAGCCATG
AAGCGCTACGCCCTGGTGCCCGGCACCATCGCCTTTACCGACGCACATATCGAGGTGGACATTACCTACGCCGAGTACTT
CGAGATGAGCGTTCGGCTGGCAGAAGCTATGAAGCGCTATGGGCTGAATACAAACCATCGGATCGTGGTGTGCAGCGAGA
ATAGCTTGCAGTTCTTCATGCCCGTGTTGGGTGCCCTGTTCATCGGTGTGGCTGTGGCCCCAGCTAACGACATCTACAAC
GAGCGCGAGCTGCTGAACAGCATGGGCATCAGCCAGCCCACCGTCGTATTCGTGAGCAAGAAAGGGCTGCAAAAGATCCT
CAACGTGCAAAAGAAGCTACCGATCATACAAAAGATCATCATCATGGATAGCAAGACCGACTACCAGGGCTTCCAAAGCA
TGTACACCTTCGTGACTTCCCATTTGCCACCCGGCTTCAACGAGTACGACTTCGTGCCCGAGAGCTTCGACCGGGACAAA
ACCATCGCCCTGATCATGAACAGTAGTGGCAGTACCGGATTGCCCAAGGGCGTAGCCCTACCGCACCGCACCGCTTGTGT
CCGATTCAGTCATGCCCGCGACCCCATCTTCGGCAACCAGATCATCCCCGTTTAAAC

YY) pBFB182 Sgf to Pme (SEQ ID NO:358)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGATGG
TATTTTGGCAAGATCACCAGACGGGAGTCAGAGCGGTTACTGCTCAATGCAGAGAACCCGAGAGGGACCTTCCTCGTGCG
AGAAAGTGAGACCACGAAAGGTGCCTACTGCCTCTCAGTGTCTGACTTCGACAACGCCAAGGGCCTCAACGTGAAGCACT
ACAAGATCCGCAAGCTGGACAGCGGCGGCTTCTACATCACCTCCCGCACCCAGTTCAACAGCCTGCAGCAGCTGGTGGCC
TACTACTCCAAACACGCCGATGGCCTGTGCCACCGCCTCACCACCGTGTGCGGTTCCGGAGGATCTACTTCGGGGTCAGG
TAAACCTGGCTCGGGTGAGGGATCGGAAATTTATGGTGAATTCGGATCCGGTGGTTCAGGTGGCAGCGGAGGAGGGTCAG
GTGGATCTGGAGGGAGCTCCGGTGCCAAAAACATTAAGAAGGGCCCAGCGCCATTCTACCCACTCGAAGACGGGACCGCC
GGCGAGCAGCTGCACAAAGCCATGAAGCGCTACGCCCTGGTGCCCGGCACCATCGCCTTTACCGACGCACATATCGAGGT
GGACATTACCTACGCCGAGTACTTCGAGATGAGCGTTCGGCTGGCAGAAGCTATGAAGCGCTATGGGCTGAATACAAACC
ATCGGATCGTGGTGTGCAGCGAGAATAGCTTGCAGTTCTTCATGCCCGTGTTGGGTGCCCTGTTCATCGGTGTGGCTGTG
GCCCCAGCTAACGACATCTACAACGAGCGCGAGCTGCTGAACAGCATGGGCATCAGCCAGCCCACCGTCGTATTCGTGAG
CAAGAAAGGGCTGCAAAAGATCCTCAACGTGCAAAAGAAGCTACCGATCATACAAAAGATCATCATCATGGATAGCAAGA
CCGACTACCAGGGCTTCCAAAGCATGTACACCTTCGTGACTTCCCATTTGCCACCCGGCTTCAACGAGTACGACTTCGTG
CCCGAGAGCTTCGACCGGGACAAAACCATCGCCCTGATCATGAACAGTAGTGGCAGTACCGGATTGCCCAAGGGCGTAGC
CCTACCGCACCGCACCGCTTGTGTCCGATTCAGTCATGCCCGCGACCCCATCTTCGGCAACCAGATCATCCCCGTTTAAA
C

ZZ) pBFB197 Sgf to Pme (SEQ ID NO:359)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGACCGGAATGTATGAAAGCTTTATTGAGTCACTGCCATTCCTT
AAATCTTTGGAGTTTTCTGAACGCCTGAAAGTAGTAGATGTGATAGGCACCAAAGTATACAACGATGGAGAACAAATCAT

FIG. 67Y

TGCTCAGGGAGATTCGGCTGATTCTTTTTTCATTGTAGAATCTGGAGAAGTGAAAATTACTATGAAAAGAAAGGGTAAAT
CAGAAGTGGAAGAGAATGGTGCAGTAGAAATCGCTCGATGCTCGCGGGGACAGTACTTTGGAGAGCTTGCCCTGGTAACT
AACAAACCTCGAGCAGCTTCTGCCCACGCCATTGGGACTGTCAAATGTTTAGCAATGGATGTGCAAGCATTTGAAAGGCT
TCTGGGACCTTGCATGGAAATTATGAAAAGGAACATCGCTACCTATGAAGAACAGTTAGTTGCCCTGTTTGGAACGAACA
TGGATATTGTTGGGAGCTCAGGAGCTTCCAAGGTGTACGACCCCGAGCAACGCAAACGCATGATCACTGGGCCTCAGTGG
TGGGCTCGCTGCAAGCAAATGAACGTGCTGGACTCCTTCATCAACTACTATGATTCCGAGAAGCACGCCGAGAACGCCGT
GATTTTTCTGCATGGTAACGCTGCCTCCAGCTACCTGTGGAGGCACGTCGTGCCTCACATCGAGCCCGTGGCTAGATGCA
TCATCCCTGATCTGATCGGAATGGGTAAGTCCGGCAAGAGCGGGAATGGCTCAGTTTAAAC

AAA) pBFB198 Sgf to Pme (SEQ ID NO:360)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGACCGGAATGTATGAAAGCTTTATTGAGTCACTGCCATTCCTT
AAATCTTTGGAGTTTTCTGAACGCCTGAAAGTAGTAGATGTGATAGGCACCAAAGTATACAACGATGGAGAACAAATCAT
TGCTCAGGGAGATTCGGCTGATTCTTTTTTCATTGTAGAATCTGGAGAAGTGAAAATTACTATGAAAAGAAAGGGTAAAT
CAGAAGTGGAAGAGAATGGTGCAGTAGAAATCGCTCGATGCTCGCGGGGACAGTACTTTGGAGAGCTTGCCCTGGTAACT
AACAAACCTCGAGCAGCTTCTGCCCACGCCATTGGGACTGTCAAATGTTTAGCAATGGATGTGCAAGCATTTGAAAGGCT
TCTGGGACCTTGCATGGAAATTATGAAAAGGAACATCGCTACCTATGAAGAACAGTTAGTTGCCCTGTTTGGAACGAACA
TGGATATTGTATCTGGAGGGAGCTCAGGAGCTTCCAAGGTGTACGACCCCGAGCAACGCAAACGCATGATCACTGGGCCT
CAGTGGTGGGCTCGCTGCAAGCAAATGAACGTGCTGGACTCCTTCATCAACTACTATGATTCCGAGAAGCACGCCGAGAA
CGCCGTGATTTTTCTGCATGGTAACGCTGCCTCCAGCTACCTGTGGAGGCACGTCGTGCCTCACATCGAGCCCGTGGCTA
GATGCATCATCCCTGATCTGATCGGAATGGGTAAGTCCGGCAAGAGCGGGAATGGCTCAGTTTAAAC

BBB) pBFB199 Sgf to Pme (SEQ ID NO:361)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGACCGGAATGTATGAAAGCTTTATTGAGTCACTGCCATTCCTT
AAATCTTTGGAGTTTTCTGAACGCCTGAAAGTAGTAGATGTGATAGGCACCAAAGTATACAACGATGGAGAACAAATCAT
TGCTCAGGGAGATTCGGCTGATTCTTTTTTCATTGTAGAATCTGGAGAAGTGAAAATTACTATGAAAAGAAAGGGTAAAT
CAGAAGTGGAAGAGAATGGTGCAGTAGAAATCGCTCGATGCTCGCGGGGACAGTACTTTGGAGAGCTTGCCCTGGTAACT
AACAAACCTCGAGCAGCTTCTGCCCACGCCATTGGGACTGTCAAATGTTTAGCAATGGATGTGCAAGCATTTGAAAGGCT
TCTGGGACCTTGCATGGAAATTATGAAAAGGAACATCGCTACCTATGAAGAACAGTTAGTTGCCCTGTTTGGAACGAACA
TGGATATTGTAGGTGGATCTGGAGGGAGCTCAGGAGCTTCCAAGGTGTACGACCCCGAGCAACGCAAACGCATGATCACT
GGGCCTCAGTGGTGGGCTCGCTGCAAGCAAATGAACGTGCTGGACTCCTTCATCAACTACTATGATTCCGAGAAGCACGC
CGAGAACGCCGTGATTTTTCTGCATGGTAACGCTGCCTCCAGCTACCTGTGGAGGCACGTCGTGCCTCACATCGAGCCCG
TGGCTAGATGCATCATCCCTGATCTGATCGGAATGGGTAAGTCCGGCAAGAGCGGGAATGGCTCAGTTTAAAC

CCC) pBFB201 Sgf to Pme (SEQ ID NO:362)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC

*FIG. 67Z*

TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGACCGGAATGTATGAAAGCTTTATTGAGTCACTGCCATTCCTT
AAATCTTTGGAGTTTTCTGAACGCCTGAAAGTAGTAGATGTGATAGGCACCAAAGTATACAACGATGGAGAACAAATCAT
TGCTCAGGGAGATTCGGCTGATTCTTTTTTCATTGTAGAATCTGGAGAAGTGAAAATTACTATGAAAAGAAAGGGTAAAT
CAGAAGTGGAAGAGAATGGTGCAGTAGAAATCGCTCGATGCTCGCGGGGACAGTACTTTGGAGAGCTTGCCCTGGTAACT
AACAAACCTCGAGCAGCTTCTGCCCACGCCATTGGGACTGTCAAATGTTTAGCAATGGATGTGCAAGCATTTGAAAGGCT
TCTGGGACCTTGCATGGAAATTATGAAAAGGAACATCGCTACCTATGAAGAACAGTTAGTTGCCCTGTTTGGAACGAACA
TGGATATTGTTGGCGGAGGGTCAGGTGGATCTGGAGGGAGCTCAGGAGCTTCCAAGGTGTACGACCCCGAGCAACGCAAA
CGCATGATCACTGGGCCTCAGTGGTGGGCTCGCTGCAAGCAAATGAACGTGCTGGACTCCTTCATCAACTACTATGATTC
CGAGAAGCACGCCGAGAACGCCGTGATTTTTCTGCATGGTAACGCTGCCTCCAGCTACCTGTGGAGGCACGTCGTGCCTC
ACATCGAGCCCGTGGCTAGATGCATCATCCCTGATCTGATCGGAATGGGTAAGTCCGGCAAGAGCGGGAATGGCTCAGTT
TAAAC

DDD) pBFB202 Sgf to Pme (SEQ ID NO:363)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGACCGGAATGTATGAAAGCTTTATTGAGTCACTGCCATTCCTT
AAATCTTTGGAGTTTTCTGAACGCCTGAAAGTAGTAGATGTGATAGGCACCAAAGTATACAACGATGGAGAACAAATCAT
TGCTCAGGGAGATTCGGCTGATTCTTTTTTCATTGTAGAATCTGGAGAAGTGAAAATTACTATGAAAAGAAAGGGTAAAT
CAGAAGTGGAAGAGAATGGTGCAGTAGAAATCGCTCGATGCTCGCGGGGACAGTACTTTGGAGAGCTTGCCCTGGTAACT
AACAAACCTCGAGCAGCTTCTGCCCACGCCATTGGGACTGTCAAATGTTTAGCAATGGATGTGCAAGCATTTGAAAGGCT
TCTGGGACCTTGCATGGAAATTATGAAAAGGAACATCGCTACCTATGAAGAACAGTTAGTTGCCCTGTTTGGAACGAACA
TGGATATTGTTGGCAGCGGCGGAGGGTCAGGTGGATCTGGAGGGAGCTCAGGAGCTTCCAAGGTGTACGACCCCGAGCAA
CGCAAACGCATGATCACTGGGCCTCAGTGGTGGGCTCGCTGCAAGCAAATGAACGTGCTGGACTCCTTCATCAACTACTA
TGATTCCGAGAAGCACGCCGAGAACGCCGTGATTTTTCTGCATGGTAACGCTGCCTCCAGCTACCTGTGGAGGCACGTCG
TGCCTCACATCGAGCCCGTGGCTAGATGCATCATCCCTGATCTGATCGGAATGGGTAAGTCCGGCAAGAGCGGGAATGGC
TCAGTTTAAAC

EEE) pBFB203 Sgf to Pme (SEQ ID NO:364)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGACCGGAATGTATGAAAGCTTTATTGAGTCACTGCCATTCCTT

AAATCTTTGGAGTTTTCTGAACGCCTGAAAGTAGTAGATGTGATAGGCACCAAAGTATACAACGATGGAGAACAAATCAT
TGCTCAGGGAGATTCGGCTGATTCTTTTTTCATTGTAGAATCTGGAGAAGTGAAAATTACTATGAAAAGAAAGGGTAAAT
CAGAAGTGGAAGAGAATGGTGCAGTAGAAATCGCTCGATGCTCGCGGGGACAGTACTTTGGAGAGCTTGCCCTGGTAACT
AACAAACCTCGAGCAGCTTCTGCCCACGCCATTGGGACTGTCAAATGTTTAGCAATGGATGTGCAAGCATTTGAAAGGCT
TCTGGGACCTTGCATGGAAATTATGAAAAGGAACATCGCTACCTATGAAGAACAGTTAGTTGCCCTGTTTGGAACGAACA
TGGATATTGTTTCCGGTGGCAGCGGCGGAGGGTCAGGTGGATCTGGAGGGAGCTCAGGAGCTTCCAAGGTGTACGACCCC
GAGCAACGCAAACGCATGATCACTGGGCCTCAGTGGTGGGCTCGCTGCAAGCAAATGAACGTGCTGGACTCCTTCATCAA
CTACTATGATTCCGAGAAGCACGCCGAGAACGCCGTGATTTTTCTGCATGGTAACGCTGCCTCCAGCTACCTGTGGAGGC
ACGTCGTGCCTCACATCGAGCCCGTGGCTAGATGCATCATCCCTGATCTGATCGGAATGGGTAAGTCCGGCAAGAGCGGG
AATGGCTCAGTTTAAAC

FFF) pBFB205 Sgf to Pme (SEQ ID NO:365)

*FIG. 67AA*

GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGACCGGAATGTATGAAAGCTTTATTGAGTCACTGCCATTCCTT
AAATCTTTGGAGTTTTCTGAACGCCTGAAAGTAGTAGATGTGATAGGCACCAAAGTATACAACGATGGAGAACAAATCAT
TGCTCAGGGAGATTCGGCTGATTCTTTTTTCATTGTAGAATCTGGAGAAGTGAAAATTACTATGAAAAGAAAGGGTAAAT
CAGAAGTGGAAGAGAATGGTGCAGTAGAAATCGCTCGATGCTCGCGGGGACAGTACTTTGGAGAGCTTGCCCTGGTAACT
AACAAACCTCGAGCAGCTTCTGCCCACGCCATTGGGACTGTCAAATGTTTAGCAATGGATGTGCAAGCATTTGAAAGGCT
TCTGGGACCTTGCATGGAAATTATGAAAAGGAACATCGCTACCTATGAAGAACAGTTAGTTGCCCTGTTTGGAACGAACA
TGGATATTGTTGGGTCCGGTGGATCCGGTGGCAGCGGAGGGACGTCAGGTGGATCTGGAGGGAGCTCAGGAGCTTCCAAG
GTGTACGACCCCGAGCAACGCAAACGCATGATCACTGGGCCTCAGTGGTGGGCTCGCTGCAAGCAAATGAACGTGCTGGA
CTCCTTCATCAACTACTATGATTCCGAGAAGCACGCCGAGAACGCCGTGATTTTTCTGCATGGTAACGCTGCCTCCAGCT
ACCTGTGGAGGCACGTCGTGCCTCACATCGAGCCCGTGGCTAGATGCATCATCCCTGATCTGATCGGAATGGGTAAGTCC
GGCAAGAGCGGGAATGGCTCAGTTTAAAC

GGG) pBFB206 Sgf to Pme (SEQ ID NO:366)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGAGCGGAGGTTCAGGCGGTTCCGGAATGTATGAAAGCTTTATT
GAGTCACTGCCATTCCTTAAATCTTTGGAGTTTTCTGAACGCCTGAAAGTAGTAGATGTGATAGGCACCAAAGTATACAA
CGATGGAGAACAAATCATTGCTCAGGGAGATTCGGCTGATTCTTTTTTCATTGTAGAATCTGGAGAAGTGAAAATTACTA
TGAAAAGAAAGGGTAAATCAGAAGTGGAAGAGAATGGTGCAGTAGAAATCGCTCGATGCTCGCGGGGACAGTACTTTGGA
GAGCTTGCCCTGGTAACTAACAAACCTCGAGCAGCTTCTGCCCACGCCATTGGGACTGTCAAATGTTTAGCAATGGATGT
GCAAGCATTTGAAAGGCTTCTGGGACCTTGCATGGAAATTATGAAAAGGAACATCGCTACCTATGAAGAACAGTTAGTTG
CCCTGTTTGGAACGAACATGGATATTGTAGGGTCAGGTGGATCTGGAGGGAGCTCAGGAGCTTCCAAGGTGTACGACCCC
GAGCAACGCAAACGCATGATCACTGGGCCTCAGTGGTGGGCTCGCTGCAAGCAAATGAACGTGCTGGACTCCTTCATCAA
CTACTATGATTCCGAGAAGCACGCCGAGAACGCCGTGATTTTTCTGCATGGTAACGCTGCCTCCAGCTACCTGTGGAGGC
ACGTCGTGCCTCACATCGAGCCCGTGGCTAGATGCATCATCCCTGATCTGATCGGAATGGGTAAGTCCGGCAAGAGCGGG
AATGGCTCAGTTTAAAC

HHH) pBFB207 Sgf to Pme (SEQ ID NO:367)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGAGCGGAGGTTCAGGCGGTTCCGGAGGAGGTTCTGGCGGATCA
GGCGGTTCGGGGATGTATGAAAGCTTTATTGAGTCACTGCCATTCCTTAAATCTTTGGAGTTTTCTGAACGCCTGAAAGT
AGTAGATGTGATAGGCACCAAAGTATACAACGATGGAGAACAAATCATTGCTCAGGGAGATTCGGCTGATTCTTTTTTCA
TTGTAGAATCTGGAGAAGTGAAAATTACTATGAAAAGAAAGGGTAAATCAGAAGTGGAAGAGAATGGTGCAGTAGAAATC
GCTCGATGCTCGCGGGGACAGTACTTTGGAGAGCTTGCCCTGGTAACTAACAAACCTCGAGCAGCTTCTGCCCACGCCAT
TGGGACTGTCAAATGTTTAGCAATGGATGTGCAAGCATTTGAAAGGCTTCTGGGACCTTGCATGGAAATTATGAAAAGGA
ACATCGCTACCTATGAAGAACAGTTAGTTGCCCTGTTTGGAACGAACATGGATATTGTTGGGTCCGGTGGATCCGGTGGC

FIG. 67AB

AGCGGAGGGACGTCAGGTGGATCTGGAGGGAGCTCAGGAGCTTCCAAGGTGTACGACCCCGAGCAACGCAAACGCATGAT
CACTGGGCCTCAGTGGTGGGCTCGCTGCAAGCAAATGAACGTGCTGGACTCCTTCATCAACTACTATGATTCCGAGAAGC
ACGCCGAGAACGCCGTGATTTTTCTGCATGGTAACGCTGCCTCCAGCTACCTGTGGAGGCACGTCGTGCCTCACATCGAG
CCCGTGGCTAGATGCATCATCCCTGATCTGATCGGAATGGGTAAGTCCGGCAAGAGCGGGAATGGCTCAGTTTAAAC

III) pBFB208 Sgf to Pme (SEQ ID NO:368)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGAGCGGAGGTTCAGGCGGTTCCGGAGGAGGTTCTGGCGGATCA
GGCGGTTCGGGGATGTATGAAAGCTTTATTGAGTCACTGCCATTCCTTAAATCTTTGGAGTTTTCTGAACGCCTGAAAGT
AGTAGATGTGATAGGCACCAAAGTATACAACGATGGAGAACAAATCATTGCTCAGGGAGATTCGGCTGATTCTTTTTTCA
TTGTAGAATCTGGAGAAGTGAAAATTACTATGAAAAGAAAGGGTAAATCAGAAGTGGAAGAGAATGGTGCAGTAGAAATC
GCTCGATGCTCGCGGGGACAGTACTTTGGAGAGCTTGCCCTGGTAACTAACAAACCTCGAGCAGCTTCTGCCCACGCCAT
TGGGACTGTCAAATGTTTAGCAATGGATGTGCAAGCATTTGAAAGGCTTCTGGGACCTTGCATGGAAATTATGAAAAGGA
ACATCGCTACCTATGAAGAACAGTTAGTTGCCCTGTTTGGAACGAACATGGATATTGTTGGGAGCTCAGGAGCTTCCAAG
GTGTACGACCCCGAGCAACGCAAACGCATGATCACTGGGCCTCAGTGGTGGGCTCGCTGCAAGCAAATGAACGTGCTGGA
CTCCTTCATCAACTACTATGATTCCGAGAAGCACGCCGAGAACGCCGTGATTTTTCTGCATGGTAACGCTGCCTCCAGCT
ACCTGTGGAGGCACGTCGTGCCTCACATCGAGCCCGTGGCTAGATGCATCATCCCTGATCTGATCGGAATGGGTAAGTCC
GGCAAGAGCGGGAATGGCTCAGTTTAAAC

JJJ) pBFB209 Sgf to Pme (SEQ ID NO:369)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGAGCGGAGGTTCAGGCGGTTCCGGAGGAGGTTCTGGCGGATCA
GGCGGTTCGGGGATGTATGAAAGCTTTATTGAGTCACTGCCATTCCTTAAATCTTTGGAGTTTTCTGAACGCCTGAAAGT
AGTAGATGTGATAGGCACCAAAGTATACAACGATGGAGAACAAATCATTGCTCAGGGAGATTCGGCTGATTCTTTTTTCA
TTGTAGAATCTGGAGAAGTGAAAATTACTATGAAAAGAAAGGGTAAATCAGAAGTGGAAGAGAATGGTGCAGTAGAAATC
GCTCGATGCTCGCGGGGACAGTACTTTGGAGAGCTTGCCCTGGTAACTAACAAACCTCGAGCAGCTTCTGCCCACGCCAT
TGGGACTGTCAAATGTTTAGCAATGGATGTGCAAGCATTTGAAAGGCTTCTGGGACCTTGCATGGAAATTATGAAAAGGA
ACATCGCTACCTATGAAGAACAGTTAGTTGCCCTGTTTGGAACGAACATGGATATTGTAGGGTCAGGTGGATCTGGAGGG
AGCTCAGGAGCTTCCAAGGTGTACGACCCCGAGCAACGCAAACGCATGATCACTGGGCCTCAGTGGTGGGCTCGCTGCAA
GCAAATGAACGTGCTGGACTCCTTCATCAACTACTATGATTCCGAGAAGCACGCCGAGAACGCCGTGATTTTTCTGCATG
GTAACGCTGCCTCCAGCTACCTGTGGAGGCACGTCGTGCCTCACATCGAGCCCGTGGCTAGATGCATCATCCCTGATCTG
ATCGGAATGGGTAAGTCCGGCAAGAGCGGGAATGGCTCAGTTTAAAC

KKK) pBFB210 Sgf to Pme (SEQ ID NO:370)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGAGCGGAATGTATGAGGAATTCCTTAGTAAAGTCTCTATTTTA

FIG. 67AC

GAGTCTCTGGACAAGTGGGAACGTCTTACGGTAGCTGATGCATTGGAACCAGTGCAGTTTGAAGATGGGCAGAAGATTGT
GGTGCAGGGAGAACCAGGGGATGAGTTCTTCATTATTTTAGAGGGGTCAGCTGCTGTGCTACAACGTCGGTCAGAAAATG
AAGAGTTTGTTGAAGTGGGAAGATTGGGGCCTTCTGATTATTTTGGTGAAATTGCACTACTGATGAATCGTCCTCGTGCT
GCCACAGTTGTTGCTCGTGGCCCCTTGAAGTGCGTTAAGCTGGACCGACCTAGATTTGAACGTGTTCTTGGCCCATGCTC
AGACATCCTCAAACGAAACATCCAGCAGTACAACAGTTTTGTGTCACTGTCTGTCGGGTCCGGTGGATCCGGTGGCAGCG
GAGGGACGTCAGGTGGATCTGGAGGGAGCTCAGGAGCTTCCAAGGTGTACGACCCCGAGCAACGCAAACGCATGATCACT
GGGCCTCAGTGGTGGGCTCGCTGCAAGCAAATGAACGTGCTGGACTCCTTCATCAACTACTATGATTCCGAGAAGCACGC
CGAGAACGCCGTGATTTTTCTGCATGGTAACGCTGCCTCCAGCTACCTGTGGAGGCACGTCGTGCCTCACATCGAGCCCG
TGGCTAGATGCATCATCCCTGATCTGATCGGAATGGGTAAGTCCGGCAAGAGCGGGAATGGCTCAGTTTAAAC

LLL) pBFB211 Sgf to Pme (SEQ ID NO:371)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGAGCGGAATGTATGAGGAATTCCTTAGTAAAGTCTCTATTTTA
GAGTCTCTGGACAAGTGGGAACGTCTTACGGTAGCTGATGCATTGGAACCAGTGCAGTTTGAAGATGGGCAGAAGATTGT
GGTGCAGGGAGAACCAGGGGATGAGTTCTTCATTATTTTAGAGGGGTCAGCTGCTGTGCTACAACGTCGGTCAGAAAATG
AAGAGTTTGTTGAAGTGGGAAGATTGGGGCCTTCTGATTATTTTGGTGAAATTGCACTACTGATGAATCGTCCTCGTGCT
GCCACAGTTGTTGCTCGTGGCCCCTTGAAGTGCGTTAAGCTGGACCGACCTAGATTTGAACGTGTTCTTGGCCCATGCTC
AGACATCCTCAAACGAAACATCCAGCAGTACAACAGTTTTGTGTCACTGTCTGTCGGGAGCTCAGGAGCTTCCAAGGTGT
ACGACCCCGAGCAACGCAAACGCATGATCACTGGGCCTCAGTGGTGGGCTCGCTGCAAGCAAATGAACGTGCTGGACTCC
TTCATCAACTACTATGATTCCGAGAAGCACGCCGAGAACGCCGTGATTTTTCTGCATGGTAACGCTGCCTCCAGCTACCT
GTGGAGGCACGTCGTGCCTCACATCGAGCCCGTGGCTAGATGCATCATCCCTGATCTGATCGGAATGGGTAAGTCCGGCA
AGAGCGGGAATGGCTCAGTTTAAAC

MMM) pBFB212 Sgf to Pme (SEQ ID NO:372)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGAGCGGAGGTTCAGGCGGTTCCGGAATGTATGAGGAATTCCTT
AGTAAAGTCTCTATTTTAGAGTCTCTGGACAAGTGGGAACGTCTTACGGTAGCTGATGCATTGGAACCAGTGCAGTTTGA
AGATGGGCAGAAGATTGTGGTGCAGGGAGAACCAGGGGATGAGTTCTTCATTATTTTAGAGGGGTCAGCTGCTGTGCTAC
AACGTCGGTCAGAAAATGAAGAGTTTGTTGAAGTGGGAAGATTGGGGCCTTCTGATTATTTTGGTGAAATTGCACTACTG
ATGAATCGTCCTCGTGCTGCCACAGTTGTTGCTCGTGGCCCCTTGAAGTGCGTTAAGCTGGACCGACCTAGATTTGAACG
TGTTCTTGGCCCATGCTCAGACATCCTCAAACGAAACATCCAGCAGTACAACAGTTTTGTGTCACTGTCTGTAGGGTCAG
GTGGATCTGGAGGGAGCTCAGGAGCTTCCAAGGTGTACGACCCCGAGCAACGCAAACGCATGATCACTGGGCCTCAGTGG
TGGGCTCGCTGCAAGCAAATGAACGTGCTGGACTCCTTCATCAACTACTATGATTCCGAGAAGCACGCCGAGAACGCCGT
GATTTTTCTGCATGGTAACGCTGCCTCCAGCTACCTGTGGAGGCACGTCGTGCCTCACATCGAGCCCGTGGCTAGATGCA
TCATCCCTGATCTGATCGGAATGGGTAAGTCCGGCAAGAGCGGGAATGGCTCAGTTTAAAC

NNN) pBFB213 Sgf to Pme (SEQ ID NO:373)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC

*FIG. 67AD*

GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGAGCGGAGGTTCAGGCGGTTCCGGAGGAGGTTCTGGCGGATCA
GGCGGTTCGGGGATGTATGAGGAATTCCTTAGTAAAGTCTCTATTTTAGAGTCTCTGGACAAGTGGGAACGTCTTACGGT
AGCTGATGCATTGGAACCAGTGCAGTTTGAAGATGGGCAGAAGATTGTGGTGCAGGGAGAACCAGGGGATGAGTTCTTCA
TTATTTTAGAGGGGTCAGCTGCTGTGCTACAACGTCGGTCAGAAAATGAAGAGTTTGTTGAAGTGGGAAGATTGGGGCCT
TCTGATTATTTTGGTGAAATTGCACTACTGATGAATCGTCCTCGTGCTGCCACAGTTGTTGCTCGTGGCCCCTTGAAGTG
CGTTAAGCTGGACCGACCTAGATTTGAACGTGTTCTTGGCCCATGCTCAGACATCCTCAAACGAAACATCCAGCAGTACA
ACAGTTTTGTGTCACTGTCTGTCGGGTCCGGTGGATCCGGTGGCAGCGGAGGGACGTCAGGTGGATCTGGAGGGAGCTCA
GGAGCTTCCAAGGTGTACGACCCCGAGCAACGCAAACGCATGATCACTGGGCCTCAGTGGTGGGCTCGCTGCAAGCAAAT
GAACGTGCTGGACTCCTTCATCAACTACTATGATTCCGAGAAGCACGCCGAGAACGCCGTGATTTTTCTGCATGGTAACG
CTGCCTCCAGCTACCTGTGGAGGCACGTCGTGCCTCACATCGAGCCCGTGGCTAGATGCATCATCCCTGATCTGATCGGA
ATGGGTAAGTCCGGCAAGAGCGGGAATGGCTCAGTTTAAAC

OOO) pBFB22 Sgf to Pme (SEQ ID NO:374)
GCGATCGCCATGGCCAAAAACATTAAGAAGGCCCAGCGCCATTCTACCCACTCGAAGACGGGACCGCCGGCGAGCAGCTG
CACAAAGCCATGAAGCGCTACGCCCTGGTGCCCGGCACCATCGCCTTTACCGACGCACATATCGAGGTGGACATTACCTA
CGCCGAGTACTTCGAGATGAGCGTTCGGCTGGCAGAAGCTATGAAGCGCTATGGGCTGAATACAAACCATCGGATCGTGG
TGTGCAGCGAGAATAGCTTGCAGTTCTTCATGCCCGTGTTGGGTGCCCTGTTCATCGGTGTGGCTGTGGCCCCAGCTAAC
GACATCTACAACGAGCGCGAGCTGCTGAACAGCATGGGCATCAGCCAGCCCACCGTCGTATTCGTGAGCAAGAAAGGGCT
GCAAAAGATCCTCAACGTGCAAAAGAAGCTACCGATCATACAAAAGATCATCATCATGGATAGCAAGACCGACTACCAGG
GCTTCCAAAGCATGTACACCTTCGTGACTTCCCATTTGCCACCCGGCTTCAACGAGTACGACTTCGTGCCCGAGAGCTTC
GACCGGGACAAAACCATCGCCCTGATCATGAACAGTAGTGGCAGTACCGGATTGCCCAAGGGCGTAGCCCTACCGCACCG
CACCGCTTGTGTCCGATTCAGTCATGCCCGCGACCCCATCTTCGGCAACCAGATCATCCCCGACACCGCTATCCTCAGCG
TGGTGCCATTTCACCACGGCTTCGGCATGTTCACCACGCTGGGCTACTTGATCTGCGGCTTTCGGGTCGTGCTCATGTAC
CGCTTCGAGGAGGAGCTATTCTTGCGCAGCTTGCAAGACTATAAGATTCAATCTGCCCTGCTGGTGCCCACACTATTTAG
CTTCTTCGCTAAGAGCACTCTCATCGACAAGTACGACCTAAGCAACTTGCACGAGATCGCCAGCGGCGGGGCGCCGCTCA
GCAAGGAGGTAGGTGAGGCCGTGGCCAAACGCTTCCACCTACCAGGCATCCGCCAGGGCTACGGCCTGACAGAAACAACC
AGCGCCATTCTGATCACCCCCGAAGGGGACGACAAGCCTGGCGCAGTAGGCAAGGTGGTGCCCTTCTTCGAGGCTAAGGT
GGTGGACTTGGACACCGGTAAGACACTGGGTGTGAACCAGCGCGGCGAGCTGTGCGTCCGTGGCCCCATGATCATGAGCG
GCTACGTTAACAACCCCGAGGCTACAAACGCTCTCATCGACAAGGACGGCTGGCTGCACAGCGGCGACATCGCCTACTGG
GACGAGGACGAGCACTTCTTCATCGTGGACCGGCTGAAGAGCCTGATCAAATACAAGGGCTACCAGGTAGCCCCAGCCGA
ACTGGAGAGCATCCTGCTGCAACACCCCAACATCTTCGACGCCGGGGTCGCCGGCCTGCCCGACGACGATGCCGGCGAGC
TGCCCGCCGCAGTCGTCGTGCTGGAACACGGTAAAACCATGACCGAGAAGGAGATCGTGGACTATGTGGCCAGCCAGGTT
ACAACCGCCAAGAAGCTGCGCGGTGGTGTTGTGTTCGTGGACGAGGTGCCTAAAGGACTGACCGGCAAGTTGGACGCCCG
CAAGATCCGCGAGATTCTCATTAAGGCCAAGAAGGTTTAAAC

PPP) pBFB225 Sgf to Pme (SEQ ID NO:375)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAGGAGGTTCTGGCGGATCAGGCGGTTCGGGGCTCAGCGAGGAGATGATTGCTGAGTTCAAAGCTGC
CTTTGACATGTTTGATGCGGACGGTGGTGGGGACATCAGCACCAAGGAGTTGGGCACGGTGATGAGGATGCTGGGCCAGA
ACCCCACCAAAGAGGAGCTGGATGCCATCATCGAGGAGGTGGACGAGGATGGCAGCGGCACCATCGACTTCGAGGAGTTC
CTGGTGATGATGGTGCGCCAGATGAAAGAGGACGCCAAGGGCAAGTCTGAGGAGGAGCTGGCCAACTGCTTCCGCATCTT
CGACAAGGATGCTAATGGGTTCATCGACATCGAGGAGCTGGGTGAGATTCTCAGGGCCACTGGGGAGCACGTCATCGAGG
AGGACATAGAAGACCTCATGAAGGATTCAGACAAGGATAATAATGGCCGCATTGACTTCGATGAGTTCCTGAAGATGATG
GAGGGTGTGCAGGGATCCGGTGGATCCGGTGGCAGCGGAGGGACGTCAGGTGGATCTGGAGGGAGCTCCGGTGCCAAAAA

FIG. 67AE

CATTAAGAAGGGCCCAGCGCCATTCTACCCACTCGAAGACGGGACCGCCGGCGAGCAGCTGCACAAAGCCATGAAGCGCT
ACGCCCTGGTGCCCGGCACCATCGCCTTTACCGACGCACATATCGAGGTGGACATTACCTACGCCGAGTACTTCGAGATG
AGCGTTCGGCTGGCAGAAGCTATGAAGCGCTATGGGCTGAATACAAACCATCGGATCGTGGTGTGCAGCGAGAATAGCTT
GCAGTTCTTCATGCCCGTGTTGGGTGCCCTGTTCATCGGTGTGGCTGTGGCCCCAGCTAACGACATCTACAACGAGCGCG
AGCTGCTGAACAGCATGGGCATCAGCCAGCCCACCGTCGTATTCGTGAGCAAGAAAGGGCTGCAAAAGATCCTCAACGTG
CAAAAGAAGCTACCGATCATACAAAAGATCATCATCATGGATAGCAAGACCGACTACCAGGGCTTCCAAAGCATGTACAC
CTTCGTGACTTCCCATTTGCCACCCGGCTTCAACGAGTACGACTTCGTGCCCGAGAGCTTCGACCGGGACAAAACCATCG
CCCTGATCATGAACAGTAGTGGCAGTACCGGATTGCCCAAGGGCGTAGCCCTACCGCACCGCACCGCTTGTGTCCGATTC
AGTCATGCCCGCGACCCCATCTTCGGCAACCAGATCATCCCCGTTTAAAC

QQQ) pBFB226 Sgf to Pme (SEQ ID NO:376)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGACTCAGCGAGGAGATGATTGCTGAGTTCAAAGCTGCCTTTGACATGTTTGATGCGGACGGTGGTGG
GGACATCAGCACCAAGGAGTTGGGCACGGTGATGAGGATGCTGGGCCAGAACCCCACCAAAGAGGAGCTGGATGCCATCA
TCGAGGAGGTGGACGAGGATGGCAGCGGCACCATCGACTTCGAGGAGTTCCTGGTGATGATGGTGCGCCAGATGAAAGAG
GACGCCAAGGGCAAGTCTGAGGAGGAGCTGGCCAACTGCTTCCGCATCTTCGACAAGGATGCTAATGGGTTCATCGACAT
CGAGGAGCTGGGTGAGATTCTCAGGGCCACTGGGGAGCACGTCATCGAGGAGGACATAGAAGACCTCATGAAGGATTCAG
ACAAGGATAATAATGGCCGCATTGACTTCGATGAGTTCCTGAAGATGATGGAGGGTGTGCAAGGGTCAGGTGGATCTGGA
GGGAGCTCCGGTGCCAAAAACATTAAGAAGGGCCCAGCGCCATTCTACCCACTCGAAGACGGGACCGCCGGCGAGCAGCT
GCACAAAGCCATGAAGCGCTACGCCCTGGTGCCCGGCACCATCGCCTTTACCGACGCACATATCGAGGTGGACATTACCT
ACGCCGAGTACTTCGAGATGAGCGTTCGGCTGGCAGAAGCTATGAAGCGCTATGGGCTGAATACAAACCATCGGATCGTG
GTGTGCAGCGAGAATAGCTTGCAGTTCTTCATGCCCGTGTTGGGTGCCCTGTTCATCGGTGTGGCTGTGGCCCCAGCTAA
CGACATCTACAACGAGCGCGAGCTGCTGAACAGCATGGGCATCAGCCAGCCCACCGTCGTATTCGTGAGCAAGAAAGGGC
TGCAAAAGATCCTCAACGTGCAAAAGAAGCTACCGATCATACAAAAGATCATCATCATGGATAGCAAGACCGACTACCAG
GGCTTCCAAAGCATGTACACCTTCGTGACTTCCCATTTGCCACCCGGCTTCAACGAGTACGACTTCGTGCCCGAGAGCTT
CGACCGGGACAAAACCATCGCCCTGATCATGAACAGTAGTGGCAGTACCGGATTGCCCAAGGGCGTAGCCCTACCGCACC
GCACCGCTTGTGTCCGATTCAGTCATGCCCGCGACCCCATCTTCGGCAACCAGATCATCCCCGTTTAAAC

RRR) pBFB227 Sgf to Pme (SEQ ID NO:377)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGACTC
AGCGAGGAGATGATTGCTGAGTTCAAAGCTGCCTTTGACATGTTTGATGCGGACGGTGGTGGGGACATCAGCACCAAGGA
GTTGGGCACGGTGATGAGGATGCTGGGCCAGAACCCCACCAAAGAGGAGCTGGATGCCATCATCGAGGAGGTGGACGAGG
ATGGCAGCGGCACCATCGACTTCGAGGAGTTCCTGGTGATGATGGTGCGCCAGATGAAAGAGGACGCCAAGGGCAAGTCT
GAGGAGGAGCTGGCCAACTGCTTCCGCATCTTCGACAAGGATGCTAATGGGTTCATCGACATCGAGGAGCTGGGTGAGAT
TCTCAGGGCCACTGGGGAGCACGTCATCGAGGAGGACATAGAAGACCTCATGAAGGATTCAGACAAGGATAATAATGGCC

FIG. 67AF

GCATTGACTTCGATGAGTTCCTGAAGATGATGGAGGGTGTGCAGGGGAGCTCCGGTGCCAAAAACATTAAGAAGGGCCCA
GCGCCATTCTACCCACTCGAAGACGGGACCGCCGGCGAGCAGCTGCACAAAGCCATGAAGCGCTACGCCCTGGTGCCCGG
CACCATCGCCTTTACCGACGCACATATCGAGGTGGACATTACCTACGCCGAGTACTTCGAGATGAGCGTTCGGCTGGCAG
AAGCTATGAAGCGCTATGGGCTGAATACAAACCATCGGATCGTGGTGTGCAGCGAGAATAGCTTGCAGTTCTTCATGCCC
GTGTTGGGTGCCCTGTTCATCGGTGTGGCTGTGGCCCCAGCTAACGACATCTACAACGAGCGCGAGCTGCTGAACAGCAT
GGGCATCAGCCAGCCCACCGTCGTATTCGTGAGCAAGAAAGGGCTGCAAAAGATCCTCAACGTGCAAAAGAAGCTACCGA
TCATACAAAAGATCATCATCATGGATAGCAAGACCGACTACCAGGGCTTCCAAAGCATGTACACCTTCGTGACTTCCCAT
TTGCCACCCGGCTTCAACGAGTACGACTTCGTGCCCGAGAGCTTCGACCGGGACAAAACCATCGCCCTGATCATGAACAG
TAGTGGCAGTACCGGATTGCCCAAGGGCGTAGCCCTACCGCACCGCACCGCTTGTGTCCGATTCAGTCATGCCCGCGACC
CCATCTTCGGCAACCAGATCATCCCCGTTTAAAC

SSS) pBFB228 Sgf to Pme (SEQ ID NO:378)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGAGCGGATGGTATTTTGGCAAGATCACCAGACGGGAGTCAGAG
CGGTTACTGCTCAATGCAGAGAACCCGAGAGGGACCTTCCTCGTGCGAGAAAGTGAGACCACGAAAGGTGCCTACTGCCT
CTCAGTGTCTGACTTCGACAACGCCAAGGGCCTCAACGTGAAGCACTACAAGATCCGCAAGCTGGACAGCGGCGGCTTCT
ACATCACCTCCCGCACCCAGTTCAACAGCCTGCAGCAGCTGGTGGCCTACTACTCCAAACACGCCGATGGCCTGTGCCAC
CGCCTCACCACCGTGTGCGGTTCCGGAGGATCTACTTCGGGGTCAGGTAAACCTGGCTCGGGTGAGGGATCGGAAATTTA
TGGTCAATTCGGGAGCTCAGGAGCTTCCAAGGTGTACGACCCCGAGCAACGCAAACGCATGATCACTGGGCCTCAGTGGT
GGGCTCGCTGCAAGCAAATGAACGTGCTGGACTCCTTCATCAACTACTATGATTCCGAGAAGCACGCCGAGAACGCCGTG
ATTTTTCTGCATGGTAACGCTGCCTCCAGCTACCTGTGGAGGCACGTCGTGCCTCACATCGAGCCCGTGGCTAGATGCAT
CATCCCTGATCTGATCGGAATGGGTAAGTCCGGCAAGAGCGGGAATGGCTCAGTTTAAAC

TTT) pBFB229 Sgf to Pme (SEQ ID NO:379)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGAGCGGATGGTATTTTGGCAAGATCACCAGACGGGAGTCAGAG
CGGTTACTGCTCAATGCAGAGAACCCGAGAGGGACCTTCCTCGTGCGAGAAAGTGAGACCACGAAAGGTGCCTACTGCCT
CTCAGTGTCTGACTTCGACAACGCCAAGGGCCTCAACGTGAAGCACTACAAGATCCGCAAGCTGGACAGCGGCGGCTTCT
ACATCACCTCCCGCACCCAGTTCAACAGCCTGCAGCAGCTGGTGGCCTACTACTCCAAACACGCCGATGGCCTGTGCCAC
CGCCTCACCACCGTGTGCGGTTCCGGAGGATCTACTTCGGGGTCAGGTAAACCTGGCTCGGGTGAGGGATCGGAAATTTA
TGGTGAATTCGGATCCGGGTCAGGTGGATCTGGAGGGAGCTCAGGAGCTTCCAAGGTGTACGACCCCGAGCAACGCAAAC
GCATGATCACTGGGCCTCAGTGGTGGGCTCGCTGCAAGCAAATGAACGTGCTGGACTCCTTCATCAACTACTATGATTCC
GAGAAGCACGCCGAGAACGCCGTGATTTTTCTGCATGGTAACGCTGCCTCCAGCTACCTGTGGAGGCACGTCGTGCCTCA
CATCGAGCCCGTGGCTAGATGCATCATCCCTGATCTGATCGGAATGGGTAAGTCCGGCAAGAGCGGGAATGGCTCAGTTT
AAAC

UUU) pBFB230 Sgf to Pme (SEQ ID NO:380)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC

*FIG. 67AG*

GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGAGCGGATGGTATTTTGGCAAGATCACCAGACGGGAGTCAGAG
CGGTTACTGCTCAATGCAGAGAACCCCGAGAGGGACCTTCCTCGTGCGAGAAAGTGAGACCACGAAAGGTGCCTACTGCCT
CTCAGTGTCTGACTTCGACAACGCCAAGGGCCTCAACGTGAAGCACTACAAGATCCGCAAGCTGGACAGCGGCGGCTTCT
ACATCACCTCCCGCACCCAGTTCAACAGCCTGCAGCAGCTGGTGGCCTACTACTCCAAACACGCCGATGGCCTGTGCCAC
CGCCTCACCACCGTGTGCGGTTCCGGAGGATCTACTTCGGGGTCAGGTAAACCTGGCTCGGGTGAGGGATCGGAAATTTA
TGGTGAATTCGGATCCGGTGGTTCAGGTGGCAGCGGAGGAGGGTCAGGTGGATCTGGAGGGAGCTCAGGAGCTTCCAAGG
TGTACGACCCCGAGCAACGCAAACGCATGATCACTGGGCCTCAGTGGTGGGCTCGCTGCAAGCAAATGAACGTGCTGGAC
TCCTTCATCAACTACTATGATTCCGAGAAGCACGCCGAGAACGCCGTGATTTTTCTGCATGGTAACGCTGCCTCCAGCTA
CCTGTGGAGGCACGTCGTGCCTCACATCGAGCCCGTGGCTAGATGCATCATCCCTGATCTGATCGGAATGGGTAAGTCCG
GCAAGAGCGGGAATGGCTCAGTTTAAAC

VVV) pBFB232 Sgf to Pme (SEQ ID NO:381)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGAGCGGAGGTTCAGGCGGTTCCGGAGGAGGTTCTGGCGGATCA
GGCGGTTCGGGGTCTATCATGAACACTGTCAAGAGTCTCACGGAAAGTGCGCGTTGCAGTCTCTTCCTTGTCAGAGGTGA
CGTACTTGAAGCGCATTTTGAGGATGGTAACGTCGTTACAATCCCTAGGGGTGCAGGTATTGCCGGATATGTGGCGCAAA
CTGGTGAGACTGTTAATATTGTTGATGCCTACGCCGATGACCGCTTTAACCGTGAGGTTGACAAGGCTACTGGGTACCGT
ACAAAGACGATACTCTGCATGCCTGTGATGTACGAAGGAACGATTGTGGCTGTTGCCCAACTGATTAATAAATTGGATCT
GACAACTGAGAGTGGATTGCGCCTACCTCGTGTGTTCGGAAAACGTGACGAGGAGCTGTTCCAAACCTTCTCTATGTTTG
CTGGCGCCTCACTACGTGGGTCCGGTGGATCCGGTGGCAGCGGAGGGACGTCAGGTGGATCTGGAGGGAGCTCAGGAGCT
TCCAAGGTGTACGACCCCGAGCAACGCAAACGCATGATCACTGGGCCTCAGTGGTGGGCTCGCTGCAAGCAAATGAACGT
GCTGGACTCCTTCATCAACTACTATGATTCCGAGAAGCACGCCGAGAACGCCGTGATTTTTCTGCATGGTAACGCTGCCT
CCAGCTACCTGTGGAGGCACGTCGTGCCTCACATCGAGCCCGTGGCTAGATGCATCATCCCTGATCTGATCGGAATGGGT
AAGTCCGGCAAGAGCGGGAATGGCTCAGTTTAAAC

WWW) pBFB247 Sgf to Pme (SEQ ID NO:382)
GCGATCGCCATGAAGGGCGTAGCCCTACCGCACCGCACCGCTTGTGTCCGATTCAGTCATGCCCGCGACCCCATCTTCGG
CAACCAGATCATCCCCGACACCGCTATCCTCAGCGTGGTGCCATTTCACCACGGCTTCGGCATGTTCACCACGCTGGGCT
ACTTGATCTGCGGCTTTCGGGTCGTGCTCATGTACCGCTTCGAGGAGGAGCTATTCTTGCGCAGCTTGCAAGACTATAAG
ATTCAATCTGCCCTGCTGGTGCCCACACTATTTAGCTTCTTCGCTAAGAGCACTCTCATCGACAAGTACGACCTAAGCAA
CTTGCACGAGATCGCCAGCGGCGGGGCGCCGCTCAGCAAGGAGGTAGGTGAGGCCGTGGCCAAACGCTTCCACCTACCAG
GCATCCGCCAGGGCTACGGCCTGACAGAAACAACCAGCGCCATTCTGATCACCCCCGAAGGGGACGACAAGCCTGGCGCA
GTAGGCAAGGTGGTGCCCTTCTTCGAGGCTAAGGTGGTGGACTTGGACACCGGTAAGACACTGGGTGTGAACCAGCGCGG
CGAGCTGTGCGTCCGTGGCCCCATGATCATGAGCGGCTACGTTAACAACCCCGAGGCTACAAACGCTCTCATCGACAAGG
ACGGCTGGCTGCACAGCGGCGACATCGCCTACTGGGACGAGGACGAGCACTTCTTCATCGTGGACCGGCTGAAGAGCCTG
ATCAAATACAAGGGCTACCAGGTAGCCCCAGCCGAACTGGAGAGCATCCTGCTGCAACACCCCAACATCTTCGACGCCGG
GGTCGCCGGCCTGCCCGACGACGATGCCGGCGAGCTGCCCGCCGCAGTCGTCGTGCTGGAACACGGTAAAACCATGACCG
AGAAGGAGATCGTGGACTATGTGGCCAGCCAGGTTACAACCGCCAAGAAGCTGCGCGGTGGTGTTGTGTTCGTGGACGAG
GTGCCTAAAGGACTGACCGGCAAGTTGGACGCCCGCAAGATCCGCGAGATTCTCATTAAGGCCAAGAAGGGCTCGAGCGG
AGGTTCAGGCGGTTCCGGAGGAGGTATGTATGAAAGCTTTATTGAGTCACTGCCATTCCTTAAATCTTTGGAGTTTTCTG
AACGCCTGAAAGTAGTAGATGTGATAGGCACCAAAGTATACAACGATGGAGAACAAATCATTGCTCAGGGAGATTCGGCT
GATTCTTTTTTCATTGTAGAATCTGGAGAAGTGAAAATTACTATGAAAAGAAAGGGTAAATCAGAAGTGGAAGAGAATGG
TGCAGTAGAAATCGCTCGATGCTCGCGGGGACAGTACTTTGGAGAGCTTGCCCTGGTAACTAACAAACCTCGAGCAGCTT
CTGCCCACGCCATTGGGACTGTCAAATGTTTAGCAATGGATGTGCAAGCATTTGAAAGGCTTCTGGGACCTTGCATGGAA
ATTATGAAAAGGAACATCGCTACCTATGAAGAACAGTTAGTTGCCCTGTTTGGAACGAACATGGATATTGTAGCCAAAAA
CATTAAGAAGGGCCCAGCGCCATTCTACCCACTCGAAGACGGGACCGCCGGCGAGCAGCTGCACAAAGCCATGAAGCGCT
ACGCCCTGGTGCCCGGCACCATCGCCTTTACCGACGCACATATCGAGGTGGACATTACCTACGCCGAGTACTTCGAGATG
AGCGTTCGGCTGGCAGAAGCTATGAACCGCTATGGGCTGAATACAAACCATCGGATCGTGGTGTGCAGCGAGAATAGCTT

FIG. 67AH

GCAGTTCTTCATGCCCGTGTTGGGTGCCCTGTTCATCGGTGTGGCTGTGGCCCCAGCTAACGACATCTACAACGAGCGCG
AGCTGCTGAACAGCATGGGCATCAGCCAGCCCACCGTCGTATTCGTGAGCAAGAAAGGGCTGCAAAAGATCCTCAACGTG
CAAAAGAAGCTACCGATCATACAAAAGATCATCATCATGGATAGCAAGACCGACTACCAGGGCTTCCAAAGCATGTACAC
CTTCGTGACTTCCCATTTGCCACCCGGCTTCAACGAGTACGACTTCGTGCCCGAGAGCTTCGACCGGGACAAAACCATCG
CCCTGATCATGAACAGTGTTTAAAC

XXX) pBFB251 Sgf to Pme (SEQ ID NO:383)
GCGATCGCCATGAGTGGCAGTACCGGATTGCCCAAGGGCGTAGCCCTACCGCACCGCACCGCTTGTGTCCGATTCAGTCA
TGCCCGCGACCCCATCTTCGGCAACCAGATCATCCCCGACACCGCTATCCTCAGCGTGGTGCCATTTCACCACGGCTTCG
GCATGTTCACCACGCTGGGCTACTTGATCTGCGGCTTTCGGGTCGTGCTCATGTACCGCTTCGAGGAGGAGCTATTCTTG
CGCAGCTTGCAAGACTATAAGATTCAATCTGCCCTGCTGGTGCCCACACTATTTAGCTTCTTCGCTAAGAGCACTCTCAT
CGACAAGTACGACCTAAGCAACTTGCACGAGATCGCCAGCGGCGGGGCGCCGCTCAGCAAGGAGGTAGGTGAGGCCGTGG
CCAAACGCTTCCACCTACCAGGCATCCGCCAGGGCTACGGCCTGACAGAAACAACCAGCGCCATTCTGATCACCCCCGAA
GGGGACGACAAGCCTGGCGCAGTAGGCAAGGTGGTGCCCTTCTTCGAGGCTAAGGTGGTGGACTTGGACACCGGTAAGAC
ACTGGGTGTGAACCAGCGCGGCGAGCTGTGCGTCCGTGGCCCCATGATCATGAGCGGCTACGTTAACAACCCCGAGGCTA
CAAACGCTCTCATCGACAAGGACGGCTGGCTGCACAGCGGCGACATCGCCTACTGGGACGAGGACGAGCACTTCTTCATC
GTGGACCGGCTGAAGAGCCTGATCAAATACAAGGGCTACCAGGTAGCCCCAGCCGAACTGGAGAGCATCCTGCTGCAACA
CCCCAACATCTTCGACGCCGGGGTCGCCGGCCTGCCCGACGACGATGCCGGCGAGCTGCCCGCCGCAGTCGTCGTGCTGG
AACACGGTAAAACCATGACCGAGAAGGAGATCGTGGACTATGTGGCCAGCCAGGTTACAACCGCCAAGAAGCTGCGCGGT
GGTGTTGTGTTCGTGGACGAGGTGCCTAAAGGACTGACCGGCAAGTTGGACGCCCGCAAGATCCGCGAGATTCTCATTAA
GGCCAAGAAGGGCTCGAGCGGAGGTTCAGGCGGTTCCGGAGGAGGTATGTATGAAAGCTTTATTGAGTCACTGCCATTCC
TTAAATCTTTGGAGTTTTCTGAACGCCTGAAAGTAGTAGATGTGATAGGCACCAAAGTATACAACGATGGAGAACAAATC
ATTGCTCAGGGAGATTCGGCTGATTCTTTTTTCATTGTAGAATCTGGAGAAGTGAAAATTACTATGAAAAGAAAGGGTAA
ATCAGAAGTGGAAGAGAATGGTGCAGTAGAAATCGCTCGATGCTCGCGGGGACAGTACTTTGGAGAGCTTGCCCTGGTAA
CTAACAAACCTCGAGCAGCTTCTGCCCACGCCATTGGGACTGTCAAATGTTTAGCAATGGATGTGCAAGCATTTGAAAGG
CTTCTGGGACCTTGCATGGAAATTATGAAAAGGAACATCGCTACCTATGAAGAACAGTTAGTTGCCCTGTTTGGAACGAA
CATGGATATTGTAGCCAAAAACATTAAGAAGGGCCCAGCGCCATTCTACCCACTCGAAGACGGGACCGCCGGCGAGCAGC
TGCACAAAGCCATGAAGCGCTACGCCCTGGTGCCCGGCACCATCGCCTTTACCGACGCACATATCGAGGTGGACATTACC
TACGCCGAGTACTTCGAGATGAGCGTTCGGCTGGCAGAAGCTATGAAGCGCTATGGGCTGAATACAAACCATCGGATCGT
GGTGTGCAGCGAGAATAGCTTGCAGTTCTTCATGCCCGTGTTGGGTGCCCTGTTCATCGGTGTGGCTGTGGCCCCAGCTA
ACGACATCTACAACGAGCGCGAGCTGCTGAACAGCATGGGCATCAGCCAGCCCACCGTCGTATTCGTGAGCAAGAAAGGG
CTGCAAAAGATCCTCAACGTGCAAAAGAAGCTACCGATCATACAAAAGATCATCATCATGGATAGCAAGACCGACTACCA
GGGCTTCCAAAGCATGTACACCTTCGTGACTTCCCATTTGCCACCCGGCTTCAACGAGTACGACTTCGTGCCCGAGAGCT
TCGACCGGGACAAAACCATCGCCCTGATCATGAACAGTGTTTAAAC

YYY) pBFB252 Sgf to Pme (SEQ ID NO:384)
GCGATCGCCATGGGCACCATCGCCTTTACCGACGCACATATCGAGGTGGACATTACCTACGCCGAGTACTTCGAGATGAG
CGTTCGGCTGGCAGAAGCTATGAAGCGCTATGGGCTGAATACAAACCATCGGATCGTGGTGTGCAGCGAGAATAGCTTGC
AGTTCTTCATGCCCGTGTTGGGTGCCCTGTTCATCGGTGTGGCTGTGGCCCCAGCTAACGACATCTACAACGAGCGCGAG
CTGCTGAACAGCATGGGCATCAGCCAGCCCACCGTCGTATTCGTGAGCAAGAAAGGGCTGCAAAAGATCCTCAACGTGCA
AAAGAAGCTACCGATCATACAAAAGATCATCATCATGGATAGCAAGACCGACTACCAGGGCTTCCAAAGCATGTACACCT
TCGTGACTTCCCATTTGCCACCCGGCTTCAACGAGTACGACTTCGTGCCCGAGAGCTTCGACCGGGACAAAACCATCGCC
CTGATCATGAACAGTAGTGGCAGTACCGGATTGCCCAAGGGCGTAGCCCTACCGCACCGCACCGCTTGTGTCCGATTCAG
TCATGCCCGCGACCCCATCTTCGGCAACCAGATCATCCCCGACACCGCTATCCTCAGCGTGGTGCCATTTCACCACGGCT
TCGGCATGTTCACCACGCTGGGCTACTTGATCTGCGGCTTTCGGGTCGTGCTCATGTACCGCTTCGAGGAGGAGCTATTC
TTGCGCAGCTTGCAAGACTATAAGATTCAATCTGCCCTGCTGGTGCCCACACTATTTAGCTTCTTCGCTAAGAGCACTCT
CATCGACAAGTACGACCTAAGCAACTTGCACGAGATCGCCAGCGGCGGGGCGCCGCTCAGCAAGGAGGTAGGTGAGGCCG
TGGCCAAACGCTTCCACCTACCAGGCATCCGCCAGGGCTACGGCCTGACAGAAACAACCAGCGCCATTCTGATCACCCCC
GAAGGGGACGACAAGCCTGGCGCAGTAGGCAAGGTGGTGCCCTTCTTCGAGGCTAAGGTGGTGGACTTGGACACCGGTAA
GACACTGGGTGTGAACCAGCGCGGCGAGCTGTGCGTCCGTGGCCCCATGATCATGAGCGGCTACGTTAACAACCCCGAGG
CTACAAACGCTCTCATCGACAAGGACGGCTGGCTGCACAGCGGCGACATCGCCTACTGGGACGAGGACGAGCACTTCTTC
ATCGTGGACCGGCTGAAGAGCCTGATCAAATACAAGGGCTACCAGGTAGCCCCAGCCGAACTGGAGAGCATCCTGCTGCA
ACACCCCAACATCTTCGACGCCGGGGTCGCCGGCCTGCCCGACGACGATGCCGGCGAGCTGCCCGCCGCAGTCGTCGTGC
TGGAACACGGTAAAACCATGACCGAGAAGGAGATCGTGGACTATGTGGCCAGCCAGGTTACAACCGCCAAGAAGCTGCGC
GGTGGTGTTGTGTTCGTGGACGAGGTGCCTAAAGGACTGACCGGCAAGTTGGACGCCCGCAAGATCCGCGAGATTCTCAT
TAAGGCCAAGAAGGGCTCGAGCGGAGGTTCAGGCGGTTCCGGAGGAGGTATGTATGAAAGCTTTATTGAGTCACTGCCAT
TCCTTAAATCTTTGGAGTTTTCTGAACGCCTGAAAGTAGTAGATGTGATAGGCACCAAAGTATACAACGATGGAGAACAA

FIG. 67AI

ATCATTGCTCAGGGAGATTCGGCTGATTCTTTTTTCATTGTAGAATCTGGAGAAGTGAAAATTACTATGAAAAGAAAGGG
TAAATCAGAAGTGGAAGAGAATGGTGCAGTAGAAATCGCTCGATGCTCGCGGGGACAGTACTTTGGAGAGCTTGCCCTGG
TAACTAACAAACCTCGAGCAGCTTCTGCCCACGCCATTGGGACTGTCAAATGTTTAGCAATGGATGTGCAAGCATTTGAA
AGGCTTCTGGGACCTTGCATGGAAATTATGAAAAGGAACATCGCTACCTATGAAGAACAGTTAGTTGCCCTGTTTGGAAC
GAACATGGATATTGTAGCCAAAAACATTAAGAAGGGCCCAGCGCCATTCTACCCACTCGAAGACGGGACCGCCGGCGAGC
AGCTGCACAAAGCCATGAAGCGCTACGCCCTGGTTTAAAC

ZZZ) pBFB253 Sgf to Pme (SEQ ID NO:385)
GCGATCGCCATGGAGGTGGACATTACCTACGCCGAGTACTTCGAGATGAGCGTTCGGCTGGCAGAAGCTATGAAGCGCTA
TGGGCTGAATACAAACCATCGGATCGTGGTGTGCAGCGAGAATAGCTTGCAGTTCTTCATGCCCGTGTTGGGTGCCCTGT
TCATCGGTGTGGCTGTGGCCCCAGCTAACGACATCTACAACGAGCGCGAGCTGCTGAACAGCATGGGCATCAGCCAGCCC
ACCGTCGTATTCGTGAGCAAGAAAGGGCTGCAAAAGATCCTCAACGTGCAAAAGAAGCTACCGATCATACAAAAGATCAT
CATCATGGATAGCAAGACCGACTACCAGGGCTTCCAAAGCATGTACACCTTCGTGACTTCCCATTTGCCACCCGGCTTCA
ACGAGTACGACTTCGTGCCCGAGAGCTTCGACCGGGACAAAACCATCGCCCTGATCATGAACAGTAGTGGCAGTACCGGA
TTGCCCAAGGGCGTAGCCCTACCGCACCGCACCGCTTGTGTCCGATTCAGTCATGCCCGCGACCCCATCTTCGGCAACCA
GATCATCCCCGACACCGCTATCCTCAGCGTGGTGCCATTTCACCACGGCTTCGGCATGTTCACCACGCTGGGCTACTTGA
TCTGCGGCTTTCGGGTCGTGCTCATGTACCGCTTCGAGGAGGAGCTATTCTTGCGCAGCTTGCAAGACTATAAGATTCAA
TCTGCCCTGCTGGTGCCCACACTATTTAGCTTCTTCGCTAAGAGCACTCTCATCGACAAGTACGACCTAAGCAACTTGCA
CGAGATCGCCAGCGGCGGGGCGCCGCTCAGCAAGGAGGTAGGTGAGGCCGTGGCCAAACGCTTCCACCTACCAGGCATCC
GCCAGGGCTACGGCCTGACAGAAACAACCAGCGCCATTCTGATCACCCCCGAAGGGGACGACAAGCCTGGCGCAGTAGGC
AAGGTGGTGCCCTTCTTCGAGGCTAAGGTGGTGGACTTGGACACCGGTAAGACACTGGGTGTGAACCAGCGCGGCGAGCT
GTGCGTCCGTGGCCCCATGATCATGAGCGGCTACGTTAACAACCCCGAGGCTACAAACGCTCTCATCGACAAGGACGGCT
GGCTGCACAGCGGCGACATCGCCTACTGGGACGAGGACGAGCACTTCTTCATCGTGGACCGGCTGAAGAGCCTGATCAAA
TACAAGGGCTACCAGGTAGCCCCAGCCGAACTGGAGAGCATCCTGCTGCAACACCCCAACATCTTCGACGCCGGGGTCGC
CGGCCTGCCCGACGACGATGCCGGCGAGCTGCCCGCCGCAGTCGTCGTGCTGGAACACGGTAAAACCATGACCGAGAAGG
AGATCGTGGACTATGTGGCCAGCCAGGTTACAACCGCCAAGAAGCTGCGCGGTGGTGTTGTGTTCGTGGACGAGGTGCCT
AAAGGACTGACCGGCAAGTTGGACGCCCGCAAGATCCGCGAGATTCTCATTAAGGCCAAGAAGGGCTCGAGCGGAGGTTC
AGGCGGTTCCGGAGGAGGTATGTATGAAAGCTTTATTGAGTCACTGCCATTCCTTAAATCTTTGGAGTTTTCTGAACGCC
TGAAAGTAGTAGATGTGATAGGCACCAAAGTATACAACGATGGAGAACAAATCATTGCTCAGGGAGATTCGGCTGATTCT
TTTTTCATTGTAGAATCTGGAGAAGTGAAAATTACTATGAAAAGAAAGGGTAAATCAGAAGTGGAAGAGAATGGTGCAGT
AGAAATCGCTCGATGCTCGCGGGGACAGTACTTTGGAGAGCTTGCCCTGGTAACTAACAAACCTCGAGCAGCTTCTGCCC
ACGCCATTGGGACTGTCAAATGTTTAGCAATGGATGTGCAAGCATTTGAAAGGCTTCTGGGACCTTGCATGGAAATTATG
AAAAGGAACATCGCTACCTATGAAGAACAGTTAGTTGCCCTGTTTGGAACGAACATGGATATTGTAGCCAAAAACATTAA
GAAGGGCCCAGCGCCATTCTACCCACTCGAAGACGGGACCGCCGGCGAGCAGCTGCACAAAGCCATGAAGCGCTACGCCC
TGGTGCCCGGCACCATCGCCTTTACCGACGCAGTTTAAAC

AAAA) pBFB254 Sgf to Pme (SEQ ID NO:386)
GCGATCGCCATGGACAAAACCATCGCCCTGATCATGAACAGTAGTGGCAGTACCGGATTGCCCAAGGGCGTAGCCCTACC
GCACCGCACCGCTTGTGTCCGATTCAGTCATGCCCGCGACCCCATCTTCGGCAACCAGATCATCCCCGACACCGCTATCC
TCAGCGTGGTGCCATTTCACCACGGCTTCGGCATGTTCACCACGCTGGGCTACTTGATCTGCGGCTTTCGGGTCGTGCTC
ATGTACCGCTTCGAGGAGGAGCTATTCTTGCGCAGCTTGCAAGACTATAAGATTCAATCTGCCCTGCTGGTGCCCACACT
ATTTAGCTTCTTCGCTAAGAGCACTCTCATCGACAAGTACGACCTAAGCAACTTGCACGAGATCGCCAGCGGCGGGGCGC
CGCTCAGCAAGGAGGTAGGTGAGGCCGTGGCCAAACGCTTCCACCTACCAGGCATCCGCCAGGGCTACGGCCTGACAGAA
ACAACCAGCGCCATTCTGATCACCCCCGAAGGGGACGACAAGCCTGGCGCAGTAGGCAAGGTGGTGCCCTTCTTCGAGGC
TAAGGTGGTGGACTTGGACACCGGTAAGACACTGGGTGTGAACCAGCGCGGCGAGCTGTGCGTCCGTGGCCCCATGATCA
TGAGCGGCTACGTTAACAACCCCGAGGCTACAAACGCTCTCATCGACAAGGACGGCTGGCTGCACAGCGGCGACATCGCC
TACTGGGACGAGGACGAGCACTTCTTCATCGTGGACCGGCTGAAGAGCCTGATCAAATACAAGGGCTACCAGGTAGCCCC
AGCCGAACTGGAGAGCATCCTGCTGCAACACCCCAACATCTTCGACGCCGGGGTCGCCGGCCTGCCCGACGACGATGCCG
GCGAGCTGCCCGCCGCAGTCGTCGTGCTGGAACACGGTAAAACCATGACCGAGAAGGAGATCGTGGACTATGTGGCCAGC
CAGGTTACAACCGCCAAGAAGCTGCGCGGTGGTGTTGTGTTCGTGGACGAGGTGCCTAAAGGACTGACCGGCAAGTTGGA
CGCCCGCAAGATCCGCGAGATTCTCATTAAGGCCAAGAAGGGCTCGAGCGGAGGTTCAGGCGGTTCCGGAGGAGGTATGT
ATGAAAGCTTTATTGAGTCACTGCCATTCCTTAAATCTTTGGAGTTTTCTGAACGCCTGAAAGTAGTAGATGTGATAGGC
ACCAAAGTATACAACGATGGAGAACAAATCATTGCTCAGGGAGATTCGGCTGATTCTTTTTTCATTGTAGAATCTGGAGA
AGTGAAAATTACTATGAAAAGAAAGGGTAAATCAGAAGTGGAAGAGAATGGTGCAGTAGAAATCGCTCGATGCTCGCGGG
GACAGTACTTTGGAGAGCTTGCCCTGGTAACTAACAAACCTCGAGCAGCTTCTGCCCACGCCATTGGGACTGTCAAATGT
TTAGCAATGGATGTGCAAGCATTTGAAAGGCTTCTGGGACCTTGCATGGAAATTATGAAAAGGAACATCGCTACCTATGA
AGAACAGTTAGTTGCCCTGTTTGGAACGAACATGGATATTGTAGCCAAAAACATTAAGAAGGGCCCAGCGCCATTCTACC

FIG. 67AJ

CACTCGAAGACGGGACCGCCGGCGAGCAGCTGCACAAAGCCATGAAGCGCTACGCCCTGGTGCCCGGCACCATCGCCTTT
ACCGACGCACATATCGAGGTGGACATTACCTACGCCGAGTACTTCGAGATGAGCGTTCGGCTGGCAGAAGCTATGAAGCG
CTATGGGCTGAATACAAACCATCGGATCGTGGTGTGCAGCGAGAATAGCTTGCAGTTCTTCATGCCCGTGTTGGGTGCCC
TGTTCATCGGTGTGGCTGTGGCCCCAGCTAACGACATCTACAACGAGCGCGAGCTGCTGAACAGCATGGGCATCAGCCAG
CCCACCGTCGTATTCGTGAGCAAGAAAGGGCTGCAAAAGATCCTCAACGTGCAAAAGAAGCTACCGATCATACAAAAGAT
CATCATCATGGATAGCAAGACCGACTACCAGGGCTTCCAAAGCATGTACACCTTCGTGACTTCCCATTTGCCACCCGGCT
TCAACGAGTACGACTTCGTGCCCGAGAGCTTCGTTTAAAC

BBBB) pBFB255 Sgf to Pme (SEQ ID NO:387)
GCGATCGCCATGATCTTCGGCAACCAGATCATCCCCGACACCGCTATCCTCAGCGTGGTGCCATTTCACCACGGCTTCGG
CATGTTCACCACGCTGGGCTACTTGATCTGCGGCTTTCGGGTCGTGCTCATGTACCGCTTCGAGGAGGAGCTATTCTTGC
GCAGCTTGCAAGACTATAAGATTCAATCTGCCCTGCTGGTGCCCACACTATTTAGCTTCTTCGCTAAGAGCACTCTCATC
GACAAGTACGACCTAAGCAACTTGCACGAGATCGCCAGCGGCGGGGCGCCGCTCAGCAAGGAGGTAGGTGAGGCCGTGGC
CAAACGCTTCCACCTACCAGGCATCCGCCAGGGCTACGGCCTGACAGAAACAACCAGCGCCATTCTGATCACCCCCGAAG
GGGACGACAAGCCTGGCGCAGTAGGCAAGGTGGTGCCCTTCTTCGAGGCTAAGGTGGTGGACTTGGACACCGGTAAGACA
CTGGGTGTGAACCAGCGCGGCGAGCTGTGCGTCCGTGGCCCCATGATCATGAGCGGCTACGTTAACAACCCCGAGGCTAC
AAACGCTCTCATCGACAAGGACGGCTGGCTGCACAGCGGCGACATCGCCTACTGGGACGAGGACGAGCACTTCTTCATCG
TGGACCGGCTGAAGAGCCTGATCAAATACAAGGGCTACCAGGTAGCCCCAGCCGAACTGGAGAGCATCCTGCTGCAACAC
CCCAACATCTTCGACGCCGGGGTCGCCGGCCTGCCCGACGACGATGCCGGCGAGCTGCCCGCCGCAGTCGTCGTGCTGGA
ACACGGTAAAACCATGACCGAGAAGGAGATCGTGGACTATGTGGCCAGCCAGGTTACAACCGCCAAGAAGCTGCGCGGTG
GTGTTGTGTTCGTGGACGAGGTGCCTAAAGGACTGACCGGCAAGTTGGACGCCCGCAAGATCCGCGAGATTCTCATTAAG
GCCAAGAAGGGCTCGAGCGGAGGTTCAGGCGGTTCCGGAGGAGGTATGTATGAAAGCTTTATTGAGTCACTGCCATTCCT
TAAATCTTTGGAGTTTTCTGAACGCCTGAAAGTAGTAGATGTGATAGGCACCAAAGTATACAACGATGGAGAACAAATCA
TTGCTCAGGGAGATTCGGCTGATTCTTTTTTCATTGTAGAATCTGGAGAAGTGAAAATTACTATGAAAAGAAAGGGTAAA
TCAGAAGTGGAAGAGAATGGTGCAGTAGAAATCGCTCGATGCTCGCGGGGACAGTACTTTGGAGAGCTTGCCCTGGTAAC
TAACAAACCTCGAGCAGCTTCTGCCCACGCCATTGGGACTGTCAAATGTTTAGCAATGGATGTGCAAGCATTTGAAAGGC
TTCTGGGACCTTGCATGGAAATTATGAAAAGGAACATCGCTACCTATGAAGAACAGTTAGTTGCCCTGTTTGGAACGAAC
ATGGATATTGTAGCCAAAAACATTAAGAAGGGCCCAGCGCCATTCTACCCACTCGAAGACGGGACCGCCGGCGAGCAGCT
GCACAAAGCCATGAAGCGCTACGCCCTGGTGCCCGGCACCATCGCCTTTACCGACGCACATATCGAGGTGGACATTACCT
ACGCCGAGTACTTCGAGATGAGCGTTCGGCTGGCAGAAGCTATGAAGCGCTATGGGCTGAATACAAACCATCGGATCGTG
GTGTGCAGCGAGAATAGCTTGCAGTTCTTCATGCCCGTGTTGGGTGCCCTGTTCATCGGTGTGGCTGTGGCCCCAGCTAA
CGACATCTACAACGAGCGCGAGCTGCTGAACAGCATGGGCATCAGCCAGCCCACCGTCGTATTCGTGAGCAAGAAAGGGC
TGCAAAAGATCCTCAACGTGCAAAAGAAGCTACCGATCATACAAAAGATCATCATCATGGATAGCAAGACCGACTACCAG
GGCTTCCAAAGCATGTACACCTTCGTGACTTCCCATTTGCCACCCGGCTTCAACGAGTACGACTTCGTGCCCGAGAGCTT
CGACCGGGACAAAACCATCGCCCTGATCATGAACAGTAGTGGCAGTACCGGATTGCCCAAGGGCGTAGCCCTACCGCACC
GCACCGCTTGTGTCCGATTCAGTCATGCCCGCGTTTAAAC

CCCC) pBFB264 Sgf to Pme (SEQ ID NO:388)
GCGATCGCCATGCATCGGATCGTGGTGTGCAGCGAGAATAGCTTGCAGTTCTTCATGCCCGTGTTGGGTGCCCTGTTCAT
CGGTGTGGCTGTGGCCCCAGCTAACGACATCTACAACGAGCGCGAGCTGCTGAACAGCATGGGCATCAGCCAGCCCACCG
TCGTATTCGTGAGCAAGAAAGGGCTGCAAAAGATCCTCAACGTGCAAAAGAAGCTACCGATCATACAAAAGATCATCATC
ATGGATAGCAAGACCGACTACCAGGGCTTCCAAAGCATGTACACCTTCGTGACTTCCCATTTGCCACCCGGCTTCAACGA
GTACGACTTCGTGCCCGAGAGCTTCGACCGGGACAAAACCATCGCCCTGATCATGAACAGTAGTGGCAGTACCGGATTGC
CCAAGGGCGTAGCCCTACCGCACCGCACCGCTTGTGTCCGATTCAGTCATGCCCGCGACCCCATCTTCGGCAACCAGATC
ATCCCCGACACCGCTATCCTCAGCGTGGTGCCATTTCACCACGGCTTCGGCATGTTCACCACGCTGGGCTACTTGATCTG
CGGCTTTCGGGTCGTGCTCATGTACCGCTTCGAGGAGGAGCTATTCTTGCGCAGCTTGCAAGACTATAAGATTCAATCTG
CCCTGCTGGTGCCCACACTATTTAGCTTCTTCGCTAAGAGCACTCTCATCGACAAGTACGACCTAAGCAACTTGCACGAG
ATCGCCAGCGGCGGGGCGCCGCTCAGCAAGGAGGTAGGTGAGGCCGTGGCCAAACGCTTCCACCTACCAGGCATCCGCCA
GGGCTACGGCCTGACAGAAACAACCAGCGCCATTCTGATCACCCCCGAAGGGGACGACAAGCCTGGCGCAGTAGGCAAGG
TGGTGCCCTTCTTCGAGGCTAAGGTGGTGGACTTGGACACCGGTAAGACACTGGGTGTGAACCAGCGCGGCGAGCTGTGC
GTCCGTGGCCCCATGATCATGAGCGGCTACGTTAACAACCCCGAGGCTACAAACGCTCTCATCGACAAGGACGGCTGGCT
GCACAGCGGCGACATCGCCTACTGGGACGAGGACGAGCACTTCTTCATCGTGGACCGGCTGAAGAGCCTGATCAAATACA
AGGGCTACCAGGTAGCCCCAGCCGAACTGGAGAGCATCCTGCTGCAACACCCCAACATCTTCGACGCCGGGGTCGCCGGC
CTGCCCGACGACGATGCCGGCGAGCTGCCCGCCGCAGTCGTCGTGCTGGAACACGGTAAAACCATGACCGAGAAGGAGAT
CGTGGACTATGTGGCCAGCCAGGTTACAACCGCCAAGAAGCTGCGCGGTGGTGTTGTGTTCGTGGACGAGGTGCCTAAAG
GACTGACCGGCAAGTTGGACGCCCGCAAGATCCGCGAGATTCTCATTAAGGCCAAGAAGGGCTCGAGCGGAGGTTCAGGC
GGTTCCGGAGGAGGTATGTATGAAAGCTTTATTGAGTCACTGCCATTCCTTAAATCTTTGGAGTTTTCTGAACGCCTGAA
AGTAGTAGATGTGATAGGCACCAAAGTATACAACGATGGAGAACAAATCATTGCTCAGGGAGATTCGGCTGATTCTTTTT
TCATTGTAGAATCTGGAGAAGTGAAAATTACTATGAAAAGAAAGGGTAAATCAGAAGTGGAAGAGAATGGTGCAGTAGAA
ATCGCTCGATGCTCGCGGGGACAGTACTTTGGAGAGCTTGCCCTGGTAACTAACAAACCTCGAGCAGCTTCTGCCCACGC
CATTGGGACTGTCAAATGTTTAGCAATGGATGTGCAAGCATTTGAAAGGCTTCTGGGACCTTGCATGGAAATTATGAAAA

FIG. 67AK

GGAACATCGCTACCTATGAAGAACAGTTAGTTGCCCTGTTTGGAACGAACATGGATATTGTAGCCAAAAACATTAAGAAG
GGCCCAGCGCCATTCTACCCACTCGAAGACGGGACCGCCGGCGAGCAGCTGCACAAAGCCATGAAGCGCTACGCCCTGGT
GCCCGGCACCATCGCCTTTACCGACGCACATATCGAGGTGGACATTACCTACGCCGAGTACTTCGAGATGAGCGTTCGGC
TGGCAGAAGCTATGAAGCGCTATGGGCTGAATGTTTAAAC

DDDD) pBFB265 Sgf to Pme (SEQ ID NO:389)
GCGATCGCCATGAATAGCTTGCAGTTCTTCATGCCCGTGTTGGGTGCCCTGTTCATCGGTGTGGCTGTGGCCCCAGCTAA
CGACATCTACAACGAGCGCGAGCTGCTGAACAGCATGGGCATCAGCCAGCCCACCGTCGTATTCGTGAGCAAGAAAGGGC
TGCAAAAGATCCTCAACGTGCAAAAGAAGCTACCGATCATACAAAAGATCATCATCATGGATAGCAAGACCGACTACCAG
GGCTTCCAAAGCATGTACACCTTCGTGACTTCCCATTTGCCACCCGGCTTCAACGAGTACGACTTCGTGCCCGAGAGCTT
CGACCGGGACAAAACCATCGCCCTGATCATGAACAGTAGTGGCAGTACCGGATTGCCCAAGGGCGTAGCCCTACCGCACC
GCACCGCTTGTGTCCGATTCAGTCATGCCCGCGACCCCATCTTCGGCAACCAGATCATCCCCGACACCGCTATCCTCAGC
GTGGTGCCATTTCACCACGGCTTCGGCATGTTCACCACGCTGGGCTACTTGATCTGCGGCTTTCGGGTCGTGCTCATGTA
CCGCTTCGAGGAGGAGCTATTCTTGCGCAGCTTGCAAGACTATAAGATTCAATCTGCCCTGCTGGTGCCCACACTATTTA
GCTTCTTCGCTAAGAGCACTCTCATCGACAAGTACGACCTAAGCAACTTGCACGAGATCGCCAGCGGCGGGGCGCCGCTC
AGCAAGGAGGTAGGTGAGGCCGTGGCCAAACGCTTCCACCTACCAGGCATCCGCCAGGGCTACGGCCTGACAGAAACAAC
CAGCGCCATTCTGATCACCCCCGAAGGGGACGACAAGCCTGGCGCAGTAGGCAAGGTGGTGCCCTTCTTCGAGGCTAAGG
TGGTGGACTTGGACACCGGTAAGACACTGGGTGTGAACCAGCGCGGCGAGCTGTGCGTCCGTGGCCCCATGATCATGAGC
GGCTACGTTAACAACCCCGAGGCTACAAACGCTCTCATCGACAAGGACGGCTGGCTGCACAGCGGCGACATCGCCTACTG
GGACGAGGACGAGCACTTCTTCATCGTGGACCGGCTGAAGAGCCTGATCAAATACAAGGGCTACCAGGTAGCCCCAGCCG
AACTGGAGAGCATCCTGCTGCAACACCCCAACATCTTCGACGCCGGGGTCGCCGGCCTGCCCGACGACGATGCCGGCGAG
CTGCCCGCCGCAGTCGTCGTGCTGGAACACGGTAAAACCATGACCGAGAAGGAGATCGTGGACTATGTGGCCAGCCAGGT
TACAACCGCCAAGAAGCTGCGCGGTGGTGTTGTGTTCGTGGACGAGGTGCCTAAAGGACTGACCGGCAAGTTGGACGCCC
GCAAGATCCGCGAGATTCTCATTAAGGCCAAGAAGGGCTCGAGCGGAGGTTCAGGCGGTTCCGGAGGAGGTATGTATGAA
AGCTTTATTGAGTCACTGCCATTCCTTAAATCTTTGGAGTTTTCTGAACGCCTGAAAGTAGTAGATGTGATAGGCACCAA
AGTATACAACGATGGAGAACAAATCATTGCTCAGGGAGATTCGGCTGATTCTTTTTTCATTGTAGAATCTGGAGAAGTGA
AAATTACTATGAAAAGAAAGGGTAAATCAGAAGTGGAAGAGAATGGTGCAGTAGAAATCGCTCGATGCTCGCGGGGACAG
TACTTTGGAGAGCTTGCCCTGGTAACTAACAAACCTCGAGCAGCTTCTGCCCACGCCATTGGGACTGTCAAATGTTTAGC
AATGGATGTGCAAGCATTTGAAAGGCTTCTGGGACCTTGCATGGAAATTATGAAAAGGAACATCGCTACCTATGAAGAAC
AGTTAGTTGCCCTGTTTGGAACGAACATGGATATTGTAGCCAAAAACATTAAGAAGGGCCCAGCGCCATTCTACCCACTC
GAAGACGGGACCGCCGGCGAGCAGCTGCACAAAGCCATGAAGCGCTACGCCCTGGTGCCCGGCACCATCGCCTTTACCGA
CGCACATATCGAGGTGGACATTACCTACGCCGAGTACTTCGAGATGAGCGTTCGGCTGGCAGAAGCTATGAAGCGCTATG
GGCTGAATACAAACCATCGGATCGTGGTGTGCGTTTAAAC

EEEE) pBFB266 Sgf to Pme (SEQ ID NO:390)
GCGATCGCCATGATCTACAACGAGCGCGAGCTGCTGAACAGCATGGGCATCAGCCAGCCCACCGTCGTATTCGTGAGCAA
GAAAGGGCTGCAAAAGATCCTCAACGTGCAAAAGAAGCTACCGATCATACAAAAGATCATCATCATGGATAGCAAGACCG
ACTACCAGGGCTTCCAAAGCATGTACACCTTCGTGACTTCCCATTTGCCACCCGGCTTCAACGAGTACGACTTCGTGCCC
GAGAGCTTCGACCGGGACAAAACCATCGCCCTGATCATGAACAGTAGTGGCAGTACCGGATTGCCCAAGGGCGTAGCCCT
ACCGCACCGCACCGCTTGTGTCCGATTCAGTCATGCCCGCGACCCCATCTTCGGCAACCAGATCATCCCCGACACCGCTA
TCCTCAGCGTGGTGCCATTTCACCACGGCTTCGGCATGTTCACCACGCTGGGCTACTTGATCTGCGGCTTTCGGGTCGTG
CTCATGTACCGCTTCGAGGAGGAGCTATTCTTGCGCAGCTTGCAAGACTATAAGATTCAATCTGCCCTGCTGGTGCCCAC
ACTATTTAGCTTCTTCGCTAAGAGCACTCTCATCGACAAGTACGACCTAAGCAACTTGCACGAGATCGCCAGCGGCGGGG
CGCCGCTCAGCAAGGAGGTAGGTGAGGCCGTGGCCAAACGCTTCCACCTACCAGGCATCCGCCAGGGCTACGGCCTGACA
GAAACAACCAGCGCCATTCTGATCACCCCCGAAGGGGACGACAAGCCTGGCGCAGTAGGCAAGGTGGTGCCCTTCTTCGA
GGCTAAGGTGGTGGACTTGGACACCGGTAAGACACTGGGTGTGAACCAGCGCGGCGAGCTGTGCGTCCGTGGCCCCATGA
TCATGAGCGGCTACGTTAACAACCCCGAGGCTACAAACGCTCTCATCGACAAGGACGGCTGGCTGCACAGCGGCGACATC
GCCTACTGGGACGAGGACGAGCACTTCTTCATCGTGGACCGGCTGAAGAGCCTGATCAAATACAAGGGCTACCAGGTAGC
CCCAGCCGAACTGGAGAGCATCCTGCTGCAACACCCCAACATCTTCGACGCCGGGGTCGCCGGCCTGCCCGACGACGATG
CCGGCGAGCTGCCCGCCGCAGTCGTCGTGCTGGAACACGGTAAAACCATGACCGAGAAGGAGATCGTGGACTATGTGGCC
AGCCAGGTTACAACCGCCAAGAAGCTGCGCGGTGGTGTTGTGTTCGTGGACGAGGTGCCTAAAGGACTGACCGGCAAGTT
GGACGCCCGCAAGATCCGCGAGATTCTCATTAAGGCCAAGAAGGGCTCGAGCGGAGGTTCAGGCGGTTCCGGAGGAGGTA
TGTATGAAAGCTTTATTGAGTCACTGCCATTCCTTAAATCTTTGGAGTTTTCTGAACGCCTGAAAGTAGTAGATGTGATA

FIG. 67AL

GGCACCAAAGTATACAACGATGGAGAACAAATCATTGCTCAGGGAGATTCGGCTGATTCTTTTTTCATTGTAGAATCTGG
AGAAGTGAAAATTACTATGAAAAGAAAGGGTAAATCAGAAGTGGAAGAGAATGGTGCAGTAGAAATCGCTCGATGCTCGC
GGGGACAGTACTTTGGAGAGCTTGCCCTGGTAACTAACAAACCTCGAGCAGCTTCTGCCCACGCCATTGGGACTGTCAAA
TGTTTAGCAATGGATGTGCAAGCATTTGAAAGGCTTCTGGGACCTTGCATGGAAATTATGAAAAGGAACATCGCTACCTA
TGAAGAACAGTTAGTTGCCCTGTTTGGAACGAACATGGATATTGTAGCCAAAAACATTAAGAAGGGCCCAGCGCCATTCT
ACCCACTCGAAGACGGGACCGCCGGCGAGCAGCTGCACAAAGCCATGAAGCGCTACGCCCTGGTGCCCGGCACCATCGCC
TTTACCGACGCACATATCGAGGTGGACATTACCTACGCCGAGTACTTCGAGATGAGCGTTCGGCTGGCAGAAGCTATGAA
GCGCTATGGGCTGAATACAAACCATCGGATCGTGGTGTGCAGCGAGAATAGCTTGCAGTTCTTCATGCCCGTGTTGGGTG
CCCTGTTCATCGGTGTGGCTGTGGCCCCAGCTGTTTAAAC

FFFF) pBFB267 Sgf to Pme (SEQ ID NO:391)
GCGATCGCCATGATCATACAAAAGATCATCATCATGGATAGCAAGACCGACTACCAGGGCTTCCAAAGCATGTACACCTT
CGTGACTTCCCATTTGCCACCCGGCTTCAACGAGTACGACTTCGTGCCCGAGAGCTTCGACCGGGACAAAACCATCGCCC
TGATCATGAACAGTAGTGGCAGTACCGGATTGCCCAAGGGCGTAGCCCTACCGCACCGCACCGCTTGTGTCCGATTCAGT
CATGCCCGCGACCCCATCTTCGGCAACCAGATCATCCCCGACACCGCTATCCTCAGCGTGGTGCCATTTCACCACGGCTT
CGGCATGTTCACCACGCTGGGCTACTTGATCTGCGGCTTTCGGGTCGTGCTCATGTACCGCTTCGAGGAGGAGCTATTCT
TGCGCAGCTTGCAAGACTATAAGATTCAATCTGCCCTGCTGGTGCCCACACTATTTAGCTTCTTCGCTAAGAGCACTCTC
ATCGACAAGTACGACCTAAGCAACTTGCACGAGATCGCCAGCGGCGGGGCGCCGCTCAGCAAGGAGGTAGGTGAGGCCGT
GGCCAAACGCTTCCACCTACCAGGCATCCGCCAGGGCTACGGCCTGACAGAAACAACCAGCGCCATTCTGATCACCCCCG
AAGGGGACGACAAGCCTGGCGCAGTAGGCAAGGTGGTGCCCTTCTTCGAGGCTAAGGTGGTGGACTTGGACACCGGTAAG
ACACTGGGTGTGAACCAGCGCGGCGAGCTGTGCGTCCGTGGCCCCATGATCATGAGCGGCTACGTTAACAACCCCGAGGC
TACAAACGCTCTCATCGACAAGGACGGCTGGCTGCACAGCGGCGACATCGCCTACTGGGACGAGGACGAGCACTTCTTCA
TCGTGGACCGGCTGAAGAGCCTGATCAAATACAAGGGCTACCAGGTAGCCCCAGCCGAACTGGAGAGCATCCTGCTGCAA
CACCCCAACATCTTCGACGCCGGGGTCGCCGGCCTGCCCGACGACGATGCCGGCGAGCTGCCCGCCGCAGTCGTCGTGCT
GGAACACGGTAAAACCATGACCGAGAAGGAGATCGTGGACTATGTGGCCAGCCAGGTTACAACCGCCAAGAAGCTGCGCG
GTGGTGTTGTGTTCGTGGACGAGGTGCCTAAAGGACTGACCGGCAAGTTGGACGCCCGCAAGATCCGCGAGATTCTCATT
AAGGCCAAGAAGGGCTCGAGCGGAGGTTCAGGCGGTTCCGGAGGAGGTATGTATGAAAGCTTTATTGAGTCACTGCCATT
CCTTAAATCTTTGGAGTTTTCTGAACGCCTGAAAGTAGTAGATGTGATAGGCACCAAAGTATACAACGATGGAGAACAAA
TCATTGCTCAGGGAGATTCGGCTGATTCTTTTTTCATTGTAGAATCTGGAGAAGTGAAAATTACTATGAAAAGAAAGGGT
AAATCAGAAGTGGAAGAGAATGGTGCAGTAGAAATCGCTCGATGCTCGCGGGGACAGTACTTTGGAGAGCTTGCCCTGGT
AACTAACAAACCTCGAGCAGCTTCTGCCCACGCCATTGGGACTGTCAAATGTTTAGCAATGGATGTGCAAGCATTTGAAA
GGCTTCTGGGACCTTGCATGGAAATTATGAAAAGGAACATCGCTACCTATGAAGAACAGTTAGTTGCCCTGTTTGGAACG
AACATGGATATTGTAGCCAAAAACATTAAGAAGGGCCCAGCGCCATTCTACCCACTCGAAGACGGGACCGCCGGCGAGCA
GCTGCACAAAGCCATGAAGCGCTACGCCCTGGTGCCCGGCACCATCGCCTTTACCGACGCACATATCGAGGTGGACATTA
CCTACGCCGAGTACTTCGAGATGAGCGTTCGGCTGGCAGAAGCTATGAAGCGCTATGGGCTGAATACAAACCATCGGATC
GTGGTGTGCAGCGAGAATAGCTTGCAGTTCTTCATGCCCGTGTTGGGTGCCCTGTTCATCGGTGTGGCTGTGGCCCCAGC
TAACGACATCTACAACGAGCGCGAGCTGCTGAACAGCATGGGCATCAGCCAGCCCACCGTCGTATTCGTGAGCAAGAAAG
GGCTGCAAAAGATCCTCAACGTGCAAAAGAAGGTTTAAAC

GGGG) pBFB268 Sgf to Pme (SEQ ID NO:392)
GCGATCGCCATGTTCCAAAGCATGTACACCTTCGTGACTTCCCATTTGCCACCCGGCTTCAACGAGTACGACTTCGTGCC
CGAGAGCTTCGACCGGGACAAAACCATCGCCCTGATCATGAACAGTAGTGGCAGTACCGGATTGCCCAAGGGCGTAGCCC
TACCGCACCGCACCGCTTGTGTCCGATTCAGTCATGCCCGCGACCCCATCTTCGGCAACCAGATCATCCCCGACACCGCT
ATCCTCAGCGTGGTGCCATTTCACCACGGCTTCGGCATGTTCACCACGCTGGGCTACTTGATCTGCGGCTTTCGGGTCGT
GCTCATGTACCGCTTCGAGGAGGAGCTATTCTTGCGCAGCTTGCAAGACTATAAGATTCAATCTGCCCTGCTGGTGCCCA
CACTATTTAGCTTCTTCGCTAAGAGCACTCTCATCGACAAGTACGACCTAAGCAACTTGCACGAGATCGCCAGCGGCGGG
GCGCCGCTCAGCAAGGAGGTAGGTGAGGCCGTGGCCAAACGCTTCCACCTACCAGGCATCCGCCAGGGCTACGGCCTGAC
AGAAACAACCAGCGCCATTCTGATCACCCCCGAAGGGGACGACAAGCCTGGCGCAGTAGGCAAGGTGGTGCCCTTCTTCG
AGGCTAAGGTGGTGGACTTGGACACCGGTAAGACACTGGGTGTGAACCAGCGCGGCGAGCTGTGCGTCCGTGGCCCCATG
ATCATGAGCGGCTACGTTAACAACCCCGAGGCTACAAACGCTCTCATCGACAAGGACGGCTGGCTGCACAGCGGCGACAT
CGCCTACTGGGACGAGGACGAGCACTTCTTCATCGTGGACCGGCTGAAGAGCCTGATCAAATACAAGGGCTACCAGGTAG
CCCCAGCCGAACTGGAGAGCATCCTGCTGCAACACCCCAACATCTTCGACGCCGGGGTCGCCGGCCTGCCCGACGACGAT
GCCGGCGAGCTGCCCGCCGCAGTCGTCGTGCTGGAACACGGTAAAACCATGACCGAGAAGGAGATCGTGGACTATGTGGC
CAGCCAGGTTACAACCGCCAAGAAGCTGCGCGGTGGTGTTGTGTTCGTGGACGAGGTGCCTAAAGGACTGACCGGCAAGT
TGGACGCCCGCAAGATCCGCGAGATTCTCATTAAGGCCAAGAAGGGCTCGAGCGGAGGTTCAGGCGGTTCCGGAGGAGGT
ATGTATGAAAGCTTTATTGAGTCACTGCCATTCCTTAAATCTTTGGAGTTTTCTGAACGCCTGAAAGTAGTAGATGTGAT
AGGCACCAAAGTATACAACGATGGAGAACAAATCATTGCTCAGGGAGATTCGGCTGATTCTTTTTTCATTGTAGAATCTG

FIG. 67AM

GAGAAGTGAAAATTACTATGAAAAGAAAGGGTAAATCAGAAGTGGAAGAGAATGGTGCAGTAGAAATCGCTCGATGCTCG
CGGGGACAGTACTTTGGAGAGCTTGCCCTGGTAACTAACAAACCTCGAGCAGCTTCTGCCCACGCCATTGGGACTGTCAA
ATGTTTAGCAATGGATGTGCAAGCATTTGAAAGGCTTCTGGGACCTTGCATGGAAATTATGAAAAGGAACATCGCTACCT
ATGAAGAACAGTTAGTTGCCCTGTTTGGAACGAACATGGATATTGTAGCCAAAAACATTAAGAAGGGCCCAGCGCCATTC
TACCCACTCGAAGACGGGACCGCCGGCGAGCAGCTGCACAAAGCCATGAAGCGCTACGCCCTGGTGCCCGGCACCATCGC
CTTTACCGACGCACATATCGAGGTGGACATTACCTACGCCGAGTACTTCGAGATGAGCGTTCGGCTGGCAGAAGCTATGA
AGCGCTATGGGCTGAATACAAACCATCGGATCGTGGTGTGCAGCGAGAATAGCTTGCAGTTCTTCATGCCCGTGTTGGGT
GCCCTGTTCATCGGTGTGGCTGTGGCCCCAGCTAACGACATCTACAACGAGCGCGAGCTGCTGAACAGCATGGGCATCAG
CCAGCCCACCGTCGTATTCGTGAGCAAGAAAGGGCTGCAAAAGATCCTCAACGTGCAAAAGAAGCTACCGATCATACAAA
AGATCATCATCATGGATAGCAAGACCGACTACGTTTAAAC

HHHH) pBFB269 Sgf to Pme (SEQ ID NO:393)
GCGATCGCCATGGGCTTCAACGAGTACGACTTCGTGCCCGAGAGCTTCGACCGGGACAAAACCATCGCCCTGATCATGAA
CAGTAGTGGCAGTACCGGATTGCCCAAGGGCGTAGCCCTACCGCACCGCACCGCTTGTGTCCGATTCAGTCATGCCCGCG
ACCCCATCTTCGGCAACCAGATCATCCCCGACACCGCTATCCTCAGCGTGGTGCCATTTCACCACGGCTTCGGCATGTTC
ACCACGCTGGGCTACTTGATCTGCGGCTTTCGGGTCGTGCTCATGTACCGCTTCGAGGAGGAGCTATTCTTGCGCAGCTT
GCAAGACTATAAGATTCAATCTGCCCTGCTGGTGCCCACACTATTTAGCTTCTTCGCTAAGAGCACTCTCATCGACAAGT
ACGACCTAAGCAACTTGCACGAGATCGCCAGCGGCGGGGCGCCGCTCAGCAAGGAGGTAGGTGAGGCCGTGGCCAAACGC
TTCCACCTACCAGGCATCCGCCAGGGCTACGGCCTGACAGAAACAACCAGCGCCATTCTGATCACCCCCGAAGGGGACGA
CAAGCCTGGCGCAGTAGGCAAGGTGGTGCCCTTCTTCGAGGCTAAGGTGGTGGACTTGGACACCGGTAAGACACTGGGTG
TGAACCAGCGCGGCGAGCTGTGCGTCCGTGGCCCCATGATCATGAGCGGCTACGTTAACAACCCCGAGGCTACAAACGCT
CTCATCGACAAGGACGGCTGGCTGCACAGCGGCGACATCGCCTACTGGGACGAGGACGAGCACTTCTTCATCGTGGACCG
GCTGAAGAGCCTGATCAAATACAAGGGCTACCAGGTAGCCCCAGCCGAACTGGAGAGCATCCTGCTGCAACACCCCAACA
TCTTCGACGCCGGGGTCGCCGGCCTGCCCGACGACGATGCCGGCGAGCTGCCCGCCGCAGTCGTCGTGCTGGAACACGGT
AAAACCATGACCGAGAAGGAGATCGTGGACTATGTGGCCAGCCAGGTTACAACCGCCAAGAAGCTGCGCGGTGGTGTTGT
GTTCGTGGACGAGGTGCCTAAAGGACTGACCGGCAAGTTGGACGCCCGCAAGATCCGCGAGATTCTCATTAAGGCCAAGA
AGGGCTCGAGCGGAGGTTCAGGCGGTTCCGGAGGAGGTATGTATGAAAGCTTTATTGAGTCACTGCCATTCCTTAAATCT
TTGGAGTTTTCTGAACGCCTGAAAGTAGTAGATGTGATAGGCACCAAAGTATACAACGATGGAGAACAAATCATTGCTCA
GGGAGATTCGGCTGATTCTTTTTTCATTGTAGAATCTGGAGAAGTGAAAATTACTATGAAAAGAAAGGGTAAATCAGAAG
TGGAAGAGAATGGTGCAGTAGAAATCGCTCGATGCTCGCGGGGACAGTACTTTGGAGAGCTTGCCCTGGTAACTAACAAA
CCTCGAGCAGCTTCTGCCCACGCCATTGGGACTGTCAAATGTTTAGCAATGGATGTGCAAGCATTTGAAAGGCTTCTGGG
ACCTTGCATGGAAATTATGAAAAGGAACATCGCTACCTATGAAGAACAGTTAGTTGCCCTGTTTGGAACGAACATGGATA
TTGTAGCCAAAAACATTAAGAAGGGCCCAGCGCCATTCTACCCACTCGAAGACGGGACCGCCGGCGAGCAGCTGCACAAA
GCCATGAAGCGCTACGCCCTGGTGCCCGGCACCATCGCCTTTACCGACGCACATATCGAGGTGGACATTACCTACGCCGA
GTACTTCGAGATGAGCGTTCGGCTGGCAGAAGCTATGAAGCGCTATGGGCTGAATACAAACCATCGGATCGTGGTGTGCA
GCGAGAATAGCTTGCAGTTCTTCATGCCCGTGTTGGGTGCCCTGTTCATCGGTGTGGCTGTGGCCCCAGCTAACGACATC
TACAACGAGCGCGAGCTGCTGAACAGCATGGGCATCAGCCAGCCCACCGTCGTATTCGTGAGCAAGAAAGGGCTGCAAAA
GATCCTCAACGTGCAAAAGAAGCTACCGATCATACAAAAGATCATCATCATGGATAGCAAGACCGACTACCAGGGCTTCC
AAAGCATGTACACCTTCGTGACTTCCCATTTGGTTTAAAC

IIII) pBFB276 Sgf to Pme (SEQ ID NO:394)
GCGATCGCCATGTCCTTCATCAACTACTATGATTCCGAGAAGCACGCCGAGAACGCCGTGATTTTTCTGCATGGTAACGC
TGCCTCCAGCTACCTGTGGAGGCACGTCGTGCCTCACATCGAGCCCGTGGCTAGATGCATCATCCCTGATCTGATCGGAA
TGGGTAAGTCCGGCAAGAGCGGGAATGGCTCATATCGCCTCCTGGATCACTACAAGTACCTCACCGCTTGGTTCGAGCTG
CTGAACCTTCCAAAGAAAATCATCTTTGTGGGCCACGACTGGGGGGCTTGTCTGGCCTTTCACTACTCCTACGAGCACCA
AGACAAGATCAAGGCCATCGTCCATGCTGAGAGTGTCGTGGACGTGATCGAGTCCTGGGACGAGTGGCCTGACATCGAGG
AGGATATCGCCCTGATCAAGAGCGAAGAGGGCGAGAAAATGGTGCTTGAGAATAACTTCTTCGTCGAGACCATGCTCCCA
AGCAAGATCATGCGGAAACTGGAGCCTGAGGAGTTCGCTGCCTACCTGGAGCCATTCAAGGAGAAGGGCGAGGTTAGACG
GCCTACCCTCTCCTGGCCTCGCGAGATCCCTCTCGTTAAGGGAGGCAAGCCCGACGTCGTCCAGATTGTCCGCAACTACA
ACGCCTACCTTCGGGCCAGCGACGATCTGCCTAAGATGTTCATCGAGTCCGACCCTGGGTTCTTTTCCAACGCTATTGTC
GAGGGAGCTAAGAAGTTCCCTAACACCGAGTTCGTGAAGGTGAAGGGCCTCCACTTCAGCCAGGAGGACGCTCCAGATGA
AATGGGTAAGTACATCAAGAGCTTCGTGGAGCGCGTGCTGAAGAACGAGCAGGGCTCGACCGGAATGTATGAAAGCTTTA
TTGAGTCACTGCCATTCCTTAAATCTTTGGAGTTTTCTGAACGCCTGAAAGTAGTAGATGTGATAGGCACCAAAGTATAC
AACGATGGAGAACAAATCATTGCTCAGGGAGATTCGGCTGATTCTTTTTTCATTGTAGAATCTGGAGAAGTGAAAATTAC
TATGAAAAGAAAGGGTAAATCAGAAGTGGAAGAGAATGGTGCAGTAGAAATCGCTCGATGCTCGCGGGGACAGTACTTTG
GAGAGCTTGCCCTGGTAACTAACAAACCTCGAGCAGCTTCTGCCCACGCCATTGGGACTGTCAAATGTTTAGCAATGGAT
GTGCAAGCATTTGAAAGGCTTCTGGGACCTTGCATGGAAATTATGAAAAGGAACATCGCTACCTATGAAGAACAGTTAGT

FIG. 67AN

TGCCCTGTTTGGAACGAACATGGATATTGTTGGGTCCGGTGGATCCGGTGGCAGCGGAGGGACGTCAGGTGGATCTGGAG
GGAGCTCAGGAGCTTCCAAGGTGTACGACCCCGAGCAACGCAAACGCATGATCACTGGGCCTCAGTGGTGGGCTCGCTGC
AAGCAAATGAACGTGCTGTGAGTTTAAAC

JJJJ) pBFB277 Sgf to Pme (SEQ ID NO:395)
GCGATCGCCATGGCCGAGAACGCCGTGATTTTTCTGCATGGTAACGCTGCCTCCAGCTACCTGTGGAGGCACGTCGTGCC
TCACATCGAGCCCGTGGCTAGATGCATCATCCCTGATCTGATCGGAATGGGTAAGTCCGGCAAGAGCGGGAATGGCTCAT
ATCGCCTCCTGGATCACTACAAGTACCTCACCGCTTGGTTCGAGCTGCTGAACCTTCCAAAGAAAATCATCTTTGTGGGC
CACGACTGGGGGGCTTGTCTGGCCTTTCACTACTCCTACGAGCACCAAGACAAGATCAAGGCCATCGTCCATGCTGAGAG
TGTCGTGGACGTGATCGAGTCCTGGGACGAGTGGCCTGACATCGAGGAGGATATCGCCCTGATCAAGAGCGAAGAGGGCG
AGAAAATGGTGCTTGAGAATAACTTCTTCGTCGAGACCATGCTCCCAAGCAAGATCATGCGGAAACTGGAGCCTGAGGAG
TTCGCTGCCTACCTGGAGCCATTCAAGGAGAAGGGCGAGGTTAGACGGCCTACCCTCTCCTGGCCTCGCGAGATCCCTCT
CGTTAAGGGAGGCAAGCCCGACGTCGTCCAGATTGTCCGCAACTACAACGCCTACCTTCGGGCCAGCGACGATCTGCCTA
AGATGTTCATCGAGTCCGACCCTGGGTTCTTTTCCAACGCTATTGTCGAGGGAGCTAAGAAGTTCCCTAACACCGAGTTC
GTGAAGGTGAAGGGCCTCCACTTCAGCCAGGAGGACGCTCCAGATGAAATGGGTAAGTACATCAAGAGCTTCGTGGAGCG
CGTGCTGAAGAACGAGCAGGGCTCGACCGGAATGTATGAAAGCTTTATTGAGTCACTGCCATTCCTTAAATCTTTGGAGT
TTTCTGAACGCCTGAAAGTAGTAGATGTGATAGGCACCAAAGTATACAACGATGGAGAACAAATCATTGCTCAGGGAGAT
TCGGCTGATTCTTTTTTCATTGTAGAATCTGGAGAAGTGAAAATTACTATGAAAAGAAAGGGTAAATCAGAAGTGGAAGA
GAATGGTGCAGTAGAAATCGCTCGATGCTCGCGGGGACAGTACTTTGGAGAGCTTGCCCTGGTAACTAACAAACCTCGAG
CAGCTTCTGCCCACGCCATTGGGACTGTCAAATGTTTAGCAATGGATGTGCAAGCATTTGAAAGGCTTCTGGGACCTTGC
ATGGAAATTATGAAAAGGAACATCGCTACCTATGAAGAACAGTTAGTTGCCCTGTTTGGAACGAACATGGATATTGTTGG
GTCCGGTGGATCCGGTGGCAGCGGAGGGACGTCAGGTGGATCTGGAGGGAGCTCAGGAGCTTCCAAGGTGTACGACCCCG
AGCAACGCAAACGCATGATCACTGGGCCTCAGTGGTGGGCTCGCTGCAAGCAAATGAACGTGCTGGACTCCTTCATCAAC
TACTATGATTCCGAGAAGTGAGTTTAAAC

KKKK) pBFB278 Sgf to Pme (SEQ ID NO:396)
GCGATCGCCATGGTGGCTAGATGCATCATCCCTGATCTGATCGGAATGGGTAAGTCCGGCAAGAGCGGGAATGGCTCATA
TCGCCTCCTGGATCACTACAAGTACCTCACCGCTTGGTTCGAGCTGCTGAACCTTCCAAAGAAAATCATCTTTGTGGGCC
ACGACTGGGGGGCTTGTCTGGCCTTTCACTACTCCTACGAGCACCAAGACAAGATCAAGGCCATCGTCCATGCTGAGAGT
GTCGTGGACGTGATCGAGTCCTGGGACGAGTGGCCTGACATCGAGGAGGATATCGCCCTGATCAAGAGCGAAGAGGGCGA
GAAAATGGTGCTTGAGAATAACTTCTTCGTCGAGACCATGCTCCCAAGCAAGATCATGCGGAAACTGGAGCCTGAGGAGT
TCGCTGCCTACCTGGAGCCATTCAAGGAGAAGGGCGAGGTTAGACGGCCTACCCTCTCCTGGCCTCGCGAGATCCCTCTC
GTTAAGGGAGGCAAGCCCGACGTCGTCCAGATTGTCCGCAACTACAACGCCTACCTTCGGGCCAGCGACGATCTGCCTAA
GATGTTCATCGAGTCCGACCCTGGGTTCTTTTCCAACGCTATTGTCGAGGGAGCTAAGAAGTTCCCTAACACCGAGTTCG
TGAAGGTGAAGGGCCTCCACTTCAGCCAGGAGGACGCTCCAGATGAAATGGGTAAGTACATCAAGAGCTTCGTGGAGCGC
GTGCTGAAGAACGAGCAGGGCTCGACCGGAATGTATGAAAGCTTTATTGAGTCACTGCCATTCCTTAAATCTTTGGAGTT
TTCTGAACGCCTGAAAGTAGTAGATGTGATAGGCACCAAAGTATACAACGATGGAGAACAAATCATTGCTCAGGGAGATT
CGGCTGATTCTTTTTTCATTGTAGAATCTGGAGAAGTGAAAATTACTATGAAAAGAAAGGGTAAATCAGAAGTGGAAGAG
AATGGTGCAGTAGAAATCGCTCGATGCTCGCGGGGACAGTACTTTGGAGAGCTTGCCCTGGTAACTAACAAACCTCGAGC
AGCTTCTGCCCACGCCATTGGGACTGTCAAATGTTTAGCAATGGATGTGCAAGCATTTGAAAGGCTTCTGGGACCTTGCA
TGGAAATTATGAAAAGGAACATCGCTACCTATGAAGAACAGTTAGTTGCCCTGTTTGGAACGAACATGGATATTGTTGGG
TCCGGTGGATCCGGTGGCAGCGGAGGGACGTCAGGTGGATCTGGAGGGAGCTCAGGAGCTTCCAAGGTGTACGACCCCGA
GCAACGCAAACGCATGATCACTGGGCCTCAGTGGTGGGCTCGCTGCAAGCAAATGAACGTGCTGGACTCCTTCATCAACT
ACTATGATTCCGAGAAGCACGCCGAGAACGCCGTGATTTTTCTGCATGGTAACGCTGCCTCCAGCTACCTGTGGAGGCAC
GTCGTGCCTCACATCGAGTGAGTTTAAAC

LLLL) pBFB279 Sgf to Pme (SEQ ID NO:397)
GCGATCGCCATGAAGAAAATCATCTTTGTGGGCCACGACTGGGGGGCTTGTCTGGCCTTTCACTACTCCTACGAGCACCA
AGACAAGATCAAGGCCATCGTCCATGCTGAGAGTGTCGTGGACGTGATCGAGTCCTGGGACGAGTGGCCTGACATCGAGG
AGGATATCGCCCTGATCAAGAGCGAAGAGGGCGAGAAAATGGTGCTTGAGAATAACTTCTTCGTCGAGACCATGCTCCCA
AGCAAGATCATGCGGAAACTGGAGCCTGAGGAGTTCGCTGCCTACCTGGAGCCATTCAAGGAGAAGGGCGAGGTTAGACG
GCCTACCCTCTCCTGGCCTCGCGAGATCCCTCTCGTTAAGGGAGGCAAGCCCGACGTCGTCCAGATTGTCCGCAACTACA
ACGCCTACCTTCGGGCCAGCGACGATCTGCCTAAGATGTTCATCGAGTCCGACCCTGGGTTCTTTTCCAACGCTATTGTC
GAGGGAGCTAAGAAGTTCCCTAACACCGAGTTCGTGAAGGTGAAGGGCCTCCACTTCAGCCAGGAGGACGCTCCAGATGA
AATGGGTAAGTACATCAAGAGCTTCGTGGAGCGCGTGCTGAAGAACGAGCAGGGCTCGACCGGAATGTATGAAAGCTTTA
TTGAGTCACTGCCATTCCTTAAATCTTTGGAGTTTTCTGAACGCCTGAAAGTAGTAGATGTGATAGGCACCAAAGTATAC
AACGATGGAGAACAAATCATTGCTCAGGGAGATTCGGCTGATTCTTTTTTCATTGTAGAATCTGGAGAAGTGAAAATTAC

FIG. 67AO

TATGAAAAGAAAGGGTAAATCAGAAGTGGAAGAGAATGGTGCAGTAGAAATCGCTCGATGCTCGCGGGGACAGTACTTTG
GAGAGCTTGCCCTGGTAACTAACAAACCTCGAGCAGCTTCTGCCCACGCCATTGGGACTGTCAAATGTTTAGCAATGGAT
GTGCAAGCATTTGAAAGGCTTCTGGGACCTTGCATGGAAATTATGAAAAGGAACATCGCTACCTATGAAGAACAGTTAGT
TGCCCTGTTTGGAACGAACATGGATATTGTTGGGTCCGGTGGATCCGGTGGCAGCGGAGGGACGTCAGGTGGATCTGGAG
GGAGCTCAGGAGCTTCCAAGGTGTACGACCCCGAGCAACGCAAACGCATGATCACTGGGCCTCAGTGGTGGGCTCGCTGC
AAGCAAATGAACGTGCTGGACTCCTTCATCAACTACTATGATTCCGAGAAGCACGCCGAGAACGCCGTGATTTTTCTGCA
TGGTAACGCTGCCTCCAGCTACCTGTGGAGGCACGTCGTGCCTCACATCGAGCCCGTGGCTAGATGCATCATCCCTGATC
TGATCGGAATGGGTAAGTCCGGCAAGAGCGGGAATGGCTCATATCGCCTCCTGGATCACTACAAGTACCTCACCGCTTGG
TTCGAGCTGCTGAACCTTTGAGTTTAAAC

MMMM) pBFB280 Sgf to Pme (SEQ ID NO:398)
GCGATCGCCATGTCCTGGGACGAGTGGCCTGACATCGAGGAGGATATCGCCCTGATCAAGAGCGAAGAGGGCGAGAAAAT
GGTGCTTGAGAATAACTTCTTCGTCGAGACCATGCTCCCAAGCAAGATCATGCGGAAACTGGAGCCTGAGGAGTTCGCTG
CCTACCTGGAGCCATTCAAGGAGAAGGGCGAGGTTAGACGGCCTACCCTCTCCTGGCCTCGCGAGATCCCTCTCGTTAAG
GGAGGCAAGCCCGACGTCGTCCAGATTGTCCGCAACTACAACGCCTACCTTCGGGCCAGCGACGATCTGCCTAAGATGTT
CATCGAGTCCGACCCTGGGTTCTTTTCCAACGCTATTGTCGAGGGAGCTAAGAAGTTCCCTAACACCGAGTTCGTGAAGG
TGAAGGGCCTCCACTTCAGCCAGGAGGACGCTCCAGATGAAATGGGTAAGTACATCAAGAGCTTCGTGGAGCGCGTGCTG
AAGAACGAGCAGGGCTCGACCGGAATGTATGAAAGCTTTATTGAGTCACTGCCATTCCTTAAATCTTTGGAGTTTTCTGA
ACGCCTGAAAGTAGTAGATGTGATAGGCACCAAAGTATACAACGATGGAGAACAAATCATTGCTCAGGGAGATTCGGCTG
ATTCTTTTTTCATTGTAGAATCTGGAGAAGTGAAAATTACTATGAAAAGAAAGGGTAAATCAGAAGTGGAAGAGAATGGT
GCAGTAGAAATCGCTCGATGCTCGCGGGGACAGTACTTTGGAGAGCTTGCCCTGGTAACTAACAAACCTCGAGCAGCTTC
TGCCCACGCCATTGGGACTGTCAAATGTTTAGCAATGGATGTGCAAGCATTTGAAAGGCTTCTGGGACCTTGCATGGAAA
TTATGAAAAGGAACATCGCTACCTATGAAGAACAGTTAGTTGCCCTGTTTGGAACGAACATGGATATTGTTGGGTCCGGT
GGATCCGGTGGCAGCGGAGGGACGTCAGGTGGATCTGGAGGGAGCTCAGGAGCTTCCAAGGTGTACGACCCCGAGCAACG
CAAACGCATGATCACTGGGCCTCAGTGGTGGGCTCGCTGCAAGCAAATGAACGTGCTGGACTCCTTCATCAACTACTATG
ATTCCGAGAAGCACGCCGAGAACGCCGTGATTTTTCTGCATGGTAACGCTGCCTCCAGCTACCTGTGGAGGCACGTCGTG
CCTCACATCGAGCCCGTGGCTAGATGCATCATCCCTGATCTGATCGGAATGGGTAAGTCCGGCAAGAGCGGGAATGGCTC
ATATCGCCTCCTGGATCACTACAAGTACCTCACCGCTTGGTTCGAGCTGCTGAACCTTCCAAAGAAAATCATCTTTGTGG
GCCACGACTGGGGGGCTTGTCTGGCCTTTCACTACTCCTACGAGCACCAAGACAAGATCAAGGCCATCGTCCATGCTGAG
AGTGTCGTGGACGTGATCTGAGTTTAAAC

NNNN) pBFB281 Sgf to Pme (SEQ ID NO:399)
GCGATCGCCATGGAGGGCGAGAAAATGGTGCTTGAGAATAACTTCTTCGTCGAGACCATGCTCCCAAGCAAGATCATGCG
GAAACTGGAGCCTGAGGAGTTCGCTGCCTACCTGGAGCCATTCAAGGAGAAGGGCGAGGTTAGACGGCCTACCCTCTCCT
GGCCTCGCGAGATCCCTCTCGTTAAGGGAGGCAAGCCCGACGTCGTCCAGATTGTCCGCAACTACAACGCCTACCTTCGG
GCCAGCGACGATCTGCCTAAGATGTTCATCGAGTCCGACCCTGGGTTCTTTTCCAACGCTATTGTCGAGGGAGCTAAGAA
GTTCCCTAACACCGAGTTCGTGAAGGTGAAGGGCCTCCACTTCAGCCAGGAGGACGCTCCAGATGAAATGGGTAAGTACA
TCAAGAGCTTCGTGGAGCGCGTGCTGAAGAACGAGCAGGGCTCGACCGGAATGTATGAAAGCTTTATTGAGTCACTGCCA
TTCCTTAAATCTTTGGAGTTTTCTGAACGCCTGAAAGTAGTAGATGTGATAGGCACCAAAGTATACAACGATGGAGAACA
AATCATTGCTCAGGGAGATTCGGCTGATTCTTTTTTCATTGTAGAATCTGGAGAAGTGAAAATTACTATGAAAAGAAAGG
GTAAATCAGAAGTGGAAGAGAATGGTGCAGTAGAAATCGCTCGATGCTCGCGGGGACAGTACTTTGGAGAGCTTGCCCTG
GTAACTAACAAACCTCGAGCAGCTTCTGCCCACGCCATTGGGACTGTCAAATGTTTAGCAATGGATGTGCAAGCATTTGA
AAGGCTTCTGGGACCTTGCATGGAAATTATGAAAAGGAACATCGCTACCTATGAAGAACAGTTAGTTGCCCTGTTTGGAA
CGAACATGGATATTGTTGGGTCCGGTGGATCCGGTGGCAGCGGAGGGACGTCAGGTGGATCTGGAGGGAGCTCAGGAGCT
TCCAAGGTGTACGACCCCGAGCAACGCAAACGCATGATCACTGGGCCTCAGTGGTGGGCTCGCTGCAAGCAAATGAACGT
GCTGGACTCCTTCATCAACTACTATGATTCCGAGAAGCACGCCGAGAACGCCGTGATTTTTCTGCATGGTAACGCTGCCT
CCAGCTACCTGTGGAGGCACGTCGTGCCTCACATCGAGCCCGTGGCTAGATGCATCATCCCTGATCTGATCGGAATGGGT
AAGTCCGGCAAGAGCGGGAATGGCTCATATCGCCTCCTGGATCACTACAAGTACCTCACCGCTTGGTTCGAGCTGCTGAA
CCTTCCAAAGAAAATCATCTTTGTGGGCCACGACTGGGGGGCTTGTCTGGCCTTTCACTACTCCTACGAGCACCAAGACA
AGATCAAGGCCATCGTCCATGCTGAGAGTGTCGTGGACGTGATCGAGTCCTGGGACGAGTGGCCTGACATCGAGGAGGAT
ATCGCCCTGATCAAGAGCTGAGTTTAAAC

OOOO) pBFB282 Sgf to Pme (SEQ ID NO:400)
GCGATCGCCATGCTGGAGCCTGAGGAGTTCGCTGCCTACCTGGAGCCATTCAAGGAGAAGGGCGAGGTTAGACGGCCTAC
CCTCTCCTGGCCTCGCGAGATCCCTCTCGTTAAGGGAGGCAAGCCCGACGTCGTCCAGATTGTCCGCAACTACAACGCCT
ACCTTCGGGCCAGCGACGATCTGCCTAAGATGTTCATCGAGTCCGACCCTGGGTTCTTTTCCAACGCTATTGTCGAGGGA
GCTAAGAAGTTCCCTAACACCGAGTTCGTGAAGGTGAAGGGCCTCCACTTCAGCCAGGAGGACGCTCCAGATGAAATGGG

*FIG. 67*AP

TAAGTACATCAAGAGCTTCGTGGAGCGCGTGCTGAAGAACGAGCAGGGCTCGACCGGAATGTATGAAAGCTTTATTGAGT
CACTGCCATTCCTTAAATCTTTGGAGTTTTCTGAACGCCTGAAAGTAGTAGATGTGATAGGCACCAAAGTATACAACGAT
GGAGAACAAATCATTGCTCAGGGAGATTCGGCTGATTCTTTTTTCATTGTAGAATCTGGAGAAGTGAAAATTACTATGAA
AAGAAAGGGTAAATCAGAAGTGGAAGAGAATGGTGCAGTAGAAATCGCTCGATGCTCGCGGGGACAGTACTTTGGAGAGC
TTGCCCTGGTAACTAACAAACCTCGAGCAGCTTCTGCCCACGCCATTGGGACTGTCAAATGTTTAGCAATGGATGTGCAA
GCATTTGAAAGGCTTCTGGGACCTTGCATGGAAATTATGAAAAGGAACATCGCTACCTATGAAGAACAGTTAGTTGCCCT
GTTTGGAACGAACATGGATATTGTTGGGTCCGGTGGATCCGGTGGCACCCGAGGGACGTCAGGTCGATCTGGAGGGAGCT
CAGGAGCTTCCAAGGTGTACGACCCCGAGCAACGCAAACGCATGATCACTGGGCCTCAGTGGTGGGCTCGCTGCAAGCAA
ATGAACGTGCTGGACTCCTTCATCAACTACTATGATTCCGAGAAGCACGCCGAGAACGCCGTGATTTTTCTGCATGGTAA
CGCTGCCTCCAGCTACCTGTGGAGGCACGTCGTGCCTCACATCGAGCCCGTGGCTAGATGCATCATCCCTGATCTGATCG
GAATGGGTAAGTCCGGCAAGAGCGGGAATGGCTCATATCGCCTCCTGGATCACTACAAGTACCTCACCGCTTGGTTCGAG
CTGCTGAACCTTCCAAAGAAAATCATCTTTGTGGGCCACGACTGGGGGGCTTGTCTGGCCTTTCACTACTCCTACGAGCA
CCAAGACAAGATCAAGGCCATCGTCCATGCTGAGAGTGTCGTGGACGTGATCGAGTCCTGGGACGAGTGGCCTGACATCG
AGGAGGATATCGCCCTGATCAAGAGCGAAGAGGGCGAGAAAATGGTGCTTGAGAATAACTTCTTCGTCGAGACCATGCTC
CCAAGCAAGATCATGCGGTGAGTTTAAAC

PPPP) pBFB283 Sgf to Pme (SEQ ID NO:401)
GCGATCGCCATGAAGGGCGAGGTTAGACGGCCTACCCTCTCCTGGCCTCGCGAGATCCCTCTCGTTAAGGGAGGCAAGCC
CGACGTCGTCCAGATTGTCCGCAACTACAACGCCTACCTTCGGGCCAGCGACGATCTGCCTAAGATGTTCATCGAGTCCG
ACCCTGGGTTCTTTTCCAACGCTATTGTCGAGGGAGCTAAGAAGTTCCCTAACACCGAGTTCGTGAAGGTGAAGGGCCTC
CACTTCAGCCAGGAGGACGCTCCAGATGAAATGGGTAAGTACATCAAGAGCTTCGTGGAGCGCGTGCTGAAGAACGAGCA
GGGCTCGACCGGAATGTATGAAAGCTTTATTGAGTCACTGCCATTCCTTAAATCTTTGGAGTTTTCTGAACGCCTGAAAG
TAGTAGATGTGATAGGCACCAAAGTATACAACGATGGAGAACAAATCATTGCTCAGGGAGATTCGGCTGATTCTTTTTTC
ATTGTAGAATCTGGAGAAGTGAAAATTACTATGAAAAGAAAGGGTAAATCAGAAGTGGAAGAGAATGGTGCAGTAGAAAT
CGCTCGATGCTCGCGGGGACAGTACTTTGGAGAGCTTGCCCTGGTAACTAACAAACCTCGAGCAGCTTCTGCCCACGCCA
TTGGGACTGTCAAATGTTTAGCAATGGATGTGCAAGCATTTGAAAGGCTTCTGGGACCTTGCATGGAAATTATGAAAAGG
AACATCGCTACCTATGAAGAACAGTTAGTTGCCCTGTTTGGAACGAACATGGATATTGTTGGGTCCGGTGGATCCGGTGG
CAGCGGAGGGACGTCAGGTGGATCTGGAGGGAGCTCAGGAGCTTCCAAGGTGTACGACCCCGAGCAACGCAAACGCATGA
TCACTGGGCCTCAGTGGTGGGCTCGCTGCAAGCAAATGAACGTGCTGGACTCCTTCATCAACTACTATGATTCCGAGAAG
CACGCCGAGAACGCCGTGATTTTTCTGCATGGTAACGCTGCCTCCAGCTACCTGTGGAGGCACGTCGTGCCTCACATCGA
GCCCGTGGCTAGATGCATCATCCCTGATCTGATCGGAATGGGTAAGTCCGGCAAGAGCGGGAATGGCTCATATCGCCTCC
TGGATCACTACAAGTACCTCACCGCTTGGTTCGAGCTGCTGAACCTTCCAAAGAAAATCATCTTTGTGGGCCACGACTGG
GGGGCTTGTCTGGCCTTTCACTACTCCTACGAGCACCAAGACAAGATCAAGGCCATCGTCCATGCTGAGAGTGTCGTGGA
CGTGATCGAGTCCTGGGACGAGTGGCCTGACATCGAGGAGGATATCGCCCTGATCAAGAGCGAAGAGGGCGAGAAAATGG
TGCTTGAGAATAACTTCTTCGTCGAGACCATGCTCCCAAGCAAGATCATGCGGAAACTGGAGCCTGAGGAGTTCGCTGCC
TACCTGGAGCCATTCAAGTGAGTTTAAAC

QQQQ) pBFB284 Sgf to Pme (SEQ ID NO:402)
GCGATCGCCATGAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGACCGGAATGTATGAAAGCTTTATTGAGTCACTGCCATTCCTT
AAATCTTTGGAGTTTTCTGAACGCCTGAAAGTAGTAGATGTGATAGGCACCAAAGTATACAACGATGGAGAACAAATCAT
TGCTCAGGGAGATTCGGCTGATTCTTTTTTCATTGTAGAATCTGGAGAAGTGAAAATTACTATGAAAAGAAAGGGTAAAT
CAGAAGTGGAAGAGAATGGTGCAGTAGAAATCGCTCGATGCTCGCGGGGACAGTACTTTGGAGAGCTTGCCCTGGTAACT
AACAAACCTCGAGCAGCTTCTGCCCACGCCATTGGGACTGTCAAATGTTTAGCAATGGATGTGCAAGCATTTGAAAGGCT
TCTGGGACCTTGCATGGAAATTATGAAAAGGAACATCGCTACCTATGAAGAACAGTTAGTTGCCCTGTTTGGAACGAACA
TGGATATTGTTGGGTCCGGTGGATCCGGTGGCAGCGGAGGGACGTCAGGTGGATCTGGAGGGAGCTCAGGAGCTTCCAAG
GTGTACGACCCCGAGCAACGCAAACGCATGATCACTGGGCCTCAGTGGTGGGCTCGCTGCAAGCAAATGAACGTGCTGGA
CTCCTTCATCAACTACTATGATTCCGAGAAGCACGCCGAGAACGCCGTGATTTTTCTGCATGGTAACGCTGCCTCCAGCT
ACCTGTGGAGGCACGTCGTGCCTCACATCGAGCCCGTGGCTAGATGCATCATCCCTGATCTGATCGGAATGGGTAAGTCC
GGCAAGAGCGGGAATGGCTCATATCGCCTCCTGGATCACTACAAGTACCTCACCGCTTGGTTCGAGCTGCTGAACCTTCC
AAAGAAAATCATCTTTGTGGGCCACGACTGGGGGGCTTGTCTGGCCTTTCACTACTCCTACGAGCACCAAGACAAGATCA
AGGCCATCGTCCATGCTGAGAGTGTCGTGGACGTGATCGAGTCCTGGGACGAGTGGCCTGACATCGAGGAGGATATCGCC
CTGATCAAGAGCGAAGAGGGCGAGAAAATGGTGCTTGAGAATAACTTCTTCGTCGAGACCATGCTCCCAAGCAAGATCAT
GCGGAAACTGGAGCCTGAGGAGTTCGCTGCCTACCTGGAGCCATTCAAGGAGAAGGGCGAGGTTAGACGGCCTACCCTCT
CCTGGCCTCGCGAGATCCCTCTCGTTAAGGGAGGCAAGCCCGACGTCGTCCAGATTGTCCGCAACTACAACGCCTACCTT
CGGGCCAGCGACGATCTGTGAGTTTAAAC

*FIG. 67AQ*

RRRR) pBFB285 Sgf to Pme (SEQ ID NO:403)
GCGATCGCCATGGGGTTCTTTTCCAACGCTATTGTCGAGGGAGCTAAGAAGTTCCCTAACACCGAGTTCGTGAAGGTGAA
GGGCCTCCACTTCAGCCAGGAGGACGCTCCAGATGAAATGGGTAAGTACATCAAGAGCTTCGTGGAGCGCGTGCTGAAGA
ACGAGCAGGGCTCGACCGGAATGTATGAAAGCTTTATTGAGTCACTGCCATTCCTTAAATCTTTGGAGTTTTCTGAACGC
CTGAAAGTAGTAGATGTGATAGGCACCAAAGTATACAACGATGGAGAACAAATCATTGCTCAGGGAGATTCGGCTGATTC
TTTTTTCATTGTAGAATCTGGAGAAGTGAAAATTACTATGAAAAGAAAGGGTAAATCAGAAGTGGAAGAGAATGGTGCAG
TAGAAATCGCTCGATGCTCGCGGGGACAGTACTTTGGAGAGCTTGCCCTGGTAACTAACAAACCTCGAGCAGCTTCTGCC
CACGCCATTGGGACTGTCAAATGTTTAGCAATGGATGTGCAAGCATTTGAAAGGCTTCTGGGACCTTGCATGGAAATTAT
GAAAAGGAACATCGCTACCTATGAAGAACAGTTAGTTGCCCTGTTTGGAACGAACATGGATATTGTTGGGTCCGGTGGAT
CCGGTGGCAGCGGAGGGACGTCAGGTGGATCTGGAGGGAGCTCAGGAGCTTCCAAGGTGTACGACCCCGAGCAACGCAAA
CGCATGATCACTGGGCCTCAGTGGTGGGCTCGCTGCAAGCAAATGAACGTGCTGGACTCCTTCATCAACTACTATGATTC
CGAGAAGCACGCCGAGAACGCCGTGATTTTTCTGCATGGTAACGCTGCCTCCAGCTACCTGTGGAGGCACGTCGTGCCTC
ACATCGAGCCCGTGGCTAGATGCATCATCCCTGATCTGATCGGAATGGGTAAGTCCGGCAAGAGCGGGAATGGCTCATAT
CGCCTCCTGGATCACTACAAGTACCTCACCGCTTGGTTCGAGCTGCTGAACCTTCCAAAGAAAATCATCTTTGTGGGCCA
CGACTGGGGGGCTTGTCTGGCCTTTCACTACTCCTACGAGCACCAAGACAAGATCAAGGCCATCGTCCATGCTGAGAGTG
TCGTGGACGTGATCGAGTCCTGGGACGAGTGGCCTGACATCGAGGAGGATATCGCCCTGATCAAGAGCGAAGAGGGCGAG
AAAATGGTGCTTGAGAATAACTTCTTCGTCGAGACCATGCTCCCAAGCAAGATCATGCGGAAACTGGAGCCTGAGGAGTT
CGCTGCCTACCTGGAGCCATTCAAGGAGAAGGGCGAGGTTAGACGGCCTACCCTCTCCTGGCCTCGCGAGATCCCTCTCG
TTAAGGGAGGCAAGCCCGACGTCGTCCAGATTGTCCGCAACTACAACGCCTACCTTCGGGCCAGCGACGATCTGCCTAAG
ATGTTCATCGAGTCCGACTGAGTTTAAAC

SSSS) pBFB286 Sgf to Pme (SEQ ID NO:404)
GCGATCGCCATGAACACCGAGTTCGTGAAGGTGAAGGGCCTCCACTTCAGCCAGGAGGACGCTCCAGATGAAATGGGTAA
GTACATCAAGAGCTTCGTGGAGCGCGTGCTGAAGAACGAGCAGGGCTCGACCGGAATGTATGAAAGCTTTATTGAGTCAC
TGCCATTCCTTAAATCTTTGGAGTTTTCTGAACGCCTGAAAGTAGTAGATGTGATAGGCACCAAAGTATACAACGATGGA
GAACAAATCATTGCTCAGGGAGATTCGGCTGATTCTTTTTTCATTGTAGAATCTGGAGAAGTGAAAATTACTATGAAAAG
AAAGGGTAAATCAGAAGTGGAAGAGAATGGTGCAGTAGAAATCGCTCGATGCTCGCGGGGACAGTACTTTGGAGAGCTTG
CCCTGGTAACTAACAAACCTCGAGCAGCTTCTGCCCACGCCATTGGGACTGTCAAATGTTTAGCAATGGATGTGCAAGCA
TTTGAAAGGCTTCTGGGACCTTGCATGGAAATTATGAAAAGGAACATCGCTACCTATGAAGAACAGTTAGTTGCCCTGTT
TGGAACGAACATGGATATTGTTGGGTCCGGTGGATCCGGTGGCAGCGGAGGGACGTCAGGTGGATCTGGAGGGAGCTCAG
GAGCTTCCAAGGTGTACGACCCCGAGCAACGCAAACGCATGATCACTGGGCCTCAGTGGTGGGCTCGCTGCAAGCAAATG
AACGTGCTGGACTCCTTCATCAACTACTATGATTCCGAGAAGCACGCCGAGAACGCCGTGATTTTTCTGCATGGTAACGC
TGCCTCCAGCTACCTGTGGAGGCACGTCGTGCCTCACATCGAGCCCGTGGCTAGATGCATCATCCCTGATCTGATCGGAA
TGGGTAAGTCCGGCAAGAGCGGGAATGGCTCATATCGCCTCCTGGATCACTACAAGTACCTCACCGCTTGGTTCGAGCTG
CTGAACCTTCCAAAGAAAATCATCTTTGTGGGCCACGACTGGGGGGCTTGTCTGGCCTTTCACTACTCCTACGAGCACCA
AGACAAGATCAAGGCCATCGTCCATGCTGAGAGTGTCGTGGACGTGATCGAGTCCTGGGACGAGTGGCCTGACATCGAGG
AGGATATCGCCCTGATCAAGAGCGAAGAGGGCGAGAAAATGGTGCTTGAGAATAACTTCTTCGTCGAGACCATGCTCCCA
AGCAAGATCATGCGGAAACTGGAGCCTGAGGAGTTCGCTGCCTACCTGGAGCCATTCAAGGAGAAGGGCGAGGTTAGACG
GCCTACCCTCTCCTGGCCTCGCGAGATCCCTCTCGTTAAGGGAGGCAAGCCCGACGTCGTCCAGATTGTCCGCAACTACA
ACGCCTACCTTCGGGCCAGCGACGATCTGCCTAAGATGTTCATCGAGTCCGACCCTGGGTTCTTTTCCAACGCTATTGTC
GAGGGAGCTAAGAAGTTCTGAGTTTAAAC

TTTT) pBFB287 Sgf to Pme (SEQ ID NO:405)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGACCGGAATGTATGAAAGCTTTATTGAGTCACTGCCATTCCTT
AAATCTTTGGAGTTTTCTGAACGCCTGAAAGTAGTAGATGTGATAGGCACCAAAGTATACAACGATGGAGAACAAATCAT
TGCTCAGGGAGATTCGGCTGATTCTTTTTTCATTGTAGAATCTGGAGAAGTGAAAATTACTATGAAAAGAAAGGGTAAAT
CAGAAGTGGAAGAGAATGGTGCAGTAGAAATCGCTCGATGCTCGCGGGGACAGTACTTTGGAGAGCTTGCCCTGGTAACT
AACAAACCTCGAGCAGCTTCTGCCCACGCCATTGGGACTGTCAAATGTTTAGCAATGGATGTGCAAGCATTTGAAAGGCT

*FIG. 67AR*

TCTGGGACCTTGCATGGAAATTATGAAAAGGAACATCGCTACCTATGAAGAACAGTTAGTTGCCCTGTTTGGAACGAACA
TGGATATTGTTGGGTCCGGTGGATCCGGTGGCAGCGGAGGGACGTCAGGTGGATCTGGAGGGAGCTCAGGAGCTTCCAAG
GTGTACGACCCCGAGCAACGCAAACGCATGATCACTGGGCCTCAGTGGTGGGCTCGCTGCAAGCAAATGAACGTGCTGGA
CTCCTTCATCAACTACTATGATTCCGAGAAGCACGCCGAGAACGCCGTGATTTTTCTGCATGGTAACGCTGCCTCCAGCT
ACCTGTGGAGGCACGTCGTGCCTCACATCGAGCCCGTGGCTAGATGCATCATCCCTGATCTGATCGGAATGGGTAAGTCC
GGCAAGAGCGGGAATGGCTCAGTTTAAAC

UUUU) pBFB290 Sgf to Pme (SEQ ID NO:406)
GCGATCGCCATGAAGGAGAGTGCTCAGGGAGGAATCGGCGAGGCTATCGTTGACATCCCTGAGATCCCAGGATTCAAAGA
TCTGGAACCAATGGAACAATTTATAGCGCAGGTCGACCTTTGTGTGGACTGTACTACCGGATGCCTGAAGGGACTTGCAA
ATGTCCAATGTAGCGATCTCCTGAAGAAATGGCTCCCCCAGAGATGTGCAACCTTTGCGAGCAAGATACAGGGGCAAGTC
GATAAGATTAAGGGCGCCGGTGGAGACGGCTCGACCGGAATGTATGAAAGCTTTATTGAGTCACTGCCATTCCTTAAATC
TTTGGAGTTTTCTGAACGCCTGAAAGTAGTAGATGTGATAGGCACCAAAGTATACAACGATGGAGAACAAATCATTGCTC
AGGGAGATTCGGCTGATTCTTTTTTCATTGTAGAATCTGGAGAAGTGAAAATTACTATGAAAAGAAAGGGTAAATCAGAA
GTGGAAGAGAATGGTGCAGTAGAAATCGCTCGATGCTCGCGGGGACAGTACTTTGGAGAGCTTGCCCTGGTAACTAACAA
ACCTCGAGCAGCTTCTGCCCACGCCATTGGGACTGTCAAATGTTTAGCAATGGATGTGCAAGCATTTGAAAGGCTTCTGG
GACCTTGCATGGAAATTATGAAAAGGAACATCGCTACCTATGAAGAACAGTTAGTTGCCCTGTTTGGAACGAACATGGAT
ATTGTTGGGAGCTCCGGTAAGCCAACCGAGAACAATGAAGATTTTAACATTGTGGCCGTCGCAAGCAATTTTGCCACCAC
TGATCTGGACGCAGACAGGGGCAAGCTGCCGGGAAAAAAACTGCCCCTGGAGGTGTTGAAAGAGATGGAGGCAAACGCCA
GAAAGGCCGGCTGCACACGCGGTTGTCTGATTTGCTTGTCTCACATCAAGTGCACACCCAAAATGAAGAAATTTATCCCG
GGCAGGTGCCACACATACGAGGGATGAGTTTAAAC

VVVV) pBFB291 Sgf to Pme (SEQ ID NO:407)
GCGATCGCCATGAAGGAGAGTGCTCAGGGAGGAATCGGCGAGGCTATCGTTGACATCCCTGAGATCCCAGGATTCAAAGA
TCTGGAACCAATGGAACAATTTATAGCGCAGGTCGACCTTTGTGTGGACTGTACTACCGGATGCCTGAAGGGACTTGCAA
ATGTCCAATGTAGCGATCTCCTGAAGAAATGGCTCCCCCAGAGATGTGCAACCTTTGCGAGCAAGATACAGGGGCAAGTC
GATAAGATTAAGGGCGCCGGTGGAGACGGCTCGAGCGGAGGTTCAGGCGGTTCCGGAATGTATGAAAGCTTTATTGAGTC
ACTGCCATTCCTTAAATCTTTGGAGTTTTCTGAACGCCTGAAAGTAGTAGATGTGATAGGCACCAAAGTATACAACGATG
GAGAACAAATCATTGCTCAGGGAGATTCGGCTGATTCTTTTTTCATTGTAGAATCTGGAGAAGTGAAAATTACTATGAAA
AGAAAGGGTAAATCAGAAGTGGAAGAGAATGGTGCAGTAGAAATCGCTCGATGCTCGCGGGGACAGTACTTTGGAGAGCT
TGCCCTGGTAACTAACAAACCTCGAGCAGCTTCTGCCCACGCCATTGGGACTGTCAAATGTTTAGCAATGGATGTGCAAG
CATTTGAAAGGCTTCTGGGACCTTGCATGGAAATTATGAAAAGGAACATCGCTACCTATGAAGAACAGTTAGTTGCCCTG
TTTGGAACGAACATGGATATTGTAGGGTCAGGTGGATCTGGAGGGAGCTCCGGTAAGCCAACCGAGAACAATGAAGATTT
TAACATTGTGGCCGTCGCAAGCAATTTTGCCACCACTGATCTGGACGCAGACAGGGGCAAGCTGCCGGGAAAAAAACTGC
CCCTGGAGGTGTTGAAAGAGATGGAGGCAAACGCCAGAAAGGCCGGCTGCACACGCGGTTGTCTGATTTGCTTGTCTCAC
ATCAAGTGCACACCCAAAATGAAGAAATTTATCCCGGGCAGGTGCCACACATACGAGGGATGAGTTTAAAC

WWWW) pBFB292 Sgf to Pme (SEQ ID NO:408)
GCGATCGCCATGAAGGAGAGTGCTCAGGGAGGAATCGGCGAGGCTATCGTTGACATCCCTGAGATCCCAGGATTCAAAGA
TCTGGAACCAATGGAACAATTTATAGCGCAGGTCGACCTTTGTGTGGACTGTACTACCGGATGCCTGAAGGGACTTGCAA
ATGTCCAATGTAGCGATCTCCTGAAGAAATGGCTCCCCCAGAGATGTGCAACCTTTGCGAGCAAGATACAGGGGCAAGTC
GATAAGATTAAGGGCGCCGGTGGAGACGGCTCGAGCGGAGGTTCAGGCGGTTCCGGAGGAGGTTCTGGCGGATCAGGCGG
TTCGGGGATGTATGAAAGCTTTATTGAGTCACTGCCATTCCTTAAATCTTTGGAGTTTTCTGAACGCCTGAAAGTAGTAG
ATGTGATAGGCACCAAAGTATACAACGATGGAGAACAAATCATTGCTCAGGGAGATTCGGCTGATTCTTTTTTCATTGTA
GAATCTGGAGAAGTGAAAATTACTATGAAAAGAAAGGGTAAATCAGAAGTGGAAGAGAATGGTGCAGTAGAAATCGCTCG
ATGCTCGCGGGGACAGTACTTTGGAGAGCTTGCCCTGGTAACTAACAAACCTCGAGCAGCTTCTGCCCACGCCATTGGGA
CTGTCAAATGTTTAGCAATGGATGTGCAAGCATTTGAAAGGCTTCTGGGACCTTGCATGGAAATTATGAAAAGGAACATC
GCTACCTATGAAGAACAGTTAGTTGCCCTGTTTGGAACGAACATGGATATTGTTGGGTCCGGTGGATCCGGTGGCAGCGG
AGGGACGTCAGGTGGATCTGGAGGGAGCTCCGGTAAGCCAACCGAGAACAATGAAGATTTTAACATTGTGGCCGTCGCAA
GCAATTTTGCCACCACTGATCTGGACGCAGACAGGGGCAAGCTGCCGGGAAAAAAACTGCCCCTGGAGGTGTTGAAAGAG
ATGGAGGCAAACGCCAGAAAGGCCGGCTGCACACGCGGTTGTCTGATTTGCTTGTCTCACATCAAGTGCACACCCAAAAT
GAAGAAATTTATCCCGGGCAGGTGCCACACATACGAGGGATGAGTTTAAAC

XXXX) pBFB293 Sgf to Pme (SEQ ID NO:409)
GCGATCGCCATGGCTATCGTTGACATCCTGAGATCCCAGGATTCAAAGATCTGGAACCAATGGAACAATTTATAGCGCAG
GTCGACCTTTGTGTGGACTGTACTACCGGATGCCTGAAGGGACTTGCAAATGTCCAATGTAGCGATCTCCTGAAGAAATG
GCTCCCCCAGAGATGTGCAACCTTTGCGAGCAAGATACAGGGGCAAGTCGATAAGATTAAGGGCGCCGGTGGAGACGGCT

FIG. 67AS

CGACCGGAATGTATGAAAGCTTTATTGAGTCACTGCCATTCCTTAAATCTTTGGAGTTTTCTGAACGCCTGAAAGTAGTA
GATGTGATAGGCACCAAAGTATACAACGATGGAGAACAAATCATTGCTCAGGGAGATTCGGCTGATTCTTTTTTCATTGT
AGAATCTGGAGAAGTGAAAATTACTATGAAAAGAAAGGGTAAATCAGAAGTGGAAGAGAATGGTGCAGTAGAAATCGCTC
GATGCTCGCGGGGACAGTACTTTGGAGAGCTTGCCCTGGTAACTAACAAACCTCGAGCAGCTTCTGCCCACGCCATTGGG
ACTGTCAAATGTTTAGCAATGGATGTGCAAGCATTTGAAAGGCTTCTGGGACCTTGCATGGAAATTATGAAAAGGAACAT
CGCTACCTATGAAGAACAGTTAGTTGCCCTGTTTGGAACGAACATGGATATTGTTGGGAGCTCCGGTAAGCCAACCGAGA
ACAATGAAGATTTTAACATTGTGGCCGTCGCAAGCAATTTTGCCACCACTGATCTGGACGCAGACAGGGGCAAGCTGCCG
GGAAAAAAACTGCCCCTGGAGGTGTTGAAAGAGATGGAGGCAAACGCCAGAAAGGCCGGCTGCACACGCGGTTGTCTGAT
TTGCTTGTCTCACATCAAGTGCACACCCAAAATGAAGAAATTTATCCCGGGCAGGTGCCACACATACGAGGGAGACAAGG
AGAGTGCTCAGGGAGGAATCGGCTGAGTTTAAAC

YYYY) pBFB294 Sgf to Pme (SEQ ID NO:410)
GCGATCGCCATGGCTATCGTTGACATCCCTGAGATCCCAGGATTCAAAGATCTGGAACCAATGGAACAATTTATAGCGCA
GGTCGACCTTTGTGTGGACTGTACTACCGGATGCCTGAAGGGACTTGCAAATGTCCAATGTAGCGATCTCCTGAAGAAAT
GGCTCCCCCAGAGATGTGCAACCTTTGCGAGCAAGATACAGGGGCAAGTCGATAAGATTAAGGGCGCCGGTGGAGACGGC
TCGAGCGGAGGTTCAGGCGGTTCCGGAATGTATGAAAGCTTTATTGAGTCACTGCCATTCCTTAAATCTTTGGAGTTTTC
TGAACGCCTGAAAGTAGTAGATGTGATAGGCACCAAAGTATACAACGATGGAGAACAAATCATTGCTCAGGGAGATTCGG
CTGATTCTTTTTTCATTGTAGAATCTGGAGAAGTGAAAATTACTATGAAAAGAAAGGGTAAATCAGAAGTGGAAGAGAAT
GGTGCAGTAGAAATCGCTCGATGCTCGCGGGGACAGTACTTTGGAGAGCTTGCCCTGGTAACTAACAAACCTCGAGCAGC
TTCTGCCCACGCCATTGGGACTGTCAAATGTTTAGCAATGGATGTGCAAGCATTTGAAAGGCTTCTGGGACCTTGCATGG
AAATTATGAAAAGGAACATCGCTACCTATGAAGAACAGTTAGTTGCCCTGTTTGGAACGAACATGGATATTGTAGGGTCA
GGTGGATCTGGAGGGAGCTCCGGTAAGCCAACCGAGAACAATGAAGATTTTAACATTGTGGCCGTCGCAAGCAATTTTGC
CACCACTGATCTGGACGCAGACAGGGGCAAGCTGCCGGGAAAAAAACTGCCCCTGGAGGTGTTGAAAGAGATGGAGGCAA
ACGCCAGAAAGGCCGGCTGCACACGCGGTTGTCTGATTTGCTTGTCTCACATCAAGTGCACACCCAAAATGAAGAAATTT
ATCCCGGGCAGGTGCCACACATACGAGGGAGACAAGGAGAGTGCTCAGGGAGGAATCGGCTGAGTTTAAAC
ZZZZ) pBFB295 Sgf to Pme (SEQ ID NO:411)
GCGATCGCCATGGCTATCGTTGACATCCCTGAGATCCCAGGATTCAAAGATCTGGAACCAATGGAACAATTTATAGCGCA
GGTCGACCTTTGTGTGGACTGTACTACCGGATGCCTGAAGGGACTTGCAAATGTCCAATGTAGCGATCTCCTGAAGAAAT
GGCTCCCCCAGAGATGTGCAACCTTTGCGAGCAAGATACAGGGGCAAGTCGATAAGATTAAGGGCGCCGGTGGAGACGGC
TCGAGCGGAGGTTCAGGCGGTTCCGGAGGAGGTTCTGGCGGATCAGGCGGTTCGGGGATGTATGAAAGCTTTATTGAGTC
ACTGCCATTCCTTAAATCTTTGGAGTTTTCTGAACGCCTGAAAGTAGTAGATGTGATAGGCACCAAAGTATACAACGATG
GAGAACAAATCATTGCTCAGGGAGATTCGGCTGATTCTTTTTTCATTGTAGAATCTGGAGAAGTGAAAATTACTATGAAA
AGAAAGGGTAAATCAGAAGTGGAAGAGAATGGTGCAGTAGAAATCGCTCGATGCTCGCGGGGACAGTACTTTGGAGAGCT
TGCCCTGGTAACTAACAAACCTCGAGCAGCTTCTGCCCACGCCATTGGGACTGTCAAATGTTTAGCAATGGATGTGCAAG
CATTTGAAAGGCTTCTGGGACCTTGCATGGAAATTATGAAAAGGAACATCGCTACCTATGAAGAACAGTTAGTTGCCCTG
TTTGGAACGAACATGGATATTGTTGGGTCCGGTGGATCCGGTGGCAGCGGAGGGACGTCAGGTGGATCTGGAGGGAGCTC
CGGTAAGCCAACCGAGAACAATGAAGATTTTAACATTGTGGCCGTCGCAAGCAATTTTGCCACCACTGATCTGGACGCAG
ACAGGGGCAAGCTGCCGGGAAAAAAACTGCCCCTGGAGGTGTTGAAAGAGATGGAGGCAAACGCCAGAAAGGCCGGCTGC
ACACGCGGTTGTCTGATTTGCTTGTCTCACATCAAGTGCACACCCAAAATGAAGAAATTTATCCCGGGCAGGTGCCACAC
ATACGAGGGAGACAAGGAGAGTGCTCAGGGAGGAATCGGCTGAGTTTAAAC

AAAAA) pBFB296 Sgf to Pme (SEQ ID NO:412)
GCGATCGCCATGGAAAAAAACTGCCCCTGGAGGTGTTGAAAGAGATGGAGGCAAACGCCAGAAAGGCCGGCTGCACACG
CGGTTGTCTGATTTGCTTGTCTCACATCAAGTGCACACCCAAAATGAAGAAATTTATCCCGGGCAGGTGCCACACATACG
AGGGAGACAAGGAGAGTGCTCAGGGAGGAATCGGCGAGGCTATCGTTGACATCCCTGAGATCCCAGGATTCAAAGATCTG
GAACCAATGGAACAATTTATAGCGCAGGTCGACCTTTGTGTGGACTGTACTACCGGATGCCTGAAGGGACTTGCAAATGT
CCAATGTAGCGATCTCCTGAAGAAATGGCTCCCCCAGAGATGTGCAACCTTTGCGAGCAAGATACAGGGGCAAGTCGATA
AGATTAAGGGCGCCGGTGGAGACGGCTCGACCGGAATGTATGAAAGCTTTATTGAGTCACTGCCATTCCTTAAATCTTTG
GAGTTTTCTGAACGCCTGAAAGTAGTAGATGTGATAGGCACCAAAGTATACAACGATGGAGAACAAATCATTGCTCAGGG
AGATTCGGCTGATTCTTTTTTCATTGTAGAATCTGGAGAAGTGAAAATTACTATGAAAAGAAAGGGTAAATCAGAAGTGG
AAGAGAATGGTGCAGTAGAAATCGCTCGATGCTCGCGGGGACAGTACTTTGGAGAGCTTGCCCTGGTAACTAACAAACCT
CGAGCAGCTTCTGCCCACGCCATTGGGACTGTCAAATGTTTAGCAATGGATGTGCAAGCATTTGAAAGGCTTCTGGGACC
TTGCATGGAAATTATGAAAAGGAACATCGCTACCTATGAAGAACAGTTAGTTGCCCTGTTTGGAACGAACATGGATATTG
TTGGGAGCTCCGGTAAGCCAACCGAGAACAATGAAGATTTTAACATTGTGGCCGTCGCAAGCAATTTTGCCACCACTGAT
CTGGACGCAGACAGGGGCAAGCTGTGAGTTTAAAC

BBBBB) pBFB297 Sgf to Pme (SEQ ID NO:413)

*FIG. 67AT*

GCGATCGCCATGGGAAAAAAACTGCCCCTGGAGGTGTTGAAAGAGATGGAGGCAAACGCCAGAAAGGCCGGCTGCACACG
CGGTTGTCTGATTTGCTTGTCTCACATCAAGTGCACACCCAAAATGAAGAAATTTATCCCGGGCAGGTGCCACACATACG
AGGGAGACAAGGAGAGTGCTCAGGGAGGAATCGGCGAGGCTATCGTTGACATCCCTGAGATCCCAGGATTCAAAGATCTG
GAACCAATGGAACAATTTATAGCGCAGGTCGACCTTTGTGTGGACTGTACTACCGGATGCCTGAAGGGACTTGCAAATGT
CCAATGTAGCGATCTCCTGAAGAAATGGCTCCCCCAGAGATGTGCAACCTTTGCGAGCAAGATACAGGGGCAAGTCGATA
AGATTAAGGGCGCCGGTGGAGACGGCTCGAGCGGAGGTTCAGGCGGTTCCGGAATGTATGAAAGCTTTATTGAGTCACTG
CCATTCCTTAAATCTTTGGAGTTTTCTGAACGCCTGAAAGTAGTAGATGTGATAGGCACCAAAGTATACAACGATGGAGA
ACAAATCATTGCTCAGGGAGATTCGGCTGATTCTTTTTTCATTGTAGAATCTGGAGAAGTGAAAATTACTATGAAAAGAA
AGGGTAAATCAGAAGTGGAAGAGAATGGTGCAGTAGAAATCGCTCGATGCTCGCGGGGACAGTACTTTGGAGAGCTTGCC
CTGGTAACTAACAAACCTCGAGCAGCTTCTGCCCACGCCATTGGGACTGTCAAATGTTTAGCAATGGATGTGCAAGCATT
TGAAAGGCTTCTGGGACCTTGCATGGAAATTATGAAAAGGAACATCGCTACCTATGAAGAACAGTTAGTTGCCCTGTTTG
GAACGAACATGGATATTGTAGGGTCAGGTGGATCTGGAGGGAGCTCCGGTAAGCCAACCGAGAACAATGAAGATTTTAAC
ATTGTGGCCGTCGCAAGCAATTTTGCCACCACTGATCTGGACGCAGACAGGGGCAAGCTGTGAGTTTAAAC

CCCCC) pBFB298 Sgf to Pme (SEQ ID NO:414)
GCGATCGCCATGGGAAAAAAACTGCCCCTGGAGGTGTTGAAAGAGATGGAGGCAAACGCCAGAAAGGCCGGCTGCACACG
CGGTTGTCTGATTTGCTTGTCTCACATCAAGTGCACACCCAAAATGAAGAAATTTATCCCGGGCAGGTGCCACACATACG
AGGGAGACAAGGAGAGTGCTCAGGGAGGAATCGGCGAGGCTATCGTTGACATCCCTGAGATCCCAGGATTCAAAGATCTG
GAACCAATGGAACAATTTATAGCGCAGGTCGACCTTTGTGTGGACTGTACTACCGGATGCCTGAAGGGACTTGCAAATGT
CCAATGTAGCGATCTCCTGAAGAAATGGCTCCCCCAGAGATGTGCAACCTTTGCGAGCAAGATACAGGGGCAAGTCGATA
AGATTAAGGGCGCCGGTGGAGACGGCTCGAGCGGAGGTTCAGGCGGTTCCGGAGGAGGTTCTGGCGGATCAGGCGGTTCG
GGGATGTATGAAAGCTTTATTGAGTCACTGCCATTCCTTAAATCTTTGGAGTTTTCTGAACGCCTGAAAGTAGTAGATGT
GATAGGCACCAAAGTATACAACGATGGAGAACAAATCATTGCTCAGGGAGATTCGGCTGATTCTTTTTTCATTGTAGAAT
CTGGAGAAGTGAAAATTACTATGAAAAGAAAGGGTAAATCAGAAGTGGAAGAGAATGGTGCAGTAGAAATCGCTCGATGC
TCGCGGGGACAGTACTTTGGAGAGCTTGCCCTGGTAACTAACAAACCTCGAGCAGCTTCTGCCCACGCCATTGGGACTGT
CAAATGTTTAGCAATGGATGTGCAAGCATTTGAAAGGCTTCTGGGACCTTGCATGGAAATTATGAAAAGGAACATCGCTA
CCTATGAAGAACAGTTAGTTGCCCTGTTTGGAACGAACATGGATATTGTTGGGTCCGGTGGATCCGGTGGCAGCGGAGGG
ACGTCAGGTGGATCTGGAGGGAGCTCCGGTAAGCCAACCGAGAACAATGAAGATTTTAACATTGTGGCCGTCGCAAGCAA
TTTTGCCACCACTGATCTGGACGCAGACAGGGGCAAGCTGTGAGTTTAAAC

DDDDD) pBFB299 Sgf to Pme (SEQ ID NO:415)
GCGATCGCCATGTGCACACGCGGTTGTCTGATTTGCTTGTCTCACATCAAGTGCACACCCAAAATGAAGAAATTTATCCC
GGGCAGGTGCCACACATACGAGGGAGACAAGGAGAGTGCTCAGGGAGGAATCGGCGAGGCTATCGTTGACATCCCTGAGA
TCCCAGGATTCAAAGATCTGGAACCAATGGAACAATTTATAGCGCAGGTCGACCTTTGTGTGGACTGTACTACCGGATGC
CTGAAGGGACTTGCAAATGTCCAATGTAGCGATCTCCTGAAGAAATGGCTCCCCCAGAGATGTGCAACCTTTGCGAGCAA
GATACAGGGGCAAGTCGATAAGATTAAGGGCGCCGGTGGAGACGGCTCGACCGGAATGTATGAAAGCTTTATTGAGTCAC
TGCCATTCCTTAAATCTTTGGAGTTTTCTGAACGCCTGAAAGTAGTAGATGTGATAGGCACCAAAGTATACAACGATGGA
GAACAAATCATTGCTCAGGGAGATTCGGCTGATTCTTTTTTCATTGTAGAATCTGGAGAAGTGAAAATTACTATGAAAAG
AAAGGGTAAATCAGAAGTGGAAGAGAATGGTGCAGTAGAAATCGCTCGATGCTCGCGGGGACAGTACTTTGGAGAGCTTG
CCCTGGTAACTAACAAACCTCGAGCAGCTTCTGCCCACGCCATTGGGACTGTCAAATGTTTAGCAATGGATGTGCAAGCA
TTTGAAAGGCTTCTGGGACCTTGCATGGAAATTATGAAAAGGAACATCGCTACCTATGAAGAACAGTTAGTTGCCCTGTT
TGGAACGAACATGGATATTGTTGGGAGCTCCGGTAAGCCAACCGAGAACAATGAAGATTTTAACATTGTGGCCGTCGCAA
GCAATTTTGCCACCACTGATCTGGACGCAGACAGGGGCAAGCTGCCGGGAAAAAAACTGCCCCTGGAGGTGTTGAAAGAG
ATGGAGGCAAACGCCAGAAAGGCCTGAGTTTAAAC

EEEEE) pBFB300 Sgf to Pme (SEQ ID NO:416)
GCGATCGCCATGTGCACACGCGGTTGTCTGATTTGCTTGTCTCACATCAAGTGCACACCCAAAATGAAGAAATTTATCCC
GGGCAGGTGCCACACATACGAGGGAGACAAGGAGAGTGCTCAGGGAGGAATCGGCGAGGCTATCGTTGACATCCCTGAGA
TCCCAGGATTCAAAGATCTGGAACCAATGGAACAATTTATAGCGCAGGTCGACCTTTGTGTGGACTGTACTACCGGATGC
CTGAAGGGACTTGCAAATGTCCAATGTAGCGATCTCCTGAAGAAATGGCTCCCCCAGAGATGTGCAACCTTTGCGAGCAA
GATACAGGGGCAAGTCGATAAGATTAAGGGCGCCGGTGGAGACGGCTCGAGCGGAGGTTCAGGCGGTTCCGGAATGTATG
AAAGCTTTATTGAGTCACTGCCATTCCTTAAATCTTTGGAGTTTTCTGAACGCCTGAAAGTAGTAGATGTGATAGGCACC
AAAGTATACAACGATGGAGAACAAATCATTGCTCAGGGAGATTCGGCTGATTCTTTTTTCATTGTAGAATCTGGAGAAGT
GAAAATTACTATGAAAAGAAAGGGTAAATCAGAAGTGGAAGAGAATGGTGCAGTAGAAATCGCTCGATGCTCGCGGGGAC
AGTACTTTGGAGAGCTTGCCCTGGTAACTAACAAACCTCGAGCAGCTTCTGCCCACGCCATTGGGACTGTCAAATGTTTA
GCAATGGATGTGCAAGCATTTGAAAGGCTTCTGGGACCTTGCATGGAAATTATGAAAAGGAACATCGCTACCTATGAAGA
ACAGTTAGTTGCCCTGTTTGGAACGAACATGGATATTGTAGGGTCAGGTGGATCTGGAGGGAGCTCCGGTAAGCCAACCG

*FIG. 67*AU

AGAACAATGAAGATTTTAACATTGTGGCCGTCGCAAGCAATTTTGCCACCACTGATCTGGACGCAGACAGGGGCAAGCTG
CCGGGAAAAAAACTGCCCCTGGAGGTGTTGAAAGAGATGGAGGCAAACGCCAGAAAGGCCTGAGTTTAAAC

FFFFF) pBFB301 Sgf to Pme (SEQ ID NO:417)
GCGATCGCCATGTGCACACGCGGTTGTCTGATTTGCTTGTCTCACATCAAGTGCACACCCAAAATGAAGAAATTTATCCC
GGGCAGGTGCCACACATACGAGGGAGACAAGGAGAGTGCTCAGGGAGGAATCGGCGAGGCTATCGTTGACATCCCTGAGA
TCCCAGGATTCAAAGATCTGGAACCAATGGAACAATTTATAGCGCAGGTCGACCTTTGTGTGGACTGTACTACCGGATGC
CTGAAGGGACTTGCAAATGTCCAATGTAGCGATCTCCTGAAGAAATGGCTCCCCCAGAGATGTGCAACCTTTGCGAGCAA
GATACAGGGGCAAGTCGATAAGATTAAGGGCGCCGGTGGAGACGGCTCGAGCGGAGGTTCAGGCGGTTCCGGAGGAGGTT
CTGGCGGATCAGGCGGTTCGGGGATGTATGAAAGCTTTATTGAGTCACTGCCATTCCTTAAATCTTTGGAGTTTTCTGAA
CGCCTGAAAGTAGTAGATGTGATAGGCACCAAAGTATACAACGATGGAGAACAAATCATTGCTCAGGGAGATTCGGCTGA
TTCTTTTTTCATTGTAGAATCTGGAGAAGTGAAAATTACTATGAAAAGAAAGGGTAAATCAGAAGTGGAAGAGAATGGTG
CAGTAGAAATCGCTCGATGCTCGCGGGGACAGTACTTTGGAGAGCTTGCCCTGGTAACTAACAAACCTCGAGCAGCTTCT
GCCCACGCCATTGGGACTGTCAAATGTTTAGCAATGGATGTGCAAGCATTTGAAAGGCTTCTGGGACCTTGCATGGAAAT
TATGAAAAGGAACATCGCTACCTATGAAGAACAGTTAGTTGCCCTGTTTGGAACGAACATGGATATTGTTGGGTCCGGTG
GATCCGGTGGCAGCGGAGGGACGTCAGGTGGATCTGGAGGGAGCTCCGGTAAGCCAACCGAGAACAATGAAGATTTTAAC
ATTGTGGCCGTCGCAAGCAATTTTGCCACCACTGATCTGGACGCAGACAGGGGCAAGCTGCCGGGAAAAAAACTGCCCCT
GGAGGTGTTGAAAGAGATGGAGGCAAACGCCAGAAAGGCCTGAGTTTAAAC

GGGGG) pBFB302 Sgf to Pme (SEQ ID NO:418)
GCGATCGCCATGAAAATGAAGAAATTTATCCCGGGCAGGTGCCACACATACGAGGGAGACAAGGAGAGTGCTCAGGGAGG
AATCGGCGAGGCTATCGTTGACATCCCTGAGATCCCAGGATTCAAAGATCTGGAACCAATGGAACAATTTATAGCGCAGG
TCGACCTTTGTGTGGACTGTACTACCGGATGCCTGAAGGGACTTGCAAATGTCCAATGTAGCGATCTCCTGAAGAAATGG
CTCCCCCAGAGATGTGCAACCTTTGCGAGCAAGATACAGGGGCAAGTCGATAAGATTAAGGGCGCCGGTGGAGACGGCTC
GACCGGAATGTATGAAAGCTTTATTGAGTCACTGCCATTCCTTAAATCTTTGGAGTTTTCTGAACGCCTGAAAGTAGTAG
ATGTGATAGGCACCAAAGTATACAACGATGGAGAACAAATCATTGCTCAGGGAGATTCGGCTGATTCTTTTTTCATTGTA
GAATCTGGAGAAGTGAAAATTACTATGAAAAGAAAGGGTAAATCAGAAGTGGAAGAGAATGGTGCAGTAGAAATCGCTCG
ATGCTCGCGGGGACAGTACTTTGGAGAGCTTGCCCTGGTAACTAACAAACCTCGAGCAGCTTCTGCCCACGCCATTGGGA
CTGTCAAATGTTTAGCAATGGATGTGCAAGCATTTGAAAGGCTTCTGGGACCTTGCATGGAAATTATGAAAAGGAACATC
GCTACCTATGAAGAACAGTTAGTTGCCCTGTTTGGAACGAACATGGATATTGTTGGGAGCTCCGGTAAGCCAACCGAGAA
CAATGAAGATTTTAACATTGTGGCCGTCGCAAGCAATTTTGCCACCACTGATCTGGACGCAGACAGGGGCAAGCTGCCGG
GAAAAAAACTGCCCCTGGAGGTGTTGAAAGAGATGGAGGCAAACGCCAGAAAGGCCGGCTGCACACGCGGTTGTCTGATT
TGCTTGTCTCACATCAAGTGCACATGAGTTTAAAC

HHHHH) pBFB303 Sgf to Pme (SEQ ID NO:419)
GCGATCGCCATGAAAATGAAGAAATTTATCCCGGGCAGGTGCCACACATACGAGGGAGACAAGGAGAGTGCTCAGGGAGG
AATCGGCGAGGCTATCGTTGACATCCCTGAGATCCCAGGATTCAAAGATCTGGAACCAATGGAACAATTTATAGCGCAGG
TCGACCTTTGTGTGGACTGTACTACCGGATGCCTGAAGGGACTTGCAAATGTCCAATGTAGCGATCTCCTGAAGAAATGG
CTCCCCCAGAGATGTGCAACCTTTGCGAGCAAGATACAGGGGCAAGTCGATAAGATTAAGGGCGCCGGTGGAGACGGCTC
GAGCGGAGGTTCAGGCGGTTCCGGAATGTATGAAAGCTTTATTGAGTCACTGCCATTCCTTAAATCTTTGGAGTTTTCTG
AACGCCTGAAAGTAGTAGATGTGATAGGCACCAAAGTATACAACGATGGAGAACAAATCATTGCTCAGGGAGATTCGGCT
GATTCTTTTTTCATTGTAGAATCTGGAGAAGTGAAAATTACTATGAAAAGAAAGGGTAAATCAGAAGTGGAAGAGAATGG
TGCAGTAGAAATCGCTCGATGCTCGCGGGGACAGTACTTTGGAGAGCTTGCCCTGGTAACTAACAAACCTCGAGCAGCTT
CTGCCCACGCCATTGGGACTGTCAAATGTTTAGCAATGGATGTGCAAGCATTTGAAAGGCTTCTGGGACCTTGCATGGAA
ATTATGAAAAGGAACATCGCTACCTATGAAGAACAGTTAGTTGCCCTGTTTGGAACGAACATGGATATTGTAGGGTCAGG
TGGATCTGGAGGGAGCTCCGGTAAGCCAACCGAGAACAATGAAGATTTTAACATTGTGGCCGTCGCAAGCAATTTTGCCA
CCACTGATCTGGACGCAGACAGGGGCAAGCTGCCGGGAAAAAAACTGCCCCTGGAGGTGTTGAAAGAGATGGAGGCAAAC
GCCAGAAAGGCCGGCTGCACACGCGGTTGTCTGATTTGCTTGTCTCACATCAAGTGCACATGAGTTTAAAC

IIIII) pBFB304 Sgf to Pme (SEQ ID NO:420)
GCGATCGCCATGAAAATGAAGAAATTTATCCCGGGCAGGTGCCACACATACGAGGGAGACAAGGAGAGTGCTCAGGGAGG
AATCGGCGAGGCTATCGTTGACATCCCTGAGATCCCAGGATTCAAAGATCTGGAACCAATGGAACAATTTATAGCGCAGG
TCGACCTTTGTGTGGACTGTACTACCGGATGCCTGAAGGGACTTGCAAATGTCCAATGTAGCGATCTCCTGAAGAAATGG
CTCCCCCAGAGATGTGCAACCTTTGCGAGCAAGATACAGGGGCAAGTCGATAAGATTAAGGGCGCCGGTGGAGACGGCTC
GAGCGGAGGTTCAGGCGGTTCCGGAGGAGGTTCTGGCGGATCAGGCGGTTCGGGGATGTATGAAAGCTTTATTGAGTCAC
TGCCATTCCTTAAATCTTTGGAGTTTTCTGAACGCCTGAAAGTAGTAGATGTGATAGGCACCAAAGTATACAACGATGGA
GAACAAATCATTGCTCAGGGAGATTCGGCTGATTCTTTTTTCATTGTAGAATCTGGAGAAGTGAAAATTACTATGAAAAG

*FIG. 67AV*

AAAGGGTAAATCAGAAGTGGAAGAGAATGGTGCAGTAGAAATCGCTCGATGCTCGCGGGGACAGTACTTTGGAGAGCTTG
CCCTGGTAACTAACAAACCTCGAGCAGCTTCTGCCCACGCCATTGGGACTGTCAAATGTTTAGCAATGGATGTGCAAGCA
TTTGAAAGGCTTCTGGGACCTTGCATGGAAATTATGAAAAGGAACATCGCTACCTATGAAGAACAGTTAGTTGCCCTGTT
TGGAACGAACATGGATATTGTTGGGTCCGGTGGATCCGGTGGCAGCGGAGGGACGTCAGGTGGATCTGGAGGGAGCTCCG
GTAAGCCAACCGAGAACAATGAAGATTTTAACATTGTGGCCGTCGCAAGCAATTTTGCCACCACTGATCTGGACGCAGAC
AGGGGCAAGCTGCCGGGAAAAAAACTGCCCCTGGAGGTGTTGAAAGAGATGGAGGCAAACGCCAGAAAGGCCGGCTGCAC
ACGCGGTTGTCTGATTTGCTTGTCTCACATCAAGTGCACATGAGTTTAAAC

JJJJJ) pBFB305 Sgf to Pme (SEQ ID NO:421)
GCGATCGCCATGGGCAGGTGCCACACATACGAGGGAGACAAGGAGAGTGCTCAGGGAGGAATCGGCGAGGCTATCGTTGA
CATCCCTGAGATCCCAGGATTCAAAGATCTGGAACCAATGGAACAATTTATAGCGCAGGTCGACCTTTGTGTGGACTGTA
CTACCGGATGCCTGAAGGGACTTGCAAATGTCCAATGTAGCGATCTCCTGAAGAAATGGCTCCCCCAGAGATGTGCAACC
TTTGCGAGCAAGATACAGGGGCAAGTCGATAAGATTAAGGGCGCCGGTGGAGACGGCTCGACCGGAATGTATGAAAGCTT
TATTGAGTCACTGCCATTCCTTAAATCTTTGGAGTTTTCTGAACGCCTGAAAGTAGTAGATGTGATAGGCACCAAAGTAT
ACAACGATGGAGAACAAATCATTGCTCAGGGAGATTCGGCTGATTCTTTTTTCATTGTAGAATCTGGAGAAGTGAAAATT
ACTATGAAAAGAAAGGGTAAATCAGAAGTGGAAGAGAATGGTGCAGTAGAAATCGCTCGATGCTCGCGGGGACAGTACTT
TGGAGAGCTTGCCCTGGTAACTAACAAACCTCGAGCAGCTTCTGCCCACGCCATTGGGACTGTCAAATGTTTAGCAATGG
ATGTGCAAGCATTTGAAAGGCTTCTGGGACCTTGCATGGAAATTATGAAAAGGAACATCGCTACCTATGAAGAACAGTTA
GTTGCCCTGTTTGGAACGAACATGGATATTGTTGGGAGCTCCGGTAAGCCAACCGAGAACAATGAAGATTTTAACATTGT
GGCCGTCGCAAGCAATTTTGCCACCACTGATCTGGACGCAGACAGGGGCAAGCTGCCGGGAAAAAAACTGCCCCTGGAGG
TGTTGAAAGAGATGGAGGCAAACGCCAGAAAGGCCGGCTGCACACGCGGTTGTCTGATTTGCTTGTCTCACATCAAGTGC
ACACCCAAAATGAAGAAATTTATCTGAGTTTAAAC

KKKKK) pBFB306 Sgf to Pme (SEQ ID NO:422)
GCGATCGCCATGGGCAGGTGCCACACATACGAGGGAGACAAGGAGAGTGCTCAGGGAGGAATCGGCGAGGCTATCGTTGA
CATCCCTGAGATCCCAGGATTCAAAGATCTGGAACCAATGGAACAATTTATAGCGCAGGTCGACCTTTGTGTGGACTGTA
CTACCGGATGCCTGAAGGGACTTGCAAATGTCCAATGTAGCGATCTCCTGAAGAAATGGCTCCCCCAGAGATGTGCAACC
TTTGCGAGCAAGATACAGGGGCAAGTCGATAAGATTAAGGGCGCCGGTGGAGACGGCTCGAGCGGAGGTTCAGGCGGTTC
CGGAATGTATGAAAGCTTTATTGAGTCACTGCCATTCCTTAAATCTTTGGAGTTTTCTGAACGCCTGAAAGTAGTAGATG
TGATAGGCACCAAAGTATACAACGATGGAGAACAAATCATTGCTCAGGGAGATTCGGCTGATTCTTTTTTCATTGTAGAA
TCTGGAGAAGTGAAAATTACTATGAAAAGAAAGGGTAAATCAGAAGTGGAAGAGAATGGTGCAGTAGAAATCGCTCGATG
CTCGCGGGGACAGTACTTTGGAGAGCTTGCCCTGGTAACTAACAAACCTCGAGCAGCTTCTGCCCACGCCATTGGGACTG
TCAAATGTTTAGCAATGGATGTGCAAGCATTTGAAAGGCTTCTGGGACCTTGCATGGAAATTATGAAAAGGAACATCGCT
ACCTATGAAGAACAGTTAGTTGCCCTGTTTGGAACGAACATGGATATTGTAGGGTCAGGTGGATCTGGAGGGAGCTCCGG
TAAGCCAACCGAGAACAATGAAGATTTTAACATTGTGGCCGTCGCAAGCAATTTTGCCACCACTGATCTGGACGCAGACA
GGGGCAAGCTGCCGGGAAAAAAACTGCCCCTGGAGGTGTTGAAAGAGATGGAGGCAAACGCCAGAAAGGCCGGCTGCACA
CGCGGTTGTCTGATTTGCTTGTCTCACATCAAGTGCACACCCAAAATGAAGAAATTTATCTGAGTTTAAAC

LLLLL) pBFB307 Sgf to Pme (SEQ ID NO:423)
GCGATCGCCATGGGCAGGTGCCACACATACGAGGGAGACAAGGAGAGTGCTCAGGGAGGAATCGGCGAGGCTATCGTTGA
CATCCCTGAGATCCCAGGATTCAAAGATCTGGAACCAATGGAACAATTTATAGCGCAGGTCGACCTTTGTGTGGACTGTA
CTACCGGATGCCTGAAGGGACTTGCAAATGTCCAATGTAGCGATCTCCTGAAGAAATGGCTCCCCCAGAGATGTGCAACC
TTTGCGAGCAAGATACAGGGGCAAGTCGATAAGATTAAGGGCGCCGGTGGAGACGGCTCGAGCGGAGGTTCAGGCGGTTC
CGGAGGAGGTTCTGGCGGATCAGGCGGTTCGGGGATGTATGAAAGCTTTATTGAGTCACTGCCATTCCTTAAATCTTTGG
AGTTTTCTGAACGCCTGAAAGTAGTAGATGTGATAGGCACCAAAGTATACAACGATGGAGAACAAATCATTGCTCAGGGA
GATTCGGCTGATTCTTTTTTCATTGTAGAATCTGGAGAAGTGAAAATTACTATGAAAAGAAAGGGTAAATCAGAAGTGGA
AGAGAATGGTGCAGTAGAAATCGCTCGATGCTCGCGGGGACAGTACTTTGGAGAGCTTGCCCTGGTAACTAACAAACCTC
GAGCAGCTTCTGCCCACGCCATTGGGACTGTCAAATGTTTAGCAATGGATGTGCAAGCATTTGAAAGGCTTCTGGGACCT
TGCATGGAAATTATGAAAAGGAACATCGCTACCTATGAAGAACAGTTAGTTGCCCTGTTTGGAACGAACATGGATATTGT
TGGGTCCGGTGGATCCGGTGGCAGCGGAGGGACGTCAGGTGGATCTGGAGGGAGCTCCGGTAAGCCAACCGAGAACAATG
AAGATTTTAACATTGTGGCCGTCGCAAGCAATTTTGCCACCACTGATCTGGACGCAGACAGGGGCAAGCTGCCGGGAAAA
AAACTGCCCCTGGAGGTGTTGAAAGAGATGGAGGCAAACGCCAGAAAGGCCGGCTGCACACGCGGTTGTCTGATTTGCTT
GTCTCACATCAAGTGCACACCCAAAATGAAGAAATTTATCTGAGTTTAAAC

MMMMM) pBFB308 Sgf to Pme (SEQ ID NO:424)
GCGATCGCCATGATCCCTGAGATCCCAGGATTCAAAGATCTGGAACCAATGGAACAATTTATAGCGCAGGTCGACCTTTG
TGTGGACTGTACTACCGGATGCCTGAAGGGACTTGCAAATGTCCAATGTAGCGATCTCCTGAAGAAATGGCTCCCCCAGA

FIG. 67AW

GATGTGCAACCTTTGCGAGCAAGATACAGGGGCAAGTCGATAAGATTAAGGGCGCCGGTGGAGACGGCTCGACCGGAATG
TATGAAAGCTTTATTGAGTCACTGCCATTCCTTAAATCTTTGGAGTTTTCTGAACGCCTGAAAGTAGTAGATGTGATAGG
CACCAAAGTATACAACGATGGAGAACAAATCATTGCTCAGGGAGATTCGGCTGATTCTTTTTTCATTGTAGAATCTGGAG
AAGTGAAAATTACTATGAAAAGAAAGGGTAAATCAGAAGTGGAAGAGAATGGTGCAGTAGAAATCGCTCGATGCTCGCGG
GGACAGTACTTTGGAGAGCTTGCCCTGGTAACTAACAAACCTCGAGCAGCTTCTGCCCACGCCATTGGGACTGTCAAATG
TTTAGCAATGGATGTGCAAGCATTTGAAAGGCTTCTGGGACCTTGCATGGAAATTATGAAAAGGAACATCGCTACCTATG
AAGAACAGTTAGTTGCCCTGTTTGGAACGAACATGGATATTGTTGGGAGCTCCGGTAAGCCAACCGAGAACAATGAAGAT
TTTAACATTGTGGCCGTCGCAAGCAATTTTGCCACCACTGATCTGGACGCAGACAGGGGCAAGCTGCCGGGAAAAAAACT
GCCCCTGGAGGTGTTGAAAGAGATGGAGGCAAACGCCAGAAAGGCCGGCTGCACACGCGGTTGTCTGATTTGCTTGTCTC
ACATCAAGTGCACACCCAAAATGAAGAAATTTATCCCGGGCAGGTGCCACACATACGAGGGAGACAAGGAGAGTGCTCAG
GGAGGAATCGGCGAGGCTATCGTTTGAGTTTAAAC

NNNNN) pBFB309 Sgf to Pme (SEQ ID NO:425)
GCGATCGCCATGATCCCTGAGATCCCAGGATTCAAAGATCTGGAACCAATGGAACAATTTATAGCGCAGGTCGACCTTTG
TGTGGACTGTACTACCGGATGCCTGAAGGGACTTGCAAATGTCCAATGTAGCGATCTCCTGAAGAAATGGCTCCCCCAGA
GATGTGCAACCTTTGCGAGCAAGATACAGGGGCAAGTCGATAAGATTAAGGGCGCCGGTGGAGACGGCTCGAGCGGAGGT
TCAGGCGGTTCCGGAATGTATGAAAGCTTTATTGAGTCACTGCCATTCCTTAAATCTTTGGAGTTTTCTGAACGCCTGAA
AGTAGTAGATGTGATAGGCACCAAAGTATACAACGATGGAGAACAAATCATTGCTCAGGGAGATTCGGCTGATTCTTTTT
TCATTGTAGAATCTGGAGAAGTGAAAATTACTATGAAAAGAAAGGGTAAATCAGAAGTGGAAGAGAATGGTGCAGTAGAA
ATCGCTCGATGCTCGCGGGGACAGTACTTTGGAGAGCTTGCCCTGGTAACTAACAAACCTCGAGCAGCTTCTGCCCACGC
CATTGGGACTGTCAAATGTTTAGCAATGGATGTGCAAGCATTTGAAAGGCTTCTGGGACCTTGCATGGAAATTATGAAAA
GGAACATCGCTACCTATGAAGAACAGTTAGTTGCCCTGTTTGGAACGAACATGGATATTGTAGGGTCAGGTGGATCTGGA
GGGAGCTCCGGTAAGCCAACCGAGAACAATGAAGATTTTAACATTGTGGCCGTCGCAAGCAATTTTGCCACCACTGATCT
GGACGCAGACAGGGGCAAGCTGCCGGGAAAAAAACTGCCCCTGGAGGTGTTGAAAGAGATGGAGGCAAACGCCAGAAAGG
CCGGCTGCACACGCGGTTGTCTGATTTGCTTGTCTCACATCAAGTGCACACCCAAAATGAAGAAATTTATCCCGGGCAGG
TGCCACACATACGAGGGAGACAAGGAGAGTGCTCAGGGAGGAATCGGCGAGGCTATCGTTTGAGTTTAAAC

OOOOO) pBFB310 Sgf to Pme (SEQ ID NO:426)
GCGATCGCCATGATCCCTGAGATCCCAGGATTCAAAGATCTGGAACCAATGGAACAATTTATAGCGCAGGTCGACCTTTG
TGTGGACTGTACTACCGGATGCCTGAAGGGACTTGCAAATGTCCAATGTAGCGATCTCCTGAAGAAATGGCTCCCCCAGA
GATGTGCAACCTTTGCGAGCAAGATACAGGGGCAAGTCGATAAGATTAAGGGCGCCGGTGGAGACGGCTCGAGCGGAGGT
TCAGGCGGTTCCGGAGGAGGTTCTGGCGGATCAGGCGGTTCGGGGATGTATGAAAGCTTTATTGAGTCACTGCCATTCCT
TAAATCTTTGGAGTTTTCTGAACGCCTGAAAGTAGTAGATGTGATAGGCACCAAAGTATACAACGATGGAGAACAAATCA
TTGCTCAGGGAGATTCGGCTGATTCTTTTTTCATTGTAGAATCTGGAGAAGTGAAAATTACTATGAAAAGAAAGGGTAAA
TCAGAAGTGGAAGAGAATGGTGCAGTAGAAATCGCTCGATGCTCGCGGGGACAGTACTTTGGAGAGCTTGCCCTGGTAAC
TAACAAACCTCGAGCAGCTTCTGCCCACGCCATTGGGACTGTCAAATGTTTAGCAATGGATGTGCAAGCATTTGAAAGGC
TTCTGGGACCTTGCATGGAAATTATGAAAAGGAACATCGCTACCTATGAAGAACAGTTAGTTGCCCTGTTTGGAACGAAC
ATGGATATTGTTGGGTCCGGTGGATCCGGTGGCAGCGGAGGGACGTCAGGTGGATCTGGAGGGAGCTCCGGTAAGCCAAC
CGAGAACAATGAAGATTTTAACATTGTGGCCGTCGCAAGCAATTTTGCCACCACTGATCTGGACGCAGACAGGGGCAAGC
TGCCGGGAAAAAAACTGCCCCTGGAGGTGTTGAAAGAGATGGAGGCAAACGCCAGAAAGGCCGGCTGCACACGCGGTTGT
CTGATTTGCTTGTCTCACATCAAGTGCACACCCAAAATGAAGAAATTTATCCCGGGCAGGTGCCACACATACGAGGGAGA
CAAGGAGAGTGCTCAGGGAGGAATCGGCGAGGCTATCGTTTGAGTTTAAAC

PPPPP) pBFB311 Sgf to Pme (SEQ ID NO:427)
GCGATCGCCATGGAACAATTTATAGCGCAGGTCGACCTTTGTGTGGACTGTACTACCGGATGCCTGAAGGGACTTGCAAA
TGTCCAATGTAGCGATCTCCTGAAGAAATGGCTCCCCCAGAGATGTGCAACCTTTGCGAGCAAGATACAGGGGCAAGTCG
ATAAGATTAAGGGCGCCGGTGGAGACGGCTCGACCGGAATGTATGAAAGCTTTATTGAGTCACTGCCATTCCTTAAATCT
TTGGAGTTTTCTGAACGCCTGAAAGTAGTAGATGTGATAGGCACCAAAGTATACAACGATGGAGAACAAATCATTGCTCA
GGGAGATTCGGCTGATTCTTTTTTCATTGTAGAATCTGGAGAAGTGAAAATTACTATGAAAAGAAAGGGTAAATCAGAAG
TGGAAGAGAATGGTGCAGTAGAAATCGCTCGATGCTCGCGGGGACAGTACTTTGGAGAGCTTGCCCTGGTAACTAACAAA
CCTCGAGCAGCTTCTGCCCACGCCATTGGGACTGTCAAATGTTTAGCAATGGATGTGCAAGCATTTGAAAGGCTTCTGGG
ACCTTGCATGGAAATTATGAAAAGGAACATCGCTACCTATGAAGAACAGTTAGTTGCCCTGTTTGGAACGAACATGGATA
TTGTTGGGAGCTCCGGTAAGCCAACCGAGAACAATGAAGATTTTAACATTGTGGCCGTCGCAAGCAATTTTGCCACCACT
GATCTGGACGCAGACAGGGGCAAGCTGCCGGGAAAAAAACTGCCCCTGGAGGTGTTGAAAGAGATGGAGGCAAACGCCAG
AAAGGCCGGCTGCACACGCGGTTGTCTGATTTGCTTGTCTCACATCAAGTGCACACCCAAAATGAAGAAATTTATCCCGG
GCAGGTGCCACACATACGAGGGAGACAAGGAGAGTGCTCAGGGAGGAATCGGCGAGGCTATCGTTGACATCCCTGAGATC
CCAGGATTCAAAGATCTGGAATGAGTTTAAAC

*FIG. 67AX*

QQQQQ) pBFB312 Sgf to Pme (SEQ ID NO:428)
GCGATCGCCATGGAACAATTTATAGCGCAGGTCGACCTTTGTGTGGACTGTACTACCGGATGCCTGAAGGGACTTGCAAA
TGTCCAATGTAGCGATCTCCTGAAGAAATGGCTCCCCCAGAGATGTGCAACCTTTGCGAGCAAGATACAGGGGCAAGTCG
ATAAGATTAAGGGCGCCGGTGGAGACGGCTCGAGCGGAGGTTCAGGCGGTTCCGGAATGTATGAAAGCTTTATTGAGTCA
CTGCCATTCCTTAAATCTTTGGAGTTTTCTGAACGCCTGAAAGTAGTAGATGTGATAGGCACCAAAGTATACAACGATGG
AGAACAAATCATTGCTCAGGGAGATTCGGCTGATTCTTTTTTCATTGTAGAATCTGGAGAAGTGAAAATTACTATGAAAA
GAAAGGGTAAATCAGAAGTGGAAGAGAATGGTGCAGTAGAAATCGCTCGATGCTCGCGGGGACAGTACTTTGGAGAGCTT
GCCCTGGTAACTAACAAACCTCGAGCAGCTTCTGCCCACGCCATTGGGACTGTCAAATGTTTAGCAATGGATGTGCAAGC
ATTTGAAAGGCTTCTGGGACCTTGCATGGAAATTATGAAAAGGAACATCGCTACCTATGAAGAACAGTTAGTTGCCCTGT
TTGGAACGAACATGGATATTGTAGGGTCAGGTGGATCTGGAGGGAGCTCCGGTAAGCCAACCGAGAACAATGAAGATTTT
AACATTGTGGCCGTCGCAAGCAATTTTGCCACCACTGATCTGGACGCAGACAGGGGCAAGCTGCCGGGAAAAAAACTGCC
CCTGGAGGTGTTGAAAGAGATGGAGGCAAACGCCAGAAAGGCCGGCTGCACACGCGGTTGTCTGATTTGCTTGTCTCACA
TCAAGTGCACACCCAAAATGAAGAAATTTATCCCGGGCAGGTGCCACACATACGAGGGAGACAAGGAGAGTGCTCAGGGA
GGAATCGGCGAGGCTATCGTTGACATCCCTGAGATCCCAGGATTCAAAGATCTGGAATGAGTTTAAAC

RRRRR) pBFB313 Sgf to Pme (SEQ ID NO:429)
GCGATCGCCATGGAACAATTTATAGCGCAGGTCGACCTTTGTGTGGACTGTACTACCGGATGCCTGAAGGGACTTGCAAA
TGTCCAATGTAGCGATCTCCTGAAGAAATGGCTCCCCCAGAGATGTGCAACCTTTGCGAGCAAGATACAGGGGCAAGTCG
ATAAGATTAAGGGCGCCGGTGGAGACGGCTCGAGCGGAGGTTCAGGCGGTTCCGGAGGAGGTTCTGGCGGATCAGGCGGT
TCGGGGATGTATGAAAGCTTTATTGAGTCACTGCCATTCCTTAAATCTTTGGAGTTTTCTGAACGCCTGAAAGTAGTAGA
TGTGATAGGCACCAAAGTATACAACGATGGAGAACAAATCATTGCTCAGGGAGATTCGGCTGATTCTTTTTTCATTGTAG
AATCTGGAGAAGTGAAAATTACTATGAAAAGAAAGGGTAAATCAGAAGTGGAAGAGAATGGTGCAGTAGAAATCGCTCGA
TGCTCGCGGGGACAGTACTTTGGAGAGCTTGCCCTGGTAACTAACAAACCTCGAGCAGCTTCTGCCCACGCCATTGGGAC
TGTCAAATGTTTAGCAATGGATGTGCAAGCATTTGAAAGGCTTCTGGGACCTTGCATGGAAATTATGAAAAGGAACATCG
CTACCTATGAAGAACAGTTAGTTGCCCTGTTTGGAACGAACATGGATATTGTTGGGTCCGGTGGATCCGGTGGCAGCGGA
GGGACGTCAGGTGGATCTGGAGGGAGCTCCGGTAAGCCAACCGAGAACAATGAAGATTTTAACATTGTGGCCGTCGCAAG
CAATTTTGCCACCACTGATCTGGACGCAGACAGGGGCAAGCTGCCGGGAAAAAAACTGCCCCTGGAGGTGTTGAAAGAGA
TGGAGGCAAACGCCAGAAAGGCCGGCTGCACACGCGGTTGTCTGATTTGCTTGTCTCACATCAAGTGCACACCCAAAATG
AAGAAATTTATCCCGGGCAGGTGCCACACATACGAGGGAGACAAGGAGAGTGCTCAGGGAGGAATCGGCGAGGCTATCGT
TGACATCCCTGAGATCCCAGGATTCAAAGATCTGGAATGAGTTTAAAC

SSSSS) pBFB314 Sgf to Pme (SEQ ID NO:430)
GCGATCGCCATGCAGAGATGTGCAACCTTTGCGAGCAAGATACAGGGGCAAGTCGATAAGATTAAGGGCGCCGGTGGAGA
CGGCTCGACCGGAATGTATGAAAGCTTTATTGAGTCACTGCCATTCCTTAAATCTTTGGAGTTTTCTGAACGCCTGAAAG
TAGTAGATGTGATAGGCACCAAAGTATACAACGATGGAGAACAAATCATTGCTCAGGGAGATTCGGCTGATTCTTTTTTC
ATTGTAGAATCTGGAGAAGTGAAAATTACTATGAAAAGAAAGGGTAAATCAGAAGTGGAAGAGAATGGTGCAGTAGAAAT
CGCTCGATGCTCGCGGGGACAGTACTTTGGAGAGCTTGCCCTGGTAACTAACAAACCTCGAGCAGCTTCTGCCCACGCCA
TTGGGACTGTCAAATGTTTAGCAATGGATGTGCAAGCATTTGAAAGGCTTCTGGGACCTTGCATGGAAATTATGAAAAGG
AACATCGCTACCTATGAAGAACAGTTAGTTGCCCTGTTTGGAACGAACATGGATATTGTTGGGAGCTCCGGTAAGCCAAC
CGAGAACAATGAAGATTTTAACATTGTGGCCGTCGCAAGCAATTTTGCCACCACTGATCTGGACGCAGACAGGGGCAAGC
TGCCGGGAAAAAAACTGCCCCTGGAGGTGTTGAAAGAGATGGAGGCAAACGCCAGAAAGGCCGGCTGCACACGCGGTTGT
CTGATTTGCTTGTCTCACATCAAGTGCACACCCAAAATGAAGAAATTTATCCCGGGCAGGTGCCACACATACGAGGGAGA
CAAGGAGAGTGCTCAGGGAGGAATCGGCGAGGCTATCGTTGACATCCCTGAGATCCCAGGATTCAAAGATCTGGAACCAA
TGGAACAATTTATAGCGCAGGTCGACCTTTGTGTGGACTGTACTACCGGATGCCTGAAGGGACTTGCAAATGTCCAATGT
AGCGATCTCCTGAAGAAATGGCTCTGAGTTTAAAC

TTTTT) pBFB315 Sgf to Pme (SEQ ID NO:431)
GCGATCGCCATGCAGAGATGTGCAACCTTTGCGAGCAAGATACAGGGGCAAGTCGATAAGATTAAGGGCGCCGGTGGAGA
CGGCTCGAGCGGAGGTTCAGGCGGTTCCGGAATGTATGAAAGCTTTATTGAGTCACTGCCATTCCTTAAATCTTTGGAGT
TTTCTGAACGCCTGAAAGTAGTAGATGTGATAGGCACCAAAGTATACAACGATGGAGAACAAATCATTGCTCAGGGAGAT
TCGGCTGATTCTTTTTTCATTGTAGAATCTGGAGAAGTGAAAATTACTATGAAAAGAAAGGGTAAATCAGAAGTGGAAGA
GAATGGTGCAGTAGAAATCGCTCGATGCTCGCGGGGACAGTACTTTGGAGAGCTTGCCCTGGTAACTAACAAACCTCGAG
CAGCTTCTGCCCACGCCATTGGGACTGTCAAATGTTTAGCAATGGATGTGCAAGCATTTGAAAGGCTTCTGGGACCTTGC
ATGGAAATTATGAAAAGGAACATCGCTACCTATGAAGAACAGTTAGTTGCCCTGTTTGGAACGAACATGGATATTGTAGG
GTCAGGTGGATCTGGAGGGAGCTCCGGTAAGCCAACCGAGAACAATGAAGATTTTAACATTGTGGCCGTCGCAAGCAATT
TTGCCACCACTGATCTGGACGCAGACAGGGGCAAGCTGCCGGGAAAAAAACTGCCCCTGGAGGTGTTGAAAGAGATGGAG

*FIG. 67AY*

GCAAACGCCAGAAAGGCCGGCTGCACACGCGGTTGTCTGATTTGCTTGTCTCACATCAAGTGCACACCCAAAATGAAGAA
ATTTATCCCGGGCAGGTGCCACACATACGAGGGAGACAAGGAGAGTGCTCAGGGAGGAATCGGCGAGGCTATCGTTGACA
TCCCTGAGATCCCAGGATTCAAAGATCTGGAACCAATGGAACAATTTATAGCGCAGGTCGACCTTTGTGTGGACTGTACT
ACCGGATGCCTGAAGGGACTTGCAAATGTCCAATGTAGCGATCTCCTGAAGAAATGGCTCTGAGTTTAAAC

UUUUU) pBFB316 Sgf to Pme (SEQ ID NO:432)
GCGATCGCCATGCAGAGATGTGCAACCTTTGCGAGCAAGATACAGGGGCAAGTCGATAAGATTAAGGGCGCCGGTGGAGA
CGGCTCGAGCGGAGGTTCAGGCGGTTCCGGAGGAGGTTCTGGCGGATCAGGCGGTTCGGGGATGTATGAAAGCTTTATTG
AGTCACTGCCATTCCTTAAATCTTTGGAGTTTTCTGAACGCCTGAAAGTAGTAGATGTGATAGGCACCAAAGTATACAAC
GATGGAGAACAAATCATTGCTCAGGGAGATTCGGCTGATTCTTTTTTCATTGTAGAATCTGGAGAAGTGAAAATTACTAT
GAAAAGAAAGGGTAAATCAGAAGTGGAAGAGAATGGTGCAGTAGAAATCGCTCGATGCTCGCGGGGACAGTACTTTGGAG
AGCTTGCCCTGGTAACTAACAAACCTCGAGCAGCTTCTGCCCACGCCATTGGGACTGTCAAATGTTTAGCAATGGATGTG
CAAGCATTTGAAAGGCTTCTGGGACCTTGCATGGAAATTATGAAAAGGAACATCGCTACCTATGAAGAACAGTTAGTTGC
CCTGTTTGGAACGAACATGGATATTGTTGGGTCCGGTGGATCCGGTGGCAGCGGAGGGACGTCAGGTGGATCTGGAGGGA
GCTCCGGTAAGCCAACCGAGAACAATGAAGATTTTAACATTGTGGCCGTCGCAAGCAATTTTGCCACCACTGATCTGGAC
GCAGACAGGGGCAAGCTGCCGGGAAAAAAACTGCCCCTGGAGGTGTTGAAAGAGATGGAGGCAAACGCCAGAAAGGCCGG
CTGCACACGCGGTTGTCTGATTTGCTTGTCTCACATCAAGTGCACACCCAAAATGAAGAAATTTATCCCGGGCAGGTGCC
ACACATACGAGGGAGACAAGGAGAGTGCTCAGGGAGGAATCGGCGAGGCTATCGTTGACATCCCTGAGATCCCAGGATTC
AAAGATCTGGAACCAATGGAACAATTTATAGCGCAGGTCGACCTTTGTGTGGACTGTACTACCGGATGCCTGAAGGGACT
TGCAAATGTCCAATGTAGCGATCTCCTGAAGAAATGGCTCTGAGTTTAAAC

VVVVV) pBFB335 Sgf to Pme (SEQ ID NO:433)
GCGATCGCCATGACCGCTATCCTCAGCGTGGTGCCATTTCACCACGGCTTCGGCATGTTCACCACGCTGGGCTACTTGAT
CTGCGGCTTTCGGGTCGTGCTCATGTACCGCTTCGAGGAGGAGCTATTCTTGCGCAGCTTGCAAGACTATAAGATTCAAT
CTGCCCTGCTGGTGCCCACACTATTTAGCTTCTTCGCTAAGAGCACTCTCATCGACAAGTACGACCTAAGCAACTTGCAC
GAGATCGCCAGCGGCGGGGCGCCGCTCAGCAAGGAGGTAGGTGAGGCCGTGGCCAAACGCTTCCACCTACCAGGCATCCG
CCAGGGCTACGGCCTGACAGAAACAACCAGCGCCATTCTGATCACCCCCGAAGGGGACGACAAGCCTGGCGCAGTAGGCA
AGGTGGTGCCCTTCTTCGAGGCTAAGGTGGTGGACTTGGACACTGGTAAGACACTGGGTGTGAACCAGCGCGGCGAGCTG
TGCGTCCGTGGCCCCATGATCATGAGCGGCTACGTTAACAACCCCGAGGCTACAAACGCTCTCATCGACAAGGACGGCTG
GCTGCACAGCGGCGACATCGCCTACTGGGACGAGGACGAGCACTTCTTCATCGTGGACCGGCTGAAGAGCCTGATCAAAT
ACAAGGGCTACCAGGTAGCCCCAGCCGAACTGGAGAGCATCCTGCTGCAACACCCCAACATCTTCGACGCCGGGGTCGCC
GGCCTGCCCGACGACGATGCCGGCGAGCTGCCCGCCGCAGTCGTCGTGCTGGAACACGGTAAAACCATGACCGAGAAGGA
GATCGTGGACTATGTGGCCAGCCAGGTTACAACCGCCAAGAAGCTGCGCGGTGGTGTTGTGTTCGTGGACGAGGTGCCTA
AAGGACTGACCGGCAAGTTGGACGCCCGCAAGATCCGCGAGATTCTCATTAAGGCCAAGAAGGGCTCGAGCGGACGAAAG
AGAGATCGGCTGGGGACCCTGGGGATTGGCGGGAGCTCTGGGGGAGGGTCTGGGGGTGGTGGTAGTGGCGGTGGGAACGG
CAGGTTCCTGACACTTAAGCCTCTTCCGGATAGTATTATCCAGGAGTCCCTTGAGATCCAGCAAGGGGTGAATCCTTTTT
TTATCGGGCGAAGCGAGGACTGTAATTGCAAGATCGAAGATAACAGACTCAGTAGAGTGCACTGCTTTATTTCAAGAAG
AGGCACGCAGTGGGAAAATCTATGTACGAATCCCCAGCTCAGGGCCTCGACGATATTTGGTACTGTCATACAGGCACAAA
TGTATCCTACCTGAATAACAATCGAATGATCCAAGGCACCAAATTCCTTCTGCAGGATGGCGACGAAATCAAGATTATCT
GGGATAAGAATAACAAATTCGTTATAGGTTTTAAGGTCGAGATCAATGATACAACCGGGCTCTTCAACGAGGGGCTGGGT
ATGCTGCAGGAGCAGCGGGTCGTACTGAAGCAGACTGCTGAAGAGAAAGACCTCGTAAAGAAACTTGGATCCGGAGGCGC
CAAAAACATTAAGAAGGGCCCAGCGCCATTCTACCCACTCGAAGACGGGACCGCCGGCGAGCAGCTGCACAAAGCCATGA
AGCGCTACGCCCTGGTGCCCGGCACCATCGCCTTTACCGACGCACATATCGAGGTGGACATTACCTACGCCGAGTACTTC
GAGATGAGCGTTCGGCTGGCAGAAGCTATGAAGCGCTATGGGCTGAATACAAACCATCGGATCGTGGTGTGCAGCGAGAA
TAGCTTGCAGTTCTTCATGCCCGTGTTGGGTGCCCTGTTCATCGGTGTGGCTGTGGCCCCAGCTAACGACATCTACAACG
AGCGCGAGCTGCTGAACAGCATGGGCATCAGCCAGCCCACCGTCGTATTCGTGAGCAAGAAAGGGCTGCAAAAGATCCTC
AACGTGCAAAAGAAGCTACCGATCATACAAAAGATCATCATCATGGATAGCAAGACCGACTACCAGGGCTTCCAAAGCAT
GTACACCTTCGTGACTTCCCATTTGCCACCCGGCTTCAACGAGTACGACTTCGTGCCCGAGAGCTTCGACCGGGACAAAA
CCATCGCCCTGATCATGAACAGTAGTGGCAGTACCGGATTGCCCAAGGGCGTAGCCCTACCGCACCGCACCGCTTGTGTC
CGATTCAGTCATGCCCGCGACCCCATCTTCGGCAACCAGATCATCCCCTGAGTTTAAAC

WWWWW) pBFB336 Sgf to Pme (SEQ ID NO:434)
GCGATCGCCATGACCGCTATCCTCAGCGTGGTGCCATTTCACCACGGCTTCGGCATGTTCACCACGCTGGGCTACTTGAT
CTGCGGCTTTCGGGTCGTGCTCATGTACCGCTTCGAGGAGGAGCTATTCTTGCGCAGCTTGCAAGACTATAAGATTCAAT
CTGCCCTGCTGGTGCCCACACTATTTAGCTTCTTCGCTAAGAGCACTCTCATCGACAAGTACGACCTAAGCAACTTGCAC
GAGATCGCCAGCGGCGGGGCGCCGCTCAGCAAGGAGGTAGGTGAGGCCGTGGCCAAACGCTTCCACCTACCAGGCATCCG
CCAGGGCTACGGCCTGACAGAAACAACCAGCGCCATTCTGATCACCCCCGAAGGGGACGACAAGCCTGGCGCAGTAGGCA

FIG. 67AZ

AGGTGGTGCCCTTCTTCGAGGCTAAGGTGGTGGACTTGGACACTGGTAAGACACTGGGTGTGAACCAGCGCGGCGAGCTG
TGCGTCCGTGGCCCCATGATCATGAGCGGCTACGTTAACAACCCCGAGGCTACAAACGCTCTCATCGACAAGGACGGCTG
GCTGCACAGCGGCGACATCGCCTACTGGGACGAGGACGAGCACTTCTTCATCGTGGACCGGCTGAAGAGCCTGATCAAAT
ACAAGGGCTACCAGGTAGCCCCAGCCGAACTGGAGAGCATCCTGCTGCAACACCCCAACATCTTCGACGCCGGGGTCGCC
GGCCTGCCCGACGACGATGCCGGCGAGCTGCCCGCCGCAGTCGTCGTGCTGGAACACGGTAAAACCATGACCGAGAAGGA
GATCGTGGACTATGTGGCCAGCCAGGTTACAACCGCCAAGAAGCTGCGCGGTGGTGTTGTGTTCGTGGACGAGGTGCCTA
AAGGACTGACCGGCAAGTTGGACGCCCGCAAGATCCGCGAGATTCTCATTAAGGCCAAGAAGGGAGGTTCTGGAGGATCT
GGCTCGAGCGGACGAAAGAGAGATCGGCTGGGGACCCTGGGGATTGGCGGGAGCTCTGGGGGAGGGTCTGGGGGTGGTGG
TAGTGGCGGTGGGAACGGCAGGTTCCTGACACTTAAGCCTCTTCCGGATAGTATTATCCAGGAGTCCCTTGAGATCCAGC
AAGGGGTGAATCCTTTTTTTATCGGGCGAAGCGAGGACTGTAATTGCAAGATCGAAGATAACAGACTCAGTAGAGTGCAC
TGCTTTATTTTCAAGAAGAGGCACGCAGTGGGAAAATCTATGTACGAATCCCCAGCTCAGGGCCTCGACGATATTTGGTA
CTGTCATACAGGCACAAATGTATCCTACCTGAATAACAATCGAATGATCCAAGGCACCAAATTCCTTCTGCAGGATGGCG
ACGAAATCAAGATTATCTGGGATAAGAATAACAAATTCGTTATAGGTTTTAAGGTCGAGATCAATGATACAACCGGGCTC
TTCAACGAGGGGCTGGGTATGCTGCAGGAGCAGCGGGTCGTACTGAAGCAGACTGCTGAAGAGAAAGACCTCGTAAAGAA
ACTTGGATCCGGAGGCTCCGGCGGCTCCGGCGGAGCCAAAAACATTAAGAAGGGCCCAGCGCCATTCTACCCACTCGAAG
ACGGGACCGCCGGCGAGCAGCTGCACAAAGCCATGAAGCGCTACGCCCTGGTGCCCGGCACCATCGCCTTTACCGACGCA
CATATCGAGGTGGACATTACCTACGCCGAGTACTTCGAGATGAGCGTTCGGCTGGCAGAAGCTATGAAGCGCTATGGGCT
GAATACAAACCATCGGATCGTGGTGTGCAGCGAGAATAGCTTGCAGTTCTTCATGCCCGTGTTGGGTGCCCTGTTCATCG
GTGTGGCTGTGGCCCCAGCTAACGACATCTACAACGAGCGCGAGCTGCTGAACAGCATGGGCATCAGCCAGCCCACCGTC
GTATTCGTGAGCAAGAAAGGGCTGCAAAAGATCCTCAACGTGCAAAAGAAGCTACCGATCATACAAAAGATCATCATCAT
GGATAGCAAGACCGACTACCAGGGCTTCCAAAGCATGTACACCTTCGTGACTTCCCATTTGCCACCCGGCTTCAACGAGT
ACGACTTCGTGCCCGAGAGCTTCGACCGGGACAAAACCATCGCCCTGATCATGAACAGTAGTGGCAGTACCGGATTGCCC
AAGGGCGTAGCCCTACCGCACCGCACCGCTTGTGTCCGATTCAGTCATGCCCGCGACCCCATCTTCGGCAACCAGATCAT
CCCCTGAGTTTAAAC

XXXXX) pBFB337 Sgf to Pme (SEQ ID NO:435)
GCGATCGCCATGACCGCTATCCTCAGCGTGGTGCCATTTCACCACGGCTTCGGCATGTTCACCACGCTGGGCTACTTGAT
CTGCGGCTTTCGGGTCGTGCTCATGTACCGCTTCGAGGAGGAGCTATTCTTGCGCAGCTTGCAAGACTATAAGATTCAAT
CTGCCCTGCTGGTGCCCACACTATTTAGCTTCTTCGCTAAGAGCACTCTCATCGACAAGTACGACCTAAGCAACTTGCAC
GAGATCGCCAGCGGCGGGGCGCCGCTCAGCAAGGAGGTAGGTGAGGCCGTGGCCAAACGCTTCCACCTACCAGGCATCCG
CCAGGGCTACGGCCTGACAGAAACAACCAGCGCCATTCTGATCACCCCCGAAGGGGACGACAAGCCTGGCGCAGTAGGCA
AGGTGGTGCCCTTCTTCGAGGCTAAGGTGGTGGACTTGGACACTGGTAAGACACTGGGTGTGAACCAGCGCGGCGAGCTG
TGCGTCCGTGGCCCCATGATCATGAGCGGCTACGTTAACAACCCCGAGGCTACAAACGCTCTCATCGACAAGGACGGCTG
GCTGCACAGCGGCGACATCGCCTACTGGGACGAGGACGAGCACTTCTTCATCGTGGACCGGCTGAAGAGCCTGATCAAAT
ACAAGGGCTACCAGGTAGCCCCAGCCGAACTGGAGAGCATCCTGCTGCAACACCCCAACATCTTCGACGCCGGGGTCGCC
GGCCTGCCCGACGACGATGCCGGCGAGCTGCCCGCCGCAGTCGTCGTGCTGGAACACGGTAAAACCATGACCGAGAAGGA
GATCGTGGACTATGTGGCCAGCCAGGTTACAACCGCCAAGAAGCTGCGCGGTGGTGTTGTGTTCGTGGACGAGGTGCCTA
AAGGACTGACCGGCAAGTTGGACGCCCGCAAGATCCGCGAGATTCTCATTAAGGCCAAGAAGGGTTCATCTGGTGGATCA
GGTGGAAGTGGAGGAGGTTCTGGAGGATCTGGCTCGAGCGGACGAAAGAGAGATCGGCTGGGGACCCTGGGGATTGGCGG
GAGCTCTGGGGGAGGGTCTGGGGGTGGTGGTAGTGGCGGTGGGAACGGCAGGTTCCTGACACTTAAGCCTCTTCCGGATA
GTATTATCCAGGAGTCCCTTGAGATCCAGCAAGGGGTGAATCCTTTTTTTATCGGGCGAAGCGAGGACTGTAATTGCAAG
ATCGAAGATAACAGACTCAGTAGAGTGCACTGCTTTATTTTCAAGAAGAGGCACGCAGTGGGAAAATCTATGTACGAATC
CCCAGCTCAGGGCCTCGACGATATTTGGTACTGTCATACAGGCACAAATGTATCCTACCTGAATAACAATCGAATGATCC
AAGGCACCAAATTCCTTCTGCAGGATGGCGACGAAATCAAGATTATCTGGGATAAGAATAACAAATTCGTTATAGGTTTT
AAGGTCGAGATCAATGATACAACCGGGCTCTTCAACGAGGGGCTGGGTATGCTGCAGGAGCAGCGGGTCGTACTGAAGCA
CACTGCTGAAGAGAAAGACCTCGTAAAGAAACTTGGATCCGGAGGCTCCGGCGGCTCCGGCGGAACCTCAGGAGGCAGTG
GAGGAAGTTCTGGAGCCAAAAACATTAAGAAGGGCCCAGCGCCATTCTACCCACTCGAAGACGGGACCGCCGGCGAGCAG
CTGCACAAAGCCATGAAGCGCTACGCCCTGGTGCCCGGCACCATCGCCTTTACCGACGCACATATCGAGGTGGACATTAC
CTACGCCGAGTACTTCGAGATGAGCGTTCGGCTGGCAGAAGCTATGAAGCGCTATGGGCTGAATACAAACCATCGGATCG
TGGTGTGCAGCGAGAATAGCTTGCAGTTCTTCATGCCCGTGTTGGGTGCCCTGTTCATCGGTGTGGCTGTGGCCCCAGCT
AACGACATCTACAACGAGCGCGAGCTGCTGAACAGCATGGGCATCAGCCAGCCCACCGTCGTATTCGTGAGCAAGAAAGG
GCTGCAAAAGATCCTCAACGTGCAAAAGAAGCTACCGATCATACAAAAGATCATCATCATGGATAGCAAGACCGACTACC
AGGGCTTCCAAAGCATGTACACCTTCGTGACTTCCCATTTGCCACCCGGCTTCAACGAGTACGACTTCGTGCCCGAGAGC
TTCGACCGGGACAAAACCATCGCCCTGATCATGAACAGTAGTGGCAGTACCGGATTGCCCAAGGGCGTAGCCCTACCGCA
CCGCACCGCTTGTGTCCGATTCAGTCATGCCCGCGACCCCATCTTCGGCAACCAGATCATCCCCTGAGTTTAAAC

YYYYY) pBFB338 Sgf to Pme (SEQ ID NO:436)

FIG. 67BA

GCGATCGCCATGCCTGGCGCAGTAGGCAAGGTGGTGCCCTTCTTCGAGGCTAAGGTGGTGGACTTGGACACCGGTAAGAC
ACTGGGTGTGAACCAGCGCGGCGAGCTGTGCGTCCGTGGCCCCATGATCATGAGCGGCTACGTTAACAACCCCGAGGCTA
CAAACGCTCTCATCGACAAGGACGGCTGGCTGCACAGCGGCGACATCGCCTACTGGGACGAGGACGAGCACTTCTTCATC
GTGGACCGGCTGAAGAGCCTGATCAAATACAAGGGCTACCAGGTAGCCCCAGCCGAACTGGAGAGCATCCTGCTGCAACA
CCCCAACATCTTCGACGCCGGGGTCGCCGGCCTGCCCGACGACGATGCCGGCGAGCTGCCCGCCGCAGTCGTCGTGCTGG
AACACGGTAAAACCATGACCGAGAAGGAGATCGTGGACTATGTGGCCAGCCAGGTTACAACCGCCAAGAAGCTGCGCGGT
GGTGTTGTGTTCGTGGACGAGGTGCCTAAAGGACTGACCGGCAAGTTGGACGCCCGCAAGATCCGCGAGATTCTCATTAA
GGCCAAGAAGGGCTCGAGCGGACGAAAGAGAGATCGGCTGGGGACCCTGGGGATTGGCGGGAGCTCTGGGGGAGGGTCTG
GGGGTGGTGGTAGTGGCGGTGGGAACGGCAGGTTCCTGACACTTAAGCCTCTTCCGGATAGTATTATCCAGGAGTCCCTT
GAGATCCAGCAAGGGGTGAATCCTTTTTTTATCGGGCGAAGCGAGGACTGTAATTGCAAGATCGAAGATAACAGACTCAG
TAGAGTGCACTGCTTTATTTTCAAGAAGAGGCACGCAGTGGGAAAATCTATGTACGAATCCCCAGCTCAGGGCCTCGACG
ATATTTGGTACTGTCATACAGGCACAAATGTATCCTACCTGAATAACAATCGAATGATCCAAGGCACCAAATTCCTTCTG
CAGGATGGCGACGAAATCAAGATTATCTGGGATAAGAATAACAAATTCGTTATAGGTTTTAAGGTCGAGATCAATGATAC
AACCGGGCTCTTCAACGAGGGGCTGGGTATGCTGCAGGAGCAGCGGGTCGTACTGAAGCAGACTGCTGAAGAGAAAGACC
TCGTAAAGAAACTTGGATCCGGAGGCGCCAAAAACATTAAGAAGGGCCCAGCGCCATTCTACCCACTCGAAGACGGGACC
GCCGGCGAGCAGCTGCACAAAGCCATGAAGCGCTACGCCCTGGTGCCCGGCACCATCGCCTTTACCGACGCACATATCGA
GGTGGACATTACCTACGCCGAGTACTTCGAGATGAGCGTTCGGCTGGCAGAAGCTATGAAGCGCTATGGGCTGAATACAA
ACCATCGGATCGTGGTGTGCAGCGAGAATAGCTTGCAGTTCTTCATGCCCGTGTTGGGTGCCCTGTTCATCGGTGTGGCT
GTGGCCCCAGCTAACGACATCTACAACGAGCGCGAGCTGCTGAACAGCATGGGCATCAGCCAGCCCACCGTCGTATTCGT
GAGCAAGAAAGGGCTGCAAAAGATCCTCAACGTGCAAAAGAAGCTACCGATCATACAAAAGATCATCATCATGGATAGCA
AGACCGACTACCAGGGCTTCCAAAGCATGTACACCTTCGTGACTTCCCATTTGCCACCCGGCTTCAACGAGTACGACTTC
GTGCCCGAGAGCTTCGACCGGGACAAAACCATCGCCCTGATCATGAACAGTAGTGGCAGTACCGGATTGCCCAAGGGCGT
AGCCCTACCGCACCGCACCGCTTGTGTCCGATTCAGTCATGCCCGCGACCCCATCTTCGGCAACCAGATCATCCCCGACA
CCGCTATCCTCAGCGTGGTGCCATTTCACCACGGCTTCGGCATGTTCACCACGCTGGGCTACTTGATCTGCGGCTTTCGG
GTCGTGCTCATGTACCGCTTCGAGGAGGAGCTATTCTTGCGCAGCTTGCAAGACTATAAGATTCAATCTGCCCTGCTGGT
GCCCACACTATTTAGCTTCTTCGCTAAGAGCACTCTCATCGACAAGTACGACCTAAGCAACTTGCACGAGATCGCCAGCG
GCGGGGCGCCGCTCAGCAAGGAGGTAGGTGAGGCCGTGGCCAAACGCTTCCACCTACCAGGCATCCGCCAGGGCTACGGC
CTGACAGAAACAACCAGCGCCATTCTGATCACCCCCGAAGGGTGAGTTTAAAC

ZZZZZ) pBFB339 Sgf to Pme (SEQ ID NO:437)
CGATCGCCATGCCTGGCGCAGTAGGCAAGGTGGTGCCCTTCTTCGAGGCTAAGGTGGTGGACTTGGACACCGGTAAGACA
CTGGGTGTGAACCAGCGCGGCGAGCTGTGCGTCCGTGGCCCCATGATCATGAGCGGCTACGTTAACAACCCCGAGGCTAC
AAACGCTCTCATCGACAAGGACGGCTGGCTGCACAGCGGCGACATCGCCTACTGGGACGAGGACGAGCACTTCTTCATCG
TGGACCGGCTGAAGAGCCTGATCAAATACAAGGGCTACCAGGTAGCCCCAGCCGAACTGGAGAGCATCCTGCTGCAACAC
CCCAACATCTTCGACGCCGGGGTCGCCGGCCTGCCCGACGACGATGCCGGCGAGCTGCCCGCCGCAGTCGTCGTGCTGGA
ACACGGTAAAACCATGACCGAGAAGGAGATCGTGGACTATGTGGCCAGCCAGGTTACAACCGCCAAGAAGCTGCGCGGTG
GTGTTGTGTTCGTGGACGAGGTGCCTAAAGGACTGACCGGCAAGTTGGACGCCCGCAAGATCCGCGAGATTCTCATTAAG
GCCAAGAAGGGAGGTTCTGGAGGATCTGGCTCGAGCGGACGAAAGAGAGATCGGCTGGGGACCCTGGGGATTGGCGGGAG
CTCTGGGGGAGGGTCTGGGGGTGGTGGTAGTGGCGGTGGGAACGGCAGGTTCCTGACACTTAAGCCTCTTCCGGATAGTA
TTATCCAGGAGTCCCTTGAGATCCAGCAAGGGGTGAATCCTTTTTTTATCGGGCGAAGCGAGGACTGTAATTGCAAGATC
GAAGATAACAGACTCAGTAGAGTGCACTGCTTTATTTTCAAGAAGAGGCACGCAGTGGGAAAATCTATGTACGAATCCCC
AGCTCAGGGCCTCGACGATATTTGGTACTGTCATACAGGCACAAATGTATCCTACCTGAATAACAATCGAATGATCCAAG
GCACCAAATTCCTTCTGCAGGATGGCGACGAAATCAAGATTATCTGGGATAAGAATAACAAATTCGTTATAGGTTTTAAG
GTCGAGATCAATGATACAACCGGGCTCTTCAACGAGGGGCTGGGTATGCTGCAGGAGCAGCGGGTCGTACTGAAGCAGAC
TGCTGAAGAGAAAGACCTCGTAAAGAAACTTGGATCCGGAGGCTCCGGCGGCTCCGGCGGAGCCAAAAACATTAAGAAGG
GCCCAGCGCCATTCTACCCACTCGAAGACGGGACCGCCGGCGAGCAGCTGCACAAAGCCATGAAGCGCTACGCCCTGGTG
CCCGGCACCATCGCCTTTACCGACGCACATATCGAGGTGGACATTACCTACGCCGAGTACTTCGAGATGAGCGTTCGGCT
GGCAGAAGCTATGAAGCGCTATGGGCTGAATACAAACCATCGGATCGTGGTGTGCAGCGAGAATAGCTTGCAGTTCTTCA
TGCCCGTGTTGGGTGCCCTGTTCATCGGTGTGGCTGTGGCCCCAGCTAACGACATCTACAACGAGCGCGAGCTGCTGAAC
AGCATGGGCATCAGCCAGCCCACCGTCGTATTCGTGAGCAAGAAAGGGCTGCAAAAGATCCTCAACGTGCAAAAGAAGCT
ACCGATCATACAAAAGATCATCATCATGGATAGCAAGACCGACTACCAGGGCTTCCAAAGCATGTACACCTTCGTGACTT
CCCATTTGCCACCCGGCTTCAACGAGTACGACTTCGTGCCCGAGAGCTTCGACCGGGACAAAACCATCGCCCTGATCATG
AACAGTAGTGGCAGTACCGGATTGCCCAAGGGCGTAGCCCTACCGCACCGCACCGCTTGTGTCCGATTCAGTCATGCCCG
CGACCCCATCTTCGGCAACCAGATCATCCCCGACACCGCTATCCTCAGCGTGGTGCCATTTCACCACGGCTTCGGCATGT
TCACCACGCTGGGCTACTTGATCTGCGGCTTTCGGGTCGTGCTCATGTACCGCTTCGAGGAGGAGCTATTCTTGCGCAGC
TTGCAAGACTATAAGATTCAATCTGCCCTGCTGGTGCCCACACTATTTAGCTTCTTCGCTAAGAGCACTCTCATCGACAA
GTACGACCTAAGCAACTTGCACGAGATCGCCAGCGGCGGGGCGCCGCTCAGCAAGGAGGTAGGTGAGGCCGTGGCCAAAC

FIG. 67BB

GCTTCCACCTACCAGGCATCCGCCAGGGCTACGGCCTGACAGAAACAACCAGCGCCATTCTGATCACCCCCGAAGGGTGA
GTTTAAAC

AAAAAA) pBFB340 Sgf to Pme (SEQ ID NO:438)
GCGATCGCCATGCCTGGCGCAGTAGGCAAGGTGGTGCCCTTCTTCGAGGCTAAGGTGGTGGACTTGGACACCGGTAAGAC
ACTGGGTGTGAACCAGCGCGGCGAGCTGTGCGTCCGTGGCCCCATGATCATGAGCGGCTACGTTAACAACCCCGAGGCTA
CAAACGCTCTCATCGACAAGGACGGCTGGCTGCACAGCGGCGACATCGCCTACTGGGACGAGGACGAGCACTTCTTCATC
GTGGACCGGCTGAAGAGCCTGATCAAATACAAGGGCTACCAGGTAGCCCCAGCCGAACTGGAGAGCATCCTGCTGCAACA
CCCCAACATCTTCGACGCCGGGGTCGCCGGCCTGCCCGACGACGATGCCGGCGAGCTGCCCGCCGCAGTCGTCGTGCTGG
AACACGGTAAAACCATGACCGAGAAGGAGATCGTGGACTATGTGGCCAGCCAGGTTACAACCGCCAAGAAGCTGCGCGGT
GGTGTTGTGTTCGTGGACGAGGTGCCTAAAGGACTGACCGGCAAGTTGGACGCCCGCAAGATCCGCGAGATTCTCATTAA
GGCCAAGAAGGGTTCATCTGGTGGATCAGGTGGAAGTGGAGGAGGTTCTGGAGGATCTGGCTCGAGCGGACGAAAGAGAG
ATCGGCTGGGGACCCTGGGGATTGGCGGGAGCTCTGGGGGAGGGTCTGGGGGTGGTGGTAGTGGCGGTGGGAACGGCAGG
TTCCTGACACTTAAGCCTCTTCCGGATAGTATTATCCAGGAGTCCCTTGAGATCCAGCAAGGGGTGAATCCTTTTTTTAT
CGGGCGAAGCGAGGACTGTAATTGCAAGATCGAAGATAACAGACTCAGTAGAGTGCACTGCTTTATTTTCAAGAAGAGGC
ACGCAGTGGGAAAATCTATGTACGAATCCCCAGCTCAGGGCCTCGACGATATTTGGTACTGTCATACAGGCACAAATGTA
TCCTACCTGAATAACAATCGAATGATCCAAGGCACCAAATTCCTTCTGCAGGATGGCGACGAAATCAAGATTATCTGGGA
TAAGAATAACAAATTCGTTATAGGTTTTAAGGTCGAGATCAATGATACAACCGGGCTCTTCAACGAGGGGCTGGGTATGC
TGCAGGAGCAGCGGGTCGTACTGAAGCAGACTGCTGAAGAGAAAGACCTCGTAAAGAAACTTGGATCCGGAGGCTCCGGC
GGCTCCGGCGGAACCTCAGGAGGCAGTGGAGGAAGTTCTGGAGCCAAAAACATTAAGAAGGGCCCAGCGCCATTCTACCC
ACTCGAAGACGGGACCGCCGGCGAGCAGCTGCACAAAGCCATGAAGCGCTACGCCCTGGTGCCCGGCACCATCGCCTTTA
CCGACGCACATATCGAGGTGGACATTACCTACGCCGAGTACTTCGAGATGAGCGTTCGGCTGGCAGAAGCTATGAAGCGC
TATGGGCTGAATACAAACCATCGGATCGTGGTGTGCAGCGAGAATAGCTTGCAGTTCTTCATGCCCGTGTTGGGTGCCCT
GTTCATCGGTGTGGCTGTGGCCCCAGCTAACGACATCTACAACGAGCGCGAGCTGCTGAACAGCATGGGCATCAGCCAGC
CCACCGTCGTATTCGTGAGCAAGAAAGGGCTGCAAAAGATCCTCAACGTGCAAAAGAAGCTACCGATCATACAAAAGATC
ATCATCATGGATAGCAAGACCGACTACCAGGGCTTCCAAAGCATGTACACCTTCGTGACTTCCCATTTGCCACCCGGCTT
CAACGAGTACGACTTCGTGCCCGAGAGCTTCGACCGGGACAAAACCATCGCCCTGATCATGAACAGTAGTGGCAGTACCG
GATTGCCCAAGGGCGTAGCCCTACCGCACCGCACCGCTTGTGTCCGATTCAGTCATGCCCGCGACCCCATCTTCGGCAAC
CAGATCATCCCCGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGTGAGTTTAAAC

BBBBBB) pBFB341 Sgf to Pme (SEQ ID NO:439)
GCGATCGCCATGAATAGCTTGCAGTTCTTCATGCCCGTGTTGGGTGCCCTGTTCATCGGTGTGGCTGTGGCCCCAGCTAA
CGACATCTACAACGAGCGCGAGCTGCTGAACAGCATGGGCATCAGCCAGCCCACCGTCGTATTCGTGAGCAAGAAAGGGC
TGCAAAAGATCCTCAACGTGCAAAAGAAGCTACCGATCATACAAAAGATCATCATCATGGATAGCAAGACCGACTACCAG
GGCTTCCAAAGCATGTACACCTTCGTGACTTCCCATTTGCCACCCGGCTTCAACGAGTACGACTTCGTGCCCGAGAGCTT
CGACCGGGACAAAACCATCGCCCTGATCATGAACAGTAGTGGCAGTACCGGATTGCCCAAGGGCGTAGCCCTACCGCACC
GCACCGCTTGTGTCCGATTCAGTCATGCCCGCGACCCCATCTTCGGCAACCAGATCATCCCCGACACCGCTATCCTCAGC
GTGGTGCCATTTCACCACGGCTTCGGCATGTTCACCACGCTGGGCTACTTGATCTGCGGCTTTCGGGTCGTGCTCATGTA
CCGCTTCGAGGAGGAGCTATTCTTGCGCAGCTTGCAAGACTATAAGATTCAATCTGCCCTGCTGGTGCCCACACTATTTA
GCTTCTTCGCTAAGAGCACTCTCATCGACAAGTACGACCTAAGCAACTTGCACGAGATCGCCAGCGGCGGGGCGCCGCTC
AGCAAGGAGGTAGGTGAGGCCGTGGCCAAACGCTTCCACCTACCAGGCATCCGCCAGGGCTACGGCCTGACAGAAACAAC
CAGCGCCATTCTGATCACCCCCGAAGGGGACGACAAGCCTGGCGCAGTAGGCAAGGTGGTGCCCTTCTTCGAGGCTAAGG
TGGTGGACTTGGACACCGGTAAGACACTGGGTGTGAACCAGCGCGGCGAGCTGTGCGTCCGTGGCCCCATGATCATGAGC
GGCTACGTTAACAACCCCGAGGCTACAAACGCTCTCATCGACAAGGACGGCTGGCTGCACAGCGGCGACATCGCCTACTG
GGACGAGGACGAGCACTTCTTCATCGTGGACCGGCTGAAGAGCCTGATCAAATACAAGGGCTACCAGGTAGCCCCAGCCG
AACTGGAGAGCATCCTGCTGCAACACCCCAACATCTTCGACGCCGGGGTCGCCGGCCTGCCCGACGACGATGCCGGCGAG
CTGCCCGCCGCAGTCGTCGTGCTGGAACACGGTAAAACCATGACCGAGAAGGAGATCGTGGACTATGTGGCCAGCCAGGT
TACAACCGCCAAGAAGCTGCGCGGTGGTGTTGTGTTCGTGGACGAGGTGCCTAAAGGACTGACCGGCAAGTTGGACGCCC
GCAAGATCCGCGAGATTCTCATTAAGGCCAAGAAGGGCTCGAGCGGACGAAAGAGAGATCGGCTGGGGACCCTGGGGATT
GGCGGGAGCTCTGGGGGAGGGTCTGGGGGTGGTGGTAGTGGCGGTGGGAACGGCAGGTTCCTGACACTTAAGCCTCTTCC
GGATAGTATTATCCAGGAGTCCCTTGAGATCCAGCAAGGGGTGAATCCTTTTTTTATCGGGCGAAGCGAGGACTGTAATT
GCAAGATCGAAGATAACAGACTCAGTAGAGTGCACTGCTTTATTTTCAAGAAGAGGCACGCAGTGGGAAAATCTATGTAC
GAATCCCCAGCTCAGGGCCTCGACGATATTTGGTACTGTCATACAGGCACAAATGTATCCTACCTGAATAACAATCGAAT

*FIG. 67*BC

GATCCAAGGCACCAAATTCCTTCTGCAGGATGGCGACGAAATCAAGATTATCTGGGATAAGAATAACAAATTCGTTATAG
GTTTTAAGGTCGAGATCAATGATACAACCGGGCTCTTCAACGAGGGGCTGGGTATGCTGCAGGAGCAGCGGGTCGTACTG
AAGCAGACTGCTGAAGAGAAAGACCTCGTAAAGAAACTTGGATCCGGAGGCGCCAAAAACATTAAGAAGGGCCCAGCGCC
ATTCTACCCACTCGAAGACGGGACCGCCGGCGAGCAGCTGCACAAAGCCATGAAGCGCTACGCCCTGGTGCCCGGCACCA
TCGCCTTTACCGACGCACATATCGAGGTGGACATTACCTACGCCGAGTACTTCGAGATGAGCGTTCGGCTGGCAGAAGCT
ATGAAGCGCTATGGGCTGAATACAAACCATCGGATCGTGGTGTGCAGCTGAGTTTAAAC

CCCCCC) pBFB342 Sgf to Pme (SEQ ID NO:440)
GCGATCGCCATGAATAGCTTGCAGTTCTTCATGCCCGTGTTGGGTGCCCTGTTCATCGGTGTGGCTGTGGCCCCAGCTAA
CGACATCTACAACGAGCGCGAGCTGCTGAACAGCATGGGCATCAGCCAGCCCACCGTCGTATTCGTGAGCAAGAAAGGGC
TGCAAAAGATCCTCAACGTGCAAAAGAAGCTACCGATCATACAAAAGATCATCATCATGGATAGCAAGACCGACTACCAG
GGCTTCCAAAGCATGTACACCTTCGTGACTTCCCATTTGCCACCCGGCTTCAACGAGTACGACTTCGTGCCCGAGAGCTT
CGACCGGGACAAAACCATCGCCCTGATCATGAACAGTAGTGGCAGTACCGGATTGCCCAAGGGCGTAGCCCTACCGCACC
GCACCGCTTGTGTCCGATTCAGTCATGCCCGCGACCCCATCTTCGGCAACCAGATCATCCCCGACACCGCTATCCTCAGC
GTGGTGCCATTTCACCACGGCTTCGGCATGTTCACCACGCTGGGCTACTTGATCTGCGGCTTTCGGGTCGTGCTCATGTA
CCGCTTCGAGGAGGAGCTATTCTTGCGCAGCTTGCAAGACTATAAGATTCAATCTGCCCTGCTGGTGCCCACACTATTTA
GCTTCTTCGCTAAGAGCACTCTCATCGACAAGTACGACCTAAGCAACTTGCACGAGATCGCCAGCGGCGGGGCGCCGCTC
AGCAAGGAGGTAGGTGAGGCCGTGGCCAAACGCTTCCACCTACCAGGCATCCGCCAGGGCTACGGCCTGACAGAAACAAC
CAGCGCCATTCTGATCACCCCCGAAGGGGACGACAAGCCTGGCGCAGTAGGCAAGGTGGTGCCCTTCTTCGAGGCTAAGG
TGGTGGACTTGGACACCGGTAAGACACTGGGTGTGAACCAGCGCGGCGAGCTGTGCGTCCGTGGCCCCATGATCATGAGC
GGCTACGTTAACAACCCCGAGGCTACAAACGCTCTCATCGACAAGGACGGCTGGCTGCACAGCGGCGACATCGCCTACTG
GGACGAGGACGAGCACTTCTTCATCGTGGACCGGCTGAAGAGCCTGATCAAATACAAGGGCTACCAGGTAGCCCCAGCCG
AACTGGAGAGCATCCTGCTGCAACACCCCAACATCTTCGACGCCGGGGTCGCCGGCCTGCCCGACGACGATGCCGGCGAG
CTGCCCGCCGCAGTCGTCGTGCTGGAACACGGTAAAACCATGACCGAGAAGGAGATCGTGGACTATGTGGCCAGCCAGGT
TACAACCGCCAAGAAGCTGCGCGGTGGTGTTGTGTTCGTGGACGAGGTGCCTAAAGGACTGACCGGCAAGTTGGACGCCC
GCAAGATCCGCGAGATTCTCATTAAGGCCAAGAAGGGAGGTTCTGGAGGATCTGGCTCGAGCGGACGAAAGAGAGATCGG
CTGGGGACCCTGGGGATTGGCGGGAGCTCTGGGGGAGGGTCTGGGGGTGGTGGTAGTGGCGGTGGGAACGGCAGGTTCCT
GACACTTAAGCCTCTTCCGGATAGTATTATCCAGGAGTCCCTTGAGATCCAGCAAGGGGTGAATCCTTTTTTTATCGGGC
GAAGCGAGGACTGTAATTGCAAGATCGAAGATAACAGACTCAGTAGAGTGCACTGCTTTATTTTCAAGAAGAGGCACGCA
GTGGGAAAATCTATGTACGAATCCCCAGCTCAGGGCCTCGACGATATTTGGTACTGTCATACAGGCACAAATGTATCCTA
CCTGAATAACAATCGAATGATCCAAGGCACCAAATTCCTTCTGCAGGATGGCGACGAAATCAAGATTATCTGGGATAAGA
ATAACAAATTCGTTATAGGTTTTAAGGTCGAGATCAATGATACAACCGGGCTCTTCAACGAGGGGCTGGGTATGCTGCAG
GAGCAGCGGGTCGTACTGAAGCAGACTGCTGAAGAGAAAGACCTCGTAAAGAAACTTGGATCCGGAGGCTCCGGCGGCTC
CGGCGGAGCCAAAAACATTAAGAAGGGCCCAGCGCCATTCTACCCACTCGAAGACGGGACCGCCGGCGAGCAGCTGCACA
AAGCCATGAAGCGCTACGCCCTGGTGCCCGGCACCATCGCCTTTACCGACGCACATATCGAGGTGGACATTACCTACGCC
GAGTACTTCGAGATGAGCGTTCGGCTGGCAGAAGCTATGAAGCGCTATGGGCTGAATACAAACCATCGGATCGTGGTGTG
CAGCTGAGTTTAAAC

DDDDDD) pBFB343 Sgf to Pme (SEQ ID NO:441)
GCGATCGCCATGAATAGCTTGCAGTTCTTATGCCCGTGTTGGGTGCCCTGTTCATCGGTGTGGCTGTGGCCCCAGCTAAC
GACATCTACAACGAGCGCGAGCTGCTGAACAGCATGGGCATCAGCCAGCCCACCGTCGTATTCGTGAGCAAGAAAGGGCT
GCAAAAGATCCTCAACGTGCAAAAGAAGCTACCGATCATACAAAAGATCATCATCATGGATAGCAAGACCGACTACCAGG
GCTTCCAAAGCATGTACACCTTCGTGACTTCCCATTTGCCACCCGGCTTCAACGAGTACGACTTCGTGCCCGAGAGCTTC
GACCGGGACAAAACCATCGCCCTGATCATGAACAGTAGTGGCAGTACCGGATTGCCCAAGGGCGTAGCCCTACCGCACCG
CACCGCTTGTGTCCGATTCAGTCATGCCCGCGACCCCATCTTCGGCAACCAGATCATCCCCGACACCCCTATCCTCAGCG
TGGTGCCATTTCACCACGGCTTCGGCATGTTCACCACGCTGGGCTACTTGATCTGCGGCTTTCGGGTCGTGCTCATGTAC
CGCTTCGAGGAGGAGCTATTCTTGCGCAGCTTGCAAGACTATAAGATTCAATCTGCCCTGCTGGTGCCCACACTATTTAG
CTTCTTCGCTAAGAGCACTCTCATCGACAAGTACGACCTAAGCAACTTGCACGAGATCGCCAGCGGCGGGGCGCCGCTCA
GCAAGGAGGTAGGTGAGGCCGTGGCCAAACGCTTCCACCTACCAGGCATCCGCCAGGGCTACGGCCTGACAGAAACAACC
AGCGCCATTCTGATCACCCCCGAAGGGGACGACAAGCCTGGCGCAGTAGGCAAGGTGGTGCCCTTCTTCGAGGCTAAGGT
GGTGGACTTGGACACCGGTAAGACACTGGGTGTGAACCAGCGCGGCGAGCTGTGCGTCCGTGGCCCCATGATCATGAGCG
GCTACGTTAACAACCCCGAGGCTACAAACGCTCTCATCGACAAGGACGGCTGGCTGCACAGCGGCGACATCGCCTACTGG
GACGAGGACGAGCACTTCTTCATCGTGGACCGGCTGAAGAGCCTGATCAAATACAAGGGCTACCAGGTAGCCCCAGCCGA
ACTGGAGAGCATCCTGCTGCAACACCCCAACATCTTCGACGCCGGGGTCGCCGGCCTGCCCGACGACGATGCCGGCGAGC
TGCCCGCCGCAGTCGTCGTGCTGGAACACGGTAAAACCATGACCGAGAAGGAGATCGTGGACTATGTGGCCAGCCAGGTT
ACAACCGCCAAGAAGCTGCGCGGTGGTGTTGTGTTCGTGGACGAGGTGCCTAAAGGACTGACCGGCAAGTTGGACGCCCG
CAAGATCCGCGAGATTCTCATTAAGGCCAAGAAGGGTTCATCTGGTGGATCAGGTGGAAGTGGAGGAGGTTCTGGAGGAT

FIG. 67BD

CTGGCTCGAGCGGACGAAAGAGAGATCGGCTGGGGACCCTGGGGATTGGCGGGAGCTCTGGGGGAGGGTCTGGGGGTGGT
GGTAGTGGCGGTGGGAACGGCAGGTTCCTGACACTTAAGCCTCTTCCGGATAGTATTATCCAGGAGTCCCTTGAGATCCA
GCAAGGGGTGAATCCTTTTTTTATCGGGCGAAGCGAGGACTGTAATTGCAAGATCGAAGATAACAGACTCAGTAGAGTGC
ACTGCTTTATTTTCAAGAAGAGGCACGCAGTGGGAAAATCTATGTACGAATCCCCAGCTCAGGGCCTCGACGATATTTGG
TACTGTCATACAGGCACAAATGTATCCTACCTGAATAACAATCGAATGATCCAAGGCACCAAATTCCTTCTGCAGGATGG
CGACGAAATCAAGATTATCTGGGATAAGAATAACAAATTCGTTATAGGTTTTAAGGTCGAGATCAATGATACAACCGGGC
TCTTCAACGAGGGGCTGGGTATGCTGCAGGAGCAGCGGGTCGTACTGAAGCAGACTGCTGAAGAGAAAGACCTCGTAAAG
AAACTTGGATCCGGAGGCTCCGGCGGCTCCGGCGGAACCTCAGGAGGCAGTGGAGGAAGTTCTGGAGCCAAAAACATTAA
GAAGGGCCCAGCGCCATTCTACCCACTCGAAGACGGGACCGCCGGCGAGCAGCTGCACAAAGCCATGAAGCGCTACGCCC
TGGTGCCCGGCACCATCGCCTTTACCGACGCACATATCGAGGTGGACATTACCTACGCCGAGTACTTCGAGATGAGCGTT
CGGCTGGCAGAAGCTATGAAGCGCTATGGGCTGAATACAAACCATCGGATCGTGGTGTGCAGCTGAGTTTAAAC

EEEEEE) pBFB344 Sgf to Pme (SEQ ID NO:442)
GCGATCGCCATGTTGCACGAGATCGCCAGCGGCGGGGCGCCGCTCAGCAAGGAGGTAGGTGAGGCCGTGGCCAAACGCTT
CCACCTACCAGGCATCCGCCAGGGCTACGGCCTGACAGAAACAACCAGCGCCATTCTGATCACCCCCGAAGGGGACGACA
AGCCTGGCGCAGTAGGCAAGGTGGTGCCCTTCTTCGAGGCTAAGGTGGTGGACTTGGACACCGGTAAGACACTGGGTGTG
AACCAGCGCGGCGAGCTGTGCGTCCGTGGCCCCATGATCATGAGCGGCTACGTTAACAACCCCGAGGCTACAAACGCTCT
CATCGACAAGGACGGCTGGCTGCACAGCGGCGACATCGCCTACTGGGACGAGGACGAGCACTTCTTCATCGTGGACCGGC
TGAAGAGCCTGATCAAATACAAGGGCTACCAGGTAGCCCCAGCCGAACTGGAGAGCATCCTGCTGCAACACCCCAACATC
TTCGACGCCGGGGTCGCCGGCCTGCCCGACGACGATGCCGGCGAGCTGCCCGCCGCAGTCGTCGTGCTGGAACACGGTAA
AACCATGACCGAGAAGGAGATCGTGGACTATGTGGCCAGCCAGGTTACAACCGCCAAGAAGCTGCGCGGTGGTGTTGTGT
TCGTGGACGAGGTGCCTAAAGGACTGACCGGCAAGTTGGACGCCCGCAAGATCCGCGAGATTCTCATTAAGGCCAAGAAG
GGCTCGAGCGGACGAAAGAGAGATCGGCTGGGGACCCTGGGGATTGGCGGGAGCTCTGGGGGAGGGTCTGGGGGTGGTGG
TAGTGGCGGTGGGAACGGCAGGTTCCTGACACTTAAGCCTCTTCCGGATAGTATTATCCAGGAGTCCCTTGAGATCCAGC
AAGGGGTGAATCCTTTTTTTATCGGGCGAAGCGAGGACTGTAATTGCAAGATCGAAGATAACAGACTCAGTAGAGTGCAC
TGCTTTATTTTCAAGAAGAGGCACGCAGTGGGAAAATCTATGTACGAATCCCCAGCTCAGGGCCTCGACGATATTTGGTA
CTGTCATACAGGCACAAATGTATCCTACCTGAATAACAATCGAATGATCCAAGGCACCAAATTCCTTCTGCAGGATGGCG
ACGAAATCAAGATTATCTGGGATAAGAATAACAAATTCGTTATAGGTTTTAAGGTCGAGATCAATGATACAACCGGGCTC
TTCAACGAGGGGCTGGGTATGCTGCAGGAGCAGCGGGTCGTACTGAAGCAGACTGCTGAAGAGAAAGACCTCGTAAAGAA
ACTTGGATCCGGAGGCGCCAAAAACATTAAGAAGGGCCCAGCGCCATTCTACCCACTCGAAGACGGGACCGCCGGCGAGC
AGCTGCACAAAGCCATGAAGCGCTACGCCCTGGTGCCCGGCACCATCGCCTTTACCGACGCACATATCGAGGTGGACATT
ACCTACGCCGAGTACTTCGAGATGAGCGTTCGGCTGGCAGAAGCTATGAAGCGCTATGGGCTGAATACAAACCATCGGAT
CGTGGTGTGCAGCGAGAATAGCTTGCAGTTCTTCATGCCCGTGTTGGGTGCCCTGTTCATCGGTGTGGCTGTGGCCCCAG
CTAACGACATCTACAACGAGCGCGAGCTGCTGAACAGCATGGGCATCAGCCAGCCCACCGTCGTATTCGTGAGCAAGAAA
GGGCTGCAAAAGATCCTCAACGTGCAAAAGAAGCTACCGATCATACAAAAGATCATCATCATGGATAGCAAGACCGACTA
CCAGGGCTTCCAAAGCATGTACACCTTCGTGACTTCCCATTTGCCACCCGGCTTCAACGAGTACGACTTCGTGCCCGAGA
GCTTCGACCGGGACAAAACCATCGCCCTGATCATGAACAGTAGTGGCAGTACCGGATTGCCCAAGGGCGTAGCCCTACCG
CACCGCACCGCTTGTGTCCGATTCAGTCATGCCCGCGACCCCATCTTCGGCAACCAGATCATCCCCGACACCGCTATCCT
CAGCGTGGTGCCATTTCACCACGGCTTCGGCATGTTCACCACGCTGGGCTACTTGATCTGCGGCTTTCGGGTCGTGCTCA
TGTACCGCTTCGAGGAGGAGCTATTCTTGCGCAGCTTGCAAGACTATAAGATTCAATCTGCCCTGCTGGTGCCCACACTA
TTTAGCTTCTTCGCTAAGAGCACTCTCATCGACAAGTACGACCTAAGCTGAGTTTAAAC

FFFFFF) pBFB345 Sgf to Pme (SEQ ID NO:443)
GCGATCGCCATGTTGCACGAGATCGCCAGCGGCGGGGCGCCGCTCAGCAAGGAGGTAGGTGAGGCCGTGGCCAAACGCTT
CCACCTACCAGGCATCCGCCAGGGCTACGGCCTGACAGAAACAACCAGCGCCATTCTGATCACCCCCGAAGGGGACGACA
AGCCTGGCGCAGTAGGCAAGGTGGTGCCCTTCTTCGAGGCTAAGGTGGTGGACTTGGACACCGGTAAGACACTGGGTGTG
AACCAGCGCGGCGAGCTGTGCGTCCGTGGCCCCATGATCATGAGCGGCTACGTTAACAACCCCGAGGCTACAAACGCTCT
CATCGACAAGGACGGCTGGCTGCACAGCGGCGACATCGCCTACTGGGACGAGGACGAGCACTTCTTCATCGTGGACCGGC
TGAAGAGCCTGATCAAATACAAGGGCTACCAGGTAGCCCCAGCCGAACTGGAGAGCATCCTGCTGCAACACCCCAACATC
TTCGACGCCGGGGTCGCCGGCCTGCCCGACGACGATGCCGGCGAGCTGCCCGCCGCAGTCGTCGTGCTGGAACACGGTAA
AACCATGACCGAGAAGGAGATCGTGGACTATGTGGCCAGCCAGGTTACAACCGCCAAGAAGCTGCGCGGTGGTGTTGTGT
TCGTGGACGAGGTGCCTAAAGGACTGACCGGCAAGTTGGACGCCCGCAAGATCCGCGAGATTCTCATTAAGGCCAAGAAG
GGAGGTTCTGGAGGATCTGGCTCGAGCGGACGAAAGAGAGATCGGCTGGGGACCCTGGGGATTGGCGGGAGCTCTGGGGG
AGGGTCTGGGGGTGGTGGTAGTGGCGGTGGGAACGGCAGGTTCCTGACACTTAAGCCTCTTCCGGATAGTATTATCCAGG
AGTCCCTTGAGATCCAGCAAGGGGTGAATCCTTTTTTTATCGGGCGAAGCGAGGACTGTAATTGCAAGATCGAAGATAAC
AGACTCAGTAGAGTGCACTGCTTTATTTTCAAGAAGAGGCACGCAGTGGGAAAATCTATGTACGAATCCCCAGCTCAGGG
CCTCGACGATATTTGGTACTGTCATACAGGCACAAATGTATCCTACCTGAATAACAATCGAATGATCCAAGGCACCAAAT

*FIG. 67BE*

TCCTTCTGCAGGATGGCGACGAAATCAAGATTATCTGGGATAAGAATAACAAATTCGTTATAGGTTTTAAGGTCGAGATC
AATGATACAACCGGGCTCTTCAACGAGGGGCTGGGTATGCTGCAGGAGCAGCGGGTCGTACTGAAGCAGACTGCTGAAGA
GAAAGACCTCGTAAAGAAACTTGGATCCGGAGGCTCCGGCGGCTCCGGCGGAGCCAAAAACATTAAGAAGGGCCCAGCGC
CATTCTACCCACTCGAAGACGGGACCGCCGGCGAGCAGCTGCACAAAGCCATGAAGCGCTACGCCCTGGTGCCCGGCACC
ATCGCCTTTACCGACGCACATATCGAGGTGGACATTACCTACGCCGAGTACTTCGAGATGAGCGTTCGGCTGGCAGAAGC
TATGAAGCGCTATGGGCTGAATACAAACCATCGGATCGTGGTGTGCAGCGAGAATAGCTTGCAGTTCTTCATGCCCGTGT
TGGGTGCCCTGTTCATCGGTGTGGCTGTGGCCCCAGCTAACGACATCTACAACGAGCGCGAGCTGCTGAACAGCATGGGC
ATCAGCCAGCCCACCGTCGTATTCGTGAGCAAGAAAGGGCTGCAAAAGATCCTCAACGTGCAAAAGAAGCTACCGATCAT
ACAAAAGATCATCATCATGGATAGCAAGACCGACTACCAGGGCTTCCAAAGCATGTACACCTTCGTGACTTCCCATTTGC
CACCCGGCTTCAACGAGTACGACTTCGTGCCCGAGAGCTTCGACCGGGACAAAACCATCGCCCTGATCATGAACAGTAGT
GGCAGTACCGGATTGCCCAAGGGCGTAGCCCTACCGCACCGCACCGCTTGTGTCCGATTCAGTCATGCCCGCGACCCCAT
CTTCGGCAACCAGATCATCCCCGACACCGCTATCCTCAGCGTGGTGCCATTTCACCACGGCTTCGGCATGTTCACCACGC
TGGGCTACTTGATCTGCGGCTTTCGGGTCGTGCTCATGTACCGCTTCGAGGAGGAGCTATTCTTGCGCAGCTTGCAAGAC
TATAAGATTCAATCTGCCCTGCTGGTGCCCACACTATTTAGCTTCTTCGCTAAGAGCACTCTCATCGACAAGTACGACCT
AAGCTGAGTTTAAAC

GGGGGG) pBFB346 Sgf to Pme (SEQ ID NO:444)
GCGATCGCCATGTTGCACGAGATCGCCAGCGGCGGGGCGCCGCTCAGCAAGGAGGTAGGTGAGGCCGTGGCCAAACGCTT
CCACCTACCAGGCATCCGCCAGGGCTACGGCCTGACAGAAACAACCAGCGCCATTCTGATCACCCCCGAAGGGGACGACA
AGCCTGGCGCAGTAGGCAAGGTGGTGCCCTTCTTCGAGGCTAAGGTGGTGGACTTGGACACCGGTAAGACACTGGGTGTG
AACCAGCGCGGCGAGCTGTGCGTCCGTGGCCCCATGATCATGAGCGGCTACGTTAACAACCCCGAGGCTACAAACGCTCT
CATCGACAAGGACGGCTGGCTGCACAGCGGCGACATCGCCTACTGGGACGAGGACGAGCACTTCTTCATCGTGGACCGGC
TGAAGAGCCTGATCAAATACAAGGGCTACCAGGTAGCCCCAGCCGAACTGGAGAGCATCCTGCTGCAACACCCCAACATC
TTCGACGCCGGGGTCGCCGGCCTGCCCGACGACGATGCCGGCGAGCTGCCCGCCGCAGTCGTCGTGCTGGAACACGGTAA
AACCATGACCGAGAAGGAGATCGTGGACTATGTGGCCAGCCAGGTTACAACCGCCAAGAAGCTGCGCGGTGGTGTTGTGT
TCGTGGACGAGGTGCCTAAAGGACTGACCGGCAAGTTGGACGCCCGCAAGATCCGCGAGATTCTCATTAAGGCCAAGAAG
GGTTCATCTGGTGGATCAGGTGGAAGTGGAGGAGGTTCTGGAGGATCTGGCTCGAGCGGACGAAAGAGAGATCGGCTGGG
GACCCTGGGGATTGGCGGGAGCTCTGGGGGAGGGTCTGGGGGTGGTGGTAGTGGCGGTGGGAACGGCAGGTTCCTGACAC
TTAAGCCTCTTCCGGATAGTATTATCCAGGAGTCCCTTGAGATCCAGCAAGGGGTGAATCCTTTTTTTATCGGGCGAAGC
GAGGACTGTAATTGCAAGATCGAAGATAACAGACTCAGTAGAGTGCACTGCTTTATTTTCAAGAAGAGGCACGCAGTGGG
AAAATCTATGTACGAATCCCCAGCTCAGGGCCTCGACGATATTTGGTACTGTCATACAGGCACAAATGTATCCTACCTGA
ATAACAATCGAATGATCCAAGGCACCAAATTCCTTCTGCAGGATGGCGACGAAATCAAGATTATCTGGGATAAGAATAAC
AAATTCGTTATAGGTTTTAAGGTCGAGATCAATGATACAACCGGGCTCTTCAACGAGGGGCTGGGTATGCTGCAGGAGCA
GCGGGTCGTACTGAAGCAGACTGCTGAAGAGAAAGACCTCGTAAAGAAACTTGGATCCGGAGGCTCCGGCGGCTCCGGCG
GAACCTCAGGAGGCAGTGGAGGAAGTTCTGGAGCCAAAAACATTAAGAAGGGCCCAGCGCCATTCTACCCACTCGAAGAC
GGGACCGCCGGCGAGCAGCTGCACAAAGCCATGAAGCGCTACGCCCTGGTGCCCGGCACCATCGCCTTTACCGACGCACA
TATCGAGGTGGACATTACCTACGCCGAGTACTTCGAGATGAGCGTTCGGCTGGCAGAAGCTATGAAGCGCTATGGGCTGA
ATACAAACCATCGGATCGTGGTGTGCAGCGAGAATAGCTTGCAGTTCTTCATGCCCGTGTTGGGTGCCCTGTTCATCGGT
GTGGCTGTGGCCCCAGCTAACGACATCTACAACGAGCGCGAGCTGCTGAACAGCATGGGCATCAGCCAGCCCACCGTCGT
ATTCGTGAGCAAGAAAGGGCTGCAAAAGATCCTCAACGTGCAAAAGAAGCTACCGATCATACAAAAGATCATCATCATGG
ATAGCAAGACCGACTACCAGGGCTTCCAAAGCATGTACACCTTCGTGACTTCCCATTTGCCACCCGGCTTCAACGAGTAC
GACTTCGTGCCCGAGAGCTTCGACCGGGACAAAACCATCGCCCTGATCATGAACAGTAGTGGCAGTACCGGATTGCCCAA
GGGCGTAGCCCTACCGCACCGCACCGCTTGTGTCCGATTCAGTCATGCCCGCGACCCCATCTTCGGCAACCAGATCATCC
CCGACACCGCTATCCTCAGCGTGGTGCCATTTCACCACGGCTTCGGCATGTTCACCACGCTGGGCTACTTGATCTGCGGC
TTTCGGGTCGTGCTCATGTACCGCTTCGAGGAGGAGCTATTCTTGCGCAGCTTGCAAGACTATAAGATTCAATCTGCCCT
GCTGGTGCCCACACTATTTAGCTTCTTCGCTAAGAGCACTCTCATCGACAAGTACGACCTAAGCTGAGTTTAAAC

HHHHHH) pBFB350 Sgf to Pme (SEQ ID NO:445)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGAGCGGACGAAAGAGAGATCGGCTGGGGACCCTGGGGATTGGC

*FIG. 67*BF

GGGAGCTCTGGGGGAGGGTCTGGGGGTGGTGGTAGTGGCGGTGGGAACGGCAGGTTCCTGACACTTAAGCCTCTTCCGGA
TAGTATTATCCAGGAGTCCCTTGAGATCCAGCAAGGGGTGAATCCTTTTTTTATCGGGCGAAGCGAGGACTGTAATTGCA
AGATCGAAGATAACAGACTCAGTAGAGTGCACTGCTTTATTTTCAAGAAGAGGCACGCAGTGGGAAAATCTATGTACGAA
TCCCCAGCTCAGGGCCTCGACGATATTTGGTACTGTCATACAGGCACAAATGTATCCTACCTGAATAACAATCGAATGAT
CCAAGGCACCAAATTCCTTCTGCAGGATGGCGACGAAATCAAGATTATCTGGGATAAGAATAACAAATTCGTTATAGGTT
TTAAGGTCGAGATCAATGATACAACCGGGCTCTTCAACGAGGGGCTGGGTATGCTGCAGGAGCAGCGGGTCGTACTGAAG
CAGACTGCTGAAGAGAAAGACCTCGTAAAGAAACTTGGATCCGGAGGCGCTTCCAAGGTGTACGACCCCGAGCAACGCAA
ACGCATGATCACTGGGCCTCAGTGGTGGGCTCGCTGCAAGCAAATGAACGTGCTGGACTCCTTCATCAACTACTATGATT
CCGAGAAGCACGCCGAGAACGCCGTGATTTTTCTGCATGGTAACGCTGCCTCCAGCTACCTGTGGAGGCACGTCGTGCCT
CACATCGAGCCCGTGGCTAGATGCATCATCCCTGATCTGATCGGAATGGGTAAGTCCGGCAAGAGCGGGAATGGCTGAGT
TTAAAC

IIIIII) pBFB351 Sgf to Pme (SEQ ID NO:446)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGAGGTTCTGGAGGATCTGGCTCGAGCGGACGAAAGAGAGATCGGCTG
GGGACCCTGGGGATTGGCGGGAGCTCTGGGGGAGGGTCTGGGGGTGGTGGTAGTGGCGGTGGGAACGGCAGGTTCCTGAC
ACTTAAGCCTCTTCCGGATAGTATTATCCAGGAGTCCCTTGAGATCCAGCAAGGGGTGAATCCTTTTTTTATCGGGCGAA
GCGAGGACTGTAATTGCAAGATCGAAGATAACAGACTCAGTAGAGTGCACTGCTTTATTTTCAAGAAGAGGCACGCAGTG
GGAAAATCTATGTACGAATCCCCAGCTCAGGGCCTCGACGATATTTGGTACTGTCATACAGGCACAAATGTATCCTACCT
GAATAACAATCGAATGATCCAAGGCACCAAATTCCTTCTGCAGGATGGCGACGAAATCAAGATTATCTGGGATAAGAATA
ACAAATTCGTTATAGGTTTTAAGGTCGAGATCAATGATACAACCGGGCTCTTCAACGAGGGGCTGGGTATGCTGCAGGAG
CAGCGGGTCGTACTGAAGCAGACTGCTGAAGAGAAAGACCTCGTAAAGAAACTTGGATCCGGAGGCTCCGGCGGCTCCGG
CGGAGCTTCCAAGGTGTACGACCCCGAGCAACGCAAACGCATGATCACTGGGCCTCAGTGGTGGGCTCGCTGCAAGCAAA
TGAACGTGCTGGACTCCTTCATCAACTACTATGATTCCGAGAAGCACGCCGAGAACGCCGTGATTTTTCTGCATGGTAAC
GCTGCCTCCAGCTACCTGTGGAGGCACGTCGTGCCTCACATCGAGCCCGTGGCTAGATGCATCATCCCTGATCTGATCGG
AATGGGTAAGTCCGGCAAGAGCGGGAATGGCTGAGTTTAAAC

JJJJJJ) pBFB352 Sgf to Pme (SEQ ID NO:447)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGTTCATCTGGTGGATCAGGTGGAAGTGGAGGAGGTTCTGGAGGATCT
GGCTCGAGCGGACGAAAGAGAGATCGGCTGGGGACCCTGGGGATTGGCGGGAGCTCTGGGGGAGGGTCTGGGGGTGGTGG
TAGTGGCGGTGGGAACGGCAGGTTCCTGACACTTAAGCCTCTTCCGGATAGTATTATCCAGGAGTCCCTTGAGATCCAGC
AAGGGGTGAATCCTTTTTTTATCGGGCGAAGCGAGGACTGTAATTGCAAGATCGAAGATAACAGACTCAGTAGAGTGCAC
TGCTTTATTTTCAAGAAGAGGCACGCAGTGGGAAAATCTATGTACGAATCCCCAGCTCAGGGCCTCGACGATATTTGGTA
CTGTCATACAGGCACAAATGTATCCTACCTGAATAACAATCGAATGATCCAAGGCACCAAATTCCTTCTGCAGGATGGCG
ACGAAATCAAGATTATCTGGGATAAGAATAACAAATTCGTTATAGGTTTTAAGGTCGAGATCAATGATACAACCGGGCTC
TTCAACGAGGGGCTGGGTATGCTGCAGGAGCAGCGGGTCGTACTGAAGCAGACTGCTGAAGAGAAAGACCTCGTAAAGAA
ACTTGGATCCGGAGGCTCCGGCGGCTCCGGCGGAACCTCAGGAGGCAGTGGAGGAAGTTCTGGAGCTTCCAAGGTGTACG
ACCCCGAGCAACGCAAACGCATGATCACTGGGCCTCAGTGGTGGGCTCGCTGCAAGCAAATGAACGTGCTGGACTCCTTC
ATCAACTACTATGATTCCGAGAAGCACGCCGAGAACGCCGTGATTTTTCTGCATGGTAACGCTGCCTCCAGCTACCTGTG
GAGGCACGTCGTGCCTCACATCGAGCCCGTGGCTAGATGCATCATCCCTGATCTGATCGGAATGGGTAAGTCCGGCAAGA
GCGGGAATGGCTGAGTTTAAAC

FIG. 67BG

KKKKKK) pBFB353 Sgf to Pme (SEQ ID NO:448)
GCGATCGCCATGGCCGAGAACGCCGTGATTTTTCTGCATGGTAACGCTGCCTCCAGCTACCTGTGGAGGCACGTCGTGCC
TCACATCGAGCCCGTGGCTAGATGCATCATCCCTGATCTGATCGGAATGGGTAAGTCCGGCAAGAGCGGGAATGGCTCAT
ATCGCCTCCTGGATCACTACAAGTACCTCACCGCTTGGTTCGAGCTGCTGAACCTTCCAAAGAAAATCATCTTTGTGGGC
CACGACTGGGGGGCTTGTCTGGCCTTTCACTACTCCTACGAGCACCAAGACAAGATCAAGGCCATCGTCCATGCTGAGAG
TGTCGTGGACGTGATCGAGTCCTGGGACGAGTGGCCTGACATCGAGGAGGATATCGCCCTGATCAAGAGCGAAGAGGGCG
AGAAAATGGTGCTTGAGAATAACTTCTTCGTCGAGACCATGCTCCCAAGCAAGATCATGCGGAAACTGGAGCCTGAGGAG
TTCGCTGCCTACCTGGAGCCATTCAAGGAGAAGGGCGAGGTTAGACGGCCTACCCTCTCCTGGCCTCGCGAGATCCCTCT
CGTTAAGGGAGGCAAGCCCGACGTCGTCCAGATTGTCCGCAACTACAACGCCTACCTTCGGGCCAGCGACGATCTGCCTA
AGATGTTCATCGAGTCCGACCCTGGGTTCTTTTCCAACGCTATTGTCGAGGGAGCTAAGAAGTTCCCTAACACCGAGTTC
GTGAAGGTGAAGGGCCTCCACTTCAGCCAGGAGGACGCTCCAGATGAAATGGGTAAGTACATCAAGAGCTTCGTGGAGCG
CGTGCTGAAGAACGAGCAGGGCTCGAGCGGACGAAAGAGAGATCGGCTGGGGACCCTGGGGATTGGCGGGAGCTCTGGGG
GAGGGTCTGGGGGTGGTGGTAGTGGCGGTGGGAACGGCAGGTTCCTGACACTTAAGCCTCTTCCGGATAGTATTATCCAG
GAGTCCCTTGAGATCCAGCAAGGGGTGAATCCTTTTTTTATCGGGCGAAGCGAGGACTGTAATTGCAAGATCGAAGATAA
CAGACTCAGTAGAGTGCACTGCTTTATTTTCAAGAAGAGGCACGCAGTGGGAAAATCTATGTACGAATCCCCAGCTCAGG
GCCTCGACGATATTTGGTACTGTCATACAGGCACAAATGTATCCTACCTGAATAACAATCGAATGATCCAAGGCACCAAA
TTCCTTCTGCAGGATGGCGACGAAATCAAGATTATCTGGGATAAGAATAACAAATTCGTTATAGGTTTTAAGGTCGAGAT
CAATGATACAACCGGGCTCTTCAACGAGGGGCTGGGTATGCTGCAGGAGCAGCGGGTCGTACTGAAGCAGACTGCTGAAG
AGAAAGACCTCGTAAAGAAACTTGGATCCGGAGGCGCTTCCAAGGTGTACGACCCCGAGCAACGCAAACGCATGATCACT
GGGCCTCAGTGGTGGGCTCGCTGCAAGCAAATGAACGTGCTGGACTCCTTCATCAACTACTATGATTCCGAGAAGTGAGT
TTAAAC

LLLLLL) pBFB354 Sgf to Pme (SEQ ID NO:449)
GCGATCGCCATGGCCGAGAACGCCGTGATTTTTCTGCATGGTAACGCTGCCTCCAGCTACCTGTGGAGGCACGTCGTGCC
TCACATCGAGCCCGTGGCTAGATGCATCATCCCTGATCTGATCGGAATGGGTAAGTCCGGCAAGAGCGGGAATGGCTCAT
ATCGCCTCCTGGATCACTACAAGTACCTCACCGCTTGGTTCGAGCTGCTGAACCTTCCAAAGAAAATCATCTTTGTGGGC
CACGACTGGGGGGCTTGTCTGGCCTTTCACTACTCCTACGAGCACCAAGACAAGATCAAGGCCATCGTCCATGCTGAGAG
TGTCGTGGACGTGATCGAGTCCTGGGACGAGTGGCCTGACATCGAGGAGGATATCGCCCTGATCAAGAGCGAAGAGGGCG
AGAAAATGGTGCTTGAGAATAACTTCTTCGTCGAGACCATGCTCCCAAGCAAGATCATGCGGAAACTGGAGCCTGAGGAG
TTCGCTGCCTACCTGGAGCCATTCAAGGAGAAGGGCGAGGTTAGACGGCCTACCCTCTCCTGGCCTCGCGAGATCCCTCT
CGTTAAGGGAGGCAAGCCCGACGTCGTCCAGATTGTCCGCAACTACAACGCCTACCTTCGGGCCAGCGACGATCTGCCTA
AGATGTTCATCGAGTCCGACCCTGGGTTCTTTTCCAACGCTATTGTCGAGGGAGCTAAGAAGTTCCCTAACACCGAGTTC
GTGAAGGTGAAGGGCCTCCACTTCAGCCAGGAGGACGCTCCAGATGAAATGGGTAAGTACATCAAGAGCTTCGTGGAGCG
CGTGCTGAAGAACGAGCAGGGAGGTTCTGGAGGATCTGGCTCGAGCGGACGAAAGAGAGATCGGCTGGGGACCCTGGGGA
TTGGCGGGAGCTCTGGGGGAGGGTCTGGGGGTGGTGGTAGTGGCGGTGGGAACGGCAGGTTCCTGACACTTAAGCCTCTT
CCGGATAGTATTATCCAGGAGTCCCTTGAGATCCAGCAAGGGGTGAATCCTTTTTTTATCGGGCGAAGCGAGGACTGTAA
TTGCAAGATCGAAGATAACAGACTCAGTAGAGTGCACTGCTTTATTTTCAAGAAGAGGCACGCAGTGGGAAAATCTATGT
ACGAATCCCCAGCTCAGGGCCTCGACGATATTTGGTACTGTCATACAGGCACAAATGTATCCTACCTGAATAACAATCGA
ATGATCCAAGGCACCAAATTCCTTCTGCAGGATGGCGACGAAATCAAGATTATCTGGGATAAGAATAACAAATTCGTTAT
AGGTTTTAAGGTCGAGATCAATGATACAACCGGGCTCTTCAACGAGGGGCTGGGTATGCTGCAGGAGCAGCGGGTCGTAC
TGAAGCAGACTGCTGAAGAGAAAGACCTCGTAAAGAAACTTGGATCCGGCGGCTCCGGCGGCTCCGGCGGAGCTTCCAAG
GTGTACGACCCCGAGCAACGCAAACGCATGATCACTGGGCCTCAGTGGTGGGCTCGCTGCAAGCAAATGAACGTGCTGGA
CTCCTTCATCAACTACTATGATTCCGAGAAGTGAGTTTAAAC

MMMMMM) pBFB355 Sgf to Pme (SEQ ID NO:450)
GCGATCGCCATGGCCGAGAACGCCGTGATTTTTCTGCATGGTAACGCTGCCTCCAGCTACCTGTGGAGGCACGTCGTGCC
TCACATCGAGCCCGTGGCTAGATGCATCATCCCTGATCTGATCGGAATGGGTAAGTCCGGCAAGAGCGGGAATGGCTCAT
ATCGCCTCCTGGATCACTACAAGTACCTCACCGCTTGGTTCGAGCTGCTGAACCTTCCAAAGAAAATCATCTTTGTGGGC
CACGACTGGGGGGCTTGTCTGGCCTTTCACTACTCCTACGAGCACCAAGACAAGATCAAGGCCATCGTCCATGCTGAGAG
TGTCGTGGACGTGATCGAGTCCTGGGACGAGTGGCCTGACATCGAGGAGGATATCGCCCTGATCAAGAGCGAAGAGGGCG
AGAAAATGGTGCTTGAGAATAACTTCTTCGTCGAGACCATGCTCCCAAGCAAGATCATGCGGAAACTGGAGCCTGAGGAG
TTCGCTGCCTACCTGGAGCCATTCAAGGAGAAGGGCGAGGTTAGACGGCCTACCCTCTCCTGGCCTCGCGAGATCCCTCT
CGTTAAGGGAGGCAAGCCCGACGTCGTCCAGATTGTCCGCAACTACAACGCCTACCTTCGGGCCAGCGACGATCTGCCTA
AGATGTTCATCGAGTCCGACCCTGGGTTCTTTTCCAACGCTATTGTCGAGGGAGCTAAGAAGTTCCCTAACACCGAGTTC
GTGAAGGTGAAGGGCCTCCACTTCAGCCAGGAGGACGCTCCAGATGAAATGGGTAAGTACATCAAGAGCTTCGTGGAGCG
CGTGCTGAAGAACGAGCAGGGTTCATCTGGTGGATCAGGTGGAAGTGGAGGAGGTTCTGGAGGATCTGGCTCGAGCGGAC
GAAAGAGAGATCGGCTGGGGACCCTGGGGATTGGCGGGAGCTCTGGGGGAGGGTCTGGGGGTGGTGGTAGTGGCGGTGGG

*FIG. 67BH*

AACGGCAGGTTCCTGACACTTAAGCCTCTTCCGGATAGTATTATCCAGGAGTCCCTTGAGATCCAGCAAGGGGTGAATCC
TTTTTTTATCGGGCGAAGCGAGGACTGTAATTGCAAGATCGAAGATAACAGACTCAGTAGAGTGCACTGCTTTATTTTCA
AGAAGAGGCACGCAGTGGGAAAATCTATGTACGAATCCCCAGCTCAGGGCCTCGACGATATTTGGTACTGTCATACAGGC
ACAAATGTATCCTACCTGAATAACAATCGAATGATCCAAGGCACCAAATTCCTTCTGCAGGATGGCGACGAAATCAAGAT
TATCTGGGATAAGAATAACAAATTCGTTATAGGTTTTAAGGTCGAGATCAATGATACAACCGGGCTCTTCAACGAGGGGC
TGGGTATGCTGCAGGAGCAGCGGGTCGTACTGAAGCAGACTGCTGAAGAGAAAGACCTCGTAAAGAAACTTGGATCCGGA
GGCTCCGGCGGCTCCGGCGGAACCTCAGGAGGCAGTGGAGGAAGTTCTGGAGCTTCCAAGGTGTACGACCCCGAGCAACG
CAAACGCATGATCACTGGGCCTCAGTGGTGGGCTCGCTGCAAGCAAATGAACGTGCTGGACTCCTTCATCAACTACTATG
ATTCCGAGAAGTGAGTTTAAAC

NNNNNN) pBFB356 Sgf to Pme (SEQ ID NO:451)
GCGATCGCCATGAAGAAAATCATCTTTGTGGGCCACGACTGGGGGGCTTGTCTGGCCTTTCACTACTCCTACGAGCACCA
AGACAAGATCAAGGCCATCGTCCATGCTGAGAGTGTCGTGGACGTGATCGAGTCCTGGGACGAGTGGCCTGACATCGAGG
AGGATATCGCCCTGATCAAGAGCGAAGAGGGCGAGAAAATGGTGCTTGAGAATAACTTCTTCGTCGAGACCATGCTCCCA
AGCAAGATCATGCGGAAACTGGAGCCTGAGGAGTTCGCTGCCTACCTGGAGCCATTCAAGGAGAAGGGCGAGGTTAGACG
GCCTACCCTCTCCTGGCCTCGCGAGATCCCTCTCGTTAAGGGAGGCAAGCCCGACGTCGTCCAGATTGTCCGCAACTACA
ACGCCTACCTTCGGGCCAGCGACGATCTGCCTAAGATGTTCATCGAGTCCGACCCTGGGTTCTTTTCCAACGCTATTGTC
GAGGGAGCTAAGAAGTTCCCTAACACCGAGTTCGTGAAGGTGAAGGGCCTCCACTTCAGCCAGGAGGACGCTCCAGATGA
AATGGGTAAGTACATCAAGAGCTTCGTGGAGCGCGTGCTGAAGAACGAGCAGGGCTCGAGCGGACGAAAGAGAGATCGGC
TGGGGACCCTGGGGATTGGCGGGAGCTCTGGGGGAGGGTCTGGGGGTGGTGGTAGTGGCGGTGGGAACGGCAGGTTCCTG
ACACTTAAGCCTCTTCCGGATAGTATTATCCAGGAGTCCCTTGAGATCCAGCAAGGGGTGAATCCTTTTTTTATCGGGCG
AAGCGAGGACTGTAATTGCAAGATCGAAGATAACAGACTCAGTAGAGTGCACTGCTTTATTTTCAAGAAGAGGCACGCAG
TGGGAAAATCTATGTACGAATCCCCAGCTCAGGGCCTCGACGATATTTGGTACTGTCATACAGGCACAAATGTATCCTAC
CTGAATAACAATCGAATGATCCAAGGCACCAAATTCCTTCTGCAGGATGGCGACGAAATCAAGATTATCTGGGATAAGAA
TAACAAATTCGTTATAGGTTTTAAGGTCGAGATCAATGATACAACCGGGCTCTTCAACGAGGGGCTGGGTATGCTGCAGG
AGCAGCGGGTCGTACTGAAGCAGACTGCTGAAGAGAAAGACCTCGTAAAGAAACTTGGATCCGGAGGCGCTTCCAAGGTG
TACGACCCCGAGCAACGCAAACGCATGATCACTGGGCCTCAGTGGTGGGCTCGCTGCAAGCAAATGAACGTGCTGGACTC
CTTCATCAACTACTATGATTCCGAGAAGCACGCCGAGAACGCCGTGATTTTTCTGCATGGTAACGCTGCCTCCAGCTACC
TGTGGAGGCACGTCGTGCCTCACATCGAGCCCGTGGCTAGATGCATCATCCCTGATCTGATCGGAATGGGTAAGTCCGGC
AAGAGCGGGAATGGCTCATATCGCCTCCTGGATCACTACAAGTACCTCACCGCTTGGTTCGAGCTGCTGAACCTTTGAGT
TTAAAC

OOOOOO) pBFB357 Sgf to Pme (SEQ ID NO:452)
GCGATCGCCATGAAGAAAATCATCTTTGTGGGCCACGACTGGGGGGCTTGTCTGGCCTTTCACTACTCCTACGAGCACCA
AGACAAGATCAAGGCCATCGTCCATGCTGAGAGTGTCGTGGACGTGATCGAGTCCTGGGACGAGTGGCCTGACATCGAGG
AGGATATCGCCCTGATCAAGAGCGAAGAGGGCGAGAAAATGGTGCTTGAGAATAACTTCTTCGTCGAGACCATGCTCCCA
AGCAAGATCATGCGGAAACTGGAGCCTGAGGAGTTCGCTGCCTACCTGGAGCCATTCAAGGAGAAGGGCGAGGTTAGACG
GCCTACCCTCTCCTGGCCTCGCGAGATCCCTCTCGTTAAGGGAGGCAAGCCCGACGTCGTCCAGATTGTCCGCAACTACA
ACGCCTACCTTCGGGCCAGCGACGATCTGCCTAAGATGTTCATCGAGTCCGACCCTGGGTTCTTTTCCAACGCTATTGTC
GAGGGAGCTAAGAAGTTCCCTAACACCGAGTTCGTGAAGGTGAAGGGCCTCCACTTCAGCCAGGAGGACGCTCCAGATGA
AATGGGTAAGTACATCAAGAGCTTCGTGGAGCGCGTGCTGAAGAACGAGCAGGGAGGTTCTGGAGGATCTGGCTCGAGCG
GACGAAAGAGAGATCGGCTGGGGACCCTGGGGATTGGCGGGAGCTCTGGGGGAGGGTCTGGGGGTGGTGGTAGTGGCGGT
GGGAACGGCAGGTTCCTGACACTTAAGCCTCTTCCGGATAGTATTATCCAGGAGTCCCTTGAGATCCAGCAAGGGGTGAA
TCCTTTTTTTATCGGGCGAAGCGAGGACTGTAATTGCAAGATCGAAGATAACAGACTCAGTAGAGTGCACTGCTTTATTT
TCAAGAAGAGGCACGCAGTGGGAAAATCTATGTACGAATCCCCAGCTCAGGGCCTCGACGATATTTGGTACTGTCATACA
GGCACAAATGTATCCTACCTGAATAACAATCGAATGATCCAAGGCACCAAATTCCTTCTGCAGGATGGCGACGAAATCAA
GATTATCTGGGATAAGAATAACAAATTCGTTATAGGTTTTAAGGTCGAGATCAATGATACAACCGGGCTCTTCAACGAGG
GGCTGGGTATGCTGCAGGAGCAGCGGGTCGTACTGAAGCAGACTGCTGAAGAGAAAGACCTCGTAAAGAAACTTGGATCC
GGCGGCTCCGGCGGAGCTTCCAAGGTGTACGACCCCGAGCAACGCAAACGCATGATCACTGGGCCTCAGTGGTGGGCTCG
CTGCAAGCAAATGAACGTGCTGGACTCCTTCATCAACTACTATGATTCCGAGAAGCACGCCGAGAACGCCGTGATTTTTC
TGCATGGTAACGCTGCCTCCAGCTACCTGTGGAGGCACGTCGTGCCTCACATCGAGCCCGTGGCTAGATGCATCATCCCT
GATCTGATCGGAATGGGTAAGTCCGGCAAGAGCGGGAATGGCTCATATCGCCTCCTGGATCACTACAAGTACCTCACCGC
TTGGTTCGAGCTGCTGAACCTTTGAGTTTAAAC

PPPPPP) pBFB358 Sgf to Pme (SEQ ID NO:453)
GCGATCGCCATGAAGAAAATCATCTTTGTGGGCCACGACTGGGGGGCTTGTCTGGCCTTTCACTACTCCTACGAGCACCA
AGACAAGATCAAGGCCATCGTCCATGCTGAGAGTGTCGTGGACGTGATCGAGTCCTGGGACGAGTGGCCTGACATCGAGG

FIG. 67BI

AGGATATCGCCCTGATCAAGAGCGAAGAGGGCGAGAAAATGGTGCTTGAGAATAACTTCTTCGTCGAGACCATGCTCCCA
AGCAAGATCATGCGGAAACTGGAGCCTGAGGAGTTCGCTGCCTACCTGGAGCCATTCAAGGAGAAGGGCGAGGTTAGACG
GCCTACCCTCTCCTGGCCTCGCGAGATCCCTCTCGTTAAGGGAGGCAAGCCCGACGTCGTCCAGATTGTCCGCAACTACA
ACGCCTACCTTCGGGCCAGCGACGATCTGCCTAAGATGTTCATCGAGTCCGACCCTGGGTTCTTTTCCAACGCTATTGTC
GAGGGAGCTAAGAAGTTCCCTAACACCGAGTTCGTGAAGGTGAAGGGCCTCCACTTCAGCCAGGAGGACGCTCCAGATGA
AATGGGTAAGTACATCAAGAGCTTCGTGGAGCGCGTGCTGAAGAACGAGCAGGGTTCATCTGGTGGATCAGGTGGAAGTG
GAGGAGGTTCTGGAGGATCTGGCTCGAGCGGACGAAAGAGAGATCGGCTGGGGACCCTGGGGATTGGCGGGAGCTCTGGG
GGAGGGTCTGGGGGTGGTGGTAGTGGCGGTGGGAACGGCAGGTTCCTGACACTTAAGCCTCTTCCGGATAGTATTATCCA
GGAGTCCCTTGAGATCCAGCAAGGGGTGAATCCTTTTTTTATCGGGCGAAGCGAGGACTGTAATTGCAAGATCGAAGATA
ACAGACTCAGTAGAGTGCACTGCTTTATTTTCAAGAAGAGGCACGCAGTGGGAAAATCTATGTACGAATCCCCAGCTCAG
GGCCTCGACGATATTTGGTACTGTCATACAGGCACAAATGTATCCTACCTGAATAACAATCGAATGATCCAAGGCACCAA
ATTCCTTCTGCAGGATGGCGACGAAATCAAGATTATCTGGGATAAGAATAACAAATTCGTTATAGGTTTTAAGGTCGAGA
TCAATGATACAACCGGGCTCTTCAACGAGGGGCTGGGTATGCTGCAGGAGCAGCGGGTCGTACTGAAGCAGACTGCTGAA
GAGAAAGACCTCGTAAAGAAACTTGGATCCGGAGGCTCCGGCGGCTCCGGCGGAACCTCAGGAGGCAGTGGAGGAAGTTC
TGGAGCTTCCAAGGTGTACGACCCCGAGCAACGCAAACGCATGATCACTGGGCCTCAGTGGTGGGCTCGCTGCAAGCAAA
TGAACGTGCTGGACTCCTTCATCAACTACTATGATTCCGAGAAGCACGCCGAGAACGCCGTGATTTTTCTGCATGGTAAC
GCTGCCTCCAGCTACCTGTGGAGGCACGTCGTGCCTCACATCGAGCCCGTGGCTAGATGCATCATCCCTGATCTGATCGG
AATGGGTAAGTCCGGCAAGAGCGGGAATGGCTCATATCGCCTCCTGGATCACTACAAGTACCTCACCGCTTGGTTCGAGC
TGCTGAACCTTTGAGTTTAAAC

QQQQQQ) pBFB359 Sgf to Pme (SEQ ID NO:454)
GCGATCGCCATGTCCTTCATCAACTACTTGATTCCGAGAAGCACGCCGAGAACGCCGTGATTTTTCTGCATGGTAACGCT
GCCTCCAGCTACCTGTGGAGGCACGTCGTGCCTCACATCGAGCCCGTGGCTAGATGCATCATCCCTGATCTGATCGGAAT
GGGTAAGTCCGGCAAGAGCGGGAATGGCTCATATCGCCTCCTGGATCACTACAAGTACCTCACCGCTTGGTTCGAGCTGC
TGAACCTTCCAAAGAAAATCATCTTTGTGGGCCACGACTGGGGGGCTTGTCTGGCCTTTCACTACTCCTACGAGCACCAA
GACAAGATCAAGGCCATCGTCCATGCTGAGAGTGTCGTGGACGTGATCGAGTCCTGGGACGAGTGGCCTGACATCGAGGA
GGATATCGCCCTGATCAAGAGCGAAGAGGGCGAGAAAATGGTGCTTGAGAATAACTTCTTCGTCGAGACCATGCTCCCAA
GCAAGATCATGCGGAAACTGGAGCCTGAGGAGTTCGCTGCCTACCTGGAGCCATTCAAGGAGAAGGGCGAGGTTAGACGG
CCTACCCTCTCCTGGCCTCGCGAGATCCCTCTCGTTAAGGGAGGCAAGCCCGACGTCGTCCAGATTGTCCGCAACTACAA
CGCCTACCTTCGGGCCAGCGACGATCTGCCTAAGATGTTCATCGAGTCCGACCCTGGGTTCTTTTCCAACGCTATTGTCG
AGGGAGCTAAGAAGTTCCCTAACACCGAGTTCGTGAAGGTGAAGGGCCTCCACTTCAGCCAGGAGGACGCTCCAGATGAA
ATGGGTAAGTACATCAAGAGCTTCGTGGAGCGCGTGCTGAAGAACGAGCAGGGCTCGAGCGGACGAAAGAGAGATCGGCT
GGGGACCCTGGGGATTGGCGGGAGCTCTGGGGGAGGGTCTGGGGGTGGTGGTAGTGGCGGTGGGAACGGCAGGTTCCTGA
CACTTAAGCCTCTTCCGGATAGTATTATCCAGGAGTCCCTTGAGATCCAGCAAGGGGTGAATCCTTTTTTTATCGGGCGA
AGCGAGGACTGTAATTGCAAGATCGAAGATAACAGACTCAGTAGAGTGCACTGCTTTATTTTCAAGAAGAGGCACGCAGT
GGGAAAATCTATGTACGAATCCCCAGCTCAGGGCCTCGACGATATTTGGTACTGTCATACAGGCACAAATGTATCCTACC
TGAATAACAATCGAATGATCCAAGGCACCAAATTCCTTCTGCAGGATGGCGACGAAATCAAGATTATCTGGGATAAGAAT
AACAAATTCGTTATAGGTTTTAAGGTCGAGATCAATGATACAACCGGGCTCTTCAACGAGGGGCTGGGTATGCTGCAGGA
GCAGCGGGTCGTACTGAAGCAGACTGCTGAAGAGAAAGACCTCGTAAAGAAACTTGGATCCGGAGGCGCTTCCAAGGTGT
ACGACCCCGAGCAACGCAAACGCATGATCACTGGGCCTCAGTGGTGGGCTCGCTGCAAGCAAATGAACGTGCTGTGAGTT
TAAAC

RRRRRR) pBFB360 Sgf to Pme (SEQ ID NO:455)
GCGATCGCCATGTCCTTCATCAACTACTATGATTCCGAGAAGCACGCCGAGAACGCCGTGATTTTTCTGCATGGTAACGC
TGCCTCCAGCTACCTGTGGAGGCACGTCGTGCCTCACATCGAGCCCGTGGCTAGATGCATCATCCCTGATCTGATCGGAA
TGGGTAAGTCCGGCAAGAGCGGGAATGGCTCATATCGCCTCCTGGATCACTACAAGTACCTCACCGCTTGGTTCGAGCTG
CTGAACCTTCCAAAGAAAATCATCTTTGTGGGCCACGACTGGGGGGCTTGTCTGGCCTTTCACTACTCCTACGAGCACCA
AGACAAGATCAAGGCCATCGTCCATGCTGAGAGTGTCGTGGACGTGATCGAGTCCTGGGACGAGTGGCCTGACATCGAGG
AGGATATCGCCCTGATCAAGAGCGAAGAGGGCGAGAAAATGGTGCTTGAGAATAACTTCTTCGTCGAGACCATGCTCCCA
AGCAAGATCATGCGGAAACTGGAGCCTGAGGAGTTCGCTGCCTACCTGGAGCCATTCAAGGAGAAGGGCGAGGTTAGACG
GCCTACCCTCTCCTGGCCTCGCGAGATCCCTCTCGTTAAGGGAGGCAAGCCCGACGTCGTCCAGATTGTCCGCAACTACA
ACGCCTACCTTCGGGCCAGCGACGATCTGCCTAAGATGTTCATCGAGTCCGACCCTGGGTTCTTTTCCAACGCTATTGTC
GAGGGAGCTAAGAAGTTCCCTAACACCGAGTTCGTGAAGGTGAAGGGCCTCCACTTCAGCCAGGAGGACGCTCCAGATGA
AATGGGTAAGTACATCAAGAGCTTCGTGGAGCGCGTGCTGAAGAACGAGCAGGGAGGTTCTGGAGGATCTGGCTCGAGCG
GACGAAAGAGAGATCGGCTGGGGACCCTGGGGATTGGCGGGAGCTCTGGGGGAGGGTCTGGGGGTGGTGGTAGTGGCGGT
GGGAACGGCAGGTTCCTGACACTTAAGCCTCTTCCGGATAGTATTATCCAGGAGTCCCTTGAGATCCAGCAAGGGGTGAA
TCCTTTTTTTATCGGGCGAAGCGAGGACTGTAATTGCAAGATCGAAGATAACAGACTCAGTAGAGTGCACTGCTTTATTT

FIG. 67BJ

TCAAGAAGAGGCACGCAGTGGGAAAATCTATGTACGAATCCCCAGCTCAGGGCCTCGACGATATTTGGTACTGTCATACA
GGCACAAATGTATCCTACCTGAATAACAATCGAATGATCCAAGGCACCAAATTCCTTCTGCAGGATGGCGACGAAATCAA
GATTATCTGGGATAAGAATAACAAATTCGTTATAGGTTTTAAGGTCGAGATCAATGATACAACCGGGCTCTTCAACGAGG
GGCTGGGTATGCTGCAGGAGCAGCGGGTCGTACTGAAGCAGACTGCTGAAGAGAAAGACCTCGTAAAGAAACTTGGATCC
GGAGGCTCCGGCGGCTCCGGCGGAGCTTCCAAGGTGTACGACCCCGAGCAACGCAAACGCATGATCACTGGGCCTCAGTG
GTGGGCTCGCTGCAAGCAAATGAACGTGCTGTGAGTTTAAAC

SSSSSS) pBFB361 Sgf to Pme (SEQ ID NO:456)
GCGATCGCCATGTCCTTCATCAACTACTATGATTCCGAGAAGCACGCCGAGAACGCCGTGATTTTTCTGCATGGTAACGC
TGCCTCCAGCTACCTGTGGAGGCACGTCGTGCCTCACATCGAGCCCGTGGCTAGATGCATCATCCCTGATCTGATCGGAA
TGGGTAAGTCCGGCAAGAGCGGGAATGGCTCATATCGCCTCCTGGATCACTACAAGTACCTCACCGCTTGGTTCGAGCTG
CTGAACCTTCCAAAGAAAATCATCTTTGTGGGCCACGACTGGGGGGCTTGTCTGGCCTTTCACTACTCCTACGAGCACCA
AGACAAGATCAAGGCCATCGTCCATGCTGAGAGTGTCGTGGACGTGATCGAGTCCTGGGACGAGTGGCCTGACATCGAGG
AGGATATCGCCCTGATCAAGAGCGAAGAGGGCGAGAAAATGGTGCTTGAGAATAACTTCTTCGTCGAGACCATGCTCCCA
AGCAAGATCATGCGGAAACTGGAGCCTGAGGAGTTCGCTGCCTACCTGGAGCCATTCAAGGAGAAGGGCGAGGTTAGACG
GCCTACCCTCTCCTGGCCTCGCGAGATCCCTCTCGTTAAGGGAGGCAAGCCCGACGTCGTCCAGATTGTCCGCAACTACA
ACGCCTACCTTCGGGCCAGCGACGATCTGCCTAAGATGTTCATCGAGTCCGACCCTGGGTTCTTTTCCAACGCTATTGTC
GAGGGAGCTAAGAAGTTCCCTAACACCGAGTTCGTGAAGGTGAAGGGCCTCCACTTCAGCCAGGAGGACGCTCCAGATGA
AATGGGTAAGTACATCAAGAGCTTCGTGGAGCGCGTGCTGAAGAACGAGCAGGGTTCATCTGGTGGATCAGGTGGAAGTG
GAGGAGGTTCTGGAGGATCTGGCTCGAGCGGACGAAAGAGAGATCGGCTGGGGACCCTGGGGATTGGCGGGAGCTCTGGG
GGAGGGTCTGGGGGTGGTGGTAGTGGCGGTGGGAACGGCAGGTTCCTGACACTTAAGCCTCTTCCGGATAGTATTATCCA
GGAGTCCCTTGAGATCCAGCAAGGGGTGAATCCTTTTTTTATCGGGCGAAGCGAGGACTGTAATTGCAAGATCGAAGATA
ACAGACTCAGTAGAGTGCACTGCTTTATTTTCAAGAAGAGGCACGCAGTGGGAAAATCTATGTACGAATCCCCAGCTCAG
GGCCTCGACGATATTTGGTACTGTCATACAGGCACAAATGTATCCTACCTGAATAACAATCGAATGATCCAAGGCACCAA
ATTCCTTCTGCAGGATGGCGACGAAATCAAGATTATCTGGGATAAGAATAACAAATTCGTTATAGGTTTTAAGGTCGAGA
TCAATGATACAACCGGGCTCTTCAACGAGGGGCTGGGTATGCTGCAGGAGCAGCGGGTCGTACTGAAGCAGACTGCTGAA
GAGAAAGACCTCGTAAAGAAACTTGGATCCGGAGGCTCCGGCGGCTCCGGCGGAACCTCAGGAGGCAGTGGAGGAAGTTC
TGGAGCTTCCAAGGTGTACGACCCCGAGCAACGCAAACGCATGATCACTGGGCCTCAGTGGTGGGCTCGCTGCAAGCAAA
TGAACGTGCTGTGAGTTTAAAC

TTTTTT) pBFB362 Sgf to Pme (SEQ ID NO:457)
GCGATCGCCATGGTGGCTAGATGCATCATCCCTGATCTGATCGGAATGGGTAAGTCCGGCAAGAGCGGGAATGGCTCATA
TCGCCTCCTGGATCACTACAAGTACCTCACCGCTTGGTTCGAGCTGCTGAACCTTCCAAAGAAAATCATCTTTGTGGGCC
ACGACTGGGGGGCTTGTCTGGCCTTTCACTACTCCTACGAGCACCAAGACAAGATCAAGGCCATCGTCCATGCTGAGAGT
GTCGTGGACGTGATCGAGTCCTGGGACGAGTGGCCTGACATCGAGGAGGATATCGCCCTGATCAAGAGCGAAGAGGGCGA
GAAAATGGTGCTTGAGAATAACTTCTTCGTCGAGACCATGCTCCCAAGCAAGATCATGCGGAAACTGGAGCCTGAGGAGT
TCGCTGCCTACCTGGAGCCATTCAAGGAGAAGGGCGAGGTTAGACGGCCTACCCTCTCCTGGCCTCGCGAGATCCCTCTC
GTTAAGGGAGGCAAGCCCGACGTCGTCCAGATTGTCCGCAACTACAACGCCTACCTTCGGGCCAGCGACGATCTGCCTAA
GATGTTCATCGAGTCCGACCCTGGGTTCTTTTCCAACGCTATTGTCGAGGGAGCTAAGAAGTTCCCTAACACCGAGTTCG
TGAAGGTGAAGGGCCTCCACTTCAGCCAGGAGGACGCTCCAGATGAAATGGGTAAGTACATCAAGAGCTTCGTGGAGCGC
GTGCTGAAGAACGAGCAGGGCTCGAGCGGACGAAAGAGAGATCGGCTGGGGACCCTGGGGATTGGCGGGAGCTCTGGGGG
AGGGTCTGGGGGTGGTGGTAGTGGCGGTGGGAACGGCAGGTTCCTGACACTTAAGCCTCTTCCGGATAGTATTATCCAGG
AGTCCCTTGAGATCCAGCAAGGGGTGAATCCTTTTTTTATCGGGCGAAGCGAGGACTGTAATTGCAAGATCGAAGATAAC
AGACTCAGTAGAGTGCACTGCTTTATTTTCAAGAAGAGGCACGCAGTGGGAAAATCTATGTACGAATCCCCAGCTCAGGG
CCTCGACGATATTTGGTACTGTCATACAGGCACAAATGTATCCTACCTGAATAACAATCGAATGATCCAAGGCACCAAAT
TCCTTCTGCAGGATGGCGACGAAATCAAGATTATCTGGGATAAGAATAACAAATTCGTTATAGGTTTTAAGGTCGAGATC
AATGATACAACCGGGCTCTTCAACGAGGGGCTGGGTATGCTGCAGGAGCAGCGGGTCGTACTGAAGCAGACTGCTGAAGA
GAAAGACCTCGTAAAGAAACTTGGATCCGGAGGCGCTTCCAAGGTGTACGACCCCGAGCAACGCAAACGCATGATCACTG
GGCCTCAGTGGTGGGCTCGCTGCAAGCAAATGAACGTGCTGGACTCCTTCATCAACTACTATGATTCCGAGAAGCACGCC
GAGAACGCCGTGATTTTTCTGCATGGTAACGCTGCCTCCAGCTACCTGTGGAGGCACGTCGTGCCTCACATCGAGTGAGT
TTAAAC

UUUUUU) pBFB363 Sgf to Pme (SEQ ID NO:458)
GCGATCGCCATGGTGGCTAGATGCATCATCCCTGATCTGATCGGAATGGGTAAGTCCGGCAAGAGCGGGAATGGCTCATA
TCGCCTCCTGGATCACTACAAGTACCTCACCGCTTGGTTCGAGCTGCTGAACCTTCCAAAGAAAATCATCTTTGTGGGCC
ACGACTGGGGGGCTTGTCTGGCCTTTCACTACTCCTACGAGCACCAAGACAAGATCAAGGCCATCGTCCATGCTGAGAGT
GTCGTGGACGTGATCGAGTCCTGGGACGAGTGGCCTGACATCGAGGAGGATATCGCCCTGATCAAGAGCGAAGAGGGCGA

*FIG. 67BK*

GAAAATGGTGCTTGAGAATAACTTCTTCGTCGAGACCATGCTCCCAAGCAAGATCATGCGGAAACTGGAGCCTGAGGAGT
TCGCTGCCTACCTGGAGCCATTCAAGGAGAAGGGCGAGGTTAGACGGCCTACCCTCTCCTGGCCTCGCGAGATCCCTCTC
GTTAAGGGAGGCAAGCCCGACGTCGTCCAGATTGTCCGCAACTACAACGCCTACCTTCGGGCCAGCGACGATCTGCCTAA
GATGTTCATCGAGTCCGACCCTGGGTTCTTTTCCAACGCTATTGTCGAGGGAGCTAAGAAGTTCCCTAACACCGAGTTCG
TGAAGGTGAAGGGCCTCCACTTCAGCCAGGAGGACGCTCCAGATGAAATGGGTAAGTACATCAAGAGCTTCGTGGAGCGC
GTGCTGAAGAACGAGCAGGGAGGTTCTGGAGGATCTGGCTCGAGCGGACGAAAGAGAGATCGGCTGGGGACCCTGGGGAT
TGGCGGGAGCTCTGGGGGAGGGTCTGGGGGTGGTGGTAGTGGCGGTGGGAACGGCAGGTTCCTGACACTTAAGCCTCTTC
CGGATAGTATTATCCAGGAGTCCCTTGAGATCCAGCAAGGGGTGAATCCTTTTTTTATCGGGCGAAGCGAGGACTGTAAT
TGCAAGATCGAAGATAACAGACTCAGTAGAGTGCACTGCTTTATTTTCAAGAAGAGGCACGCAGTGGGAAAATCTATGTA
CGAATCCCCAGCTCAGGGCCTCGACGATATTTGGTACTGTCATACAGGCACAAATGTATCCTACCTGAATAACAATCGAA
TGATCCAAGGCACCAAATTCCTTCTGCAGGATGGCGACGAAATCAAGATTATCTGGGATAAGAATAACAAATTCGTTATA
GGTTTTAAGGTCGAGATCAATGATACAACCGGGCTCTTCAACGAGGGGCTGGGTATGCTGCAGGAGCAGCGGGTCGTACT
GAAGCAGACTGCTGAAGAGAAAGACCTCGTAAAGAAACTTGGATCCGGAGGCTCCGGCGGCTCCGGCGGAGCTTCCAAGG
TGTACGACCCCGAGCAACGCAAACGCATGATCACTGGGCCTCAGTGGTGGGCTCGCTGCAAGCAAATGAACGTGCTGGAC
TCCTTCATCAACTACTATGATTCCGAGAAGCACGCCGAGAACGCCGTGATTTTTCTGCATGGTAACGCTGCCTCCAGCTA
CCTGTGGAGGCACGTCGTGCCTCACATCGAGTGAGTTTAAAC

VVVVVV) pBFB364 Sgf to Pme (SEQ ID NO:459)
GCGATCGCCATGGTGGCTAGATGCATCATCCCTGATCTGATCGGAATGGGTAAGTCCGGCAAGAGCGGGAATGGCTCATA
TCGCCTCCTGGATCACTACAAGTACCTCACCGCTTGGTTCGAGCTGCTGAACCTTCCAAAGAAAATCATCTTTGTGGGCC
ACGACTGGGGGGCTTGTCTGGCCTTTCACTACTCCTACGAGCACCAAGACAAGATCAAGGCCATCGTCCATGCTGAGAGT
GTCGTGGACGTGATCGAGTCCTGGGACGAGTGGCCTGACATCGAGGAGGATATCGCCCTGATCAAGAGCGAAGAGGGCGA
GAAAATGGTGCTTGAGAATAACTTCTTCGTCGAGACCATGCTCCCAAGCAAGATCATGCGGAAACTGGAGCCTGAGGAGT
TCGCTGCCTACCTGGAGCCATTCAAGGAGAAGGGCGAGGTTAGACGGCCTACCCTCTCCTGGCCTCGCGAGATCCCTCTC
GTTAAGGGAGGCAAGCCCGACGTCGTCCAGATTGTCCGCAACTACAACGCCTACCTTCGGGCCAGCGACGATCTGCCTAA
GATGTTCATCGAGTCCGACCCTGGGTTCTTTTCCAACGCTATTGTCGAGGGAGCTAAGAAGTTCCCTAACACCGAGTTCG
TGAAGGTGAAGGGCCTCCACTTCAGCCAGGAGGACGCTCCAGATGAAATGGGTAAGTACATCAAGAGCTTCGTGGAGCGC
GTGCTGAAGAACGAGCAGGGTTCATCTGGTGGATCAGGTGGAAGTGGAGGAGGTTCTGGAGGATCTGGCTCGAGCGGACG
AAAGAGAGATCGGCTGGGGACCCTGGGGATTGGCGGGAGCTCTGGGGGAGGGTCTGGGGGTGGTGGTAGTGGCGGTGGGA
ACGGCAGGTTCCTGACACTTAAGCCTCTTCCGGATAGTATTATCCAGGAGTCCCTTGAGATCCAGCAAGGGGTGAATCCT
TTTTTTATCGGGCGAAGCGAGGACTGTAATTGCAAGATCGAAGATAACAGACTCAGTAGAGTGCACTGCTTTATTTTCAA
GAAGAGGCACGCAGTGGGAAAATCTATGTACGAATCCCCAGCTCAGGGCCTCGACGATATTTGGTACTGTCATACAGGCA
CAAATGTATCCTACCTGAATAACAATCGAATGATCCAAGGCACCAAATTCCTTCTGCAGGATGGCGACGAAATCAAGATT
ATCTGGGATAAGAATAACAAATTCGTTATAGGTTTTAAGGTCGAGATCAATGATACAACCGGGCTCTTCAACGAGGGGCT
GGGTATGCTGCAGGAGCAGCGGGTCGTACTGAAGCAGACTGCTGAAGAGAAAGACCTCGTAAAGAAACTTGGATCCGGAG
GCTCCGGCGGCTCCGGCGGAACCTCAGGAGGCAGTGGAGGAAGTTCTGGAGCTTCCAAGGTGTACGACCCCGAGCAACGC
AAACGCATGATCACTGGGCCTCAGTGGTGGGCTCGCTGCAAGCAAATGAACGTGCTGGACTCCTTCATCAACTACTATGA
TTCCGAGAAGCACGCCGAGAACGCCGTGATTTTTCTGCATGGTAACGCTGCCTCCAGCTACCTGTGGAGGCACGTCGTGC
CTCACATCGAGTGAGTTTAAAC

WWWWWW) pBFB368 Sgf to Pme (SEQ ID NO:460)
GCGATCGCCATGACCGCTATCCTCAGCGTGGTGCCATTTCACCACGGCTTCGGCATGTTCACCACGCTGGGCTACTTGAT
CTGCGGCTTTCGGGTCGTGCTCATGTACCGCTTCGAGGAGGAGCTATTCTTGCGCAGCTTGCAAGACTATAAGATTCAAT
CTGCCCTGCTGGTGCCCACACTATTTAGCTTCTTCGCTAAGAGCACTCTCATCGACAAGTACGACCTAAGCAACTTGCAC
GAGATCGCCAGCGGCGGGGCGCCGCTCAGCAAGGAGGTAGGTGAGGCCGTGGCCAAACGCTTCCACCTACCAGGCATCCG
CCAGGGCTACGGCCTGACAGAAACAACCAGCGCCATTCTGATCACCCCCGAAGGGGACGACAAGCCTGGCGCAGTAGGCA
AGGTGGTGCCCTTCTTCGAGGCTAAGGTGGTGGACTTGGACACTGGTAAGACACTGGGTGTGAACCAGCGCGGCGAGCTG
TGCGTCCGTGGCCCCATGATCATGAGCGGCTACGTTAACAACCCCGAGGCTACAAACGCTCTCATCGACAAGGACGGCTG
GCTGCACAGCGGCGACATCGCCTACTGGGACGAGGACGAGCACTTCTTCATCGTGGACCGGCTGAAGAGCCTGATCAAAT
ACAAGGGCTACCAGGTAGCCCCAGCCGAACTGGAGAGCATCCTGCTGCAACACCCCAACATCTTCGACGCCGGGGTCGCC
GGCCTGCCCGACGACGATGCCGGCGAGCTGCCCGCCGCAGTCGTCGTGCTGGAACACGGTAAAACCATGACCGAGAAGGA
GATCGTGGACTATGTGGCCAGCCAGGTTACAACCGCCAAGAAGCTGCGCGGTGGTGTTGTGTTCGTGGACGAGGTGCCTA
AAGGACTGACCGGCAAGTTGGACGCCCGCAAGATCCGCGAGATTCTCATTAAGGCCAAGAAGGGCTCGAGCGGATGGTAT
TTTGGCAAGATCACCAGACGGGAGTCAGAGCGGTTACTGCTCAATGCAGAGAACCCGAGAGGGACCTTCCTCGTGCGAGA
AAGTGAGACCACGAAAGGTGCCTACTGCCTCTCAGTGTCTGACTTCGACAACGCCAAGGGCCTCAACGTGAAGCACTACA
AGATCCGCAAGCTGGACAGCGGCGGCTTCTACATCACCTCCCGCACCCAGTTCAACAGCCTGCAGCAGCTGGTGGCCTAC
TACTCCAAACACGCCGATGGCCTGTGCCACCGCCTCACCACCGTGTGCGGTTCCGGAGGATCTACTTCGGGGTCAGGTAA

*FIG. 67BL*

ACCTGGCTCGGGTGAGGGATCGGAAATTTATGGTGAATTCGGGAGCTCCGGTGCCAAAAACATTAAGAAGGGCCCAGCGC
CATTCTACCCACTCGAAGACGGGACCGCCGGCGAGCAGCTGCACAAAGCCATGAAGCGCTACGCCCTGGTGCCCGGCACC
ATCGCCTTTACCGACGCACATATCGAGGTGGACATTACCTACGCCGAGTACTTCGAGATGAGCGTTCGGCTGGCAGAAGC
TATGAAGCGCTATGGGCTGAATACAAACCATCGGATCGTGGTGTGCAGCGAGAATAGCTTGCAGTTCTTCATGCCCGTGT
TGGGTGCCCTGTTCATCGGTGTGGCTGTGGCCCCAGCTAACGACATCTACAACGAGCGCGAGCTGCTGAACAGCATGGGC
ATCAGCCAGCCCACCGTCGTATTCGTGAGCAAGAAAGGGCTGCAAAAGATCCTCAACGTGCAAAAGAAGCTACCGATCAT
ACAAAAGATCATCATCATGGATAGCAAGACCGACTACCAGGGCTTCCAAAGCATGTACACCTTCGTGACTTCCCATTTGC
CACCCGGCTTCAACGAGTACGACTTCGTGCCCGAGAGCTTCGACCGGGACAAAACCATCGCCCTGATCATGAACAGTAGT
GGCAGTACCGGATTGCCCAAGGGCGTAGCCCTACCGCACCGCACCGCTTGTGTCCGATTCAGTCATGCCCGCGACCCCAT
CTTCGGCAACCAGATCATCCCCTGAGTTTAAAC

XXXXXX) pBFB369 Sgf to Pme (SEQ ID NO:461)
GCGATCGCCATGACCGCTATCCTCAGCGTGGTGCCATTTCACCACGGCTTCGGCATGTTCACCACGCTGGGCTACTTGAT
CTGCGGCTTTCGGGTCGTGCTCATGTACCGCTTCGAGGAGGAGCTATTCTTGCGCAGCTTGCAAGACTATAAGATTCAAT
CTGCCCTGCTGGTGCCCACACTATTTAGCTTCTTCGCTAAGAGCACTCTCATCGACAAGTACGACCTAAGCAACTTGCAC
GAGATCGCCAGCGGCGGGGCGCCGCTCAGCAAGGAGGTAGGTGAGGCCGTGGCCAAACGCTTCCACCTACCAGGCATCCG
CCAGGGCTACGGCCTGACAGAAACAACCAGCGCCATTCTGATCACCCCCGAAGGGGACGACAAGCCTGGCGCAGTAGGCA
AGGTGGTGCCCTTCTTCGAGGCTAAGGTGGTGGACTTGGACACTGGTAAGACACTGGGTGTGAACCAGCGCGGCGAGCTG
TGCGTCCGTGGCCCCATGATCATGAGCGGCTACGTTAACAACCCCGAGGCTACAAACGCTCTCATCGACAAGGACGGCTG
GCTGCACAGCGGCGACATCGCCTACTGGGACGAGGACGAGCACTTCTTCATCGTGGACCGGCTGAAGAGCCTGATCAAAT
ACAAGGGCTACCAGGTAGCCCCAGCCGAACTGGAGAGCATCCTGCTGCAACACCCCAACATCTTCGACGCCGGGGTCGCC
GGCCTGCCCGACGACGATGCCGGCGAGCTGCCCGCCGCAGTCGTCGTGCTGGAACACGGTAAAACCATGACCGAGAAGGA
GATCGTGGACTATGTGGCCAGCCAGGTTACAACCGCCAAGAAGCTGCGCGGTGGTGTTGTGTTCGTGGACGAGGTGCCTA
AAGGACTGACCGGCAAGTTGGACGCCCGCAAGATCCGCGAGATTCTCATTAAGGCCAAGAAGGGCTCGAGCGGAGGTTCA
GGCGGTTCCGGATGGTATTTTGGCAAGATCACCAGACGGGAGTCAGAGCGGTTACTGCTCAATGCAGAGAACCCGAGAGG
GACCTTCCTCGTGCGAGAAAGTGAGACCACGAAAGGTGCCTACTGCCTCTCAGTGTCTGACTTCGACAACGCCAAGGGCC
TCAACGTGAAGCACTACAAGATCCGCAAGCTGGACAGCGGCGGCTTCTACATCACCTCCCGCACCCAGTTCAACAGCCTG
CAGCAGCTGGTGGCCTACTACTCCAAACACGCCGATGGCCTGTGCCACCGCCTCACCACCGTGTGCGGTTCCGGAGGATC
TACTTCGGGGTCAGGTAAACCTGGCTCGGGTGAGGGATCGGAAATTTATGGTGAATTCGGATCCGGGTCAGGTGGATCTG
GAGGGAGCTCCGGTGCCAAAAACATTAAGAAGGGCCCAGCGCCATTCTACCCACTCGAAGACGGGACCGCCGGCGAGCAG
CTGCACAAAGCCATGAAGCGCTACGCCCTGGTGCCCGGCACCATCGCCTTTACCGACGCACATATCGAGGTGGACATTAC
CTACGCCGAGTACTTCGAGATGAGCGTTCGGCTGGCAGAAGCTATGAAGCGCTATGGGCTGAATACAAACCATCGGATCG
TGGTGTGCAGCGAGAATAGCTTGCAGTTCTTCATGCCCGTGTTGGGTGCCCTGTTCATCGGTGTGGCTGTGGCCCCAGCT
AACGACATCTACAACGAGCGCGAGCTGCTGAACAGCATGGGCATCAGCCAGCCCACCGTCGTATTCGTGAGCAAGAAAGG
GCTGCAAAAGATCCTCAACGTGCAAAAGAAGCTACCGATCATACAAAAGATCATCATCATGGATAGCAAGACCGACTACC
AGGGCTTCCAAAGCATGTACACCTTCGTGACTTCCCATTTGCCACCCGGCTTCAACGAGTACGACTTCGTGCCCGAGAGC
TTCGACCGGGACAAAACCATCGCCCTGATCATGAACAGTAGTGGCAGTACCGGATTGCCCAAGGGCGTAGCCCTACCGCA
CCGCACCGCTTGTGTCCGATTCAGTCATGCCCGCGACCCCATCTTCGGCAACCAGATCATCCCCTGAGTTTAAAC

YYYYYY) pBFB370 Sgf to Pme (SEQ ID NO:462)
GCGATCGCCATGACCGCTATCCTCAGCGTGGTGCCATTTCACCACGGCTTCGGCATGTTCACCACGCTGGGCTACTTGAT
CTGCGGCTTTCGGGTCGTGCTCATGTACCGCTTCGAGGAGGAGCTATTCTTGCGCAGCTTGCAAGACTATAAGATTCAAT
CTGCCCTGCTGGTGCCCACACTATTTAGCTTCTTCGCTAAGAGCACTCTCATCGACAAGTACGACCTAAGCAACTTGCAC
GAGATCGCCAGCGGCGGGGCGCCGCTCAGCAAGGAGGTAGGTGAGGCCGTGGCCAAACGCTTCCACCTACCAGGCATCCG
CCAGGGCTACGGCCTGACAGAAACAACCAGCGCCATTCTGATCACCCCCGAAGGGGACGACAAGCCTGGCGCAGTAGGCA
AGGTGGTGCCCTTCTTCGAGGCTAAGGTGGTGGACTTGGACACTGGTAAGACACTGGGTGTGAACCAGCGCGGCGAGCTG
TGCGTCCGTGGCCCCATGATCATGAGCGGCTACGTTAACAACCCCGAGGCTACAAACGCTCTCATCGACAAGGACGGCTG
GCTGCACAGCGGCGACATCGCCTACTGGGACGAGGACGAGCACTTCTTCATCGTGGACCGGCTGAAGAGCCTGATCAAAT
ACAAGGGCTACCAGGTAGCCCCAGCCGAACTGGAGAGCATCCTGCTGCAACACCCCAACATCTTCGACGCCGGGGTCGCC
GGCCTGCCCGACGACGATGCCGGCGAGCTGCCCGCCGCAGTCGTCGTGCTGGAACACGGTAAAACCATGACCGAGAAGGA
GATCGTGGACTATGTGGCCAGCCAGGTTACAACCGCCAAGAAGCTGCGCGGTGGTGTTGTGTTCGTGGACGAGGTGCCTA
AAGGACTGACCGGCAAGTTGGACGCCCGCAAGATCCGCGAGATTCTCATTAAGGCCAAGAAGGGCTCGAGCGGAGGTTCA
GGCGGTTCCGGAGGAGGTTCTGGCGGATCAGGCGGTTCGGGGTGGTATTTTGGCAAGATCACCAGACGGGAGTCAGAGCG
GTTACTGCTCAATGCAGAGAACCCGAGAGGGACCTTCCTCGTGCGAGAAAGTGAGACCACGAAAGGTGCCTACTGCCTCT
CAGTGTCTGACTTCGACAACGCCAAGGGCCTCAACGTGAAGCACTACAAGATCCGCAAGCTGGACAGCGGCGGCTTCTAC
ATCACCTCCCGCACCCAGTTCAACAGCCTGCAGCAGCTGGTGGCCTACTACTCCAAACACGCCGATGGCCTGTGCCACCG
CCTCACCACCGTGTGCGGTTCCGGAGGATCTACTTCGGGGTCAGGTAAACCTGGCTCGGGTGAGGGATCGGAAATTTATG

*FIG. 67*BM

GTGAATTCGGATCCGGTGGTTCAGGTGGCAGCGGAGGAGGGTCAGGTGGATCTGGAGGGAGCTCCGGTGCCAAAAACATT
AAGAAGGGCCCAGCGCCATTCTACCCACTCGAAGACGGGACCGCCGGCGAGCAGCTGCACAAAGCCATGAAGCGCTACGC
CCTGGTGCCCGGCACCATCGCCTTTACCGACGCACATATCGAGGTGGACATTACCTACGCCGAGTACTTCGAGATGAGCG
TTCGGCTGGCAGAAGCTATGAAGCGCTATGGGCTGAATACAAACCATCGGATCGTGGTGTGCAGCGAGAATAGCTTGCAG
TTCTTCATGCCCGTGTTGGGTGCCCTGTTCATCGGTGTGGCTGTGGCCCCAGCTAACGACATCTACAACGAGCGCGAGCT
GCTGAACAGCATGGGCATCAGCCAGCCCACCGTCGTATTCGTGAGCAAGAAAGGGCTGCAAAAGATCCTCAACGTGCAAA
AGAAGCTACCGATCATACAAAAGATCATCATCATGGATAGCAAGACCGACTACCAGGGCTTCCAAAGCATGTACACCTTC
GTGACTTCCCATTTGCCACCCGGCTTCAACGAGTACGACTTCGTGCCCGAGAGCTTCGACCGGGACAAAACCATCGCCCT
GATCATGAACAGTAGTGGCAGTACCGGATTGCCCAAGGGCGTAGCCCTACCGCACCGCACCGCTTGTGTCCGATTCAGTC
ATGCCCGCGACCCCATCTTCGGCAACCAGATCATCCCCTGAGTTTAAAC

ZZZZZZ) pBFB371 Sgf to Pme (SEQ ID NO:463)
GCGATCGCCATGCCTGGCGCAGTAGGCAAGGTGGTGCCCTTCTTCGAGGCTAAGGTGGTGGACTTGGACACCGGTAAGAC
ACTGGGTGTGAACCAGCGCGGCGAGCTGTGCGTCCGTGGCCCCATGATCATGAGCGGCTACGTTAACAACCCCGAGGCTA
CAAACGCTCTCATCGACAAGGACGGCTGGCTGCACAGCGGCGACATCGCCTACTGGGACGAGGACGAGCACTTCTTCATC
GTGGACCGGCTGAAGAGCCTGATCAAATACAAGGGCTACCAGGTAGCCCCAGCCGAACTGGAGAGCATCCTGCTGCAACA
CCCCAACATCTTCGACGCCGGGGTCGCCGGCCTGCCCGACGACGATGCCGGCGAGCTGCCCGCCGCAGTCGTCGTGCTGG
AACACGGTAAAACCATGACCGAGAAGGAGATCGTGGACTATGTGGCCAGCCAGGTTACAACCGCCAAGAAGCTGCGCGGT
GGTGTTGTGTTCGTGGACGAGGTGCCTAAAGGACTGACCGGCAAGTTGGACGCCCGCAAGATCCGCGAGATTCTCATTAA
GGCCAAGAAGGGCTCGACCGGATGGTATTTTGGCAAGATCACCAGACGGGAGTCAGAGCGGTTACTGCTCAATGCAGAGA
ACCCGAGAGGGACCTTCCTCGTGCGAGAAAGTGAGACCACGAAAGGTGCCTACTGCCTCTCAGTGTCTGACTTCGACAAC
GCCAAGGGCCTCAACGTGAAGCACTACAAGATCCGCAAGCTGGACAGCGGCGGCTTCTACATCACCTCCCGCACCCAGTT
CAACAGCCTGCAGCAGCTGGTGGCCTACTACTCCAAACACGCCGATGGCCTGTGCCACCGCCTCACCACCGTGTGCGGTT
CCGGAGGATCTACTTCGGGGTCAGGTAAACCTGGCTCGGGTGAGGGATCGGAAATTTATGGTGAATTCGGGAGCTCCGGT
GCCAAAAACATTAAGAAGGGCCCAGCGCCATTCTACCCACTCGAAGACGGGACCGCCGGCGAGCAGCTGCACAAAGCCAT
GAAGCGCTACGCCCTGGTGCCCGGCACCATCGCCTTTACCGACGCACATATCGAGGTGGACATTACCTACGCCGAGTACT
TCGAGATGAGCGTTCGGCTGGCAGAAGCTATGAAGCGCTATGGGCTGAATACAAACCATCGGATCGTGGTGTGCAGCGAG
AATAGCTTGCAGTTCTTCATGCCCGTGTTGGGTGCCCTGTTCATCGGTGTGGCTGTGGCCCCAGCTAACGACATCTACAA
CGAGCGCGAGCTGCTGAACAGCATGGGCATCAGCCAGCCCACCGTCGTATTCGTGAGCAAGAAAGGGCTGCAAAAGATCC
TCAACGTGCAAAAGAAGCTACCGATCATACAAAAGATCATCATCATGGATAGCAAGACCGACTACCAGGGCTTCCAAAGC
ATGTACACCTTCGTGACTTCCCATTTGCCACCCGGCTTCAACGAGTACGACTTCGTGCCCGAGAGCTTCGACCGGGACAA
AACCATCGCCCTGATCATGAACAGTAGTGGCAGTACCGGATTGCCCAAGGGCGTAGCCCTACCGCACCGCACCGCTTGTG
TCCGATTCAGTCATGCCCGCGACCCCATCTTCGGCAACCAGATCATCCCCGACACCGCTATCCTCAGCGTGGTGCCATTT
CACCACGGCTTCGGCATGTTCACCACGCTGGGCTACTTGATCTGCGGCTTTCGGGTCGTGCTCATGTACCGCTTCGAGGA
GGAGCTATTCTTGCGCAGCTTGCAAGACTATAAGATTCAATCTGCCCTGCTGGTGCCCACACTATTTAGCTTCTTCGCTA
AGAGCACTCTCATCGACAAGTACGACCTAAGCAACTTGCACGAGATCGCCAGCGGCGGGGCGCCGCTCAGCAAGGAGGTA
GGTGAGGCCGTGGCCAAACGCTTCCACCTACCAGGCATCCGCCAGGGCTACGGCCTGACAGAAACAACCAGCGCCATTCT
GATCACCCCCGAAGGGTGAGTTTAAAC

AAAAAAA) pBFB372 Sgf to Pme (SEQ ID NO:464)
GCGATCGCCATGCCTGGCGCAGTAGGCAAGGTGGTGCCCTTCTTCGAGGCTAAGGTGGTGGACTTGGACACCGGTAAGAC
ACTGGGTGTGAACCAGCGCGGCGAGCTGTGCGTCCGTGGCCCCATGATCATGAGCGGCTACGTTAACAACCCCGAGGCTA
CAAACGCTCTCATCGACAAGGACGGCTGGCTGCACAGCGGCGACATCGCCTACTGGGACGAGGACGAGCACTTCTTCATC
GTGGACCGGCTGAAGAGCCTGATCAAATACAAGGGCTACCAGGTAGCCCCAGCCGAACTGGAGAGCATCCTGCTGCAACA
CCCCAACATCTTCGACGCCGGGGTCGCCGGCCTGCCCGACGACGATGCCGGCGAGCTGCCCGCCGCAGTCGTCGTGCTGG
AACACGGTAAAACCATGACCGAGAAGGAGATCGTGGACTATGTGGCCAGCCAGGTTACAACCGCCAAGAAGCTGCGCGGT
GGTGTTGTGTTCGTGGACGAGGTGCCTAAAGGACTGACCGGCAAGTTGGACGCCCGCAAGATCCGCGAGATTCTCATTAA
GGCCAAGAAGGGCTCGAGCGGAGGTTCAGGCGGTTCCGGATGGTATTTTGGCAAGATCACCAGACGGGAGTCAGAGCGGT
TACTGCTCAATGCAGAGAACCCGAGAGGGACCTTCCTCGTGCGAGAAAGTGAGACCACGAAAGGTGCCTACTGCCTCTCA
GTGTCTGACTTCGACAACGCCAAGGGCCTCAACGTGAAGCACTACAAGATCCGCAAGCTGGACAGCGGCGGCTTCTACAT
CACCTCCCGCACCCAGTTCAACAGCCTGCAGCAGCTGGTGGCCTACTACTCCAAACACGCCGATGGCCTGTGCCACCGCC
TCACCACCGTGTGCGGTTCCGGAGGATCTACTTCGGGGTCAGGTAAACCTGGCTCGGGTGAGGGATCGGAAATTTATGGT
GAATTCGGATCCGGGTCAGGTGGATCTGGAGGGAGCTCCGGTGCCAAAAACATTAAGAAGGGCCCAGCGCCATTCTACCC
ACTCGAAGACGGGACCGCCGGCGAGCAGCTGCACAAAGCCATGAAGCGCTACGCCCTGGTGCCCGGCACCATCGCCTTTA
CCGACGCACATATCGAGGTGGACATTACCTACGCCGAGTACTTCGAGATGAGCGTTCGGCTGGCAGAAGCTATGAAGCGC
TATGGGCTGAATACAAACCATCGGATCGTGGTGTGCAGCGAGAATAGCTTGCAGTTCTTCATGCCCGTGTTGGGTGCCCT
GTTCATCGGTGTGGCTGTGGCCCCAGCTAACGACATCTACAACGAGCGCGAGCTGCTGAACAGCATGGGCATCAGCCAGC

*FIG. 67*BN

CCACCGTCGTATTCGTGAGCAAGAAAGGGCTGCAAAAGATCCTCAACGTGCAAAAGAAGCTACCGATCATACAAAAGATC
ATCATCATGGATAGCAAGACCGACTACCAGGGCTTCCAAAGCATGTACACCTTCGTGACTTCCCATTTGCCACCCGGCTT
CAACGAGTACGACTTCGTGCCCGAGAGCTTCGACCGGGACAAAACCATCGCCCTGATCATGAACAGTAGTGGCAGTACCG
GATTGCCCAAGGGCGTAGCCCTACCGCACCGCACCGCTTGTGTCCGATTCAGTCATGCCCGCGACCCCATCTTCGGCAAC
CAGATCATCCCCGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGTGAGTTTAAAC

BBBBBBB) pBFB373 Sgf to Pme (SEQ ID NO:465)
GCGATCGCCATGCCTGGCGCAGTAGGCAAGGTGGTGCCCTTCTTCGAGGCTAAGGTGGTGGACTTGGACACCGGTAAGAC
ACTGGGTGTGAACCAGCGCGGCGAGCTGTGCGTCCGTGGCCCCATGATCATGAGCGGCTACGTTAACAACCCCGAGGCTA
CAAACGCTCTCATCGACAAGGACGGCTGGCTGCACAGCGGCGACATCGCCTACTGGGACGAGGACGAGCACTTCTTCATC
GTGGACCGGCTGAAGAGCCTGATCAAATACAAGGGCTACCAGGTAGCCCCAGCCGAACTGGAGAGCATCCTGCTGCAACA
CCCCAACATCTTCGACGCCGGGGTCGCCGGCCTGCCCGACGACGATGCCGGCGAGCTGCCCGCCGCAGTCGTCGTGCTGG
AACACGGTAAAACCATGACCGAGAAGGAGATCGTGGACTATGTGGCCAGCCAGGTTACAACCGCCAAGAAGCTGCGCGGT
GGTGTTGTGTTCGTGGACGAGGTGCCTAAAGGACTGACCGGCAAGTTGGACGCCCGCAAGATCCGCGAGATTCTCATTAA
GGCCAAGAAGGGCTCGAGCGGAGGTTCAGGCGGTTCCGGAGGAGGTTCTGGCGGATCAGGCGGTTCGGGGTGGTATTTTG
GCAAGATCACCAGACGGGAGTCAGAGCGGTTACTGCTCAATGCAGAGAACCCGAGAGGGACCTTCCTCGTGCGAGAAAGT
GAGACCACGAAAGGTGCCTACTGCCTCTCAGTGTCTGACTTCGACAACGCCAAGGGCCTCAACGTGAAGCACTACAAGAT
CCGCAAGCTGGACAGCGGCGGCTTCTACATCACCTCCCGCACCCAGTTCAACAGCCTGCAGCAGCTGGTGGCCTACTACT
CCAAACACGCCGATGGCCTGTGCCACCGCCTCACCACCGTGTGCGGTTCCGGAGGATCTACTTCGGGGTCAGGTAAACCT
GGCTCGGGTGAGGGATCGGAAATTTATGGTGAATTCGGATCCGGTGGTTCAGGTGGCAGCGGAGGAGGGTCAGGTGGATC
TGGAGGGAGCTCCGGTGCCAAAAACATTAAGAAGGGCCCAGCGCCATTCTACCCACTCGAAGACGGGACCGCCGGCGAGC
AGCTGCACAAAGCCATGAAGCGCTACGCCCTGGTGCCCGGCACCATCGCCTTTACCGACGCACATATCGAGGTGGACATT
ACCTACGCCGAGTACTTCGAGATGAGCGTTCGGCTGGCAGAAGCTATGAAGCGCTATGGGCTGAATACAAACCATCGGAT
CGTGGTGTGCAGCGAGAATAGCTTGCAGTTCTTCATGCCCGTGTTGGGTGCCCTGTTCATCGGTGTGGCTGTGGCCCCAG
CTAACGACATCTACAACGAGCGCGAGCTGCTGAACAGCATGGGCATCAGCCAGCCCACCGTCGTATTCGTGAGCAAGAAA
GGGCTGCAAAAGATCCTCAACGTGCAAAAGAAGCTACCGATCATACAAAAGATCATCATCATGGATAGCAAGACCGACTA
CCAGGGCTTCCAAAGCATGTACACCTTCGTGACTTCCCATTTGCCACCCGGCTTCAACGAGTACGACTTCGTGCCCGAGA
GCTTCGACCGGGACAAAACCATCGCCCTGATCATGAACAGTAGTGGCAGTACCGGATTGCCCAAGGGCGTAGCCCTACCG
CACCGCACCGCTTGTGTCCGATTCAGTCATGCCCGCGACCCCATCTTCGGCAACCAGATCATCCCCGACACCGCTATCCT
CAGCGTGGTGCCATTTCACCACGGCTTCGGCATGTTCACCACGCTGGGCTACTTGATCTGCGGCTTTCGGGTCGTGCTCA
TGTACCGCTTCGAGGAGGAGCTATTCTTGCGCAGCTTGCAAGACTATAAGATTCAATCTGCCCTGCTGGTGCCCACACTA
TTTAGCTTCTTCGCTAAGAGCACTCTCATCGACAAGTACGACCTAAGCAACTTGCACGAGATCGCCAGCGGCGGGGCGCC
GCTCAGCAAGGAGGTAGGTGAGGCCGTGGCCAAACGCTTCCACCTACCAGGCATCCGCCAGGGCTACGGCCTGACAGAAA
CAACCAGCGCCATTCTGATCACCCCCGAAGGGTGAGTTTAAAC

CCCCCCC) pBFB374 Sgf to Pme (SEQ ID NO:466)
GCGATCGCCATGAATAGCTTGCAGTTCTTCATGCCCGTGTTGGGTGCCCTGTTCATCGGTGTGGCTGTGGCCCCAGCTAA
CGACATCTACAACGAGCGCGAGCTGCTGAACAGCATGGGCATCAGCCAGCCCACCGTCGTATTCGTGAGCAAGAAAGGGC
TGCAAAAGATCCTCAACGTGCAAAAGAAGCTACCGATCATACAAAAGATCATCATCATGGATAGCAAGACCGACTACCAG
GGCTTCCAAAGCATGTACACCTTCGTGACTTCCCATTTGCCACCCGGCTTCAACGAGTACGACTTCGTGCCCGAGAGCTT
CGACCGGGACAAAACCATCGCCCTGATCATGAACAGTAGTGGCAGTACCGGATTGCCCAAGGGCGTAGCCCTACCGCACC
GCACCGCTTGTGTCCGATTCAGTCATGCCCGCGACCCCATCTTCGGCAACCAGATCATCCCCGACACCGCTATCCTCAGC
GTGGTGCCATTTCACCACGGCTTCGGCATGTTCACCACGCTGGGCTACTTGATCTGCGGCTTTCGGGTCGTGCTCATGTA
CCGCTTCGAGGAGGAGCTATTCTTGCGCAGCTTGCAAGACTATAAGATTCAATCTGCCCTGCTGGTGCCCACACTATTTA
GCTTCTTCGCTAAGAGCACTCTCATCGACAAGTACGACCTAAGCAACTTGCACGAGATCGCCAGCGGCGGGGCGCCGCTC
AGCAAGGAGGTAGGTGAGGCCGTGGCCAAACGCTTCCACCTACCAGGCATCCGCCAGGGCTACGGCCTGACAGAAACAAC
CAGCGCCATTCTGATCACCCCCGAAGGGGACGACAAGCCTGGCGCAGTAGGCAAGGTGGTGCCCTTCTTCGAGGCTAAGG
TGGTGGACTTGGACACCGGTAAGACACTGGGTGTGAACCAGCGCGGCGAGCTGTGCGTCCGTGGCCCCATGATCATGAGC
GGCTACGTTAACAACCCCGAGGCTACAAACGCTCTCATCGACAAGGACGGCTGGCTGCACAGCGGCGACATCGCCTACTG
GGACGAGGACGAGCACTTCTTCATCGTGGACCGGCTGAAGAGCCTGATCAAATACAAGGGCTACCAGGTAGCCCCAGCCG
AACTGGAGAGCATCCTGCTGCAACACCCCAACATCTTCGACGCCGGGGTCGCCGGCCTGCCCGACGACGATGCCGGCGAG
CTGCCCGCCGCAGTCGTCGTGCTGGAACACGGTAAAACCATGACCGAGAAGGAGATCGTGGACTATGTGGCCAGCCAGGT
TACAACCGCCAAGAAGCTGCGCGGTGGTGTTGTGTTCGTGGACGAGGTGCCTAAAGGACTGACCGGCAAGTTGGACGCCC

FIG. 67BO

GCAAGATCCGCGAGATTCTCATTAAGGCCAAGAAGGGCTCGAGCGGATGGTATTTTGGCAAGATCACCAGACGGGAGTCA
GAGCGGTTACTGCTCAATGCAGAGAACCCGAGAGGGACCTTCCTCGTGCGAGAAAGTGAGACCACGAAAGGTGCCTACTG
CCTCTCAGTGTCTGACTTCGACAACGCCAAGGGCCTCAACGTGAAGCACTACAAGATCCGCAAGCTGGACAGCGGCGGCT
TCTACATCACCTCCCGCACCCAGTTCAACAGCCTGCAGCAGCTGGTGGCCTACTACTCCAAACACGCCGATGGCCTGTGC
CACCGCCTCACCACCGTGTGCGGTTCCGGAGGATCTACTTCGGGGTCAGGTAAACCTGGCTCGGGTGAGGGATCGGAAAT
TTATGGTGAATTCGGGAGCTCCGGTGCCAAAAACATTAAGAAGGGCCCAGCGCCATTCTACCCACTCGAAGACGGGACCG
CCGGCGAGCAGCTGCACAAAGCCATGAAGCGCTACGCCCTGGTGCCCGGCACCATCGCCTTTACCGACGCACATATCGAG
GTGGACATTACCTACGCCGAGTACTTCGAGATGAGCGTTCGGCTGGCAGAAGCTATGAAGCGCTATGGGCTCAATACAAA
CCATCGGATCGTGGTGTGCAGCTGAGTTTAAAC

DDDDDDD) pBFB375 Sgf to Pme (SEQ ID NO:467)
GCGATCGCCATGAATAGCTTGCAGTTCTTCATGCCCGTGTTGGGTGCCCTGTTCATCGGTGTGGCTGTGGCCCCAGCTAA
CGACATCTACAACGAGCGCGAGCTGCTGAACAGCATGGGCATCAGCCAGCCCACCGTCGTATTCGTGAGCAAGAAAGGGC
TGCAAAAGATCCTCAACGTGCAAAAGAAGCTACCGATCATACAAAAGATCATCATCATGGATAGCAAGACCGACTACCAG
GGCTTCCAAAGCATGTACACCTTCGTGACTTCCCATTTGCCACCCGGCTTCAACGAGTACGACTTCGTGCCCGAGAGCTT
CGACCGGGACAAAACCATCGCCCTGATCATGAACAGTAGTGGCAGTACCGGATTGCCCAAGGGCGTAGCCCTACCGCACC
GCACCGCTTGTGTCCGATTCAGTCATGCCCGCGACCCCATCTTCGGCAACCAGATCATCCCCGACACCGCTATCCTCAGC
GTGGTGCCATTTCACCACGGCTTCGGCATGTTCACCACGCTGGGCTACTTGATCTGCGGCTTTCGGGTCGTGCTCATGTA
CCGCTTCGAGGAGGAGCTATTCTTGCGCAGCTTGCAAGACTATAAGATTCAATCTGCCCTGCTGGTGCCCACACTATTTA
GCTTCTTCGCTAAGAGCACTCTCATCGACAAGTACGACCTAAGCAACTTGCACGAGATCGCCAGCGGCGGGGCGCCGCTC
AGCAAGGAGGTAGGTGAGGCCGTGGCCAAACGCTTCCACCTACCAGGCATCCGCCAGGGCTACGGCCTGACAGAAACAAC
CAGCGCCATTCTGATCACCCCCGAAGGGGACGACAAGCCTGGCGCAGTAGGCAAGGTGGTGCCCTTCTTCGAGGCTAAGG
TGGTGGACTTGGACACCGGTAAGACACTGGGTGTGAACCAGCGCGGCGAGCTGTGCGTCCGTGGCCCCATGATCATGAGC
GGCTACGTTAACAACCCCGAGGCTACAAACGCTCTCATCGACAAGGACGGCTGGCTGCACAGCGGCGACATCGCCTACTG
GGACGAGGACGAGCACTTCTTCATCGTGGACCGGCTGAAGAGCCTGATCAAATACAAGGGCTACCAGGTAGCCCCAGCCG
AACTGGAGAGCATCCTGCTGCAACACCCCAACATCTTCGACGCCGGGGTCGCCGGCCTGCCCGACGACGATGCCGGCGAG
CTGCCCGCCGCAGTCGTCGTGCTGGAACACGGTAAAACCATGACCGAGAAGGAGATCGTGGACTATGTGGCCAGCCAGGT
TACAACCGCCAAGAAGCTGCGCGGTGGTGTTGTGTTCGTGGACGAGGTGCCTAAAGGACTGACCGGCAAGTTGGACGCCC
GCAAGATCCGCGAGATTCTCATTAAGGCCAAGAAGGGCTCGAGCGGAGGTTCAGGCGGTTCCGGATGGTATTTTGGCAAG
ATCACCAGACGGGAGTCAGAGCGGTTACTGCTCAATGCAGAGAACCCGAGAGGGACCTTCCTCGTGCGAGAAAGTGAGAC
CACGAAAGGTGCCTACTGCCTCTCAGTGTCTGACTTCGACAACGCCAAGGGCCTCAACGTGAAGCACTACAAGATCCGCA
AGCTGGACAGCGGCGGCTTCTACATCACCTCCCGCACCCAGTTCAACAGCCTGCAGCAGCTGGTGGCCTACTACTCCAAA
CACGCCGATGGCCTGTGCCACCGCCTCACCACCGTGTGCGGTTCCGGAGGATCTACTTCGGGGTCAGGTAAACCTGGCTC
GGGTGAGGGATCGGAAATTTATGGTGAATTCGGGTCAGGTGGATCTGGAGGGAGCTCCGGTGCCAAAAACATTAAGAAGG
GCCCAGCGCCATTCTACCCACTCGAAGACGGGACCGCCGGCGAGCAGCTGCACAAAGCCATGAAGCGCTACGCCCTGGTG
CCCGGCACCATCGCCTTTACCGACGCACATATCGAGGTGGACATTACCTACGCCGAGTACTTCGAGATGAGCGTTCGGCT
GGCAGAAGCTATGAAGCGCTATGGGCTGAATACAAACCATCGGATCGTGGTGTGCAGCTGAGTTTAAAC

EEEEEEE) pBFB377 Sgf to Pme (SEQ ID NO:468)
GCGATCGCCATGTTGCACGAGATCGCCAGCGGCGGGGCGCCGCTCAGCAAGGAGGTAGGTGAGGCCGTGGCCAAACGCTT
CCACCTACCAGGCATCCGCCAGGGCTACGGCCTGACAGAAACAACCAGCGCCATTCTGATCACCCCCGAAGGGGACGACA
AGCCTGGCGCAGTAGGCAAGGTGGTGCCCTTCTTCGAGGCTAAGGTGGTGGACTTGGACACCGGTAAGACACTGGGTGTG
AACCAGCGCGGCGAGCTGTGCGTCCGTGGCCCCATGATCATGAGCGGCTACGTTAACAACCCCGAGGCTACAAACGCTCT
CATCGACAAGGACGGCTGGCTGCACAGCGGCGACATCGCCTACTGGGACGAGGACGAGCACTTCTTCATCGTGGACCGGC
TGAAGAGCCTGATCAAATACAAGGGCTACCAGGTAGCCCCAGCCGAACTGGAGAGCATCCTGCTGCAACACCCCAACATC
TTCGACGCCGGGGTCGCCGGCCTGCCCGACGACGATGCCGGCGAGCTGCCCGCCGCAGTCGTCGTGCTGGAACACGGTAA
AACCATGACCGAGAAGGAGATCGTGGACTATGTGGCCAGCCAGGTTACAACCGCCAAGAAGCTGCGCGGTGGTGTTGTGT
TCGTGGACGAGGTGCCTAAAGGACTGACCGGCAAGTTGGACGCCCGCAAGATCCGCGAGATTCTCATTAAGGCCAAGAAG
GGCTCGACCGGATGGTATTTTGGCAAGATCACCAGACGGGAGTCAGAGCGGTTACTGCTCAATGCAGAGAACCCGAGAGG
GACCTTCCTCGTGCGAGAAAGTGAGACCACGAAAGGTGCCTACTGCCTCTCAGTGTCTGACTTCGACAACGCCAAGGGCC
TCAACGTGAAGCACTACAAGATCCGCAAGCTGGACAGCGGCGGCTTCTACATCACCTCCCGCACCCAGTTCAACAGCCTG
CAGCAGCTGGTGGCCTACTACTCCAAACACGCCGATGGCCTGTGCCACCGCCTCACCACCGTGTGCGGTTCCGGAGGATC
TACTTCGGGGTCAGGTAAACCTGGCTCGGGTGAGGGATCGGAAATTTATGGTGAATTCGGGAGCTCCGGTGCCAAAAACA
TTAAGAAGGGCCCAGCGCCATTCTACCCACTCGAAGACGGGACCGCCGGCGAGCAGCTGCACAAAGCCATGAAGCGCTAC
GCCCTGGTGCCCGGCACCATCGCCTTTACCGACGCACATATCGAGGTGGACATTACCTACGCCGAGTACTTCGAGATGAG
CGTTCGGCTGGCAGAAGCTATGAAGCGCTATGGGCTGAATACAAACCATCGGATCGTGGTGTGCAGCGAGAATAGCTTGC
AGTTCTTCATGCCCGTGTTGGGTGCCCTGTTCATCGGTGTGGCTGTGGCCCCAGCTAACGACATCTACAACGAGCGCGAG

FIG. 67BP

CTGCTGAACAGCATGGGCATCAGCCAGCCCACCGTCGTATTCGTGAGCAAGAAAGGGCTGCAAAAGATCCTCAACGTGCA
AAAGAAGCTACCGATCATACAAAAGATCATCATCATGGATAGCAAGACCGACTACCAGGGCTTCCAAAGCATGTACACCT
TCGTGACTTCCCATTTGCCACCCGGCTTCAACGAGTACGACTTCGTGCCCGAGAGCTTCGACCGGGACAAAACCATCGCC
CTGATCATGAACAGTAGTGGCAGTACCGGATTGCCCAAGGGCGTAGCCCTACCGCACCGCACCGCTTGTGTCCGATTCAG
TCATGCCCGCGACCCCATCTTCGGCAACCAGATCATCCCCGACACCGCTATCCTCAGCGTGGTGCCATTTCACCACGGCT
TCGGCATGTTCACCACGCTGGGCTACTTGATCTGCGGCTTTCGGGTCGTGCTCATGTACCGCTTCGAGGAGGAGCTATTC
TTGCGCAGCTTGCAAGACTATAAGATTCAATCTGCCCTGCTGGTGCCCACACTATTTAGCTTCTTCGCTAAGAGCACTCT
CATCGACAAGTACGACCTAAGCTGAGTTTAAAC

FFFFFFF) pBFB378 Sgf to Pme (SEQ ID NO:469)
GCGATCGCCATGTTGCACGAGATCGCCAGCGGCGGGGCGCCGCTCAGCAAGGAGGTAGGTGAGGCCGTGGCCAAACGCTT
CCACCTACCAGGCATCCGCCAGGGCTACGGCCTGACAGAAACAACCAGCGCCATTCTGATCACCCCCGAAGGGGACGACA
AGCCTGGCGCAGTAGGCAAGGTGGTGCCCTTCTTCGAGGCTAAGGTGGTGGACTTGGACACCGGTAAGACACTGGGTGTG
AACCAGCGCGGCGAGCTGTGCGTCCGTGGCCCCATGATCATGAGCGGCTACGTTAACAACCCCGAGGCTACAAACGCTCT
CATCGACAAGGACGGCTGGCTGCACAGCGGCGACATCGCCTACTGGGACGAGGACGAGCACTTCTTCATCGTGGACCGGC
TGAAGAGCCTGATCAAATACAAGGGCTACCAGGTAGCCCCAGCCGAACTGGAGAGCATCCTGCTGCAACACCCCAACATC
TTCGACGCCGGGGTCGCCGGCCTGCCCGACGACGATGCCGGCGAGCTGCCCGCCGCAGTCGTCGTGCTGGAACACGGTAA
AACCATGACCGAGAAGGAGATCGTGGACTATGTGGCCAGCCAGGTTACAACCGCCAAGAAGCTGCGCGGTGGTGTTGTGT
TCGTGGACGAGGTGCCTAAAGGACTGACCGGCAAGTTGGACGCCCGCAAGATCCGCGAGATTCTCATTAAGGCCAAGAAG
GGCTCGAGCGGAGGTTCAGGCGGTTCCGGATGGTATTTTGGCAAGATCACCAGACGGGAGTCAGAGCGGTTACTGCTCAA
TGCAGAGAACCCGAGAGGGACCTTCCTCGTGCGAGAAAGTGAGACCACGAAAGGTGCCTACTGCCTCTCAGTGTCTGACT
TCGACAACGCCAAGGGCCTCAACGTGAAGCACTACAAGATCCGCAAGCTGGACAGCGGCGGCTTCTACATCACCTCCCGC
ACCCAGTTCAACAGCCTGCAGCAGCTGGTGGCCTACTACTCCAAACACGCCGATGGCCTGTGCCACCGCCTCACCACCGT
GTGCGGTTCCGGAGGATCTACTTCGGGGTCAGGTAAACCTGGCTCGGGTGAGGGATCGGAAATTTATGGTGAATTCGGAT
CCGGGTCAGGTGGATCTGGAGGGAGCTCCGGTGCCAAAAACATTAAGAAGGGCCCAGCGCCATTCTACCCACTCGAAGAC
GGGACCGCCGGCGAGCAGCTGCACAAAGCCATGAAGCGCTACGCCCTGGTGCCCGGCACCATCGCCTTTACCGACGCACA
TATCGAGGTGGACATTACCTACGCCGAGTACTTCGAGATGAGCGTTCGGCTGGCAGAAGCTATGAAGCGCTATGGGCTGA
ATACAAACCATCGGATCGTGGTGTGCAGCGAGAATAGCTTGCAGTTCTTCATGCCCGTGTTGGGTGCCCTGTTCATCGGT
GTGGCTGTGGCCCCAGCTAACGACATCTACAACGAGCGCGAGCTGCTGAACAGCATGGGCATCAGCCAGCCCACCGTCGT
ATTCGTGAGCAAGAAAGGGCTGCAAAAGATCCTCAACGTGCAAAAGAAGCTACCGATCATACAAAAGATCATCATCATGG
ATAGCAAGACCGACTACCAGGGCTTCCAAAGCATGTACACCTTCGTGACTTCCCATTTGCCACCCGGCTTCAACGAGTAC
GACTTCGTGCCCGAGAGCTTCGACCGGGACAAAACCATCGCCCTGATCATGAACAGTAGTGGCAGTACCGGATTGCCCAA
GGGCGTAGCCCTACCGCACCGCACCGCTTGTGTCCGATTCAGTCATGCCCGCGACCCCATCTTCGGCAACCAGATCATCC
CCGACACCGCTATCCTCAGCGTGGTGCCATTTCACCACGGCTTCGGCATGTTCACCACGCTGGGCTACTTGATCTGCGGC
TTTCGGGTCGTGCTCATGTACCGCTTCGAGGAGGAGCTATTCTTGCGCAGCTTGCAAGACTATAAGATTCAATCTGCCCT
GCTGGTGCCCACACTATTTAGCTTCTTCGCTAAGAGCACTCTCATCGACAAGTACGACCTAAGCTGAGTTTAAAC

GGGGGGG) pBFB379 Sgf to Pme (SEQ ID NO:470)
GCGATCGCCATGTTGCACGAGATCGCCAGCGGCGGGGCGCCGCTCAGCAAGGAGGTAGGTGAGGCCGTGGCCAAACGCTT
CCACCTACCAGGCATCCGCCAGGGCTACGGCCTGACAGAAACAACCAGCGCCATTCTGATCACCCCCGAAGGGGACGACA
AGCCTGGCGCAGTAGGCAAGGTGGTGCCCTTCTTCGAGGCTAAGGTGGTGGACTTGGACACCGGTAAGACACTGGGTGTG
AACCAGCGCGGCGAGCTGTGCGTCCGTGGCCCCATGATCATGAGCGGCTACGTTAACAACCCCGAGGCTACAAACGCTCT
CATCGACAAGGACGGCTGGCTGCACAGCGGCGACATCGCCTACTGGGACGAGGACGAGCACTTCTTCATCGTGGACCGGC
TGAAGAGCCTGATCAAATACAAGGGCTACCAGGTAGCCCCAGCCGAACTGGAGAGCATCCTGCTGCAACACCCCAACATC
TTCGACGCCGGGGTCGCCGGCCTGCCCGACGACGATGCCGGCGAGCTGCCCGCCGCAGTCGTCGTGCTGGAACACGGTAA
AACCATGACCGAGAAGGAGATCGTGGACTATGTGGCCAGCCAGGTTACAACCGCCAAGAAGCTGCGCGGTGGTGTTGTGT
TCGTGGACGAGGTGCCTAAAGGACTGACCGGCAAGTTGGACGCCCGCAAGATCCGCGAGATTCTCATTAAGGCCAAGAAG
GGCTCGAGCGGAGGTTCAGGCGGTTCCGGAGGAGGTTCTGGCGGATCAGGCGGTTCGGGGTGGTATTTTGGCAAGATCAC
CAGACGGGAGTCAGAGCGGTTACTGCTCAATGCAGAGAACCCGAGAGGGACCTTCCTCGTGCGAGAAAGTGAGACCACGA
AAGGTGCCTACTGCCTCTCAGTGTCTGACTTCGACAACGCCAAGGGCCTCAACGTGAAGCACTACAAGATCCGCAAGCTG
GACAGCGGCGGCTTCTACATCACCTCCCGCACCCAGTTCAACAGCCTGCAGCAGCTGGTGGCCTACTACTCCAAACACGC
CGATGGCCTGTGCCACCGCCTCACCACCGTGTGCGGTTCCGGAGGATCTACTTCGGGGTCAGGTAAACCTGGCTCGGGTG
AGGGATCGGAAATTTATGGTGAATTCGGATCCGGTGGTTCAGGTGGCAGCGGAGGAGGGTCAGGTGGATCTGGAGGGAGC
TCCGGTGCCAAAAACATTAAGAAGGGCCCAGCGCCATTCTACCCACTCGAAGACGGGACCGCCGGCGAGCAGCTGCACAA
AGCCATGAAGCGCTACGCCCTGGTGCCCGGCACCATCGCCTTTACCGACGCACATATCGAGGTGGACATTACCTACGCCG
AGTACTTCGAGATGAGCGTTCGGCTGGCAGAAGCTATGAAGCGCTATGGGCTGAATACAAACCATCGGATCGTGGTGTGC
AGCGAGAATAGCTTGCAGTTCTTCATGCCCGTGTTGGGTGCCCTGTTCATCGGTGTGGCTGTGGCCCCAGCTAACGACAT

FIG. 67BQ

CTACAACGAGCGCGAGCTGCTGAACAGCATGGGCATCAGCCAGCCCACCGTCGTATTCGTGAGCAAGAAAGGGCTGCAAA
AGATCCTCAACGTGCAAAAGAAGCTACCGATCATACAAAAGATCATCATCATGGATAGCAAGACCGACTACCAGGGCTTC
CAAAGCATGTACACCTTCGTGACTTCCCATTTGCCACCCGGCTTCAACGAGTACGACTTCGTGCCCGAGAGCTTCGACCG
GGACAAAACCATCGCCCTGATCATGAACAGTAGTGGCAGTACCGGATTGCCCAAGGGCGTAGCCCTACCGCACCGCACCG
CTTGTGTCCGATTCAGTCATGCCCGCGACCCCATCTTCGGCAACCAGATCATCCCCGACACCGCTATCCTCAGCGTGGTG
CCATTTCACCACGGCTTCGGCATGTTCACCACGCTGGGCTACTTGATCTGCGGCTTTCGGGTCGTGCTCATGTACCGCTT
CGAGGAGGAGCTATTCTTGCGCAGCTTGCAAGACTATAAGATTCAATCTGCCCTGCTGGTGCCCACACTATTTAGCTTCT
TCGCTAAGAGCACTCTCATCGACAAGTACGACCTAAGCTGAGTTTAAAC

HHHHHHH) pBFB380 Sgf to Pme (SEQ ID NO:471)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGAGCGGATGGTATTTTGGCAAGATCACCAGACGGGAGTCAGAG
CGGTTACTGCTCAATGCAGAGAACCCGAGAGGGACCTTCCTCGTGCGAGAAAGTGAGACCACGAAAGGTGCCTACTGCCT
CTCAGTGTCTGACTTCGACAACGCCAAGGGCCTCAACGTGAAGCACTACAAGATCCGCAAGCTGGACAGCGGCGGCTTCT
ACATCACCTCCCGCACCCAGTTCAACAGCCTGCAGCAGCTGGTGGCCTACTACTCCAAACACGCCGATGGCCTGTGCCAC
CGCCTCACCACCGTGTGCGGTTCCGGAGGATCTACTTCGGGGTCAGGTAAACCTGGCTCGGGTGAGGGATCGGAAATTTA
TGGTGAATTCGGGAGCTCCGGTGCTTCCAAGGTGTACGACCCCGAGCAACGCAAACGCATGATCACTGGGCCTCAGTGGT
GGGCTCGCTGCAAGCAAATGAACGTGCTGGACTCCTTCATCAACTACTATGATTCCGAGAAGCACGCCGAGAACGCCGTG
ATTTTTCTGCATGGTAACGCTGCCTCCAGCTACCTGTGGAGGCACGTCGTGCCTCACATCGAGCCCGTGGCTAGATGCAT
CATCCCTGATCTGATCGGAATGGGTAAGTCCGGCAAGAGCGGGAATGGCTGAGTTTAAAC

IIIIIII) pBFB381 Sgf to Pme (SEQ ID NO:472)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGAGCGGAGGTTCAGGCGGTTCCGGATGGTATTTTGGCAAGATC
ACCAGACGGGAGTCAGAGCGGTTACTGCTCAATGCAGAGAACCCGAGAGGGACCTTCCTCGTGCGAGAAAGTGAGACCAC
GAAAGGTGCCTACTGCCTCTCAGTGTCTGACTTCGACAACGCCAAGGGCCTCAACGTGAAGCACTACAAGATCCGCAAGC
TGGACAGCGGCGGCTTCTACATCACCTCCCGCACCCAGTTCAACAGCCTGCAGCAGCTGGTGGCCTACTACTCCAAACAC
GCCGATGGCCTGTGCCACCGCCTCACCACCGTGTGCGGTTCCGGAGGATCTACTTCGGGGTCAGGTAAACCTGGCTCGGG
TGAGGGATCGGAAATTTATGGTGAATTCGGATCCGGGTCAGGTGGATCTGGAGGGAGCTCCGGTGCTTCCAAGGTGTACG
ACCCCGAGCAACGCAAACGCATGATCACTGGGCCTCAGTGGTGGGCTCGCTGCAAGCAAATGAACGTGCTGGACTCCTTC
ATCAACTACTATGATTCCGAGAAGCACGCCGAGAACGCCGTGATTTTTCTGCATGGTAACGCTGCCTCCAGCTACCTGTG
GAGGCACGTCGTGCCTCACATCGAGCCCGTGGCTAGATGCATCATCCCTGATCTGATCGGAATGGGTAAGTCCGGCAAGA
GCGGGAATGGCTGAGTTTAAAC

JJJJJJJ) pBFB383 Sgf to Pme (SEQ ID NO:473)
GCGATCGCCATGGCCGAGAACGCCGTGATTTTTCTGCATGGTAACGCTGCCTCCAGCTACCTGTGGAGGCACGTCGTGCC
TCACATCGAGCCCGTGGCTAGATGCATCATCCCTGATCTGATCGGAATGGGTAAGTCCGGCAAGAGCGGGAATGGCTCAT
ATCGCCTCCTGGATCACTACAAGTACCTCACCGCTTGGTTCGAGCTGCTGAACCTTCCAAAGAAAATCATCTTTGTGGGC
CACGACTGGGGGGCTTGTCTGGCCTTTCACTACTCCTACGAGCACCAAGACAAGATCAAGGCCATCGTCCATGCTGAGAG
TGTCGTGGACGTGATCGAGTCCTGGGACGAGTGGCCTGACATCGAGGAGGATATCGCCCTGATCAAGAGCGAAGAGGGCG
AGAAAATGGTGCTTGAGAATAACTTCTTCGTCGAGACCATGCTCCCAAGCAAGATCATGCGGAAACTGGAGCCTGAGGAG
TTCGCTGCCTACCTGGAGCCATTCAAGGAGAAGGGCGAGGTTAGACGGCCTACCCTCTCCTGGCCTCGCGAGATCCCTCT
CGTTAAGGGAGGCAAGCCCGACGTCGTCCAGATTGTCCGCAACTACAACGCCTACCTTCGGGCCAGCGACGATCTGCCTA

*FIG. 67*BR

AGATGTTCATCGAGTCCGACCCTGGGTTCTTTTCCAACGCTATTGTCGAGGGAGCTAAGAAGTTCCCTAACACCGAGTTC
GTGAAGGTGAAGGGCCTCCACTTCAGCCAGGAGGACGCTCCAGATGAAATGGGTAAGTACATCAAGAGCTTCGTGGAGCG
CGTGCTGAAGAACGAGCAGGGCTCGAGCGGATGGTATTTTGGCAAGATCACCAGACGGGAGTCAGAGCGGTTACTGCTCA
ATGCAGAGAACCCGAGAGGGACCTTCCTCGTGCGAGAAAGTGAGACCACGAAAGGTGCCTACTGCCTCTCAGTGTCTGAC
TTCGACAACGCCAAGGGCCTCAACGTGAAGCACTACAAGATCCGCAAGCTGGACAGCGGCGGCTTCTACATCACCTCCCG
CACCCAGTTCAACAGCCTGCAGCAGCTGGTGGCCTACTACTCCAAACACGCCGATGGCCTGTGCCACCGCCTCACCACCG
TGTGCGGTTCCGGAGGATCTACTTCGGGGTCAGGTAAACCTGGCTCGGGTGAGGGATCGGAAATTTATGGTGAATTCGGG
AGCTCCGGTGCTTCCAAGGTGTACGACCCCGAGCAACGCAAACGCATGATCACTGGGCCTCAGTGGTGGGCTCGCTGCAA
GCAAATGAACGTGCTGGACTCCTTCATCAACTACTATGATTCCGAGAAGTGAGTTTAAAC

KKKKKKK) pBFB384 Sgf to Pme (SEQ ID NO:474)
GCGATCGCCATGGCCGAGAACGCCGTGATTTTTCTGCATGGTAACGCTGCCTCCAGCTACCTGTGGAGGCACGTCGTGCC
TCACATCGAGCCCGTGGCTAGATGCATCATCCCTGATCTGATCGGAATGGGTAAGTCCGGCAAGAGCGGGAATGGCTCAT
ATCGCCTCCTGGATCACTACAAGTACCTCACCGCTTGGTTCGAGCTGCTGAACCTTCCAAAGAAAATCATCTTTGTGGGC
CACGACTGGGGGGCTTGTCTGGCCTTTCACTACTCCTACGAGCACCAAGACAAGATCAAGGCCATCGTCCATGCTGAGAG
TGTCGTGGACGTGATCGAGTCCTGGGACGAGTGGCCTGACATCGAGGAGGATATCGCCCTGATCAAGAGCGAAGAGGGCG
AGAAAATGGTGCTTGAGAATAACTTCTTCGTCGAGACCATGCTCCCAAGCAAGATCATGCGGAAACTGGAGCCTGAGGAG
TTCGCTGCCTACCTGGAGCCATTCAAGGAGAAGGGCGAGGTTAGACGGCCTACCCTCTCCTGGCCTCGCGAGATCCCTCT
CGTTAAGGGAGGCAAGCCCGACGTCGTCCAGATTGTCCGCAACTACAACGCCTACCTTCGGGCCAGCGACGATCTGCCTA
AGATGTTCATCGAGTCCGACCCTGGGTTCTTTTCCAACGCTATTGTCGAGGGAGCTAAGAAGTTCCCTAACACCGAGTTC
GTGAAGGTGAAGGGCCTCCACTTCAGCCAGGAGGACGCTCCAGATGAAATGGGTAAGTACATCAAGAGCTTCGTGGAGCG
CGTGCTGAAGAACGAGCAGGGCTCGAGCGGAGGTTCAGGCGGTTCCGGATGGTATTTTGGCAAGATCACCAGACGGGAGT
CAGAGCGGTTACTGCTCAATGCAGAGAACCCGAGAGGGACCTTCCTCGTGCGAGAAAGTGAGACCACGAAAGGTGCCTAC
TGCCTCTCAGTGTCTGACTTCGACAACGCCAAGGGCCTCAACGTGAAGCACTACAAGATCCGCAAGCTGGACAGCGGCGG
CTTCTACATCACCTCCCGCACCCAGTTCAACAGCCTGCAGCAGCTGGTGGCCTACTACTCCAAACACGCCGATGGCCTGT
GCCACCGCCTCACCACCGTGTGCGGTTCCGGAGGATCTACTTCGGGGTCAGGTAAACCTGGCTCGGGTGAGGGATCGGAA
ATTTATGGTGAATTCGGATCCGGGTCAGGTGGATCTGGAGGGAGCTCCGGTGCTTCCAAGGTGTACGACCCCGAGCAACG
CAAACGCATGATCACTGGGCCTCAGTGGTGGGCTCGCTGCAAGCAAATGAACGTGCTGGACTCCTTCATCAACTACTATG
ATTCCGAGAAGTGAGTTTAAAC

LLLLLLL) pBFB386 Sgf to Pme (SEQ ID NO:475)
GCGATCGCCATGAAGAAAATCATCTTTGTGGGCCACGACTGGGGGGCTTGTCTGGCCTTTCACTACTCCTACGAGCACCA
AGACAAGATCAAGGCCATCGTCCATGCTGAGAGTGTCGTGGACGTGATCGAGTCCTGGGACGAGTGGCCTGACATCGAGG
AGGATATCGCCCTGATCAAGAGCGAAGAGGGCGAGAAAATGGTGCTTGAGAATAACTTCTTCGTCGAGACCATGCTCCCA
AGCAAGATCATGCGGAAACTGGAGCCTGAGGAGTTCGCTGCCTACCTGGAGCCATTCAAGGAGAAGGGCGAGGTTAGACG
GCCTACCCTCTCCTGGCCTCGCGAGATCCCTCTCGTTAAGGGAGGCAAGCCCGACGTCGTCCAGATTGTCCGCAACTACA
ACGCCTACCTTCGGGCCAGCGACGATCTGCCTAAGATGTTCATCGAGTCCGACCCTGGGTTCTTTTCCAACGCTATTGTC
GAGGGAGCTAAGAAGTTCCCTAACACCGAGTTCGTGAAGGTGAAGGGCCTCCACTTCAGCCAGGAGGACGCTCCAGATGA
AATGGGTAAGTACATCAAGAGCTTCGTGGAGCGCGTGCTGAAGAACGAGCAGGGCTCGAGCGGATGGTATTTTGGCAAGA
TCACCAGACGGGAGTCAGAGCGGTTACTGCTCAATGCAGAGAACCCGAGAGGGACCTTCCTCGTGCGAGAAAGTGAGACC
ACGAAAGGTGCCTACTGCCTCTCAGTGTCTGACTTCGACAACGCCAAGGGCCTCAACGTGAAGCACTACAAGATCCGCAA
GCTGGACAGCGGCGGCTTCTACATCACCTCCCGCACCCAGTTCAACAGCCTGCAGCAGCTGGTGGCCTACTACTCCAAAC
ACGCCGATGGCCTGTGCCACCGCCTCACCACCGTGTGCGGTTCCGGAGGATCTACTTCGGGGTCAGGTAAACCTGGCTCG
GGTGAGGGATCGGAAATTTATGGTGAATTCGGGAGCTCCGGTGCTTCCAAGGTGTACGACCCCGAGCAACGCAAACGCAT
GATCACTGGGCCTCAGTGGTGGGCTCGCTGCAAGCAAATGAACGTGCTGGACTCCTTCATCAACTACTATGATTCCGAGA
AGCACGCCGAGAACGCCGTGATTTTTCTGCATGGTAACGCTGCCTCCAGCTACCTGTGGAGGCACGTCGTGCCTCACATC
GAGCCCGTGGCTAGATGCATCATCCCTGATCTGATCGGAATGGGTAAGTCCGGCAAGAGCGGGAATGGCTCATATCGCCT
CCTGGATCACTACAAGTACCTCACCGCTTGGTTCGAGCTGCTGAACCTTTGAGTTTAAAC

MMMMMMM) pBFB387 Sgf to Pme (SEQ ID NO:476)
GCGATCGCCATGAAGAAAATCATCTTTGTGGGCCACGACTGGGGGGCTTGTCTGGCCTTTCACTACTCCTACGAGCACCA
AGACAAGATCAAGGCCATCGTCCATGCTGAGAGTGTCGTGGACGTGATCGAGTCCTGGGACGAGTGGCCTGACATCGAGG
AGGATATCGCCCTGATCAAGAGCGAAGAGGGCGAGAAAATGGTGCTTGAGAATAACTTCTTCGTCGAGACCATGCTCCCA
AGCAAGATCATGCGGAAACTGGAGCCTGAGGAGTTCGCTGCCTACCTGGAGCCATTCAAGGAGAAGGGCGAGGTTAGACG
GCCTACCCTCTCCTGGCCTCGCGAGATCCCTCTCGTTAAGGGAGGCAAGCCCGACGTCGTCCAGATTGTCCGCAACTACA
ACGCCTACCTTCGGGCCAGCGACGATCTGCCTAAGATGTTCATCGAGTCCGACCCTGGGTTCTTTTCCAACGCTATTGTC
GAGGGAGCTAAGAAGTTCCCTAACACCGAGTTCGTGAAGGTGAAGGGCCTCCACTTCAGCCAGGAGGACGCTCCAGATGA

*FIG. 67BS*

AATGGGTAAGTACATCAAGAGCTTCGTGGAGCGCGTGCTGAAGAACGAGCAGGGCTCGAGCGGAGGTTCAGGCGGTTCCG
GATGGTATTTTGGCAAGATCACCAGACGGGAGTCAGAGCGGTTACTGCTCAATGCAGAGAACCCGAGAGGGACCTTCCTC
GTGCGAGAAAGTGAGACCACGAAAGGTGCCTACTGCCTCTCAGTGTCTGACTTCGACAACGCCAAGGGCCTCAACGTGAA
GCACTACAAGATCCGCAAGCTGGACAGCGGCGGCTTCTACATCACCTCCCGCACCCAGTTCAACAGCCTGCAGCAGCTGG
TGGCCTACTACTCCAAACACGCCGATGGCCTGTGCCACCGCCTCACCACCGTGTGCGGTTCCGGAGGATCTACTTCGGGG
TCAGGTAAACCTGGCTCGGGTGAGGGATCGGAAATTTATGGTGAATTCGGATCCGGGTCAGGTGGATCTGGAGGGAGCTC
CGGTGCTTCCAAGGTGTACGACCCCGAGCAACGCAAACGCATGATCACTGGGCCTCAGTGGTGGGCTCGCTGCAAGCAAA
TGAACGTGCTGGACTCCTTCATCAACTACTATGATTCCGAGAAGCACGCCGAGAACGCCGTGATTTTTCTGCATGGTAAC
GCTGCCTCCAGCTACCTGTGGAGGCACGTCGTGCCTCACATCGAGCCCGTGGCTAGATGCATCATCCCTGATCTGATCGG
AATGGGTAAGTCCGGCAAGAGCGGGAATGGCTCATATCGCCTCCTGGATCACTACAAGTACCTCACCGCTTGGTTCGAGC
TGCTGAACCTTTGAGTTTAAAC

NNNNNNN) pBFB389 Sgf to Pme (SEQ ID NO:477)
GCGATCGCCATGTCCTTCATCAACTACTATGATTCCGAGAAGCACGCCGAGAACGCCGTGATTTTTCTGCATGGTAACGC
TGCCTCCAGCTACCTGTGGAGGCACGTCGTGCCTCACATCGAGCCCGTGGCTAGATGCATCATCCCTGATCTGATCGGAA
TGGGTAAGTCCGGCAAGAGCGGGAATGGCTCATATCGCCTCCTGGATCACTACAAGTACCTCACCGCTTGGTTCGAGCTG
CTGAACCTTCCAAAGAAAATCATCTTTGTGGGCCACGACTGGGGGGCTTGTCTGGCCTTTCACTACTCCTACGAGCACCA
AGACAAGATCAAGGCCATCGTCCATGCTGAGAGTGTCGTGGACGTGATCGAGTCCTGGGACGAGTGGCCTGACATCGAGG
AGGATATCGCCCTGATCAAGAGCGAAGAGGGCGAGAAAATGGTGCTTGAGAATAACTTCTTCGTCGAGACCATGCTCCCA
AGCAAGATCATGCGGAAACTGGAGCCTGAGGAGTTCGCTGCCTACCTGGAGCCATTCAAGGAGAAGGGCGAGGTTAGACG
GCCTACCCTCTCCTGGCCTCGCGAGATCCCTCTCGTTAAGGGAGGCAAGCCCGACGTCGTCCAGATTGTCCGCAACTACA
ACGCCTACCTTCGGGCCAGCGACGATCTGCCTAAGATGTTCATCGAGTCCGACCCTGGGTTCTTTTCCAACGCTATTGTC
GAGGGAGCTAAGAAGTTCCCTAACACCGAGTTCGTGAAGGTGAAGGGCCTCCACTTCAGCCAGGAGGACGCTCCAGATGA
AATGGGTAAGTACATCAAGAGCTTCGTGGAGCGCGTGCTGAAGAACGAGCAGGGCTCGAGCGGATGGTATTTTGGCAAGA
TCACCAGACGGGAGTCAGAGCGGTTACTGCTCAATGCAGAGAACCCGAGAGGGACCTTCCTCGTGCGAGAAAGTGAGACC
ACGAAAGGTGCCTACTGCCTCTCAGTGTCTGACTTCGACAACGCCAAGGGCCTCAACGTGAAGCACTACAAGATCCGCAA
GCTGGACAGCGGCGGCTTCTACATCACCTCCCGCACCCAGTTCAACAGCCTGCAGCAGCTGGTGGCCTACTACTCCAAAC
ACGCCGATGGCCTGTGCCACCGCCTCACCACCGTGTGCGGTTCCGGAGGATCTACTTCGGGGTCAGGTAAACCTGGCTCG
GGTGAGGGATCGGAAATTTATGGTGAATTCGGGAGCTCCGGTGCTTCCAAGGTGTACGACCCCGAGCAACGCAAACGCAT
GATCACTGGGCCTCAGTGGTGGGCTCGCTGCAAGCAAATGAACGTGCTGTGAGTTTAAAC

OOOOOOO) pBFB39 Sgf to Pme (SEQ ID NO:478)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAATG
TATGAAAGCTTTATTGAGTCACTGCCATTCCTTAAATCTTTGGAGTTTTCTGAACGCCTGAAAGTAGTAGATGTGATAGG
CACCAAAGTATACAACGATGGAGAACAAATCATTGCTCAGGGAGATTCGGCTGATTCTTTTTTCATTGTAGAATCTGGAG
AAGTGAAAATTACTATGAAAAGAAAGGGTAAATCAGAAGTGGAAGAGAATGGTGCAGTAGAAATCGCTCGATGCTCGCGG
GGACAGTACTTTGGAGAGCTTGCCCTGGTAACTAACAAACCTCGAGCAGCTTCTGCCCACGCCATTGGGACTGTCAAATG
TTTAGCAATGGATGTGCAAGCATTTGAAAGGCTTCTGGGACCTTGCATGGAAATTATGAAAAGGAACATCGCTACCTATG
AAGAACAGTTAGTTGCCCTGTTTGGAACGAACATGGATATTGTAGGGTCAGGTGGATCTGGAGGGAGCTCCGGTGCCAAA
AACATTAAGAAGGGCCCAGCGCCATTCTACCCACTCGAAGACGGGACCGCCGGCGAGCAGCTGCACAAAGCCATGAAGCG
CTACGCCCTGGTGCCCGGCACCATCGCCTTTACCGACGCACATATCGAGGTGGACATTACCTACGCCGAGTACTTCGAGA
TGAGCGTTCGGCTGGCAGAAGCTATGAAGCGCTATGGGCTGAATACAAACCATCGGATCGTGGTGTGCAGCGAGAATAGC
TTGCAGTTCTTCATGCCCGTGTTGGGTGCCCTGTTCATCGGTGTGGCTGTGGCCCCAGCTAACGACATCTACAACGAGCG
CGAGCTGCTGAACAGCATGGGCATCAGCCAGCCCACCGTCGTATTCGTGAGCAAGAAAGGGCTGCAAAAGATCCTCAACG
TGCAAAAGAAGCTACCGATCATACAAAAGATCATCATCATGGATAGCAAGACCGACTACCAGGGCTTCCAAAGCATGTAC
ACCTTCGTGACTTCCCATTTGCCACCCGGCTTCAACGAGTACGACTTCGTGCCCGAGAGCTTCGACCGGGACAAAACCAT

*FIG. 67*BT

CGCCCTGATCATGAACAGTAGTGGCAGTACCGGATTGCCCAAGGGCGTAGCCCTACCGCACCGCACCGCTTGTGTCCGAT
TCAGTCATGCCCGCGACCCCATCTTCGGCAACCAGATCATCCCCGTTTAAAC

PPPPPPP) pBFB390 Sgf to Pme (SEQ ID NO:479)
GCGATCGCCATGTCCTTCATCAACTACTATGATTCCGAGAAGCACGCCGAGAACGCCGTGATTTTTCTGCATGGTAACGC
TGCCTCCAGCTACCTGTGGAGGCACGTCGTGCCTCACATCGAGCCCGTGGCTAGATGCATCATCCCTGATCTGATCGGAA
TGGGTAAGTCCGGCAAGAGCGGGAATGGCTCATATCGCCTCCTGGATCACTACAAGTACCTCACCGCTTGGTTCGAGCTG
CTGAACCTTCCAAAGAAAATCATCTTTGTGGGCCACGACTGGGGGGCTTGTCTGGCCTTTCACTACTCCTACGAGCACCA
AGACAAGATCAAGGCCATCGTCCATGCTGAGAGTGTCGTGGACGTGATCGAGTCCTGGGACGAGTGGCCTGACATCGAGG
AGGATATCGCCCTGATCAAGAGCGAAGAGGGCGAGAAAATGGTGCTTGAGAATAACTTCTTCGTCGAGACCATGCTCCCA
AGCAAGATCATGCGGAAACTGGAGCCTGAGGAGTTCGCTGCCTACCTGGAGCCATTCAAGGAGAAGGGCGAGGTTAGACG
GCCTACCCTCTCCTGGCCTCGCGAGATCCCTCTCGTTAAGGGAGGCAAGCCCGACGTCGTCCAGATTGTCCGCAACTACA
ACGCCTACCTTCGGGCCAGCGACGATCTGCCTAAGATGTTCATCGAGTCCGACCCTGGGTTCTTTTCCAACGCTATTGTC
GAGGGAGCTAAGAAGTTCCCTAACACCGAGTTCGTGAAGGTGAAGGGCCTCCACTTCAGCCAGGAGGACGCTCCAGATGA
AATGGGTAAGTACATCAAGAGCTTCGTGGAGCGCGTGCTGAAGAACGAGCAGGGCTCGAGCGGAGGTTCAGGCGGTTCCG
GATGGTATTTTGGCAAGATCACCAGACGGGAGTCAGAGCGGTTACTGCTCAATGCAGAGAACCCGAGAGGGACCTTCCTC
GTGCGAGAAAGTGAGACCACGAAAGGTGCCTACTGCCTCTCAGTGTCTGACTTCGACAACGCCAAGGGCCTCAACGTGAA
GCACTACAAGATCCGCAAGCTGGACAGCGGCGGCTTCTACATCACCTCCCGCACCCAGTTCAACAGCCTGCAGCAGCTGG
TGGCCTACTACTCCAAACACGCCGATGGCCTGTGCCACCGCCTCACCACCGTGTGCGGTTCCGGAGGATCTACTTCGGGG
TCAGGTAAACCTGGCTCGGGTGAGGGATCGGAAATTTATGGTGAATTCGGATCCGGGTCAGGTGGATCTGGAGGGAGCTC
CGGTGCTTCCAAGGTGTACGACCCCGAGCAACGCAAACGCATGATCACTGGGCCTCAGTGGTGGGCTCGCTGCAAGCAAA
TGAACGTGCTGTGAGTTTAAAC

QQQQQQQ) pBFB392 Sgf to Pme (SEQ ID NO:480)
GCGATCGCCATGGTGGCTAGATGCATCATCCCTGATCTGATCGGAATGGGTAAGTCCGGCAAGAGCGGGAATGGCTCATA
TCGCCTCCTGGATCACTACAAGTACCTCACCGCTTGGTTCGAGCTGCTGAACCTTCCAAAGAAAATCATCTTTGTGGGCC
ACGACTGGGGGGCTTGTCTGGCCTTTCACTACTCCTACGAGCACCAAGACAAGATCAAGGCCATCGTCCATGCTGAGAGT
GTCGTGGACGTGATCGAGTCCTGGGACGAGTGGCCTGACATCGAGGAGGATATCGCCCTGATCAAGAGCGAAGAGGGCGA
GAAAATGGTGCTTGAGAATAACTTCTTCGTCGAGACCATGCTCCCAAGCAAGATCATGCGGAAACTGGAGCCTGAGGAGT
TCGCTGCCTACCTGGAGCCATTCAAGGAGAAGGGCGAGGTTAGACGGCCTACCCTCTCCTGGCCTCGCGAGATCCCTCTC
GTTAAGGGAGGCAAGCCCGACGTCGTCCAGATTGTCCGCAACTACAACGCCTACCTTCGGGCCAGCGACGATCTGCCTAA
GATGTTCATCGAGTCCGACCCTGGGTTCTTTTCCAACGCTATTGTCGAGGGAGCTAAGAAGTTCCCTAACACCGAGTTCG
TGAAGGTGAAGGGCCTCCACTTCAGCCAGGAGGACGCTCCAGATGAAATGGGTAAGTACATCAAGAGCTTCGTGGAGCGC
GTGCTGAAGAACGAGCAGGGCTCGAGCGGATGGTATTTTGGCAAGATCACCAGACGGGAGTCAGAGCGGTTACTGCTCAA
TGCAGAGAACCCGAGAGGGACCTTCCTCGTGCGAGAAAGTGAGACCACGAAAGGTGCCTACTGCCTCTCAGTGTCTGACT
TCGACAACGCCAAGGGCCTCAACGTGAAGCACTACAAGATCCGCAAGCTGGACAGCGGCGGCTTCTACATCACCTCCCGC
ACCCAGTTCAACAGCCTGCAGCAGCTGGTGGCCTACTACTCCAAACACGCCGATGGCCTGTGCCACCGCCTCACCACCGT
GTGCGGTTCCGGAGGATCTACTTCGGGGTCAGGTAAACCTGGCTCGGGTGAGGGATCGGAAATTTATGGTGAATTCGGGA
GCTCCGGTGCTTCCAAGGTGTACGACCCCGAGCAACGCAAACGCATGATCACTGGGCCTCAGTGGTGGGCTCGCTGCAAG
CAAATGAACGTGCTGGACTCCTTCATCAACTACTATGATTCCGAGAAGCACGCCGAGAACGCCGTGATTTTTCTGCATGG
TAACGCTGCCTCCAGCTACCTGTGGAGGCACGTCGTGCCTCACATCGAGTGAGTTTAAAC

RRRRRRR) pBFB393 Sgf to Pme (SEQ ID NO:481)
GCGATCGCCATGGTGGCTAGATGCATCATCCCTGATCTGATCGGAATGGGTAAGTCCGGCAAGAGCGGGAATGGCTCATA
TCGCCTCCTGGATCACTACAAGTACCTCACCGCTTGGTTCGAGCTGCTGAACCTTCCAAAGAAAATCATCTTTGTGGGCC
ACGACTGGGGGGCTTGTCTGGCCTTTCACTACTCCTACGAGCACCAAGACAAGATCAAGGCCATCGTCCATGCTGAGAGT
GTCGTGGACGTGATCGAGTCCTGGGACGAGTGGCCTGACATCGAGGAGGATATCGCCCTGATCAAGAGCGAAGAGGGCGA
GAAAATGGTGCTTGAGAATAACTTCTTCGTCGAGACCATGCTCCCAAGCAAGATCATGCGGAAACTGGAGCCTGAGGAGT
TCGCTGCCTACCTGGAGCCATTCAAGGAGAAGGGCGAGGTTAGACGGCCTACCCTCTCCTGGCCTCGCGAGATCCCTCTC
GTTAAGGGAGGCAAGCCCGACGTCGTCCAGATTGTCCGCAACTACAACGCCTACCTTCGGGCCAGCGACGATCTGCCTAA
GATGTTCATCGAGTCCGACCCTGGGTTCTTTTCCAACGCTATTGTCGAGGGAGCTAAGAAGTTCCCTAACACCGAGTTCG
TGAAGGTGAAGGGCCTCCACTTCAGCCAGGAGGACGCTCCAGATGAAATGGGTAAGTACATCAAGAGCTTCGTGGAGCGC
GTGCTGAAGAACGAGCAGGGCTCGAGCGGAGGTTCAGGCGGTTCCGGATGGTATTTTGGCAAGATCACCAGACGGGAGTC
AGAGCGGTTACTGCTCAATGCAGAGAACCCGAGAGGGACCTTCCTCGTGCGAGAAAGTGAGACCACGAAAGGTGCCTACT
GCCTCTCAGTGTCTGACTTCGACAACGCCAAGGGCCTCAACGTGAAGCACTACAAGATCCGCAAGCTGGACAGCGGCGGC
TTCTACATCACCTCCCGCACCCAGTTCAACAGCCTGCAGCAGCTGGTGGCCTACTACTCCAAACACGCCGATGGCCTGTG
CCACCGCCTCACCACCGTGTGCGGTTCCGGAGGATCTACTTCGGGGTCAGGTAAACCTGGCTCGGGTGAGGGATCGGAAA

FIG. 67BU

TTTATGGTGAATTCGGATCCGGGTCAGGTGGATCTGGAGGGAGCTCCGGTGCTTCCAAGGTGTACGACCCCGAGCAACGC
AAACGCATGATCACTGGGCCTCAGTGGTGGGCTCGCTGCAAGCAAATGAACGTGCTGGACTCCTTCATCAACTACTATGA
TTCCGAGAAGCACGCCGAGAACGCCGTGATTTTTCTGCATGGTAACGCTGCCTCCAGCTACCTGTGGAGGCACGTCGTGC
CTCACATCGAGTGAGTTTAAAC

SSSSSSS) pBFB395 Sgf to Pme (SEQ ID NO:482)
GCGATCGCCATGTTTACGTTGGCAGATTTCGTTGGAGACTGGCAACAGACAGCTGGATACAACCAAGATCAAGTGTTAGA
ACAAGGAGGATTGTCTAGTCTGTTCCAAGCCCTGGGAGTGTCAGTCACCCCAATCCAGAAAGTTGTACTGTCTGGGGAGA
ATGGCGGGAGCTCTGGTGGAGGGTCTGGGGGTGTGGCCATCCTCTGGCATGAGATGTGGCATGAAGGCCTGGAAGAGGCA
TCTCGTTTGTACTTTGGGGAAAGGAACGTGAAAGGCATGTTTGAGGTGCTGGAGCCCTTGCATGCTATGATGGAACGGGG
CCCCCAGACTCTGAAGGAAACATCCTTTAATCAGGCCTATGGTCGAGATTTAATGGAGGCCCAAGAGTGGTGCAGGAAGT
ACATGAAATCAGGGAATGTCAAGGACCTCACCCAAGCCTGGGACCTCTATTATCATGTGTTCCGACGAATCTCATGAGTT
TAAAC

TTTTTTT) pBFB396 Sgf to Pme (SEQ ID NO:483)
GCGATCGCCATGTTTACGTTGGCAGATTTCGTTGGAGACTGGCAACAGACAGCTGGATACAACCAAGATCAAGTGTTAGA
ACAAGGAGGATTGTCTAGTCTGTTCCAAGCCCTGGGAGTGTCAGTCACCCCAATCCAGAAAGTTGTGCTGTCTGGGGAGA
ATGGGTTAAAAGCTGATATTCATGTCATCATCCCTTACGAGGGACTCAGTGGTTTTCAAATGGGTCTGATTGAAATGATC
TTCAAAGTTGTTTACCCCGTGGATGGCGGGAGCTCTGGTGGAGGGTCTGGGGGTGTGGCCATCCTCTGGCATGAGATGTG
GCATGAAGGCCTGGAAGAGGCATCTCGTTTGTACTTTGGGGAAAGGAACGTGAAAGGCATGTTTGAGGTGCTGGAGCCCT
TGCATGCTATGATGGAACGGGGCCCCCAGACTCTGAAGGAAACATCCTTTAATCAGGCCTATGGTCGAGATTTAATGGAG
GCCCAAGAGTGGTGCAGGAAGTACATGAAATCAGGGAATGTCAAGGACCTCACCCAAGCCTGGGACCTCTATTATCATGT
GTTCCGACGAATCTCATGAGTTTAAAC

UUUUUUU) pBFB397 Sgf to Pme (SEQ ID NO:484)
GCGATCGCCATGTTTACGTTGGCAGATTTCGTTGGAGACTGGCAACAGACAGCTGGATACAACCAAGATCAAGTGTTAGA
ACAAGGAGGATTGTCTAGTCTGTTCCAAGCCCTGGGAGTGTCAGTCACCCCAATCCAGAAAGTTGTACTGTCTGGGGAGA
ATGGCTCGACCGGAATGTATGAAAGCTTTATTGAGTCACTGCCATTCCTTAAATCTTTGGAGTTTTCTGAACGCCTGAAA
GTAGTAGATGTGATAGGCACCAAAGTATACAACGATGGAGAACAAATCATTGCTCAGGGAGATTCGGCTGATTCTTTTTT
CATTGTAGAATCTGGAGAAGTGAAAATTACTATGAAAAGAAAGGGTAAATCAGAAGTGGAAGAGAATGGTGCAGTAGAAA
TCGCTCGATGCTCGCGGGGACAGTACTTTGGAGAGCTTGCCCTGGTAACTAACAAACCTCGAGCAGCTTCTGCCCACGCC
ATTGGGACTGTCAAATGTTTAGCAATGGATGTGCAAGCATTTGAAAGGCTTCTGGGACCTTGCATGGAAATTATGAAAAG
GAACATCGCTACCTATGAAGAACAGTTAGTTGCCCTGTTTGGAACGAACATGGATATTGTTGGAGCTCCGGTGGGTTAA
AAGCTGATATTCATGTCATCATCCCTTACGAGGGACTCAGTGGTTTTCAAATGGGTCTGATTGAAATGATCTTCAAAGTT
GTTTACCCAGTGGATGATCATCATTTCAAGATTATTCTCCATTATGGTACACTCGTTATTGACGGTGTGACACCAAACAT
GATTGACTACTTTGGACGCCCTTACCCTGGAATTGCTGTGTTTGACGGCAAGCAGATCACAGTTACTGGAACTCTGTGGA
ACGGCAACAAGATCTATGATGAGCGCCTGATCAACCCAGATGGTTCACTCCTCTTCCGCGTTACTATCAATGGAGTCACC
GGATGGCGCCTTTGCGAGAACATTCTTGCCTGAGTTTAAAC

VVVVVVV) pBFB398 Sgf to Pme (SEQ ID NO:485)
GCGATCGCCATGTTTACGTTGGCAGATTTCGTTGGAGACTGGCAACAGACAGCTGGATACAACCAAGATCAAGTGTTAGA
ACAAGGAGGATTGTCTAGTCTGTTCCAAGCCCTGGGAGTGTCAGTCACCCCAATCCAGAAAGTTGTACTGTCTGGGGAGA
ATGGCTCGAGCGGAGGTTCAGGCGGTTCCGGAATGTATGAAAGCTTTATTGAGTCACTGCCATTCCTTAAATCTTTGGAG
TTTTCTGAACGCCTGAAAGTAGTAGATGTGATAGGCACCAAAGTATACAACGATGGAGAACAAATCATTGCTCAGGGAGA
TTCGGCTGATTCTTTTTTCATTGTAGAATCTGGAGAAGTGAAAATTACTATGAAAAGAAAGGGTAAATCAGAAGTGGAAG
AGAATGGTGCAGTAGAAATCGCTCGATGCTCGCGGGGACAGTACTTTGGAGAGCTTGCCCTGGTAACTAACAAACCTCGA
GCAGCTTCTGCCCACGCCATTGGGACTGTCAAATGTTTAGCAATGGATGTGCAAGCATTTGAAAGGCTTCTGGGACCTTG
CATGGAAATTATGAAAAGGAACATCGCTACCTATGAAGAACAGTTAGTTGCCCTGTTTGGAACGAACATGGATATTGTAG
GGTCAGGTGGATCTGGAGGGAGCTCCGGTGGGTTAAAAGCTGATATTCATGTCATAATCCCTTACGAGGGACTCAGTGGT
TTTCAAATGGGTCTGATTGAAATGATCTTCAAAGTTGTTTACCCAGTGGATGATCATCATTTCAAGATTATTCTCCATTA
TGGTACACTCGTTATTGACGGTGTGACACCAAACATGATTGACTACTTTGGACGCCCTTACCCTGGAATTGCTGTGTTTG
ACGGCAAGCAGATCACAGTTACTGGAACTCTGTGGAACGGCAACAAGATCTATGATGAGCGCCTGATCAACCCAGATGGT
TCACTCCTCTTCCGCGTTACTATCAATGGAGTCACCGGATGGCGCCTTTGCGAGAACATTCTTGCCTGAGTTTAAAC

WWWWWWW) pBFB399 Sgf to Pme (SEQ ID NO:486)
GCGATCGCCATGTTTACGTTGGCAGATTTCGTTGGAGACTGGCAACAGACAGCTGGATACAACCAAGATCAAGTGTTAGA
ACAAGGAGGATTGTCTAGTCTGTTCCAAGCCCTGGGAGTGTCAGTCACCCCAATCCAGAAAGTTGTACTGTCTGGGGAGA

*FIG. 67BV*

ATGGCTCGAGCGGAGGTTCAGGCGGTTCCGGAGGAGGTTCTGGCGGATCAGGCGGTTCGGGGATGTATGAAAGCTTTATT
GAGTCACTGCCATTCCTTAAATCTTTGGAGTTTTCTGAACGCCTGAAAGTAGTAGATGTGATAGGCACCAAAGTATACAA
CGATGGAGAACAAATCATTGCTCAGGGAGATTCGGCTGATTCTTTTTTCATTGTAGAATCTGGAGAAGTGAAAATTACTA
TGAAAAGAAAGGGTAAATCAGAAGTGGAAGAGAATGGTGCAGTAGAAATCGCTCGATGCTCGCGGGGACAGTACTTTGGA
GAGCTTGCCCTGGTAACTAACAAACCTCGAGCAGCTTCTGCCCACGCCATTGGGACTGTCAAATGTTTAGCAATGGATGT
GCAAGCATTTGAAAGGCTTCTGGGACCTTGCATGGAAATTATGAAAAGGAACATCGCTACCTATGAAGAACAGTTAGTTG
CCCTGTTTGGAACGAACATGGATATTGTTGGGTCCGGTGGATCCGGTGGCAGCGGAGGGACGTCAGGTGGATCTGGAGGG
AGCTCCGGTGGGTTAAAAGCTGATATTCATGTCATCATCCCTTACGAGGGACTCAGTGGTTTTCAAATGGGTCTGATTGA
AATGATCTTCAAAGTTGTTTACCCAGTGGATGATCATCATTTCAAGATTATTCTCCATTATGGTACACTCGTTATTGACG
GTGTGACACCAAACATGATTGACTACTTTGGACGCCCTTACCCTGGAATTGCTGTGTTTGACGGCAAGCAGATCACAGTT
ACTGGAACTCTGTGGAACGGCAACAAGATCTATGATGAGCGCCTGATCAACCCAGATGGTTCACTCCTCTTCCGCGTTAC
TATCAATGGAGTCACCGGATGGCGCCTTTGCGAGAACATTCTTGCCTGAGTTTAAAC

XXXXXXX) pBFB40 Sgf to Pme (SEQ ID NO:487)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAATG
TATGAAAGCTTTATTGAGTCACTGCCATTCCTTAAATCTTTGGAGTTTTCTGAACGCCTGAAAGTAGTAGATGTGATAGG
CACCAAAGTATACAACGATGGAGAACAAATCATTGCTCAGGGAGATTCGGCTGATTCTTTTTTCATTGTAGAATCTGGAG
AAGTGAAAATTACTATGAAAAGAAAGGGTAAATCAGAAGTGGAAGAGAATGGTGCAGTAGAAATCGCTCGATGCTCGCGG
GGACAGTACTTTGGAGAGCTTGCCCTGGTAACTAACAAACCTCGAGCAGCTTCTGCCCACGCCATTGGGACTGTCAAATG
TTTAGCAATGGATGTGCAAGCATTTGAAAGGCTTCTGGGACCTTGCATGGAAATTATGAAAAGGAACATCGCTACCTATG
AAGAACAGTTAGTTGCCCTGTTTGGAACGAACATGGATATTGTTGGGTCCGGTGGATCCGGTGGCAGCGGAGGGACGTCA
GGTGGATCTGGAGGGAGCTCCGGTGCCAAAAACATTAAGAAGGGCCCAGCGCCATTCTACCCACTCGAAGACGGGACCGC
CGGCGAGCAGCTGCACAAAGCCATGAAGCGCTACGCCCTGGTGCCCGGCACCATCGCCTTTACCGACGCACATATCGAGG
TGGACATTACCTACGCCGAGTACTTCGAGATGAGCGTTCGGCTGGCAGAAGCTATGAAGCGCTATGGGCTGAATACAAAC
CATCGGATCGTGGTGTGCAGCGAGAATAGCTTGCAGTTCTTCATGCCCGTGTTGGGTGCCCTGTTCATCGGTGTGGCTGT
GGCCCCAGCTAACGACATCTACAACGAGCGCGAGCTGCTGAACAGCATGGGCATCAGCCAGCCCACCGTCGTATTCGTGA
GCAAGAAAGGGCTGCAAAAGATCCTCAACGTGCAAAAGAAGCTACCGATCATACAAAAGATCATCATCATGGATAGCAAG
ACCGACTACCAGGGCTTCCAAAGCATGTACACCTTCGTGACTTCCCATTTGCCACCCGGCTTCAACGAGTACGACTTCGT
GCCCGAGAGCTTCGACCGGGACAAAACCATCGCCCTGATCATGAACAGTAGTGGCAGTACCGGATTGCCCAAGGGCGTAG
CCCTACCGCACCGCACCGCTTGTGTCCGATTCAGTCATGCCCGCGACCCCATCTTCGGCAACCAGATCATCCCCGTTTAA
AC

YYYYYYY) pBFB400 Sgf to Pme (SEQ ID NO:488)
GCGATCGCCATGTTTACGTTGGCAGATTTCGTTGGAGACTGGCAACAGACAGCTGGATACAACCAAGATCAAGTGTTAGA
ACAAGGAGGATTGTCTAGTCTGTTCCAAGCCCTGGGAGTGTCAGTCACCCCAATCCAGAAAGTTGTGCTGTCTGGGGAGA
ATGGGTTAAAAGCTGATATTCATGTCATCATCCCTTACGAGGGACTCAGTGGTTTTCAAATGGGTCTGATTGAAATGATC
TTCAAAGTTGTTTACCCCGTGGATGGCTCGACCGGAATGTATGAAAGCTTTATTGAGTCACTGCCATTCCTTAAATCTTT
GGAGTTTTCTGAACGCCTGAAAGTAGTAGATGTGATAGGCACCAAAGTATACAACGATGGAGAACAAATCATTGCTCAGG
GAGATTCGGCTGATTCTTTTTTCATTGTAGAATCTGGAGAAGTGAAAATTACTATGAAAAGAAAGGGTAAATCAGAAGTG
GAAGAGAATGGTGCAGTAGAAATCGCTCGATGCTCGCGGGGACAGTACTTTGGAGAGCTTGCCCTGGTAACTAACAAACC
TCGAGCAGCTTCTGCCCACGCCATTGGGACTGTCAAATGTTTAGCAATGGATGTGCAAGCATTTGAAAGGCTTCTGGGAC
CTTGCATGGAAATTATGAAAAGGAACATCGCTACCTATGAAGAACAGTTAGTTGCCCTGTTTGGAACGAACATGGATATT
GTTGGGAGCTCCGGTGATCATCATTTCAAGATTATTCTCCATTATGGTACACTCGTTATTGACGGTGTGACACCAAACAT
GATTGACTACTTTGGACGCCCTTACCCTGGAATTGCTGTGTTTGACGGCAAGCAGATCACAGTTACTGGAACTCTGTGGA
ACGGCAACAAGATCTATGATGAGCGCCTGATCAACCCAGATGGTTCACTCCTCTTCCGCGTTACTATCAATGGAGTCACC
GGATGGCGCCTTTGCGAGAACATTCTTGCCTGAGTTTAAAC

FIG. 67BW

ZZZZZZZ) pBFB401 Sgf to Pme (SEQ ID NO:489)
GCGATCGCCATGTTTACGTTGGCAGATTTCGTTGGAGACTGGCAACAGACAGCTGGATACAACCAAGATCAAGTGTTAGA
ACAAGGAGGATTGTCTAGTCTGTTCCAAGCCCTGGGAGTGTCAGTCACCCCAATCCAGAAAGTTGTGCTGTCTGGGGAGA
ATGGGTTAAAAGCTGATATTCATGTCATCATCCCTTACGAGGGACTCAGTGGTTTTCAAATGGGTCTGATTGAAATGATC
TTCAAAGTTGTTTACCCCGTGGATGGCTCGAGCGGAGGTTCAGGCGGTTCCGGAATGTATGAAAGCTTTATTGAGTCACT
GCCATTCCTTAAATCTTTGGAGTTTTCTGAACGCCTGAAAGTAGTAGATGTGATAGGCACCAAAGTATACAACGATGGAG
AACAAATCATTGCTCAGGGAGATTCGGCTGATTCTTTTTTCATTGTAGAATCTGGAGAAGTGAAAATTACTATGAAAAGA
AAGGGTAAATCAGAAGTGGAAGAGAATGGTGCAGTAGAAATCGCTCGATGCTCGCGGGGACAGTACTTTGGAGAGCTTGC
CCTGGTAACTAACAAACCTCGAGCAGCTTCTGCCCACGCCATTGGGACTGTCAAATGTTTAGCAATGGATGTGCAAGCAT
TTGAAAGGCTTCTGGGACCTTGCATGGAAATTATGAAAAGGAACATCGCTACCTATGAAGAACAGTTAGTTGCCCTGTTT
GGAACGAACATGGATATTGTAGGGTCAGGTGGATCTGGAGGGAGCTCCGGTGATCATCATTTCAAGATTATTCTCCATTA
TGGTACACTCGTTATTGACGGTGTGACACCAAACATGATTGACTACTTTGGACGCCCTTACCCTGGAATTGCTGTGTTTG
ACGGCAAGCAGATCACAGTTACTGGAACTCTGTGGAACGGCAACAAGATCTATGATGAGCGCCTGATCAACCCAGATGGT
TCACTCCTCTTCCGCGTTACTATCAATGGAGTCACCGGATGGCGCCTTTGCGAGAACATTCTTGCCTGAGTTTAAAC

AAAAAAAA) pBFB402 Sgf to Pme (SEQ ID NO:490)
GCGATCGCCATGTTTACGTTGGCAGATTTCGTTGGAGACTGGCAACAGACAGCTGGATACAACCAAGATCAAGTGTTAGA
ACAAGGAGGATTGTCTAGTCTGTTCCAAGCCCTGGGAGTGTCAGTCACCCCAATCCAGAAAGTTGTGCTGTCTGGGGAGA
ATGGGTTAAAAGCTGATATTCATGTCATCATCCCTTACGAGGGACTCAGTGGTTTTCAAATGGGTCTGATTGAAATGATC
TTCAAAGTTGTTTACCCCGTGGATGGCTCGAGCGGAGGTTCAGGCGGTTCCGGAGGAGGTTCTGGCGGATCAGGCGGTTC
GGGGATGTATGAAAGCTTTATTGAGTCACTGCCATTCCTTAAATCTTTGGAGTTTTCTGAACGCCTGAAAGTAGTAGATG
TGATAGGCACCAAAGTATACAACGATGGAGAACAAATCATTGCTCAGGGAGATTCGGCTGATTCTTTTTTCATTGTAGAA
TCTGGAGAAGTGAAAATTACTATGAAAAGAAAGGGTAAATCAGAAGTGGAAGAGAATGGTGCAGTAGAAATCGCTCGATG
CTCGCGGGGACAGTACTTTGGAGAGCTTGCCCTGGTAACTAACAAACCTCGAGCAGCTTCTGCCCACGCCATTGGGACTG
TCAAATGTTTAGCAATGGATGTGCAAGCATTTGAAAGGCTTCTGGGACCTTGCATGGAAATTATGAAAAGGAACATCGCT
ACCTATGAAGAACAGTTAGTTGCCCTGTTTGGAACGAACATGGATATTGTTGGGTCCGGTGGATCCGGTGGCAGCGGAGG
GACGTCAGGTGGATCTGGAGGGAGCTCCGGTGATCATCATTTCAAGATTATTCTCCATTATGGTACACTCGTTATTGACG
GTGTGACACCAAACATGATTGACTACTTTGGACGCCCTTACCCTGGAATTGCTGTGTTTGACGGCAAGCAGATCACAGTT
ACTGGAACTCTGTGGAACGGCAACAAGATCTATGATGAGCGCCTGATCAACCCAGATGGTTCACTCCTCTTCCGCGTTAC
TATCAATGGAGTCACCGGATGGCGCCTTTGCGAGAACATTCTTGCCTGAGTTTAAAC

BBBBBBBB) pBFB41 Sgf to Pme (SEQ ID NO:491)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAATGTATGAAAGCTTTATTGAGTCACTGCCATTCCTTAAATCTTTGGAGTTTTCTGAACGCCTGAA
AGTAGTAGATGTGATAGGCACCAAAGTATACAACGATGGAGAACAAATCATTGCTCAGGGAGATTCGGCTGATTCTTTTT
TCATTGTAGAATCTGGAGAAGTGAAAATTACTATGAAAAGAAAGGGTAAATCAGAAGTGGAAGAGAATGGTGCAGTAGAA
ATCGCTCGATGCTCGCGGGGACAGTACTTTGGAGAGCTTGCCCTGGTAACTAACAAACCTCGAGCAGCTTCTGCCCACGC
CATTGGGACTGTCAAATGTTTAGCAATGGATGTGCAAGCATTTGAAAGGCTTCTGGGACCTTGCATGGAAATTATGAAAA
GGAACATCGCTACCTATGAAGAACAGTTAGTTGCCCTGTTTGGAACGAACATGGATATTGTTGGGAGCTCCGGTGCCAAA
AACATTAAGAAGGGCCCAGCGCCATTCTACCCACTCGAAGACGGGACCGCCGGCGAGCAGCTGCACAAAGCCATGAAGCG
CTACGCCCTGGTGCCCGGCACCATCGCCTTTACCGACGCACATATCGAGGTGGACATTACCTACGCCGAGTACTTCGAGA
TGAGCGTTCGGCTGGCAGAAGCTATGAAGCGCTATGGGCTGAATACAAACCATCGGATCGTGGTGTGCAGCGAGAATAGC
TTGCAGTTCTTCATGCCCGTGTTGGGTGCCCTGTTCATCGGTGTGGCTGTGGCCCCAGCTAACGACATCTACAACGAGCG
CGAGCTGCTGAACAGCATGGGCATCAGCCAGCCCACCGTCGTATTCGTGAGCAAGAAAGGGCTGCAAAAGATCCTCAACG
TGCAAAAGAAGCTACCGATCATACAAAAGATCATCATCATGGATAGCAAGACCGACTACCAGGGCTTCCAAAGCATGTAC

*FIG. 67BX*

ACCTTCGTGACTTCCCATTTGCCACCCGGCTTCAACGAGTACGACTTCGTGCCCGAGAGCTTCGACCGGGACAAAACCAT
CGCCCTGATCATGAACAGTAGTGGCAGTACCGGATTGCCCAAGGGCGTAGCCCTACCGCACCGCACCGCTTGTGTCCGAT
TCAGTCATGCCCGCGACCCCATCTTCGGCAACCAGATCATCCCCGTTTAAAC

CCCCCCCC) pBFB42 Sgf to Pme (SEQ ID NO:492)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAATGTATGAAAGCTTTATTGAGTCACTGCCATTCCTTAAATCTTTGGAGTTTTCTGAACGCCTGAA
AGTAGTAGATGTGATAGGCACCAAAGTATACAACGATGGAGAACAAATCATTGCTCAGGGAGATTCGGCTGATTCTTTTT
TCATTGTAGAATCTGGAGAAGTGAAAATTACTATCAAAAGAAAGGGTAAATCAGAAGTGGAAGAGAATGGTGCAGTACAA
ATCGCTCGATGCTCGCGGGGACAGTACTTTGGAGAGCTTGCCCTGGTAACTAACAAACCTCGAGCAGCTTCTGCCCACGC
CATTGGGACTGTCAAATGTTTAGCAATGGATGTGCAAGCATTTGAAAGGCTTCTGGGACCTTGCATGGAAATTATGAAAA
GGAACATCGCTACCTATGAAGAACAGTTAGTTGCCCTGTTTGGAACGAACATGGATATTGTTGGGTCCGGTGGATCCGGT
GGCAGCGGAGGGACGTCAGGTGGATCTGGAGGGAGCTCCGGTGCCAAAAACATTAAGAAGGGCCCAGCGCCATTCTACCC
ACTCGAAGACGGGACCGCCGGCGAGCAGCTGCACAAAGCCATGAAGCGCTACGCCCTGGTGCCCGGCACCATCGCCTTTA
CCGACGCACATATCGAGGTGGACATTACCTACGCCGAGTACTTCGAGATGAGCGTTCGGCTGGCAGAAGCTATGAAGCGC
TATGGGCTGAATACAAACCATCGGATCGTGGTGTGCAGCGAGAATAGCTTGCAGTTCTTCATGCCCGTGTTGGGTGCCCT
GTTCATCGGTGTGGCTGTGGCCCCAGCTAACGACATCTACAACGAGCGCGAGCTGCTGAACAGCATGGGCATCAGCCAGC
CCACCGTCGTATTCGTGAGCAAGAAAGGGCTGCAAAAGATCCTCAACGTGCAAAAGAAGCTACCGATCATACAAAAGATC
ATCATCATGGATAGCAAGACCGACTACCAGGGCTTCCAAAGCATGTACACCTTCGTGACTTCCCATTTGCCACCCGGCTT
CAACGAGTACGACTTCGTGCCCGAGAGCTTCGACCGGGACAAAACCATCGCCCTGATCATGAACAGTAGTGGCAGTACCG
GATTGCCCAAGGGCGTAGCCCTACCGCACCGCACCGCTTGTGTCCGATTCAGTCATGCCCGCGACCCCATCTTCGGCAAC
CAGATCATCCCCGTTTAAAC

DDDDDDDD) pBFB45 Sgf to Pme (SEQ ID NO:493)
GCGATCGCCATGACGTCAGCAATTTTAACGGTAATACCTTTCCACCATGGTTTTGGTATGATGACCACATTAGGATACTT
TACTTGTGGATTCCGAGTTGTTCTAATGCACACGTTTGAAGAAAAACTATTTCTACAATCATTACAAGATTATAAAGTGG
AAAGTACTTTACTTGTACCAACATTAATGGCATTTCTTGCAAAAAGTGCATTAGTTGAAAAGTACGATTTATCGCACTTA
AAAGAAATTGCATCTGGTGGCGCACCTTTATCAAAAGAAATTGGGGAGATGGTGAAAAAACGGTTTAAATTAAACTTTGT
CAGGCAAGGGTATGGATTAACAGAAACCACTTCGGCTGTTTTAATTACACCGAAAGGTGACGCCAAACCGGGATCAACTG
GTAAAATAGTACCATTACACGCTGTTAAAGTTGTCGATCCTACAACAGGAAAAATTTTGGGGCCAAATGAACCTGGAGAA
TTGTATTTTAAAGGCCCGATGATAATGAAGGGTTATTATAATAATGAAGAAGCTACTAAAGCAATTATTGATAATGACGG
ATGGTTGCGCTCTGGTGATATTGCTTATTATGACAATGATGGCCATTTTTATATTGTGGACAGGCTGAAGTCACTGATTA
AATATAAAGGTTATCAGGTTGCACCTGCTGAAATTGAGGGAATACTCTTACAACATCCGTATATTGTTGATGCCGGCGTT
ACTGGTATACCGGATGAAGCCGCGGGCGAGCTTCCAGCTGCAGGTGTTGTAGTACAGACTGGAAAATATCTAAACGAACA
AATCGTACAAGATTATGTTGCCAGTCAAGTTTCAACAGCCAAATGGCTACGTGGTGGGGTGAAATTTTTGGATGAAATTC
CCAAAGGATCAACTGGAAAAATTGACAGAAAAGTGTTAAGACAAATGTTAGAAAAACACACCAATGGCTCGAGCGGAGGT
TCAGGCGGTTCCGGAGGAGGTTCTGGCGGATCAGGCGGTTCGCGAGGAGGTGGCACCGGTGGATCCGGTGGCAGCGGAGG
GACGTCAGGTGGATCTGGAGGGAGCTCCGGTGATAAGAATATTTTATATGGGCCCGAACCATTTTATCCCTTGGAAGATG
GGACGGCTGGAGAACAGATGTTTGACGCATTATCTCGTTATGCAGCTATTCCGGGCTGCATAGCATTGACAAATGCTCAT
ACAAAAGAAAATGTTTTATATGAAGAGTTTCTGAAACTGTCGTGTCGTTTAGCGGAAAGTTTTAAAAAGTATGGATTAAA
ACAAAACGACACAATAGCGGTGTGTAGCGAAAATAGTCTGCAATTTTTCCTTCCTGTAATTGCATCATTGTATCTTGGAA
TAATTGTGGCACCTGTTAACGATAAATACATTGAACGTGAATTAATACACAGTCTTGGTATTGTAAAACCACGCATAGTT
TTTTGCTCCAAGAATACTTTTCAAAAAGTACTGAATGTAAAATCTAAATTAAAATCTATTGAAACTATTATTATATTAGA
CTTAAATGAAGACTTAGGAGGTTATCAATGCCTCAACAACTTTATTTCTCAAAATTCCGATAGTAATCTGGACGTAAAAA
AATTTAAACCCTATTCTTTTAATCGAGACGATCAGGTTGCGTCGATTATGTTTTCTTCTGGTACAACTGGTCTGCCGAAG

*FIG. 67*BY

GGAGTCATGCTAACTCACAAGAATATTGTTGCACGATTTTCTATTGCAAAAGATCCTACTTTTGGTAACGCAATTAATCC
CGTTTAAAC

EEEEEEEE) pBFB51 Sgf to Pme (SEQ ID NO:494)
GCGATCGCCATGACGTCAGCAATTTTAACGGTAATACCTTTCCACCATGGTTTTGGTATGATGACCACATTAGGATACTT
TACTTGTGGATTCCGAGTTGTTCTAATGCACACGTTTGAAGAAAAACTATTTCTACAATCATTACAAGATTATAAAGTGG
AAAGTACTTTACTTGTACCAACATTAATGGCATTTCTTGCAAAAAGTGCATTAGTTGAAAAGTACGATTTATCGCACTTA
AAAGAAATTGCATCTGGTGGCGCACCTTTATCAAAAGAAATTGGGGAGATGGTGAAAAAACGGTTTAAATTAAACTTTGT
CAGGCAAGGGTATGGATTAACAGAAACCACTTCGGCTGTTTTAATTACACCGAAAGGTGACGCCAAACCGGGATCAACTG
GTAAAATAGTACCATTACACGCTGTTAAAGTTGTCGATCCTACAACAGGAAAAATTTTGGGGCCAAATGAACCTGGAGAA
TTGTATTTTAAAGGCCCGATGATAATGAAGGGTTATTATAATAATGAAGAAGCTACTAAAGCAATTATTGATAATGACGG
ATGGTTGCGCTCTGGTGATATTGCTTATTATGACAATGATGGCCATTTTTATATTGTGGACAGGCTGAAGTCACTGATTA
AATATAAAGGTTATCAGGTTGCACCTGCTGAAATTGAGGGAATACTCTTACAACATCCGTATATTGTTGATGCCGGCGTT
ACTGGTATACCGGATGAAGCCGCGGGCGAGCTTCCAGCTGCAGGTGTTGTAGTACAGACTGGAAAATATCTAAACGAACA
AATCGTACAAGATTATGTTGCCAGTCAAGTTTCAACAGCCAAATGGCTACGTGGTGGGGTGAAATTTTTGGATGAAATTC
CCAAAGGATCAACTGGAAAAATTGACAGAAAAGTGTTAAGACAAATGTTAGAAAAACACACCAATGGCTCGACCGGAATG
TATGAAAGCTTTATTGAGTCACTGCCATTCCTTAAATCTTTGGAGTTTTCTGAACGCCTGAAAGTAGTAGATGTGATAGG
CACCAAAGTATACAACGATGGAGAACAAATCATTGCTCAGGGAGATTCGGCTGATTCTTTTTTCATTGTAGAATCTGGAG
AAGTGAAAATTACTATGAAAAGAAAGGGTAAATCAGAAGTGGAAGAGAATGGTGCAGTAGAAATCGCTCGATGCTCGCGG
GGACAGTACTTTGGAGAGCTTGCCCTGGTAACTAACAAACCTCGAGCAGCTTCTGCCCACGCCATTGGGACTGTCAAATG
TTTAGCAATGGATGTGCAAGCATTTGAAAGGCTTCTGGGACCTTGCATGGAAATTATGAAAAGGAACATCGCTACCTATG
AAGAACAGTTAGTTGCCCTGTTTGGAACGAACATGGATATTGTTGGGAGCTCCGGTGATAAGAATATTTTATATGGGCCC
GAACCATTTTATCCCTTGGAAGATGGGACGGCTGGAGAACAGATGTTTGACGCATTATCTCGTTATGCAGCTATTCCGGG
CTGCATAGCATTGACAAATGCTCATACAAAAGAAAATGTTTTATATGAAGAGTTTCTGAAACTGTCGTGTCGTTAGCGG
AAAGTTTTAAAAAGTATGGATTAAAACAAAACGACACAATAGCGGTGTGTAGCGAAAATAGTCTGCAATTTTTCCTTCCT
GTAATTGCATCATTGTATCTTGGAATAATTGTGGCACCTGTTAACGATAAATACATTGAACGTGAATTAATACACAGTCT
TGGTATTGTAAAACCACGCATAGTTTTTTGCTCCAAGAATACTTTTCAAAAAGTACTGAATGTAAAATCTAAATTAAAAT
CTATTGAAACTATTATTATATTAGACTTAAATGAAGACTTAGGAGGTTATCAATGCCTCAACAACTTTATTTCTCAAAAT
TCCGATAGTAATCTCGACGTAAAAAAATTTAAACCCTATTCTTTTAATCGAGACGATCAGGTTGCGTCGATTATGTTTTC
TTCTGGTACAACTGGTCTGCCGAAGGGAGTCATGCTAACTCACAAGAATATTGTTGCACGATTTTCTATTGCAAAAGATC
CTACTTTTGGTAACGCAATTAATCCCGTTTAAAC

FFFFFFFF) pBFB52 Sgf to Pme (SEQ ID NO:495)
GCGATCGCCATGACGTCAGCAATTTTAACGGTAATACCTTTCCACCATGGTTTTGGTATGATGACCACATTAGGATACTT
TACTTGTGGATTCCGAGTTGTTCTAATGCACACGTTTGAAGAAAAACTATTTCTACAATCATTACAAGATTATAAAGTGG
AAAGTACTTTACTTGTACCAACATTAATGGCATTTCTTGCAAAAAGTGCATTAGTTGAAAAGTACGATTTATCGCACTTA
AAAGAAATTGCATCTGGTGGCGCACCTTTATCAAAAGAAATTGGGGAGATGGTGAAAAAACGGTTTAAATTAAACTTTGT
CAGGCAAGGGTATGGATTAACAGAAACCACTTCGGCTGTTTTAATTACACCGAAAGGTGACGCCAAACCGGGATCAACTG
GTAAAATAGTACCATTACACGCTGTTAAAGTTGTCGATCCTACAACAGGAAAAATTTTGGGGCCAAATGAACCTGGAGAA
TTGTATTTTAAAGGCCCGATGATAATGAAGGGTTATTATAATAATGAAGAAGCTACTAAAGCAATTATTGATAATGACGG
ATGGTTGCGCTCTGGTGATATTGCTTATTATGACAATGATGGCCATTTTTATATTGTGGACAGGCTGAAGTCACTGATTA
AATATAAAGGTTATCAGGTTGCACCTGCTGAAATTGAGGGAATACTCTTACAACATCCGTATATTGTTGATGCCGGCGTT
ACTGGTATACCGGATGAAGCCGCGGGCGAGCTTCCAGCTGCAGGTGTTGTAGTACAGACTGGAAAATATCTAAACGAACA
AATCGTACAAGATTATGTTGCCAGTCAAGTTTCAACAGCCAAATGGCTACGTGGTGGGGTGAAATTTTTGGATGAAATTC
CCAAAGGATCAACTGGAAAAATTGACAGAAAAGTGTTAAGACAAATGTTAGAAAAACACACCAATGGCTCGAGCGGAGGT
TCAGGCGGTTCCGGAGGAGGTTCTGGCGGATCAGGCGGTTCGGGGATGTATGAAAGCTTTATTGAGTCACTGCCATTCCT
TAAATCTTTGGAGTTTTCTGAACGCCTGAAAGTAGTAGATGTGATAGGCACCAAAGTATACAACGATGGAGAACAAATCA
TTGCTCAGGGAGATTCGGCTGATTCTTTTTTCATTGTAGAATCTGGAGAAGTGAAAATTACTATGAAAAGAAAGGGTAAA
TCAGAAGTGGAAGAGAATGGTGCAGTAGAAATCGCTCGATGCTCGCGGGGACAGTACTTTGGAGAGCTTGCCCTGGTAAC
TAACAAACCTCGAGCAGCTTCTGCCCACGCCATTGGGACTGTCAAATGTTTAGCAATGGATGTGCAAGCATTTGAAAGGC
TTCTGGGACCTTGCATGGAAATTATGAAAAGGAACATCGCTACCTATGAAGAACAGTTAGTTGCCCTGTTTGGAACGAAC
ATGGATATTGTTGGGTCCGGTGGATCCGGTGGCAGCGGAGGGACGTCAGGTGGATCTGGAGGGAGCTCCGGTGATAAGAA
TATTTTATATGGGCCCGAACCATTTTATCCCTTGGAAGATGGGACGGCTGGAGAACAGATGTTTGACGCATTATCTCGTT
ATGCAGCTATTCCGGGCTGCATAGCATTGACAAATGCTCATACAAAAGAAAATGTTTTATATGAAGAGTTTCTGAAACTG
TCGTGTCGTTTAGCGGAAAGTTTTAAAAAGTATGGATTAAAACAAAACGACACAATAGCGGTGTGTAGCGAAAATAGTCT
GCAATTTTTCCTTCCTGTAATTGCATCATTGTATCTTGGAATAATTGTGGCACCTGTTAACGATAAATACATTGAACGTG
AATTAATACACAGTCTTGGTATTGTAAAACCACGCATAGTTTTTTGCTCCAAGAATACTTTTCAAAAAGTACTGAATGTA

*FIG. 67*BZ

AAATCTAAATTAAAATCTATTGAAACTATTATTATATTAGACTTAAATGAAGACTTAGGAGGTTATCAATGCCTCAACAA
CTTTATTTCTCAAAATTCCGATAGTAATCTGGACGTAAAAAAATTTAAACCCTATTCTTTTAATCGAGACGATCAGGTTG
CGTCGATTATGTTTTCTTCTGGTACAACTGGTCTGCCGAAGGGAGTCATGCTAACTCACAAGAATATTGTTGCACGATTT
TCTATTGCAAAAGATCCTACTTTTGGTAACGCAATTAATCCCGTTTAAAC

GGGGGGGG) pBFB54 Sgf to Pme (SEQ ID NO:496)
GCGATCGCCATGGGCGTGACTGTGCTGGTGTATCTGCCTTTCTTTCACGCCTTTGGTTTCTCTATTACCCTGGGCTATTT
CATGGTCGGCTTGCGTGTCATCATGTTTCGTCGCTTCGACCAAGAAGCCTTCTTGAAGGCTATTCAAGACTACGAGGTGC
GTTCCGTGATCAACGTCCCTTCAGTCATTTTGTTCCTGAGCAAATCTCCTTTGGTTGACAAGTATGATCTGAGCAGCTTG
CGTGAGCTGTGCTGTGGCGCTGCTCCTTTGGCCAAAGAAGTGGCCGAGGTCGCTGCTAAGCGTCTGAACCTCCCTGGTAT
CCGCTGCGGTTTTGGTTTGACTGAGAGCACTTCTGCTAACATCCATAGCTTGCGAGACGAGTTTAAGTCTGGTAGCCTGG
GTCGCGTGACTCCTCTTATGGCTGCAAAGATCGCCGACCGTGAGACCGGCAAAGCACTGGGCCCAAATCAAGTCGGTGAA
TTGTGTATTAAGGGCCCTATGGTCTCTAAAGGCTACGTGAACAATGTGGAGGCCACTAAAGAAGCCATTGATGATGATGG
CTGGCTCCATAGCGGCGACTTCGGTTACTATGATGAGGACGAACACTTCTATGTGGTCGATCGCTACAAAGAATTGATTA
AGTACAAAGGCTCTCAAGTCGCACCAGCCGAACTGGAAGAAATTTTGCTGAAGAACCCTTGTATCCGCGACGTGGCCGTC
GTGGGTATCCCAGACTTGGAAGCTGGCGAGTTGCCTAGCGCCTTTGTGGTGAAACAACCCGGCAAGGAGATCACTGCTAA
GGAGGTCTACGACTATTTGGCCGAGCGCGTGTCTCACACCAAATATCTGCGTGGCGGCGTCCGCTTCGTCGATTCTATTC
CACGCAACGTTACCGGTAAGATCACTCGTAAAGAGTTGCTGAAGCAACTCCTCGAAAAAGCTGGCGGCGGCTCGACCGGA
ATGTATGAAAGCTTTATTGAGTCACTGCCATTCCTTAAATCTTTGGAGTTTTCTGAACGCCTGAAAGTAGTAGATGTGAT
AGGCACCAAAGTATACAACGATGGAGAACAAATCATTGCTCAGGGAGATTCGGCTGATTCTTTTTTCATTGTAGAATCTG
GAGAAGTGAAAATTACTATGAAAAGAAAGGGTAAATCAGAAGTGGAAGAGAATGGTGCAGTAGAAATCGCTCGATGCTCG
CGGGGACAGTACTTTGGAGAGCTTGCCCTGGTAACTAACAAACCTCGAGCAGCTTCTGCCCACGCCATTGGGACTGTCAA
ATGTTTAGCAATGGATGTGCAAGCATTTGAAAGGCTTCTGGGACCTTGCATGGAAATTATGAAAAGGAACATCGCTACCT
ATGAAGAACAGTTAGTTGCCCTGTTTGGAACGAACATGGATATTGTTGGGAGCTCCGGTGAAAAGAACGTGATCTACGGC
CCAGAACCACTGCATCCACTGGAAGACCTCACCGCTGGTGAGATGCTCTTCCGAGCACTGCGTAAACATAGTCACCTCCC
TCAAGCACTCGTGGACGTCGTGGGAGACGAGAGCCTCTCCTACAAAGAATTTTTCGAAGCTACTGTGCTGTTGGCCCAAA
GCCTCCATAATTGTGGGTACAAAATGAACGATGTGGTGAGCATTTGTGCTGAGAATAACACTCGCTTCTTTATTCCTGTA
ATCGCTGCTTGGTACATCGGCATGATTGTCGCCCCTGTGAATGAATCTTACATCCCAGATGAGCTGTGTAAGGTTATGGG
TATTAGCAAACCTCAAATCGTCTTTACTACCAAAAACATCTTGAATAAGGTCTTGGAAGTCCAGTCTCGTACTAACTTCA
TCAAACGCATCATTATTCTGGATACCGTCGAAAACATCCACGGCTGTGAGAGCCTCCCTAACTTCATCTCTCGTTACAGC
GATGGTAATATCGCTAATTTCAAGCCCTTGCATTTTGATCCAGTCGAGCAAGTGGCCGCTATTTTGTGCTCCTCCGGCAC
CACTGGTTTGCCTAAAGGTGTCATGCAGACTCACCAGAATATCTGTGTGCGTTTGATCCACGCTCTCGACCCTCGTGTGG
GTACTCAATTGATCCCTGTTTAAAC

HHHHHHHH) pBFB55 Sgf to Pme (SEQ ID NO:497)
GCGATCGCCATGGGCGTGACTGTGCTGGTTATCTGCCTTTCTTTCACGCCTTTGGTTTCTCTATTACCCTGGGCTATTTC
ATGGTCGGCTTGCGTGTCATCATGTTTCGTCGCTTCGACCAAGAAGCCTTCTTGAAGGCTATTCAAGACTACGAGGTGCG
TTCCGTGATCAACGTCCCTTCAGTCATTTTGTTCCTGAGCAAATCTCCTTTGGTTGACAAGTATGATCTGAGCAGCTTGC
GTGAGCTGTGCTGTGGCGCTGCTCCTTTGGCCAAAGAAGTGGCCGAGGTCGCTGCTAAGCGTCTGAACCTCCCTGGTATC
CGCTGCGGTTTTGGTTTGACTGAGAGCACTTCTGCTAACATCCATAGCTTGCGAGACGAGTTTAAGTCTGGTAGCCTGGG
TCGCGTGACTCCTCTTATGGCTGCAAAGATCGCCGACCGTGAGACCGGCAAAGCACTGGGCCCAAATCAAGTCGGTGAAT
TGTGTATTAAGGGCCCTATGGTCTCTAAAGGCTACGTGAACAATGTGGAGGCCACTAAAGAAGCCATTGATGATGATGGC
TGGCTCCATAGCGGCGACTTCGGTTACTATGATGAGGACGAACACTTCTATGTGGTCGATCGCTACAAAGAATTGATTAA
GTACAAAGGCTCTCAAGTCGCACCAGCCGAACTGGAAGAAATTTTGCTGAAGAACCCTTGTATCCGCGACGTGGCCGTCG
TGGGTATCCCAGACTTGGAAGCTGGCGAGTTGCCTAGCGCCTTTGTGGTGAAACAACCCGGCAAGGAGATCACTGCTAAG
GAGGTCTACGACTATTTGGCCGAGCGCGTGTCTCACACCAAATATCTGCGTGGCGGCGTCCGCTTCGTCGATTCTATTCC
ACGCAACGTTACCGGTAAGATCACTCGTAAAGAGTTGCTGAAGCAACTCCTCGAAAAAGCTGGCGGCGGCTCGAGCGGAG
GTTCAGGCGGTTCCGGAGGAGGTTCTGGCGGATCAGGCGGTTCGGGGATGTATGAAAGCTTTATTGAGTCACTGCCATTC
CTTAAATCTTTGGAGTTTTCTGAACGCCTGAAAGTAGTAGATGTGATAGGCACCAAAGTATACAACGATGGAGAACAAAT
CATTGCTCAGGGAGATTCGGCTGATTCTTTTTTCATTGTAGAATCTGGAGAAGTGAAAATTACTATGAAAAGAAAGGGTA
AATCAGAAGTGGAAGAGAATGGTGCAGTAGAAATCGCTCGATGCTCGCGGGGACAGTACTTTGGAGAGCTTGCCCTGGTA
ACTAACAAACCTCGAGCAGCTTCTGCCCACGCCATTGGGACTGTCAAATGTTTAGCAATGGATGTGCAAGCATTTGAAAG
GCTTCTGGGACCTTGCATGGAAATTATGAAAAGGAACATCGCTACCTATGAAGAACAGTTAGTTGCCCTGTTTGGAACGA
ACATGGATATTGTTGGGTCCGGTGGATCCGGTGGCAGCGGAGGGACGTCAGGTGGATCTGGAGGGAGCTCCGGTGAAAAG
AACGTGATCTACGGCCCAGAACCACTGCATCCACTGGAAGACCTCACCGCTGGTGAGATGCTCTTCCGAGCACTGCGTAA
ACATAGTCACCTCCCTCAAGCACTCGTGGACGTCGTGGGAGACGAGAGCCTCTCCTACAAAGAATTTTTCGAAGCTACTG
TGCTGTTGGCCCAAAGCCTCCATAATTGTGGGTACAAAATGAACGATGTGGTGAGCATTTGTGCTGAGAATAACACTCGC

*FIG. 67CA*

TTCTTTATTCCTGTAATCGCTGCTTGGTACATCGGCATGATTGTCGCCCCTGTGAATGAATCTTACATCCCAGATGAGCT
GTGTAAGGTTATGGGTATTAGCAAACCTCAAATCGTCTTTACTACCAAAAACATCTTGAATAAGGTCTTGGAAGTCCAGT
CTCGTACTAACTTCATCAAACGCATCATTATTCTGGATACCGTCGAAAACATCCACGGCTGTGAGAGCCTCCCTAACTTC
ATCTCTCGTTACAGCGATGGTAATATCGCTAATTTCAAGCCCTTGCATTTTGATCCAGTCGAGCAAGTGGCCGCTATTTT
GTGCTCCTCCGGCACCACTGGTTTGCCTAAAGGTGTCATGCAGACTCACCAGAATATCTGTGTGCGTTTGATCCACGCTC
TCGACCCTCGTGTGGGTACTCAATTGATCCCTGTTTAAAC

IIIIIII) pBFB56 Sgf to Pme (SEQ ID NO:498)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAATG
TATGAGGAATTCCTTAGTAAAGTCTCTATTTTAGAGTCTCTGGACAAGTGGGAACGTCTTACGGTAGCTGATGCATTGGA
ACCAGTGCAGTTTGAAGATGGGCAGAAGATTGTGGTGCAGGGAGAACCAGGGGATGAGTTCTTCATTATTTTAGAGGGGT
CAGCTGCTGTGCTACAACGTCGGTCAGAAAATGAAGAGTTTGTTGAAGTGGGAAGATTGGGGCCTTCTGATTATTTTGGT
GAAATTGCACTACTGATGAATCGTCCTCGTGCTGCCACAGTTGTTGCTCGTGGCCCCTTGAAGTGCGTTAAGCTGGACCG
ACCTAGATTTGAACGTGTTCTTGGCCCATGCTCAGACATCCTCAAACGAAACATCCAGCAGTACAACAGTTTTGTGTCAC
TGTCTGTCGGGAGCTCCGGTGCCAAAAACATTAAGAAGGGCCCAGCGCCATTCTACCCACTCGAAGACGGGACCGCCGGC
GAGCAGCTGCACAAAGCCATGAAGCGCTACGCCCTGGTGCCCGGCACCATCGCCTTTACCGACGCACATATCGAGGTGGA
CATTACCTACGCCGAGTACTTCGAGATGAGCGTTCGGCTGGCAGAAGCTATGAAGCGCTATGGGCTGAATACAAACCATC
GGATCGTGGTGTGCAGCGAGAATAGCTTGCAGTTCTTCATGCCCGTGTTGGGTGCCCTGTTCATCGGTGTGGCTGTGGCC
CCAGCTAACGACATCTACAACGAGCGCGAGCTGCTGAACAGCATGGGCATCAGCCAGCCCACCGTCGTATTCGTGAGCAA
GAAAGGGCTGCAAAAGATCCTCAACGTGCAAAAGAAGCTACCGATCATACAAAAGATCATCATCATGGATAGCAAGACCG
ACTACCAGGGCTTCCAAAGCATGTACACCTTCGTGACTTCCCATTTGCCACCCGGCTTCAACGAGTACGACTTCGTGCCC
GAGAGCTTCGACCGGGACAAAACCATCGCCCTGATCATGAACAGTAGTGGCAGTACCGGATTGCCCAAGGGCGTAGCCCT
ACCGCACCGCACCGCTTGTGTCCGATTCAGTCATGCCCGCGACCCCATCTTCGGCAACCAGATCATCCCCGTTTAAAC

JJJJJJJ) pBFB58 Sgf to Pme (SEQ ID NO:499)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAGGAGGTTCTGGCGGATCAGGCGGTTCGGGGATGTATGAGGAATTCCTTAGTAAAGTCTCTATTTT
AGAGTCTCTGGACAAGTGGGAACGTCTTACGGTAGCTGATGCATTGGAACCAGTGCAGTTTGAAGATGGGCAGAAGATTG
TGGTGCAGGGAGAACCAGGGGATGAGTTCTTCATTATTTTAGAGGGGTCAGCTGCTGTGCTACAACGTCGGTCAGAAAAT
GAAGAGTTTGTTGAAGTGGGAAGATTGGGGCCTTCTGATTATTTTGGTGAAATTGCACTACTGATGAATCGTCCTCGTGC
TGCCACAGTTGTTGCTCGTGGCCCCTTGAAGTGCGTTAAGCTGGACCGACCTAGATTTGAACGTGTTCTTGGCCCATGCT
CAGACATCCTCAAACGAAACATCCAGCAGTACAACAGTTTTGTGTCACTGTCTGTCGGGTCCGGTGGATCCGGTGGCAGC
GGAGGGACGTCAGGTGGATCTGGAGGGAGCTCCGGTGCCAAAAACATTAAGAAGGGCCCAGCGCCATTCTACCCACTCGA
AGACGGGACCGCCGGCGAGCAGCTGCACAAAGCCATGAAGCGCTACGCCCTGGTGCCCGGCACCATCGCCTTTACCGACG
CACATATCGAGGTGGACATTACCTACGCCGAGTACTTCGAGATGAGCGTTCGGCTGGCAGAAGCTATGAAGCGCTATGGG

*FIG. 67CB*

CTGAATACAAACCATCGGATCGTGGTGTGCAGCGAGAATAGCTTGCAGTTCTTCATGCCCGTGTTGGGTGCCCTGTTCAT
CGGTGTGGCTGTGGCCCCAGCTAACGACATCTACAACGAGCGCGAGCTGCTGAACAGCATGGGCATCAGCCAGCCCACCG
TCGTATTCGTGAGCAAGAAAGGGCTGCAAAAGATCCTCAACGTGCAAAAGAAGCTACCGATCATACAAAAGATCATCATC
ATGGATAGCAAGACCGACTACCAGGGCTTCCAAAGCATGTACACCTTCGTGACTTCCCATTTGCCACCCGGCTTCAACGA
GTACGACTTCGTGCCCGAGAGCTTCGACCGGGACAAAACCATCGCCCTGATCATGAACAGTAGTGGCAGTACCGGATTGC
CCAAGGGCGTAGCCCTACCGCACCGCACCGCTTGTGTCCGATTCAGTCATGCCCGCGACCCCATCTTCGGCAACCAGATC
ATCCCCGTTTAAAC

KKKKKKKK) pBFB8 Sgf to Pme (SEQ ID NO:500)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAGGAGGTTCTGGCGGATCAGGCGGTTCGCGAGGAGGTGGCACCGGTGGATCCGGTGGCAGCGGAGG
GACGTCAGGTGGATCTGGAGGGAGCTCCGGTGCCAAAAACATTAAGAAGGGCCCAGCGCCATTCTACCCACTCGAAGACG
GGACCGCCGGCGAGCAGCTGCACAAAGCCATGAAGCGCTACGCCCTGGTGCCCGGCACCATCGCCTTTACCGACGCACAT
ATCGAGGTGGACATTACCTACGCCGAGTACTTCGAGATGAGCGTTCGGCTGGCAGAAGCTATGAAGCGCTATGGGCTGAA
TACAAACCATCGGATCGTGGTGTGCAGCGAGAATAGCTTGCAGTTCTTCATGCCCGTGTTGGGTGCCCTGTTCATCGGTG
TGGCTGTGGCCCCAGCTAACGACATCTACAACGAGCGCGAGCTGCTGAACAGCATGGGCATCAGCCAGCCCACCGTCGTA
TTCGTGAGCAAGAAAGGGCTGCAAAAGATCCTCAACGTGCAAAAGAAGCTACCGATCATACAAAAGATCATCATCATGGA
TAGCAAGACCGACTACCAGGGCTTCCAAAGCATGTACACCTTCGTGACTTCCCATTTGCCACCCGGCTTCAACGAGTACG
ACTTCGTGCCCGAGAGCTTCGACCGGGACAAAACCATCGCCCTGATCATGAACAGTAGTGGCAGTACCGGATTGCCCAAG
GGCGTAGCCCTACCGCACCGCACCGCTTGTGTCCGATTCAGTCATGCCCGCGACCCCATCTTCGGCAACCAGATCATCCC
CGTTTAAAC

LLLLLLLL) pBFB89 Sgf to Pme (SEQ ID NO:501)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGATGTATGAAAGCTTT
ATTGAGTCACTGCCATTCCTTAAATCTTTGGAGTTTTCTGAACGCCTGAAAGTAGTAGATGTGATAGGCACCAAAGTATA
CAACGATGGAGAACAAATCATTGCTCAGGGAGATTCGGCTGATTCTTTTTTCATTGTAGAATCTGGAGAAGTGAAAATTA
CTATGAAAAGAAAGGGTAAATCAGAAGTGGAAGAGAATGGTGCAGTAGAAATCGCTCGATGCTCGCGGGGACAGTACTTT
GGAGAGCTTGCCCTGGTAACTAACAAACCTCGAGCAGCTTCTGCCCACGCCATTGGGACTGTCAAATGTTTAGCAATGGA
TGTGCAAGCATTTGAAAGGCTTCTGGGACCTTGCATGGAAATTATGAAAAGGAACATCGCTACCTATGAAGAACAGTTAG
TTGCCCTGTTTGGAACGAACATGGATATTGTAGCCAAAAACATTAAGAAGGGCCCAGCGCCATTCTACCCACTCGAAGAC
GGGACCGCCGGCGAGCAGCTGCACAAAGCCATGAAGCGCTACGCCCTGGTGCCCGGCACCATCGCCTTTACCGACGCACA
TATCGAGGTGGACATTACCTACGCCGAGTACTTCGAGATGAGCGTTCGGCTGGCAGAAGCTATGAAGCGCTATGGGCTGA
ATACAAACCATCGGATCGTGGTGTGCAGCGAGAATAGCTTGCAGTTCTTCATGCCCGTGTTGGGTGCCCTGTTCATCGGT
GTGGCTGTGGCCCCAGCTAACGACATCTACAACGAGCGCGAGCTGCTGAACAGCATGGGCATCAGCCAGCCCACCGTCGT
ATTCGTGAGCAAGAAAGGGCTGCAAAAGATCCTCAACGTGCAAAAGAAGCTACCGATCATACAAAAGATCATCATCATGG

FIG. 67CC

ATAGCAAGACCGACTACCAGGGCTTCCAAAGCATGTACACCTTCGTGACTTCCCATTTGCCACCCGGCTTCAACGAGTAC
GACTTCGTGCCCGAGAGCTTCGACCGGGACAAAACCATCGCCCTGATCATGAACAGTAGTGGCAGTACCGGATTGCCCAA
GGGCGTAGCCCTACCGCACCGCACCGCTTGTGTCCGATTCAGTCATGCCCGCGACCCCATCTTCGGCAACCAGATCATCC
CCGTTTAAAC

MMMMMMMM) pBFB9 Sgf to Pme (SEQ ID NO:502)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAATG
TATGAAAGCTTTATTGAGTCACTGCCATTCCTTAAATCTTTGGAGTTTTCTGAACGCCTGAAAGTAGTAGATGTGATAGG
CACCAAAGTATACAACGATGGAGAACAAATCATTGCTCAGGGAGATTCGGCTGATTCTTTTTTCATTGTAGAATCTGGAG
AAGTGAAAATTACTATGAAAAGAAAGGGTAAATCAGAAGTGGAAGAGAATGGTGCAGTAGAAATCGCTCGATGCTCGCGG
GGACAGTACTTTGGAGAGCTTGCCCTGGTAACTAACAAACCTCGAGCAGCTTCTGCCCACGCCATTGGGACTGTCAAATG
TTTAGCAATGGATGTGCAAGCATTTGAAAGGCTTCTGGGACCTTGCATGGAAATTATGAAAAGGAACATCGCTACCTATG
AAGAACAGTTAGTTGCCCTGTTTGGAACGAACATGGATATTGTTGGGAGCTCCGGTGCCAAAAACATTAAGAAGGGCCCA
GCGCCATTCTACCCACTCGAAGACGGGACCGCCGGCGAGCAGCTGCACAAAGCCATGAAGCGCTACGCCCTGGTGCCCGG
CACCATCGCCTTTACCGACGCACATATCGAGGTGGACATTACCTACGCCGAGTACTTCGAGATGAGCGTTCGGCTGGCAG
AAGCTATGAAGCGCTATGGGCTGAATACAAACCATCGGATCGTGGTGTGCAGCGAGAATAGCTTGCAGTTCTTCATGCCC
GTGTTGGGTGCCCTGTTCATCGGTGTGGCTGTGGCCCCAGCTAACGACATCTACAACGAGCGCGAGCTGCTGAACAGCAT
GGGCATCAGCCAGCCCACCGTCGTATTCGTGAGCAAGAAAGGGCTGCAAAAGATCCTCAACGTGCAAAAGAAGCTACCGA
TCATACAAAAGATCATCATCATGGATAGCAAGACCGACTACCAGGGCTTCCAAAGCATGTACACCTTCGTGACTTCCCAT
TTGCCACCCGGCTTCAACGAGTACGACTTCGTGCCCGAGAGCTTCGACCGGGACAAAACCATCGCCCTGATCATGAACAG
TAGTGGCAGTACCGGATTGCCCAAGGGCGTAGCCCTACCGCACCGCACCGCTTGTGTCCGATTCAGTCATGCCCGCGACC
CCATCTTCGGCAACCAGATCATCCCCGTTTAAAC

NNNNNNNN) pBFB90 Sgf to Pme (SEQ ID NO:503)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGATGTATGAAAGCTTT
ATTGAGTCACTGCCATTCCTTAAATCTTTGGAGTTTTCTGAACGCCTGAAAGTAGTAGATGTGATAGGCACCAAAGTATA
CAACGATGGAGAACAAATCATTGCTCAGGGAGATTCGGCTGATTCTTTTTTCATTGTAGAATCTGGAGAAGTGAAAATTA
CTATGAAAAGAAAGGGTAAATCAGAAGTGGAAGAGAATGGTGCAGTAGAAATCGCTCGATGCTCGCGGGGACAGTACTTT
GGAGAGCTTGCCCTGGTAACTAACAAACCTCGAGCAGCTTCTGCCCACGCCATTGGGACTGTCAAATGTTTAGCAATGGA
TGTGCAAGCATTTGAAAGGCTTCTGGGACCTTGCATGGAAATTATGAAAAGGAACATCGCTACCTATGAAGAACAGTTAG
TTGCCCTGTTTGGAACGAACATGGATATTGTATCCGGTGCCAAAAACATTAAGAAGGGCCCAGCGCCATTCTACCCACTC
GAAGACGGGACCGCCGGCGAGCAGCTGCACAAAGCCATGAAGCGCTACGCCCTGGTGCCCGGCACCATCGCCTTTACCGA
CGCACATATCGAGGTGGACATTACCTACGCCGAGTACTTCGAGATGAGCGTTCGGCTGGCAGAAGCTATGAAGCGCTATG
GGCTGAATACAAACCATCGGATCGTGGTGTGCAGCGAGAATAGCTTGCAGTTCTTCATGCCCGTGTTGGGTGCCCTGTTC
ATCGGTGTGGCTGTGGCCCCAGCTAACGACATCTACAACGAGCGCGAGCTGCTGAACAGCATGGGCATCAGCCAGCCCAC

FIG. 67CD

CGTCGTATTCGTGAGCAAGAAAGGGCTGCAAAAGATCCTCAACGTGCAAAAGAAGCTACCGATCATACAAAAGATCATCA
TCATGGATAGCAAGACCGACTACCAGGGCTTCCAAAGCATGTACACCTTCGTGACTTCCCATTTGCCACCCGGCTTCAAC
GAGTACGACTTCGTGCCCGAGAGCTTCGACCGGGACAAAACCATCGCCCTGATCATGAACAGTAGTGGCAGTACCGGATT
GCCCAAGGGCGTAGCCCTACCGCACCGCACCGCTTGTGTCCGATTCAGTCATGCCCGCGACCCCATCTTCGGCAACCAGA
TCATCCCCGTTTAAAC

OOOOOOOO) pBFB91 Sgf to Pme (SEQ ID NO:504)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGATGTATGAAAGCTTT
ATTGAGTCACTGCCATTCCTTAAATCTTTGGAGTTTTCTGAACGCCTGAAAGTAGTAGATGTGATAGGCACCAAAGTATA
CAACGATGGAGAACAAATCATTGCTCAGGGAGATTCGGCTGATTCTTTTTTCATTGTAGAATCTGGAGAAGTGAAAATTA
CTATGAAAAGAAAGGGTAAATCAGAAGTGGAAGAGAATGGTGCAGTAGAAATCGCTCGATGCTCGCGGGGACAGTACTTT
GGAGAGCTTGCCCTGGTAACTAACAAACCTCGAGCAGCTTCTGCCCACGCCATTGGGACTGTCAAATGTTTAGCAATGGA
TGTGCAAGCATTTGAAAGGCTTCTGGGACCTTGCATGGAAATTATGAAAAGGAACATCGCTACCTATGAAGAACAGTTAG
TTGCCCTGTTTGGAACGAACATGGATATTGTTGGGAGCTCCGGTGCCAAAAACATTAAGAAGGGCCCAGCGCCATTCTAC
CCACTCGAAGACGGGACCGCCGGCGAGCAGCTGCACAAAGCCATGAAGCGCTACGCCCTGGTGCCCGGCACCATCGCCTT
TACCGACGCACATATCGAGGTGGACATTACCTACGCCGAGTACTTCGAGATGAGCGTTCGGCTGGCAGAAGCTATGAAGC
GCTATGGGCTGAATACAAACCATCGGATCGTGGTGTGCAGCGAGAATAGCTTGCAGTTCTTCATGCCCGTGTTGGGTGCC
CTGTTCATCGGTGTGGCTGTGGCCCCAGCTAACGACATCTACAACGAGCGCGAGCTGCTGAACAGCATGGGCATCAGCCA
GCCCACCGTCGTATTCGTGAGCAAGAAAGGGCTGCAAAAGATCCTCAACGTGCAAAAGAAGCTACCGATCATACAAAAGA
TCATCATCATGGATAGCAAGACCGACTACCAGGGCTTCCAAAGCATGTACACCTTCGTGACTTCCCATTTGCCACCCGGC
TTCAACGAGTACGACTTCGTGCCCGAGAGCTTCGACCGGGACAAAACCATCGCCCTGATCATGAACAGTAGTGGCAGTAC
CGGATTGCCCAAGGGCGTAGCCCTACCGCACCGCACCGCTTGTGTCCGATTCAGTCATGCCCGCGACCCCATCTTCGGCA
ACCAGATCATCCCCGTTTAAAC

PPPPPPPP) pBFB92 Sgf to Pme (SEQ ID NO:505)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGATGTATGAAAGCTTT
ATTGAGTCACTGCCATTCCTTAAATCTTTGGAGTTTTCTGAACGCCTGAAAGTAGTAGATGTGATAGGCACCAAAGTATA
CAACGATGGAGAACAAATCATTGCTCAGGGAGATTCGGCTGATTCTTTTTTCATTGTAGAATCTGGAGAAGTGAAAATTA
CTATGAAAAGAAAGGGTAAATCAGAAGTGGAAGAGAATGGTGCAGTAGAAATCGCTCGATGCTCGCGGGGACAGTACTTT
GGAGAGCTTGCCCTGGTAACTAACAAACCTCGAGCAGCTTCTGCCCACGCCATTGGGACTGTCAAATGTTTAGCAATGGA
TGTGCAAGCATTTGAAAGGCTTCTGGGACCTTGCATGGAAATTATGAAAAGGAACATCGCTACCTATGAAGAACAGTTAG
TTGCCCTGTTTGGAACGAACATGGATATTGTATCTGGAGGGAGCTCCGGTGCCAAAAACATTAAGAAGGGCCCAGCGCCA
TTCTACCCACTCGAAGACGGGACCGCCGGCGAGCAGCTGCACAAAGCCATGAAGCGCTACGCCCTGGTGCCCGGCACCAT
CGCCTTTACCGACGCACATATCGAGGTGGACATTACCTACGCCGAGTACTTCGAGATGAGCGTTCGGCTGGCAGAAGCTA
TGAAGCGCTATGGGCTGAATACAAACCATCGGATCGTGGTGTGCAGCGAGAATAGCTTGCAGTTCTTCATGCCCGTGTTG

*FIG. 67CE*

GGTGCCCTGTTCATCGGTGTGGCTGTGGCCCCCAGCTAACGACATCTACAACGAGCGCGAGCTGCTGAACAGCATGGGCAT
CAGCCAGCCCACCGTCGTATTCGTGAGCAAGAAAGGGCTGCAAAAGATCCTCAACGTGCAAAAGAAGCTACCGATCATAC
AAAAGATCATCATCATGGATAGCAAGACCGACTACCAGGGCTTCCAAAGCATGTACACCTTCGTGACTTCCCATTTGCCA
CCCGGCTTCAACGAGTACGACTTCGTGCCCGAGAGCTTCGACCGGGACAAAACCATCGCCCTGATCATGAACAGTAGTGG
CAGTACCGGATTGCCCAAGGGCGTAGCCCTACCGCACCGCACCGCTTGTGTCCGATTCAGTCATGCCCGCGACCCCATCT
TCGGCAACCAGATCATCCCCGTTTAAAC

QQQQQQQQ) pBFB93 Sgf to Pme (SEQ ID NO:506)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGATGTATGAAAGCTTT
ATTGAGTCACTGCCATTCCTTAAATCTTTGGAGTTTTCTGAACGCCTGAAAGTAGTAGATGTGATAGGCACCAAAGTATA
CAACGATGGAGAACAAATCATTGCTCAGGGAGATTCGGCTGATTCTTTTTTCATTGTAGAATCTGGAGAAGTGAAAATTA
CTATGAAAAGAAAGGGTAAATCAGAAGTGGAAGAGAATGGTGCAGTAGAAATCGCTCGATGCTCGCGGGGACAGTACTTT
GGAGAGCTTGCCCTGGTAACTAACAAACCTCGAGCAGCTTCTGCCCACGCCATTGGGACTGTCAAATGTTTAGCAATGGA
TGTGCAAGCATTTGAAAGGCTTCTGGGACCTTGCATGGAAATTATGAAAAGGAACATCGCTACCTATGAAGAACAGTTAG
TTGCCCTGTTTGGAACGAACATGGATATTGTAGGTGGATCTGGAGGGAGCTCCGGTGCCAAAAACATTAAGAAGGGCCCA
GCGCCATTCTACCCACTCGAAGACGGGACCGCCGGCGAGCAGCTGCACAAAGCCATGAAGCGCTACGCCCTGGTGCCCGG
CACCATCGCCTTTACCGACGCACATATCGAGGTGGACATTACCTACGCCGAGTACTTCGAGATGAGCGTTCGGCTGGCAG
AAGCTATGAAGCGCTATGGGCTGAATACAAACCATCGGATCGTGGTGTGCAGCGAGAATAGCTTGCAGTTCTTCATGCCC
GTGTTGGGTGCCCTGTTCATCGGTGTGGCTGTGGCCCCAGCTAACGACATCTACAACGAGCGCGAGCTGCTGAACAGCAT
GGGCATCAGCCAGCCCACCGTCGTATTCGTGAGCAAGAAAGGGCTGCAAAAGATCCTCAACGTGCAAAAGAAGCTACCGA
TCATACAAAAGATCATCATCATGGATAGCAAGACCGACTACCAGGGCTTCCAAAGCATGTACACCTTCGTGACTTCCCAT
TTGCCACCCGGCTTCAACGAGTACGACTTCGTGCCCGAGAGCTTCGACCGGGACAAAACCATCGCCCTGATCATGAACAG
TAGTGGCAGTACCGGATTGCCCAAGGGCGTAGCCCTACCGCACCGCACCGCTTGTGTCCGATTCAGTCATGCCCGCGACC
CCATCTTCGGCAACCAGATCATCCCCGTTTAAAC

RRRRRRRR) pBFB94 Sgf to Pme (SEQ ID NO:507)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGATGTATGAAAGCTTT
ATTGAGTCACTGCCATTCCTTAAATCTTTGGAGTTTTCTGAACGCCTGAAAGTAGTAGATGTGATAGGCACCAAAGTATA
CAACGATGGAGAACAAATCATTGCTCAGGGAGATTCGGCTGATTCTTTTTTCATTGTAGAATCTGGAGAAGTGAAAATTA
CTATGAAAAGAAAGGGTAAATCAGAAGTGGAAGAGAATGGTGCAGTAGAAATCGCTCGATGCTCGCGGGGACAGTACTTT
GGAGAGCTTGCCCTGGTAACTAACAAACCTCGAGCAGCTTCTGCCCACGCCATTGGGACTGTCAAATGTTTAGCAATGGA
TGTGCAAGCATTTGAAAGGCTTCTGGGACCTTGCATGGAAATTATGAAAAGGAACATCGCTACCTATGAAGAACAGTTAG
TTGCCCTGTTTGGAACGAACATGGATATTGTAGGGTCAGGTGGATCTGGAGGGAGCTCCGGTGCCAAAAACATTAAGAAG
GGCCCAGCGCCATTCTACCCACTCGAAGACGGGACCGCCGGCGAGCAGCTGCACAAAGCCATGAAGCGCTACGCCCTGGT
GCCCGGCACCATCGCCTTTACCGACGCACATATCGAGGTGGACATTACCTACGCCGAGTACTTCGAGATGAGCGTTCGGC

FIG. 67CF

TGGCAGAAGCTATGAAGCGCTATGGGCTGAATACAAACCATCGGATCGTGGTGTGCAGCGAGAATAGCTTGCAGTTCTTC
ATGCCCGTGTTGGGTGCCCTGTTCATCGGTGTGGCTGTGGCCCCAGCTAACGACATCTACAACGAGCGCGAGCTGCTGAA
CAGCATGGGCATCAGCCAGCCCACCGTCGTATTCGTGAGCAAGAAAGGGCTGCAAAAGATCCTCAACGTGCAAAAGAAGC
TACCGATCATACAAAAGATCATCATCATGGATAGCAAGACCGACTACCAGGGCTTCCAAAGCATGTACACCTTCGTGACT
TCCCATTTGCCACCCGGCTTCAACGAGTACGACTTCGTGCCCGAGAGCTTCGACCGGGACAAAACCATCGCCCTGATCAT
GAACAGTAGTGGCAGTACCGGATTGCCCAAGGGCGTAGCCCTACCGCACCGCACCGCTTGTGTCCGATTCAGTCATGCCC
GCGACCCCATCTTCGGCAACCAGATCATCCCCGTTTAAAC

SSSSSSSS) pBFB95 Sgf to Pme (SEQ ID NO:508)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGATGTATGAA
AGCTTTATTGAGTCACTGCCATTCCTTAAATCTTTGGAGTTTTCTGAACGCCTGAAAGTAGTAGATGTGATAGGCACCAA
AGTATACAACGATGGAGAACAAATCATTGCTCAGGGAGATTCGGCTGATTCTTTTTTCATTGTAGAATCTGGAGAAGTGA
AAATTACTATGAAAAGAAAGGGTAAATCAGAAGTGGAAGAGAATGGTGCAGTAGAAATCGCTCGATGCTCGCGGGGACAG
TACTTTGGAGAGCTTGCCCTGGTAACTAACAAACCTCGAGCAGCTTCTGCCCACGCCATTGGGACTGTCAAATGTTTAGC
AATGGATGTGCAAGCATTTGAAAGGCTTCTGGGACCTTGCATGGAAATTATGAAAAGGAACATCGCTACCTATGAAGAAC
AGTTAGTTGCCCTGTTTGGAACGAACATGGATATTGTAGCCAAAAACATTAAGAAGGGCCCAGCGCCATTCTACCCACTC
GAAGACGGGACCGCCGGCGAGCAGCTGCACAAAGCCATGAAGCGCTACGCCCTGGTGCCCGGCACCATCGCCTTTACCGA
CGCACATATCGAGGTGGACATTACCTACGCCGAGTACTTCGAGATGAGCGTTCGGCTGGCAGAAGCTATGAAGCGCTATG
GGCTGAATACAAACCATCGGATCGTGGTGTGCAGCGAGAATAGCTTGCAGTTCTTCATGCCCGTGTTGGGTGCCCTGTTC
ATCGGTGTGGCTGTGGCCCCAGCTAACGACATCTACAACGAGCGCGAGCTGCTGAACAGCATGGGCATCAGCCAGCCCAC
CGTCGTATTCGTGAGCAAGAAAGGGCTGCAAAAGATCCTCAACGTGCAAAAGAAGCTACCGATCATACAAAAGATCATCA
TCATGGATAGCAAGACCGACTACCAGGGCTTCCAAAGCATGTACACCTTCGTGACTTCCCATTTGCCACCCGGCTTCAAC
GAGTACGACTTCGTGCCCGAGAGCTTCGACCGGGACAAAACCATCGCCCTGATCATGAACAGTAGTGGCAGTACCGGATT
GCCCAAGGGCGTAGCCCTACCGCACCGCACCGCTTGTGTCCGATTCAGTCATGCCCGCGACCCCATCTTCGGCAACCAGA
TCATCCCCGTTTAAAC

TTTTTTTT) pBFB96 Sgf to Pme (SEQ ID NO:509)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGATGTATGAA
AGCTTTATTGAGTCACTGCCATTCCTTAAATCTTTGGAGTTTTCTGAACGCCTGAAAGTAGTAGATGTGATAGGCACCAA
AGTATACAACGATGGAGAACAAATCATTGCTCAGGGAGATTCGGCTGATTCTTTTTTCATTGTAGAATCTGGAGAAGTGA
AAATTACTATGAAAAGAAAGGGTAAATCAGAAGTGGAAGAGAATGGTGCAGTAGAAATCGCTCGATGCTCGCGGGGACAG
TACTTTGGAGAGCTTGCCCTGGTAACTAACAAACCTCGAGCAGCTTCTGCCCACGCCATTGGGACTGTCAAATGTTTAGC
AATGGATGTGCAAGCATTTGAAAGGCTTCTGGGACCTTGCATGGAAATTATGAAAAGGAACATCGCTACCTATGAAGAAC
AGTTAGTTGCCCTGTTTGGAACGAACATGGATATTGTATCCGGTGCCAAAAACATTAAGAAGGGCCCAGCGCCATTCTAC
CCACTCGAAGACGGGACCGCCGGCGAGCAGCTGCACAAAGCCATGAAGCGCTACGCCCTGGTGCCCGGCACCATCGCCTT

FIG. 67CG

TACCGACGCACATATCGAGGTGGACATTACCTACGCCGAGTACTTCGAGATGAGCGTTCGGCTGGCAGAAGCTATGAAGC
GCTATGGGCTGAATACAAACCATCGGATCGTGGTGTGCAGCGAGAATAGCTTGCAGTTCTTCATGCCCGTGTTGGGTGCC
CTGTTCATCGGTGTGGCTGTGGCCCCAGCTAACGACATCTACAACGAGCGCGAGCTGCTGAACAGCATGGGCATCAGCCA
GCCCACCGTCGTATTCGTGAGCAAGAAAGGGCTGCAAAAGATCCTCAACGTGCAAAAGAAGCTACCGATCATACAAAAGA
TCATCATCATGGATAGCAAGACCGACTACCAGGGCTTCCAAAGCATGTACACCTTCGTGACTTCCCATTTGCCACCCGGC
TTCAACGAGTACGACTTCGTGCCCGAGAGCTTCGACCGGGACAAAACCATCGCCCTGATCATGAACAGTAGTGGCAGTAC
CGGATTGCCCAAGGGCGTAGCCCTACCGCACCGCACCGCTTGTGTCCGATTCAGTCATGCCCGCGACCCCATCTTCGGCA
ACCAGATCATCCCCGTTTAAAC

UUUUUUUU) pBFB97 Sgf to Pme (SEQ ID NO:510)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGATGTATGAA
AGCTTTATTGAGTCACTGCCATTCCTTAAATCTTTGGAGTTTTCTGAACGCCTGAAAGTAGTAGATGTGATAGGCACCAA
AGTATACAACGATGGAGAACAAATCATTGCTCAGGGAGATTCGGCTGATTCTTTTTTCATTGTAGAATCTGGAGAAGTGA
AAATTACTATGAAAAGAAAGGGTAAATCAGAAGTGGAAGAGAATGGTGCAGTAGAAATCGCTCGATGCTCGCGGGGACAG
TACTTTGGAGAGCTTGCCCTGGTAACTAACAAACCTCGAGCAGCTTCTGCCCACGCCATTGGGACTGTCAAATGTTTAGC
AATGGATGTGCAAGCATTTGAAAGGCTTCTGGGACCTTGCATGGAAATTATGAAAAGGAACATCGCTACCTATGAAGAAC
AGTTAGTTGCCCTGTTTGGAACGAACATGGATATTGTTGGGAGCTCCGGTGCCAAAAACATTAAGAAGGGCCCAGCGCCA
TTCTACCCACTCGAAGACGGGACCGCCGGCGAGCAGCTGCACAAAGCCATGAAGCGCTACGCCCTGGTGCCCGGCACCAT
CGCCTTTACCGACGCACATATCGAGGTGGACATTACCTACGCCGAGTACTTCGAGATGAGCGTTCGGCTGGCAGAAGCTA
TGAAGCGCTATGGGCTGAATACAAACCATCGGATCGTGGTGTGCAGCGAGAATAGCTTGCAGTTCTTCATGCCCGTGTTG
GGTGCCCTGTTCATCGGTGTGGCTGTGGCCCCAGCTAACGACATCTACAACGAGCGCGAGCTGCTGAACAGCATGGGCAT
CAGCCAGCCCACCGTCGTATTCGTGAGCAAGAAAGGGCTGCAAAAGATCCTCAACGTGCAAAAGAAGCTACCGATCATAC
AAAAGATCATCATCATGGATAGCAAGACCGACTACCAGGGCTTCCAAAGCATGTACACCTTCGTGACTTCCCATTTGCCA
CCCGGCTTCAACGAGTACGACTTCGTGCCCGAGAGCTTCGACCGGGACAAAACCATCGCCCTGATCATGAACAGTAGTGG
CAGTACCGGATTGCCCAAGGGCGTAGCCCTACCGCACCGCACCGCTTGTGTCCGATTCAGTCATGCCCGCGACCCCATCT
TCGGCAACCAGATCATCCCCGTTTAAAC

VVVVVVVV) pBFB98 Sgf to Pme (SEQ ID NO:511)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGATGTATGAA
AGCTTTATTGAGTCACTGCCATTCCTTAAATCTTTGGAGTTTTCTGAACGCCTGAAAGTAGTAGATGTGATAGGCACCAA
AGTATACAACGATGGAGAACAAATCATTGCTCAGGGAGATTCGGCTGATTCTTTTTTCATTGTAGAATCTGGAGAAGTGA
AAATTACTATGAAAAGAAAGGGTAAATCAGAAGTGGAAGAGAATGGTGCAGTAGAAATCGCTCGATGCTCGCGGGGACAG
TACTTTGGAGAGCTTGCCCTGGTAACTAACAAACCTCGAGCAGCTTCTGCCCACGCCATTGGGACTGTCAAATGTTTAGC
AATGGATGTGCAAGCATTTGAAAGGCTTCTGGGACCTTGCATGGAAATTATGAAAAGGAACATCGCTACCTATGAAGAAC
AGTTAGTTGCCCTGTTTGGAACGAACATGGATATTGTATCTGGAGGGAGCTCCGGTGCCAAAAACATTAAGAAGGGCCCA

*FIG. 67CH*

GCGCCATTCTACCCACTCGAAGACGGGACCGCCGGCGAGCAGCTGCACAAAGCCATGAAGCGCTACGCCCTGGTGCCCGG
CACCATCGCCTTTACCGACGCACATATCGAGGTGGACATTACCTACGCCGAGTACTTCGAGATGAGCGTTCGGCTGGCAG
AAGCTATGAAGCGCTATGGGCTGAATACAAACCATCGGATCGTGGTGTGCAGCGAGAATAGCTTGCAGTTCTTCATGCCC
GTGTTGGGTGCCCTGTTCATCGGTGTGGCTGTGGCCCCAGCTAACGACATCTACAACGAGCGCGAGCTGCTGAACAGCAT
GGGCATCAGCCAGCCCACCGTCGTATTCGTGAGCAAGAAAGGGCTGCAAAAGATCCTCAACGTGCAAAAGAAGCTACCGA
TCATACAAAAGATCATCATCATGGATAGCAAGACCGACTACCAGGGCTTCCAAAGCATGTACACCTTCGTGACTTCCCAT
TTGCCACCCGGCTTCAACGAGTACGACTTCGTGCCCGAGAGCTTCGACCGGGACAAAACCATCGCCCTGATCATGAACAG
TAGTGGCAGTACCGGATTGCCCAAGGGCGTAGCCCTACCGCACCGCACCGCTTGTGTCCGATTCAGTCATGCCCGCGACC
CCATCTTCGGCAACCAGATCATCCCCGTTTAAAC

WWWWWWWW) pBFB99 Sgf to Pme (SEQ ID NO:512)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGATGTATGAA
AGCTTTATTGAGTCACTGCCATTCCTTAAATCTTTGGAGTTTTCTGAACGCCTGAAAGTAGTAGATGTGATAGGCACCAA
AGTATACAACGATGGAGAACAAATCATTGCTCAGGGAGATTCGGCTGATTCTTTTTTCATTGTAGAATCTGGAGAAGTGA
AAATTACTATGAAAAGAAAGGGTAAATCAGAAGTGGAAGAGAATGGTGCAGTAGAAATCGCTCGATGCTCGCGGGGACAG
TACTTTGGAGAGCTTGCCCTGGTAACTAACAAACCTCGAGCAGCTTCTGCCCACGCCATTGGGACTGTCAAATGTTTAGC
AATGGATGTGCAAGCATTTGAAAGGCTTCTGGGACCTTGCATGGAAATTATGAAAAGGAACATCGCTACCTATGAAGAAC
AGTTAGTTGCCCTGTTTGGAACGAACATGGATATTGTAGGTGGATCTGGAGGGAGCTCCGGTGCCAAAAACATTAAGAAG
GGCCCAGCGCCATTCTACCCACTCGAAGACGGGACCGCCGGCGAGCAGCTGCACAAAGCCATGAAGCGCTACGCCCTGGT
GCCCGGCACCATCGCCTTTACCGACGCACATATCGAGGTGGACATTACCTACGCCGAGTACTTCGAGATGAGCGTTCGGC
TGGCAGAAGCTATGAAGCGCTATGGGCTGAATACAAACCATCGGATCGTGGTGTGCAGCGAGAATAGCTTGCAGTTCTTC
ATGCCCGTGTTGGGTGCCCTGTTCATCGGTGTGGCTGTGGCCCCAGCTAACGACATCTACAACGAGCGCGAGCTGCTGAA
CAGCATGGGCATCAGCCAGCCCACCGTCGTATTCGTGAGCAAGAAAGGGCTGCAAAAGATCCTCAACGTGCAAAAGAAGC
TACCGATCATACAAAAGATCATCATCATGGATAGCAAGACCGACTACCAGGGCTTCCAAAGCATGTACACCTTCGTGACT
TCCCATTTGCCACCCGGCTTCAACGAGTACGACTTCGTGCCCGAGAGCTTCGACCGGGACAAAACCATCGCCCTGATCAT
GAACAGTAGTGGCAGTACCGGATTGCCCAAGGGCGTAGCCCTACCGCACCGCACCGCTTGTGTCCGATTCAGTCATGCCC
GCGACCCCATCTTCGGCAACCAGATCATCCCCGTTTAAAC

XXXXXXXX) 201325_15_A1 Sgf to Pme (SEQ ID NO:513)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGAGCGGAGGTTCAGGCGGTTCCGGAGGAGGTTCTGGCGGATCA
GGCGGTTCGCGAGGAGGTGGCACCGGTGGATCCGGTGGCAGCGGAGGGACGTCAGGTGGATCTGGAGGGAGCTCAGGAGC
TTCCAAGGTGTACGACCCCGAGCAACGCAAACGCATGATCACTGGGCCTCAGTGGTGGGCTCGCTGCAAGCAAATGAACG
TGCTGGACTCCTTCATCAACTACTATGATTCCGAGAAGCACGCCGAGAACGCCGTGATTTTTCTGCATGGTAACGCTGCC
TCCAGCTACCTGTGGAGGCACGTCGTGCCTCACATCGAGCCCGTGGCTAGATGCATCATCCCTGATCTGATCGGAATGGG
TAAGTCCGGCAAGAGCGGGAATGGCTCAGTTTAAAC

YYYYYYYY) 201325_15_B6 Sgf to Pme (SEQ ID NO:514)

*FIG. 67CI*

GCGATCGCCATGCCTCTCGTTAAGGGAGGCAAGCCCGACGTCGTCCAGATTGTCCGCAACTACAACGCCTACCTTCGGGC
CAGCGACGATCTGCCTAAGATGTTCATCGAGTCCGACCCTGGGTTCTTTTCCAACGCTATTGTCGAGGGAGCTAAGAAGT
TCCCTAACACCGAGTTCGTGAAGGTGAAGGGCCTCCACTTCAGCCAGGAGGACGCTCCAGATGAAATGGGTAAGTACATC
AAGAGCTTCGTGGAGCGCGTGCTGAAGAACGAGCAGGGCTCGAGCGGAGGTTCAGGCGGTTCCGGAGGAGGTTCTGGCGG
ATCAGGCGGTTCGCGAGGAGGTGGCACCGGTGGATCCGGTGGCAGCGGAGGGACGTCAGGTGGATCTGGAGGGAGCTCAG
GAGCTTCCAAGGTGTACGACCCCGAGCAACGCAAACGCATGATCACTGGGCCTCAGTGGTGGGCTCGCTGCAAGCAAATG
AACGTGCTGGACTCCTTCATCAACTACTATGATTCCGAGAAGCACGCCGAGAACGCCGTGATTTTTCTGCATGGTAACGC
TGCCTCCAGCTACCTGTGGAGGCACGTCGTGCCTCACATCGAGCCCGTGGCTAGATGCATCATCCCTGATCTGATCGGAA
TGGGTAAGTCCGGCAAGAGCGGGAATGGCTCATATCGCCTCCTGGATCACTACAAGTACCTCACCGCTTGGTTCGAGCTG
CTGAACCTTCCAAAGAAAATCATCTTTGTGGGCCACGACTGGGGGGCTTGTCTGGCCTTTCACTACTCCTACGAGCACCA
AGACAAGATCAAGGCCATCGTCCATGCTGAGAGTGTCGTGGACGTGATCGAGTCCTGGGACGAGTGGCCTGACATCGAGG
AGGATATCGCCCTGATCAAGAGCGAAGAGGGCGAGAAAATGGTGCTTGAGAATAACTTCTTCGTCGAGACCATGCTCCCA
AGCAAGATCATGCGGAAACTGGAGCCTGAGGAGTTCGCTGCCTACCTGGAGCCATTCAAGGAGAAGGGCGAGGTTAGACG
GCCTACCCTCTCCTGGCCTCGCGAGATCGTTTAAAC

ZZZZZZZZ) 201325_165_A2 Sgf to Pme (SEQ ID NO:515)
GCGATCGCCATGGCTTCCAAGGTGTACGACCCCGAGCAACGCAAACGCATGATCACTGGGCCTCAGTGGTGGGCTCGCTG
CAAGCAAATGAACGTGCTGGACTCCTTCATCAACTACTATGATTCCGAGAAGCACGCCGAGAACGCCGTGATTTTTCTGC
ATGGTAACGCTGCCTCCAGCTACCTGTGGAGGCACGTCGTGCCTCACATCGAGCCCGTGGCTAGATGCATCATCCCTGAT
CTGATCGGAATGGGTAAGTCCGGCAAGAGCGGGAATGGCTCAGGCTCGAGCGGAGGTTCAGGCGGTTCCGGAGGAGGTTC
TGGCGGATCAGGCGGTTCGCGAGGAGGTGGCACCGGTGGATCCGGTGGCAGCGGAGGGACGTCAGGTGGATCTGGAGGGA
GCTCCGGTTATCGCCTCCTGGATCACTACAAGTACCTCACCGCTTGGTTCGAGCTGCTGAACCTTCCAAAGAAAATCATC
TTTGTGGGCCACGACTGGGGGGCTTGTCTGGCCTTTCACTACTCCTACGAGCACCAAGACAAGATCAAGGCCATCGTCCA
TGCTGAGAGTGTCGTGGACGTGATCGAGTCCTGGGACGAGTGGCCTGACATCGAGGAGGATATCGCCCTGATCAAGAGCG
AAGAGGGCGAGAAAATGGTGCTTGAGAATAACTTCTTCGTCGAGACCATGCTCCCAAGCAAGATCATGCGGAAACTGGAG
CCTGAGGAGTTCGCTGCCTACCTGGAGCCATTCAAGGAGAAGGGCGAGGTTAGACGGCCTACCCTCTCCTGGCCTCGCGA
GATCCCTCTCGTTAAGGGAGGCAAGCCCGACGTCGTCCAGATTGTCCGCAACTACAACGCCTACCTTCGGGCCAGCGACG
ATCTGCCTAAGATGTTCATCGAGTCCGACCCTGGGTTCTTTTCCAACGCTATTGTCGAGGGAGCTAAGAAGTTCCCTAAC
ACCGAGTTCGTGAAGGTGAAGGGCCTCCACTTCAGCCAGGAGGACGCTCCAGATGAAATGGGTAAGTACATCAAGAGCTT
CGTGGAGCGCGTGCTGAAGAACGAGCAGGTTTAAAC

AAAAAAAAA) 201325_165_C5 Sgf to Pme (SEQ ID NO:516)
GCGATCGCCATGGCTTCCAAGGTGTACGACCCCGAGCAACGCAAACGCATGATCACTGGGCCTCAGTGGTGGGCTCGCTG
CAAGCAAATGAACGTGCTGGACTCCTTCATCAACTACTATGATTCCGAGAAGCACGCCGAGAACGCCGTGATTTTTCTGC
ATGGTAACGCTGCCTCCAGCTACCTGTGGAGGCACGTCGTGCCTCACATCGAGCCCGTGGCTAGATGCATCATCCCTGAT
CTGATCGGAATGGGTAAGTCCGGCAAGAGCGGGAATGGCTCATATCGCCTCCTGGATCACTACAAGTACCTCACCGCTTG
GTTCGAGCTGCTGAACCTTCCAAAGAAAATCATCTTTGTGGGCCACGACTGGGGGGCTTGTCTGGCCTTTCACTACTCCT
ACGAGCACCAAGACAAGATCAAGGCCATCGTCCATGCTGAGAGTGTCGTGGACGTGATCGAGTCCTGGGACGAGTGGCCT
GACATCGAGGAGGATATCGCCCTGATCAAGAGCGAAGAGGGCGAGAAAATGGTGCTTGAGAATAACTTCTTCGTCGAGAC
CATGCTCCCAAGCAAGATCATGCGGAAACTGGAGCCTGAGGAGTTCGCTGCCTACCTGGAGCCATTCAAGGAGAAGGGCG
AGGTTAGACGGCCTACCCTCTCCTGGCCTCGCGAGATCCCTCTCGTTAAGGGAGGCGGCTCGAGCGGAGGTTCAGGCGGT
TCCGGAGGAGGTTCTGGCGGATCAGGCGGTTCGCGAGGAGGTGGCACCGGTGGATCCGGTGGCAGCGGAGGGACGTCAGG
TGGATCTGGAGGGAGCTCCGGTAAGCCCGACGTCGTCCAGATTGTCCGCAACTACAACGCCTACCTTCGGGCCAGCGACG
ATCTGCCTAAGATGTTCATCGAGTCCGACCCTGGGTTCTTTTCCAACGCTATTGTCGAGGGAGCTAAGAAGTTCCCTAAC
ACCGAGTTCGTGAAGGTGAAGGGCCTCCACTTCAGCCAGGAGGACGCTCCAGATGAAATGGGTAAGTACATCAAGAGCTT
CGTGGAGCGCGTGCTGAAGAACGAGCAGGTTTAAAC

BBBBBBBBB) 201325_177_B7 Sgf to Pme (SEQ ID NO:517)
GCGATCGCCATGGCTTCCAAGGTGTACGACCCCGAGCAACGCAAACGCATGATCACTGGGCCTCAGTGGTGGGCTCGCTG
CAAGCAAATGAACGTGCTGGACTCCTTCATCAACTACTATGATTCCGAGAAGCACGCCGAGAACGCCGTGATTTTTCTGC
ATGGTAACGCTGCCTCCAGCTACCTGTGGAGGCACGTCGTGCCTCACATCGAGCCCGTGGCTAGATGCATCATCCCTGAT
CTGATCGGAATGGGTAAGTCCGGCAAGAGCGGGAATGGCTCATATCGCCTCCTGGATCACTACAAGTACCTCACCGCTTG
GTTCGAGCTGCTGAACCTTCCAAAGAAAATCATCTTTGTGGGCCACGACTGGGGGGCTTGTCTGGCCTTTCACTACTCCT
ACGAGCACCAAGACAAGATCAAGGCCATCGTCCATGCTGAGAGTGTCGTGGACGTGATCGAGTCCTGGGACGAGTGGCCT
GACATCGAGGAGGATATCGCCCTGATCAAGAGCGAAGAGGGCGAGAAAATGGTGCTTGAGAATAACTTCTTCGTCGAGAC
CATGCTCCCAAGCAAGATCATGCGGAAACTGGAGCCTGAGGAGTTCGCTGCCTACCTGGAGCCATTCAAGGAGAAGGGCG
AGGTTAGACGGCCTACCCTCTCCTGGCCTCGCGAGATCGGCTCGAGCGGAGGTTCAGGCGGTTCCGGAGGAGGTTCTGGC

FIG. 67CJ

GGATCAGGCGGTTCGCGAGGAGGTGGCACCGGTGGATCCGGTGGCAGCGGAGGGACGTCAGGTGGATCTGGAGGGAGCTC
CGGTCCTCTCGTTAAGGGAGGCAAGCCCGACGTCGTCCAGATTGTCCGCAACTACAACGCCTACCTTCGGGCCAGCGACG
ATCTGCCTAAGATGTTCATCGAGTCCGACCCTGGGTTCTTTTCCAACGCTATTGTCGAGGGAGCTAAGAAGTTCCCTAAC
ACCGAGTTCGTGAAGGTGAAGGGCCTCCACTTCAGCCAGGAGGACGCTCCAGATGAAATGGGTAAGTACATCAAGAGCTT
CGTGGAGCGCGTGCTGAAGAACGAGCAGGTTTAAAC

CCCCCCCCC) 201325_33_C9 Sgf to Pme (SEQ ID NO:518)
GCGATCGCCATGGCTTCCAAGGTGTACGACCCCGAGCAACGCAAACGCATGATCACTGGGCCTCAGTGGTGGGCTCGCTG
CAAGCAAATGAACGTGCTGGACTCCTTCATCAACTACTATGATTCCGAGAAGCACGCCGAGAACGCCGTGATTTTTCTGC
ATGGTAACGCTGCCTCCAGCTACCTGTGGAGGCACGTCGTGCCTCACATCGAGCCCGTGGCTAGATGCATCATCCCTGAT
CTGATCGGAATGGGTAAGTCCGGCAAGAGCGGGAATGGCTCATATCGCCTCCTGGATCACTACAAGTACCTCACCGCTTG
GTTCGAGCTGCTGAACCTTCCAAAGAAAATCATCTTTGTGGGCCACGACTGGGGGGCTTGTCTGGCCTTTCACTACTCCT
ACGAGCACCAAGACAAGATCAAGGCCATCGTCCATGCTGAGAGTGTCGTGGACGTGATCGAGTCCTGGGACGAGTGGCCT
GACATCGAGGAGGATATCGCCCTGATCAAGAGCGAAGAGGGCGAGAAAATGGTGCTTGAGAATAACTTCTTCGTCGAGAC
CATGCTCCCAAGCAAGATCATGCGGAAACTGGAGCCTGAGGAGTTCGCTGCCTACCTGGAGCCATTCAAGGAGAAGGGCG
AGGTTAGACGGCCTACCCTCTCCTGGCCTCGCGAGATCGGCTCGACCGGAATGTATGAAAGCTTTATTGAGTCACTGCCA
TTCCTTAAATCTTTGGAGTTTTCTGAACGCCTGAAAGTAGTAGATGTGATAGGCACCAAAGTATACAACGATGGAGAACA
AATCATTGCTCAGGGAGATTCGGCTGATTCTTTTTTCATTGTAGAATCTGGAGAAGTGAAAATTACTATGAAAAGAAAGG
GTAAATCAGAAGTGGAAGAGAATGGTGCAGTAGAAATCGCTCGATGCTCGCGGGGACAGTACTTTGGAGAGCTTGCCCTG
GTAACTAACAAACCTCGAGCAGCTTCTGCCCACGCCATTGGGACTGTCAAATGTTTAGCAATGGATGTGCAAGCATTTGA
AAGGCTTCTGGGACCTTGCATGGAAATTATGAAAAGGAACATCGCTACCTATGAAGAACAGTTAGTTGCCCTGTTTGGAA
CGAACATGGATATTGTTGGGTCCGGTGGATCCGGTGGCAGCGGAGGGACGTCAGGTGGATCTGGAGGGAGCTCCGGTCCT
CTCGTTAAGGGAGGCAAGCCCGACGTCGTCCAGATTGTCCGCAACTACAACGCCTACCTTCGGGCCAGCGACGATCTGCC
TAAGATGTTCATCGAGTCCGACCCTGGGTTCTTTTCCAACGCTATTGTCGAGGGAGCTAAGAAGTTCCCTAACACCGAGT
TCGTGAAGGTGAAGGGCCTCCACTTCAGCCAGGAGGACGCTCCAGATGAAATGGGTAAGTACATCAAGAGCTTCGTGGAG
CGCGTGCTGAAGAACGAGCAGGTTTAAAC

DDDDDDDDD) 201325_44_H6 Sgf to Pme (SEQ ID NO:519)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGACCGGAATGTATGAAAGCTTTATTGAGTCACTGCCATTCCTT
AAATCTTTGGAGTTTTCTGAACGCCTGAAAGTAGTAGATGTGATAGGCACCAAAGTATACAACGATGGAGAACAAATCAT
TGCTCAGGGAGATTCGGCTGATTCTTTTTTCATTGTAGAATCTGGAGAAGTGAAAATTACTATGAAAAGAAAGGGTAAAT
CAGAAGTGGAAGAGAATGGTGCAGTAGAAATCGCTCGATGCTCGCGGGGACAGTACTTTGGAGAGCTTGCCCTGGTAACT
AACAAACCTCGAGCAGCTTCTGCCCACGCCATTGGGACTGTCAAATGTTTAGCAATGGATGTGCAAGCATTTGAAAGGCT
TCTGGGACCTTGCATGGAAATTATGAAAAGGAACATCGCTACCTATGAAGAACAGTTAGTTGCCCTGTTTGGAACGAACA
TGGATATTGTTGGGTCCGGTGGATCCGGTGGCAGCGGAGGGACGTCAGGTGGATCTGGAGGGAGCTCAGGAGCTTCCAAG
GTGTACGACCCCGAGCAACGCAAACGCATGATCACTGGGCCTCAGTGGTGGGCTCGCTGCAAGCAAATGAACGTGCTGGA
CTCCTTCATCAACTACTATGATTCCGAGAAGCACGCCGAGAACGCCGTGATTTTTCTGCATGGTAACGCTGCCTCCAGCT
ACCTGTGGAGGCACGTCGTGCCTCACATCGAGCCCGTGGCTAGATGCATCATCCCTGATCTGATCGGAATGGGTAAGTCC
GGCAAGAGCGGGAATGGCTCAGTTTAAAC

EEEEEEEEE) 201325_50_A7 Sgf to Pme (SEQ ID NO:520)
GCGATCGCCATGGCTTCCAAGGTGTACGACCCCGAGCAACGCAAACGCATGATCACTGGGCCTCAGTGGTGGGCTCGCTG
CAAGCAAATGAACGTGCTGGACTCCTTCATCAACTACTATGATTCCGAGAAGCACGCCGAGAACGCCGTGATTTTTCTGC
ATGGTAACGCTGCCTCCAGCTACCTGTGGAGGCACGTCGTGCCTCACATCGAGCCCGTGGCTAGATGCATCATCCCTGAT
CTGATCGGAATGGGTAAGTCCGGCAAGAGCGGGAATGGCTCATATCGCCTCCTGGATCACTACAAGTACCTCACCGCTTG
GTTCGAGCTGCTGAACCTTCCAAAGAAAATCATCTTTGTGGGCCACGACTGGGGGGCTTGTCTGGCCTTTCACTACTCCT
ACGAGCACCAAGACAAGATCAAGGCCATCGTCCATGCTGAGAGTGTCGTGGACGTGATCGAGTCCTGGGACGAGTGGCCT
GACATCGAGGAGGATATCGCCCTGATCAAGAGCGAAGAGGGCGAGAAAATGGTGCTTGAGAATAACTTCTTCGTCGAGAC
CATGCTCCCAAGCAAGATCATGCGGAAACTGGAGCCTGAGGAGTTCGCTGCCTACCTGGAGCCATTCAAGGAGAAGGGCG

*FIG. 67CK*

AGGTTAGACGGCCTACCCTCTCCTGGCCTCGCGAGATCCCTCTCGTTAAGGGAGGCAAGCCCGACGTCGTCCAGATTGTC
CGCAACTACAACGCCTACCTTCGGGCCAGCGACGATCTGCCTAAGATGTTCATCGAGTCCGACCCTGGGTTCTTTTCCAA
CGCTATTGTCGAGGGAGCTAAGAAGTTCCCTAACACCGAGTTCGTGAAGGTGAAGGGCCTCCACTTCAGCCAGGAGGACG
CTCCAGATGAAATGGGTAAGTACATCAAGAGCTTCGTGGAGCGCGTGCTGAAGAACGAGCAGGTTTAAAC

FFFFFFFFF) 201325_50_D12 Sgf to Pme (SEQ ID NO:521)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GCGAGATCCCTCTCGTTAAGGGAGGCAAGCCCGACGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGAGCGGAGGTTCAGGCGGTTCCGGAATGTATGAAAGCTTTATT
GAGTCACTGCCATTCCTTAAATCTTTGGAGTTTTCTGAACGCCTGAAAGTAGTAGATGTGATAGGCACCAAAGTATACAA
CGATGGAGAACAAATCATTGCTCAGGGAGATTCGGCTGATTCTTTTTTCATTGTAGAATCTGGAGAAGTGAAAATTACTA
TGAAAAGAAAGGGTAAATCAGAAGTGGAAGAGAATGGTGCAGTAGAAATCGCTCGATGCTCGCGGGGACAGTACTTTGGA
GAGCTTGCCCTGGTAACTAACAAACCTCGAGCAGCTTCTGCCCACGCCATTGGGACTGTCAAATGTTTAGCAATGGATGT
GCAAGCATTTGAAAGGCTTCTGGGACCTTGCATGGAAATTATGAAAAGGAACATCGCTACCTATGAAGAACAGTTAGTTG
CCCTGTTTGGAACGAACATGGATATTGTTGGGAGCTCAGGAGCTTCCAAGGTGTACGACCCCGAGCAACGCAAACGCATG
ATCACTGGGCCTCAGTGGTGGGCTCGCTGCAAGCAAATGAACGTGCTGGACTCCTTCATCAACTACTATGATTCCGAGAA
GCACGCCGAGAACGCCGTGATTTTTCTGCATGGTAACGCTGCCTCCAGCTACCTGTGGAGGCACGTCGTGCCTCACATCG
AGCCCGTGGCTAGATGCATCATCCCTGATCTGATCGGAATGGGTAAGTCCGGCAAGAGCGGGAATGGCTCAGTTTAAAC

GGGGGGGGG) 201325_54_E12 Sgf to Pme (SEQ ID NO:522)
GCGATCGCCATGCCTCTCGTTAAGGGAGGCAAGCCCGACGTCGTCCAGATTGTCCGCAACTACAACGCCTACCTTCGGGC
CAGCGACGATCTGCCTAAGATGTTCATCGAGTCCGACCCTGGGTTCTTTTCCAACGCTATTGTCGAGGGAGCTAAGAAGT
TCCCTAACACCGAGTTCGTGAAGGTGAAGGGCCTCCACTTCAGCCAGGAGGACGCTCCAGATGAAATGGGTAAGTACATC
AAGAGCTTCGTGGAGCGCGTGCTGAAGAACGAGCAGGGCTCGAGCGGAGGTTCAGGCGGTTCCGGAATGTATGAAAGCTT
TATTGAGTCACTGCCATTCCTTAAATCTTTGGAGTTTTCTGAACGCCTGAAAGTAGTAGATGTGATAGGCACCAAAGTAT
ACAACGATGGAGAACAAATCATTGCTCAGGGAGATTCGGCTGATTCTTTTTTCATTGTAGAATCTGGAGAAGTGAAAATT
ACTATGAAAAGAAAGGGTAAATCAGAAGTGGAAGAGAATGGTGCAGTAGAAATCGCTCGATGCTCGCGGGGACAGTACTT
TGGAGAGCTTGCCCTGGTAACTAACAAACCTCGAGCAGCTTCTGCCCACGCCATTGGGACTGTCAAATGTTTAGCAATGG
ATGTGCAAGCATTTGAAAGGCTTCTGGGACCTTGCATGGAAATTATGAAAAGGAACATCGCTACCTATGAAGAACAGTTA
GTTGCCCTGTTTGGAACGAACATGGATATTGTTGGGTCCGGTGGATCCGGTGGCAGCGGAGGGACGTCAGGTGGATCTGG
AGGGAGCTCAGGAGCTTCCAAGGTGTACGACCCCGAGCAACGCAAACGCATGATCACTGGGCCTCAGTGGTGGGCTCGCT
GCAAGCAAATGAACGTGCTGGACTCCTTCATCAACTACTATGATTCCGAGAAGCACGCCGAGAACGCCGTGATTTTTCTG
CATGGTAACGCTGCCTCCAGCTACCTGTGGAGGCACGTCGTGCCTCACATCGAGCCCGTGGCTAGATGCATCATCCCTGA
TCTGATCGGAATGGGTAAGTCCGGCAAGAGCGGGAATGGCTCATATCGCCTCCTGGATCACTACAAGTACCTCACCGCTT
GGTTCGAGCTGCTGAACCTTCCAAAGAAAATCATCTTTGTGGGCCACGACTGGGGGGCTTGTCTGGCCTTTCACTACTCC
TACGAGCACCAAGACAAGATCAAGGCCATCGTCCATGCTGAGAGTGTCGTGGACGTGATCGAGTCCTGGGACGAGTGGCC
TGACATCGAGGAGGATATCGCCCTGATCAAGAGCGAAGAGGGCGAGAAAATGGTGCTTGAGAATAACTTCTTCGTCGAGA
CCATGCTCCCAAGCAAGATCATGCGGAAACTGGAGCCTGAGGAGTTCGCTGCCTACCTGGAGCCATTCAAGGAGAAGGGC
GAGGTTAGACGGCCTACCCTCTCCTGGCCTCGCGAGATCGTTTAAAC

HHHHHHHHH) 201325_54_E2 Sgf to Pme (SEQ ID NO:523)
GCGATCGCCATGCCTCTCGTTAAGGGAGGCAAGCCCGACGTCGTCCAGATTGTCCGCAACTACAACGCCTACCTTCGGGC
CAGCGACGATCTGCCTAAGATGTTCATCGAGTCCGACCCTGGGTTCTTTTCCAACGCTATTGTCGAGGGAGCTAAGAAGT
TCCCTAACACCGAGTTCGTGAAGGTGAAGGGCCTCCACTTCAGCCAGGAGGACGCTCCAGATGAAATGGGTAAGTACATC
AAGAGCTTCGTGGAGCGCGTGCTGAAGAACGAGCAGGGCTCGAGCGGAGGTTCAGGCGGTTCCGGAATGTATGAAAGCTT
TATTGAGTCACTGCCATTCCTTAAATCTTTGGAGTTTTCTGAACGCCTGAAAGTAGTAGATGTGATAGGCACCAAAGTAT
ACAACGATGGAGAACAAATCATTGCTCAGGGAGATTCGGCTGATTCTTTTTTCATTGTAGAATCTGGAGAAGTGAAAATT
ACTATGAAAAGAAAGGGTAAATCAGAAGTGGAAGAGAATGGTGCAGTAGAAATCGCTCGATGCTCGCGGGGACAGTACTT
TGGAGAGCTTGCCCTGGTAACTAACAAACCTCGAGCAGCTTCTGCCCACGCCATTGGGACTGTCAAATGTTTAGCAATGG
ATGTGCAAGCATTTGAAAGGCTTCTGGGACCTTGCATGGAAATTATGAAAAGGAACATCGCTACCTATGAAGAACAGTTA
GTTGCCCTGTTTGGAACGAACATGGATATTGTTGGGAGCTCAGGAGCTTCCAAGGTGTACGACCCCGAGCAACGCAAACG

FIG. 67CL

CATGATCACTGGGCCTCAGTGGTGGGCTCGCTGCAAGCAAATGAACGTGCTGGACTCCTTCATCAACTACTATGATTCCG
AGAAGCACGCCGAGAACGCCGTGATTTTTCTGCATGGTAACGCTGCCTCCAGCTACCTGTGGAGGCACGTCGTGCCTCAC
ATCGAGCCCGTGGCTAGATGCATCATCCCTGATCTGATCGGAATGGGTAAGTCCGGCAAGAGCGGGAATGGCTCATATCG
CCTCCTGGATCACTACAAGTACCTCACCGCTTGGTTCGAGCTGCTGAACCTTCCAAAGAAAATCATCTTTGTGGGCCACG
ACTGGGGGGCTTGTCTGGCCTTTCACTACTCCTACGAGCACCAAGACAAGATCAAGGCCATCGTCCATGCTGAGAGTGTC
GTGGACGTGATCGAGTCCTGGGACGAGTGGCCTGACATCGAGGAGGATATCGCCCTGATCAAGAGCGAAGAGGGCGAGAA
AATGGTGCTTGAGAATAACTTCTTCGTCGAGACCATGCTCCCAAGCAAGATCATGCGGAAACTGGAGCCTGAGGAGTTCG
CTGCCTACCTGGAGCCATTCAAGGAGAAGGGCGAGGTTAGACGGCCTACCCTCTCCTGGCCTCGCGAGATCGTTTAAAC

IIIIIIIII) 201325_58_E11 Sgf to Pme (SEQ ID NO:524)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GCGAGATCCCTCTCGTTAAGGGAGGCAAGCCCGACGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGAGCGGAGGTTCAGGCGGTTCCGGAATGTATGAAAGCTTTATT
GAGTCACTGCCATTCCTTAAATCTTTGGAGTTTTCTGAACGCCTGAAAGTAGTAGATGTGATAGGCACCAAAGTATACAA
CGATGGAGAACAAATCATTGCTCAGGGAGATTCGGCTGATTCTTTTTTCATTGTAGAATCTGGAGAAGTGAAAATTACTA
TGAAAAGAAAGGGTAAATCAGAAGTGGAAGAGAATGGTGCAGTAGAAATCGCTCGATGCTCGCGGGGACAGTACTTTGGA
GAGCTTGCCCTGGTAACTAACAAACCTCGAGCAGCTTCTGCCCACGCCATTGGGACTGTCAAATGTTTAGCAATGGATGT
GCAAGCATTTGAAAGGCTTCTGGGACCTTGCATGGAAATTATGAAAAGGAACATCGCTACCTATGAAGAACAGTTAGTTG
CCCTGTTTGGAACGAACATGGATATTGTTGGGTCCGGTGGATCCGGTGGCAGCGGAGGGACGTCAGGTGGATCTGGAGGG
AGCTCAGGAGCTTCCAAGGTGTACGACCCCGAGCAACGCAAACGCATGATCACTGGGCCTCAGTGGTGGGCTCGCTGCAA
GCAAATGAACGTGCTGGACTCCTTCATCAACTACTATGATTCCGAGAAGCACGCCGAGAACGCCGTGATTTTTCTGCATG
GTAACGCTGCCTCCAGCTACCTGTGGAGGCACGTCGTGCCTCACATCGAGCCCGTGGCTAGATGCATCATCCCTGATCTG
ATCGGAATGGGTAAGTCCGGCAAGAGCGGGAATGGCTCAGTTTAAAC

JJJJJJJJJ) 201325_78_E5 Sgf to Pme (SEQ ID NO:525)
GCGATCGCCATGTATCGCCTCCTGGATCACTACAAGTACCTCACCGCTTGGTTCGAGCTGCTGAACCTTCCAAAGAAAAT
CATCTTTGTGGGCCACGACTGGGGGGCTTGTCTGGCCTTTCACTACTCCTACGAGCACCAAGACAAGATCAAGGCCATCG
TCCATGCTGAGAGTGTCGTGGACGTGATCGAGTCCTGGGACGAGTGGCCTGACATCGAGGAGGATATCGCCCTGATCAAG
AGCGAAGAGGGCGAGAAAATGGTGCTTGAGAATAACTTCTTCGTCGAGACCATGCTCCCAAGCAAGATCATGCGGAAACT
GGAGCCTGAGGAGTTCGCTGCCTACCTGGAGCCATTCAAGGAGAAGGGCGAGGTTAGACGGCCTACCCTCTCCTGGCCTC
GTGAGATCCCTCTCGTTAAGGGAGGCAAGCCCGATGTCGTCCAGATTGTCCGCAACTACAACGCCTACCTTCGGGCCAGC
GACGATCTGCCTAAGATGTTCATCGAGTCCGACCCTGGGTTCTTTTCCAACGCTATTGTCGAGGGAGCTAAGAAGTTCCC
TAACACCGAGTTCGTGAAGGTGAAGGGCCTCCACTTCAGCCAGGAGGACGCTCCAGATGAAATGGGTAAGTACATCAAGA
GCTTCGTGGAGCGCGTGCTGAAGAACGAGCAGGGCTCGACCGGAATGTATGAAAGCTTTATTGAGTCACTGCCATTCCTT
AAATCTTTGGAGTTTTCTGAACGCCTGAAAGTAGTAGATGTGATAGGCACCAAAGTATACAACGATGGAGAACAAATCAT
TGCTCAGGGAGATTCGGCTGATTCTTTTTTCATTGTAGAATCTGGAGAAGTGAAAATTACTATGAAAAGAAAGGGTAAAT
CAGAAGTGGAAGAGAATGGTGCAGTAGAAATCGCTCGATGCTCGCGGGGACAGTACTTTGGAGAGCTTGCCCTGGTAACT
AACAAACCTCGAGCAGCTTCTGCCCACGCCATTGGGACTGTCAAATGTTTAGCAATGGATGTGCAAGCATTTGAAAGGCT
TCTGGGACCTTGCATGGAAATTATGAAAAGGAACATCGCTACCTATGAAGAACAGTTAGTTGCCCTGTTTGGAACGAACA
TGGATATTGTTGGGTCCGGTGGATCCGGTGGCAGCGGAGGGACGTCAGGTGGATCTGGAGGGAGCTCAGGAGCTTCCAAG
GTGTACGACCCCGAGCAACGCAAACGCATGATCACTGGGCCTCAGTGGTGGGCTCGCTGCAAGCAAATGAACGTGCTGGA
CTCCTTCATCAACTACTATGATTCCGAGAAGCACGCCGAGAACGCCGTGATTTTTCTGCATGGTAACGCTGCCTCCAGCT
ACCTGTGGAGGCACGTCGTGCCTCACATCGAGCCCGTGGCTAGATGCATCATCCCTGATCTGATCGGAATGGGTAAGTCC
GGCAAGAGCGGGAATGGCTCAGTTTAAAC

KKKKKKKKK) 201325_86_B1 Sgf to Pme (SEQ ID NO:526)
GCGATCGCCATGGCTTCCAAGGTGTACGACCCCGAGCAACGCAAACGCATGATCACTGGGCCTCAGTGGTGGGCTCGCTG
CAAGCAAATGAACGTGCTGGACTCCTTCATCAACTACTATGATTCCGAGAAGCACGCCGAGAACGCCGTGATTTTTCTGC
ATGGTAACGCTGCCTCCAGCTACCTGTGGAGGCACGTCGTGCCTCACATCGAGCCCGTGGCTAGATGCATCATCCCTGAT
CTGATCGGAATGGGTAAGTCCGGCAAGAGCGGGAATGGCTCATATCGCCTCCTGGATCACTACAAGTACCTCACCGCTTG
GTTCGAGCTGCTGAACCTTCCAAAGAAAATCATCTTTGTGGGCCACGACTGGGGGGCTTGTCTGGCCTTTCACTACTCCT

FIG. 67CM

ACGAGCACCAAGACAAGATCAAGGCCATCGTCCATGCTGAGAGTGTCGTGGACGTGATCGAGTCCTGGGACGAGTGGCCT
GACATCGAGGAGGATATCGCCCTGATCAAGAGCGAAGAGGGCGAGAAAATGGTGCTTGAGAATAACTTCTTCGTCGAGAC
CATGCTCCCAAGCAAGATCATGCGGAAACTGGAGCCTGAGGAGTTCGCTGCCTACCTGGAGCCATTCAAGGAGAAGGGCG
AGGTTAGACGGCCTACCCTCTCCTGGCCTCGCGAGATCCCTCTCGTTAAGGGAGGCGGCTCGACCGGAATGTATGAAAGC
TTTATTGAGTCACTGCCATTCCTTAAATCTTTGGAGTTTTCTGAACGCCTGAAAGTAGTAGATGTGATAGGCACCAAAGT
ATACAACGATGGAGAACAAATCATTGCTCAGGGAGATTCGGCTGATTCTTTTTTCATTGTAGAATCTGGAGAAGTGAAAA
TTACTATGAAAAGAAAGGGTAAATCAGAAGTGGAAGAGAATGGTGCAGTAGAAATCGCTCGATGCTCGCGGGGACAGTAC
TTTGGAGAGCTTGCCCTGGTAACTAACAAACCTCGAGCAGCTTCTGCCCACGCCATTGGGACTGTCAAATGTTTAGCAAT
GGATGTGCAAGCATTTGAAAGGCTTCTGGGACCTTGCATGGAAATTATGAAAAGGAACATCGCTACCTATGAAGAACAGT
TAGTTGCCCTGTTTGGAACGAACATGGATATTGTTGGGTCCGGTGGATCCGGTGGCAGCGGAGGGACGTCAGGTGGATCT
GGAGGGAGCTCCGGTAAGCCCGACGTCGTCCAGATTGTCCGCAACTACAACGCCTACCTTCGGGCCAGCGACGATCTGCC
TAAGATGTTCATCGAGTCCGACCCTGGGTTCTTTTCCAACGCTATTGTCGAGGGAGCTAAGAAGTTCCCTAACACCGAGT
TCGTGAAGGTGAAGGGCCTCCACTTCAGCCAGGAGGACGCTCCAGATGAAATGGGTAAGTACATCAAGAGCTTCGTGGAG
CGCGTGCTGAAGAACGAGCAGGTTTAAAC

LLLLLLLLL) 201360_17_A3 Sgf to Pme (SEQ ID NO:527)
GCGATCGCCATGGCTTCCAAGGTGTACGACCCCGAGCAACGCAAACGCATGATCACTGGGCCTCAGTGGTGGGCTCGCTG
CAAGCAAATGAACGTGCTGGACTCCTTCATCAACTACTATGATTCCGAGAAGCACGCCGAGAACGCCGTGATTTTTCTGC
ATGGTAACGCTGCCTCCAGCTACCTGTGGAGGCACGTCGTGCCTCACATCGAGCCCGTGGCTAGATGCATCATCCCTGAT
CTGATCGGAATGGGTAAGTCCGGCAAGAGCGGGAATGGCTCAGGCTCGACCGGAATGTATGAAAGCTTTATTGAGTCACT
GCCATTCCTTAAATCTTTGGAGTTTTCTGAACGCCTGAAAGTAGTAGATGTGATAGGCACCAAAGTATACAACGATGGAG
AACAAATCATTGCTCAGGGAGATTCGGCTGATTCTTTTTTCATTGTAGAATCTGGAGAAGTGAAAATTACTATGAAAAGA
AAGGGTAAATCAGAAGTGGAAGAGAATGGTGCAGTAGAAATCGCTCGATGCTCGCGGGGACAGTACTTTGGAGAGCTTGC
CCTGGTAACTAACAAACCTCGAGCAGCTTCTGCCCACGCCATTGGGACTGTCAAATGTTTAGCAATGGATGTGCAAGCAT
TTGAAAGGCTTCTGGGACCTTGCATGGAAATTATGAAAAGGAACATCGCTACCTATGAAGAACAGTTAGTTGCCCTGTTT
GGAACGAACATGGATATTGTTGGGAGCTCCGGTTATCGCCTCCTGGATCACTACAAGTACCTCACCGCTTGGTTCGAGCT
GCTGAACCTTCCAAAGAAAATCATCTTTGTGGGCCACGACTGGGGGGCTTGTCTGGCCTTTCACTACTCCTACGAGCACC
AAGACAAGATCAAGGCCATCGTCCATGCTGAGAGTGTCGTGGACGTGATCGAGTCCTGGGACGAGTGGCCTGACATCGAG
GAGGATATCGCCCTGATCAAGAGCGAAGAGGGCGAGAAAATGGTGCTTGAGAATAACTTCTTCGTCGAGACCATGCTCCC
AAGCAAGATCATGCGGAAACTGGAGCCTGAGGAGTTCGCTGCCTACCTGGAGCCATTCAAGGAGAAGGGCGAGGTTAGAC
GGCCTACCCTCTCCTGGCCTCGCGAGATCCCTCTCGTTAAGGGAGGCAAGCCCGACGTCGTCCAGATTGTCCGCAACTAC
AACGCCTACCTTCGGGCCAGCGACGATCTGCCTAAGATGTTCATCGAGTCCGACCCTGGGTTCTTTTCCAACGCTATTGT
CGAGGGAGCTAAGAAGTTCCCTAACACCGAGTTCGTGAAGGTGAAGGGCCTCCACTTCAGCCAGGAGGACGCTCCAGATG
AAATGGGTAAGTACATCAAGAGCTTCGTGGAGCGCGTGCTGAAGAACGAGCAGGTTTAAAC

MMMMMMMMM) 201360_17_D7 Sgf to Pme (SEQ ID NO:528)
GCGATCGCCATGGCTTCCAAGGTGTACGACCCCGAGCAACGCAAACGCATGATCACTGGGCCTCAGTGGTGGGCTCGCTG
CAAGCAAATGAACGTGCTGGACTCCTTCATCAACTACTATGATTCCGAGAAGCACGCCGAGAACGCCGTGATTTTTCTGC
ATGGTAACGCTGCCTCCAGCTACCTGTGGAGGCACGTCGTGCCTCACATCGAGCCCGTGGCTAGATGCATCATCCCTGAT
CTGATCGGAATGGGTAAGTCCGGCAAGAGCGGGAATGGCTCAGGCTCGAGCGGAGGTTCAGGCGGTTCCGGAATGTATGA
AAGCTTTATTGAGTCACTGCCATTCCTTAAATCTTTGGAGTTTTCTGAACGCCTGAAAGTAGTAGATGTGATAGGCACCA
AAGTATACAACGATGGAGAACAAATCATTGCTCAGGGAGATTCGGCTGATTCTTTTTTCATTGTAGAATCTGGAGAAGTG
AAAATTACTATGAAAAGAAAGGGTAAATCAGAAGTGGAAGAGAATGGTGCAGTAGAAATCGCTCGATGCTCGCGGGGACA
GTACTTTGGAGAGCTTGCCCTGGTAACTAACAAACCTCGAGCAGCTTCTGCCCACGCCATTGGGACTGTCAAATGTTTAG
CAATGGATGTGCAAGCATTTGAAAGGCTTCTGGGACCTTGCATGGAAATTATGAAAAGGAACATCGCTACCTATGAAGAA
CAGTTAGTTGCCCTGTTTGGAACGAACATGGATATTGTTGGGAGCTCCGGTTATCGCCTCCTGGATCACTACAAGTACCT
CACCGCTTGGTTCGAGCTGCTGAACCTTCCAAAGAAAATCATCTTTGTGGGCCACGACTGGGGGGCTTGTCTGGCCTTTC
ACTACTCCTACGAGCACCAAGACAAGATCAAGGCCATCGTCCATGCTGAGAGTGTCGTGGACGTGATCGAGTCCTGGGAC
GAGTGGCCTGACATCGAGGAGGATATCGCCCTGATCAAGAGCGAAGAGGGCGAGAAAATGGTGCTTGAGAATAACTTCTT
CGTCGAGACCATGCTCCCAAGCAAGATCATGCGGAAACTGGAGCCTGAGGAGTTCGCTGCCTACCTGGAGCCATTCAAGG
AGAAGGGCGAGGTTAGACGGCCTACCCTCTCCTGGCCTCGCGAGATCCCTCTCGTTAAGGGAGGCAAGCCCGACGTCGTC
CAGATTGTCCGCAACTACAACGCCTACCTTCGGGCCAGCGACGATCTGCCTAAGATGTTCATCGAGTCCGACCCTGGGTT
CTTTTCCAACGCTATTGTCGAGGGAGCTAAGAAGTTCCCTAACACCGAGTTCGTGAAGGTGAAGGGCCTCCACTTCAGCC
AGGAGGACGCTCCAGATGAAATGGGTAAGTACATCAAGAGCTTCGTGGAGCGCGTGCTGAAGAACGAGCAGGTTTAAAC

NNNNNNNNN) 201360_19_E9 Sgf to Pme (SEQ ID NO:529)

FIG. 67CN

GCGATCGCCATGGCTTCCAAGGTGTACGACCCCGAGCAACGCAAACGCATGATCACTGGGCCTCAGTGGTGGGCTCGCTG
CAAGCAAATGAACGTGCTGGACTCCTTCATCAACTACTATGATTCCGAGAAGCACGCCGAGAACGCCGTGATTTTTCTGC
ATGGTAACGCTGCCTCCAGCTACCTGTGGAGGCACGTCGTGCCTCACATCGAGCCCGTGGCTAGATGCATCATCCCTGAT
CTGATCGGAATGGGTAAGTCCGGCAAGAGCGGGAATGGCTCATATCGCCTCCTGGATCACTACAAGTACCTCACCGCTTG
GTTCGAGCTGCTGAACCTTCCAAAGAAAATCATCTTTGTGGGCCACGACTGGGGGGCTTGTCTGGCCTTTCACTACTCCT
ACGAGCACCAAGACAAGATCAAGGCCATCGTCCATGCTGAGAGTGTCGTGGACGTGATCGAGTCCTGGGACGAGTGGCCT
GACATCGAGGAGGATATCGCCCTGATCAAGAGCGAAGAGGGCGAGAAAATGGTGCTTGAGAATAACTTCTTCGTCGAGAC
CATGCTCCCAAGCAAGATCATGCGGAAACTGGAGCCTGAGGAGTTCGCTGCCTACCTGGAGCCATTCAAGGAGAAGGGCG
AGGTTAGACGGCCTACCCTCTCCTGGCCTCGCGAGATCCCTCTCGTTAAGGGAGGCGGCTCGACCGGAATGTATGAAAGC
TTTATTGAGTCACTGCCATTCCTTAAATCTTTGGAGTTTTCTGAACGCCTGAAAGTAGTAGATGTGATAGGCACCAAAGT
ATACAACGATGGAGAACAAATCATTGCTCAGGGAGATTCGGCTGATTCTTTTTTCATTGTAGAATCTGGAGAAGTGAAAA
TTACTATGAAAAGAAAGGGTAAATCAGAAGTGGAAGAGAATGGTGCAGTAGAAATCGCTCGATGCTCGCGGGGACAGTAC
TTTGGAGAGCTTGCCCTGGTAACTAACAAACCTCGAGCAGCTTCTGCCCACGCCATTGGGACTGTCAAATGTTTAGCAAT
GGATGTGCAAGCATTTGAAAGGCTTCTGGGACCTTGCATGGAAATTATGAAAAGGAACATCGCTACCTATGAAGAACAGT
TAGTTGCCCTGTTTGGAACGAACATGGATATTGTTGGGAGCTCCGGTAAGCCCGACGTCGTCCAGATTGTCCGCAACTAC
AACGCCTACCTTCGGGCCAGCGACGATCTGCCTAAGATGTTCATCGAGTCCGACCCTGGGTTCTTTTCCAACGCTATTGT
CGAGGGAGCTAAGAAGTTCCCTAACACCGAGTTCGTGAAGGTGAAGGGCCTCCACTTCAGCCAGGAGGACGCTCCAGATG
AAATGGGTAAGTACATCAAGAGCTTCGTGGAGCGCGTGCTGAAGAACGAGCAGGTTTAAAC

OOOOOOOOO) 201360_24_A1 Sgf to Pme (SEQ ID NO:530)
GCGATCGCCATGGCTTCCAAGGTGTACGACCCCGAGCAACAAACGCATGATCACTGGGCCTCAGTGGTGGGCTCGCTGCA
AGCAAATGAACGTGCTGGACTCCTTCATCAACTACTATGATTCCGAGAAGCACGCCGAGAACGCCGTGATTTTTCTGCAT
GGTAACGCTGCCTCCAGCTACCTGTGGAGGCACGTCGTGCCTCACATCGAGCCCGTGGCTAGATGCATCATCCCTGATCT
GATCGGAATGGGTAAGTCCGGCAAGAGCGGGAATGGCTCATATCGCCTCCTGGATCACTACAAGTACCTCACCGCTTGGT
TCGAGCTGCTGAACCTTCCAAAGAAAATCATCTTTGTGGGCCACGACTGGGGGGCTTGTCTGGCCTTTCACTACTCCTAC
GAGCACCAAGACAAGATCAAGGCCATCGTCCATGCTGAGAGTGTCGTGGACGTGATCGAGTCCTGGGACGAGTGGCCTGA
CATCGAGGAGGATATCGCCCTGATCAAGAGCGAAGAGGGCGAGAAAATGGTGCTTGAGAATAACTTCTTCGTCGAGACCA
TGCTCCCAAGCAAGATCATGCGGAAACTGGAGCCTGAGGAGTTCGCTGCCTACCTGGAGCCATTCAAGGAGAAGGGCGAG
GTTAGACGGCCTACCCTCTCCTGGCCTCGCGAGATCGGCTCGACCGGAATGTATGAAAGCTTTATTGAGTCACTGCCATT
CCTTAAATCTTTGGAGTTTTCTGAACGCCTGAAAGTAGTAGATGTGATAGGCACCAAAGTATACAACGATGGAGAACAAA
TCATTGCTCAGGGAGATTCGGCTGATTCTTTTTTCATTGTAGAATCTGGAGAAGTGAAAATTACTATGAAAAGAAAGGGT
AAATCAGAAGTGGAAGAGAATGGTGCAGTAGAAATCGCTCGATGCTCGCGGGGACAGTACTTTGGAGAGCTTGCCCTGGT
AACTAACAAACCTCGAGCAGCTTCTGCCCACGCCATTGGGACTGTCAAATGTTTAGCAATGGATGTGCAAGCATTTGAAA
GGCTTCTGGGACCTTGCATGGAAATTATGAAAAGGAACATCGCTACCTATGAAGAACAGTTAGTTGCCCTGTTTGGAACG
AACATGGATATTGTTGGGAGCTCCGGTCCTCTCGTTAAGGGAGGCAAGCCCGACGTCGTCCAGATTGTCCGCAACTACAA
CGCCTACCTTCGGGCCAGCGACGATCTGCCTAAGATGTTCATCGAGTCCGACCCTGGGTTCTTTTCCAACGCTATTGTCG
AGGGAGCTAAGAAGTTCCCTAACACCGAGTTCGTGAAGGTGAAGGGCCTCCACTTCAGCCAGGAGGACGCTCCAGATGAA
ATGGGTAAGTACATCAAGAGCTTCGTGGAGCGCGTGCTGAAGAACGAGCAGGTTTAAAC

PPPPPPPPP) 201360_24_A10 Sgf to Pme (SEQ ID NO:531)
GCGATCGCCATGGCTTCCAAGGTGTACGACCCCGAGCAACGCAAACGCATGATCACTGGGCCTCAGTGGTGGGCTCGCTG
CAAGCAAATGAACGTGCTGGACTCCTTCATCAACTACTATGATTCCGAGAAGCACGCCGAGAACGCCGTGATTTTTCTGC
ATGGTAACGCTGCCTCCAGCTACCTGTGGAGGCACGTCGTGCCTCACATCGAGCCCGTGGCTAGATGCATCATCCCTGAT
CTGATCGGAATGGGTAAGTCCGGCAAGAGCGGGAATGGCTCATATCGCCTCCTGGATCACTACAAGTACCTCACCGCTTG
GTTCGAGCTGCTGAACCTTCCAAAGAAAATCATCTTTGTGGGCCACGACTGGGGGGCTTGTCTGGCCTTTCACTACTCCT
ACGAGCACCAAGACAAGATCAAGGCCATCGTCCATGCTGAGAGTGTCGTGGACGTGATCGAGTCCTGGGACGAGTGGCCT
GACATCGAGGAGGATATCGCCCTGATCAAGAGCGAAGAGGGCGAGAAAATGGTGCTTGAGAATAACTTCTTCGTCGAGAC
CATGCTCCCAAGCAAGATCATGCGGAAACTGGAGCCTGAGGAGTTCGCTGCCTACCTGGAGCCATTCAAGGAGAAGGGCG
AGGTTAGACGGCCTACCCTCTCCTGGCCTCGCGAGATCGGCTCGACCGGAATGTATGAAAGCTTTATTGAGTCACTGCCA
TTCCTTAAATCTTTGGAGTTTTCTGAACGCCTGAAAGTAGTAGATGTGATAGGCACCAAAGTATACAACGATGGAGAACA
AATCATTGCTCAGGGAGATTCGGCTGATTCTTTTTTCATTGTAGAATCTGGAGAAGTGAAAATTACTATGAAAAGAAAGG
GTAAATCAGAAGTGGAAGAGAATGGTGCAGTAGAAATCGCTCGATGCTCGCGGGGACAGTACTTTGGAGAGCTTGCCCTG
GTAACTAACAAACCTCGAGCAGCTTCTGCCCACGCCATTGGGACTGTCAAATGTTTAGCAATGGATGTGCAAGCATTTGA
AAGGCTTCTGGGACCTTGCATGGAAATTATGAAAAGGAACATCGCTACCTATGAAGAACAGTTAGTTGCCCTGTTTGGAA
CGAACATGGATATTGTTGGGTCCGGTGGATCCGGTGGCAGCGGAGGGACGTCAGGTGGATCTGGAGGGAGCTCCGGTCCT
CTCGTTAAGGGAGGCAAGCCCGACGTCGTCCAGATTGTCCGCAACTACAACGCCTACCTTCGGGCCAGCGACGATCTGCC
TAAGATGTTCATCGAGTCCGACCCTGGGTTCTTTTCCAACGCTATTGTCGAGGGAGCTAAGAAGTTCCCTAACACCGAGT

FIG. 67CO

TCGTGAAGGTGAAGGGCCTCCACTTCAGCCAGGAGGACGCTCCAGATGAAATGGGTAAGTACATCAAGAGCTTCGTGGAG
CGCGTGCTGAAGAACGAGCAGGTTTAAAC

QQQQQQQQ) 201360_24_C5 Sgf to Pme (SEQ ID NO:532)
GCGATCGCCATGGCTTCCAAGGTGTACGACCCCGAGCAACGCAAACGCATGATCACTGGGCCTCAGTGGTGGGCTCGCTG
CAAGCAAATGAACGTGCTGGACTCCTTCATCAACTACTATGATTCCGAGAAGCACGCCGAGAACGCCGTGATTTTTCTGC
ATGGTAACGCTGCCTCCAGCTACCTGTGGAGGCACGTCGTGCCTCACATCGAGCCCGTGGCTAGATGCATCATCCCTGAT
CTGATCGGAATGGGTAAGTCCGGCAAGAGCGGGAATGGCTCATATCGCCTCCTGGATCACTACAAGTACCTCACCGCTTG
GTTCGAGCTGCTGAACCTTCCAAAGAAAATCATCTTTGTGGGCCACGACTGGGGGGCTTGTCTGGCCTTTCACTACTCCT
ACGAGCACCAAGACAAGATCAAGGCCATCGTCCATGCTGAGAGTGTCGTGGACGTGATCGAGTCCTGGGACGAGTGGCCT
GACATCGAGGAGGATATCGCCCTGATCAAGAGCGAAGAGGGCGAGAAAATGGTGCTTGAGAATAACTTCTTCGTCGAGAC
CATGCTCCCAAGCAAGATCATGCGGAAACTGGAGCCTGAGGAGTTCGCTGCCTACCTGGAGCCATTCAAGGAGAAGGGCG
AGGTTAGACGGCCTACCCTCTCCTGGCCTCGCGAGATCGGCTCGAGCGGAGGTTCAGGCGGTTCCGGAATGTATGAAAGC
TTTATTGAGTCACTGCCATTCCTTAAATCTTTGGAGTTTTCTGAACGCCTGAAAGTAGTAGATGTGATAGGCACCAAAGT
ATACAACGATGGAGAACAAATCATTGCTCAGGGAGATTCGGCTGATTCTTTTTTCATTGTAGAATCTGGAGAAGTGAAAA
TTACTATGAAAAGAAAGGGTAAATCAGAAGTGGAAGAGAATGGTGCAGTAGAAATCGCTCGATGCTCGCGGGGACAGTAC
TTTGGAGAGCTTGCCCTGGTAACTAACAAACCTCGAGCAGCTTCTGCCCACGCCATTGGGACTGTCAAATGTTTAGCAAT
GGATGTGCAAGCATTTGAAAGGCTTCTGGGACCTTGCATGGAAATTATGAAAAGGAACATCGCTACCTATGAAGAACAGT
TAGTTGCCCTGTTTGGAACGAACATGGATATTGTTGGGAGCTCCGGTCCTCTCGTTAAGGGAGGCAAGCCCGACGTCGTC
CAGATTGTCCGCAACTACAACGCCTACCTTCGGGCCAGCGACGATCTGCCTAAGATGTTCATCGAGTCCGACCCTGGGTT
CTTTTCCAACGCTATTGTCGAGGGAGCTAAGAAGTTCCCTAACACCGAGTTCGTGAAGGTGAAGGGCCTCCACTTCAGCC
AGGAGGACGCTCCAGATGAAATGGGTAAGTACATCAAGAGCTTCGTGGAGCGCGTGCTGAAGAACGAGCAGGTTTAAAC

RRRRRRRR) 201360_24_E11 Sgf to Pme (SEQ ID NO:533)
GCGATCGCCATGGCTTCCAAGGTGTACGACCCCGAGCAACGCAAACGCATGATCACTGGGCCTCAGTGGTGGGCTCGCTG
CAAGCAAATGAACGTGCTGGACTCCTTCATCAACTACTATGATTCCGAGAAGCACGCCGAGAACGCCGTGATTTTTCTGC
ATGGTAACGCTGCCTCCAGCTACCTGTGGAGGCACGTCGTGCCTCACATCGAGCCCGTGGCTAGATGCATCATCCCTGAT
CTGATCGGAATGGGTAAGTCCGGCAAGAGCGGGAATGGCTCATATCGCCTCCTGGATCACTACAAGTACCTCACCGCTTG
GTTCGAGCTGCTGAACCTTCCAAAGAAAATCATCTTTGTGGGCCACGACTGGGGGGCTTGTCTGGCCTTTCACTACTCCT
ACGAGCACCAAGACAAGATCAAGGCCATCGTCCATGCTGAGAGTGTCGTGGACGTGATCGAGTCCTGGGACGAGTGGCCT
GACATCGAGGAGGATATCGCCCTGATCAAGAGCGAAGAGGGCGAGAAAATGGTGCTTGAGAATAACTTCTTCGTCGAGAC
CATGCTCCCAAGCAAGATCATGCGGAAACTGGAGCCTGAGGAGTTCGCTGCCTACCTGGAGCCATTCAAGGAGAAGGGCG
AGGTTAGACGGCCTACCCTCTCCTGGCCTCGCGAGATCGGCTCGAGCGGAGGTTCAGGCGGTTCCGGAATGTATGAAAGC
TTTATTGAGTCACTGCCATTCCTTAAATCTTTGGAGTTTTCTGAACGCCTGAAAGTAGTAGATGTGATAGGCACCAAAGT
ATACAACGATGGAGAACAAATCATTGCTCAGGGAGATTCGGCTGATTCTTTTTTCATTGTAGAATCTGGAGAAGTGAAAA
TTACTATGAAAAGAAAGGGTAAATCAGAAGTGGAAGAGAATGGTGCAGTAGAAATCGCTCGATGCTCGCGGGGACAGTAC
TTTGGAGAGCTTGCCCTGGTAACTAACAAACCTCGAGCAGCTTCTGCCCACGCCATTGGGACTGTCAAATGTTTAGCAAT
GGATGTGCAAGCATTTGAAAGGCTTCTGGGACCTTGCATGGAAATTATGAAAAGGAACATCGCTACCTATGAAGAACAGT
TAGTTGCCCTGTTTGGAACGAACATGGATATTGTTGGGTCCGGTGGATCCGGTGGCAGCGGAGGGACGTCAGGTGGATCT
GGAGGGAGCTCCGGTCCTCTCGTTAAGGGAGGCAAGCCCGACGTCGTCCAGATTGTCCGCAACTACAACGCCTACCTTCG
GGCCAGCGACGATCTGCCTAAGATGTTCATCGAGTCCGACCCTGGGTTCTTTTCCAACGCTATTGTCGAGGGAGCTAAGA
AGTTCCCTAACACCGAGTTCGTGAAGGTGAAGGGCCTCCACTTCAGCCAGGAGGACGCTCCAGATGAAATGGGTAAGTAC
ATCAAGAGCTTCGTGGAGCGCGTGCTGAAGAACGAGCAGGTTTAAAC

SSSSSSSSS) 201360_65_A1 Sgf to Pme (SEQ ID NO:534)
GCGATCGCCATGGCTTCCAAGGTGTACGACCCCGAGCAACGCAAACGCATGATCACTGGGCCTCAGTGGTGGGCTCGCTG
CAAGCAAATGAACGTGCTGGACTCCTTCATCAACTACTATGATTCCGAGAAGCACGCCGAGAACGCCGTGATTTTTCTGC
ATGGTAACGCTGCCTCCAGCTACCTGTGGAGGCACGTCGTGCCTCACATCGAGCCCGTGGCTAGATGCATCATCCCTGAT
CTGATCGGAATGGGTAAGTCCGGCAAGAGCGGGAATGGCTCATATCGCCTCCTGGATCACTACAAGTACCTCACCGCTTG
GTTCGAGCTGCTGAACCTTCCAAAGAAAATCATCTTTGTGGGCCACGACTGGGGGGCTTGTCTGGCCTTTCACTACTCCT
ACGAGCACCAAGACAAGATCAAGGCCATCGTCCATGCTGAGAGTGTCGTGGACGTGATCGAGTCCTGGGACGAGTGGCCT
GACATCGAGGAGGATATCGCCCTGATCAAGAGCGAAGAGGGCGAGAAAATGGTGCTTGAGAATAACTTCTTCGTCGAGAC
CATGCTCCCAAGCAAGATCATGCGGAAACTGGAGCCTGAGGAGTTCGCTGCCTACCTGGAGCCATTCAAGGAGAAGGGCG
AGGTTAGACGGCCTACCCTCTCCTGGCCTCGCGAGATCCCTCTCGTTAAGGGAGGCGGCTCGACCGGAATGTATGAAAGC
TTTATTGAGTCACTGCCATTCCTTAAATCTTTGGAGTTTTCTGAACGCCTGAAAGTAGTAGATGTGATAGGCACCAAAGT
ATACAACGATGGAGAACAAATCATTGCTCAGGGAGATTCGGCTGATTCTTTTTTCATTGTAGAATCTGGAGAAGTGAAAA
TTACTATGAAAAGAAAGGGTAAATCAGAAGTGGAAGAGAATGGTGCAGTAGAAATCGCTCGATGCTCGCGGGGACAGTAC

*FIG. 67CP*

TTTGGAGAGCTTGCCCTGGTAACTAACAAACCTCGAGCAGCTTCTGCCCACGCCATTGGGACTGTCAAATGTTTAGCAAT
GGATGTGCAAGCATTTGAAAGGCTTCTGGGACCTTGCATGGAAATTATGAAAAGGAACATCGCTACCTATGAAGAACAGT
TAGTTGCCCTGTTTGGAACGAACATGGATATTGTTGGGTCCGGTGGATCCGGTGGCAGCGGAGGGACGTCAGGTGGATCT
GGAGGGAGCTCCGGTAAGCCCGACGTCGTCCAGATTGTCCGCAACTACAACGCCTACCTTCGGGCCAGCGACGATCTGCC
TAAGATGTTCATCGAGTCCGACCCTGGGTTCTTTTCCAACGCTATTGTCGAGGGAGCTAAGAAGTTCCCTAACACCGAGT
TCGTGAAGGTGAAGGGCCTCCACTTCAGCCAGGAGGACGCTCCAGATGAAATGGGTAAGTACATCAAGAGCTTCGTGGAG
CGCGTGCTGAAGAACGAGCAGGTTTAAAC

TTTTTTTTT) 201518_104_04 Sgf to Pme (SEQ ID NO:535)
GCGATCGCCATGTTTACGTTGGCAGATTTCGTTGGAGACTGGCAACAGACAGCTGGATACAACCAAGATCAAGTGTTAGA
ACAAGGAGGATTGTCTAGTCTGTTCCAAGCCCTGGGAGTGTCAGTCACCCCAATCCAGAAAGTTGTGCTGTCTGGGGAGA
ATGGGTTAAAAGCTGATATTCATGTCATCATCCCTTACGAGGGACTCAGTGGTTTTCAAATGGGTCTGATTGAAATGATC
TTCAAAGTTGTTTACCCCGTGGATGGCGGGAGCTCTGGTGGAGGGTCTGGGGGTGTGGCCATCCTCTGGCATGAGATGTG
GCATGAAGGCCTGGAAGAGGCATCTCGTTTGTACTTTGGGGAAAGGAACGTGAAAGGCATGTTTGAGGTGCTGGAGCCCT
TGCATGCTATGATGGAACGGGGCCCCCAGACTCTGAAGGAAACATCCTTTAATCAGGCCTATGGTCGAGATTTAATGGAG
GCCCAAGAGTGGTGCAGGAAGTACATGAAATCAGGGAATGTCAAGGACCTCACCCAAGCCTGGGACCTCTATTATCATGT
GTTCCGACGAATCTCATGAGTTTAAAC

UUUUUUUUU) 201518_110_4_1 Sgf to Pme (SEQ ID NO:536)
GCGATCGCCATGTTTACGTTGGCAGATTTCGTTGGAGACTGGCAACAGACAGCTGGATACAACCAAGATCAAGTGTTAGA
ACAAGGAGGATTGTCTAGTCTGTTCCAAGCCCTGGGAGTGTCAGTCACCCCAATCCAGAAAGTTGTACTGTCTGGGGAGA
ATGGCGGGAGCTCTGGTGGAGGGTCTGGGGGTGTGGCCATCCTCTGGCATGAGATGTGGCATGAAGGCCTGGAAGAGGCA
TCTCGTTTGTACTTTGGGGAAAGGAACGTGAAAGGCATGTTTGAGGTGCTGGAGCCCTTGCATGCTATGATGGAACGGGG
CCCCCAGACTCTGAAGGAAACATCCTTTAATCAGGCCTATGGTCGAGATTTAATGGAGGCCCAAGAGTGGTGCAGGAAGT
ACATGAAATCAGGGAATGTCAAGGACCTCACCCAAGCCTGGGACCTCTATTATCATGTGTTCCGACGAATCTCATGAGTT
TAAAC

VVVVVVVVV) 201518_129_03 Sgf to Pme (SEQ ID NO:537)
GCGATCGCCATGGGGTTAAAAGCTGATATTCATGTCATCATCCCTTACGAGGGACTCAGTGGTTTTCAAATGGGTCTGAT
TGAAATGATCTTCAAAGTTGTTTACCCAGTGGATGATCATCATTTCAAGATTATTCTCCATTATGGTACACTCGTTATTG
ACGGTGTGACACCAAACATGATTGACTACTTTGGACGCCCTTACCCTGGAATTGCTGTGTTTGACGGCAAGCAGATCACA
GTTACTGGAACTCTGTGGAACGGCAACAAGATCTATGATGAGCGCCTGATCAACCCAGATGGTTCACTCCTCTTCCGCGT
TACTATCAATGGAGTCACCGGATGGCGCCTTTGCGAGAACATTCTTGCCGGAGGGAGCTCTGGTGGAGGGTCTGGGGGTG
GAGTGCAGGTGGAAACCATCTCCCCAGGAGACGGGCGCACCTTCCCCAAGCGCGGCCAGACCTGCGTGGTGCACTACACC
GGGATGCTTGAAGATGGAAAGAAATTTGATTCCTCCCGGGACAGAAACAAGCCCTTTAAGTTTATGCTAGGCAAGCAGGA
GGTGATCCGAGGCTGGGAAGAAGGGGTTGCCCAGATGAGTGTGGGTCAGAGAGCCAAACTGACTATATCTCCAGATTATG
CCTATGGTGCCACTGGGCACCCAGGCATCATCCCACCACATGCCACTCTCGTCTTCGATGTGGAGCTTCTAAAACTGGAA
TGAGTTTAAAC

WWWWWWWWW) 201518_129_06 Sgf to Pme (SEQ ID NO:538)
GCGATCGCCATGGATCATCATTTCAAGATTATTCTCCATTATGGTACACTCGTTATTGACGGTGTGACACCAAACATGAT
TGACTACTTTGGACGCCCTTACCCTGGAATTGCTGTGTTTGACGGCAAGCAGATCACAGTTACTGGAACTCTGTGGAACG
GCAACAAGATCTATGATGAGCGCCTGATCAACCCAGATGGTTCACTCCTCTTCCGCGTTACTATCAATGGAGTCACCGGA
TGGCGCCTTTGCGAGAACATTCTTGCCGGCGGGAGCTCTGGTGGAGGGTCTGGGGGTGGAGTGCAGGTGGAAACCATCTC
CCCAGGAGACGGGCGCACCTTCCCCAAGCGCGGCCAGACCTGCGTGGTGCACTACACCGGGATGCTTGAAGATGGAAAGA
AATTTGATTCCTCCCGGGACAGAAACAAGCCCTTTAAGTTTATGCTAGGCAAGCAGGAGGTGATCCGAGGCTGGGAAGAA
GGGGTTGCCCAGATGAGTGTGGGTCAGAGAGCCAAACTGACTATATCTCCAGATTATGCCTATGGTGCCACTGGGCACCC
AGGCATCATCCCACCACATGCCACTCTCGTCTTCGATGTGGAGCTTCTAAAACTGGAATGAGTTTAAAC

XXXXXXXXX) 201518_45_08 Sgf to Pme (SEQ ID NO:539)
GCGATCGCCATGGTGTTTACGTTGGCAGATTTCGTTGGAGACTGGCAACAGACAGCTGGATACAACCAAGATCAAGTGTT
AGAACAAGGAGGATTGTCTAGTCTGTTCCAAGCCCTGGCAGTGTCAGTCACCCCAATCCAGAAAGTTGTGCTGTCTGGGG
AGAATGGGTTAAAAGCTGATATTCATGTCATCATCCCTTACGAGGGACTCAGTGGTTTTCAAATGGGTCTGATTGAAATG
ATCTTCAAAGTTGTTTACCCAGTGGATGATCATCATTTCAAGATTATTCTCCATTATGGTACACTCGTTATTGACGGTGT
GACACCAAACATGATTGACTACTTTGGACGCCCTTACCCTGGAATTGCTGTGTTTGACGGCAAGCAGATCACAGTTACTG
GAACTCTGTGGAACGGCAACAAGATCTATGATGAGCGCCTGATCAACCCAGATGGTTCACTCCTCTTCCGCGTTACTATC
AATGGAGTCACCGGATGGCGCCTTTGCGAGAACATTCTTGCCTAATGTTTAAAC

FIG. 67CQ

YYYYYYYYY) 201518_54_06 Sgf to Pme (SEQ ID NO:540)
GCGATCGCCATGGTGTTTACGTTGGCAGATTTCGTTGGAGACTGGCAACAGACAGCTGGATACAACCAAGATCAAGTGTT
AGAACAAGGAGGATTGTCTAGTCTGTTCCAAGCCCTGGGAGTGTCAGTCACCCCAATCCAGAAAGTTGTGCTGTCTGGGG
AGAATGGGTTAAAAGCTGATATTCATGTCATCATCCCTTACGAGGGACTCAGTGGTTTTCAAATGGGTCTGATTGAAATG
ATCTTCAAAGTTGTTTACCCAGTGGATGATCATCATTTCAAGATTATTCTCCATTATGGTACACTCGTTATTGACGGTGT
GACACCAAACATGATTGACTACTTTGGACGCCCTTACCCTGGAATTGCTGTGTTTGACGGCAAGCAGATCACAGTTACTG
GAACTCTGTGGAACGGCAACAAGATCTATGATGAGCGCCTGATCAACCCAGATGGTTCACTCCTCTTCCGCGTTACTATC
AATGGAGTCACCGGATGGCGCCTTTGCGAGAACATTCTTGCCTAATGTTTAAAC

ZZZZZZZZZ) 201518_57_A11 Sgf to Pme (SEQ ID NO:541)
GCGATCGCCATGGTGTTTACGTTGGCAGATTTCGTTGGAGACTGGCAACAGACAGCTGGATACAACCAAGATCAAGTGTT
AGAACAAGGAGGATTGTCTAGTCTGTTCCAAGCCCTGGGAGTGTCAGTCACCCCAATCCAGAAAGTTGTGCTGTCTGGGG
AGAATGGGTTAAAAGCTGATATTCATGTCATCATCCCTTACGAGGGACTCAGTGGTTTTCAAATGGGTCTGATTGAAATG
ATCTTCAAAGTTGTTTACCCCGTGGATGTTTAAAC

AAAAAAAAAA) 201518_57_A2 Sgf to Pme (SEQ ID NO:542)
GCGATCGCCATGGTGTTTACGTTGGCAGATTTCGTTGGAGACTGGCAACAGACAGCTGGATACAACCAAGATCAAGTGTT
AGAACAAGGAGGATTGTCTAGTCTGTTCCAAGCCCTGGGAGTGTCAGTCACCCCAATCCAGAAAGTTGTACTGTCTGGGG
AGAATGTTTAAAC

BBBBBBBBBB) 201518_57_D9 Sgf to Pme (SEQ ID NO:543)
GCGATCGCCGGGTTAAAAGCTGATATTCATGTCATCATCCCTTACGAGGGACTCAGTGGTTTTCAAATGGGTCTGATTGA
AATGATCTTCAAAGTTGTTTACCCAGTGGATGATCATCATTTCAAGATTATTCTCCATTATGGTACACTCGTTATTGACG
GTGTGACACCAAACATGATTGACTACTTTGGAAGACCTTACCCTGGAATTGCTGTATTTGACGGCAAGCAGATCACAGTT
ACTGGAACTCTGTGGAACGGCAACAAGATCTATGATGAGCGCCTGATCAACCCAGATGGTTCACTCCTCTTCCGCGTTAC
TATCAATGGAGTCACCGGATGGCGCCTTTGCGAGAACATTCTTGCCGTTTAAAC

CCCCCCCCCC) 201518_57_E6 Sgf to Pme (SEQ ID NO:544)
GCGATCGCCATGGTGTTTACGTTGGCAGATTTCGTTGGAGACTGGCAACAGACAGCTGGATACAACCAAGATCAAGTGTT
AGAACAAGGAGGATTGTCTAGTCTGTTCCAAGCCCTGGGAGTGTCAGTCACCCCAATCCAGAAAGTTGTACTGTCTGGGG
AGAATGTTTAAAC

DDDDDDDDDD) 201518_57_G3 Sgf to Pme (SEQ ID NO:545)
GCGATCGCCATGGTGTTTACGTTGGCAGATTTCGTTGGAGACTGGCAACAGACAGCTGGATACAACCAAGATCAAGTGTT
AGAACAAGGAGGATTGTCTAGTCTGTTCCAAGCCCTGGGAGTGTCAGTCACCCCAATCCAGAAAGTTGTGCTGTCTGGGG
AGAATGGGTTAAAAGCTGATATTCATGTCATCATCCCTTACGAGGGACTCAGTGGTTTTCAAATGGGTCTGATTGAAATG
ATCTTCAAAGTTGTTTACCCCGTGGATGTTTAAAC

EEEEEEEEEE) 201518_57_H12 Sgf to Pme (SEQ ID NO:546)
GCGATCGCCGATCATCATTTCAAGATTATTCTCCATTATGGTACACTCGTTATTGACGGTGTGACACCAAACATGATTGA
CTACTTTGGACGCCCTTACCCTGGAATTGCTGTGTTTGACGGCAAGCAGATCACAGTTACTGGAACTCTGTGGAACGGCA
ACAAGATCTATGATGAGCGCCTGATCAACCCAGATGGTTCACTCCTCTTCCGCGTTACTATCAATGGAGTCACCGGATGG
CGCCTTTGCGAGAACATTCTTGCCGTTTAAAC

FFFFFFFFFF) 201518_61_H3 Sgf to Pme (SEQ ID NO:547)
GCGATCGCCGATCATCATTTCAAGATTATTCTCCATTATGGTACACTCGTTATTGACGGTGTGACACCAAACATGATTGA
CTACTTTGGACGCCCTTACCCTGGAATTGCTGTGTTTGACGGCAAGCAGATCACAGTTACTGGAACTCTGTGGAACGGCA
ACAAGATCTATGATGAGCGCCTGATCAACCCAGATGGTTCACTCCTCTTCCGCGTTACTATCAATGGAGTCACCGGATGG
CGCCTTTGCGAGAACATTCTTGCCGTTTAAAC

GGGGGGGGGG) pBFB105 Sgf to Pme (SEQ ID NO:548)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG

*FIG. 67CR*

GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGACCGGAGGT
TCAATGTATGAAAGCTTTATTGAGTCACTGCCATTCCTTAAATCTTTGGAGTTTTCTGAACGCCTGAAAGTAGTAGATGT
GATAGGCACCAAAGTATACAACGATGGAGAACAAATCATTGCTCAGGGAGATTCGGCTGATTCTTTTTTCATTGTAGAAT
CTGGAGAAGTGAAAATTACTATGAAAAGAAAGGGTAAATCAGAAGTGGAAGAGAATGGTGCAGTAGAAATCGCTCGATGC
TCGCGGGGACAGTACTTTGGAGAGCTTGCCCTGGTAACTAACAAACCTCGAGCAGCTTCTGCCCACGCCATTGGGACTGT
CAAATGTTTAGCAATGGATGTGCAAGCATTTGAAAGGCTTCTGGGACCTTGCATGGAAATTATGAAAAGGAACATCGCTA
CCTATGAAGAACAGTTAGTTGCCCTGTTTGGAACGAACATGGATATTGTTGCCAAAAACATTAAGAAGGGCCCAGCGCCA
TTCTACCCACTCGAAGACGGGACCGCCGGCGAGCAGCTGCACAAAGCCATGAAGCGCTACGCCCTGGTGCCCGGCACCAT
CGCCTTTACCGACGCACATATCGAGGTGGACATTACCTACGCCGAGTACTTCGAGATGAGCGTTCGGCTGGCAGAAGCTA
TGAAGCGCTATGGGCTGAATACAAACCATCGGATCGTGGTGTGCAGCGAGAATAGCTTGCAGTTCTTCATGCCCGTGTTG
GGTGCCCTGTTCATCGGTGTGGCTGTGGCCCCAGCTAACGACATCTACAACGAGCGCGAGCTGCTGAACAGCATGGGCAT
CAGCCAGCCCACCGTCGTATTCGTGAGCAAGAAAGGGCTGCAAAAGATCCTCAACGTGCAAAAGAAGCTACCGATCATAC
AAAAGATCATCATCATGGATAGCAAGACCGACTACCAGGGCTTCCAAAGCATGTACACCTTCGTGACTTCCCATTTGCCA
CCCGGCTTCAACGAGTACGACTTCGTGCCCGAGAGCTTCGACCGGGACAAAACCATCGCCCTGATCATGAACAGTAGTGG
CAGTACCGGATTGCCCAAGGGCGTAGCCCTACCGCACCGCACCGCTTGTGTCCGATTCAGTCATGCCCGCGACCCCATCT
TCGGCAACCAGATCATCCCCGTTTAAAC

HHHHHHHHH) pBFB141 Sgf to Pme (SEQ ID NO:549)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAATGTATGAAAGCTTTATTGAGTCACTGCCATTCCTTAAATCTTTGGAGTTTTCTGAACGCCTGAA
AGTAGTAGATGTGATAGGCACCAAAGTATACAACGATGGAGAACAAATCATTGCTCAGGGAGATTCGGCTGATTCTTTTT
TCATTGTAGAATCTGGAGAAGTGAAAATTACTATGAAAAGAAAGGGTAAATCAGAAGTGGAAGAGAATGGTGCAGTAGAA
ATCGCTCGATGCTCGCGGGGACAGTACTTTGGAGAGCTTGCCCTGGTAACTAACAAACCTCGAGCAGCTTCTGCCCACGC
CATTGGGACTGTCAAATGTTTAGCAATGGATGTGCAAGCATTTGAAAGGCTTCTGGGACCTTGCATGGAAATTATGAAAA
GGAACATCGCTACCTATGAAGAACAGTTAGTTGCCCTGTTTGGAACGAACATGGATATTGTAGCCAAAAACATTAAGAAG
GGCCCAGCGCCATTCTACCCACTCGAAGACGGGACCGCCGGCGAGCAGCTGCACAAAGCCATGAAGCGCTACGCCCTGGT
GCCCGGCACCATCGCCTTTACCGACGCACATATCGAGGTGGACATTACCTACGCCGAGTACTTCGAGATGAGCGTTCGGC
TGGCAGAAGCTATGAAGCGCTATGGGCTGAATACAAACCATCGGATCGTGGTGTGCAGCGAGAATAGCTTGCAGTTCTTC
ATGCCCGTGTTGGGTGCCCTGTTCATCGGTGTGGCTGTGGCCCCAGCTAACGACATCTACAACGAGCGCGAGCTGCTGAA
CAGCATGGGCATCAGCCAGCCCACCGTCGTATTCGTGAGCAAGAAAGGGCTGCAAAAGATCCTCAACGTGCAAAAGAAGC
TACCGATCATACAAAAGATCATCATCATGGATAGCAAGACCGACTACCAGGGCTTCCAAAGCATGTACACCTTCGTGACT
TCCCATTTGCCACCCGGCTTCAACGAGTACGACTTCGTGCCCGAGAGCTTCGACCGGGACAAAACCATCGCCCTGATCAT
GAACAGTAGTGGCAGTACCGGATTGCCCAAGGGCGTAGCCCTACCGCACCGCACCGCTTGTGTCCGATTCAGTCATGCCC
GCGACCCCATCTTCGGCAACCAGATCATCCCCGTTTAAAC

IIIIIIIII) pBFB248 Sgf to Pme (SEQ ID NO:550)
GCGATCGCCATGGAGGAGGAGCTATTCTTGCGCAGCTTGCAAGACTATAAGATTCAATCTGCCCTGCTGGTGCCCACACT
ATTTAGCTTCTTCGCTAAGAGCACTCTCATCGACAAGTACGACCTAAGCAACTTGCACGAGATCGCCAGCGGCGGGGCGC
CGCTCAGCAAGGAGGTAGGTGAGGCCGTGGCCAAACGCTTCCACCTACCAGGCATCCGCCAGGGCTACGGCCTGACAGAA
ACAACCAGCGCCATTCTGATCACCCCCGAAGGGGACGACAAGCCTGGCGCAGTAGGCAAGGTGGTGCCCTTCTTCGAGGC

FIG. 67CS

TAAGGTGGTGGACTTGGACACCGGTAAGACACTGGGTGTGAACCAGCGCGGCGAGCTGTGCGTCCGTGGCCCCATGATCA
TGAGCGGCTACGTTAACAACCCCGAGGCTACAAACGCTCTCATCGACAAGGACGGCTGGCTGCACAGCGGCGACATCGCC
TACTGGGACGAGGACGAGCACTTCTTCATCGTGGACCGGCTGAAGAGCCTGATCAAATACAAGGGCTACCAGGTAGCCCC
AGCCGAACTGGAGAGCATCCTGCTGCAACACCCCAACATCTTCGACGCCGGGGTCGCCGGCCTGCCCGACGACGATGCCG
GCGAGCTGCCCGCCGCAGTCGTCGTGCTGGAACACGGTAAAACCATGACCGAGAAGGAGATCGTGGACTATGTGGCCAGC
CAGGTTACAACCGCCAAGAAGCTGCGCGGTGGTGTTGTGTTCGTGGACGAGGTGCCTAAAGGACTGACCGGCAAGTTGGA
CGCCCGCAAGATCCGCGAGATTCTCATTAAGGCCAAGAAGGGCTCGAGCGGAGGTTCAGGCGGTTCCGGAGGAGGTATGT
ATGAAAGCTTTATTGAGTCACTGCCATTCCTTAAATCTTTGGAGTTTTCTGAACGCCTGAAAGTAGTAGATGTGATAGGC
ACCAAAGTATACAACGATGGAGAACAAATCATTGCTCAGGGAGATTCGGCTGATTCTTTTTTCATTGTAGAATCTGGAGA
AGTGAAAATTACTATGAAAAGAAAGGGTAAATCAGAAGTGGAAGAGAATGGTGCAGTAGAAATCGCTCGATGCTCGCGGG
GACAGTACTTTGGAGAGCTTGCCCTGGTAACTAACAAACCTCGAGCAGCTTCTGCCCACGCCATTGGGACTGTCAAATGT
TTAGCAATGGATGTGCAAGCATTTGAAAGGCTTCTGGGACCTTGCATGGAAATTATGAAAAGGAACATCGCTACCTATGA
AGAACAGTTAGTTGCCCTGTTTGGAACGAACATGGATATTGTAGCCAAAAACATTAAGAAGGGCCCAGCGCCATTCTACC
CACTCGAAGACGGGACCGCCGGCGAGCAGCTGCACAAAGCCATGAAGCGCTACGCCCTGGTGCCCGGCACCATCGCCTTT
ACCGACGCACATATCGAGGTGGACATTACCTACGCCGAGTACTTCGAGATGAGCGTTCGGCTGGCAGAAGCTATGAAGCG
CTATGGGCTGAATACAAACCATCGGATCGTGGTGTGCAGCGAGAATAGCTTGCAGTTCTTCATGCCCGTGTTGGGTGCCC
TGTTCATCGGTGTGGCTGTGGCCCCAGCTAACGACATCTACAACGAGCGCGAGCTGCTGAACAGCATGGGCATCAGCCAG
CCCACCGTCGTATTCGTGAGCAAGAAAGGGCTGCAAAAGATCCTCAACGTGCAAAAGAAGCTACCGATCATACAAAAGAT
CATCATCATGGATAGCAAGACCGACTACCAGGGCTTCCAAAGCATGTACACCTTCGTGACTTCCCATTTGCCACCCGGCT
TCAACGAGTACGACTTCGTGCCCGAGAGCTTCGACCGGGACAAAACCATCGCCCTGATCATGAACAGTAGTGGCAGTACC
GGATTGCCCAAGGGCGTAGCCCTACCGCACCGCACCGCTTGTGTCCGATTCAGTCATGCCCGCGACCCCATCTTCGGCAA
CCAGATCATCCCCGACACCGCTATCCTCAGCGTGGTGCCATTTCACCACGGCTTCGGCATGTTCACCACGCTGGGCTACT
TGATCTGCGGCTTTCGGGTCGTGCTCATGTACGTTTAAAC

JJJJJJJJJ) pBFB249 Sgf to Pme (SEQ ID NO:551)
GCGATCGCCATGCCTGGCGCAGTAGGCAAGGTGGTGCCCTTCTTCGAGGCTAAGGTGGTGGACTTGGACACCGGTAAGAC
ACTGGGTGTGAACCAGCGCGGCGAGCTGTGCGTCCGTGGCCCCATGATCATGAGCGGCTACGTTAACAACCCCGAGGCTA
CAAACGCTCTCATCGACAAGGACGGCTGGCTGCACAGCGGCGACATCGCCTACTGGGACGAGGACGAGCACTTCTTCATC
GTGGACCGGCTGAAGAGCCTGATCAAATACAAGGGCTACCAGGTAGCCCCAGCCGAACTGGAGAGCATCCTGCTGCAACA
CCCCAACATCTTCGACGCCGGGGTCGCCGGCCTGCCCGACGACGATGCCGGCGAGCTGCCCGCCGCAGTCGTCGTGCTGG
AACACGGTAAAACCATGACCGAGAAGGAGATCGTGGACTATGTGGCCAGCCAGGTTACAACCGCCAAGAAGCTGCGCGGT
GGTGTTGTGTTCGTGGACGAGGTGCCTAAAGGACTGACCGGCAAGTTGGACGCCCGCAAGATCCGCGAGATTCTCATTAA
GGCCAAGAAGGGCTCGAGCGGAGGTTCAGGCGGTTCCGGAGGAGGTATGTATGAAAGCTTTATTGAGTCACTGCCATTCC
TTAAATCTTTGGAGTTTTCTGAACGCCTGAAAGTAGTAGATGTGATAGGCACCAAAGTATACAACGATGGAGAACAAATC
ATTGCTCAGGGAGATTCGGCTGATTCTTTTTTCATTGTAGAATCTGGAGAAGTGAAAATTACTATGAAAAGAAAGGGTAA
ATCAGAAGTGGAAGAGAATGGTGCAGTAGAAATCGCTCGATGCTCGCGGGGACAGTACTTTGGAGAGCTTGCCCTGGTAA
CTAACAAACCTCGAGCAGCTTCTGCCCACGCCATTGGGACTGTCAAATGTTTAGCAATGGATGTGCAAGCATTTGAAAGG
CTTCTGGGACCTTGCATGGAAATTATGAAAAGGAACATCGCTACCTATGAAGAACAGTTAGTTGCCCTGTTTGGAACGAA
CATGGATATTGTAGCCAAAAACATTAAGAAGGGCCCAGCGCCATTCTACCCACTCGAAGACGGGACCGCCGGCGAGCAGC
TGCACAAAGCCATGAAGCGCTACGCCCTGGTGCCCGGCACCATCGCCTTTACCGACGCACATATCGAGGTGGACATTACC
TACGCCGAGTACTTCGAGATGAGCGTTCGGCTGGCAGAAGCTATGAAGCGCTATGGGCTGAATACAAACCATCGGATCGT
GGTGTGCAGCGAGAATAGCTTGCAGTTCTTCATGCCCGTGTTGGGTGCCCTGTTCATCGGTGTGGCTGTGGCCCCAGCTA
ACGACATCTACAACGAGCGCGAGCTGCTGAACAGCATGGGCATCAGCCAGCCCACCGTCGTATTCGTGAGCAAGAAAGGG
CTGCAAAAGATCCTCAACGTGCAAAAGAAGCTACCGATCATACAAAAGATCATCATCATGGATAGCAAGACCGACTACCA
GGGCTTCCAAAGCATGTACACCTTCGTGACTTCCCATTTGCCACCCGGCTTCAACGAGTACGACTTCGTGCCCGAGAGCT
TCGACCGGGACAAAACCATCGCCCTGATCATGAACAGTAGTGGCAGTACCGGATTGCCCAAGGGCGTAGCCCTACCGCAC
CGCACCGCTTGTGTCCGATTCAGTCATGCCCGCGACCCCATCTTCGGCAACCAGATCATCCCCGACACCGCTATCCTCAG
CGTGGTGCCATTTCACCACGGCTTCGGCATGTTCACCACGCTGGGCTACTTGATCTGCGGCTTTCGGGTCGTGCTCATGT
ACCGCTTCGAGGAGGAGCTATTCTTGCGCAGCTTGCAAGACTATAAGATTCAATCTGCCCTGCTGGTGCCCACACTATTT
AGCTTCTTCGCTAAGAGCACTCTCATCGACAAGTACGACCTAAGCAACTTGCACGAGATCGCCAGCGGCGGGGCGCCGCT
CAGCAAGGAGGTAGGTGAGGCCGTGGCCAAACGCTTCCACCTACCAGGCATCCGCCAGGGCTACGGCCTGACAGAAACAA
CCAGCGCCATTCTGATCACTCCAGAAGGGGTTTAAAC

KKKKKKKKK) pBFB257 Sgf to Pme (SEQ ID NO:552)
GCGATCGCCATGTTTCACCACGGCTTCGGCATGTTCACCACGCTGGGCTACTTGATCTGCGGCTTTCGGGTCGTGCTCAT
GTACCGCTTCGAGGAGGAGCTATTCTTGCGCAGCTTGCAAGACTATAAGATTCAATCTGCCCTGCTGGTGCCCACACTAT
TTAGCTTCTTCGCTAAGAGCACTCTCATCGACAAGTACGACCTAAGCAACTTGCACGAGATCGCCAGCGGCGGGGCGCCG

*FIG. 67*CT

```
CTCAGCAAGGAGGTAGGTGAGGCCGTGGCCAAACGCTTCCACCTACCAGGCATCCGCCAGGGCTACGGCCTGACAGAAAC
AACCAGCGCCATTCTGATCACCCCCGAAGGGGACGACAAGCCTGGCGCAGTAGGCAAGGTGGTGCCCTTCTTCGAGGCTA
AGGTGGTGGACTTGGACACCGGTAAGACACTGGGTGTGAACCAGCGCGGCGAGCTGTGCGTCCGTGGCCCCATGATCATG
AGCGGCTACGTTAACAACCCCGAGGCTACAAACGCTCTCATCGACAAGGACGGCTGGCTGCACAGCGGCGACATCGCCTA
CTGGGACGAGGACGAGCACTTCTTCATCGTGGACCGGCTGAAGAGCCTGATCAAATACAAGGGCTACCAGGTAGCCCCAG
CCGAACTGGAGAGCATCCTGCTGCAACACCCCAACATCTTCGACGCCGGGGTCGCCGGCCTGCCCGACGACGATGCCGGC
GAGCTGCCCGCCGCAGTCGTCGTGCTGGAACACGGTAAAACCATGACCGAGAAGGAGATCGTGGACTATGTGGCCAGCCA
GGTTACAACCGCCAAGAAGCTGCGCGGTGGTGTTGTGTTCGTGGACGAGGTGCCTAAAGGACTGACCGGCAAGTTGGACG
CCCGCAAGATCCGCGAGATTCTCATTAAGGCCAAGAAGGGCTCGAGCGGAGGTTCAGGCGGTTCCGGAGGAGGTATGTAT
GAAAGCTTTATTGAGTCACTGCCATTCCTTAAATCTTTGGAGTTTTCTGAACGCCTGAAAGTAGTAGATGTGATAGGCAC
CAAAGTATACAACGATGGAGAACAAATCATTGCTCAGGGAGATTCGGCTGATTCTTTTTTCATTGTAGAATCTGGAGAAG
TGAAAATTACTATGAAAAGAAAGGGTAAATCAGAAGTGGAAGAGAATGGTGCAGTAGAAATCGCTCGATGCTCGCGGGGA
CAGTACTTTGGAGAGCTTGCCCTGGTAACTAACAAACCTCGAGCAGCTTCTGCCCACGCCATTGGGACTGTCAAATGTTT
AGCAATGGATGTGCAAGCATTTGAAAGGCTTCTGGGACCTTGCATGGAAATTATGAAAAGGAACATCGCTACCTATGAAG
AACAGTTAGTTGCCCTGTTTGGAACGAACATGGATATTGTAGCCAAAAACATTAAGAAGGGCCCAGCGCCATTCTACCCA
CTCGAAGACGGGACCGCCGGCGAGCAGCTGCACAAAGCCATGAAGCGCTACGCCCTGGTGCCCGGCACCATCGCCTTTAC
CGACGCACATATCGAGGTGGACATTACCTACGCCGAGTACTTCGAGATGAGCGTTCGGCTGGCAGAAGCTATGAAGCGCT
ATGGGCTGAATACAAACCATCGGATCGTGGTGTGCAGCGAGAATAGCTTGCAGTTCTTCATGCCCGTGTTGGGTGCCCTG
TTCATCGGTGTGGCTGTGGCCCCAGCTAACGACATCTACAACGAGCGCGAGCTGCTGAACAGCATGGGCATCAGCCAGCC
CACCGTCGTATTCGTGAGCAAGAAAGGGCTGCAAAAGATCCTCAACGTGCAAAAGAAGCTACCGATCATACAAAAGATCA
TCATCATGGATAGCAAGACCGACTACCAGGGCTTCCAAAGCATGTACACCTTCGTGACTTCCCATTTGCCACCCGGCTTC
AACGAGTACGACTTCGTGCCCGAGAGCTTCGACCGGGACAAAACCATCGCCCTGATCATGAACAGTAGTGGCAGTACCGG
ATTGCCCAAGGGCGTAGCCCTACCGCACCGCACCGCTTGTGTCCGATTCAGTCATGCCCGCGACCCCATCTTCGGCAACC
AGATCATCCCCGACACCGCTATCCTCAGCGTGGTTTAAAC

LLLLLLLLLL) pBFB259    Sgf to Pme    (SEQ ID NO:553)
GCGATCGCCATGTTGCACGAGATCGCCAGCGGCGGGGCGCCGCTCAGCAAGGAGGTAGGTGAGGCCGTGGCCAAACGCTT
CCACCTACCAGGCATCCGCCAGGGCTACGGCCTGACAGAAACAACCAGCGCCATTCTGATCACCCCCGAAGGGGACGACA
AGCCTGGCGCAGTAGGCAAGGTGGTGCCCTTCTTCGAGGCTAAGGTGGTGGACTTGGACACCGGTAAGACACTGGGTGTG
AACCAGCGCGGCGAGCTGTGCGTCCGTGGCCCCATGATCATGAGCGGCTACGTTAACAACCCCGAGGCTACAAACGCTCT
CATCGACAAGGACGGCTGGCTGCACAGCGGCGACATCGCCTACTGGGACGAGGACGAGCACTTCTTCATCGTGGACCGGC
TGAAGAGCCTGATCAAATACAAGGGCTACCAGGTAGCCCCAGCCGAACTGGAGAGCATCCTGCTGCAACACCCCAACATC
TTCGACGCCGGGGTCGCCGGCCTGCCCGACGACGATGCCGGCGAGCTGCCCGCCGCAGTCGTCGTGCTGGAACACGGTAA
AACCATGACCGAGAAGGAGATCGTGGACTATGTGGCCAGCCAGGTTACAACCGCCAAGAAGCTGCGCGGTGGTGTTGTGT
TCGTGGACGAGGTGCCTAAAGGACTGACCGGCAAGTTGGACGCCCGCAAGATCCGCGAGATTCTCATTAAGGCCAAGAAG
GGCTCGAGCGGAGGTTCAGGCGGTTCCGGAGGAGGTATGTATGAAAGCTTTATTGAGTCACTGCCATTCCTTAAATCTTT
GGAGTTTTCTGAACGCCTGAAAGTAGTAGATGTGATAGGCACCAAAGTATACAACGATGGAGAACAAATCATTGCTCAGG
GAGATTCGGCTGATTCTTTTTTCATTGTAGAATCTGGAGAAGTGAAAATTACTATGAAAAGAAAGGGTAAATCAGAAGTG
GAAGAGAATGGTGCAGTAGAAATCGCTCGATGCTCGCGGGGACAGTACTTTGGAGAGCTTGCCCTGGTAACTAACAAACC
TCGAGCAGCTTCTGCCCACGCCATTGGGACTGTCAAATGTTTAGCAATGGATGTGCAAGCATTTGAAAGGCTTCTGGGAC
CTTGCATGGAAATTATGAAAAGGAACATCGCTACCTATGAAGAACAGTTAGTTGCCCTGTTTGGAACGAACATGGATATT
GTAGCCAAAAACATTAAGAAGGGCCCAGCGCCATTCTACCCACTCGAAGACGGGACCGCCGGCGAGCAGCTGCACAAAGC
CATGAAGCGCTACGCCCTGGTGCCCGGCACCATCGCCTTTACCGACGCACATATCGAGGTGGACATTACCTACGCCGAGT
ACTTCGAGATGAGCGTTCGGCTGGCAGAAGCTATGAAGCGCTATGGGCTGAATACAAACCATCGGATCGTGGTGTGCAGC
GAGAATAGCTTGCAGTTCTTCATGCCCGTGTTGGGTGCCCTGTTCATCGGTGTGGCTGTGGCCCCAGCTAACGACATCTA
CAACGAGCGCGAGCTGCTGAACAGCATGGGCATCAGCCAGCCCACCGTCGTATTCGTGAGCAAGAAAGGGCTGCAAAAGA
TCCTCAACGTGCAAAAGAAGCTACCGATCATACAAAAGATCATCATCATGGATAGCAAGACCGACTACCAGGGCTTCCAA
AGCATGTACACCTTCGTGACTTCCCATTTGCCACCCGGCTTCAACGAGTACGACTTCGTGCCCGAGAGCTTCGACCGGGA
CAAAACCATCGCCCTGATCATGAACAGTAGTGGCAGTACCGGATTGCCCAAGGGCGTAGCCCTACCGCACCGCACCGCTT
GTGTCCGATTCAGTCATGCCCGCGACCCCATCTTCGGCAACCAGATCATCCCCGACACCGCTATCCTCAGCGTGGTGCCA
TTTCACCACGGCTTCGGCATGTTCACCACGCTGGGCTACTTGATCTGCGGCTTTCGGGTCGTGCTCATGTACCGCTTCGA
GGAGGAGCTATTCTTGCGCAGCTTGCAAGACTATAAGATTCAATCTGCCCTGCTGGTGCCCACACTATTTAGCTTCTTCG
CTAAGAGCACTCTCATCGACAAGTACGACCTAGTTTAAAC

MMMMMMMMMM) pBFB260    Sgf to Pme    (SEQ ID NO:554)
GCGATCGCCATGGCGCCGCTCAGCAAGGAGGTAGGTGAGGCCGTGGCCAAACGCTTCCACCTACCAGGCATCCGCCAGGG
CTACGGCCTGACAGAAACAACCAGCGCCATTCTGATCACCCCCGAAGGGGACGACAAGCCTGGCGCAGTAGGCAAGGTGG
```

*FIG. 67CU*

TGCCCTTCTTCGAGGCTAAGGTGGTGGACTTGGACACCGGTAAGACACTGGGTGTGAACCAGCGCGGCGAGCTGTGCGTC
CGTGGCCCCATGATCATGAGCGGCTACGTTAACAACCCCGAGGCTACAAACGCTCTCATCGACAAGGACGGCTGGCTGCA
CAGCGGCGACATCGCCTACTGGGACGAGGACGAGCACTTCTTCATCGTGGACCGGCTGAAGAGCCTGATCAAATACAAGG
GCTACCAGGTAGCCCCAGCCGAACTGGAGAGCATCCTGCTGCAACACCCCAACATCTTCGACGCCGGGGTCGCCGGCCTG
CCCGACGACGATGCCGGCGAGCTGCCCGCCGCAGTCGTCGTGCTGGAACACGGTAAAACCATGACCGAGAAGGAGATCGT
GGACTATGTGGCCAGCCAGGTTACAACCGCCAAGAAGCTGCGCGGTGGTGTTGTGTTCGTGGACGAGGTGCCTAAAGGAC
TGACCGGCAAGTTGGACGCCCGCAAGATCCGCGAGATTCTCATTAAGGCCAAGAAGGGCTCGAGCGGAGGTTCAGGCGGT
TCCGGAGGAGGTATGTATGAAAGCTTTATTGAGTCACTGCCATTCCTTAAATCTTTGGAGTTTTCTGAACGCCTGAAAGT
AGTAGATGTGATAGGCACCAAAGTATACAACGATGGAGAACAAATCATTGCTCAGGGAGATTCGGCTGATTCTTTTTTCA
TTGTAGAATCTGGAGAAGTGAAAATTACTATGAAAAGAAAGGGTAAATCAGAAGTGGAAGAGAATGGTGCAGTAGAAATC
GCTCGATGCTCGCGGGGACAGTACTTTGGAGAGCTTGCCCTGGTAACTAACAAACCTCGAGCAGCTTCTGCCCACGCCAT
TGGGACTGTCAAATGTTTAGCAATGGATGTGCAAGCATTTGAAAGGCTTCTGGGACCTTGCATGGAAATTATGAAAAGGA
ACATCGCTACCTATGAAGAACAGTTAGTTGCCCTGTTTGGAACGAACATGGATATTGTAGCCAAAAACATTAAGAAGGGC
CCAGCGCCATTCTACCCACTCGAAGACGGGACCGCCGGCGAGCAGCTGCACAAAGCCATGAAGCGCTACGCCCTGGTGCC
CGGCACCATCGCCTTTACCGACGCACATATCGAGGTGGACATTACCTACGCCGAGTACTTCGAGATGAGCGTTCGGCTGG
CAGAAGCTATGAAGCGCTATGGGCTGAATACAAACCATCGGATCGTGGTGTGCAGCGAGAATAGCTTGCAGTTCTTCATG
CCCGTGTTGGGTGCCCTGTTCATCGGTGTGGCTGTGGCCCCAGCTAACGACATCTACAACGAGCGCGAGCTGCTGAACAG
CATGGGCATCAGCCAGCCCACCGTCGTATTCGTGAGCAAGAAAGGGCTGCAAAAGATCCTCAACGTGCAAAAGAAGCTAC
CGATCATACAAAAGATCATCATCATGGATAGCAAGACCGACTACCAGGGCTTCCAAAGCATGTACACCTTCGTGACTTCC
CATTTGCCACCCGGCTTCAACGAGTACGACTTCGTGCCCGAGAGCTTCGACCGGGACAAAACCATCGCCCTGATCATGAA
CAGTAGTGGCAGTACCGGATTGCCCAAGGGCGTAGCCCTACCGCACCGCACCGCTTGTGTCCGATTCAGTCATGCCCGCG
ACCCCATCTTCGGCAACCAGATCATCCCCGACACCGCTATCCTCAGCGTGGTGCCATTTCACCACGGCTTCGGCATGTTC
ACCACGCTGGGCTACTTGATCTGCGGCTTTCGGGTCGTGCTCATGTACCGCTTCGAGGAGGAGCTATTCTTGCGCAGCTT
GCAAGACTATAAGATTCAATCTGCCCTGCTGGTGCCCACACTATTTAGCTTCTTCGCTAAGAGCACTCTCATCGACAAGT
ACGACCTAAGCAACTTGCACGAGATCGCCAGCGTTTAAAC

NNNNNNNNNN) pBFB261 Sgf to Pme (SEQ ID NO:555)
GCGATCGCCATGACCGGTAAGACACTGGGTGTGAACCAGCGCGGCGAGCTGTGCGTCCGTGGCCCCATGATCATGAGCGG
CTACGTTAACAACCCCGAGGCTACAAACGCTCTCATCGACAAGGACGGCTGGCTGCACAGCGGCGACATCGCCTACTGGG
ACGAGGACGAGCACTTCTTCATCGTGGACCGGCTGAAGAGCCTGATCAAATACAAGGGCTACCAGGTAGCCCCAGCCGAA
CTGGAGAGCATCCTGCTGCAACACCCCAACATCTTCGACGCCGGGGTCGCCGGCCTGCCCGACGACGATGCCGGCGAGCT
GCCCGCCGCAGTCGTCGTGCTGGAACACGGTAAAACCATGACCGAGAAGGAGATCGTGGACTATGTGGCCAGCCAGGTTA
CAACCGCCAAGAAGCTGCGCGGTGGTGTTGTGTTCGTGGACGAGGTGCCTAAAGGACTGACCGGCAAGTTGGACGCCCGC
AAGATCCGCGAGATTCTCATTAAGGCCAAGAAGGGCTCGAGCGGAGGTTCAGGCGGTTCCGGAGGAGGTATGTATGAAAG
CTTTATTGAGTCACTGCCATTCCTTAAATCTTTGGAGTTTTCTGAACGCCTGAAAGTAGTAGATGTGATAGGCACCAAAG
TATACAACGATGGAGAACAAATCATTGCTCAGGGAGATTCGGCTGATTCTTTTTTCATTGTAGAATCTGGAGAAGTGAAA
ATTACTATGAAAAGAAAGGGTAAATCAGAAGTGGAAGAGAATGGTGCAGTAGAAATCGCTCGATGCTCGCGGGGACAGTA
CTTTGGAGAGCTTGCCCTGGTAACTAACAAACCTCGAGCAGCTTCTGCCCACGCCATTGGGACTGTCAAATGTTTAGCAA
TGGATGTGCAAGCATTTGAAAGGCTTCTGGGACCTTGCATGGAAATTATGAAAAGGAACATCGCTACCTATGAAGAACAG
TTAGTTGCCCTGTTTGGAACGAACATGGATATTGTAGCCAAAAACATTAAGAAGGGCCCAGCGCCATTCTACCCACTCGA
AGACGGGACCGCCGGCGAGCAGCTGCACAAAGCCATGAAGCGCTACGCCCTGGTGCCCGGCACCATCGCCTTTACCGACG
CACATATCGAGGTGGACATTACCTACGCCGAGTACTTCGAGATGAGCGTTCGGCTGGCAGAAGCTATGAAGCGCTATGGG
CTGAATACAAACCATCGGATCGTGGTGTGCAGCGAGAATAGCTTGCAGTTCTTCATGCCCGTGTTGGGTGCCCTGTTCAT
CGGTGTGGCTGTGGCCCCAGCTAACGACATCTACAACGAGCGCGAGCTGCTGAACAGCATGGGCATCAGCCAGCCCACCG
TCGTATTCGTGAGCAAGAAAGGGCTGCAAAAGATCCTCAACGTGCAAAAGAAGCTACCGATCATACAAAAGATCATCATC
ATGGATAGCAAGACCGACTACCAGGGCTTCCAAAGCATGTACACCTTCGTGACTTCCCATTTGCCACCCGGCTTCAACGA
GTACGACTTCGTGCCCGAGAGCTTCGACCGGGACAAAACCATCGCCCTGATCATGAACAGTAGTGGCAGTACCGGATTGC
CCAAGGGCGTAGCCCTACCGCACCGCACCGCTTGTGTCCGATTCAGTCATGCCCGCGACCCCATCTTCGGCAACCAGATC
ATCCCCGACACCGCTATCCTCAGCGTGGTGCCATTTCACCACGGCTTCGGCATGTTCACCACGCTGGGCTACTTGATCTG
CGGCTTTCGGGTCGTGCTCATGTACCGCTTCGAGGAGGAGCTATTCTTGCGCAGCTTGCAAGACTATAAGATTCAATCTG
CCCTGCTGGTGCCCACACTATTTAGCTTCTTCGCTAAGAGCACTCTCATCGACAAGTACGACCTAAGCAACTTGCACGAG
ATCGCCAGCGGCGGGGCGCCGCTCAGCAAGGAGGTAGGTGAGGCCGTGGCCAAACGCTTCCACCTACCAGGCATCCGCCA
GGGCTACGGCCTGACAGAAACAACCAGCGCCATTCTGATCACCCCCGAAGGGGACGACAAGCCTGGCGCAGTAGGCAAGG
TGGTGCCCTTCTTCGAGGCTAAGGTGGTGGACGTTTAAAC

OOOOOOOOOO) pBFB262 Sgf to Pme (SEQ ID NO:556)

FIG. 67CV

GCGATCGCCATGAACCCCGAGGCTACAAACGCTCTCATCGACAAGGACGGCTGGCTGCACAGCGGCGACATCGCCTACTG
GGACGAGGACGAGCACTTCTTCATCGTGGACCGGCTGAAGAGCCTGATCAAATACAAGGGCTACCAGGTAGCCCCAGCCG
AACTGGAGAGCATCCTGCTGCAACACCCCAACATCTTCGACGCCGGGGTCGCCGGCCTGCCCGACGACGATGCCGGCGAG
CTGCCCGCCGCAGTCGTCGTGCTGGAACACGGTAAAACCATGACCGAGAAGGAGATCGTGGACTATGTGGCCAGCCAGGT
TACAACCGCCAAGAAGCTGCGCGGTGGTGTTGTGTTCGTGGACGAGGTGCCTAAAGGACTGACCGGCAAGTTGGACGCCC
GCAAGATCCGCGAGATTCTCATTAAGGCCAAGAAGGGCTCGAGCGGAGGTTCAGGCGGTTCCGGAGGAGGTATGTATGAA
AGCTTTATTGAGTCACTGCCATTCCTTAAATCTTTGGAGTTTTCTGAACGCCTGAAAGTAGTAGATGTGATAGGCACCAA
AGTATACAACGATGGAGAACAAATCATTGCTCAGGGAGATTCGGCTGATTCTTTTTTCATTGTAGAATCTGGAGAAGTGA
AAATTACTATGAAAAGAAAGGGTAAATCAGAAGTGGAAGAGAATGGTGCAGTAGAAATCGCTCGATGCTCGCGGGGACAG
TACTTTGGAGAGCTTGCCCTGGTAACTAACAAACCTCGAGCAGCTTCTGCCCACGCCATTGGGACTGTCAAATGTTTAGC
AATGGATGTGCAAGCATTTGAAAGGCTTCTGGGACCTTGCATGGAAATTATGAAAAGGAACATCGCTACCTATGAAGAAC
AGTTAGTTGCCCTGTTTGGAACGAACATGGATATTGTAGCCAAAAACATTAAGAAGGGCCCAGCGCCATTCTACCCACTC
GAAGACGGGACCGCCGGCGAGCAGCTGCACAAAGCCATGAAGCGCTACGCCCTGGTGCCCGGCACCATCGCCTTTACCGA
CGCACATATCGAGGTGGACATTACCTACGCCGAGTACTTCGAGATGAGCGTTCGGCTGGCAGAAGCTATGAAGCGCTATG
GGCTGAATACAAACCATCGGATCGTGGTGTGCAGCGAGAATAGCTTGCAGTTCTTCATGCCCGTGTTGGGTGCCCTGTTC
ATCGGTGTGGCTGTGGCCCCAGCTAACGACATCTACAACGAGCGCGAGCTGCTGAACAGCATGGGCATCAGCCAGCCCAC
CGTCGTATTCGTGAGCAAGAAAGGGCTGCAAAAGATCCTCAACGTGCAAAAGAAGCTACCGATCATACAAAAGATCATCA
TCATGGATAGCAAGACCGACTACCAGGGCTTCCAAAGCATGTACACCTTCGTGACTTCCCATTTGCCACCCGGCTTCAAC
GAGTACGACTTCGTGCCCGAGAGCTTCGACCGGGACAAAACCATCGCCCTGATCATGAACAGTAGTGGCAGTACCGGATT
GCCCAAGGGCGTAGCCCTACCGCACCGCACCGCTTGTGTCCGATTCAGTCATGCCCGCGACCCCATCTTCGGCAACCAGA
TCATCCCCGACACCGCTATCCTCAGCGTGGTGCCATTTCACCACGGCTTCGGCATGTTCACCACGCTGGGCTACTTGATC
TGCGGCTTTCGGGTCGTGCTCATGTACCGCTTCGAGGAGGAGCTATTCTTGCGCAGCTTGCAAGACTATAAGATTCAATC
TGCCCTGCTGGTGCCCACACTATTTAGCTTCTTCGCTAAGAGCACTCTCATCGACAAGTACGACCTAAGCAACTTGCACG
AGATCGCCAGCGGCGGGGCGCCGCTCAGCAAGGAGGTAGGTGAGGCCGTGGCCAAACGCTTCCACCTACCAGGCATCCGC
CAGGGCTACGGCCTGACAGAAACAACCAGCGCCATTCTGATCACCCCCGAAGGGGACGACAAGCCTGGCGCAGTAGGCAA
GGTGGTGCCCTTCTTCGAGGCTAAGGTGGTGGACTTGGACACCGGTAAGACACTGGGTGTGAACCAGCGCGGCGAGCTGT
GCGTCCGTGGCCCCATGATCATGAGCGGCTACGTTTAAAC

PPPPPPPPPP) pBFB270 Sgf to Pme (SEQ ID NO:557)
GCGATCGCCATGGACCGGCTGAAGAGCCTGATCAAATACAAGGGCTACCAGGTAGCCCCAGCCGAACTGGAGAGCATCCT
GCTGCAACACCCCAACATCTTCGACGCCGGGGTCGCCGGCCTGCCCGACGACGATGCCGGCGAGCTGCCCGCCGCAGTCG
TCGTGCTGGAACACGGTAAAACCATGACCGAGAAGGAGATCGTGGACTATGTGGCCAGCCAGGTTACAACCGCCAAGAAG
CTGCGCGGTGGTGTTGTGTTCGTGGACGAGGTGCCTAAAGGACTGACCGGCAAGTTGGACGCCCGCAAGATCCGCGAGAT
TCTCATTAAGGCCAAGAAGGGCTCGAGCGGAGGTTCAGGCGGTTCCGGAGGAGGTATGTATGAAAGCTTTATTGAGTCAC
TGCCATTCCTTAAATCTTTGGAGTTTTCTGAACGCCTGAAAGTAGTAGATGTGATAGGCACCAAAGTATACAACGATGGA
GAACAAATCATTGCTCAGGGAGATTCGGCTGATTCTTTTTTCATTGTAGAATCTGGAGAAGTGAAAATTACTATGAAAAG
AAAGGGTAAATCAGAAGTGGAAGAGAATGGTGCAGTAGAAATCGCTCGATGCTCGCGGGGACAGTACTTTGGAGAGCTTG
CCCTGGTAACTAACAAACCTCGAGCAGCTTCTGCCCACGCCATTGGGACTGTCAAATGTTTAGCAATGGATGTGCAAGCA
TTTGAAAGGCTTCTGGGACCTTGCATGGAAATTATGAAAAGGAACATCGCTACCTATGAAGAACAGTTAGTTGCCCTGTT
TGGAACGAACATGGATATTGTAGCCAAAAACATTAAGAAGGGCCCAGCGCCATTCTACCCACTCGAAGACGGGACCGCCG
GCGAGCAGCTGCACAAAGCCATGAAGCGCTACGCCCTGGTGCCCGGCACCATCGCCTTTACCGACGCACATATCGAGGTG
GACATTACCTACGCCGAGTACTTCGAGATGAGCGTTCGGCTGGCAGAAGCTATGAAGCGCTATGGGCTGAATACAAACCA
TCGGATCGTGGTGTGCAGCGAGAATAGCTTGCAGTTCTTCATGCCCGTGTTGGGTGCCCTGTTCATCGGTGTGGCTGTGG
CCCCAGCTAACGACATCTACAACGAGCGCGAGCTGCTGAACAGCATGGGCATCAGCCAGCCCACCGTCGTATTCGTGAGC
AAGAAAGGGCTGCAAAAGATCCTCAACGTGCAAAAGAAGCTACCGATCATACAAAAGATCATCATCATGGATAGCAAGAC
CGACTACCAGGGCTTCCAAAGCATGTACACCTTCGTGACTTCCCATTTGCCACCCGGCTTCAACGAGTACGACTTCGTGC
CCGAGAGCTTCGACCGGGACAAAACCATCGCCCTGATCATGAACAGTAGTGGCAGTACCGGATTGCCCAAGGGCGTAGCC
CTACCGCACCGCACCGCTTGTGTCCGATTCAGTCATGCCCGCGACCCCATCTTCGGCAACCAGATCATCCCCGACACCGC
TATCCTCAGCGTGGTGCCATTTCACCACGGCTTCGGCATGTTCACCACGCTGGGCTACTTGATCTGCGGCTTTCGGGTCG
TGCTCATGTACCGCTTCGAGGAGGAGCTATTCTTGCGCAGCTTGCAAGACTATAAGATTCAATCTGCCCTGCTGGTGCCC
ACACTATTTAGCTTCTTCGCTAAGAGCACTCTCATCGACAAGTACGACCTAAGCAACTTGCACGAGATCGCCAGCGGCGG
GGCGCCGCTCAGCAAGGAGGTAGGTGAGGCCGTGGCCAAACGCTTCCACCTACCAGGCATCCGCCAGGGCTACGGCCTGA
CAGAAACAACCAGCGCCATTCTGATCACCCCCGAAGGGGACGACAAGCCTGGCGCAGTAGGCAAGGTGGTGCCCTTCTTC
GAGGCTAAGGTGGTGGACTTGGACACCGGTAAGACACTGGGTGTGAACCAGCGCGGCGAGCTGTGCGTCCGTGGCCCCAT
GATCATGAGCGGCTACGTTAACAACCCCGAGGCTACAAACGCTCTCATCGACAAGGACGGCTGGCTGCACAGCGGCGACA
TCGCCTACTGGGACGAGGACGAGCACTTCTTCGTTTAAAC

FIG. 67CW

QQQQQQQQQ) pBFB271 Sgf to Pme (SEQ ID NO:558)
GCGATCGCCATGTTGATCTGCGGCTTTCGGGTCGTGCTCATGTACCGCTTCGAGGAGGAGCTATTCTTGCGCAGCTTGCA
AGACTATAAGATTCAATCTGCCCTGCTGGTGCCCACACTATTTAGCTTCTTCGCTAAGAGCACTCTCATCGACAAGTACG
ACCTAAGCAACTTGCACGAGATCGCCAGCGGCGGGGCGCCGCTCAGCAAGGAGGTAGGTGAGGCCGTGGCCAAACGCTTC
CACCTACCAGGCATCCGCCAGGGCTACGGCCTGACAGAAACAACCAGCGCCATTCTGATCACCCCCGAAGGGGACGACAA
GCCTGGCGCAGTAGGCAAGGTGGTGCCCTTCTTCGAGGCTAAGGTGGTGGACTTGGACACCGGTAAGACACTGGGTGTGA
ACCAGCGCGGCGAGCTGTGCGTCCGTGGCCCCATGATCATGAGCGGCTACGTTAACAACCCCGAGGCTACAAACGCTCTC
ATCGACAAGGACGGCTGGCTGCACAGCGGCGACATCGCCTACTGGGACGAGGACGAGCACTTCTTCATCGTGGACCGGCT
GAAGAGCCTGATCAAATACAAGGGCTACCAGGTAGCCCCAGCCGAACTGGAGAGCATCCTGCTGCAACACCCCAACATCT
TCGACGCCGGGGTCGCCGGCCTGCCCGACGACGATGCCGGCGAGCTGCCCGCCGCAGTCGTCGTGCTGGAACACGGTAAA
ACCATGACCGAGAAGGAGATCGTGGACTATGTGGCCAGCCAGGTTACAACCGCCAAGAAGCTGCGCGGTGGTGTTGTGTT
CGTGGACGAGGTGCCTAAAGGACTGACCGGCAAGTTGGACGCCCGCAAGATCCGCGAGATTCTCATTAAGGCCAAGAAGG
GCTCGAGCGGAGGTTCAGGCGGTTCCGGAGGAGGTATGTATGAAAGCTTTATTGAGTCACTGCCATTCCTTAAATCTTTG
GAGTTTTCTGAACGCCTGAAAGTAGTAGATGTGATAGGCACCAAAGTATACAACGATGGAGAACAAATCATTGCTCAGGG
AGATTCGGCTGATTCTTTTTTCATTGTAGAATCTGGAGAAGTGAAAATTACTATGAAAAGAAAGGGTAAATCAGAAGTGG
AAGAGAATGGTGCAGTAGAAATCGCTCGATGCTCGCGGGGACAGTACTTTGGAGAGCTTGCCCTGGTAACTAACAAACCT
CGAGCAGCTTCTGCCCACGCCATTGGGACTGTCAAATGTTTAGCAATGGATGTGCAAGCATTTGAAAGGCTTCTGGGACC
TTGCATGGAAATTATGAAAAGGAACATCGCTACCTATGAAGAACAGTTAGTTGCCCTGTTTGGAACGAACATGGATATTG
TAGCCAAAAACATTAAGAAGGGCCCAGCGCCATTCTACCCACTCGAAGACGGGACCGCCGGCGAGCAGCTGCACAAAGCC
ATGAAGCGCTACGCCCTGGTGCCCGGCACCATCGCCTTTACCGACGCACATATCGAGGTGGACATTACCTACGCCGAGTA
CTTCGAGATGAGCGTTCGGCTGGCAGAAGCTATGAAGCGCTATGGGCTGAATACAAACCATCGGATCGTGGTGTGCAGCG
AGAATAGCTTGCAGTTCTTCATGCCCGTGTTGGGTGCCCTGTTCATCGGTGTGGCTGTGGCCCCAGCTAACGACATCTAC
AACGAGCGCGAGCTGCTGAACAGCATGGGCATCAGCCAGCCCACCGTCGTATTCGTGAGCAAGAAAGGGCTGCAAAAGAT
CCTCAACGTGCAAAAGAAGCTACCGATCATACAAAAGATCATCATCATGGATAGCAAGACCGACTACCAGGGCTTCCAAA
GCATGTACACCTTCGTGACTTCCCATTTGCCACCCGGCTTCAACGAGTACGACTTCGTGCCCGAGAGCTTCGACCGGGAC
AAAACCATCGCCCTGATCATGAACAGTAGTGGCAGTACCGGATTGCCCAAGGGCGTAGCCCTACCGCACCGCACCGCTTG
TGTCCGATTCAGTCATGCCCGCGACCCCATCTTCGGCAACCAGATCATCCCCGACACCGCTATCCTCAGCGTGGTGCCAT
TTCACCACGGCTTCGGCATGTTCACCACGCTGGTTTAAAC

RRRRRRRRR) pBFB272 Sgf to Pme (SEQ ID NO:559)
GCGATCGCCATGAAAACCATGACCGAGAAGGAGATCGTGGACTATGTGGCCAGCCAGGTTACAACCGCCAAGAAGCTGCG
CGGTGGTGTTGTGTTCGTGGACGAGGTGCCTAAAGGACTGACCGGCAAGTTGGACGCCCGCAAGATCCGCGAGATTCTCA
TTAAGGCCAAGAAGGGCTCGAGCGGAGGTTCAGGCGGTTCCGGAGGAGGTATGTATGAAAGCTTTATTGAGTCACTGCCA
TTCCTTAAATCTTTGGAGTTTTCTGAACGCCTGAAAGTAGTAGATGTGATAGGCACCAAAGTATACAACGATGGAGAACA
AATCATTGCTCAGGGAGATTCGGCTGATTCTTTTTTCATTGTAGAATCTGGAGAAGTGAAAATTACTATGAAAAGAAAGG
GTAAATCAGAAGTGGAAGAGAATGGTGCAGTAGAAATCGCTCGATGCTCGCGGGGACAGTACTTTGGAGAGCTTGCCCTG
GTAACTAACAAACCTCGAGCAGCTTCTGCCCACGCCATTGGGACTGTCAAATGTTTAGCAATGGATGTGCAAGCATTTGA
AAGGCTTCTGGGACCTTGCATGGAAATTATGAAAAGGAACATCGCTACCTATGAAGAACAGTTAGTTGCCCTGTTTGGAA
CGAACATGGATATTGTAGCCAAAAACATTAAGAAGGGCCCAGCGCCATTCTACCCACTCGAAGACGGGACCGCCGGCGAG
CAGCTGCACAAAGCCATGAAGCGCTACGCCCTGGTGCCCGGCACCATCGCCTTTACCGACGCACATATCGAGGTGGACAT
TACCTACGCCGAGTACTTCGAGATGAGCGTTCGGCTGGCAGAAGCTATGAAGCGCTATGGGCTGAATACAAACCATCGGA
TCGTGGTGTGCAGCGAGAATAGCTTGCAGTTCTTCATGCCCGTGTTGGGTGCCCTGTTCATCGGTGTGGCTGTGGCCCCA
GCTAACGACATCTACAACGAGCGCGAGCTGCTGAACAGCATGGGCATCAGCCAGCCCACCGTCGTATTCGTGAGCAAGAA
AGGGCTGCAAAAGATCCTCAACGTGCAAAAGAAGCTACCGATCATACAAAAGATCATCATCATGGATAGCAAGACCGACT
ACCAGGGCTTCCAAAGCATGTACACCTTCGTGACTTCCCATTTGCCACCCGGCTTCAACGAGTACGACTTCGTGCCCGAG
AGCTTCGACCGGGACAAAACCATCGCCCTGATCATGAACAGTAGTGGCAGTACCGGATTGCCCAAGGGCGTAGCCCTACC
GCACCGCACCGCTTGTGTCCGATTCAGTCATGCCCGCGACCCCATCTTCGGCAACCAGATCATCCCCGACACCGCTATCC
TCAGCGTGGTGCCATTTCACCACGGCTTCGGCATGTTCACCACGCTGGGCTACTTGATCTGCGGCTTTCGGGTCGTGCTC
ATGTACCGCTTCGAGGAGGAGCTATTCTTGCGCAGCTTGCAAGACTATAAGATTCAATCTGCCCTGCTGGTGCCCACACT
ATTTAGCTTCTTCGCTAAGAGCACTCTCATCGACAAGTACGACCTAAGCAACTTGCACGAGATCGCCAGCGGCGGGGCGC
CGCTCAGCAAGGAGGTAGGTGAGGCCGTGGCCAAACGCTTCCACCTACCAGGCATCCGCCAGGGCTACGGCCTGACAGAA
ACAACCAGCGCCATTCTGATCACCCCCGAAGGGGACGACAAGCCTGGCGCAGTAGGCAAGGTGGTGCCCTTCTTCGAGGC
TAAGGTGGTGGACTTGGACACCGGTAAGACACTGGGTGTGAACCAGCGCGGCGAGCTGTGCGTCCGTGGCCCCATGATCA
TGAGCGGCTACGTTAACAACCCCGAGGCTACAAACGCTCTCATCGACAAGGACGGCTGGCTGCACAGCGGCGACATCGCC
TACTGGGACGAGGACGAGCACTTCTTCATCGTGGACCGGCTGAAGAGCCTGATCAAATACAAGGGCTACCAGGTAGCCCC
AGCCGAACTGGAGAGCATCCTGCTGCAACACCCCAACATCTTCGACGCCGGGGTCGCCGGCCTGCCCGACGACGATGCCG
GCGAGCTGCCCGCCGCAGTCGTCGTGCTGGAAGTTTAAAC

*FIG. 67CX*

SSSSSSSSSS) pBFB317 Sgf to Pme (SEQ ID NO:560)
GCGATCGCCATGGAGGAGGAGCTATTCTTGCGCAGCTTGCAAGACTATAAGATTCAATCTGCCCTGCTGGTGCCCACACT
ATTTAGCTTCTTCGCTAAGAGCACTCTCATCGACAAGTACGACCTAAGCAACTTGCACGAGATCGCCAGCGGCGGGGCGC
CGCTCAGCAAGGAGGTAGGTGAGGCCGTGGCCAAACGCTTCCACCTACCAGGCATCCGCCAGGGCTACGGCCTGACAGAA
ACAACCAGCGCCATTCTGATCACCCCCGAAGGGGACGACAAGCCTGGCGCAGTAGGCAAGGTGGTGCCCTTCTTCGAGGC
TAAGGTGGTGGACTTGGACACCGGTAAGACACTGGGTGTGAACCAGCGCGGCGAGCTGTGCGTCCGTGGCCCCATGATCA
TGAGCGGCTACGTTAACAACCCCGAGGCTACAAACGCTCTCATCGACAAGGACGGCTGGCTGCACAGCGGCGACATCGCC
TACTGGGACGAGGACGAGCACTTCTTCATCGTGGACCGGCTGAAGAGCCTGATCAAATACAAGGGCTACCAGGTAGCCCC
AGCCGAACTGGAGAGCATCCTGCTGCAACACCCCAACATCTTCGACGCCGGGGTCGCCGGCCTGCCCGACGACGATGCCG
GCGAGCTGCCCGCCGCAGTCGTCGTGCTGGAACACGGTAAAACCATGACCGAGAAGGAGATCGTGGACTATGTGGCCAGC
CAGGTTACAACCGCCAAGAAGCTGCGCGGTGGTGTTGTGTTCGTGGACGAGGTGCCTAAAGGACTGACCGGCAAGTTGGA
CGCCCGCAAGATCCGCGAGATTCTCATTAAGGCCAAGAAGGGCTCGAGCGGAGGTTCAGGCGGTTCCGGAGGAGGTATGT
ATGAAAGCTTTATTGAGTCACTGCCATTCCTTAAATCTTTGGAGTTTTCTGAACGCCTGAAAGTAGTAGATGTGATAGGC
ACCAAAGTATACAACGATGGAGAACAAATCATTGCTCAGGGAGATTCGGCTGATTCTTTTTTCATTGTAGAATCTGGAGA
AGTGAAAATTACTATGAAAAGAAAGGGTAAATCAGAAGTGGAAGAGAATGGTGCAGTAGAAATCGCTCGATGCTCGCGGG
GACAGTACTTTGGAGAGCTTGCCCTGGTAACTAACAAACCTCGAGCAGCTTCTGCCCACGCCATTGGGACTGTCAAATGT
TTAGCAATGGATGTGCAAGCATTTGAAAGGCTTCTGGGACCTTGCATGGAAATTATGAAAAGGAACATCGCTACCTATGA
AGAACAGTTAGTTGCCCTGTTTGGAACGAACATGGATATTGTAGCCAAAAACATTAAGAAGGGCCCAGCGCCATTCTACC
CACTCGAAGACGGGACCGCCGGCGAGCAGCTGCACAAAGCCATGAAGCGCTACGCCCTGGTGCCCGGCACCATCGCCTTT
ACCGACGCACATATCGAGGTGGACATTACCTACGCCGAGTACTTCGAGATGAGCGTTCGGCTGGCAGAAGCTATGAAGCG
CTATGGGCTGAATACAAACCATCGGATCGTGGTGTGCAGCGAGAATAGCTTGCAGTTCTTCATGCCCGTGTTGGGTGCCC
TGTTCATCGGTGTGGCTGTGGCCCCAGCTAACGACATCTACAACGAGCGCGAGCTGCTGAACAGCATGGGCATCAGCCAG
CCCACCGTCGTATTCGTGAGCAAGAAAGGGCTGCAAAAGATCCTCAACGTGCAAAAGAAGCTACCGATCATACAAAAGAT
CATCATCATGGATAGCAAGACCGACTACCAGGGCTTCCAAAGCATGTACACCTTCGTGACTTCCCATTTGCCACCCGGCT
TCAACGAGTACGACTTCGTGCCCGAGAGCTTCGACCGGGACAAAACCATCGCCCTGATCATGAACAGTAGTGGCAGTACC
GGATTGCCCAAGGGCGTAGCCCTACCGCACCGCACCGCTTGTGTCCGATTCAGTCATGCCCGCGACCCCATCTTCGGCAA
CCAGATCATCCCCGACACCGCTATCCTCAGCGTGGTGCCATTTCACCACGGCTTCGGCATGTTCACCACGCTGGGCTACT
TGATCTGCGGCTTTCGGGTCGTGCTCATGTACGTTTAAAC

TTTTTTTTTT) pBFB318 Sgf to Pme (SEQ ID NO:561)
GCGATCGCCATGCCTGGCGCAGTAGGCAAGGTGGTGCCCTTCTTCGAGGCTAAGGTGGTGGACTTGGACACCGGTAAGAC
ACTGGGTGTGAACCAGCGCGGCGAGCTGTGCGTCCGTGGCCCCATGATCATGAGCGGCTACGTTAACAACCCCGAGGCTA
CAAACGCTCTCATCGACAAGGACGGCTGGCTGCACAGCGGCGACATCGCCTACTGGGACGAGGACGAGCACTTCTTCATC
GTGGACCGGCTGAAGAGCCTGATCAAATACAAGGGCTACCAGGTAGCCCCAGCCGAACTGGAGAGCATCCTGCTGCAACA
CCCCAACATCTTCGACGCCGGGGTCGCCGGCCTGCCCGACGACGATGCCGGCGAGCTGCCCGCCGCAGTCGTCGTGCTGG
AACACGGTAAAACCATGACCGAGAAGGAGATCGTGGACTATGTGGCCAGCCAGGTTACAACCGCCAAGAAGCTGCGCGGT
GGTGTTGTGTTCGTGGACGAGGTGCCTAAAGGACTGACCGGCAAGTTGGACGCCCGCAAGATCCGCGAGATTCTCATTAA
GGCCAAGAAGGGCTCGAGCGGAGGTTCAGGCGGTTCCGGAGGAGGTATGTATGAAAGCTTTATTGAGTCACTGCCATTCC
TTAAATCTTTGGAGTTTTCTGAACGCCTGAAAGTAGTAGATGTGATAGGCACCAAAGTATACAACGATGGAGAACAAATC
ATTGCTCAGGGAGATTCGGCTGATTCTTTTTTCATTGTAGAATCTGGAGAAGTGAAAATTACTATGAAAAGAAAGGGTAA
ATCAGAAGTGGAAGAGAATGGTGCAGTAGAAATCGCTCGATGCTCGCGGGGACAGTACTTTGGAGAGCTTGCCCTGGTAA
CTAACAAACCTCGAGCAGCTTCTGCCCACGCCATTGGGACTGTCAAATGTTTAGCAATGGATGTGCAAGCATTTGAAAGG
CTTCTGGGACCTTGCATGGAAATTATGAAAAGGAACATCGCTACCTATGAAGAACAGTTAGTTGCCCTGTTTGGAACGAA
CATGGATATTGTAGCCAAAAACATTAAGAAGGGCCCAGCGCCATTCTACCCACTCGAAGACGGGACCGCCGGCGAGCAGC
TGCACAAAGCCATGAAGCGCTACGCCCTGGTGCCCGGCACCATCGCCTTTACCGACGCACATATCGAGGTGGACATTACC
TACGCCGAGTACTTCGAGATGAGCGTTCGGCTGGCAGAAGCTATGAAGCGCTATGGGCTGAATACAAACCATCGGATCGT
GGTGTGCAGCGAGAATAGCTTGCAGTTCTTCATGCCCGTGTTGGGTGCCCTGTTCATCGGTGTGGCTGTGGCCCCAGCTA
ACGACATCTACAACGAGCGCGAGCTGCTGAACAGCATGGGCATCAGCCAGCCCACCGTCGTATTCGTGAGCAAGAAAGGG
CTGCAAAAGATCCTCAACGTGCAAAAGAAGCTACCGATCATACAAAAGATCATCATCATGGATAGCAAGACCGACTACCA
GGGCTTCCAAAGCATGTACACCTTCGTGACTTCCCATTTGCCACCCGGCTTCAACGAGTACGACTTCGTGCCCGAGAGCT
TCGACCGGGACAAAACCATCGCCCTGATCATGAACAGTAGTGGCAGTACCGGATTGCCCAAGGGCGTAGCCCTACCGCAC
CGCACCGCTTGTGTCCGATTCAGTCATGCCCGCGACCCCATCTTCGGCAACCAGATCATCCCCGACACCGCTATCCTCAG
CGTGGTGCCATTTCACCACGGCTTCGGCATGTTCACCACGCTGGGCTACTTGATCTGCGGCTTTCGGGTCGTGCTCATGT
ACCGCTTCGAGGAGGAGCTATTCTTGCGCAGCTTGCAAGACTATAAGATTCAATCTGCCCTGCTGGTGCCCACACTATTT
AGCTTCTTCGCTAAGAGCACTCTCATCGACAAGTACGACCTAAGCAACTTGCACGAGATCGCCAGCGGCGGGGCGCCGCT

*FIG. 67CY*

CAGCAAGGAGGTAGGTGAGGCCGTGGCCAAACGCTTCCACCTACCAGGCATCCGCCAGGGCTACGGCCTGACAGAAACAA
CCAGCGCCATTCTGATCACTCCAGAAGGGGTTTAAAC

UUUUUUUUUU) pBFB319 Sgf to Pme (SEQ ID NO:562)
GCGATCGCCATGGAGGTGGACATTACCTACGCCGAGTACTTCGAGATGAGCGTTCGGCTGGCAGAAGCTATGAAGCGCTA
TGGGCTGAATACAAACCATCGGATCGTGGTGTGCAGCGAGAATAGCTTGCAGTTCTTCATGCCCGTGTTGGGTGCCCTGT
TCATCGGTGTGGCTGTGGCCCCAGCTAACGACATCTACAACGAGCGCGAGCTGCTGAACAGCATGGGCATCAGCCAGCCC
ACCGTCGTATTCGTGAGCAAGAAAGGGCTGCAAAAGATCCTCAACGTGCAAAAGAAGCTACCGATCATACAAAAGATCAT
CATCATGGATAGCAAGACCGACTACCAGGGCTTCCAAAGCATGTACACCTTCGTGACTTCCCATTTGCCACCCGGCTTCA
ACGAGTACGACTTCGTGCCCGAGAGCTTCGACCGGGACAAAACCATCGCCCTGATCATGAACAGTAGTGGCAGTACCGGA
TTGCCCAAGGGCGTAGCCCTACCGCACCGCACCGCTTGTGTCCGATTCAGTCATGCCCGCGACCCCATCTTCGGCAACCA
GATCATCCCCGACACCGCTATCCTCAGCGTGGTGCCATTTCACCACGGCTTCGGCATGTTCACCACGCTGGGCTACTTGA
TCTGCGGCTTTCGGGTCGTGCTCATGTACCGCTTCGAGGAGGAGCTATTCTTGCGCAGCTTGCAAGACTATAAGATTCAA
TCTGCCCTGCTGGTGCCCACACTATTTAGCTTCTTCGCTAAGAGCACTCTCATCGACAAGTACGACCTAAGCAACTTGCA
CGAGATCGCCAGCGGCGGGGCGCCGCTCAGCAAGGAGGTAGGTGAGGCCGTGGCCAAACGCTTCCACCTACCAGGCATCC
GCCAGGGCTACGGCCTGACAGAAACAACCAGCGCCATTCTGATCACCCCCGAAGGGGACGACAAGCCTGGCGCAGTAGGC
AAGGTGGTGCCCTTCTTCGAGGCTAAGGTGGTGGACTTGGACACCGGTAAGACACTGGGTGTGAACCAGCGCGGCGAGCT
GTGCGTCCGTGGCCCCATGATCATGAGCGGCTACGTTAACAACCCCGAGGCTACAAACGCTCTCATCGACAAGGACGGCT
GGCTGCACAGCGGCGACATCGCCTACTGGGACGAGGACGAGCACTTCTTCATCGTGGACCGGCTGAAGAGCCTGATCAAA
TACAAGGGCTACCAGGTAGCCCCAGCCGAACTGGAGAGCATCCTGCTGCAACACCCCAACATCTTCGACGCCGGGGTCGC
CGGCCTGCCCGACGACGATGCCGGCGAGCTGCCCGCCGCAGTCGTCGTGCTGGAACACGGTAAAACCATGACCGAGAAGG
AGATCGTGGACTATGTGGCCAGCCAGGTTACAACCGCCAAGAAGCTGCGCGGTGGTGTTGTGTTCGTGGACGAGGTGCCT
AAAGGACTGACCGGCAAGTTGGACGCCCGCAAGATCCGCGAGATTCTCATTAAGGCCAAGAAGGGCTCGAGCGGAGGTTC
AGGCGGTTCCGGAGGAGGTATGTATGAAAGCTTTATTGAGTCACTGCCATTCCTTAAATCTTTGGAGTTTTCTGAACGCC
TGAAAGTAGTAGATGTGATAGGCACCAAAGTATACAACGATGGAGAACAAATCATTGCTCAGGGAGATTCGGCTGATTCT
TTTTTCATTGTAGAATCTGGAGAAGTGAAAATTACTATGAAAAGAAAGGGTAAATCAGAAGTGGAAGAGAATGGTGCAGT
AGAAATCGCTCGATGCTCGCGGGGACAGTACTTTGGAGAGCTTGCCCTGGTAACTAACAAACCTCGAGCAGCTTCTGCCC
ACGCCATTGGGACTGTCAAATGTTTAGCAATGGATGTGCAAGCATTTGAAAGGCTTCTGGGACCTTGCATGGAAATTATG
AAAAGGAACATCGCTACCTATGAAGAACAGTTAGTTGCCCTGTTTGGAACGAACATGGATATTGTAGCCAAAAACATTAA
GAAGGGCCCAGCGCCATTCTACCCACTCGAAGACGGGACCGCCGGCGAGCAGCTGCACAAAGCCATGAAGCGCTACGCCC
TGGTGCCCGGCACCATCGCCTTTACCGACGCAGTTTAAAC

VVVVVVVVVV) pBFB321 Sgf to Pme (SEQ ID NO:563)
GCGATCGCCATGATCTTCGGCAACCAGATCATCCCCGACACCGCTATCCTCAGCGTGGTGCCATTTCACCACGGCTTCGG
CATGTTCACCACGCTGGGCTACTTGATCTGCGGCTTTCGGGTCGTGCTCATGTACCGCTTCGAGGAGGAGCTATTCTTGC
GCAGCTTGCAAGACTATAAGATTCAATCTGCCCTGCTGGTGCCCACACTATTTAGCTTCTTCGCTAAGAGCACTCTCATC
GACAAGTACGACCTAAGCAACTTGCACGAGATCGCCAGCGGCGGGGCGCCGCTCAGCAAGGAGGTAGGTGAGGCCGTGGC
CAAACGCTTCCACCTACCAGGCATCCGCCAGGGCTACGGCCTGACAGAAACAACCAGCGCCATTCTGATCACCCCCGAAG
GGGACGACAAGCCTGGCGCAGTAGGCAAGGTGGTGCCCTTCTTCGAGGCTAAGGTGGTGGACTTGGACACCGGTAAGACA
CTGGGTGTGAACCAGCGCGGCGAGCTGTGCGTCCGTGGCCCCATGATCATGAGCGGCTACGTTAACAACCCCGAGGCTAC
AAACGCTCTCATCGACAAGGACGGCTGGCTGCACAGCGGCGACATCGCCTACTGGGACGAGGACGAGCACTTCTTCATCG
TGGACCGGCTGAAGAGCCTGATCAAATACAAGGGCTACCAGGTAGCCCCAGCCGAACTGGAGAGCATCCTGCTGCAACAC
CCCAACATCTTCGACGCCGGGGTCGCCGGCCTGCCCGACGACGATGCCGGCGAGCTGCCCGCCGCAGTCGTCGTGCTGGA
ACACGGTAAAACCATGACCGAGAAGGAGATCGTGGACTATGTGGCCAGCCAGGTTACAACCGCCAAGAAGCTGCGCGGTG
GTGTTGTGTTCGTGGACGAGGTGCCTAAAGGACTGACCGGCAAGTTGGACGCCCGCAAGATCCGCGAGATTCTCATTAAG
GCCAAGAAGGGCTCGAGCGGAGGTTCAGGCGGTTCCGGAGGAGGTATGTATGAAAGCTTTATTGAGTCACTGCCATTCCT
TAAATCTTTGGAGTTTTCTGAACGCCTGAAAGTAGTAGATGTGATAGGCACCAAAGTATACAACGATGGAGAACAAATCA
TTGCTCAGGGAGATTCGGCTGATTCTTTTTTCATTGTAGAATCTGGAGAAGTGAAAATTACTATGAAAAGAAAGGGTAAA
TCAGAAGTGGAAGAGAATGGTGCAGTAGAAATCGCTCGATGCTCGCGGGGACAGTACTTTGGAGAGCTTGCCCTGGTAAC
TAACAAACCTCGAGCAGCTTCTGCCCACGCCATTGGGACTGTCAAATGTTTAGCAATGGATGTGCAAGCATTTGAAAGGC
TTCTGGGACCTTGCATGGAAATTATGAAAAGGAACATCGCTACCTATGAAGAACAGTTAGTTGCCCTGTTTGGAACGAAC
ATGGATATTGTAGCCAAAAACATTAAGAAGGGCCCAGCGCCATTCTACCCACTCGAAGACGGGACCGCCGGCGAGCAGCT
GCACAAAGCCATGAAGCGCTACGCCCTGGTGCCCGGCACCATCGCCTTTACCGACGCACATATCGAGGTGGACATTACCT
ACGCCGAGTACTTCGAGATGAGCGTTCGGCTGGCAGAAGCTATGAAGCGCTATGGGCTGAATACAAACCATCGGATCGTG
GTGTGCAGCGAGAATAGCTTGCAGTTCTTCATGCCCGTGTTGGGTGCCCTGTTCATCGGTGTGGCTGTGGCCCCAGCTAA
CGACATCTACAACGAGCGCGAGCTGCTGAACAGCATGGGCATCAGCCAGCCCACCGTCGTATTCGTGAGCAAGAAAGGGC
TGCAAAAGATCCTCAACGTGCAAAAGAAGCTACCGATCATACAAAAGATCATCATCATGGATAGCAAGACCGACTACCAG

FIG. 67CZ

GGCTTCCAAAGCATGTACACCTTCGTGACTTCCCATTTGCCACCCGGCTTCAACGAGTACGACTTCGTGCCCGAGAGCTT
CGACCGGGACAAAACCATCGCCCTGATCATGAACAGTAGTGGCAGTACCGGATTGCCCAAGGGCGTAGCCCTACCGCACC
GCACCGCTTGTGTCCGATTCAGTCATGCCCGCGTTTAAAC

WWWWWWWWWW) pBFB322 Sgf to Pme (SEQ ID NO:564)
GCGATCGCCATGGACACCGCTATCCTCAGCGTGGTGCCATTTCACCACGGCTTCGGCATGTTCACCACGCTGGGCTACTT
GATCTGCGGCTTTCGGGTCGTGCTCATGTACCGCTTCGAGGAGGAGCTATTCTTGCGCAGCTTGCAAGACTATAAGATTC
AATCTGCCCTGCTGGTGCCCACACTATTTAGCTTCTTCGCTAAGAGCACTCTCATCGACAAGTACGACCTAAGCAACTTG
CACGAGATCGCCAGCGGCGGGGCGCCGCTCAGCAAGGAGGTAGGTGAGGCCGTGGCCAAACGCTTCCACCTACCAGGCAT
CCGCCAGGGCTACGGCCTGACAGAAACAACCAGCGCCATTCTGATCACCCCCGAAGGGGACGACAAGCCTGGCGCAGTAG
GCAAGGTGGTGCCCTTCTTCGAGGCTAAGGTGGTGGACTTGGACACTGGTAAGACACTGGGTGTGAACCAGCGCGGCGAG
CTGTGCGTCCGTGGCCCCATGATCATGAGCGGCTACGTTAACAACCCCGAGGCTACAAACGCTCTCATCGACAAGGACGG
CTGGCTGCACAGCGGCGACATCGCCTACTGGGACGAGGACGAGCACTTCTTCATCGTGGACCGGCTGAAGAGCCTGATCA
AATACAAGGGCTACCAGGTAGCCCCAGCCGAACTGGAGAGCATCCTGCTGCAACACCCCAACATCTTCGACGCCGGGGTC
GCCGGCCTGCCCGACGACGATGCCGGCGAGCTGCCCGCCGCAGTCGTCGTGCTGGAACACGGTAAAACCATGACCGAGAA
GGAGATCGTGGACTATGTGGCCAGCCAGGTTACAACCGCCAAGAAGCTGCGCGGTGGTGTTGTGTTCGTGGACGAGGTGC
CTAAAGGACTGACCGGCAAGTTGGACGCCCGCAAGATCCGCGAGATTCTCATTAAGGCCAAGAAGGGCTCGAGCGGAGGT
TCAGGCGGTTCCGGAGGAGGTATGTATGAAAGCTTTATTGAGTCACTGCCATTCCTTAAATCTTTGGAGTTTTCTGAACG
CCTGAAAGTAGTAGATGTGATAGGCACCAAAGTATACAACGATGGAGAACAAATCATTGCTCAGGGAGATTCGGCTGATT
CTTTTTTCATTGTAGAATCTGGAGAAGTGAAAATTACTATGAAAAGAAAGGGTAAATCAGAAGTGGAAGAGAATGGTGCA
GTAGAAATCGCTCGATGCTCGCGGGGACAGTACTTTGGAGAGCTTGCCCTGGTAACTAACAAACCTCGAGCAGCTTCTGC
CCACGCCATTGGGACTGTCAAATGTTTAGCAATGGATGTGCAAGCATTTGAAAGGCTTCTGGGACCTTGCATGGAAATTA
TGAAAAGGAACATCGCTACCTATGAAGAACAGTTAGTTGCCCTGTTTGGAACGAACATGGATATTGTAGCCAAAAACATT
AAGAAGGGCCCAGCGCCATTCTACCCACTCGAAGACGGGACCGCCGGCGAGCAGCTGCACAAAGCCATGAAGCGCTACGC
CCTGGTGCCCGGCACCATCGCCTTTACCGACGCACATATCGAGGTGGACATTACCTACGCCGAGTACTTCGAGATGAGCG
TTCGGCTGGCAGAAGCTATGAAGCGCTATGGGCTGAATACAAACCATCGGATCGTGGTGTGCAGCGAGAATAGCTTGCAG
TTCTTCATGCCCGTGTTGGGTGCCCTGTTCATCGGTGTGGCTGTGGCCCCAGCTAACGACATCTACAACGAGCGCGAGCT
GCTGAACAGCATGGGCATCAGCCAGCCCACCGTCGTATTCGTGAGCAAGAAAGGGCTGCAAAAGATCCTCAACGTGCAAA
AGAAGCTACCGATCATACAAAAGATCATCATCATGGATAGCAAGACCGACTACCAGGGCTTCCAAAGCATGTACACCTTC
GTGACTTCCCATTTGCCACCCGGCTTCAACGAGTACGACTTCGTGCCCGAGAGCTTCGACCGGGACAAAACCATCGCCCT
GATCATGAACAGTAGTGGCAGTACCGGATTGCCCAAGGGCGTAGCCCTACCGCACCGCACCGCTTGTGTCCGATTCAGTC
ATGCCCGCGACCCCATCTTCGGCAACCAGATCATCCCCGTTTAAAC

XXXXXXXXXX) pBFB325 Sgf to Pme (SEQ ID NO:565)
GCGATCGCCATGTTGCACGAGATCGCCAGCGGCGGGGCGCCGCTCAGCAAGGAGGTAGGTGAGGCCGTGGCCAAACGCTT
CCACCTACCAGGCATCCGCCAGGGCTACGGCCTGACAGAAACAACCAGCGCCATTCTGATCACCCCCGAAGGGGACGACA
AGCCTGGCGCAGTAGGCAAGGTGGTGCCCTTCTTCGAGGCTAAGGTGGTGGACTTGGACACCGGTAAGACACTGGGTGTG
AACCAGCGCGGCGAGCTGTGCGTCCGTGGCCCCATGATCATGAGCGGCTACGTTAACAACCCCGAGGCTACAAACGCTCT
CATCGACAAGGACGGCTGGCTGCACAGCGGCGACATCGCCTACTGGGACGAGGACGAGCACTTCTTCATCGTGGACCGGC
TGAAGAGCCTGATCAAATACAAGGGCTACCAGGTAGCCCCAGCCGAACTGGAGAGCATCCTGCTGCAACACCCCAACATC
TTCGACGCCGGGGTCGCCGGCCTGCCCGACGACGATGCCGGCGAGCTGCCCGCCGCAGTCGTCGTGCTGGAACACGGTAA
AACCATGACCGAGAAGGAGATCGTGGACTATGTGGCCAGCCAGGTTACAACCGCCAAGAAGCTGCGCGGTGGTGTTGTGT
TCGTGGACGAGGTGCCTAAAGGACTGACCGGCAAGTTGGACGCCCGCAAGATCCGCGAGATTCTCATTAAGGCCAAGAAG
GGCTCGAGCGGAGGTTCAGGCGGTTCCGGAGGAGGTATGTATGAAAGCTTTATTGAGTCACTGCCATTCCTTAAATCTTT
GGAGTTTTCTGAACGCCTGAAAGTAGTAGATGTGATAGGCACCAAAGTATACAACGATGGAGAACAAATCATTGCTCAGG
GAGATTCGGCTGATTCTTTTTTCATTGTAGAATCTGGAGAAGTGAAAATTACTATGAAAAGAAAGGGTAAATCAGAAGTG
GAAGAGAATGGTGCAGTAGAAATCGCTCGATGCTCGCGGGGACAGTACTTTGGAGAGCTTGCCCTGGTAACTAACAAACC
TCGAGCAGCTTCTGCCCACGCCATTGGGACTGTCAAATGTTTAGCAATGGATGTGCAAGCATTTGAAAGGCTTCTGGGAC
CTTGCATGGAAATTATGAAAAGGAACATCGCTACCTATGAAGAACAGTTAGTTGCCCTGTTTGGAACGAACATGGATATT
GTAGCCAAAAACATTAAGAAGGGCCCAGCGCCATTCTACCCACTCGAAGACGGGACCGCCGGCGAGCAGCTGCACAAAGC
CATGAAGCGCTACGCCCTGGTGCCCGGCACCATCGCCTTTACCGACGCACATATCGAGGTGGACATTACCTACGCCGAGT
ACTTCGAGATGAGCGTTCGGCTGGCAGAAGCTATGAAGCGCTATGGGCTGAATACAAACCATCGGATCGTGGTGTGCAGC
GAGAATAGCTTGCAGTTCTTCATGCCCGTGTTGGGTGCCCTGTTCATCGGTGTGGCTGTGGCCCCAGCTAACGACATCTA
CAACGAGCGCGAGCTGCTGAACAGCATGGGCATCAGCCAGCCCACCGTCGTATTCGTGAGCAAGAAAGGGCTGCAAAAGA
TCCTCAACGTGCAAAAGAAGCTACCGATCATACAAAAGATCATCATCATGGATAGCAAGACCGACTACCAGGGCTTCCAA
AGCATGTACACCTTCGTGACTTCCCATTTGCCACCCGGCTTCAACGAGTACGACTTCGTGCCCGAGAGCTTCGACCGGGA
CAAAACCATCGCCCTGATCATGAACAGTAGTGGCAGTACCGGATTGCCCAAGGGCGTAGCCCTACCGCACCGCACCGCTT

FIG. 67DA

GTGTCCGATTCAGTCATGCCCGCGACCCCATCTTCGGCAACCAGATCATCCCCGACACCGCTATCCTCAGCGTGGTGCCA
TTTCACCACGGCTTCGGCATGTTCACCACGCTGGGCTACTTGATCTGCGGCTTTCGGGTCGTGCTCATGTACCGCTTCGA
GGAGGAGCTATTCTTGCGCAGCTTGCAAGACTATAAGATTCAATCTGCCCTGCTGGTGCCCACACTATTTAGCTTCTTCG
CTAAGAGCACTCTCATCGACAAGTACGACCTAGTTTAAAC

YYYYYYYYYY) pBFB326 Sgf to Pme (SEQ ID NO:566)
GCGATCGCCATGACCGGTAAGACACTGGGTGTGAACCAGCGCGGCGAGCTGTGCGTCCGTGGCCCCATGATCATGAGCGG
CTACGTTAACAACCCCGAGGCTACAAACGCTCTCATCGACAAGGACGGCTGGCTGCACAGCGGCGACATCGCCTACTGGG
ACGAGGACGAGCACTTCTTCATCGTGGACCGGCTGAAGAGCCTGATCAAATACAAGGGCTACCAGGTAGCCCCAGCCGAA
CTGGAGAGCATCCTGCTGCAACACCCCAACATCTTCGACGCCGGGGTCGCCGGCCTGCCCGACGACGATGCCGGCGAGCT
GCCCGCCGCAGTCGTCGTGCTGGAACACGGTAAAACCATGACCGAGAAGGAGATCGTGGACTATGTGGCCAGCCAGGTTA
CAACCGCCAAGAAGCTGCGCGGTGGTGTTGTGTTCGTGGACGAGGTGCCTAAAGGACTGACCGGCAAGTTGGACGCCCGC
AAGATCCGCGAGATTCTCATTAAGGCCAAGAAGGGCTCGAGCGGAGGTTCAGGCGGTTCCGGAGGAGGTATGTATGAAAG
CTTTATTGAGTCACTGCCATTCCTTAAATCTTTGGAGTTTTCTGAACGCCTGAAAGTAGTAGATGTGATAGGCACCAAAG
TATACAACGATGGAGAACAAATCATTGCTCAGGGAGATTCGGCTGATTCTTTTTTCATTGTAGAATCTGGAGAAGTGAAA
ATTACTATGAAAAGAAAGGGTAAATCAGAAGTGGAAGAGAATGGTGCAGTAGAAATCGCTCGATGCTCGCGGGGACAGTA
CTTTGGAGAGCTTGCCCTGGTAACTAACAAACCTCGAGCAGCTTCTGCCCACGCCATTGGGACTGTCAAATGTTTAGCAA
TGGATGTGCAAGCATTTGAAAGGCTTCTGGGACCTTGCATGGAAATTATGAAAAGGAACATCGCTACCTATGAAGAACAG
TTAGTTGCCCTGTTTGGAACGAACATGGATATTGTAGCCAAAAACATTAAGAAGGGCCCAGCGCCATTCTACCCACTCGA
AGACGGGACCGCCGGCGAGCAGCTGCACAAAGCCATGAAGCGCTACGCCCTGGTGCCCGGCACCATCGCCTTTACCGACG
CACATATCGAGGTGGACATTACCTACGCCGAGTACTTCGAGATGAGCGTTCGGCTGGCAGAAGCTATGAAGCGCTATGGG
CTGAATACAAACCATCGGATCGTGGTGTGCAGCGAGAATAGCTTGCAGTTCTTCATGCCCGTGTTGGGTGCCCTGTTCAT
CGGTGTGGCTGTGGCCCCAGCTAACGACATCTACAACGAGCGCGAGCTGCTGAACAGCATGGGCATCAGCCAGCCCACCG
TCGTATTCGTGAGCAAGAAAGGGCTGCAAAAGATCCTCAACGTGCAAAAGAAGCTACCGATCATACAAAAGATCATCATC
ATGGATAGCAAGACCGACTACCAGGGCTTCCAAAGCATGTACACCTTCGTGACTTCCCATTTGCCACCCGGCTTCAACGA
GTACGACTTCGTGCCCGAGAGCTTCGACCGGGACAAAACCATCGCCCTGATCATGAACAGTAGTGGCAGTACCGGATTGC
CCAAGGGCGTAGCCCTACCGCACCGCACCGCTTGTGTCCGATTCAGTCATGCCCGCGACCCCATCTTCGGCAACCAGATC
ATCCCCGACACCGCTATCCTCAGCGTGGTGCCATTTCACCACGGCTTCGGCATGTTCACCACGCTGGGCTACTTGATCTG
CGGCTTTCGGGTCGTGCTCATGTACCGCTTCGAGGAGGAGCTATTCTTGCGCAGCTTGCAAGACTATAAGATTCAATCTG
CCCTGCTGGTGCCCACACTATTTAGCTTCTTCGCTAAGAGCACTCTCATCGACAAGTACGACCTAAGCAACTTGCACGAG
ATCGCCAGCGGCGGGGCGCCGCTCAGCAAGGAGGTAGGTGAGGCCGTGGCCAAACGCTTCCACCTACCAGGCATCCGCCA
GGGCTACGGCCTGACAGAAACAACCAGCGCCATTCTGATCACCCCCGAAGGGGACGACAAGCCTGGCGCAGTAGGCAAGG
TGGTGCCCTTCTTCGAGGCTAAGGTGGTGGACGTTTAAAC

ZZZZZZZZZZ) pBFB327 Sgf to Pme (SEQ ID NO:567)
GCGATCGCCATGAACCCCGAGGCTACAAACGCTCTCATCGACAAGGACGGCTGGCTGCACAGCGGCGACATCGCCTACTG
GGACGAGGACGAGCACTTCTTCATCGTGGACCGGCTGAAGAGCCTGATCAAATACAAGGGCTACCAGGTAGCCCCAGCCG
AACTGGAGAGCATCCTGCTGCAACACCCCAACATCTTCGACGCCGGGGTCGCCGGCCTGCCCGACGACGATGCCGGCGAG
CTGCCCGCCGCAGTCGTCGTGCTGGAACACGGTAAAACCATGACCGAGAAGGAGATCGTGGACTATGTGGCCAGCCAGGT
TACAACCGCCAAGAAGCTGCGCGGTGGTGTTGTGTTCGTGGACGAGGTGCCTAAAGGACTGACCGGCAAGTTGGACGCCC
GCAAGATCCGCGAGATTCTCATTAAGGCCAAGAAGGGCTCGAGCGGAGGTTCAGGCGGTTCCGGAGGAGGTATGTATGAA
AGCTTTATTGAGTCACTGCCATTCCTTAAATCTTTGGAGTTTTCTGAACGCCTGAAAGTAGTAGATGTGATAGGCACCAA
AGTATACAACGATGGAGAACAAATCATTGCTCAGGGAGATTCGGCTGATTCTTTTTTCATTGTAGAATCTGGAGAAGTGA
AAATTACTATGAAAAGAAAGGGTAAATCAGAAGTGGAAGAGAATGGTGCAGTAGAAATCGCTCGATGCTCGCGGGGACAG
TACTTTGGAGAGCTTGCCCTGGTAACTAACAAACCTCGAGCAGCTTCTGCCCACGCCATTGGGACTGTCAAATGTTTAGC
AATGGATGTGCAAGCATTTGAAAGGCTTCTGGGACCTTGCATGGAAATTATGAAAAGGAACATCGCTACCTATGAAGAAC
AGTTAGTTGCCCTGTTTGGAACGAACATGGATATTGTAGCCAAAAACATTAAGAAGGGCCCAGCGCCATTCTACCCACTC
GAAGACGGGACCGCCGGCGAGCAGCTGCACAAAGCCATGAAGCGCTACGCCCTGGTGCCCGGCACCATCGCCTTTACCGA
CGCACATATCGAGGTGGACATTACCTACGCCGAGTACTTCGAGATGAGCGTTCGGCTGGCAGAAGCTATGAAGCGCTATG
GGCTGAATACAAACCATCGGATCGTGGTGTGCAGCGAGAATAGCTTGCAGTTCTTCATGCCCGTGTTGGGTGCCCTGTTC
ATCGGTGTGGCTGTGGCCCCAGCTAACGACATCTACAACGAGCGCGAGCTGCTGAACAGCATGGGCATCAGCCAGCCCAC
CGTCGTATTCGTGAGCAAGAAAGGGCTGCAAAAGATCCTCAACGTGCAAAAGAAGCTACCGATCATACAAAAGATCATCA
TCATGGATAGCAAGACCGACTACCAGGGCTTCCAAAGCATGTACACCTTCGTGACTTCCCATTTGCCACCCGGCTTCAAC
GAGTACGACTTCGTGCCCGAGAGCTTCGACCGGGACAAAACCATCGCCCTGATCATGAACAGTAGTGGCAGTACCGGATT
GCCCAAGGGCGTAGCCCTACCGCACCGCACCGCTTGTGTCCGATTCAGTCATGCCCGCGACCCCATCTTCGGCAACCAGA
TCATCCCCGACACCGCTATCCTCAGCGTGGTGCCATTTCACCACGGCTTCGGCATGTTCACCACGCTGGGCTACTTGATC
TGCGGCTTTCGGGTCGTGCTCATGTACCGCTTCGAGGAGGAGCTATTCTTGCGCAGCTTGCAAGACTATAAGATTCAATC

FIG. 67DB

TGCCCTGCTGGTGCCCACACTATTTAGCTTCTTCGCTAAGAGCACTCTCATCGACAAGTACGACCTAAGCAACTTGCACG
AGATCGCCAGCGGCGGGGCGCCGCTCAGCAAGGAGGTAGGTGAGGCCGTGGCCAAACGCTTCCACCTACCAGGCATCCGC
CAGGGCTACGGCCTGACAGAAACAACCAGCGCCATTCTGATCACCCCCGAAGGGGACGACAAGCCTGGCGCAGTAGGCAA
GGTGGTGCCCTTCTTCGAGGCTAAGGTGGTGGACTTGGACACCGGTAAGACACTGGGTGTGAACCAGCGCGGCGAGCTGT
GCGTCCGTGGCCCCATGATCATGAGCGGCTACGTTTAAAC

AAAAAAAAAAA) pBFB328 Sgf to Pme (SEQ ID NO:568)
GCGATCGCCATGCATCGGATCGTGGTGTGCAGCGAGAATAGCTTGCAGTTCTTCATGCCCGTGTTGGGTGCCCTGTTCAT
CGGTGTGGCTGTGGCCCCAGCTAACGACATCTACAACGAGCGCGAGCTGCTGAACAGCATGGGCATCAGCCAGCCCACCG
TCGTATTCGTGAGCAAGAAAGGGCTGCAAAAGATCCTCAACGTGCAAAAGAAGCTACCGATCATACAAAAGATCATCATC
ATGGATAGCAAGACCGACTACCAGGGCTTCCAAAGCATGTACACCTTCGTGACTTCCCATTTGCCACCCGGCTTCAACGA
GTACGACTTCGTGCCCGAGAGCTTCGACCGGGACAAAACCATCGCCCTGATCATGAACAGTAGTGGCAGTACCGGATTGC
CCAAGGGCGTAGCCCTACCGCACCGCACCGCTTGTGTCCGATTCAGTCATGCCCGCGACCCCATCTTCGGCAACCAGATC
ATCCCCGACACCGCTATCCTCAGCGTGGTGCCATTTCACCACGGCTTCGGCATGTTCACCACGCTGGGCTACTTGATCTG
CGGCTTTCGGGTCGTGCTCATGTACCGCTTCGAGGAGGAGCTATTCTTGCGCAGCTTGCAAGACTATAAGATTCAATCTG
CCCTGCTGGTGCCCACACTATTTAGCTTCTTCGCTAAGAGCACTCTCATCGACAAGTACGACCTAAGCAACTTGCACGAG
ATCGCCAGCGGCGGGGCGCCGCTCAGCAAGGAGGTAGGTGAGGCCGTGGCCAAACGCTTCCACCTACCAGGCATCCGCCA
GGGCTACGGCCTGACAGAAACAACCAGCGCCATTCTGATCACCCCCGAAGGGGACGACAAGCCTGGCGCAGTAGGCAAGG
TGGTGCCCTTCTTCGAGGCTAAGGTGGTGGACTTGGACACCGGTAAGACACTGGGTGTGAACCAGCGCGGCGAGCTGTGC
GTCCGTGGCCCCATGATCATGAGCGGCTACGTTAACAACCCCGAGGCTACAAACGCTCTCATCGACAAGGACGGCTGGCT
GCACAGCGGCGACATCGCCTACTGGGACGAGGACGAGCACTTCTTCATCGTGGACCGGCTGAAGAGCCTGATCAAATACA
AGGGCTACCAGGTAGCCCCAGCCGAACTGGAGAGCATCCTGCTGCAACACCCCAACATCTTCGACGCCGGGGTCGCCGGC
CTGCCCGACGACGATGCCGGCGAGCTGCCCGCCGCAGTCGTCGTGCTGGAACACGGTAAAACCATGACCGAGAAGGAGAT
CGTGGACTATGTGGCCAGCCAGGTTACAACCGCCAAGAAGCTGCGCGGTGGTGTTGTGTTCGTGGACGAGGTGCCTAAAG
GACTGACCGGCAAGTTGGACGCCCGCAAGATCCGCGAGATTCTCATTAAGGCCAAGAAGGGCTCGAGCGGAGGTTCAGGC
GGTTCCGGAGGAGGTATGTATGAAAGCTTTATTGAGTCACTGCCATTCCTTAAATCTTTGGAGTTTTCTGAACGCCTGAA
AGTAGTAGATGTGATAGGCACCAAAGTATACAACGATGGAGAACAAATCATTGCTCAGGGAGATTCGGCTGATTCTTTTT
TCATTGTAGAATCTGGAGAAGTGAAAATTACTATGAAAAGAAAGGGTAAATCAGAAGTGGAAGAGAATGGTGCAGTAGAA
ATCGCTCGATGCTCGCGGGGACAGTACTTTGGAGAGCTTGCCCTGGTAACTAACAAACCTCGAGCAGCTTCTGCCCACGC
CATTGGGACTGTCAAATGTTTAGCAATGGATGTGCAAGCATTTGAAAGGCTTCTGGGACCTTGCATGGAAATTATGAAAA
GGAACATCGCTACCTATGAAGAACAGTTAGTTGCCCTGTTTGGAACGAACATGGATATTGTAGCCAAAAACATTAAGAAG
GGCCCAGCGCCATTCTACCCACTCGAAGACGGGACCGCCGGCGAGCAGCTGCACAAAGCCATGAAGCGCTACGCCCTGGT
GCCCGGCACCATCGCCTTTACCGACGCACATATCGAGGTGGACATTACCTACGCCGAGTACTTCGAGATGAGCGTTCGGC
TGGCAGAAGCTATGAAGCGCTATGGGCTGAATGTTTAAAC

BBBBBBBBBBB) pBFB329 Sgf to Pme (SEQ ID NO:569)
GCGATCGCCATGAATAGCTTGCAGTTCTTCATGCCCGTGTTGGGTGCCCTGTTCATCGGTGTGGCTGTGGCCCCAGCTAA
CGACATCTACAACGAGCGCGAGCTGCTGAACAGCATGGGCATCAGCCAGCCCACCGTCGTATTCGTGAGCAAGAAAGGGC
TGCAAAAGATCCTCAACGTGCAAAAGAAGCTACCGATCATACAAAAGATCATCATCATGGATAGCAAGACCGACTACCAG
GGCTTCCAAAGCATGTACACCTTCGTGACTTCCCATTTGCCACCCGGCTTCAACGAGTACGACTTCGTGCCCGAGAGCTT
CGACCGGGACAAAACCATCGCCCTGATCATGAACAGTAGTGGCAGTACCGGATTGCCCAAGGGCGTAGCCCTACCGCACC
GCACCGCTTGTGTCCGATTCAGTCATGCCCGCGACCCCATCTTCGGCAACCAGATCATCCCCGACACCGCTATCCTCAGC
GTGGTGCCATTTCACCACGGCTTCGGCATGTTCACCACGCTGGGCTACTTGATCTGCGGCTTTCGGGTCGTGCTCATGTA
CCGCTTCGAGGAGGAGCTATTCTTGCGCAGCTTGCAAGACTATAAGATTCAATCTGCCCTGCTGGTGCCCACACTATTTA
GCTTCTTCGCTAAGAGCACTCTCATCGACAAGTACGACCTAAGCAACTTGCACGAGATCGCCAGCGGCGGGGCGCCGCTC
AGCAAGGAGGTAGGTGAGGCCGTGGCCAAACGCTTCCACCTACCAGGCATCCGCCAGGGCTACGGCCTGACAGAAACAAC
CAGCGCCATTCTGATCACCCCCGAAGGGGACGACAAGCCTGGCGCAGTAGGCAAGGTGGTGCCCTTCTTCGAGGCTAAGG
TGGTGGACTTGGACACCGGTAAGACACTGGGTGTGAACCAGCGCGGCGAGCTGTGCGTCCGTGGCCCCATGATCATGAGC
GGCTACGTTAACAACCCCGAGGCTACAAACGCTCTCATCGACAAGGACGGCTGGCTGCACAGCGGCGACATCGCCTACTG
GGACGAGGACGAGCACTTCTTCATCGTGGACCGGCTGAAGAGCCTGATCAAATACAAGGGCTACCAGGTAGCCCCAGCCG
AACTGGAGAGCATCCTGCTGCAACACCCCAACATCTTCGACGCCGGGGTCGCCGGCCTGCCCGACGACGATGCCGGCGAG
CTGCCCGCCGCAGTCGTCGTGCTGGAACACGGTAAAACCATGACCGAGAAGGAGATCGTGGACTATGTGGCCAGCCAGGT
TACAACCGCCAAGAAGCTGCGCGGTGGTGTTGTGTTCGTGGACGAGGTGCCTAAAGGACTGACCGGCAAGTTGGACGCCC
GCAAGATCCGCGAGATTCTCATTAAGGCCAAGAAGGGCTCGAGCGGAGGTTCAGGCGGTTCCGGAGGAGGTATGTATGAA
AGCTTTATTGAGTCACTGCCATTCCTTAAATCTTTGGAGTTTTCTGAACGCCTGAAAGTAGTAGATGTGATAGGCACCAA
AGTATACAACGATGGAGAACAAATCATTGCTCAGGGAGATTCGGCTGATTCTTTTTTCATTGTAGAATCTGGAGAAGTGA
AAATTACTATGAAAAGAAAGGGTAAATCAGAAGTGGAAGAGAATGGTGCAGTAGAAATCGCTCGATGCTCGCGGGGACAG

FIG. 67DC

TACTTTGGAGAGCTTGCCCTGGTAACTAACAAACCTCGAGCAGCTTCTGCCCACGCCATTGGGACTGTCAAATGTTTAGC
AATGGATGTGCAAGCATTTGAAAGGCTTCTGGGACCTTGCATGGAAATTATGAAAAGGAACATCGCTACCTATGAAGAAC
AGTTAGTTGCCCTGTTTGGAACGAACATGGATATTGTAGCCAAAAACATTAAGAAGGGCCCAGCGCCATTCTACCCACTC
GAAGACGGGACCGCCGGCGAGCAGCTGCACAAAGCCATGAAGCGCTACGCCCTGGTGCCCGGCACCATCGCCTTTACCGA
CGCACATATCGAGGTGGACATTACCTACGCCGAGTACTTCGAGATGAGCGTTCGGCTGGCAGAAGCTATGAAGCGCTATG
GGCTGAATACAAACCATCGGATCGTGGTGTGCGTTTAAAC

CCCCCCCCCCC) pBFB403 Sgf to Pme (SEQ ID NO:570)
GCGATCGCCATGGCCAAAAACATTAAGAAGGGCCCAGCGCCATTCTACCCACTCGAAGACGGGACCGCCGGCGAGCAGCT
GCACAAAGCCATGAAGCGCTACGCCCTGGTGCCCGGCACCATCGCCTTTACCGACGCACATATCGAGGTGGACATTACCT
ACGCCGAGTACTTCGAGATGAGCGTTCGGCTGGCAGAAGCTATGAAGCGCTATGGGCTGAATACAAACCATCGGATCGTG
GTGTGCAGCGAGAATAGCTTGCAGTTCTTCATGCCCGTGTTGGGTGCCCTGTTCATCGGTGTGGCTGTGGCCCCAGCTAA
CGACATCTACAACGAGCGCGAGCTGCTGAACAGCATGGGCATCAGCCAGCCCACCGTCGTATTCGTGAGCAAGAAAGGGC
TGCAAAAGATCCTCAACGTGCAAAAGAAGCTACCGATCATACAAAAGATCATCATCATGGATAGCAAGACCGACTACCAG
GGCTTCCAAAGCATGTACACCTTCGTGACTTCCCATTTGCCACCCGGCTTCAACGAGTACGACTTCGTGCCCGAGAGCTT
CGACCGGGACAAAACCATCGCCCTGATCATGAACAGTAGTGGCAGTACCGGATTGCCCAAGGGCGTAGCCCTACCGCACC
GCACCGCTTGTGTCCGATTCAGTCATGCCCGCGACCCCATCTTCGGCAACCAGATCATCCCCGGCTCGACCGGAATGTAT
GAAAGCTTTATTGAGTCACTGCCATTCCTTAAATCTTTGGAGTTTTCTGAACGCCTGAAAGTAGTAGATGTGATAGGCAC
CAAAGTATACAACGATGGAGAACAAATCATTGCTCAGGGAGATTCGGCTGATTCTTTTTTCATTGTAGAATCTGGAGAAG
TGAAAATTACTATGAAAAGAAAGGGTAAATCAGAAGTGGAAGAGAATGGTGCAGTAGAAATCGCTCGATGCTCGCGGGGA
CAGTACTTTGGAGAGCTTGCCCTGGTAACTAACAAACCTCGAGCAGCTTCTGCCCACGCCATTGGGACTGTCAAATGTTT
AGCAATGGATGTGCAAGCATTTGAAAGGCTTCTGGGACCTTGCATGGAAATTATGAAAAGGAACATCGCTACCTATGAAG
AACAGTTAGTTGCCCTGTTTGGAACGAACATGGATATTGTTGGGAGCTCCGGTGACACCGCTATCCTCAGCGTGGTGCCA
TTTCACCACGGCTTCGGCATGTTCACCACGCTGGGCTACTTGATCTGCGGCTTTCGGGTCGTGCTCATGTACCGCTTCGA
GGAGGAGCTATTCTTGCGCAGCTTGCAAGACTATAAGATTCAATCTGCCCTGCTGGTGCCCACACTATTTAGCTTCTTCG
CTAAGAGCACTCTCATCGACAAGTACGACCTAAGCAACTTGCACGAGATCGCCAGCGGCGGGGCGCCGCTCAGCAAGGAG
GTAGGTGAGGCCGTGGCCAAACGCTTCCACCTACCAGGCATCCGCCAGGGCTACGGCCTGACAGAAACAACCAGCGCCAT
TCTGATCACCCCCGAAGGGGACGACAAGCCTGGCGCAGTAGGCAAGGTGGTGCCCTTCTTCGAGGCTAAGGTGGTGGACT
TGGACACTGGTAAGACACTGGGTGTGAACCAGCGCGGCGAGCTGTGCGTCCGTGGCCCCATGATCATGAGCGGCTACGTT
AACAACCCCGAGGCTACAAACGCTCTCATCGACAAGGACGGCTGGCTGCACAGCGGCGACATCGCCTACTGGGACGAGGA
CGAGCACTTCTTCATCGTGGACCGGCTGAAGAGCCTGATCAAATACAAGGGCTACCAGGTAGCCCCAGCCGAACTGGAGA
GCATCCTGCTGCAACACCCCAACATCTTCGACGCCGGGGTCGCCGGCCTGCCCGACGACGATGCCGGCGAGCTGCCCGCC
GCAGTCGTCGTGCTGGAACACGGTAAAACCATGACCGAGAAGGAGATCGTGGACTATGTGGCCAGCCAGGTTACAACCGC
CAAGAAGCTGCGCGGTGGTGTTGTGTTCGTGGACGAGGTGCCTAAAGGACTGACCGGCAAGTTGGACGCCCGCAAGATCC
GCGAGATTCTCATTAAGGCCAAGAAGTAGGTTTAAAC

DDDDDDDDDDD) pBFB404 Sgf to Pme (SEQ ID NO:571)
GCGATCGCCATGGCCAAAAACATTAAGAAGGGCCCAGCGCCATTCTACCCACTCGAAGACGGGACCGCCGGCGAGCAGCT
GCACAAAGCCATGAAGCGCTACGCCCTGGTGCCCGGCACCATCGCCTTTACCGACGCACATATCGAGGTGGACATTACCT
ACGCCGAGTACTTCGAGATGAGCGTTCGGCTGGCAGAAGCTATGAAGCGCTATGGGCTGAATACAAACCATCGGATCGTG
GTGTGCAGCGAGAATAGCTTGCAGTTCTTCATGCCCGTGTTGGGTGCCCTGTTCATCGGTGTGGCTGTGGCCCCAGCTAA
CGACATCTACAACGAGCGCGAGCTGCTGAACAGCATGGGCATCAGCCAGCCCACCGTCGTATTCGTGAGCAAGAAAGGGC
TGCAAAAGATCCTCAACGTGCAAAAGAAGCTACCGATCATACAAAAGATCATCATCATGGATAGCAAGACCGACTACCAG
GGCTTCCAAAGCATGTACACCTTCGTGACTTCCCATTTGCCACCCGGCTTCAACGAGTACGACTTCGTGCCCGAGAGCTT
CGACCGGGACAAAACCATCGCCCTGATCATGAACAGTAGTGGCAGTACCGGATTGCCCAAGGGCGTAGCCCTACCGCACC
GCACCGCTTGTGTCCGATTCAGTCATGCCCGCGACCCCATCTTCGGCAACCAGATCATCCCCGGCTCGAGCGGAGGTTCA
GGCGGTTCCGGAATGTATGAAAGCTTTATTGAGTCACTGCCATTCCTTAAATCTTTGGAGTTTTCTGAACGCCTGAAAGT
AGTAGATGTGATAGGCACCAAAGTATACAACGATGGAGAACAAATCATTGCTCAGGGAGATTCGGCTGATTCTTTTTTCA
TTGTAGAATCTGGAGAAGTGAAAATTACTATGAAAAGAAAGGGTAAATCAGAAGTGGAAGAGAATGGTGCAGTAGAAATC
GCTCGATGCTCGCGGGGACAGTACTTTGGAGAGCTTGCCCTGGTAACTAACAAACCTCGAGCAGCTTCTGCCCACGCCAT
TGGGACTGTCAAATGTTTAGCAATGGATGTGCAAGCATTTGAAAGGCTTCTGGGACCTTGCATGGAAATTATGAAAAGGA
ACATCGCTACCTATGAAGAACAGTTAGTTGCCCTGTTTGGAACGAACATGGATATTGTAGGGTCAGGTGGATCTGGAGGG
AGCTCCGGTGACACCGCTATCCTCAGCGTGGTGCCATTTCACCACGGCTTCGGCATGTTCACCACGCTGGGCTACTTGAT
CTGCGGCTTTCGGGTCGTGCTCATGTACCGCTTCGAGGAGGAGCTATTCTTGCGCAGCTTGCAAGACTATAAGATTCAAT
CTGCCCTGCTGGTGCCCACACTATTTAGCTTCTTCGCTAAGAGCACTCTCATCGACAAGTACGACCTAAGCAACTTGCAC
GAGATCGCCAGCGGCGGGGCGCCGCTCAGCAAGGAGGTAGGTGAGGCCGTGGCCAAACGCTTCCACCTACCAGGCATCCG
CCAGGGCTACGGCCTGACAGAAACAACCAGCGCCATTCTGATCACCCCCGAAGGGGACGACAAGCCTGGCGCAGTAGGCA

*FIG. 67DD*

AGGTGGTGCCCTTCTTCGAGGCTAAGGTGGTGGACTTGGACACTGGTAAGACACTGGGTGTGAACCAGCGCGGCGAGCTG
TGCGTCCGTGGCCCCATGATCATGAGCGGCTACGTTAACAACCCCGAGGCTACAAACGCTCTCATCGACAAGGACGGCTG
GCTGCACAGCGGCGACATCGCCTACTGGGACGAGGACGAGCACTTCTTCATCGTGGACCGGCTGAAGAGCCTGATCAAAT
ACAAGGGCTACCAGGTAGCCCCAGCCGAACTGGAGAGCATCCTGCTGCAACACCCCAACATCTTCGACGCCGGGGTCGCC
GGCCTGCCCGACGACGATGCCGGCGAGCTGCCCGCCGCAGTCGTCGTGCTGGAACACGGTAAAACCATGACCGAGAAGGA
GATCGTGGACTATGTGGCCAGCCAGGTTACAACCGCCAAGAAGCTGCGCGGTGGTGTTGTGTTCGTGGACGAGGTGCCTA
AAGGACTGACCGGCAAGTTGGACGCCCGCAAGATCCGCGAGATTCTCATTAAGGCCAAGAAGTAGGTTTAAAC

EEEEEEEEEEE) pBFB405 Sgf to Pme (SEQ ID NO:572)
GCGATCGCCATGGCCAAAAACATTAAGAAGGGCCCGCGCCATTCTACCCACTCGAAGACGGGACCGCCGGCGAGCAGCTG
CACAAAGCCATGAAGCGCTACGCCCTGGTGCCCGGCACCATCGCCTTTACCGACGCACATATCGAGGTGGACATTACCTA
CGCCGAGTACTTCGAGATGAGCGTTCGGCTGGCAGAAGCTATGAAGCGCTATGGGCTGAATACAAACCATCGGATCGTGG
TGTGCAGCGAGAATAGCTTGCAGTTCTTCATGCCCGTGTTGGGTGCCCTGTTCATCGGTGTGGCTGTGGCCCCAGCTAAC
GACATCTACAACGAGCGCGAGCTGCTGAACAGCATGGGCATCAGCCAGCCCACCGTCGTATTCGTGAGCAAGAAAGGGCT
GCAAAAGATCCTCAACGTGCAAAAGAAGCTACCGATCATACAAAAGATCATCATCATGGATAGCAAGACCGACTACCAGG
GCTTCCAAAGCATGTACACCTTCGTGACTTCCCATTTGCCACCCGGCTTCAACGAGTACGACTTCGTGCCCGAGAGCTTC
GACCGGGACAAAACCATCGCCCTGATCATGAACAGTAGTGGCAGTACCGGATTGCCCAAGGGCGTAGCCCTACCGCACCG
CACCGCTTGTGTCCGATTCAGTCATGCCCGCGACCCCATCTTCGGCAACCAGATCATCCCCGGCTCGAGCGGAGGTTCAG
GCGGTTCCGGAGGAGGTTCTGGCGGATCAGGCGGTTCGGGGATGTATGAAAGCTTTATTGAGTCACTGCCATTCCTTAAA
TCTTTGGAGTTTTCTGAACGCCTGAAAGTAGTAGATGTGATAGGCACCAAAGTATACAACGATGGAGAACAAATCATTGC
TCAGGGAGATTCGGCTGATTCTTTTTTCATTGTAGAATCTGGAGAAGTGAAAATTACTATGAAAAGAAAGGGTAAATCAG
AAGTGGAAGAGAATGGTGCAGTAGAAATCGCTCGATGCTCGCGGGGACAGTACTTTGGAGAGCTTGCCCTGGTAACTAAC
AAACCTCGAGCAGCTTCTGCCCACGCCATTGGGACTGTCAAATGTTTAGCAATGGATGTGCAAGCATTTGAAAGGCTTCT
GGGACCTTGCATGGAAATTATGAAAAGGAACATCGCTACCTATGAAGAACAGTTAGTTGCCCTGTTTGGAACGAACATGG
ATATTGTTGGGTCCGGTGGATCCGGTGGCAGCGGAGGGACGTCAGGTGGATCTGGAGGGAGCTCCGGTGACACCGCTATC
CTCAGCGTGGTGCCATTTCACCACGGCTTCGGCATGTTCACCACGCTGGGCTACTTGATCTGCGGCTTTCGGGTCGTGCT
CATGTACCGCTTCGAGGAGGAGCTATTCTTGCGCAGCTTGCAAGACTATAAGATTCAATCTGCCCTGCTGGTGCCCACAC
TATTTAGCTTCTTCGCTAAGAGCACTCTCATCGACAAGTACGACCTAAGCAACTTGCACGAGATCGCCAGCGGCGGGGCG
CCGCTCAGCAAGGAGGTAGGTGAGGCCGTGGCCAAACGCTTCCACCTACCAGGCATCCGCCAGGGCTACGGCCTGACAGA
AACAACCAGCGCCATTCTGATCACCCCCGAAGGGGACGACAAGCCTGGCGCAGTAGGCAAGGTGGTGCCCTTCTTCGAGG
CTAAGGTGGTGGACTTGGACACTGGTAAGACACTGGGTGTGAACCAGCGCGGCGAGCTGTGCGTCCGTGGCCCCATGATC
ATGAGCGGCTACGTTAACAACCCCGAGGCTACAAACGCTCTCATCGACAAGGACGGCTGGCTGCACAGCGGCGACATCGC
CTACTGGGACGAGGACGAGCACTTCTTCATCGTGGACCGGCTGAAGAGCCTGATCAAATACAAGGGCTACCAGGTAGCCC
CAGCCGAACTGGAGAGCATCCTGCTGCAACACCCCAACATCTTCGACGCCGGGGTCGCCGGCCTGCCCGACGACGATGCC
GGCGAGCTGCCCGCCGCAGTCGTCGTGCTGGAACACGGTAAAACCATGACCGAGAAGGAGATCGTGGACTATGTGGCCAG
CCAGGTTACAACCGCCAAGAAGCTGCGCGGTGGTGTTGTGTTCGTGGACGAGGTGCCTAAAGGACTGACCGGCAAGTTGG
ACGCCCGCAAGATCCGCGAGATTCTCATTAAGGCCAAGAAGTAGGTTTAAAC

FFFFFFFFFFF) pBFB406 Sgf to Pme (SEQ ID NO:573)
GCGATCGCCATGGCCAAAAACATTAAGAAGGGCCCAGCGCCATTCTACCCACTCGAAGACGGGACCGCCGGCGAGCAGCT
GCACAAAGCCATGAAGCGCTACGCCCTGGTGCCCGGCACCATCGCCTTTACCGACGCACATATCGAGGTGGACATTACCT
ACGCCGAGTACTTCGAGATGAGCGTTCGGCTGGCAGAAGCTATGAAGCGCTATGGGCTGAATACAAACCATCGGATCGTG
GTGTGCAGCGAGAATAGCTTGCAGTTCTTCATGCCCGTGTTGGGTGCCCTGTTCATCGGTGTGGCTGTGGCCCCAGCTAA
CGACATCTACAACGAGCGCGAGCTGCTGAACAGCATGGGCATCAGCCAGCCCACCGTCGTATTCGTGAGCAAGAAAGGGC
TGCAAAAGATCCTCAACGTGCAAAAGAAGCTACCGATCATACAAAAGATCATCATCATGGATAGCAAGACCGACTACCAG
GGCTTCCAAAGCATGTACACCTTCGTGACTTCCCATTTGCCACCCGGCTTCAACGAGTACGACTTCGTGCCCGAGAGCTT
CGACCGGGACAAAACCATCGCCCTGATCATGAACAGTAGTGGCAGTACCGGATTGCCCAAGGGCGTAGCCCTACCGCACC
GCACCGCTTGTGTCCGATTCAGTCATGCCCGCGACCCCATCTTCGGCAACCAGATCATCCCCGACACCGCTATCCTCAGC
GTGGTGCCATTTCACCACGGCTTCGGCATGTTCACCACGCTGGGCTACTTGATCTGCGGCTTTCGGGTCGTGCTCATGTA
CCGCTTCGAGGAGGAGCTATTCTTGCGCAGCTTGCAAGACTATAAGATTCAATCTGCCCTGCTGGTGCCCACACTATTTA
GCTTCTTCGCTAAGAGCACTCTCATCGACAAGTACGACCTAAGCAACTTGCACGAGATCGCCAGCGGCGGGGCGCCGCTC
AGCAAGGAGGTAGGTGAGGCCGTGGCCAAACGCTTCCACCTACCAGGCATCCGCCAGGGCTACGGCCTGACAGAAACAAC
CAGCGCCATTCTGATCACCCCCGAAGGGGGCTCGACCGGAATGTATGAAAGCTTTATTGAGTCACTGCCATTCCTTAAAT
CTTTGGAGTTTTCTGAACGCCTGAAAGTAGTAGATGTGATAGGCACCAAAGTATACAACGATGGAGAACAAATCATTGCT
CAGGGAGATTCGGCTGATTCTTTTTTCATTGTAGAATCTGGAGAAGTGAAAATTACTATGAAAAGAAAGGGTAAATCAGA
AGTGGAAGAGAATGGTGCAGTAGAAATCGCTCGATGCTCGCGGGGACAGTACTTTGGAGAGCTTGCCCTGGTAACTAACA
AACCTCGAGCAGCTTCTGCCCACGCCATTGGGACTGTCAAATGTTTAGCAATGGATGTGCAAGCATTTGAAAGGCTTCTG

FIG. 67DE

GGACCTTGCATGGAAATTATGAAAAGGAACATCGCTACCTATGAAGAACAGTTAGTTGCCCTGTTTGGAACGAACATGGA
TATTGTTGGGAGCTCCGGTCCTGGCGCAGTAGGCAAGGTGGTGCCCTTCTTCGAGGCTAAGGTGGTGGACTTGGACACTG
GTAAGACACTGGGTGTGAACCAGCGCGGCGAGCTGTGCGTCCGTGGCCCCATGATCATGAGCGGCTACGTTAACAACCCC
GAGGCTACAAACGCTCTCATCGACAAGGACGGCTGGCTGCACAGCGGCGACATCGCCTACTGGGACGAGGACGAGCACTT
CTTCATCGTGGACCGGCTGAAGAGCCTGATCAAATACAAGGGCTACCAGGTAGCCCCAGCCGAACTGGAGAGCATCCTGC
TGCAACACCCCAACATCTTCGACGCCGGGGTCGCCGGCCTGCCCGACGACGATGCCGGCGAGCTGCCCGCCGCAGTCGTC
GTGCTGGAACACGGTAAAACCATGACCGAGAAGGAGATCGTGGACTATGTGGCCAGCCAGGTTACAACCGCCAAGAAGCT
GCGCGGTGGTGTTGTGTTCGTGGACGAGGTGCCTAAAGGACTGACCGGCAAGTTGGACGCCCGCAAGATCCGCGAGATTC
TCATTAAGGCCAAGAAGTAGGTTTAAAC

GGGGGGGGGGG) pBFB407 Sgf to Pme (SEQ ID NO:574)
GCGATCGCCATGGCCAAAAACATTAAGAAGGGCCCAGCGCCATTCTACCCACTCGAAGACGGGACCGCCGGCGAGCAGCT
GCACAAAGCCATGAAGCGCTACGCCCTGGTGCCCGGCACCATCGCCTTTACCGACGCACATATCGAGGTGGACATTACCT
ACGCCGAGTACTTCGAGATGAGCGTTCGGCTGGCAGAAGCTATGAAGCGCTATGGGCTGAATACAAACCATCGGATCGTG
GTGTGCAGCGAGAATAGCTTGCAGTTCTTCATGCCCGTGTTGGGTGCCCTGTTCATCGGTGTGGCTGTGGCCCCAGCTAA
CGACATCTACAACGAGCGCGAGCTGCTGAACAGCATGGGCATCAGCCAGCCCACCGTCGTATTCGTGAGCAAGAAAGGGC
TGCAAAAGATCCTCAACGTGCAAAAGAAGCTACCGATCATACAAAAGATCATCATCATGGATAGCAAGACCGACTACCAG
GGCTTCCAAAGCATGTACACCTTCGTGACTTCCCATTTGCCACCCGGCTTCAACGAGTACGACTTCGTGCCCGAGAGCTT
CGACCGGGACAAAACCATCGCCCTGATCATGAACAGTAGTGGCAGTACCGGATTGCCCAAGGGCGTAGCCCTACCGCACC
GCACCGCTTGTGTCCGATTCAGTCATGCCCGCGACCCCATCTTCGGCAACCAGATCATCCCCGACACCGCTATCCTCAGC
GTGGTGCCATTTCACCACGGCTTCGGCATGTTCACCACGCTGGGCTACTTGATCTGCGGCTTTCGGGTCGTGCTCATGTA
CCGCTTCGAGGAGGAGCTATTCTTGCGCAGCTTGCAAGACTATAAGATTCAATCTGCCCTGCTGGTGCCCACACTATTTA
GCTTCTTCGCTAAGAGCACTCTCATCGACAAGTACGACCTAAGCAACTTGCACGAGATCGCCAGCGGCGGGGCGCCGCTC
AGCAAGGAGGTAGGTGAGGCCGTGGCCAAACGCTTCCACCTACCAGGCATCCGCCAGGGCTACGGCCTGACAGAAACAAC
CAGCGCCATTCTGATCACCCCCGAAGGGGGCTCGAGCGGAGGTTCAGGCGGTTCCGGAATGTATGAAAGCTTTATTGAGT
CACTGCCATTCCTTAAATCTTTGGAGTTTTCTGAACGCCTGAAAGTAGTAGATGTGATAGGCACCAAAGTATACAACGAT
GGAGAACAAATCATTGCTCAGGGAGATTCGGCTGATTCTTTTTTCATTGTAGAATCTGGAGAAGTGAAAATTACTATGAA
AAGAAAGGGTAAATCAGAAGTGGAAGAGAATGGTGCAGTAGAAATCGCTCGATGCTCGCGGGGACAGTACTTTGGAGAGC
TTGCCCTGGTAACTAACAAACCTCGAGCAGCTTCTGCCCACGCCATTGGGACTGTCAAATGTTTAGCAATGGATGTGCAA
GCATTTGAAAGGCTTCTGGGACCTTGCATGGAAATTATGAAAAGGAACATCGCTACCTATGAAGAACAGTTAGTTGCCCT
GTTTGGAACGAACATGGATATTGTAGGGTCAGGTGGATCTGGAGGGAGCTCCGGTCCTGGCGCAGTAGGCAAGGTGGTGC
CCTTCTTCGAGGCTAAGGTGGTGGACTTGGACACTGGTAAGACACTGGGTGTGAACCAGCGCGGCGAGCTGTGCGTCCGT
GGCCCCATGATCATGAGCGGCTACGTTAACAACCCCGAGGCTACAAACGCTCTCATCGACAAGGACGGCTGGCTGCACAG
CGGCGACATCGCCTACTGGGACGAGGACGAGCACTTCTTCATCGTGGACCGGCTGAAGAGCCTGATCAAATACAAGGGCT
ACCAGGTAGCCCCAGCCGAACTGGAGAGCATCCTGCTGCAACACCCCAACATCTTCGACGCCGGGGTCGCCGGCCTGCCC
GACGACGATGCCGGCGAGCTGCCCGCCGCAGTCGTCGTGCTGGAACACGGTAAAACCATGACCGAGAAGGAGATCGTGGA
CTATGTGGCCAGCCAGGTTACAACCGCCAAGAAGCTGCGCGGTGGTGTTGTGTTCGTGGACGAGGTGCCTAAAGGACTGA
CCGGCAAGTTGGACGCCCGCAAGATCCGCGAGATTCTCATTAAGGCCAAGAAGTAGGTTTAAAC

HHHHHHHHHHH) pBFB408 Sgf to Pme (SEQ ID NO:575)
GCGATCGCCATGGCCAAAAACATTAAGAAGGGCCCAGCGCCATTCTACCCACTCGAAGACGGGACCGCCGGCGAGCAGCT
GCACAAAGCCATGAAGCGCTACGCCCTGGTGCCCGGCACCATCGCCTTTACCGACGCACATATCGAGGTGGACATTACCT
ACGCCGAGTACTTCGAGATGAGCGTTCGGCTGGCAGAAGCTATGAAGCGCTATGGGCTGAATACAAACCATCGGATCGTG
GTGTGCAGCGAGAATAGCTTGCAGTTCTTCATGCCCGTGTTGGGTGCCCTGTTCATCGGTGTGGCTGTGGCCCCAGCTAA
CGACATCTACAACGAGCGCGAGCTGCTGAACAGCATGGGCATCAGCCAGCCCACCGTCGTATTCGTGAGCAAGAAAGGGC
TGCAAAAGATCCTCAACGTGCAAAAGAAGCTACCGATCATACAAAAGATCATCATCATGGATAGCAAGACCGACTACCAG
GGCTTCCAAAGCATGTACACCTTCGTGACTTCCCATTTGCCACCCGGCTTCAACGAGTACGACTTCGTGCCCGAGAGCTT
CGACCGGGACAAAACCATCGCCCTGATCATGAACAGTAGTGGCAGTACCGGATTGCCCAAGGGCGTAGCCCTACCGCACC
GCACCGCTTGTGTCCGATTCAGTCATGCCCGCGACCCCATCTTCGGCAACCAGATCATCCCCGACACCGCTATCCTCAGC
GTGGTGCCATTTCACCACGGCTTCGGCATGTTCACCACGCTGGGCTACTTGATCTGCGGCTTTCGGGTCGTGCTCATGTA
CCGCTTCGAGGAGGAGCTATTCTTGCGCAGCTTGCAAGACTATAAGATTCAATCTGCCCTGCTGGTGCCCACACTATTTA
GCTTCTTCGCTAAGAGCACTCTCATCGACAAGTACGACCTAAGCAACTTGCACGAGATCGCCAGCGGCGGGGCGCCGCTC
AGCAAGGAGGTAGGTGAGGCCGTGGCCAAACGCTTCCACCTACCAGGCATCCGCCAGGGCTACGGCCTGACAGAAACAAC
CAGCGCCATTCTGATCACCCCCGAAGGGGGCTCGAGCGGAGGTTCAGGCGGTTCCGGAGGAGGTTCTGGCGGATCAGGCG
GTTCGGGGATGTATGAAAGCTTTATTGAGTCACTGCCATTCCTTAAATCTTTGGAGTTTTCTGAACGCCTGAAAGTAGTA
GATGTGATAGGCACCAAAGTATACAACGATGGAGAACAAATCATTGCTCAGGGAGATTCGGCTGATTCTTTTTTCATTGT
AGAATCTGGAGAAGTGAAAATTACTATGAAAAGAAAGGGTAAATCAGAAGTGGAAGAGAATGGTGCAGTAGAAATCGCTC

FIG. 67DF

GATGCTCGCGGGGACAGTACTTTGGAGAGCTTGCCCTGGTAACTAACAAACCTCGAGCAGCTTCTGCCCACGCCATTGGG
ACTGTCAAATGTTTAGCAATGGATGTGCAAGCATTTGAAAGGCTTCTGGGACCTTGCATGGAAATTATGAAAAGGAACAT
CGCTACCTATGAAGAACAGTTAGTTGCCCTGTTTGGAACGAACATGGATATTGTTGGGTCCGGTGGATCCGGTGGCAGCG
GAGGGACGTCAGGTGGATCTGGAGGGAGCTCCGGTCCTGGCGCAGTAGGCAAGGTGGTGCCCTTCTTCGAGGCTAAGGTG
GTGGACTTGGACACTGGTAAGACACTGGGTGTGAACCAGCGCGGCGAGCTGTGCGTCCGTGGCCCCATGATCATGAGCGG
CTACGTTAACAACCCCGAGGCTACAAACGCTCTCATCGACAAGGACGGCTGGCTGCACAGCGGCGACATCGCCTACTGGG
ACGAGGACGAGCACTTCTTCATCGTGGACCGGCTGAAGAGCCTGATCAAATACAAGGGCTACCAGGTAGCCCCAGCCGAA
CTGGAGAGCATCCTGCTGCAACACCCCAACATCTTCGACGCCGGGGTCGCCGGCCTGCCCGACGACGATGCCGGCGAGCT
GCCCGCCGCAGTCGTCGTGCTGGAACACGGTAAAACCATGACCGAGAAGGAGATCGTGGACTATGTGGCCAGCCAGGTTA
CAACCGCCAAGAAGCTGCGCGGTGGTGTTGTGTTCGTGGACGAGGTGCCTAAAGGACTGACCGGCAAGTTGGACGCCCGC
AAGATCCGCGAGATTCTCATTAAGGCCAAGAAGTAGGTTTAAAC

IIIIIIIIII) pBFB409 Sgf to Pme (SEQ ID NO:576)
GCGATCGCCATGGCCAAAAACATTAAGAAGGGCCCAGCGCCATTCTACCCACTCGAAGACGGGACCGCCGGCGAGCAGCT
GCACAAAGCCATGAAGCGCTACGCCCTGGTGCCCGGCACCATCGCCTTTACCGACGCACATATCGAGGTGGACATTACCT
ACGCCGAGTACTTCGAGATGAGCGTTCGGCTGGCAGAAGCTATGAAGCGCTATGGGCTGAATACAAACCATCGGATCGTG
GTGTGCAGCGGCTCGACCGGAATGTATGAAAGCTTTATTGAGTCACTGCCATTCCTTAAATCTTTGGAGTTTTCTGAACG
CCTGAAAGTAGTAGATGTGATAGGCACCAAAGTATACAACGATGGAGAACAAATCATTGCTCAGGGAGATTCGGCTGATT
CTTTTTTCATTGTAGAATCTGGAGAAGTGAAAATTACTATGAAAAGAAAGGGTAAATCAGAAGTGGAAGAGAATGGTGCA
GTAGAAATCGCTCGATGCTCGCGGGGACAGTACTTTGGAGAGCTTGCCCTGGTAACTAACAAACCTCGAGCAGCTTCTGC
CCACGCCATTGGGACTGTCAAATGTTTAGCAATGGATGTGCAAGCATTTGAAAGGCTTCTGGGACCTTGCATGGAAATTA
TGAAAAGGAACATCGCTACCTATGAAGAACAGTTAGTTGCCCTGTTTGGAACGAACATGGATATTGTTGGAGCTCCGGT
GAGAATAGCTTGCAGTTCTTCATGCCCGTGTTGGGTGCCCTGTTCATCGGTGTGGCTGTGGCCCCAGCTAACGACATCTA
CAACGAGCGCGAGCTGCTGAACAGCATGGGCATCAGCCAGCCCACCGTCGTATTCGTGAGCAAGAAAGGGCTGCAAAAGA
TCCTCAACGTGCAAAAGAAGCTACCGATCATACAAAAGATCATCATCATGGATAGCAAGACCGACTACCAGGGCTTCCAA
AGCATGTACACCTTCGTGACTTCCCATTTGCCACCCGGCTTCAACGAGTACGACTTCGTGCCCGAGAGCTTCGACCGGGA
CAAAACCATCGCCCTGATCATGAACAGTAGTGGCAGTACCGGATTGCCCAAGGGCGTAGCCCTACCGCACCGCACCGCTT
GTGTCCGATTCAGTCATGCCCGCGACCCCATCTTCGGCAACCAGATCATCCCCGACACCGCTATCCTCAGCGTGGTGCCA
TTTCACCACGGCTTCGGCATGTTCACCACGCTGGGCTACTTGATCTGCGGCTTTCGGGTCGTGCTCATGTACCGCTTCGA
GGAGGAGCTATTCTTGCGCAGCTTGCAAGACTATAAGATTCAATCTGCCCTGCTGGTGCCCACACTATTTAGCTTCTTCG
CTAAGAGCACTCTCATCGACAAGTACGACCTAAGCAACTTGCACGAGATCGCCAGCGGCGGGGCGCCGCTCAGCAAGGAG
GTAGGTGAGGCCGTGGCCAAACGCTTCCACCTACCAGGCATCCGCCAGGGCTACGGCCTGACAGAAACAACCAGCGCCAT
TCTGATCACCCCCGAAGGGCCTGGCGCAGTAGGCAAGGTGGTGCCCTTCTTCGAGGCTAAGGTGGTGGACTTGGACACTG
GTAAGACACTGGGTGTGAACCAGCGCGGCGAGCTGTGCGTCCGTGGCCCCATGATCATGAGCGGCTACGTTAACAACCCC
GAGGCTACAAACGCTCTCATCGACAAGGACGGCTGGCTGCACAGCGGCGACATCGCCTACTGGGACGAGGACGAGCACTT
CTTCATCGTGGACCGGCTGAAGAGCCTGATCAAATACAAGGGCTACCAGGTAGCCCCAGCCGAACTGGAGAGCATCCTGC
TGCAACACCCCAACATCTTCGACGCCGGGGTCGCCGGCCTGCCCGACGACGATGCCGGCGAGCTGCCCGCCGCAGTCGTC
GTGCTGGAACACGGTAAAACCATGACCGAGAAGGAGATCGTGGACTATGTGGCCAGCCAGGTTACAACCGCCAAGAAGCT
GCGCGGTGGTGTTGTGTTCGTGGACGAGGTGCCTAAAGGACTGACCGGCAAGTTGGACGCCCGCAAGATCCGCGAGATTC
TCATTAAGGCCAAGAAGTAGGTTTAAAC

JJJJJJJJJJ) pBFB410 Sgf to Pme (SEQ ID NO:577)
GCGATCGCCATGGCCAAAAACATTAAGAAGGGCCCAGCGCCATTCTACCCACTCGAAGACGGGACCGCCGGCGAGCAGCT
GCACAAAGCCATGAAGCGCTACGCCCTGGTGCCCGGCACCATCGCCTTTACCGACGCACATATCGAGGTGGACATTACCT
ACGCCGAGTACTTCGAGATGAGCGTTCGGCTGGCAGAAGCTATGAAGCGCTATGGGCTGAATACAAACCATCGGATCGTG
GTGTGCAGCGGCTCGAGCGGAGGTTCAGGCGGTTCCGGAATGTATGAAAGCTTTATTGAGTCACTGCCATTCCTTAAATC
TTTGGAGTTTTCTGAACGCCTGAAAGTAGTAGATGTGATAGGCACCAAAGTATACAACGATGGAGAACAAATCATTGCTC
AGGGAGATTCGGCTGATTCTTTTTTCATTGTAGAATCTGGAGAAGTGAAAATTACTATGAAAAGAAAGGGTAAATCAGAA
GTGGAAGAGAATGGTGCAGTAGAAATCGCTCGATGCTCGCGGGGACAGTACTTTGGAGAGCTTGCCCTGGTAACTAACAA
ACCTCGAGCAGCTTCTGCCCACGCCATTGGGACTGTCAAATGTTTAGCAATGGATGTGCAAGCATTTGAAAGGCTTCTGG
GACCTTGCATGGAAATTATGAAAAGGAACATCGCTACCTATGAAGAACAGTTAGTTGCCCTGTTTGGAACGAACATGGAT
ATTGTAGGGTCAGGTGGATCTGGAGGGAGCTCCGGTGAGAATAGCTTGCAGTTCTTCATGCCCGTGTTGGGTGCCCTGTT
CATCGGTGTGGCTGTGGCCCCAGCTAACGACATCTACAACGAGCGCGAGCTGCTGAACAGCATGGGCATCAGCCAGCCCA
CCGTCGTATTCGTGAGCAAGAAAGGGCTGCAAAAGATCCTCAACGTGCAAAAGAAGCTACCGATCATACAAAAGATCATC
ATCATGGATAGCAAGACCGACTACCAGGGCTTCCAAAGCATGTACACCTTCGTGACTTCCCATTTGCCACCCGGCTTCAA
CGAGTACGACTTCGTGCCCGAGAGCTTCGACCGGGACAAAACCATCGCCCTGATCATGAACAGTAGTGGCAGTACCGGAT
TGCCCAAGGGCGTAGCCCTACCGCACCGCACCGCTTGTGTCCGATTCAGTCATGCCCGCGACCCCATCTTCGGCAACCAG

*FIG. 67DG*

ATCATCCCCGACACCGCTATCCTCAGCGTGGTGCCATTTCACCACGGCTTCGGCATGTTCACCACGCTGGGCTACTTGAT
CTGCGGCTTTCGGGTCGTGCTCATGTACCGCTTCGAGGAGGAGCTATTCTTGCGCAGCTTGCAAGACTATAAGATTCAAT
CTGCCCTGCTGGTGCCCACACTATTTAGCTTCTTCGCTAAGAGCACTCTCATCGACAAGTACGACCTAAGCAACTTGCAC
GAGATCGCCAGCGGCGGGGCGCCGCTCAGCAAGGAGGTAGGTGAGGCCGTGGCCAAACGCTTCCACCTACCAGGCATCCG
CCAGGGCTACGGCCTGACAGAAACAACCAGCGCCATTCTGATCACCCCCGAAGGGCCTGGCGCAGTAGGCAAGGTGGTGC
CCTTCTTCGAGGCTAAGGTGGTGGACTTGGACACTGGTAAGACACTGGGTGTGAACCAGCGCGGCGAGCTGTGCGTCCGT
GGCCCCATGATCATGAGCGGCTACGTTAACAACCCCGAGGCTACAAACGCTCTCATCGACAAGGACGGCTGGCTGCACAG
CGGCGACATCGCCTACTGGGACGAGGACGAGCACTTCTTCATCGTGGACCGGCTGAAGAGCCTGATCAAATACAAGGGCT
ACCAGGTAGCCCCAGCCGAACTGGAGAGCATCCTGCTGCAACACCCCAACATCTTCGACGCCGGGGTCGCCGGCCTGCCC
GACGACGATGCCGGCGAGCTGCCCGCCGCAGTCGTCGTGCTGGAACACGGTAAAACCATGACCGAGAAGGAGATCGTGGA
CTATGTGGCCAGCCAGGTTACAACCGCCAAGAAGCTGCGCGGTGGTGTTGTGTTCGTGGACGAGGTGCCTAAAGGACTGA
CCGGCAAGTTGGACGCCCGCAAGATCCGCGAGATTCTCATTAAGGCCAAGAAGTAGGTTTAAAC

KKKKKKKKKK) pBFB411 Sgf to Pme (SEQ ID NO:578)
GCGATCGCCATGGCCAAAAACATTAAGAAGGGCCCAGCGCCATTCTACCCACTCGAAGACGGGACCGCCGGCGAGCAGCT
GCACAAAGCCATGAAGCGCTACGCCCTGGTGCCCGGCACCATCGCCTTTACCGACGCACATATCGAGGTGGACATTACCT
ACGCCGAGTACTTCGAGATGAGCGTTCGGCTGGCAGAAGCTATGAAGCGCTATGGGCTGAATACAAACCATCGGATCGTG
GTGTGCAGCGGCTCGAGCGGAGGTTCAGGCGGTTCCGGAGGAGGTTCTGGCGGATCAGGCGGTTCGGGGATGTATGAAAG
CTTTATTGAGTCACTGCCATTCCTTAAATCTTTGGAGTTTTCTGAACGCCTGAAAGTAGTAGATGTGATAGGCACCAAAG
TATACAACGATGGAGAACAAATCATTGCTCAGGGAGATTCGGCTGATTCTTTTTTCATTGTAGAATCTGGAGAAGTGAAA
ATTACTATGAAAAGAAAGGGTAAATCAGAAGTGGAAGAGAATGGTGCAGTAGAAATCGCTCGATGCTCGCGGGGACAGTA
CTTTGGAGAGCTTGCCCTGGTAACTAACAAACCTCGAGCAGCTTCTGCCCACGCCATTGGGACTGTCAAATGTTTAGCAA
TGGATGTGCAAGCATTTGAAAGGCTTCTGGGACCTTGCATGGAAATTATGAAAAGGAACATCGCTACCTATGAAGAACAG
TTAGTTGCCCTGTTTGGAACGAACATGGATATTGTTGGGTCCGGTGGATCCGGTGGCAGCGGAGGGACGTCAGGTGGATC
TGGAGGGAGCTCCGGTGAGAATAGCTTGCAGTTCTTCATGCCCGTGTTGGGTGCCCTGTTCATCGGTGTGGCTGTGGCCC
CAGCTAACGACATCTACAACGAGCGCGAGCTGCTGAACAGCATGGGCATCAGCCAGCCCACCGTCGTATTCGTGAGCAAG
AAAGGGCTGCAAAAGATCCTCAACGTGCAAAAGAAGCTACCGATCATACAAAAGATCATCATCATGGATAGCAAGACCGA
CTACCAGGGCTTCCAAAGCATGTACACCTTCGTGACTTCCCATTTGCCACCCGGCTTCAACGAGTACGACTTCGTGCCCG
AGAGCTTCGACCGGGACAAAACCATCGCCCTGATCATGAACAGTAGTGGCAGTACCGGATTGCCCAAGGGCGTAGCCCTA
CCGCACCGCACCGCTTGTGTCCGATTCAGTCATGCCCGCGACCCCATCTTCGGCAACCAGATCATCCCCGACACCGCTAT
CCTCAGCGTGGTGCCATTTCACCACGGCTTCGGCATGTTCACCACGCTGGGCTACTTGATCTGCGGCTTTCGGGTCGTGC
TCATGTACCGCTTCGAGGAGGAGCTATTCTTGCGCAGCTTGCAAGACTATAAGATTCAATCTGCCCTGCTGGTGCCCACA
CTATTTAGCTTCTTCGCTAAGAGCACTCTCATCGACAAGTACGACCTAAGCAACTTGCACGAGATCGCCAGCGGCGGGGC
GCCGCTCAGCAAGGAGGTAGGTGAGGCCGTGGCCAAACGCTTCCACCTACCAGGCATCCGCCAGGGCTACGGCCTGACAG
AAACAACCAGCGCCATTCTGATCACCCCCGAAGGGCCTGGCGCAGTAGGCAAGGTGGTGCCCTTCTTCGAGGCTAAGGTG
GTGGACTTGGACACTGGTAAGACACTGGGTGTGAACCAGCGCGGCGAGCTGTGCGTCCGTGGCCCCATGATCATGAGCGG
CTACGTTAACAACCCCGAGGCTACAAACGCTCTCATCGACAAGGACGGCTGGCTGCACAGCGGCGACATCGCCTACTGGG
ACGAGGACGAGCACTTCTTCATCGTGGACCGGCTGAAGAGCCTGATCAAATACAAGGGCTACCAGGTAGCCCCAGCCGAA
CTGGAGAGCATCCTGCTGCAACACCCCAACATCTTCGACGCCGGGGTCGCCGGCCTGCCCGACGACGATGCCGGCGAGCT
GCCCGCCGCAGTCGTCGTGCTGGAACACGGTAAAACCATGACCGAGAAGGAGATCGTGGACTATGTGGCCAGCCAGGTTA
CAACCGCCAAGAAGCTGCGCGGTGGTGTTGTGTTCGTGGACGAGGTGCCTAAAGGACTGACCGGCAAGTTGGACGCCCGC
AAGATCCGCGAGATTCTCATTAAGGCCAAGAAGTAGGTTTAAAC

LLLLLLLLLL) pBFB412 Sgf to Pme (SEQ ID NO:579)
GCGATCGCCATGGCCAAAAACATTAAGAAGGGCCCAGCGCCATTCTACCCACTCGAAGACGGGACCGCCGGCGAGCAGCT
GCACAAAGCCATGAAGCGCTACGCCCTGGTGCCCGGCACCATCGCCTTTACCGACGCACATATCGAGGTGGACATTACCT
ACGCCGAGTACTTCGAGATGAGCGTTCGGCTGGCAGAAGCTATGAAGCGCTATGGGCTGAATACAAACCATCGGATCGTG
GTGTGCAGCGAGAATAGCTTGCAGTTCTTCATGCCCGTGTTGGGTGCCCTGTTCATCGGTGTGGCTGTGGCCCCAGCTAA
CGACATCTACAACGAGCGCGAGCTGCTGAACAGCATGGGCATCAGCCAGCCCACCGTCGTATTCGTGAGCAAGAAAGGGC
TGCAAAAGATCCTCAACGTGCAAAAGAAGCTACCGATCATACAAAAGATCATCATCATGGATAGCAAGACCGACTACCAG
GGCTTCCAAAGCATGTACACCTTCGTGACTTCCCATTTGCCACCCGGCTTCAACGAGTACGACTTCGTGCCCGAGAGCTT
CGACCGGGACAAAACCATCGCCCTGATCATGAACAGTAGTGGCAGTACCGGATTGCCCAAGGGCGTAGCCCTACCGCACC
GCACCGCTTGTGTCCGATTCAGTCATGCCCGCGACCCCATCTTCGGCAACCAGATCATCCCCGACACCGCTATCCTCAGC
GTGGTGCCATTTCACCACGGCTTCGGCATGTTCACCACGCTGGGCTACTTGATCTGCGGCTTTCGGGTCGTGCTCATGTA
CCGCTTCGAGGAGGAGCTATTCTTGCGCAGCTTGCAAGACTATAAGATTCAATCTGCCCTGCTGGTGCCCACACTATTTA
GCTTCTTCGCTAAGAGCACTCTCATCGACAAGTACGACCTAAGCGGCTCGACCGGAATGTATGAAAGCTTTATTGAGTCA
CTGCCATTCCTTAAATCTTTGGAGTTTTCTGAACGCCTGAAAGTAGTAGATGTGATAGGCACCAAAGTATACAACGATGG

*FIG. 67DH*

AGAACAAATCATTGCTCAGGGAGATTCGGCTGATTCTTTTTCATTGTAGAATCTGGAGAAGTGAAAATTACTATGAAAA
GAAAGGGTAAATCAGAAGTGGAAGAGAATGGTGCAGTAGAAATCGCTCGATGCTCGCGGGACAGTACTTTGGAGAGCTT
GCCCTGGTAACTAACAAACCTCGAGCAGCTTCTGCCCACGCCATTGGGACTGTCAAATGTTTAGCAATGGATGTGCAAGC
ATTTGAAAGGCTTCTGGGACCTTGCATGGAAATTATGAAAAGGAACATCGCTACCTATGAAGAACAGTTAGTTGCCCTGT
TTGGAACGAACATGGATATTGTTGGGAGCTCCGGTAACTTGCACGAGATCGCCAGCGGCGGGGCGCCGCTCAGCAAGGAG
GTAGGTGAGGCCGTGGCCAAACGCTTCCACCTACCAGGCATCCGCCAGGGCTACGGCCTGACAGAAACAACCAGCGCCAT
TCTGATCACCCCCGAAGGGCCTGGCGCAGTAGGCAAGGTGGTGCCCTTCTTCGAGGCTAAGGTGGTGGACTTGGACACTG
GTAAGACACTGGGTGTGAACCAGCGCGGCGAGCTGTGCGTCCGTGGCCCCATGATCATGAGCGGCTACGTTAACAACCCC
GAGGCTACAAACGCTCTCATCGACAAGGACGGCTGGCTGCACAGCGGCGACATCGCCTACTGGGACGAGGACGAGCACTT
CTTCATCGTGGACCGGCTGAAGAGCCTGATCAAATACAAGGGCTACCAGGTAGCCCCAGCCGAACTGGAGAGCATCCTGC
TGCAACACCCCAACATCTTCGACGCCGGGGTCGCCGGCCTGCCCGACGACGATGCCGGCGAGCTGCCCGCCGCAGTCGTC
GTGCTGGAACACGGTAAAACCATGACCGAGAAGGAGATCGTGGACTATGTGGCCAGCCAGGTTACAACCGCCAAGAAGCT
GCGCGGTGGTGTTGTGTTCGTGGACGAGGTGCCTAAAGGACTGACCGGCAAGTTGGACGCCCGCAAGATCCGCGAGATTC
TCATTAAGGCCAAGAAGTAGGTTTAAAC

MMMMMMMMMMM) pBFB413 Sgf to Pme (SEQ ID NO:580)
GCGATCGCCATGGCCAAAAACATTAAGAAGGGCCCAGCGCCATTCTACCCACTCGAAGACGGGACCGCCGGCGAGCAGCT
GCACAAAGCCATGAAGCGCTACGCCCTGGTGCCCGGCACCATCGCCTTTACCGACGCACATATCGAGGTGGACATTACCT
ACGCCGAGTACTTCGAGATGAGCGTTCGGCTGGCAGAAGCTATGAAGCGCTATGGGCTGAATACAAACCATCGGATCGTG
GTGTGCAGCGAGAATAGCTTGCAGTTCTTCATGCCCGTGTTGGGTGCCCTGTTCATCGGTGTGGCTGTGGCCCCAGCTAA
CGACATCTACAACGAGCGCGAGCTGCTGAACAGCATGGGCATCAGCCAGCCCACCGTCGTATTCGTGAGCAAGAAAGGGC
TGCAAAAGATCCTCAACGTGCAAAAGAAGCTACCGATCATACAAAAGATCATCATCATGGATAGCAAGACCGACTACCAG
GGCTTCCAAAGCATGTACACCTTCGTGACTTCCCATTTGCCACCCGGCTTCAACGAGTACGACTTCGTGCCCGAGAGCTT
CGACCGGGACAAAACCATCGCCCTGATCATGAACAGTAGTGGCAGTACCGGATTGCCCAAGGGCGTAGCCCTACCGCACC
GCACCGCTTGTGTCCGATTCAGTCATGCCCGCGACCCCATCTTCGGCAACCAGATCATCCCCGACACCGCTATCCTCAGC
GTGGTGCCATTTCACCACGGCTTCGGCATGTTCACCACGCTGGGCTACTTGATCTGCGGCTTTCGGGTCGTGCTCATGTA
CCGCTTCGAGGAGGAGCTATTCTTGCGCAGCTTGCAAGACTATAAGATTCAATCTGCCCTGCTGGTGCCCACACTATTTA
GCTTCTTCGCTAAGAGCACTCTCATCGACAAGTACGACCTAAGCGGCTCGAGCGGAGGTTCAGGCGGTTCCGGAATGTAT
GAAAGCTTTATTGAGTCACTGCCATTCCTTAAATCTTTGGAGTTTTCTGAACGCCTGAAAGTAGTAGATGTGATAGGCAC
CAAAGTATACAACGATGGAGAACAAATCATTGCTCAGGGAGATTCGGCTGATTCTTTTTTCATTGTAGAATCTGGAGAAG
TGAAAATTACTATGAAAAGAAAGGGTAAATCAGAAGTGGAAGAGAATGGTGCAGTAGAAATCGCTCGATGCTCGCGGGGA
CAGTACTTTGGAGAGCTTGCCCTGGTAACTAACAAACCTCGAGCAGCTTCTGCCCACGCCATTGGGACTGTCAAATGTTT
AGCAATGGATGTGCAAGCATTTGAAAGGCTTCTGGGACCTTGCATGGAAATTATGAAAAGGAACATCGCTACCTATGAAG
AACAGTTAGTTGCCCTGTTTGGAACGAACATGGATATTGTAGGGTCAGGTGGATCTGGAGGGAGCTCCGGTAACTTGCAC
GAGATCGCCAGCGGCGGGGCGCCGCTCAGCAAGGAGGTAGGTGAGGCCGTGGCCAAACGCTTCCACCTACCAGGCATCCG
CCAGGGCTACGGCCTGACAGAAACAACCAGCGCCATTCTGATCACCCCCGAAGGGCCTGGCGCAGTAGGCAAGGTGGTGC
CCTTCTTCGAGGCTAAGGTGGTGGACTTGGACACTGGTAAGACACTGGGTGTGAACCAGCGCGGCGAGCTGTGCGTCCGT
GGCCCCATGATCATGAGCGGCTACGTTAACAACCCCGAGGCTACAAACGCTCTCATCGACAAGGACGGCTGGCTGCACAG
CGGCGACATCGCCTACTGGGACGAGGACGAGCACTTCTTCATCGTGGACCGGCTGAAGAGCCTGATCAAATACAAGGGCT
ACCAGGTAGCCCCAGCCGAACTGGAGAGCATCCTGCTGCAACACCCCAACATCTTCGACGCCGGGGTCGCCGGCCTGCCC
GACGACGATGCCGGCGAGCTGCCCGCCGCAGTCGTCGTGCTGGAACACGGTAAAACCATGACCGAGAAGGAGATCGTGGA
CTATGTGGCCAGCCAGGTTACAACCGCCAAGAAGCTGCGCGGTGGTGTTGTGTTCGTGGACGAGGTGCCTAAAGGACTGA
CCGGCAAGTTGGACGCCCGCAAGATCCGCGAGATTCTCATTAAGGCCAAGAAGTAGGTTTAAAC

NNNNNNNNNNN) pBFB414 Sgf to Pme (SEQ ID NO:581)
GCGATCGCCATGGCCAAAAACATTAAGAAGGGCCCAGCGCCATTCTACCCACTCGAAGACGGGACCGCCGGCGAGCAGCT
GCACAAAGCCATGAAGCGCTACGCCCTGGTGCCCGGCACCATCGCCTTTACCGACGCACATATCGAGGTGGACATTACCT
ACGCCGAGTACTTCGAGATGAGCGTTCGGCTGGCAGAAGCTATGAAGCGCTATGGGCTGAATACAAACCATCGGATCGTG
GTGTGCAGCGAGAATAGCTTGCAGTTCTTCATGCCCGTGTTGGGTGCCCTGTTCATCGGTGTGGCTGTGGCCCCAGCTAA
CGACATCTACAACGAGCGCGAGCTGCTGAACAGCATGGGCATCAGCCAGCCCACCGTCGTATTCGTGAGCAAGAAAGGGC
TGCAAAAGATCCTCAACGTGCAAAAGAAGCTACCGATCATACAAAAGATCATCATCATGGATAGCAAGACCGACTACCAG
GGCTTCCAAAGCATGTACACCTTCGTGACTTCCCATTTGCCACCCGGCTTCAACGAGTACGACTTCGTGCCCGAGAGCTT
CGACCGGGACAAAACCATCGCCCTGATCATGAACAGTAGTGGCAGTACCGGATTGCCCAAGGGCGTAGCCCTACCGCACC
GCACCGCTTGTGTCCGATTCAGTCATGCCCGCGACCCCATCTTCGGCAACCAGATCATCCCCGACACCGCTATCCTCAGC
GTGGTGCCATTTCACCACGGCTTCGGCATGTTCACCACGCTGGGCTACTTGATCTGCGGCTTTCGGGTCGTGCTCATGTA
CCGCTTCGAGGAGGAGCTATTCTTGCGCAGCTTGCAAGACTATAAGATTCAATCTGCCCTGCTGGTGCCCACACTATTTA
GCTTCTTCGCTAAGAGCACTCTCATCGACAAGTACGACCTAAGCGGCTCGAGCGGAGGTTCAGGCGGTTCCGGAGGAGGT

FIG. 67DI

TCTGGCGGATCAGGCGGTTCGGGGATGTATGAAAGCTTTATTGAGTCACTGCCATTCCTTAAATCTTTGGAGTTTTCTGA
ACGCCTGAAAGTAGTAGATGTGATAGGCACCAAAGTATACAACGATGGAGAACAAATCATTGCTCAGGGAGATTCGGCTG
ATTCTTTTTTCATTGTAGAATCTGGAGAAGTGAAAATTACTATGAAAAGAAAGGGTAAATCAGAAGTGGAAGAGAATGGT
GCAGTAGAAATCGCTCGATGCTCGCGGGGACAGTACTTTGGAGAGCTTGCCCTGGTAACTAACAAACCTCGAGCAGCTTC
TGCCCACGCCATTGGGACTGTCAAATGTTTAGCAATGGATGTGCAAGCATTTGAAAGGCTTCTGGGACCTTGCATGGAAA
TTATGAAAAGGAACATCGCTACCTATGAAGAACAGTTAGTTGCCCTGTTTGGAACGAACATGGATATTGTTGGGTCCGGT
GGATCCGGTGGCAGCGGAGGGACGTCAGGTGGATCTGGAGGGAGCTCCGGTAACTTGCACGAGATCGCCAGCGGCGGGGC
GCCGCTCAGCAAGGAGGTAGGTGAGGCCGTGGCCAAACGCTTCCACCTACCAGGCATCCGCCAGGGCTACGGCCTGACAG
AAACAACCAGCGCCATTCTGATCACCCCCGAAGGGCCTGGCGCAGTAGGCAAGGTGGTGCCCTTCTTCGAGGCTAAGGTG
GTGGACTTGGACACTGGTAAGACACTGGGTGTGAACCAGCGCGGCGAGCTGTGCGTCCGTGGCCCCATGATCATGAGCGG
CTACGTTAACAACCCCGAGGCTACAAACGCTCTCATCGACAAGGACGGCTGGCTGCACAGCGGCGACATCGCCTACTGGG
ACGAGGACGAGCACTTCTTCATCGTGGACCGGCTGAAGAGCCTGATCAAATACAAGGGCTACCAGGTAGCCCCAGCCGAA
CTGGAGAGCATCCTGCTGCAACACCCCAACATCTTCGACGCCGGGGTCGCCGGCCTGCCCGACGACGATGCCGGCGAGCT
GCCCGCCGCAGTCGTCGTGCTGGAACACGGTAAAACCATGACCGAGAAGGAGATCGTGGACTATGTGGCCAGCCAGGTTA
CAACCGCCAAGAAGCTGCGCGGTGGTGTTGTGTTCGTGGACGAGGTGCCTAAAGGACTGACCGGCAAGTTGGACGCCCGC
AAGATCCGCGAGATTCTCATTAAGGCCAAGAAGTAGGTTTAAAC

OOOOOOOOOOO) pBFB415 Sgf to Pme (SEQ ID NO:582)
GCGATCGCCATGGGGTTAAAAGCTGATATTCATGTCATCATCCCTTACGAGGGACTCAGTGGTTTTCAAATGGGTCTGAT
TGAAATGATCTTCAAAGTTGTTTACCCAGTGGATGATCATCATTTCAAGATTATTCTCCATTATGGTACACTCGTTATTG
ACGGTGTGACACCAAACATGATTGACTACTTTGGACGCCCTTACCCTGGAATTGCTGTGTTTGACGGCAAGCAGATCACA
GTTACTGGAACTCTGTGGAACGGCAACAAGATCTATGATGAGCGCCTGATCAACCCAGATGGTTCACTCCTCTTCCGCGT
TACTATCAATGGAGTCACCGGATGGCGCCTTTGCGAGAACATTCTTGCCGGAGGGAGCTCTGGTGGAGGGTCTGGGGGTG
GAGTGCAGGTGGAAACCATCTCCCCAGGAGACGGGCGCACCTTCCCCAAGCGCGGCCAGACCTGCGTGGTGCACTACACC
GGGATGCTTGAAGATGGAAAGAAATTTGATTCCTCCCGGGACAGAAACAAGCCCTTTAAGTTTATGCTAGGCAAGCAGGA
GGTGATCCGAGGCTGGGAAGAAGGGGTTGCCCAGATGAGTGTGGGTCAGAGAGCCAAACTGACTATATCTCCAGATTATG
CCTATGGTGCCACTGGGCACCCAGGCATCATCCCACCACATGCCACTCTCGTCTTCGATGTGGAGCTTCTAAAACTGGAA
TGAGTTTAAAC

PPPPPPPPPPP) pBFB416 Sgf to Pme (SEQ ID NO:583)
GCGATCGCCATGGATCATCATTTCAAGATTATTCTCCATTATGGTACACTCGTTATTGACGGTGTGACACCAAACATGAT
TGACTACTTTGGACGCCCTTACCCTGGAATTGCTGTGTTTGACGGCAAGCAGATCACAGTTACTGGAACTCTGTGGAACG
GCAACAAGATCTATGATGAGCGCCTGATCAACCCAGATGGTTCACTCCTCTTCCGCGTTACTATCAATGGAGTCACCGGA
TGGCGCCTTTGCGAGAACATTCTTGCCGGCGGGAGCTCTGGTGGAGGGTCTGGGGGTGGAGTGCAGGTGGAAACCATCTC
CCCAGGAGACGGGCGCACCTTCCCCAAGCGCGGCCAGACCTGCGTGGTGCACTACACCGGGATGCTTGAAGATGGAAAGA
AATTTGATTCCTCCCGGGACAGAAACAAGCCCTTTAAGTTTATGCTAGGCAAGCAGGAGGTGATCCGAGGCTGGGAAGAA
GGGGTTGCCCAGATGAGTGTGGGTCAGAGAGCCAAACTGACTATATCTCCAGATTATGCCTATGGTGCCACTGGGCACCC
AGGCATCATCCCACCACATGCCACTCTCGTCTTCGATGTGGAGCTTCTAAAACTGGAATGAGTTTAAAC

QQQQQQQQQQQ) pBFB417 Sgf to Pme (SEQ ID NO:584)
GCGATCGCCATGACCGCTATCCTCAGCGTGGTGCCATTTCACCACGGCTTCGGCATGTTCACCACGCTGGGCTACTTGAT
CTGCGGCTTTCGGGTCGTGCTCATGTACCGCTTCGAGGAGGAGCTATTCTTGCGCAGCTTGCAAGACTATAAGATTCAAT
CTGCCCTGCTGGTGCCCACACTATTTAGCTTCTTCGCTAAGAGCACTCTCATCGACAAGTACGACCTAAGCAACTTGCAC
GAGATCGCCAGCGGCGGGGCGCCGCTCAGCAAGGAGGTAGGTGAGGCCGTGGCCAAACGCTTCCACCTACCAGGCATCCG
CCAGGGCTACGGCCTGACAGAAACAACCAGCGCCATTCTGATCACCCCCGAAGGGGACGACAAGCCTGGCGCAGTAGGCA
AGGTGGTGCCCTTCTTCGAGGCTAAGGTGGTGGACTTGGACACTGGTAAGACACTGGGTGTGAACCAGCGCGGCGAGCTG
TGCGTCCGTGGCCCCATGATCATGAGCGGCTACGTTAACAACCCCGAGGCTACAAACGCTCTCATCGACAAGGACGGCTG
GCTGCACAGCGGCGACATCGCCTACTGGGACGAGGACGAGCACTTCTTCATCGTGGACCGGCTGAAGAGCCTGATCAAAT
ACAAGGGCTACCAGGTAGCCCCAGCCGAACTGGAGAGCATCCTGCTGCAACACCCCAACATCTTCGACGCCGGGGTCGCC
GGCCTGCCCGACGACGATGCCGGCGAGCTGCCCGCCGCAGTCGTCGTGCTGGAACACGGTAAAACCATGACCGAGAAGGA
GATCGTGGACTATGTGGCCAGCCAGGTTACAACCGCCAAGAAGCTGCGCGGTGGTGTTGTGTTCGTGGACGAGGTGCCTA
AAGGACTGACCGGCAAGTTGGACGCCCGCAAGATCCGCGAGATTCTCATTAAGGCCAAGAAGGGTAGTGGCGGTGGGAAC
GGCAGGTTCCTGACACTTAAGCCTCTTCCGGATAGTATTATCCAGGAGTCCCTTGAGATCCAGCAAGGGGTGAATCCTTT
TTTTATCGGGCGAAGCGAGGACTGTAATTGCAAGATCGAAGATAACAGACTCAGTAGAGTGCACTGCTTTATTTTCAAGA
AGAGGCACGCAGTGGGAAAATCTATGTACGAATCCCCAGCTCAGGGCCTCGACGATATTTGGTACTGTCATACAGGCACA
AATGTATCCTACCTGAATAACAATCGAATGATCCAAGGCACCAAATTCCTTCTGCAGGATGGCGACGAAATCAAGATTAT
CTGGGATAAGAATAACAAATTCGTTATAGGTTTTAAGGTCGAGATCAATGATACAACCGGGCTCTTCAACGAGGGGCTGG

FIG. 67DJ

GTATGCTGCAGGAGCAGCGGGTCGTACTGAAGCAGACTGCTGAAGAGAAAGACCTCGTAAAGAAACTTGGAGGCTCGAGC
GGACGAAAGAGAGATCGGCTGGGGACCCTGGGGATTGGAGGGAGCTCCGGTGCCAAAAACATTAAGAAGGGCCCAGCGCC
ATTCTACCCACTCGAAGACGGGACCGCCGGCGAGCAGCTGCACAAAGCCATGAAGCGCTACGCCCTGGTGCCCGGCACCA
TCGCCTTTACCGACGCACATATCGAGGTGGACATTACCTACGCCGAGTACTTCGAGATGAGCGTTCGGCTGGCAGAAGCT
ATGAAGCGCTATGGGCTGAATACAAACCATCGGATCGTGGTGTGCAGCGAGAATAGCTTGCAGTTCTTCATGCCCGTGTT
GGGTGCCCTGTTCATCGGTGTGGCTGTGGCCCCAGCTAACGACATCTACAACGAGCGCGAGCTGCTGAACAGCATGGGCA
TCAGCCAGCCCACCGTCGTATTCGTGAGCAAGAAAGGGCTGCAAAAGATCCTCAACGTGCAAAAGAAGCTACCGATCATA
CAAAAGATCATCATCATGGATAGCAAGACCGACTACCAGGGCTTCCAAAGCATGTACACCTTCGTGACTTCCCATTTGCC
ACCCGGCTTCAACGAGTACGACTTCGTGCCCGAGAGCTTCGACCGGGACAAAACCATCGCCCTGATCATGAACAGTAGTG
GCAGTACCGGATTGCCCAAGGGCGTAGCCCTACCGCACCGCACCGCTTGTGTCCGATTCAGTCATGCCCGCGACCCCATC
TTCGGCAACCAGATCATCCCCTGAGTTTAAAC

RRRRRRRRRRR) pBFB418 Sgf to Pme (SEQ ID NO:585)
GCGATCGCCATGACCGCTATCCTCAGCGTGGTGCCATTTCACCACGGCTTCGGCATGTTCACCACGCTGGGCTACTTGAT
CTGCGGCTTTCGGGTCGTGCTCATGTACCGCTTCGAGGAGGAGCTATTCTTGCGCAGCTTGCAAGACTATAAGATTCAAT
CTGCCCTGCTGGTGCCCACACTATTTAGCTTCTTCGCTAAGAGCACTCTCATCGACAAGTACGACCTAAGCAACTTGCAC
GAGATCGCCAGCGGCGGGGCGCCGCTCAGCAAGGAGGTAGGTGAGGCCGTGGCCAAACGCTTCCACCTACCAGGCATCCG
CCAGGGCTACGGCCTGACAGAAACAACCAGCGCCATTCTGATCACCCCCGAAGGGGACGACAAGCCTGGCGCAGTAGGCA
AGGTGGTGCCCTTCTTCGAGGCTAAGGTGGTGGACTTGGACACTGGTAAGACACTGGGTGTGAACCAGCGCGGCGAGCTG
TGCGTCCGTGGCCCCATGATCATGAGCGGCTACGTTAACAACCCCGAGGCTACAAACGCTCTCATCGACAAGGACGGCTG
GCTGCACAGCGGCGACATCGCCTACTGGGACGAGGACGAGCACTTCTTCATCGTGGACCGGCTGAAGAGCCTGATCAAAT
ACAAGGGCTACCAGGTAGCCCCAGCCGAACTGGAGAGCATCCTGCTGCAACACCCCAACATCTTCGACGCCGGGGTCGCC
GGCCTGCCCGACGACGATGCCGGCGAGCTGCCCGCCGCAGTCGTCGTGCTGGAACACGGTAAAACCATGACCGAGAAGGA
GATCGTGGACTATGTGGCCAGCCAGGTTACAACCGCCAAGAAGCTGCGCGGTGGTGTTGTGTTCGTGGACGAGGTGCCTA
AAGGACTGACCGGCAAGTTGGACGCCCGCAAGATCCGCGAGATTCTCATTAAGGCCAAGAAGGGAGGGTCTGGGGGTGGT
GGTAGTGGCGGTGGGAACGGCAGGTTCCTGACACTTAAGCCTCTTCCGGATAGTATTATCCAGGAGTCCCTTGAGATCCA
GCAAGGGGTGAATCCTTTTTTTATCGGGCGAAGCGAGGACTGTAATTGCAAGATCGAAGATAACAGACTCAGTAGAGTGC
ACTGCTTTATTTTCAAGAAGAGGCACGCAGTGGGAAAATCTATGTACGAATCCCCAGCTCAGGGCCTCGACGATATTTGG
TACTGTCATACAGGCACAAATGTATCCTACCTGAATAACAATCGAATGATCCAAGGCACCAAATTCCTTCTGCAGGATGG
CGACGAAATCAAGATTATCTGGGATAAGAATAACAAATTCGTTATAGGTTTTAAGGTCGAGATCAATGATACAACCGGGC
TCTTCAACGAGGGGCTGGGTATGCTGCAGGAGCAGCGGGTCGTACTGAAGCAGACTGCTGAAGAGAAAGACCTCGTAAAG
AAACTTGGAGGCTCGAGCGGACGAAAGAGAGATCGGCTGGGGACCCTGGGGATTGGGAGCTCCGGCTCCGGCGGCTCCGG
CGGAGCCAAAAACATTAAGAAGGGCCCAGCGCCATTCTACCCACTCGAAGACGGGACCGCCGGCGAGCAGCTGCACAAAG
CCATGAAGCGCTACGCCCTGGTGCCCGGCACCATCGCCTTTACCGACGCACATATCGAGGTGGACATTACCTACGCCGAG
TACTTCGAGATGAGCGTTCGGCTGGCAGAAGCTATGAAGCGCTATGGGCTGAATACAAACCATCGGATCGTGGTGTGCAG
CGAGAATAGCTTGCAGTTCTTCATGCCCGTGTTGGGTGCCCTGTTCATCGGTGTGGCTGTGGCCCCAGCTAACGACATCT
ACAACGAGCGCGAGCTGCTGAACAGCATGGGCATCAGCCAGCCCACCGTCGTATTCGTGAGCAAGAAAGGGCTGCAAAAG
ATCCTCAACGTGCAAAAGAAGCTACCGATCATACAAAAGATCATCATCATGGATAGCAAGACCGACTACCAGGGCTTCCA
AAGCATGTACACCTTCGTGACTTCCCATTTGCCACCCGGCTTCAACGAGTACGACTTCGTGCCCGAGAGCTTCGACCGGG
ACAAAACCATCGCCCTGATCATGAACAGTAGTGGCAGTACCGGATTGCCCAAGGGCGTAGCCCTACCGCACCGCACCGCT
TGTGTCCGATTCAGTCATGCCCGCGACCCCATCTTCGGCAACCAGATCATCCCCTGAGTTTAAAC

SSSSSSSSSSS) pBFB419 Sgf to Pme (SEQ ID NO:586)
GCGATCGCCATGACCGCTATCCTCAGCGTGGTGCCATTTCACCACGGCTTCGGCATGTTCACCACGCTGGGCTACTTGAT
CTGCGGCTTTCGGGTCGTGCTCATGTACCGCTTCGAGGAGGAGCTATTCTTGCGCAGCTTGCAAGACTATAAGATTCAAT
CTGCCCTGCTGGTGCCCACACTATTTAGCTTCTTCGCTAAGAGCACTCTCATCGACAAGTACGACCTAAGCAACTTGCAC
GAGATCGCCAGCGGCGGGGCGCCGCTCAGCAAGGAGGTAGGTGAGGCCGTGGCCAAACGCTTCCACCTACCAGGCATCCG
CCAGGGCTACGGCCTGACAGAAACAACCAGCGCCATTCTGATCACCCCCGAAGGGGACGACAAGCCTGGCGCAGTAGGCA
AGGTGGTGCCCTTCTTCGAGGCTAAGGTGGTGGACTTGGACACTGGTAAGACACTGGGTGTGAACCAGCGCGGCGAGCTG
TGCGTCCGTGGCCCCATGATCATGAGCGGCTACGTTAACAACCCCGAGGCTACAAACGCTCTCATCGACAAGGACGGCTG
GCTGCACAGCGGCGACATCGCCTACTGGGACGAGGACGAGCACTTCTTCATCGTGGACCGGCTGAAGAGCCTGATCAAAT
ACAAGGGCTACCAGGTAGCCCCAGCCGAACTGGAGAGCATCCTGCTGCAACACCCCAACATCTTCGACGCCGGGGTCGCC
GGCCTGCCCGACGACGATGCCGGCGAGCTGCCCGCCGCAGTCGTCGTGCTGGAACACGGTAAAACCATGACCGAGAAGGA
GATCGTGGACTATGTGGCCAGCCAGGTTACAACCGCCAAGAAGCTGCGCGGTGGTGTTGTGTTCGTGGACGAGGTGCCTA
AAGGACTGACCGGCAAGTTGGACGCCCGCAAGATCCGCGAGATTCTCATTAAGGCCAAGAAGGGCTCGAGCGGAGGTTCA
GGCGGTTCCGGAGGAGGTTCTGGCGGATCAGGCGGTTCGGGAGGGAACGGCAGGTTCCTGACACTTAAGCCTCTTCCGGA
TAGTATTATCCAGGAGTCCCTTGAGATCCAGCAAGGGGTGAATCCTTTTTTTATCGGGCGAAGCGAGGACTGTAATTGCA

FIG. 67DK

AGATCGAAGATAACAGACTCAGTAGAGTGCACTGCTTTATTTTCAAGAAGAGGCACGCAGTGGGAAAATCTATGTACGAA
TCCCCAGCTCAGGGCCTCGACGATATTTGGTACTGTCATACAGGCACAAATGTATCCTACCTGAATAACAATCGAATGAT
CCAAGGCACCAAATTCCTTCTGCAGGATGGCGACGAAATCAAGATTATCTGGGATAAGAATAACAAATTCGTTATAGGTT
TTAAGGTCGAGATCAATGATACAACCGGGCTCTTCAACGAGGGGCTGGGTATGCTGCAGGAGCAGCGGGTCGTACTGAAG
CAGACTGCTGAAGAGAAAGACCTCGTAAAGAAACTTGGAGGCTCGAGCGGACGAAAGAGAGATCGGCTGGGGACCCTGGG
GATTGGGTCCGGTGGATCCGGTGGCAGCGGAGGGACGTCAGGTGGATCTGGAGGGAGCTCCGGTGCCAAAAACATTAAGA
AGGGCCCAGCGCCATTCTACCCACTCGAAGACGGGACCGCCGGCGAGCAGCTGCACAAAGCCATGAAGCGCTACGCCCTG
GTGCCCGGCACCATCGCCTTTACCGACGCACATATCGAGGTGGACATTACCTACGCCGAGTACTTCGAGATGAGCGTTCG
GCTGGCAGAAGCTATGAAGCGCTATGGGCTGAATACAAACCATCGGATCGTGGTGTGCAGCGAGAATAGCTTGCAGTTCT
TCATGCCCGTGTTGGGTGCCCTGTTCATCGGTGTGGCTGTGGCCCCAGCTAACGACATCTACAACGAGCGCGAGCTGCTG
AACAGCATGGGCATCAGCCAGCCCACCGTCGTATTCGTGAGCAAGAAAGGGCTGCAAAAGATCCTCAACGTGCAAAAGAA
GCTACCGATCATACAAAAGATCATCATCATGGATAGCAAGACCGACTACCAGGGCTTCCAAAGCATGTACACCTTCGTGA
CTTCCCATTTGCCACCCGGCTTCAACGAGTACGACTTCGTGCCCGAGAGCTTCGACCGGGACAAAACCATCGCCCTGATC
ATGAACAGTAGTGGCAGTACCGGATTGCCCAAGGGCGTAGCCCTACCGCACCGCACCGCTTGTGTCCGATTCAGTCATGC
CCGCGACCCCATCTTCGGCAACCAGATCATCCCCTGAGTTTAAAC

TTTTTTTTTTT) pBFB420 Sgf to Pme (SEQ ID NO:587)
GCGATCGCCATGCCTGGCGCAGTAGGCAAGGTGGTGCCCTTCTTCGAGGCTAAGGTGGTGGACTTGGACACCGGTAAGAC
ACTGGGTGTGAACCAGCGCGGCGAGCTGTGCGTCCGTGGCCCCATGATCATGAGCGGCTACGTTAACAACCCCGAGGCTA
CAAACGCTCTCATCGACAAGGACGGCTGGCTGCACAGCGGCGACATCGCCTACTGGGACGAGGACGAGCACTTCTTCATC
GTGGACCGGCTGAAGAGCCTGATCAAATACAAGGGCTACCAGGTAGCCCCAGCCGAACTGGAGAGCATCCTGCTGCAACA
CCCCAACATCTTCGACGCCGGGGTCGCCGGCCTGCCCGACGACGATGCCGGCGAGCTGCCCGCCGCAGTCGTCGTGCTGG
AACACGGTAAAACCATGACCGAGAAGGAGATCGTGGACTATGTGGCCAGCCAGGTTACAACCGCCAAGAAGCTGCGCGGT
GGTGTTGTGTTCGTGGACGAGGTGCCTAAAGGACTGACCGGCAAGTTGGACGCCCGCAAGATCCGCGAGATTCTCATTAA
GGCCAAGAAGGGTAGTGGCGGTGGGAACGGCAGGTTCCTGACACTTAAGCCTCTTCCGGATAGTATTATCCAGGAGTCCC
TTGAGATCCAGCAAGGGGTGAATCCTTTTTTTATCGGGCGAAGCGAGGACTGTAATTGCAAGATCGAAGATAACAGACTC
AGTAGAGTGCACTGCTTTATTTTCAAGAAGAGGCACGCAGTGGGAAAATCTATGTACGAATCCCCAGCTCAGGGCCTCGA
CGATATTTGGTACTGTCATACAGGCACAAATGTATCCTACCTGAATAACAATCGAATGATCCAAGGCACCAAATTCCTTC
TGCAGGATGGCGACGAAATCAAGATTATCTGGGATAAGAATAACAAATTCGTTATAGGTTTTAAGGTCGAGATCAATGAT
ACAACCGGGCTCTTCAACGAGGGGCTGGGTATGCTGCAGGAGCAGCGGGTCGTACTGAAGCAGACTGCTGAAGAGAAAGA
CCTCGTAAAGAAACTTGGAGGCTCGAGCGGACGAAAGAGAGATCGGCTGGGGACCCTGGGGATTGGAGGGAGCTCCGGTG
CCAAAAACATTAAGAAGGGCCCAGCGCCATTCTACCCACTCGAAGACGGGACCGCCGGCGAGCAGCTGCACAAAGCCATG
AAGCGCTACGCCCTGGTGCCCGGCACCATCGCCTTTACCGACGCACATATCGAGGTGGACATTACCTACGCCGAGTACTT
CGAGATGAGCGTTCGGCTGGCAGAAGCTATGAAGCGCTATGGGCTGAATACAAACCATCGGATCGTGGTGTGCAGCGAGA
ATAGCTTGCAGTTCTTCATGCCCGTGTTGGGTGCCCTGTTCATCGGTGTGGCTGTGGCCCCAGCTAACGACATCTACAAC
GAGCGCGAGCTGCTGAACAGCATGGGCATCAGCCAGCCCACCGTCGTATTCGTGAGCAAGAAAGGGCTGCAAAAGATCCT
CAACGTGCAAAAGAAGCTACCGATCATACAAAAGATCATCATCATGGATAGCAAGACCGACTACCAGGGCTTCCAAAGCA
TGTACACCTTCGTGACTTCCCATTTGCCACCCGGCTTCAACGAGTACGACTTCGTGCCCGAGAGCTTCGACCGGGACAAA
ACCATCGCCCTGATCATGAACAGTAGTGGCAGTACCGGATTGCCCAAGGGCGTAGCCCTACCGCACCGCACCGCTTGTGT
CCGATTCAGTCATGCCCGCGACCCCATCTTCGGCAACCAGATCATCCCCGACACCGCTATCCTCAGCGTGGTGCCATTTC
ACCACGGCTTCGGCATGTTCACCACGCTGGGCTACTTGATCTGCGGCTTTCGGGTCGTGCTCATGTACCGCTTCGAGGAG
GAGCTATTCTTGCGCAGCTTGCAAGACTATAAGATTCAATCTGCCCTGCTGGTGCCCACACTATTTAGCTTCTTCGCTAA
GAGCACTCTCATCGACAAGTACGACCTAAGCAACTTGCACGAGATCGCCAGCGGCGGGGCGCCGCTCAGCAAGGAGGTAG
GTGAGGCCGTGGCCAAACGCTTCCACCTACCAGGCATCCGCCAGGGCTACGGCCTGACAGAAACAACCAGCGCCATTCTG
ATCACCCCCGAAGGGTGAGTTTAAAC

UUUUUUUUUUU) pBFB421 Sgf to Pme (SEQ ID NO:588)
GCGATCGCCATGCCTGGCGCAGTAGGCAAGGTGGTGCCCTTCTTCGAGGCTAAGGTGGTGGACTTGGACACCGGTAAGAC
ACTGGGTGTGAACCAGCGCGGCGAGCTGTGCGTCCGTGGCCCCATGATCATGAGCGGCTACGTTAACAACCCCGAGGCTA
CAAACGCTCTCATCGACAAGGACGGCTGGCTGCACAGCGGCGACATCGCCTACTGGGACGAGGACGAGCACTTCTTCATC
GTGGACCGGCTGAAGAGCCTGATCAAATACAAGGGCTACCAGGTAGCCCCAGCCGAACTGGAGAGCATCCTGCTGCAACA
CCCCAACATCTTCGACGCCGGGGTCGCCGGCCTGCCCGACGACGATGCCGGCGAGCTGCCCGCCGCAGTCGTCGTGCTGG
AACACGGTAAAACCATGACCGAGAAGGAGATCGTGGACTATGTGGCCAGCCAGGTTACAACCGCCAAGAAGCTGCGCGGT
GGTGTTGTGTTCGTGGACGAGGTGCCTAAAGGACTGACCGGCAAGTTGGACGCCCGCAAGATCCGCGAGATTCTCATTAA
GGCCAAGAAGGGAGGGTCTGGGGGTGGTGGTAGTGGCGGTGGGAACGGCAGGTTCCTGACACTTAAGCCTCTTCCGGATA
GTATTATCCAGGAGTCCCTTGAGATCCAGCAAGGGGTGAATCCTTTTTTTATCGGGCGAAGCGAGGACTGTAATTGCAAG
ATCGAAGATAACAGACTCAGTAGAGTGCACTGCTTTATTTTCAAGAAGAGGCACGCAGTGGGAAAATCTATGTACGAATC

FIG. 67DL

CCCAGCTCAGGGCCTCGACGATATTTGGTACTGTCATACAGGCACAAATGTATCCTACCTGAATAACAATCGAATGATCC
AAGGCACCAAATTCCTTCTGCAGGATGGCGACGAAATCAAGATTATCTGGGATAAGAATAACAAATTCGTTATAGGTTTT
AAGGTCGAGATCAATGATACAACCGGGCTCTTCAACGAGGGGCTGGGTATGCTGCAGGAGCAGCGGGTCGTACTGAAGCA
GACTGCTGAAGAGAAAGACCTCGTAAAGAAACTTGGAGGCTCGAGCGGACGAAAGAGAGATCGGCTGGGGACCCTGGGGA
TTGGGAGCTCCGGCTCCGGCGGCTCCGGCGGAGCCAAAAACATTAAGAAGGGCCCAGCGCCATTCTACCCACTCGAAGAC
GGGACCGCCGGCGAGCAGCTGCACAAAGCCATGAAGCGCTACGCCCTGGTGCCCGGCACCATCGCCTTTACCGACGCACA
TATCGAGGTGGACATTACCTACGCCGAGTACTTCGAGATGAGCGTTCGGCTGGCAGAAGCTATGAAGCGCTATGGGCTGA
ATACAAACCATCGGATCGTGGTGTGCAGCGAGAATAGCTTGCAGTTCTTCATGCCCGTGTTGGGTGCCCTGTTCATCGGT
GTGGCTGTGGCCCCAGCTAACGACATCTACAACGAGCGCGAGCTGCTGAACAGCATGGGCATCAGCCAGCCCACCGTCGT
ATTCGTGAGCAAGAAAGGGCTGCAAAAGATCCTCAACGTGCAAAAGAAGCTACCGATCATACAAAAGATCATCATCATGG
ATAGCAAGACCGACTACCAGGGCTTCCAAAGCATGTACACCTTCGTGACTTCCCATTTGCCACCCGGCTTCAACGAGTAC
GACTTCGTGCCCGAGAGCTTCGACCGGGACAAAACCATCGCCCTGATCATGAACAGTAGTGGCAGTACCGGATTGCCCAA
GGGCGTAGCCCTACCGCACCGCACCGCTTGTGTCCGATTCAGTCATGCCCGCGACCCCATCTTCGGCAACCAGATCATCC
CCGACACCGCTATCCTCAGCGTGGTGCCATTTCACCACGGCTTCGGCATGTTCACCACGCTGGGCTACTTGATCTGCGGC
TTTCGGGTCGTGCTCATGTACCGCTTCGAGGAGGAGCTATTCTTGCGCAGCTTGCAAGACTATAAGATTCAATCTGCCCT
GCTGGTGCCCACACTATTTAGCTTCTTCGCTAAGAGCACTCTCATCGACAAGTACGACCTAAGCAACTTGCACGAGATCG
CCAGCGGCGGGGCGCCGCTCAGCAAGGAGGTAGGTGAGGCCGTGGCCAAACGCTTCCACCTACCAGGCATCCGCCAGGGC
TACGGCCTGACAGAAACAACCAGCGCCATTCTGATCACCCCCGAAGGGTGAGTTTAAAC

VVVVVVVVVVV) pBFB422 Sgf to Pme (SEQ ID NO:589)
GCGATCGCCATGCCTGGCGCAGTAGGCAAGGTGGTGCCTTCTTCGAGGCTAAGGTGGTGGACTTGGACACCGGTAAGACA
CTGGGTGTGAACCAGCGCGGCGAGCTGTGCGTCCGTGGCCCCATGATCATGAGCGGCTACGTTAACAACCCCGAGGCTAC
AAACGCTCTCATCGACAAGGACGGCTGGCTGCACAGCGGCGACATCGCCTACTGGGACGAGGACGAGCACTTCTTCATCG
TGGACCGGCTGAAGAGCCTGATCAAATACAAGGGCTACCAGGTAGCCCCAGCCGAACTGGAGAGCATCCTGCTGCAACAC
CCCAACATCTTCGACGCCGGGGTCGCCGGCCTGCCCGACGACGATGCCGGCGAGCTGCCCGCCGCAGTCGTCGTGCTGGA
ACACGGTAAAACCATGACCGAGAAGGAGATCGTGGACTATGTGGCCAGCCAGGTTACAACCGCCAAGAAGCTGCGCGGTG
GTGTTGTGTTCGTGGACGAGGTGCCTAAAGGACTGACCGGCAAGTTGGACGCCCGCAAGATCCGCGAGATTCTCATTAAG
GCCAAGAAGGGTTCATCTGGTGGATCAGGTGGAAGTGGAGGAGGTTCTGGAGGATCTGGCGGGAACGGCAGGTTCCTGAC
ACTTAAGCCTCTTCCGGATAGTATTATCCAGGAGTCCCTTGAGATCCAGCAAGGGGTGAATCCTTTTTTTATCGGGCGAA
GCGAGGACTGTAATTGCAAGATCGAAGATAACAGACTCAGTAGAGTGCACTGCTTTATTTTCAAGAAGAGGCACGCAGTG
GGAAAATCTATGTACGAATCCCCAGCTCAGGGCCTCGACGATATTTGGTACTGTCATACAGGCACAAATGTATCCTACCT
GAATAACAATCGAATGATCCAAGGCACCAAATTCCTTCTGCAGGATGGCGACGAAATCAAGATTATCTGGGATAAGAATA
ACAAATTCGTTATAGGTTTTAAGGTCGAGATCAATGATACAACCGGGCTCTTCAACGAGGGGCTGGGTATGCTGCAGGAG
CAGCGGGTCGTACTGAAGCAGACTGCTGAAGAGAAAGACCTCGTAAAGAAACTTGGAGGCTCGAGCGGACGAAAGAGAGA
TCGGCTGGGGACCCTGGGGATTGGGAGCTCCGGCTCCGGCGGCTCCGGCGGAACCTCAGGAGGCAGTGGAGGAAGTTCTG
GAGCCAAAAACATTAAGAAGGGCCCAGCGCCATTCTACCCACTCGAAGACGGGACCGCCGGCGAGCAGCTGCACAAAGCC
ATGAAGCGCTACGCCCTGGTGCCCGGCACCATCGCCTTTACCGACGCACATATCGAGGTGGACATTACCTACGCCGAGTA
CTTCGAGATGAGCGTTCGGCTGGCAGAAGCTATGAAGCGCTATGGGCTGAATACAAACCATCGGATCGTGGTGTGCAGCG
AGAATAGCTTGCAGTTCTTCATGCCCGTGTTGGGTGCCCTGTTCATCGGTGTGGCTGTGGCCCCAGCTAACGACATCTAC
AACGAGCGCGAGCTGCTGAACAGCATGGGCATCAGCCAGCCCACCGTCGTATTCGTGAGCAAGAAAGGGCTGCAAAAGAT
CCTCAACGTGCAAAAGAAGCTACCGATCATACAAAAGATCATCATCATGGATAGCAAGACCGACTACCAGGGCTTCCAAA
GCATGTACACCTTCGTGACTTCCCATTTGCCACCCGGCTTCAACGAGTACGACTTCGTGCCCGAGAGCTTCGACCGGGAC
AAAACCATCGCCCTGATCATGAACAGTAGTGGCAGTACCGGATTGCCCAAGGGCGTAGCCCTACCGCACCGCACCGCTTG
TGTCCGATTCAGTCATGCCCGCGACCCCATCTTCGGCAACCAGATCATCCCCGACACCGCTATCCTCAGCGTGGTGCCAT
TTCACCACGGCTTCGGCATGTTCACCACGCTGGGCTACTTGATCTGCGGCTTTCGGGTCGTGCTCATGTACCGCTTCGAG
GAGGAGCTATTCTTGCGCAGCTTGCAAGACTATAAGATTCAATCTGCCCTGCTGGTGCCCACACTATTTAGCTTCTTCGC
TAAGAGCACTCTCATCGACAAGTACGACCTAAGCAACTTGCACGAGATCGCCAGCGGCGGGGCGCCGCTCAGCAAGGAGG
TAGGTGAGGCCGTGGCCAAACGCTTCCACCTACCAGGCATCCGCCAGGGCTACGGCCTGACAGAAACAACCAGCGCCATT
CTGATCACCCCCGAAGGGTGAGTTTAAAC

WWWWWWWWWWW) pBFB423 Sgf to Pme (SEQ ID NO:590)
GCGATCGCCATGAAGAAAATCATCTTTGTGGGCCACGACTGGGGGGCTTGTCTGGCCTTTCACTACTCCTACGAGCACCA
AGACAAGATCAAGGCCATCGTCCATGCTGAGAGTGTCGTGGACGTGATCGAGTCCTGGGACGAGTGGCCTGACATCGAGG
AGGATATCGCCCTGATCAAGAGCGAAGAGGGCGAGAAAATGGTGCTTGAGAATAACTTCTTCGTCGAGACCATGCTCCCA
AGCAAGATCATGCGGAAACTGGAGCCTGAGGAGTTCGCTGCCTACCTGGAGCCATTCAAGGAGAAGGGCGAGGTTAGACG
GCCTACCCTCTCCTGGCCTCGCGAGATCCCTCTCGTTAAGGGAGGCAAGCCCGACGTCGTCCAGATTGTCCGCAACTACA
ACGCCTACCTTCGGGCCAGCGACGATCTGCCTAAGATGTTCATCGAGTCCGACCCTGGGTTCTTTTCCAACGCTATTGTC

FIG. 67DM

GAGGGAGCTAAGAAGTTCCCTAACACCGAGTTCGTGAAGGTGAAGGGCCTCCACTTCAGCCAGGAGGACGCTCCAGATGA
AATGGGTAAGTACATCAAGAGCTTCGTGGAGCGCGTGCTGAAGAACGAGCAGGGTAGTGGCGGTGGAACGGCAGGTTCC
TGACACTTAAGCCTCTTCCGGATAGTATTATCCAGGAGTCCCTTGAGATCCAGCAAGGGGTGAATCCTTTTTTTATCGGG
CGAAGCGAGGACTGTAATTGCAAGATCGAAGATAACAGACTCAGTAGAGTGCACTGCTTTATTTTCAAGAAGAGGCACGC
AGTGGGAAAATCTATGTACGAATCCCCAGCTCAGGGCCTCGACGATATTTGGTACTGTCATACAGGCACAAATGTATCCT
ACCTGAATAACAATCGAATGATCCAAGGCACCAAATTCCTTCTGCAGGATGGCGACGAAATCAAGATTATCTGGGATAAG
AATAACAAATTCGTTATAGGTTTTAAGGTCGAGATCAATGATACAACCGGGCTCTTCAACGAGGGGCTGGGTATGCTGCA
GGAGCAGCGGGTCGTACTGAAGCAGACTGCTGAAGAGAAAGACCTCGTAAAGAAACTTGGAGGCTCGAGCGGACGAAAGA
GAGATCGGCTGGGGACCCTGGGGATTGGAGGGAGCTCAGGAGCTTCCAAGGTGTACGACCCCGAGCAACGCAAACGCATG
ATCACTGGGCCTCAGTGGTGGGCTCGCTGCAAGCAAATGAACGTGCTGGACTCCTTCATCAACTACTATGATTCCGAGAA
GCACGCCGAGAACGCCGTGATTTTTCTGCATGGTAACGCTGCCTCCAGCTACCTGTGGAGGCACGTCGTGCCTCACATCG
AGCCCGTGGCTAGATGCATCATCCCTGATCTGATCGGAATGGGTAAGTCCGGCAAGAGCGGGAATGGCTCATATCGCCTC
CTGGATCACTACAAGTACCTCACCGCTTGGTTCGAGCTGCTGAACCTTTGAGTTTAAAC

XXXXXXXXXXX) pBFB424 Sgf to Pme (SEQ ID NO:591)
GCGATCGCCATGAAGAAAATCATCTTTGTGGGCCACGACTGGGGGGCTTGTCTGGCCTTTCACTACTCCTACGAGCACCA
AGACAAGATCAAGGCCATCGTCCATGCTGAGAGTGTCGTGGACGTGATCGAGTCCTGGGACGAGTGGCCTGACATCGAGG
AGGATATCGCCCTGATCAAGAGCGAAGAGGGCGAGAAAATGGTGCTTGAGAATAACTTCTTCGTCGAGACCATGCTCCCA
AGCAAGATCATGCGGAAACTGGAGCCTGAGGAGTTCGCTGCCTACCTGGAGCCATTCAAGGAGAAGGGCGAGGTTAGACG
GCCTACCCTCTCCTGGCCTCGCGAGATCCCTCTCGTTAAGGGAGGCAAGCCCGACGTCGTCCAGATTGTCCGCAACTACA
ACGCCTACCTTCGGGCCAGCGACGATCTGCCTAAGATGTTCATCGAGTCCGACCCTGGGTTCTTTTCCAACGCTATTGTC
GAGGGAGCTAAGAAGTTCCCTAACACCGAGTTCGTGAAGGTGAAGGGCCTCCACTTCAGCCAGGAGGACGCTCCAGATGA
AATGGGTAAGTACATCAAGAGCTTCGTGGAGCGCGTGCTGAAGAACGAGCAGGGTTCATCTGGTGGATCAGGTGGAAGTG
GAGGGAACGGCAGGTTCCTGACACTTAAGCCTCTTCCGGATAGTATTATCCAGGAGTCCCTTGAGATCCAGCAAGGGGTG
AATCCTTTTTTTATCGGGCGAAGCGAGGACTGTAATTGCAAGATCGAAGATAACAGACTCAGTAGAGTGCACTGCTTTAT
TTTCAAGAAGAGGCACGCAGTGGGAAAATCTATGTACGAATCCCCAGCTCAGGGCCTCGACGATATTTGGTACTGTCATA
CAGGCACAAATGTATCCTACCTGAATAACAATCGAATGATCCAAGGCACCAAATTCCTTCTGCAGGATGGCGACGAAATC
AAGATTATCTGGGATAAGAATAACAAATTCGTTATAGGTTTTAAGGTCGAGATCAATGATACAACCGGGCTCTTCAACGA
GGGGCTGGGTATGCTGCAGGAGCAGCGGGTCGTACTGAAGCAGACTGCTGAAGAGAAAGACCTCGTAAAGAAACTTGGAG
GCTCGAGCGGACGAAAGAGAGATCGGCTGGGGACCCTGGGGATTGGGAGCTCCGGCAGTGGAGGAAGTTCTGGAGCTTCC
AAGGTGTACGACCCCGAGCAACGCAAACGCATGATCACTGGGCCTCAGTGGTGGGCTCGCTGCAAGCAAATGAACGTGCT
GGACTCCTTCATCAACTACTATGATTCCGAGAAGCACGCCGAGAACGCCGTGATTTTTCTGCATGGTAACGCTGCCTCCA
GCTACCTGTGGAGGCACGTCGTGCCTCACATCGAGCCCGTGGCTAGATGCATCATCCCTGATCTGATCGGAATGGGTAAG
TCCGGCAAGAGCGGGAATGGCTCATATCGCCTCCTGGATCACTACAAGTACCTCACCGCTTGGTTCGAGCTGCTGAACCT
TTGAGTTTAAAC

YYYYYYYYYYY) pBFB425 Sgf to Pme (SEQ ID NO:592)
GCGATCGCCATGAAGAAAATCATCTTTGTGGGCCACGACTGGGGGGCTTGTCTGGCCTTTCACTACTCCTACGAGCACCA
AGACAAGATCAAGGCCATCGTCCATGCTGAGAGTGTCGTGGACGTGATCGAGTCCTGGGACGAGTGGCCTGACATCGAGG
AGGATATCGCCCTGATCAAGAGCGAAGAGGGCGAGAAAATGGTGCTTGAGAATAACTTCTTCGTCGAGACCATGCTCCCA
AGCAAGATCATGCGGAAACTGGAGCCTGAGGAGTTCGCTGCCTACCTGGAGCCATTCAAGGAGAAGGGCGAGGTTAGACG
GCCTACCCTCTCCTGGCCTCGCGAGATCCCTCTCGTTAAGGGAGGCAAGCCCGACGTCGTCCAGATTGTCCGCAACTACA
ACGCCTACCTTCGGGCCAGCGACGATCTGCCTAAGATGTTCATCGAGTCCGACCCTGGGTTCTTTTCCAACGCTATTGTC
GAGGGAGCTAAGAAGTTCCCTAACACCGAGTTCGTGAAGGTGAAGGGCCTCCACTTCAGCCAGGAGGACGCTCCAGATGA
AATGGGTAAGTACATCAAGAGCTTCGTGGAGCGCGTGCTGAAGAACGAGCAGGGTTCATCTGGTGGATCAGGTGGAAGTG
GAGGAGGTTCTGGAGGATCTGGCGGGAACGGCAGGTTCCTGACACTTAAGCCTCTTCCGGATAGTATTATCCAGGAGTCC
CTTGAGATCCAGCAAGGGGTGAATCCTTTTTTTATCGGGCGAAGCGAGGACTGTAATTGCAAGATCGAAGATAACAGACT
CAGTAGAGTGCACTGCTTTATTTTCAAGAAGAGGCACGCAGTGGGAAAATCTATGTACGAATCCCCAGCTCAGGGCCTCG
ACGATATTTGGTACTGTCATACAGGCACAAATGTATCCTACCTGAATAACAATCGAATGATCCAAGGCACCAAATTCCTT
CTGCAGGATGGCGACGAAATCAAGATTATCTGGGATAAGAATAACAAATTCGTTATAGGTTTTAAGGTCGAGATCAATGA
TACAACCGGGCTCTTCAACGAGGGGCTGGGTATGCTGCAGGAGCAGCGGGTCGTACTGAAGCAGACTGCTGAAGAGAAAG
ACCTCGTAAAGAAACTTGGAGGCTCGAGCGGACGAAAGAGAGATCGGCTGGGGACCCTGGGGATTGGGAGCTCCGGCTCC
GGCGGCTCCGGCGGAACCTCAGGAGGCAGTGGAGGAAGTTCTGGAGCTTCCAAGGTGTACGACCCCGAGCAACGCAAACG
CATGATCACTGGGCCTCAGTGGTGGGCTCGCTGCAAGCAAATGAACGTGCTGGACTCCTTCATCAACTACTATGATTCCG
AGAAGCACGCCGAGAACGCCGTGATTTTTCTGCATGGTAACGCTGCCTCCAGCTACCTGTGGAGGCACGTCGTGCCTCAC
ATCGAGCCCGTGGCTAGATGCATCATCCCTGATCTGATCGGAATGGGTAAGTCCGGCAAGAGCGGGAATGGCTCATATCG
CCTCCTGGATCACTACAAGTACCTCACCGCTTGGTTCGAGCTGCTGAACCTTTGAGTTTAAAC

FIG. 67DN

ZZZZZZZZZZZ) pBFB426 Sgf to Pme (SEQ ID NO:593)
GCGATCGCCATGGCCGAGAACGCCGTGATTTTTCTGCATGGTAACGCTGCCTCCAGCTACCTGTGGAGGCACGTCGTGCC
TCACATCGAGCCCGTGGCTAGATGCATCATCCCTGATCTGATCGGAATGGGTAAGTCCGGCAAGAGCGGGAATGGCTCAT
ATCGCCTCCTGGATCACTACAAGTACCTCACCGCTTGGTTCGAGCTGCTGAACCTTCCAAAGAAAATCATCTTTGTGGGC
CACGACTGGGGGGCTTGTCTGGCCTTTCACTACTCCTACGAGCACCAAGACAAGATCAAGGCCATCGTCCATGCTGAGAG
TGTCGTGGACGTGATCGAGTCCTGGGACGAGTGGCCTGACATCGAGGAGGATATCGCCCTGATCAAGAGCGAAGAGGGCG
AGAAAATGGTGCTTGAGAATAACTTCTTCGTCGAGACCATGCTCCCAAGCAAGATCATGCGGAAACTGGAGCCTGAGGAG
TTCGCTGCCTACCTGGAGCCATTCAAGGAGAAGGGCGAGGTTAGACGGCCTACCCTCTCCTGGCCTCGCGAGATCCCTCT
CGTTAAGGGAGGCAAGCCCGACGTCGTCCAGATTGTCCGCAACTACAACGCCTACCTTCGGGCCAGCGACGATCTGCCTA
AGATGTTCATCGAGTCCGACCCTGGGTTCTTTTCCAACGCTATTGTCGAGGGAGCTAAGAAGTTCCCTAACACCGAGTTC
GTGAAGGTGAAGGGCCTCCACTTCAGCCAGGAGGACGCTCCAGATGAAATGGGTAAGTACATCAAGAGCTTCGTGGAGCG
CGTGCTGAAGAACGAGCAGGGTAGTGGCGGTGGGAACGGCAGGTTCCTGACACTTAAGCCTCTTCCGGATAGTATTATCC
AGGAGTCCCTTGAGATCCAGCAAGGGGTGAATCCTTTTTTTATCGGGCGAAGCGAGGACTGTAATTGCAAGATCGAAGAT
AACAGACTCAGTAGAGTGCACTGCTTTATTTTCAAGAAGAGGCACGCAGTGGGAAAATCTATGTACGAATCCCCAGCTCA
GGGCCTCGACGATATTTGGTACTGTCATACAGGCACAAATGTATCCTACCTGAATAACAATCGAATGATCCAAGGCACCA
AATTCCTTCTGCAGGATGGCGACGAAATCAAGATTATCTGGGATAAGAATAACAAATTCGTTATAGGTTTTAAGGTCGAG
ATCAATGATACAACCGGGCTCTTCAACGAGGGGCTGGGTATGCTGCAGGAGCAGCGGGTCGTACTGAAGCAGACTGCTGA
AGAGAAAGACCTCGTAAAGAAACTTGGAGGCTCGAGCGGACGAAAGAGAGATCGGCTGGGGACCCTGGGGATTGGAGGGA
GCTCAGGAGCTTCCAAGGTGTACGACCCCGAGCAACGCAAACGCATGATCACTGGGCCTCAGTGGTGGGCTCGCTGCAAG
CAAATGAACGTGCTGGACTCCTTCATCAACTACTATGATTCCGAGAAGTGAGTTTAAAC

AAAAAAAAAAAA) pBFB427 Sgf to Pme (SEQ ID NO:594)
GCGATCGCCATGGCCGAGAACGCCGTGATTTTTCTGCATGGTAACGCTGCCTCCAGCTACCTGTGGAGGCACGTCGTGCC
TCACATCGAGCCCGTGGCTAGATGCATCATCCCTGATCTGATCGGAATGGGTAAGTCCGGCAAGAGCGGGAATGGCTCAT
ATCGCCTCCTGGATCACTACAAGTACCTCACCGCTTGGTTCGAGCTGCTGAACCTTCCAAAGAAAATCATCTTTGTGGGC
CACGACTGGGGGGCTTGTCTGGCCTTTCACTACTCCTACGAGCACCAAGACAAGATCAAGGCCATCGTCCATGCTGAGAG
TGTCGTGGACGTGATCGAGTCCTGGGACGAGTGGCCTGACATCGAGGAGGATATCGCCCTGATCAAGAGCGAAGAGGGCG
AGAAAATGGTGCTTGAGAATAACTTCTTCGTCGAGACCATGCTCCCAAGCAAGATCATGCGGAAACTGGAGCCTGAGGAG
TTCGCTGCCTACCTGGAGCCATTCAAGGAGAAGGGCGAGGTTAGACGGCCTACCCTCTCCTGGCCTCGCGAGATCCCTCT
CGTTAAGGGAGGCAAGCCCGACGTCGTCCAGATTGTCCGCAACTACAACGCCTACCTTCGGGCCAGCGACGATCTGCCTA
AGATGTTCATCGAGTCCGACCCTGGGTTCTTTTCCAACGCTATTGTCGAGGGAGCTAAGAAGTTCCCTAACACCGAGTTC
GTGAAGGTGAAGGGCCTCCACTTCAGCCAGGAGGACGCTCCAGATGAAATGGGTAAGTACATCAAGAGCTTCGTGGAGCG
CGTGCTGAAGAACGAGCAGGGTTCATCTGGTGGATCAGGTGGAAGTGGAGGGAACGGCAGGTTCCTGACACTTAAGCCTC
TTCCGGATAGTATTATCCAGGAGTCCCTTGAGATCCAGCAAGGGGTGAATCCTTTTTTTATCGGGCGAAGCGAGGACTGT
AATTGCAAGATCGAAGATAACAGACTCAGTAGAGTGCACTGCTTTATTTTCAAGAAGAGGCACGCAGTGGGAAAATCTAT
GTACGAATCCCCAGCTCAGGGCCTCGACGATATTTGGTACTGTCATACAGGCACAAATGTATCCTACCTGAATAACAATC
GAATGATCCAAGGCACCAAATTCCTTCTGCAGGATGGCGACGAAATCAAGATTATCTGGGATAAGAATAACAAATTCGTT
ATAGGTTTTAAGGTCGAGATCAATGATACAACCGGGCTCTTCAACGAGGGGCTGGGTATGCTGCAGGAGCAGCGGGTCGT
ACTGAAGCAGACTGCTGAAGAGAAAGACCTCGTAAAGAAACTTGGAGGCTCGAGCGGACGAAAGAGAGATCGGCTGGGGA
CCCTGGGGATTGGGAGCTCCGGCAGTGGAGGAAGTTCTGGAGCTTCCAAGGTGTACGACCCCGAGCAACGCAAACGCATG
ATCACTGGGCCTCAGTGGTGGGCTCGCTGCAAGCAAATGAACGTGCTGGACTCCTTCATCAACTACTATGATTCCGAGAA
GTGAGTTTAAAC

BBBBBBBBBBBB) pBFB428 Sgf to Pme (SEQ ID NO:595)
GCGATCGCCATGGCCGAGAACGCCGTGATTTTTCTGCATGGTAACGCTGCCTCCAGCTACCTGTGGAGGCACGTCGTGCC
TCACATCGAGCCCGTGGCTAGATGCATCATCCCTGATCTGATCGGAATGGGTAAGTCCGGCAAGAGCGGGAATGGCTCAT
ATCGCCTCCTGGATCACTACAAGTACCTCACCGCTTGGTTCGAGCTGCTGAACCTTCCAAAGAAAATCATCTTTGTGGGC
CACGACTGGGGGGCTTGTCTGGCCTTTCACTACTCCTACGAGCACCAAGACAAGATCAAGGCCATCGTCCATGCTGAGAG
TGTCGTGGACGTGATCGAGTCCTGGGACGAGTGGCCTGACATCGAGGAGGATATCGCCCTGATCAAGAGCGAAGAGGGCG
AGAAAATGGTGCTTGAGAATAACTTCTTCGTCGAGACCATGCTCCCAAGCAAGATCATGCGGAAACTGGAGCCTGAGGAG
TTCGCTGCCTACCTGGAGCCATTCAAGGAGAAGGGCGAGGTTAGACGGCCTACCCTCTCCTGGCCTCGCGAGATCCCTCT
CGTTAAGGGAGGCAAGCCCGACGTCGTCCAGATTGTCCGCAACTACAACGCCTACCTTCGGGCCAGCCACGATCTGCCTA
AGATGTTCATCGAGTCCGACCCTGGGTTCTTTTCCAACGCTATTGTCGAGGGAGCTAAGAAGTTCCCTAACACCGAGTTC
GTGAAGGTGAAGGGCCTCCACTTCAGCCAGGAGGACGCTCCAGATGAAATGGGTAAGTACATCAAGAGCTTCGTGGAGCG
CGTGCTGAAGAACGAGCAGGGTTCATCTGGTGGATCAGGTGGAAGTGGAGGAGGTTCTGGAGGATCTGGCGGGAACGGCA
GGTTCCTGACACTTAAGCCTCTTCCGGATAGTATTATCCAGGAGTCCCTTGAGATCCAGCAAGGGGTGAATCCTTTTTTT

FIG. 67DO

ATCGGGCGAAGCGAGGACTGTAATTGCAAGATCGAAGATAACAGACTCAGTAGAGTGCACTGCTTTATTTTCAAGAAGAG
GCACGCAGTGGGAAAATCTATGTACGAATCCCCAGCTCAGGGCCTCGACGATATTTGGTACTGTCATACAGGCACAAATG
TATCCTACCTGAATAACAATCGAATGATCCAAGGCACCAAATTCCTTCTGCAGGATGGCGACGAAATCAAGATTATCTGG
GATAAGAATAACAAATTCGTTATAGGTTTTAAGGTCGAGATCAATGATACAACCGGGCTCTTCAACGAGGGGCTGGGTAT
GCTGCAGGAGCAGCGGGTCGTACTGAAGCAGACTGCTGAAGAGAAAGACCTCGTAAAGAAACTTGGAGGCTCGAGCGGAC
GAAAGAGAGATCGGCTGGGGACCCTGGGGATTGGGAGCTCCGGCTCCGGCGGC

CCCCCCCCCCCC) pBFB7 (not Sgf I to Pme I; ORF only) (SEQ ID NO:596)
ATGGATACTGCGATTTTAAGTGTTGTTCCATTCCATCACGGTTTTGGAATGTTTACTACACTCGGATATTTGATATGTGG
ATTTCGAGTCGTCTTAATGTATAGATTTGAAGAAGAGCTGTTTCTGAGGAGCCTTCAGGATTACAAGATTCAAAGTGCGC
TGCTGGTGCCAACCCTATTCTCCTTCTTCGCCAAAAGCACTCTGATTGACAAATACGATTTATCTAATTTACACGAAATT
GCTTCTGGTGGCGCTCCCCTCTCTAAGGAAGTCGGGGAAGCGGTTGCCAAGAGGTTCCATCTGCCAGGTATCAGGCAAGG
ATATGGGCTCACTGAGACTACATCAGCTATTCTGATTACACCCGAGGGGGATGATAAACCGGGCGCGGTCGGTAAAGTTG
TTCCATTTTTTGAAGCGAAGGTTGTGGATCTGGATACCGGGAAAACGCTGGGCGTTAATCAAAGAGGCGAACTGTGTGTG
AGAGGTCCTATGATTATGTCCGGTTATGTAAACAATCCGGAAGCGACCAACGCCTTGATTGACAAGGATGGATGGCTACA
TTCTGGAGACATAGCTTACTGGGACGAAGACGAACACTTCTTCATCGTTGACCGCCTGAAGTCTCTGATTAAGTACAAAG
GCTATCAGGTGGCTCCCGCTGAATTGGAATCCATCTTGCTCCAACACCCCAACATCTTCGACGCAGGTGTCGCAGGTCTT
CCCGACGATGACGCCGGTGAACTTCCCGCCGCCGTTGTTGTTTTGGAGCACGGAAAGACGATGACGGAAAAAGAGATCGT
GGATTACGTCGCCAGTCAAGTAACAACCGCGAAAAAGTTGCGCGGAGGAGTTGTGTTTGTGGACGAAGTACCGAAAGGTC
TTACCGGAAAACTCGACGCAAGAAAAATCAGAGAGATCCTCATAAAGGCCAAGAAGCTCGAGGGAAGCGGTGGCGGAGGT
CTGACTGAGGAGCAGATTGCAGAGTTCAAGGAGGCCTTCTCCCTCTTTGACAAGGATGGAGATGGCACTATCACCACCAA
GGAGTTGGGGACAGTGATGAGATCCCTGGGACAGAACCCCACTGAAGCAGAGCTGCAGGATATGATCAATGAGGTGGATG
CAGATGGGAACGGGACCATTGACTTCCCGGAGTTCCTGACCATGATGGCCAGAAAGATGAAGGACACAGACAGTGAGGAG
GAGATCCGAGAGGCGTTCCGTGTCTTTGACAAGGATGGGAATGGCTACATCAGCGCCGCAGAGCTGCGTCACGTAATGAC
GAACCTGGGGGAGAAGCTGACCGATGAGGAGGTGGATGAGATGATCAGGGAGGCTGACATCGATGGAGATGGCCAGGTCA
ATTATGAAGAGTTTGTACAGATGATGACTGCAGGAGGCGGCGGTAGCGGTCCATGGGCCAAAAACATAAAGAAAGGCCCG
GCGCCATTCTATCCGCTGGAAGATGGAACCGCTGGAGAGCAACTGCATAAGGCTATGAAGAGATACGCCCTGGTTCCTGG
AACAATTGCTTTTACAGATGCACATATCGAGGTGGACATCACTTACGCTGAGTACTTCGAAATGTCCGTTCGGTTGGCAG
AAGCTATGAAACGATATGGGCTGAATACAAATCACAGAATCGTCGTATGCAGTGAAAACTCTCTTCAATTCTTTATGCCG
GTGTTGGGCGCGTTATTTATCGGAGTTGCAGTTGCGCCCGCGAACGACATTTATAATGAACGTGAATTGCTCAACAGTAT
GGGCATTTCGCAGCCTACCGTGGTGTTCGTTTCCAAAAAGGGGTTGCAAAAAATTTTGAACGTGCAAAAAAAGCTCCCAA
TCATCCAAAAAATTATTATCATGGATTCTAAAACGGATTACCAGGGATTTCAGTCGATGTACACGTTCGTCACATCTCAT
CTACCTCCCGGTTTTAATGAATACGATTTTGTGCCAGAGTCCTTCGATAGGGACAAGACAATTGCACTGATCATGAACTC
CTCTGGATCTACTGGTCTGCCTAAAGGTGTCGCTCTGCCTCATAGAACTGCCTGCGTGAGATTCTCGCATGCCAGAGATC
CTATTTTTGGCAATCAAATCATTCCTtaa

*DDDDDDDDDDDD) 201360_17_A12 Sgf to Pme (SEQ ID NO:597)*
GCGATCGCATGgcttccaaggtgtacgaccccgagcaacgcaaacgcatgatcactgggcctcagtggtgggctcgctgc
Aagcaaatgaacgtgctggactccttcatcaactactatgattccgagaagcacgccgagaacgccgtgatttttctgca
tggtaacgctgcctccagctacctgtggaggcacgtcgtgcctcacatcgagcccgtggctagatgcatcatccctgatc
tgatcggaatgggtaagtccggcaagagcgggaatggcTCAggCTCGAcCGGAatgtatgaaagctttattgagtcactg
ccattccttaaatctttggagttttctgaacgcctgaaagtagtagatgtgataggcaccaaagtatacaacgatggaga
acaaatcattgctcagggagattcggctgattctttttcattgtagaatctggagaagtgaaaattactatgaaaagaa
agggtaaatcagaagtggaagagaatggtgcagtagaaatcgctcgatgctcgcggggacagtactttggagagcttgcc
ctggtaactaacaaacctcgagcagcttctgcccacgccattgggactgtcaaatgtttagcaatggatgtgcaagcatt
tgaaaggcttctgggaccttgcatggaaattatgaaaaggaacatcgctacctatgaagaacagttagttgccctgtttg
gaacgaacatggatattgttgggtCCGGTGGATCCGGTGGCAGCGGAGGGACGTCAGGTGGATCTGGAGGGAGCTCcggt
TATCGCCTCCTGGATCACTACAAGTACCTCACCGCTTGGTTCGAGCTGCTGAACCTTCCAAAGAAAATCATCTTTGTGGG
CCACGACTGGGGGGCTTGTCTGGCCTTTCACTACTCCTACGAGCACCAAGACAAGATCAAGGCCATCGTCCATGCTGAGA
GTGTCGTGGACGTGATCGAGTCCTGGGACGAGTGGCCTGACATCGAGGAGGATATCGCCCTGATCAAGAGCGAAGAGGGC
GAGAAAATGGTGCTTGAGAATAACTTCTTCGTCGAGACCATGCTCCCAAGCAAGATCATGCGGAAACTGGAGCCTGAGGA
GTTCGCTGCCTACCTGGAGCCATTCAAGGAGAAGGGCGAGGTTAGACGGCCTACCCTCTCCTGGCCTCGCGAGATCCCTC
TCGTTAAGGGAGGCAAGCCCGACGTCGTCCAGATTGTCCGCAACTACAACGCCTACCTTCGGGCCAGCGACGATCTGCCT
AAGATGTTCATCGAGTCCGACCCTGGGTTCTTTTCCAACGCTATTGTCGAGGGAGCTAAGAAGTTCCCTAACACCGAGTT
CGTGAAGGTGAAGGGCCTCCACTTCAGCCAGGAGGACGCTCCAGATGAAATGGGTAAGTACATCAAGAGCTTCGTGGAGC
GCGTGCTGAAGAACGAGCAgGTTTAAAC

*FIG. 67*DP

PERMUTED AND NONPERMUTED LUCIFERASE BIOSENSORS

CROSS-REFERENCE TO RELATED APPLICATIONS

This is a divisional of U.S. application Ser. No. 11/732,105, filed Apr. 2, 2007, now U.S. Pat. No. 9,359,635, which claims benefit under 35 U.S.C. § 119(e) of U.S. Provisional Application No. 60/788,608, filed Apr. 3, 2006, U.S. Provisional Application No. 60/879,771, filed Jan. 10, 2007, and U.S. Provisional Application No. 60/901,133, filed Feb. 14, 2007, the disclosures of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Feb. 12, 2018, is named 016026-9474-US04-SEQ-LIST.txt and is 589,571 bytes in size.

FIELD OF THE INVENTION

This invention relates to the field of biochemical assays and reagents. More specifically, this invention relates to modified luciferases and to methods for their use.

BACKGROUND

Luciferases are enzymes that catalyze the oxidation of a substrate (e.g., luciferin) with the concomitant release of photons of light. Luciferases have been isolated from numerous species, including Coleopteran arthropods and many sea creatures. Because it is easily detectable and its activity can be quantified with high precision, luciferases have been used widely to study gene expression and protein localization. Unlike green fluorescent protein (GFP), which requires up to 30 minutes to form chromophore, the products of luciferases can be detected immediately upon completion of synthesis of the polypeptide chain (if substrate and oxygen are also present). In addition, no post-translational modifications are required for enzymatic activity, and the enzyme contains no prosthetic groups, bound cofactors, or disulfide bonds. Luciferases are useful reporters in numerous species and in a wide variety of cells.

Luciferases possess additional features that render them particularly useful as reporter molecules for biosensing, i.e., molecules which reveal molecular properties of a system. Biosensors (i.e., sensors which comprise a biological component) generally function by means of a two-step process: signal generation mediated through a biological component, and signal transduction and/or amplification through an electrical component. Signal generation is typically achieved through binding, energy transfer or catalysis. Signal generation by enzymatic catalysis can be particularly useful due to the inherent efficiency and specificity of these chemical processes. Most catalytic reactions generate less than the energy of hydrolysis for two molecules of ATP, or about 70 kJ/mole. However, the luminescence elicited by luciferases has much higher energy content. For instance, the reaction catalyzed by firefly luciferase (560 nm) emits 214 kJ/mole of energy. Furthermore, luciferases are also highly efficient at converting chemical energy into photons, i.e., they have high quantum yields. Luciferases are thus extremely efficient for generating detectable signals.

Luciferase biosensors have been described. For example, Sala-Newby et al. (1991) disclose that a *Photinus pyralis* luciferase cDNA was modified to generate cyclic AMP-dependent protein kinase phosphorylation sites. In particular, a valine at position 217 was mutated to arginine to generate a site, RRFS (SEQ ID NO:117), and the heptapeptide kemptide, the phosphorylation site of the porcine pyruvate kinase, was added at the N- or C-terminus of the luciferase. Sala-Newby et al. relate that the proteins carrying phosphorylation sites were characterized for their specific activity, pI, effect of pH on the color of the light emitted, and effect of the catalytic subunit of protein kinase A in the presence of ATP. They found that only one of the recombinant proteins (RRFS; SEQ ID NO:117) was significantly different from wild-type luciferase and that the RRFS (SEQ ID NO:117) mutant had a lower specific activity, lower pH optimum, emitted greener light at low pH and, when phosphorylated, decreased its activity by up to 80%. It is disclosed that the latter effect was reversed by phosphatase.

Waud et al. (1996) engineered protein kinase recognition sequences and proteinase sites into a *Photinus pyralis* luciferase cDNA. Two domains of the luciferase were modified by Waud et al.; one between amino acids 209 and 227 and the other at the C-terminus, between amino acids 537 and 550. Waud et al. disclose that the mutation of amino acids between residues 209 and 227 reduced bioluminescent activity to less than 1% of wild-type recombinant, while engineering peptide sequences at the C-terminus resulted in specific activities ranging from 0.06%-120% of the wild-type recombinant luciferase. Waud et al. also disclose that addition of a cyclic AMP dependent protein kinase catalytic subunit to a variant luciferase incorporating the kinase recognition sequence, LRRASLG (SEQ ID NO:1), with a serine at amino acid position 543, resulted in a 30% reduction activity. Alkaline phosphatase treatment restored activity. Waud et al. further disclose that the bioluminescent activity of a variant luciferase containing a thrombin recognition sequence, LVPRES (SEQ ID NO:2), with the cleavage site positioned between amino acids 542 and 543, decreased by 50% when incubated in the presence of thrombin.

Ozawa et al. (2001) describe a biosensor based on protein splicing-induced complementation of rationally designed fragments of firefly luciferase. Protein splicing is a post-translational protein modification through which inteins (internal proteins) are excised out from a precursor fusion protein, ligating the flanking exteins (external proteins) into a contiguous polypeptide. It is disclosed that the N- and C-terminal intein DnaE from *Synechocystis* sp. PCC6803 were each fused respectively to N- and C-terminal fragments of a luciferase. Protein-protein interactions trigger the folding of DnaE intein, resulting in protein splicing, and thereby the extein of ligated luciferase recovers its enzymatic activity. Ozawa et al. disclose that the interaction between known binding partners, phosphorylated insulin receptor substrate 1 (IRS-1) and its target N-terminal SH2 domain of PI 3-kinase, was monitored using a split luciferase in the presence insulin.

Paulmurugan et al. (2002) employed a split firefly luciferase-based assay to monitor the interaction of two proteins, i.e., MyoD and Id, in cell cultures and in mice using both complementation strategy and an intein-mediated reconstitution strategy. To retain reporter activity, in the complementation strategy, fusion proteins need protein interaction, i.e., via the interaction of the protein partners MyoD and Id, while in the reconstitution strategy, the new complete beetle luciferase formed via intein-mediated splicing maintains it activity even in the absence of a continuing interaction between the protein partners.

A protein fragment complementation assay is disclosed in Michnick et al. (U.S. Pat. Nos. 6,270,964, 6,294,330 and 6,428,951). Specifically, Michnick describe a split murine dihydrofolate reductase (DHFR) gene-based assay in which an N-terminal fragment of DHFR and a C-terminal fragment of DHFR are each fused to a GCN4 leucine zipper sequence. DHFR activity was detected in cells which expressed both fusion proteins. Michnick et al. also describe another complementation approach in which nested sets of S1 nuclease generated deletions in the aminoglycoside kinase (AK) gene are introduced into a leucine zipper construct, and the resulting sets of constructs introduced to cells and screened for AK activity.

What is needed is an improved recombinant luciferase for use as a biosensor, e.g., in detecting cellular events such as protein-protein interactions, intracellular signal transduction, or physiological transformations, with a high degree of specificity and a high signal sensitivity.

SUMMARY OF THE INVENTION

The invention provides an improved gene product, e.g., a modified luciferase such as a modified beetle luciferase, such as a firefly or click beetle luciferase, an anthozoan luciferase such as a *Renilla* luciferase, or a crustacean luciferase, which, in the presence of one or more molecules of interest, such as cAMP, cGMP, a kinase, a phosphatase, or calcium, has one or more altered activities. In one embodiment, the amino acid sequence of the modified luciferase is different than the amino acid sequence of a corresponding unmodified (native, wild-type or parental, e.g., a mutant luciferase with one or more substitutions) luciferase as a result of one or more modifications at a site (residue) or in a region which is tolerant to modification, e.g., tolerant to an insertion, a deletion, circular permutation, or any combination thereof. In one embodiment, the regions which are tolerant to modification include surface loops between secondary structures, such as beta sheets or alpha helices, found on the native, wild-type luciferase. One or more modifications may be internal relative to the N- or C-terminus of the unmodified luciferase, and/or may be at the N- and/or C-terminus of the unmodified luciferase, e.g., a deletion of luciferase sequences and/or insertion of one or more amino acid residues optionally including luciferase sequences at the modification site, thereby yielding a modified luciferase. A deletion within the scope of the invention includes a deletion of one or more amino acid residues at a site or in a region of a luciferase sequence that is tolerant to a deletion. The modification(s) may include circular permutation and the introduction (insertion) of one or more discreet (isolated) heterologous amino acid sequences, at least one of which directly or indirectly interacts with a molecule of interest, and optionally may include the deletion of one or more amino acids, e.g., at a site(s) or in a region(s) tolerant to modification including the N- and/or C-terminus of the unmodified luciferase, so long as the resulting modified luciferase has bioluminescent activity before and/or after the interaction with the molecule of interest, e.g., bioluminescent activity is altered after interaction with the molecule of interest. In one embodiment, the modification may be the absence of a peptide bond in the modified luciferase between two amino acids which are linked via a peptide bond in the corresponding unmodified luciferase, in conjunction with a peptide bond in the modified luciferase between residues found at or near the N-terminal and C-terminal residues of the corresponding unmodified luciferase, yielding a circularly permuted luciferase, which optionally includes one or more isolated heterologous amino acid sequences, at least one of which directly or indirectly interacts with a molecule of interest. In one embodiment, the one or more heterologous amino acid sequences, which directly or indirectly interact with a molecule of interest, which sequences are in a circularly permuted luciferase at or near sequences corresponding to the N-terminal and/or C-terminal residues of the corresponding unmodified luciferase. In another embodiment, the one or more heterologous amino acid sequences which directly or indirectly interact with a molecule of interest are at or near the N-terminal and/or C-terminal residues of the circularly permuted or noncircularly permuted luciferase. In one embodiment, the one or more heterologous amino acid sequences which directly or indirectly interact with a molecule of interest in a circularly permuted luciferase are at site(s) or in a region(s) tolerant to modification which is/are not at or near the N-terminal and/or C-terminal residues of the circularly permuted luciferase, i.e., the heterologous sequences are internal to the N- and C-termini. In one embodiment, the circularly permuted luciferase is modified to include two or more heterologous amino acid sequences, which heterologous amino acid sequences are independently at or near sequences corresponding to the N-terminal and/or C-terminal residues of the corresponding unmodified luciferase, at or near the N-terminal and/or C-terminal residues of the circularly permuted luciferase, at site(s) or in a region(s) tolerant to modification which is/are not at or near the N-terminal and/or C-terminal residues of the circularly permuted or noncircularly permuted luciferase, or any combination thereof. In one embodiment, the heterologous amino acid sequences each interact directly or indirectly with a different molecule of interest. In a further embodiment, a circularly permuted luciferase includes at least two heterologous amino acid sequences which interact with each other in the presence or absence of particular exogenous agents. The two heterologous amino acid sequences may contain the same or different sequences. Moreover, the modified luciferase may include deletions at the N- and C-terminus of 1 to about 10 or about 30, residues, or any integer in between, e.g., 15 residues, corresponding to the N- or C-terminus of the unmodified luciferase. The length of the deletion may be greater than 30 residues depending on the particular luciferase and the length of a desirable deletion may be determined by routine deletion analysis. The modified luciferase may be employed to detect reversible interactions, e.g., binding of two or more molecules, formation of disulfide bonds or other conformational changes, changes in conditions, such as pH, temperature or solvent hydrophobicity, or irreversible interactions, via an alteration in the activity of the modified luciferase, such as an alteration in light intensity, color or kinetic profile. The modified luciferase may also be employed to detect interactions that result in structural modifications of the modified luciferase, e.g., phosphorylation by a kinase or bond cleavage by a protease.

As described below, in-frame insertions resulting in modified click beetle luciferases with detectable activity were at residue 21, 25, 117, 358, 376, 379, 398, 399, 400, 401, 402, 403, 405, 406, 407, 409 or 490 of click beetle luciferase, i.e., those residues and/or regions near those residues are tolerant to modification. As also described below, in-frame insertions resulting in modified firefly luciferases with detectable activity were at residue 7, 121, 233, 267, 294, 303, 361, 540 or 541 of firefly luciferase, i.e., those residues and/or regions near those residues are tolerant to modifications. Additional residues or regions tolerant to modification are also described herein below.

Thus, a beetle luciferase may be modified at a residue, for instance, residue 21, 25, 117, 358, 376, 379, 398, 399, 400, 401, 402, 403, 405, 406, 407, 409 or 490, or in a region corresponding to residue 15 to 30, e.g., residue 21 or 25, residue 112 to 122, e.g., residue 117, residue 352 to 362, for instance, residue 358, residue 371 to 384, e.g., residue 379, residue 393 to 414, or residue 485 to 495, of a click beetle luciferase, or at residue 7, 37, 47, 75, 83, 107, 121, 144, 160, 174, 188, 198, 205, 225, 233, 242, 255, 268, 308, 316, 358, 377, 403, 435, 490 or 540, or in a region corresponding to residue 2 to 12, residue 32 to 53, e.g., residue 32 to 43 or residue 42 to 52, residue 70 to 88, e.g., residue 70 to 80 or residue 78 to 88, residue 102 to 126, e.g., residue 102 to 112 or residue 116 to 126, residue 139 to 165, residue 183 to 203, residue 220 to 247, e.g., residue 228 to 238, residue 262 to 273, residue 303 to 313, residue 353 to 408, residue 485 to 495, or residue 535 to 546 of a firefly luciferase. Corresponding positions may be identified by aligning luciferase sequences using, for instance, sequence alignment programs. Residues or regions in a luciferase tolerant to modification may be employed as sites to circularly permute the luciferase, for an insertion, or to "split" the luciferase into two molecules that may be employed in protein complementation or protein splicing assays.

The invention further includes a modified anthozoan luciferase having at least one modification at a site or in a region which is tolerant to modification, including but not limited to at a residue corresponding to residue 2, 30, 31, 42, 45, 46, 68, 69, 90, 91, 92, 110, 111, 150, 151, 168, 169, 193, 207, 208, 223, 224, 251, 259, 274, or 311 or in a region corresponding to residue 2 to 12, residue 26 to 36, residue 37 to 47, residue 64 to 74, residue 86 to 97, e.g., residue 90 or 91, residue 96 to 116, residue 147 to 157, residue 218 to 234, e.g., residue 223, 234, 228, 229 or 230, or residue 301 to 311 of a *Renilla* luciferase (Genbank ID AF025843). Corresponding positions may be identified by aligning luciferase sequences using, for instance, sequence alignment programs. Residues or regions in a luciferase tolerant to modification may be employed as sites to circularly permute the luciferase, for an insertion, or to "split" the luciferase into two molecules that may be employed in protein complementation or protein splicing assays.

Further included is a modified crustacean luciferase, e.g., a copepod luciferase, having at least one modification at a site or in a region which is tolerant to modification, including but not limited to in a region corresponding to residue 43 to 53, residue 63 to 73, residue 79 to 89, residue 95 to 105, residue 105 to 115, residue 109 to 119, residue 121 to 131 or residue 157 to 168 of a *Gaussia* luciferase, e.g., see FIG. 41, or in a region corresponding to residue 45 to 55 or residue 79 to 89 of a mature *Oplophorus* luciferase. Corresponding positions may be identified by aligning luciferase sequences using, for instance, sequence alignment programs. Residues or regions in a luciferase tolerant to modification may be employed as sites to circularly permute the luciferase, for an insertion or to "split" the luciferase into two molecules that may be employed in protein complementation or protein splicing assays.

In one embodiment, the modified luciferase has a detectable activity and includes an insertion of one or more amino acids relative to a corresponding unmodified luciferase at a site or in a region which is tolerant to modification, which insertion includes an amino acid sequence which directly interacts with a molecule of interest, e.g., an insertion which includes a recognition sequence for the molecule of interest, or indirectly interacts with the molecule of interest, e.g., via another molecule. In one embodiment, a modified luciferase comprises an insertion of 2 or more, e.g., 3, 4, 5, 10, 20, 50, 100, 200, 300 or more, but less than about 1000, or any integer in between, amino acid residues. For instance, an insertion of an IP3 sequence may include about 700 amino acid residues. In one embodiment, the modified luciferase with an insertion further comprises a deletion of luciferase sequences, e.g., a deletion of 1 or more, but less than about 100, for instance less than 50, 40, 30, 20, 10 or 5, or any integer in between, residues.

In one embodiment, the invention provides circularly permuted luciferases further modified to include an insertion of an amino acid sequence which directly interacts with a molecule of interest, e.g., an insertion which includes a recognition sequence for the molecule of interest, or indirectly acts with the molecule of interest, e.g., via another molecule. For example, as described hereinbelow, luciferases having a N- and/or C-terminus as well as an internal residue or region which are tolerant to modification were circularly permuted at tolerant residues or regions and at different tolerant residues or regions, and one or more heterologous amino acid sequences were inserted, at least one of which directly or indirectly interacts with a molecule of interest. The resulting modified luciferase was shown to have an alteration in detectable activity in the presence of the molecule of interest.

In one embodiment, circularly permuted beetle luciferases, circularly permuted decapod crustecean luciferases (e.g., *Oplophorus* luciferase), or circularly permuted *Renilla* luciferases having a cAMP or cGMP binding site were shown to have altered luciferase activity in the presence of a cyclic nucleotide, e.g., cAMP or cGMP. Cyclic nucleotide binding sites useful in the luciferases of the invention may have G(E/Q/K)(L/K/S/I)(A/I/C/G)(L/I)X(P/V/T/R/E)R(A/T/H/S)(A/S)(V/T/S/N/W) (SEQ ID NO:118), where X is 2 to 6 amino acids. cAMP binding sites (domains) useful in the circularly permuted luciferases of the invention include but are not limited to cAMP binding sites in exchange protein directly activated by cAMP (Epac) (Bos et al., 2003; and see, for instance, NCBI Accession No. AF115480), including Epac 2B, Epac 1, and Epac IIA, cyclic nucleotide gated ion channels such as hyperpolarization-activated cyclic nucleotide modulated channel (Zagotta et al., 2003), neuropathy target esterase (Dremier et al., 2003), PKA regulatory type IIβ subunit (see, e.g., NCBI Accession No. M124921), e.g., PKA IIβA and PKA IIβB, PKA regulatory type Iα subunit, e.g., PKA IαA and PKA IαB, PKG IIA, PKG IIB, and catabolite activating protein. Also described herein, a noncircularly permuted *Renilla* luciferase and a non-circularly permuted decapod crustecean luciferase having a cAMP binding site had altered luciferase activity in the present of cAMP. cGMP binding sites useful in the circularly permuted luciferases of the invention include but are not limited to cGMP binding sites in a cGMP dependent protein kinase (GK), e.g., GK I, or a GAF regulatory region in phosphodiesterases (PDEs), e.g., PDE2 or PDE5, adenyl cyclases, or FnlA. In one embodiment, the cyclic nucleotide binding domain containing luciferase of the invention further includes a subcellular localization signal, which is useful to detect subcellular localization and/or concentration of cyclic nucleotides.

As described hereinbelow, luciferase biosensors were prepared with insertions of various sequences representing at least four different structural fold classes. In particular, one of the fold classes participates in the modulation of numerous enzymes through different small molecule interactions. Moreover, insertion of an allosteric domain, i.e., one that changes structural conformation upon binding another molecule, into a luciferase of the invention may be used to detect conformational changes, e.g., phosphorylation or protease cleavage.

Hence, in one embodiment, a modified luciferase of the invention comprises an amino acid sequence which is circularly permuted relative to the amino acid sequence of a corresponding luciferase, such as an unmodified wild type luciferase, resulting in a new N- and C-terminus in the circularly permuted luciferase, at least one of which is at a site or in a region which is tolerant to modification, and is engineered to have functionality by introducing a heterologous amino acid sequence which directly or indirectly interacts with, for instance, a cyclic nucleotide. In another embodiment, the circularly permuted luciferase includes other modifications, including but not limited to insertions and/or deletions internal to the N- or C-terminus of the circularly permuted luciferase, for instance, another insertion and/or a deletion, e.g., at or near the N- and C-terminus of the corresponding unmodified luciferase such as at residues corresponding to residues 1 to about 10 or about 30, or any integer in between, of the N-terminus and/or corresponding to the last residue or about the last 30, e.g., last 15, or any integer in between 1 and 30, residues of the C-terminus of the corresponding unmodified luciferase.

In one embodiment, in the absence of the molecule of interest, the activity of a modified luciferase of the invention is less than the activity of a corresponding unmodified luciferase, e.g., the reporter activity of the modified luciferase is about 0.001%, 0.01%, 0.1%, 1%, 10%, 20%, 50%, 70% or more, but less than 100% that of a corresponding unmodified luciferase, the activity of which modified luciferase is optionally detectable. In another embodiment, in the absence of the molecule of interest, the activity of a modified luciferase of the invention is substantially the same or greater than the activity of a corresponding unmodified luciferase, e.g., the reporter activity of the modified luciferase of the invention is about 1.5-fold, e.g., at least 2-, 3- or 5-fold or more, that of a corresponding unmodified luciferase. In the presence of the molecule of interest, the activity of the modified luciferase of the invention is detectably altered. For instance, a detectable alteration in activity of a modified luciferase in the presence of the molecule of interest is an alteration of at least 0.001%, 0.01%, 0.1%, 1%, 10%, or 100%, and up to 2-fold, 4-fold, 10-fold, 100-fold, 1,000-fold, 10,000-fold or more, relative to the activity of the modified luciferase in the absence of the molecule of interest. Thus, the physical proximity of the molecule of interest which interacts with a modification present in the modified luciferase but not the corresponding unmodified luciferase, alters, e.g., decreases, eliminates or increases, the activity of the modified luciferase. For example, a modified beetle, anthozoan luciferase or decapod crustecean may be a circularly permuted beetle, anthozoan or decapod crustecean luciferase with a cAMP binding site. The luminescent signal of such a modified luciferase in the presence of cAMP may be decreased, eliminated or increased relative to the luminescent signal of the modified luciferase in the absence of cAMP or the luminescent signal of the corresponding unmodified beetle, anthozoan or decapod crustecean luciferase in the presence or absence of cAMP.

Accordingly, a modified luciferase of the invention may be employed as a biosensor.

The invention also provides an isolated nucleic acid molecule (polynucleotide) comprising a nucleic acid sequence encoding a modified luciferase of the invention. Further provided is an isolated nucleic acid molecule comprising a nucleic acid sequence encoding fusion protein comprising a modified luciferase and one or more amino acid residues at the N-terminus (a N-terminal fusion partner) and/or C-terminus (a C-terminal fusion partner) of the modified luciferase. Thus, as used herein, a "fusion protein" is a polypeptide which includes one or more amino acids at the N-terminus and/or C-terminus of a modified luciferase of the invention. Preferably, the presence of one or more fusion partners in the fusion protein does not substantially alter the detectable activity of the fusion protein relative to a corresponding modified luciferase. The N- or C-terminal fusion partner may be a sequence used for purification, e.g., a glutathione S-transferase (GST) or a polyHis sequence, a sequence intended to alter a property of the modified luciferase, e.g., a protein destabilization sequence, a protein or nucleic acid interaction sequence (e.g, a binding sequence), a subcellular localization sequence, or a sequence which has a property which is distinguishable from one or more properties of the luciferase in the fusion protein. In one embodiment, the fusion protein comprises a modified luciferase and a fusion partner which is a reporter protein that is different than the luciferase, which reporter protein is useful as an intramolecular control, e.g., a fluorescent protein or another luciferase. In another embodiment, the invention includes a vector comprising a nucleic acid sequence encoding a fusion protein comprising a modified luciferase of the invention and a nucleic acid fragment which encodes a reporter protein that is different than the luciferase in the modified luciferase. Optionally, optimized nucleic acid sequences, e.g., human codon optimized sequences, encoding at least the luciferase, and preferably the modified luciferase or a fusion protein comprising a modified luciferase, are employed in the nucleic acid molecules of the invention, as those optimized sequences can increase the strength of the signal for luciferase. The optimization of nucleic acid sequences is known to the art, see, for example, WO 02/16944.

The invention also includes a stable cell line that expresses a modified luciferase, or fusion protein of the invention, as well as an expression cassette comprising a nucleic acid molecule encoding the modified luciferase or fusion protein of the invention, and a vecto (e.g., a plasmid, virus, or defective viral particles) capable of expressing the nucleic acid molecule of the invention in a host cell. Preferably, the expression cassette comprises a promoter, e.g., a constitutive or regulatable promoter, operably linked to the nucleic acid sequence. In one embodiment, the expression cassette contains an inducible promoter. Also provided is a host cell, e.g., a prokaryotic cell or an eukaryotic cell such as a plant or vertebrate cell, e.g., a mammalian cell, including but not limited to a human, non-human primate, canine, feline, bovine, equine, ovine or rodent (e.g., rabbit, rat, ferret or mouse) cell, which comprises the expression cassette or vector of the invention, and a kit which comprises the nucleic acid molecule, expression cassette, vector, host cell or modified luciferase or fusion protein of the invention.

A modified luciferase of the invention may be employed in applications where unmodified luciferases cannot, such as, as a functional reporter to measure or detect various conditions or molecules of interest, e.g., steroids via insertion of a hormone receptor binding site, for instance, an estrogen binding domain, a calcium binding domain, a protease via insertion of a protease recognition site, or cyclic nucleotides via insertion of a cyclic nucleotide binding site.

For instance, a vector encoding a modified luciferase comprising an insertion of a cAMP binding site, or a modified luciferase comprising an insertion of a cAMP binding site, is mixed with a sample, e.g., a cell, cell lysate, in vitro transcription/translation mixture, or supernatant, and the activity of the modified luciferase in the sample detected or determined, e.g., optionally at one or more time points, and optionally relative to a corresponding unmodified luciferase, or similarly modified luciferase having reduced interaction with cAMP (e.g., further modified by mutations to specific amino acids to reduce the binding affinity with cAMP), or a control sample without cAMP or having a differing amount of cAMP. An alteration in luminescent activity in the sample, for instance, over time, and/or relative to a control, e.g., a cell having a specified amount of cAMP, indicates the presence or amount of cAMP in the sample, or change in amount of cAMP related to experimental condition. In one embodiment, a cell is contacted with a vector comprising a promoter, e.g., a regulatable or constitutive promoter, and a nucleic acid sequence encoding a modified luciferase of the invention which comprises an insertion which interacts with the cyclic nucleotide. In one embodiment, a transfected cell is cultured under conditions in which the promoter induces transient expression of the modified luciferase, and the presence or amount of luminescence determined. In another embodiment, a modified luciferase of the invention which comprises an insertion which interacts with the cyclic nucleotide and a sample suspected of having a cyclic nucleotide are mixed. Then the amount of luminescence is determined. The invention thus provides a method of detecting the amount of a cyclic nucleotide.

In one embodiment, the modified luciferase is a modified anthozoan luciferase such as a modified *Renilla* luciferase. In one embodiment, the modified anthozoan luciferase is a circularly permuted anthozoan luciferase such as a circularly permuted *Renilla* luciferase. In another embodiment, the modified anthozoan luciferase is not circularly permuted. The modified anthozoan luciferase has one or more heterologous amino acid sequences, including at least one which directly or indirectly interacts with a molecule of interest. In one embodiment, the amino acid sequence is one which, during or after interaction with the molecule of interest, undergoes a conformational change, which in turn alters the activity of the luciferase, e.g., a modified *Renilla* luciferase with such an amino acid sequence is useful to detect allosteric interactions.

In one embodiment, the modified luciferase is a modified decapod crustecean luciferase such as a modified *Oplophorus* luciferase. In one embodiment, the modified decapod crustecean luciferase is a circularly permuted decapod crustecean luciferase such as a circularly permuted *Oplophorus* luciferase. In another embodiment, the modified decapod crustecean luciferase is not circularly permuted. The modified decapod crustecean luciferase has one or more heterologous amino acid sequences, including at least one which directly or indirectly interacts with a molecule of interest. In one embodiment, the amino acid sequence is one which, during or after interaction with the molecule of interest, undergoes a conformational change, which in turn alters the activity of the luciferase, e.g., a modified *Oplophorus* luciferase with such an amino acid sequence is useful to detect allosteric interactions.

Exemplary amino acid sequences of interest to fuse to a modified anthozoan luciferase or a modified decapod crustacean luciferase of the invention include but are not limited to an enterokinase site, a protease cleavage site, e.g., a site for a caspase, for instance, a caspase 3 cleavage site, a caspase 8 cleavage site, PSA, or a viral protease such as a Rhinovirus protease cleavage site, a SARS protease cleavage site, or a TEV protease cleavage site (NLYFQG; SEQ ID NO:119), a cyclic nucleotide binding site, a hormone binding site, a calcium binding domain such as calmodulin which is regulated by EGTA and $CaCl_2$, or a double fusion with sequences that interact with each other and optionally are modulated by an exogenous agent, e.g., FKBP and FRB, where rapamycin induces binding and FK506 promotes dissociation of binding; a domain from PKA-R and a domain from PKA-C, which may be regulated by cAMP; a domain from SH2 and a domain that is capable of being phosphorylated, which may be regulated by for instance a tyrosine kinase or a phosphatase; a domain from 14-3-3t and a domain that is capable of being phosphorylated, which may be regulated by for example, cAMP-PKA; a domain from WW and a domain that is capable of being phosphorylated, which may be regulated by for example a Ser-Thr kinase; a domain from dihydrofolate reductase (DHFR), which may be regulated by methotrexate (MTX) or BisMTX; a domain from gyrase B (GyrB), which may be regulated by coumermycin or novobiocin; or a double fusion with sequences from the same domain. Thus, in one embodiment, the circularly permuted anthozoan luciferase or a modified decapod crustacean luciferase is modified to include two or more heterologous sequences, which heterologous sequences are independently at or near sequences corresponding to the N-terminal and/or C-terminal residues of the corresponding unmodified luciferase, at or near the N-terminal and/or C-terminal residues of the circularly permuted luciferase, at site(s) or in a region(s) tolerant to modification which is not at or near the N-terminal and/or C-terminal residues of the circularly permuted luciferase, or any combination thereof, wherein the two heterologous amino acid sequence may interact with different molecules of interest.

Further provided are methods of identifying one or more agents that directly or indirectly modulate a molecule of interest.

In one embodiment, the invention provides a method to detect, or determine the activity of, a molecule of interest in a cell. The method includes providing a luminogenic reaction mixture comprising a cell with a vector having a nucleic acid sequence comprising an open reading frame for a modified luciferase, e.g., a modified beetle luciferase. The modified luciferase has an insertion relative to a corresponding unmodified luciferase, which insertion is at a residue or in a region in a luciferase sequence which is tolerant to modification. The insertion includes an amino acid sequence which directly or indirectly interacts with a molecule of interest relative to the corresponding unmodified luciferase. The mixture is at about 20° C. to about 47° C., e.g., about 37° C. to about 45° C. Luminescence in the mixture is then detected or determined, thereby detecting or determining the presence, amount or activity of the molecule in the cell. As described hereinbelow, incubating a luminogenic reaction mixture with cells encoding a luciferase that is a biosensor for cAMP at physiological temperatures and/or conditions, e.g., about 37° C. and/or about 5% $CO_2$, for a period of time prior to addition of a test agent provided faster responses and a greater dynamic range.

Also provided is the use of a biosensor of the invention for imaging in cells or multicellular organisms, e.g., living mammals.

BRIEF DESCRIPTION OF THE FIGURES

FIG. 1. Positions of Tn5 insertions (bolded) in a click beetle luciferase (amino acid sequence corresponds to SEQ ID NO:3).

FIG. 2. Amino acid sequence of a parental (unmodified) firefly luciferase (luc+) (SEQ ID NO:210).

FIG. 5C. Epac amino acid sequences (SEQ ID NOS: 13-14) and Epac DNA sequence (SEQ ID NO:15) modified for *E. coli* expression.

FIG. 9A) Dose response kinetics. FIG. 9B) RLU at 300 seconds.

FIG. 20. Sequence of CPM-FF Luc (SEQ ID NO:16).

FIG. 26. Additional sites for modification of a firefly luciferase.

FIG. 29. Constructs with an insertion of RIIβB in a noncircularly permuted *Renilla* luciferase.

FIG. 31. Constructs with RIIβB in a circularly permuted *Renilla* luciferase and varying linker lengths.

FIG. 33. Constructs with RIαB in a circularly permuted *Renilla* luciferase.

FIG. 35A) RLU. FIG. 35B) Fold induction.

FIG. 35A) RLU. FIG. 35B) Fold induction.

FIG. 40A) SKF38393. FIG. 40B) SCH23390.

FIG. 50. Comparison of bioluminescent GPCR assays with various agonists.

FIG. 51. Comparison of bioluminescent GPCR assays with various antagonists.

FIG. 52A-FIG. 52D. Detection of intracellular changes in cAMP with a CPM RLuc/RIIβB cAMP biosensor. FIG. 52A) Comparison of detection with different promoters. FIG. 52B) Forskolin induction. FIG. 52C) SK38393 induction. FIG. 52D) Dopamine induction.

FIG. 55A and FIG. 55B. Nucleic acid sequences for *Oplophorus* luciferase and fusions constructs thereof (SEQ ID NOs:205, 206, 207, 208, 209).

FIG. 64A) 50/50 split site. FIG. 64B) 84/85 split site. FIG. 64C) 112/113 split site. FIG. 64D) 134/135 split site.

FIG. 65. Serine/threonine kinase/phosphatase constructs. Peptide sequences specifically identified in the table are: EIYGEFGSSG (SEQ ID NO:267), EIYGEF-GSSGGSGGSG (SEQ ID NO:268), EIYGEF-GSSGGSGGSGGGSGGSGGSG (SEQ ID NO:269), GSSG (SEQ ID NO:270), GSTSGSGKPGSGEGSEIYGEFGSSG (SEQ ID NO:271), GSTSGSGKPGSGEGSEIYGEF-GSGGSGGSSG (SEQ ID NO:272), GSTSGSGKPGSGEG-SEIYGEFGSGGSGGSGGGSGGSGGSSG (SEQ ID NO:273), GSTSGSGKPGSGEGSEIYGEF-GSGSGGSGGSSG (SEQ ID NO:274), GSTG (SEQ ID NO:275), GSSGGSGGSG (SEQ ID NO:276), GSSGGSGGSGGGSGGSGGSG (SEQ ID NO:277), GSGGSGGSGGTSGGSGGSSG (SEQ ID NO:278), GSS-GRKRDRLGTLGIGGSSGGGSGGGGSGG (SEQ ID NO:279), GGSGGSGSSGRKRDRLGTL-GIGGSSGGGSGGGGSGG (SEQ ID NO:280), GSGGSGGSGG (SEQ ID NO:281), GSSGGSGGSGGGSGGSGSSGRKRDRLGTL-GIGGSSGGGSGGGGSGG (SEQ ID NO:282), RKRDRL-GTLGIGGSSGGGSGGGGSGG (SEQ ID NO:283), GGSS-GRKRDRLGTLGIGGSSG (SEQ ID NO:284), GGSSGRKRDRLGTLGIGSSGSGGSGG (SEQ ID NO:285), GGSSGRKRDRLGTL-GIGSGGSGGSGGTSGGSGGSSG (SEQ ID NO:287), GSSGGSGGSGGGSGGSG (SEQ ID NO:288), GGSS-GRKRDRLGTLGIGSSGSGGSGGTSGGSGGSSG (SEQ ID NO:289), GSSGGSGGSGGGRKRDRLGTL-GIGGSSGGGSGGGGSGG (SEQ ID NO:290), GSGGSGGSSG (SEQ ID NO:291), GSSGGSGGSGGGSGGSGGSGRKRDRLGTL-GIGGSSGGGSGGGGSGG (SEQ ID NO:292), GSGG (SEQ ID NO:293), and GGSGGGGSGG (SEQ ID NO:294).

FIG. 67A-67DP. Representative nucleic acid sequences (SEQ ID NOS:308-597).

DETAILED DESCRIPTION OF THE INVENTION

Definitions

Figure 3:
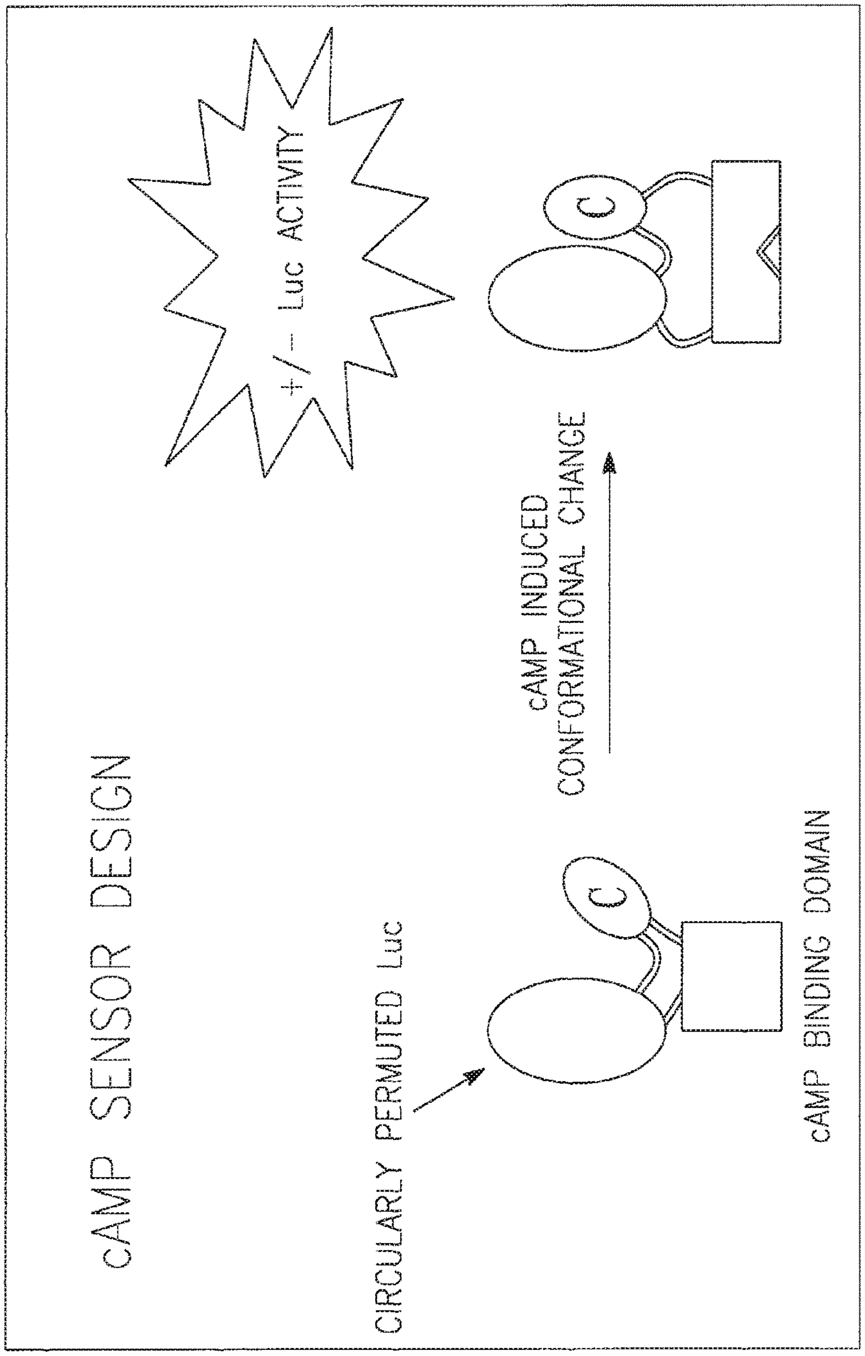
FIG. 3. Schematic of a luminescent cAMP binding assay with a circularly permuted luciferase.
Figure 4:
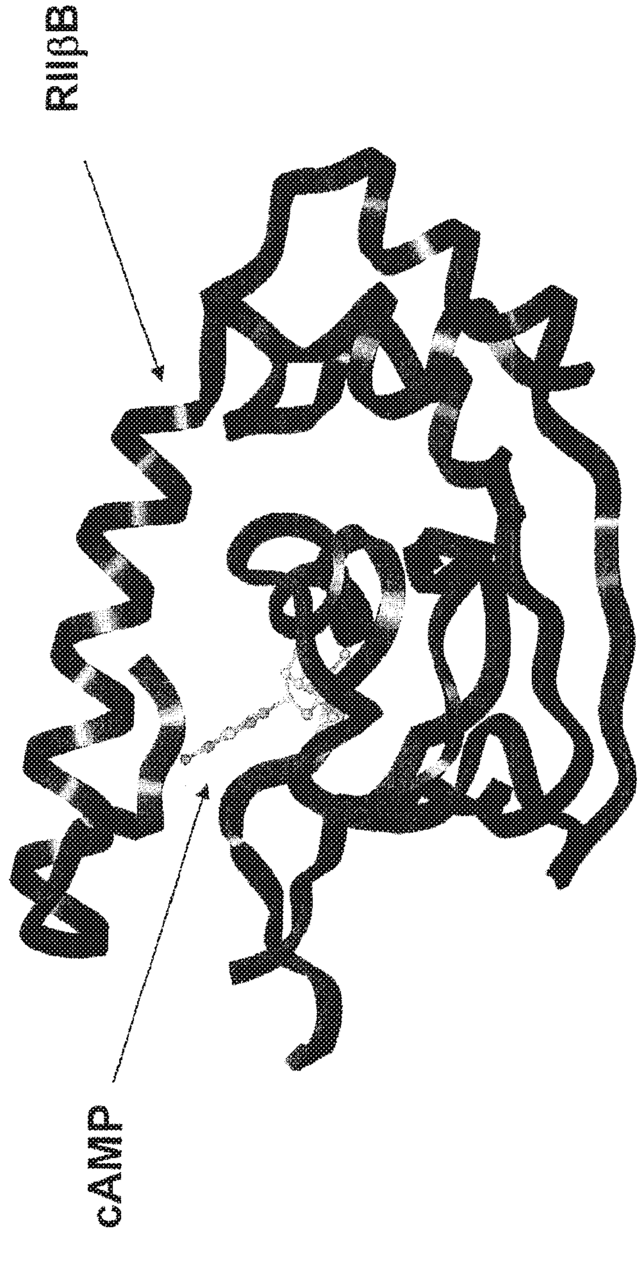
FIG. 4. PKA regulatory subunit type IIβ (RIIβB). X-ray crystal structure of rat RIIβB amino acids 264-412 (PDB 1CX4). RIIβB is rendered as a red ribbon; cAMP is rendered as ball and stick. The primary sequence similarity between rat (amino acids 264-412) and human RIIβB (amino acids 266-414) is 96.6% (program Megallign, DNAStar).

The term "nucleic acid molecule", "polynucleotide", or "nucleic acid sequence" as used herein, refers to nucleic acid, DNA or RNA, that comprises coding sequences necessary for the production of a polypeptide or protein precursor. The encoded polypeptide may be a full-length polypeptide, a fragment thereof (less than full-length), or a fusion of either the full-length polypeptide or fragment thereof with another polypeptide, yielding a fusion polypeptide.

A "nucleic acid", as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence, i.e., a linear order of nucleotides. A "polynucleotide", as used herein, is a nucleic acid containing a sequence that is greater than about 100 nucleotides in length.

An "oligonucleotide" or "primer", as used herein, is a short polynucleotide or a portion of a polynucleotide. An oligonucleotide typically contains a sequence of about two to about one hundred bases. The word "oligo" is sometimes used in place of the word "oligonucleotide".

Nucleic acid molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. Typically, promoter and enhancer elements that direct transcription of a linked gene (e.g., open reading frame or coding region) are generally located 5' or upstream of the coding region. However, enhancer elements can exert their effect even when located 3' of the promoter element and the coding region. Transcription termination and polyadenylation signals are located 3' or downstream of the coding region.

The term "codon" as used herein, is a basic genetic coding unit, consisting of a sequence of three nucleotides that specify a particular amino acid to be incorporated into a polypeptide chain, or a start or stop signal. The term "coding region" when used in reference to structural gene refers to the nucleotide sequences that encode the amino acids found in the nascent polypeptide as a result of translation of a mRNA molecule. Typically, the coding region is bounded on the 5' side by the nucleotide triplet "ATG" which encodes the initiator methionine and on the 3' side by a stop codon (e.g., TAA, TAG, TGA). In some cases the coding region is also known to initiate by a nucleotide triplet "TTG".

The term "gene" refers to a DNA sequence that comprises coding sequences and optionally control sequences necessary for the production of a polypeptide from the DNA sequence.

As used herein, the term "heterologous" nucleic acid sequence or protein refers to a sequence that relative to a reference sequence has a different source, e.g., originates from a foreign species, or, if from the same species, it may be substantially modified from the original form.

Nucleic acids are known to contain different types of mutations. A "point" mutation refers to an alteration in the sequence of a nucleotide at a single base position from the wild-type sequence. Mutations may also refer to insertion or deletion of one or more bases, so that the nucleic acid sequence differs from a reference, e.g., a wild-type, sequence.

As used herein, the terms "hybridize" and "hybridization" refer to the annealing of a complementary sequence to the target nucleic acid, i.e., the ability of two polymers of nucleic acid (polynucleotides) containing complementary sequences to anneal through base pairing. The terms "annealed" and "hybridized" are used interchangeably throughout, and are intended to encompass any specific and reproducible interaction between a complementary sequence and a target nucleic acid, including binding of regions having only partial complementarity. Certain bases not commonly found in natural nucleic acids may be included in the nucleic acids of the present invention and include, for example, inosine and 7-deazaguanine. Those skilled in the art of nucleic acid technology can determine duplex stability empirically considering a number of variables including, for example, the length of the complementary sequence, base composition and sequence of the oligonucleotide, ionic strength and incidence of mismatched base pairs. The stability of a nucleic acid duplex is measured by the melting temperature, or "$T_m$". The $T_m$ of a particular nucleic acid duplex under specified conditions is the temperature at which on average half of the base pairs have disassociated.

The term "recombinant DNA molecule" means a hybrid DNA sequence comprising at least two nucleotide sequences not normally found together in nature.

The term "vector" is used in reference to nucleic acid molecules into which fragments of DNA may be inserted or cloned and can be used to transfer DNA segment(s) into a cell and capable of replication in a cell. Vectors may be derived from plasmids, bacteriophages, viruses, cosmids, and the like.

The terms "recombinant vector" and "expression vector" as used herein refer to DNA or RNA sequences containing a desired coding sequence and appropriate DNA or RNA sequences necessary for the expression of the operably linked coding sequence in a particular host organism. Prokaryotic expression vectors include a promoter, a ribosome binding site, an origin of replication for autonomous replication in a host cell and possibly other sequences, e.g. an optional operator sequence, optional restriction enzyme sites. A promoter is defined as a DNA sequence that directs RNA polymerase to bind to DNA and to initiate RNA synthesis. Eukaryotic expression vectors include a promoter, optionally a polyadenylation signal and optionally an enhancer sequence.

A polynucleotide having a nucleotide sequence encoding a protein or polypeptide means a nucleic acid sequence comprising the coding region of a gene, or in other words the nucleic acid sequence encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region. Other regulatory elements include, but are not limited to, transcription factor binding sites, splicing signals, polyadenylation signals, termination signals and enhancer elements.

Transcriptional control signals in eukaryotes comprise "promoter" and "enhancer" elements. Promoters and enhancers consist of short arrays of DNA sequences that interact specifically with cellular proteins involved in transcription. Promoter and enhancer elements have been isolated from a variety of eukaryotic sources including genes in yeast, insect and mammalian cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types. For example, the SV40 early gene enhancer is very active in a wide variety of cell types from many mammalian species and has been widely used for the expression of proteins in mammalian cells. Two other examples of promoter/enhancer elements active in a broad range of mammalian cell types are those from the human elongation factor 1 gene and the long terminal repeats of the Rous sarcoma virus; and the human cytomegalovirus.

The term "promoter/enhancer" denotes a segment of DNA containing sequences capable of providing both promoter and enhancer functions (i.e., the functions provided by a promoter element and an enhancer element as described above). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques) such that transcription of the gene is directed by the linked enhancer/promoter.

The presence of "splicing signals" on an expression vector often results in higher levels of expression of the recombinant transcript in eukaryotic host cells. Splicing signals mediate the removal of introns from the primary RNA transcript and consist of a splice donor and acceptor site. A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly (A) signal. The SV40 poly(A) signal is contained on a 237 bp BamH I/Bcl I restriction fragment and directs both termination and polyadenylation.

Eukaryotic expression vectors may also contain "viral replicons" or "viral origins of replication." Viral replicons are viral DNA sequences that allow for the extrachromosomal replication of a vector in a host cell expressing the appropriate replication factors. Vectors containing either the SV40 or polyoma virus origin of replication replicate to high copy number (up to $10^4$ copies/cell) in cells that express the appropriate viral T antigen. In contrast, vectors containing the replicons from bovine papillomavirus or Epstein-Barr virus replicate extrachromosomally at low copy number (about 100 copies/cell).

The term "in vitro" refers to an artificial environment and to processes or reactions that occur within an artificial environment. In vitro environments include, but are not limited to, test tubes and cell lysates. The term "in vivo" refers to the natural environment (e.g., an animal or a cell) and to processes or reaction that occur within a natural environment.

The term "expression system" refers to any assay or system for determining (e.g., detecting) the expression of a gene of interest. Those skilled in the field of molecular biology will understand that any of a wide variety of expression systems may be used. A wide range of suitable mammalian cells are available from a wide range of source (e.g., the American Type Culture Collection, Rockland, Md.). The method of transformation or transfection and the choice of expression vehicle will depend on the host system selected. Transformation and transfection methods are well known to the art. Expression systems include in vitro gene expression assays where a gene of interest (e.g., a reporter gene) is linked to a regulatory sequence and the expression of the gene is monitored following treatment with an agent that inhibits or induces expression of the gene. Detection of gene expression can be through any suitable means including, but not limited to, detection of expressed mRNA or protein (e.g., a detectable product of a reporter gene) or through a detectable change in the phenotype of a cell expressing the gene of interest. Expression systems may also comprise assays where a cleavage event or other nucleic acid or cellular change is detected.

The term "wild-type" as used herein, refers to a gene or gene product that has the characteristics of that gene or gene product isolated from a naturally occurring source. A wild-type gene is that which is most frequently observed in a population and is thus arbitrarily designated the "wild-type" form of the gene. In contrast, the term "mutant" refers to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "isolated" when used in relation to a nucleic acid, as in "isolated oligonucleotide" or "isolated polynucleotide" refers to a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., the oligonucleotide may single-stranded), but may contain both the sense and anti-sense strands (i.e., the oligonucleotide may be double-stranded).

By "peptide," "protein" and "polypeptide" is meant any chain of amino acids, regardless of length or post-translational modification (e.g., glycosylation or phosphorylation). The nucleic acid molecules of the invention may also encode a variant of a naturally-occurring protein or polypeptide fragment thereof, which has an amino acid sequence that is at least 85%, 90%, 95% or 99% identical to the amino acid sequence of the naturally-occurring (native or wild-type) protein from which it is derived. The term "fusion polypeptide" or "fusion protein" refers to a chimeric protein containing a reference protein (e.g., luciferase) joined at the N- and/or C-terminus to one or more heterologous sequences (e.g., a non-luciferase polypeptide). In some embodiments, a modified polypeptide, fusion polypeptide or a portion of a full-length polypeptide of the invention, may retain at least some of the activity of a corresponding full-length functional (nonchimeric) polypeptide. In other embodiments, in the absence of an exogenous agent or molecule of interest, a modified polypeptide, fusion polypeptide or portion of a full-length functional polypeptide of the invention, may lack activity relative to a corresponding full-length functional polypeptide. In other embodiments, a modified polypeptide, fusion polypeptide or portion of a full-length functional polypeptide of the invention in the presence of an exogenous agent may retain at least some or have substantially the same activity, or alternatively lack activity, relative to a corresponding full-length functional polypeptide.

Polypeptide molecules are said to have an "amino terminus" (N-terminus) and a "carboxy terminus" (C-terminus) because peptide linkages occur between the backbone amino group of a first amino acid residue and the backbone carboxyl group of a second amino acid residue. The terms "N-terminal" and "C-terminal" in reference to polypeptide sequences refer to regions of polypeptides including portions of the N-terminal and C-terminal regions of the polypeptide, respectively. A sequence that includes a portion of the N-terminal region of polypeptide includes amino acids predominantly from the N-terminal half of the polypeptide chain, but is not limited to such sequences. For example, an N-terminal sequence may include an interior portion of the polypeptide sequence including bases from both the N-terminal and C-terminal halves of the polypeptide. The same applies to C-terminal regions. N-terminal and C-terminal regions may, but need not, include the amino acid defining the ultimate N-terminus and C-terminus of the polypeptide, respectively.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

The terms "cell," "cell line," "host cell," as used herein, are used interchangeably, and all such designations include progeny or potential progeny of these designations. By "transformed cell" is meant a cell into which (or into an ancestor of which) has been introduced a nucleic acid molecule of the invention. Optionally, a nucleic acid molecule of the invention may be introduced into a suitable cell line so as to create a stably-transfected cell line capable of producing the protein or polypeptide encoded by the gene. Vectors, cells, and methods for constructing such cell lines are well known in the art. The words "transformants" or "transformed cells" include the primary transformed cells derived from the originally transformed cell without regard to the number of transfers. All progeny may not be precisely identical in DNA content, due to deliberate or inadvertent mutations. Nonetheless, mutant progeny that have the same functionality as screened for in the originally transformed cell are included in the definition of transformants.

The term "homology" refers to a degree of complementarity between two or more sequences. There may be partial homology or complete homology (i.e., identity). Homology is often measured using sequence analysis software (e.g., Sequence Analysis Software Package of the Genetics Computer Group. University of Wisconsin Biotechnology Center. 1710 University Avenue. Madison, Wis. 53705). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide is present in a form or setting that is different from that in which it is found in nature. In contrast, non-isolated polypeptides (e.g., proteins and enzymes) are found in the state they exist in nature.

The term "purified" or "to purify" means the result of any process that removes some of a contaminant from the component of interest, such as a protein or nucleic acid. The percent of a purified component is thereby increased in the sample.

As used herein, "pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a "substantially pure" composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide is produced.

As used herein, the term "poly-histidine tract" or (His tag) refers to a molecule comprising two to ten histidine residues, e.g., a poly-histidine tract of five to ten residues. A poly-histidine tract allows the affinity purification of a covalently linked molecule on an immobilized metal, e.g., nickel, zinc, cobalt or copper, chelate column or through an interaction with another molecule (e.g., an antibody reactive with the His tag).

A "protein destabilization sequence" includes, but is not limited to, a PEST sequence, for example, a PEST sequence from cyclin, e.g., mitotic cyclins, uracil permease or ODC, a sequence from the C-terminal region of a short-lived protein such as ODC, early response proteins such as cytokines, lymphokines, protooncogenes, e.g., c-myc or c-fos, MyoD, HMG CoA reductase, or S-adenosyl methionine decarboxylase, CL sequences, a cyclin destruction box, or N-degron.

As used herein, a "marker gene" or "reporter gene" is a gene that imparts a distinct phenotype to cells expressing the gene and thus permits cells having the gene to be distinguished from cells that do not have the gene. Such genes may encode either a selectable or screenable marker, depending on whether the marker confers a trait which one can 'select' for by chemical means, i.e., through the use of a selective agent (e.g., a herbicide, antibiotic, or the like), or whether it is simply a "reporter" trait that one can identify through observation or testing, i.e., by 'screening'. Elements of the present disclosure are exemplified in detail through the use of particular marker genes. Of course, many examples of suitable marker genes or reporter genes are known to the art and can be employed in the practice of the invention. Therefore, it will be understood that the following discussion is exemplary rather than exhaustive. In light of the techniques disclosed herein and the general recombinant techniques which are known in the art, the present invention renders possible the alteration of any gene. Exemplary reporter proteins are encoded by nucleic acid molecules comprising modified reporter genes including, but are not limited to, modifications of a neo gene, a β-gal gene, a gus gene, a cat gene, a gpt gene, a hyg gene, a hisD gene, a ble gene, a mprt gene, a bar gene, a nitrilase gene, a galactopyranoside gene, a xylosidase gene, a thymidine kinase gene, an arabinosidase gene, a mutant acetolactate synthase gene (ALS) or acetoacid synthase gene (AAS), a methotrexate-resistant dhfr gene, a dalapon dehalogenase gene, a mutated anthranilate synthase gene that confers resistance to 5-methyl tryptophan (WO 97/26366), an R-locus gene, a β-lactamase gene, a xy/E gene, an α-amylase gene, a tyrosinase gene, a luciferase (luc) gene, (e.g., a *Renilla reniformis* luciferase gene, a firefly luciferase gene, or a click beetle luciferase (*Pyrophorus plagiophthalamus*) gene), an aequorin gene, a red fluorescent protein gene, or a green fluorescent protein gene.

All amino acid residues identified herein are in the natural L-configuration. In keeping with standard polypeptide nomenclature, abbreviations for amino acid residues are as shown in the following Table of Correspondence.

TABLE OF CORRESPONDENCE

| 1-Letter | 3-Letter | AMINO ACID |
|---|---|---|
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |

-continued

| TABLE OF CORRESPONDENCE | | |
|---|---|---|
| 1-Letter | 3-Letter | AMINO ACID |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

I. Methods to Identify Residues or Regions of a Luciferase which are Tolerant to Modification Numerous methods are available to identify sites and/or regions in a luciferase gene which may be modified, e.g., disrupted, yet when transcribed and translated, yield a desirable, for instance, a readily detectable, gene product. For instance, amplification reactions may be employed to delete and/or insert nucleotides for one or more amino acid residues in a luciferase gene. Alternatively, transposons may be employed to prepare libraries of insertional mutations. Transposons are mobile DNA sequences found in the genomes of prokaryotes and eukaryotes. Transposon tagging has long been recognized as a powerful research tool for randomly distributing primer binding sites, creating gene "knockouts," and introducing a physical tag or a genetic tag into large target DNAs. Insertions in a reporter gene useful to prepare the modified luciferases of the invention are those which are internal, in frame insertions in the coding region for the luciferase.

One frequently used transposition system is the Tn5 system isolated from gram-negative bacteria. The Tn5 transposase is a small, single subunit enzyme that has been cloned and purified to high specific activity, and carries out transposition without the need for host cell factors. Moreover, Tn5 transposon insertions into target DNA are highly random, and proceed by a simple process. Tn5 transposase will transpose any DNA sequence contained between its short 19 basepair Mosaic End (ME) Tn5 transposase recognition sequences.

The GPS-M Mutagenesis System uses TnsABC*Transposase to insert a Tn7-based transposon randomly into a DNA target. Target DNA may be a plasmid, cosmid, BAC or purified chromosomal DNA. If the insertion site is within a translated gene segment, this will normally result in a null (loss of function) mutation. There is minimal site preference for insertion, so disruption of any open reading frame is possible. Due to target immunity, only one insertion occurs per DNA molecule in vivo over a distance of about 190 kb. Therefore, the in vitro reaction produces a population of target DNA molecules each containing the transposable element at a different position.

The transposon donor can be modified by adding to or replacing the antibiotic, e.g., kanamycin, resistance marker. The donor plasmid may be grown in standard laboratory *E. coli* strains, and the vector backbone carries a different antibiotic marker, e.g., $Amp^r$, than the transposon and an origin of replication. To destroy unreacted donor molecules and avoid undesirable reaction products, the donor can be destroyed by digestion with a rare-cutting enzyme, for instance, PI-SceI (VDE). For applications in which the mutagenized DNA is transformed into naturally-competent organisms (which take up single DNA strands), the gaps are filled-in and ligated.

Once sites tolerant to modification in a luciferase sequence are identified, insertions, deletions and permutations, or any combination thereof, of the sequences may be prepared. With regard to permuted sequences, Plainkum et al. (2003) reported that circularly permuted forms of ribonuclease A having new N- and C-termini and a peptide linker containing a protease recognition site linking the original N- and C-termini had reduced ribonuclease activity due to steric occlusion of the active site. Plainkum et al. found that cleavage of the circularly permuted ribonuclease A with the protease increased the activity of the protein, presumably by removing the block to the active site. In the case of luciferase, the N- and C-termini are separated by about 40 angstroms, a distance equivalent to 5-6 amino acids. Circularly permuted firefly luciferases were prepared, one of which had a new N-terminus at Asp(234) and a new C-terminus at Pro(233) and a recognition site for the protease enterokinase which cleaves on the carboxyl terminal side of Asp(4)Lys (see U.S. published application 20050153310 and PCT/US2004/032705). The activity of the fused mutant protein was increased about 90- to about 150-fold by treatment with enterokinase (FIG. 3). Other biosensors included a caspase-3 DEVD cleavage site (FIG. 3), a PSA cleavage site, e.g., Ala-Asn-Lys-Ile-Ser-Tyr-Gln-Ser-Ser-Ser-Thr-Glu (SEQ ID NO:17), a Rhinovirus protease site, e.g., Leu-Glu-Val-Leu-Phe-Gln-Gly-Pro (SEQ ID NO:19), and a SARS virus protease site, e.g., TSAVLQSGFR (SEQ ID NO:20), inserted into the circularly permuted firefly luciferase or a click beetle luciferase (CP1: R=Asn401 and CP2: R=Arg223) (see U.S. published application 20050153310 and PCT/US2004/032705). CP2 has an insertion at a position in click beetle luciferase which corresponds to position 234 in firefly luciferase. As described hereinbelow, circularly permuted *Renilla* lucferases were prepared.

The biosensors of the invention include but are not limited to those in which the heterologous amino acid sequence includes a protein binding domain, such as one that binds IL-17RA, e.g., IL-17A, or the IL-17A binding domain of IL-17RA, Jun binding domain of Erg, or the EG binding domain of Jun; a potassium channel voltage sensing domain, e.g., one useful to detect protein conformational changes, the GTPase binding domain of a Cdc42 or rac target, or other GTPase binding domains, domains associated with kinase or phosphotase activity, e.g., regulatory myosin light chain, PKCδ, pleckstrin containing PH and DEP domains, other phosphorylation recognition domains and substrates; glucose binding protein domains, glutamate/aspartate binding protein domains, PKA or a cAMP-dependent binding substrate, InsP3 receptors, GKI, PDE, estrogen receptor ligand binding domains, apoK1-er, or calmodulin binding domains.

In one embodiment, the biosensor is useful to detect a GTPase, e.g., binding of Cdc42 or Rac to a EBFP, EGFP PAK fragment, Raichu-Rac, Raichu-Cdc42, integrin alphav-beta3, IBB of importin-a, DMCA or NBD-Ras of CRaf1 (for Ras activation), binding domain of Ras/Rap Ral RBD with Ras prenylation sequence. In one embodiment, the biosensor detects PI(4,5)P2 (e.g., using PH-PCLdelta1, PH-GRP1), PI(4,5)P2 or PI(4)P (e.g., PH-OSBP), PI(3,4,5)P3 (e.g., using PH-ARNO, or PH-BTK, or PH-Cytohesin1), PI(3,4,5)P3 or PI(3,4)P2 (e.g., using PH Akt), PI(3)P (e.g., using FYVE-EEA1), or Ca2+ (cytosolic) (e.g., using calmodulin, or C2 domain of PKC.

In one embodiment, the domain is one with a phosphorylated tyrosine (e.g., in Src, Ab1 and EGFR), that detects phosphorylation of ErbB2, phosphorylation of tyrosine in Src, Ab1 and EGFR, activation of MKA2 (e.g., using MK2), cAMP induced phosphorylation, activation of PKA, e.g., using KID of CREG, phosphorylation of CrkII, e.g., using SH2 domain pTyr peptide, binding of bZIP transcription factors and REL proteins, e.g., bFos and bJun ATF2 and Jun, or p65 NFkappaB, or microtubule binding, e.g., using kinesin.

Thus, the invention includes luciferase biosensors including circularly permuted luciferases, which luciferase sequence may include deletions of residues at the original (wild type) N- or C-termini, or both, e.g., deletion of 1 to 3 or more residues at the N-terminus and 1 to 6 or more residues at the C-terminus, as well as sequences that directly or indirectly interact with a molecule of interest.

II. Exemplary Polynucleotides and Proteins

The invention includes a modified luciferase encompassing any amino acid sequence which provides a polypeptide having a detectable activity, e.g., luminescent activity, as well as protein fragments thereof, which are recombinantly or synthetically synthesized. The luciferase sequences of a modified luciferase are the same or are substantially the same as the amino acid sequence of a corresponding unmodified luciferase. A polypeptide or peptide having substantially the same sequence means that an amino acid sequence is largely, but may not entirely be, the same and retains a functional activity of the sequence to which it is related. In general, two amino acid sequences are substantially the same or substantially homologous if they are at least 70% identical, e.g., have at least 80%, 90%, 95% or more identity.

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms “homology” and “identity” in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Methods of alignment of sequence for comparison are well-known in the art. Optimal alignment of sequences for comparison can be conducted by the local homology algorithm of Smith et al. (1981), by the homology alignment algorithm of Needleman et al. (1970), by the search for similarity method of Person et al. (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988); Higgins et al. (1989); Corpet et al. (1988); Huang et al. (1992); and Pearson et al. (1994). The ALIGN program is based on the algorithm of Myers and Miller (1988). The BLAST programs of Altschul et al. (1990), are based on the algorithm of Karlin and Altschul (1990).

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences (see, e.g., Karlin & Altschul (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989).

In particular, a polypeptide may be substantially related but for a conservative variation. A conservative variation denotes the replacement of an amino acid residue by another, biologically similar residue. Examples of conservative variations include the substitution of one hydrophobic residue such as isoleucine, valine, leucine or methionine for another, or the substitution of one polar residue for another such as the substitution of arginine for lysine, glutamic for aspartic acids, or glutamine for asparagine, and the like. Other illustrative examples of conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine.

In one embodiment, a polynucleotide of the invention is optimized for expression in a particular host. As used herein, optimization includes codon optimization as well as, in eukaryotic cells, introduction of a Kozak sequence, and/or one or more introns. Thus, a nucleic acid molecule may have a codon composition that differs from that of a wild-type nucleic acid sequence encoding an unmodified luciferase at more than 30%, 35%, 40% or more than 45%, e.g., 50%, 55%, 60% or more of the codons. Preferred codons for use in the invention are those which are employed more frequently than at least one other codon for the same amino acid in a particular organism and, more preferably, are also not low-usage codons in that organism and are not low-usage codons in the organism used to clone or screen for the expression of the nucleic acid molecule. Moreover, preferred codons for certain amino acids (i.e., those amino acids that have three or more codons), may include two or more codons that are employed more frequently than the other (non-preferred) codon(s). The presence of codons in the nucleic acid molecule that are employed more frequently in one organism than in another organism results in a nucleic acid molecule which, when introduced into the cells of the organism that employs those codons more frequently, is expressed in those cells at a level that is greater than the expression of the wild-type or parent nucleic acid sequence in those cells.

In one embodiment of the invention, the codons that are different are those employed more frequently in a mammal, while in another embodiment the codons that are different are those employed more frequently in a plant. A particular type of mammal, e.g., human, may have a different set of preferred codons than another type of mammal. Likewise, a particular type of plant may have a different set of preferred codons than another type of plant. In one embodiment of the invention, the majority of the codons which differ are ones that are preferred codons in a desired host cell. Preferred codons for mammals (e.g., humans) and plants are known to the art (e.g., Wada et al., 1990). For example, preferred human codons include, but are not limited to, CGC (Arg), CTG (Leu), TCT (Ser), AGC (Ser), ACC (Thr), CCA (Pro), CCT (Pro), GCC (Ala), GGC (Gly), GTG (Val), ATC (Ile), ATT (Ile), AAG (Lys), AAC (Asn), CAG (Gln), CAC (His), GAG (Glu), GAC (Asp), TAC (Tyr), TGC (Cys) and TTC (Phe) (Wada et al., 1990). Thus, preferred "humanized" synthetic nucleic acid molecules of the invention have a codon composition which differs from a wild type nucleic acid sequence by having an increased number of the preferred human codons, e.g. CGC, CTG, TCT, AGC, ACC, CCA, CCT, GCC, GGC, GTG, ATC, ATT, AAG, AAC, CAG, CAC, GAG, GAC, TAC, TGC, TTC, or any combination thereof. For example, the nucleic acid molecule of the invention may have an increased number of CTG or TTG leucine-encoding codons, GTG or GTC valine-encoding codons, GGC or GGT glycine-encoding codons, ATC or ATT isoleucine-encoding codons, CCA or CCT proline-encoding codons, CGC or CGT arginine-encoding codons, AGC or TCT serine-encoding codons, ACC or ACT threonine-encoding codon, GCC or GCT alanine-encoding codons, or any combination thereof, relative to the wild-type nucleic acid sequence. Similarly, nucleic acid molecules having an increased number of codons that are employed more frequently in plants, have a codon composition which differs from a wild-type nucleic acid sequence by having an increased number of the plant codons including, but not limited to, CGC (Arg), CTT (Leu), TCT (Ser), TCC (Ser), ACC (Thr), CCA (Pro), CCT (Pro), GCT (Ser), GGA (Gly), GTG (Val), ATC (Ile), ATT (Ile), AAG (Lys), AAC (Asn), CAA (Gln), CAC (His), GAG (Glu), GAC (Asp), TAC (Tyr), TGC (Cys), TTC (Phe), or any combination thereof (Murray et al., 1989). Preferred codons may differ for different types of plants (Wada et al., 1990).

The modified luciferase proteins or fusion proteins of the invention may be prepared by recombinant methods or by solid phase chemical peptide synthesis methods. Such methods have been known in the art since the early 1960's (Merrifield, 1963) (See also Stewart et al., Solid Phase Peptide Synthesis, 2$^{nd}$ ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of Geysen et al. (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, e.g., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

III. Fusion Partners Useful with the Modified Luciferase of the Invention

The polynucleotide of the invention which encodes a modified luciferase may be employed with other nucleic acid sequences, e.g., a native sequence such as a cDNA or one which has been manipulated in vitro, e.g., to prepare N-terminal, C-terminal, or N- and C-terminal fusion proteins, e.g., a fusion with a protein encoded by a different reporter gene including a selectable marker. Many examples of suitable fusion partners are known to the art and can be employed in the practice of the invention.

Fusion partners include but are not limited to affinity domains or other functional protein sequences, such as those having an enzymatic activity. For example, a functional protein sequence may encode a kinase catalytic domain (Hanks and Hunter, 1995), producing a fusion protein that can enzymatically add phosphate moieties to particular amino acids, or may encode a Src Homology 2 (SH2)

domain (Sadowski et al., 1986; Mayer and Baltimore, 1993), producing a fusion protein that specifically binds to phosphorylated tyrosines.

Affinity domains are generally peptide sequences that can interact with a binding partner, e.g., such as one immobilized on a solid support. DNA sequences encoding multiple consecutive single amino acids, such as histidine, when fused to the expressed protein, may be used for one-step purification of the recombinant protein by high affinity binding to a resin column, such as nickel sepharose. Sequences encoding peptides, such as the chitin binding domain (which binds to chitin), glutathione-S-transferase (which binds to glutathione), biotin (which binds to avidin and strepavidin), and the like, can also be used for facilitating purification of the protein of interest. The affinity domain can be separated from the protein of interest by methods well known in the art, including the use of inteins (protein self-splicing elements (Chong et al., 1997). Exemplary affinity domains include HisV5 (HHHHH) (SEQ ID NO:4), HisX6 (HHHHHH) (SEQ ID NO:5), C-myc (EQKLISEEDL) (SEQ ID NO:6), Flag (DYKDDDDK) (SEQ ID NO:7), SteptTag (WSHPQFEK) (SEQ ID NO:8), hemagluttinin, e.g., HA Tag (YPYDVPDYA) (SEQ ID NO:9), GST, thioredoxin, cellulose binding domain, RYIRS (SEQ ID NO:10), Phe-His-His-Thr (SEQ ID NO:11), chitin binding domain, S-peptide, T7 peptide, SH2 domain, C-end RNA tag, WEAAAREACCRECCARA (SEQ ID NO:12), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin $D_{9K}$, calbindin $D_{28K}$, and calretinin, inteins, biotin, streptavidin, MyoD, Id, leucine zipper sequences, and maltose binding protein. In one embodiment, the fusion partner is a sequence useful to purify a fusion protein, e.g., a His or GST tag, and in one embodiment the purification tag is fused to the N- or C-terminus of a circularly permuted luciferase.

Another class of fusion partners includes a protein encoded by a reporter gene, including, but are not limited to, a neo gene, a β-gal gene, a gus gene, a cat gene, a gpt gene, a hyg gene, a hisD gene, a ble gene, a mprt gene, a bar gene, a nitrilase gene, a galactopyranoside gene, a xylosidase gene, a thymidine kinase gene, an arabinosidase gene, a mutant acetolactate synthase gene (ALS) or acetoacid synthase gene (AAS), a methotrexate-resistant dhfr gene, a dalapon dehalogenase gene, a mutated anthranilate synthase gene that confers resistance to 5-methyl tryptophan (WO 97/26366), an R-locus gene, a β-lactamase gene, a xy/E gene, an α-amylase gene, a tyrosinase gene, an anthozoan luciferase (luc) gene, (e.g., a *Renilla reniformis* luciferase gene), an aequorin gene, a red fluorescent protein gene, or a green fluorescent protein gene. Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA, and proteins that are inserted or trapped in the cell membrane.

IV. Vectors and Host Cells Encoding the Modified Luciferase or Fusions Thereof

Once a desirable nucleic acid molecule encoding a modified luciferase or a fusion thereof is prepared, an expression cassette encoding the modified luciferase or a fusion protein comprising the modified luciferase is prepared. For example, a nucleic acid molecule comprising a nucleic acid sequence encoding a modified luciferase is optionally operably linked to transcription regulatory sequences, e.g., one or more enhancers, a promoter, a transcription termination sequence or a combination thereof, to form an expression cassette. The nucleic acid molecule or expression cassette may be introduced to a vector, e.g., a plasmid or viral vector, which optionally includes a selectable marker gene, and the vector introduced to a cell of interest, for example, a prokaryotic cell such as *E. coli, Streptomyces* spp., *Bacillus* spp., *Staphylococcus* spp. and the like, as well as eukaryotic cells including a plant (dicot or monocot), fungus, yeast, e.g., *Pichia, Saccharomyces* or *Schizosaccharomyces*, or a mammalian cell. Preferred mammalian cells include bovine, caprine, ovine, canine, feline, non-human primate, e.g., simian, and human cells. Preferred mammalian cell lines include, but are not limited to, CHO, COS, 293, Hela, CV-1, SH-SY5Y, HEK293, and NIH3T3 cells.

The expression of an encoded modified luciferase may be controlled by any promoter capable of expression in prokaryotic cells or eukaryotic cells. Preferred prokaryotic promoters include, but are not limited to, SP6, T7, T5, tac, bla, trp, gal, lac or maltose promoters. Preferred eukaryotic promoters include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE. The nucleic acid molecule, expression cassette and/or vector of the invention may be introduced to a cell by any method including, but not limited to, calcium-mediated transformation, electroporation, microinjection, lipofection and the like.

V. Exemplary Uses

The modified luciferases or fusions thereof are useful for any purpose including, but not limited to, detecting the amount or presence of a particular molecule (a biosensor), isolating a particular molecule, detecting conformational changes in a particular molecule, e.g., due to binding, phosphorylation or ionization, facilitating high or low throughput screening, detecting protein-protein, protein-DNA or other protein-based interactions, or selecting or evolving biosensors. For instance, a modified luciferase or a fusion thereof, is useful to detect, e.g., in an in vitro or cell-based assay, the amount, presence or activity of a particular kinase (for example, by inserting a kinase site into a reporter protein), RNAi (e.g., by inserting a sequence suspected of being recognized by RNAi into a coding sequence for a reporter protein, then monitoring reporter activity after addition of RNAi), or protease, such as one to detect the presence of a particular viral protease, which in turn is indicator of the presence of the virus, or an antibody; to screen for inhibitors, e.g., protease inhibitors; to identify recognition sites or to detect substrate specificity, e.g., using a modified luciferase with a selected recognition sequence or a library of modified luciferases having a plurality of different sequences with a single molecule of interest or a plurality (for instance, a library) of molecules; to select or evolve biosensors or molecules of interest, e.g., proteases; or to detect protein-protein interactions via complementation or binding, e.g., in an in vitro or cell-based approach. In one embodiment, a modified luciferase which includes an insertion is contacted with a random library or mutated library of molecules, and molecules identified which interact with the insertion. In another embodiment, a library of modified luciferases having a plurality insertions is contacted with a molecule, and modified luciferases which interact with the molecule identified. In one embodiment, a modified luciferase or fusion thereof, is useful to detect, e.g., in an in vitro or cell-based assay, the amount or presence of cAMP or cGMP (for example, by inserting a cAMP or cGMP binding site into a circularly permuted luciferase), to screen for inhibitors or activators, e.g., inhibitors or activators of cAMP or cGMP, inhibitors or activators of cAMP binding to a cAMP binding site or inhibitors or activators of G protein coupled receptors (GPCR), to identify recognition sites or to detect substrate specificity, e.g., using a modified luciferase with a selected recognition sequence or a library of modified luciferases having a plurality of different sequences with a single molecule of interest or a plurality (for instance, a library) of molecules, to select or evolve cAMP or cGMP binding sites, or in whole animal imaging.

The invention also provides methods to monitor the expression, location and/or trafficking of molecules in a cell, as well as to monitor changes in microenvironments within a cell, using a modified luciferase or a fusion protein thereof. In one embodiment, a modified luciferase comprises a recognition site for a molecule, and when the molecule interacts with the recognition site, that results in an increase in activity, and so can be employed to detect or determine the presence or amount of the molecule. For example, in one embodiment, a modified luciferase comprises an internal insertion containing two domains which interact with each other under certain conditions. In one embodiment, one domain in the insertion contains an amino acid which can be phosphorylated and the other domain is a phosphoamino acid binding domain. In the presence of the appropriate kinase or phosphatase, the two domains in the insertion interact and change the conformation of the modified luciferase resulting in an alteration in the detectable activity of the modified luciferase. In another embodiment, a modified luciferase comprises a recognition site for a molecule, and when the molecule interacts with the recognition site, results in an increase in activity, and so can be employed to detect or determine the presence of amount or the other molecule.

Two-hybrid systems are extremely powerful methods for detecting protein:protein interactions in vivo as well as identifying residues/domains involved in protein:protein interactions. The basis of two-hybrid systems is the modular domains found in some transcription factors: a DNA-binding domain, which binds to a specific DNA sequence, and a transcriptional activation domain, which interacts with the basal transcriptional machinery (Sadowski, 1988). A transcriptional activation domain in association with a DNA-binding domain may promote the assembly of RNA polymerase II complexes at the TATA box and increase transcription. In the CheckMate™ Mammalian Two-Hybrid System (Promega Corp., Madison, Wis.), the DNA-binding domain and the transcriptional activation domain, produced by separate plasmids, are closely associated when one protein ("X") fused to a DNA-binding domain interacts with a second protein ("Y") fused to a transcriptional activation domain. In this system, interaction between proteins X and Y results in transcription of either a reporter gene or a selectable marker gene. In particular, the pBIND Vector contains a yeast GAL4 DNA-binding domain upstream of a multiple cloning region, and a pACT Vector contains the herpes simplex virus VP16 activation domain upstream of a multiple cloning region. In addition, the pBIND Vector expresses the *Renilla reniformis* luciferase. The two genes encoding the two potentially interactive proteins of interest are cloned into pBIND and pACT Vectors to generate fusion proteins with the DNA-binding domain of GAL4 and the activation domain of VP16, respectively. The pG5luc Vector contains five GAL4 binding sites upstream of a minimal TATA box, which in turn, is upstream of the firefly luciferase gene (luc+). The pGAL4 and pVP16 fusion constructs are transfected along with pG5luc Vector into mammalian cells. Two to three days after transfection the cells are lysed, and the amount of *Renilla* luciferase and firefly luciferase can be quantitated using the Dual-Luciferase® Reporter Assay System (Promega Cat. # E1910). Interaction between the two test proteins, as GAL4 and VP16 fusion constructs, results in an increase in firefly luciferase expression over the negative controls. A modified luciferase of the invention, e.g., one which is deleted at a site or region which is tolerant to modification (a N-terminal fragment), is fused to a DNA binding domain while the remainder of the luciferase (the C-terminal fragment) is fused to a transcriptional activator domain.

The invention also provides methods of screening for agents ("test" agents) capable of modulating the amount of a molecule of interest such as a cyclic nucleotide. "Modulation" refers to an alteration of a property; such enhancement or inhibition of a biological or chemical activity, where the alteration may be contingent on the occurrence of a specific event, such as activation of a signal transduction pathway, and/or may be manifest only in particular cell types. A "modulator" refers to an agent (naturally occurring or non-naturally occurring), such as, for example, a biological macromolecule (e.g., nucleic acid, protein, non-peptide, or organic molecule), small molecules, an extract made from biological materials such as bacteria, plants, fungi, or animal (particularly mammalian) cells or tissues, or any other agent. Modulators are evaluated for potential activity as inhibitors or activators (directly or indirectly) of a biological process or processes (e.g., agonist, partial antagonist, partial agonist, or antagonist) by inclusion in the screening assays described herein. The activities (or activity) of a modulator may be known, unknown or partially known. Such modulators can be screened using the methods of the invention. The term "test agent" refers to an agent to be tested by one or more screening method(s) of the invention as a putative modulator. Usually, various predetermined concentrations are used for screening such as 0.01 μM, 0.1 μM, 1.0 μM, and 10.0 μM. Controls can include the measurement of a signal in the absence of the test agent, comparison to an agent known to modulate the target, or comparison to a sample (e. a cell, tissue or organism) before, during and/or after contacting with the test agent.

In one embodiment, the method includes screening for agents that modulate protease activity. For example, in one embodiment, a method of identifying an agent capable of modulating apoptosis is provided. Caspase family proteases have been associated with apoptosis. Thus, the method includes contacting a sample suspected of containing a caspase-family protease with an agent suspected of modulating the caspase activity, and a modified luciferase having a cleavage site cleavable by the caspase. The activity of the modified luciferase is detected in the sample before and after contacting with the test agent. An increase in activity after contacting with the agent is indicative of an agent that inhibits apoptosis and a decrease is indicative of an agent that activates apoptosis.

Accordingly, the invention provides a screening system useful for identifying agents which modulate the cleavage of recognition sequence present in a modified luciferase protein of the invention and detecting its activity. This allows one to rapidly screen for protease activity modulators. Utilization of the screening system described herein provides a sensitive and rapid means to identify agents which modulate (e.g., inhibit or activate) a protease, for example, a caspase family protease.

A modified luciferase protein of the invention is thus useful as a substrate to study agents or conditions that modulate an interaction between an insertion in the modified luciferase protein and a molecule of interest. In particular, the invention contemplates modified luciferase proteins in which the insertion includes an amino acid sequence that is a cleavage site for an enzyme of interest. Thus, when the molecule of interest is a protease, the insertion comprises a peptide containing a cleavage recognition sequence for the protease. A cleavage recognition sequence for a protease is a specific amino acid sequence recognized by the protease during proteolytic cleavage. Accordingly, the invention provides methods to determine the amount of a protease in a sample by contacting the sample with a modified luciferase polypeptide of the invention and measuring changes in luciferase activity. The modified luciferase protein of the invention can be used for, among other things, monitoring the activity of a protease inside a cell that expresses the modified luciferase.

In one embodiment, a modified luciferase of the invention is thus useful as a substrate to study agents or conditions that modulate an interaction between a cyclic nucleotide binding site in the modified luciferase and a molecule of interest such as a cyclic nucleotide, agents or conditions that modulate the presence or amount of a cyclic nucleotide, or agents or conditions that modulate molecules such as receptors that are associated with intracellular cyclic nucleotide concentrations. In particular, the invention contemplates modified luciferase proteins in which the insertion includes a cAMP or cGMP binding site. Thus, when the molecule of interest is cAMP or cGMP, the invention provides a method to determine the presence or the amount of cAMP or cGMP in a sample by contacting the sample with a modified luciferase polypeptide of the invention and measuring changes in luciferase activity. The modified luciferase protein of the invention can be used for, among other things, monitoring the amount or presence of cAMP or cGMP or molecules that alter the amount or presence of cAMP or cGMP inside a cell that has the modified luciferase.

The assays of the invention can be used to screen drugs to identify compounds that alter the amount, for example, of cyclic nucleotide or alter the binding of a cyclic nucleotide to a cyclic nucleotide binding site. In one embodiment, the assay is performed on a sample in vitro containing cAMP. A sample containing a known amount of cAMP is mixed with a modified luciferase of the invention and with a test agent. The amount of the luciferase activity in the sample is then determined. Then the amount of activity per mole of cAMP in the presence of the test agent may be compared with the activity per mole of cAMP in the absence of the test agent. A difference indicates that the test agent alters the amount of cAMP or binding of cAMP to the cAMP binding site.

In one embodiment, cells are conditioned or contacted with an agent suspected of directly or indirectly modulating, for instance, cAMP amount or binding. The cells or cells in culture are lysed and cAMP amount measured. For example, a lysed cell sample containing a known or unknown amount of cAMP is mixed with a modified luciferase of the invention. The amount of cAMP in the sample is then determined as above by determining the degree of modified luciferase activity in a control or non-treated sample and the treated lysed cellular sample. The activity or inhibition can be calculated based on a per microgram or milligram protein in the sample. Typically, the difference is calibrated against standard measurements to yield an absolute amount of cAMP.

The materials and composition for use in the assay of the invention are ideally suited for the preparation of a kit. Such a kit may comprise a carrier means containing one or more container means such as vials, tubes, and the like, each of the container means comprising one of the separate elements to be used in the method. One of the containers comprises a modified luciferase or polynucleotide (e.g., in the form of a vector) of the invention. A second container may contain a substrate for the modified luciferase.

The invention will be further described by the following non-limiting examples.

Example I

Sites Tolerant to Modification in Click Beetle and Firefly Luciferases

Positions in click beetle and firefly luciferases that are tolerant to modification and certain modified luciferases are disclosed in U.S. published application 20050153310 and PCT/US2004/032705, the disclosures of which are incorporated by reference herein (see also FIG. 1 and Table 1.)

TABLE 1

| Inserted after Amino Acid in Firefly Luciferases | % Activity |
|---|---|
| 7 | 10 |
| 121 | 5-10 |
| 233 | 50-75 |
| 267 | 2 |
| 294 | 3 |
| 303 | 5-10 |
| 361 | 3-5 |
| 540 | 15 |
| 541 | 75 |

Example II

Circular Permuted Firefly Luciferase Fusion to cAMP Binding Site cAMP is one of the most important second messengers for cellular signal transduction. cAMP assays are extremely important for G-protein coupled receptor (GPCR) drug discovery. To identify biosensors for cAMP, cAMP binding sites were fused to circularly permuted firefly luciferases (CPM-FF Luc) (FIG. 5A and FIG. 5B) (pBFB8, pBFB9, pBFB10, pBFB11, pBFB22, pBFB40, pBFB41, pBFB42). One CPM-FF Luc cAMP binding site fusion employed the cAMP binding site from human Epac1 (Exchange protein directly activated by cAMP) (Bos, 2003). Previous studies showed that a single chain fragment from human Epac1 (residues 157 to 316) binds cAMP (Nikolaev, *J. Biol. Chem.*, 279, 37215 (2004)). A second CPM-FF Luc/cAMP binding site fusion employed the B domain from the human PKA regulatory subunit type IIB (CPM-FF Luc/RIIβB).

Materials and Methods

A DNA fragment encoding residues 157-316 of human Epac1 was synthesized, which included some silent nucleotide changes to potentially increase the expression in *E. coli*

(FIG. 5C). Two primers were used to generate a PCR fragment of EPAC1 with XhoI and NcoI sites at the 5' and 3' ends, respectively:

```
                                    (SEQ ID NO: 22)
5' primer:   atgcctcgagGAAGAAGAACTTGCTGAAGCTG

                                    (SEQ ID NO: 23)
3' primer:   atgccatggAACTCCATGTTCTTCTAAACGC
```

Figure 6:
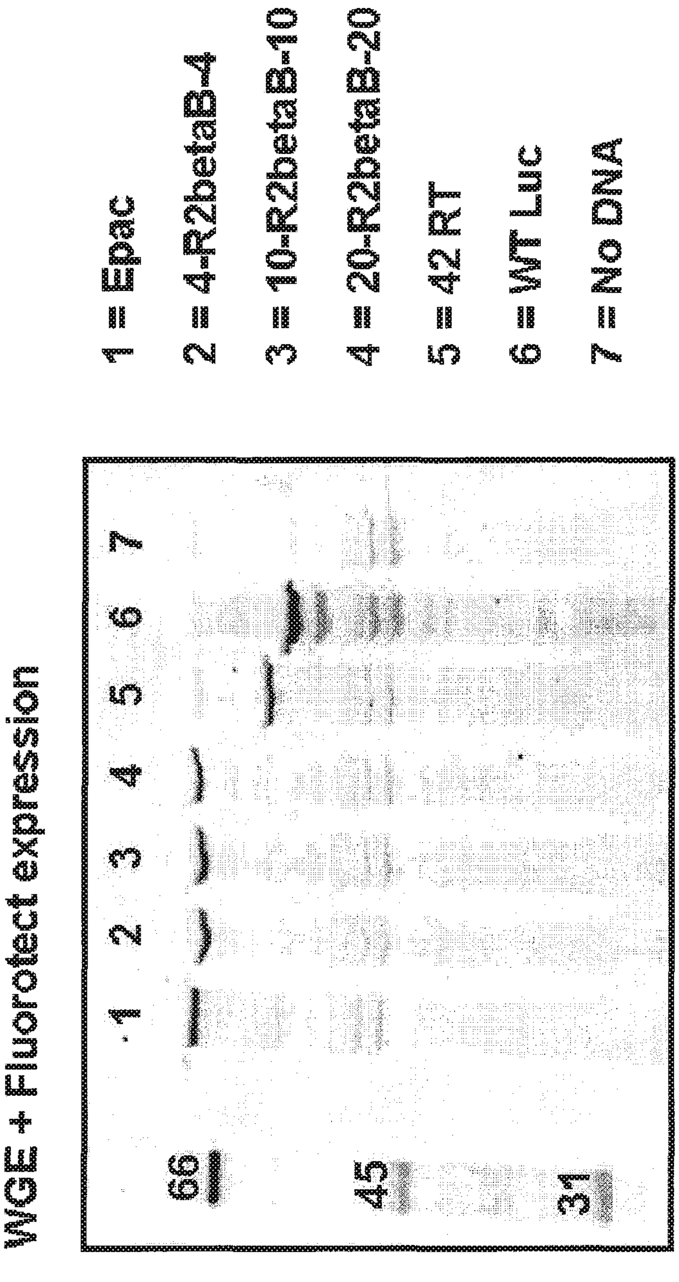
FIG. 6. SDS-PAGE analysis of in vitro transcription/translation products of circularly permuted beetle luciferases with cAMP binding sites. Expression of CPM-FF Luc/RIIβB fusion proteins with X/Y linker lengths of (X=4, Y=4), (X=10,Y=10), and (X=20,Y=20) amino acid residues.

The resulting PCR fragment was digested and cloned into XhoI and NcoI sites of a circularly permuted beetle luciferase construct. The resulting plasmids expressed a modified firefly (pSPLuc+, Promega Corporation) luciferase with EPAC1 inserted between the original N- and C-termini. The correct size of the fusion protein was verified by TnT cell-free expression and SDS-PAGE (FIG. 6). This construct was identified as FF105.

DNA encoding RIIβB was inserted into a novel expression vector encoding CPM-FF Luc/RIIβB fusions [Luc2.0 (234-544)-linker X-human RIIβ (residues 266-414)-linker Y-Luc (4-233)]. By using unique combinations of restriction enzymes, various constructs were generated with RIIβB fused to CPM-FF Luc with a variety of X/Y peptide linker lengths.

Synthesis of a CPM-FF Luc Expression Plasmid for Subsequent Insertion of RIIβB

Figure 5A:
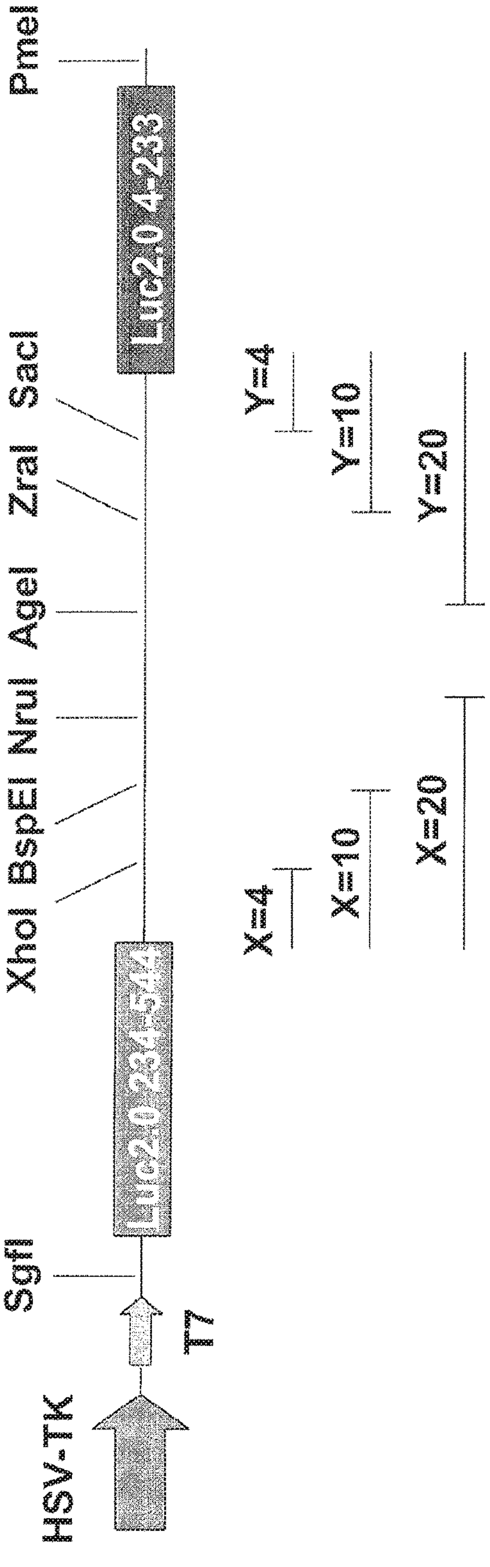
FIG. 5A. Circularly permuted firefly luciferase (CPM-FF Luc) expression plasmid. HSV-TK or T7 promoters were utilized to express the circularly permuted firefly luciferase in mammalian cells or in lysates, respectively. Amino acids 544 and 4 of firefly luciferase are linked by a Gly/Ser rich 42 amino acid peptide (SEQ ID NO:196).

A synthetic 1816 bp fragment encoding CPM-FF Luc (DNA 2.0; SEQ ID NO:16, see FIG. 20) was digested with HindIII/XbaI and ligated to the 3265 bp HindIII/XbaI fragment of pGL4.74 (Promega Corp.). The resultant plasmid encodes a circularly permuted mutant of synthetic luciferase (Luc2.0; Promega Corp.) with amino acids 544 and 4 of firefly luciferase connected by a 42 amino acid Gly/Ser rich peptide [Luc2.0 (234-544)-42 aa Gly/Ser rich peptide-Luc2.0 (4-233)] (pBFB8). FIG. 5A depicts this parent CPM-FF Luc expression plasmid (pBFB8) and the unique restriction sites used to create various linker lengths and to insert the cAMP domain. This fusion protein can be expressed in vitro or in vivo using T7 or HSV-TK promoters, respectively. In addition, SgfI and PmeI restriction enzyme sites were included at the 5' and 3' ends to facilitate subsequent transfer of this open reading frame to additional plasmids (Flexi vector system; Promega Corp.).

Figure 5B:
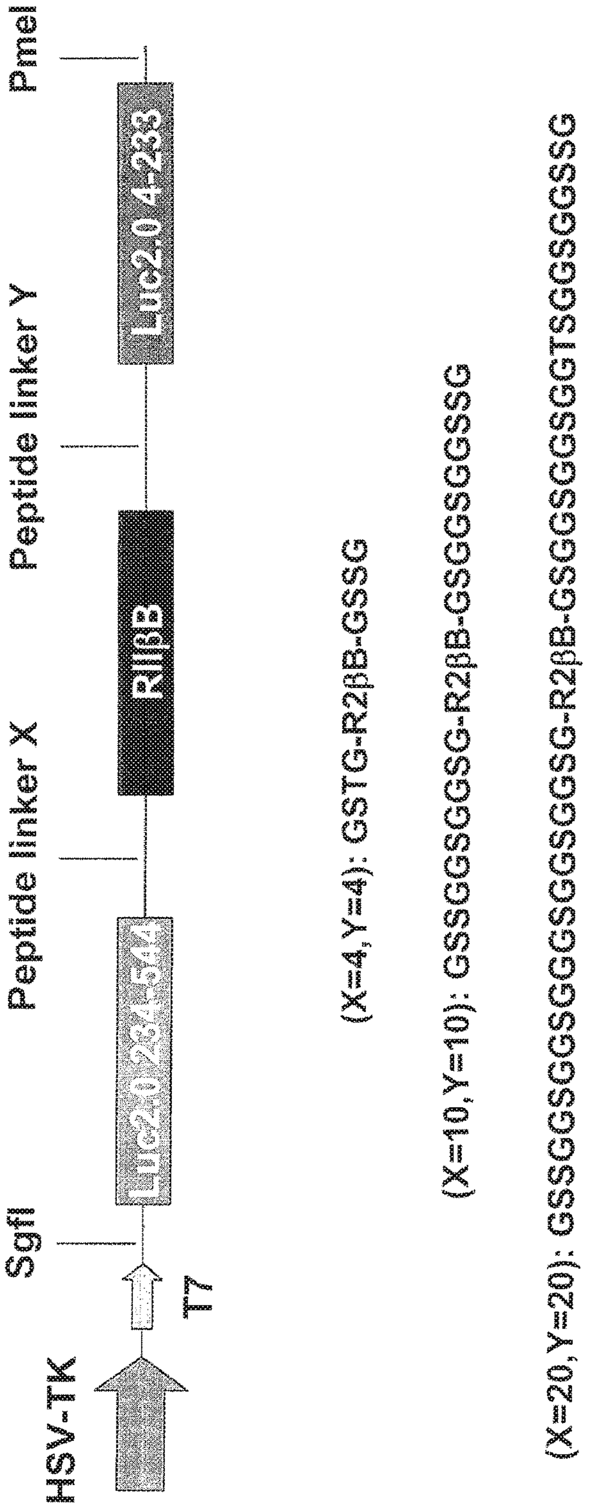
FIG. 5B. Expression plasmids for CPM-FF Luc fusions to RIIβB (CPM-FF Luc/RIIβB). Unique combinations of restriction enzymes allowed DNA encoding RIIβB to be ligated in-frame to generate plasmids that encode CPM-FF Luc/RIIβB fusion proteins with various X/Y peptide linker lengths (GSTG corresponds to SEQ ID NO:122; GSSG corresponds to SEQ ID NO:197; GSSGGSGGSG corresponds to SEQ ID NO:198, GSGGSGGSSG corresponds to SEQ ID NO:199; GSSGGSGGSGGGSGGSGGSG corresponds to SEQ ID NO:200; and GSGGSGGSGGTSGGSGGSSG corresponds to SEQ ID NO:201).

Synthesis of Plasmids Encoding CPM-FF Luc/RIIβB Fusion Proteins with X/Y Linker Lengths of (X=4,Y=4; pBFB9), (X=10,Y=10; pBFB10), and (X=20,Y=20; pBFB11) Amino Acid Residues The plasmid DNA construct described above was digested with unique restriction enzymes present in the multiple cloning site (MCS) linking the DNA fragments encoding Luc2.0 (233-544) and Luc2.0 (4-233) to allow synthesis of CPM-FF Luc/RIIβB expression constructs with X/Y linker lengths of (X=4,Y=4), (X=10,Y=10), and (X=20,Y=20) amino acid residues. FIG. 5B depicts the linkers lengths flanking the RIIβB domain to create pBFB9 (X=4, Y=4), pBFB10 (X=10, Y=10) and pBFB11 (X=20, Y=20).

To synthesize the construct with (X=4,Y=4) linker lengths, primers 5'-AAA AAA GTC GAC CGG AAT GTA TGA AAG CTT TAT TGA GTC ACT GCC-3' (SEQ ID NO:25; BFB51) and 5'-AAA AAA GAG CTC CCA ACA ATA TCC ATG TTC GTT CCA AAC-3' (SEQ ID NO:26; BFB20) were used to amplify RIIβB DNA from ATCC 10625233 (Genbank ID BC075800). The resultant product was digested with SalI/SacI restriction enzymes and ligated into the parent CPM-FF Luc expression plasmid (pBFB8) digested with XhoI/SacI. This new construct was identified as pBFB9.

To synthesize the construct with (X=10,Y=10) linker lengths, primers 5'-AAA AAA TCC GGA ATG TAT GAA AGC TTT ATT GAG TCA CTG CC-3' (SEQ ID NO:211; BFB21) and 5'-AAA AAA AGG CCT ACA ATA TCC ATG TTC GTT CCA AAC-3' (SEQ ID NO:27; BFB22) were used to amplify RIIβB DNA from ATCC 10625233 (Genbank ID BC075800). The resultant product was digested with BspEI/StuI restriction enzymes and ligated into the parent CPM-FF Luc expression plasmid (pBFB8) digested with BspEI/ZraI. This new construct was identified as pBFB10.

To synthesize the construct with (X=20,Y=20) linker lengths, primers 5'-AAA AAA CCC GGG ATG TAT GAA AGC TTT ATT GAG TCA CTG CC-3' (SEQ ID NO:28; BFB23) and 5'-AAA AAA TCC GGA CCC AAC AAT ATC CAT GTT CGT TCC AAA C-3' (SEQ ID NO:29; BFB24) were used to amplify RIIβB DNA from ATCC 10625233 (Genbank ID BC075800). The resultant product was digested with BspEI/SmaI restriction enzymes and ligated into the parent CPM-FF Luc expression plasmid (pBFB8) digested with AgeI/NruI. This new construct was identified as pBFB11.

Expression of CPM-FF Luc/RIIβB Fusion Proteins with X/Y Linker Lengths of (X=4,Y=4), (X=10,Y=10), and (X=20,Y=20) Amino Acid Residues.

The synthesis of fusion proteins of the predicted size was confirmed for the CPM-FF Luc/RIIβB fusion proteins with X/Y linker lengths of (X=4,Y=4; pBFB9), (X=10,Y=10; pBFB10), and (X=20,Y=20; pBFB11) amino acid residues using the TNT® T7 Coupled Wheat Germ Extract System (Promega Corp.) together with the FluoroTect GreenLys in vitro Translation Labeling System (Promega Corp.). Briefly, the following components were assembled according to the manufacturer's recommended protocol:

400 ng plasmid DNA
10 μL TnT Wheat Germ Extract
0.8 μL TNT reaction buffer
0.4 μL T7 polymerase
0.4 μL amino acid mixture
0.4 μL rRNasin
0.4 μL FluoroTect GreenLys label
$dH_2O$ to 20 μL total volume Following incubation at 30° C. for 1.5 hours, 5 μL of TNT reaction was resolved via SDS-PAGE following the manufacturer's protocol (NuPAGE Novex 4-12% bis-tris gel, Invitrogen Corp.). Translated proteins were subsequently visualized via fluorimager (Typhoon Variable Mode Imager, Amersham Biosciences). Densitometry analysis (ImageQuant, GE Healthcare) indicated that the CPM-FF Luc/RIIβB fusion proteins with variable X/Y linker lengths were expressed similarly to the CPM-FF Luc fusion proteins having the 42 amino acid Gly/Ser rich peptide (pBFB8) and Epac1 (FF105).

Functional Characterization of CPM-FF Luc/RIIβB Fusion Proteins with X/Y Linker Lengths of (X=4,Y=4; pBFB9), (X=10,Y=10; pBFB10), and (X=20,Y=20; pBFB11) Amino Acid Residues Luciferase activity in the presence and absence of 100 μM cAMP was measured for the CPM-FF Luc/RIIβB fusion proteins with X/Y linker lengths of (X=4,Y=4; pBFB9), (X=10,Y=10; pBFB10), and (X=20,Y=20; pBFB11) amino acid residues following expression using the TNT® T7 Coupled Reticulocyte Lysate System (Promega Corp.). Briefly, the following components were assembled according to the manufacturer's recommended protocol:

400 ng plasmid DNA
10 μL Rabbit Retic Extract
0.8 μL TNT reaction buffer
0.4 μL T7 polymerase
0.4 μL amino acid mixture
0.4 μL rRNasin
$dH_2O$ to 20 μL total volume Following incubation at 30° C. for 1.5 hours, the respective fusion proteins were incubated in the presence or absence of 100 μM cAMP by combining 9 μL of TNT® reaction with 1 μL of 1 mM cAMP stock or $dH_2O$. Following incubation for 10 minutes at room temperature, 1 μL of sample was added to 100 μL of Luciferase Assay Reagent (LAR; Promega Corp.) solution+/−100 μM cAMP (90 μL LAR+10 μL 1 mM cAMP stock or $dH_2O$). Luminescence was measured using a Veritas Microplate Luminometer (Turner Biosystems; program Bright-Glo).

Dose Response Experiment Using CPM-FF Luc/RIIβB Fusion Proteins with X/Y Linker Lengths of (X=4,Y=4; pBFB9), (X=10,Y=10; pBFB10), and (X=20,Y=20; pBFB11) Amino Acid Residues The cAMP dose response of CPM-FF Luc/RIIβB fusion proteins with X/Y linker lengths of (X=4,Y=4; pBFB9), (X=10,Y=10; pBFB10), and (X=20,Y=20; pBFB11) amino acid residues was measured following expression using the TNT® T7 Coupled Reticulocyte Lysate System (Promega Corp.). Briefly, the following components were assembled according to the manufacturer's recommended protocol:

2000 ng plasmid DNA
50 μL Rabbit Retic Extract
4 μL TNT reaction buffer
2 μL T7 polymerase
2 μL amino acid mixture
2 μL rRNasin
$dH_2O$ to 100 μL total volume Following incubation at 30° C. for 2 hours, the respective fusion proteins were incubated with varying concentrations of cAMP by combining 9 μL of TnT® reaction with 1 μL of cAMP stock solution (final concentrations of 0, 0.01, 0.025, 0.1, 0.25, 1, 2.5, 10, 25, or 100 μM cAMP). Following incubation at room temperature for ≥25 minutes, 1 μL of sample was added to 100 μL of Luciferase Assay Reagent (LAR; Promega Corp.) with the respective concentration of cAMP (90 μL LAR+10 μL cAMP stock solution). Luminescence was measured using a Veritas Microplate Luminometer (Turner Biosystems; program Bright-Glo).

Selectivity of the CPM-FF Luca/RIIβB Fusion Protein with X/Y Linker Length of (X=10,Y=10; pBFB10) Amino Acid Residues The selectivity of the CPM-FF Luc/RIIβB fusion protein with X/Y linker length of (X=10,Y=10; pBFB10) amino acid residues for cAMP activation relative to other cyclic nucleotides was measured following expression using the TNT® T7 Coupled Reticulocyte Lysate System (Promega Corp.). Briefly, the following components were assembled according to the manufacturer's recommended protocol:

6000 ng plasmid DNA
150 μL Rabbit Retic Extract
12 μL TNT reaction buffer
6 μL T7 polymerase
6 μL amino acid mixture
6 μL rRNasin
$dH_2O$ to 300 μL total volume Following incubation at 30° C. for 2.3 hours, the fusion protein was incubated with varying concentrations of cAMP, cGMP, or N6-benzoyl cAMP by combining 9 μL of TNT® reaction with 1 μL of cyclic nucleotide stock solution (final concentrations of 0, 0.01, 0.025, 0.1, 0.25, 1, 2.5, 10, 25, or 100 μM cAMP). Following incubation at room temperature for ≥29 minutes, 1 μL of sample was added to 100 μL of Luciferase Assay Reagent (LAR; Promega Corp.) with the respective concentration of cyclic nucleotide (90 μL LAR+10 μL cyclic nucleotide stock solution). Luminescence was measured using a Veritas Microplate Luminometer (Turner Biosystems; program Bright-Glo).

Results

Figure 7:
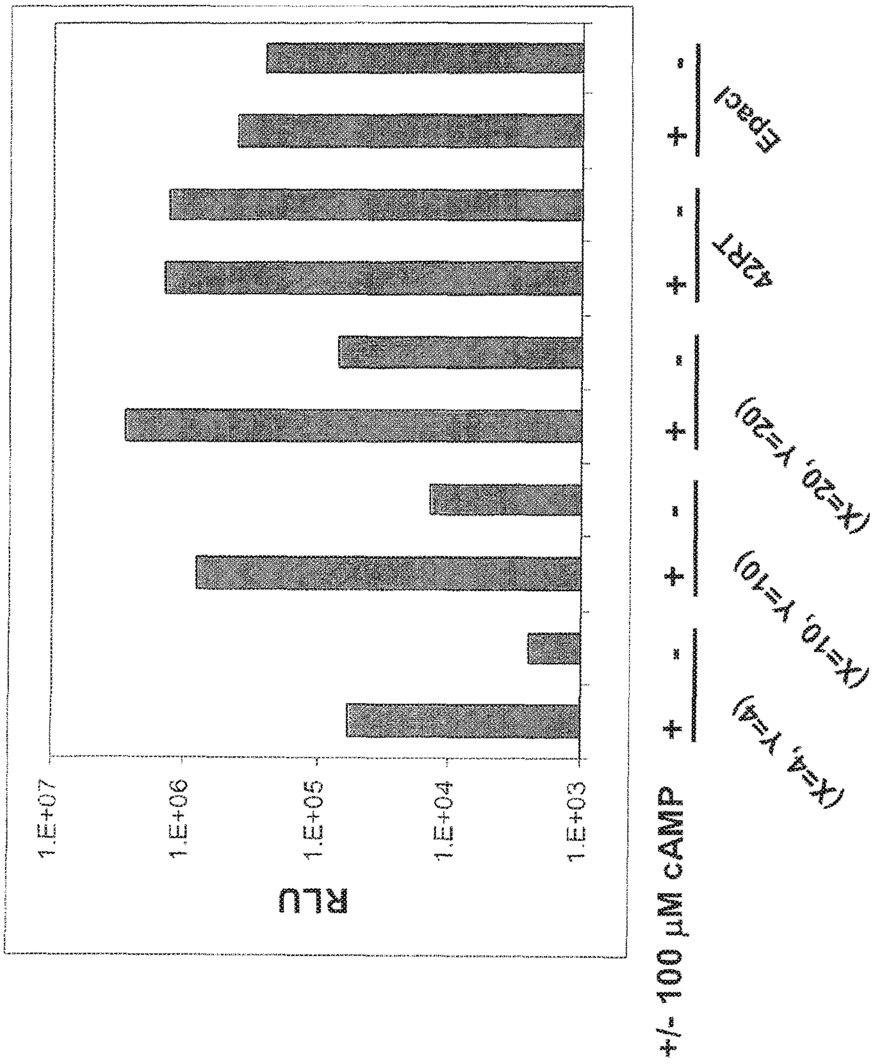
FIG. 7. Functional characterization of CPM-FF Luc/RIIβB based cAMP sensors with X/Y linker lengths of (X=4,Y=4), (X=10,Y=10), and (X=20,Y=20) amino acid residues.

Protein kinase A regulatory subunit type IIβ (PRKAR2B), has two cAMP binding sites, A and B. The cAMP binding site from the B domain (RIIβB) was used to prepare a circularly permutated luciferase (CPM-FF Luc) with RIIβB (CPM-FF Luc/RIIβB). CPM-FF Luc/RIIβB fusion proteins with X/Y linker lengths of (X=4,Y=4; pBFB9), (X=10, Y=10; pBFB10), and (X=20,Y=20; pBFB11) amino acid residues each showed an induction of luciferase activity in the presence of 100 μM cAMP of 23-, 58-, and 39-fold, respectively (FIG. 7). As expected, no cAMP regulation was seen for the CPM-FF Luc fusion protein having the 42 amino acid Gly/Ser rich peptide (pBFB8). In addition to RIIβB, the cAMP binding site from Epac1 was used to generate a cAMP sensor (FF105). However, the fold induction in luciferase activity was less than the RIIβB based sensor (FIG. 7).

Figure 8A:
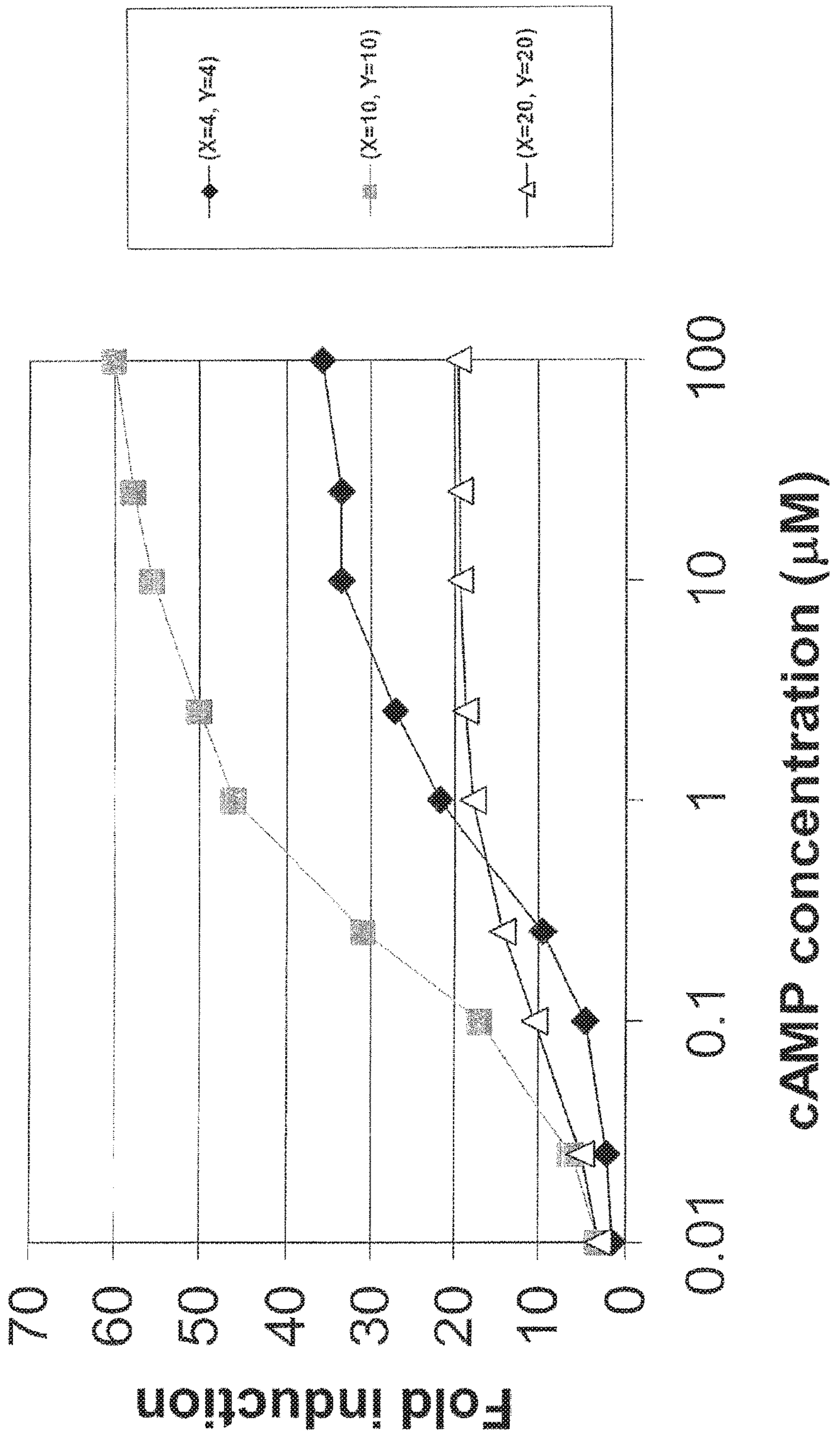
FIG. 8A. Dose response experiment using CPM-FF Luc/RIIβB based cAMP sensors with X/Y linker lengths of (X=4,Y=4), (X=10,Y=10), and (X=20,Y=20) amino acid residues.
Figure 8B:
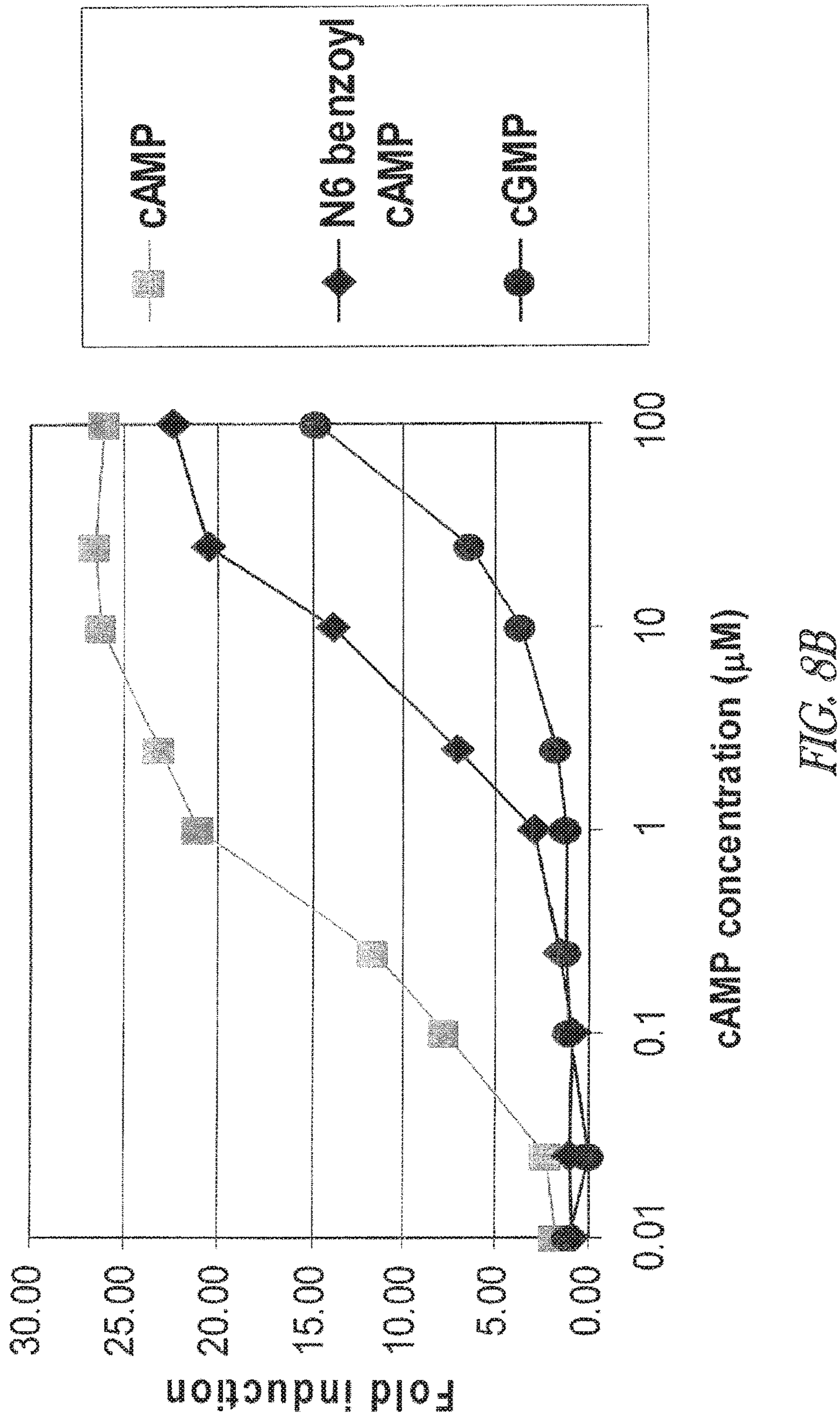
FIG. 8B. Selectivity of the CPM-FF Luc/RIIbB based cAMP sensor with X/Y linker lengths of (X=10,Y=10) amino acid residues.

Each CPM-FF Luc/RIIβB fusion protein showed a unique dose response with variable values for the effective concentration for 50% maximal fold induction (FIG. 8A). The CPM-FF Luc/RIIβB fusion protein with X/Y linker length of (X=10,Y=10; pBFB10) amino acid residues showed enhanced selectivity for binding to cAMP relative to other cyclic nucleotides (FIG. 8B).

Example III

Circularly Permuted *Renilla* Luciferases with cAMP Binding Sites

Materials and Methods

Figure 5D:
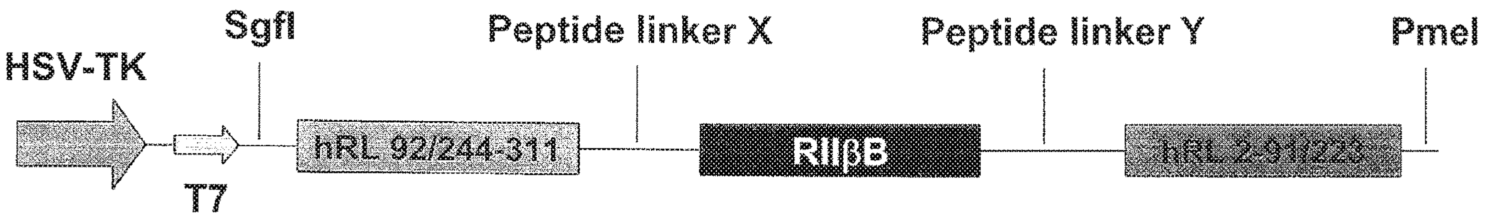
FIG. 5D. Circularly permuted *Renilla* luciferase (CPM-hRL) expression plasmid and constructs expressing fusions of CPM-hRL to RIIβB (CPM-hRL/RIIβB). Unique combinations of restriction enzymes allowed DNA encoding RIIβB to be ligated in-frame to generate plasmids that encode CPM-hRL/RIIβB fusion proteins with various X/Y peptide linker lengths (GSTG corresponds to SEQ ID NO:122; GSSG corresponds to SEQ ID NO:197; GSSGGSGGSG corresponds to SEQ ID NO:198; GSGGSGGSGGTSGGSGGSSG corresponds to SEQ ID NO:201). The Gly/Ser rich 42 amino acid peptide corresponds to SEQ ID NO:196.

Four humanized *Renilla* luciferase DNA fragments were amplified from either pF5RK or phRL-null vectors (Promega Corp.) and cloned into the CPM-FF Luc fusion protein construct=[Luc2.0 (234-544)-42 amino acid Gly/Ser rich peptide-Luc2.0 (4-233)] (pBFB8; FIG. 5A) to generate a circularly permuted *Renilla* luciferase open reading frame (CPM-hRL) split either between positions Ser91/Tyr92 or Ile223/Pro224 (FIG. 5D). The sequencing primers used to generate the four humanized *Renilla* luciferase DNA fragments were: 5'-ATGGGCGATCGCCatgtatcgcctcctggatcactacaag-3' (hRL92 Se; FF273; SEQ ID NO:110); 5'-ATGGGCGATCGCCatgcctctcgttaagggaggcaagc-3' (hRL224 Se; FF277; SEQ ID NO:111); 5'-gcatCTCGAGccctgctcgttcttcagcacgcgc-3' (hRL311/XhoI; FF294; SEQ ID NO:112); 5'-atgcGAGCTCaggagcttccaaggtgtacgacccg-3' (hRL2 SacI; FF295; SEQ ID NO:113); 5'-TTGTGTTTAAACtgagccattcccgctcttgccg-3'(hRL91/PmeI; FF276; SEQ ID NO:114); and 5'-TTGTGTTTAAACgatctcgcgaggccaggagagg-3' (hRL223 PmeI; FF278; SEQ ID NO:115). Primer pairs FF273/FF294 and FF277/FF294 were used to amplify the C terminal fragment of the humanized *Renilla* luciferase DNA (hRL 92-311 and hRL 224-311, respectively). The resultant products were digested with SgfI/XhoI restriction enzymes and ligated into the parent CPM-FF Luc fusion protein construct=[Luc2.0 (234-544)-42 amino acid Gly/Ser rich peptide-Luc2.0 (4-233)], pBFB8, digested with SgfI/XhoI. Primer pairs FF276/FF295 and FF278/FF295 were used to amplify the N terminal fragments of the humanized *Renilla* luciferase DNA (hRL 2-91 and hRL 2-223, respectively). The resultant products were digested with SacI/PmeI restriction enzymes and ligated into the intermediate CPM-FF Luc/hRL plasmid encoding [hRL (92-311 or 224-311)-42 amino acid Gly/Ser rich peptide-Luc2.0 (4-233)] digested with SacI/PmeI. This resulted in the generation of CPM-hRL expression vectors where the circularly permuted hRL luciferase fragments are fused by a 42 amino acid Gly/Ser rich peptide (identical to the Gly/Ser rich peptide of FIG. 5A, 201325.15.A1 (CPM91); 201325.15.B6 (CPM223)). The sequence encoding human RIIβB amino acids 266-414 (Genbank ID BC075800) was cloned into subsets of the unique restriction enzyme sites that encode amino acids present in the Gly/Ser rich peptide as previously described for the CPM-FF Luc/RIIβB cAMP sensors (FIG. 5D). The resulting constructs encode CPM-hRL/RIIβB fusions with either X=4, Y=20 (201325.44.H6 (CPM91); 201325.33.C9 (CPM223)), X=10, Y=4 (201325.50.D12 (CPM91); 201325.54.E2 (CPM223)) or X=10, Y=20 (201325.58.E11 (CPM91); 201325.54.E12 (CPM223)) Gly/Ser rich linkers fused to the N- and C-termini of RIIβB, respectively (FIG. 5D). In addition, the full length hRL open reading frame was cloned into the SgfI/PmeI sites of the CPM-FF Luc expression plasmid encoding Luc2.0 (234-544)-42 amino acid Gly/Ser rich peptide-Luc2.0 (4-233) (201325.50.A7, FIG. 5A).

One μg purified plasmid DNA per 50 μl Wheat Germ TnT® (Promega cat# L4140) reaction was used to express the protein products. Wheat Germ TnT® reactions were carried out at 30° C. for 1 hour in the presence of FluoroTect™ $Green_{Lys}$ tRNA (Promega cat#L5001). The CPM-hRL constructs were expressed together with the following controls: CPM-FF Luc/RIIβB with X=10, Y=4 (pBFB41), full length *Renilla* luciferase (201325.50.A7), and a "no DNA" (negative control). Fifteen μl of each lysate was mixed with either 1.5 μl 1 mM cAMP (Promega cat# V642A, 100 μM final concentration) or water (Promega cat#P119C) and incubated for 10 minutes at room temperature. Seventy five μl of 1× *Renilla* Luciferase Assay Lysis Buffer (5× *Renilla* Luciferase Assay Lysis Buffer (Promega cat#E291A) plus water (Promega cat#P119C) was added to the *Renilla* luciferase reaction and "no DNA" samples, mixed, and 20 μl of each mixture was added in triplicate to a 96 well white flat bottom plate. Two μl of the CPM-FF Luc/RIIβB with X=10, Y=4 linkers sample (pBFB41) was added in triplicate to a 96 well white flat bottom plate. One hundred μl of *Renilla* Luciferase Assay Buffer plus 1× *Renilla* Luciferase Assay Substrate (Promega Corp.; cat# E2820) was added to each of the *Renilla* luciferase and "no DNA" wells. One hundred μl of Luciferase Assay Buffer plus Luciferase Assay Substrate (Promega Corp.; cat# E1500) was added to each well containing the CPM-FF Luc/RIIβB with X=10, Y=4 linkers (pBFB41). Luminescence was measured using a Veritas Luminometer. Prior to cAMP incubation, 10 μl of each lysate was size fractionated on an SDS-PAGE gel. Fluorescent protein products were visualized on a Typhoon imager.

Results

Figure 10A:
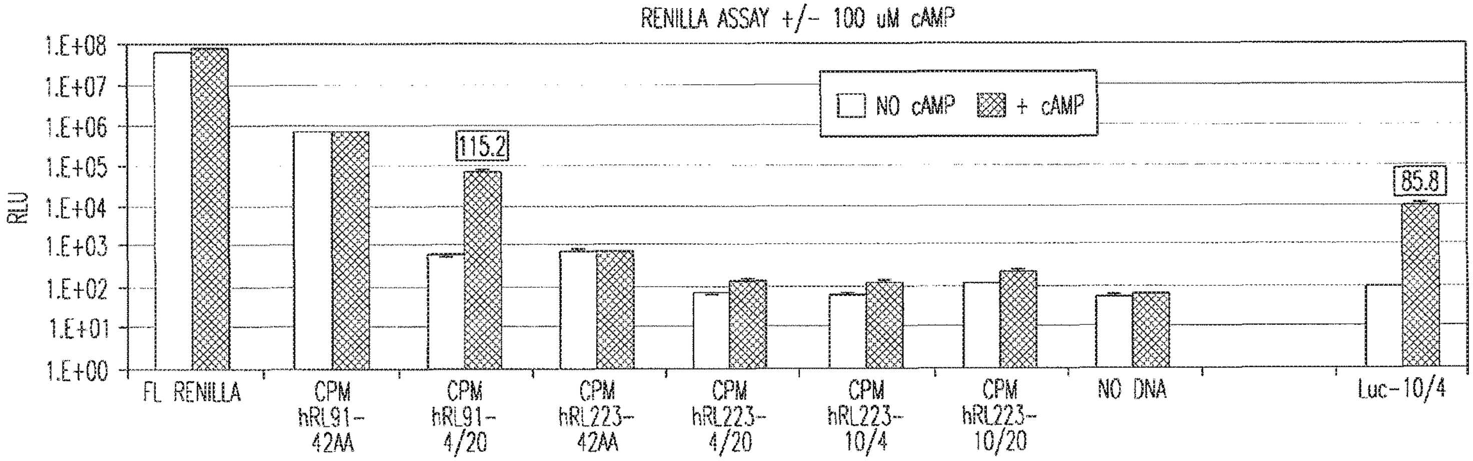
FIG. 10A and FIG. 10B. Comparison of RLU activity for cAMP binding site containing circularly permuted *Renilla* luciferases.
Figure 10B:
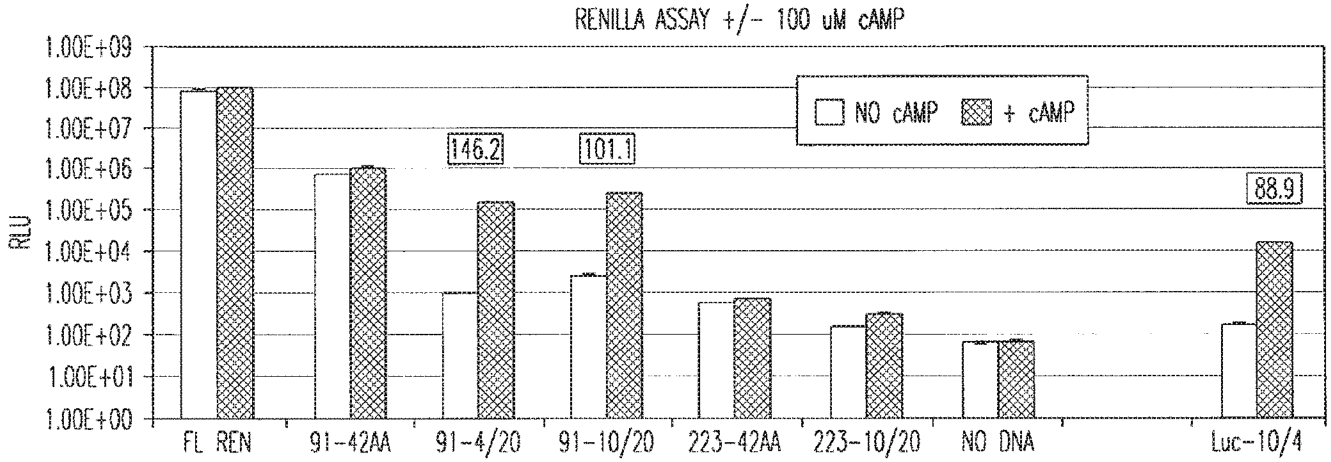

Wheat Germ TnT® reactions resulted in approximately equal amounts of each construct protein. There was no visible protein product from the "no DNA" sample. The full length *Renilla* luciferase construct (201325.50.A7) resulted in about 100-fold more luminescence than the CPM-hRL91-42aa construct (201325.15.A1) and about 100,000-fold more luminescence than the CPM-hRL223-42aa construct (201325.15.B6). The RIIβB constructs CPM-hRL91-4aa-RIIβB-20aa (201325.44.H6) and CPM-hRL91-10aa-RIIβB-20aa (201325.58.E11) gave more luminescence when incubated with 100 μM cAMP than water (115- to 146-fold and 100-fold, respectively). The RIIβB constructs CPM-hRL223-4aa-RIIβB-20aa (201325.33.C9), CPM-hRL223-10aa-RIIβB-4aa (201325.54.E2) and CPM-hRL223-10aa-RIIβB-20aa (201325.54.E12) gave 1.7- to 2.1-fold more luminescence when incubated with 100 μM cAMP than water. The full length *Renilla* luciferase (201325.50.A7), CPM-hRL91-42aa (201325.15.A1), and CPM-hRL223-42aa constructs (201325.15.B6) did not change with cAMP incubation more than 1.3-fold as compared to water. The CPM-FF Luc/RIIβB sensor with X=10, Y=4 linkers construct (pBFB41) gave 85-90-fold more luminescence in the presence of cAMP. The "no DNA" reaction had low luminescence (1,000,000-fold less than full length *Renilla* luciferase) and did not change with cAMP incubation (see FIG. 10A and FIG. 10B).

Example IV

In Vitro Detection of cAMP with CPM-FF Luc/RIIβB cAMP Biosensors

Materials and Methods

To demonstrate the efficacy of cAMP measurement in cell lysates and in the presence of cell lysis detergents, CPM-FF Luc/RIIβB fusion protein with X/Y linker lengths of (X=10, Y=10; pBFB10) was expressed using the TNT® T7 Coupled Reticulocyte Lysate System (Promega Corp.). Briefly, the following components were assembled according to the manufacturers recommended protocol and incubated at 30° C. for 1.5 hours:

1000 ng plasmid DNA
25 μL Rabbit Retic Extract
2 μL TNT reaction buffer
1 μL T7 polymerase
1 μL amino acid mixture
1 μL rRNasin
$dH_2O$ to 50 μL total volume To simulate the experimental conditions of cAMP measurement following detergent mediated lysis of cells, the following components were mixed at room temperature with final concentrations of 0, 0.01, 0.025, 0.1, 0.25, 1, 2.5, 10, and 25 μM cAMP:

0.5 μL TNT® expressed cAMP sensor
19.5 μL Wheat Germ Extract (Promega Corp.; cat# L4140, part# L411A)
5 μL cAMP stock solution
25 μL Bright-Glo assay reagent (Promega Corp., cat# E2610)

The assembled reaction was immediately mixed and the luciferase activity was measured continuously using a Turner 20/20N luminometer at 1 measurement per second (Turner Biosystems).

In some experiments, to enhance signal stability and luminescence, the reaction mixture includes 4 mM luciferin (Promega Bioscience), 2 mM Coenzyme A (Sigma), 10 mM ATP (Pharmacia), 10 mM DTT (Promega), 16 mM magnesium sulfate, 150 mM HEPES, pH 8.0 (Fisher), 1% Tergitol N101 (Sigma), 1% Mazu DF101, and 1 mM CDTA (Sigma). In vitro translated CPM-FF Luc/RIIβB cAMP biosensors were synthesized using TnT® Coupled Rabbit Reticulocyte System (Promega) using 1 μg of plasmid DNA for 50 μl total reaction volume and added to the reaction mixture immediately prior to assaying for cAMP (addition of 1 μl of translated product per 100 μl of assay reagent). 100 μl of assay reagent plus sensor was then added to either 100 μl of cell culture or 100 μl of cAMP diluted in complete media (DMEM/F12+10% FBS).

Cell Culture

For the in vitro analyses, HEK-293 cells were plated in a 96 well plate and grown to 50-90% confluency in 100 μl DMEM/F12 (Invitrogen) with 10% FBS (Hyclone) at 37° C. with 5% $CO_2$. Cells were stimulated with 0.02 to 250 μM forskolin (Sigma) where the forskolin was diluted by 2-fold dilutions in the complete media.

Standard Curve with cAMP 1 mM cAMP (Promega) was diluted into complete DMEM/F12 media with 10% FBS using a concentration range of 0.005 to 50 μM cAMP, where cAMP is serially diluted by 2-fold dilutions. 100 μl of cAMP was mixed with 100 μl of Homogeneous cAMP Luminescent Assay Reagent.

Results

Figure 9A:
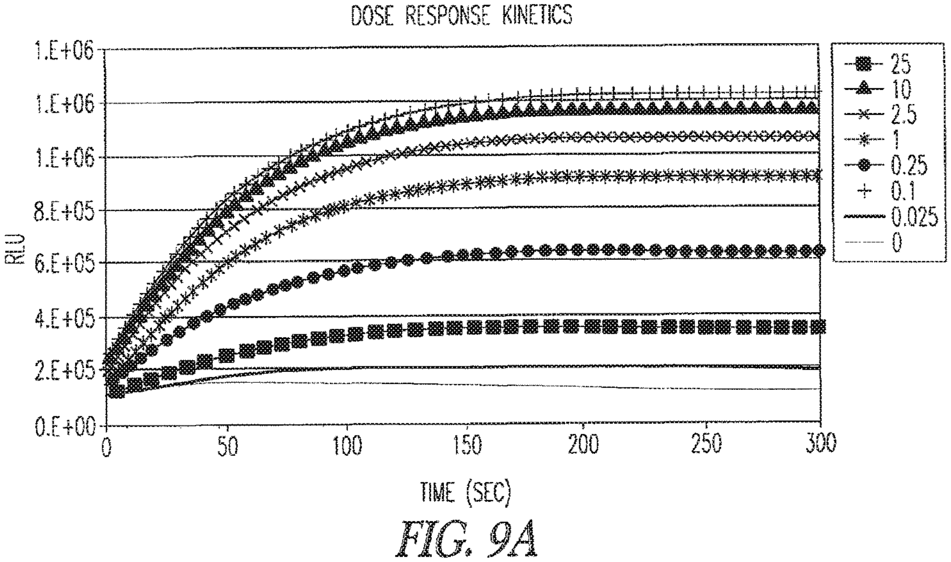
FIG. 9A and FIG. 9B. Homogeneous cAMP assay data from reactions with CPM-FF Luc/RIIβB cAMP biosensor with X/Y linker lengths of (X=10, Y=10).
Figure 9B:
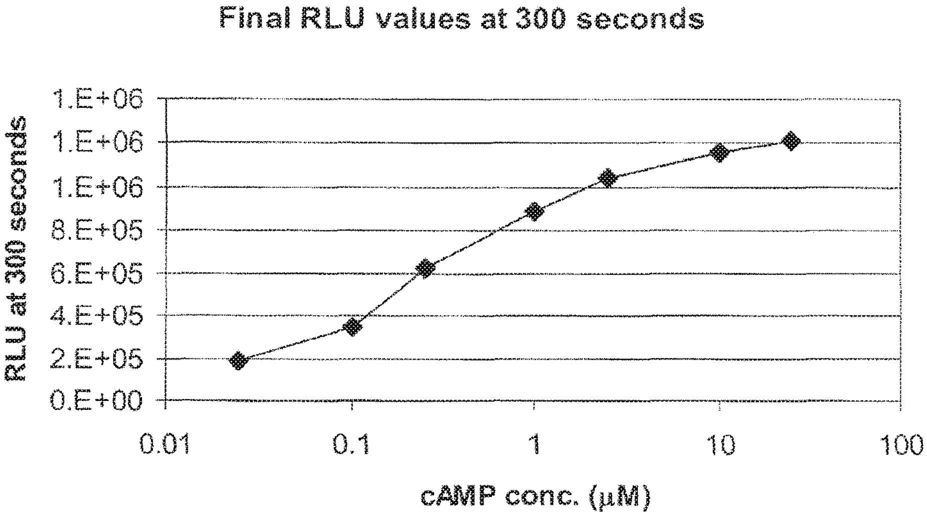
Figure 11A:
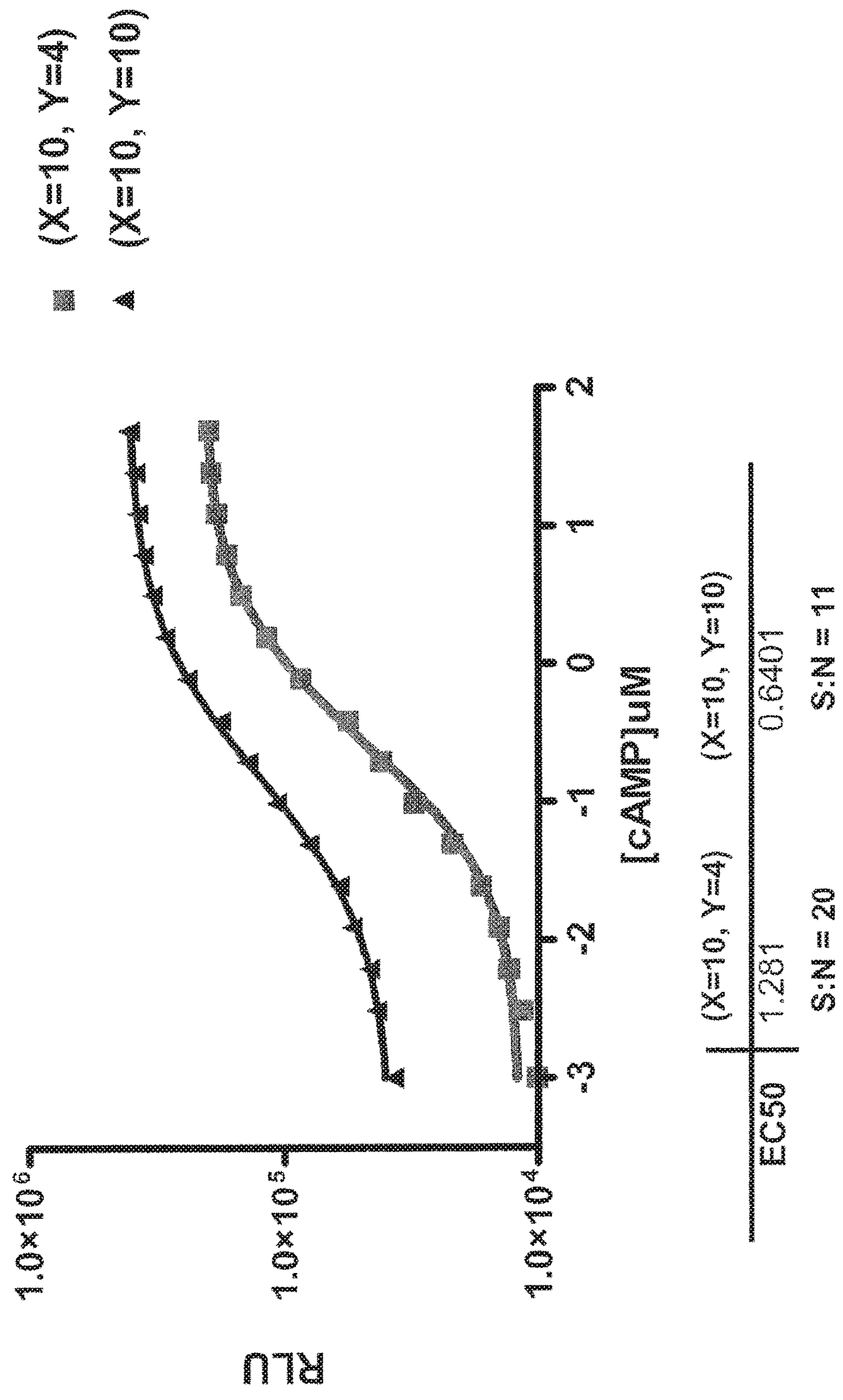
FIG. 11A and FIG. 11B. Measurement of cAMP concentrations in lysates of forskolin treated HEK293 cells with two different CPM-FF Luc/RIIβB cAMP biosensors.
Figure 11B:
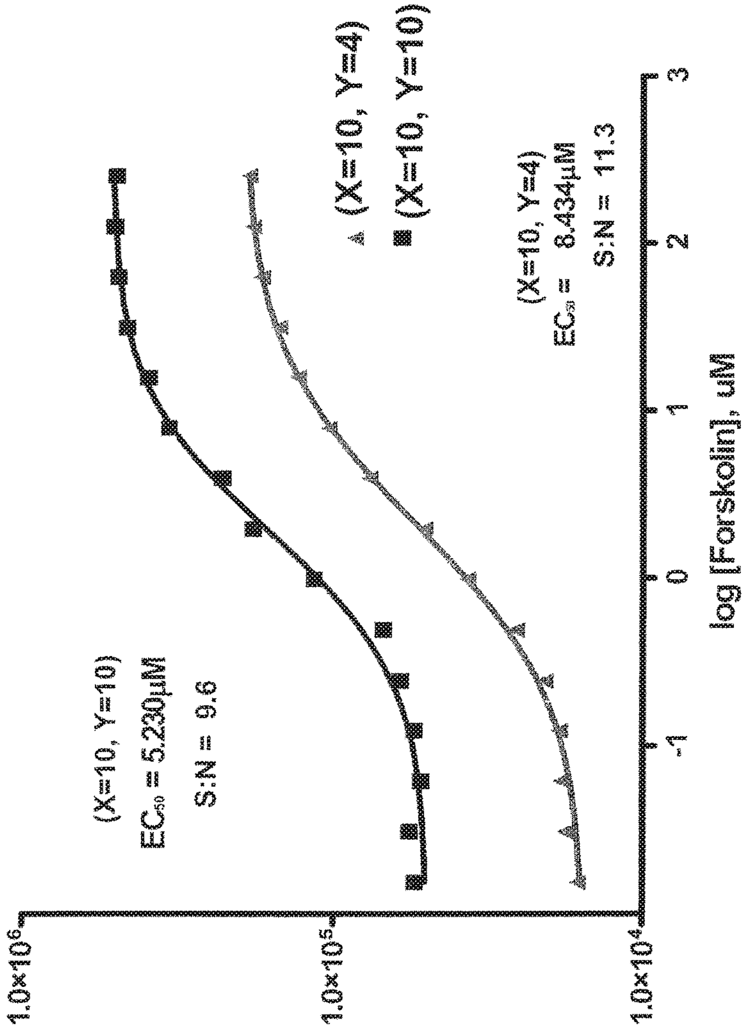

CPM-FF Luc/RIIβB cAMP sensors functioned in a variety of lysis buffers and with a variety of luciferase reagents. Furthermore, the CPM-FF Luc/RIIβB cAMP sensors were employed in homogenous assay formats for detection of cAMP in vitro (FIG. 9A, FIG. 9B, FIG. 11A and FIG. 11B). For example, using wheat germ extract, dose dependent values of luciferase activity developed within approximately three minutes with a dynamic range of cAMP detection between 0.025 to 25 μM cAMP (FIG. 9A and FIG. 9B). In an additional example using an optimized reagent formulation, in vitro detection of cAMP showed a signal to background ratio of 20 and an $EC_{50}$ of 1.28 μM for the CPM-FF Luc/RIIβB cAMP sensor with X/Y linker lengths of X=10, Y=4 (pBFB41) (FIG. 11A). Similarly, using the same optimized reagent formulation, in vitro detection of cAMP showed a signal to background ratio of 11 and an $EC_{50}$ of 0.64 μM for the CPM-FF Luc/RIIβB cAMP sensor with X/Y linker lengths of (X=10, Y=10) (pBFB10) (FIG. 11A). The present cAMP assay has the following advantages: a bioluminescence readout, which reduces compound interference; a homogenous one-step format; and the specificity that requires both binding and the capability of inducing a conformational change.

Example V

Intracellular Detection of Changes in cAMP Concentration Using CPM-FF Luc/RIIβB cAMP Biosensors Cell Culture Cells were cultured in 60 ml in DMEM/F12 with HEPES buffer (Invitrogen) with 10% FBS at 37° C. with 5% $CO_2$.

Plasmids

The ORF encoding the CPM-FF Luc/RIIβB based cAMP biosensor with X/Y linker lengths of (X=10, Y=0) was transferred to Flexi vector pF4K (Flexi vector system; Promega Corp.). The resultant plasmid construct (pBFB141) utilizes an upstream CMV promoter for expression of the associated cAMP biosensor in mammalian cells.

Transfections

Cells were transfected with TransIt®-LT1 Reagent (MIRUS) using 0.3 μl TransIt®-LT1 reagent and 0.15 μg DNA per well of a 96 well plate. Cells were allowed to grow overnight and were assayed the next day.

Modulation of Biosensor

Approximately 1 day after transfection, cells were removed from the incubator and equilibrated to room temperature. A 5 μl aliquot of 100 mM Luciferin EF was added to a total of 90 μl of cell culture plus transfection reagent to give a final concentration of approximately 5 mM luciferin. Cells were then incubated at room temperature for at least 90 minutes. After 90 minutes at room temperature, baseline measurements of luminescence were measured using a 96 well Veritas Luminometer (Turner Biosystems; integration time of 0.5 seconds per well). Cells were then induced with 10 μM isopreterenol (CalBiochem), 50 mM forskolin (Sigma) or not induced (0.1% DMSO, Sigma) and luminescence was measured continuously for about 30 minutes. After 30 minutes, 10 mM propranolol (Sigma) was added to cells with isopreterenol and 0.1% DMSO was added to all other samples. Luminescence was then measured continuously for the next 30 minutes. A final addition of 50 μM forskolin was added to the isopreterenol/propranolol sample and 0.1% DMSO was added to all other samples. Luminescence was then measured continuously for the next half hour. Samples were measured in sets of 12 replicates. 10× stocks of isopreterenol, propranolol, forskolin and DMSO were made in 1×PBS (Invitrogen).

Results

Figure 11C:
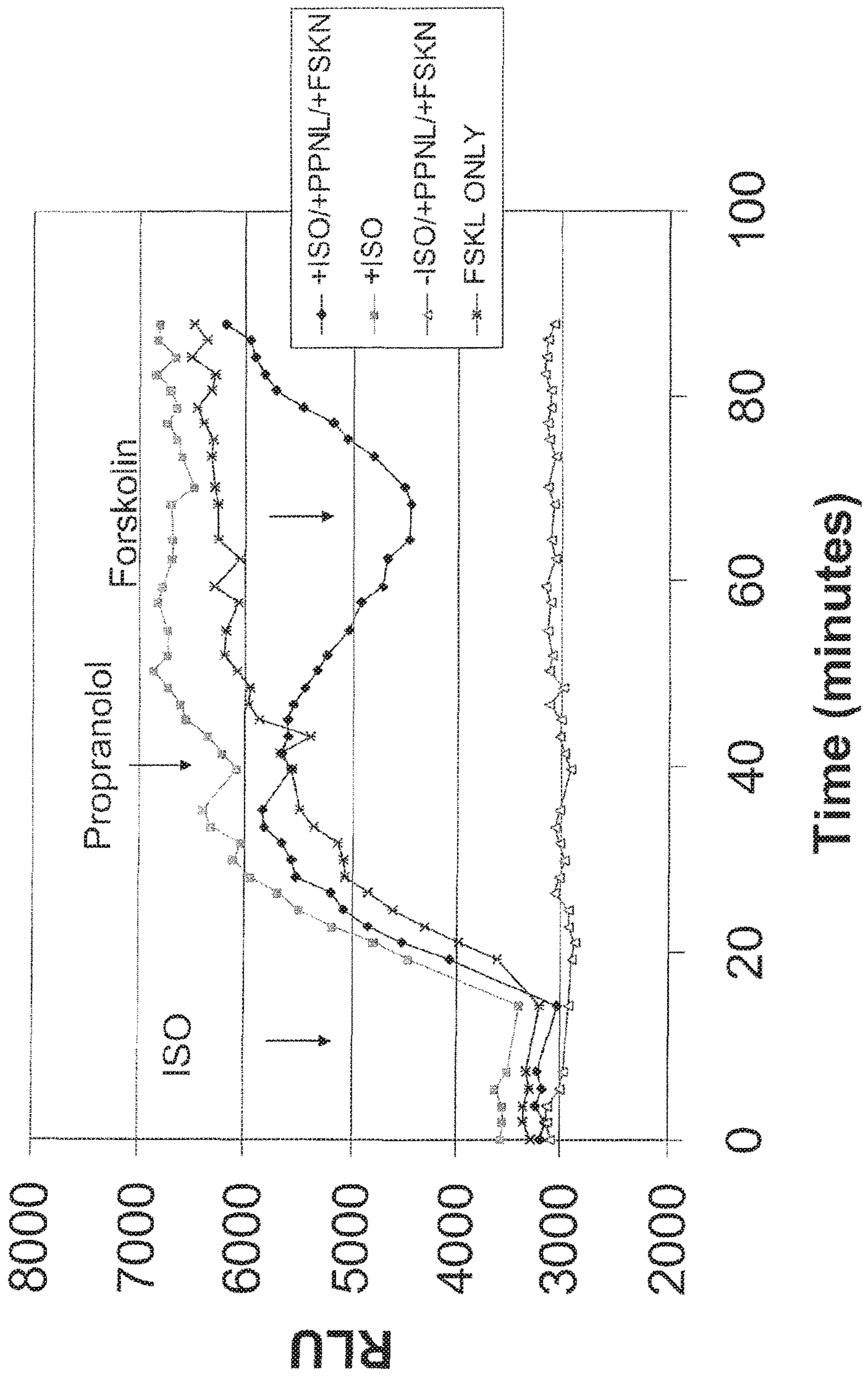
FIG. 11C. RLU over time in HEK293 cells transiently transfected with DNA encoding CPM-FF Luc/RIIβB based cAMP luciferase biosensor with X/Y linker lengths of (X=10, Y=0).

To measure changes in the intracellular concentration of cAMP, HEK 293 cells were transiently transfected with the CPM-FF Luc/RIIβB (X=10, Y=0, pBFB141) construct followed by treatment with compounds known to increase the intracellular cAMP concentration through GPCR activation (isopreterenol, β-adrenergic receptor agonist), decrease intracellular cAMP concentration through GPCR inhibition (propranolol, β-adrenergic receptor antagonist), or increase intracellular cAMP concentration through activation of adenylate cyclase (forskolin). Both isopreterenol and forskolin treatment alone increased light output from transfected cells approximately 2-fold, reflecting an increase in intracellular cAMP concentration (FIG. 11C). In addition, the temporal response of changes in cAMP concentration was followed by treating transfected cells with isoperterenol, propranolol, followed by forskolin (FIG. 11C). Wild type luciferase and the CPM-FF Luc/RIIβB fusion protein expressing the 42 amino acid Gly/Ser rich peptide (pBFB8) were also tested and showed no specific response to addition of known modulators of intracellular cAMP concentration.

Example VI

Light Output and Fold Induction Vary as a Function of X/Y Peptide Linker Lengths for CPM-FF Luc/RIIβB Based cAMP Sensors A. Synthesis of Plasmids Encoding CPM-FF Luc/RIIβB Based cAMP Sensors with Variable X/Y Peptide Linker Lengths To generate a set of CPM-FF Luc/RIIβB based cAMP sensors with variable X/Y peptide linker lengths of [2x (x=0-5), 2y (y=0-5)], plasmids encoding sensors of (X=0, Y=0, pBFB89), (X=2,Y=2, pBFB96), (X=6,Y=6, pBFB108), and (X=8,Y=8, pBFB115) were synthesized using splice overlap extension PCR (SOE PCR). Once acquired, standard molecular cloning techniques were used to exchange DNA fragments between plasmids encoding CPM-FF Luc/RIIβB based cAMP sensors with (X=0,Y=0), (X=2,Y=2), (X=4,Y=4), (X=6,Y=6), (X=8,Y=8), and (X=10,Y=10) peptide linkers to generate all remaining clones in this set. In addition, SOE PCR was used to synthesize clones in [10+2n (n=0-5), 0] and [10, −2n (n=1-7)] sets (Table 2).

TABLE 2

| | | |
|---|---|---|
| pBFB89 | X = 0, Y = 0 | RIIβB (SEQ ID NO: 124) |
| pBFB90 | X = 0, Y = 2 | RIIβB-SG (SEQ ID NO: 125) |
| pBFB91 | X = 0, Y = 4 | RIIβB-GSSG (SEQ ID NO: 126) |
| pBFB92 | X = 0, Y = 6 | RIIβB-SGGSSG (SEQ ID NO: 127) |
| pBFB93 | X = 0, Y = 8 | RIIβB-GGSGGSSG (SEQ ID NO: 128) |
| pBFB94 | X = 0, Y = 10 | RIIβB-GSGGSGGSSG (SEQ ID NO: 129) |
| pBFB95 | X = 2, Y = 0 | GS-RIIβB (SEQ ID NO: 130) |
| pBFB96 | X = 2, Y = 2 | GS-RIIβB-SG (SEQ ID NO: 131) |
| pBFB97 | X = 2, Y = 4 | GS-RIIβB-GSSG (SEQ ID NO: 132) |
| pBFB98 | X = 2, Y = 6 | GS-RIIβB-SGGSSG (SEQ ID NO: 133) |
| pBFB99 | X = 2, Y = 8 | GS-RIIβB-GGSGGSSG (SEQ ID NO: 134) |
| pBFB100 | X = 2, Y = 10 | GS-RIIβB-GSGGSGGSSG (SEQ ID NO: 135) |
| pBFB101 | X = 4, Y = 0 | GSTG-RIIβB (SEQ ID NO: 136) |
| pBFB102 | X = 4, Y = 2 | GSTG-RIIβB-SG (SEQ ID NO: 137) |
| pBFB9 | X = 4, Y = 4 | GSTG-RIIβB-GSSG (SEQ ID NO: 138) |
| pBFB103 | X = 4, Y = 6 | GSTG-RIIβB-SGGSSG (SEQ ID NO: 139) |
| pBFB104 | X = 4, Y = 8 | GSTG-RIIβB-GGSGGSSG (SEQ ID NO: 140) |
| pBFB39 | X = 4, Y = 10 | GSTG-RIIβB-GSGGSGGSSG (SEQ ID NO: 141) |
| pBFB105 | X = 6, Y = 0 | GSTGGS-RIIβB (SEQ ID NO: 142) |
| pBFB106 | X = 6, Y = 2 | GSTGGS-RIIβB-SG (SEQ ID NO: 143) |
| pBFB107 | X = 6, Y = 4 | GSTGGS-RIIβB-GSSG (SEQ ID NO: 144) |
| pBFB108 | X = 6, Y = 6 | GSTGGS-RIIβB-SGGSSG (SEQ ID NO: 145) |
| pBFB109 | X = 6, Y = 8 | GSTGGS-RIIβB-GGSGGSSG (SEQ ID NO: 146) |
| pBFB110 | X = 6, Y = 10 | GSTGGS-RIIβB-GSGGSGGSSG (SEQ ID NO: 147) |
| pBFB111 | X = 8, Y = 0 | GSTGGSGG-RIIβB (SEQ ID NO: 148) |
| pBFB112 | X = 8, Y = 2 | GSTGGSGG-RIIβB-SG (SEQ ID NO: 149) |
| pBFB113 | X = 8, Y = 4 | GSTGGSGG-RIIβB-GSSG (SEQ ID NO: 150) |
| pBFB114 | X = 8, Y = 6 | GSTGGSGG-RIIβB-SGGSSG (SEQ ID NO: 151) |
| pBFB115 | X = 8, Y = 8 | GSTGGSGG-RIIβB-GGSGGSSG (SEQ ID NO: 152) |
| pBFB116 | X = 8, Y = 10 | GSTGGSGG-RIIβB-GSGGSGGSSG (SEQ ID NO: 153) |
| pBFB117 | X = 10, Y = 0 | GSSGGSGGSG-RIIβB (SEQ ID NO: 154) |
| pBFB118 | X = 10, Y = 2 | GSSGGSGGSG-RIIβB-SG (SEQ ID NO: 155) |
| pBFB41 | X = 10, Y = 4 | GSSGGSGGSG-RIIβB-GSSG (SEQ ID NO: 156) |
| pBFB119 | X = 10, Y = 6 | GSSGGSGGSG-RIIβB-SGGSSG (SEQ ID NO: 157) |
| pBFB120 | X = 10, Y = 8 | GSSGGSGGSG-RIIβB-GGSGGSSG (SEQ ID NO: 158) |
| pBFB 10 | X = 10, Y = 10 | GSSGGSGGSG-RIIβB-GSGGSGGSSG (SEQ ID NO: 159) |
| pBFB128 | X = 10, Y = -2 | GSSGGSGGSG-RIIβB (266-412) (SEQ ID NO: 160) |
| pBFB129 | X = 10, Y = -4 | GSSGGSGGSG-RIIβB (266-410) (SEQ ID NO: 161) |
| pBFB130 | X = 10, Y = -6 | GSSGGSGGSG-(266-408) (SEQ ID NO: 162) |
| pBFB131 | X = 10, Y = -8 | GSSGGSGGSG-RIIβB (266-406) (SEQ ID NO: 163) |

TABLE 2-continued

| | | |
|---|---|---|
| pBFB132 | X = 10, Y = −10 | GSSGGSGGSG-RIIβB (266-404) (SEQ ID NO: 164) |
| pBFB133 | X = 10, Y = −12 | GSSGGSGGSG-RIIβB (266-402) (SEQ ID NO: 165) |
| pBFB134 | X = 10, Y = −14 | GSSGGSGGSG-RIIβB (266-400) (SEQ ID NO: 166) |
| pBFB135 | X = 12, Y = 0 | GSSGGSGGSGGG-RIIβB (SEQ ID NO: 167) |
| pBFB136 | X = 14, Y = 0 | GSSGGSGGSGGGSG-RIIβB (SEQ ID NO: 168) |
| pBFB137 | X = 16, Y = 0 | GSSGGSGGSGGGSGGS-RIIβB (SEQ ID NO: 169) |
| pBFB138 | X = 18, Y = 0 | GSSGGSGGSGGGSGGSGG-RIIβB (SEQ ID NO: 170) |
| pBFB139 | X = 20, Y = 0 | GSSGGSGGSGGGSGGSGGSG-RIIβB (SEQ ID NO: 171) |

(RIIβB corresponds to amino acids 266-414 of Genbank ID AAH75800)

i. Synthesis of a Plasmid Encoding a CPM-FF Luc/RIIβB Based cAMP Sensor Lacking Peptide Linkers (X=0,Y=0; pBFB89)

To synthesize the construct lacking peptide linkers (X=0, Y=0), three separate primer pairs were used to amplify RIIβB DNA to generate three separate PCR products. Primer pair 5'-CCT CGA ACA CCG AGC GAC C-3' (SEQ ID NO:31) and 5'-GCA GTG ACT CAA TAA AGC TTT CAT ACA TCT TCT TGG CCT TAA TGA GAA TCT CG-3' (SEQ ID NO:18) were used to generate product #1; primer pair 5'-CGA GAT TCT CAT TAA GGC CAA GAA GAT GTA TGA AAG CTT TAT TGA GTC ACT GC-3' (SEQ ID NO:32) and 5'-GGC CCT TCT TAA TGT TTT TGG CTA CAA TAT CCA TGT TCG TTC CAA ACA G-3' (SEQ ID NO:33) were used to generate product 2; and primer pair 5'-CTG TTT GGA ACG AAC ATG GAT ATT GTA GCC AAA AAC ATT AAG AAG GGC C-3' (SEQ ID NO:34) and 5'-GTA TCT TAT CAT GTC TGC TCG AAG CG-3 (SEQ ID NO:35) were used to generate product 3. SOE PCR of the three products yielded the full-length PCR product, which was subsequently digested with SgfI/XbaI restriction enzymes and ligated into the parent CPM-FF Luc expression plasmid (pBFB8) digested with SgfI/XbaI.

ii. Synthesis of a Plasmid Encoding a CPM-FF Luc/RIIβB Based cAMP Sensor with (X=2,Y=2; pBFB96) Peptide Linker Lengths To synthesize the construct with peptide linkers (X=2, Y=2), three separate primer pairs were used to amplify RIIβB to generate three separate PCR products. Primer pair 5'-CCT CGA ACA CCG AGC GAC C-3' (SEQ ID NO:36; BFB31) and 5'-CAA TAA AGC TTT CAT ACA TCG AGC CCT TCT TGG CCT TAA TGA GAA TCT CG-3' (SEQ ID NO:37; BFB120) were used to generate product 1; primer pair 5'-CGA GAT TCT CAT TAA GGC CAA GAA GGG CTC GAT GTA TGA AAG CTT TAT TG-3' (SEQ ID NO:38; BFB119) and 5'-CTT CTT AAT GTT TTT GGC ACC GGA TAC AAT ATC CAT GTT CGT TCC AAA CAG-3' (SEQ ID NO:39; BFB122) were used to generate product 2; and primer pair 5'-CTG TTT GGA ACG AAC ATG GAT ATT GTA TCC GGT GCC AAA AAC ATT AAG AAG-3' (SEQ ID NO:40; BFB122) and 5'-GTA TCT TAT CAT GTC TGC TCG AAG CG-3' (SEQ ID NO:41; BFB34) were used to generate product 3. SOE PCR of the three products yielded the full-length PCR product, which was subsequently digested with SgfI/l XbaI restriction enzymes and ligated into the parent CPM-FF Luc expression plasmid (pBFB8) digested with SgfI/XbaI.

iii. Synthesis of a Plasmid Encoding a CPM-FF Luc/RIIβB Based cAMP Sensor with (X=6,Y=6; pBFB108) Peptide Linker Lengths To synthesize the construct with peptide linkers (X=6, Y=6), primers 5'-AAA AAA AAA GTC GAC CGG AGG TTC AAT GTA TGA AAG CTT TAT TGA GTC ACT GC-3' (SEQ ID NO:42; BFB123) and 5'-AAA AAA GAG CTC CCT CCA GAT ACA ATA TCC ATG TTC GTT CCA AAC AG-3' (SEQ ID NO:43; BFB124) were used to PCR amplify RIIβB DNA. The resultant product was digested with SalI/SacI restriction enzymes and ligated into the parent CPM-FF Luc expression plasmid (pBFB8) digested with XhoI/SacI.

iv. Synthesis of a Plasmid Encoding a CPM-FF Luc/RIIβB Based cAMP Sensor with (X=8,Y=8; pBFB115) Peptide Linker Lengths To synthesize the construct with peptide linkers (X=8, Y=8), primers 5'-AAA AAA GTC GAC CGG AGG TTC AGG CGG TAT GTA TGA AAG CTT TAT TGA GTC ACT GC-3' (SEQ ID NO:44; BFB125) and 5'-AAA AAA GAG CTC CCT CCA GAT CCA CCT ACA ATA TCC ATG TTC GTT CCA AAC AG-3' (SEQ ID NO:116; BFB126) were used to PCR amplify RIIβB DNA. The resultant product was digested with SalI/SacI restriction enzymes and ligated into the parent CPM-FF Luc expression plasmid (pBFB8) digested with XhoI/SacI.

v. Synthesis of Plasmids Encoding the Remaining CPM-FF Luc/RIIβB Based cAMP Sensors with Peptide Linker Lengths in the Set [2x (x=0-5), 2y (y=0-5)]

XhoI/XbaI or XmnI/XbaI restriction enzyme digests were performed on plasmids encoding CPM-Luc/RIIβB based cAMP sensors with peptide linker lengths of (X=0,Y=0), (X=2,Y=2), (X=4,Y=4), (X=6,Y=6), (X=8,Y=8), and (X=10,Y=10). In each case, the restriction enzyme digest generates two fragments: a smaller fragment encoding a C-terminal portion of RIIβB, linker Y, and the Luc2.0 4-233 fragment; and a larger fragment containing all remaining elements of the original plasmid, including the sequences encoding Luc2.0 234-544, linker X, and an N-terminal portion of RIIβB. To generate all 36 clones in the [2x (x=0-5), 2y (y=0-5)] set, the smaller fragments were ligated to the larger fragments from the various restriction enzyme digests.

vi. Synthesis of Plasmids Encoding CPM-FF Luc/RIIβB Based cAMP Sensors with Peptide Linker Lengths in the Set [10+2n (n=1-5), 0]

To synthesize the plasmid encoding the CPM-FF Luc/RIIβB based cAMP sensor with peptide linker length (X=12, Y=0; pBFB135), two separate primer pairs were used to amplify RIIβB to generate two separate PCR products. Primer pair 5'-AAA AAA TCC GGA GGA GGT ATG TAT GAA AGC TTT ATT GAG TCA CTG C-3' (SEQ ID NO:46 BFB142) and 5'-GGC CCT TCT TAA TGT TTT TGG CTA CAA TAT CCA TGT TCG TTC CAA ACA G-3' (SEQ ID NO:47; BFB118) were used to generate product #1; primer pair 5'-CTG TTT GGA ACG AAC ATG GAT ATT GTA GCC AAA AAC ATT AAG AAG GGC C-3' (SEQ ID NO:48; BFB117) and 5'-GTA TCT TAT CAT GTC TGC TCG AAG CG-3' (SEQ ID NO:49; BFB34) were used to generate product 2. SOE PCR of the two products yielded the full-length PCR product, which was subsequently digested with BspEI/XbaI restriction enzymes and ligated into the parent CPM-FF Luc expression plasmid (pBFB8) digested with BspEI/XbaI.

To synthesize the plasmid encoding the CPM-FF Luc/RIIβB based cAMP sensor with peptide linker length (X=14, Y=0; pBFB136), two separate primer pairs were used to amplify RIIβB to generate two separate PCR products. Primer pair 5'-AAA AAA TCC GGA GGA GGT TCT GGC ATG TAT GAA AGC TTT ATT GAG TCA CTG C-3' (SEQ ID NO:45; BFB143) and 5'-GGC CCT TCT TAA TGT TTT TGG CTA CAA TAT CCA TGT TCG TTC CAA ACA G-3' (SEQ ID NO:21; BFB118) were used to generate product 1; primer pair 5'-CTG TTT GGA ACG AAC ATG GAT ATT GTA GCC AAA AAC ATT AAG AAG GGC C-3' (SEQ ID NO:24; BFB117) and 5'-GTA TCT TAT CAT GTC TGC TCG AAG CG-3' (SEQ ID NO:30; BFB34) were used to generate product 2. SOE PCR of the two products yielded the full-length PCR product, which was subsequently digested with BspEI/XbaI restriction enzymes and ligated into the parent CPM-FF Luc expression plasmid (pBFB8) digested with BspEI/XbaI.

To synthesize the plasmid encoding the CPM-FF Luc/RIIβB based cAMP sensor with peptide linker length (X=16, Y=0; pBFB137), two separate primer pairs were used to amplify RIIβB to generate two separate PCR products. Primer pair 5'-ATA AAT TCC GGA GGA GGT TCT GGC GGA TCA ATG TAT GAA AGC TTT ATT GAG TCA CTG C-3' (SEQ ID NO:50; BFB144) and 5'-GGC CCT TCT TAA TGT TTT TGG CTA CAA TAT CCA TGT TCG TTC CAA ACA G-3' (SEQ ID NO:51; BFB118) were used to generate product 1; primer pair 5'-CTG TTT GGA ACG AAC ATG GAT ATT GTA GCC AAA AAC ATT AAG AAG GGC C-3' (SEQ ID NO:52; BFB117) and 5'-GTA TCT TAT CAT GTC TGC TCG AAG CG-3' (SEQ ID NO:53; BFB34) were used to generate product 2. SOE PCR of the two products yielded the full-length PCR product, which was subsequently digested with BspEI/XbaI restriction enzymes and ligated into the parent CPM-FF Luc expression plasmid (pBFB8) digested with BspEI/XbaI.

To synthesize the plasmid encoding the CPM-FF Luc/RIIβB based cAMP sensor with peptide linker length (X=18, Y=0; pBFB138), two separate primer pairs were used to amplify RIIβB to generate two separate PCR products. Primer pair 5'-AAA AAT TCC GGA GGA GGT TCT GGC GGA TCA GGC GGT ATG TAT GAA AGC TTT ATT GAG TCA CTG C-3' (SEQ ID NO:54; BFB145) and 5'-GGC CCT TCT TAA TGT TTT TGG CTA CAA TAT CCA TGT TCG TTC CAA ACA G-3' (SEQ ID NO:55; BFB118) were used to generate product 1; primer pair 5'-CTG TTT GGA ACG AAC ATG GAT ATT GTA GCC AAA AAC ATT AAG AAG GGC C-3' (SEQ ID NO:56; BFB117) and 5'-GTA TCT TAT CAT GTC TGC TCG AAG CG-3' (SEQ ID NO:57; BFB34) were used to generate product 2. SOE PCR of the two products yielded the full-length PCR product, which was subsequently digested with BspEI/XbaI restriction enzymes and ligated into the parent CPM-FF Luc expression plasmid (pBFB8) digested with BspEI/XbaI.

vii. Synthesis of Plasmids Encoding CPM-FF Luc/RIIβB Based cAMP Sensors with Peptide Linker Lengths in the Set [10, −2n (n=1-7)]

To synthesize the plasmid encoding the CPM-FF Luc/RIIβB based cAMP sensor with an N-terminal peptide linker length of (X=10), lacking a C-terminal peptide linker, with RIIβB residues 266-412 (10, −2; pBFB128), two separate primer pairs were used to amplify RIIβB DNA to generate two separate PCR products. Primer pair 5'-AAA AAA GTC GAC CGG AGG TTC AGG CGG TTC-3' (SEQ ID NO:58; BFB127) and 5'-GGC CCT TCT TAA TGT TTT TGG CAT CCA TGT TCG TTC CAA ACA GG-3' (SEQ ID NO:59; BFB128) were used to generate product 1; primer pair 5'-CCT GTT TGG AAC GAA CAT GGA TGC CAA AAA CAT TAA GAA GGG CC-3' (SEQ ID NO:60; BFB129) and 5'-GTA TCT TAT CAT GTC TGC TCG AAG CG-3' (SEQ ID NO:61; BFB34) were used to generate product 2. SOE PCR of the two products yielded the full-length PCR product, which was subsequently digested with SalI/XbaI restriction enzymes and ligated into the parent CPM-FF Luc expression plasmid (pBFB8) digested with XhoI/XbaI.

To synthesize the plasmid encoding the CPM-FF Luc/RIIβB based cAMP sensor with an N-terminal peptide linker length of (X=10), lacking a C-terminal peptide linker, with RIIβB residues 266-410 (10, −4; pBFB129), two separate primer pairs were used to amplify RIIβB DNA to generate two separate PCR products. Primer pair 5'-AAAAAAGTCGACCGGAGGTTCAGGCGGTTC-3' (SEQ ID NO:62; BFB127) and 5'-GGCCCTTCTTAATGTTTTTGGCGTTCGTTCCAAACAGGGCAACTAAC-3' (SEQ ID NO:63; BFB130) were used to generate product #1; primer pair 5'-GTTAGTTGCCCTGTTTGGAACGAACGCCAAAAACATTAAGAAGGGCC-3' (SEQ ID NO:64; BFB131) and 5'-GTATCTTATCATGTCTGCTCGAAGCG-3' (SEQ ID NO:65; BFB34) were used to generate product 2. SOE PCR of the two products yielded the full-length PCR product, which was subsequently digested with SalI/XbaI restriction enzymes and ligated into the parent CPM-FF Luc expression plasmid (pBFB8) digested with XhoI/XbaI.

To synthesize the plasmid encoding the CPM-FF Luc/RIIβB based cAMP sensor with an N-terminal peptide linker length of (X=10), lacking a C-terminal peptide linker, with RIIβB residues 266-408 (10, −6; pBFB130), two separate primer pairs were used to amplify RIIβB DNA to generate two separate PCR products. Primer pair 5'-AAAAAAGTCGACCGGAGGTTCAGGCGGTTC-3' (SEQ ID NO:66; BFB127) and 5'-GGCCCTTCTTAATGTTTTTGGCTCCAAACAGGGCAACTAACTGTTCTTC-3' (SEQ ID NO:67; BFB132) were used to generate product 1; primer pair 5'-GAAGAACAGTTAGTTGCCCTGTTTGGAGCCAAAAACATTAAGAAGGG CC-3' (SEQ ID NO:68; BFB133) and 5'-GTATCTTATCATGTCTGCTCGAAGCG-3' (SEQ ID NO:69; BFB34) were used to generate product 2. SOE PCR of the two products yielded the full-length PCR product, which was subsequently digested with SalI XbaI restriction enzymes and ligated into the parent CPM-FF Luc expression plasmid (pBFB8) digested with XhoI/XbaI.

To synthesize the plasmid encoding the CPM-FF Luc/RIIβB based cAMP sensor with an N-terminal peptide linker length of (X=10), lacking a C-terminal peptide linker, with RIIβB residues 266-406 (10, −8; pBFB131), two separate primer pairs were used to amplify RIIβB DNA to generate two separate PCR products. Primer pair 5'-AAAAAAGTCGACCGGAGGTTCAGGCGGTTC-3' (SEQ ID NO:70; BFB127) and 5'-GGCCCTTCTTAATGTTTTTGGCCAGGGCAACTAACTGTTCTTCATAGG-3' (SEQ ID NO:71; BFB134) were used to generate product 1; primer pair 5'-CCTATGAAGAACAGTTAGTTGCCCTGGC-CAAAAACATTAAGAAGGGC C-3' (SEQ ID NO:72; BFB135) and 5'-GTATCTTATCATGTCTGCTCGAAGCG-3' (SEQ ID NO:73; BFB34) were used to generate product 2. SOE PCR of the two products yielded the full-length PCR product, which was subsequently digested with SalI/XbaI restriction enzymes and ligated into the parent CPM-FF Luc expression plasmid (pBFB8) digested with XhoI/XbaI.

To synthesize the plasmid encoding the CPM-FF Luc/RIIβB based cAMP sensor with an N-terminal peptide linker length of (X=10), lacking a C-terminal peptide linker, with RIIβB residues 266-404 (10, −10; pBFB132), two separate primer pairs were used to amplify RIIβB DNA to generate two separate PCR products. Primer pair 5'-AAAAAAGTC-GACCGGAGGTTCAGGCGGTTC-3' (SEQ ID NO:74; BFB127) and 5'-GGCCCTTCTTAATGTTTTTG-GCAACTAACTGTTCTTCATAGGTAGCGAT G-3' (SEQ ID NO:75; BFB136) were used to generate product 1; primer pair 5'-CATCGCTACCTATGAAGAACAGTTAGT-TGCCAAAAACATTAAGAAGG GCC-3' (SEQ ID NO:76; BFB137) and 5'-GTATCTTATCATGTCTGCTCGAAGCG-3' (SEQ ID NO:77; BFB34) were used to generate product 2. SOE PCR of the two products yielded the full-length PCR product, which was subsequently digested with SalI XbaI restriction enzymes and ligated into the parent CPM-FF Luc expression plasmid (pBFB8) digested with XhoI/XbaI.

To synthesize the plasmid encoding the CPM-FF Luc/RIIβB based cAMP sensor with an N-terminal peptide linker length of (X=10), lacking a C-terminal peptide linker, with RIIβB residues 266-402 (10, −12; pBFB133), two separate primer pairs were used to amplify RIIβB DNA to generate two separate PCR products. Primer pair 5'-AAAAAAGTC-GACCGGAGGTTCAGGCGGTTC-3' (SEQ ID NO:78; BFB127) and 5'-GGCCCTTCTTAATGTTTTTGGCCTGT-TCTTCATAGGTAGCGATGTTCC-3' (SEQ ID NO:79; BFB138) were used to generate product 1; primer pair 5'-GGAACATCGCTACCTATGAAGAACAGGC-CAAAAACATTAAGAAGGGC C-3' (SEQ ID NO:80; BFB139) and 5'-GTATCTTATCATGTCTGCTCGAAGCG-3' (SEQ ID NO:81; BFB34) were used to generate product 2. SOE PCR of the two products yielded the full-length PCR product, which was subsequently digested with SalI/XbaI restriction enzymes and ligated into the parent CPM-FF Luc expression plasmid (pBFB8) digested with XhoI/XbaI.

To synthesize the plasmid encoding the CPM-FF Luc/RIIβB based cAMP sensor with an N-terminal peptide linker length of (X=10), lacking a C-terminal peptide linker, with R2βB residues 266-400 (10, −14; pBFB134), two separate primer pairs were used to amplify RIIβB DNA to generate two separate PCR products. Primer pair 5'-AAAAAAGTC-GACCGGAGGTTCAGGCGGTTC-3' (SEQ ID NO:82; BFB127) and 5'-GGCCCTTCTTAATGTTTTTGGCT-TCATAGGTAGCGATGTTCCTTTTC-3' (SEQ ID NO:83; BFB140) were used to generate product 1; primer pair 5'-GAAAAGGAACATCGCTACCTATGAAGC-CAAAAACATTAAGAAGGGCC-3' (SEQ ID NO:84; BFB141) and 5'-GTATCTTATCATGTCTGCTCGAAGCG-3' (SEQ ID NO:85; BFB34) were used to generate product 2. SOE PCR of the two products yielded the full-length PCR product, which was subsequently digested with SalI/XbaI restriction enzymes and ligated into the parent CPM-FF Luc expression plasmid (pBFB8) digested with XhoI/XbaI.

B. Functional Characterization of CPM-FF Luc/RIIβB Based cAMP Sensors with Variable X/Y Peptide Linker Lengths i. Functional Characterization of CPM-FF Luc/RIIβB Based cAMP Sensors with X/Y Peptide Linkers in the Set [2x (x=0-5), 2y (y=0-5)]

Figure 12:
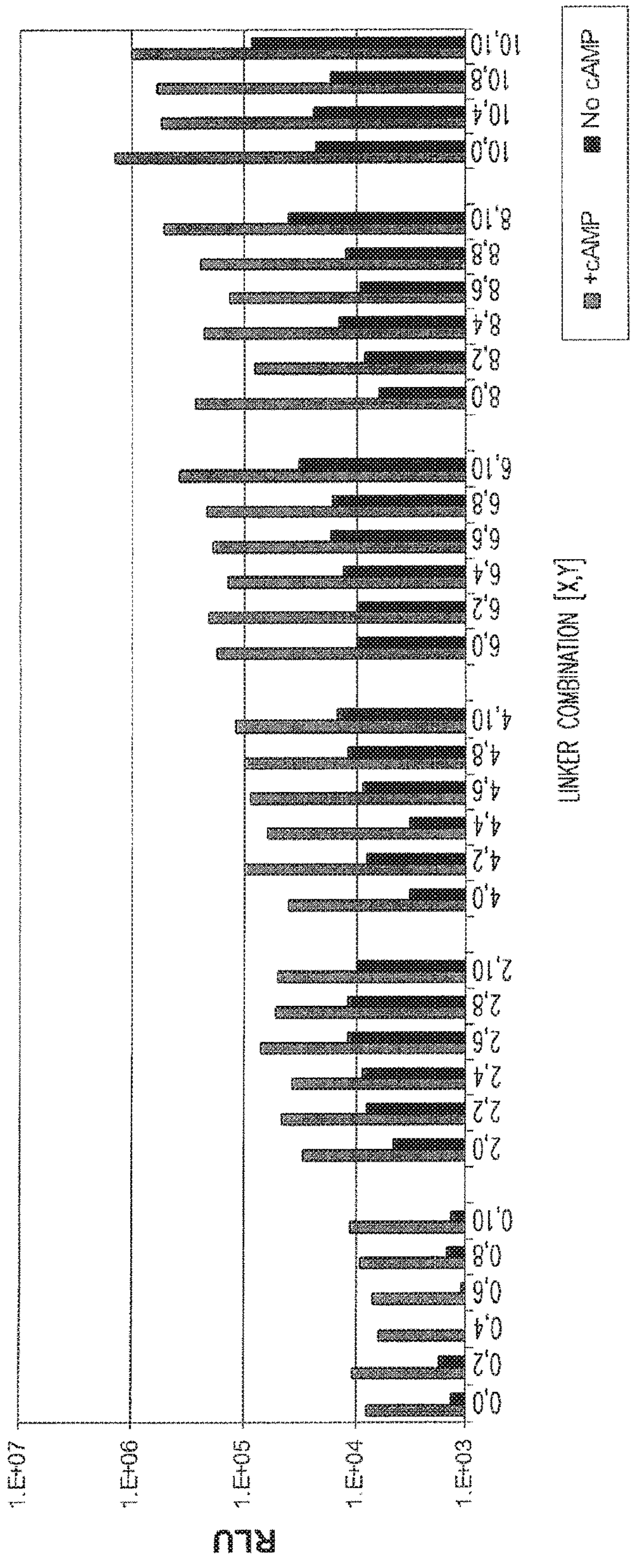
FIG. 12. Functional characterization of the CPM-FF Luc/RIIβB cAMP biosensors with X/Y linker lengths in the set [2x (x=0-5), 2y (y=0-5)] amino acid residues. Luciferase activity in the presence and absence of 100 μM cAMP. Linker combinations (10, 2) and (10, 6) not shown.
Figure 13:
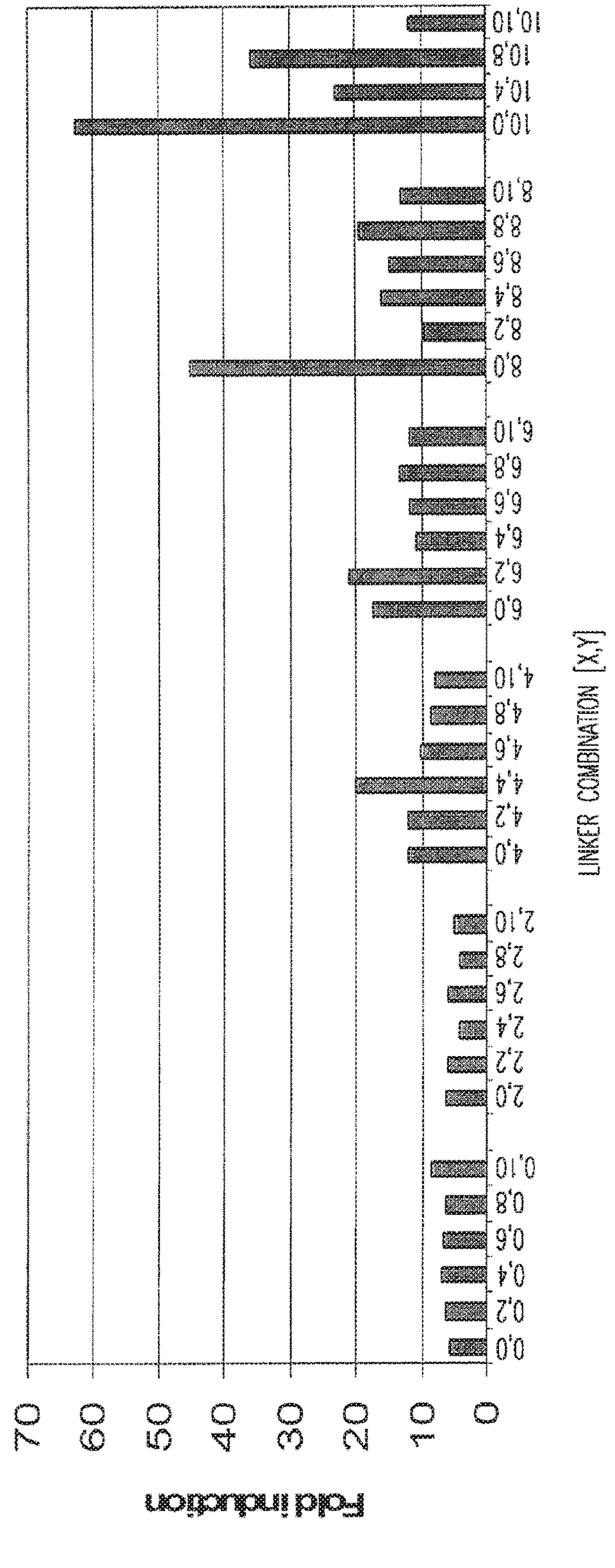
FIG. 13. Functional characterization of the CPM-FF Luc/RIIβB cAMP sensors with X/Y linker lengths in the set [2x (x=0-5), 2y (y=0-5)] amino acid residues. Fold induction in luciferase activity in the presence of 100 μM cAMP. Linker combinations (10, 2) and (10, 6) not shown.
Figure 14:
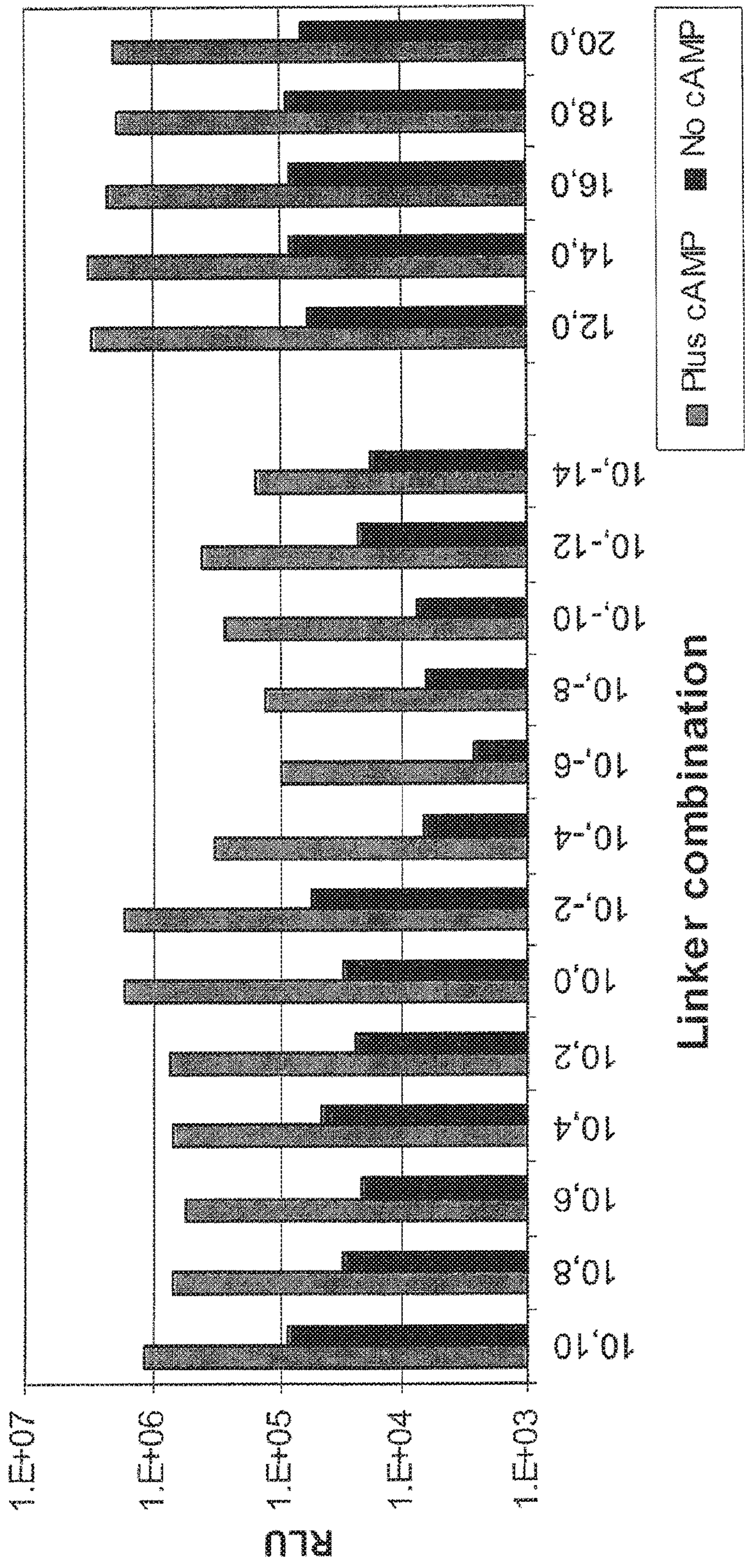
FIG. 14. Functional characterization of the CPM-FF Luc/RIIβB cAMP sensors with X/Y linker lengths in the sets [10, −2n (n=1-7)], [10, 2n (n=1-5)], and [10+2n (n=1-5), 0] amino acid residues. Luciferase activity in the presence or absence of 100 μM cAMP.
Figure 15:
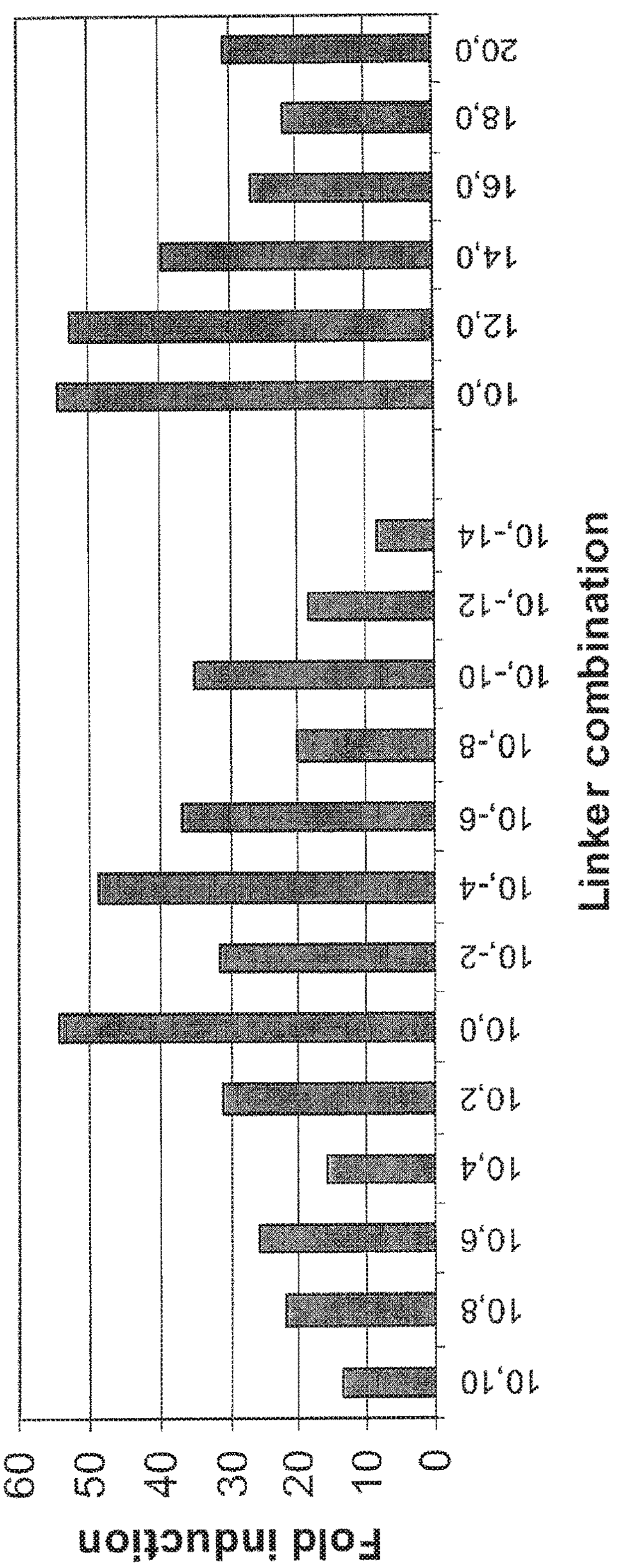
FIG. 15. Functional characterization of the CPM-FF Luc/RIIβB cAMP sensors with X/Y linker lengths in the sets [10, −2n (n=1-7)], [10, 2n (n=1-5)], and [10+2n (n=1-5), 0] amino acid residues. Fold induction in luciferase activity in the presence of 100 μM cAMP.

Luciferase activity in the presence and absence of cAMP was measured for the CPM-FF Luc/RIIβB cAMP sensors with X/Y linker lengths in the set [2x (x=0-5), 2y (y=0-5)] following expression using the TNT® T7 Coupled Reticulocyte Lysate System (Promega Corp.). Briefly, the following components were assembled according to the manufacturer's recommended protocol:

400 ng plasmid DNA
10 μL Rabbit Retic Extract
0.8 μL TNT reaction buffer
0.4 μL T7 polymerase
0.4 μL amino acid mixture
0.4 μL rRNasin
$dH_2O$ to 20 μL total volume Following incubation at 30° C. for 1.5 hours, the respective fusion proteins were incubated in the presence or absence of 100 μM cAMP by combining 9 μL of TNT® reaction with 1 μL of 1 mM cAMP stock or $dH_2O$. Following incubation for ≥15 minutes at room temperature, 1 μL of sample was added to 100 μL of Luciferase Assay Reagent (LAR; Promega Corp.) solution+/−100 μM cAMP (90 μL LAR+10 μL 1 mM cAMP stock or $dH_2O$). Luminescence was measured using a Veritas Microplate Luminometer (Turner Biosystems; program Bright-Glo). Overall, a trend was observed with CPM-FF Luc/RIIβB fusions with X/Y linker lengths in the set [2x (x=0-5), 2y (y=0-5)] where increasing luciferase activity was measured in the presence or absence of 100 μM cAMP with increasing peptide linker length (FIG. 12). In addition, a second trend was observed where the fold induction of luciferase activity in the presence of 100 μM cAMP increased with increasing peptide linker length (FIG. 13).

ii. Functional Characterization of CPM-FF Luc/RIIβB Based cAMP Sensors with X/Y Peptide Linkers in the Sets [10, −2n (n=1-7)], [10, 2n (n=1-5)], and [10+2n (n=0-5), 0] Amino Acid Residues Luciferase activity in the presence and absence of 100 μM cAMP was measured for the CPM-FF Luc/RIIβB cAMP sensors with X/Y linker lengths in the sets [10, −2n (n=1-7)], [10, 2n (n=1-5)], and [10+2n (n=0-5), 0] amino acid residues following expression using the TNT® T7 Coupled Reticulocyte Lysate System (Promega Corp.). Briefly, the following components were assembled according to the manufacturer's recommended protocol:

400 ng plasmid DNA
10 μL Rabbit Retic Extract
0.8 μL TNT reaction buffer
0.4 μL T7 polymerase
0.4 μL amino acid mixture
0.4 μL rRNasin
$dH_2O$ to 20 μL total volume Following incubation at 30° C. for 1 hour, the respective fusion proteins were incubated in the presence or absence of 100 μM cAMP by combining 9 μL of TNT® reaction with 1 μL of 1 mM cAMP stock or $dH_2O$. Following incubation at room temperature for ≥9 minutes, 1 μL of sample was added to 100 μL of Luciferase Assay Reagent (LAR; Promega Corp.) solution+/−100 μM cAMP (90 μL LAR+10 μL 1 mM cAMP stock or $dH_2O$). Luminescence was measured using a Veritas Microplate Luminometer (Turner Biosystems; program Bright-Glo). In general, luciferase activity in the presence or absence of 100 μM cAMP decreased with increasing C-terminal truncation of RIIβB for CPM-FF Luc/RIIβB cAMP sensors lacking C-terminal peptide linkers (FIG. 14). In addition, the maximal fold induction in the presence of 100 μM cAMP for CPM-FF Luc/RIIβB cAMP sensors of the set [10, −2n (n=1-7)] and [10, 2n (n=1-5)] was the sensor with peptide linkers of (X=10, Y=0; pBFB117). Moreover, CPM-FF Luc/RIIβB cAMP sensors of the set [10+2n (n=0-5), 0] showed a maximal fold induction for the sensor with peptide linkers of (X=10, Y=0; pBFB117) amino acid residues (FIG. 15).

Example VII

A cAMP Biosensor with Circularly Permuted Click Beetle Luciferase and the B Domain from the PKA Regulatory Subunit Type IIβ

A. Synthesis of a CPM-Click Beetle Luc Expression Plasmid for Subsequent Insertion of RIIβB (pBFB53)

To synthesize a click beetle variant of the plasmid synthesized in Example X, part A, primers 5'-TATAATGCTAGCGATCGCCATGGGCGTGACTGTGCTGGTGTATC-3' (SEQ ID NO:86; BFB94) and 5'-TTTTTTCTCGAGCCGCCGCCAGCTTTTTCGAGG-3' (SEQ ID NO:87; BFB95) were used to amplify the click beetle equivalent of the firefly luciferase fragment encoding residues 234-544 (click beetle luciferase amino acids 231-542) from plasmid pCBG68-basic (Genbank Acc# AY258593; Promega Corp). The resultant product was digested with NheI/XhoI restriction enzymes and ligated into the parent CPM-FF Luc (pBFB8) expression plasmid digested with NheI/XhoI to give plasmid intermediate 1. Subsequently, primers 5'-AAAAAAGAGCTCCGGTGAAAAGAACGTGATCTACGGCC-3' (SEQ ID NO:88; BFB96) and 5'-AAAAAATCTAGAGTTTAAACAGGGATCAATTGAGTACCCACAC-3' (SEQ ID NO:89; BFB97) were used to amplify the click beetle equivalent of the firefly luciferase fragment encoding residues 4-233 (click beetle luciferase amino acids 5-230) from plasmid pCBG68-basic (Genbank Acc# AY258593; Promega Corp). The resultant product was digested with SacI/XbaI restriction enzymes and ligated into plasmid intermediate 1 described above digested with SacI/XbaI.

B. Synthesis of Plasmids Encoding CPM-Click Beetle Luc/RIIβB Fusion Proteins with Peptide Linkers of (X=4, Y=4; pBFB54) and (X=10, Y=4; pBFB55) Amino Acid Residues.

To synthesize the construct with (X=4,Y=4) linker lengths, primers 5'-AAA AAA GTC GAC CGG AAT GTA TGA AAG CTT TAT TGA GTC ACT GCC-3' (SEQ ID NO:90; BFB51) and 5'-AAA AAA GAG CTC CCA ACA ATA TCC ATG TTC GTT CCA AAC-3' (SEQ ID NO:91; BFB20) were used to amplify RIIβB DNA from ATCC 10625233 (Genbank ID BC075800). The resultant product was digested with SalI/SacI restriction enzymes and ligated into the parent CPM-Click Beetle Luc (pBFB53).

To synthesize the construct with (X=10,Y=4) linker lengths, primers 5'-AAA AAA GAG CTC CCA ACA ATA TCC ATG TTC GTT CCA AAC-3' (SEQ ID NO:92; BFB20) and 5'-AAA AAA TCC GGA ATG TAT GAA AGC TTT ATT GAG TCA CTG CC-3' (SEQ ID NO:93; BFB21) were used to amplify RIIβB DNA from ATCC 10625233 (Genbank ID BC075800). The resultant product was digested with BspEI/SacI restriction enzymes and ligated into the parent CPM-Click Beetle Luc (pBFB53) expression plasmid digested with BspEI/SacI.

B. Functional Characterization of CPM-Click Beetle Luc/RIIβB Fusion Proteins with Peptide Linkers of (X=4, Y=4; pBFB54) and (X=10, Y=4; pBFB55) Amino Acid Residues.

Figure 16A:
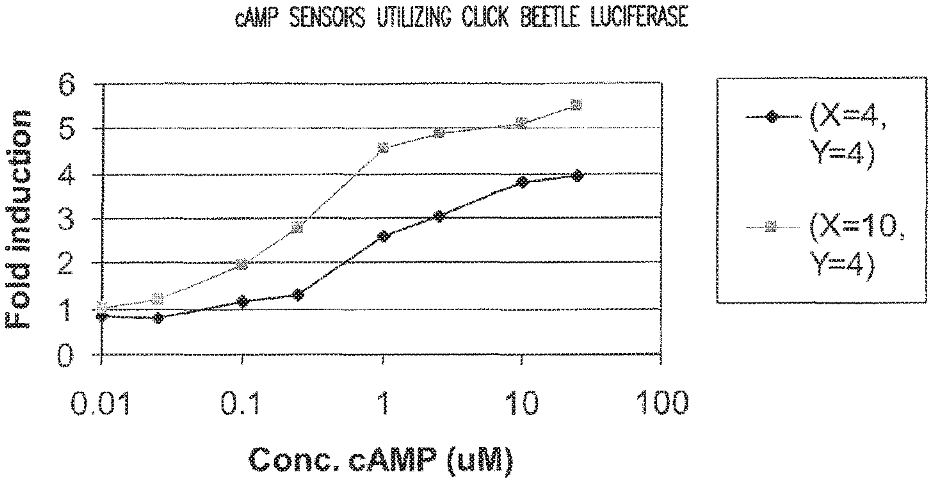
FIG. 16A and FIG. 16B. Comparison of dose response experiment using the CPM-click beetle Luc/RIIβB cAMP sensors with X/Y linker lengths of (X=4, Y=4) and (X=10, Y=4) amino acid residues and the corresponding CPM-FF luciferases.
Figure 16B:
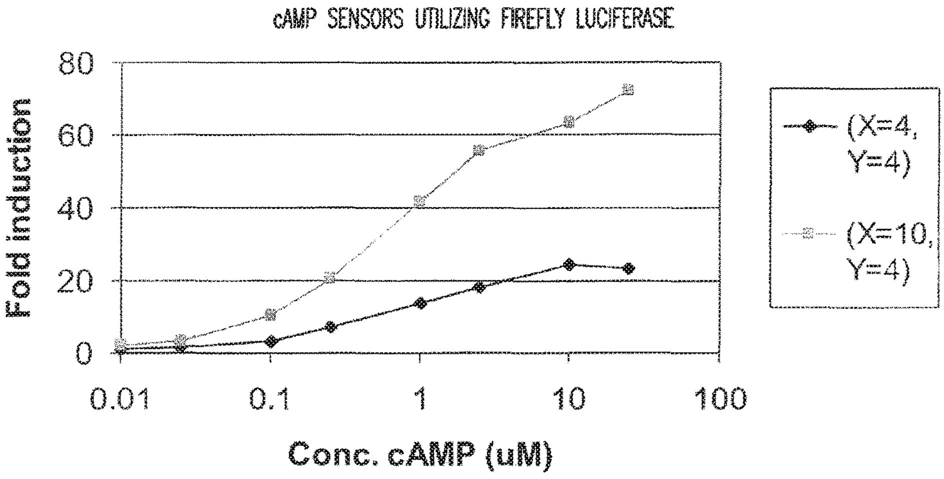

The cAMP dose response of CPM-click beetle Luc/RIIβB fusion proteins with X/Y linker lengths of (X=4,Y=4; pBFB54) and (X=10,Y=4; pBFB55) amino acid residues was measured following expression using the TNT® T7 Coupled Reticulocyte Lysate System (Promega Corp.). Briefly, the following components were assembled according to the manufacturers recommended protocol:

- 2400 ng plasmid DNA
- 60 μL Rabbit Retic Extract
- 4.8 μL TNT reaction buffer
- 2.4 μL T7 polymerase
- 2.4 μL amino acid mixture
- 2.4 μL rRNasin
- $dH_2O$ to 120 μL total volume Following incubation at 30° C. for 1.5 hours, the respective fusion proteins were incubated with varying concentrations of cAMP by combining 9 μL of TNT® reaction with 1 μL of cAMP stock solution (final concentrations of 0, 0.01, 0.025, 0.1, 0.25, 1, 2.5, 10, and 25 μM cAMP). Following equilibration at room temperature for approximately 20 minutes, 1 μL of sample was added to 100 μL of Luciferase Assay Reagent (LAR; Promega Corp.) solution containing the respective concentration of cAMP (90 μL LAR+10 μL cAMP stock solution). Luminescence was measured using a Veritas Microplate Luminometer (Turner Biosystems; program Bright-Glo). CPM-click beetle Luc/RIIβB fusion proteins with X/Y linker lengths of (X=4,Y=4; pBFB54) and (X=10,Y=4; pBFB55) amino acid residues showed fold inductions in luciferase activity at 25 μM cAMP of 4.0 and 5.5, respectively. However, the fold induction for the click beetle luciferase based cAMP sensors was less than the fold induction of the firefly luciferase based sensors at all concentrations tested (FIG. 16A and FIG. 16B).

Example VIII

A cAMP Biosensor Utilizing Circularly Permuted Firefly Luciferase and the B Domain from the PKA Regulatory Subunit Type Iα

DNA encoding the B domain from the human PKA regulatory subunit type Iα (RIαB) was ligated into an expression vector encoding CPM-FF Luc/RIαB fusions [Luc2.0 (234-544)-linker X-human RIα (residues 245-381)-linker Y-Luc2.0 (4-233)].

A. Synthesis of CPM-FF Luc/RIαB Fusion Proteins with Peptide Linkers of (X=4, Y=4; pBFB56) and (X=20, Y=20; pBFB58) Amino Acid Residues To synthesize the construct with (X=4,Y=4) linker lengths, primers 5'-ATATAACTCGAGCGGAATGTATGAGGAATTCCTTAGTAAAGTCTCTATTT TAG-3' (SEQ ID NO:94; BFB98) and 5'-AAAAAAGAGCTCCCGACAGACAGTGACACAAAACTGTTGTAC-3' (SEQ ID NO:95; BFB99) were used to amplify RIαB DNA (Genbank Acc# BC036285). The resultant product was digested with XhoI/SacI restriction enzymes and ligated into the parent CPM-FF Luc (pBFB8) expression plasmid digested with XhoI/SacI.

To synthesize the construct with (X=20,Y=20) linker lengths, primers 5'-ATTAAACCCGGGATGTATGAGGAATTCCTTAGTAAAGTCTCTATTTTAG-3' (SEQ ID NO:96; BFB102) and 5'-AAAAAATCCGGACCCGACAGACAGTGACACAAAACTGTTGTAC-3' (SEQ ID NO:97; BFB103) were used to amplify RIαB DNA from (Genbank Acc# BC036285. The resultant product was digested with SmaI BspEI restriction enzymes and ligated into the parent CPM-FF Luc (pBFB8) expression plasmid digested with NruI/AgeI.

Figure 17A:
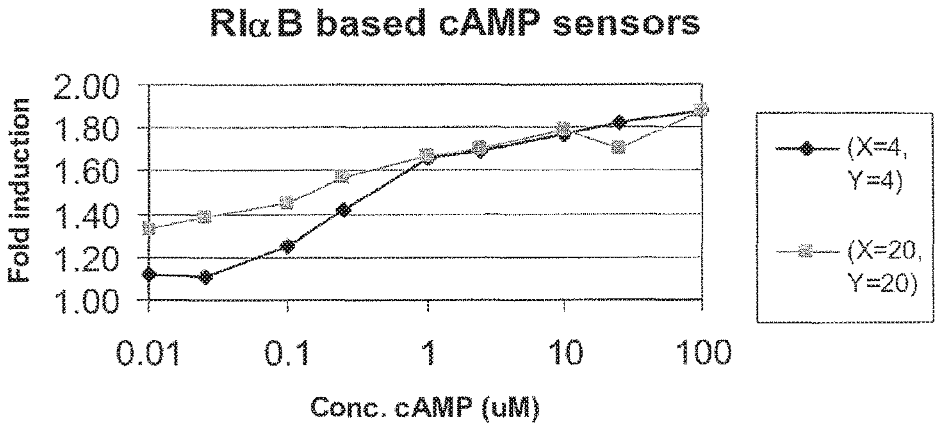
FIG. 17A and FIG. 17B. Comparison of dose response experiment using the CPM-FF Luc/RIαB cAMP sensors with X/Y linker lengths of (X=4, Y=4) and (X=20, Y=20) amino acid residues and the corresponding CPM-FF Luc/RIIβB.
Figure 17B:
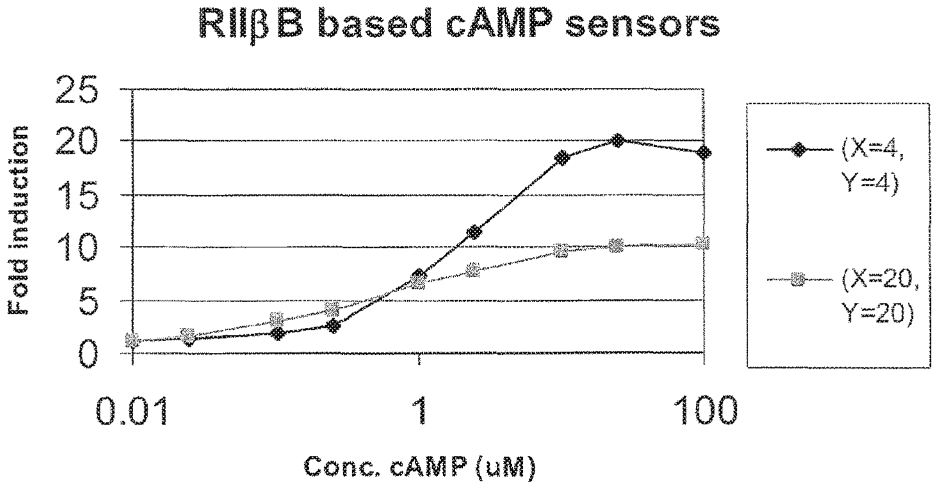

B. Functional Characterization of CPM-FF Luc/RIαB Fusion Proteins with Peptide Linkers of (X=4, Y=4; pBFB56) and (X=20, Y=20; pBFB58) Amino Acid Residues The cAMP dose response of CPM-FF Luc/RIαB fusion proteins with X/Y linker lengths of (X=4, Y=4; pBFB56) and (X=20, Y=20; pBFB58) amino acid residues was measured following expression using the TNT® T7 Coupled Reticulocyte Lysate System (Promega Corp.). Briefly, the following components were assembled according to the manufacturer's recommended protocol:

- 2400 ng plasmid DNA
- 60 μL Rabbit Retic Extract
- 4.8 μL TNT reaction buffer
- 2.4 μL T7 polymerase
- 2.4 μL amino acid mixture
- 2.4 μL rRNasin
- $dH_2O$ to 120 μL total volume Following incubation at 30° C. for 1.5 hours, the respective fusion proteins were incubated with varying concentrations of cAMP by combining 9 μL of TNT® reaction with 1 μL of cAMP stock solution (final concentrations of 0, 0.01, 0.025, 0.1, 0.25, 1, 2.5, 10, 25, and 100 μM cAMP). Following equilibration at room temperature for ≥10 minutes, 1 μL of sample was added to 100 μL of Luciferase Assay Reagent (LAR; Promega Corp.) solution containing the respective concentration of cAMP (90 μL LAR+10 μL cAMP stock solution). Luminescence was measured using a Veritas Microplate Luminometer (Turner Biosystems; program Bright-Glo). CPM-FF Luc/RIαB fusion proteins with X/Y linker lengths of (X=4, Y=4; pBFB56) and (X=20, Y=20; pBFB58) amino acid residues showed fold inductions in luciferase activity at 100 μM cAMP of 1.8. However, the fold induction for the RIαB based cAMP sensors was less than the fold induction of the RIIβB based sensors at concentrations ≥0.025 μM (FIG. 17A and FIG. 17B).

Example IX

A cAMP Biosensor Utilizing a Circularly Permuted Thermal Stable Luciferase and the B Domain from the PKA Regulatory Subunit Type IIβ

A. Synthesis of a CPM-Thermal Stable Luc Expression Plasmid for Subsequent Insertion of RIIβB (pBFB45)

To synthesize a thermal stable luciferase (UltraGlo luciferase, Promega Corp.) primers 5'-AATTAAGCTAGC-GATCGCCATGACGTCAGCAATTTTAACGG-TAATACC-3' (SEQ ID NO:98; BFB88) and 5'-TTTTTTCTCGAGCCATTGGTGT-GTTTTTCTAACATTTGTCTTAAC-3' (SEQ ID NO:99; BFB89) were used to amplify the UltraGlo luciferase equivalent of the firefly luciferase fragment encoding residues 234-544 (UltraGlo luciferase residues 233-543). The resultant product was digested with NheI/XhoI restriction enzymes and ligated into the parent CPM-FF Luc (pBFB8) expression plasmid digested with NheI/XhoI to give plasmid intermediate 1. Subsequently, primers 5'-AATTTT-GAGCTCCGGTGATAAGAATATTTTATATGGGC-CCGAAC-3' (SEQ ID NO:100; BFB90) and 5'-AAAAAATCTAGAGTTTAAACGGGATTAATTGCGT-TACCAAAAGTAG-3 (SEQ ID NO:101; BFB91) were used to amplify the click beetle equivalent of the firefly luciferase fragment encoding residues 4-233 (UltraGlo luciferase residues 3-232). The resultant product was digested with SacI/XbaI restriction enzymes and ligated into plasmid intermediate 1 described above digested with SacI/XbaI.

B. Synthesis of Plasmids Encoding CPM-Thermal Stable Luc/RIIβB Fusion Proteins with Peptide Linkers of (X=4, Y=4; pBFB51) and (X=20, Y=20; pBFB52) Amino Acid Residues To synthesize the plasmid encoding the CPM-Thermal Stable Luc/RIIβB fusion protein with (X=4,Y=4) linker lengths, primers 5'-AAA AAA GTC GAC CGG AAT GTA TGA AAG CTT TAT TGA GTC ACT GCC-3' (SEQ ID NO:102; BFB51) and 5'-AAA AAA GAG CTC CCA ACA ATA TCC ATG TTC GTT CCA AAC-3' (SEQ ID NO:103; BFB20) were used to amplify RIIβB DNA from ATCC 10625233 (Genbank ID BC075800). The resultant product was digested with SalI/SacI restriction enzymes and ligated into the parent CPM-Thermal Stable Luc expression plasmid (pBFB45) described above digested with XhoI/SacI.

To synthesize the plasmid encoding the CPM-Thermal Stable Luc/RIIβB fusion protein with (X=20,Y=20) linker lengths, primers 5'-AAA AAA CCC GGG ATG TAT GAA AGC TTT ATT GAG TCA CTG CC-3' (SEQ ID NO:104; BFB23) and 5'-AAA AAA TCC GGA CCC AAC AAT ATC CAT GTT CGT TCC AAA C-3' (SEQ ID NO:105; BFB24) were used to amplify RIIβB DNA from ATCC 10625233 (Genbank ID BC075800). The resultant product was digested with BspEI/SmaI restriction enzymes and ligated into the parent CPM-Thermal Stable Luc expression plasmid described above digested with AgeI/NruI.

Figure 18A:
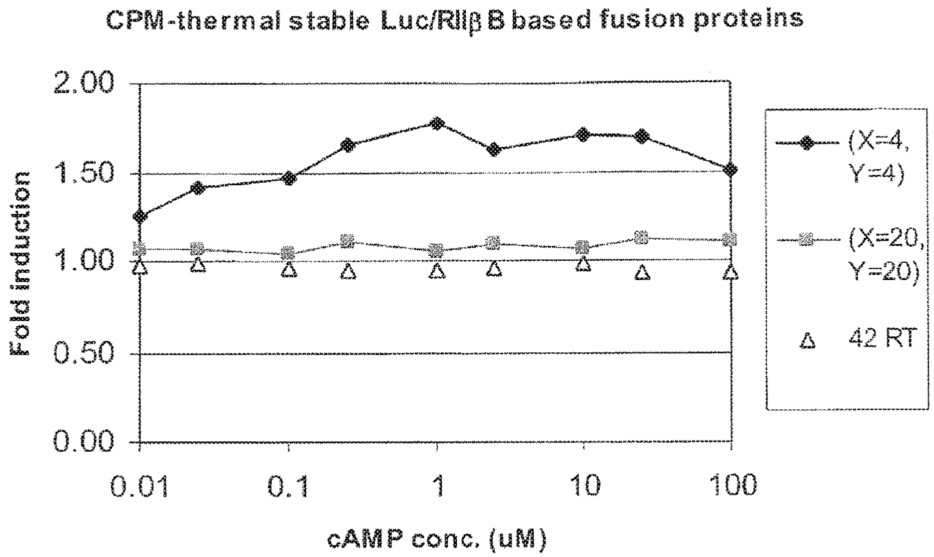
FIG. 18A and FIG. 18B. Comparison of dose response experiment using the CPM-thermal stable Luc/RIIβB cAMP sensors with X/Y linker lengths of (X=4, Y=4) and (X=20, Y=20) amino acid residues and the corresponding CPM-FF luciferases.
Figure 18B:
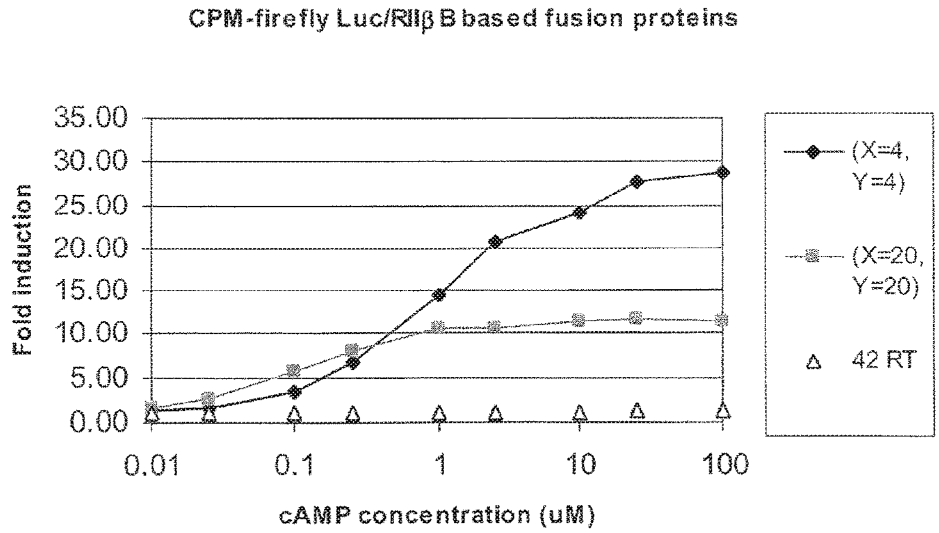

C. Functional Characterization of CPM-Thermal Stable Luc/RIIβB Fusion Proteins with Peptide Linkers of (X=4, Y=4; pBFB51) and (X=20, Y=20; pBFB52) Amino Acid Residues The cAMP dose response of CPM-Thermal Stable Luc/RIIβB fusion proteins with X/Y linker lengths of (X=4, Y=4; pBFB51) and (X=20, Y=20; pBFB52) amino acid residues was measured following expression using the TNT® T7 Coupled Reticulocyte Lysate System (Promega Corp.). Briefly, the following components were assembled according to the manufacturer's recommended protocol:

- 2400 ng plasmid DNA
- 60 μL Rabbit Retic Extract
- 4.8 μL TNT reaction buffer
- 2.4 μL T7 polymerase
- 2.4 μL amino acid mixture
- 2.4 μL rRNasin
- $dH_2O$ to 120 μL total volume Following incubation at 30° C. for 1.5 hours, the respective fusion proteins were incubated with varying concentrations of cAMP by combining 9 μL of TNT® reaction with 1 μL of cAMP stock solution (final concentrations of 0, 0.01, 0.025, 0.1, 0.25, 1, 2.5, 10, 25, and 100 μM cAMP). Following equilibration at room temperature for ≥19 minutes, 1 μL of sample was added to 100 μL of Luciferase Assay Reagent (LAR; Promega Corp.) solution containing the respective concentration of cAMP (90 μL LAR+10 μL cAMP stock solution). Luminescence was measured using a Veritas Microplate Luminometer (Turner Biosystems; program Bright-Glo). The CPM-Thermal Stable Luc/RIIβB fusion protein with X/Y linker lengths of X=4, Y=4 amino acid residues (pBFB51) showed a fold induction in luciferase activity at 100 μM cAMP of 1.5 (FIG. 18A and FIG. 18B). However, the CPM-Thermal Stable Luc/RIIβB fusion protein with X/Y linker lengths of X=20, Y=20 amino acid residues (pBFB52) was unresponsive to cAMP (FIG. 18A and FIG. 18B). In both cases, the fold induction in luciferase activity for CPM-Thermal Stable Luc/RIIβB based cAMP sensors was less than the fold induction of the firefly luciferase based sensors at concentrations ≥0.025 μM (FIG. 18A and FIG. 18B).

Example X

Intracellular Detection of Changes in cAMP Concentration Using CPM *Renilla* Luciferase/RIIβB Biosensor (Forskolin Titration)

Cell Culture

100 μl HEK-293 cells were plated in a 96 well plate and grown to 70-90% confluency in DMEM/F12 with HEPES buffer (Invitrogen) with 10% FBS at 37° C. with 5% $CO_2$.

Transfections

Cells were transfected with TransIt®-LT1 Reagent (MIRUS) using 0.3 μl TransIt®-LT1 reagent and 0.15 μg DNA (CPM-hRL/RIIβB cAMP biosensor with X/Y peptide linker lengths of (X=4, Y=20) (201325.78.E5)) per well of a 96-well plate. Cells were allowed to grow overnight and were assayed the next day.

Modulation of Biosensor

Figure 19:
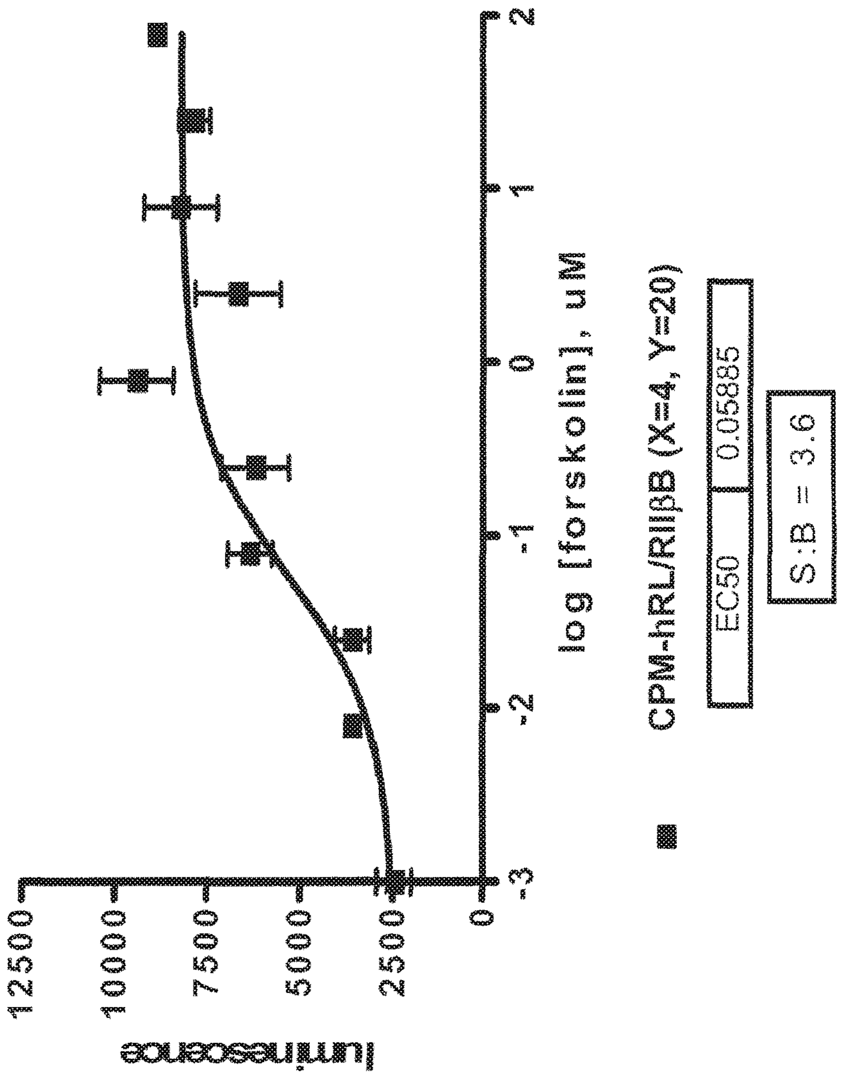
FIG. 19. Monitoring changes in cAMP concentration in HEK293 cells using a CPM-hRL/RIIβB cAMP biosensor with X/Y linker lengths of (X=4, Y=20).

Approximately 1 day after transfection, cells were removed from incubator and equilibrated to room temperature. A 10 μl aliquot of 600 μM EnduRen Live Cell Substrate (Promega) was added to a total of 100 μl of cell culture to give a final concentration of approximately 60 μM coelentrazine. Cells were then incubated at room temperature for at least 15 minutes. After 15 minutes at room temperature, baseline measurements of luminescence were measured using a 96-well Veritas Luminometer (Turner) at 0.5 seconds per well. Cells were then induced with 0.025 μM-250 μM forskolin (Sigma) or not induced (0.1% DMSO (Sigma)) and luminescence was measured continuously for about 30 minutes (FIG. 19). Samples were measured in sets of 5 replicates per concentration of forskolin. $EC_{50}$s were calculated using GraphPad Prism for Windows, Version 4.

Results

Light output increased from cells transfected with DNA encoding the CPM-hRL/RIIβB cAMP biosensor with X/Y peptide linker lengths of (X=4, Y=20) (201325.78.E5) following stimulation with forskolin (FIG. 19). Maximal levels of forskolin induced light output 3.6-fold above that of untreated cells. In addition, the $EC_{50}$ of the forskolin response was 0.059 μM (FIG. 19).

Example XI

A cGMP Biosensor Utilizing Circularly Permuted Firefly Luciferase and the B Domain from the cGMP Activated Protein Kinase (GKI-B) or Human Phosphodiesterase 2A (PDE2A)

cGMP is an important cellular second messenger with a variety of physiological functions, particularly in the cardiovascular and nervous systems. A series of cGMP sensors were prepared by fusing a circularly permuted firefly luciferase to a cGMP binding domain.

A. Synthesis of Plasmids Encoding CPM-FF Luc/GKI-B Fusion Proteins with Peptide Linkers of (X=4, Y=4) and (X=10, Y=10) Amino Acid Residues.

To synthesize the construct with (X=4,Y=4) linker lengths, primers 5'-AAAAAACTCGAGCGGATTAAAAAGCGTTCCAACATTCCAG-3' (SEQ ID NO:106; BFB151) and 5'-AAAAAAGAGCTCCCAGACAGCTTCAGGTTGGCGAAG-3' (SEQ ID NO:107; BFB163) were used to amplify human GKI-B DNA (Origene, cat # TC116252; Genbank Acc # NM_006258), for instance, DNA corresponding to residues 231 to 350 (pBFB164, pBFB165) or 231 to 373 (pBFB171, pBFB172). The resultant product was digested with XhoI/SacI restriction enzymes and ligated into the parent CPM-FF Luc expression plasmid (pBFB8) digested with XhoI/SacI.

To synthesize the construct with (X=10,Y=10) linker lengths, primers 5'-AAAAAATCCGGATTAAAAAGCGTTCCAACATTCCAG-3' (SEQ ID NO:108; BFB153) and 5'-AAAAAAAGGCCTGACAGCTTCAGGTTGGCGAAG-3' (SEQ ID NO:109; BFB164) were used to amplify human GKI-B DNA (Origene, cat # TC116252; Genbank Acc # NM_006258). The resultant product was digested with BspEI/StuI restriction enzymes and ligated into the parent CPM-FF Luc expression plasmid (pBFB8) digested with BspEI/ZraI.

B. Functional Characterization of CPM-FF Luc/GKI-B Fusion Proteins with X/Y Linker Lengths of (X=4,Y=4) and (X=10,Y=10) Amino Acid Residues Luciferase activity in the presence and absence of 100 μM cGMP was measured for the CPM-FF Luc/GKI-B fusion proteins with X/Y linker lengths of (X=4,Y=4) and (X=10, Y=10) amino acid residues following expression using the TNT® T7 Coupled Reticulocyte Lysate System (Promega Corp.). Briefly, the following components were assembled according to the manufacturer's recommended protocol:

400 ng plasmid DNA
10 μL Rabbit Retic Extract
0.8 μL TNT reaction buffer
0.4 μL T7 polymerase
0.4 μL amino acid mixture
0.4 μL rRNasin
$dH_2O$ to 20 μL total volume Following incubation at 30° C. for 1 hour, the respective fusion proteins were incubated in the presence or absence of 100 μM cGMP by combining 9 μL of TNT® reaction with 1 μL of 1 mM cGMP stock or $dH_2O$. Following incubation for ≥10 minutes at room temperature, 1 μL of sample was added to 100 μL of Luciferase Assay Reagent (LAR; Promega Corp.) solution+/−100 μM cGMP (90 μL LAR+10 μL 1 mM cGMP stock or $dH_2O$). Luminescence was measured using a Veritas Microplate Luminometer (Turner Biosystems; program Bright-Glo). The CPM-FF Luc/GKI-B fusion protein with (X=4, Y=4) linker lengths (pBFB171) showed a 2-fold decrease in luciferase activity in the presence of 100 μM cGMP. In addition, the CPM-FF Luc/GKI-B fusion protein with (X=10, Y=10) linker lengths (pBFB172) showed a 1.5-fold decrease in luciferase activity in the presence of 100 μM cGMP.

TABLE 2

| pBFB | Linker combination | RLU with 100 μM cGMP | RLU with No cGMP |
|---|---|---|---|
| pBFB171 | (X = 4, Y = 4) | 247,801 | 497,938 |
| pBFB172 | (X = 10, Y = 10) | 1,148,496 | 1,707,449 |

C. Synthesis of Plasmids Encoding CPM-FF Luc/Human Phosphodiesterase 2A (PDE2A; Genbank NM_002599; Amino Acid Residues 416-549)

DNA sequences encoding circularly permuted firefly luciferase constructs with engineered N- and C-termini at residues 234 and 233, respectively, were fused to a sequence encoding human PDE2A, which has a different protein fold relative to the RIIβB domain [Met-(Luc2.0 234-544)-(Linker X)-(human PDE2A 416-549)-(Linker Y)-(Luc2.0

Figure 21:
FIG. 21. Schematic of CPM-FF Luc GAF constructs. GSTG corresponds to SEQ ID NO:122; GSSG corresponds to SEQ ID NO:197; GSSGGSGGSG corresponds to SEQ ID NO:198; GSGGSGGSSG corresponds to SEQ ID NO:199; GSSGGSGGSGGGSGGSGGSG corresponds to SEQ ID NO:200; GSGGSGGSGGTSGGSGGSSG corresponds to SEQ ID NO:201; and the 42 RT control peptide corresponds to SEQ ID NO:196.
Figure 22:
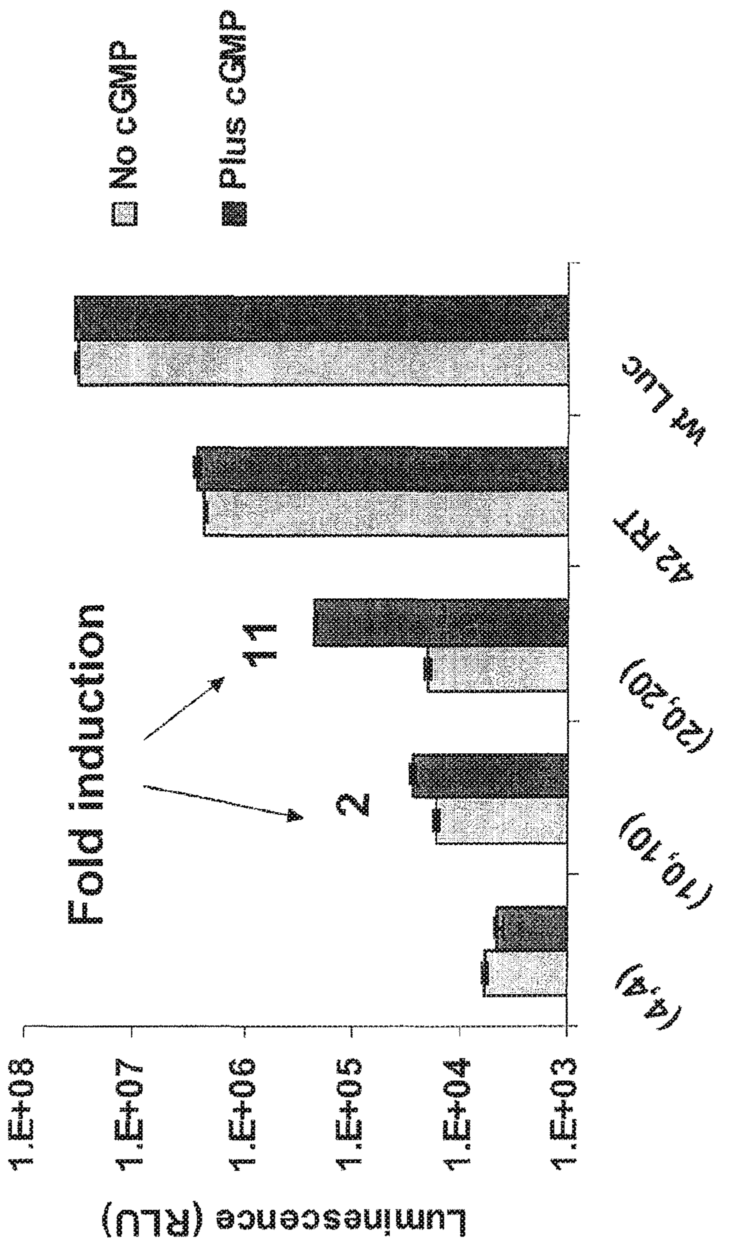
FIG. 22. RLU for various CPM-FF Luc GAF constructs in the presence and absence of cGMP.
Figure 23:
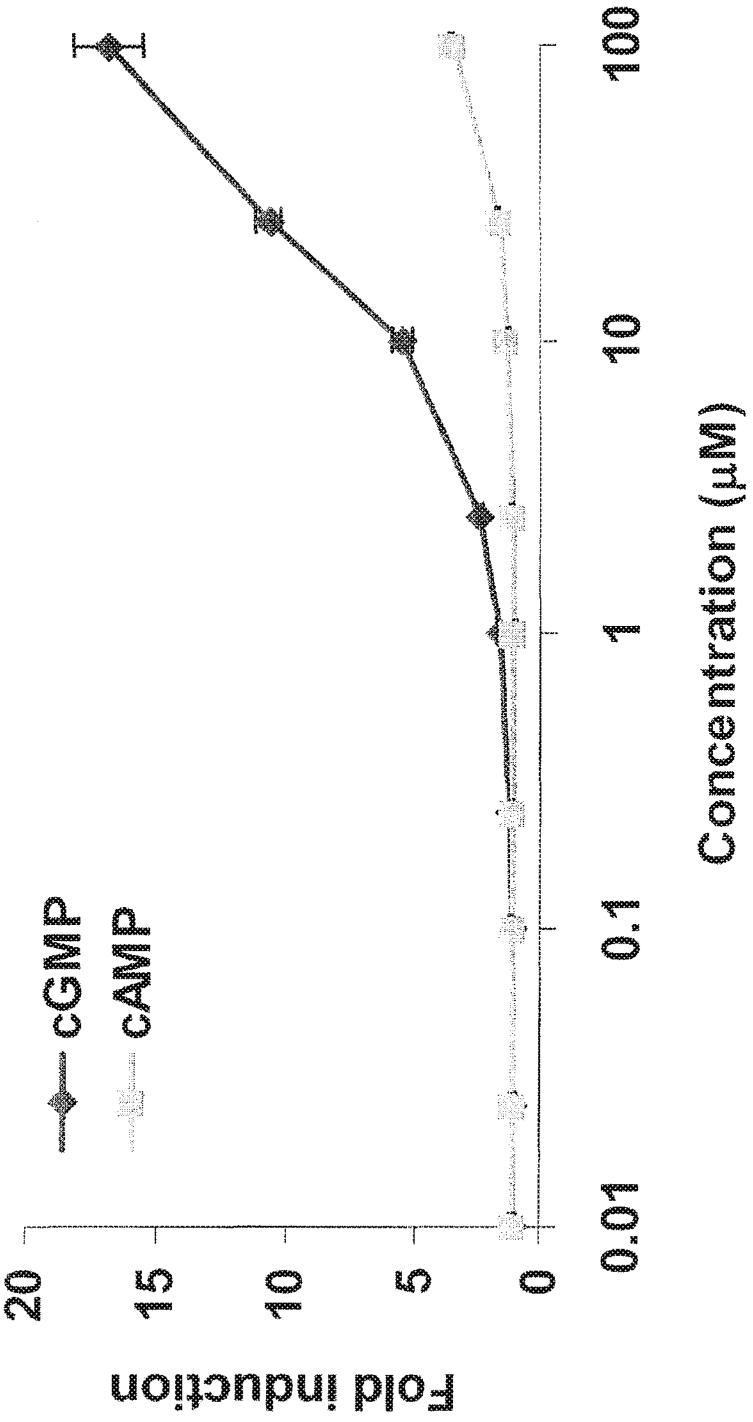
FIG. 23. Fold induction with increasing concentrations of cGMP or cAMP for a CPM-FF Luc GAF construct.

4-233)-Val]. The cGMP binding domain from human PDE2A belongs to a large family of small molecule binding units called GAF domains. Constructs were made with X/Y linker lengths of (pBFB167; X=4, Y=4) (pBFB168; X=10, Y=10), and (pBFB169; X=20, Y=20) amino acid residues (FIG. 21). PDE2A based biosensors were identified with 2 and 11 fold induction in luminescence activity in the presence of 100 μM cGMP for constructs with (pBFB168; X=10, Y=10) and (pBFB169; X=20, Y=20) amino acid linkers, respectively, following expression in vitro using the T7 Coupled Reticulocyte Lysate System (FIG. 22). Moreover, activation of these biosensors by cGMP was found to be dose dependent and selective over cAMP in separate experiments following expression using the T7 Coupled Reticulocyte Lysate System (pBFB169; FIG. 23).

Thus, these cGMP sensors are useful for the detection of changes in cGMP concentration in vitro, and these biosensors will likely be useful for detecting changes in cGMP concentration in living cells for use in cell culture experiments or for whole animal imaging studies.

Example XII

Luciferase Calcium Biosensors

Calcium biosensors were prepared by fusing sequences encoding a circularly permuted firefly luciferase having engineered N- and C-termini at residues 234 and 233, respectively, to sequences encoding protein domains that bind calcium. One type of calcium biosensor utilized a mutant of fast chicken skeletal muscle troponin C (TnC) (amino acids 15-163; N109D, D111N, N145D, D147N; Genbank NM_205450) [Met-(Luc2.0 234-544)-(Linker X)-(TnC)-(Linker Y)-(Luc2.0 4-233)-Val], and the second type of calcium biosensor utilized human calmodulin (CaM) (amino acids 5-148; Genbank BC005137) [Met-Luc+ (234-544)-(Linker X)-human Calmodulin (5-148)-(Linker Y)-Luc+ (4-233)].

Figure 24:
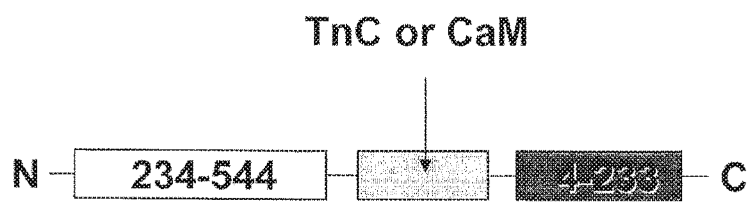
FIG. 24. Schematic of CPM-FF Luc calcium biosensors. GSTG corresponds to SEQ ID NO:122; GSSG corresponds to SEQ ID NO:197; GSSGGSGGSG corresponds to SEQ ID NO:198, GSGGSGGSSG corresponds to SEQ ID NO:199; GSSGGSGGSGGGSGGSGGSG corresponds to SEQ ID NO:200; and GSGGSGGSGGTSGGSGGSSG corresponds to SEQ ID NO:201; the 42 RT control peptide corresponds to SEQ ID NO:196; LEGSGGGG corresponds to SEQ ID NO:202; and GGGGSGPW corresponds to SEQ ID NO:203.
Figure 25:
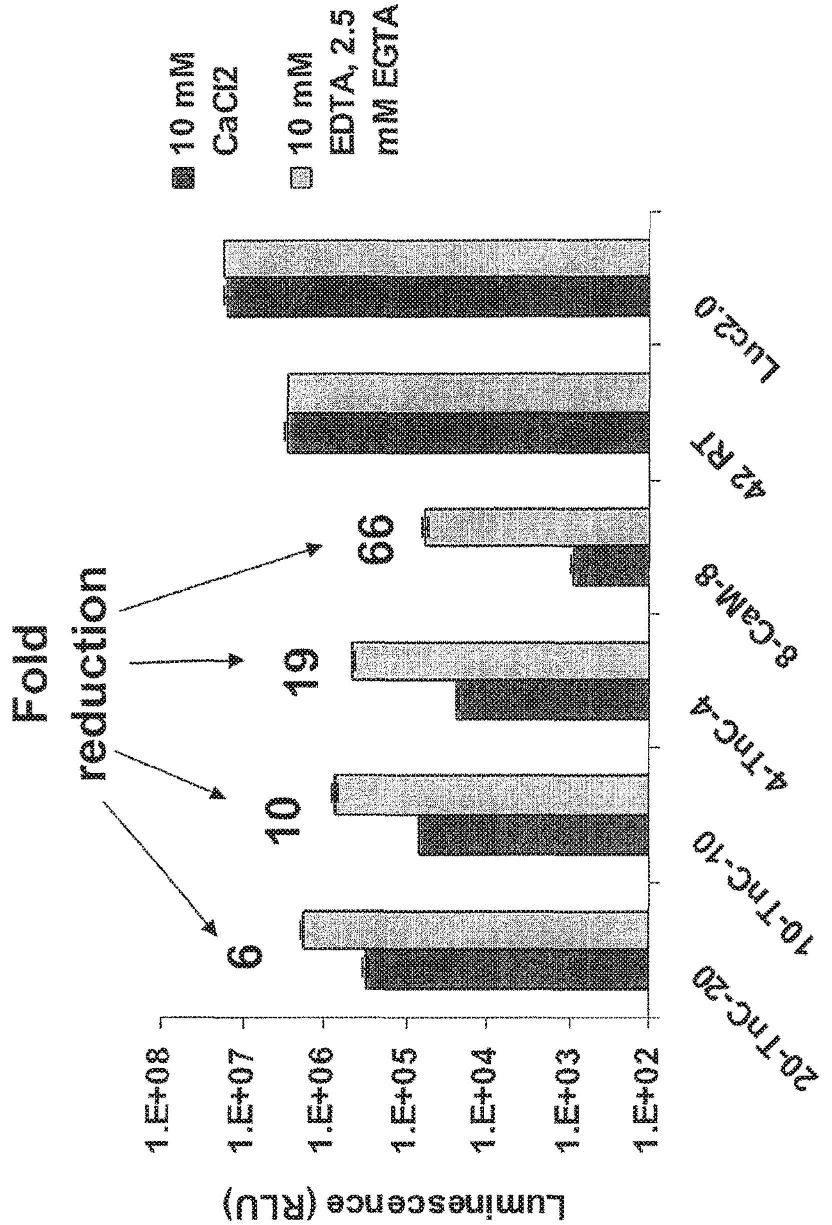
FIG. 25. RLU for various CPM-FF Luc calcium biosensors in the presence of $CaCl_2$ or EDTA and EGTA.

CPM-FF Luc/TnC and CPM-FF Luc/CaM constructs with varying X/Y peptide linker lengths were expressed in vitro using the T7 Coupled Reticulocyte Lysate System (pBFB225, pBFB226, pBFB227, pBFB7; FIG. 24). Reactions were then supplemented with 10 mM $CaCl_2$ or 10 mM EDTA plus 2.5 mM EGTA. A maximal response was seen for a CPM-FF Luc/CaM biosensor with (X=8, Y=8; pBFB7), where X=LEGSGGGG (SEQ ID NO:306) and Y=GGGGSGPW (SEQ ID NO:307), with a greater than 60 fold reduction in luminescence activity in the presence of calcium. Similar responses, although of lower magnitude, were seen for CPM-FF Luc/CaM constructs with different X/Y peptide linker lengths (pBFB225, pBFB226, pBFB227). No response was seen for a control construct having a random 42 amino acid linker or for wild-type firefly luciferase (pBFB8 and pBFB22; FIG. 25).

These biosensors will likely be useful for the detection of changes in calcium concentration both in vitro and inside living cells.

Example XIII cAMP Biosensors Using Multiple Sites of Modification in Firefly Luciferase

Additional sites of modification, such as circular permutation, can be used for the development of a firefly luciferase biosensor, e.g., a cAMP biosensor. Above, a cAMP biosensor was prepared using a circularly permuted mutant of firefly luciferase with the primary structure Met-(Luc2.0 residues 234-544)-GSSGGSGGSGGG-RIIβB-(Luc2.0 residues 4-233)-Val (SEQ ID NO:184; RIIβB is the B cAMP binding domain from human PKA regulatory domain type IIβ amino acids 266-414). Analogous constructs were prepared using firefly luciferase mutants circularly permuted at additional residues. Overall, twenty-three independent constructs were tested that encoded fusion proteins of the following type: Met-(Luc2.0 residues X-544)-GSSGGSGGSGGG-RIIβB-(Luc2.0 residues 4-Y)-Val (GSSGGSGGSGGG corresponds to SEQ ID NO:121; FIG. 26 lists X/Y values for the various constructs). For each of these constructs, excluding the construct with circular permutation at residue 255, a site was chosen in a solvent exposed surface loop bounded by secondary structures such as a beta sheet or alpha helix, for circular permutation using PDB file 1LCI. Solvent exposed surface loops may be more amenable as sites of modification, such as circular permutation, than sites buried in the protein core or sites that are involved in alpha or beta structures. This is supported by the lack of activity seen for the construct with circular permutation at 255, where Tyr255 is a component of an alpha helix that is buried in the protein core. This collection of constructs represents the majority, but not all, surface turns seen in the 1LCI crystal structure.

Figure 27A:
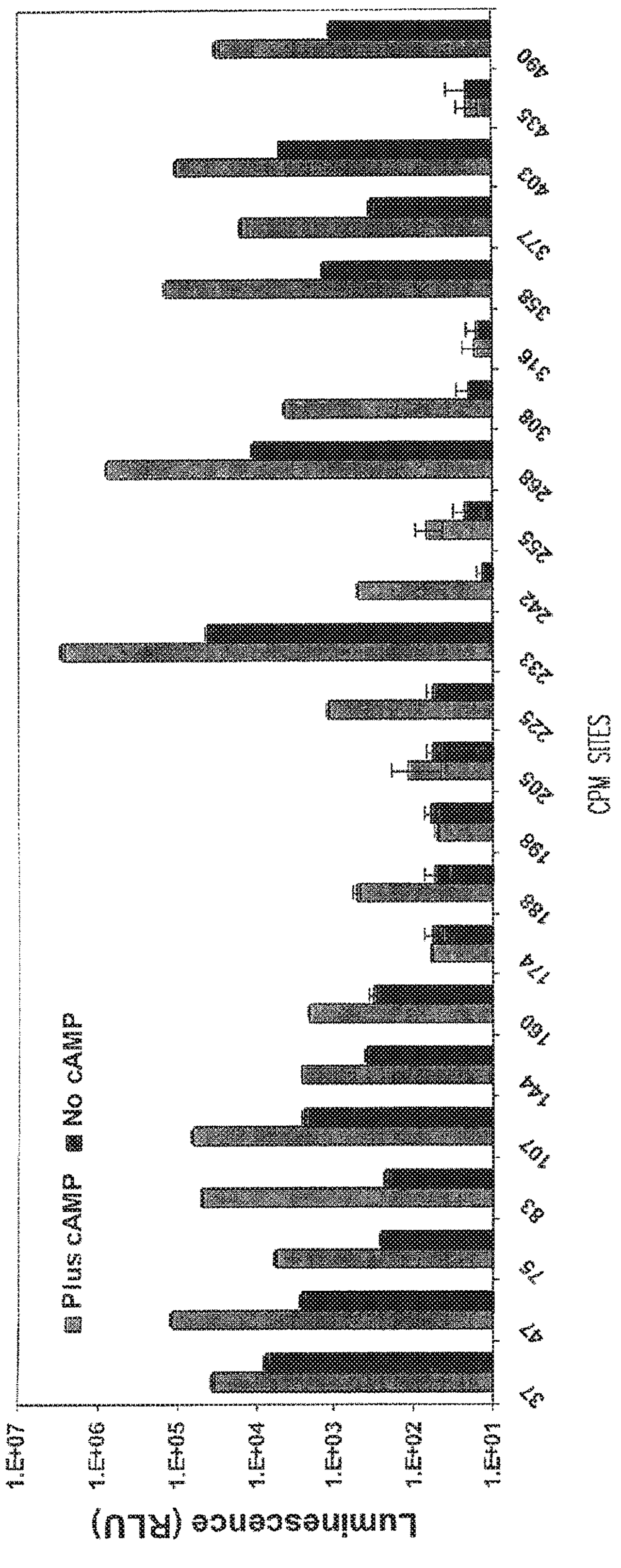
FIG. 27A and FIG. 27B. RLU (FIG. 27A) and fold induction (FIG. 27B) in vitro for CPM-FF Luc cAMP biosensors at various sites.
Figure 27B:
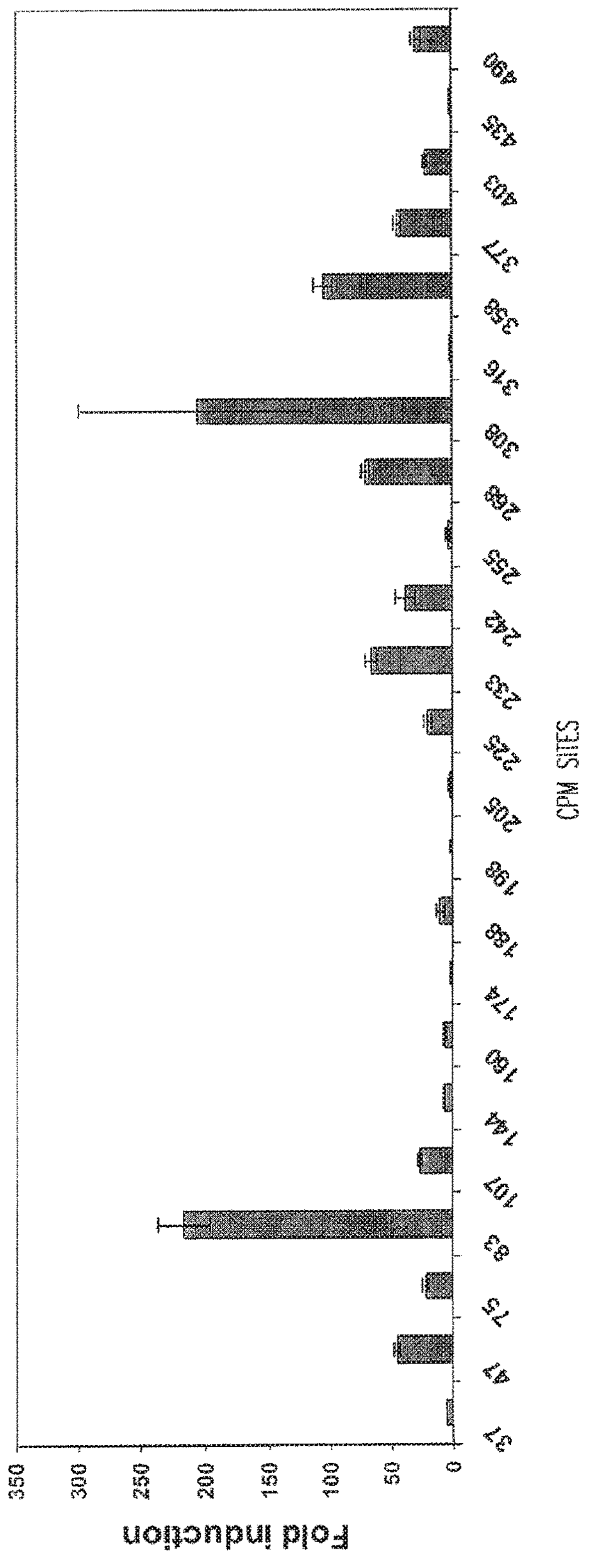
Figure 28:
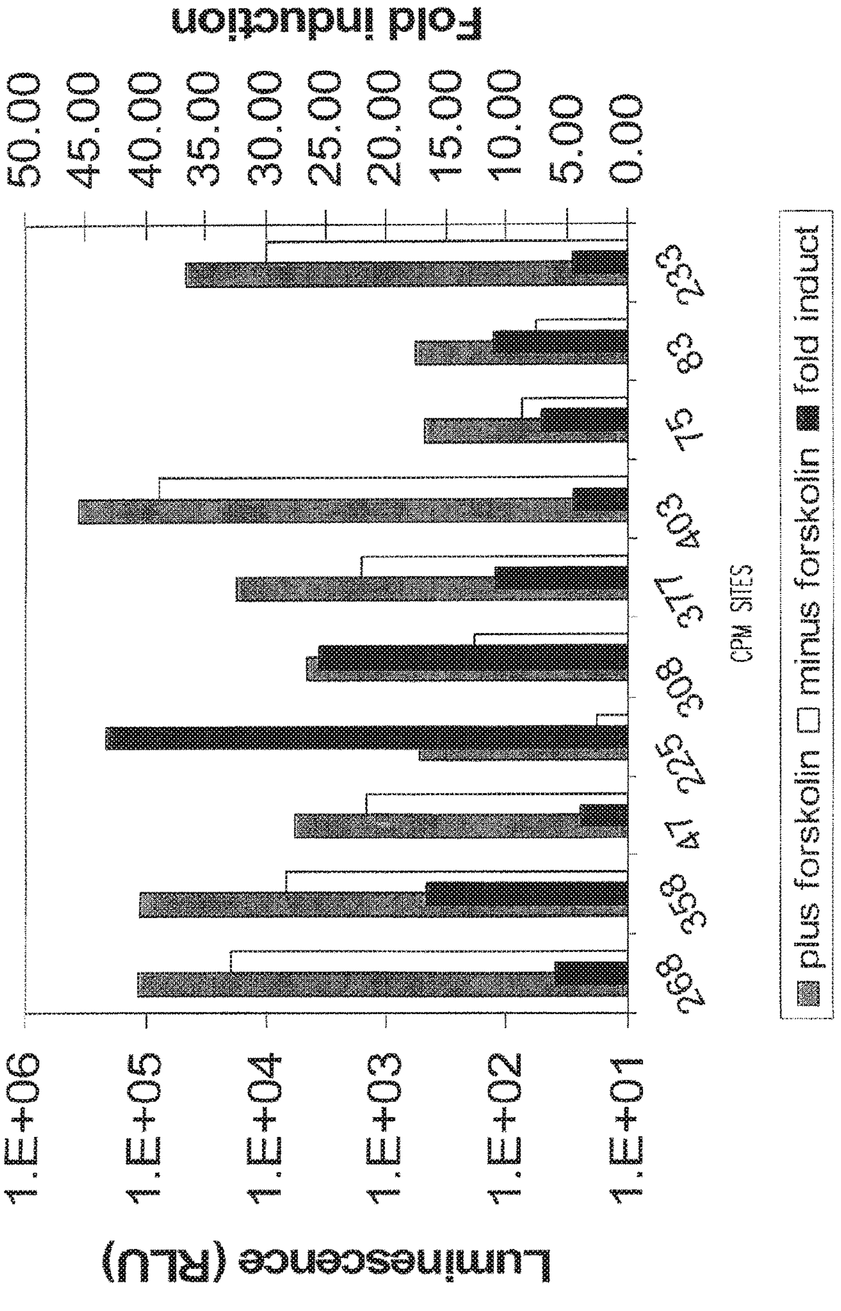
FIG. 28. RLU and fold induction in vivo for CPM-FF Luc cAMP biosensors at various sites.

Following expression using the TNT T7 Coupled Reticulocyte Lysate System, a number of different sites of circular permutation were identified where luminescence activity exceeded the background detection levels of the luminometer and fold inductions in the presence of 100 μM cAMP were greater than two-fold (CPM sites: 37, 47, 75, 83, 107, 144, 160, 188, 225, 233, 242, 268, 308, 358, 377, 403, and 490). In addition, constructs were identified where the fold induction in luminescence activity was greater than CPM 233, with maximal fold activation values greater than 200 fold in this experiment. DNA encoding select constructs was transferred to a mammalian expression vector containing a CMV promoter (pF9A; Promega Corp.). The constructs were: pBFB317 (CPM site 268), pBFB318 (CPM site 358), pBFB319 (CPM site 47), pBFB321 (CPM site 225), pBFB322 (CPM site 233), pBFB325 (CPM site 308), pBFB326 (CPM site 377), pBFB327 (CPM site 403), pBFB328 (CPM site 75), and pBFB329 (CPM site 83) (see FIG. 26 for X, Y values). Following transient transfection with DNA encoding the various Met-(Luc2.0 residues X-544)-GSSGGSGGSGGG-RIIβB-(Luc2.0 residues 4-Y)-Val (GSSGGSGGSGGG corresponds to SEQ ID NO:121) constructs, HEK293 cells were treated with 50 μM forskolin to activate endogenous adenylate cyclase. Following incubation for 16 minutes, luminescence was measured from the live cell populations. As predicted, the various constructs functioned as cAMP biosensors inside living cells. Interestingly, constructs that showed the highest fold induction inside cells were not the same constructs with the highest fold induction in vitro (compare FIG. 27A, FIG. 27B and FIG. 28).

Example XIV

A Nonpermuted *Renilla* Luciferase cAMP Biosensor

As described herein, circularly permuted *Renilla* luciferase constructs can be employed as a biosensor. Nonpermuted *Renilla* luciferase constructs having RIIβB inserted into sites tolerant to modification, e.g., between residues 91/92, 223/224 or 229/230, were prepared. Constructs were generated as described above. They are: hRL (1-91)-4 amino acid peptide linker-RIIBetaB-4 amino acid peptide linker-hRL (92-311) (201360.17.A3), hRL(1-91)-4 amino acid peptide linker-RIIBetaB-20 amino acid peptide linker-hRL992-311) (201360.17.A12), hRL(1-91)-10 amino acid peptide linker-RIIBetaB-4 amino acid linker-hRL(92-311) (201360.17.D7), hRL(1-91)-42 amino acid peptide linker-hRL(92-311) (201325.165.A2), hRL(1-223)-4 amino acid peptide linker-RIIBetaB-4 amino acid linker-hRL(224-311) (201360.24.A1), hRL(1-223)-4 amino acid peptide linker-RIIBetaB-20 amino acid linker-hRL(224-311) (201360.24.A10), hRL(1-223)-10 amino acid peptide linker-RIIBetaB-4 amino acid linker-hRL(224-311) (201360.24.C5), hRL(1-223)-10 amino acid peptide linker-RIIBetaB-20 amino acid linker-hRL(224-311) (201360.24.E11), hRL(1-223)-42 amino acid peptide linker-hRL(224-311) (201325.177.B7), hRL(1-229)-4 amino acid peptide linker-RIIBetaB-4 amino acid linker-hRL(230-311) (201360.19.E9), hRL(1-229)-4 amino acid peptide linker-RIIBetaB-20 amino acid linker-hRL(230-311) (201360.54.A1), hRL(1-229)-42 amino acid peptide linker-hRL(230-311) (201325.165.C5) (FIG. 29).

Protein was expressed from the constructs using the TnT T7 Coupled Wheat Germ Lysate System, 17 μL of TNT reaction was mixed with 17 μL of 300 mM HEPES/200 mM thiourea (pH about 7.5) supplemented with 3.4 μL of 1 mM cAMP stock or $dH_2O$; reactions were allowed to incubate at room temperature for approximately 10 minutes. Ten μL of each sample was added to a 96 well plate well in triplicate and luminescence was measured using 100 μL of *Renilla* luciferase assay reagent on a Glomax luminometer.

Figure 30A:
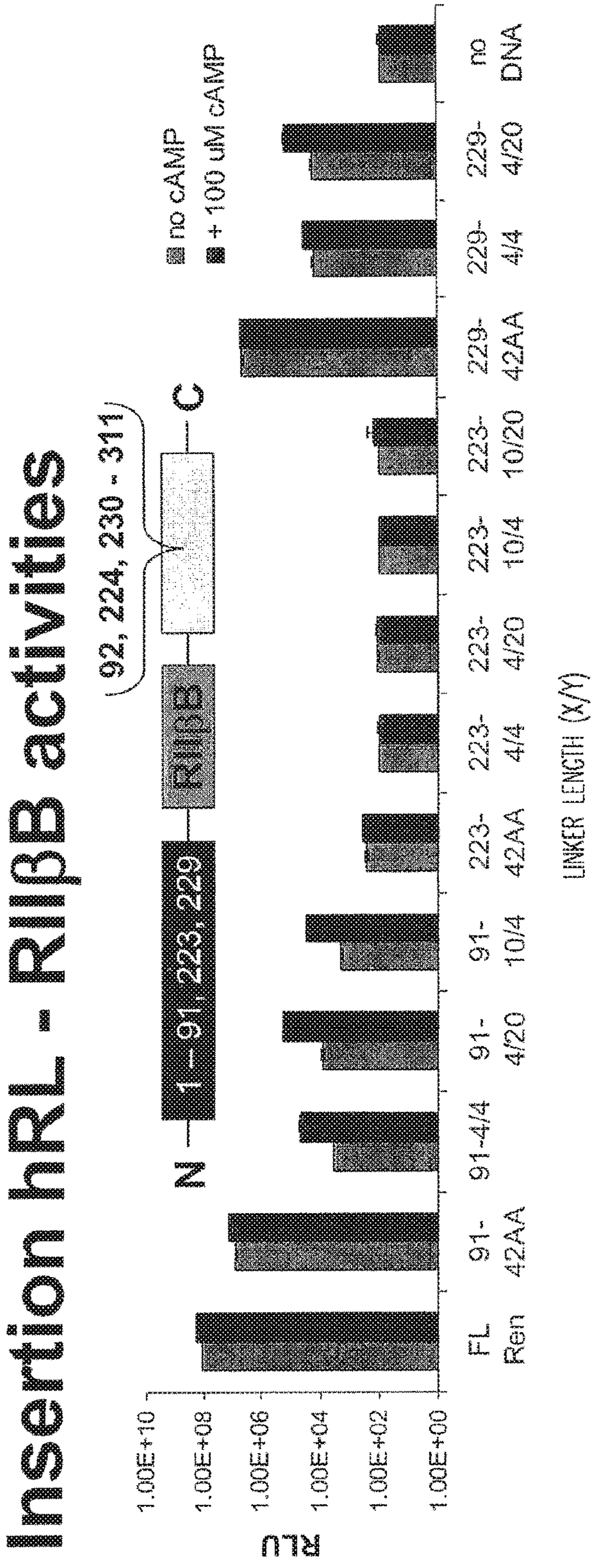
FIG. 30A and FIG. 30B. RLU (FIG. 30A) and fold induction (FIG. 30B) for the constructs shown in FIG. 29.
Figure 30B:
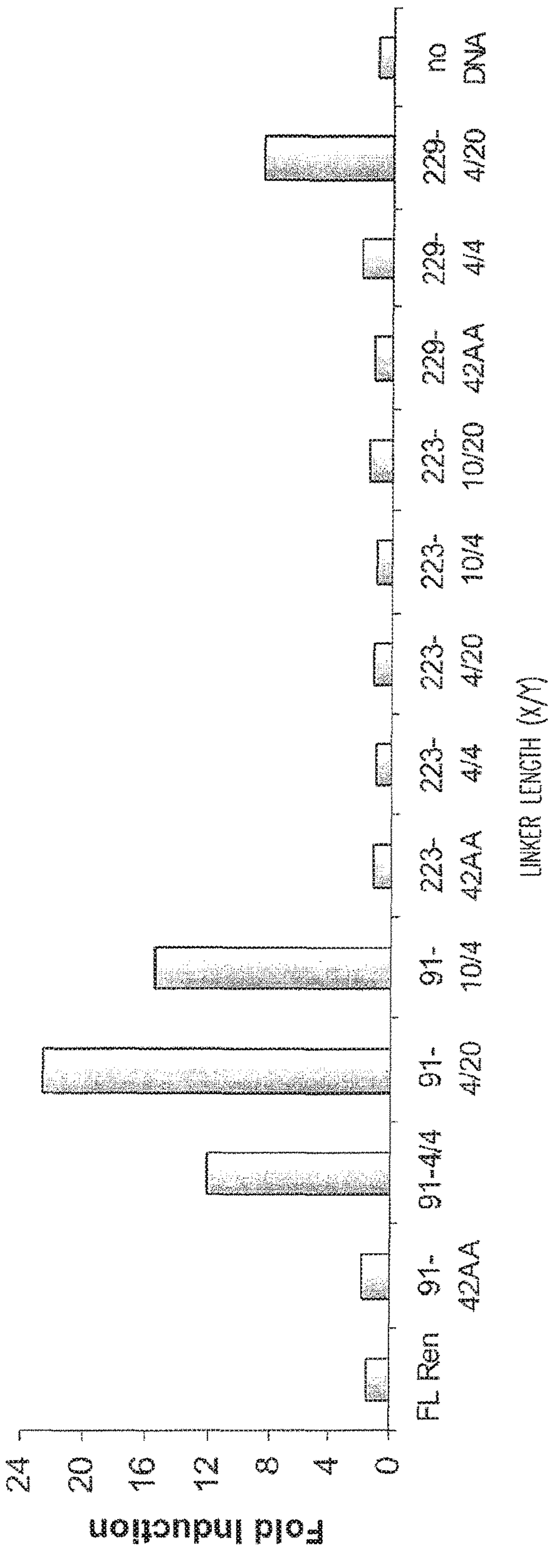

The hRL(1-91)-linker-RIIBetaB-linker-hRL(92-311) proteins were induced by about 12 to 23 fold, the hRL(1-223)-linker RIIBetaB-linker-hRL(224-311) proteins were not induced and the hRL(1-229)-linker-RIIBetaB-(230-311) proteins were induced by about 2 to 9 fold. None of the 42 amino acid linker constructs were induced, nor were the full length *Renilla* luciferase construct (201325.50.A7) or the "no DNA" controls (FIG. 30A and FIG. 30B).

Example XV

Figure 32A:
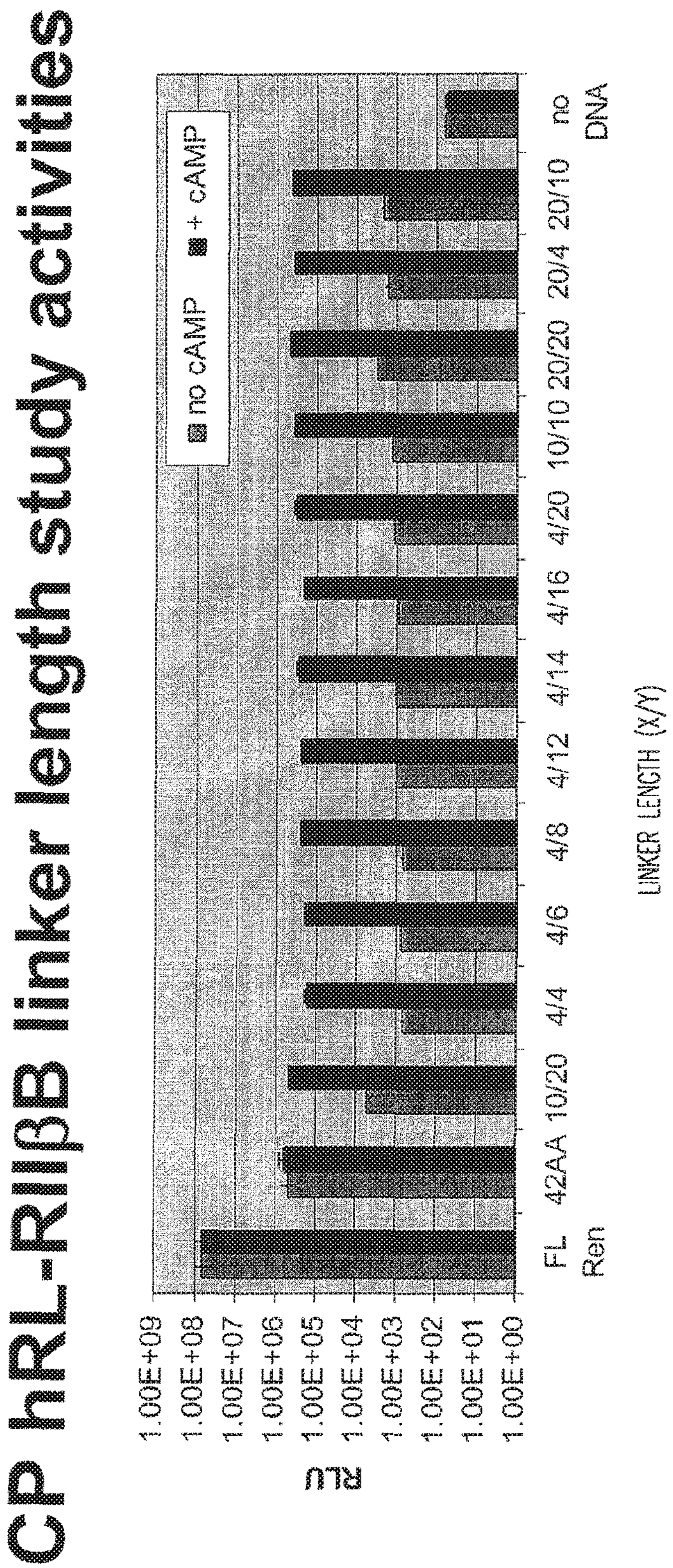
FIG. 32A and FIG. 32B. RLU (FIG. 32A) and fold induction (FIG. 32B) for the constructs in FIG. 31.
Figure 32B:
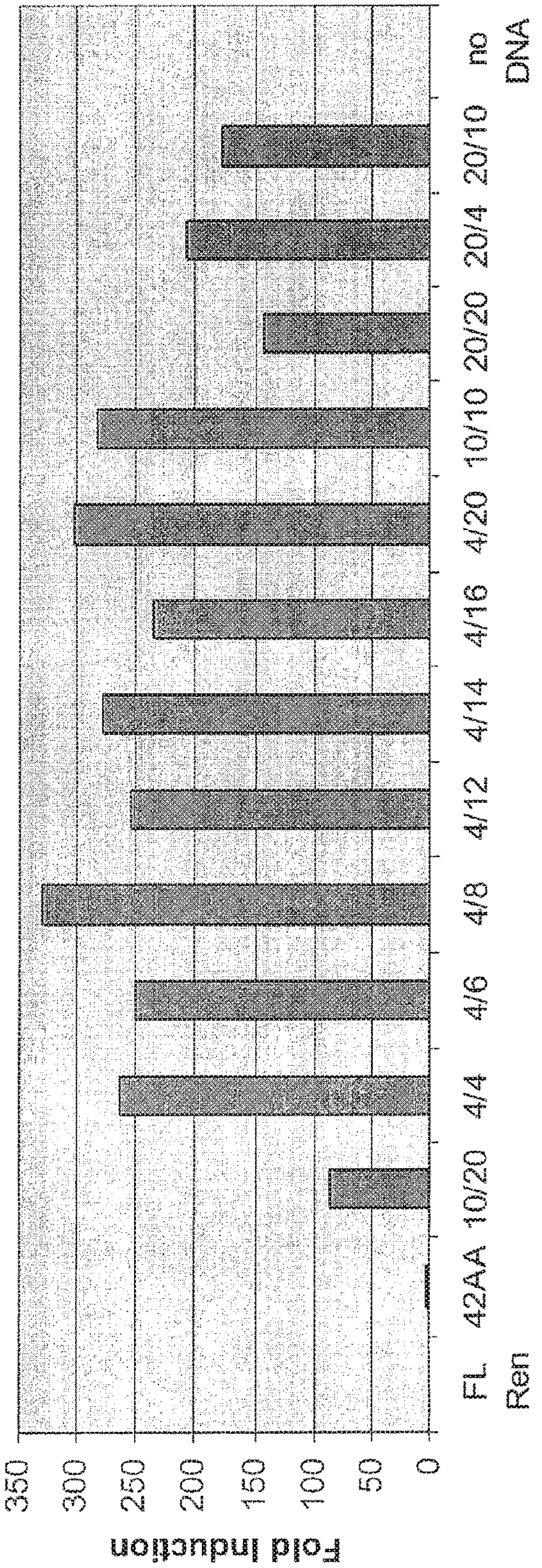

Light Output and Fold Induction Vary as a Function of X/Y Peptide Linker Lengths for CPM-hRL91 Luc/RIIβB Based cAMP Sensors Constructs encoding CPM-hRL91 Luc/RIIβB based cAMP sensors with variable X/Y peptide linker lengths were generated (FIG. 31). Protein was expressed from the constructs using the TnT T7 Coupled Wheat Germ Lysate System, 17 μL of TNT reaction was mixed with 17 μL of 300 mM HEPES/200 mM thiourea (pH about 7.5) supplemented with 3.4 μL of 1 mM cAMP stock or $dH_2O$; reactions were allowed to incubate at room temperature for approximately 10 minutes. Ten μL of each sample was added to a 96 well plate well in triplicate and luminescence was measured using 100 μL of *Renilla* luciferase assay reagent on a Glomax luminometer. As shown in FIG. 32A and FIG. 32B, light output and fold induction varied with linker length. Fold induction ranged from about 87 to 331. The 42 amino acid linker construct, the full length *Renilla* luciferase construct and the "no DNA" control were not induced (FIG. 32A and FIG. 32B).

Example XVI

Figure 34A:
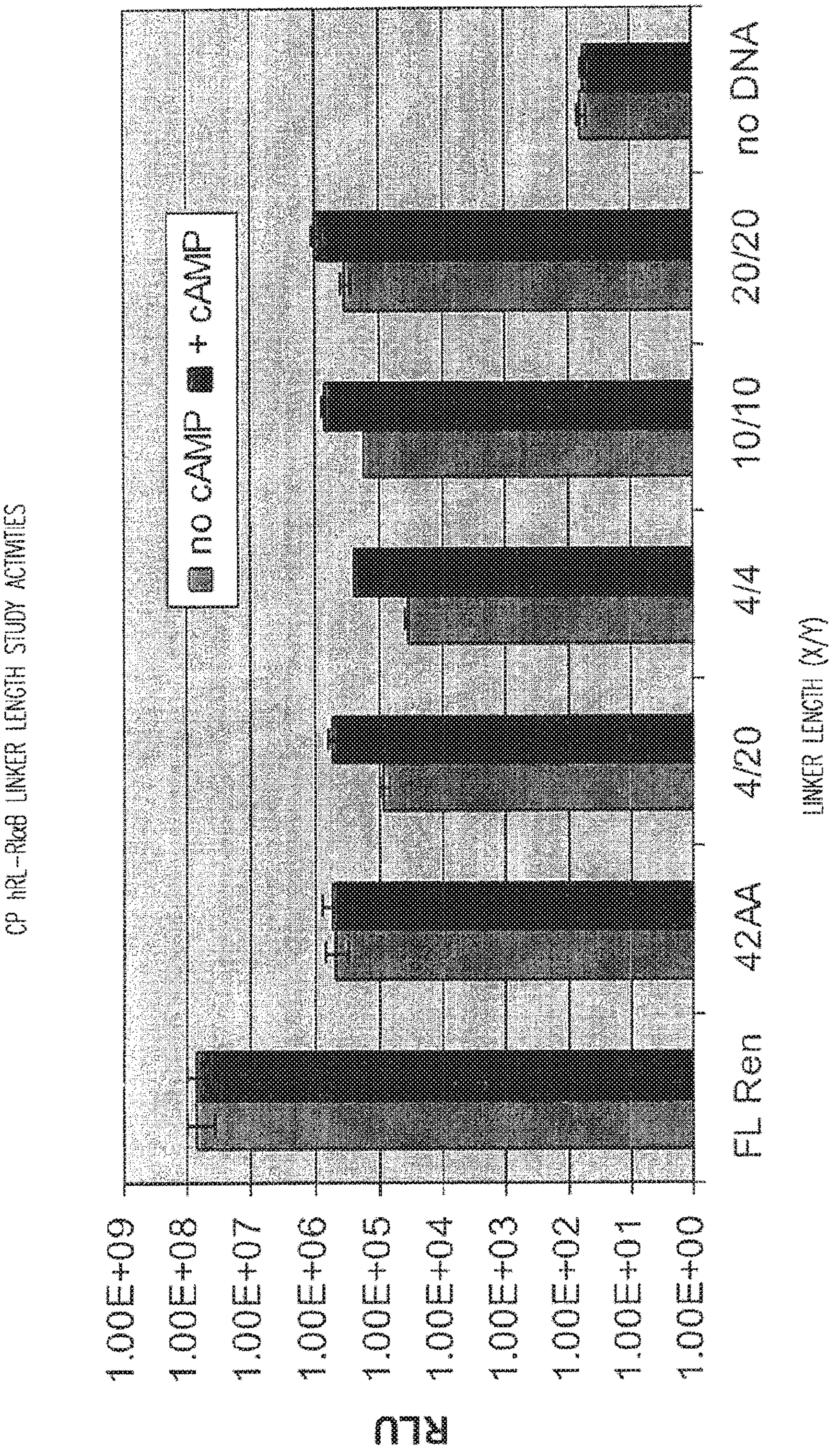
FIG. 34A and FIG. 34B. RLU (FIG. 34A) and fold induction (FIG. 34B) for the constructs in FIG. 33.
Figure 34B:
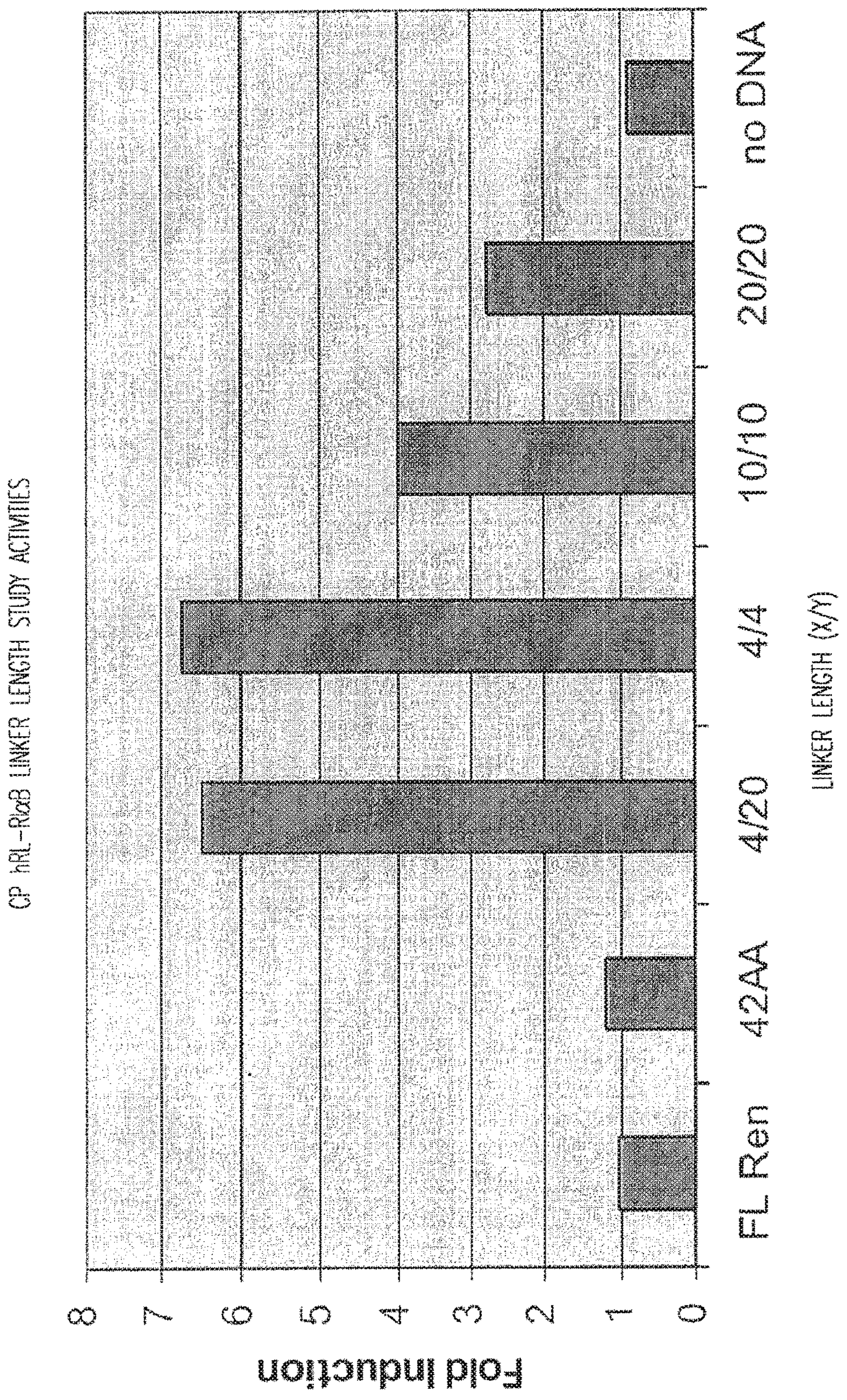
Figure 35A:
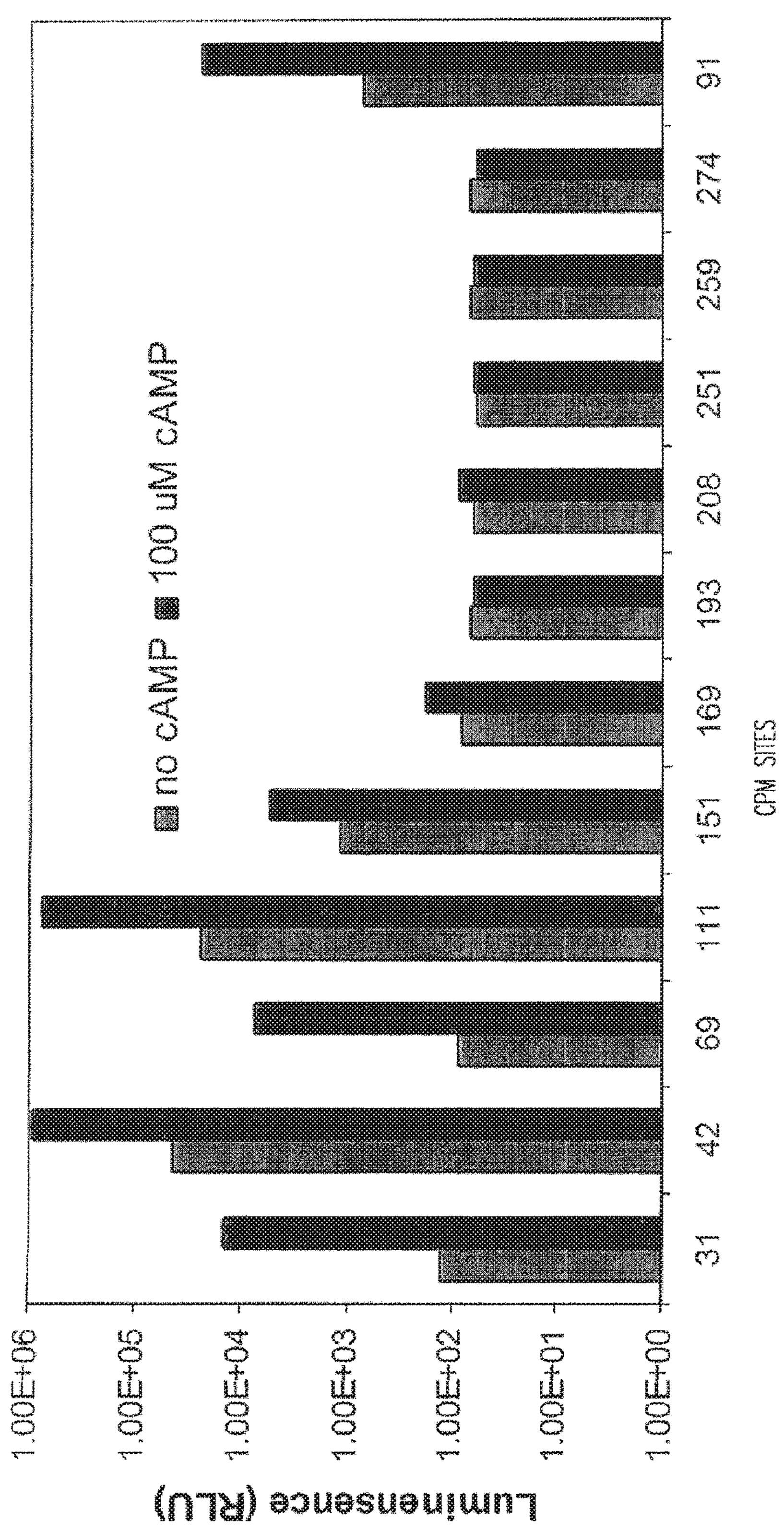
FIG. 35A and FIG. 35B. Activity test in vitro. Construct pBFB287 was used for the 91 site. Following expression using the TnT T7 Coupled Rabbit Reticulocyte Lysate System, 8.5 μL of TNT reaction was mixed with 8.5 μL of 300 mM HEPES/200 mM thiourea (pH about 7.5) supplemented with 1.7 μL of 1 mM cAMP stock or $dH_2O$; reactions were allowed to incubate at room temperature for approximately 10 minutes. Five μL of each sample was added to a 96 well plate well in triplicate and luminescence was measured using 100 μL of *Renilla* luciferase assay reagent on a Glomax luminometer.
Figure 35B:
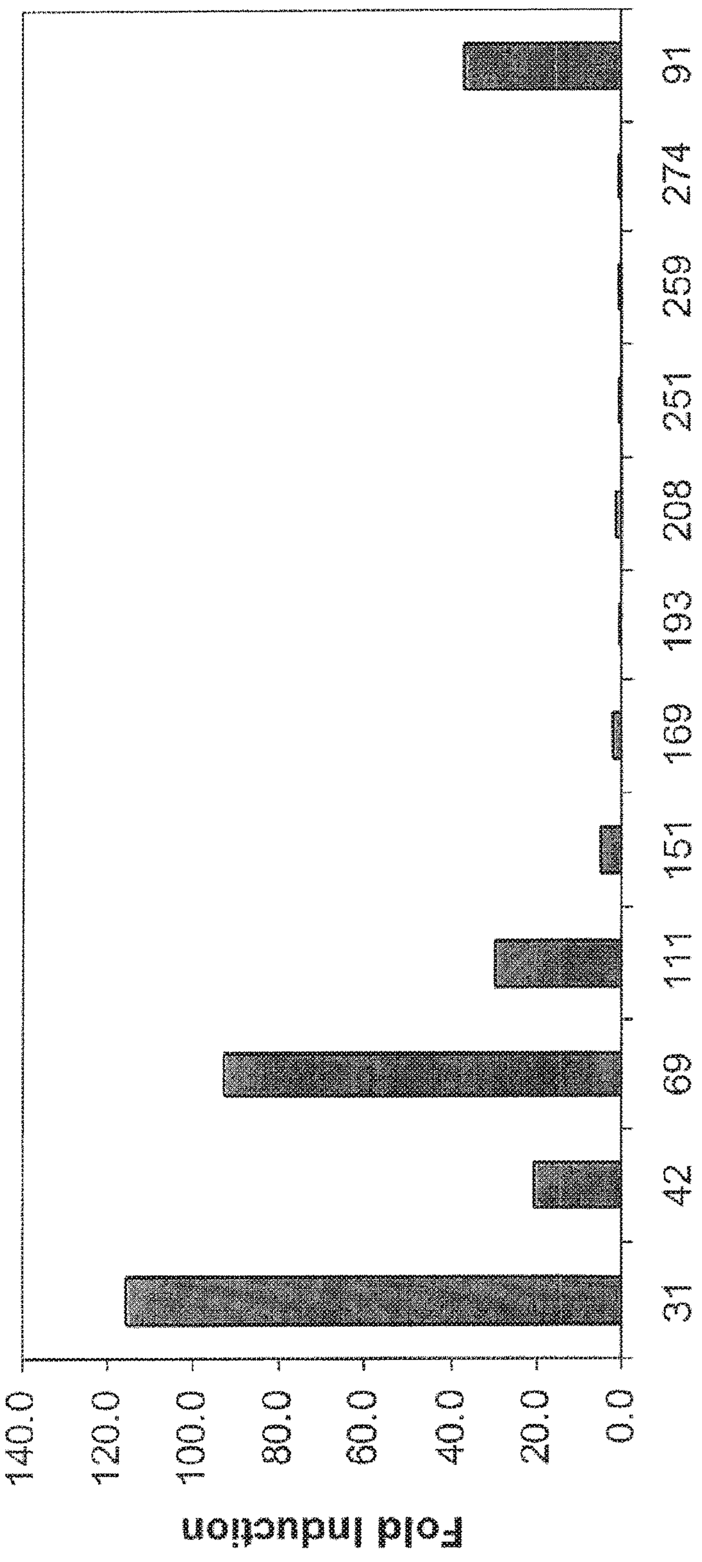
Figure 36A:
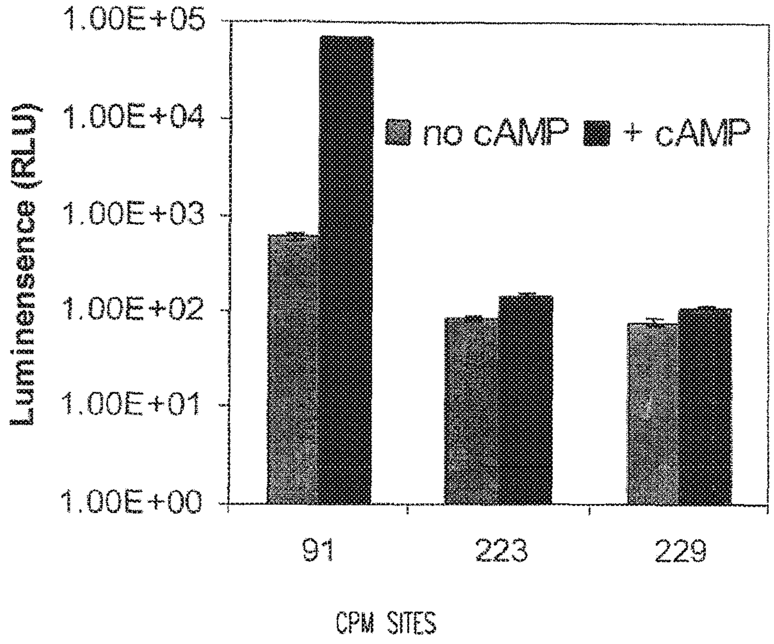
FIG. 36A and FIG. 36B. Activity test in vitro. Construct 201325.44.H6 was used for the 91 site. Following expression using the TnT T7 Coupled Wheat Germ Extract System, 15 μL of TNT reaction was supplemented with 1.5 μL of 1 mM cAMP stock or $dH_2O$; reactions were allowed to incubate at room temperature for approximately 10 minutes. 15 μL of this mixture was then added to 75 ul 1× *Renilla* Lysis Buffer and 20 μL of each sample was added to a 96 well plate well in triplicate and luminescence was measured using 100 μL of *Renilla* luciferase assay reagent on a Glomax luminometer for the 91 and 223 constructs. For the 229 construct, cAMP induction was measured as described in FIG. 35A and FIG. 35B.
Figure 36B:
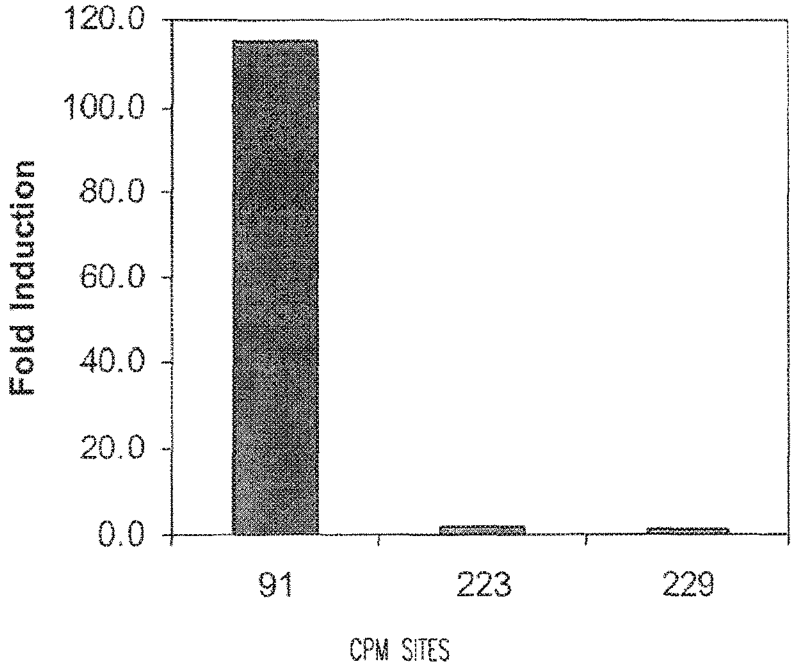

A cAMP Biosensor Utilizing Circularly Permuted *Renilla* Luciferase and the B Domain from the PKA Regulatory Subunit Type Iα or a GAF Domain DNA encoding the B domain from the human PKA regulatory subunit type Iα (RIαB) was ligated into an expression vector encoding CPM-hRL91 Luc/RIαB fusions [hRL (92-311)-linker X-human RIα (residues 245-381)-linker Y-hRL (1-91)]; (X=4, Y=20; pBFB210), (X=4, Y=4; pBFB211), (X=10, Y=10; pBFB212) and (X=20, Y=20; pBFB213) (FIG. 33). Protein was expressed from the constructs using the TnT T7 Coupled Wheat Germ Lysate System, 17 μL of TNT reaction was mixed with 17 μL of 300 mM HEPES/200 mM thiourea (pH about 7.5) supplemented with 3.4 μL of 1 mM cAMP stock or $dH_2O$; reactions were allowed to incubate at room temperature for approximately 10 minutes. Ten μL of each sample was added to a 96 well plate well in triplicate and luminescence was measured using 100 μL of *Renilla* luciferase assay reagent on a Glomax luminometer. As shown in FIG. 34A and FIG. 34B, light output and fold induction varied with linker length. Fold induction ranged from about 2.8 to 6.8. The 42 amino acid linker construct (201325.15.A1), the full length *Renilla* construct (201325.50.A7) and the "no DNA" control were not induced (FIG. 34A and FIG. 34B).

An additional type of cAMP biosensor was constructed using a circularly permuted *Renilla* luciferase (hRL) and a GAF domain. The plasmid DNA construct encoding the following fusion protein: Met-(hRL 92-311)-GSSGGSGGSGGGSGGSGGSG-(GAF A domain from *Trypanosoma brucei* PDE; Genbank AF192755 amino acids 241-375)-GSGGSGGSGGTSGGSGGSSG-A-(hRL 3-91)-Val (SEQ ID NO:185) [clone pBFB232]. Following expression using the T7 Coupled Reticulocyte Lysate System, luminescence activity was measured in the presence or absence of exogenous cAMP. In the presence of cAMP, the measured activity was 7595 RLU; in the absence of cAMP, the measured activity was 298 RLU (about a 25 fold change). These results indicate that additional domains can be used in CPM hRL constructs in the generation of biosensors. This type of reagent may allow the monitoring of changes in cAMP concentration in living cells, and it also may provide distinct advantages over existing FRET-based cAMP biosensors in that assay format. Moreover, since the GAF domain is a highly conserved fold in nature responsible for binding a wide range of molecules, it is likely that additional types of CPM hRL biosensors could be made using this fold.

Example XVII cAMP Biosensors Using Multiple Sites of Modification in *Renilla* Luciferase A cAMP biosensor having a circularly permuted mutant of *Renilla* luciferase with the primary structure Met-(hRL 92-311)-GSTG-RIIβB-GSGGSGGSGGTSGGSGGSSG (hRL 2-91)-Val (SEQ ID NO:186; RIIβB is the B cAMP binding domain from human PKA regulatory domain type IIBeta amino acids 266-414) showed an increase in luminescence activity upon binding to cAMP. Analogous constructs, either "split" proteins or circularly permuted proteins, can be generated using *Renilla* luciferase mutants modified at additional residues. Overall, fourteen independent circularly permuted constructs were tested encoding fusion proteins of the following type: Met-(hRL X-311)-GSTG-RIIβB-GSGGSGGSGGTSGGSGGSSG(hRL 2-Y)-Val (GSTG corresponds to SEQ ID NO:122; GSGGSGGSGGTSGGSGGSSG corresponds to SEQ ID NO:123). The following table provides X/Y values for the fourteen constructs.

TABLE 3

| CPM site | X value | Y value | Clone ID |
|---|---|---|---|
| 31 | 32 | 30 | pBFB276 |
| 42 | 43 | 41 | pBFB277 |
| 69 | 70 | 68 | pBFB278 |
| 111 | 112 | 110 | pBFB279 |
| 151 | 152 | 150 | pBFB280 |
| 169 | 170 | 168 | pBFB281 |
| 193 | 194 | 192 | pBFB282 |
| 208 | 209 | 207 | pBFB283* |
| 251 | 252 | 250 | pBFB284 |
| 259 | 260 | 258 | pBFB285 |
| 274 | 275 | 273 | pBFB286 |
| 91 | 92 | 91 | pBFB287 and 201325.44.H6 |
| 223 | 224 | 223 | 201325.33.C9 |
| 229 | 230 | 229 | 201325.86.B1 |

*Note:
for construct pBFB283, the last amino acids at the C terminal were PFSEFKPD (SEQ ID NO: 120) instead of PFK and no Val was inserted prior to the stop codon.

For all but four of these constructs, a site was chosen in a solvent exposed surface loop for circular permutation using a homology model of *Renilla* luciferase using 1BN6 (*Rhodococcus* sp.) and 2DHD (*Xanthobacter autotrophicus*) haloalkane dehalogenase crystal structures as templates. Solvent exposed surface loops may be more amenable as sites of modification, e.g., circular permutation, than sites buried in the protein core or sites that are involved in alpha or beta structures. This hypothesis is supported by the lack of activity seen for the firefly luciferase construct with circular permutation at 255, where Tyr255 is a component of an alpha helix that is buried in the protein core. This collection of constructs represents some, but not all, of the surface turns seen in the homology model structure. Four CPM sites: 91, 111, 223 and 229, were chosen based on previous reports (Kaihara et al., 2003, Remy et al., 2005 and Paulmurugan et al., 2003). The constructs were expressed using the TNT T7 Coupled Reticulocyte Lysate System or TnT T7 Coupled Wheat Germ Extract System and tested in vitro (FIG. 35A, FIG. 35B, FIG. 36A and FIG. 36B).

The results indicate that a number of different sites of circular permutation can be used to generate a biosensor such as a cAMP biosensor. Alternative sites of circular permutation were identified with uninduced/induced levels of activity greater than the initial construct with circular permutation at 91 (CPM 91). In addition, constructs were identified where the fold induction in luminescence activity was greater than CPM 91. In addition, owing to the very low solubility of CPM 91 when expressed in *E. coli*, the additional constructs will be tested for increased solubility compared to this construct. Increased solubility may facilitate the development of an in vitro biosensor such as a cAMP detection reagent.

The results also indicate that a number of sites are not useful for circular permutation. All the sites between residues 169 and 274 had low induced and uninduced activities and the fold induction in luminescence activity was about 2 fold or lower.

Figure 37:
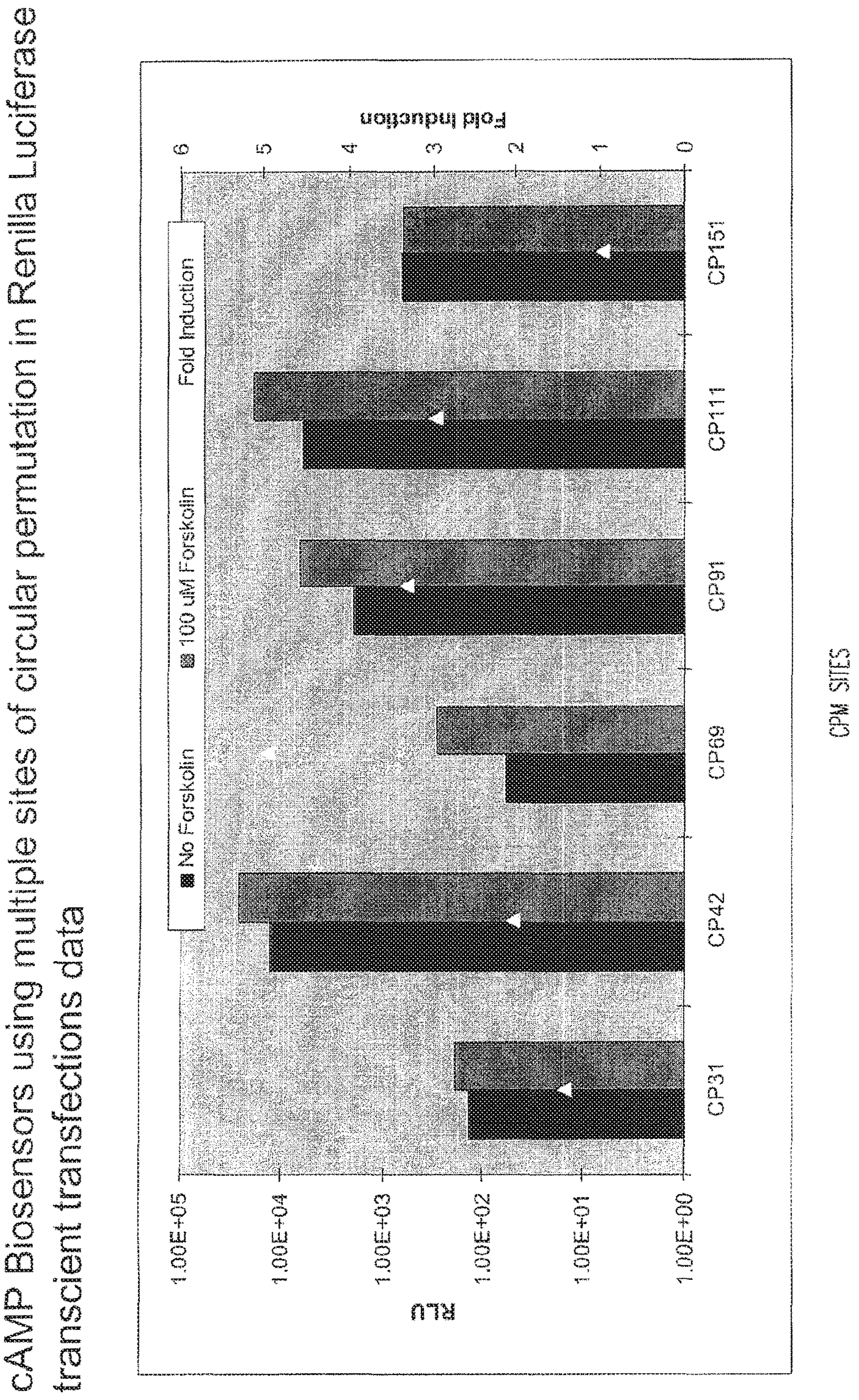
FIG. 37. Transient transfection data for CPM RLuc cAMP biosensors.

Constructs were designed in a vector backbone (pF5A; Promega Corp.) which allows for both in vitro expression (T7 promoter) as well as mammalian expression (CMV promoter). Following transient transfection with DNA encoding the various Met-(hRL residues X-311)-GSTG-RIIβB-GSGGSGGSGGTSGGSGGSSG-(hRL residues 2-Y)-Val (GSTG corresponds to SEQ ID NO:122; GSGGSGGSGGTSGGSGGSSG corresponds to SEQ ID NO:123) constructs (pBFB276, pBFB277, pBFB278, pBFB279, pBFB280, pBFB287), HEK293 cells were treated with 100 μM forskolin to activate endogenous adenylate cyclase. Following incubation for 14 minutes, luminescence was measured from the live cell populations. As predicted, the various constructs functioned as cAMP biosensors inside living cells. Interestingly, construct CPM 31 showed the highest fold induction in vitro, however, this was not the case inside cells. However, in general, the light output and fold inductions showed similar trends in vitro and in vivo (FIG. 37).

Example XVIII

A number of different genetic constructs were prepared to test the possibility of creating biosensors using *Gaussia* luciferase (Gluc) lacking the seventeen amino acid N-terminal peptide that acts as a secretion signal (Genbank AAG54095; amino acids 18-185). *Gaussia* luciferase with or without the N-terminal signal peptide has been reported to give greater light intensity relative to other luciferases when measured from living cells (Tannous et al., 2005; Remy et al., 2006). In addition, fragments of Gluc have been used in systems of protein complementation (Gluc split at amino acid residue 110; Remy et al., 2006); thus, it is likely that Gluc will also be amenable to circular permutation at this site or other sites.

To prepare a Gluc cAMP biosensor, predictions of protein secondary structure were used to choose various sites of Gluc circular permutation: Met-(Gluc A-185)-(Linker X)-(human RilbetaB Genbank BC075800 amino acid residues 266-414)-(Linker Y)-(Gluc 18-B).

TABLE 4

| CPM site | A residue | B residue | Length Linker X | Length Linker Y | pBFB# |
|---|---|---|---|---|---|
| 100 | 101 | 99 | 4 | 4 | pBFB290 |
| 100 | 101 | 99 | 10 | 10 | pBFB291 |
| 100 | 101 | 99 | 20 | 20 | pBFB292 |
| 110 | 111 | 109 | 4 | 4 | pBFB293 |
| 110 | 111 | 109 | 10 | 10 | pBFB294 |
| 110 | 111 | 109 | 20 | 20 | pBFB295 |
| 48 | 49 | 47 | 4 | 4 | pBFB296 |
| 48 | 49 | 47 | 10 | 10 | pBFB297 |
| 48 | 49 | 47 | 20 | 20 | pBFB298 |
| 68 | 69 | 67 | 4 | 4 | pBFB299 |
| 68 | 69 | 67 | 10 | 10 | pBFB300 |
| 68 | 69 | 67 | 20 | 20 | pBFB301 |
| 84 | 85 | 83 | 4 | 4 | pBFB302 |
| 84 | 85 | 83 | 10 | 10 | pBFB303 |

TABLE 4-continued

| CPM site | A residue | B residue | Length Linker X | Length Linker Y | pBFB# |
|---|---|---|---|---|---|
| 84 | 85 | 83 | 20 | 20 | pBFB304 |
| 91 | 92 | 90 | 4 | 4 | pBFB305 |
| 91 | 92 | 90 | 10 | 10 | pBFB306 |
| 91 | 92 | 90 | 20 | 20 | pBFB307 |
| 114 | 115 | 113 | 4 | 4 | pBFB308 |
| 114 | 115 | 113 | 10 | 10 | pBFB309 |
| 114 | 115 | 113 | 20 | 20 | pBFB310 |
| 126 | 127 | 125 | 4 | 4 | pBFB311 |
| 126 | 127 | 125 | 10 | 10 | pBFB312 |
| 126 | 127 | 125 | 20 | 20 | pBFB313 |
| 162 | 163 | 161 | 4 | 4 | pBFB314 |
| 162 | 163 | 161 | 10 | 10 | pBFB315 |
| 162 | 163 | 161 | 20 | 20 | pBFB316 |

Where the various linker combinations have the sequences:

TABLE 5

| Linker combination | Sequence |
|---|---|
| (X = 4, Y = 4) | GSTG-RIIbetaB-GSSG (SEQ ID NO: 187) |
| (X = 10, Y = 10) | GSSGGSGGSG-RIIbetaB-GSGGSGGSSG (SEQ ID NO: 188) |
| (X = 20, Y = 20) | GSSGGSGGSGGGSGGSGGSG-RIIbetaB-GSGGSGGSGGTSGGSGGSSG (SEQ ID NO: 189) |

Sites useful for a Gluc cAMP may be substituted to generate biosensors for other molecules using this site of circular permutation. Moreover, sites amenable to circular permutation in one copepod luciferase are likely useful in other copepod luciferases, such as the luciferase from *Metridia longa*.

Example XIX

Figure 38A:
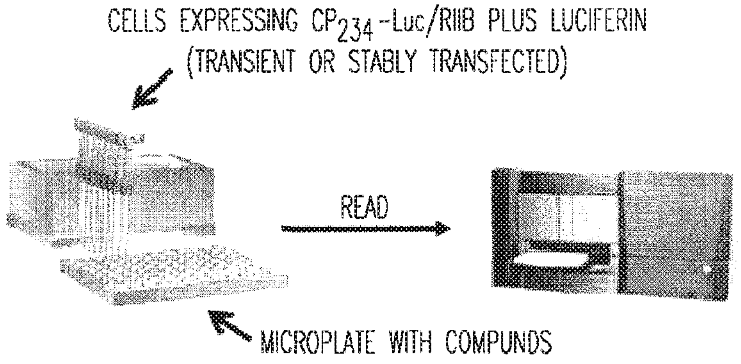
FIG. 38A. Schematic of a single step assay for GPCR with a CPM FF Luc cAMP biosensor.
Figure 38B:
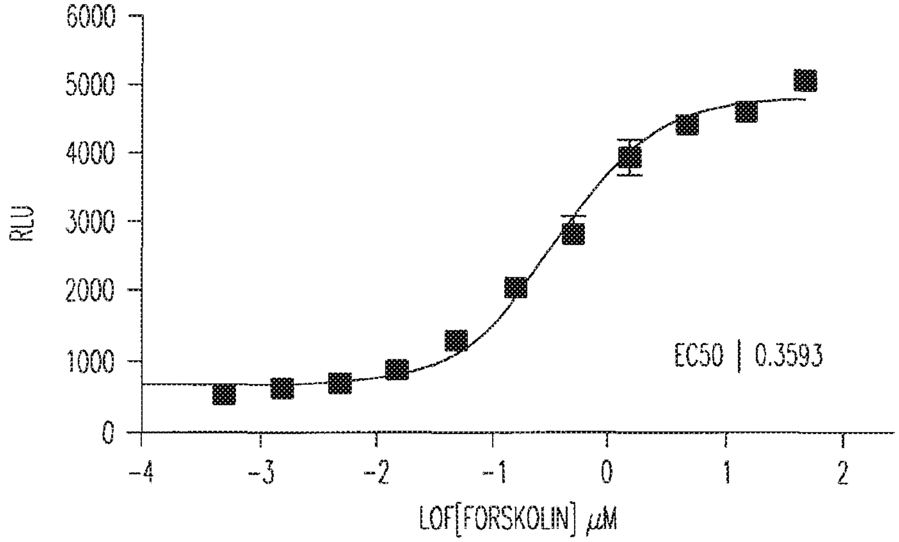
FIG. 38B. RLU versus increasing forskolin concentration in a CPM FF Luc cAMP assay.

Methods for cell-based GPCR assays can involve direct detection of intracellular signal transduction events. Among the most successful are methods using fluorescent dyes or aequorin for real-time monitoring of intracellular calcium. However, analogous technologies have been lacking for the detection of intracellular cAMP dynamics. A circularly permuted firefly luciferase with the allosteric RIIβB cAMP binding domain of Protein Kinase A is a sensor capable of emitting luminescence in proportion to the concentration of cAMP. Live cell, zero-step GPCR assays using this sensor allow the dynamic detection of changes in cAMP concentration using stable or transiently transfected cell lines. In addition, it is possible to develop a single-step homogenous assay format for detection of cAMP in vitro (FIG. 38A and FIG. 38B).

The ORF from pBFB135, under the class of biosensors called "CPM-FF Luc/RIIβB," was used to generate the transient and stable cells lines described below. These cell lines are called "CP234-Luc/RIIB," "cAMP LucSensor," "LucSensor," and "FF cAMP Sensor."

HEK293 cells stably expressing CP234-Luc/RIIB (ORF derived from pBFB135) were resuspended in complete media and mixed with 5 mM luciferin-EF. Cells were plated at $1\times10^5$ cells per well in a 96 well plate and equilibrated to room temperature for 1.5 hours. After stimulation with forskolin, luminescence was measured at 15 minutes using a GloMax™ Luminometer. The results showed that this assay generate $EC_{50}$ values of 0.36 μM for forskolin (FIG. 38A and FIG. 38B).

For a Z' measurement, $2\times10^4$ cells were aliquoted per well to a 384-well plate and equilibrated using a similar protocol. Half the plate was induced with 20 forskolin, whereas the other half remained uninduced. Luminescence was captured 15 minutes after induction using a TECAN GENios Pro™ luminometer. The fold of induction was 6.1 and Z' was 0.83. Since assays with Z' greater than 0.5 are considered good quality for high-throughput screening (HTS), the cAMP biosensor-based assay is amenable for HTS.

Figure 39:
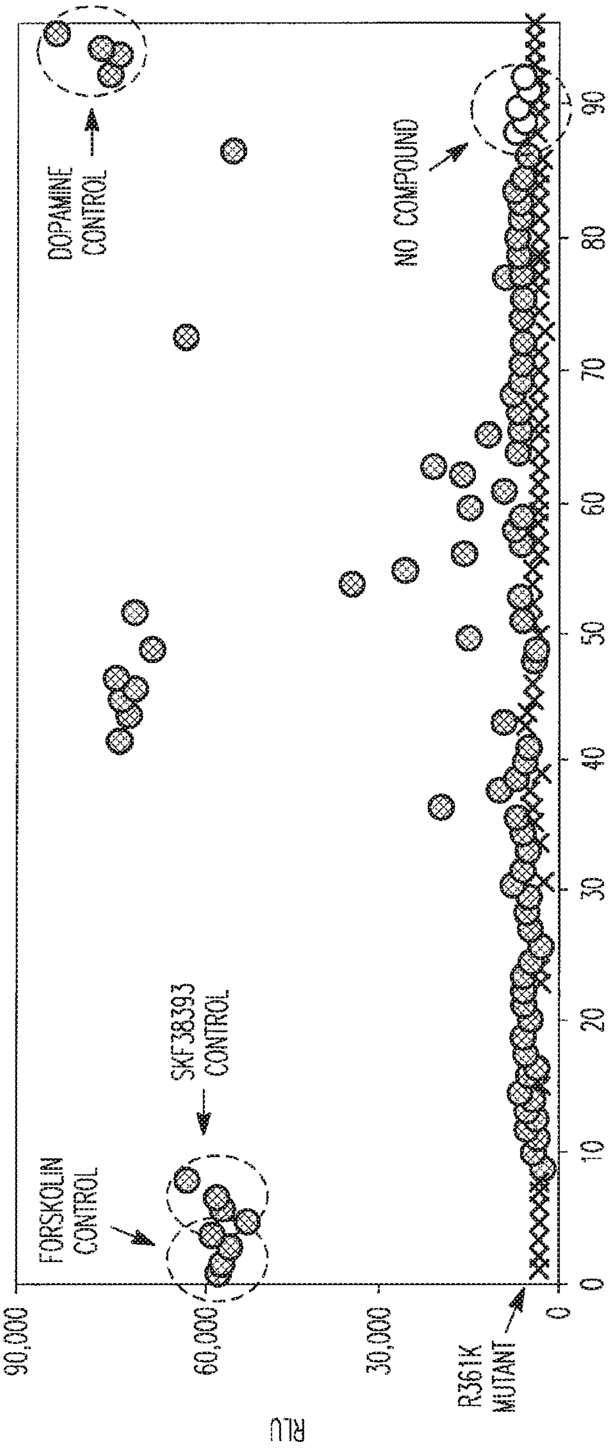
FIG. 39. Data from a screen of a library of compounds with a CPM FF Luc cAMP biosensor.

HEK293 cells stably expressing the dopamine D1 receptor were transiently transfected with plasmid DNA encoding CP234-Luc/RIIB or the R361K mutant (a mutation in the cAMP binding domain) (ORFs derived from pBFB135 and pBFB147, respectively). Cells were plated and equilibrated with luciferin-EF as described above, and compounds from a LOPAC library (plate 6) were added to each well (10 μM). Following incubation for 50 minutes, the plates were read on a TECAN GENios Pro™ luminometer. Hits that also were identified using a luciferase reporter gene assay (CRE response element) are shown in red (FIG. 39). Most hits identified by the cAMP biosensor assay correlated with hits identified by the CRE-Luc reporter assay, validating the biological relevance of the cAMP biosensor GPCR assay.

Figure 40A:
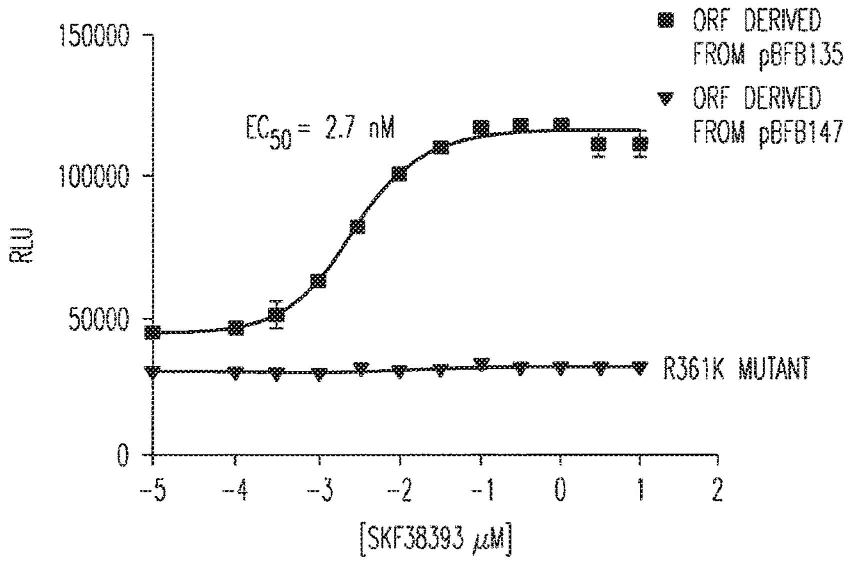
FIG. 40A and FIG. 40B. Dose response of particular compounds using a CPM FF Luc cAMP biosensor.
Figure 40B:
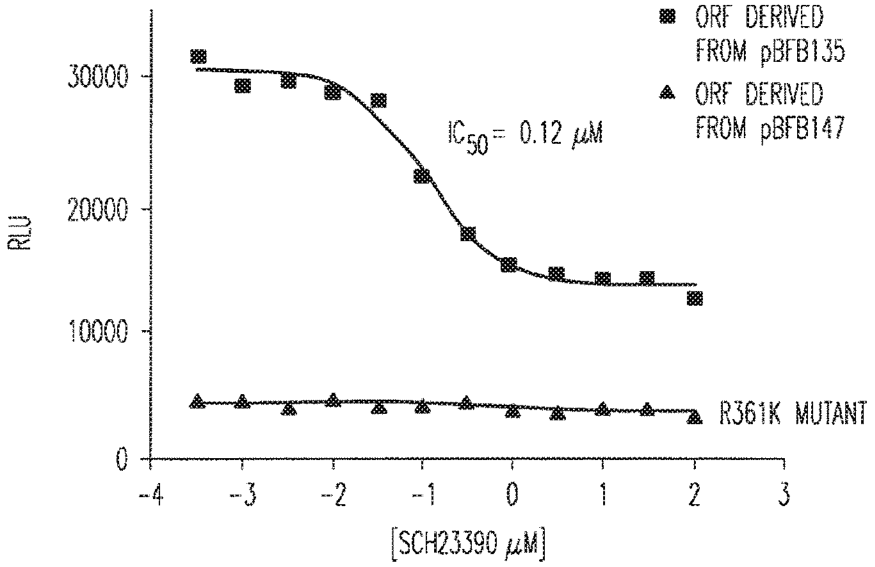

Cells were also plated and equilibrated with luciferin-EF, and then after compound addition, luminescence was measured at 40 minutes using a GloMax™ Luminometer. The pharmacokinetic parameters of $EC_{50}$ and $IC_{50}$ values generated using the cAMP biosensor assay correlated well with those reported in the literature using other methods, again validating the biological relevance of the cAMP biosensor GPCR assay (FIG. 40A and FIG. 40B).

Figures 41, 42:
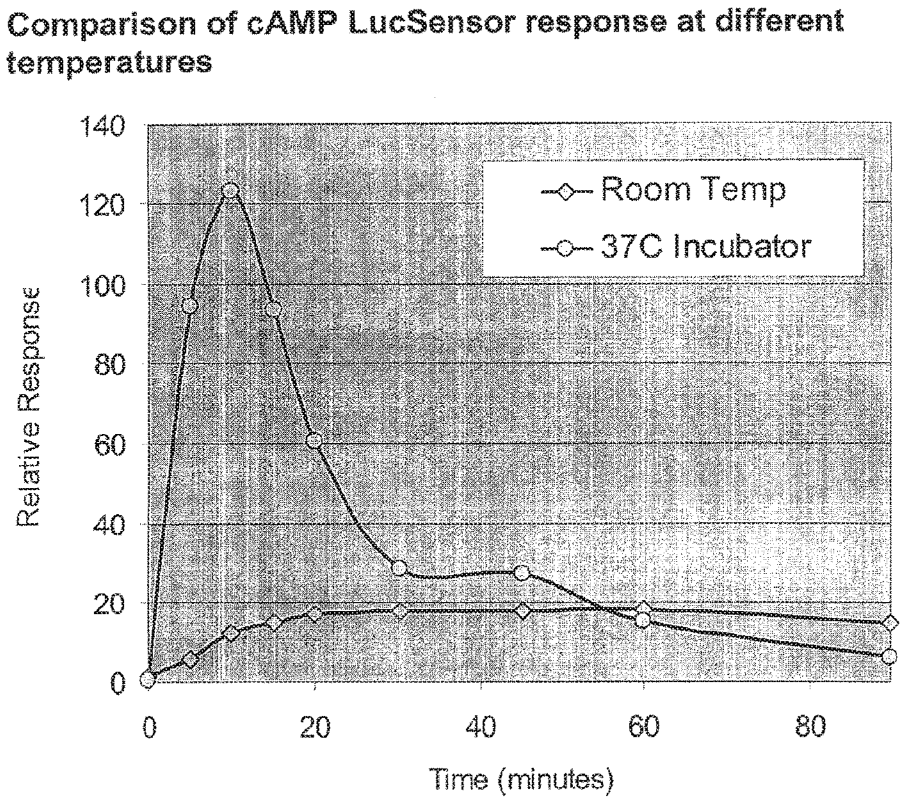
FIG. 41. Amino acid sequence of an exemplary copepod luciferase (SEQ ID NO:204; Genbank ID AAG54095).
FIG. 42. Comparison of the relative response of a CPM-FF Luc/RIIβ cAMP biosensor at room temperature and 37° C. over time.
Figure 43A:
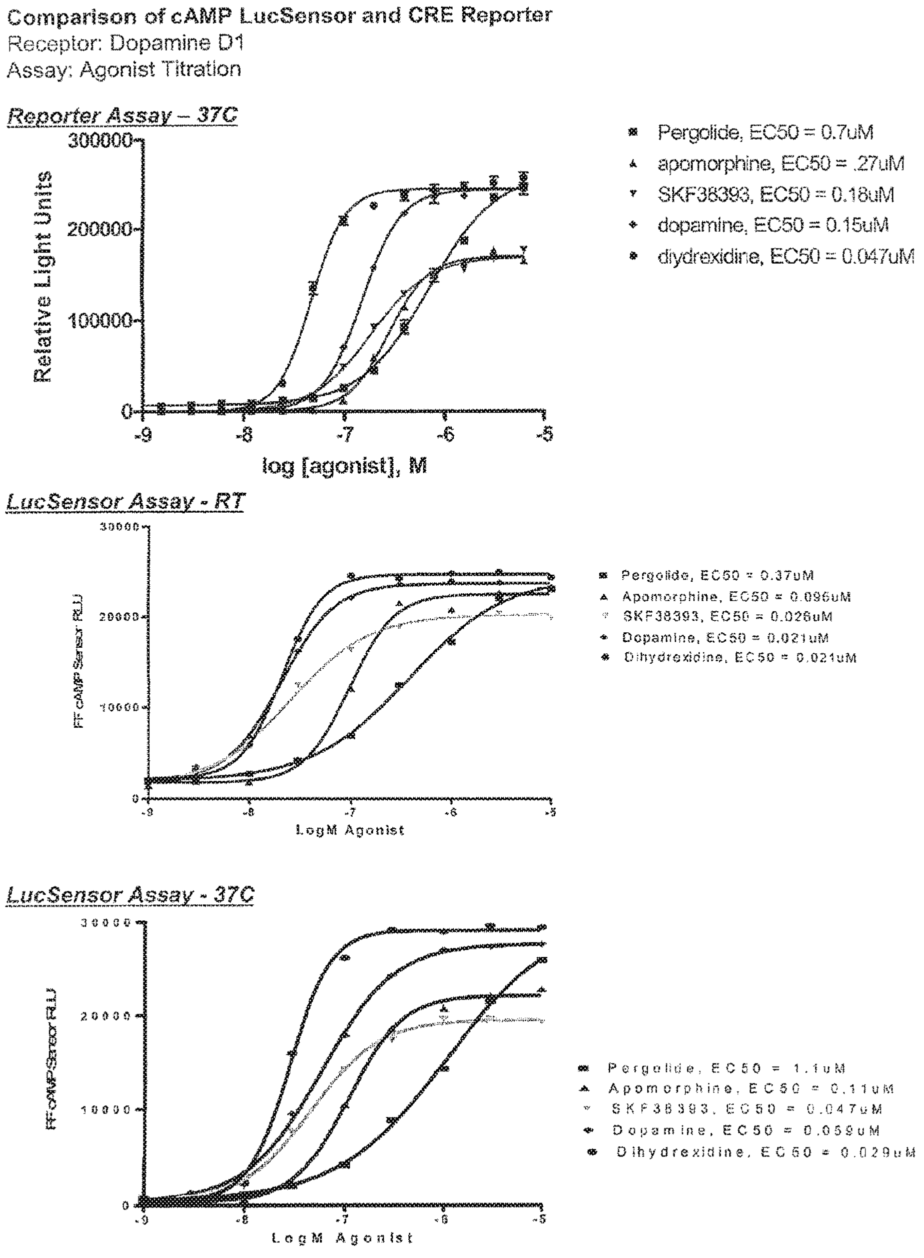
FIG. 43A and FIG. 43B. RLU for a CRE reporter and a CPM-FF Luc/RIIβ cAMP biosensor in the presence of various agonists (FIG. 43A) or antagonists (FIG. 43B) at room temperature and 37° C.
Figure 43B:
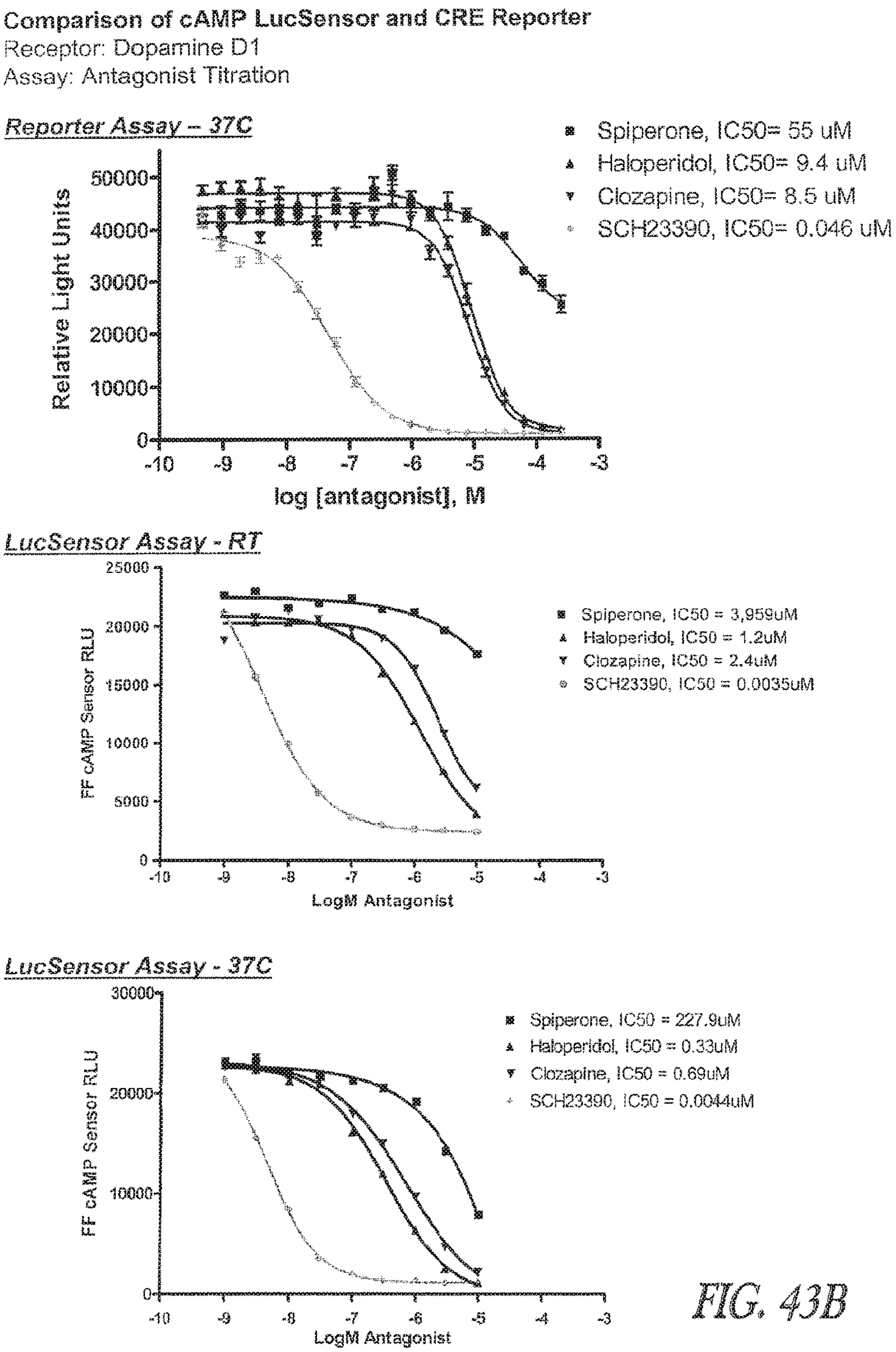

Responses were also tested in cells incubated at different temperatures (FIG. 42) and with a variety of agonists and antagonists (FIG. 43A and FIG. 43B). HEK293 cells expressing the cAMP LucSensor (ORF derived from pBFB135) and a dopamine D1 receptor were incubated with luciferin for 1.5 hours at room temperature or 37° C., then contacted with agonist or antagonist. Responses were measured on a luminometer. There was a more rapid and dynamic response to compounds when cells were incubated under physiological conditions, e.g., 37° C. and $CO_2$. The results at 37° C. were qualitatively similar to those expected for intracellular cAMP dynamics. At room temperature, there was a slower response with a lower dynamic range, which may be useful for large scale screening.

Figure 44:
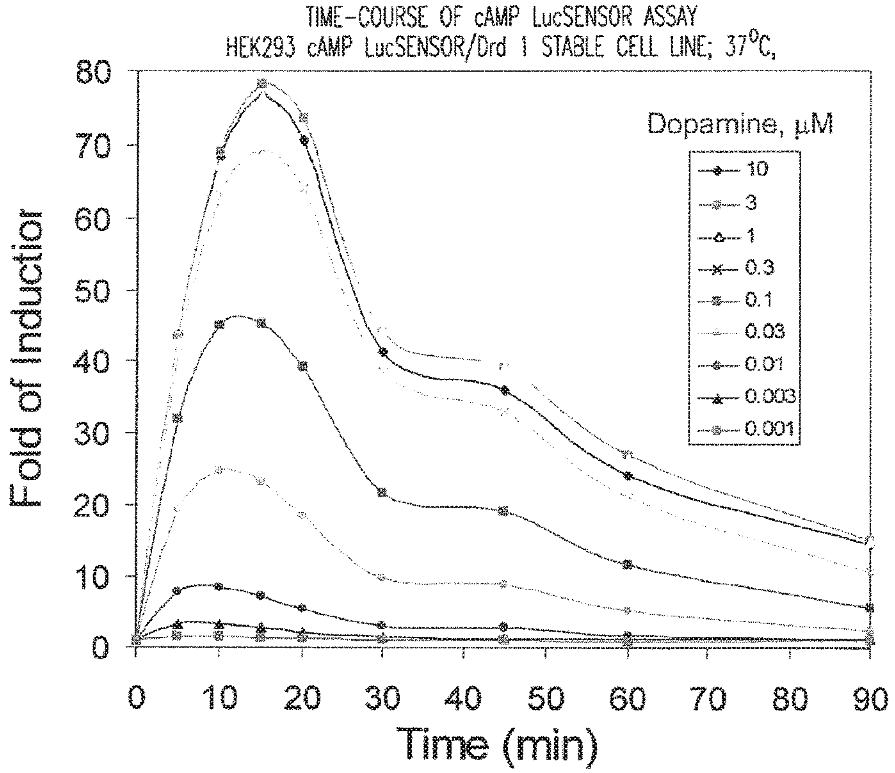
FIG. 44. Fold induction over time with cells stably transfected CPM-FF Luc/RIIβ and exposed to different amounts of dopamine at 37° C.
Figure 45:
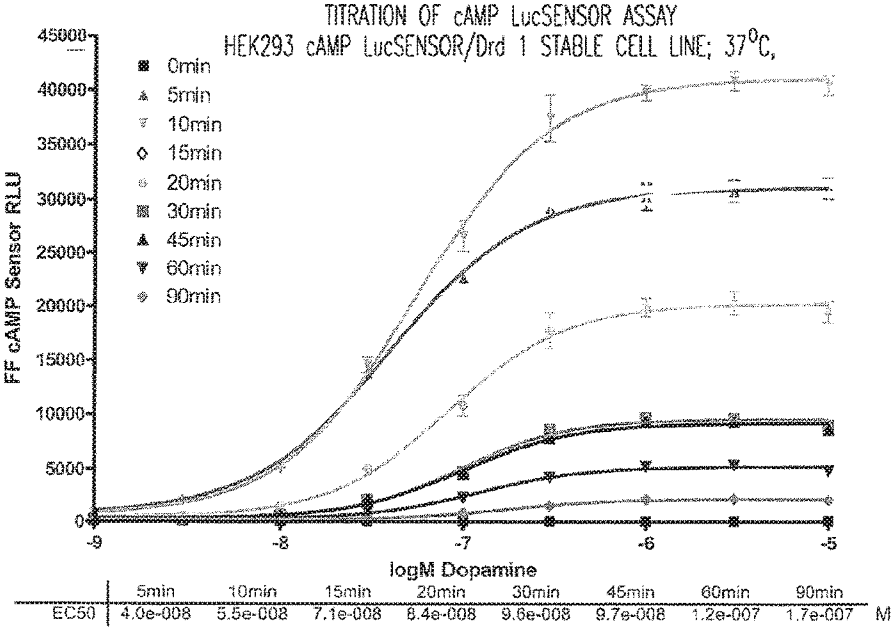
FIG. 45. RLU versus log M dopamine at 37° C.
Figure 46:
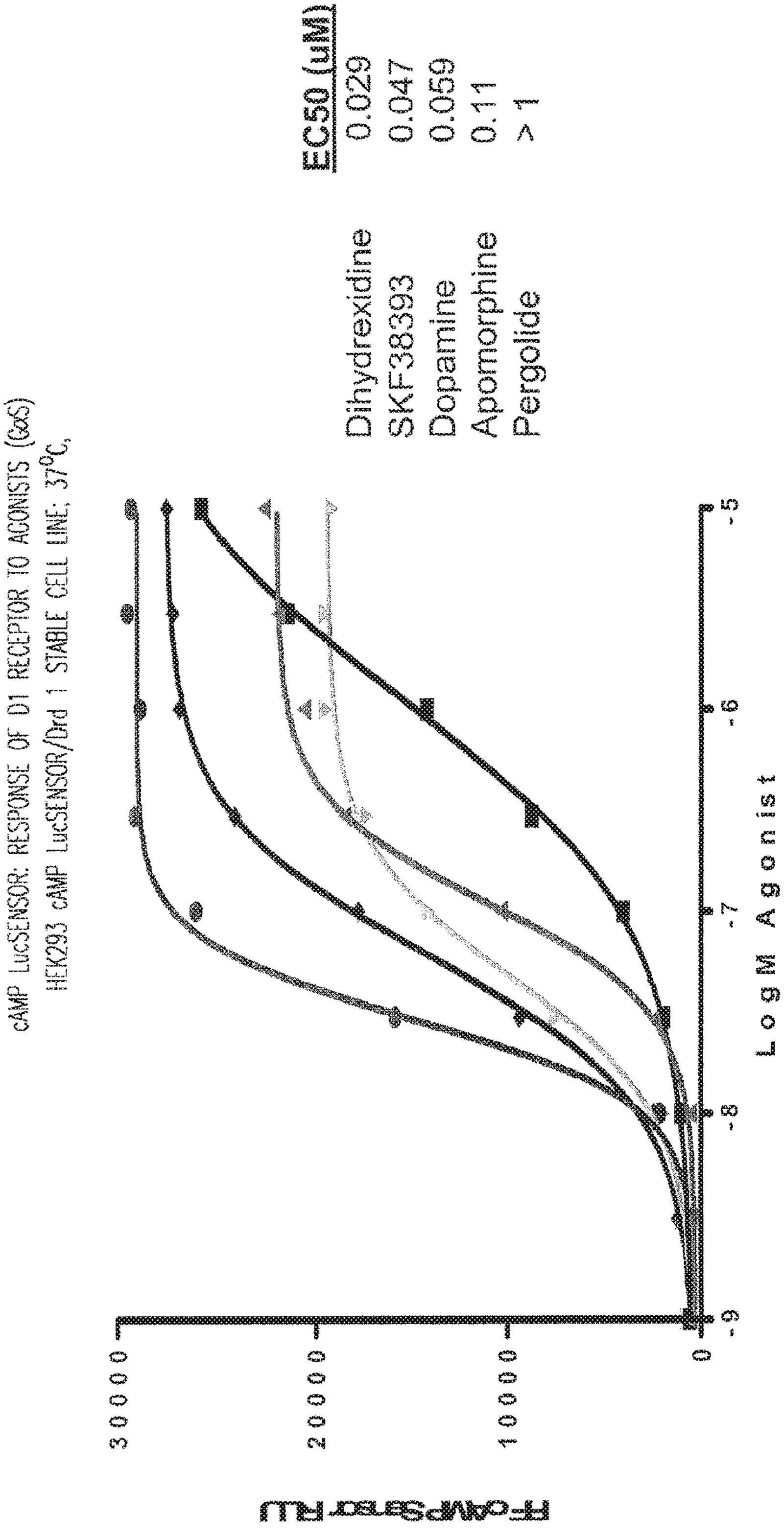
FIG. 46. Potency ranking for various agonists at 37° C.
Figure 47:
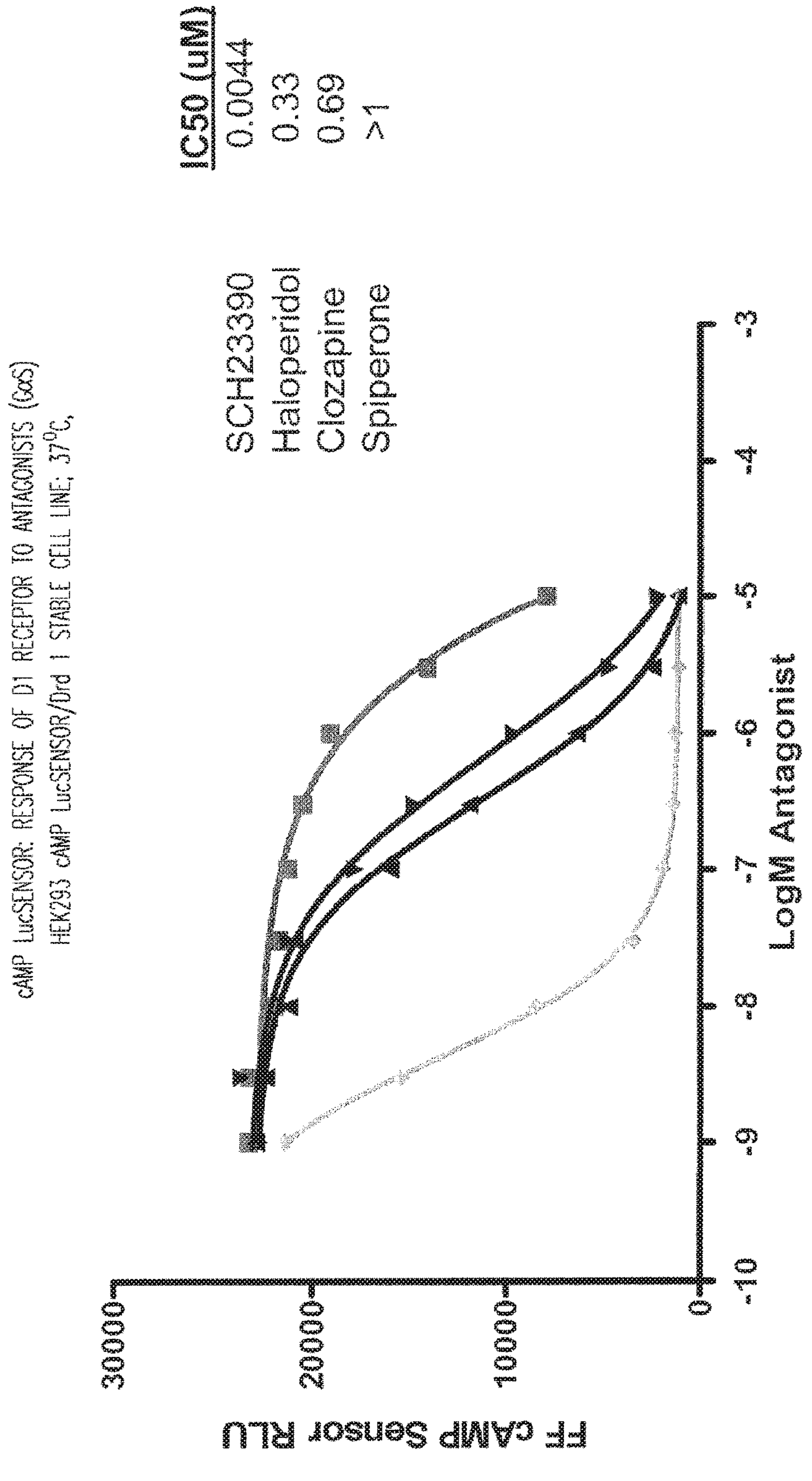
FIG. 47. Potency ranking for various antagonists at 37° C.

FIG. 44 shows a time course for fold induction in cells stably transfected with the cAMP LucSensor and contacted with different amounts of dopamine. The results show that the system allows for monitoring of cAMP dynamics in live cells in real time. Moreover, the results in FIG. 45 show that the system permits evaluation of compound potency, which is relatively consistent at different time points. FIG. 46 provides potency rankings ($EC_{50}$) and results for various agonists and shows that some compounds are partial agonists. Data for antagonist potency ($IC_{50}$) is shown in FIG. 47.

Figure 48:
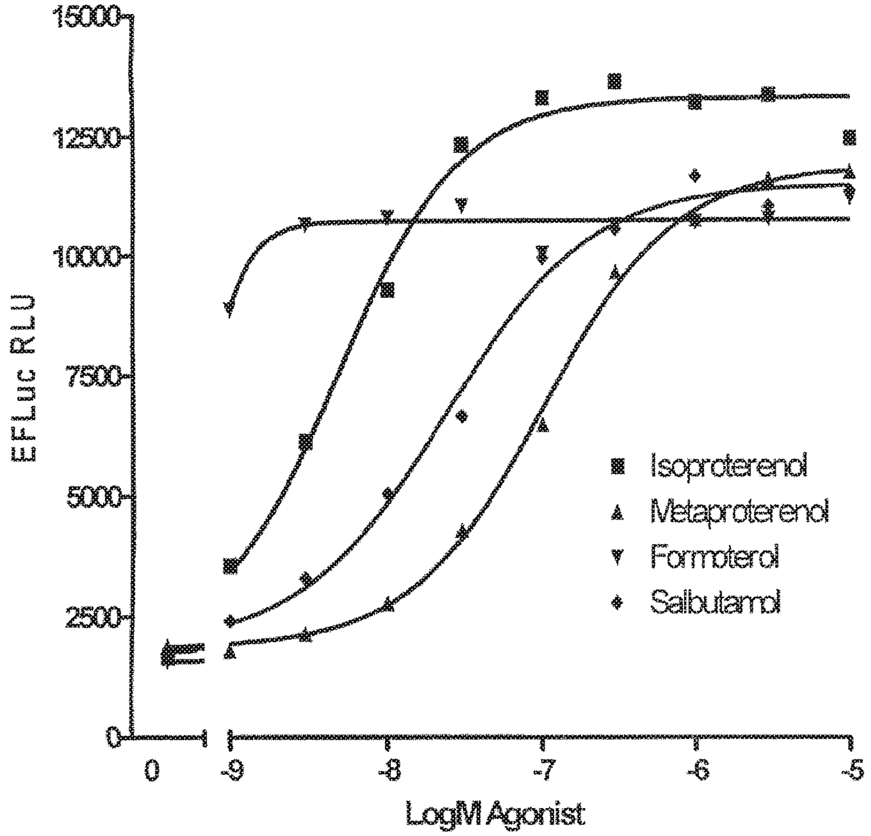
FIG. 48. Potency ranking of agonists of beta2-adrenergic receptor using HEK293/CPM-FF Luc/RIIβ. HEK293 cells stably expressing CPM-FF Luc/RIIB were stimulated with agonists of the endogenous beta-2 adrenergic receptor. Luminescence was measured after 26 minutes incubation at room temperature.
Figure 49:
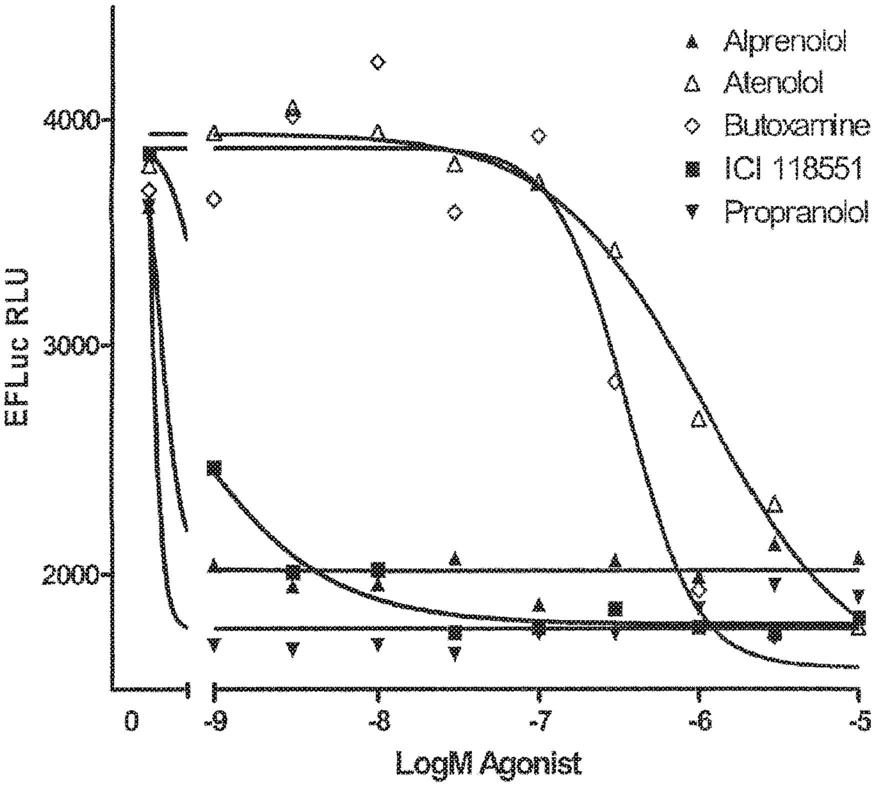
FIG. 49. Potency ranking of agonists of beta2-adrenergic receptor using HEK293. HEK293 cells stably expressing CPM-FF Luc/RIIB were incubed with antagonists in the presence of 0.033 μM isopreterenol. Luminescence was measured after 31 minute incubation at room temperature.
Figure 52A:
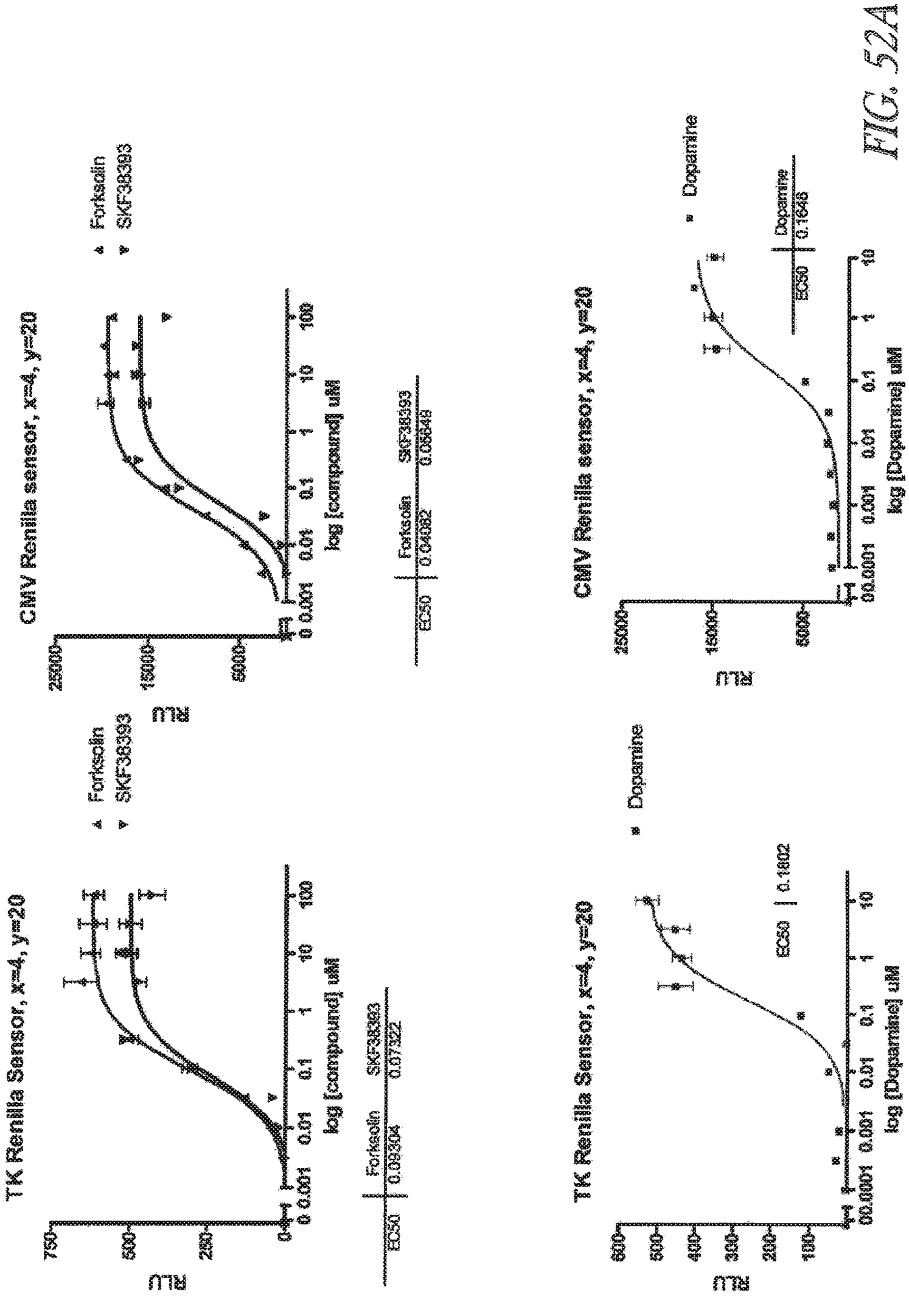
Figure 52C:
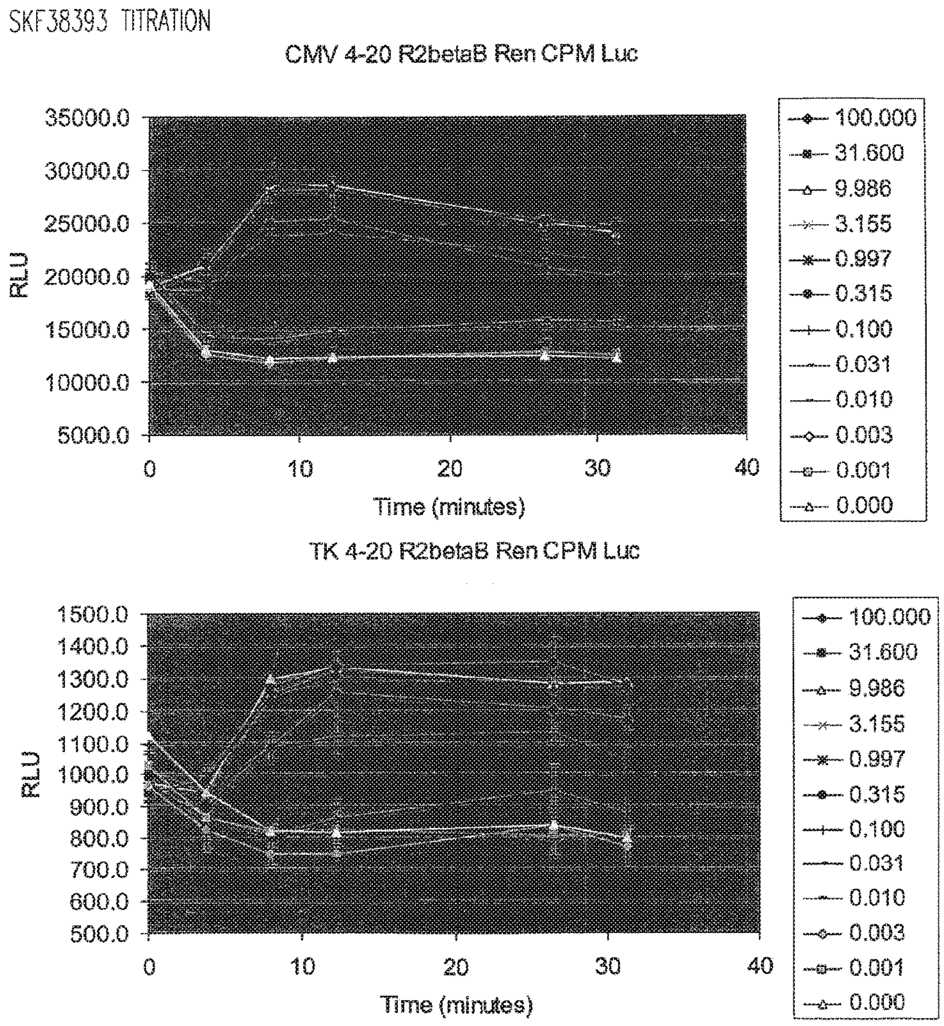
Figure 52D:
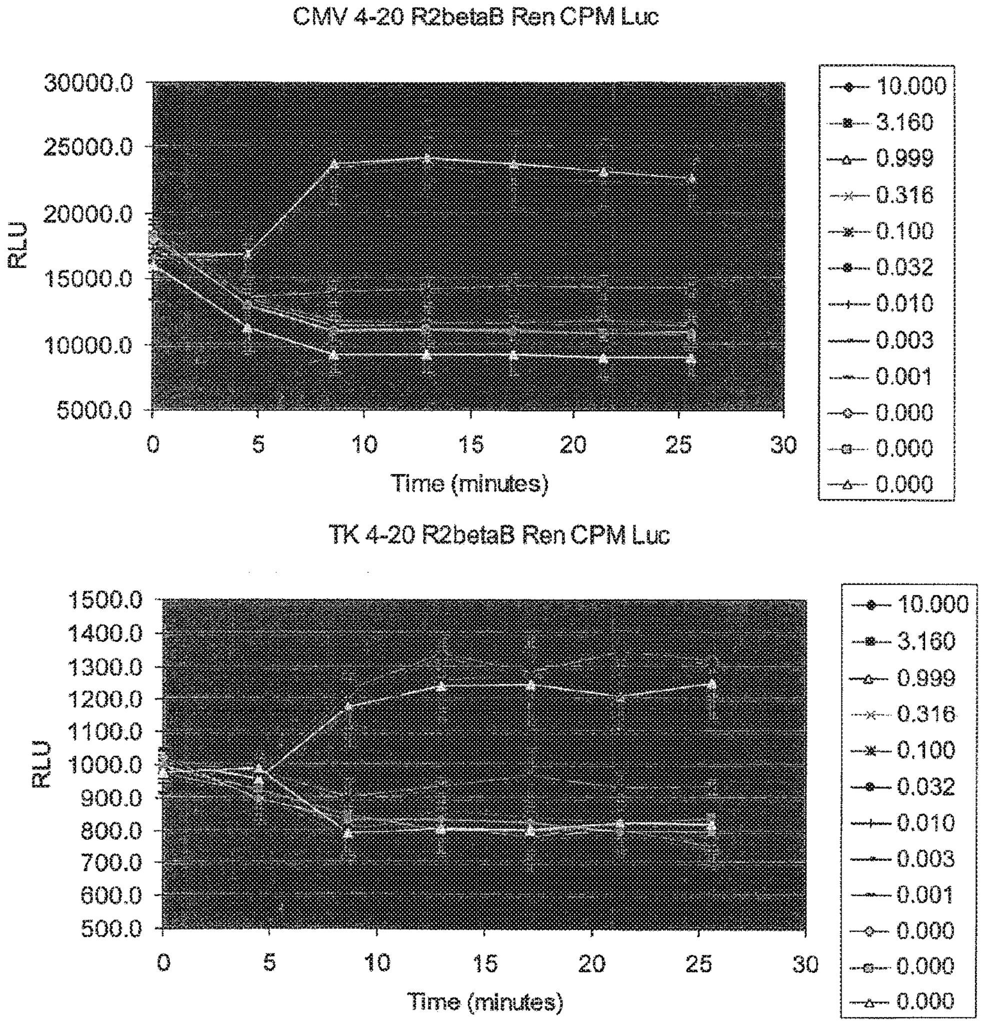

The cAMP LucSensor can also be used measure modulations of GPCR already expressed in the host cell (endogenous GPCR). An example is shown using HEK293 cells which expressed beta2-adrenergic receptor and stably transfected with the cAMP LucSensor. Following similar protocols as described for the dopamine receptor, FIG. 48 and FIG. 49 showed the potency ranking of various agonists and antagonists, respectively.

A comparison of three bioluminescent GPCR assays was conducted. The results for those assays and agonists are shown in FIG. 50. The results for the three bioluminescent assays with antagonists are shown in FIG. 51. The rankings for the tested compounds were the same in all three assays.

The increased in luminescence of the cAMP LucSensor in the presence of cAMP may be the result of an increased efficiency in a conformational change from "open" to "closed".

HEK293 cells stably expressing the dopamine D1 receptor were also transiently transfected with plasmid DNA encoding CPM-hRL Luc/RIIβB X=4, Y=20 under the CMV promoter (201325.78.E5) or TK promoter (201325.44.H6) and then stimulated with either forskolin, SKF38393 or dopamine. Wild type *Renilla* luciferase and CPM-hRL Luc without the RIIβB domain were also tested and showed no specific response to cAMP modulation (data not shown). Cells were transfected in a T75 flask with TransIt®-LT1 Reagent (MIRUS) using 60 μL TransIt®-LT1 reagent and 30 μg DNA per flask, allowed to grow over night and assayed the next day. Approximately one day after transfecting, cells were removed from incubator and trypsinized, counted and 10,000 cells per well were plated in a 96 well plate in DMEM/F12 (HEPES buffer, Invitrogen) with 10% FBS and 60 μM EnduRen Live Cell Substrate. EnduRen Live Cell Substrate (Promega) was reconstituted in 100 μL DMSO and was added to pre-warmed complete media to a final concentration of 60 μM. Cells were then incubated for at least 1 hour at 37° C. and then cooled to room temperature. After 15 minutes at room temperature, baseline measurements of luminescence were measured using a 96 well GloMax™ Luminometer at 0.5 seconds per well. Cells were then induced with 10× stocks, made in complete media, of Forskolin (Sigma), SKF38393 (Sigma), Dopamine (Sigma) or not induced (0.1% DMSO (Sigma)) and luminescence was measured continuously for about 30 minutes. Samples were measured in sets of four replicates per concentration of Forskolin, Dopamine or SKF38393. $EC_{50}$ data represents 15 minutes after induction and were calculated using GraphPad Prism for Windows, Version 4.

Similar to the CPM-FF Luc/RIIβB biosensor, the $EC_{50}$ values generated using the CPM-hRL Luc/RIIβB X=4, Y=20 biosensor (201325.44.H6 and 201325.78.E5) correlated well with those reported in the literature using other methods, again validating the biological relevance of the cAMP biosensor GPCR assay (FIG. 52A-FIG. 52D).

Example XX

Intracellular Detection of Changes in cAMP Concentration Using CPM-hRL Luc/RIIβB cAMP Biosensors Cell Culture Cells were cultured in 2 mL DMEM/F12 with HEPES buffer (Invitrogen) and 10% FBS at 37° C. with 5% $CO_2$ in a 6 well plate.

Plasmids

Three of the constructs described in Example XVII were used to detect intracellular changes of cAMP concentrations. The constructs used were: pBFB277, pBFB279 and pBFB287. HEK293 cells stably expressing CPM91-hRL/RIIβB (ORF derived from 201325.44.H6 were also used in these experiments.

Transfections

HEK293 cells were transfected with TransIt®-LT1 Reagent (MIRUS) using 6 μL TransIt®-LT1 reagent and 2 μg DNA (pBFB277, pBFB279 and pBFB287) per well of a 6 well plate. Cells were allowed to grow overnight and were assayed the next day.

Modulation of Biosensor

Approximately 1 day after transfection, cells were trypsinized, resuspended in fresh DMEM/F12 with HEPES buffer (Invitrogen) with 1% FBS and plated in a 96 well plate at approximately 10,000 cells per well. Alternatively, a HEK293 cell line stably expressing CP91-hRL/RIIβB was plated in a 96 well plate at approximately 10,000 cells per well. A 10 μL aliquot of 600 μM EnduRen was added to a total of 100 μL of cell culture to give a final concentration of approximately 5.5 μM EnduRen. Cells were then incubated at 37° C. with 5% $CO_2$. After 5 hours, the plate was removed from the incubator and allowed to cool to room temperature for at least 20 minutes. After 20 minutes, baseline measurements of luminescence were measured using a 96 well Veritas Luminometer (Turner Biosystems; integration time of 0.5 seconds per well). Cells were then induced with 10 μM isopreterenol (CalBiochem), 50 μM forskolin (Sigma) or not induced (0.1% DMSO, Sigma) and luminescence was measured continuously for about 30 minutes. After 30 minutes, 10 μM propranolol (Sigma) was added to cells already induced with isopreterenol and 0.1% DMSO was added to all other samples. Luminescence was then measured continuously for the next 30 minutes. A final addition of 50 μM forskolin was added to the isopreterenol/propranolol sample and 0.1% DMSO was added to all other samples. Luminescence was then measured continuously for the next half hour. Samples were measured in sets of 4-6 replicates. 10× stocks of isopreterenol, propranolol, forskolin and DMSO were made in DMEM/F12 with HEPES buffer (Invitrogen) and 1% FBS.

Results

Figure 53:
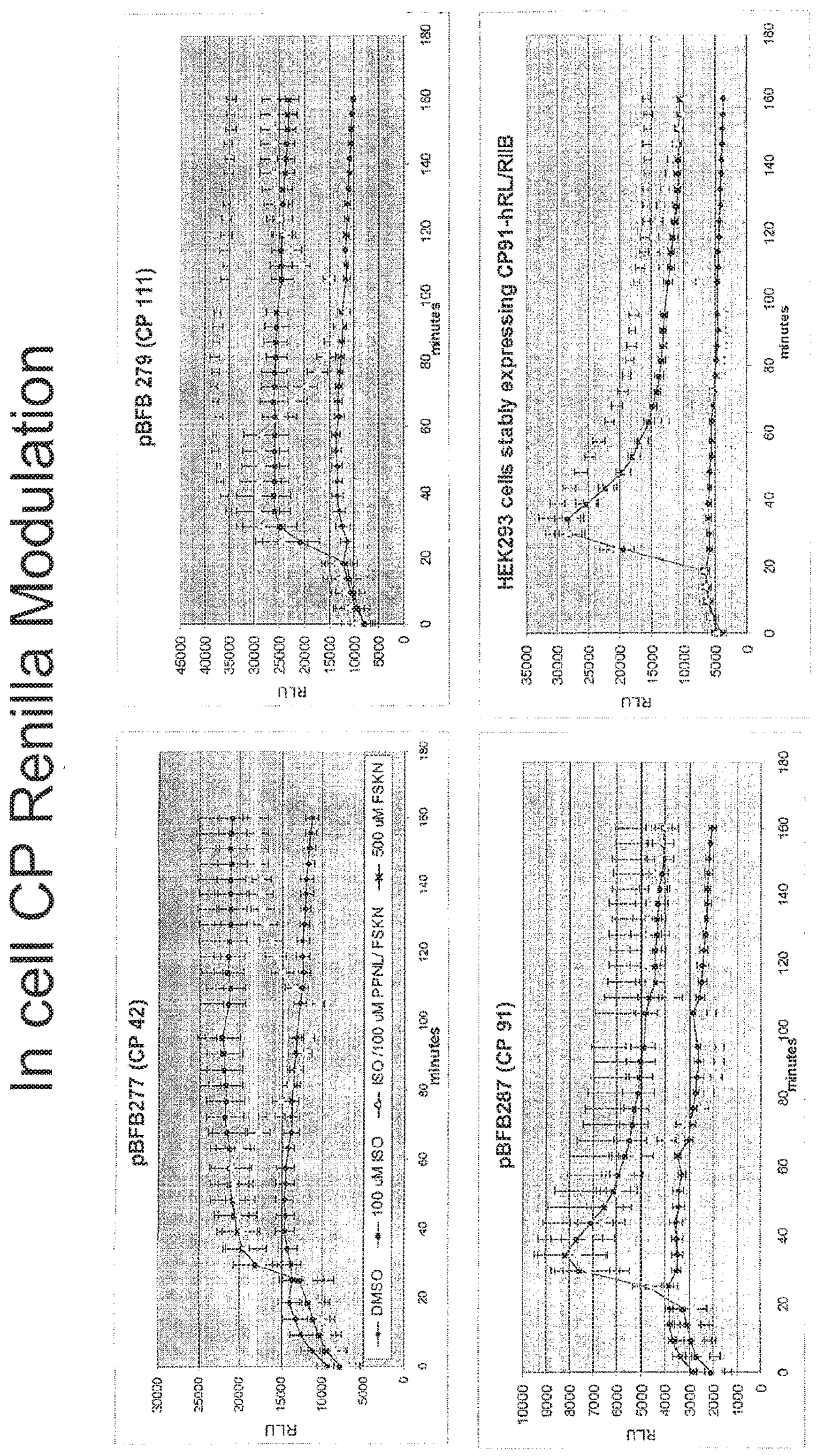
FIG. 53. Detection of intracellular changes in cAMP in cells with a CPM RLuc/RIIβB cAMP biosensor FIG. 54A and FIG. 54B. RLU for FLuc constructs with RIIβB and various linker lengths.

To measure changes in the intracellular concentration of cAMP, HEK 293 cells were transiently transfected with three CPM-hRL Luc/RIIβB (X=4, Y=20) constructs (circularly permuted at different positions within *Renilla* luciferase) followed by treatment with compounds known to increase the intracellular cAMP concentration through GPCR activation (isopreterenol, a β-adrenergic receptor agonist), decrease intracellular cAMP concentration through GPCR inhibition (propranolol, a β-adrenergic receptor antagonist), or increase intracellular cAMP concentration through activation of adenylate cyclase (forskolin). Both isopreterenol and forskolin treatment alone increased light output from transfected cells approximately 2-fold, reflecting an increase in intracellular cAMP concentration (FIG. 53). In addition, a temporal response to changes in cAMP concentration was observed by treating the cells with isoperterenol, followed by propranolol, followed by forskolin (FIG. 53). Detection of cAMP modulation using the *Renilla* luciferase biosensor was also demonstrated in HEK293 cells stably expressing CPM91-hRL/RIIβB. These data showed an about 5-fold increase in light output in response to isopreterenol and forskolin treatment (FIG. 53). Similar to the transiently transfected cells, a temporal response to changes in cAMP concentration was observed by treating the cells with isoperterenol, followed propranolol, followed by forskolin (FIG. 53).

Example XXI

Nonpermuted Firefly Luciferase cAMP Biosensors

Various nonpermuted firefly luciferase constructs having RIIβB directly inserted into sites tolerant to modification, e.g., between residues 233/234, 355/359, 82/83, and 307/308, were prepared. DNA encoding the following fusion proteins was cloned into vector pF9A:

TABLE 6

| | |
|---|---|
| pBFB403 | Met-(Luc2.0 4-233)-GSTG-RIIbetaB-GSSG-(Luc2.0 234-544) (SEQ ID NO: 172) |
| pBFB404 | Met-(Luc2.0 4-233)-GSSGGSGGSG-R2betaB-GSGGSGGSSG-(Luc2.0 234-544) (SEQ ID NO: 173) |
| pBFB405 | Met-(Luc2.0 4-233)-GSSGGSGGSGGGSGGSGGSG-R2betaB-GSGGSGGSGGTSGGSGGSSG-(Luc2.0 234-544) (SEQ ID NO: 174) |
| pBFB406 | Met-(Luc2.0 4-355)-GSTG-RIIbetaB-GSSG-(Luc2.0 359-544) (SEQ ID NO: 175) |
| pBFB407 | Met-(Luc2.0 4-355)-GSSGGSGGSG-R2betaB-GSGGSGGSSG-(Luc2.0 359-544) (SEQ ID NO: 176) |
| pBFB408 | Met-(Luc2.0 4-355)-GSSGGSGGSGGGSGGSGGSG-R2betaB-GSGGSGGSGGTSGGSGGSSG-(Luc2.0 359-544) (SEQ ID NO: 177) |
| pBFB409 | Met-(Luc2.0 4-82)-GSTG-RIIbetaB-GSSG-(Luc2.0 83-544) (SEQ ID NO: 178) |
| pBFB410 | Met-(Luc2.0 4-82)-GSSGGSGGSG-R2betaB-GSGGSGGSSG-(Luc2.0 83-544) (SEQ ID NO: 179) |
| pBFB411 | Met-(Luc2.0 4-82)-GSSGGSGGSGGGSGGSGGSG-R2betaB-GSGGSGGSGGTSGGSGGSSG-(Luc2.0 83-544) (SEQ ID NO: 180) |
| pBFB412 | Met-(Luc2.0 4-307)-GSTG-RIIbetaB-GSSG-(Luc2.0 308-544) (SEQ ID NO: 181) |
| pBFB413 | Met-(Luc2.0 4-307)-GSSGGSGGSG-R2betaB-GSGGSGGSSG-(Luc2.0 308-544) (SEQ ID NO: 182) |
| pBFB414 | Met-(Luc2.0 4-307)-GSSGGSGGSGGGSGGSGGSG-R2betaB-GSGGSGGSGGTSGGSGGSSG-(Luc2.0 308-544) (SEQ ID NO: 183) |

Luc2.0 = *Photinus pyralis* luciferase encoded by the luc2.0 gene (see Genbank ID AY738222);
RIIbetaB = residues 266-414 of human PKA regulatory subunit type II beta (Genbank BC075800)

Protein was expressed from these constructs using the TnT T7 Coupled Reticulocyte Lysate System. Following expression, 9 μL of TNT reaction was mixed with 1 μL 1 mM cAMP stock or $H_2O$, and the reactions were allowed to incubate at room temperature for approximately 15 minutes. Following incubation, 2 μL of solution was aliquoted to individual wells of a 96 well plate in triplicate. Luminescence was measured using a Glomax luminometer following injection of 100 μL of Luciferase Assay Reagent (0.5 second integration time).

Figure 54A:
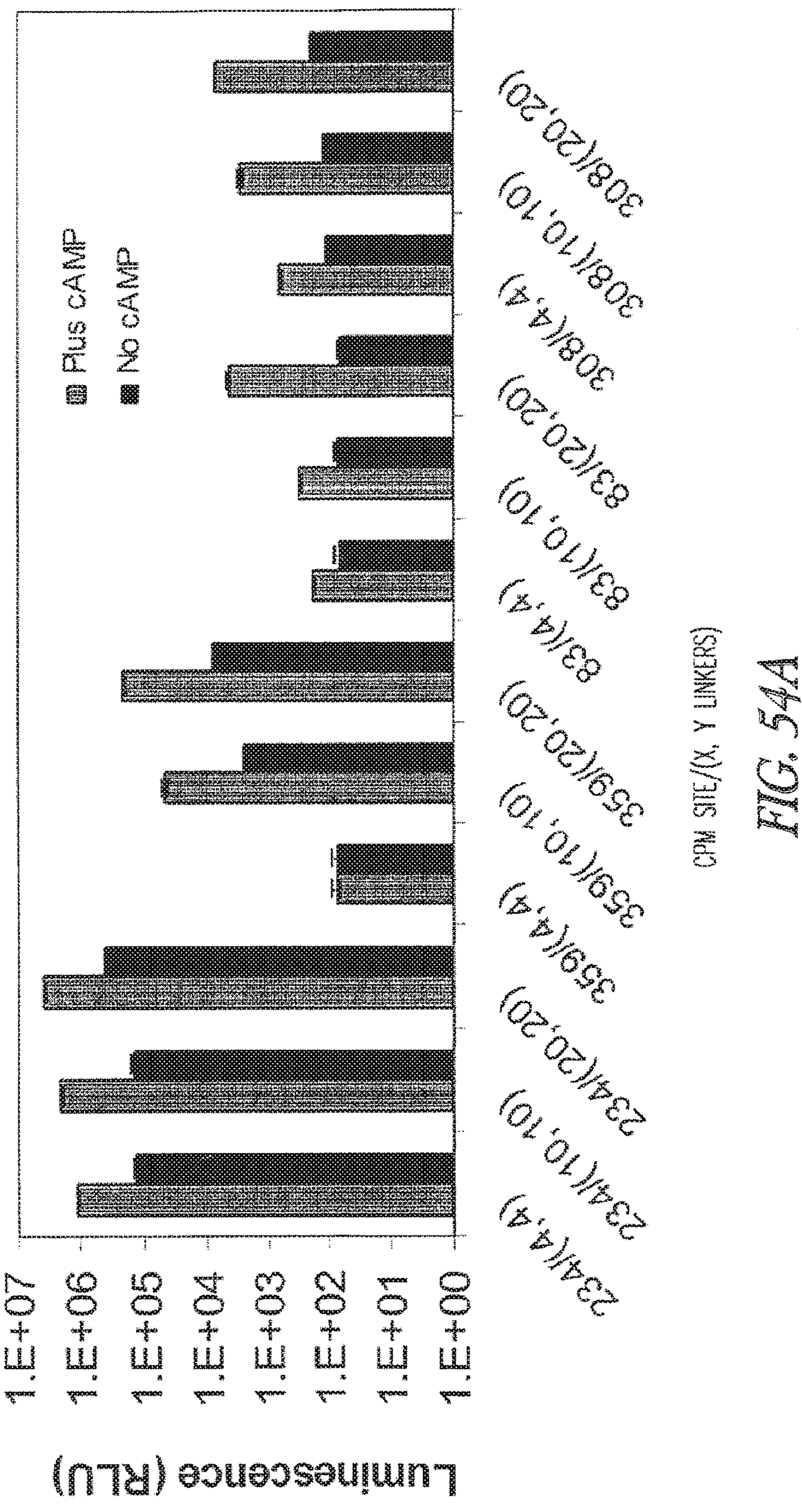
(FIG. 54A) RLU.
Figure 54B:
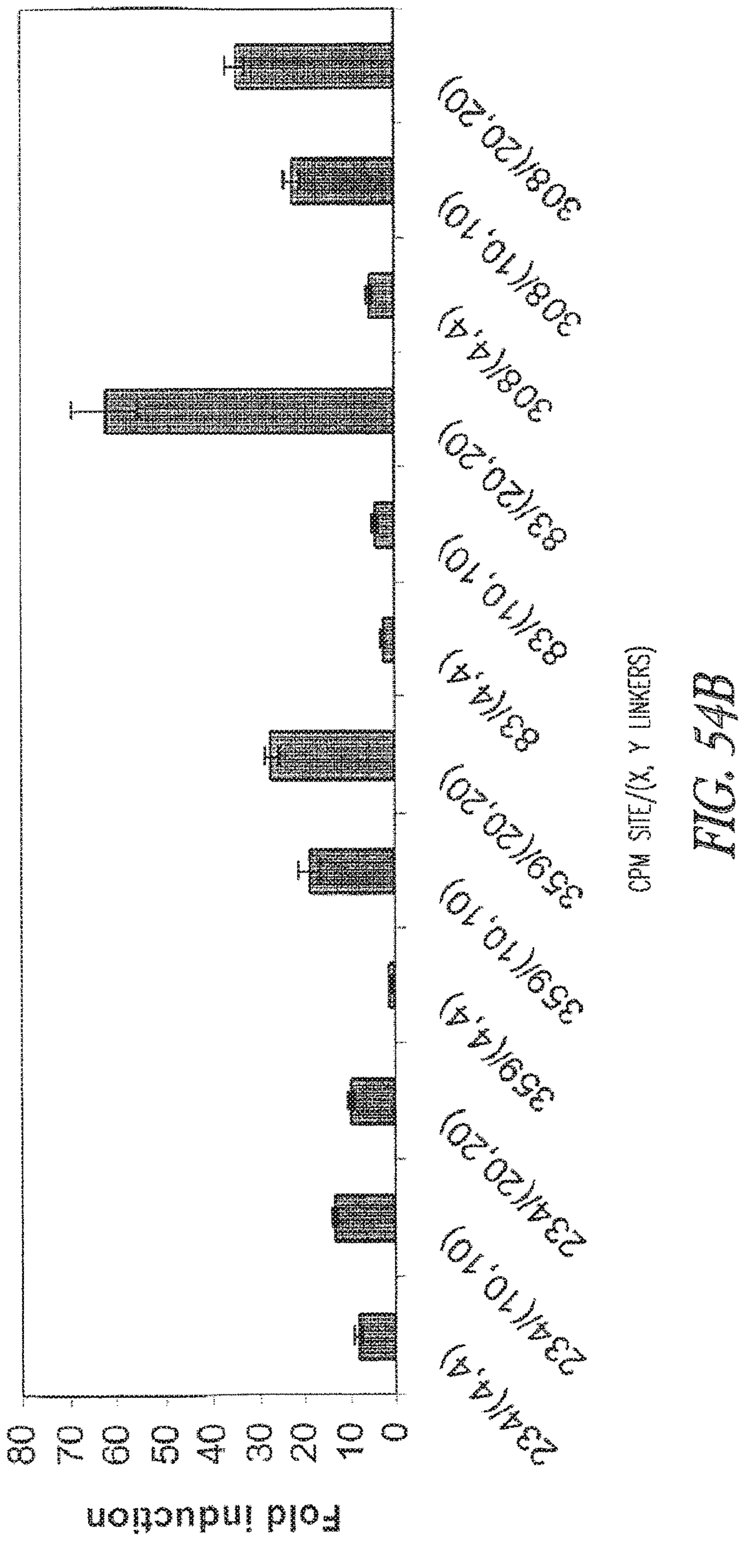
(FIG. 54B) Fold induction.

The results indicate that cAMP biosensors can be generated by direct insertion of RIIβB into any of the four chosen insertion sites (see FIG. 54A and FIG. 54B). The results also indicate that sites that are tolerant to circular permutation also appear to be tolerant to direct insertion to generate viable biosensors.

Example XXII

Nonpermuted and Permuted *Oplophorus* Luciferase cAMP Biosensors

*Oplophorus gracilirostris* luciferase (OpLuc) catalizes oxidation of coelentrazine to emit blue light. The mature form of the enzyme is 18.7 kD (169 aa). The original ORF includes 27 extra residues which represent a putative signal peptide for secretion. Removal of the putative 27 aa signal peptide resulted in about 50 fold increase in the luciferase activity. Due to its small size, OpLuc is particularly amenable to use as a biosensor or in PCA.

OpLuc is active and stable if it is present in TnT cell free extract or *E. coli* cell lysate. However, it immediately inactivates upon purification. Gel filtration showed that the luciferase (expressed in *E. coli* without the 35 kD protein found in the native organism) eluted between 13.7 and 29 kD protein standards. MW of the enzyme is 18.7 kD. Therefore, it appears that, if expressed without the 35 kD protein, the luciferase is maintained as a monomer. The enzyme remains active at pH 7.5-9 and the activity begins to decrease at pH 9.5.

Various nonpermuted *Oplophorus* luciferase (OpLuc) constructs having RIIβB directly inserted into sites tolerant to modification, e.g., between residues 50/51 and 84/85, were prepared. DNA encoding the following fusion proteins was cloned into vector pF5K:

TABLE 7

| | |
|---|---|
| pBFB397 | Met-(OpLuc 1-50)-GSTG-R2betaB-GSSG-(OpLuc 51-169) (SEQ ID NO: 190) |
| pBFB398 | Met-(OpLuc 1-50)-GSSGGSGGSG-R2betaB-GSSGGSGGSG-(OpLuc 51-169) (SEQ ID NO: 191) |
| pBFB399 | Met-(OpLuc 1-50)-GSSGGSGGSGGGSGGSGGSG-R2betaB-GSGGSGGSGGTSGGSGGSSG-(OpLuc 51-169) (SEQ ID NO: 192) |
| pBFB400 | Met-(OpLuc 1-84)-GSTG-R2betaB-GSSG-(OpLuc 85-169) (SEQ ID NO: 193) |

TABLE 7-continued

| | |
|---|---|
| pBFB401 | Met-(OpLuc 1-84)-GSSGGSGGSG-R2betaB-GSSGGSGGSG-(OpLuc 85-169) (SEQ ID NO: 194) |
| pBFB402 | Met-(OpLuc 1-84)-GSSGGSGGSGGGSGGSGGSG-R2betaB-GSGGSGGSGGTSGGSGGSSG-(OpLuc 85-169) (SEQ ID NO: 195) |

Residue '1' in the above table indicates the first residue in the mature form of the protein (lacking the signal peptide for secretion, residue 28 in Genbank AB030246);
RIIbetaB = residues 266-414 of human PKA regulatory subunit type II beta (Genbank BC075800).

Protein was expressed from these constructs using the TnT T7 Coupled Reticulocyte Lysate System. Following expression, 9 μL of TNT reaction was mixed with 1 μL 1 mM cAMP stock or $H_2O$, and the reactions were allowed to incubate at room temperature for approximately 15 minutes. Following incubation, 10 μL of 2× buffer (300 mM HEPES, pH=8.0, 200 mM thiourea) was added to each reaction, and luminescence was measured from the resulting 20 μL of solution following addition of 100 μL of *Renilla* Assay Reagent using a Turner 20/20N luminometer (1 second integration time). The results are listed in the following table:

TABLE 8

| | |
|---|---|
| pBFB397+ | 918 |
| pBFB397− | 225 |
| pBFB398+ | 4,917 |
| pBFB398− | 291 |
| pBFB399+ | 38,051 |
| pBFB399− | 356 |
| pBFB400+ | 10,369 |
| pBFB400− | 6,387 |
| pBFB401+ | 6,124 |
| pBFB401− | 2,304 |
| pBFB402+ | 62,264 |
| pBFB402− | 8,568 |
| FL Opluc+ | 25,225,870 |
| FL Opluc− | 23,231,428 |
| No DNA+ | 120 |
| No DNA− | 116 |

FL Opluc = expression of residues 28-169 of Genbank BC075800; '+' = addition of exogenous cAMP to 50 μM final concentration; '−' = no exogenous cAMP was added.

Figure 63:
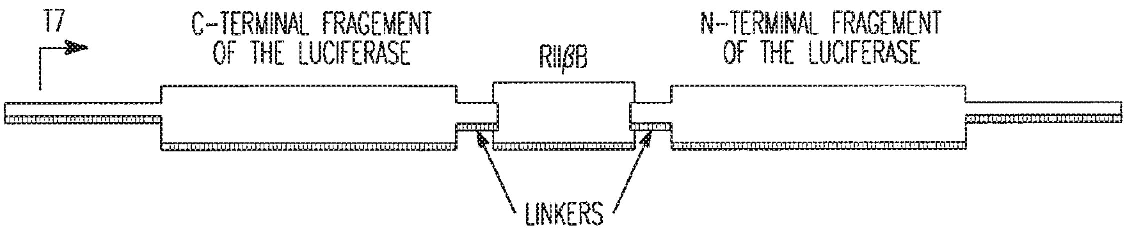
FIG. 63. CP *Oplophorus* luciferase based vector.
Figure 64A:
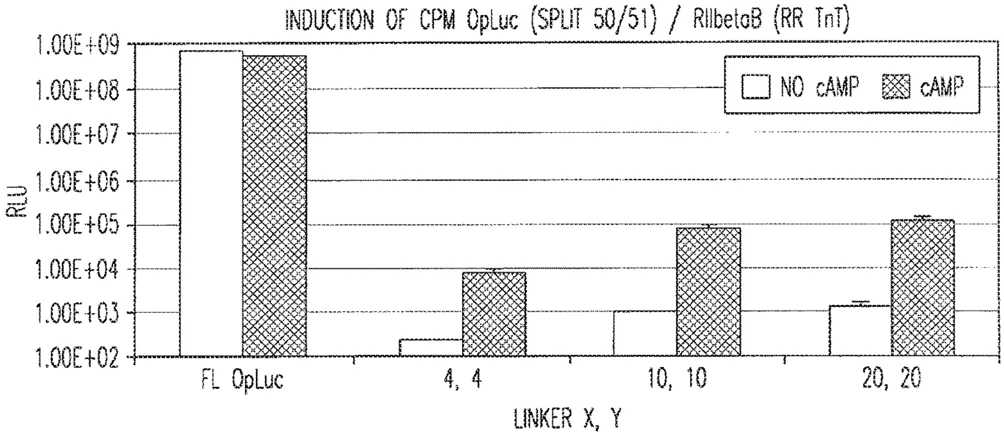
FIG. 64A-FIG. 64D. Results with RIIbetaB CP *Oplophorus* luciferase based vector. Left column indicates activity of the intact luciferase (control). Second column from left: corresponding construct with 4 aa linkers. Third column from left: -"- with 10 aa linker. Fourth column from left: -"- with 20 aa linker.
Figure 64B:
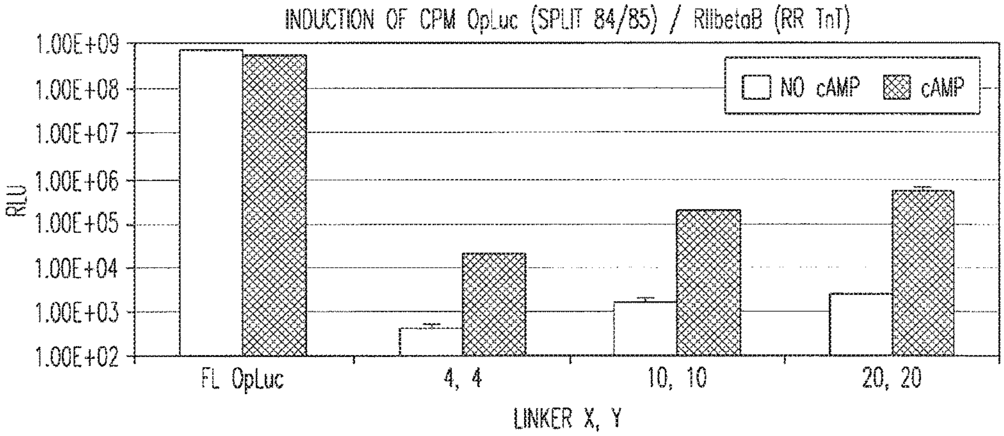
Figure 64C:
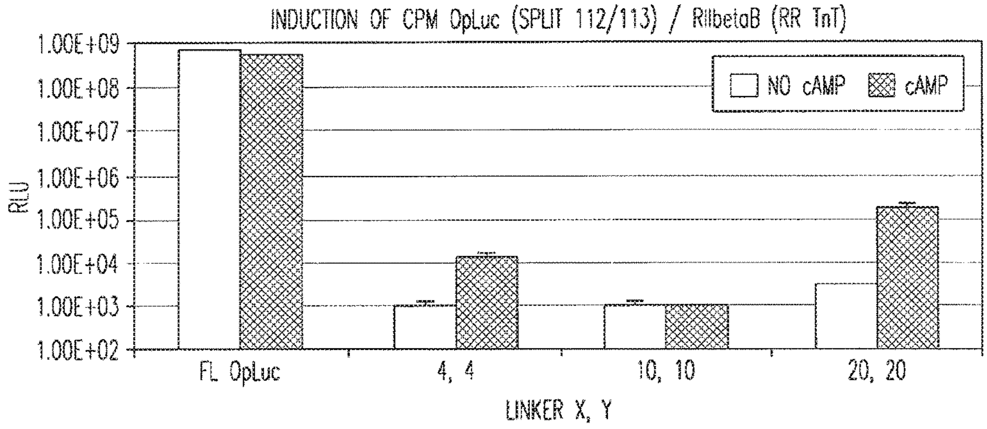
Figure 64D:
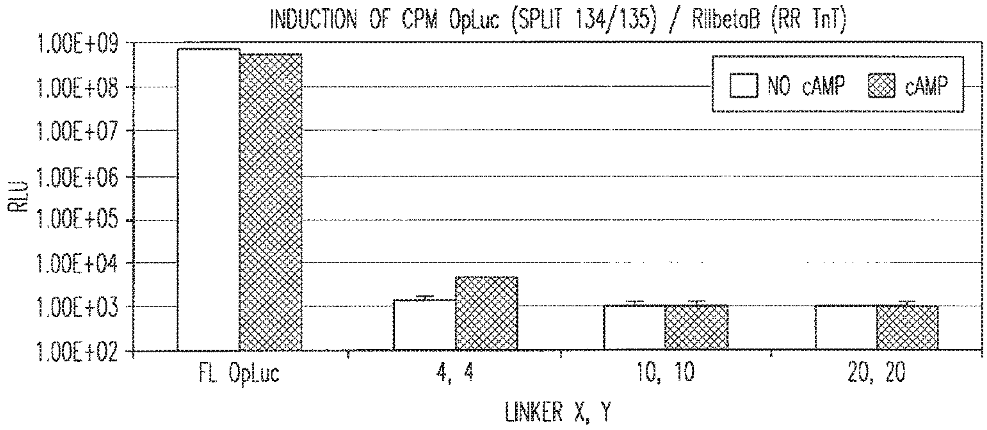

Other vectors include circularly permutated mutants of *Oplophorus* luciferase (OpLuc) with a RIIβB domain cloned into a pF4K-CMV plasmid to enable expression under T7 and CMV promoters. Various circularly permuted *Oplophorus* luciferase (OpLuc) constructs having RIIβB inserted into sites tolerant to modification were also prepared (CPM OpLuc/RIIβB). See FIG. 63. Numbers in brackets correspond to amino acid residues in the mature form of *Oplophorus* luciferase. The integers "4", "10" and "20" indicate the linkers of corresponding length. Note that Met and Val residues were added to N-terminus of the luciferase. Therefore, the position of each split in circularly permutated mutants is shifted for two amino acid residues. For example, the split marker "50-51" (referred to the residue order in the native mature form of the enzyme) occurred in-between residues 52 and 53 in the actual luciferase version used.

pF4K-CMV-[51-169]-4-RIIβB-4-[1-50]-OpLuc
pF4K-CMV-[51-169]-10-RIIβB-10-[1-50]-OpLuc
pF4K-CMV-[51-169]-20-RIIβB-20-[1-50]-OpLuc
pF4K-CMV-[85-169]-4-RIIβB-4-[1-84]-OpLuc
pF4K-CMV-[85-169]-10-RIIβB-10-[1-84]-OpLuc
pF4K-CMV-[85-169]-20-RIIβB-20-[1-84]-OpLuc
pF4K-CMV-[113-169]-4-RIIβB-4-[1-112]-OpLuc
pF4K-CMV-[113-169]-10-RIIβB-10-[1-112]-OpLuc
pF4K-CMV-[113-169]-20-RIIβB-20-[1-112]-OpLuc
pF4K-CMV-[135-169]-4-RIIβB-4-[1-134]-OpLuc
pF4K-CMV-[135-169]-10-RIIβB-10-[1-134]-OpLuc
pF4K-CMV-[135-169]-20-RIIβB-20-[1-134]-OpLuc pJ15:4809-OgLuc-2.7 kb plasmid with cloned full-size *Oplophorus* luciferase ORF (by DNA 2.0)

pJ15:4810-2.6 kb plasmid with the ORF of the mature *Oplophorus* luciferase ORF (27 aa signal peptide was deleted) (by DNA 2.0)

pF1K-OgLucS-3.7 kb. The full-size luciferase ORF was cloned into pF1K (FL OpLuc)

pF1K-OgLuc-3.6 kb. ORF of the mature luciferase was cloned into pF1K pF1K-OpLucDN-3.6 kb. Identical to pF1K-OgLuc except that first four N-terminal residues were deleted pF1K-OpLucDC-3.6 kb. Identical to pF1K-OgLuc except that last three C-terminal residues were deleted pF1K-OpLucDNDC-3.6 kb. Identical to pF1K-OgLuc except that first four N-terminal and last three C-terminal residues were deleted pFVDnK-OgLucS-4.4 kb. HaloTag was fused with the full-size luciferase ORF pFVDnK-OgLuc-4.5 kb. HaloTag was fused with ORF of the mature luciferase pFN6K-opLuc-3.6 kb. HQ-tag was introduced into N-terminus of ORF of the mature luciferase Equal amounts of CPM OpLuc/RIIβB constructs (0.1 μg of plasmid per 50 μl of reaction mixture; FIG. 64A-FIG. 64D) were expressed in a rabbit reticulocyte TnT system (Promega #L1170). After the TnT reactions were complete, cAMP was added to the final concentration of 0.1 mM and the mixtures were additionally incubated at room temperature for 15 minutes. The reactions were diluted ten fold with *Renilla* lysis buffer and luciferase activity was measured in *Renilla* reagent as recommended (*Renilla* Luciferase Assay System, #E2810, Promega Corp.).

Induction of luciferase activity was observed with all four circularly permutated luciferase constructs (FIG. 64A-FIG. 64D). The construct with the luciferase split between residues 84 and 85 demonstrated the highest induction (about 250 fold). The 20 amino acid linker supported the most efficient folding.

The results indicate that cAMP biosensors can be generated by either circular permutation or direct insertion of RIIβB into any of the above chosen insertion sites.

Example XXIII

Protein Complementation with *Oplophorus* Luciferase

To determine sites in *Oplophorus* luciferase useful for protein complementation, N- and C-terminal fusions were prepared. Vector backbones included pF3A for in vitro experiments and pF5K for in cell experiments. The following constructs were prepared: "N term-FRB", i.e., OpLuc (1-50 or 1-84) 10 aa G/S linker-FRB, "FKBP-C term", i.e., FKBP-(G4S)2 linker-OpLuc (51-170 or 85-170), "FRB-N term," i.e., FRB-(G4S)2 linker-OpLuc (1-50 or 1-84), and "C term-FKBP," i.e., OpLuc (51-170 or 85-170)-10aa G/S linker-FKBP. See table below.

| Construct | Vector | Type | Description | Figure legend |
|---|---|---|---|---|
| 201518.54.06 | pF5K | Full length | FL-OpLuc | FL OpLuc |
| 201518.57.E6 | pF5K | FRB-N term | FRB-OpLuc (1-50) | FRB-50 |
| 201518.57.G3 | pF5K | FRB-N term | FRB-OpLuc (1-84) | FRB-84 |
| 201518.101.04 | pF5K | FKBP - C term | FKBP-OpLuc (51-170) | FKBP-51 |
| 201518.57.H12 | pF5K | FKBP - C term | FKBP-OpLuc (85-170) | FKBP-85 |
| pBFB395 | pF5K | N term-FRB | OpLuc (1-50) - FRB | 50-FRB |
| pBFB396 | pF5K | N term-FRB | OpLuc (1-84) - FRB | 84-FRB |
| pBFB415 | pF5K | C term - FKBP | OpLuc (51-170) - FKBP | 51-FKBP |
| pBFB416 | pF5K | C term - FKBP | OpLuc (85-170) - FKBP | 85-FKBP |
| 201518.45.08 | pF3A | Full length | FL-OpLuc | FL OpLuc |
| 201518.57.A2 | pF3A | FRB-N term | FRB-OpLuc (1-50) | FRB-50 |
| 201518.57.A11 | pF3A | FRB-N term | FRB-OpLuc (1-84) | FRB-84 |
| 201518.57.D9 | pF3A | FKBP - C term | FKBP-OpLuc (51-170) | FKBP-51 |
| 201518.61.H3 | pF3A | FKBP - C term | FKBP-OpLuc (85-170) | FKBP-85 |
| 201518.110.4-1 | pF3A | N term-FRB | OpLuc (1-50)-FRB | 50-FRB |
| 201518.104.04 | pF3A | N term-FRB | OpLuc (1-84)-FRB | 84-FRB |
| 201518.129.03 | pF3A | C term - FKBP | OpLuc (51-170) - FKBP | 51-FKBP |
| 201518.129.06 | pF3A | C term - FKBP | OpLuc (85-170) - FKBP | 85-FKBP |

Figure 56:
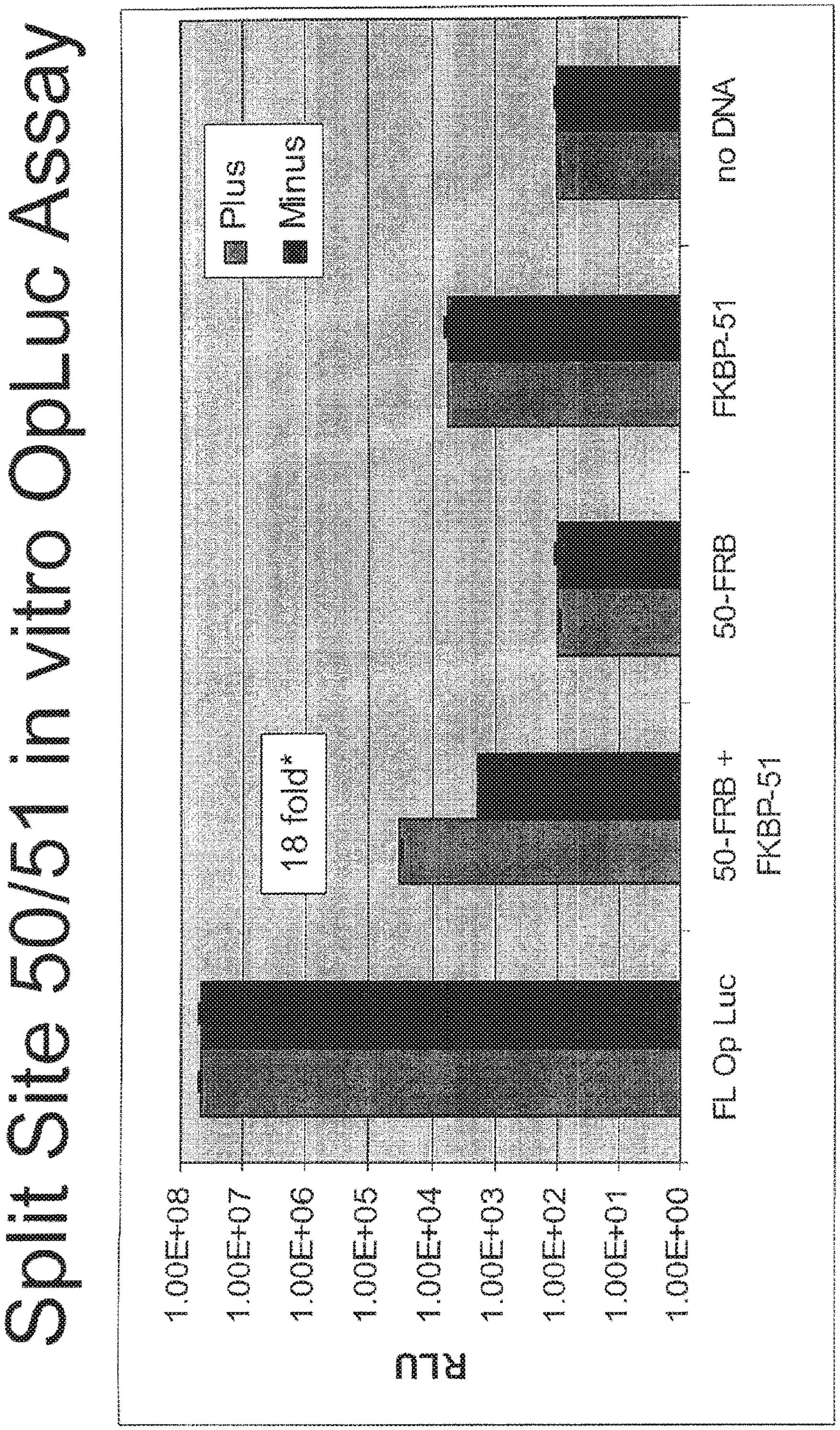
FIG. 56. RLU for *Oplophorus* luciferase fusions in an in vitro protein complementation assay (PCA). Fold induction was determined after background subtraction.
Figure 57:
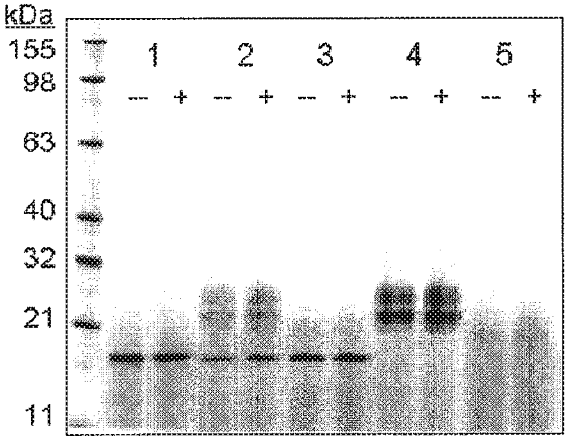
FIG. 57. SDS-PAGE analysis of *Oplophorus* luciferase (OpLuc) fusions. Lane 1) full length OpLuc; lane 2) co-expressed 50-FRB and FKBP-51; lane 3) 50-FRB; lane 4) FKBP-51; and lane 5) no DNA control.
Figure 58:
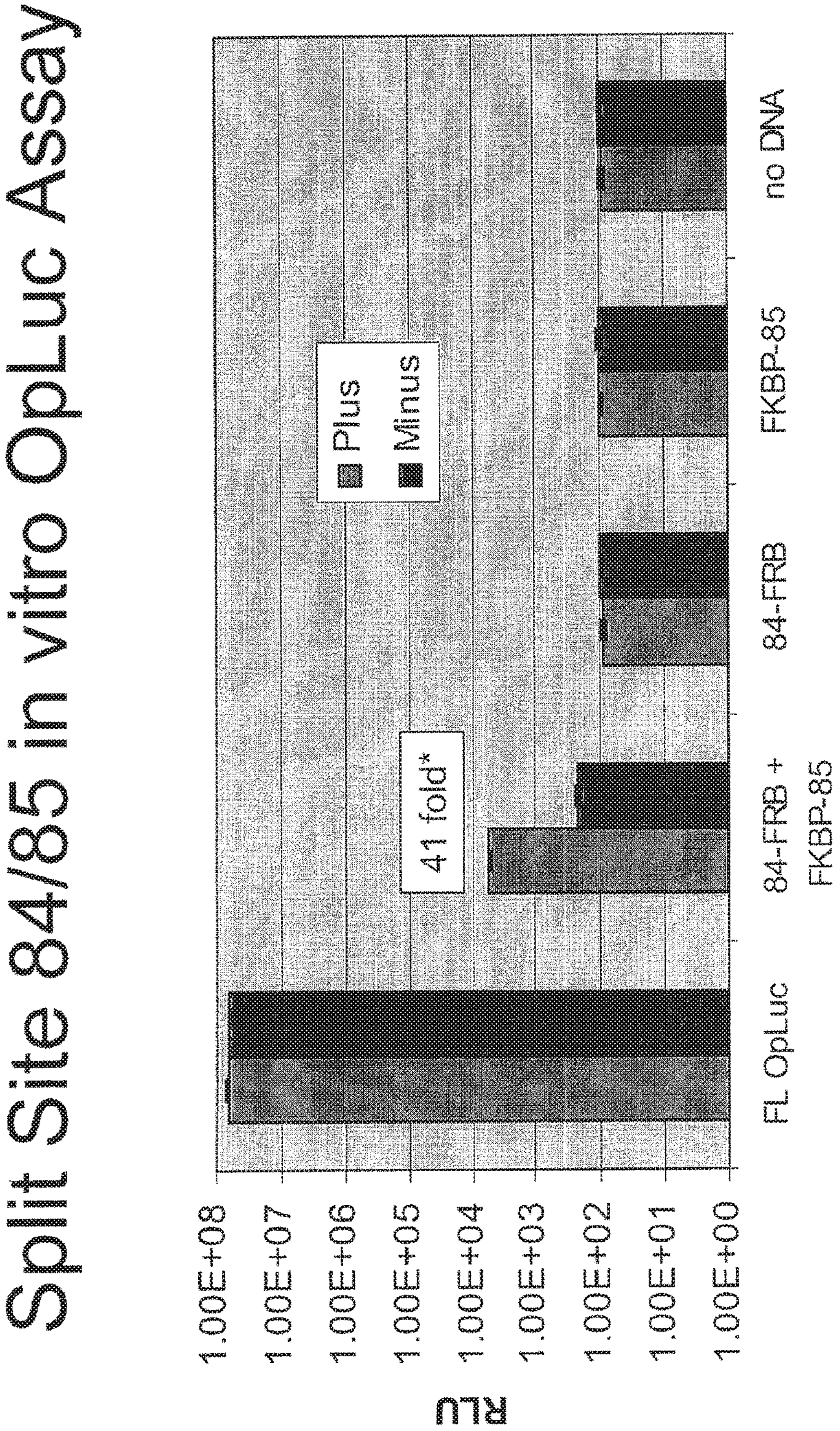
FIG. 58. RLU for *Oplophorus* luciferase fusions in an in vitro PCA. Fold induction was determined after background subtraction.
Figure 59:
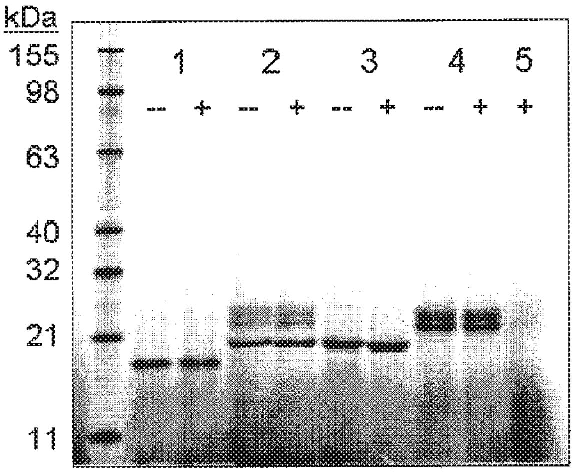
FIG. 59. SDS-PAGE analysis of *Oplophorus* luciferase fusions. Lane 1) full length OpLuc; lane 2) co-expressed 84-FRB and FKBP-85; lane 3) 84-FRB; lane 4) FKBP-85; and lane 5) no DNA control.
Figure 61:
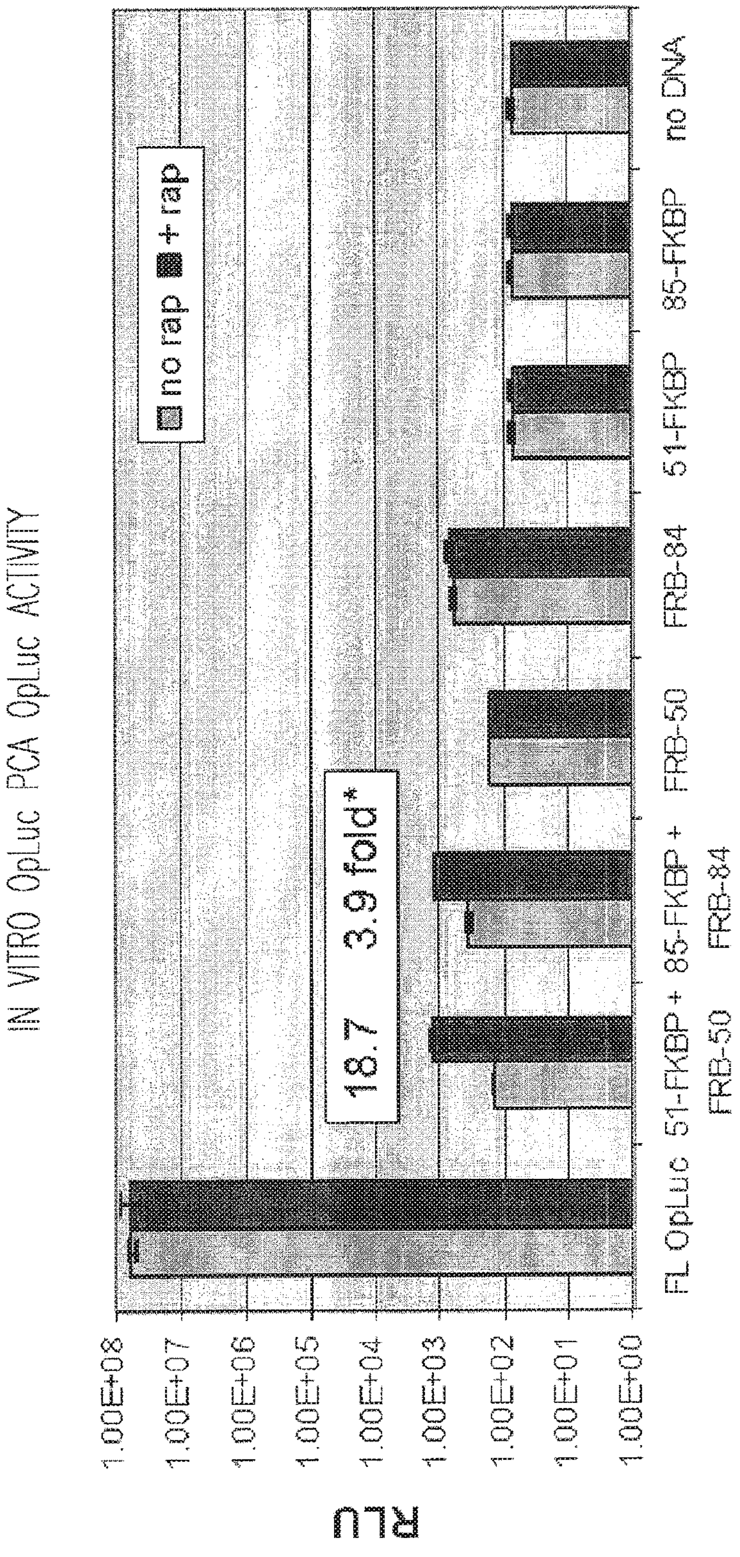
FIG. 61. RLU for *Oplophorus* luciferase circular permuted-like fusions in an in vitro PCA. Fold induction was determined after background subtraction.
Figure 62:
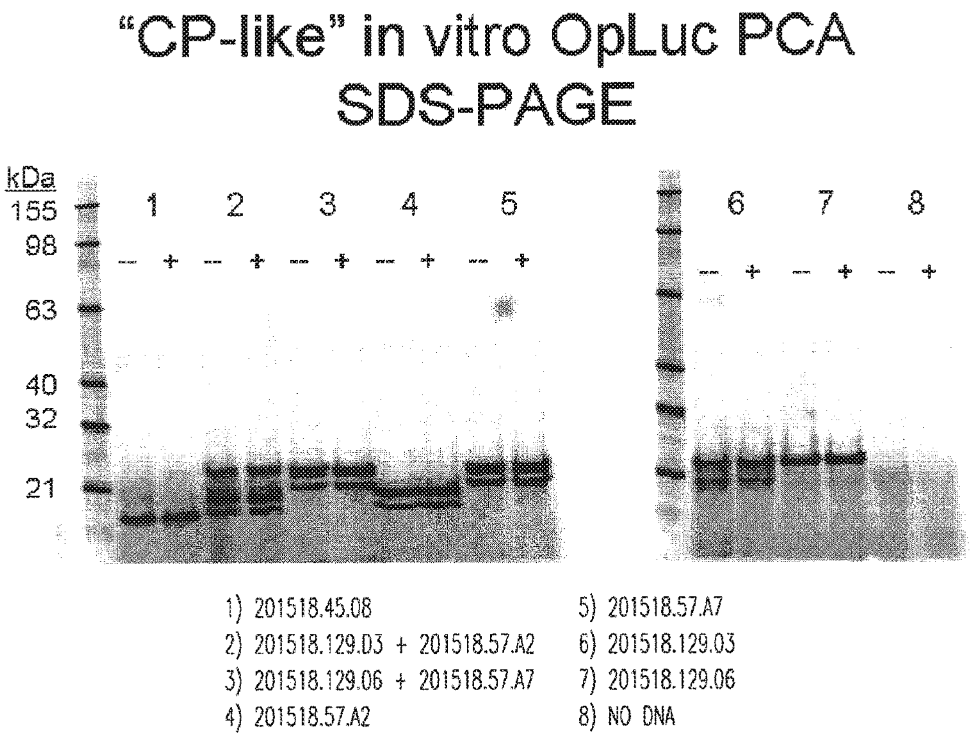
FIG. 62. SDS-PAGE analysis of *Oplophorus* luciferase circular permuted-like fusions. Lane 1) full length OpLuc; lane 2) co-expressed 51-FKBP and FRB-50; lane 3) co-expressed 85-FKBP and FRB-84; lane 4) FRB-50; lane 5) FRB-84; lane 5) 51-FKBP; lane 7) 85-FKBP; and lane 8) no DNA control. 84-FRB; lane 4) FKBP-85; and lane 5) no DNA control.

Proteins were either singly expressed or co-expressed using the TnT® SP6 High-Yield Protein Expression System at 30° C. for 2 hours (as per the manufacturer's protocol; Promega Corp.). Twenty μL lysate was incubated +/−1 μM rapamycin for 15 minutes at room temperature. Ten μL lysate was diluted 1:1 in 2×HEPES/thiourea and 5 μL was placed in a 96-well plate well, in triplicate. Luminescence was measured by addition of 100 μL *Renilla* Luciferase Assay Reagent (R-LAR) by injectors. The in vitro results for a split at positions 50/51 (50-FRB+FKBP-51) are shown in FIG. 56 and those for 84/85 (84-FRB+FKBP-85) are shown in FIG. 58. FIG. 57 and FIG. 59 show the results for the respective SDS-PAGE analyses. Five μL−/+rapamycin lysate was size fractionated on 4-12% SDS-PAGE. FIG. 61 and FIG. 62 show in vitro results for the 51-FKBP+FRB-50 and 85-FKBP+FRB-85 orientations. For the data in FIG. 62, 7.5 μL+/−rapamycin lysate was size fractionated on 4-12% SDS-PAGE.

Figure 60:
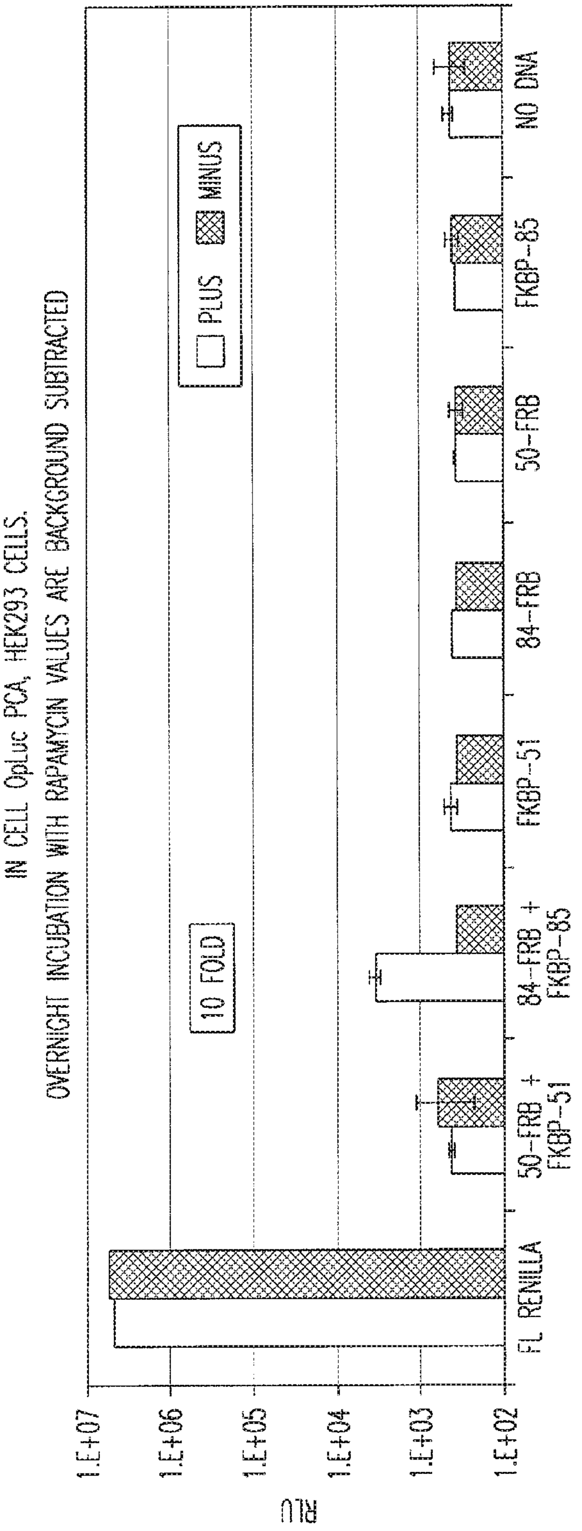
FIG. 60. RLU for *Oplophorus* luciferase fusions in a cell based PCA. N=3. ss=split site. Fold induction was determined after background subtraction.

FIG. 60 shows the in-cell results using HEK-293 cells. HEK-293 cells were transiently transfected with complimenting fragments or with the individual fragments of *Oplophorus* luciferase in a 6-well plate and incubated overnight. The next day cells were trypsinized and plated in a 96-well plate at 20,000 cells per well. At the same time 1 μM rapamycin or vehicle (DMSO) was added to the cells and they were allowed to recover overnight at 37° C. with 5% $CO_2$. The next day media was removed and 20 μL of 1× *Renilla* Luciferase Assay Lysis buffer was added to each sample and the plate was shaken for 15 minutes at 500 rpm. 100 μL of *Renilla* Luciferase Assay Reagent was injected into each well and samples were measured for 3 sec/well with a 0.5 second delay.

Example XXIV

The CPM firefly luciferase (FF Luc) and *Renilla* luciferase (hRL Luc) were also used as biosensors to assay kinase/phosphatase activities. In a manner similar to previous biosensors of cAMP, cGMP, and calcium, various circularly permuted (CPM) FF Luc and hRL Luc constructs were made to detect phosphorylation by tyrosine or serine/threonine kinases (phosphorylation on the underlined Tyr or Thr residues, respectively, in the constructs described below). The conformational change, caused by the binding of the phosphorylated peptide sequence with the tethered phosphopeptide recognition domain, may cause a modulation of the fused biosensor luciferase activity. This represents a novel class of reagents able to measure the activity of kinases, perhaps with enhanced performance characteristics relative to existing FRET-based biosensors.

The peptide sequences and recognition domains used for the tyrosine kinase and serine/threonine kinase were, respectively: peptide GSTSGSGKPGSGEGSEIYGEF (SEQ ID NO:295) or EIYGEF (SEQ ID NO:296) with phosphopeptide recognition domain human Src SH2 domain (Genbank NM_005417; aa residues 151-248) and RKRDRLGTLGI (SEQ ID NO:297) with phosphopeptide recognition domain FHA2 from Rad53p (codon optimized version of the nucleic acid sequence Genbank accession # AY693009 which aligns to bases 1717-2186; aa residues 573-730 of accession #AAT93028).

The multiple sites for CPM that were previously identified as functional for generating biosensors in FF Luc and hRL Luc were used for the construction of kinase biosensors. These constructs were either made using PCR products ligated into unique restriction sites or Splicing by Overlapping Extension PCR (SOE-PCR). The FF Luc constructs were made in the pF9A backbone and the hRL Luc constructs were made in the pF5A backbone, except for plasmids pBFB174, 175, 176, 178, 179, 180, 181, 182, 228, 229 and 230 which were made in the modified pGL4.74 backbone described in Example II.

The following constructs were made: Met-(Luc2.0 or hRL C-terminal fragment)-(Linker X)-(peptide phosphorylated by kinase)-(linker)-(phosphopeptide recognition domain)-(Linker Y)-(Luc2.0 or hRL N-terminal fragment)-Val. Constructs were also made in which the order of the peptide phosphorylated by the kinase and the phosphopeptide recognition domain were switched. In addition, the following constructs were made for the tyrosine kinase FF Luc biosensor: Met-(short peptide phosphorylated by kinase)-(linker X)-(Luc2.0)-(linker)-(phosphopeptide recognition domain)-Val. See FIG. 65.

Tyrosine Kinase Constructs

1) Met-(Luc2.0 234-544)-GSSG-(human Src SH2 domain)-GSG-GSTSGSGKPGSGEGSEIYGEF-(Linker Y)-(Luc2.0 4-233)-Val, where Y=GSGGSGGSSG (SEQ ID NO:291), or GSGGSGGSGGGSGGSGGSSG (SEQ ID NO:286). (GSSG corresponds to SEQ ID NO:270; GSGGSTSGSGKPGSGEGSEIYGEF corresponds to SEQ ID NO:298). Clones pBFB180, 181, 182, 365, 366, 367.

2) Met-EIYGEF-(Linker X)-(Luc2.0 4-544)-GSSG-(human Src SH2 domain), where X=GSSG (SEQ ID NO:270), GSSGGSGGSG (SEQ ID NO:276), or GSSGGSGGSGGGSGGSGGSG (SEQ ID NO:277). (EIYGEF corresponds to SEQ ID NO:296). Clones pBFB174, 175, 176.

3) Met-(hRL 92-311)-GSG-(human Src SH2 domain)-GSG-GSTSGSGKPGSGEGSEIYGEF-(Linker X)-GSSG-(hRL 2-91)-Val, where X=GSSG (SEQ ID NO:270), GSGGSGGSSG (SEQ ID NO:291), or GSGGSGGSGGGSGGSGGSSG (SEQ ID NO:286). (GSGGSTSGSGKPGSGEGSEIYGEF corresponds to SEQ ID NO:298). Clones pBFB228, 229, 230.

4) Met-(Luc2.0 A-544)-(Linker X)-(human Src SH2 domain)-GSTSGSGKPGSGEGSEIYGEF-(Linker Y)-(Luc2.0 4-B)-Val, where X=GSTG (SEQ ID NO:275), GSSGGSGGSG (SEQ ID NO:276), or GSSGGSGGSGGGSGGSGGSG (SEQ ID NO:277) and Y=GSSG (SEQ ID NO:270), GSGSGGSGGSSG (SEQ ID NO:299), or GSGGSGGSGGGSGGSGGSSG (SEQ ID NO:286). (GSTSGSGKPGSGEGSEIYGEF corresponds to SEQ ID NO:295). CPM sites [A, B]=[235, 233], [359, 355], [84, 82], [309, 307]. Clones pBFB368, 369, 370, 371, 372, 373, 374, 375, 376, 377, 378, 379.

5) Met-(hRL A-311)-(Linker X)-(human Src SH2 domain)-GSTSGSGKPGSGEGSEIYGEF-(Linker Y)-(hRL 3-B)-Val, where X=GSSG (SEQ ID NO:270), GSSGGSGGSG (SEQ ID NO:276), or GSSGGSGGSGGGSGGSGGSG (SEQ ID NO:277) and Y=GSSG (SEQ ID NO:270), GSGSGGSGGSSG (SEQ ID NO:299), or GSGGSGGSGGGSGGSGGSSG (SEQ ID NO:286). (GSTSGSGKPGSGEGSEIYGEF corresponds to SEQ ID NO:295). CPM sites [A, B]=[92, 91], [42, 41], [111, 110], [31, 30], [69, 68]. Clones pBFB380, 381, 382, 383, 384, 385, 386, 387, 388, 389, 390, 391, 392, 393, 394.

Serine/Threonine Kinase Constructs

1) Met-(Luc2.0A-544)-(linker X)-RKRDRLGTLGI-(GGSSGGGSGGGGSGG)-(Rad53p FHA2 domain)-(linker Y)-(Luc2.04-B), where X=GSSG (SEQ ID NO:270), GGSGGSGSSG (SEQ ID NO:300), or GSSGGSGGSGGGSGGSGSSG (SEQ ID NO:301), Y=GSSG (SEQ ID NO:270), GSGGSGGSGG (SEQ ID NO:281), or GSGGSGGSGGTSGGSGGSSG (SEQ ID NO:278). (RKRDRLGTLGIGGSSGGGSGGGGSGG corresponds to SEQ ID NO:283) CPM sites were [A, B]=[235, 233], [359, 355], [84, 82], [309, 307]. Clones pBFB335, 336, 337, 338, 339, 340, 341, 342, 343, 344, 345, 346.

2) Met-(hRL A-311)-(linker X)-RKRDRLGTLGI-(GGSSGGGSGGGGSGG)-(Rad53p FHA2 domain)-(linker Y)-(hRL 3-B), where X=GSSG (SEQ ID NO:270), GSSGGSGGSGGG (SEQ ID NO:302), or GSSGGSGGSGGGSGGSGGSG (SEQ ID NO:277), Y=GSSG (SEQ ID NO:270), GSGGSGGSSG (SEQ ID NO:291), or GSGGSGGSGGTSGGSGGSSG (SEQ ID NO:278). (RKRDRLGTLGIGGSSGGGSGGGGSGG corresponds to SEQ ID NO:283). CPM sites were [A, B]=[92, 91], [42, 41], [111, 110], [31, 30], [69, 68]. Clones pBFB350, 351, 352, 353, 354, 355, 356, 357, 358, 359, 360, 361, 362, 363, 364.

3) Met-(Luc2.0A-544)-(linker X)-(Rad53p FHA2 domain)-GGSSG-RKRDRLGTLGI-(linker Y)-(Luc2.04-B), where X=GSGG (SEQ ID NO:293), GGSGGGGSGG (SEQ ID NO:294), or GSSGGSGGSGGGSGGSGGSG (SEQ ID NO:277), Y=GGSSG (SEQ ID NO:304), GSSGSGGSGG (SEQ ID NO:305), or GSGGSGGSGGTSGGSGGSSG (SEQ ID NO:278). (GGSSGRKRDRLGTLGI corresponds to SEQ ID NO:303). CPM sites were [A, B]=[235, 233], [359, 355]. Clones pBFB417, 418, 419, 420, 421, 422.

4) Met-(hRL A-311)-(linker X)-(Rad53p FHA2 domain)-GGSSG-RKRDRLGTLGI-(linker Y)-(hRL 3-B), where X=GSGG (SEQ ID NO:293), GGSGGGGSGG (SEQ ID NO:294), or GSSGGSGGSGGGSGGSGGSG (SEQ ID NO:277), Y=GGSSG (SEQ ID NO:304), GSSGSGGSGG (SEQ ID NO:305), or GSGGSGGSGGTSGGSGGSSG (SEQ ID NO:278). (GGSSGRKRDRLGTLGI corresponds to SEQ ID NO:303). CPM sites were [A, B]=[42, 41], [111, 110]. Clones pBFB423, 424, 425, 426, 427, 428.

In Vitro Testing of a Subset of Serine/Threonine Kinase Sensors

Constructs pBFB335, 336, 338, 339, 340, 417, 418, 419, 422, 22 and 8 were tested in vitro using TNT® T7 Coupled Reticulocyte Lysate System (Promega Corp.). Briefly, the following components were assembled according to the manufacturer's recommended protocol:

1 μg plasmid DNA
25 μL Rabbit Retic Extract
2 μL TNT reaction buffer
1 μL T7 polymerase
1 μL amino acid mixture
1 μL rRNasin
$dH_2O$ to 50 μL total volume Following incubation at 30° C. for 1 hour, the respective fusion proteins were incubated in the presence or absence of 10 ng Akt1/PKB alpha recombinant enzyme (Upstate Biotechnology) by combining 2 μL of TNT® reaction with 8 μL water+4 μL 5× Reaction Buffer (40 mM MOPS/NaOH pH 7.0, 1 mM EDTA)+4 μL 5×Mg-ATP (50 mM Mg acetate, 0.5 mM ATP)+2 μL 5 ng/μL enzyme (diluted from 100 ng/ul stock diluted in PKB dilution buffer [20 mM MOPS (7.0), 1 mM EDTA, 5% glycerol, 0.05% DTT, 1 mg/ml BSA]) or 2 μL PKB dilution buffer only. Samples were then incubated at 30° C. for 20 minutes. Five μL of sample was added to 100 μL of Luciferase Assay Reagent (LAR; Promega Corp.) solution and pipetted up and down 4× rapidly to mix. Luminescence was measured using a Turner 20/20N luminometer (Turner Biosystems; 1 second integration time). All samples were measured in triplicate.

Results

Figure 66:
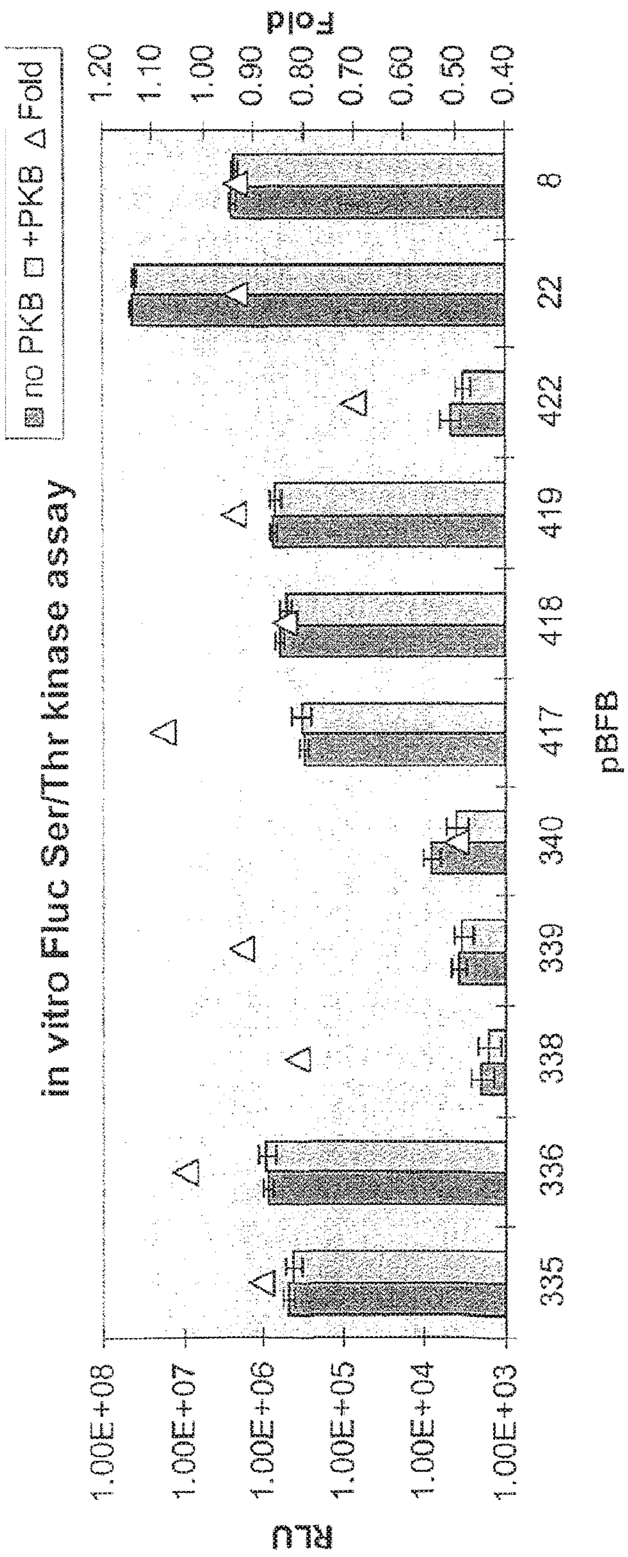
FIG. 66. In vitro Fluc serine/threonine kinase assay.

Construct pBFB340 showed a 50% decrease in luminescence plus Akt1/PKB as compared to no Akt1/PKB. The control constructs pBFB22 and pBFB8 did not change with Akt1/PKB addition (FIG. 66).

The protocol for other Serine/Threonine kinase sensors is identical to the one above except that for the CPM hRL Luc samples, 5 μL of sample are added to a 96 well plate+5 μL 2× *Renilla* lysis buffer without detergents (150 mM HEPES, 100 mM Thiourea) and 100 μL *Renilla* Assay Reagent (Promega Corp.) is added by injectors using a Veritas Microplate Luminometer and luminescence is measured (Turner Biosystems; Bright-Glo program; 3 second integration time). FF Luc samples are measured by adding 100 μL of Luciferase Assay Reagent (LAR; Promega Corp.), to 5 μL of sample in a 96 well plate, by injectors using a Veritas Microplate Luminometer and luminescence measured (Turner Biosystems; Bright-Glo program; 3 second integration time).

The tyrosine kinase sensors are tested as follows: Proteins are expressed in vitro using TNT® T7 Coupled Reticulocyte Lysate System (Promega Corp.). Briefly, the following components are assembled according to the manufacturer's recommended protocol:

1 μg plasmid DNA
25 μL Rabbit Retic Extract

2 μL TNT reaction buffer
1 μL T7 polymerase
1 μL amino acid mixture
1 μL rRNasin
$dH_2O$ to 50 μL total volume Following incubation at 30° C. for 1 hour, the respective fusion proteins are used in 50 μl kinase reactions as follows: 1× ProFlour reaction buffer (Promega Corp.)+10 μl RR TnT reaction+100 μM sodium vanadate+1 mM $MnCl_2$+1 mM MgATP+0.5 μl c-Src Kinase or water. At 0, 30 and 60 minutes after addition of Src Kinase, 10 μl aliquots are taken and stored at −20° C. until assayed. For the CPM FF Luc samples, 5 μl is transferred to a 96 well plate and 100 ul Luciferase Assay Reagent (LAR; Promega Corp.) is added by injectors using a Veritas Microplate Luminometer and luminescence will be measured (Turner Biosystems; Bright-Glo program; 3 second integration time). For the CPM hRL Luc samples, 5 μL of sample is added to a 96 well plate+5 μL 2× *Renilla* lysis buffer without detergents (150 mM HEPES, 100 mM Thiourea) and 100 μL *Renilla* Assay Reagent (Promega Corp.) is added by injectors using a Veritas Microplate Luminometer and luminescence was measured (Turner Biosystems; Bright-Glo program; 3 second integration time).

To test kinase sensors in cells, the FF Luc and CPM hRL Luc serine/threonine kinase biosensors are tested as follows: HEK293 and NIH/3T3 cells are plated in 96 well plates at a cell density of 1-1.5×$10^4$ cells per well in $CO_2$-independent media (Invitrogen)+10% FBS. They are then transfected with TransIt®-LT1 Reagent (MIRUS) using 4.2 μL TransIt®-LT1 reagent and 1.4 DNA per well. Cells are allowed to grow overnight at 37° C./10% $CO_2$. The next day the media is changed to $CO_2$-independent media+0.2% FBS to serum-starve the cells. The cells are then allowed to grow overnight at 37° C./10% $CO_2$. Approximately 2 days after transfection, the cells are equilibrated with a final concentration of 5 mM Luciferin-EF (Promega Corp.) for the FF Luc sensors or 60 μM EnduRen (Promega Corp.) for the CPM hRL Luc sensors. All cells are allowed to equilibrate for 1.5 hours at 37° C./10% $CO_2$. After 1.5 hours, baseline measurements of luminescence are measured using a Mithras LB 940 Luminometer (Berthold Technologies; integration time of 1 second per well) at 37° C. Next, half of the cells are treated with a kinase activator such as Platelet-Derived Growth Factor (PDGF, 50 ng/ml final concentration). Luminescence will then be measured continuously for the next 30 minutes at 37° C.

Example XXV

Determination of Suitable Split Points for Creating Circularly Permuted Proteins in the Absence of Three-Dimensional Protein Structure Information Method 1) Obtain the amino acid sequence of the protein of interest.
2) Use one or more computer programs to predict protein structure features that aid in the determination of suitable split points. Suitable split points are likely exposed on the protein surface. Split points that lie outside of regular secondary structure elements such as helices and sheets are less likely to disrupt protein structure and function.
   Predict surface exposed protein regions: exposed regions are likely to be hydrophilic. The distribution of hydrophilic and hydrophobic residues along a protein sequence (hydrophobicity plot/score) can be computed based on commonly used hydrophobicity scales using programs available at open access websites (e.g. ProtScale from the ExPASy proteomics server of the Swiss Institute of Bioinformatics and as part of commercial sequence analysis packages (e.g. Lasergene from DNASTAR).
   Predict protein secondary structure: such programs are available at open access websites (see list on ExPASy Proteomics Tools website and as part of commercial sequence analysis packages (e.g. Lasergene from DNASTAR).
3) Select split points based on the results from one or more prediction methods.

Example

1) Protein sequence: *Oplophorus gracilorostris* mature luciferase sequence (Genbank accession BAB13776, residues 28-196 (SEQ ID NO: 318)).
2) Predict surface exposed protein regions: calculate per-residue hydrophobicity score based on the Kyte-Doolittle hydrophobicity scale using window sizes of 5 and 7, which specify the range recommended for finding putative surface-exposed regions (Kyte J and Doolittle R F: A simple method for displaying the hydropathic character of a protein. J. Mol. Biol. 157:105, 1982).
   Predict protein secondary structure: use five different prediction algorithms:
   a. PSIPRED (Jones D T. (1999) Protein secondary structure prediction based on position-specific scoring matrices. J. Mol. Biol. 292: 195-202. McGuffin L J, Bryson K, Jones D T).
   b. JPRED (Cuff J A, Clamp M E, Siddiqui A S, Finlay M and Barton G J. 1998. Jpred: A Consensus Secondary Structure Prediction Server, Bioinformatics 14:892-893).
   c. PORTER (G Pollastri, A McLysaght. "Porter: a new, accurate server for protein secondary structure prediction". Bioinformatics, 21(8), 1719-20, 2005).
   d. SCRATCH (G Pollastri, D Przybylski, B Rost, P Baldi: Improving the prediction of protein secondary structure in three and eight classes using recurrent neural networks and profiles. Proteins, 47, 228-335, 2002).
   e. PROF (M Ouali, R King: Cascaded multiple classifiers for secondary structure prediction. Protein Science, 9, 1162-1176, 1999).
3) Compile results of protein structure feature predictions in a table for comparison. Select suitable split points in areas that are hydrophilic (low hydrophobicity score) and lie outside of predicted regular secondary structure elements (helices and sheets). See Table 9 (in three sections below).

TABLE 9

Compiled structure feature prediction results for *Oplophorus gracilorostris* mature luciferase. Secondary structure prediction results code is H = helix, E = sheet, C = coil, blank = coil. Hydrophobicity prediction score is >0 for hydrophobic and <0 for hydrophilic areas. Suitable split point examples are marked xxx in rightmost column.

| | | | | | | | Hyphobicity K-D | | |
|---|---|---|---|---|---|---|---|---|---|
| Seq # | Mature Seq | PSTPRED | JPRED | PORTER | SCRATCH | PROF | win = 7 | win = 5 | |
| 1 | F | C | | C | C | C | | | |
| 2 | T | C | | C | C | E | | | |
| 3 | L | H | | C | H | E | | 0.84 | |
| 4 | A | H | | H | H | E | | 0.84 | |
| 5 | D | H | | H | C | E | 0.81 | 1.82 | |
| 6 | F | H | | C | C | E | 0.40 | 0.98 | |
| 7 | V | H | | C | C | C | 0.09 | −0.08 | |
| 8 | G | C | | C | C | C | −0.72 | 0.44 | |
| 9 | D | C | | C | C | C | −1.00 | −0.82 | |
| 10 | W | H | | H | H | C | −0.41 | −2.36 | |
| 11 | Q | H | | H | H | H | −0.77 | −2.42 | |
| 12 | Q | H | | H | H | C | −1.38 | −1.36 | |
| 13 | T | H | | H | H | C | −1.72 | −1.26 | |
| 14 | A | C | | C | C | C | −1.72 | −0.82 | |
| 15 | G | C | | C | C | C | −2.01 | −0.82 | |
| 16 | Y | C | | C | C | C | −2.01 | −1.38 | |
| 17 | N | C | | C | C | C | −1.16 | −2.44 | |
| 18 | Q | H | | H | H | C | −0.66 | −3.06 | |
| 19 | D | H | H | H | H | E | −1.24 | −1.96 | |
| 20 | Q | H | H | H | H | E | −1.59 | −0.5 | |
| 21 | V | H | H | H | H | E | −1.49 | −0.5 | |
| 22 | L | H | H | H | H | E | −1.14 | −0.5 | |
| 23 | E | H | H | H | H | E | −0.33 | 0.12 | |
| 24 | Q | C | H | C | C | C | −0.03 | −0.8 | |
| 25 | G | C | | C | C | C | 0.27 | −0.8 | |
| 26 | G | C | | C | C | C | 0.22 | −0.26 | |
| 27 | L | H | | H | H | C | 0.11 | 0.28 | |
| 28 | S | H | H | H | H | H | 0.11 | 1.12 | |
| 29 | S | H | H | H | H | H | 0.70 | 1.76 | |
| 30 | L | H | H | H | H | H | 1.17 | 0.3 | |
| 31 | F | H | H | H | H | H | 1.17 | 0.82 | |
| 32 | Q | H | H | H | H | H | 1.21 | 1.74 | |
| 33 | A | H | H | H | H | H | 1.21 | 0.9 | |
| 34 | L | H | H | H | H | H | 1.77 | 1.18 | |
| 35 | G | C | | C | C | C | 1.27 | 1.72 | |
| 36 | V | C | | C | C | C | 0.78 | 2.2 | |
| 37 | S | C | | C | C | E | 1.67 | 1.3 | |
| 38 | V | C | | C | C | E | 1.08 | 1.06 | |
| 39 | T | C | | C | C | E | 0.22 | 1.12 | |
| 40 | P | C | | C | C | C | 0.73 | 0.58 | |
| 41 | I | H | E | C | C | C | 0.73 | −1.04 | |
| 42 | Q | H | E | E | E | E | 1.24 | −0.06 | |
| 43 | K | H | E | E | E | E | 0.69 | 1.1 | |
| 44 | V | H | E | E | E | E | 0.72 | 0.96 | |
| 45 | V | E | E | E | E | E | 0.51 | 1.5 | |
| 46 | L | E | E | E | E | E | −0.38 | 2.2 | |
| 47 | S | C | | C | C | E | −0.03 | 0.66 | |
| 48 | G | C | | C | C | C | 0.82 | −0.88 | |
| 49 | E | C | | C | C | C | −0.08 | −1.72 | |
| 50 | N | C | | C | C | C | −0.34 | −0.8 | |
| 51 | G | C | | C | C | C | 1.16 | −1.5 | xxx |
| 52 | L | C | | C | C | C | −0.57 | −0.44 | xxx |
| 53 | K | E | E | C | C | C | −0.88 | −0.44 | |
| 54 | A | E | | C | C | C | −0.02 | 0.54 | |
| 55 | D | E | E | E | C | E | 0.87 | −0.86 | |
| 56 | I | E | E | E | E | E | 1.41 | 0.76 | |
| 57 | H | E | E | E | E | E | 0.81 | 1.3 | |
| 58 | V | E | E | E | E | E | 1.10 | 2.9 | |
| 59 | I | E | E | E | E | E | 0.51 | 1.68 | |
| 60 | I | E | E | E | E | E | 0.86 | 2.06 | |
| 61 | P | E | E | E | E | E | 0.78 | 0.52 | |
| 62 | Y | C | | C | C | E | 1.04 | −0.46 | |
| 63 | E | C | | C | C | C | 0.53 | −0.6 | |
| 64 | G | C | | C | C | C | 0.34 | −0.44 | |
| 65 | L | C | | C | C | C | −0.54 | −0.26 | |
| 66 | S | C | | C | C | C | −0.16 | 1 | |
| 67 | G | C | | H | H | C | −0.06 | 0.38 | |
| 68 | F | H | H | H | H | C | 0.76 | 0 | |
| 69 | Q | H | H | H | H | C | 1.30 | 0.08 | |
| 70 | M | H | H | H | H | C | 0.49 | 0.92 | |

TABLE 9-continued

Compiled structure feature prediction results for *Oplophorus gracilorostris* mature luciferase. Secondary structure prediction results code is H = helix, E = sheet, C = coil, blank = coil. Hydrophobicity prediction score is >0 for hydrophobic and <0 for hydrophilic areas. Suitable split point examples are marked xxx in rightmost column.

| | | | | | | | Hyphobicity K-D | | |
|---|---|---|---|---|---|---|---|---|---|
| Seq # | Mature Seq | PSTPRED | JPRED | PORTER | SCRATCH | PROF | win = 7 | win = 5 | |
| 71 | G | H | H | H | H | C | 0.79 | 1.26 | |
| 72 | L | H | H | H | H | H | 1.33 | 1.26 | |
| 73 | I | H | H | H | H | H | 1.33 | 1.26 | |
| 74 | E | H | H | E | H | E | 1.29 | 2.24 | |
| 75 | M | H | H | E | H | E | 1.54 | 2.04 | |
| 76 | I | H | E | E | H | E | 2.06 | 0.36 | |
| 77 | F | H | E | E | H | E | 1.49 | 1.9 | |
| 78 | K | H | E | E | E | E | 0.81 | 2.36 | |
| 79 | V | H | E | E | E | E | 1.67 | 1.2 | |
| 80 | V | H | E | E | E | E | 1.07 | 0.32 | |
| 81 | Y | C | E | C | C | E | 0.18 | 1.94 | |
| 82 | P | C | E | C | C | E | −0.49 | 0.4 | |
| 83 | V | C | | C | C | C | −0.41 | −1.14 | 1st choice |
| 84 | D | C | | C | C | C | −0.57 | −1.52 | xxx |
| 85 | D | C | | C | C | C | −1.47 | −1.84 | xxx |
| 86 | H | C | | C | C | C | −0.82 | −2.12 | |
| 87 | H | C | | C | C | E | −0.14 | −2.2 | |
| 88 | F | E | E | E | E | E | −0.19 | −0.6 | |
| 89 | K | E | E | E | E | E | −0.16 | 0.94 | |
| 90 | I | E | E | E | E | E | 0.09 | 2.34 | |
| 91 | I | E | E | E | E | E | 0.40 | 1.14 | |
| 92 | L | E | E | E | E | E | 0.68 | 1.66 | |
| 93 | H | E | E | E | E | E | 0.79 | 0.68 | |
| 94 | Y | E | | E | C | C | 1.69 | −0.36 | |
| 95 | G | C | | C | C | C | 1.69 | −0.36 | |
| 96 | T | E | E | E | E | E | 0.80 | 1.12 | |
| 97 | L | E | E | E | E | E | 0.33 | 2.28 | |
| 98 | V | E | E | E | E | E | 1.16 | 1.66 | |
| 99 | I | E | E | E | E | E | 1.22 | 1.72 | |
| 100 | D | C | E | C | C | E | 1.09 | 1.8 | |
| 101 | G | C | | C | C | C | 0.78 | 0.82 | |
| 102 | V | C | | C | C | C | 0.57 | −0.4 | |
| 103 | T | C | | C | C | C | 0.60 | −0.4 | |
| 104 | P | C | | C | C | C | −0.29 | 0.06 | |
| 105 | N | H | | C | C | C | −0.04 | 0.12 | |
| 106 | M | H | | H | H | C | 0.31 | −0.44 | |
| 107 | I | H | | H | H | H | −0.20 | −0.38 | |
| 108 | D | H | | H | H | E | −0.62 | 0.88 | |
| 109 | Y | H | | C | H | C | −0.62 | 0.42 | |
| 110 | F | C | | C | C | C | −0.38 | −1.38 | |
| 111 | G | C | | C | C | C | −0.77 | −1 | |
| 112 | R | C | | C | C | C | −1.31 | −1 | xxx |
| 113 | P | C | | C | C | C | −0.42 | −1.00 | xxx |
| 114 | Y | C | | C | C | C | −0.08 | −1.88 | |
| 115 | P | C | | C | C | C | 0.08 | −0.08 | |
| 116 | G | C | | C | C | C | 0.43 | 0.6 | |
| 117 | I | E | E | E | E | E | 0.54 | 1.7 | |
| 118 | A | E | E | E | E | E | 0.68 | 2.58 | |
| 119 | V | E | E | E | E | E | 0.39 | 1.96 | |
| 120 | F | E | E | E | E | E | 0.18 | 0.98 | |
| 121 | D | C | | C | C | C | 0.72 | −0.16 | |
| 122 | G | C | | C | C | C | 0.14 | −1.7 | |
| 123 | K | C | | C | C | C | 0.41 | −1.36 | |
| 124 | Q | E | E | E | E | E | −0.13 | −0.8 | |
| 125 | I | E | E | E | E | E | −0.49 | 0.12 | |
| 126 | T | E | E | E | E | E | −0.18 | 0.76 | |
| 127 | V | E | E | E | E | E | 0.29 | 1.38 | |
| 128 | T | E | E | E | E | E | 0.62 | 0.34 | |
| 129 | G | E | E | E | E | E | 0.62 | 1.24 | |
| 130 | T | E | E | E | E | E | 0.08 | 0.22 | |
| 131 | L | E | E | E | C | E | −0.23 | −0.34 | |
| 132 | W | E | | C | C | C | −1.13 | −0.34 | |
| 133 | N | C | | C | C | C | −0.56 | −0.9 | |
| 134 | G | C | | C | C | C | −0.66 | −2.44 | |
| 135 | N | C | | C | C | C | −0.97 | −1.36 | |
| 136 | K | E | | C | C | E | −1.78 | −0.92 | |
| 137 | I | E | E | E | E | E | −2.18 | −1.54 | |
| 138 | Y | E | | E | E | E | −1.37 | −1.54 | |
| 139 | D | C | | E | C | E | −0.82 | −1.66 | |
| 140 | E | C | E | E | C | E | −0.82 | −1.8 | |

TABLE 9-continued

Compiled structure feature prediction results for *Oplophorus gracilorostris* mature luciferase. Secondary structure prediction results code is H = helix, E = sheet, C = coil, blank = coil. Hydrophobicity prediction score is >0 for hydrophobic and <0 for hydrophilic areas. Suitable split point examples are marked xxx in rightmost column.

| | | | | | | | Hyphobicity K-D | |
|---|---|---|---|---|---|---|---|---|
| Seq # | Mature Seq | PSTPRED | JPRED | PORTER | SCRATCH | PROF | win = 7 | win = 5 |
| 141 | R | E | E | E | E | E | −0.57 | −0.64 |
| 142 | L | E | E | E | C | E | −1.46 | −0.64 |
| 143 | I | C | | C | E | E | −1.36 | −0.26 |
| 144 | N | C | | C | C | C | −1.06 | −0.06 |
| 145 | P | C | | C | C | C | −0.24 | −0.9 |
| 146 | D | C | | C | C | C | 0.68 | −1.96 |
| 147 | G | C | | C | C | C | 0.57 | −0.5 |
| 148 | S | C | | C | C | E | −0.43 | 0.58 |
| 149 | L | E | E | E | E | E | 0.42 | 1.84 |
| 150 | L | E | E | E | E | E | 0.52 | 1.02 |
| 151 | F | E | E | E | E | E | 1.41 | 2.02 |
| 152 | R | E | E | E | E | E | 1.07 | 1.12 |
| 153 | V | E | E | E | E | E | 1.11 | 1.26 |
| 154 | T | E | E | E | E | E | 1.16 | 0 |
| 155 | I | E | E | E | E | E | 0.66 | 0.82 |
| 156 | N | C | | C | C | C | 0.30 | 0.82 |
| 157 | G | C | | C | C | C | 0.70 | 0.82 |
| 158 | V | C | | C | C | C | −0.27 | −0.16 |
| 159 | T | C | | C | C | C | 0.23 | 0.36 |
| 160 | G | H | | H | H | C | 0.01 | −0.46 |
| 161 | W | H | H | H | H | C | 0.01 | −0.54 |
| 162 | R | H | H | H | H | H | −0.33 | 0.1 |
| 163 | L | H | H | H | H | H | −0.30 | −0.52 |
| 164 | C | H | H | H | H | H | 0.20 | −1.04 |
| 165 | E | H | H | H | H | H | 0.44 | 0.16 |
| 166 | N | H | H | H | H | H | | 0.76 |
| 167 | I | H | | H | H | H | | 0.62 |
| 168 | L | C | | C | H | C | | |
| 169 | A | C | | C | C | C | | |

Thus, split sites for any protein, e.g., one to be used in PCA or one to be used as a biosensor (insertion of domain directly in-between the split sites or into a circular permuted mutant, circularly permuted at the split sites), in the absence of a three-dimensional structure, can be selected.

REFERENCES

Altschul et al., *J. Mol. Biol.,* 215:403 (1990).
Altschul et al., *Nuc. Acids Res.,* 25:3389 (1977).
Bos, Nat. Rev. *Mol. Cell. Biol.,* 4:733 (2003)
Chong et al., *Gene,* 192:271 (1997).
Corpet et al., *Nucl. Acids Res.,* 16:1088 (1988).
Dremier et. al., *FEBS Lett.,* 546:163 (2003).
Geysen et al., *Proc. Natl. Acad. Sci. USA,* 3998 (1984).
Hanks and Hunter, *FASEB J,* 9:576-595 (1995).
Henikoff & Henikoff, *Proc. Natl. Acad. Sci. USA,* 89:10915 (1989).
Higgins et al., *Gene,* 73:237 (1988).
Higgins et al., *CABIOS,* 5:157 (1989).
Huang et al., *CABIOS,* 8:155 (1992).
Kaihara et al., *Anal. Chem.,* 75:41 (2003).
Karlin & Altschul, *Proc. Natl. Acad. Sci. USA,* 90:5873 (1993).
Lee et al., *Anal. Biochem.,* 316:162 (2003).
Liu et al., *Gene,* 237:153 (1999).
Mayer and Baltimore, *Trends Cell. Biol.,* 3:8 (1993).
Merrifield, *J. Am. Chem. Soc.,* 2149 (1963).
Murray et al., *Nucl. Acids Res.,* 17:477 (1989)
Myers and Miller, *LABIOS,* 4:11 (1988).
Ozawa et al, *Analytical Chemistry,* 73:2516 (2001).
Needleman et al., *J. Mol. Biol.,* 48:443 (1976).
Paulmurugan et al., *Anal. Chem.,* 75:1584 (2003).
Paulmurugan et al., *Proc. Natl. Acad. Sci. USA,* 99:3105 (2002).
Paulmurugan et al., *PNAS,* 24:15603 (1999).
Pearson et al., *Methods Mol. Biol.,* 24:307 (1994).
Pearson et al., *Proc. Natl. Acad. Sci. USA,* 85:2444 (1985.
Plainkum et al., *Nat. Struct. Biol.,* 10:115 (2003).
Remy et al., *Biotechniques,* 38:763 (2005).
Remy et al., *Nat. Methods,* 3:977 (2006).
Sadowski, et al., *Mol. Cell. Bio.,* 6:4396 (1986).
Sala-Newby et al., *Biochem J.,* 279:727 (1991).
Sala-Newby et al., *FEBS,* 307:241 (1992).
Sambrook et al., In: *Molecular Cloning: A Laboratory Manual*, Cold Spring Harbor (1989).
Smith et al., *Adv. Appl. Math.,* 2:482 (1981).
Stewart et al., Solid Phase Peptide Synthesis, 2 ed., Pierce Chemical Co., Rockford, Ill., pp. 11-12).
Tannous et al., *Mol. Thera.,* 11:435 (2005).
Wada et al., *Nucl. Acids Res.,* 18:2367 (1990).
Wang et al., *BBRC,* 282:28 (2001).
Waud et al, *BBA,* 1292:89 (1996).
Zagotta et al., *Nature,* 425:730 (2003).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. An isolated polynucleotide comprising a nucleic acid sequence comprising an open reading frame for a modified decapod luciferase, wherein the modified decapod luciferase comprises an internal insertion relative to a corresponding unmodified decapod luciferase, which insertion is in a region corresponding to residue 45 to 55 or residue 79 to 89 of a mature *Oplophorus* luciferase of SEQ ID NO: 318, wherein the insertion comprises an amino acid which directly or indirectly interacts with a molecule of interest, and wherein the activity of the modified decapod luciferase is detectable.

2. The isolated polynucleotide of claim 1, wherein the insertion comprises a peptide substrate for a serine, threonine, tyrosine kinase, a phosphoserine peptide binding domain, a phosphothreonine peptide binding domain, a phosphotyrosine peptide binding domain, or a cyclic nucleotide binding site.

3. A vector comprising the isolated polynucleotide of claim 1.

4. An isolated host cell comprising the isolated polynucleotide of claim 1.

5. A modified decapod luciferase encoded by the polynucleotide of claim 1.

6. An isolated polynucleotide comprising a nucleic acid sequence comprising an open reading frame for a modified decapod luciferase, wherein the modified decapod luciferase is circularly-permuted, wherein the permutation is a region corresponding to residue 45 to 55 or residue 79 to 89 of a mature *Oplophorus* luciferase of SEQ ID NO: 318, wherein the modified decapod luciferase comprises an insertion relative to a corresponding unmodified decapod luciferase, wherein the insertion comprises an amino acid sequence which directly or indirectly interacts with a molecule of interest relative to the corresponding unmodified decapod luciferase, wherein the activity of the modified decapod luciferase is detectable.

7. The isolated polynucleotide of claim 6, wherein the insertion comprises a peptide substrate for a serine, threonine, tyrosine kinase, a phosphoserine peptide binding domain, a phosphothreonine peptide binding domain, a phosphotyrosine peptide binding domain, or a cyclic nucleotide binding site.

8. The isolated polynucleotide of claim 6, wherein the nucleic acid sequence encodes a fusion protein comprising the circularly permuted decapod luciferase and a tag of at least one amino acid at the N-terminus, C-terminus, or both.

9. The isolated polynucleotide of claim 6, wherein the insertion is at a sequence corresponding to the N-terminus and/or C-terminus of a corresponding noncircularly permuted decapod luciferase.

10. The isolated polynucleotide of claim 6, wherein the insertion is about 4 to about 200 amino acid residues.

11. A vector comprising the isolated polynucleotide of claim 6.

12. An isolated host cell comprising the isolated polynucleotide of claim 6.

13. A modified decapod luciferase encoded by the polynucleotide of claim 6.

14. A method to detect a molecule of interest in a cell, comprising: a) contacting a sample having cells or in vitro transcription/translation mixture and the vector of claim 3, wherein the insertion is recognized by the molecule of interest; and b) detecting or determining the activity of the modified decapod luciferase encoded by the vector, thereby detecting or determining the presence or amount of the molecule in the sample.

15. A method to detect or determine a molecule of interest in a cell, comprising: a) providing a mixture comprising the isolated host cell of claim 12 or a lysate thereof, and reagents for a luminescence reaction, wherein the circularly permuted luciferase comprises the insertion; and b) detecting or determining luminescence in the mixture, thereby detecting or determining the presence or amount of the molecule in the cell.

16. A method to detect or determine a molecule of interest in a sample, comprising: a) providing a mixture comprising a sample suspected of having cyclic nucleotide, the modified decapod luciferase of claim 13, and reagents for a luminescence reaction; and b) detecting or determining luminescence in the mixture.

17. A method to detect one or more modulators of a molecule of interest, comprising: a) providing a sample comprising one or more test agents, the isolated host cell of claim 12 or a lysate thereof, and reagents for a luminescence reaction; and b) detecting or determining luminescence in the sample.

18. A method to detect one or more modulators of a molecule of interest, comprising: a) providing a sample comprising one or more test agents, the modified decapod luciferase of claim 13 and reagents for a luminescence reaction; and b) detecting or determining luminescence in the sample.

* * * * *

SEQUENCE LISTING

```
<160> NUMBER OF SEQ ID NOS: 318

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Arg Arg Ala Ser Leu Gly
1               5


<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Val Pro Arg Glu Ser
1               5


<210> SEQ ID NO 3
<211> LENGTH: 542
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Val Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205
```

```
His Gln Asn Ile Cys Val Arg Leu Ile His Ala Leu Asp Pro Arg Val
    210                 215                 220

Gly Thr Gln Leu Ile Pro Gly Val Thr Val Leu Val Tyr Leu Pro Phe
225                 230                 235                 240

Phe His Ala Phe Gly Phe Ser Ile Thr Leu Gly Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
        275                 280                 285

Ile Leu Phe Leu Ser Lys Ser Pro Leu Val Asp Lys Tyr Asp Leu Ser
    290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Asn Ile His Ser Leu Arg Asp
            340                 345                 350

Glu Phe Lys Ser Gly Ser Leu Gly Arg Val Thr Pro Leu Met Ala Ala
        355                 360                 365

Lys Ile Ala Asp Arg Glu Thr Gly Lys Ala Leu Gly Pro Asn Gln Val
    370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Asp Gly Trp Leu His
                405                 410                 415

Ser Gly Asp Phe Gly Tyr Tyr Asp Glu Asp Glu His Phe Tyr Val Val
            420                 425                 430

Asp Arg Tyr Lys Glu Leu Ile Lys Tyr Lys Gly Ser Gln Val Ala Pro
        435                 440                 445

Ala Glu Leu Glu Glu Ile Leu Leu Lys Asn Pro Cys Ile Arg Asp Val
    450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
        515                 520                 525

Arg Lys Glu Leu Leu Lys Gln Leu Leu Glu Lys Ala Gly Gly
    530                 535                 540
```

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

```
His His His His His
1               5
```

-continued

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 5

His His His His His His
1 5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 6

Glu Gln Lys Leu Ile Ser Glu Glu Asp Leu
1 5 10

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 7

Asp Tyr Lys Asp Asp Asp Asp Lys
1 5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 8

Trp Ser His Pro Gln Phe Glu Lys
1 5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

Tyr Pro Tyr Asp Val Pro Asp Tyr Ala
1 5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

```
Arg Tyr Ile Arg Ser
1               5


<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe His His Thr
1


<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Trp Glu Ala Ala Ala Arg Glu Ala Cys Cys Arg Glu Cys Cys Ala Arg
1               5                   10                  15

Ala


<210> SEQ ID NO 13
<211> LENGTH: 170
<212> TYPE: PRT
<213> ORGANISM: Homo sapiens

<400> SEQUENCE: 13

Pro Val Gly Thr His Glu Met Glu Glu Glu Leu Ala Glu Ala Val Ala
1               5                   10                  15

Leu Leu Ser Gln Arg Gly Pro Asp Ala Leu Leu Thr Val Ala Leu Arg
            20                  25                  30

Lys Pro Pro Gly Gln Arg Thr Asp Glu Glu Leu Asp Leu Ile Phe Glu
        35                  40                  45

Glu Leu Leu His Ile Lys Ala Val Ala His Leu Ser Asn Ser Val Lys
    50                  55                  60

Arg Glu Leu Ala Ala Val Leu Leu Phe Glu Pro His Ser Lys Ala Gly
65                  70                  75                  80

Thr Val Leu Phe Ser Gln Gly Asp Lys Gly Thr Ser Trp Tyr Ile Ile
                85                  90                  95

Trp Lys Gly Ser Val Asn Val Val Thr His Gly Lys Gly Leu Val Thr
            100                 105                 110

Thr Leu His Glu Gly Asp Asp Phe Gly Gln Leu Ala Leu Val Asn Asp
        115                 120                 125

Ala Pro Arg Ala Ala Thr Ile Ile Leu Arg Glu Asp Asn Cys His Phe
    130                 135                 140

Leu Arg Val Asp Lys Gln Asp Phe Asn Arg Ile Ile Lys Asp Val Glu
145                 150                 155                 160

Ala Lys Thr Met Arg Leu Glu Glu His Gly
                165                 170


<210> SEQ ID NO 14
<211> LENGTH: 174
<212> TYPE: PRT
```

<213> ORGANISM: Homo sapiens

<400> SEQUENCE: 14

Ala Ile Ala Pro Val Gly Thr His Glu Met Glu Glu Glu Leu Ala Glu
1 5 10 15

Ala Val Ala Leu Leu Ser Gln Arg Gly Pro Asp Ala Leu Leu Thr Val
20 25 30

Ala Leu Arg Lys Pro Pro Gly Gln Arg Thr Asp Glu Glu Leu Asp Leu
35 40 45

Ile Phe Glu Glu Leu Leu His Ile Lys Ala Val Ala His Leu Ser Asn
50 55 60

Ser Val Lys Arg Glu Leu Ala Ala Val Leu Leu Phe Glu Pro His Ser
65 70 75 80

Lys Ala Gly Thr Val Leu Phe Ser Gln Gly Asp Lys Gly Thr Ser Trp
85 90 95

Tyr Ile Ile Trp Lys Gly Ser Val Asn Val Val Thr His Gly Lys Gly
100 105 110

Leu Val Thr Thr Leu His Glu Gly Asp Asp Phe Gly Gln Leu Ala Leu
115 120 125

Val Asn Asp Ala Pro Arg Ala Ala Thr Ile Ile Leu Arg Glu Asp Asn
130 135 140

Cys His Phe Leu Arg Val Asp Lys Gln Asp Phe Asn Arg Ile Ile Lys
145 150 155 160

Asp Val Glu Ala Lys Thr Met Arg Leu Glu Glu His Gly Val
165 170

<210> SEQ ID NO 15
<211> LENGTH: 527
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15
gcgatcgccc ccgtaggtac ccacgaaatg gaagaagaac ttgctgaagc tgtagcctta 60
cttagtcaac gcggacctga tgccttatta accgtagccc ttcgtaaacc tcccggccaa 120
cgcacagacg aagaactgga cctcattttt gaagaacttt tgcatattaa agccgttgcg 180
catctctcta actctgttaa acgtgaactt gctgccgtac ttctcttcga accccattca 240
aaagccggca ctgttttatt ctcccaaggt gataaaggta cttcttggta tattatttgg 300
aaaggatcag ttaacgttgt aacccacgga aaaggtctcg taactacatt acatgaagga 360
gatgattttg gacaactcgc cttagtaaat gacgccccac gtgctgccac aattattctg 420
cgcgaagaca attgccattt tttacgtgtc gataaacagg atttcaatcg tattattaaa 480
gatgtcgaag cgaaaacaat gcgtttagaa gaacatggag tttaaac 527

<210> SEQ ID NO 16
<211> LENGTH: 1816
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16
gcttaaaagc tttaatacga ctcactatag ggctagcgat cgccatggac accgctatcc 60

-continued

```
tcagcgtggt gccatttcac cacggcttcg gcatgttcac cacgctgggc tacttgatct    120
gcggctttcg ggtcgtgctc atgtaccgct tcgaggagga gctattcttg cgcagcttgc    180
aagactataa gattcaatct gccctgctgg tgcccacact atttagcttc ttcgctaaga    240
gcactctcat cgacaagtac gacctaagca acttgcacga gatcgccagc ggcggggcgc    300
cgctcagcaa ggaggtaggt gaggccgtgg ccaaacgctt ccacctacca ggcatccgcc    360
agggctacgg cctgacagaa acaaccagcg ccattctgat cacccccgaa ggggacgaca    420
agcctggcgc agtaggcaag gtggtgccct tcttcgaggc taaggtggtg gacttggaca    480
ctggtaagac actgggtgtg aaccagcgcg gcgagctgtg cgtccgtggc cccatgatca    540
tgagcggcta cgttaacaac cccgaggcta caaacgctct catcgacaag gacggctggc    600
tgcacagcgg cgacatcgcc tactgggacg aggacgagca cttcttcatc gtggaccggc    660
tgaagagcct gatcaaatac aagggctacc aggtagcccc agccgaactg gagagcatcc    720
tgctgcaaca ccccaacatc ttcgacgccg gggtcgccgg cctgcccgac gacgatgccg    780
gcgagctgcc cgccgcagtc gtcgtgctgg aacacggtaa aaccatgacc gagaaggaga    840
tcgtggacta tgtggccagc caggttacaa ccgccaagaa gctgcgcggt ggtgttgtgt    900
tcgtggacga ggtgcctaaa ggactgaccg gcaagttgga cgcccgcaag atccgcgaga    960
ttctcattaa ggccaagaag ggctcgagcg gaggttcagg cggttccgga ggaggttctg   1020
gcggatcagg cggttcgcga ggaggtggca ccggtggatc cggtggcagc ggagggacgt   1080
caggtggatc tggagggagc tccggtgcca aaaacattaa gaagggccca gcgccattct   1140
acccactcga agacgggacc gccggcgagc agctgcacaa agccatgaag cgctacgccc   1200
tggtgcccgg caccatcgcc tttaccgacg cacatatcga ggtggacatt acctacgccg   1260
agtacttcga gatgagcgtt cggctggcag aagctatgaa gcgctatggg ctgaatacaa   1320
accatcggat cgtggtgtgc agcgagaata gcttgcagtt cttcatgccc gtgttgggtg   1380
ccctgttcat cggtgtggct gtggccccag ctaacgacat ctacaacgag cgcgagctgc   1440
tgaacagcat gggcatcagc cagcccaccg tcgtattcgt gagcaagaaa gggctgcaaa   1500
agatcctcaa cgtgcaaaag aagctaccga tcatacaaaa gatcatcatc atggatagca   1560
agaccgacta ccagggcttc caaagcatgt acaccttcgt gacttcccat ttgccacccg   1620
gcttcaacga gtacgacttc gtgcccgaga gcttcgaccg ggacaaaacc atcgccctga   1680
tcatgaacag tagtggcagt accggattgc ccaagggcgt agccctaccg caccgcaccg   1740
cttgtgtccg attcagtcat gcccgcgacc ccatcttcgg caaccagatc atccccgttt   1800
aaactctaga gtcggg                                                    1816
```

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

```
Ala Asn Lys Ile Ser Tyr Gln Ser Ser Ser Thr Glu
1               5                   10
```

<210> SEQ ID NO 18
<211> LENGTH: 53
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 18

gcagtgactc aataaagctt tcatacatct tcttggcctt aatgagaatc tcg           53


<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Glu Val Leu Phe Gln Gly Pro
1               5


<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Ser Ala Val Leu Gln Ser Gly Phe Arg
1               5                   10


<210> SEQ ID NO 21
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

ggcccttctt aatgtttttg gctacaatat ccatgttcgt tccaaacag                49


<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

atgcctcgag gaagaagaac ttgctgaagc tg                                  32


<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23

atgccatgga actccatgtt cttctaaacg c                                   31


<210> SEQ ID NO 24
<211> LENGTH: 49
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 24

ctgtttggaa cgaacatgga tattgtagcc aaaaacatta agaagggcc                49


<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25

aaaaaagtcg accggaatgt atgaaagctt tattgagtca ctgcc                    45


<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26

aaaaaagagc tcccaacaat atccatgttc gttccaaac                           39


<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27

aaaaaaaggc ctacaatatc catgttcgtt ccaaac                              36


<210> SEQ ID NO 28
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28

aaaaaacccg ggatgtatga aagctttatt gagtcactgc c                        41


<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29

aaaaaatccg gacccaacaa tatccatgtt cgttccaaac                          40


<210> SEQ ID NO 30
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 30

gtatcttatc atgtctgctc gaagcg                                          26


<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31

cctcgaacac cgagcgacc                                                  19


<210> SEQ ID NO 32
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32

cgagattctc attaaggcca agaagatgta tgaaagcttt attgagtcac tgc            53


<210> SEQ ID NO 33
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33

ggcccttctt aatgtttttg gctacaatat ccatgttcgt tccaaacag                 49


<210> SEQ ID NO 34
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34

ctgtttggaa cgaacatgga tattgtagcc aaaaacatta agaagggcc                 49


<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35

gtatcttatc atgtctgctc gaagcg                                          26


<210> SEQ ID NO 36
<211> LENGTH: 19
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 36
cctcgaacac cgagcgacc 19

<210> SEQ ID NO 37
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
caataaagct ttcatacatc gagcccttct tggccttaat gagaatctcg 50

<210> SEQ ID NO 38
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cgagattctc attaaggcca agaagggctc gatgtatgaa agctttattg 50

<210> SEQ ID NO 39
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cttcttaatg tttttggcac cggatacaat atccatgttc gttccaaaca g 51

<210> SEQ ID NO 40
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ctgtttggaa cgaacatgga tattgtatcc ggtgccaaaa acattaagaa g 51

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gtatcttatc atgtctgctc gaagcg 26

<210> SEQ ID NO 42
<211> LENGTH: 53
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
aaaaaaaaag tcgaccggag gttcaatgta tgaaagcttt attgagtcac tgc 53

<210> SEQ ID NO 43
<211> LENGTH: 47
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
aaaaaagagc tccctccaga tacaatatcc atgttcgttc caaacag 47

<210> SEQ ID NO 44
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
aaaaaagtcg accggaggtt caggcggtat gtatgaaagc tttattgagt cactgc 56

<210> SEQ ID NO 45
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
aaaaaatccg gaggaggttc tggcatgtat gaaagcttta ttgagtcact gc 52

<210> SEQ ID NO 46
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46
aaaaaatccg gaggaggtat gtatgaaagc tttattgagt cactgc 46

<210> SEQ ID NO 47
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 47
ggcccttctt aatgtttttg gctacaatat ccatgttcgt tccaaacag 49

<210> SEQ ID NO 48
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
ctgtttggaa cgaacatgga tattgtagcc aaaaacatta agaagggcc 49

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 49
gtatcttatc atgtctgctc gaagcg 26

<210> SEQ ID NO 50
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 50
ataaattccg gaggaggttc tggcggatca atgtatgaaa gctttattga gtcactgc 58

<210> SEQ ID NO 51
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 51
ggcccttctt aatgtttttg gctacaatat ccatgttcgt tccaaacag 49

<210> SEQ ID NO 52
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 52
ctgtttggaa cgaacatgga tattgtagcc aaaaacatta agaagggcc 49

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 53
gtatcttatc atgtctgctc gaagcg 26

<210> SEQ ID NO 54
<211> LENGTH: 64
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 54
aaaaattccg gaggaggttc tggcggatca ggcggtatgt atgaaagctt tattgagtca 60
ctgc 64

<210> SEQ ID NO 55
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 55
ggcccttctt aatgtttttg gctacaatat ccatgttcgt tccaaacag 49

<210> SEQ ID NO 56
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 56
ctgtttggaa cgaacatgga tattgtagcc aaaaacatta agaagggcc 49

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 57
gtatcttatc atgtctgctc gaagcg 26

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 58
aaaaaagtcg accggaggtt caggcggttc 30

<210> SEQ ID NO 59
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 59
ggcccttctt aatgtttttg gcatccatgt tcgttccaaa cagg 44

<210> SEQ ID NO 60
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 60
cctgtttgga acgaacatgg atgccaaaaa cattaagaag ggcc 44

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 61
gtatcttatc atgtctgctc gaagcg 26

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 62
aaaaaagtcg accggaggtt caggcggttc 30

<210> SEQ ID NO 63
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 63
ggcccttctt aatgtttttg gcgttcgttc caaacagggc aactaac 47

<210> SEQ ID NO 64
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 64
gttagttgcc ctgtttggaa cgaacgccaa aaacattaag aagggcc 47

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 65
gtatcttatc atgtctgctc gaagcg 26

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 66
aaaaaagtcg accggaggtt caggcggttc 30

<210> SEQ ID NO 67
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 67
ggcccttctt aatgtttttg gctccaaaca gggcaactaa ctgttcttc 49

<210> SEQ ID NO 68
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 68
gaagaacagt tagttgccct gtttggagcc aaaaacatta agaagggcc 49

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 69
gtatcttatc atgtctgctc gaagcg 26

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 70
aaaaaagtcg accggaggtt caggcggttc 30

<210> SEQ ID NO 71
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 71
ggcccttctt aatgtttttg gccagggcaa ctaactgttc ttcatagg 48

<210> SEQ ID NO 72
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 72
cctatgaaga acagttagtt gccctggcca aaaacattaa gaagggcc 48

<210> SEQ ID NO 73
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 73
gtatcttatc atgtctgctc gaagcg 26

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 74
aaaaaagtcg accggaggtt caggcggttc 30

<210> SEQ ID NO 75
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 75
ggcccttctt aatgtttttg gcaactaact gttcttcata ggtagcgatg 50

<210> SEQ ID NO 76
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 76
catcgctacc tatgaagaac agttagttgc caaaaacatt aagaagggcc 50

<210> SEQ ID NO 77
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 77
gtatcttatc atgtctgctc gaagcg 26

<210> SEQ ID NO 78
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 78

-continued aaaaaagtcg accggaggtt caggcggttc 30

<210> SEQ ID NO 79
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 79
ggcccttctt aatgtttttg gcctgttctt cataggtagc gatgttcc 48

<210> SEQ ID NO 80
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 80
ggaacatcgc tacctatgaa gaacaggcca aaaacattaa gaagggcc 48

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 81
gtatcttatc atgtctgctc gaagcg 26

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 82
aaaaaagtcg accggaggtt caggcggttc 30

<210> SEQ ID NO 83
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 83
ggcccttctt aatgtttttg gcttcatagg tagcgatgtt ccttttc 47

<210> SEQ ID NO 84
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 84
gaaaaggaac atcgctacct atgaagccaa aaacattaag aagggcc 47

<210> SEQ ID NO 85
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 85
gtatcttatc atgtctgctc gaagcg 26

<210> SEQ ID NO 86
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86
tataatgcta gcgatcgcca tgggcgtgac tgtgctggtg tatc 44

<210> SEQ ID NO 87
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 87
ttttttctcg agccgccgcc agctttttcg agg 33

<210> SEQ ID NO 88
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 88
aaaaaagagc tccggtgaaa agaacgtgat ctacggcc 38

<210> SEQ ID NO 89
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 89
aaaaaatcta gagtttaaac agggatcaat tgagtaccca cac 43

<210> SEQ ID NO 90
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 90
aaaaaagtcg accggaatgt atgaaagctt tattgagtca ctgcc 45

<210> SEQ ID NO 91
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 91
aaaaaagagc tcccaacaat atccatgttc gttccaaac 39

<210> SEQ ID NO 92
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 92
aaaaaagagc tcccaacaat atccatgttc gttccaaac 39

<210> SEQ ID NO 93
<211> LENGTH: 41
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 93
aaaaaatccg gaatgtatga aagctttatt gagtcactgc c 41

<210> SEQ ID NO 94
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 94
atataactcg agcggaatgt atgaggaatt ccttagtaaa gtctctattt tag 53

<210> SEQ ID NO 95
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 95
aaaaaagagc tcccgacaga cagtgacaca aaactgttgt ac 42

<210> SEQ ID NO 96
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 96
attaaacccg ggatgtatga ggaattcctt agtaaagtct ctattttag 49

-continued

<210> SEQ ID NO 97
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 97
aaaaaatccg gacccgacag acagtgacac aaaactgttg tac 43

<210> SEQ ID NO 98
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 98
aattaagcta gcgatcgcca tgacgtcagc aattttaacg gtaatacc 48

<210> SEQ ID NO 99
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 99 tttttctcg agccattggt gtgtttttct aacatttgtc ttaac 45

<210> SEQ ID NO 100
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 100
aattttgagc tccggtgata agaatatttt atatgggccc gaac 44

<210> SEQ ID NO 101
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 101
aaaaaatcta gagtttaaac gggattaatt gcgttaccaa aagtag 46

<210> SEQ ID NO 102
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 102
aaaaaagtcg accggaatgt atgaaagctt tattgagtca ctgcc 45

<210> SEQ ID NO 103

<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
aaaaaagagc tcccaacaat atccatgttc gttccaaac 39

<210> SEQ ID NO 104
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
aaaaaacccg ggatgtatga aagctttatt gagtcactgc c 41

<210> SEQ ID NO 105
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
aaaaaatccg gacccaacaa tatccatgtt cgttccaaac 40

<210> SEQ ID NO 106
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
aaaaaactcg agcggattaa aaagcgttcc aacattccag 40

<210> SEQ ID NO 107
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
aaaaaagagc tcccagacag cttcaggttg gcgaag 36

<210> SEQ ID NO 108
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
aaaaaatccg gattaaaaag cgttccaaca ttccag 36

<210> SEQ ID NO 109
<211> LENGTH: 33

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 109
aaaaaaaggc ctgacagctt caggttggcg aag 33

<210> SEQ ID NO 110
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 110
atgggcgatc gccatgtatc gcctcctgga tcactacaag 40

<210> SEQ ID NO 111
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 111
atgggcgatc gccatgcctc tcgttaaggg aggcaagc 38

<210> SEQ ID NO 112
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 112
gcatctcgag ccctgctcgt tcttcagcac gcgc 34

<210> SEQ ID NO 113
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 113
atgcgagctc aggagcttcc aaggtgtacg acccg 35

<210> SEQ ID NO 114
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 114
ttgtgtttaa actgagccat tcccgctctt gccg 34

<210> SEQ ID NO 115
<211> LENGTH: 34
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 115
ttgtgtttaa acgatctcgc gaggccagga gagg 34

<210> SEQ ID NO 116
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 116
aaaaaagagc tccctccaga tccacctaca atatccatgt tcgttccaaa cag 53

<210> SEQ ID NO 117
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 117

Arg Arg Phe Ser
1

<210> SEQ ID NO 118
<211> LENGTH: 16
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: Glu, Gln or Lys
<220> FEATURE:
<221> NAME/KEY: MOD_RES
<222> LOCATION: (3)..(3)
<223> OTHER INFORMATION: Leu, Lys, Ser or Ile
<220> FEATURE:
<221> NAME/KEY: MOD_RES
<222> LOCATION: (4)..(4)
<223> OTHER INFORMATION: Ala, Ile, Cys or Gly
<220> FEATURE:
<221> NAME/KEY: MOD_RES
<222> LOCATION: (5)..(5)
<223> OTHER INFORMATION: Leu or Ile
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (8)..(11)
<223> OTHER INFORMATION: Any amino acid or absent
<220> FEATURE:
<221> NAME/KEY: MOD_RES
<222> LOCATION: (12)..(12)
<223> OTHER INFORMATION: Pro, Val, Thr, Arg or Glu
<220> FEATURE:
<221> NAME/KEY: MOD_RES
<222> LOCATION: (14)..(14)
<223> OTHER INFORMATION: Ala, Thr, His or Ser
<220> FEATURE:
<221> NAME/KEY: MOD_RES
<222> LOCATION: (15)..(15)

```
<223> OTHER INFORMATION: Ala or Ser
<220> FEATURE:
<221> NAME/KEY: MOD_RES
<222> LOCATION: (16)..(16)
<223> OTHER INFORMATION: Val, Thr, Ser, Asn or Trp

<400> SEQUENCE: 118

Gly Xaa Xaa Xaa Xaa Xaa Xaa Xaa Xaa Xaa Xaa Xaa Arg Xaa Xaa Xaa
1               5                   10                  15


<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Asn Leu Tyr Phe Gln Gly
1               5


<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Pro Phe Ser Glu Phe Lys Pro Asp
1               5


<210> SEQ ID NO 121
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Ser Ser Gly Gly Ser Gly Gly Ser Gly Gly Gly
1               5                   10


<210> SEQ ID NO 122
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Ser Thr Gly
1


<210> SEQ ID NO 123
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Ser Gly Gly Ser Gly Gly Ser Gly Gly Thr Ser Gly Gly Ser Gly
```

-continued

```
1               5                   10                  15

Gly Ser Ser Gly
            20


<210> SEQ ID NO 124
<211> LENGTH: 149
<212> TYPE: PRT
<213> ORGANISM: Homo sapiens

<400> SEQUENCE: 124

Met Tyr Glu Ser Phe Ile Glu Ser Leu Pro Phe Leu Lys Ser Leu Glu
1               5                   10                  15

Phe Ser Glu Arg Leu Lys Val Val Asp Val Ile Gly Thr Lys Val Tyr
            20                  25                  30

Asn Asp Gly Glu Gln Ile Ile Ala Gln Gly Asp Ser Ala Asp Ser Phe
        35                  40                  45

Phe Ile Val Glu Ser Gly Glu Val Lys Ile Thr Met Lys Arg Lys Gly
    50                  55                  60

Lys Ser Glu Val Glu Glu Asn Gly Ala Val Glu Ile Ala Arg Cys Ser
65                  70                  75                  80

Arg Gly Gln Tyr Phe Gly Glu Leu Ala Leu Val Thr Asn Lys Pro Arg
                85                  90                  95

Ala Ala Ser Ala His Ala Ile Gly Thr Val Lys Cys Leu Ala Met Asp
            100                 105                 110

Val Gln Ala Phe Glu Arg Leu Leu Gly Pro Cys Met Glu Ile Met Lys
        115                 120                 125

Arg Asn Ile Ala Thr Tyr Glu Glu Gln Leu Val Ala Leu Phe Gly Thr
    130                 135                 140

Asn Met Asp Ile Val
145


<210> SEQ ID NO 125
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Met Tyr Glu Ser Phe Ile Glu Ser Leu Pro Phe Leu Lys Ser Leu Glu
1               5                   10                  15

Phe Ser Glu Arg Leu Lys Val Val Asp Val Ile Gly Thr Lys Val Tyr
            20                  25                  30

Asn Asp Gly Glu Gln Ile Ile Ala Gln Gly Asp Ser Ala Asp Ser Phe
        35                  40                  45

Phe Ile Val Glu Ser Gly Glu Val Lys Ile Thr Met Lys Arg Lys Gly
    50                  55                  60

Lys Ser Glu Val Glu Glu Asn Gly Ala Val Glu Ile Ala Arg Cys Ser
65                  70                  75                  80

Arg Gly Gln Tyr Phe Gly Glu Leu Ala Leu Val Thr Asn Lys Pro Arg
                85                  90                  95

Ala Ala Ser Ala His Ala Ile Gly Thr Val Lys Cys Leu Ala Met Asp
            100                 105                 110

Val Gln Ala Phe Glu Arg Leu Leu Gly Pro Cys Met Glu Ile Met Lys
        115                 120                 125

Arg Asn Ile Ala Thr Tyr Glu Glu Gln Leu Val Ala Leu Phe Gly Thr
```

```
    130                 135                 140

Asn Met Asp Ile Val Ser Gly
145                 150


<210> SEQ ID NO 126
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Met Tyr Glu Ser Phe Ile Glu Ser Leu Pro Phe Leu Lys Ser Leu Glu
1               5                   10                  15

Phe Ser Glu Arg Leu Lys Val Val Asp Val Ile Gly Thr Lys Val Tyr
            20                  25                  30

Asn Asp Gly Glu Gln Ile Ile Ala Gln Gly Asp Ser Ala Asp Ser Phe
        35                  40                  45

Phe Ile Val Glu Ser Gly Glu Val Lys Ile Thr Met Lys Arg Lys Gly
    50                  55                  60

Lys Ser Glu Val Glu Glu Asn Gly Ala Val Glu Ile Ala Arg Cys Ser
65                  70                  75                  80

Arg Gly Gln Tyr Phe Gly Glu Leu Ala Leu Val Thr Asn Lys Pro Arg
                85                  90                  95

Ala Ala Ser Ala His Ala Ile Gly Thr Val Lys Cys Leu Ala Met Asp
            100                 105                 110

Val Gln Ala Phe Glu Arg Leu Leu Gly Pro Cys Met Glu Ile Met Lys
        115                 120                 125

Arg Asn Ile Ala Thr Tyr Glu Glu Gln Leu Val Ala Leu Phe Gly Thr
    130                 135                 140

Asn Met Asp Ile Val Gly Ser Ser Gly
145                 150


<210> SEQ ID NO 127
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met Tyr Glu Ser Phe Ile Glu Ser Leu Pro Phe Leu Lys Ser Leu Glu
1               5                   10                  15

Phe Ser Glu Arg Leu Lys Val Val Asp Val Ile Gly Thr Lys Val Tyr
            20                  25                  30

Asn Asp Gly Glu Gln Ile Ile Ala Gln Gly Asp Ser Ala Asp Ser Phe
        35                  40                  45

Phe Ile Val Glu Ser Gly Glu Val Lys Ile Thr Met Lys Arg Lys Gly
    50                  55                  60

Lys Ser Glu Val Glu Glu Asn Gly Ala Val Glu Ile Ala Arg Cys Ser
65                  70                  75                  80

Arg Gly Gln Tyr Phe Gly Glu Leu Ala Leu Val Thr Asn Lys Pro Arg
                85                  90                  95

Ala Ala Ser Ala His Ala Ile Gly Thr Val Lys Cys Leu Ala Met Asp
            100                 105                 110

Val Gln Ala Phe Glu Arg Leu Leu Gly Pro Cys Met Glu Ile Met Lys
```

```
        115                 120                 125

Arg Asn Ile Ala Thr Tyr Glu Glu Gln Leu Val Ala Leu Phe Gly Thr
    130                 135                 140

Asn Met Asp Ile Val Ser Gly Gly Ser Ser Gly
145                 150                 155


<210> SEQ ID NO 128
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Met Tyr Glu Ser Phe Ile Glu Ser Leu Pro Phe Leu Lys Ser Leu Glu
1               5                   10                  15

Phe Ser Glu Arg Leu Lys Val Val Asp Val Ile Gly Thr Lys Val Tyr
            20                  25                  30

Asn Asp Gly Glu Gln Ile Ile Ala Gln Gly Asp Ser Ala Asp Ser Phe
        35                  40                  45

Phe Ile Val Glu Ser Gly Glu Val Lys Ile Thr Met Lys Arg Lys Gly
    50                  55                  60

Lys Ser Glu Val Glu Glu Asn Gly Ala Val Glu Ile Ala Arg Cys Ser
65                  70                  75                  80

Arg Gly Gln Tyr Phe Gly Glu Leu Ala Leu Val Thr Asn Lys Pro Arg
                85                  90                  95

Ala Ala Ser Ala His Ala Ile Gly Thr Val Lys Cys Leu Ala Met Asp
            100                 105                 110

Val Gln Ala Phe Glu Arg Leu Leu Gly Pro Cys Met Glu Ile Met Lys
        115                 120                 125

Arg Asn Ile Ala Thr Tyr Glu Glu Gln Leu Val Ala Leu Phe Gly Thr
    130                 135                 140

Asn Met Asp Ile Val Gly Gly Ser Gly Gly Ser Ser Gly
145                 150                 155


<210> SEQ ID NO 129
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Met Tyr Glu Ser Phe Ile Glu Ser Leu Pro Phe Leu Lys Ser Leu Glu
1               5                   10                  15

Phe Ser Glu Arg Leu Lys Val Val Asp Val Ile Gly Thr Lys Val Tyr
            20                  25                  30

Asn Asp Gly Glu Gln Ile Ile Ala Gln Gly Asp Ser Ala Asp Ser Phe
        35                  40                  45

Phe Ile Val Glu Ser Gly Glu Val Lys Ile Thr Met Lys Arg Lys Gly
    50                  55                  60

Lys Ser Glu Val Glu Glu Asn Gly Ala Val Glu Ile Ala Arg Cys Ser
65                  70                  75                  80

Arg Gly Gln Tyr Phe Gly Glu Leu Ala Leu Val Thr Asn Lys Pro Arg
                85                  90                  95

Ala Ala Ser Ala His Ala Ile Gly Thr Val Lys Cys Leu Ala Met Asp
```

```
            100                 105                 110

Val Gln Ala Phe Glu Arg Leu Leu Gly Pro Cys Met Glu Ile Met Lys
        115                 120                 125

Arg Asn Ile Ala Thr Tyr Glu Glu Gln Leu Val Ala Leu Phe Gly Thr
    130                 135                 140

Asn Met Asp Ile Val Gly Ser Gly Gly Ser Gly Gly Ser Ser Gly
145                 150                 155


<210> SEQ ID NO 130
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gly Ser Met Tyr Glu Ser Phe Ile Glu Ser Leu Pro Phe Leu Lys Ser
1               5                   10                  15

Leu Glu Phe Ser Glu Arg Leu Lys Val Val Asp Val Ile Gly Thr Lys
            20                  25                  30

Val Tyr Asn Asp Gly Glu Gln Ile Ile Ala Gln Gly Asp Ser Ala Asp
        35                  40                  45

Ser Phe Phe Ile Val Glu Ser Gly Glu Val Lys Ile Thr Met Lys Arg
    50                  55                  60

Lys Gly Lys Ser Glu Val Glu Glu Asn Gly Ala Val Glu Ile Ala Arg
65                  70                  75                  80

Cys Ser Arg Gly Gln Tyr Phe Gly Glu Leu Ala Leu Val Thr Asn Lys
                85                  90                  95

Pro Arg Ala Ala Ser Ala His Ala Ile Gly Thr Val Lys Cys Leu Ala
            100                 105                 110

Met Asp Val Gln Ala Phe Glu Arg Leu Leu Gly Pro Cys Met Glu Ile
        115                 120                 125

Met Lys Arg Asn Ile Ala Thr Tyr Glu Glu Gln Leu Val Ala Leu Phe
    130                 135                 140

Gly Thr Asn Met Asp Ile Val
145                 150


<210> SEQ ID NO 131
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gly Ser Met Tyr Glu Ser Phe Ile Glu Ser Leu Pro Phe Leu Lys Ser
1               5                   10                  15

Leu Glu Phe Ser Glu Arg Leu Lys Val Val Asp Val Ile Gly Thr Lys
            20                  25                  30

Val Tyr Asn Asp Gly Glu Gln Ile Ile Ala Gln Gly Asp Ser Ala Asp
        35                  40                  45

Ser Phe Phe Ile Val Glu Ser Gly Glu Val Lys Ile Thr Met Lys Arg
    50                  55                  60

Lys Gly Lys Ser Glu Val Glu Glu Asn Gly Ala Val Glu Ile Ala Arg
65                  70                  75                  80

Cys Ser Arg Gly Gln Tyr Phe Gly Glu Leu Ala Leu Val Thr Asn Lys
```

```
                85                  90                  95

Pro Arg Ala Ala Ser Ala His Ala Ile Gly Thr Val Lys Cys Leu Ala
            100                 105                 110

Met Asp Val Gln Ala Phe Glu Arg Leu Leu Gly Pro Cys Met Glu Ile
        115                 120                 125

Met Lys Arg Asn Ile Ala Thr Tyr Glu Glu Gln Leu Val Ala Leu Phe
    130                 135                 140

Gly Thr Asn Met Asp Ile Val Ser Gly
145                 150


<210> SEQ ID NO 132
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gly Ser Met Tyr Glu Ser Phe Ile Glu Ser Leu Pro Phe Leu Lys Ser
1               5                   10                  15

Leu Glu Phe Ser Glu Arg Leu Lys Val Val Asp Val Ile Gly Thr Lys
            20                  25                  30

Val Tyr Asn Asp Gly Glu Gln Ile Ile Ala Gln Gly Asp Ser Ala Asp
        35                  40                  45

Ser Phe Phe Ile Val Glu Ser Gly Glu Val Lys Ile Thr Met Lys Arg
    50                  55                  60

Lys Gly Lys Ser Glu Val Glu Glu Asn Gly Ala Val Glu Ile Ala Arg
65                  70                  75                  80

Cys Ser Arg Gly Gln Tyr Phe Gly Glu Leu Ala Leu Val Thr Asn Lys
                85                  90                  95

Pro Arg Ala Ala Ser Ala His Ala Ile Gly Thr Val Lys Cys Leu Ala
            100                 105                 110

Met Asp Val Gln Ala Phe Glu Arg Leu Leu Gly Pro Cys Met Glu Ile
        115                 120                 125

Met Lys Arg Asn Ile Ala Thr Tyr Glu Glu Gln Leu Val Ala Leu Phe
    130                 135                 140

Gly Thr Asn Met Asp Ile Val Gly Ser Ser Gly
145                 150                 155


<210> SEQ ID NO 133
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gly Ser Met Tyr Glu Ser Phe Ile Glu Ser Leu Pro Phe Leu Lys Ser
1               5                   10                  15

Leu Glu Phe Ser Glu Arg Leu Lys Val Val Asp Val Ile Gly Thr Lys
            20                  25                  30

Val Tyr Asn Asp Gly Glu Gln Ile Ile Ala Gln Gly Asp Ser Ala Asp
        35                  40                  45

Ser Phe Phe Ile Val Glu Ser Gly Glu Val Lys Ile Thr Met Lys Arg
    50                  55                  60

Lys Gly Lys Ser Glu Val Glu Glu Asn Gly Ala Val Glu Ile Ala Arg
```

65 70 75 80

Cys Ser Arg Gly Gln Tyr Phe Gly Glu Leu Ala Leu Val Thr Asn Lys
85 90 95

Pro Arg Ala Ala Ser Ala His Ala Ile Gly Thr Val Lys Cys Leu Ala
100 105 110

Met Asp Val Gln Ala Phe Glu Arg Leu Leu Gly Pro Cys Met Glu Ile
115 120 125

Met Lys Arg Asn Ile Ala Thr Tyr Glu Glu Gln Leu Val Ala Leu Phe
130 135 140

Gly Thr Asn Met Asp Ile Val Ser Gly Gly Ser Ser Gly
145 150 155

<210> SEQ ID NO 134
<211> LENGTH: 159
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 134

Gly Ser Met Tyr Glu Ser Phe Ile Glu Ser Leu Pro Phe Leu Lys Ser
1 5 10 15

Leu Glu Phe Ser Glu Arg Leu Lys Val Val Asp Val Ile Gly Thr Lys
20 25 30

Val Tyr Asn Asp Gly Glu Gln Ile Ile Ala Gln Gly Asp Ser Ala Asp
35 40 45

Ser Phe Phe Ile Val Glu Ser Gly Glu Val Lys Ile Thr Met Lys Arg
50 55 60

Lys Gly Lys Ser Glu Val Glu Glu Asn Gly Ala Val Glu Ile Ala Arg
65 70 75 80

Cys Ser Arg Gly Gln Tyr Phe Gly Glu Leu Ala Leu Val Thr Asn Lys
85 90 95

Pro Arg Ala Ala Ser Ala His Ala Ile Gly Thr Val Lys Cys Leu Ala
100 105 110

Met Asp Val Gln Ala Phe Glu Arg Leu Leu Gly Pro Cys Met Glu Ile
115 120 125

Met Lys Arg Asn Ile Ala Thr Tyr Glu Glu Gln Leu Val Ala Leu Phe
130 135 140

Gly Thr Asn Met Asp Ile Val Gly Gly Ser Gly Gly Ser Ser Gly
145 150 155

<210> SEQ ID NO 135
<211> LENGTH: 161
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 135

Gly Ser Met Tyr Glu Ser Phe Ile Glu Ser Leu Pro Phe Leu Lys Ser
1 5 10 15

Leu Glu Phe Ser Glu Arg Leu Lys Val Val Asp Val Ile Gly Thr Lys
20 25 30

Val Tyr Asn Asp Gly Glu Gln Ile Ile Ala Gln Gly Asp Ser Ala Asp
35 40 45

Ser Phe Phe Ile Val Glu Ser Gly Glu Val Lys Ile Thr Met Lys Arg 50 55 60

Lys Gly Lys Ser Glu Val Glu Glu Asn Gly Ala Val Glu Ile Ala Arg
65 70 75 80

Cys Ser Arg Gly Gln Tyr Phe Gly Glu Leu Ala Leu Val Thr Asn Lys
85 90 95

Pro Arg Ala Ala Ser Ala His Ala Ile Gly Thr Val Lys Cys Leu Ala
100 105 110

Met Asp Val Gln Ala Phe Glu Arg Leu Leu Gly Pro Cys Met Glu Ile
115 120 125

Met Lys Arg Asn Ile Ala Thr Tyr Glu Glu Gln Leu Val Ala Leu Phe
130 135 140

Gly Thr Asn Met Asp Ile Val Gly Ser Gly Gly Ser Gly Gly Ser Ser
145 150 155 160

Gly

<210> SEQ ID NO 136
<211> LENGTH: 153
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 136

Gly Ser Thr Gly Met Tyr Glu Ser Phe Ile Glu Ser Leu Pro Phe Leu
1 5 10 15

Lys Ser Leu Glu Phe Ser Glu Arg Leu Lys Val Val Asp Val Ile Gly
20 25 30

Thr Lys Val Tyr Asn Asp Gly Glu Gln Ile Ile Ala Gln Gly Asp Ser
35 40 45

Ala Asp Ser Phe Phe Ile Val Glu Ser Gly Glu Val Lys Ile Thr Met
50 55 60

Lys Arg Lys Gly Lys Ser Glu Val Glu Glu Asn Gly Ala Val Glu Ile
65 70 75 80

Ala Arg Cys Ser Arg Gly Gln Tyr Phe Gly Glu Leu Ala Leu Val Thr
85 90 95

Asn Lys Pro Arg Ala Ala Ser Ala His Ala Ile Gly Thr Val Lys Cys
100 105 110

Leu Ala Met Asp Val Gln Ala Phe Glu Arg Leu Leu Gly Pro Cys Met
115 120 125

Glu Ile Met Lys Arg Asn Ile Ala Thr Tyr Glu Glu Gln Leu Val Ala
130 135 140

Leu Phe Gly Thr Asn Met Asp Ile Val
145 150

<210> SEQ ID NO 137
<211> LENGTH: 155
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 137

Gly Ser Thr Gly Met Tyr Glu Ser Phe Ile Glu Ser Leu Pro Phe Leu
1 5 10 15

Lys Ser Leu Glu Phe Ser Glu Arg Leu Lys Val Val Asp Val Ile Gly
20 25 30

Thr Lys Val Tyr Asn Asp Gly Glu Gln Ile Ile Ala Gln Gly Asp Ser
35 40 45

Ala Asp Ser Phe Phe Ile Val Glu Ser Gly Glu Val Lys Ile Thr Met
50 55 60

Lys Arg Lys Gly Lys Ser Glu Val Glu Glu Asn Gly Ala Val Glu Ile
65 70 75 80

Ala Arg Cys Ser Arg Gly Gln Tyr Phe Gly Glu Leu Ala Leu Val Thr
85 90 95

Asn Lys Pro Arg Ala Ala Ser Ala His Ala Ile Gly Thr Val Lys Cys
100 105 110

Leu Ala Met Asp Val Gln Ala Phe Glu Arg Leu Leu Gly Pro Cys Met
115 120 125

Glu Ile Met Lys Arg Asn Ile Ala Thr Tyr Glu Glu Gln Leu Val Ala
130 135 140

Leu Phe Gly Thr Asn Met Asp Ile Val Ser Gly
145 150 155

<210> SEQ ID NO 138
<211> LENGTH: 157
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 138

Gly Ser Thr Gly Met Tyr Glu Ser Phe Ile Glu Ser Leu Pro Phe Leu
1 5 10 15

Lys Ser Leu Glu Phe Ser Glu Arg Leu Lys Val Val Asp Val Ile Gly
20 25 30

Thr Lys Val Tyr Asn Asp Gly Glu Gln Ile Ile Ala Gln Gly Asp Ser
35 40 45

Ala Asp Ser Phe Phe Ile Val Glu Ser Gly Glu Val Lys Ile Thr Met
50 55 60

Lys Arg Lys Gly Lys Ser Glu Val Glu Glu Asn Gly Ala Val Glu Ile
65 70 75 80

Ala Arg Cys Ser Arg Gly Gln Tyr Phe Gly Glu Leu Ala Leu Val Thr
85 90 95

Asn Lys Pro Arg Ala Ala Ser Ala His Ala Ile Gly Thr Val Lys Cys
100 105 110

Leu Ala Met Asp Val Gln Ala Phe Glu Arg Leu Leu Gly Pro Cys Met
115 120 125

Glu Ile Met Lys Arg Asn Ile Ala Thr Tyr Glu Glu Gln Leu Val Ala
130 135 140

Leu Phe Gly Thr Asn Met Asp Ile Val Gly Ser Ser Gly
145 150 155

<210> SEQ ID NO 139
<211> LENGTH: 159
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 139

Gly Ser Thr Gly Met Tyr Glu Ser Phe Ile Glu Ser Leu Pro Phe Leu
1 5 10 15

```
Lys Ser Leu Glu Phe Ser Glu Arg Leu Lys Val Val Asp Val Ile Gly
            20                  25                  30

Thr Lys Val Tyr Asn Asp Gly Glu Gln Ile Ile Ala Gln Gly Asp Ser
        35                  40                  45

Ala Asp Ser Phe Phe Ile Val Glu Ser Gly Glu Val Lys Ile Thr Met
    50                  55                  60

Lys Arg Lys Gly Lys Ser Glu Val Glu Glu Asn Gly Ala Val Glu Ile
65                  70                  75                  80

Ala Arg Cys Ser Arg Gly Gln Tyr Phe Gly Glu Leu Ala Leu Val Thr
                85                  90                  95

Asn Lys Pro Arg Ala Ala Ser Ala His Ala Ile Gly Thr Val Lys Cys
            100                 105                 110

Leu Ala Met Asp Val Gln Ala Phe Glu Arg Leu Leu Gly Pro Cys Met
        115                 120                 125

Glu Ile Met Lys Arg Asn Ile Ala Thr Tyr Glu Glu Gln Leu Val Ala
    130                 135                 140

Leu Phe Gly Thr Asn Met Asp Ile Val Ser Gly Gly Ser Ser Gly
145                 150                 155
```

<210> SEQ ID NO 140
<211> LENGTH: 161
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 140

```
Gly Ser Thr Gly Met Tyr Glu Ser Phe Ile Glu Ser Leu Pro Phe Leu
1               5                   10                  15

Lys Ser Leu Glu Phe Ser Glu Arg Leu Lys Val Val Asp Val Ile Gly
            20                  25                  30

Thr Lys Val Tyr Asn Asp Gly Glu Gln Ile Ile Ala Gln Gly Asp Ser
        35                  40                  45

Ala Asp Ser Phe Phe Ile Val Glu Ser Gly Glu Val Lys Ile Thr Met
    50                  55                  60

Lys Arg Lys Gly Lys Ser Glu Val Glu Glu Asn Gly Ala Val Glu Ile
65                  70                  75                  80

Ala Arg Cys Ser Arg Gly Gln Tyr Phe Gly Glu Leu Ala Leu Val Thr
                85                  90                  95

Asn Lys Pro Arg Ala Ala Ser Ala His Ala Ile Gly Thr Val Lys Cys
            100                 105                 110

Leu Ala Met Asp Val Gln Ala Phe Glu Arg Leu Leu Gly Pro Cys Met
        115                 120                 125

Glu Ile Met Lys Arg Asn Ile Ala Thr Tyr Glu Glu Gln Leu Val Ala
    130                 135                 140

Leu Phe Gly Thr Asn Met Asp Ile Val Gly Gly Ser Gly Gly Ser Ser
145                 150                 155                 160

Gly
```

<210> SEQ ID NO 141
<211> LENGTH: 163
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 141

Gly Ser Thr Gly Met Tyr Glu Ser Phe Ile Glu Ser Leu Pro Phe Leu
1 5 10 15

Lys Ser Leu Glu Phe Ser Glu Arg Leu Lys Val Val Asp Val Ile Gly
20 25 30

Thr Lys Val Tyr Asn Asp Gly Glu Gln Ile Ile Ala Gln Gly Asp Ser
35 40 45

Ala Asp Ser Phe Phe Ile Val Glu Ser Gly Glu Val Lys Ile Thr Met
50 55 60

Lys Arg Lys Gly Lys Ser Glu Val Glu Glu Asn Gly Ala Val Glu Ile
65 70 75 80

Ala Arg Cys Ser Arg Gly Gln Tyr Phe Gly Glu Leu Ala Leu Val Thr
85 90 95

Asn Lys Pro Arg Ala Ala Ser Ala His Ala Ile Gly Thr Val Lys Cys
100 105 110

Leu Ala Met Asp Val Gln Ala Phe Glu Arg Leu Leu Gly Pro Cys Met
115 120 125

Glu Ile Met Lys Arg Asn Ile Ala Thr Tyr Glu Glu Gln Leu Val Ala
130 135 140

Leu Phe Gly Thr Asn Met Asp Ile Val Gly Ser Gly Gly Ser Gly Gly
145 150 155 160

Ser Ser Gly

<210> SEQ ID NO 142
<211> LENGTH: 155
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 142

Gly Ser Thr Gly Gly Ser Met Tyr Glu Ser Phe Ile Glu Ser Leu Pro
1 5 10 15

Phe Leu Lys Ser Leu Glu Phe Ser Glu Arg Leu Lys Val Val Asp Val
20 25 30

Ile Gly Thr Lys Val Tyr Asn Asp Gly Glu Gln Ile Ile Ala Gln Gly
35 40 45

Asp Ser Ala Asp Ser Phe Phe Ile Val Glu Ser Gly Glu Val Lys Ile
50 55 60

Thr Met Lys Arg Lys Gly Lys Ser Glu Val Glu Glu Asn Gly Ala Val
65 70 75 80

Glu Ile Ala Arg Cys Ser Arg Gly Gln Tyr Phe Gly Glu Leu Ala Leu
85 90 95

Val Thr Asn Lys Pro Arg Ala Ala Ser Ala His Ala Ile Gly Thr Val
100 105 110

Lys Cys Leu Ala Met Asp Val Gln Ala Phe Glu Arg Leu Leu Gly Pro
115 120 125

Cys Met Glu Ile Met Lys Arg Asn Ile Ala Thr Tyr Glu Glu Gln Leu
130 135 140

Val Ala Leu Phe Gly Thr Asn Met Asp Ile Val
145 150 155

<210> SEQ ID NO 143
<211> LENGTH: 157

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gly Ser Thr Gly Gly Ser Met Tyr Glu Ser Phe Ile Glu Ser Leu Pro
1               5                   10                  15

Phe Leu Lys Ser Leu Glu Phe Ser Glu Arg Leu Lys Val Val Asp Val
            20                  25                  30

Ile Gly Thr Lys Val Tyr Asn Asp Gly Glu Gln Ile Ile Ala Gln Gly
        35                  40                  45

Asp Ser Ala Asp Ser Phe Phe Ile Val Glu Ser Gly Glu Val Lys Ile
    50                  55                  60

Thr Met Lys Arg Lys Gly Lys Ser Glu Val Glu Glu Asn Gly Ala Val
65                  70                  75                  80

Glu Ile Ala Arg Cys Ser Arg Gly Gln Tyr Phe Gly Glu Leu Ala Leu
                85                  90                  95

Val Thr Asn Lys Pro Arg Ala Ala Ser Ala His Ala Ile Gly Thr Val
            100                 105                 110

Lys Cys Leu Ala Met Asp Val Gln Ala Phe Glu Arg Leu Leu Gly Pro
        115                 120                 125

Cys Met Glu Ile Met Lys Arg Asn Ile Ala Thr Tyr Glu Glu Gln Leu
    130                 135                 140

Val Ala Leu Phe Gly Thr Asn Met Asp Ile Val Ser Gly
145                 150                 155


<210> SEQ ID NO 144
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gly Ser Thr Gly Gly Ser Met Tyr Glu Ser Phe Ile Glu Ser Leu Pro
1               5                   10                  15

Phe Leu Lys Ser Leu Glu Phe Ser Glu Arg Leu Lys Val Val Asp Val
            20                  25                  30

Ile Gly Thr Lys Val Tyr Asn Asp Gly Glu Gln Ile Ile Ala Gln Gly
        35                  40                  45

Asp Ser Ala Asp Ser Phe Phe Ile Val Glu Ser Gly Glu Val Lys Ile
    50                  55                  60

Thr Met Lys Arg Lys Gly Lys Ser Glu Val Glu Glu Asn Gly Ala Val
65                  70                  75                  80

Glu Ile Ala Arg Cys Ser Arg Gly Gln Tyr Phe Gly Glu Leu Ala Leu
                85                  90                  95

Val Thr Asn Lys Pro Arg Ala Ala Ser Ala His Ala Ile Gly Thr Val
            100                 105                 110

Lys Cys Leu Ala Met Asp Val Gln Ala Phe Glu Arg Leu Leu Gly Pro
        115                 120                 125

Cys Met Glu Ile Met Lys Arg Asn Ile Ala Thr Tyr Glu Glu Gln Leu
    130                 135                 140

Val Ala Leu Phe Gly Thr Asn Met Asp Ile Val Gly Ser Ser Gly
145                 150                 155
```

<210> SEQ ID NO 145
<211> LENGTH: 161
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 145

```
Gly Ser Thr Gly Gly Ser Met Tyr Glu Ser Phe Ile Glu Ser Leu Pro
1               5                   10                  15

Phe Leu Lys Ser Leu Glu Phe Ser Glu Arg Leu Lys Val Val Asp Val
            20                  25                  30

Ile Gly Thr Lys Val Tyr Asn Asp Gly Glu Gln Ile Ile Ala Gln Gly
        35                  40                  45

Asp Ser Ala Asp Ser Phe Phe Ile Val Glu Ser Gly Glu Val Lys Ile
    50                  55                  60

Thr Met Lys Arg Lys Gly Lys Ser Glu Val Glu Glu Asn Gly Ala Val
65                  70                  75                  80

Glu Ile Ala Arg Cys Ser Arg Gly Gln Tyr Phe Gly Glu Leu Ala Leu
                85                  90                  95

Val Thr Asn Lys Pro Arg Ala Ala Ser Ala His Ala Ile Gly Thr Val
            100                 105                 110

Lys Cys Leu Ala Met Asp Val Gln Ala Phe Glu Arg Leu Leu Gly Pro
        115                 120                 125

Cys Met Glu Ile Met Lys Arg Asn Ile Ala Thr Tyr Glu Glu Gln Leu
    130                 135                 140

Val Ala Leu Phe Gly Thr Asn Met Asp Ile Val Ser Gly Gly Ser Ser
145                 150                 155                 160

Gly
```

<210> SEQ ID NO 146
<211> LENGTH: 163
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 146

```
Gly Ser Thr Gly Gly Ser Met Tyr Glu Ser Phe Ile Glu Ser Leu Pro
1               5                   10                  15

Phe Leu Lys Ser Leu Glu Phe Ser Glu Arg Leu Lys Val Val Asp Val
            20                  25                  30

Ile Gly Thr Lys Val Tyr Asn Asp Gly Glu Gln Ile Ile Ala Gln Gly
        35                  40                  45

Asp Ser Ala Asp Ser Phe Phe Ile Val Glu Ser Gly Glu Val Lys Ile
    50                  55                  60

Thr Met Lys Arg Lys Gly Lys Ser Glu Val Glu Glu Asn Gly Ala Val
65                  70                  75                  80

Glu Ile Ala Arg Cys Ser Arg Gly Gln Tyr Phe Gly Glu Leu Ala Leu
                85                  90                  95

Val Thr Asn Lys Pro Arg Ala Ala Ser Ala His Ala Ile Gly Thr Val
            100                 105                 110

Lys Cys Leu Ala Met Asp Val Gln Ala Phe Glu Arg Leu Leu Gly Pro
        115                 120                 125

Cys Met Glu Ile Met Lys Arg Asn Ile Ala Thr Tyr Glu Glu Gln Leu
```

130 135 140

Val Ala Leu Phe Gly Thr Asn Met Asp Ile Val Gly Gly Ser Gly Gly
145 150 155 160

Ser Ser Gly

<210> SEQ ID NO 147
<211> LENGTH: 165
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 147

Gly Ser Thr Gly Gly Ser Met Tyr Glu Ser Phe Ile Glu Ser Leu Pro
1 5 10 15

Phe Leu Lys Ser Leu Glu Phe Ser Glu Arg Leu Lys Val Val Asp Val
20 25 30

Ile Gly Thr Lys Val Tyr Asn Asp Gly Glu Gln Ile Ile Ala Gln Gly
35 40 45

Asp Ser Ala Asp Ser Phe Phe Ile Val Glu Ser Gly Glu Val Lys Ile
50 55 60

Thr Met Lys Arg Lys Gly Lys Ser Glu Val Glu Glu Asn Gly Ala Val
65 70 75 80

Glu Ile Ala Arg Cys Ser Arg Gly Gln Tyr Phe Gly Glu Leu Ala Leu
85 90 95

Val Thr Asn Lys Pro Arg Ala Ala Ser Ala His Ala Ile Gly Thr Val
100 105 110

Lys Cys Leu Ala Met Asp Val Gln Ala Phe Glu Arg Leu Leu Gly Pro
115 120 125

Cys Met Glu Ile Met Lys Arg Asn Ile Ala Thr Tyr Glu Glu Gln Leu
130 135 140

Val Ala Leu Phe Gly Thr Asn Met Asp Ile Val Gly Ser Gly Gly Ser
145 150 155 160

Gly Gly Ser Ser Gly
165

<210> SEQ ID NO 148
<211> LENGTH: 157
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 148

Gly Ser Thr Gly Gly Ser Gly Gly Met Tyr Glu Ser Phe Ile Glu Ser
1 5 10 15

Leu Pro Phe Leu Lys Ser Leu Glu Phe Ser Glu Arg Leu Lys Val Val
20 25 30

Asp Val Ile Gly Thr Lys Val Tyr Asn Asp Gly Glu Gln Ile Ile Ala
35 40 45

Gln Gly Asp Ser Ala Asp Ser Phe Phe Ile Val Glu Ser Gly Glu Val
50 55 60

Lys Ile Thr Met Lys Arg Lys Gly Lys Ser Glu Val Glu Glu Asn Gly
65 70 75 80

Ala Val Glu Ile Ala Arg Cys Ser Arg Gly Gln Tyr Phe Gly Glu Leu
85 90 95

Ala Leu Val Thr Asn Lys Pro Arg Ala Ala Ser Ala His Ala Ile Gly
100 105 110

Thr Val Lys Cys Leu Ala Met Asp Val Gln Ala Phe Glu Arg Leu Leu
115 120 125

Gly Pro Cys Met Glu Ile Met Lys Arg Asn Ile Ala Thr Tyr Glu Glu
130 135 140

Gln Leu Val Ala Leu Phe Gly Thr Asn Met Asp Ile Val
145 150 155

<210> SEQ ID NO 149
<211> LENGTH: 159
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 149

Gly Ser Thr Gly Gly Ser Gly Gly Met Tyr Glu Ser Phe Ile Glu Ser
1 5 10 15

Leu Pro Phe Leu Lys Ser Leu Glu Phe Ser Glu Arg Leu Lys Val Val
20 25 30

Asp Val Ile Gly Thr Lys Val Tyr Asn Asp Gly Glu Gln Ile Ile Ala
35 40 45

Gln Gly Asp Ser Ala Asp Ser Phe Phe Ile Val Glu Ser Gly Glu Val
50 55 60

Lys Ile Thr Met Lys Arg Lys Gly Lys Ser Glu Val Glu Glu Asn Gly
65 70 75 80

Ala Val Glu Ile Ala Arg Cys Ser Arg Gly Gln Tyr Phe Gly Glu Leu
85 90 95

Ala Leu Val Thr Asn Lys Pro Arg Ala Ala Ser Ala His Ala Ile Gly
100 105 110

Thr Val Lys Cys Leu Ala Met Asp Val Gln Ala Phe Glu Arg Leu Leu
115 120 125

Gly Pro Cys Met Glu Ile Met Lys Arg Asn Ile Ala Thr Tyr Glu Glu
130 135 140

Gln Leu Val Ala Leu Phe Gly Thr Asn Met Asp Ile Val Ser Gly
145 150 155

<210> SEQ ID NO 150
<211> LENGTH: 161
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 150

Gly Ser Thr Gly Gly Ser Gly Gly Met Tyr Glu Ser Phe Ile Glu Ser
1 5 10 15

Leu Pro Phe Leu Lys Ser Leu Glu Phe Ser Glu Arg Leu Lys Val Val
20 25 30

Asp Val Ile Gly Thr Lys Val Tyr Asn Asp Gly Glu Gln Ile Ile Ala
35 40 45

Gln Gly Asp Ser Ala Asp Ser Phe Phe Ile Val Glu Ser Gly Glu Val
50 55 60

Lys Ile Thr Met Lys Arg Lys Gly Lys Ser Glu Val Glu Glu Asn Gly
65 70 75 80

```
Ala Val Glu Ile Ala Arg Cys Ser Arg Gly Gln Tyr Phe Gly Glu Leu
                85                  90                  95

Ala Leu Val Thr Asn Lys Pro Arg Ala Ala Ser Ala His Ala Ile Gly
            100                 105                 110

Thr Val Lys Cys Leu Ala Met Asp Val Gln Ala Phe Glu Arg Leu Leu
        115                 120                 125

Gly Pro Cys Met Glu Ile Met Lys Arg Asn Ile Ala Thr Tyr Glu Glu
    130                 135                 140

Gln Leu Val Ala Leu Phe Gly Thr Asn Met Asp Ile Val Gly Ser Ser
145                 150                 155                 160

Gly
```

<210> SEQ ID NO 151
<211> LENGTH: 163
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 151

```
Gly Ser Thr Gly Gly Ser Gly Gly Met Tyr Glu Ser Phe Ile Glu Ser
1               5                   10                  15

Leu Pro Phe Leu Lys Ser Leu Glu Phe Ser Glu Arg Leu Lys Val Val
            20                  25                  30

Asp Val Ile Gly Thr Lys Val Tyr Asn Asp Gly Glu Gln Ile Ile Ala
        35                  40                  45

Gln Gly Asp Ser Ala Asp Ser Phe Phe Ile Val Glu Ser Gly Glu Val
    50                  55                  60

Lys Ile Thr Met Lys Arg Lys Gly Lys Ser Glu Val Glu Glu Asn Gly
65                  70                  75                  80

Ala Val Glu Ile Ala Arg Cys Ser Arg Gly Gln Tyr Phe Gly Glu Leu
                85                  90                  95

Ala Leu Val Thr Asn Lys Pro Arg Ala Ala Ser Ala His Ala Ile Gly
            100                 105                 110

Thr Val Lys Cys Leu Ala Met Asp Val Gln Ala Phe Glu Arg Leu Leu
        115                 120                 125

Gly Pro Cys Met Glu Ile Met Lys Arg Asn Ile Ala Thr Tyr Glu Glu
    130                 135                 140

Gln Leu Val Ala Leu Phe Gly Thr Asn Met Asp Ile Val Ser Gly Gly
145                 150                 155                 160

Ser Ser Gly
```

<210> SEQ ID NO 152
<211> LENGTH: 165
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 152

```
Gly Ser Thr Gly Gly Ser Gly Gly Met Tyr Glu Ser Phe Ile Glu Ser
1               5                   10                  15

Leu Pro Phe Leu Lys Ser Leu Glu Phe Ser Glu Arg Leu Lys Val Val
            20                  25                  30

Asp Val Ile Gly Thr Lys Val Tyr Asn Asp Gly Glu Gln Ile Ile Ala
```

-continued 35 40 45

Gln Gly Asp Ser Ala Asp Ser Phe Phe Ile Val Glu Ser Gly Glu Val
50 55 60

Lys Ile Thr Met Lys Arg Lys Gly Lys Ser Glu Val Glu Glu Asn Gly
65 70 75 80

Ala Val Glu Ile Ala Arg Cys Ser Arg Gly Gln Tyr Phe Gly Glu Leu
85 90 95

Ala Leu Val Thr Asn Lys Pro Arg Ala Ala Ser Ala His Ala Ile Gly
100 105 110

Thr Val Lys Cys Leu Ala Met Asp Val Gln Ala Phe Glu Arg Leu Leu
115 120 125

Gly Pro Cys Met Glu Ile Met Lys Arg Asn Ile Ala Thr Tyr Glu Glu
130 135 140

Gln Leu Val Ala Leu Phe Gly Thr Asn Met Asp Ile Val Gly Gly Ser
145 150 155 160

Gly Gly Ser Ser Gly
165

<210> SEQ ID NO 153
<211> LENGTH: 167
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 153

Gly Ser Thr Gly Gly Ser Gly Gly Met Tyr Glu Ser Phe Ile Glu Ser
1 5 10 15

Leu Pro Phe Leu Lys Ser Leu Glu Phe Ser Glu Arg Leu Lys Val Val
20 25 30

Asp Val Ile Gly Thr Lys Val Tyr Asn Asp Gly Glu Gln Ile Ile Ala
35 40 45

Gln Gly Asp Ser Ala Asp Ser Phe Phe Ile Val Glu Ser Gly Glu Val
50 55 60

Lys Ile Thr Met Lys Arg Lys Gly Lys Ser Glu Val Glu Glu Asn Gly
65 70 75 80

Ala Val Glu Ile Ala Arg Cys Ser Arg Gly Gln Tyr Phe Gly Glu Leu
85 90 95

Ala Leu Val Thr Asn Lys Pro Arg Ala Ala Ser Ala His Ala Ile Gly
100 105 110

Thr Val Lys Cys Leu Ala Met Asp Val Gln Ala Phe Glu Arg Leu Leu
115 120 125

Gly Pro Cys Met Glu Ile Met Lys Arg Asn Ile Ala Thr Tyr Glu Glu
130 135 140

Gln Leu Val Ala Leu Phe Gly Thr Asn Met Asp Ile Val Gly Ser Gly
145 150 155 160

Gly Ser Gly Gly Ser Ser Gly
165

<210> SEQ ID NO 154
<211> LENGTH: 159
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 154

Gly Ser Ser Gly Gly Ser Gly Gly Ser Gly Met Tyr Glu Ser Phe Ile
1 5 10 15

Glu Ser Leu Pro Phe Leu Lys Ser Leu Glu Phe Ser Glu Arg Leu Lys
20 25 30

Val Val Asp Val Ile Gly Thr Lys Val Tyr Asn Asp Gly Glu Gln Ile
35 40 45

Ile Ala Gln Gly Asp Ser Ala Asp Ser Phe Phe Ile Val Glu Ser Gly
50 55 60

Glu Val Lys Ile Thr Met Lys Arg Lys Gly Lys Ser Glu Val Glu Glu
65 70 75 80

Asn Gly Ala Val Glu Ile Ala Arg Cys Ser Arg Gly Gln Tyr Phe Gly
85 90 95

Glu Leu Ala Leu Val Thr Asn Lys Pro Arg Ala Ala Ser Ala His Ala
100 105 110

Ile Gly Thr Val Lys Cys Leu Ala Met Asp Val Gln Ala Phe Glu Arg
115 120 125

Leu Leu Gly Pro Cys Met Glu Ile Met Lys Arg Asn Ile Ala Thr Tyr
130 135 140

Glu Glu Gln Leu Val Ala Leu Phe Gly Thr Asn Met Asp Ile Val
145 150 155

<210> SEQ ID NO 155
<211> LENGTH: 161
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 155

Gly Ser Ser Gly Gly Ser Gly Gly Ser Gly Met Tyr Glu Ser Phe Ile
1 5 10 15

Glu Ser Leu Pro Phe Leu Lys Ser Leu Glu Phe Ser Glu Arg Leu Lys
20 25 30

Val Val Asp Val Ile Gly Thr Lys Val Tyr Asn Asp Gly Glu Gln Ile
35 40 45

Ile Ala Gln Gly Asp Ser Ala Asp Ser Phe Phe Ile Val Glu Ser Gly
50 55 60

Glu Val Lys Ile Thr Met Lys Arg Lys Gly Lys Ser Glu Val Glu Glu
65 70 75 80

Asn Gly Ala Val Glu Ile Ala Arg Cys Ser Arg Gly Gln Tyr Phe Gly
85 90 95

Glu Leu Ala Leu Val Thr Asn Lys Pro Arg Ala Ala Ser Ala His Ala
100 105 110

Ile Gly Thr Val Lys Cys Leu Ala Met Asp Val Gln Ala Phe Glu Arg
115 120 125

Leu Leu Gly Pro Cys Met Glu Ile Met Lys Arg Asn Ile Ala Thr Tyr
130 135 140

Glu Glu Gln Leu Val Ala Leu Phe Gly Thr Asn Met Asp Ile Val Ser
145 150 155 160

Gly

<210> SEQ ID NO 156
<211> LENGTH: 163
<212> TYPE: PRT

<213> ORGANISM: Artificial Sequence
<220> FEATURE:
<223> OTHER INFORMATION: Description of Artificial Sequence: Synthetic
polypeptide

<400> SEQUENCE: 156

```
Gly Ser Ser Gly Gly Ser Gly Gly Ser Gly Met Tyr Glu Ser Phe Ile
1               5                   10                  15

Glu Ser Leu Pro Phe Leu Lys Ser Leu Glu Phe Ser Glu Arg Leu Lys
            20                  25                  30

Val Val Asp Val Ile Gly Thr Lys Val Tyr Asn Asp Gly Glu Gln Ile
        35                  40                  45

Ile Ala Gln Gly Asp Ser Ala Asp Ser Phe Phe Ile Val Glu Ser Gly
    50                  55                  60

Glu Val Lys Ile Thr Met Lys Arg Lys Gly Lys Ser Glu Val Glu Glu
65                  70                  75                  80

Asn Gly Ala Val Glu Ile Ala Arg Cys Ser Arg Gly Gln Tyr Phe Gly
                85                  90                  95

Glu Leu Ala Leu Val Thr Asn Lys Pro Arg Ala Ala Ser Ala His Ala
            100                 105                 110

Ile Gly Thr Val Lys Cys Leu Ala Met Asp Val Gln Ala Phe Glu Arg
        115                 120                 125

Leu Leu Gly Pro Cys Met Glu Ile Met Lys Arg Asn Ile Ala Thr Tyr
    130                 135                 140

Glu Glu Gln Leu Val Ala Leu Phe Gly Thr Asn Met Asp Ile Val Gly
145                 150                 155                 160

Ser Ser Gly
```

<210> SEQ ID NO 157
<211> LENGTH: 165
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 157

```
Gly Ser Ser Gly Gly Ser Gly Gly Ser Gly Met Tyr Glu Ser Phe Ile
1               5                   10                  15

Glu Ser Leu Pro Phe Leu Lys Ser Leu Glu Phe Ser Glu Arg Leu Lys
            20                  25                  30

Val Val Asp Val Ile Gly Thr Lys Val Tyr Asn Asp Gly Glu Gln Ile
        35                  40                  45

Ile Ala Gln Gly Asp Ser Ala Asp Ser Phe Phe Ile Val Glu Ser Gly
    50                  55                  60

Glu Val Lys Ile Thr Met Lys Arg Lys Gly Lys Ser Glu Val Glu Glu
65                  70                  75                  80

Asn Gly Ala Val Glu Ile Ala Arg Cys Ser Arg Gly Gln Tyr Phe Gly
                85                  90                  95

Glu Leu Ala Leu Val Thr Asn Lys Pro Arg Ala Ala Ser Ala His Ala
            100                 105                 110

Ile Gly Thr Val Lys Cys Leu Ala Met Asp Val Gln Ala Phe Glu Arg
        115                 120                 125

Leu Leu Gly Pro Cys Met Glu Ile Met Lys Arg Asn Ile Ala Thr Tyr
    130                 135                 140

Glu Glu Gln Leu Val Ala Leu Phe Gly Thr Asn Met Asp Ile Val Ser
145                 150                 155                 160
```

```
Gly Gly Ser Ser Gly
                165


<210> SEQ ID NO 158
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Gly Ser Ser Gly Gly Ser Gly Gly Ser Gly Met Tyr Glu Ser Phe Ile
1               5                   10                  15

Glu Ser Leu Pro Phe Leu Lys Ser Leu Glu Phe Ser Glu Arg Leu Lys
            20                  25                  30

Val Val Asp Val Ile Gly Thr Lys Val Tyr Asn Asp Gly Glu Gln Ile
        35                  40                  45

Ile Ala Gln Gly Asp Ser Ala Asp Ser Phe Phe Ile Val Glu Ser Gly
    50                  55                  60

Glu Val Lys Ile Thr Met Lys Arg Lys Gly Lys Ser Glu Val Glu Glu
65                  70                  75                  80

Asn Gly Ala Val Glu Ile Ala Arg Cys Ser Arg Gly Gln Tyr Phe Gly
                85                  90                  95

Glu Leu Ala Leu Val Thr Asn Lys Pro Arg Ala Ala Ser Ala His Ala
            100                 105                 110

Ile Gly Thr Val Lys Cys Leu Ala Met Asp Val Gln Ala Phe Glu Arg
        115                 120                 125

Leu Leu Gly Pro Cys Met Glu Ile Met Lys Arg Asn Ile Ala Thr Tyr
    130                 135                 140

Glu Glu Gln Leu Val Ala Leu Phe Gly Thr Asn Met Asp Ile Val Gly
145                 150                 155                 160

Gly Ser Gly Gly Ser Ser Gly
                165


<210> SEQ ID NO 159
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Gly Ser Ser Gly Gly Ser Gly Gly Ser Gly Met Tyr Glu Ser Phe Ile
1               5                   10                  15

Glu Ser Leu Pro Phe Leu Lys Ser Leu Glu Phe Ser Glu Arg Leu Lys
            20                  25                  30

Val Val Asp Val Ile Gly Thr Lys Val Tyr Asn Asp Gly Glu Gln Ile
        35                  40                  45

Ile Ala Gln Gly Asp Ser Ala Asp Ser Phe Phe Ile Val Glu Ser Gly
    50                  55                  60

Glu Val Lys Ile Thr Met Lys Arg Lys Gly Lys Ser Glu Val Glu Glu
65                  70                  75                  80

Asn Gly Ala Val Glu Ile Ala Arg Cys Ser Arg Gly Gln Tyr Phe Gly
                85                  90                  95

Glu Leu Ala Leu Val Thr Asn Lys Pro Arg Ala Ala Ser Ala His Ala
            100                 105                 110
```

```
Ile Gly Thr Val Lys Cys Leu Ala Met Asp Val Gln Ala Phe Glu Arg
        115                 120                 125

Leu Leu Gly Pro Cys Met Glu Ile Met Lys Arg Asn Ile Ala Thr Tyr
    130                 135                 140

Glu Glu Gln Leu Val Ala Leu Phe Gly Thr Asn Met Asp Ile Val Gly
145                 150                 155                 160

Ser Gly Gly Ser Gly Gly Ser Ser Gly
                165
```

```
<210> SEQ ID NO 160
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Gly Ser Ser Gly Gly Ser Gly Gly Ser Gly Met Tyr Glu Ser Phe Ile
1               5                   10                  15

Glu Ser Leu Pro Phe Leu Lys Ser Leu Glu Phe Ser Glu Arg Leu Lys
            20                  25                  30

Val Val Asp Val Ile Gly Thr Lys Val Tyr Asn Asp Gly Glu Gln Ile
        35                  40                  45

Ile Ala Gln Gly Asp Ser Ala Asp Ser Phe Phe Ile Val Glu Ser Gly
    50                  55                  60

Glu Val Lys Ile Thr Met Lys Arg Lys Gly Lys Ser Glu Val Glu Glu
65                  70                  75                  80

Asn Gly Ala Val Glu Ile Ala Arg Cys Ser Arg Gly Gln Tyr Phe Gly
                85                  90                  95

Glu Leu Ala Leu Val Thr Asn Lys Pro Arg Ala Ala Ser Ala His Ala
            100                 105                 110

Ile Gly Thr Val Lys Cys Leu Ala Met Asp Val Gln Ala Phe Glu Arg
        115                 120                 125

Leu Leu Gly Pro Cys Met Glu Ile Met Lys Arg Asn Ile Ala Thr Tyr
    130                 135                 140

Glu Glu Gln Leu Val Ala Leu Phe Gly Thr Asn Met Asp
145                 150                 155
```

```
<210> SEQ ID NO 161
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Gly Ser Ser Gly Gly Ser Gly Gly Ser Gly Met Tyr Glu Ser Phe Ile
1               5                   10                  15

Glu Ser Leu Pro Phe Leu Lys Ser Leu Glu Phe Ser Glu Arg Leu Lys
            20                  25                  30

Val Val Asp Val Ile Gly Thr Lys Val Tyr Asn Asp Gly Glu Gln Ile
        35                  40                  45

Ile Ala Gln Gly Asp Ser Ala Asp Ser Phe Phe Ile Val Glu Ser Gly
    50                  55                  60

Glu Val Lys Ile Thr Met Lys Arg Lys Gly Lys Ser Glu Val Glu Glu
65                  70                  75                  80
```

```
Asn Gly Ala Val Glu Ile Ala Arg Cys Ser Arg Gly Gln Tyr Phe Gly
                85                  90                  95

Glu Leu Ala Leu Val Thr Asn Lys Pro Arg Ala Ala Ser Ala His Ala
            100                 105                 110

Ile Gly Thr Val Lys Cys Leu Ala Met Asp Val Gln Ala Phe Glu Arg
        115                 120                 125

Leu Leu Gly Pro Cys Met Glu Ile Met Lys Arg Asn Ile Ala Thr Tyr
    130                 135                 140

Glu Glu Gln Leu Val Ala Leu Phe Gly Thr Asn
145                 150                 155


<210> SEQ ID NO 162
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gly Ser Ser Gly Gly Ser Gly Gly Ser Gly Met Tyr Glu Ser Phe Ile
1               5                   10                  15

Glu Ser Leu Pro Phe Leu Lys Ser Leu Glu Phe Ser Glu Arg Leu Lys
            20                  25                  30

Val Val Asp Val Ile Gly Thr Lys Val Tyr Asn Asp Gly Glu Gln Ile
        35                  40                  45

Ile Ala Gln Gly Asp Ser Ala Asp Ser Phe Phe Ile Val Glu Ser Gly
    50                  55                  60

Glu Val Lys Ile Thr Met Lys Arg Lys Gly Lys Ser Glu Val Glu Glu
65                  70                  75                  80

Asn Gly Ala Val Glu Ile Ala Arg Cys Ser Arg Gly Gln Tyr Phe Gly
                85                  90                  95

Glu Leu Ala Leu Val Thr Asn Lys Pro Arg Ala Ala Ser Ala His Ala
            100                 105                 110

Ile Gly Thr Val Lys Cys Leu Ala Met Asp Val Gln Ala Phe Glu Arg
        115                 120                 125

Leu Leu Gly Pro Cys Met Glu Ile Met Lys Arg Asn Ile Ala Thr Tyr
    130                 135                 140

Glu Glu Gln Leu Val Ala Leu Phe Gly
145                 150


<210> SEQ ID NO 163
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Gly Ser Ser Gly Gly Ser Gly Gly Ser Gly Met Tyr Glu Ser Phe Ile
1               5                   10                  15

Glu Ser Leu Pro Phe Leu Lys Ser Leu Glu Phe Ser Glu Arg Leu Lys
            20                  25                  30

Val Val Asp Val Ile Gly Thr Lys Val Tyr Asn Asp Gly Glu Gln Ile
        35                  40                  45

Ile Ala Gln Gly Asp Ser Ala Asp Ser Phe Phe Ile Val Glu Ser Gly
    50                  55                  60
```

```
Glu Val Lys Ile Thr Met Lys Arg Lys Gly Lys Ser Glu Val Glu Glu
65                  70                  75                  80

Asn Gly Ala Val Glu Ile Ala Arg Cys Ser Arg Gly Gln Tyr Phe Gly
                85                  90                  95

Glu Leu Ala Leu Val Thr Asn Lys Pro Arg Ala Ala Ser Ala His Ala
            100                 105                 110

Ile Gly Thr Val Lys Cys Leu Ala Met Asp Val Gln Ala Phe Glu Arg
        115                 120                 125

Leu Leu Gly Pro Cys Met Glu Ile Met Lys Arg Asn Ile Ala Thr Tyr
    130                 135                 140

Glu Glu Gln Leu Val Ala Leu
145                 150


<210> SEQ ID NO 164
<211> LENGTH: 149
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Gly Ser Ser Gly Gly Ser Gly Gly Ser Gly Met Tyr Glu Ser Phe Ile
1               5                   10                  15

Glu Ser Leu Pro Phe Leu Lys Ser Leu Glu Phe Ser Glu Arg Leu Lys
            20                  25                  30

Val Val Asp Val Ile Gly Thr Lys Val Tyr Asn Asp Gly Glu Gln Ile
        35                  40                  45

Ile Ala Gln Gly Asp Ser Ala Asp Ser Phe Phe Ile Val Glu Ser Gly
    50                  55                  60

Glu Val Lys Ile Thr Met Lys Arg Lys Gly Lys Ser Glu Val Glu Glu
65                  70                  75                  80

Asn Gly Ala Val Glu Ile Ala Arg Cys Ser Arg Gly Gln Tyr Phe Gly
                85                  90                  95

Glu Leu Ala Leu Val Thr Asn Lys Pro Arg Ala Ala Ser Ala His Ala
            100                 105                 110

Ile Gly Thr Val Lys Cys Leu Ala Met Asp Val Gln Ala Phe Glu Arg
        115                 120                 125

Leu Leu Gly Pro Cys Met Glu Ile Met Lys Arg Asn Ile Ala Thr Tyr
    130                 135                 140

Glu Glu Gln Leu Val
145


<210> SEQ ID NO 165
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Gly Ser Ser Gly Gly Ser Gly Gly Ser Gly Met Tyr Glu Ser Phe Ile
1               5                   10                  15

Glu Ser Leu Pro Phe Leu Lys Ser Leu Glu Phe Ser Glu Arg Leu Lys
            20                  25                  30

Val Val Asp Val Ile Gly Thr Lys Val Tyr Asn Asp Gly Glu Gln Ile
        35                  40                  45
```

Ile Ala Gln Gly Asp Ser Ala Asp Ser Phe Phe Ile Val Glu Ser Gly
50 55 60

Glu Val Lys Ile Thr Met Lys Arg Lys Gly Lys Ser Glu Val Glu Glu
65 70 75 80

Asn Gly Ala Val Glu Ile Ala Arg Cys Ser Arg Gly Gln Tyr Phe Gly
85 90 95

Glu Leu Ala Leu Val Thr Asn Lys Pro Arg Ala Ala Ser Ala His Ala
100 105 110

Ile Gly Thr Val Lys Cys Leu Ala Met Asp Val Gln Ala Phe Glu Arg
115 120 125

Leu Leu Gly Pro Cys Met Glu Ile Met Lys Arg Asn Ile Ala Thr Tyr
130 135 140

Glu Glu Gln
145

<210> SEQ ID NO 166
<211> LENGTH: 145
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 166

Gly Ser Ser Gly Gly Ser Gly Gly Ser Gly Met Tyr Glu Ser Phe Ile
1 5 10 15

Glu Ser Leu Pro Phe Leu Lys Ser Leu Glu Phe Ser Glu Arg Leu Lys
20 25 30

Val Val Asp Val Ile Gly Thr Lys Val Tyr Asn Asp Gly Glu Gln Ile
35 40 45

Ile Ala Gln Gly Asp Ser Ala Asp Ser Phe Phe Ile Val Glu Ser Gly
50 55 60

Glu Val Lys Ile Thr Met Lys Arg Lys Gly Lys Ser Glu Val Glu Glu
65 70 75 80

Asn Gly Ala Val Glu Ile Ala Arg Cys Ser Arg Gly Gln Tyr Phe Gly
85 90 95

Glu Leu Ala Leu Val Thr Asn Lys Pro Arg Ala Ala Ser Ala His Ala
100 105 110

Ile Gly Thr Val Lys Cys Leu Ala Met Asp Val Gln Ala Phe Glu Arg
115 120 125

Leu Leu Gly Pro Cys Met Glu Ile Met Lys Arg Asn Ile Ala Thr Tyr
130 135 140

Glu
145

<210> SEQ ID NO 167
<211> LENGTH: 161
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 167

Gly Ser Ser Gly Gly Ser Gly Gly Ser Gly Gly Gly Met Tyr Glu Ser
1 5 10 15

Phe Ile Glu Ser Leu Pro Phe Leu Lys Ser Leu Glu Phe Ser Glu Arg
20 25 30

Leu Lys Val Val Asp Val Ile Gly Thr Lys Val Tyr Asn Asp Gly Glu
35 40 45

Gln Ile Ile Ala Gln Gly Asp Ser Ala Asp Ser Phe Phe Ile Val Glu
50 55 60

Ser Gly Glu Val Lys Ile Thr Met Lys Arg Lys Gly Lys Ser Glu Val
65 70 75 80

Glu Glu Asn Gly Ala Val Glu Ile Ala Arg Cys Ser Arg Gly Gln Tyr
85 90 95

Phe Gly Glu Leu Ala Leu Val Thr Asn Lys Pro Arg Ala Ala Ser Ala
100 105 110

His Ala Ile Gly Thr Val Lys Cys Leu Ala Met Asp Val Gln Ala Phe
115 120 125

Glu Arg Leu Leu Gly Pro Cys Met Glu Ile Met Lys Arg Asn Ile Ala
130 135 140

Thr Tyr Glu Glu Gln Leu Val Ala Leu Phe Gly Thr Asn Met Asp Ile
145 150 155 160

Val

<210> SEQ ID NO 168
<211> LENGTH: 163
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 168

Gly Ser Ser Gly Gly Ser Gly Gly Ser Gly Gly Gly Ser Gly Met Tyr
1 5 10 15

Glu Ser Phe Ile Glu Ser Leu Pro Phe Leu Lys Ser Leu Glu Phe Ser
20 25 30

Glu Arg Leu Lys Val Val Asp Val Ile Gly Thr Lys Val Tyr Asn Asp
35 40 45

Gly Glu Gln Ile Ile Ala Gln Gly Asp Ser Ala Asp Ser Phe Phe Ile
50 55 60

Val Glu Ser Gly Glu Val Lys Ile Thr Met Lys Arg Lys Gly Lys Ser
65 70 75 80

Glu Val Glu Glu Asn Gly Ala Val Glu Ile Ala Arg Cys Ser Arg Gly
85 90 95

Gln Tyr Phe Gly Glu Leu Ala Leu Val Thr Asn Lys Pro Arg Ala Ala
100 105 110

Ser Ala His Ala Ile Gly Thr Val Lys Cys Leu Ala Met Asp Val Gln
115 120 125

Ala Phe Glu Arg Leu Leu Gly Pro Cys Met Glu Ile Met Lys Arg Asn
130 135 140

Ile Ala Thr Tyr Glu Glu Gln Leu Val Ala Leu Phe Gly Thr Asn Met
145 150 155 160

Asp Ile Val

<210> SEQ ID NO 169
<211> LENGTH: 165
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 169

Gly Ser Ser Gly Gly Ser Gly Gly Ser Gly Gly Gly Ser Gly Gly Ser
1 5 10 15

Met Tyr Glu Ser Phe Ile Glu Ser Leu Pro Phe Leu Lys Ser Leu Glu
20 25 30

Phe Ser Glu Arg Leu Lys Val Val Asp Val Ile Gly Thr Lys Val Tyr
35 40 45

Asn Asp Gly Glu Gln Ile Ile Ala Gln Gly Asp Ser Ala Asp Ser Phe
50 55 60

Phe Ile Val Glu Ser Gly Glu Val Lys Ile Thr Met Lys Arg Lys Gly
65 70 75 80

Lys Ser Glu Val Glu Glu Asn Gly Ala Val Glu Ile Ala Arg Cys Ser
85 90 95

Arg Gly Gln Tyr Phe Gly Glu Leu Ala Leu Val Thr Asn Lys Pro Arg
100 105 110

Ala Ala Ser Ala His Ala Ile Gly Thr Val Lys Cys Leu Ala Met Asp
115 120 125

Val Gln Ala Phe Glu Arg Leu Leu Gly Pro Cys Met Glu Ile Met Lys
130 135 140

Arg Asn Ile Ala Thr Tyr Glu Glu Gln Leu Val Ala Leu Phe Gly Thr
145 150 155 160

Asn Met Asp Ile Val
165

<210> SEQ ID NO 170
<211> LENGTH: 167
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 170

Gly Ser Ser Gly Gly Ser Gly Gly Ser Gly Gly Gly Ser Gly Gly Ser
1 5 10 15

Gly Gly Met Tyr Glu Ser Phe Ile Glu Ser Leu Pro Phe Leu Lys Ser
20 25 30

Leu Glu Phe Ser Glu Arg Leu Lys Val Val Asp Val Ile Gly Thr Lys
35 40 45

Val Tyr Asn Asp Gly Glu Gln Ile Ile Ala Gln Gly Asp Ser Ala Asp
50 55 60

Ser Phe Phe Ile Val Glu Ser Gly Glu Val Lys Ile Thr Met Lys Arg
65 70 75 80

Lys Gly Lys Ser Glu Val Glu Glu Asn Gly Ala Val Glu Ile Ala Arg
85 90 95

Cys Ser Arg Gly Gln Tyr Phe Gly Glu Leu Ala Leu Val Thr Asn Lys
100 105 110

Pro Arg Ala Ala Ser Ala His Ala Ile Gly Thr Val Lys Cys Leu Ala
115 120 125

Met Asp Val Gln Ala Phe Glu Arg Leu Leu Gly Pro Cys Met Glu Ile
130 135 140

Met Lys Arg Asn Ile Ala Thr Tyr Glu Glu Gln Leu Val Ala Leu Phe
145 150 155 160

Gly Thr Asn Met Asp Ile Val
165

<210> SEQ ID NO 171
<211> LENGTH: 169
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 171

Gly Ser Ser Gly Gly Ser Gly Gly Ser Gly Gly Gly Ser Gly Gly Ser
1 5 10 15

Gly Gly Ser Gly Met Tyr Glu Ser Phe Ile Glu Ser Leu Pro Phe Leu
20 25 30

Lys Ser Leu Glu Phe Ser Glu Arg Leu Lys Val Val Asp Val Ile Gly
35 40 45

Thr Lys Val Tyr Asn Asp Gly Glu Gln Ile Ile Ala Gln Gly Asp Ser
50 55 60

Ala Asp Ser Phe Phe Ile Val Glu Ser Gly Glu Val Lys Ile Thr Met
65 70 75 80

Lys Arg Lys Gly Lys Ser Glu Val Glu Glu Asn Gly Ala Val Glu Ile
85 90 95

Ala Arg Cys Ser Arg Gly Gln Tyr Phe Gly Glu Leu Ala Leu Val Thr
100 105 110

Asn Lys Pro Arg Ala Ala Ser Ala His Ala Ile Gly Thr Val Lys Cys
115 120 125

Leu Ala Met Asp Val Gln Ala Phe Glu Arg Leu Leu Gly Pro Cys Met
130 135 140

Glu Ile Met Lys Arg Asn Ile Ala Thr Tyr Glu Glu Gln Leu Val Ala
145 150 155 160

Leu Phe Gly Thr Asn Met Asp Ile Val
165

<210> SEQ ID NO 172
<211> LENGTH: 699
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 172

Met Ala Lys Asn Ile Lys Lys Gly Pro Ala Pro Phe Tyr Pro Leu Glu
1 5 10 15

Asp Gly Thr Ala Gly Glu Gln Leu His Lys Ala Met Lys Arg Tyr Ala
20 25 30

Leu Val Pro Gly Thr Ile Ala Phe Thr Asp Ala His Ile Glu Val Asp
35 40 45

Ile Thr Tyr Ala Glu Tyr Phe Glu Met Ser Val Arg Leu Ala Glu Ala
50 55 60

Met Lys Arg Tyr Gly Leu Asn Thr Asn His Arg Ile Val Val Cys Ser
65 70 75 80

Glu Asn Ser Leu Gln Phe Phe Met Pro Val Leu Gly Ala Leu Phe Ile
85 90 95

Gly Val Ala Val Ala Pro Ala Asn Asp Ile Tyr Asn Glu Arg Glu Leu
100 105 110

Leu Asn Ser Met Gly Ile Ser Gln Pro Thr Val Val Phe Val Ser Lys
115 120 125

-continued

```
Lys Gly Leu Gln Lys Ile Leu Asn Val Gln Lys Lys Leu Pro Ile Ile
    130                 135                 140

Gln Lys Ile Ile Ile Met Asp Ser Lys Thr Asp Tyr Gln Gly Phe Gln
145                 150                 155                 160

Ser Met Tyr Thr Phe Val Thr Ser His Leu Pro Pro Gly Phe Asn Glu
                165                 170                 175

Tyr Asp Phe Val Pro Glu Ser Phe Asp Arg Asp Lys Thr Ile Ala Leu
            180                 185                 190

Ile Met Asn Ser Ser Gly Ser Thr Gly Leu Pro Lys Gly Val Ala Leu
        195                 200                 205

Pro His Arg Thr Ala Cys Val Arg Phe Ser His Ala Arg Asp Pro Ile
    210                 215                 220

Phe Gly Asn Gln Ile Ile Pro Gly Ser Thr Gly Met Tyr Glu Ser Phe
225                 230                 235                 240

Ile Glu Ser Leu Pro Phe Leu Lys Ser Leu Glu Phe Ser Glu Arg Leu
                245                 250                 255

Lys Val Val Asp Val Ile Gly Thr Lys Val Tyr Asn Asp Gly Glu Gln
            260                 265                 270

Ile Ile Ala Gln Gly Asp Ser Ala Asp Ser Phe Phe Ile Val Glu Ser
        275                 280                 285

Gly Glu Val Lys Ile Thr Met Lys Arg Lys Gly Lys Ser Glu Val Glu
    290                 295                 300

Glu Asn Gly Ala Val Glu Ile Ala Arg Cys Ser Arg Gly Gln Tyr Phe
305                 310                 315                 320

Gly Glu Leu Ala Leu Val Thr Asn Lys Pro Arg Ala Ala Ser Ala His
                325                 330                 335

Ala Ile Gly Thr Val Lys Cys Leu Ala Met Asp Val Gln Ala Phe Glu
            340                 345                 350

Arg Leu Leu Gly Pro Cys Met Glu Ile Met Lys Arg Asn Ile Ala Thr
        355                 360                 365

Tyr Glu Glu Gln Leu Val Ala Leu Phe Gly Thr Asn Met Asp Ile Val
    370                 375                 380

Gly Ser Ser Gly Asp Thr Ala Ile Leu Ser Val Val Pro Phe His His
385                 390                 395                 400

Gly Phe Gly Met Phe Thr Thr Leu Gly Tyr Leu Ile Cys Gly Phe Arg
                405                 410                 415

Val Val Leu Met Tyr Arg Phe Glu Glu Glu Leu Phe Leu Arg Ser Leu
            420                 425                 430

Gln Asp Tyr Lys Ile Gln Ser Ala Leu Leu Val Pro Thr Leu Phe Ser
        435                 440                 445

Phe Phe Ala Lys Ser Thr Leu Ile Asp Lys Tyr Asp Leu Ser Asn Leu
    450                 455                 460

His Glu Ile Ala Ser Gly Gly Ala Pro Leu Ser Lys Glu Val Gly Glu
465                 470                 475                 480

Ala Val Ala Lys Arg Phe His Leu Pro Gly Ile Arg Gln Gly Tyr Gly
                485                 490                 495

Leu Thr Glu Thr Thr Ser Ala Ile Leu Ile Thr Pro Glu Gly Asp Asp
            500                 505                 510

Lys Pro Gly Ala Val Gly Lys Val Val Pro Phe Phe Glu Ala Lys Val
        515                 520                 525

Val Asp Leu Asp Thr Gly Lys Thr Leu Gly Val Asn Gln Arg Gly Glu
    530                 535                 540

Leu Cys Val Arg Gly Pro Met Ile Met Ser Gly Tyr Val Asn Asn Pro
```

-continued 545 550 555 560

Glu Ala Thr Asn Ala Leu Ile Asp Lys Asp Gly Trp Leu His Ser Gly
565 570 575

Asp Ile Ala Tyr Trp Asp Glu Asp Glu His Phe Phe Ile Val Asp Arg
580 585 590

Leu Lys Ser Leu Ile Lys Tyr Lys Gly Tyr Gln Val Ala Pro Ala Glu
595 600 605

Leu Glu Ser Ile Leu Leu Gln His Pro Asn Ile Phe Asp Ala Gly Val
610 615 620

Ala Gly Leu Pro Asp Asp Asp Ala Gly Glu Leu Pro Ala Ala Val Val
625 630 635 640

Val Leu Glu His Gly Lys Thr Met Thr Glu Lys Glu Ile Val Asp Tyr
645 650 655

Val Ala Ser Gln Val Thr Thr Ala Lys Lys Leu Arg Gly Gly Val Val
660 665 670

Phe Val Asp Glu Val Pro Lys Gly Leu Thr Gly Lys Leu Asp Ala Arg
675 680 685

Lys Ile Arg Glu Ile Leu Ile Lys Ala Lys Lys
690 695

<210> SEQ ID NO 173
<211> LENGTH: 711
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 173

Met Ala Lys Asn Ile Lys Lys Gly Pro Ala Pro Phe Tyr Pro Leu Glu
1 5 10 15

Asp Gly Thr Ala Gly Glu Gln Leu His Lys Ala Met Lys Arg Tyr Ala
20 25 30

Leu Val Pro Gly Thr Ile Ala Phe Thr Asp Ala His Ile Glu Val Asp
35 40 45

Ile Thr Tyr Ala Glu Tyr Phe Glu Met Ser Val Arg Leu Ala Glu Ala
50 55 60

Met Lys Arg Tyr Gly Leu Asn Thr Asn His Arg Ile Val Val Cys Ser
65 70 75 80

Glu Asn Ser Leu Gln Phe Phe Met Pro Val Leu Gly Ala Leu Phe Ile
85 90 95

Gly Val Ala Val Ala Pro Ala Asn Asp Ile Tyr Asn Glu Arg Glu Leu
100 105 110

Leu Asn Ser Met Gly Ile Ser Gln Pro Thr Val Val Phe Val Ser Lys
115 120 125

Lys Gly Leu Gln Lys Ile Leu Asn Val Gln Lys Lys Leu Pro Ile Ile
130 135 140

Gln Lys Ile Ile Ile Met Asp Ser Lys Thr Asp Tyr Gln Gly Phe Gln
145 150 155 160

Ser Met Tyr Thr Phe Val Thr Ser His Leu Pro Pro Gly Phe Asn Glu
165 170 175

Tyr Asp Phe Val Pro Glu Ser Phe Asp Arg Asp Lys Thr Ile Ala Leu
180 185 190

Ile Met Asn Ser Ser Gly Ser Thr Gly Leu Pro Lys Gly Val Ala Leu
195 200 205

-continued

```
Pro His Arg Thr Ala Cys Val Arg Phe Ser His Ala Arg Asp Pro Ile
    210                 215                 220

Phe Gly Asn Gln Ile Ile Pro Gly Ser Ser Gly Gly Ser Gly Gly Ser
225                 230                 235                 240

Gly Met Tyr Glu Ser Phe Ile Glu Ser Leu Pro Phe Leu Lys Ser Leu
                245                 250                 255

Glu Phe Ser Glu Arg Leu Lys Val Val Asp Val Ile Gly Thr Lys Val
            260                 265                 270

Tyr Asn Asp Gly Glu Gln Ile Ile Ala Gln Gly Asp Ser Ala Asp Ser
        275                 280                 285

Phe Phe Ile Val Glu Ser Gly Glu Val Lys Ile Thr Met Lys Arg Lys
    290                 295                 300

Gly Lys Ser Glu Val Glu Glu Asn Gly Ala Val Glu Ile Ala Arg Cys
305                 310                 315                 320

Ser Arg Gly Gln Tyr Phe Gly Glu Leu Ala Leu Val Thr Asn Lys Pro
                325                 330                 335

Arg Ala Ala Ser Ala His Ala Ile Gly Thr Val Lys Cys Leu Ala Met
            340                 345                 350

Asp Val Gln Ala Phe Glu Arg Leu Leu Gly Pro Cys Met Glu Ile Met
        355                 360                 365

Lys Arg Asn Ile Ala Thr Tyr Glu Glu Gln Leu Val Ala Leu Phe Gly
    370                 375                 380

Thr Asn Met Asp Ile Val Gly Ser Gly Gly Ser Gly Gly Ser Ser Gly
385                 390                 395                 400

Asp Thr Ala Ile Leu Ser Val Val Pro Phe His His Gly Phe Gly Met
                405                 410                 415

Phe Thr Thr Leu Gly Tyr Leu Ile Cys Gly Phe Arg Val Val Leu Met
            420                 425                 430

Tyr Arg Phe Glu Glu Glu Leu Phe Leu Arg Ser Leu Gln Asp Tyr Lys
        435                 440                 445

Ile Gln Ser Ala Leu Leu Val Pro Thr Leu Phe Ser Phe Phe Ala Lys
    450                 455                 460

Ser Thr Leu Ile Asp Lys Tyr Asp Leu Ser Asn Leu His Glu Ile Ala
465                 470                 475                 480

Ser Gly Gly Ala Pro Leu Ser Lys Glu Val Gly Glu Ala Val Ala Lys
                485                 490                 495

Arg Phe His Leu Pro Gly Ile Arg Gln Gly Tyr Gly Leu Thr Glu Thr
            500                 505                 510

Thr Ser Ala Ile Leu Ile Thr Pro Glu Gly Asp Asp Lys Pro Gly Ala
        515                 520                 525

Val Gly Lys Val Val Pro Phe Phe Glu Ala Lys Val Val Asp Leu Asp
    530                 535                 540

Thr Gly Lys Thr Leu Gly Val Asn Gln Arg Gly Glu Leu Cys Val Arg
545                 550                 555                 560

Gly Pro Met Ile Met Ser Gly Tyr Val Asn Asn Pro Glu Ala Thr Asn
                565                 570                 575

Ala Leu Ile Asp Lys Asp Gly Trp Leu His Ser Gly Asp Ile Ala Tyr
            580                 585                 590

Trp Asp Glu Asp Glu His Phe Phe Ile Val Asp Arg Leu Lys Ser Leu
        595                 600                 605

Ile Lys Tyr Lys Gly Tyr Gln Val Ala Pro Ala Glu Leu Glu Ser Ile
    610                 615                 620

Leu Leu Gln His Pro Asn Ile Phe Asp Ala Gly Val Ala Gly Leu Pro
```

-continued

```
625                 630                 635                 640

Asp Asp Asp Ala Gly Glu Leu Pro Ala Ala Val Val Val Leu Glu His
                645                 650                 655

Gly Lys Thr Met Thr Glu Lys Glu Ile Val Asp Tyr Val Ala Ser Gln
            660                 665                 670

Val Thr Thr Ala Lys Lys Leu Arg Gly Gly Val Val Phe Val Asp Glu
        675                 680                 685

Val Pro Lys Gly Leu Thr Gly Lys Leu Asp Ala Arg Lys Ile Arg Glu
    690                 695                 700

Ile Leu Ile Lys Ala Lys Lys
705                 710


<210> SEQ ID NO 174
<211> LENGTH: 731
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Met Ala Lys Asn Ile Lys Lys Gly Pro Ala Pro Phe Tyr Pro Leu Glu
1               5                   10                  15

Asp Gly Thr Ala Gly Glu Gln Leu His Lys Ala Met Lys Arg Tyr Ala
            20                  25                  30

Leu Val Pro Gly Thr Ile Ala Phe Thr Asp Ala His Ile Glu Val Asp
        35                  40                  45

Ile Thr Tyr Ala Glu Tyr Phe Glu Met Ser Val Arg Leu Ala Glu Ala
    50                  55                  60

Met Lys Arg Tyr Gly Leu Asn Thr Asn His Arg Ile Val Val Cys Ser
65                  70                  75                  80

Glu Asn Ser Leu Gln Phe Phe Met Pro Val Leu Gly Ala Leu Phe Ile
                85                  90                  95

Gly Val Ala Val Ala Pro Ala Asn Asp Ile Tyr Asn Glu Arg Glu Leu
            100                 105                 110

Leu Asn Ser Met Gly Ile Ser Gln Pro Thr Val Val Phe Val Ser Lys
        115                 120                 125

Lys Gly Leu Gln Lys Ile Leu Asn Val Gln Lys Lys Leu Pro Ile Ile
    130                 135                 140

Gln Lys Ile Ile Ile Met Asp Ser Lys Thr Asp Tyr Gln Gly Phe Gln
145                 150                 155                 160

Ser Met Tyr Thr Phe Val Thr Ser His Leu Pro Pro Gly Phe Asn Glu
                165                 170                 175

Tyr Asp Phe Val Pro Glu Ser Phe Asp Arg Asp Lys Thr Ile Ala Leu
            180                 185                 190

Ile Met Asn Ser Ser Gly Ser Thr Gly Leu Pro Lys Gly Val Ala Leu
        195                 200                 205

Pro His Arg Thr Ala Cys Val Arg Phe Ser His Ala Arg Asp Pro Ile
    210                 215                 220

Phe Gly Asn Gln Ile Ile Pro Gly Ser Ser Gly Gly Ser Gly Gly Ser
225                 230                 235                 240

Gly Gly Gly Ser Gly Gly Ser Gly Gly Ser Gly Met Tyr Glu Ser Phe
                245                 250                 255

Ile Glu Ser Leu Pro Phe Leu Lys Ser Leu Glu Phe Ser Glu Arg Leu
            260                 265                 270
```

```
Lys Val Val Asp Val Ile Gly Thr Lys Val Tyr Asn Asp Gly Glu Gln
        275                 280                 285

Ile Ile Ala Gln Gly Asp Ser Ala Asp Ser Phe Phe Ile Val Glu Ser
    290                 295                 300

Gly Glu Val Lys Ile Thr Met Lys Arg Lys Gly Lys Ser Glu Val Glu
305                 310                 315                 320

Glu Asn Gly Ala Val Glu Ile Ala Arg Cys Ser Arg Gly Gln Tyr Phe
                325                 330                 335

Gly Glu Leu Ala Leu Val Thr Asn Lys Pro Arg Ala Ala Ser Ala His
            340                 345                 350

Ala Ile Gly Thr Val Lys Cys Leu Ala Met Asp Val Gln Ala Phe Glu
        355                 360                 365

Arg Leu Leu Gly Pro Cys Met Glu Ile Met Lys Arg Asn Ile Ala Thr
    370                 375                 380

Tyr Glu Glu Gln Leu Val Ala Leu Phe Gly Thr Asn Met Asp Ile Val
385                 390                 395                 400

Gly Ser Gly Gly Ser Gly Gly Ser Gly Gly Thr Ser Gly Gly Ser Gly
                405                 410                 415

Gly Ser Ser Gly Asp Thr Ala Ile Leu Ser Val Val Pro Phe His His
            420                 425                 430

Gly Phe Gly Met Phe Thr Thr Leu Gly Tyr Leu Ile Cys Gly Phe Arg
        435                 440                 445

Val Val Leu Met Tyr Arg Phe Glu Glu Glu Leu Phe Leu Arg Ser Leu
    450                 455                 460

Gln Asp Tyr Lys Ile Gln Ser Ala Leu Leu Val Pro Thr Leu Phe Ser
465                 470                 475                 480

Phe Phe Ala Lys Ser Thr Leu Ile Asp Lys Tyr Asp Leu Ser Asn Leu
                485                 490                 495

His Glu Ile Ala Ser Gly Gly Ala Pro Leu Ser Lys Glu Val Gly Glu
            500                 505                 510

Ala Val Ala Lys Arg Phe His Leu Pro Gly Ile Arg Gln Gly Tyr Gly
        515                 520                 525

Leu Thr Glu Thr Thr Ser Ala Ile Leu Ile Thr Pro Glu Gly Asp Asp
    530                 535                 540

Lys Pro Gly Ala Val Gly Lys Val Val Pro Phe Phe Glu Ala Lys Val
545                 550                 555                 560

Val Asp Leu Asp Thr Gly Lys Thr Leu Gly Val Asn Gln Arg Gly Glu
                565                 570                 575

Leu Cys Val Arg Gly Pro Met Ile Met Ser Gly Tyr Val Asn Asn Pro
            580                 585                 590

Glu Ala Thr Asn Ala Leu Ile Asp Lys Asp Gly Trp Leu His Ser Gly
        595                 600                 605

Asp Ile Ala Tyr Trp Asp Glu Asp Glu His Phe Phe Ile Val Asp Arg
    610                 615                 620

Leu Lys Ser Leu Ile Lys Tyr Lys Gly Tyr Gln Val Ala Pro Ala Glu
625                 630                 635                 640

Leu Glu Ser Ile Leu Leu Gln His Pro Asn Ile Phe Asp Ala Gly Val
                645                 650                 655

Ala Gly Leu Pro Asp Asp Asp Ala Gly Glu Leu Pro Ala Ala Val Val
            660                 665                 670

Val Leu Glu His Gly Lys Thr Met Thr Glu Lys Glu Ile Val Asp Tyr
        675                 680                 685

Val Ala Ser Gln Val Thr Thr Ala Lys Lys Leu Arg Gly Gly Val Val
```

```
    690                 695                 700

Phe Val Asp Glu Val Pro Lys Gly Leu Thr Gly Lys Leu Asp Ala Arg
705                 710                 715                 720

Lys Ile Arg Glu Ile Leu Ile Lys Ala Lys Lys
                725                 730


<210> SEQ ID NO 175
<211> LENGTH: 696
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Met Ala Lys Asn Ile Lys Lys Gly Pro Ala Pro Phe Tyr Pro Leu Glu
1               5                   10                  15

Asp Gly Thr Ala Gly Glu Gln Leu His Lys Ala Met Lys Arg Tyr Ala
            20                  25                  30

Leu Val Pro Gly Thr Ile Ala Phe Thr Asp Ala His Ile Glu Val Asp
        35                  40                  45

Ile Thr Tyr Ala Glu Tyr Phe Glu Met Ser Val Arg Leu Ala Glu Ala
    50                  55                  60

Met Lys Arg Tyr Gly Leu Asn Thr Asn His Arg Ile Val Val Cys Ser
65                  70                  75                  80

Glu Asn Ser Leu Gln Phe Phe Met Pro Val Leu Gly Ala Leu Phe Ile
                85                  90                  95

Gly Val Ala Val Ala Pro Ala Asn Asp Ile Tyr Asn Glu Arg Glu Leu
            100                 105                 110

Leu Asn Ser Met Gly Ile Ser Gln Pro Thr Val Val Phe Val Ser Lys
        115                 120                 125

Lys Gly Leu Gln Lys Ile Leu Asn Val Gln Lys Lys Leu Pro Ile Ile
    130                 135                 140

Gln Lys Ile Ile Ile Met Asp Ser Lys Thr Asp Tyr Gln Gly Phe Gln
145                 150                 155                 160

Ser Met Tyr Thr Phe Val Thr Ser His Leu Pro Pro Gly Phe Asn Glu
                165                 170                 175

Tyr Asp Phe Val Pro Glu Ser Phe Asp Arg Asp Lys Thr Ile Ala Leu
            180                 185                 190

Ile Met Asn Ser Ser Gly Ser Thr Gly Leu Pro Lys Gly Val Ala Leu
        195                 200                 205

Pro His Arg Thr Ala Cys Val Arg Phe Ser His Ala Arg Asp Pro Ile
    210                 215                 220

Phe Gly Asn Gln Ile Ile Pro Asp Thr Ala Ile Leu Ser Val Val Pro
225                 230                 235                 240

Phe His His Gly Phe Gly Met Phe Thr Thr Leu Gly Tyr Leu Ile Cys
                245                 250                 255

Gly Phe Arg Val Val Leu Met Tyr Arg Phe Glu Glu Glu Leu Phe Leu
            260                 265                 270

Arg Ser Leu Gln Asp Tyr Lys Ile Gln Ser Ala Leu Leu Val Pro Thr
        275                 280                 285

Leu Phe Ser Phe Phe Ala Lys Ser Thr Leu Ile Asp Lys Tyr Asp Leu
    290                 295                 300

Ser Asn Leu His Glu Ile Ala Ser Gly Gly Ala Pro Leu Ser Lys Glu
305                 310                 315                 320
```

```
Val Gly Glu Ala Val Ala Lys Arg Phe His Leu Pro Gly Ile Arg Gln
                325                 330                 335

Gly Tyr Gly Leu Thr Glu Thr Thr Ser Ala Ile Leu Ile Thr Pro Glu
            340                 345                 350

Gly Gly Ser Thr Gly Met Tyr Glu Ser Phe Ile Glu Ser Leu Pro Phe
        355                 360                 365

Leu Lys Ser Leu Glu Phe Ser Glu Arg Leu Lys Val Val Asp Val Ile
    370                 375                 380

Gly Thr Lys Val Tyr Asn Asp Gly Glu Gln Ile Ile Ala Gln Gly Asp
385                 390                 395                 400

Ser Ala Asp Ser Phe Phe Ile Val Glu Ser Gly Glu Val Lys Ile Thr
                405                 410                 415

Met Lys Arg Lys Gly Lys Ser Glu Val Glu Glu Asn Gly Ala Val Glu
            420                 425                 430

Ile Ala Arg Cys Ser Arg Gly Gln Tyr Phe Gly Glu Leu Ala Leu Val
        435                 440                 445

Thr Asn Lys Pro Arg Ala Ala Ser Ala His Ala Ile Gly Thr Val Lys
    450                 455                 460

Cys Leu Ala Met Asp Val Gln Ala Phe Glu Arg Leu Leu Gly Pro Cys
465                 470                 475                 480

Met Glu Ile Met Lys Arg Asn Ile Ala Thr Tyr Glu Glu Gln Leu Val
                485                 490                 495

Ala Leu Phe Gly Thr Asn Met Asp Ile Val Gly Ser Ser Gly Pro Gly
            500                 505                 510

Ala Val Gly Lys Val Val Pro Phe Phe Glu Ala Lys Val Val Asp Leu
        515                 520                 525

Asp Thr Gly Lys Thr Leu Gly Val Asn Gln Arg Gly Glu Leu Cys Val
    530                 535                 540

Arg Gly Pro Met Ile Met Ser Gly Tyr Val Asn Asn Pro Glu Ala Thr
545                 550                 555                 560

Asn Ala Leu Ile Asp Lys Asp Gly Trp Leu His Ser Gly Asp Ile Ala
                565                 570                 575

Tyr Trp Asp Glu Asp Glu His Phe Phe Ile Val Asp Arg Leu Lys Ser
            580                 585                 590

Leu Ile Lys Tyr Lys Gly Tyr Gln Val Ala Pro Ala Glu Leu Glu Ser
        595                 600                 605

Ile Leu Leu Gln His Pro Asn Ile Phe Asp Ala Gly Val Ala Gly Leu
    610                 615                 620

Pro Asp Asp Asp Ala Gly Glu Leu Pro Ala Ala Val Val Val Leu Glu
625                 630                 635                 640

His Gly Lys Thr Met Thr Glu Lys Glu Ile Val Asp Tyr Val Ala Ser
                645                 650                 655

Gln Val Thr Thr Ala Lys Lys Leu Arg Gly Gly Val Val Phe Val Asp
            660                 665                 670

Glu Val Pro Lys Gly Leu Thr Gly Lys Leu Asp Ala Arg Lys Ile Arg
        675                 680                 685

Glu Ile Leu Ile Lys Ala Lys Lys
    690                 695
```

<210> SEQ ID NO 176
<211> LENGTH: 708
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 176

```
Met Ala Lys Asn Ile Lys Lys Gly Pro Ala Pro Phe Tyr Pro Leu Glu
1               5                   10                  15

Asp Gly Thr Ala Gly Glu Gln Leu His Lys Ala Met Lys Arg Tyr Ala
            20                  25                  30

Leu Val Pro Gly Thr Ile Ala Phe Thr Asp Ala His Ile Glu Val Asp
        35                  40                  45

Ile Thr Tyr Ala Glu Tyr Phe Glu Met Ser Val Arg Leu Ala Glu Ala
    50                  55                  60

Met Lys Arg Tyr Gly Leu Asn Thr Asn His Arg Ile Val Val Cys Ser
65                  70                  75                  80

Glu Asn Ser Leu Gln Phe Phe Met Pro Val Leu Gly Ala Leu Phe Ile
                85                  90                  95

Gly Val Ala Val Ala Pro Ala Asn Asp Ile Tyr Asn Glu Arg Glu Leu
            100                 105                 110

Leu Asn Ser Met Gly Ile Ser Gln Pro Thr Val Val Phe Val Ser Lys
        115                 120                 125

Lys Gly Leu Gln Lys Ile Leu Asn Val Gln Lys Lys Leu Pro Ile Ile
    130                 135                 140

Gln Lys Ile Ile Ile Met Asp Ser Lys Thr Asp Tyr Gln Gly Phe Gln
145                 150                 155                 160

Ser Met Tyr Thr Phe Val Thr Ser His Leu Pro Pro Gly Phe Asn Glu
                165                 170                 175

Tyr Asp Phe Val Pro Glu Ser Phe Asp Arg Asp Lys Thr Ile Ala Leu
            180                 185                 190

Ile Met Asn Ser Ser Gly Ser Thr Gly Leu Pro Lys Gly Val Ala Leu
        195                 200                 205

Pro His Arg Thr Ala Cys Val Arg Phe Ser His Ala Arg Asp Pro Ile
    210                 215                 220

Phe Gly Asn Gln Ile Ile Pro Asp Thr Ala Ile Leu Ser Val Val Pro
225                 230                 235                 240

Phe His His Gly Phe Gly Met Phe Thr Thr Leu Gly Tyr Leu Ile Cys
                245                 250                 255

Gly Phe Arg Val Val Leu Met Tyr Arg Phe Glu Glu Glu Leu Phe Leu
            260                 265                 270

Arg Ser Leu Gln Asp Tyr Lys Ile Gln Ser Ala Leu Leu Val Pro Thr
        275                 280                 285

Leu Phe Ser Phe Phe Ala Lys Ser Thr Leu Ile Asp Lys Tyr Asp Leu
    290                 295                 300

Ser Asn Leu His Glu Ile Ala Ser Gly Gly Ala Pro Leu Ser Lys Glu
305                 310                 315                 320

Val Gly Glu Ala Val Ala Lys Arg Phe His Leu Pro Gly Ile Arg Gln
                325                 330                 335

Gly Tyr Gly Leu Thr Glu Thr Thr Ser Ala Ile Leu Ile Thr Pro Glu
            340                 345                 350

Gly Gly Ser Ser Gly Gly Ser Gly Gly Ser Gly Met Tyr Glu Ser Phe
        355                 360                 365

Ile Glu Ser Leu Pro Phe Leu Lys Ser Leu Glu Phe Ser Glu Arg Leu
    370                 375                 380

Lys Val Val Asp Val Ile Gly Thr Lys Val Tyr Asn Asp Gly Glu Gln
385                 390                 395                 400
```

Ile Ile Ala Gln Gly Asp Ser Ala Asp Ser Phe Phe Ile Val Glu Ser
405 410 415

Gly Glu Val Lys Ile Thr Met Lys Arg Lys Gly Lys Ser Glu Val Glu
420 425 430

Glu Asn Gly Ala Val Glu Ile Ala Arg Cys Ser Arg Gly Gln Tyr Phe
435 440 445

Gly Glu Leu Ala Leu Val Thr Asn Lys Pro Arg Ala Ala Ser Ala His
450 455 460

Ala Ile Gly Thr Val Lys Cys Leu Ala Met Asp Val Gln Ala Phe Glu
465 470 475 480

Arg Leu Leu Gly Pro Cys Met Glu Ile Met Lys Arg Asn Ile Ala Thr
485 490 495

Tyr Glu Glu Gln Leu Val Ala Leu Phe Gly Thr Asn Met Asp Ile Val
500 505 510

Gly Ser Gly Gly Ser Gly Gly Ser Ser Gly Pro Gly Ala Val Gly Lys
515 520 525

Val Val Pro Phe Phe Glu Ala Lys Val Val Asp Leu Asp Thr Gly Lys
530 535 540

Thr Leu Gly Val Asn Gln Arg Gly Glu Leu Cys Val Arg Gly Pro Met
545 550 555 560

Ile Met Ser Gly Tyr Val Asn Asn Pro Glu Ala Thr Asn Ala Leu Ile
565 570 575

Asp Lys Asp Gly Trp Leu His Ser Gly Asp Ile Ala Tyr Trp Asp Glu
580 585 590

Asp Glu His Phe Phe Ile Val Asp Arg Leu Lys Ser Leu Ile Lys Tyr
595 600 605

Lys Gly Tyr Gln Val Ala Pro Ala Glu Leu Glu Ser Ile Leu Leu Gln
610 615 620

His Pro Asn Ile Phe Asp Ala Gly Val Ala Gly Leu Pro Asp Asp Asp
625 630 635 640

Ala Gly Glu Leu Pro Ala Ala Val Val Val Leu Glu His Gly Lys Thr
645 650 655

Met Thr Glu Lys Glu Ile Val Asp Tyr Val Ala Ser Gln Val Thr Thr
660 665 670

Ala Lys Lys Leu Arg Gly Gly Val Val Phe Val Asp Glu Val Pro Lys
675 680 685

Gly Leu Thr Gly Lys Leu Asp Ala Arg Lys Ile Arg Glu Ile Leu Ile
690 695 700

Lys Ala Lys Lys
705

<210> SEQ ID NO 177
<211> LENGTH: 728
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 177

Met Ala Lys Asn Ile Lys Lys Gly Pro Ala Pro Phe Tyr Pro Leu Glu
1 5 10 15

Asp Gly Thr Ala Gly Glu Gln Leu His Lys Ala Met Lys Arg Tyr Ala
20 25 30

Leu Val Pro Gly Thr Ile Ala Phe Thr Asp Ala His Ile Glu Val Asp
35 40 45

-continued

```
Ile Thr Tyr Ala Glu Tyr Phe Glu Met Ser Val Arg Leu Ala Glu Ala
    50                  55                  60

Met Lys Arg Tyr Gly Leu Asn Thr Asn His Arg Ile Val Val Cys Ser
65                  70                  75                  80

Glu Asn Ser Leu Gln Phe Phe Met Pro Val Leu Gly Ala Leu Phe Ile
                85                  90                  95

Gly Val Ala Val Ala Pro Ala Asn Asp Ile Tyr Asn Glu Arg Glu Leu
            100                 105                 110

Leu Asn Ser Met Gly Ile Ser Gln Pro Thr Val Val Phe Val Ser Lys
        115                 120                 125

Lys Gly Leu Gln Lys Ile Leu Asn Val Gln Lys Lys Leu Pro Ile Ile
    130                 135                 140

Gln Lys Ile Ile Ile Met Asp Ser Lys Thr Asp Tyr Gln Gly Phe Gln
145                 150                 155                 160

Ser Met Tyr Thr Phe Val Thr Ser His Leu Pro Pro Gly Phe Asn Glu
                165                 170                 175

Tyr Asp Phe Val Pro Glu Ser Phe Asp Arg Asp Lys Thr Ile Ala Leu
            180                 185                 190

Ile Met Asn Ser Ser Gly Ser Thr Gly Leu Pro Lys Gly Val Ala Leu
        195                 200                 205

Pro His Arg Thr Ala Cys Val Arg Phe Ser His Ala Arg Asp Pro Ile
    210                 215                 220

Phe Gly Asn Gln Ile Ile Pro Asp Thr Ala Ile Leu Ser Val Val Pro
225                 230                 235                 240

Phe His His Gly Phe Gly Met Phe Thr Thr Leu Gly Tyr Leu Ile Cys
                245                 250                 255

Gly Phe Arg Val Val Leu Met Tyr Arg Phe Glu Glu Glu Leu Phe Leu
            260                 265                 270

Arg Ser Leu Gln Asp Tyr Lys Ile Gln Ser Ala Leu Leu Val Pro Thr
        275                 280                 285

Leu Phe Ser Phe Phe Ala Lys Ser Thr Leu Ile Asp Lys Tyr Asp Leu
    290                 295                 300

Ser Asn Leu His Glu Ile Ala Ser Gly Gly Ala Pro Leu Ser Lys Glu
305                 310                 315                 320

Val Gly Glu Ala Val Ala Lys Arg Phe His Leu Pro Gly Ile Arg Gln
                325                 330                 335

Gly Tyr Gly Leu Thr Glu Thr Thr Ser Ala Ile Leu Ile Thr Pro Glu
            340                 345                 350

Gly Gly Ser Ser Gly Gly Ser Gly Gly Ser Gly Gly Gly Ser Gly Gly
        355                 360                 365

Ser Gly Gly Ser Gly Met Tyr Glu Ser Phe Ile Glu Ser Leu Pro Phe
    370                 375                 380

Leu Lys Ser Leu Glu Phe Ser Glu Arg Leu Lys Val Val Asp Val Ile
385                 390                 395                 400

Gly Thr Lys Val Tyr Asn Asp Gly Glu Gln Ile Ile Ala Gln Gly Asp
                405                 410                 415

Ser Ala Asp Ser Phe Phe Ile Val Glu Ser Gly Glu Val Lys Ile Thr
            420                 425                 430

Met Lys Arg Lys Gly Lys Ser Glu Val Glu Glu Asn Gly Ala Val Glu
        435                 440                 445

Ile Ala Arg Cys Ser Arg Gly Gln Tyr Phe Gly Glu Leu Ala Leu Val
    450                 455                 460
```

```
Thr Asn Lys Pro Arg Ala Ala Ser Ala His Ala Ile Gly Thr Val Lys
465                 470                 475                 480

Cys Leu Ala Met Asp Val Gln Ala Phe Glu Arg Leu Leu Gly Pro Cys
                485                 490                 495

Met Glu Ile Met Lys Arg Asn Ile Ala Thr Tyr Glu Glu Gln Leu Val
            500                 505                 510

Ala Leu Phe Gly Thr Asn Met Asp Ile Val Gly Ser Gly Gly Ser Gly
        515                 520                 525

Gly Ser Gly Gly Thr Ser Gly Gly Ser Gly Gly Ser Ser Gly Pro Gly
    530                 535                 540

Ala Val Gly Lys Val Val Pro Phe Phe Glu Ala Lys Val Val Asp Leu
545                 550                 555                 560

Asp Thr Gly Lys Thr Leu Gly Val Asn Gln Arg Gly Glu Leu Cys Val
                565                 570                 575

Arg Gly Pro Met Ile Met Ser Gly Tyr Val Asn Asn Pro Glu Ala Thr
            580                 585                 590

Asn Ala Leu Ile Asp Lys Asp Gly Trp Leu His Ser Gly Asp Ile Ala
        595                 600                 605

Tyr Trp Asp Glu Asp Glu His Phe Phe Ile Val Asp Arg Leu Lys Ser
    610                 615                 620

Leu Ile Lys Tyr Lys Gly Tyr Gln Val Ala Pro Ala Glu Leu Glu Ser
625                 630                 635                 640

Ile Leu Leu Gln His Pro Asn Ile Phe Asp Ala Gly Val Ala Gly Leu
                645                 650                 655

Pro Asp Asp Asp Ala Gly Glu Leu Pro Ala Ala Val Val Val Leu Glu
            660                 665                 670

His Gly Lys Thr Met Thr Glu Lys Glu Ile Val Asp Tyr Val Ala Ser
        675                 680                 685

Gln Val Thr Thr Ala Lys Lys Leu Arg Gly Gly Val Val Phe Val Asp
    690                 695                 700

Glu Val Pro Lys Gly Leu Thr Gly Lys Leu Asp Ala Arg Lys Ile Arg
705                 710                 715                 720

Glu Ile Leu Ile Lys Ala Lys Lys
                725


<210> SEQ ID NO 178
<211> LENGTH: 699
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Met Ala Lys Asn Ile Lys Lys Gly Pro Ala Pro Phe Tyr Pro Leu Glu
1               5                   10                  15

Asp Gly Thr Ala Gly Glu Gln Leu His Lys Ala Met Lys Arg Tyr Ala
            20                  25                  30

Leu Val Pro Gly Thr Ile Ala Phe Thr Asp Ala His Ile Glu Val Asp
        35                  40                  45

Ile Thr Tyr Ala Glu Tyr Phe Glu Met Ser Val Arg Leu Ala Glu Ala
    50                  55                  60

Met Lys Arg Tyr Gly Leu Asn Thr Asn His Arg Ile Val Val Cys Ser
65                  70                  75                  80

Gly Ser Thr Gly Met Tyr Glu Ser Phe Ile Glu Ser Leu Pro Phe Leu
                85                  90                  95
```

```
Lys Ser Leu Glu Phe Ser Glu Arg Leu Lys Val Val Asp Val Ile Gly
            100                 105                 110

Thr Lys Val Tyr Asn Asp Gly Glu Gln Ile Ile Ala Gln Gly Asp Ser
        115                 120                 125

Ala Asp Ser Phe Phe Ile Val Glu Ser Gly Glu Val Lys Ile Thr Met
    130                 135                 140

Lys Arg Lys Gly Lys Ser Glu Val Glu Glu Asn Gly Ala Val Glu Ile
145                 150                 155                 160

Ala Arg Cys Ser Arg Gly Gln Tyr Phe Gly Glu Leu Ala Leu Val Thr
                165                 170                 175

Asn Lys Pro Arg Ala Ala Ser Ala His Ala Ile Gly Thr Val Lys Cys
            180                 185                 190

Leu Ala Met Asp Val Gln Ala Phe Glu Arg Leu Leu Gly Pro Cys Met
        195                 200                 205

Glu Ile Met Lys Arg Asn Ile Ala Thr Tyr Glu Glu Gln Leu Val Ala
    210                 215                 220

Leu Phe Gly Thr Asn Met Asp Ile Val Gly Ser Ser Gly Glu Asn Ser
225                 230                 235                 240

Leu Gln Phe Phe Met Pro Val Leu Gly Ala Leu Phe Ile Gly Val Ala
                245                 250                 255

Val Ala Pro Ala Asn Asp Ile Tyr Asn Glu Arg Glu Leu Leu Asn Ser
            260                 265                 270

Met Gly Ile Ser Gln Pro Thr Val Val Phe Val Ser Lys Lys Gly Leu
        275                 280                 285

Gln Lys Ile Leu Asn Val Gln Lys Lys Leu Pro Ile Ile Gln Lys Ile
    290                 295                 300

Ile Ile Met Asp Ser Lys Thr Asp Tyr Gln Gly Phe Gln Ser Met Tyr
305                 310                 315                 320

Thr Phe Val Thr Ser His Leu Pro Pro Gly Phe Asn Glu Tyr Asp Phe
                325                 330                 335

Val Pro Glu Ser Phe Asp Arg Asp Lys Thr Ile Ala Leu Ile Met Asn
            340                 345                 350

Ser Ser Gly Ser Thr Gly Leu Pro Lys Gly Val Ala Leu Pro His Arg
        355                 360                 365

Thr Ala Cys Val Arg Phe Ser His Ala Arg Asp Pro Ile Phe Gly Asn
    370                 375                 380

Gln Ile Ile Pro Asp Thr Ala Ile Leu Ser Val Val Pro Phe His His
385                 390                 395                 400

Gly Phe Gly Met Phe Thr Thr Leu Gly Tyr Leu Ile Cys Gly Phe Arg
                405                 410                 415

Val Val Leu Met Tyr Arg Phe Glu Glu Glu Leu Phe Leu Arg Ser Leu
            420                 425                 430

Gln Asp Tyr Lys Ile Gln Ser Ala Leu Leu Val Pro Thr Leu Phe Ser
        435                 440                 445

Phe Phe Ala Lys Ser Thr Leu Ile Asp Lys Tyr Asp Leu Ser Asn Leu
    450                 455                 460

His Glu Ile Ala Ser Gly Gly Ala Pro Leu Ser Lys Glu Val Gly Glu
465                 470                 475                 480

Ala Val Ala Lys Arg Phe His Leu Pro Gly Ile Arg Gln Gly Tyr Gly
                485                 490                 495

Leu Thr Glu Thr Thr Ser Ala Ile Leu Ile Thr Pro Glu Gly Asp Asp
            500                 505                 510
```

-continued

Lys Pro Gly Ala Val Gly Lys Val Val Pro Phe Phe Glu Ala Lys Val
        515                 520                 525

Val Asp Leu Asp Thr Gly Lys Thr Leu Gly Val Asn Gln Arg Gly Glu
    530                 535                 540

Leu Cys Val Arg Gly Pro Met Ile Met Ser Gly Tyr Val Asn Asn Pro
545                 550                 555                 560

Glu Ala Thr Asn Ala Leu Ile Asp Lys Asp Gly Trp Leu His Ser Gly
                565                 570                 575

Asp Ile Ala Tyr Trp Asp Glu Asp Glu His Phe Phe Ile Val Asp Arg
            580                 585                 590

Leu Lys Ser Leu Ile Lys Tyr Lys Gly Tyr Gln Val Ala Pro Ala Glu
        595                 600                 605

Leu Glu Ser Ile Leu Leu Gln His Pro Asn Ile Phe Asp Ala Gly Val
    610                 615                 620

Ala Gly Leu Pro Asp Asp Asp Ala Gly Glu Leu Pro Ala Ala Val Val
625                 630                 635                 640

Val Leu Glu His Gly Lys Thr Met Thr Glu Lys Glu Ile Val Asp Tyr
                645                 650                 655

Val Ala Ser Gln Val Thr Thr Ala Lys Lys Leu Arg Gly Gly Val Val
            660                 665                 670

Phe Val Asp Glu Val Pro Lys Gly Leu Thr Gly Lys Leu Asp Ala Arg
        675                 680                 685

Lys Ile Arg Glu Ile Leu Ile Lys Ala Lys Lys
    690                 695

<210> SEQ ID NO 179
<211> LENGTH: 711
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Met Ala Lys Asn Ile Lys Lys Gly Pro Ala Pro Phe Tyr Pro Leu Glu
1               5                   10                  15

Asp Gly Thr Ala Gly Glu Gln Leu His Lys Ala Met Lys Arg Tyr Ala
            20                  25                  30

Leu Val Pro Gly Thr Ile Ala Phe Thr Asp Ala His Ile Glu Val Asp
        35                  40                  45

Ile Thr Tyr Ala Glu Tyr Phe Glu Met Ser Val Arg Leu Ala Glu Ala
    50                  55                  60

Met Lys Arg Tyr Gly Leu Asn Thr Asn His Arg Ile Val Val Cys Ser
65                  70                  75                  80

Gly Ser Ser Gly Gly Ser Gly Gly Ser Gly Met Tyr Glu Ser Phe Ile
                85                  90                  95

Glu Ser Leu Pro Phe Leu Lys Ser Leu Glu Phe Ser Glu Arg Leu Lys
            100                 105                 110

Val Val Asp Val Ile Gly Thr Lys Val Tyr Asn Asp Gly Glu Gln Ile
        115                 120                 125

Ile Ala Gln Gly Asp Ser Ala Asp Ser Phe Phe Ile Val Glu Ser Gly
    130                 135                 140

Glu Val Lys Ile Thr Met Lys Arg Lys Gly Lys Ser Glu Val Glu Glu
145                 150                 155                 160

Asn Gly Ala Val Glu Ile Ala Arg Cys Ser Arg Gly Gln Tyr Phe Gly
                165                 170                 175

-continued

```
Glu Leu Ala Leu Val Thr Asn Lys Pro Arg Ala Ala Ser Ala His Ala
            180                 185                 190

Ile Gly Thr Val Lys Cys Leu Ala Met Asp Val Gln Ala Phe Glu Arg
        195                 200                 205

Leu Leu Gly Pro Cys Met Glu Ile Met Lys Arg Asn Ile Ala Thr Tyr
    210                 215                 220

Glu Glu Gln Leu Val Ala Leu Phe Gly Thr Asn Met Asp Ile Val Gly
225                 230                 235                 240

Ser Gly Gly Ser Gly Gly Ser Ser Gly Glu Asn Ser Leu Gln Phe Phe
                245                 250                 255

Met Pro Val Leu Gly Ala Leu Phe Ile Gly Val Ala Val Ala Pro Ala
            260                 265                 270

Asn Asp Ile Tyr Asn Glu Arg Glu Leu Leu Asn Ser Met Gly Ile Ser
        275                 280                 285

Gln Pro Thr Val Val Phe Val Ser Lys Lys Gly Leu Gln Lys Ile Leu
    290                 295                 300

Asn Val Gln Lys Lys Leu Pro Ile Ile Gln Lys Ile Ile Ile Met Asp
305                 310                 315                 320

Ser Lys Thr Asp Tyr Gln Gly Phe Gln Ser Met Tyr Thr Phe Val Thr
                325                 330                 335

Ser His Leu Pro Pro Gly Phe Asn Glu Tyr Asp Phe Val Pro Glu Ser
            340                 345                 350

Phe Asp Arg Asp Lys Thr Ile Ala Leu Ile Met Asn Ser Ser Gly Ser
        355                 360                 365

Thr Gly Leu Pro Lys Gly Val Ala Leu Pro His Arg Thr Ala Cys Val
    370                 375                 380

Arg Phe Ser His Ala Arg Asp Pro Ile Phe Gly Asn Gln Ile Ile Pro
385                 390                 395                 400

Asp Thr Ala Ile Leu Ser Val Val Pro Phe His His Gly Phe Gly Met
                405                 410                 415

Phe Thr Thr Leu Gly Tyr Leu Ile Cys Gly Phe Arg Val Val Leu Met
            420                 425                 430

Tyr Arg Phe Glu Glu Glu Leu Phe Leu Arg Ser Leu Gln Asp Tyr Lys
        435                 440                 445

Ile Gln Ser Ala Leu Leu Val Pro Thr Leu Phe Ser Phe Phe Ala Lys
    450                 455                 460

Ser Thr Leu Ile Asp Lys Tyr Asp Leu Ser Asn Leu His Glu Ile Ala
465                 470                 475                 480

Ser Gly Gly Ala Pro Leu Ser Lys Glu Val Gly Glu Ala Val Ala Lys
                485                 490                 495

Arg Phe His Leu Pro Gly Ile Arg Gln Gly Tyr Gly Leu Thr Glu Thr
            500                 505                 510

Thr Ser Ala Ile Leu Ile Thr Pro Glu Gly Asp Asp Lys Pro Gly Ala
        515                 520                 525

Val Gly Lys Val Val Pro Phe Phe Glu Ala Lys Val Val Asp Leu Asp
    530                 535                 540

Thr Gly Lys Thr Leu Gly Val Asn Gln Arg Gly Glu Leu Cys Val Arg
545                 550                 555                 560

Gly Pro Met Ile Met Ser Gly Tyr Val Asn Asn Pro Glu Ala Thr Asn
                565                 570                 575

Ala Leu Ile Asp Lys Asp Gly Trp Leu His Ser Gly Asp Ile Ala Tyr
            580                 585                 590
```

```
Trp Asp Glu Asp Glu His Phe Phe Ile Val Asp Arg Leu Lys Ser Leu
        595                 600                 605

Ile Lys Tyr Lys Gly Tyr Gln Val Ala Pro Ala Glu Leu Glu Ser Ile
    610                 615                 620

Leu Leu Gln His Pro Asn Ile Phe Asp Ala Gly Val Ala Gly Leu Pro
625                 630                 635                 640

Asp Asp Asp Ala Gly Glu Leu Pro Ala Ala Val Val Val Leu Glu His
                645                 650                 655

Gly Lys Thr Met Thr Glu Lys Glu Ile Val Asp Tyr Val Ala Ser Gln
            660                 665                 670

Val Thr Thr Ala Lys Lys Leu Arg Gly Gly Val Val Phe Val Asp Glu
        675                 680                 685

Val Pro Lys Gly Leu Thr Gly Lys Leu Asp Ala Arg Lys Ile Arg Glu
    690                 695                 700

Ile Leu Ile Lys Ala Lys Lys
705                 710


<210> SEQ ID NO 180
<211> LENGTH: 731
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Met Ala Lys Asn Ile Lys Lys Gly Pro Ala Pro Phe Tyr Pro Leu Glu
1               5                   10                  15

Asp Gly Thr Ala Gly Glu Gln Leu His Lys Ala Met Lys Arg Tyr Ala
            20                  25                  30

Leu Val Pro Gly Thr Ile Ala Phe Thr Asp Ala His Ile Glu Val Asp
        35                  40                  45

Ile Thr Tyr Ala Glu Tyr Phe Glu Met Ser Val Arg Leu Ala Glu Ala
    50                  55                  60

Met Lys Arg Tyr Gly Leu Asn Thr Asn His Arg Ile Val Val Cys Ser
65                  70                  75                  80

Gly Ser Ser Gly Gly Ser Gly Gly Ser Gly Gly Gly Ser Gly Gly Ser
                85                  90                  95

Gly Gly Ser Gly Met Tyr Glu Ser Phe Ile Glu Ser Leu Pro Phe Leu
            100                 105                 110

Lys Ser Leu Glu Phe Ser Glu Arg Leu Lys Val Val Asp Val Ile Gly
        115                 120                 125

Thr Lys Val Tyr Asn Asp Gly Glu Gln Ile Ile Ala Gln Gly Asp Ser
    130                 135                 140

Ala Asp Ser Phe Phe Ile Val Glu Ser Gly Glu Val Lys Ile Thr Met
145                 150                 155                 160

Lys Arg Lys Gly Lys Ser Glu Val Glu Glu Asn Gly Ala Val Glu Ile
                165                 170                 175

Ala Arg Cys Ser Arg Gly Gln Tyr Phe Gly Glu Leu Ala Leu Val Thr
            180                 185                 190

Asn Lys Pro Arg Ala Ala Ser Ala His Ala Ile Gly Thr Val Lys Cys
        195                 200                 205

Leu Ala Met Asp Val Gln Ala Phe Glu Arg Leu Leu Gly Pro Cys Met
    210                 215                 220

Glu Ile Met Lys Arg Asn Ile Ala Thr Tyr Glu Glu Gln Leu Val Ala
225                 230                 235                 240
```

```
Leu Phe Gly Thr Asn Met Asp Ile Val Gly Ser Gly Gly Ser Gly Gly
                245                 250                 255

Ser Gly Gly Thr Ser Gly Gly Ser Gly Gly Ser Ser Gly Glu Asn Ser
            260                 265                 270

Leu Gln Phe Phe Met Pro Val Leu Gly Ala Leu Phe Ile Gly Val Ala
        275                 280                 285

Val Ala Pro Ala Asn Asp Ile Tyr Asn Glu Arg Glu Leu Leu Asn Ser
    290                 295                 300

Met Gly Ile Ser Gln Pro Thr Val Val Phe Val Ser Lys Lys Gly Leu
305                 310                 315                 320

Gln Lys Ile Leu Asn Val Gln Lys Lys Leu Pro Ile Ile Gln Lys Ile
                325                 330                 335

Ile Ile Met Asp Ser Lys Thr Asp Tyr Gln Gly Phe Gln Ser Met Tyr
            340                 345                 350

Thr Phe Val Thr Ser His Leu Pro Pro Gly Phe Asn Glu Tyr Asp Phe
        355                 360                 365

Val Pro Glu Ser Phe Asp Arg Asp Lys Thr Ile Ala Leu Ile Met Asn
    370                 375                 380

Ser Ser Gly Ser Thr Gly Leu Pro Lys Gly Val Ala Leu Pro His Arg
385                 390                 395                 400

Thr Ala Cys Val Arg Phe Ser His Ala Arg Asp Pro Ile Phe Gly Asn
                405                 410                 415

Gln Ile Ile Pro Asp Thr Ala Ile Leu Ser Val Val Pro Phe His His
            420                 425                 430

Gly Phe Gly Met Phe Thr Thr Leu Gly Tyr Leu Ile Cys Gly Phe Arg
        435                 440                 445

Val Val Leu Met Tyr Arg Phe Glu Glu Glu Leu Phe Leu Arg Ser Leu
    450                 455                 460

Gln Asp Tyr Lys Ile Gln Ser Ala Leu Leu Val Pro Thr Leu Phe Ser
465                 470                 475                 480

Phe Phe Ala Lys Ser Thr Leu Ile Asp Lys Tyr Asp Leu Ser Asn Leu
                485                 490                 495

His Glu Ile Ala Ser Gly Gly Ala Pro Leu Ser Lys Glu Val Gly Glu
            500                 505                 510

Ala Val Ala Lys Arg Phe His Leu Pro Gly Ile Arg Gln Gly Tyr Gly
        515                 520                 525

Leu Thr Glu Thr Thr Ser Ala Ile Leu Ile Thr Pro Glu Gly Asp Asp
    530                 535                 540

Lys Pro Gly Ala Val Gly Lys Val Val Pro Phe Phe Glu Ala Lys Val
545                 550                 555                 560

Val Asp Leu Asp Thr Gly Lys Thr Leu Gly Val Asn Gln Arg Gly Glu
                565                 570                 575

Leu Cys Val Arg Gly Pro Met Ile Met Ser Gly Tyr Val Asn Asn Pro
            580                 585                 590

Glu Ala Thr Asn Ala Leu Ile Asp Lys Asp Gly Trp Leu His Ser Gly
        595                 600                 605

Asp Ile Ala Tyr Trp Asp Glu Asp Glu His Phe Phe Ile Val Asp Arg
    610                 615                 620

Leu Lys Ser Leu Ile Lys Tyr Lys Gly Tyr Gln Val Ala Pro Ala Glu
625                 630                 635                 640

Leu Glu Ser Ile Leu Leu Gln His Pro Asn Ile Phe Asp Ala Gly Val
                645                 650                 655
```

```
Ala Gly Leu Pro Asp Asp Asp Ala Gly Glu Leu Pro Ala Ala Val Val
            660                 665                 670

Val Leu Glu His Gly Lys Thr Met Thr Glu Lys Glu Ile Val Asp Tyr
        675                 680                 685

Val Ala Ser Gln Val Thr Thr Ala Lys Lys Leu Arg Gly Gly Val Val
    690                 695                 700

Phe Val Asp Glu Val Pro Lys Gly Leu Thr Gly Lys Leu Asp Ala Arg
705                 710                 715                 720

Lys Ile Arg Glu Ile Leu Ile Lys Ala Lys Lys
                725                 730


<210> SEQ ID NO 181
<211> LENGTH: 699
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Met Ala Lys Asn Ile Lys Lys Gly Pro Ala Pro Phe Tyr Pro Leu Glu
1               5                   10                  15

Asp Gly Thr Ala Gly Glu Gln Leu His Lys Ala Met Lys Arg Tyr Ala
            20                  25                  30

Leu Val Pro Gly Thr Ile Ala Phe Thr Asp Ala His Ile Glu Val Asp
        35                  40                  45

Ile Thr Tyr Ala Glu Tyr Phe Glu Met Ser Val Arg Leu Ala Glu Ala
    50                  55                  60

Met Lys Arg Tyr Gly Leu Asn Thr Asn His Arg Ile Val Val Cys Ser
65                  70                  75                  80

Glu Asn Ser Leu Gln Phe Phe Met Pro Val Leu Gly Ala Leu Phe Ile
                85                  90                  95

Gly Val Ala Val Ala Pro Ala Asn Asp Ile Tyr Asn Glu Arg Glu Leu
            100                 105                 110

Leu Asn Ser Met Gly Ile Ser Gln Pro Thr Val Val Phe Val Ser Lys
        115                 120                 125

Lys Gly Leu Gln Lys Ile Leu Asn Val Gln Lys Lys Leu Pro Ile Ile
    130                 135                 140

Gln Lys Ile Ile Ile Met Asp Ser Lys Thr Asp Tyr Gln Gly Phe Gln
145                 150                 155                 160

Ser Met Tyr Thr Phe Val Thr Ser His Leu Pro Pro Gly Phe Asn Glu
                165                 170                 175

Tyr Asp Phe Val Pro Glu Ser Phe Asp Arg Asp Lys Thr Ile Ala Leu
            180                 185                 190

Ile Met Asn Ser Ser Gly Ser Thr Gly Leu Pro Lys Gly Val Ala Leu
        195                 200                 205

Pro His Arg Thr Ala Cys Val Arg Phe Ser His Ala Arg Asp Pro Ile
    210                 215                 220

Phe Gly Asn Gln Ile Ile Pro Asp Thr Ala Ile Leu Ser Val Val Pro
225                 230                 235                 240

Phe His His Gly Phe Gly Met Phe Thr Thr Leu Gly Tyr Leu Ile Cys
                245                 250                 255

Gly Phe Arg Val Val Leu Met Tyr Arg Phe Glu Glu Glu Leu Phe Leu
            260                 265                 270

Arg Ser Leu Gln Asp Tyr Lys Ile Gln Ser Ala Leu Leu Val Pro Thr
        275                 280                 285
```

-continued

```
Leu Phe Ser Phe Phe Ala Lys Ser Thr Leu Ile Asp Lys Tyr Asp Leu
    290                 295                 300

Ser Gly Ser Thr Gly Met Tyr Glu Ser Phe Ile Glu Ser Leu Pro Phe
305                 310                 315                 320

Leu Lys Ser Leu Glu Phe Ser Glu Arg Leu Lys Val Val Asp Val Ile
                325                 330                 335

Gly Thr Lys Val Tyr Asn Asp Gly Glu Gln Ile Ile Ala Gln Gly Asp
            340                 345                 350

Ser Ala Asp Ser Phe Phe Ile Val Glu Ser Gly Glu Val Lys Ile Thr
        355                 360                 365

Met Lys Arg Lys Gly Lys Ser Glu Val Glu Glu Asn Gly Ala Val Glu
    370                 375                 380

Ile Ala Arg Cys Ser Arg Gly Gln Tyr Phe Gly Glu Leu Ala Leu Val
385                 390                 395                 400

Thr Asn Lys Pro Arg Ala Ala Ser Ala His Ala Ile Gly Thr Val Lys
                405                 410                 415

Cys Leu Ala Met Asp Val Gln Ala Phe Glu Arg Leu Leu Gly Pro Cys
            420                 425                 430

Met Glu Ile Met Lys Arg Asn Ile Ala Thr Tyr Glu Glu Gln Leu Val
        435                 440                 445

Ala Leu Phe Gly Thr Asn Met Asp Ile Val Gly Ser Ser Gly Asn Leu
    450                 455                 460

His Glu Ile Ala Ser Gly Gly Ala Pro Leu Ser Lys Glu Val Gly Glu
465                 470                 475                 480

Ala Val Ala Lys Arg Phe His Leu Pro Gly Ile Arg Gln Gly Tyr Gly
                485                 490                 495

Leu Thr Glu Thr Thr Ser Ala Ile Leu Ile Thr Pro Glu Gly Asp Asp
            500                 505                 510

Lys Pro Gly Ala Val Gly Lys Val Val Pro Phe Phe Glu Ala Lys Val
        515                 520                 525

Val Asp Leu Asp Thr Gly Lys Thr Leu Gly Val Asn Gln Arg Gly Glu
    530                 535                 540

Leu Cys Val Arg Gly Pro Met Ile Met Ser Gly Tyr Val Asn Asn Pro
545                 550                 555                 560

Glu Ala Thr Asn Ala Leu Ile Asp Lys Asp Gly Trp Leu His Ser Gly
                565                 570                 575

Asp Ile Ala Tyr Trp Asp Glu Asp Glu His Phe Phe Ile Val Asp Arg
            580                 585                 590

Leu Lys Ser Leu Ile Lys Tyr Lys Gly Tyr Gln Val Ala Pro Ala Glu
        595                 600                 605

Leu Glu Ser Ile Leu Leu Gln His Pro Asn Ile Phe Asp Ala Gly Val
    610                 615                 620

Ala Gly Leu Pro Asp Asp Asp Ala Gly Glu Leu Pro Ala Ala Val Val
625                 630                 635                 640

Val Leu Glu His Gly Lys Thr Met Thr Glu Lys Glu Ile Val Asp Tyr
                645                 650                 655

Val Ala Ser Gln Val Thr Thr Ala Lys Lys Leu Arg Gly Gly Val Val
            660                 665                 670

Phe Val Asp Glu Val Pro Lys Gly Leu Thr Gly Lys Leu Asp Ala Arg
        675                 680                 685

Lys Ile Arg Glu Ile Leu Ile Lys Ala Lys Lys
    690                 695
```

<210> SEQ ID NO 182
<211> LENGTH: 711
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 182

Met Ala Lys Asn Ile Lys Lys Gly Pro Ala Pro Phe Tyr Pro Leu Glu
1 5 10 15

Asp Gly Thr Ala Gly Glu Gln Leu His Lys Ala Met Lys Arg Tyr Ala
20 25 30

Leu Val Pro Gly Thr Ile Ala Phe Thr Asp Ala His Ile Glu Val Asp
35 40 45

Ile Thr Tyr Ala Glu Tyr Phe Glu Met Ser Val Arg Leu Ala Glu Ala
50 55 60

Met Lys Arg Tyr Gly Leu Asn Thr Asn His Arg Ile Val Val Cys Ser
65 70 75 80

Glu Asn Ser Leu Gln Phe Phe Met Pro Val Leu Gly Ala Leu Phe Ile
85 90 95

Gly Val Ala Val Ala Pro Ala Asn Asp Ile Tyr Asn Glu Arg Glu Leu
100 105 110

Leu Asn Ser Met Gly Ile Ser Gln Pro Thr Val Val Phe Val Ser Lys
115 120 125

Lys Gly Leu Gln Lys Ile Leu Asn Val Gln Lys Lys Leu Pro Ile Ile
130 135 140

Gln Lys Ile Ile Ile Met Asp Ser Lys Thr Asp Tyr Gln Gly Phe Gln
145 150 155 160

Ser Met Tyr Thr Phe Val Thr Ser His Leu Pro Pro Gly Phe Asn Glu
165 170 175

Tyr Asp Phe Val Pro Glu Ser Phe Asp Arg Asp Lys Thr Ile Ala Leu
180 185 190

Ile Met Asn Ser Ser Gly Ser Thr Gly Leu Pro Lys Gly Val Ala Leu
195 200 205

Pro His Arg Thr Ala Cys Val Arg Phe Ser His Ala Arg Asp Pro Ile
210 215 220

Phe Gly Asn Gln Ile Ile Pro Asp Thr Ala Ile Leu Ser Val Val Pro
225 230 235 240

Phe His His Gly Phe Gly Met Phe Thr Thr Leu Gly Tyr Leu Ile Cys
245 250 255

Gly Phe Arg Val Val Leu Met Tyr Arg Phe Glu Glu Glu Leu Phe Leu
260 265 270

Arg Ser Leu Gln Asp Tyr Lys Ile Gln Ser Ala Leu Leu Val Pro Thr
275 280 285

Leu Phe Ser Phe Phe Ala Lys Ser Thr Leu Ile Asp Lys Tyr Asp Leu
290 295 300

Ser Gly Ser Ser Gly Gly Ser Gly Gly Ser Gly Met Tyr Glu Ser Phe
305 310 315 320

Ile Glu Ser Leu Pro Phe Leu Lys Ser Leu Glu Phe Ser Glu Arg Leu
325 330 335

Lys Val Val Asp Val Ile Gly Thr Lys Val Tyr Asn Asp Gly Glu Gln
340 345 350

Ile Ile Ala Gln Gly Asp Ser Ala Asp Ser Phe Phe Ile Val Glu Ser
355 360 365

Gly Glu Val Lys Ile Thr Met Lys Arg Lys Gly Lys Ser Glu Val Glu
370 375 380

Glu Asn Gly Ala Val Glu Ile Ala Arg Cys Ser Arg Gly Gln Tyr Phe
385 390 395 400

Gly Glu Leu Ala Leu Val Thr Asn Lys Pro Arg Ala Ala Ser Ala His
405 410 415

Ala Ile Gly Thr Val Lys Cys Leu Ala Met Asp Val Gln Ala Phe Glu
420 425 430

Arg Leu Leu Gly Pro Cys Met Glu Ile Met Lys Arg Asn Ile Ala Thr
435 440 445

Tyr Glu Glu Gln Leu Val Ala Leu Phe Gly Thr Asn Met Asp Ile Val
450 455 460

Gly Ser Gly Gly Ser Gly Gly Ser Ser Gly Asn Leu His Glu Ile Ala
465 470 475 480

Ser Gly Gly Ala Pro Leu Ser Lys Glu Val Gly Glu Ala Val Ala Lys
485 490 495

Arg Phe His Leu Pro Gly Ile Arg Gln Gly Tyr Gly Leu Thr Glu Thr
500 505 510

Thr Ser Ala Ile Leu Ile Thr Pro Glu Gly Asp Asp Lys Pro Gly Ala
515 520 525

Val Gly Lys Val Val Pro Phe Phe Glu Ala Lys Val Val Asp Leu Asp
530 535 540

Thr Gly Lys Thr Leu Gly Val Asn Gln Arg Gly Glu Leu Cys Val Arg
545 550 555 560

Gly Pro Met Ile Met Ser Gly Tyr Val Asn Asn Pro Glu Ala Thr Asn
565 570 575

Ala Leu Ile Asp Lys Asp Gly Trp Leu His Ser Gly Asp Ile Ala Tyr
580 585 590

Trp Asp Glu Asp Glu His Phe Phe Ile Val Asp Arg Leu Lys Ser Leu
595 600 605

Ile Lys Tyr Lys Gly Tyr Gln Val Ala Pro Ala Glu Leu Glu Ser Ile
610 615 620

Leu Leu Gln His Pro Asn Ile Phe Asp Ala Gly Val Ala Gly Leu Pro
625 630 635 640

Asp Asp Asp Ala Gly Glu Leu Pro Ala Ala Val Val Val Leu Glu His
645 650 655

Gly Lys Thr Met Thr Glu Lys Glu Ile Val Asp Tyr Val Ala Ser Gln
660 665 670

Val Thr Thr Ala Lys Lys Leu Arg Gly Gly Val Val Phe Val Asp Glu
675 680 685

Val Pro Lys Gly Leu Thr Gly Lys Leu Asp Ala Arg Lys Ile Arg Glu
690 695 700

Ile Leu Ile Lys Ala Lys Lys
705 710

<210> SEQ ID NO 183
<211> LENGTH: 731
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 183

Met Ala Lys Asn Ile Lys Lys Gly Pro Ala Pro Phe Tyr Pro Leu Glu

-continued

```
1               5                   10                  15

Asp Gly Thr Ala Gly Glu Gln Leu His Lys Ala Met Lys Arg Tyr Ala
            20                  25                  30

Leu Val Pro Gly Thr Ile Ala Phe Thr Asp Ala His Ile Glu Val Asp
        35                  40                  45

Ile Thr Tyr Ala Glu Tyr Phe Glu Met Ser Val Arg Leu Ala Glu Ala
    50                  55                  60

Met Lys Arg Tyr Gly Leu Asn Thr Asn His Arg Ile Val Val Cys Ser
65                  70                  75                  80

Glu Asn Ser Leu Gln Phe Phe Met Pro Val Leu Gly Ala Leu Phe Ile
                85                  90                  95

Gly Val Ala Val Ala Pro Ala Asn Asp Ile Tyr Asn Glu Arg Glu Leu
            100                 105                 110

Leu Asn Ser Met Gly Ile Ser Gln Pro Thr Val Val Phe Val Ser Lys
        115                 120                 125

Lys Gly Leu Gln Lys Ile Leu Asn Val Gln Lys Lys Leu Pro Ile Ile
    130                 135                 140

Gln Lys Ile Ile Ile Met Asp Ser Lys Thr Asp Tyr Gln Gly Phe Gln
145                 150                 155                 160

Ser Met Tyr Thr Phe Val Thr Ser His Leu Pro Pro Gly Phe Asn Glu
                165                 170                 175

Tyr Asp Phe Val Pro Glu Ser Phe Asp Arg Asp Lys Thr Ile Ala Leu
            180                 185                 190

Ile Met Asn Ser Ser Gly Ser Thr Gly Leu Pro Lys Gly Val Ala Leu
        195                 200                 205

Pro His Arg Thr Ala Cys Val Arg Phe Ser His Ala Arg Asp Pro Ile
    210                 215                 220

Phe Gly Asn Gln Ile Ile Pro Asp Thr Ala Ile Leu Ser Val Val Pro
225                 230                 235                 240

Phe His His Gly Phe Gly Met Phe Thr Thr Leu Gly Tyr Leu Ile Cys
                245                 250                 255

Gly Phe Arg Val Val Leu Met Tyr Arg Phe Glu Glu Glu Leu Phe Leu
            260                 265                 270

Arg Ser Leu Gln Asp Tyr Lys Ile Gln Ser Ala Leu Leu Val Pro Thr
        275                 280                 285

Leu Phe Ser Phe Phe Ala Lys Ser Thr Leu Ile Asp Lys Tyr Asp Leu
    290                 295                 300

Ser Gly Ser Ser Gly Gly Ser Gly Gly Ser Gly Gly Gly Ser Gly Gly
305                 310                 315                 320

Ser Gly Gly Ser Gly Met Tyr Glu Ser Phe Ile Glu Ser Leu Pro Phe
                325                 330                 335

Leu Lys Ser Leu Glu Phe Ser Glu Arg Leu Lys Val Val Asp Val Ile
            340                 345                 350

Gly Thr Lys Val Tyr Asn Asp Gly Glu Gln Ile Ile Ala Gln Gly Asp
        355                 360                 365

Ser Ala Asp Ser Phe Phe Ile Val Glu Ser Gly Glu Val Lys Ile Thr
    370                 375                 380

Met Lys Arg Lys Gly Lys Ser Glu Val Glu Glu Asn Gly Ala Val Glu
385                 390                 395                 400

Ile Ala Arg Cys Ser Arg Gly Gln Tyr Phe Gly Glu Leu Ala Leu Val
                405                 410                 415

Thr Asn Lys Pro Arg Ala Ala Ser Ala His Ala Ile Gly Thr Val Lys
            420                 425                 430
```

Cys Leu Ala Met Asp Val Gln Ala Phe Glu Arg Leu Leu Gly Pro Cys
        435                 440                 445

Met Glu Ile Met Lys Arg Asn Ile Ala Thr Tyr Glu Glu Gln Leu Val
    450                 455                 460

Ala Leu Phe Gly Thr Asn Met Asp Ile Val Gly Ser Gly Gly Ser Gly
465                 470                 475                 480

Gly Ser Gly Gly Thr Ser Gly Gly Ser Gly Gly Ser Ser Gly Asn Leu
                485                 490                 495

His Glu Ile Ala Ser Gly Gly Ala Pro Leu Ser Lys Glu Val Gly Glu
            500                 505                 510

Ala Val Ala Lys Arg Phe His Leu Pro Gly Ile Arg Gln Gly Tyr Gly
        515                 520                 525

Leu Thr Glu Thr Thr Ser Ala Ile Leu Ile Thr Pro Glu Gly Asp Asp
    530                 535                 540

Lys Pro Gly Ala Val Gly Lys Val Val Pro Phe Phe Glu Ala Lys Val
545                 550                 555                 560

Val Asp Leu Asp Thr Gly Lys Thr Leu Gly Val Asn Gln Arg Gly Glu
                565                 570                 575

Leu Cys Val Arg Gly Pro Met Ile Met Ser Gly Tyr Val Asn Asn Pro
            580                 585                 590

Glu Ala Thr Asn Ala Leu Ile Asp Lys Asp Gly Trp Leu His Ser Gly
        595                 600                 605

Asp Ile Ala Tyr Trp Asp Glu Asp Glu His Phe Phe Ile Val Asp Arg
    610                 615                 620

Leu Lys Ser Leu Ile Lys Tyr Lys Gly Tyr Gln Val Ala Pro Ala Glu
625                 630                 635                 640

Leu Glu Ser Ile Leu Leu Gln His Pro Asn Ile Phe Asp Ala Gly Val
                645                 650                 655

Ala Gly Leu Pro Asp Asp Asp Ala Gly Glu Leu Pro Ala Ala Val Val
            660                 665                 670

Val Leu Glu His Gly Lys Thr Met Thr Glu Lys Glu Ile Val Asp Tyr
        675                 680                 685

Val Ala Ser Gln Val Thr Thr Ala Lys Lys Leu Arg Gly Gly Val Val
    690                 695                 700

Phe Val Asp Glu Val Pro Lys Gly Leu Thr Gly Lys Leu Asp Ala Arg
705                 710                 715                 720

Lys Ile Arg Glu Ile Leu Ile Lys Ala Lys Lys
                725                 730

<210> SEQ ID NO 184
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Met Asp Thr Ala Ile Leu Ser Val Val Pro Phe His His Gly Phe Gly
1               5                   10                  15

Met Phe Thr Thr Leu Gly Tyr Leu Ile Cys Gly Phe Arg Val Val Leu
            20                  25                  30

Met Tyr Arg Phe Glu Glu Glu Leu Phe Leu Arg Ser Leu Gln Asp Tyr
        35                  40                  45

Lys Ile Gln Ser Ala Leu Leu Val Pro Thr Leu Phe Ser Phe Phe Ala

-continued

```
    50                  55                  60

Lys Ser Thr Leu Ile Asp Lys Tyr Asp Leu Ser Asn Leu His Glu Ile
65                  70                  75                  80

Ala Ser Gly Gly Ala Pro Leu Ser Lys Glu Val Gly Glu Ala Val Ala
                85                  90                  95

Lys Arg Phe His Leu Pro Gly Ile Arg Gln Gly Tyr Gly Leu Thr Glu
            100                 105                 110

Thr Thr Ser Ala Ile Leu Ile Thr Pro Glu Gly Asp Asp Lys Pro Gly
        115                 120                 125

Ala Val Gly Lys Val Val Pro Phe Phe Glu Ala Lys Val Val Asp Leu
    130                 135                 140

Asp Thr Gly Lys Thr Leu Gly Val Asn Gln Arg Gly Glu Leu Cys Val
145                 150                 155                 160

Arg Gly Pro Met Ile Met Ser Gly Tyr Val Asn Asn Pro Glu Ala Thr
                165                 170                 175

Asn Ala Leu Ile Asp Lys Asp Gly Trp Leu His Ser Gly Asp Ile Ala
            180                 185                 190

Tyr Trp Asp Glu Asp Glu His Phe Phe Ile Val Asp Arg Leu Lys Ser
        195                 200                 205

Leu Ile Lys Tyr Lys Gly Tyr Gln Val Ala Pro Ala Glu Leu Glu Ser
    210                 215                 220

Ile Leu Leu Gln His Pro Asn Ile Phe Asp Ala Gly Val Ala Gly Leu
225                 230                 235                 240

Pro Asp Asp Asp Ala Gly Glu Leu Pro Ala Ala Val Val Val Leu Glu
                245                 250                 255

His Gly Lys Thr Met Thr Glu Lys Glu Ile Val Asp Tyr Val Ala Ser
            260                 265                 270

Gln Val Thr Thr Ala Lys Lys Leu Arg Gly Gly Val Val Phe Val Asp
        275                 280                 285

Glu Val Pro Lys Gly Leu Thr Gly Lys Leu Asp Ala Arg Lys Ile Arg
    290                 295                 300

Glu Ile Leu Ile Lys Ala Lys Lys Gly Ser Ser Gly Gly Ser Gly Gly
305                 310                 315                 320

Ser Gly Gly Gly Met Tyr Glu Ser Phe Ile Glu Ser Leu Pro Phe Leu
                325                 330                 335

Lys Ser Leu Glu Phe Ser Glu Arg Leu Lys Val Val Asp Val Ile Gly
            340                 345                 350

Thr Lys Val Tyr Asn Asp Gly Glu Gln Ile Ile Ala Gln Gly Asp Ser
        355                 360                 365

Ala Asp Ser Phe Phe Ile Val Glu Ser Gly Glu Val Lys Ile Thr Met
    370                 375                 380

Lys Arg Lys Gly Lys Ser Glu Val Glu Glu Asn Gly Ala Val Glu Ile
385                 390                 395                 400

Ala Arg Cys Ser Arg Gly Gln Tyr Phe Gly Glu Leu Ala Leu Val Thr
                405                 410                 415

Asn Lys Pro Arg Ala Ala Ser Ala His Ala Ile Gly Thr Val Lys Cys
            420                 425                 430

Leu Ala Met Asp Val Gln Ala Phe Glu Arg Leu Leu Gly Pro Cys Met
        435                 440                 445

Glu Ile Met Lys Arg Asn Ile Ala Thr Tyr Glu Glu Gln Leu Val Ala
    450                 455                 460

Leu Phe Gly Thr Asn Met Asp Ile Val Ala Lys Asn Ile Lys Lys Gly
465                 470                 475                 480
```

Pro Ala Pro Phe Tyr Pro Leu Glu Asp Gly Thr Ala Gly Glu Gln Leu
485 490 495

His Lys Ala Met Lys Arg Tyr Ala Leu Val Pro Gly Thr Ile Ala Phe
500 505 510

Thr Asp Ala His Ile Glu Val Asp Ile Thr Tyr Ala Glu Tyr Phe Glu
515 520 525

Met Ser Val Arg Leu Ala Glu Ala Met Lys Arg Tyr Gly Leu Asn Thr
530 535 540

Asn His Arg Ile Val Val Cys Ser Glu Asn Ser Leu Gln Phe Phe Met
545 550 555 560

Pro Val Leu Gly Ala Leu Phe Ile Gly Val Ala Val Ala Pro Ala Asn
565 570 575

Asp Ile Tyr Asn Glu Arg Glu Leu Leu Asn Ser Met Gly Ile Ser Gln
580 585 590

Pro Thr Val Val Phe Val Ser Lys Lys Gly Leu Gln Lys Ile Leu Asn
595 600 605

Val Gln Lys Lys Leu Pro Ile Ile Gln Lys Ile Ile Ile Met Asp Ser
610 615 620

Lys Thr Asp Tyr Gln Gly Phe Gln Ser Met Tyr Thr Phe Val Thr Ser
625 630 635 640

His Leu Pro Pro Gly Phe Asn Glu Tyr Asp Phe Val Pro Glu Ser Phe
645 650 655

Asp Arg Asp Lys Thr Ile Ala Leu Ile Met Asn Ser Ser Gly Ser Thr
660 665 670

Gly Leu Pro Lys Gly Val Ala Leu Pro His Arg Thr Ala Cys Val Arg
675 680 685

Phe Ser His Ala Arg Asp Pro Ile Phe Gly Asn Gln Ile Ile Pro Val
690 695 700

<210> SEQ ID NO 185
<211> LENGTH: 487
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 185

Met Tyr Arg Leu Leu Asp His Tyr Lys Tyr Leu Thr Ala Trp Phe Glu
1 5 10 15

Leu Leu Asn Leu Pro Lys Lys Ile Ile Phe Val Gly His Asp Trp Gly
20 25 30

Ala Cys Leu Ala Phe His Tyr Ser Tyr Glu His Gln Asp Lys Ile Lys
35 40 45

Ala Ile Val His Ala Glu Ser Val Val Asp Val Ile Glu Ser Trp Asp
50 55 60

Glu Trp Pro Asp Ile Glu Glu Asp Ile Ala Leu Ile Lys Ser Glu Glu
65 70 75 80

Gly Glu Lys Met Val Leu Glu Asn Asn Phe Phe Val Glu Thr Met Leu
85 90 95

Pro Ser Lys Ile Met Arg Lys Leu Glu Pro Glu Glu Phe Ala Ala Tyr
100 105 110

Leu Glu Pro Phe Lys Glu Lys Gly Glu Val Arg Arg Pro Thr Leu Ser
115 120 125

Trp Pro Arg Glu Ile Pro Leu Val Lys Gly Gly Lys Pro Asp Val Val

-continued

```
    130                 135                 140

Gln Ile Val Arg Asn Tyr Asn Ala Tyr Leu Arg Ala Ser Asp Asp Leu
145                 150                 155                 160

Pro Lys Met Phe Ile Glu Ser Asp Pro Gly Phe Phe Ser Asn Ala Ile
                165                 170                 175

Val Glu Gly Ala Lys Lys Phe Pro Asn Thr Glu Phe Val Lys Val Lys
            180                 185                 190

Gly Leu His Phe Ser Gln Glu Asp Ala Pro Asp Glu Met Gly Lys Tyr
        195                 200                 205

Ile Lys Ser Phe Val Glu Arg Val Leu Lys Asn Glu Gln Gly Ser Ser
    210                 215                 220

Gly Gly Ser Gly Gly Ser Gly Gly Gly Ser Gly Gly Ser Gly Gly Ser
225                 230                 235                 240

Gly Ser Ile Met Asn Thr Val Lys Ser Leu Thr Glu Ser Ala Arg Cys
                245                 250                 255

Ser Leu Phe Leu Val Arg Gly Asp Val Leu Glu Ala His Phe Glu Asp
            260                 265                 270

Gly Asn Val Val Thr Ile Pro Arg Gly Ala Gly Ile Ala Gly Tyr Val
        275                 280                 285

Ala Gln Thr Gly Glu Thr Val Asn Ile Val Asp Ala Tyr Ala Asp Asp
    290                 295                 300

Arg Phe Asn Arg Glu Val Asp Lys Ala Thr Gly Tyr Arg Thr Lys Thr
305                 310                 315                 320

Ile Leu Cys Met Pro Val Met Tyr Glu Gly Thr Ile Val Ala Val Ala
                325                 330                 335

Gln Leu Ile Asn Lys Leu Asp Leu Thr Thr Glu Ser Gly Leu Arg Leu
            340                 345                 350

Pro Arg Val Phe Gly Lys Arg Asp Glu Glu Leu Phe Gln Thr Phe Ser
        355                 360                 365

Met Phe Ala Gly Ala Ser Leu Arg Gly Ser Gly Gly Ser Gly Gly Ser
    370                 375                 380

Gly Gly Thr Ser Gly Gly Ser Gly Gly Ser Ser Gly Ala Ser Lys Val
385                 390                 395                 400

Tyr Asp Pro Glu Gln Arg Lys Arg Met Ile Thr Gly Pro Gln Trp Trp
                405                 410                 415

Ala Arg Cys Lys Gln Met Asn Val Leu Asp Ser Phe Ile Asn Tyr Tyr
            420                 425                 430

Asp Ser Glu Lys His Ala Glu Asn Ala Val Ile Phe Leu His Gly Asn
        435                 440                 445

Ala Ala Ser Ser Tyr Leu Trp Arg His Val Val Pro His Ile Glu Pro
    450                 455                 460

Val Ala Arg Cys Ile Ile Pro Asp Leu Ile Gly Met Gly Lys Ser Gly
465                 470                 475                 480

Lys Ser Gly Asn Gly Ser Val
                485


<210> SEQ ID NO 186
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186
```

-continued

```
Met Tyr Arg Leu Leu Asp His Tyr Lys Tyr Leu Thr Ala Trp Phe Glu
1               5                   10                  15

Leu Leu Asn Leu Pro Lys Lys Ile Ile Phe Val Gly His Asp Trp Gly
            20                  25                  30

Ala Cys Leu Ala Phe His Tyr Ser Tyr Glu His Gln Asp Lys Ile Lys
        35                  40                  45

Ala Ile Val His Ala Glu Ser Val Val Asp Val Ile Glu Ser Trp Asp
    50                  55                  60

Glu Trp Pro Asp Ile Glu Glu Asp Ile Ala Leu Ile Lys Ser Glu Glu
65                  70                  75                  80

Gly Glu Lys Met Val Leu Glu Asn Asn Phe Phe Val Glu Thr Met Leu
                85                  90                  95

Pro Ser Lys Ile Met Arg Lys Leu Glu Pro Glu Glu Phe Ala Ala Tyr
            100                 105                 110

Leu Glu Pro Phe Lys Glu Lys Gly Glu Val Arg Arg Pro Thr Leu Ser
        115                 120                 125

Trp Pro Arg Glu Ile Pro Leu Val Lys Gly Gly Lys Pro Asp Val Val
    130                 135                 140

Gln Ile Val Arg Asn Tyr Asn Ala Tyr Leu Arg Ala Ser Asp Asp Leu
145                 150                 155                 160

Pro Lys Met Phe Ile Glu Ser Asp Pro Gly Phe Phe Ser Asn Ala Ile
                165                 170                 175

Val Glu Gly Ala Lys Lys Phe Pro Asn Thr Glu Phe Val Lys Val Lys
            180                 185                 190

Gly Leu His Phe Ser Gln Glu Asp Ala Pro Asp Glu Met Gly Lys Tyr
        195                 200                 205

Ile Lys Ser Phe Val Glu Arg Val Leu Lys Asn Glu Gln Gly Ser Thr
    210                 215                 220

Gly Met Tyr Glu Ser Phe Ile Glu Ser Leu Pro Phe Leu Lys Ser Leu
225                 230                 235                 240

Glu Phe Ser Glu Arg Leu Lys Val Val Asp Val Ile Gly Thr Lys Val
                245                 250                 255

Tyr Asn Asp Gly Glu Gln Ile Ile Ala Gln Gly Asp Ser Ala Asp Ser
            260                 265                 270

Phe Phe Ile Val Glu Ser Gly Glu Val Lys Ile Thr Met Lys Arg Lys
        275                 280                 285

Gly Lys Ser Glu Val Glu Glu Asn Gly Ala Val Glu Ile Ala Arg Cys
    290                 295                 300

Ser Arg Gly Gln Tyr Phe Gly Glu Leu Ala Leu Val Thr Asn Lys Pro
305                 310                 315                 320

Arg Ala Ala Ser Ala His Ala Ile Gly Thr Val Lys Cys Leu Ala Met
                325                 330                 335

Asp Val Gln Ala Phe Glu Arg Leu Leu Gly Pro Cys Met Glu Ile Met
            340                 345                 350

Lys Arg Asn Ile Ala Thr Tyr Glu Glu Gln Leu Val Ala Leu Phe Gly
        355                 360                 365

Thr Asn Met Asp Ile Val Gly Ser Gly Gly Ser Gly Gly Ser Gly Gly
    370                 375                 380

Thr Ser Gly Gly Ser Gly Gly Ser Ser Gly Thr Ser Lys Val Tyr Asp
385                 390                 395                 400

Pro Glu Gln Arg Lys Arg Met Ile Thr Gly Pro Gln Trp Trp Ala Arg
                405                 410                 415

Cys Lys Gln Met Asn Val Leu Asp Ser Phe Ile Asn Tyr Tyr Asp Ser
```

420 425 430

Glu Lys His Ala Glu Asn Ala Val Ile Phe Leu His Gly Asn Ala Ala
435 440 445

Ser Ser Tyr Leu Trp Arg His Val Val Pro His Ile Glu Pro Val Ala
450 455 460

Arg Cys Ile Ile Pro Asp Leu Ile Gly Met Gly Lys Ser Gly Lys Ser
465 470 475 480

Gly Asn Gly Ser Val
485

<210> SEQ ID NO 187
<211> LENGTH: 157
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 187

Gly Ser Thr Gly Met Tyr Glu Ser Phe Ile Glu Ser Leu Pro Phe Leu
1 5 10 15

Lys Ser Leu Glu Phe Ser Glu Arg Leu Lys Val Val Asp Val Ile Gly
20 25 30

Thr Lys Val Tyr Asn Asp Gly Glu Gln Ile Ile Ala Gln Gly Asp Ser
35 40 45

Ala Asp Ser Phe Phe Ile Val Glu Ser Gly Glu Val Lys Ile Thr Met
50 55 60

Lys Arg Lys Gly Lys Ser Glu Val Glu Glu Asn Gly Ala Val Glu Ile
65 70 75 80

Ala Arg Cys Ser Arg Gly Gln Tyr Phe Gly Glu Leu Ala Leu Val Thr
85 90 95

Asn Lys Pro Arg Ala Ala Ser Ala His Ala Ile Gly Thr Val Lys Cys
100 105 110

Leu Ala Met Asp Val Gln Ala Phe Glu Arg Leu Leu Gly Pro Cys Met
115 120 125

Glu Ile Met Lys Arg Asn Ile Ala Thr Tyr Glu Glu Gln Leu Val Ala
130 135 140

Leu Phe Gly Thr Asn Met Asp Ile Val Gly Ser Ser Gly
145 150 155

<210> SEQ ID NO 188
<211> LENGTH: 169
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 188

Gly Ser Ser Gly Gly Ser Gly Gly Ser Gly Met Tyr Glu Ser Phe Ile
1 5 10 15

Glu Ser Leu Pro Phe Leu Lys Ser Leu Glu Phe Ser Glu Arg Leu Lys
20 25 30

Val Val Asp Val Ile Gly Thr Lys Val Tyr Asn Asp Gly Glu Gln Ile
35 40 45

Ile Ala Gln Gly Asp Ser Ala Asp Ser Phe Phe Ile Val Glu Ser Gly
50 55 60

Glu Val Lys Ile Thr Met Lys Arg Lys Gly Lys Ser Glu Val Glu Glu

```
65                  70                  75                  80

Asn Gly Ala Val Glu Ile Ala Arg Cys Ser Arg Gly Gln Tyr Phe Gly
                85                  90                  95

Glu Leu Ala Leu Val Thr Asn Lys Pro Arg Ala Ala Ser Ala His Ala
            100                 105                 110

Ile Gly Thr Val Lys Cys Leu Ala Met Asp Val Gln Ala Phe Glu Arg
        115                 120                 125

Leu Leu Gly Pro Cys Met Glu Ile Met Lys Arg Asn Ile Ala Thr Tyr
    130                 135                 140

Glu Glu Gln Leu Val Ala Leu Phe Gly Thr Asn Met Asp Ile Val Gly
145                 150                 155                 160

Ser Gly Gly Ser Gly Gly Ser Ser Gly
                165
```

<210> SEQ ID NO 189
<211> LENGTH: 189
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 189

```
Gly Ser Ser Gly Gly Ser Gly Gly Ser Gly Gly Gly Ser Gly Gly Ser
1               5                   10                  15

Gly Gly Ser Gly Met Tyr Glu Ser Phe Ile Glu Ser Leu Pro Phe Leu
            20                  25                  30

Lys Ser Leu Glu Phe Ser Glu Arg Leu Lys Val Val Asp Val Ile Gly
        35                  40                  45

Thr Lys Val Tyr Asn Asp Gly Glu Gln Ile Ile Ala Gln Gly Asp Ser
    50                  55                  60

Ala Asp Ser Phe Phe Ile Val Glu Ser Gly Glu Val Lys Ile Thr Met
65                  70                  75                  80

Lys Arg Lys Gly Lys Ser Glu Val Glu Glu Asn Gly Ala Val Glu Ile
                85                  90                  95

Ala Arg Cys Ser Arg Gly Gln Tyr Phe Gly Glu Leu Ala Leu Val Thr
            100                 105                 110

Asn Lys Pro Arg Ala Ala Ser Ala His Ala Ile Gly Thr Val Lys Cys
        115                 120                 125

Leu Ala Met Asp Val Gln Ala Phe Glu Arg Leu Leu Gly Pro Cys Met
    130                 135                 140

Glu Ile Met Lys Arg Asn Ile Ala Thr Tyr Glu Glu Gln Leu Val Ala
145                 150                 155                 160

Leu Phe Gly Thr Asn Met Asp Ile Val Gly Ser Gly Gly Ser Gly Gly
                165                 170                 175

Ser Gly Gly Thr Ser Gly Gly Ser Gly Gly Ser Ser Gly
            180                 185
```

<210> SEQ ID NO 190
<211> LENGTH: 327
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 190

```
Met Phe Thr Leu Ala Asp Phe Val Gly Asp Trp Gln Gln Thr Ala Gly
```

-continued 1 5 10 15

Tyr Asn Gln Asp Gln Val Leu Glu Gln Gly Gly Leu Ser Ser Leu Phe
20 25 30

Gln Ala Leu Gly Val Ser Val Thr Pro Ile Gln Lys Val Val Leu Ser
35 40 45

Gly Glu Asn Gly Ser Thr Gly Met Tyr Glu Ser Phe Ile Glu Ser Leu
50 55 60

Pro Phe Leu Lys Ser Leu Glu Phe Ser Glu Arg Leu Lys Val Val Asp
65 70 75 80

Val Ile Gly Thr Lys Val Tyr Asn Asp Gly Glu Gln Ile Ile Ala Gln
85 90 95

Gly Asp Ser Ala Asp Ser Phe Phe Ile Val Glu Ser Gly Glu Val Lys
100 105 110

Ile Thr Met Lys Arg Lys Gly Lys Ser Glu Val Glu Glu Asn Gly Ala
115 120 125

Val Glu Ile Ala Arg Cys Ser Arg Gly Gln Tyr Phe Gly Glu Leu Ala
130 135 140

Leu Val Thr Asn Lys Pro Arg Ala Ala Ser Ala His Ala Ile Gly Thr
145 150 155 160

Val Lys Cys Leu Ala Met Asp Val Gln Ala Phe Glu Arg Leu Leu Gly
165 170 175

Pro Cys Met Glu Ile Met Lys Arg Asn Ile Ala Thr Tyr Glu Glu Gln
180 185 190

Leu Val Ala Leu Phe Gly Thr Asn Met Asp Ile Val Gly Ser Ser Gly
195 200 205

Gly Leu Lys Ala Asp Ile His Val Ile Ile Pro Tyr Glu Gly Leu Ser
210 215 220

Gly Phe Gln Met Gly Leu Ile Glu Met Ile Phe Lys Val Val Tyr Pro
225 230 235 240

Val Asp Asp His His Phe Lys Ile Ile Leu His Tyr Gly Thr Leu Val
245 250 255

Ile Asp Gly Val Thr Pro Asn Met Ile Asp Tyr Phe Gly Arg Pro Tyr
260 265 270

Pro Gly Ile Ala Val Phe Asp Gly Lys Gln Ile Thr Val Thr Gly Thr
275 280 285

Leu Trp Asn Gly Asn Lys Ile Tyr Asp Glu Arg Leu Ile Asn Pro Asp
290 295 300

Gly Ser Leu Leu Phe Arg Val Thr Ile Asn Gly Val Thr Gly Trp Arg
305 310 315 320

Leu Cys Glu Asn Ile Leu Ala
325

<210> SEQ ID NO 191
<211> LENGTH: 339
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 191

Met Phe Thr Leu Ala Asp Phe Val Gly Asp Trp Gln Gln Thr Ala Gly
1 5 10 15

Tyr Asn Gln Asp Gln Val Leu Glu Gln Gly Gly Leu Ser Ser Leu Phe
20 25 30

```
Gln Ala Leu Gly Val Ser Val Thr Pro Ile Gln Lys Val Val Leu Ser
        35                  40                  45

Gly Glu Asn Gly Ser Ser Gly Gly Ser Gly Gly Ser Gly Met Tyr Glu
    50                  55                  60

Ser Phe Ile Glu Ser Leu Pro Phe Leu Lys Ser Leu Glu Phe Ser Glu
65                  70                  75                  80

Arg Leu Lys Val Val Asp Val Ile Gly Thr Lys Val Tyr Asn Asp Gly
                85                  90                  95

Glu Gln Ile Ile Ala Gln Gly Asp Ser Ala Asp Ser Phe Phe Ile Val
            100                 105                 110

Glu Ser Gly Glu Val Lys Ile Thr Met Lys Arg Lys Gly Lys Ser Glu
        115                 120                 125

Val Glu Glu Asn Gly Ala Val Glu Ile Ala Arg Cys Ser Arg Gly Gln
    130                 135                 140

Tyr Phe Gly Glu Leu Ala Leu Val Thr Asn Lys Pro Arg Ala Ala Ser
145                 150                 155                 160

Ala His Ala Ile Gly Thr Val Lys Cys Leu Ala Met Asp Val Gln Ala
                165                 170                 175

Phe Glu Arg Leu Leu Gly Pro Cys Met Glu Ile Met Lys Arg Asn Ile
            180                 185                 190

Ala Thr Tyr Glu Glu Gln Leu Val Ala Leu Phe Gly Thr Asn Met Asp
        195                 200                 205

Ile Val Gly Ser Ser Gly Gly Ser Gly Gly Ser Gly Gly Leu Lys Ala
    210                 215                 220

Asp Ile His Val Ile Ile Pro Tyr Glu Gly Leu Ser Gly Phe Gln Met
225                 230                 235                 240

Gly Leu Ile Glu Met Ile Phe Lys Val Val Tyr Pro Val Asp Asp His
                245                 250                 255

His Phe Lys Ile Ile Leu His Tyr Gly Thr Leu Val Ile Asp Gly Val
            260                 265                 270

Thr Pro Asn Met Ile Asp Tyr Phe Gly Arg Pro Tyr Pro Gly Ile Ala
        275                 280                 285

Val Phe Asp Gly Lys Gln Ile Thr Val Thr Gly Thr Leu Trp Asn Gly
    290                 295                 300

Asn Lys Ile Tyr Asp Glu Arg Leu Ile Asn Pro Asp Gly Ser Leu Leu
305                 310                 315                 320

Phe Arg Val Thr Ile Asn Gly Val Thr Gly Trp Arg Leu Cys Glu Asn
                325                 330                 335

Ile Leu Ala


<210> SEQ ID NO 192
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Met Phe Thr Leu Ala Asp Phe Val Gly Asp Trp Gln Gln Thr Ala Gly
1               5                   10                  15

Tyr Asn Gln Asp Gln Val Leu Glu Gln Gly Gly Leu Ser Ser Leu Phe
            20                  25                  30

Gln Ala Leu Gly Val Ser Val Thr Pro Ile Gln Lys Val Val Leu Ser
        35                  40                  45
```

```
Gly Glu Asn Gly Ser Ser Gly Gly Ser Gly Gly Ser Gly Gly Gly Ser
    50                  55                  60

Gly Gly Ser Gly Gly Ser Gly Met Tyr Glu Ser Phe Ile Glu Ser Leu
65                  70                  75                  80

Pro Phe Leu Lys Ser Leu Glu Phe Ser Glu Arg Leu Lys Val Val Asp
                85                  90                  95

Val Ile Gly Thr Lys Val Tyr Asn Asp Gly Glu Gln Ile Ile Ala Gln
            100                 105                 110

Gly Asp Ser Ala Asp Ser Phe Phe Ile Val Glu Ser Gly Glu Val Lys
        115                 120                 125

Ile Thr Met Lys Arg Lys Gly Lys Ser Glu Val Glu Glu Asn Gly Ala
    130                 135                 140

Val Glu Ile Ala Arg Cys Ser Arg Gly Gln Tyr Phe Gly Glu Leu Ala
145                 150                 155                 160

Leu Val Thr Asn Lys Pro Arg Ala Ala Ser Ala His Ala Ile Gly Thr
                165                 170                 175

Val Lys Cys Leu Ala Met Asp Val Gln Ala Phe Glu Arg Leu Leu Gly
            180                 185                 190

Pro Cys Met Glu Ile Met Lys Arg Asn Ile Ala Thr Tyr Glu Glu Gln
        195                 200                 205

Leu Val Ala Leu Phe Gly Thr Asn Met Asp Ile Val Gly Ser Gly Gly
    210                 215                 220

Ser Gly Gly Ser Gly Gly Thr Ser Gly Gly Ser Gly Gly Ser Ser Gly
225                 230                 235                 240

Gly Leu Lys Ala Asp Ile His Val Ile Ile Pro Tyr Glu Gly Leu Ser
                245                 250                 255

Gly Phe Gln Met Gly Leu Ile Glu Met Ile Phe Lys Val Val Tyr Pro
            260                 265                 270

Val Asp Asp His His Phe Lys Ile Ile Leu His Tyr Gly Thr Leu Val
        275                 280                 285

Ile Asp Gly Val Thr Pro Asn Met Ile Asp Tyr Phe Gly Arg Pro Tyr
    290                 295                 300

Pro Gly Ile Ala Val Phe Asp Gly Lys Gln Ile Thr Val Thr Gly Thr
305                 310                 315                 320

Leu Trp Asn Gly Asn Lys Ile Tyr Asp Glu Arg Leu Ile Asn Pro Asp
                325                 330                 335

Gly Ser Leu Leu Phe Arg Val Thr Ile Asn Gly Val Thr Gly Trp Arg
            340                 345                 350

Leu Cys Glu Asn Ile Leu Ala
        355
```

<210> SEQ ID NO 193
<211> LENGTH: 327
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 193

```
Met Phe Thr Leu Ala Asp Phe Val Gly Asp Trp Gln Gln Thr Ala Gly
1               5                   10                  15

Tyr Asn Gln Asp Gln Val Leu Glu Gln Gly Gly Leu Ser Ser Leu Phe
            20                  25                  30

Gln Ala Leu Gly Val Ser Val Thr Pro Ile Gln Lys Val Val Leu Ser
        35                  40                  45
```

Gly Glu Asn Gly Leu Lys Ala Asp Ile His Val Ile Ile Pro Tyr Glu
50 55 60

Gly Leu Ser Gly Phe Gln Met Gly Leu Ile Glu Met Ile Phe Lys Val
65 70 75 80

Val Tyr Pro Val Asp Gly Ser Thr Gly Met Tyr Glu Ser Phe Ile Glu
85 90 95

Ser Leu Pro Phe Leu Lys Ser Leu Glu Phe Ser Glu Arg Leu Lys Val
100 105 110

Val Asp Val Ile Gly Thr Lys Val Tyr Asn Asp Gly Glu Gln Ile Ile
115 120 125

Ala Gln Gly Asp Ser Ala Asp Ser Phe Phe Ile Val Glu Ser Gly Glu
130 135 140

Val Lys Ile Thr Met Lys Arg Lys Gly Lys Ser Glu Val Glu Glu Asn
145 150 155 160

Gly Ala Val Glu Ile Ala Arg Cys Ser Arg Gly Gln Tyr Phe Gly Glu
165 170 175

Leu Ala Leu Val Thr Asn Lys Pro Arg Ala Ala Ser Ala His Ala Ile
180 185 190

Gly Thr Val Lys Cys Leu Ala Met Asp Val Gln Ala Phe Glu Arg Leu
195 200 205

Leu Gly Pro Cys Met Glu Ile Met Lys Arg Asn Ile Ala Thr Tyr Glu
210 215 220

Glu Gln Leu Val Ala Leu Phe Gly Thr Asn Met Asp Ile Val Gly Ser
225 230 235 240

Ser Gly Asp His His Phe Lys Ile Ile Leu His Tyr Gly Thr Leu Val
245 250 255

Ile Asp Gly Val Thr Pro Asn Met Ile Asp Tyr Phe Gly Arg Pro Tyr
260 265 270

Pro Gly Ile Ala Val Phe Asp Gly Lys Gln Ile Thr Val Thr Gly Thr
275 280 285

Leu Trp Asn Gly Asn Lys Ile Tyr Asp Glu Arg Leu Ile Asn Pro Asp
290 295 300

Gly Ser Leu Leu Phe Arg Val Thr Ile Asn Gly Val Thr Gly Trp Arg
305 310 315 320

Leu Cys Glu Asn Ile Leu Ala
325

<210> SEQ ID NO 194
<211> LENGTH: 339
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 194

Met Phe Thr Leu Ala Asp Phe Val Gly Asp Trp Gln Gln Thr Ala Gly
1 5 10 15

Tyr Asn Gln Asp Gln Val Leu Glu Gln Gly Gly Leu Ser Ser Leu Phe
20 25 30

Gln Ala Leu Gly Val Ser Val Thr Pro Ile Gln Lys Val Val Leu Ser
35 40 45

Gly Glu Asn Gly Leu Lys Ala Asp Ile His Val Ile Ile Pro Tyr Glu
50 55 60

Gly Leu Ser Gly Phe Gln Met Gly Leu Ile Glu Met Ile Phe Lys Val

```
65                  70                  75                  80

Val Tyr Pro Val Asp Gly Ser Ser Gly Gly Ser Gly Gly Ser Gly Met
                85                  90                  95

Tyr Glu Ser Phe Ile Glu Ser Leu Pro Phe Leu Lys Ser Leu Glu Phe
            100                 105                 110

Ser Glu Arg Leu Lys Val Val Asp Val Ile Gly Thr Lys Val Tyr Asn
        115                 120                 125

Asp Gly Glu Gln Ile Ile Ala Gln Gly Asp Ser Ala Asp Ser Phe Phe
    130                 135                 140

Ile Val Glu Ser Gly Glu Val Lys Ile Thr Met Lys Arg Lys Gly Lys
145                 150                 155                 160

Ser Glu Val Glu Glu Asn Gly Ala Val Glu Ile Ala Arg Cys Ser Arg
                165                 170                 175

Gly Gln Tyr Phe Gly Glu Leu Ala Leu Val Thr Asn Lys Pro Arg Ala
            180                 185                 190

Ala Ser Ala His Ala Ile Gly Thr Val Lys Cys Leu Ala Met Asp Val
        195                 200                 205

Gln Ala Phe Glu Arg Leu Leu Gly Pro Cys Met Glu Ile Met Lys Arg
    210                 215                 220

Asn Ile Ala Thr Tyr Glu Glu Gln Leu Val Ala Leu Phe Gly Thr Asn
225                 230                 235                 240

Met Asp Ile Val Gly Ser Ser Gly Gly Ser Gly Gly Ser Gly Asp His
                245                 250                 255

His Phe Lys Ile Ile Leu His Tyr Gly Thr Leu Val Ile Asp Gly Val
            260                 265                 270

Thr Pro Asn Met Ile Asp Tyr Phe Gly Arg Pro Tyr Pro Gly Ile Ala
        275                 280                 285

Val Phe Asp Gly Lys Gln Ile Thr Val Thr Gly Thr Leu Trp Asn Gly
    290                 295                 300

Asn Lys Ile Tyr Asp Glu Arg Leu Ile Asn Pro Asp Gly Ser Leu Leu
305                 310                 315                 320

Phe Arg Val Thr Ile Asn Gly Val Thr Gly Trp Arg Leu Cys Glu Asn
                325                 330                 335

Ile Leu Ala


<210> SEQ ID NO 195
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Met Phe Thr Leu Ala Asp Phe Val Gly Asp Trp Gln Gln Thr Ala Gly
1               5                   10                  15

Tyr Asn Gln Asp Gln Val Leu Glu Gln Gly Gly Leu Ser Ser Leu Phe
            20                  25                  30

Gln Ala Leu Gly Val Ser Val Thr Pro Ile Gln Lys Val Val Leu Ser
        35                  40                  45

Gly Glu Asn Gly Leu Lys Ala Asp Ile His Val Ile Ile Pro Tyr Glu
    50                  55                  60

Gly Leu Ser Gly Phe Gln Met Gly Leu Ile Glu Met Ile Phe Lys Val
65                  70                  75                  80

Val Tyr Pro Val Asp Gly Ser Ser Gly Gly Ser Gly Gly Ser Gly Gly
```

```
                85                  90                  95

Gly Ser Gly Gly Ser Gly Gly Ser Gly Met Tyr Glu Ser Phe Ile Glu
            100                 105                 110

Ser Leu Pro Phe Leu Lys Ser Leu Glu Phe Ser Glu Arg Leu Lys Val
        115                 120                 125

Val Asp Val Ile Gly Thr Lys Val Tyr Asn Asp Gly Glu Gln Ile Ile
    130                 135                 140

Ala Gln Gly Asp Ser Ala Asp Ser Phe Phe Ile Val Glu Ser Gly Glu
145                 150                 155                 160

Val Lys Ile Thr Met Lys Arg Lys Gly Lys Ser Glu Val Glu Glu Asn
                165                 170                 175

Gly Ala Val Glu Ile Ala Arg Cys Ser Arg Gly Gln Tyr Phe Gly Glu
            180                 185                 190

Leu Ala Leu Val Thr Asn Lys Pro Arg Ala Ala Ser Ala His Ala Ile
        195                 200                 205

Gly Thr Val Lys Cys Leu Ala Met Asp Val Gln Ala Phe Glu Arg Leu
    210                 215                 220

Leu Gly Pro Cys Met Glu Ile Met Lys Arg Asn Ile Ala Thr Tyr Glu
225                 230                 235                 240

Glu Gln Leu Val Ala Leu Phe Gly Thr Asn Met Asp Ile Val Gly Ser
                245                 250                 255

Gly Gly Ser Gly Gly Ser Gly Gly Thr Ser Gly Gly Ser Gly Gly Ser
            260                 265                 270

Ser Gly Asp His His Phe Lys Ile Ile Leu His Tyr Gly Thr Leu Val
        275                 280                 285

Ile Asp Gly Val Thr Pro Asn Met Ile Asp Tyr Phe Gly Arg Pro Tyr
    290                 295                 300

Pro Gly Ile Ala Val Phe Asp Gly Lys Gln Ile Thr Val Thr Gly Thr
305                 310                 315                 320

Leu Trp Asn Gly Asn Lys Ile Tyr Asp Glu Arg Leu Ile Asn Pro Asp
                325                 330                 335

Gly Ser Leu Leu Phe Arg Val Thr Ile Asn Gly Val Thr Gly Trp Arg
            340                 345                 350

Leu Cys Glu Asn Ile Leu Ala
        355


<210> SEQ ID NO 196
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Gly Ser Ser Gly Gly Ser Gly Gly Ser Gly Gly Gly Ser Gly Gly Ser
1               5                   10                  15

Gly Gly Ser Arg Gly Gly Gly Thr Gly Gly Ser Gly Gly Ser Gly Gly
            20                  25                  30

Thr Ser Gly Gly Ser Gly Gly Ser Ser Gly
        35                  40


<210> SEQ ID NO 197
<211> LENGTH: 4
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 197

Gly Ser Ser Gly
1

<210> SEQ ID NO 198
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gly Ser Ser Gly Gly Ser Gly Gly Ser Gly
1               5                   10

<210> SEQ ID NO 199
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gly Ser Gly Gly Ser Gly Gly Ser Ser Gly
1               5                   10

<210> SEQ ID NO 200
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Ser Ser Gly Gly Ser Gly Gly Ser Gly Gly Gly Ser Gly Gly Ser
1               5                   10                  15

Gly Gly Ser Gly
            20

<210> SEQ ID NO 201
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gly Ser Gly Gly Ser Gly Gly Ser Gly Gly Thr Ser Gly Gly Ser Gly
1               5                   10                  15

Gly Ser Ser Gly
            20

<210> SEQ ID NO 202
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Leu Glu Gly Ser Gly Gly Gly Gly
1 5

<210> SEQ ID NO 203
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 203

Gly Gly Gly Gly Ser Gly Pro Trp
1 5

<210> SEQ ID NO 204
<211> LENGTH: 185
<212> TYPE: PRT
<213> ORGANISM: Gaussia princeps

<400> SEQUENCE: 204

Met Gly Val Lys Val Leu Phe Ala Leu Ile Cys Ile Ala Val Ala Glu
1 5 10 15

Ala Lys Pro Thr Glu Asn Asn Glu Asp Phe Asn Ile Val Ala Val Ala
20 25 30

Ser Asn Phe Ala Thr Thr Asp Leu Asp Ala Asp Arg Gly Lys Leu Pro
35 40 45

Gly Lys Lys Leu Pro Leu Glu Val Leu Lys Glu Met Glu Ala Asn Ala
50 55 60

Arg Lys Ala Gly Cys Thr Arg Gly Cys Leu Ile Cys Leu Ser His Ile
65 70 75 80

Lys Cys Thr Pro Lys Met Lys Lys Phe Ile Pro Gly Arg Cys His Thr
85 90 95

Tyr Glu Gly Asp Lys Glu Ser Ala Gln Gly Gly Ile Gly Glu Ala Ile
100 105 110

Val Asp Ile Pro Glu Ile Pro Gly Phe Lys Asp Leu Glu Pro Met Glu
115 120 125

Gln Phe Ile Ala Gln Val Asp Leu Cys Val Asp Cys Thr Thr Gly Cys
130 135 140

Leu Lys Gly Leu Ala Asn Val Gln Cys Ser Asp Leu Leu Lys Lys Trp
145 150 155 160

Leu Pro Gln Arg Cys Ala Thr Phe Ala Ser Lys Ile Gln Gly Gln Val
165 170 175

Asp Lys Ile Lys Gly Ala Gly Gly Asp
180 185

<210> SEQ ID NO 205
<211> LENGTH: 517
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 205
atggtgttta cgttggcaga tttcgttgga gactggcaac agacagctgg atacaaccaa 60
gatcaagtgt tagaacaagg aggattgtct agtctgttcc aagccctggg agtgtcagtc 120
accccaatcc agaaagttgt gctgtctggg gagaatgggt taaaagctga tattcatgtc 180
atcatccctt acgagggact cagtggtttt caaatgggtc tgattgaaat gatcttcaaa 240
gttgtttacc cagtggatga tcatcatttc aagattattc tccattatgg tacactcgtt 300
attgacggtg tgacaccaaa catgattgac tactttggac gcccttaccc tggaattgct 360
gtgtttgacg gcaagcagat cacagttact ggaactctgt ggaacggcaa caagatctat 420
gatgagcgcc tgatcaaccc agatggttca ctcctcttcc gcgttactat caatggagtc 480
accggatggc gcctttgcga gaacattctt gcctaat 517

<210> SEQ ID NO 206
<211> LENGTH: 465
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 206
atgtttacgt tggcagattt cgttggagac tggcaacaga cagctggata caaccaagat 60
caagtgttag aacaaggagg attgtctagt ctgttccaag ccctgggagt gtcagtcacc 120
ccaatccaga aagttgtact gtctggggag aatggcggga gctctggtgg agggtctggg 180
ggtgtggcca tcctctggca tgagatgtgg catgaaggcc tggaagaggc atctcgtttg 240
tactttgggg aaaggaacgt gaaaggcatg tttgaggtgc tggagccctt gcatgctatg 300
atggaacggg gcccccagac tctgaaggaa acatccttta atcaggccta tggtcgagat 360
ttaatggagg cccaagagtg gtgcaggaag tacatgaaat cagggaatgt caaggacctc 420
acccaagcct gggacctcta ttatcatgtg ttccgacgaa tctca 465

<210> SEQ ID NO 207
<211> LENGTH: 567
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 207
atgtttacgt tggcagattt cgttggagac tggcaacaga cagctggata caaccaagat 60
caagtgttag aacaaggagg attgtctagt ctgttccaag ccctgggagt gtcagtcacc 120
ccaatccaga aagttgtgct gtctggggag aatgggttaa aagctgatat tcatgtcatc 180
atcccttacg agggactcag tggttttcaa atgggtctga ttgaaatgat cttcaaagtt 240
gtttaccccg tggatggcgg gagctctggt ggagggtctg ggggtgtggc catcctctgg 300
catgagatgt ggcatgaagg cctggaagag gcatctcgtt tgtactttgg ggaaaggaac 360
gtgaaaggca tgtttgaggt gctggagccc ttgcatgcta tgatggaacg gggcccccag 420
actctgaagg aaacatcctt taatcaggcc tatggtcgag atttaatgga ggcccaagag 480
tggtgcagga agtacatgaa atcagggaat gtcaaggacc tcacccaagc ctgggacctc 540
tattatcatg tgttccgacg aatctca 567

<210> SEQ ID NO 208
<211> LENGTH: 729
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 208
atgggagtgc aggtggaaac catctcccca ggagacgggc gcaccttccc caagcgcggc 60
cagacctgcg tggtgcacta caccgggatg cttgaagatg gaaagaaatt tgattcctcc 120
cgggacagaa acaagccctt taagtttatg ctaggcaagc aggaggtgat ccgaggctgg 180
gaagaagggg ttgcccagat gagtgtgggt cagagagcca aactgactat atctccagat 240
tatgcctatg gtgccactgg gcacccaggc atcatcccac cacatgccac tctcgtcttc 300
gatgtggagc ttctaaaact ggaagggcgc gccggaggtg gcggatcagg tggcggaggc 360
tccgcgatcg ccgggttaaa agctgatatt catgtcatca tcccttacga gggactcagt 420
ggttttcaaa tgggtctgat tgaaatgatc ttcaaagttg tttacccagt ggatgatcat 480
catttcaaga ttattctcca ttatggtaca ctcgttattg acggtgtgac accaaacatg 540
attgactact ttggaagacc ttaccctgga attgctgtat ttgacggcaa gcagatcaca 600
gttactggaa ctctgtggaa cggcaacaag atctatgatg agcgcctgat caacccagat 660
ggttcactcc tcttccgcgt tactatcaat ggagtcaccg gatggcgcct ttgcgagaac 720
attcttgcc 729

<210> SEQ ID NO 209
<211> LENGTH: 627
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 209
atgggagtgc aggtggaaac catctcccca ggagacgggc gcaccttccc caagcgcggc 60
cagacctgcg tggtgcacta caccgggatg cttgaagatg gaaagaaatt tgattcctcc 120
cgggacagaa acaagccctt taagtttatg ctaggcaagc aggaggtgat ccgaggctgg 180
gaagaagggg ttgcccagat gagtgtgggt cagagagcca aactgactat atctccagat 240
tatgcctatg gtgccactgg gcacccaggc atcatcccac cacatgccac tctcgtcttc 300
gatgtggagc ttctaaaact ggaagggcgc gccggaggtg gcggatcagg tggcggaggc 360
tccgcgatcg ccgatcatca tttcaagatt attctccatt atggtacact cgttattgac 420
ggtgtgacac caaacatgat tgactacttt ggacgccctt accctggaat tgctgtgttt 480
gacggcaagc agatcacagt tactggaact ctgtggaacg gcaacaagat ctatgatgag 540
cgcctgatca acccagatgg ttcactcctc ttccgcgtta ctatcaatgg agtcaccgga 600
tggcgccttt gcgagaacat tcttgcc 627

<210> SEQ ID NO 210
<211> LENGTH: 550
<212> TYPE: PRT
<213> ORGANISM: Photinus pyralis

<400> SEQUENCE: 210

Met Glu Asp Ala Lys Asn Ile Lys Lys Gly Pro Ala Pro Phe Tyr Pro
1 5 10 15

Leu Glu Asp Gly Thr Ala Gly Glu Gln Leu His Lys Ala Met Lys Arg
20 25 30

Tyr Ala Leu Val Pro Gly Thr Ile Ala Phe Thr Asp Ala His Ile Glu
35 40 45

```
Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Asp Ala Gly Glu Leu
```

-continued 465 470 475 480

Pro Ala Ala Val Val Val Leu Glu His Gly Lys Thr Met Thr Glu Lys
485 490 495

Glu Ile Val Asp Tyr Val Ala Ser Gln Val Thr Thr Ala Lys Lys Leu
500 505 510

Arg Gly Gly Val Val Phe Val Asp Glu Val Pro Lys Gly Leu Thr Gly
515 520 525

Lys Leu Asp Ala Arg Lys Ile Arg Glu Ile Leu Ile Lys Ala Lys Lys
530 535 540

Gly Gly Lys Ile Ala Val
545 550

<210> SEQ ID NO 211
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 211
aaaaaatccg gaatgtatga aagctttatt gagtcactgc c 41

<210> SEQ ID NO 212
<211> LENGTH: 733
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 212

Met Thr Ala Ile Leu Ser Val Val Pro Phe His His Gly Phe Gly Met
1 5 10 15

Phe Thr Thr Leu Gly Tyr Leu Ile Cys Gly Phe Arg Val Val Leu Met
20 25 30

Tyr Arg Phe Glu Glu Glu Leu Phe Leu Arg Ser Leu Gln Asp Tyr Lys
35 40 45

Ile Gln Ser Ala Leu Leu Val Pro Thr Leu Phe Ser Phe Phe Ala Lys
50 55 60

Ser Thr Leu Ile Asp Lys Tyr Asp Leu Ser Asn Leu His Glu Ile Ala
65 70 75 80

Ser Gly Gly Ala Pro Leu Ser Lys Glu Val Gly Glu Ala Val Ala Lys
85 90 95

Arg Phe His Leu Pro Gly Ile Arg Gln Gly Tyr Gly Leu Thr Glu Thr
100 105 110

Thr Ser Ala Ile Leu Ile Thr Pro Glu Gly Asp Asp Lys Pro Gly Ala
115 120 125

Val Gly Lys Val Val Pro Phe Phe Glu Ala Lys Val Val Asp Leu Asp
130 135 140

Thr Gly Lys Thr Leu Gly Val Asn Gln Arg Gly Glu Leu Cys Val Arg
145 150 155 160

Gly Pro Met Ile Met Ser Gly Tyr Val Asn Asn Pro Glu Ala Thr Asn
165 170 175

Ala Leu Ile Asp Lys Asp Gly Trp Leu His Ser Gly Asp Ile Ala Tyr
180 185 190

Trp Asp Glu Asp Glu His Phe Phe Ile Val Asp Arg Leu Lys Ser Leu
195 200 205

-continued

```
Ile Lys Tyr Lys Gly Tyr Gln Val Ala Pro Ala Glu Leu Glu Ser Ile
    210                 215                 220

Leu Leu Gln His Pro Asn Ile Phe Asp Ala Gly Val Ala Gly Leu Pro
225                 230                 235                 240

Asp Asp Asp Ala Gly Glu Leu Pro Ala Ala Val Val Val Leu Glu His
                245                 250                 255

Gly Lys Thr Met Thr Glu Lys Glu Ile Val Asp Tyr Val Ala Ser Gln
            260                 265                 270

Val Thr Thr Ala Lys Lys Leu Arg Gly Gly Val Val Phe Val Asp Glu
        275                 280                 285

Val Pro Lys Gly Leu Thr Gly Lys Leu Asp Ala Arg Lys Ile Arg Glu
    290                 295                 300

Ile Leu Ile Lys Ala Lys Lys Gly Ser Ser Gly Arg Lys Arg Asp Arg
305                 310                 315                 320

Leu Gly Thr Leu Gly Ile Gly Gly Ser Ser Gly Gly Gly Ser Gly Gly
                325                 330                 335

Gly Gly Ser Gly Gly Gly Asn Gly Arg Phe Leu Thr Leu Lys Pro Leu
            340                 345                 350

Pro Asp Ser Ile Ile Gln Glu Ser Leu Glu Ile Gln Gln Gly Val Asn
        355                 360                 365

Pro Phe Phe Ile Gly Arg Ser Glu Asp Cys Asn Cys Lys Ile Glu Asp
    370                 375                 380

Asn Arg Leu Ser Arg Val His Cys Phe Ile Phe Lys Lys Arg His Ala
385                 390                 395                 400

Val Gly Lys Ser Met Tyr Glu Ser Pro Ala Gln Gly Leu Asp Asp Ile
                405                 410                 415

Trp Tyr Cys His Thr Gly Thr Asn Val Ser Tyr Leu Asn Asn Asn Arg
            420                 425                 430

Met Ile Gln Gly Thr Lys Phe Leu Leu Gln Asp Gly Asp Glu Ile Lys
        435                 440                 445

Ile Ile Trp Asp Lys Asn Asn Lys Phe Val Ile Gly Phe Lys Val Glu
    450                 455                 460

Ile Asn Asp Thr Thr Gly Leu Phe Asn Glu Gly Leu Gly Met Leu Gln
465                 470                 475                 480

Glu Gln Arg Val Val Leu Lys Gln Thr Ala Glu Glu Lys Asp Leu Val
                485                 490                 495

Lys Lys Leu Gly Ser Ser Gly Ala Lys Asn Ile Lys Lys Gly Pro Ala
            500                 505                 510

Pro Phe Tyr Pro Leu Glu Asp Gly Thr Ala Gly Glu Gln Leu His Lys
        515                 520                 525

Ala Met Lys Arg Tyr Ala Leu Val Pro Gly Thr Ile Ala Phe Thr Asp
    530                 535                 540

Ala His Ile Glu Val Asp Ile Thr Tyr Ala Glu Tyr Phe Glu Met Ser
545                 550                 555                 560

Val Arg Leu Ala Glu Ala Met Lys Arg Tyr Gly Leu Asn Thr Asn His
                565                 570                 575

Arg Ile Val Val Cys Ser Glu Asn Ser Leu Gln Phe Phe Met Pro Val
            580                 585                 590

Leu Gly Ala Leu Phe Ile Gly Val Ala Val Ala Pro Ala Asn Asp Ile
        595                 600                 605

Tyr Asn Glu Arg Glu Leu Leu Asn Ser Met Gly Ile Ser Gln Pro Thr
    610                 615                 620
```

```
Val Val Phe Val Ser Lys Lys Gly Leu Gln Lys Ile Leu Asn Val Gln
625                 630                 635                 640

Lys Lys Leu Pro Ile Ile Gln Lys Ile Ile Ile Met Asp Ser Lys Thr
                645                 650                 655

Asp Tyr Gln Gly Phe Gln Ser Met Tyr Thr Phe Val Thr Ser His Leu
            660                 665                 670

Pro Pro Gly Phe Asn Glu Tyr Asp Phe Val Pro Glu Ser Phe Asp Arg
        675                 680                 685

Asp Lys Thr Ile Ala Leu Ile Met Asn Ser Ser Gly Ser Thr Gly Leu
    690                 695                 700

Pro Lys Gly Val Ala Leu Pro His Arg Thr Ala Cys Val Arg Phe Ser
705                 710                 715                 720

His Ala Arg Asp Pro Ile Phe Gly Asn Gln Ile Ile Pro
                725                 730


<210> SEQ ID NO 213
<211> LENGTH: 745
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Met Thr Ala Ile Leu Ser Val Val Pro Phe His His Gly Phe Gly Met
1               5                   10                  15

Phe Thr Thr Leu Gly Tyr Leu Ile Cys Gly Phe Arg Val Val Leu Met
            20                  25                  30

Tyr Arg Phe Glu Glu Glu Leu Phe Leu Arg Ser Leu Gln Asp Tyr Lys
        35                  40                  45

Ile Gln Ser Ala Leu Leu Val Pro Thr Leu Phe Ser Phe Phe Ala Lys
    50                  55                  60

Ser Thr Leu Ile Asp Lys Tyr Asp Leu Ser Asn Leu His Glu Ile Ala
65                  70                  75                  80

Ser Gly Gly Ala Pro Leu Ser Lys Glu Val Gly Glu Ala Val Ala Lys
                85                  90                  95

Arg Phe His Leu Pro Gly Ile Arg Gln Gly Tyr Gly Leu Thr Glu Thr
            100                 105                 110

Thr Ser Ala Ile Leu Ile Thr Pro Glu Gly Asp Asp Lys Pro Gly Ala
        115                 120                 125

Val Gly Lys Val Val Pro Phe Phe Glu Ala Lys Val Val Asp Leu Asp
    130                 135                 140

Thr Gly Lys Thr Leu Gly Val Asn Gln Arg Gly Glu Leu Cys Val Arg
145                 150                 155                 160

Gly Pro Met Ile Met Ser Gly Tyr Val Asn Asn Pro Glu Ala Thr Asn
                165                 170                 175

Ala Leu Ile Asp Lys Asp Gly Trp Leu His Ser Gly Asp Ile Ala Tyr
            180                 185                 190

Trp Asp Glu Asp Glu His Phe Phe Ile Val Asp Arg Leu Lys Ser Leu
        195                 200                 205

Ile Lys Tyr Lys Gly Tyr Gln Val Ala Pro Ala Glu Leu Glu Ser Ile
    210                 215                 220

Leu Leu Gln His Pro Asn Ile Phe Asp Ala Gly Val Ala Gly Leu Pro
225                 230                 235                 240

Asp Asp Asp Ala Gly Glu Leu Pro Ala Ala Val Val Val Leu Glu His
                245                 250                 255
```

```
Gly Lys Thr Met Thr Glu Lys Glu Ile Val Asp Tyr Val Ala Ser Gln
            260                 265                 270

Val Thr Thr Ala Lys Lys Leu Arg Gly Gly Val Val Phe Val Asp Glu
        275                 280                 285

Val Pro Lys Gly Leu Thr Gly Lys Leu Asp Ala Arg Lys Ile Arg Glu
    290                 295                 300

Ile Leu Ile Lys Ala Lys Lys Gly Gly Ser Gly Gly Ser Gly Ser Ser
305                 310                 315                 320

Gly Arg Lys Arg Asp Arg Leu Gly Thr Leu Gly Ile Gly Gly Ser Ser
                325                 330                 335

Gly Gly Gly Ser Gly Gly Gly Gly Ser Gly Gly Gly Asn Gly Arg Phe
            340                 345                 350

Leu Thr Leu Lys Pro Leu Pro Asp Ser Ile Ile Gln Glu Ser Leu Glu
        355                 360                 365

Ile Gln Gln Gly Val Asn Pro Phe Phe Ile Gly Arg Ser Glu Asp Cys
    370                 375                 380

Asn Cys Lys Ile Glu Asp Asn Arg Leu Ser Arg Val His Cys Phe Ile
385                 390                 395                 400

Phe Lys Lys Arg His Ala Val Gly Lys Ser Met Tyr Glu Ser Pro Ala
                405                 410                 415

Gln Gly Leu Asp Asp Ile Trp Tyr Cys His Thr Gly Thr Asn Val Ser
            420                 425                 430

Tyr Leu Asn Asn Asn Arg Met Ile Gln Gly Thr Lys Phe Leu Leu Gln
        435                 440                 445

Asp Gly Asp Glu Ile Lys Ile Ile Trp Asp Lys Asn Asn Lys Phe Val
    450                 455                 460

Ile Gly Phe Lys Val Glu Ile Asn Asp Thr Thr Gly Leu Phe Asn Glu
465                 470                 475                 480

Gly Leu Gly Met Leu Gln Glu Gln Arg Val Val Leu Lys Gln Thr Ala
                485                 490                 495

Glu Glu Lys Asp Leu Val Lys Lys Leu Gly Ser Gly Gly Ser Gly Gly
            500                 505                 510

Ser Gly Gly Ala Lys Asn Ile Lys Lys Gly Pro Ala Pro Phe Tyr Pro
        515                 520                 525

Leu Glu Asp Gly Thr Ala Gly Glu Gln Leu His Lys Ala Met Lys Arg
    530                 535                 540

Tyr Ala Leu Val Pro Gly Thr Ile Ala Phe Thr Asp Ala His Ile Glu
545                 550                 555                 560

Val Asp Ile Thr Tyr Ala Glu Tyr Phe Glu Met Ser Val Arg Leu Ala
                565                 570                 575

Glu Ala Met Lys Arg Tyr Gly Leu Asn Thr Asn His Arg Ile Val Val
            580                 585                 590

Cys Ser Glu Asn Ser Leu Gln Phe Phe Met Pro Val Leu Gly Ala Leu
        595                 600                 605

Phe Ile Gly Val Ala Val Ala Pro Ala Asn Asp Ile Tyr Asn Glu Arg
    610                 615                 620

Glu Leu Leu Asn Ser Met Gly Ile Ser Gln Pro Thr Val Val Phe Val
625                 630                 635                 640

Ser Lys Lys Gly Leu Gln Lys Ile Leu Asn Val Gln Lys Lys Leu Pro
                645                 650                 655

Ile Ile Gln Lys Ile Ile Ile Met Asp Ser Lys Thr Asp Tyr Gln Gly
            660                 665                 670
```

```
Phe Gln Ser Met Tyr Thr Phe Val Thr Ser His Leu Pro Pro Gly Phe
        675                 680                 685

Asn Glu Tyr Asp Phe Val Pro Glu Ser Phe Asp Arg Asp Lys Thr Ile
    690                 695                 700

Ala Leu Ile Met Asn Ser Ser Gly Ser Thr Gly Leu Pro Lys Gly Val
705                 710                 715                 720

Ala Leu Pro His Arg Thr Ala Cys Val Arg Phe Ser His Ala Arg Asp
                725                 730                 735

Pro Ile Phe Gly Asn Gln Ile Ile Pro
            740                 745


<210> SEQ ID NO 214
<211> LENGTH: 731
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Met Pro Gly Ala Val Gly Lys Val Val Pro Phe Phe Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Ser Gly Arg
            180                 185                 190

Lys Arg Asp Arg Leu Gly Thr Leu Gly Ile Gly Gly Ser Ser Gly Gly
        195                 200                 205

Gly Ser Gly Gly Gly Gly Ser Gly Gly Gly Asn Gly Arg Phe Leu Thr
    210                 215                 220

Leu Lys Pro Leu Pro Asp Ser Ile Ile Gln Glu Ser Leu Glu Ile Gln
225                 230                 235                 240

Gln Gly Val Asn Pro Phe Phe Ile Gly Arg Ser Glu Asp Cys Asn Cys
                245                 250                 255

Lys Ile Glu Asp Asn Arg Leu Ser Arg Val His Cys Phe Ile Phe Lys
            260                 265                 270

Lys Arg His Ala Val Gly Lys Ser Met Tyr Glu Ser Pro Ala Gln Gly
        275                 280                 285
```

```
Leu Asp Asp Ile Trp Tyr Cys His Thr Gly Thr Asn Val Ser Tyr Leu
    290                 295                 300

Asn Asn Asn Arg Met Ile Gln Gly Thr Lys Phe Leu Leu Gln Asp Gly
305                 310                 315                 320

Asp Glu Ile Lys Ile Ile Trp Asp Lys Asn Asn Lys Phe Val Ile Gly
                325                 330                 335

Phe Lys Val Glu Ile Asn Asp Thr Thr Gly Leu Phe Asn Glu Gly Leu
            340                 345                 350

Gly Met Leu Gln Glu Gln Arg Val Val Leu Lys Gln Thr Ala Glu Glu
        355                 360                 365

Lys Asp Leu Val Lys Lys Leu Gly Ser Ser Gly Ala Lys Asn Ile Lys
    370                 375                 380

Lys Gly Pro Ala Pro Phe Tyr Pro Leu Glu Asp Gly Thr Ala Gly Glu
385                 390                 395                 400

Gln Leu His Lys Ala Met Lys Arg Tyr Ala Leu Val Pro Gly Thr Ile
                405                 410                 415

Ala Phe Thr Asp Ala His Ile Glu Val Asp Ile Thr Tyr Ala Glu Tyr
            420                 425                 430

Phe Glu Met Ser Val Arg Leu Ala Glu Ala Met Lys Arg Tyr Gly Leu
        435                 440                 445

Asn Thr Asn His Arg Ile Val Val Cys Ser Glu Asn Ser Leu Gln Phe
    450                 455                 460

Phe Met Pro Val Leu Gly Ala Leu Phe Ile Gly Val Ala Val Ala Pro
465                 470                 475                 480

Ala Asn Asp Ile Tyr Asn Glu Arg Glu Leu Leu Asn Ser Met Gly Ile
                485                 490                 495

Ser Gln Pro Thr Val Val Phe Val Ser Lys Lys Gly Leu Gln Lys Ile
            500                 505                 510

Leu Asn Val Gln Lys Lys Leu Pro Ile Ile Gln Lys Ile Ile Ile Met
        515                 520                 525

Asp Ser Lys Thr Asp Tyr Gln Gly Phe Gln Ser Met Tyr Thr Phe Val
    530                 535                 540

Thr Ser His Leu Pro Pro Gly Phe Asn Glu Tyr Asp Phe Val Pro Glu
545                 550                 555                 560

Ser Phe Asp Arg Asp Lys Thr Ile Ala Leu Ile Met Asn Ser Ser Gly
                565                 570                 575

Ser Thr Gly Leu Pro Lys Gly Val Ala Leu Pro His Arg Thr Ala Cys
            580                 585                 590

Val Arg Phe Ser His Ala Arg Asp Pro Ile Phe Gly Asn Gln Ile Ile
        595                 600                 605

Pro Asp Thr Ala Ile Leu Ser Val Val Pro Phe His His Gly Phe Gly
    610                 615                 620

Met Phe Thr Thr Leu Gly Tyr Leu Ile Cys Gly Phe Arg Val Val Leu
625                 630                 635                 640

Met Tyr Arg Phe Glu Glu Glu Leu Phe Leu Arg Ser Leu Gln Asp Tyr
                645                 650                 655

Lys Ile Gln Ser Ala Leu Leu Val Pro Thr Leu Phe Ser Phe Phe Ala
            660                 665                 670

Lys Ser Thr Leu Ile Asp Lys Tyr Asp Leu Ser Asn Leu His Glu Ile
        675                 680                 685

Ala Ser Gly Gly Ala Pro Leu Ser Lys Glu Val Gly Glu Ala Val Ala
    690                 695                 700
```

-continued

Lys Arg Phe His Leu Pro Gly Ile Arg Gln Gly Tyr Gly Leu Thr Glu
705 710 715 720

Thr Thr Ser Ala Ile Leu Ile Thr Pro Glu Gly
725 730

<210> SEQ ID NO 215
<211> LENGTH: 743
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 215

Met Pro Gly Ala Val Gly Lys Val Val Pro Phe Phe Glu Ala Lys Val
1 5 10 15

Val Asp Leu Asp Thr Gly Lys Thr Leu Gly Val Asn Gln Arg Gly Glu
20 25 30

Leu Cys Val Arg Gly Pro Met Ile Met Ser Gly Tyr Val Asn Asn Pro
35 40 45

Glu Ala Thr Asn Ala Leu Ile Asp Lys Asp Gly Trp Leu His Ser Gly
50 55 60

Asp Ile Ala Tyr Trp Asp Glu Asp Glu His Phe Phe Ile Val Asp Arg
65 70 75 80

Leu Lys Ser Leu Ile Lys Tyr Lys Gly Tyr Gln Val Ala Pro Ala Glu
85 90 95

Leu Glu Ser Ile Leu Leu Gln His Pro Asn Ile Phe Asp Ala Gly Val
100 105 110

Ala Gly Leu Pro Asp Asp Asp Ala Gly Glu Leu Pro Ala Ala Val Val
115 120 125

Val Leu Glu His Gly Lys Thr Met Thr Glu Lys Glu Ile Val Asp Tyr
130 135 140

Val Ala Ser Gln Val Thr Thr Ala Lys Lys Leu Arg Gly Gly Val Val
145 150 155 160

Phe Val Asp Glu Val Pro Lys Gly Leu Thr Gly Lys Leu Asp Ala Arg
165 170 175

Lys Ile Arg Glu Ile Leu Ile Lys Ala Lys Lys Gly Gly Ser Gly Gly
180 185 190

Ser Gly Ser Ser Gly Arg Lys Arg Asp Arg Leu Gly Thr Leu Gly Ile
195 200 205

Gly Gly Ser Ser Gly Gly Gly Ser Gly Gly Gly Gly Ser Gly Gly Gly
210 215 220

Asn Gly Arg Phe Leu Thr Leu Lys Pro Leu Pro Asp Ser Ile Ile Gln
225 230 235 240

Glu Ser Leu Glu Ile Gln Gln Gly Val Asn Pro Phe Phe Ile Gly Arg
245 250 255

Ser Glu Asp Cys Asn Cys Lys Ile Glu Asp Asn Arg Leu Ser Arg Val
260 265 270

His Cys Phe Ile Phe Lys Lys Arg His Ala Val Gly Lys Ser Met Tyr
275 280 285

Glu Ser Pro Ala Gln Gly Leu Asp Asp Ile Trp Tyr Cys His Thr Gly
290 295 300

Thr Asn Val Ser Tyr Leu Asn Asn Asn Arg Met Ile Gln Gly Thr Lys
305 310 315 320

Phe Leu Leu Gln Asp Gly Asp Glu Ile Lys Ile Ile Trp Asp Lys Asn
325 330 335

Asn Lys Phe Val Ile Gly Phe Lys Val Glu Ile Asn Asp Thr Thr Gly
340 345 350

Leu Phe Asn Glu Gly Leu Gly Met Leu Gln Glu Gln Arg Val Val Leu
355 360 365

Lys Gln Thr Ala Glu Glu Lys Asp Leu Val Lys Lys Leu Gly Ser Gly
370 375 380

Gly Ser Gly Gly Ser Gly Gly Ala Lys Asn Ile Lys Lys Gly Pro Ala
385 390 395 400

Pro Phe Tyr Pro Leu Glu Asp Gly Thr Ala Gly Glu Gln Leu His Lys
405 410 415

Ala Met Lys Arg Tyr Ala Leu Val Pro Gly Thr Ile Ala Phe Thr Asp
420 425 430

Ala His Ile Glu Val Asp Ile Thr Tyr Ala Glu Tyr Phe Glu Met Ser
435 440 445

Val Arg Leu Ala Glu Ala Met Lys Arg Tyr Gly Leu Asn Thr Asn His
450 455 460

Arg Ile Val Val Cys Ser Glu Asn Ser Leu Gln Phe Phe Met Pro Val
465 470 475 480

Leu Gly Ala Leu Phe Ile Gly Val Ala Val Ala Pro Ala Asn Asp Ile
485 490 495

Tyr Asn Glu Arg Glu Leu Leu Asn Ser Met Gly Ile Ser Gln Pro Thr
500 505 510

Val Val Phe Val Ser Lys Lys Gly Leu Gln Lys Ile Leu Asn Val Gln
515 520 525

Lys Lys Leu Pro Ile Ile Gln Lys Ile Ile Ile Met Asp Ser Lys Thr
530 535 540

Asp Tyr Gln Gly Phe Gln Ser Met Tyr Thr Phe Val Thr Ser His Leu
545 550 555 560

Pro Pro Gly Phe Asn Glu Tyr Asp Phe Val Pro Glu Ser Phe Asp Arg
565 570 575

Asp Lys Thr Ile Ala Leu Ile Met Asn Ser Ser Gly Ser Thr Gly Leu
580 585 590

Pro Lys Gly Val Ala Leu Pro His Arg Thr Ala Cys Val Arg Phe Ser
595 600 605

His Ala Arg Asp Pro Ile Phe Gly Asn Gln Ile Ile Pro Asp Thr Ala
610 615 620

Ile Leu Ser Val Val Pro Phe His His Gly Phe Gly Met Phe Thr Thr
625 630 635 640

Leu Gly Tyr Leu Ile Cys Gly Phe Arg Val Val Leu Met Tyr Arg Phe
645 650 655

Glu Glu Glu Leu Phe Leu Arg Ser Leu Gln Asp Tyr Lys Ile Gln Ser
660 665 670

Ala Leu Leu Val Pro Thr Leu Phe Ser Phe Phe Ala Lys Ser Thr Leu
675 680 685

Ile Asp Lys Tyr Asp Leu Ser Asn Leu His Glu Ile Ala Ser Gly Gly
690 695 700

Ala Pro Leu Ser Lys Glu Val Gly Glu Ala Val Ala Lys Arg Phe His
705 710 715 720

Leu Pro Gly Ile Arg Gln Gly Tyr Gly Leu Thr Glu Thr Thr Ser Ala
725 730 735

Ile Leu Ile Thr Pro Glu Gly
740

<210> SEQ ID NO 216
<211> LENGTH: 763
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

```
Met Pro Gly Ala Val Gly Lys Val Val Pro Phe Phe Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Ser Gly Gly
            180                 185                 190

Ser Gly Gly Ser Gly Gly Gly Ser Gly Gly Ser Gly Ser Ser Gly Arg
        195                 200                 205

Lys Arg Asp Arg Leu Gly Thr Leu Gly Ile Gly Gly Ser Ser Gly Gly
    210                 215                 220

Gly Ser Gly Gly Gly Gly Ser Gly Gly Gly Asn Gly Arg Phe Leu Thr
225                 230                 235                 240

Leu Lys Pro Leu Pro Asp Ser Ile Ile Gln Glu Ser Leu Glu Ile Gln
                245                 250                 255

Gln Gly Val Asn Pro Phe Phe Ile Gly Arg Ser Glu Asp Cys Asn Cys
            260                 265                 270

Lys Ile Glu Asp Asn Arg Leu Ser Arg Val His Cys Phe Ile Phe Lys
        275                 280                 285

Lys Arg His Ala Val Gly Lys Ser Met Tyr Glu Ser Pro Ala Gln Gly
    290                 295                 300

Leu Asp Asp Ile Trp Tyr Cys His Thr Gly Thr Asn Val Ser Tyr Leu
305                 310                 315                 320

Asn Asn Asn Arg Met Ile Gln Gly Thr Lys Phe Leu Leu Gln Asp Gly
                325                 330                 335

Asp Glu Ile Lys Ile Ile Trp Asp Lys Asn Asn Lys Phe Val Ile Gly
            340                 345                 350

Phe Lys Val Glu Ile Asn Asp Thr Thr Gly Leu Phe Asn Glu Gly Leu
        355                 360                 365
```

```
Gly Met Leu Gln Glu Gln Arg Val Val Leu Lys Gln Thr Ala Glu Glu
    370                 375                 380

Lys Asp Leu Val Lys Lys Leu Gly Ser Gly Gly Ser Gly Gly Ser Gly
385                 390                 395                 400

Gly Thr Ser Gly Gly Ser Gly Gly Ser Ser Gly Ala Lys Asn Ile Lys
                405                 410                 415

Lys Gly Pro Ala Pro Phe Tyr Pro Leu Glu Asp Gly Thr Ala Gly Glu
            420                 425                 430

Gln Leu His Lys Ala Met Lys Arg Tyr Ala Leu Val Pro Gly Thr Ile
        435                 440                 445

Ala Phe Thr Asp Ala His Ile Glu Val Asp Ile Thr Tyr Ala Glu Tyr
    450                 455                 460

Phe Glu Met Ser Val Arg Leu Ala Glu Ala Met Lys Arg Tyr Gly Leu
465                 470                 475                 480

Asn Thr Asn His Arg Ile Val Val Cys Ser Glu Asn Ser Leu Gln Phe
                485                 490                 495

Phe Met Pro Val Leu Gly Ala Leu Phe Ile Gly Val Ala Val Ala Pro
            500                 505                 510

Ala Asn Asp Ile Tyr Asn Glu Arg Glu Leu Leu Asn Ser Met Gly Ile
        515                 520                 525

Ser Gln Pro Thr Val Val Phe Val Ser Lys Lys Gly Leu Gln Lys Ile
    530                 535                 540

Leu Asn Val Gln Lys Lys Leu Pro Ile Ile Gln Lys Ile Ile Ile Met
545                 550                 555                 560

Asp Ser Lys Thr Asp Tyr Gln Gly Phe Gln Ser Met Tyr Thr Phe Val
                565                 570                 575

Thr Ser His Leu Pro Pro Gly Phe Asn Glu Tyr Asp Phe Val Pro Glu
            580                 585                 590

Ser Phe Asp Arg Asp Lys Thr Ile Ala Leu Ile Met Asn Ser Ser Gly
        595                 600                 605

Ser Thr Gly Leu Pro Lys Gly Val Ala Leu Pro His Arg Thr Ala Cys
    610                 615                 620

Val Arg Phe Ser His Ala Arg Asp Pro Ile Phe Gly Asn Gln Ile Ile
625                 630                 635                 640

Pro Asp Thr Ala Ile Leu Ser Val Val Pro Phe His His Gly Phe Gly
                645                 650                 655

Met Phe Thr Thr Leu Gly Tyr Leu Ile Cys Gly Phe Arg Val Val Leu
            660                 665                 670

Met Tyr Arg Phe Glu Glu Glu Leu Phe Leu Arg Ser Leu Gln Asp Tyr
        675                 680                 685

Lys Ile Gln Ser Ala Leu Leu Val Pro Thr Leu Phe Ser Phe Phe Ala
    690                 695                 700

Lys Ser Thr Leu Ile Asp Lys Tyr Asp Leu Ser Asn Leu His Glu Ile
705                 710                 715                 720

Ala Ser Gly Gly Ala Pro Leu Ser Lys Glu Val Gly Glu Ala Val Ala
                725                 730                 735

Lys Arg Phe His Leu Pro Gly Ile Arg Gln Gly Tyr Gly Leu Thr Glu
            740                 745                 750

Thr Thr Ser Ala Ile Leu Ile Thr Pro Glu Gly
        755                 760
```

<210> SEQ ID NO 217
<211> LENGTH: 733

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 217

```
Met Asn Ser Leu Gln Phe Phe Met Pro Val Leu Gly Ala Leu Phe Ile
1               5                   10                  15

Gly Val Ala Val Ala Pro Ala Asn Asp Ile Tyr Asn Glu Arg Glu Leu
            20                  25                  30

Leu Asn Ser Met Gly Ile Ser Gln Pro Thr Val Val Phe Val Ser Lys
        35                  40                  45

Lys Gly Leu Gln Lys Ile Leu Asn Val Gln Lys Lys Leu Pro Ile Ile
    50                  55                  60

Gln Lys Ile Ile Ile Met Asp Ser Lys Thr Asp Tyr Gln Gly Phe Gln
65                  70                  75                  80

Ser Met Tyr Thr Phe Val Thr Ser His Leu Pro Pro Gly Phe Asn Glu
                85                  90                  95

Tyr Asp Phe Val Pro Glu Ser Phe Asp Arg Asp Lys Thr Ile Ala Leu
            100                 105                 110

Ile Met Asn Ser Ser Gly Ser Thr Gly Leu Pro Lys Gly Val Ala Leu
        115                 120                 125

Pro His Arg Thr Ala Cys Val Arg Phe Ser His Ala Arg Asp Pro Ile
    130                 135                 140

Phe Gly Asn Gln Ile Ile Pro Asp Thr Ala Ile Leu Ser Val Val Pro
145                 150                 155                 160

Phe His His Gly Phe Gly Met Phe Thr Thr Leu Gly Tyr Leu Ile Cys
                165                 170                 175

Gly Phe Arg Val Val Leu Met Tyr Arg Phe Glu Glu Glu Leu Phe Leu
            180                 185                 190

Arg Ser Leu Gln Asp Tyr Lys Ile Gln Ser Ala Leu Leu Val Pro Thr
        195                 200                 205

Leu Phe Ser Phe Phe Ala Lys Ser Thr Leu Ile Asp Lys Tyr Asp Leu
    210                 215                 220

Ser Asn Leu His Glu Ile Ala Ser Gly Gly Ala Pro Leu Ser Lys Glu
225                 230                 235                 240

Val Gly Glu Ala Val Ala Lys Arg Phe His Leu Pro Gly Ile Arg Gln
                245                 250                 255

Gly Tyr Gly Leu Thr Glu Thr Thr Ser Ala Ile Leu Ile Thr Pro Glu
            260                 265                 270

Gly Asp Asp Lys Pro Gly Ala Val Gly Lys Val Val Pro Phe Phe Glu
        275                 280                 285

Ala Lys Val Val Asp Leu Asp Thr Gly Lys Thr Leu Gly Val Asn Gln
    290                 295                 300

Arg Gly Glu Leu Cys Val Arg Gly Pro Met Ile Met Ser Gly Tyr Val
305                 310                 315                 320

Asn Asn Pro Glu Ala Thr Asn Ala Leu Ile Asp Lys Asp Gly Trp Leu
                325                 330                 335

His Ser Gly Asp Ile Ala Tyr Trp Asp Glu Asp Glu His Phe Phe Ile
            340                 345                 350

Val Asp Arg Leu Lys Ser Leu Ile Lys Tyr Lys Gly Tyr Gln Val Ala
        355                 360                 365

Pro Ala Glu Leu Glu Ser Ile Leu Leu Gln His Pro Asn Ile Phe Asp
    370                 375                 380
```

```
Ala Gly Val Ala Gly Leu Pro Asp Asp Asp Ala Gly Glu Leu Pro Ala
385                 390                 395                 400

Ala Val Val Val Leu Glu His Gly Lys Thr Met Thr Glu Lys Glu Ile
                405                 410                 415

Val Asp Tyr Val Ala Ser Gln Val Thr Thr Ala Lys Lys Leu Arg Gly
            420                 425                 430

Gly Val Val Phe Val Asp Glu Val Pro Lys Gly Leu Thr Gly Lys Leu
        435                 440                 445

Asp Ala Arg Lys Ile Arg Glu Ile Leu Ile Lys Ala Lys Lys Gly Ser
    450                 455                 460

Ser Gly Arg Lys Arg Asp Arg Leu Gly Thr Leu Gly Ile Gly Gly Ser
465                 470                 475                 480

Ser Gly Gly Gly Ser Gly Gly Gly Gly Ser Gly Gly Gly Asn Gly Arg
                485                 490                 495

Phe Leu Thr Leu Lys Pro Leu Pro Asp Ser Ile Ile Gln Glu Ser Leu
            500                 505                 510

Glu Ile Gln Gln Gly Val Asn Pro Phe Phe Ile Gly Arg Ser Glu Asp
        515                 520                 525

Cys Asn Cys Lys Ile Glu Asp Asn Arg Leu Ser Arg Val His Cys Phe
    530                 535                 540

Ile Phe Lys Lys Arg His Ala Val Gly Lys Ser Met Tyr Glu Ser Pro
545                 550                 555                 560

Ala Gln Gly Leu Asp Asp Ile Trp Tyr Cys His Thr Gly Thr Asn Val
                565                 570                 575

Ser Tyr Leu Asn Asn Asn Arg Met Ile Gln Gly Thr Lys Phe Leu Leu
            580                 585                 590

Gln Asp Gly Asp Glu Ile Lys Ile Ile Trp Asp Lys Asn Asn Lys Phe
        595                 600                 605

Val Ile Gly Phe Lys Val Glu Ile Asn Asp Thr Thr Gly Leu Phe Asn
    610                 615                 620

Glu Gly Leu Gly Met Leu Gln Glu Gln Arg Val Val Leu Lys Gln Thr
625                 630                 635                 640

Ala Glu Glu Lys Asp Leu Val Lys Lys Leu Gly Ser Ser Gly Ala Lys
                645                 650                 655

Asn Ile Lys Lys Gly Pro Ala Pro Phe Tyr Pro Leu Glu Asp Gly Thr
            660                 665                 670

Ala Gly Glu Gln Leu His Lys Ala Met Lys Arg Tyr Ala Leu Val Pro
        675                 680                 685

Gly Thr Ile Ala Phe Thr Asp Ala His Ile Glu Val Asp Ile Thr Tyr
    690                 695                 700

Ala Glu Tyr Phe Glu Met Ser Val Arg Leu Ala Glu Ala Met Lys Arg
705                 710                 715                 720

Tyr Gly Leu Asn Thr Asn His Arg Ile Val Val Cys Ser
                725                 730
```

<210> SEQ ID NO 218
<211> LENGTH: 745
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 218

```
Met Asn Ser Leu Gln Phe Phe Met Pro Val Leu Gly Ala Leu Phe Ile
```

-continued

```
1               5                   10                  15

Gly Val Ala Val Ala Pro Ala Asn Asp Ile Tyr Asn Glu Arg Glu Leu
            20                  25                  30

Leu Asn Ser Met Gly Ile Ser Gln Pro Thr Val Val Phe Val Ser Lys
        35                  40                  45

Lys Gly Leu Gln Lys Ile Leu Asn Val Gln Lys Lys Leu Pro Ile Ile
    50                  55                  60

Gln Lys Ile Ile Ile Met Asp Ser Lys Thr Asp Tyr Gln Gly Phe Gln
65                  70                  75                  80

Ser Met Tyr Thr Phe Val Thr Ser His Leu Pro Pro Gly Phe Asn Glu
                85                  90                  95

Tyr Asp Phe Val Pro Glu Ser Phe Asp Arg Asp Lys Thr Ile Ala Leu
            100                 105                 110

Ile Met Asn Ser Ser Gly Ser Thr Gly Leu Pro Lys Gly Val Ala Leu
        115                 120                 125

Pro His Arg Thr Ala Cys Val Arg Phe Ser His Ala Arg Asp Pro Ile
    130                 135                 140

Phe Gly Asn Gln Ile Ile Pro Asp Thr Ala Ile Leu Ser Val Val Pro
145                 150                 155                 160

Phe His His Gly Phe Gly Met Phe Thr Thr Leu Gly Tyr Leu Ile Cys
                165                 170                 175

Gly Phe Arg Val Val Leu Met Tyr Arg Phe Glu Glu Glu Leu Phe Leu
            180                 185                 190

Arg Ser Leu Gln Asp Tyr Lys Ile Gln Ser Ala Leu Leu Val Pro Thr
        195                 200                 205

Leu Phe Ser Phe Phe Ala Lys Ser Thr Leu Ile Asp Lys Tyr Asp Leu
    210                 215                 220

Ser Asn Leu His Glu Ile Ala Ser Gly Gly Ala Pro Leu Ser Lys Glu
225                 230                 235                 240

Val Gly Glu Ala Val Ala Lys Arg Phe His Leu Pro Gly Ile Arg Gln
                245                 250                 255

Gly Tyr Gly Leu Thr Glu Thr Thr Ser Ala Ile Leu Ile Thr Pro Glu
            260                 265                 270

Gly Asp Asp Lys Pro Gly Ala Val Gly Lys Val Val Pro Phe Phe Glu
        275                 280                 285

Ala Lys Val Val Asp Leu Asp Thr Gly Lys Thr Leu Gly Val Asn Gln
    290                 295                 300

Arg Gly Glu Leu Cys Val Arg Gly Pro Met Ile Met Ser Gly Tyr Val
305                 310                 315                 320

Asn Asn Pro Glu Ala Thr Asn Ala Leu Ile Asp Lys Asp Gly Trp Leu
                325                 330                 335

His Ser Gly Asp Ile Ala Tyr Trp Asp Glu Asp Glu His Phe Phe Ile
            340                 345                 350

Val Asp Arg Leu Lys Ser Leu Ile Lys Tyr Lys Gly Tyr Gln Val Ala
        355                 360                 365

Pro Ala Glu Leu Glu Ser Ile Leu Leu Gln His Pro Asn Ile Phe Asp
    370                 375                 380

Ala Gly Val Ala Gly Leu Pro Asp Asp Asp Ala Gly Glu Leu Pro Ala
385                 390                 395                 400

Ala Val Val Val Leu Glu His Gly Lys Thr Met Thr Glu Lys Glu Ile
                405                 410                 415

Val Asp Tyr Val Ala Ser Gln Val Thr Thr Ala Lys Lys Leu Arg Gly
            420                 425                 430
```

```
Gly Val Val Phe Val Asp Glu Val Pro Lys Gly Leu Thr Gly Lys Leu
        435                 440                 445

Asp Ala Arg Lys Ile Arg Glu Ile Leu Ile Lys Ala Lys Lys Gly Gly
    450                 455                 460

Ser Gly Gly Ser Gly Ser Ser Gly Arg Lys Arg Asp Arg Leu Gly Thr
465                 470                 475                 480

Leu Gly Ile Gly Gly Ser Ser Gly Gly Gly Ser Gly Gly Gly Gly Ser
                485                 490                 495

Gly Gly Gly Asn Gly Arg Phe Leu Thr Leu Lys Pro Leu Pro Asp Ser
            500                 505                 510

Ile Ile Gln Glu Ser Leu Glu Ile Gln Gln Gly Val Asn Pro Phe Phe
        515                 520                 525

Ile Gly Arg Ser Glu Asp Cys Asn Cys Lys Ile Glu Asp Asn Arg Leu
    530                 535                 540

Ser Arg Val His Cys Phe Ile Phe Lys Lys Arg His Ala Val Gly Lys
545                 550                 555                 560

Ser Met Tyr Glu Ser Pro Ala Gln Gly Leu Asp Asp Ile Trp Tyr Cys
                565                 570                 575

His Thr Gly Thr Asn Val Ser Tyr Leu Asn Asn Asn Arg Met Ile Gln
            580                 585                 590

Gly Thr Lys Phe Leu Leu Gln Asp Gly Asp Glu Ile Lys Ile Ile Trp
        595                 600                 605

Asp Lys Asn Asn Lys Phe Val Ile Gly Phe Lys Val Glu Ile Asn Asp
    610                 615                 620

Thr Thr Gly Leu Phe Asn Glu Gly Leu Gly Met Leu Gln Glu Gln Arg
625                 630                 635                 640

Val Val Leu Lys Gln Thr Ala Glu Glu Lys Asp Leu Val Lys Lys Leu
                645                 650                 655

Gly Ser Gly Gly Ser Gly Gly Ser Gly Gly Ala Lys Asn Ile Lys Lys
            660                 665                 670

Gly Pro Ala Pro Phe Tyr Pro Leu Glu Asp Gly Thr Ala Gly Glu Gln
        675                 680                 685

Leu His Lys Ala Met Lys Arg Tyr Ala Leu Val Pro Gly Thr Ile Ala
    690                 695                 700

Phe Thr Asp Ala His Ile Glu Val Asp Ile Thr Tyr Ala Glu Tyr Phe
705                 710                 715                 720

Glu Met Ser Val Arg Leu Ala Glu Ala Met Lys Arg Tyr Gly Leu Asn
                725                 730                 735

Thr Asn His Arg Ile Val Val Cys Ser
            740                 745


<210> SEQ ID NO 219
<211> LENGTH: 733
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Met Leu His Glu Ile Ala Ser Gly Gly Ala Pro Leu Ser Lys Glu Val
1               5                   10                  15

Gly Glu Ala Val Ala Lys Arg Phe His Leu Pro Gly Ile Arg Gln Gly
            20                  25                  30

Tyr Gly Leu Thr Glu Thr Thr Ser Ala Ile Leu Ile Thr Pro Glu Gly
```

```
        35                  40                  45

Asp Asp Lys Pro Gly Ala Val Gly Lys Val Val Pro Phe Phe Glu Ala
    50                  55                  60

Lys Val Val Asp Leu Asp Thr Gly Lys Thr Leu Gly Val Asn Gln Arg
65                  70                  75                  80

Gly Glu Leu Cys Val Arg Gly Pro Met Ile Met Ser Gly Tyr Val Asn
                85                  90                  95

Asn Pro Glu Ala Thr Asn Ala Leu Ile Asp Lys Asp Gly Trp Leu His
            100                 105                 110

Ser Gly Asp Ile Ala Tyr Trp Asp Glu Asp Glu His Phe Phe Ile Val
        115                 120                 125

Asp Arg Leu Lys Ser Leu Ile Lys Tyr Lys Gly Tyr Gln Val Ala Pro
    130                 135                 140

Ala Glu Leu Glu Ser Ile Leu Leu Gln His Pro Asn Ile Phe Asp Ala
145                 150                 155                 160

Gly Val Ala Gly Leu Pro Asp Asp Asp Ala Gly Glu Leu Pro Ala Ala
                165                 170                 175

Val Val Val Leu Glu His Gly Lys Thr Met Thr Glu Lys Glu Ile Val
            180                 185                 190

Asp Tyr Val Ala Ser Gln Val Thr Thr Ala Lys Lys Leu Arg Gly Gly
        195                 200                 205

Val Val Phe Val Asp Glu Val Pro Lys Gly Leu Thr Gly Lys Leu Asp
    210                 215                 220

Ala Arg Lys Ile Arg Glu Ile Leu Ile Lys Ala Lys Lys Gly Ser Ser
225                 230                 235                 240

Gly Arg Lys Arg Asp Arg Leu Gly Thr Leu Gly Ile Gly Gly Ser Ser
                245                 250                 255

Gly Gly Gly Ser Gly Gly Gly Gly Ser Gly Gly Gly Asn Gly Arg Phe
            260                 265                 270

Leu Thr Leu Lys Pro Leu Pro Asp Ser Ile Ile Gln Glu Ser Leu Glu
        275                 280                 285

Ile Gln Gln Gly Val Asn Pro Phe Phe Ile Gly Arg Ser Glu Asp Cys
    290                 295                 300

Asn Cys Lys Ile Glu Asp Asn Arg Leu Ser Arg Val His Cys Phe Ile
305                 310                 315                 320

Phe Lys Lys Arg His Ala Val Gly Lys Ser Met Tyr Glu Ser Pro Ala
                325                 330                 335

Gln Gly Leu Asp Asp Ile Trp Tyr Cys His Thr Gly Thr Asn Val Ser
            340                 345                 350

Tyr Leu Asn Asn Asn Arg Met Ile Gln Gly Thr Lys Phe Leu Leu Gln
        355                 360                 365

Asp Gly Asp Glu Ile Lys Ile Ile Trp Asp Lys Asn Asn Lys Phe Val
    370                 375                 380

Ile Gly Phe Lys Val Glu Ile Asn Asp Thr Thr Gly Leu Phe Asn Glu
385                 390                 395                 400

Gly Leu Gly Met Leu Gln Glu Gln Arg Val Val Leu Lys Gln Thr Ala
                405                 410                 415

Glu Glu Lys Asp Leu Val Lys Lys Leu Gly Ser Ser Gly Ala Lys Asn
            420                 425                 430

Ile Lys Lys Gly Pro Ala Pro Phe Tyr Pro Leu Glu Asp Gly Thr Ala
        435                 440                 445

Gly Glu Gln Leu His Lys Ala Met Lys Arg Tyr Ala Leu Val Pro Gly
    450                 455                 460
```

Thr Ile Ala Phe Thr Asp Ala His Ile Glu Val Asp Ile Thr Tyr Ala
465 470 475 480

Glu Tyr Phe Glu Met Ser Val Arg Leu Ala Glu Ala Met Lys Arg Tyr
485 490 495

Gly Leu Asn Thr Asn His Arg Ile Val Val Cys Ser Glu Asn Ser Leu
500 505 510

Gln Phe Phe Met Pro Val Leu Gly Ala Leu Phe Ile Gly Val Ala Val
515 520 525

Ala Pro Ala Asn Asp Ile Tyr Asn Glu Arg Glu Leu Leu Asn Ser Met
530 535 540

Gly Ile Ser Gln Pro Thr Val Val Phe Val Ser Lys Lys Gly Leu Gln
545 550 555 560

Lys Ile Leu Asn Val Gln Lys Lys Leu Pro Ile Ile Gln Lys Ile Ile
565 570 575

Ile Met Asp Ser Lys Thr Asp Tyr Gln Gly Phe Gln Ser Met Tyr Thr
580 585 590

Phe Val Thr Ser His Leu Pro Pro Gly Phe Asn Glu Tyr Asp Phe Val
595 600 605

Pro Glu Ser Phe Asp Arg Asp Lys Thr Ile Ala Leu Ile Met Asn Ser
610 615 620

Ser Gly Ser Thr Gly Leu Pro Lys Gly Val Ala Leu Pro His Arg Thr
625 630 635 640

Ala Cys Val Arg Phe Ser His Ala Arg Asp Pro Ile Phe Gly Asn Gln
645 650 655

Ile Ile Pro Asp Thr Ala Ile Leu Ser Val Val Pro Phe His His Gly
660 665 670

Phe Gly Met Phe Thr Thr Leu Gly Tyr Leu Ile Cys Gly Phe Arg Val
675 680 685

Val Leu Met Tyr Arg Phe Glu Glu Glu Leu Phe Leu Arg Ser Leu Gln
690 695 700

Asp Tyr Lys Ile Gln Ser Ala Leu Leu Val Pro Thr Leu Phe Ser Phe
705 710 715 720

Phe Ala Lys Ser Thr Leu Ile Asp Lys Tyr Asp Leu Ser
725 730

<210> SEQ ID NO 220
<211> LENGTH: 745
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 220

Met Leu His Glu Ile Ala Ser Gly Gly Ala Pro Leu Ser Lys Glu Val
1 5 10 15

Gly Glu Ala Val Ala Lys Arg Phe His Leu Pro Gly Ile Arg Gln Gly
20 25 30

Tyr Gly Leu Thr Glu Thr Thr Ser Ala Ile Leu Ile Thr Pro Glu Gly
35 40 45

Asp Asp Lys Pro Gly Ala Val Gly Lys Val Val Pro Phe Phe Glu Ala
50 55 60

Lys Val Val Asp Leu Asp Thr Gly Lys Thr Leu Gly Val Asn Gln Arg
65 70 75 80

Gly Glu Leu Cys Val Arg Gly Pro Met Ile Met Ser Gly Tyr Val Asn

-continued

```
                85                  90                  95

Asn Pro Glu Ala Thr Asn Ala Leu Ile Asp Lys Asp Gly Trp Leu His
            100                 105                 110

Ser Gly Asp Ile Ala Tyr Trp Asp Glu Asp Glu His Phe Phe Ile Val
        115                 120                 125

Asp Arg Leu Lys Ser Leu Ile Lys Tyr Lys Gly Tyr Gln Val Ala Pro
    130                 135                 140

Ala Glu Leu Glu Ser Ile Leu Leu Gln His Pro Asn Ile Phe Asp Ala
145                 150                 155                 160

Gly Val Ala Gly Leu Pro Asp Asp Asp Ala Gly Glu Leu Pro Ala Ala
                165                 170                 175

Val Val Val Leu Glu His Gly Lys Thr Met Thr Glu Lys Glu Ile Val
            180                 185                 190

Asp Tyr Val Ala Ser Gln Val Thr Thr Ala Lys Lys Leu Arg Gly Gly
        195                 200                 205

Val Val Phe Val Asp Glu Val Pro Lys Gly Leu Thr Gly Lys Leu Asp
    210                 215                 220

Ala Arg Lys Ile Arg Glu Ile Leu Ile Lys Ala Lys Lys Gly Gly Ser
225                 230                 235                 240

Gly Gly Ser Gly Ser Ser Gly Arg Lys Arg Asp Arg Leu Gly Thr Leu
                245                 250                 255

Gly Ile Gly Gly Ser Ser Gly Gly Gly Ser Gly Gly Gly Gly Ser Gly
            260                 265                 270

Gly Gly Asn Gly Arg Phe Leu Thr Leu Lys Pro Leu Pro Asp Ser Ile
        275                 280                 285

Ile Gln Glu Ser Leu Glu Ile Gln Gln Gly Val Asn Pro Phe Phe Ile
    290                 295                 300

Gly Arg Ser Glu Asp Cys Asn Cys Lys Ile Glu Asp Asn Arg Leu Ser
305                 310                 315                 320

Arg Val His Cys Phe Ile Phe Lys Lys Arg His Ala Val Gly Lys Ser
                325                 330                 335

Met Tyr Glu Ser Pro Ala Gln Gly Leu Asp Asp Ile Trp Tyr Cys His
            340                 345                 350

Thr Gly Thr Asn Val Ser Tyr Leu Asn Asn Asn Arg Met Ile Gln Gly
        355                 360                 365

Thr Lys Phe Leu Leu Gln Asp Gly Asp Glu Ile Lys Ile Ile Trp Asp
    370                 375                 380

Lys Asn Asn Lys Phe Val Ile Gly Phe Lys Val Glu Ile Asn Asp Thr
385                 390                 395                 400

Thr Gly Leu Phe Asn Glu Gly Leu Gly Met Leu Gln Glu Gln Arg Val
                405                 410                 415

Val Leu Lys Gln Thr Ala Glu Glu Lys Asp Leu Val Lys Lys Leu Gly
            420                 425                 430

Ser Gly Gly Ser Gly Gly Ser Gly Gly Ala Lys Asn Ile Lys Lys Gly
        435                 440                 445

Pro Ala Pro Phe Tyr Pro Leu Glu Asp Gly Thr Ala Gly Glu Gln Leu
    450                 455                 460

His Lys Ala Met Lys Arg Tyr Ala Leu Val Pro Gly Thr Ile Ala Phe
465                 470                 475                 480

Thr Asp Ala His Ile Glu Val Asp Ile Thr Tyr Ala Glu Tyr Phe Glu
                485                 490                 495

Met Ser Val Arg Leu Ala Glu Ala Met Lys Arg Tyr Gly Leu Asn Thr
            500                 505                 510
```

Asn His Arg Ile Val Val Cys Ser Glu Asn Ser Leu Gln Phe Phe Met
515 520 525

Pro Val Leu Gly Ala Leu Phe Ile Gly Val Ala Val Ala Pro Ala Asn
530 535 540

Asp Ile Tyr Asn Glu Arg Glu Leu Leu Asn Ser Met Gly Ile Ser Gln
545 550 555 560

Pro Thr Val Val Phe Val Ser Lys Lys Gly Leu Gln Lys Ile Leu Asn
565 570 575

Val Gln Lys Lys Leu Pro Ile Ile Gln Lys Ile Ile Ile Met Asp Ser
580 585 590

Lys Thr Asp Tyr Gln Gly Phe Gln Ser Met Tyr Thr Phe Val Thr Ser
595 600 605

His Leu Pro Pro Gly Phe Asn Glu Tyr Asp Phe Val Pro Glu Ser Phe
610 615 620

Asp Arg Asp Lys Thr Ile Ala Leu Ile Met Asn Ser Ser Gly Ser Thr
625 630 635 640

Gly Leu Pro Lys Gly Val Ala Leu Pro His Arg Thr Ala Cys Val Arg
645 650 655

Phe Ser His Ala Arg Asp Pro Ile Phe Gly Asn Gln Ile Ile Pro Asp
660 665 670

Thr Ala Ile Leu Ser Val Val Pro Phe His His Gly Phe Gly Met Phe
675 680 685

Thr Thr Leu Gly Tyr Leu Ile Cys Gly Phe Arg Val Val Leu Met Tyr
690 695 700

Arg Phe Glu Glu Glu Leu Phe Leu Arg Ser Leu Gln Asp Tyr Lys Ile
705 710 715 720

Gln Ser Ala Leu Leu Val Pro Thr Leu Phe Ser Phe Phe Ala Lys Ser
725 730 735

Thr Leu Ile Asp Lys Tyr Asp Leu Ser
740 745

<210> SEQ ID NO 221
<211> LENGTH: 502
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 221

Met Tyr Arg Leu Leu Asp His Tyr Lys Tyr Leu Thr Ala Trp Phe Glu
1 5 10 15

Leu Leu Asn Leu Pro Lys Lys Ile Ile Phe Val Gly His Asp Trp Gly
20 25 30

Ala Cys Leu Ala Phe His Tyr Ser Tyr Glu His Gln Asp Lys Ile Lys
35 40 45

Ala Ile Val His Ala Glu Ser Val Val Asp Val Ile Glu Ser Trp Asp
50 55 60

Glu Trp Pro Asp Ile Glu Glu Asp Ile Ala Leu Ile Lys Ser Glu Glu
65 70 75 80

Gly Glu Lys Met Val Leu Glu Asn Asn Phe Phe Val Glu Thr Met Leu
85 90 95

Pro Ser Lys Ile Met Arg Lys Leu Glu Pro Glu Glu Phe Ala Ala Tyr
100 105 110

Leu Glu Pro Phe Lys Glu Lys Gly Glu Val Arg Arg Pro Thr Leu Ser

```
        115                 120                 125

Trp Pro Arg Glu Ile Pro Leu Val Lys Gly Gly Lys Pro Asp Val Val
    130                 135                 140

Gln Ile Val Arg Asn Tyr Asn Ala Tyr Leu Arg Ala Ser Asp Asp Leu
145                 150                 155                 160

Pro Lys Met Phe Ile Glu Ser Asp Pro Gly Phe Phe Ser Asn Ala Ile
                165                 170                 175

Val Glu Gly Ala Lys Lys Phe Pro Asn Thr Glu Phe Val Lys Val Lys
            180                 185                 190

Gly Leu His Phe Ser Gln Glu Asp Ala Pro Asp Glu Met Gly Lys Tyr
        195                 200                 205

Ile Lys Ser Phe Val Glu Arg Val Leu Lys Asn Glu Gln Gly Ser Ser
    210                 215                 220

Gly Arg Lys Arg Asp Arg Leu Gly Thr Leu Gly Ile Gly Gly Ser Ser
225                 230                 235                 240

Gly Gly Gly Ser Gly Gly Gly Gly Ser Gly Gly Gly Asn Gly Arg Phe
                245                 250                 255

Leu Thr Leu Lys Pro Leu Pro Asp Ser Ile Ile Gln Glu Ser Leu Glu
            260                 265                 270

Ile Gln Gln Gly Val Asn Pro Phe Phe Ile Gly Arg Ser Glu Asp Cys
        275                 280                 285

Asn Cys Lys Ile Glu Asp Asn Arg Leu Ser Arg Val His Cys Phe Ile
    290                 295                 300

Phe Lys Lys Arg His Ala Val Gly Lys Ser Met Tyr Glu Ser Pro Ala
305                 310                 315                 320

Gln Gly Leu Asp Asp Ile Trp Tyr Cys His Thr Gly Thr Asn Val Ser
                325                 330                 335

Tyr Leu Asn Asn Asn Arg Met Ile Gln Gly Thr Lys Phe Leu Leu Gln
            340                 345                 350

Asp Gly Asp Glu Ile Lys Ile Ile Trp Asp Lys Asn Asn Lys Phe Val
        355                 360                 365

Ile Gly Phe Lys Val Glu Ile Asn Asp Thr Thr Gly Leu Phe Asn Glu
    370                 375                 380

Gly Leu Gly Met Leu Gln Glu Gln Arg Val Val Leu Lys Gln Thr Ala
385                 390                 395                 400

Glu Glu Lys Asp Leu Val Lys Lys Leu Gly Ser Ser Gly Thr Ser Lys
                405                 410                 415

Val Tyr Asp Pro Glu Gln Arg Lys Arg Met Ile Thr Gly Pro Gln Trp
            420                 425                 430

Trp Ala Arg Cys Lys Gln Met Asn Val Leu Asp Ser Phe Ile Asn Tyr
        435                 440                 445

Tyr Asp Ser Glu Lys His Ala Glu Asn Ala Val Ile Phe Leu His Gly
    450                 455                 460

Asn Ala Ala Ser Ser Tyr Leu Trp Arg His Val Val Pro His Ile Glu
465                 470                 475                 480

Pro Val Ala Arg Cys Ile Ile Pro Asp Leu Ile Gly Met Gly Lys Ser
                485                 490                 495

Gly Lys Ser Gly Asn Gly
            500
```

<210> SEQ ID NO 222
<211> LENGTH: 516
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 222

```
Met Tyr Arg Leu Leu Asp His Tyr Lys Tyr Leu Thr Ala Trp Phe Glu
1               5                   10                  15

Leu Leu Asn Leu Pro Lys Lys Ile Ile Phe Val Gly His Asp Trp Gly
            20                  25                  30

Ala Cys Leu Ala Phe His Tyr Ser Tyr Glu His Gln Asp Lys Ile Lys
        35                  40                  45

Ala Ile Val His Ala Glu Ser Val Val Asp Val Ile Glu Ser Trp Asp
    50                  55                  60

Glu Trp Pro Asp Ile Glu Glu Asp Ile Ala Leu Ile Lys Ser Glu Glu
65                  70                  75                  80

Gly Glu Lys Met Val Leu Glu Asn Asn Phe Phe Val Glu Thr Met Leu
                85                  90                  95

Pro Ser Lys Ile Met Arg Lys Leu Glu Pro Glu Glu Phe Ala Ala Tyr
            100                 105                 110

Leu Glu Pro Phe Lys Glu Lys Gly Glu Val Arg Arg Pro Thr Leu Ser
        115                 120                 125

Trp Pro Arg Glu Ile Pro Leu Val Lys Gly Gly Lys Pro Asp Val Val
    130                 135                 140

Gln Ile Val Arg Asn Tyr Asn Ala Tyr Leu Arg Ala Ser Asp Asp Leu
145                 150                 155                 160

Pro Lys Met Phe Ile Glu Ser Asp Pro Gly Phe Phe Ser Asn Ala Ile
                165                 170                 175

Val Glu Gly Ala Lys Lys Phe Pro Asn Thr Glu Phe Val Lys Val Lys
            180                 185                 190

Gly Leu His Phe Ser Gln Glu Asp Ala Pro Asp Glu Met Gly Lys Tyr
        195                 200                 205

Ile Lys Ser Phe Val Glu Arg Val Leu Lys Asn Glu Gln Gly Ser Ser
    210                 215                 220

Gly Gly Ser Gly Gly Ser Gly Gly Gly Arg Lys Arg Asp Arg Leu Gly
225                 230                 235                 240

Thr Leu Gly Ile Gly Gly Ser Ser Gly Gly Gly Ser Gly Gly Gly Gly
                245                 250                 255

Ser Gly Gly Gly Asn Gly Arg Phe Leu Thr Leu Lys Pro Leu Pro Asp
            260                 265                 270

Ser Ile Ile Gln Glu Ser Leu Glu Ile Gln Gln Gly Val Asn Pro Phe
        275                 280                 285

Phe Ile Gly Arg Ser Glu Asp Cys Asn Cys Lys Ile Glu Asp Asn Arg
    290                 295                 300

Leu Ser Arg Val His Cys Phe Ile Phe Lys Lys Arg His Ala Val Gly
305                 310                 315                 320

Lys Ser Met Tyr Glu Ser Pro Ala Gln Gly Leu Asp Asp Ile Trp Tyr
                325                 330                 335

Cys His Thr Gly Thr Asn Val Ser Tyr Leu Asn Asn Asn Arg Met Ile
            340                 345                 350

Gln Gly Thr Lys Phe Leu Leu Gln Asp Gly Asp Glu Ile Lys Ile Ile
        355                 360                 365

Trp Asp Lys Asn Asn Lys Phe Val Ile Gly Phe Lys Val Glu Ile Asn
    370                 375                 380

Asp Thr Thr Gly Leu Phe Asn Glu Gly Leu Gly Met Leu Gln Glu Gln
```

```
385                 390                 395                 400

Arg Val Val Leu Lys Gln Thr Ala Glu Glu Lys Asp Leu Val Lys Lys
                405                 410                 415

Leu Gly Ser Gly Gly Ser Gly Gly Ser Ser Gly Thr Ser Lys Val Tyr
            420                 425                 430

Asp Pro Glu Gln Arg Lys Arg Met Ile Thr Gly Pro Gln Trp Trp Ala
        435                 440                 445

Arg Cys Lys Gln Met Asn Val Leu Asp Ser Phe Ile Asn Tyr Tyr Asp
    450                 455                 460

Ser Glu Lys His Ala Glu Asn Ala Val Ile Phe Leu His Gly Asn Ala
465                 470                 475                 480

Ala Ser Ser Tyr Leu Trp Arg His Val Val Pro His Ile Glu Pro Val
                485                 490                 495

Ala Arg Cys Ile Ile Pro Asp Leu Ile Gly Met Gly Lys Ser Gly Lys
            500                 505                 510

Ser Gly Asn Gly
        515


<210> SEQ ID NO 223
<211> LENGTH: 534
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Met Tyr Arg Leu Leu Asp His Tyr Lys Tyr Leu Thr Ala Trp Phe Glu
1               5                   10                  15

Leu Leu Asn Leu Pro Lys Lys Ile Ile Phe Val Gly His Asp Trp Gly
            20                  25                  30

Ala Cys Leu Ala Phe His Tyr Ser Tyr Glu His Gln Asp Lys Ile Lys
        35                  40                  45

Ala Ile Val His Ala Glu Ser Val Val Asp Val Ile Glu Ser Trp Asp
    50                  55                  60

Glu Trp Pro Asp Ile Glu Glu Asp Ile Ala Leu Ile Lys Ser Glu Glu
65                  70                  75                  80

Gly Glu Lys Met Val Leu Glu Asn Asn Phe Phe Val Glu Thr Met Leu
                85                  90                  95

Pro Ser Lys Ile Met Arg Lys Leu Glu Pro Glu Glu Phe Ala Ala Tyr
            100                 105                 110

Leu Glu Pro Phe Lys Glu Lys Gly Glu Val Arg Arg Pro Thr Leu Ser
        115                 120                 125

Trp Pro Arg Glu Ile Pro Leu Val Lys Gly Gly Lys Pro Asp Val Val
    130                 135                 140

Gln Ile Val Arg Asn Tyr Asn Ala Tyr Leu Arg Ala Ser Asp Asp Leu
145                 150                 155                 160

Pro Lys Met Phe Ile Glu Ser Asp Pro Gly Phe Phe Ser Asn Ala Ile
                165                 170                 175

Val Glu Gly Ala Lys Lys Phe Pro Asn Thr Glu Phe Val Lys Val Lys
            180                 185                 190

Gly Leu His Phe Ser Gln Glu Asp Ala Pro Asp Glu Met Gly Lys Tyr
        195                 200                 205

Ile Lys Ser Phe Val Glu Arg Val Leu Lys Asn Glu Gln Gly Ser Ser
    210                 215                 220
```

-continued

Gly Gly Ser Gly Gly Ser Gly Gly Gly Ser Gly Gly Ser Gly Gly Ser
225 230 235 240

Gly Arg Lys Arg Asp Arg Leu Gly Thr Leu Gly Ile Gly Gly Ser Ser
245 250 255

Gly Gly Gly Ser Gly Gly Gly Gly Ser Gly Gly Gly Asn Gly Arg Phe
260 265 270

Leu Thr Leu Lys Pro Leu Pro Asp Ser Ile Ile Gln Glu Ser Leu Glu
275 280 285

Ile Gln Gln Gly Val Asn Pro Phe Phe Ile Gly Arg Ser Glu Asp Cys
290 295 300

Asn Cys Lys Ile Glu Asp Asn Arg Leu Ser Arg Val His Cys Phe Ile
305 310 315 320

Phe Lys Lys Arg His Ala Val Gly Lys Ser Met Tyr Glu Ser Pro Ala
325 330 335

Gln Gly Leu Asp Asp Ile Trp Tyr Cys His Thr Gly Thr Asn Val Ser
340 345 350

Tyr Leu Asn Asn Asn Arg Met Ile Gln Gly Thr Lys Phe Leu Leu Gln
355 360 365

Asp Gly Asp Glu Ile Lys Ile Ile Trp Asp Lys Asn Asn Lys Phe Val
370 375 380

Ile Gly Phe Lys Val Glu Ile Asn Asp Thr Thr Gly Leu Phe Asn Glu
385 390 395 400

Gly Leu Gly Met Leu Gln Glu Gln Arg Val Val Leu Lys Gln Thr Ala
405 410 415

Glu Glu Lys Asp Leu Val Lys Lys Leu Gly Ser Gly Gly Ser Gly Gly
420 425 430

Ser Gly Gly Thr Ser Gly Gly Ser Gly Gly Ser Ser Gly Thr Ser Lys
435 440 445

Val Tyr Asp Pro Glu Gln Arg Lys Arg Met Ile Thr Gly Pro Gln Trp
450 455 460

Trp Ala Arg Cys Lys Gln Met Asn Val Leu Asp Ser Phe Ile Asn Tyr
465 470 475 480

Tyr Asp Ser Glu Lys His Ala Glu Asn Ala Val Ile Phe Leu His Gly
485 490 495

Asn Ala Ala Ser Ser Tyr Leu Trp Arg His Val Val Pro His Ile Glu
500 505 510

Pro Val Ala Arg Cys Ile Ile Pro Asp Leu Ile Gly Met Gly Lys Ser
515 520 525

Gly Lys Ser Gly Asn Gly
530

<210> SEQ ID NO 224
<211> LENGTH: 502
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 224

Met Ala Glu Asn Ala Val Ile Phe Leu His Gly Asn Ala Ala Ser Ser
1 5 10 15

Tyr Leu Trp Arg His Val Val Pro His Ile Glu Pro Val Ala Arg Cys
20 25 30

Ile Ile Pro Asp Leu Ile Gly Met Gly Lys Ser Gly Lys Ser Gly Asn
35 40 45

-continued

```
Gly Ser Tyr Arg Leu Leu Asp His Tyr Lys Tyr Leu Thr Ala Trp Phe
    50                  55                  60

Glu Leu Leu Asn Leu Pro Lys Lys Ile Ile Phe Val Gly His Asp Trp
65                  70                  75                  80

Gly Ala Cys Leu Ala Phe His Tyr Ser Tyr Glu His Gln Asp Lys Ile
                85                  90                  95

Lys Ala Ile Val His Ala Glu Ser Val Val Asp Val Ile Glu Ser Trp
            100                 105                 110

Asp Glu Trp Pro Asp Ile Glu Glu Asp Ile Ala Leu Ile Lys Ser Glu
        115                 120                 125

Glu Gly Glu Lys Met Val Leu Glu Asn Asn Phe Phe Val Glu Thr Met
    130                 135                 140

Leu Pro Ser Lys Ile Met Arg Lys Leu Glu Pro Glu Glu Phe Ala Ala
145                 150                 155                 160

Tyr Leu Glu Pro Phe Lys Glu Lys Gly Glu Val Arg Arg Pro Thr Leu
                165                 170                 175

Ser Trp Pro Arg Glu Ile Pro Leu Val Lys Gly Gly Lys Pro Asp Val
            180                 185                 190

Val Gln Ile Val Arg Asn Tyr Asn Ala Tyr Leu Arg Ala Ser Asp Asp
        195                 200                 205

Leu Pro Lys Met Phe Ile Glu Ser Asp Pro Gly Phe Phe Ser Asn Ala
    210                 215                 220

Ile Val Glu Gly Ala Lys Lys Phe Pro Asn Thr Glu Phe Val Lys Val
225                 230                 235                 240

Lys Gly Leu His Phe Ser Gln Glu Asp Ala Pro Asp Glu Met Gly Lys
                245                 250                 255

Tyr Ile Lys Ser Phe Val Glu Arg Val Leu Lys Asn Glu Gln Gly Ser
            260                 265                 270

Ser Gly Arg Lys Arg Asp Arg Leu Gly Thr Leu Gly Ile Gly Gly Ser
        275                 280                 285

Ser Gly Gly Gly Ser Gly Gly Gly Gly Ser Gly Gly Gly Asn Gly Arg
    290                 295                 300

Phe Leu Thr Leu Lys Pro Leu Pro Asp Ser Ile Ile Gln Glu Ser Leu
305                 310                 315                 320

Glu Ile Gln Gln Gly Val Asn Pro Phe Phe Ile Gly Arg Ser Glu Asp
                325                 330                 335

Cys Asn Cys Lys Ile Glu Asp Asn Arg Leu Ser Arg Val His Cys Phe
            340                 345                 350

Ile Phe Lys Lys Arg His Ala Val Gly Lys Ser Met Tyr Glu Ser Pro
        355                 360                 365

Ala Gln Gly Leu Asp Asp Ile Trp Tyr Cys His Thr Gly Thr Asn Val
    370                 375                 380

Ser Tyr Leu Asn Asn Asn Arg Met Ile Gln Gly Thr Lys Phe Leu Leu
385                 390                 395                 400

Gln Asp Gly Asp Glu Ile Lys Ile Ile Trp Asp Lys Asn Asn Lys Phe
                405                 410                 415

Val Ile Gly Phe Lys Val Glu Ile Asn Asp Thr Thr Gly Leu Phe Asn
            420                 425                 430

Glu Gly Leu Gly Met Leu Gln Glu Gln Arg Val Val Leu Lys Gln Thr
        435                 440                 445

Ala Glu Glu Lys Asp Leu Val Lys Lys Leu Gly Ser Ser Gly Thr Ser
    450                 455                 460
```

```
Lys Val Tyr Asp Pro Glu Gln Arg Lys Arg Met Ile Thr Gly Pro Gln
465                 470                 475                 480

Trp Trp Ala Arg Cys Lys Gln Met Asn Val Leu Asp Ser Phe Ile Asn
                485                 490                 495

Tyr Tyr Asp Ser Glu Lys
            500


<210> SEQ ID NO 225
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Met Ala Glu Asn Ala Val Ile Phe Leu His Gly Asn Ala Ala Ser Ser
1               5                   10                  15

Tyr Leu Trp Arg His Val Val Pro His Ile Glu Pro Val Ala Arg Cys
            20                  25                  30

Ile Ile Pro Asp Leu Ile Gly Met Gly Lys Ser Gly Lys Ser Gly Asn
        35                  40                  45

Gly Ser Tyr Arg Leu Leu Asp His Tyr Lys Tyr Leu Thr Ala Trp Phe
    50                  55                  60

Glu Leu Leu Asn Leu Pro Lys Lys Ile Ile Phe Val Gly His Asp Trp
65                  70                  75                  80

Gly Ala Cys Leu Ala Phe His Tyr Ser Tyr Glu His Gln Asp Lys Ile
                85                  90                  95

Lys Ala Ile Val His Ala Glu Ser Val Val Asp Val Ile Glu Ser Trp
            100                 105                 110

Asp Glu Trp Pro Asp Ile Glu Glu Asp Ile Ala Leu Ile Lys Ser Glu
        115                 120                 125

Glu Gly Glu Lys Met Val Leu Glu Asn Asn Phe Phe Val Glu Thr Met
    130                 135                 140

Leu Pro Ser Lys Ile Met Arg Lys Leu Glu Pro Glu Glu Phe Ala Ala
145                 150                 155                 160

Tyr Leu Glu Pro Phe Lys Glu Lys Gly Glu Val Arg Arg Pro Thr Leu
                165                 170                 175

Ser Trp Pro Arg Glu Ile Pro Leu Val Lys Gly Gly Lys Pro Asp Val
            180                 185                 190

Val Gln Ile Val Arg Asn Tyr Asn Ala Tyr Leu Arg Ala Ser Asp Asp
        195                 200                 205

Leu Pro Lys Met Phe Ile Glu Ser Asp Pro Gly Phe Phe Ser Asn Ala
    210                 215                 220

Ile Val Glu Gly Ala Lys Lys Phe Pro Asn Thr Glu Phe Val Lys Val
225                 230                 235                 240

Lys Gly Leu His Phe Ser Gln Glu Asp Ala Pro Asp Glu Met Gly Lys
                245                 250                 255

Tyr Ile Lys Ser Phe Val Glu Arg Val Leu Lys Asn Glu Gln Gly Ser
            260                 265                 270

Ser Gly Gly Ser Gly Gly Ser Gly Gly Gly Arg Lys Arg Asp Arg Leu
        275                 280                 285

Gly Thr Leu Gly Ile Gly Gly Ser Ser Gly Gly Gly Ser Gly Gly Gly
    290                 295                 300

Gly Ser Gly Gly Gly Asn Gly Arg Phe Leu Thr Leu Lys Pro Leu Pro
305                 310                 315                 320
```

Asp Ser Ile Ile Gln Glu Ser Leu Glu Ile Gln Gln Gly Val Asn Pro
325 330 335

Phe Phe Ile Gly Arg Ser Glu Asp Cys Asn Cys Lys Ile Glu Asp Asn
340 345 350

Arg Leu Ser Arg Val His Cys Phe Ile Phe Lys Lys Arg His Ala Val
355 360 365

Gly Lys Ser Met Tyr Glu Ser Pro Ala Gln Gly Leu Asp Asp Ile Trp
370 375 380

Tyr Cys His Thr Gly Thr Asn Val Ser Tyr Leu Asn Asn Asn Arg Met
385 390 395 400

Ile Gln Gly Thr Lys Phe Leu Leu Gln Asp Gly Asp Glu Ile Lys Ile
405 410 415

Ile Trp Asp Lys Asn Asn Lys Phe Val Ile Gly Phe Lys Val Glu Ile
420 425 430

Asn Asp Thr Thr Gly Leu Phe Asn Glu Gly Leu Gly Met Leu Gln Glu
435 440 445

Gln Arg Val Val Leu Lys Gln Thr Ala Glu Glu Lys Asp Leu Val Lys
450 455 460

Lys Leu Gly Ser Gly Gly Ser Gly Gly Ser Ser Gly Thr Ser Lys Val
465 470 475 480

Tyr Asp Pro Glu Gln Arg Lys Arg Met Ile Thr Gly Pro Gln Trp Trp
485 490 495

Ala Arg Cys Lys Gln Met Asn Val Leu Asp Ser Phe Ile Asn Tyr Tyr
500 505 510

Asp Ser Glu Lys
515

<210> SEQ ID NO 226
<211> LENGTH: 534
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 226

Met Ala Glu Asn Ala Val Ile Phe Leu His Gly Asn Ala Ala Ser Ser
1 5 10 15

Tyr Leu Trp Arg His Val Val Pro His Ile Glu Pro Val Ala Arg Cys
20 25 30

Ile Ile Pro Asp Leu Ile Gly Met Gly Lys Ser Gly Lys Ser Gly Asn
35 40 45

Gly Ser Tyr Arg Leu Leu Asp His Tyr Lys Tyr Leu Thr Ala Trp Phe
50 55 60

Glu Leu Leu Asn Leu Pro Lys Lys Ile Ile Phe Val Gly His Asp Trp
65 70 75 80

Gly Ala Cys Leu Ala Phe His Tyr Ser Tyr Glu His Gln Asp Lys Ile
85 90 95

Lys Ala Ile Val His Ala Glu Ser Val Val Asp Val Ile Glu Ser Trp
100 105 110

Asp Glu Trp Pro Asp Ile Glu Glu Asp Ile Ala Leu Ile Lys Ser Glu
115 120 125

Glu Gly Glu Lys Met Val Leu Glu Asn Asn Phe Phe Val Glu Thr Met
130 135 140

Leu Pro Ser Lys Ile Met Arg Lys Leu Glu Pro Glu Glu Phe Ala Ala

-continued

```
145                 150                 155                 160

Tyr Leu Glu Pro Phe Lys Glu Lys Gly Glu Val Arg Arg Pro Thr Leu
                165                 170                 175

Ser Trp Pro Arg Glu Ile Pro Leu Val Lys Gly Gly Lys Pro Asp Val
            180                 185                 190

Val Gln Ile Val Arg Asn Tyr Asn Ala Tyr Leu Arg Ala Ser Asp Asp
        195                 200                 205

Leu Pro Lys Met Phe Ile Glu Ser Asp Pro Gly Phe Phe Ser Asn Ala
    210                 215                 220

Ile Val Glu Gly Ala Lys Lys Phe Pro Asn Thr Glu Phe Val Lys Val
225                 230                 235                 240

Lys Gly Leu His Phe Ser Gln Glu Asp Ala Pro Asp Glu Met Gly Lys
                245                 250                 255

Tyr Ile Lys Ser Phe Val Glu Arg Val Leu Lys Asn Glu Gln Gly Ser
            260                 265                 270

Ser Gly Gly Ser Gly Gly Ser Gly Gly Gly Ser Gly Gly Ser Gly Gly
        275                 280                 285

Ser Gly Arg Lys Arg Asp Arg Leu Gly Thr Leu Gly Ile Gly Gly Ser
    290                 295                 300

Ser Gly Gly Gly Ser Gly Gly Gly Gly Ser Gly Gly Gly Asn Gly Arg
305                 310                 315                 320

Phe Leu Thr Leu Lys Pro Leu Pro Asp Ser Ile Ile Gln Glu Ser Leu
                325                 330                 335

Glu Ile Gln Gln Gly Val Asn Pro Phe Phe Ile Gly Arg Ser Glu Asp
            340                 345                 350

Cys Asn Cys Lys Ile Glu Asp Asn Arg Leu Ser Arg Val His Cys Phe
        355                 360                 365

Ile Phe Lys Lys Arg His Ala Val Gly Lys Ser Met Tyr Glu Ser Pro
    370                 375                 380

Ala Gln Gly Leu Asp Asp Ile Trp Tyr Cys His Thr Gly Thr Asn Val
385                 390                 395                 400

Ser Tyr Leu Asn Asn Asn Arg Met Ile Gln Gly Thr Lys Phe Leu Leu
                405                 410                 415

Gln Asp Gly Asp Glu Ile Lys Ile Ile Trp Asp Lys Asn Asn Lys Phe
            420                 425                 430

Val Ile Gly Phe Lys Val Glu Ile Asn Asp Thr Thr Gly Leu Phe Asn
        435                 440                 445

Glu Gly Leu Gly Met Leu Gln Glu Gln Arg Val Val Leu Lys Gln Thr
    450                 455                 460

Ala Glu Glu Lys Asp Leu Val Lys Lys Leu Gly Ser Gly Gly Ser Gly
465                 470                 475                 480

Gly Ser Gly Gly Thr Ser Gly Gly Ser Gly Gly Ser Ser Gly Thr Ser
                485                 490                 495

Lys Val Tyr Asp Pro Glu Gln Arg Lys Arg Met Ile Thr Gly Pro Gln
            500                 505                 510

Trp Trp Ala Arg Cys Lys Gln Met Asn Val Leu Asp Ser Phe Ile Asn
        515                 520                 525

Tyr Tyr Asp Ser Glu Lys
    530
```

<210> SEQ ID NO 227
<211> LENGTH: 502
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 227

```
Met Lys Lys Ile Ile Phe Val Gly His Asp Trp Gly Ala Cys Leu Ala
1               5                   10                  15

Phe His Tyr Ser Tyr Glu His Gln Asp Lys Ile Lys Ala Ile Val His
            20                  25                  30

Ala Glu Ser Val Val Asp Val Ile Glu Ser Trp Asp Glu Trp Pro Asp
        35                  40                  45

Ile Glu Glu Asp Ile Ala Leu Ile Lys Ser Glu Glu Gly Glu Lys Met
    50                  55                  60

Val Leu Glu Asn Asn Phe Phe Val Glu Thr Met Leu Pro Ser Lys Ile
65                  70                  75                  80

Met Arg Lys Leu Glu Pro Glu Glu Phe Ala Ala Tyr Leu Glu Pro Phe
                85                  90                  95

Lys Glu Lys Gly Glu Val Arg Arg Pro Thr Leu Ser Trp Pro Arg Glu
            100                 105                 110

Ile Pro Leu Val Lys Gly Gly Lys Pro Asp Val Val Gln Ile Val Arg
        115                 120                 125

Asn Tyr Asn Ala Tyr Leu Arg Ala Ser Asp Asp Leu Pro Lys Met Phe
    130                 135                 140

Ile Glu Ser Asp Pro Gly Phe Phe Ser Asn Ala Ile Val Glu Gly Ala
145                 150                 155                 160

Lys Lys Phe Pro Asn Thr Glu Phe Val Lys Val Lys Gly Leu His Phe
                165                 170                 175

Ser Gln Glu Asp Ala Pro Asp Glu Met Gly Lys Tyr Ile Lys Ser Phe
            180                 185                 190

Val Glu Arg Val Leu Lys Asn Glu Gln Gly Ser Ser Gly Arg Lys Arg
        195                 200                 205

Asp Arg Leu Gly Thr Leu Gly Ile Gly Gly Ser Ser Gly Gly Gly Ser
    210                 215                 220

Gly Gly Gly Gly Ser Gly Gly Gly Asn Gly Arg Phe Leu Thr Leu Lys
225                 230                 235                 240

Pro Leu Pro Asp Ser Ile Ile Gln Glu Ser Leu Glu Ile Gln Gln Gly
                245                 250                 255

Val Asn Pro Phe Phe Ile Gly Arg Ser Glu Asp Cys Asn Cys Lys Ile
            260                 265                 270

Glu Asp Asn Arg Leu Ser Arg Val His Cys Phe Ile Phe Lys Lys Arg
        275                 280                 285

His Ala Val Gly Lys Ser Met Tyr Glu Ser Pro Ala Gln Gly Leu Asp
    290                 295                 300

Asp Ile Trp Tyr Cys His Thr Gly Thr Asn Val Ser Tyr Leu Asn Asn
305                 310                 315                 320

Asn Arg Met Ile Gln Gly Thr Lys Phe Leu Leu Gln Asp Gly Asp Glu
                325                 330                 335

Ile Lys Ile Ile Trp Asp Lys Asn Asn Lys Phe Val Ile Gly Phe Lys
            340                 345                 350

Val Glu Ile Asn Asp Thr Thr Gly Leu Phe Asn Glu Gly Leu Gly Met
        355                 360                 365

Leu Gln Glu Gln Arg Val Val Leu Lys Gln Thr Ala Glu Glu Lys Asp
    370                 375                 380

Leu Val Lys Lys Leu Gly Ser Ser Gly Thr Ser Lys Val Tyr Asp Pro
```

385 390 395 400

Glu Gln Arg Lys Arg Met Ile Thr Gly Pro Gln Trp Trp Ala Arg Cys
405 410 415

Lys Gln Met Asn Val Leu Asp Ser Phe Ile Asn Tyr Tyr Asp Ser Glu
420 425 430

Lys His Ala Glu Asn Ala Val Ile Phe Leu His Gly Asn Ala Ala Ser
435 440 445

Ser Tyr Leu Trp Arg His Val Val Pro His Ile Glu Pro Val Ala Arg
450 455 460

Cys Ile Ile Pro Asp Leu Ile Gly Met Gly Lys Ser Gly Lys Ser Gly
465 470 475 480

Asn Gly Ser Tyr Arg Leu Leu Asp His Tyr Lys Tyr Leu Thr Ala Trp
485 490 495

Phe Glu Leu Leu Asn Leu
500

<210> SEQ ID NO 228
<211> LENGTH: 516
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 228

Met Lys Lys Ile Ile Phe Val Gly His Asp Trp Gly Ala Cys Leu Ala
1 5 10 15

Phe His Tyr Ser Tyr Glu His Gln Asp Lys Ile Lys Ala Ile Val His
20 25 30

Ala Glu Ser Val Val Asp Val Ile Glu Ser Trp Asp Glu Trp Pro Asp
35 40 45

Ile Glu Glu Asp Ile Ala Leu Ile Lys Ser Glu Glu Gly Glu Lys Met
50 55 60

Val Leu Glu Asn Asn Phe Phe Val Glu Thr Met Leu Pro Ser Lys Ile
65 70 75 80

Met Arg Lys Leu Glu Pro Glu Glu Phe Ala Ala Tyr Leu Glu Pro Phe
85 90 95

Lys Glu Lys Gly Glu Val Arg Arg Pro Thr Leu Ser Trp Pro Arg Glu
100 105 110

Ile Pro Leu Val Lys Gly Gly Lys Pro Asp Val Val Gln Ile Val Arg
115 120 125

Asn Tyr Asn Ala Tyr Leu Arg Ala Ser Asp Asp Leu Pro Lys Met Phe
130 135 140

Ile Glu Ser Asp Pro Gly Phe Phe Ser Asn Ala Ile Val Glu Gly Ala
145 150 155 160

Lys Lys Phe Pro Asn Thr Glu Phe Val Lys Val Lys Gly Leu His Phe
165 170 175

Ser Gln Glu Asp Ala Pro Asp Glu Met Gly Lys Tyr Ile Lys Ser Phe
180 185 190

Val Glu Arg Val Leu Lys Asn Glu Gln Gly Ser Ser Gly Gly Ser Gly
195 200 205

Gly Ser Gly Gly Gly Arg Lys Arg Asp Arg Leu Gly Thr Leu Gly Ile
210 215 220

Gly Gly Ser Ser Gly Gly Gly Ser Gly Gly Gly Gly Ser Gly Gly Gly
225 230 235 240

```
Asn Gly Arg Phe Leu Thr Leu Lys Pro Leu Pro Asp Ser Ile Ile Gln
                245                 250                 255

Glu Ser Leu Glu Ile Gln Gln Gly Val Asn Pro Phe Phe Ile Gly Arg
            260                 265                 270

Ser Glu Asp Cys Asn Cys Lys Ile Glu Asp Asn Arg Leu Ser Arg Val
        275                 280                 285

His Cys Phe Ile Phe Lys Lys Arg His Ala Val Gly Lys Ser Met Tyr
    290                 295                 300

Glu Ser Pro Ala Gln Gly Leu Asp Asp Ile Trp Tyr Cys His Thr Gly
305                 310                 315                 320

Thr Asn Val Ser Tyr Leu Asn Asn Asn Arg Met Ile Gln Gly Thr Lys
                325                 330                 335

Phe Leu Leu Gln Asp Gly Asp Glu Ile Lys Ile Ile Trp Asp Lys Asn
            340                 345                 350

Asn Lys Phe Val Ile Gly Phe Lys Val Glu Ile Asn Asp Thr Thr Gly
        355                 360                 365

Leu Phe Asn Glu Gly Leu Gly Met Leu Gln Glu Gln Arg Val Val Leu
    370                 375                 380

Lys Gln Thr Ala Glu Glu Lys Asp Leu Val Lys Lys Leu Gly Ser Gly
385                 390                 395                 400

Gly Ser Gly Gly Ser Ser Gly Thr Ser Lys Val Tyr Asp Pro Glu Gln
                405                 410                 415

Arg Lys Arg Met Ile Thr Gly Pro Gln Trp Trp Ala Arg Cys Lys Gln
            420                 425                 430

Met Asn Val Leu Asp Ser Phe Ile Asn Tyr Tyr Asp Ser Glu Lys His
        435                 440                 445

Ala Glu Asn Ala Val Ile Phe Leu His Gly Asn Ala Ala Ser Ser Tyr
    450                 455                 460

Leu Trp Arg His Val Val Pro His Ile Glu Pro Val Ala Arg Cys Ile
465                 470                 475                 480

Ile Pro Asp Leu Ile Gly Met Gly Lys Ser Gly Lys Ser Gly Asn Gly
                485                 490                 495

Ser Tyr Arg Leu Leu Asp His Tyr Lys Tyr Leu Thr Ala Trp Phe Glu
            500                 505                 510

Leu Leu Asn Leu
        515


<210> SEQ ID NO 229
<211> LENGTH: 534
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Met Lys Lys Ile Ile Phe Val Gly His Asp Trp Gly Ala Cys Leu Ala
1               5                   10                  15

Phe His Tyr Ser Tyr Glu His Gln Asp Lys Ile Lys Ala Ile Val His
            20                  25                  30

Ala Glu Ser Val Val Asp Val Ile Glu Ser Trp Asp Glu Trp Pro Asp
        35                  40                  45

Ile Glu Glu Asp Ile Ala Leu Ile Lys Ser Glu Glu Gly Glu Lys Met
    50                  55                  60

Val Leu Glu Asn Asn Phe Phe Val Glu Thr Met Leu Pro Ser Lys Ile
65                  70                  75                  80
```

-continued

```
Met Arg Lys Leu Glu Pro Glu Glu Phe Ala Ala Tyr Leu Glu Pro Phe
                85                  90                  95

Lys Glu Lys Gly Glu Val Arg Arg Pro Thr Leu Ser Trp Pro Arg Glu
            100                 105                 110

Ile Pro Leu Val Lys Gly Gly Lys Pro Asp Val Val Gln Ile Val Arg
        115                 120                 125

Asn Tyr Asn Ala Tyr Leu Arg Ala Ser Asp Asp Leu Pro Lys Met Phe
    130                 135                 140

Ile Glu Ser Asp Pro Gly Phe Phe Ser Asn Ala Ile Val Glu Gly Ala
145                 150                 155                 160

Lys Lys Phe Pro Asn Thr Glu Phe Val Lys Val Lys Gly Leu His Phe
                165                 170                 175

Ser Gln Glu Asp Ala Pro Asp Glu Met Gly Lys Tyr Ile Lys Ser Phe
            180                 185                 190

Val Glu Arg Val Leu Lys Asn Glu Gln Gly Ser Ser Gly Gly Ser Gly
        195                 200                 205

Gly Ser Gly Gly Gly Ser Gly Gly Ser Gly Gly Ser Gly Arg Lys Arg
    210                 215                 220

Asp Arg Leu Gly Thr Leu Gly Ile Gly Gly Ser Ser Gly Gly Gly Ser
225                 230                 235                 240

Gly Gly Gly Gly Ser Gly Gly Gly Asn Gly Arg Phe Leu Thr Leu Lys
                245                 250                 255

Pro Leu Pro Asp Ser Ile Ile Gln Glu Ser Leu Glu Ile Gln Gln Gly
            260                 265                 270

Val Asn Pro Phe Phe Ile Gly Arg Ser Glu Asp Cys Asn Cys Lys Ile
        275                 280                 285

Glu Asp Asn Arg Leu Ser Arg Val His Cys Phe Ile Phe Lys Lys Arg
    290                 295                 300

His Ala Val Gly Lys Ser Met Tyr Glu Ser Pro Ala Gln Gly Leu Asp
305                 310                 315                 320

Asp Ile Trp Tyr Cys His Thr Gly Thr Asn Val Ser Tyr Leu Asn Asn
                325                 330                 335

Asn Arg Met Ile Gln Gly Thr Lys Phe Leu Leu Gln Asp Gly Asp Glu
            340                 345                 350

Ile Lys Ile Ile Trp Asp Lys Asn Asn Lys Phe Val Ile Gly Phe Lys
        355                 360                 365

Val Glu Ile Asn Asp Thr Thr Gly Leu Phe Asn Glu Gly Leu Gly Met
    370                 375                 380

Leu Gln Glu Gln Arg Val Val Leu Lys Gln Thr Ala Glu Glu Lys Asp
385                 390                 395                 400

Leu Val Lys Lys Leu Gly Ser Gly Gly Ser Gly Gly Ser Gly Gly Thr
                405                 410                 415

Ser Gly Gly Ser Gly Gly Ser Ser Gly Thr Ser Lys Val Tyr Asp Pro
            420                 425                 430

Glu Gln Arg Lys Arg Met Ile Thr Gly Pro Gln Trp Trp Ala Arg Cys
        435                 440                 445

Lys Gln Met Asn Val Leu Asp Ser Phe Ile Asn Tyr Tyr Asp Ser Glu
    450                 455                 460

Lys His Ala Glu Asn Ala Val Ile Phe Leu His Gly Asn Ala Ala Ser
465                 470                 475                 480

Ser Tyr Leu Trp Arg His Val Val Pro His Ile Glu Pro Val Ala Arg
                485                 490                 495
```

-continued

```
Cys Ile Ile Pro Asp Leu Ile Gly Met Gly Lys Ser Gly Lys Ser Gly
            500                 505                 510

Asn Gly Ser Tyr Arg Leu Leu Asp His Tyr Lys Tyr Leu Thr Ala Trp
        515                 520                 525

Phe Glu Leu Leu Asn Leu
    530


<210> SEQ ID NO 230
<211> LENGTH: 502
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Met Ser Phe Ile Asn Tyr Tyr Asp Ser Glu Lys His Ala Glu Asn Ala
1               5                   10                  15

Val Ile Phe Leu His Gly Asn Ala Ala Ser Ser Tyr Leu Trp Arg His
            20                  25                  30

Val Val Pro His Ile Glu Pro Val Ala Arg Cys Ile Ile Pro Asp Leu
        35                  40                  45

Ile Gly Met Gly Lys Ser Gly Lys Ser Gly Asn Gly Ser Tyr Arg Leu
    50                  55                  60

Leu Asp His Tyr Lys Tyr Leu Thr Ala Trp Phe Glu Leu Leu Asn Leu
65                  70                  75                  80

Pro Lys Lys Ile Ile Phe Val Gly His Asp Trp Gly Ala Cys Leu Ala
                85                  90                  95

Phe His Tyr Ser Tyr Glu His Gln Asp Lys Ile Lys Ala Ile Val His
            100                 105                 110

Ala Glu Ser Val Val Asp Val Ile Glu Ser Trp Asp Glu Trp Pro Asp
        115                 120                 125

Ile Glu Glu Asp Ile Ala Leu Ile Lys Ser Glu Glu Gly Glu Lys Met
    130                 135                 140

Val Leu Glu Asn Asn Phe Phe Val Glu Thr Met Leu Pro Ser Lys Ile
145                 150                 155                 160

Met Arg Lys Leu Glu Pro Glu Glu Phe Ala Ala Tyr Leu Glu Pro Phe
                165                 170                 175

Lys Glu Lys Gly Glu Val Arg Arg Pro Thr Leu Ser Trp Pro Arg Glu
            180                 185                 190

Ile Pro Leu Val Lys Gly Gly Lys Pro Asp Val Val Gln Ile Val Arg
        195                 200                 205

Asn Tyr Asn Ala Tyr Leu Arg Ala Ser Asp Asp Leu Pro Lys Met Phe
    210                 215                 220

Ile Glu Ser Asp Pro Gly Phe Phe Ser Asn Ala Ile Val Glu Gly Ala
225                 230                 235                 240

Lys Lys Phe Pro Asn Thr Glu Phe Val Lys Val Lys Gly Leu His Phe
                245                 250                 255

Ser Gln Glu Asp Ala Pro Asp Glu Met Gly Lys Tyr Ile Lys Ser Phe
            260                 265                 270

Val Glu Arg Val Leu Lys Asn Glu Gln Gly Ser Ser Gly Arg Lys Arg
        275                 280                 285

Asp Arg Leu Gly Thr Leu Gly Ile Gly Gly Ser Ser Gly Gly Gly Ser
    290                 295                 300

Gly Gly Gly Gly Ser Gly Gly Gly Asn Gly Arg Phe Leu Thr Leu Lys
305                 310                 315                 320
```

```
Pro Leu Pro Asp Ser Ile Ile Gln Glu Ser Leu Glu Ile Gln Gln Gly
                325                 330                 335

Val Asn Pro Phe Phe Ile Gly Arg Ser Glu Asp Cys Asn Cys Lys Ile
            340                 345                 350

Glu Asp Asn Arg Leu Ser Arg Val His Cys Phe Ile Phe Lys Lys Arg
        355                 360                 365

His Ala Val Gly Lys Ser Met Tyr Glu Ser Pro Ala Gln Gly Leu Asp
    370                 375                 380

Asp Ile Trp Tyr Cys His Thr Gly Thr Asn Val Ser Tyr Leu Asn Asn
385                 390                 395                 400

Asn Arg Met Ile Gln Gly Thr Lys Phe Leu Leu Gln Asp Gly Asp Glu
                405                 410                 415

Ile Lys Ile Ile Trp Asp Lys Asn Asn Lys Phe Val Ile Gly Phe Lys
            420                 425                 430

Val Glu Ile Asn Asp Thr Thr Gly Leu Phe Asn Glu Gly Leu Gly Met
        435                 440                 445

Leu Gln Glu Gln Arg Val Val Leu Lys Gln Thr Ala Glu Glu Lys Asp
    450                 455                 460

Leu Val Lys Lys Leu Gly Ser Ser Gly Thr Ser Lys Val Tyr Asp Pro
465                 470                 475                 480

Glu Gln Arg Lys Arg Met Ile Thr Gly Pro Gln Trp Trp Ala Arg Cys
                485                 490                 495

Lys Gln Met Asn Val Leu
            500


<210> SEQ ID NO 231
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Met Ser Phe Ile Asn Tyr Tyr Asp Ser Glu Lys His Ala Glu Asn Ala
1               5                   10                  15

Val Ile Phe Leu His Gly Asn Ala Ala Ser Ser Tyr Leu Trp Arg His
            20                  25                  30

Val Val Pro His Ile Glu Pro Val Ala Arg Cys Ile Ile Pro Asp Leu
        35                  40                  45

Ile Gly Met Gly Lys Ser Gly Lys Ser Gly Asn Gly Ser Tyr Arg Leu
    50                  55                  60

Leu Asp His Tyr Lys Tyr Leu Thr Ala Trp Phe Glu Leu Leu Asn Leu
65                  70                  75                  80

Pro Lys Lys Ile Ile Phe Val Gly His Asp Trp Gly Ala Cys Leu Ala
                85                  90                  95

Phe His Tyr Ser Tyr Glu His Gln Asp Lys Ile Lys Ala Ile Val His
            100                 105                 110

Ala Glu Ser Val Val Asp Val Ile Glu Ser Trp Asp Glu Trp Pro Asp
        115                 120                 125

Ile Glu Glu Asp Ile Ala Leu Ile Lys Ser Glu Glu Gly Glu Lys Met
    130                 135                 140

Val Leu Glu Asn Asn Phe Phe Val Glu Thr Met Leu Pro Ser Lys Ile
145                 150                 155                 160

Met Arg Lys Leu Glu Pro Glu Glu Phe Ala Ala Tyr Leu Glu Pro Phe
```

165 170 175

Lys Glu Lys Gly Glu Val Arg Arg Pro Thr Leu Ser Trp Pro Arg Glu
180 185 190

Ile Pro Leu Val Lys Gly Gly Lys Pro Asp Val Val Gln Ile Val Arg
195 200 205

Asn Tyr Asn Ala Tyr Leu Arg Ala Ser Asp Asp Leu Pro Lys Met Phe
210 215 220

Ile Glu Ser Asp Pro Gly Phe Phe Ser Asn Ala Ile Val Glu Gly Ala
225 230 235 240

Lys Lys Phe Pro Asn Thr Glu Phe Val Lys Val Lys Gly Leu His Phe
245 250 255

Ser Gln Glu Asp Ala Pro Asp Glu Met Gly Lys Tyr Ile Lys Ser Phe
260 265 270

Val Glu Arg Val Leu Lys Asn Glu Gln Gly Ser Ser Gly Gly Ser Gly
275 280 285

Gly Ser Gly Gly Gly Arg Lys Arg Asp Arg Leu Gly Thr Leu Gly Ile
290 295 300

Gly Gly Ser Ser Gly Gly Gly Ser Gly Gly Gly Gly Ser Gly Gly Gly
305 310 315 320

Asn Gly Arg Phe Leu Thr Leu Lys Pro Leu Pro Asp Ser Ile Ile Gln
325 330 335

Glu Ser Leu Glu Ile Gln Gln Gly Val Asn Pro Phe Phe Ile Gly Arg
340 345 350

Ser Glu Asp Cys Asn Cys Lys Ile Glu Asp Asn Arg Leu Ser Arg Val
355 360 365

His Cys Phe Ile Phe Lys Lys Arg His Ala Val Gly Lys Ser Met Tyr
370 375 380

Glu Ser Pro Ala Gln Gly Leu Asp Asp Ile Trp Tyr Cys His Thr Gly
385 390 395 400

Thr Asn Val Ser Tyr Leu Asn Asn Asn Arg Met Ile Gln Gly Thr Lys
405 410 415

Phe Leu Leu Gln Asp Gly Asp Glu Ile Lys Ile Ile Trp Asp Lys Asn
420 425 430

Asn Lys Phe Val Ile Gly Phe Lys Val Glu Ile Asn Asp Thr Thr Gly
435 440 445

Leu Phe Asn Glu Gly Leu Gly Met Leu Gln Glu Gln Arg Val Val Leu
450 455 460

Lys Gln Thr Ala Glu Glu Lys Asp Leu Val Lys Lys Leu Gly Ser Gly
465 470 475 480

Gly Ser Gly Gly Ser Ser Gly Thr Ser Lys Val Tyr Asp Pro Glu Gln
485 490 495

Arg Lys Arg Met Ile Thr Gly Pro Gln Trp Trp Ala Arg Cys Lys Gln
500 505 510

Met Asn Val Leu
515

<210> SEQ ID NO 232
<211> LENGTH: 534
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 232

```
Met Ser Phe Ile Asn Tyr Tyr Asp Ser Glu Lys His Ala Glu Asn Ala
1               5                   10                  15

Val Ile Phe Leu His Gly Asn Ala Ala Ser Ser Tyr Leu Trp Arg His
            20                  25                  30

Val Val Pro His Ile Glu Pro Val Ala Arg Cys Ile Ile Pro Asp Leu
        35                  40                  45

Ile Gly Met Gly Lys Ser Gly Lys Ser Gly Asn Gly Ser Tyr Arg Leu
    50                  55                  60

Leu Asp His Tyr Lys Tyr Leu Thr Ala Trp Phe Glu Leu Leu Asn Leu
65                  70                  75                  80

Pro Lys Lys Ile Ile Phe Val Gly His Asp Trp Gly Ala Cys Leu Ala
                85                  90                  95

Phe His Tyr Ser Tyr Glu His Gln Asp Lys Ile Lys Ala Ile Val His
            100                 105                 110

Ala Glu Ser Val Val Asp Val Ile Glu Ser Trp Asp Glu Trp Pro Asp
        115                 120                 125

Ile Glu Glu Asp Ile Ala Leu Ile Lys Ser Glu Glu Gly Glu Lys Met
    130                 135                 140

Val Leu Glu Asn Asn Phe Phe Val Glu Thr Met Leu Pro Ser Lys Ile
145                 150                 155                 160

Met Arg Lys Leu Glu Pro Glu Glu Phe Ala Ala Tyr Leu Glu Pro Phe
                165                 170                 175

Lys Glu Lys Gly Glu Val Arg Arg Pro Thr Leu Ser Trp Pro Arg Glu
            180                 185                 190

Ile Pro Leu Val Lys Gly Gly Lys Pro Asp Val Val Gln Ile Val Arg
        195                 200                 205

Asn Tyr Asn Ala Tyr Leu Arg Ala Ser Asp Asp Leu Pro Lys Met Phe
    210                 215                 220

Ile Glu Ser Asp Pro Gly Phe Phe Ser Asn Ala Ile Val Glu Gly Ala
225                 230                 235                 240

Lys Lys Phe Pro Asn Thr Glu Phe Val Lys Val Lys Gly Leu His Phe
                245                 250                 255

Ser Gln Glu Asp Ala Pro Asp Glu Met Gly Lys Tyr Ile Lys Ser Phe
            260                 265                 270

Val Glu Arg Val Leu Lys Asn Glu Gln Gly Ser Ser Gly Gly Ser Gly
        275                 280                 285

Gly Ser Gly Gly Gly Ser Gly Gly Ser Gly Gly Ser Gly Arg Lys Arg
    290                 295                 300

Asp Arg Leu Gly Thr Leu Gly Ile Gly Gly Ser Ser Gly Gly Gly Ser
305                 310                 315                 320

Gly Gly Gly Gly Ser Gly Gly Gly Asn Gly Arg Phe Leu Thr Leu Lys
                325                 330                 335

Pro Leu Pro Asp Ser Ile Ile Gln Glu Ser Leu Glu Ile Gln Gln Gly
            340                 345                 350

Val Asn Pro Phe Phe Ile Gly Arg Ser Glu Asp Cys Asn Cys Lys Ile
        355                 360                 365

Glu Asp Asn Arg Leu Ser Arg Val His Cys Phe Ile Phe Lys Lys Arg
    370                 375                 380

His Ala Val Gly Lys Ser Met Tyr Glu Ser Pro Ala Gln Gly Leu Asp
385                 390                 395                 400

Asp Ile Trp Tyr Cys His Thr Gly Thr Asn Val Ser Tyr Leu Asn Asn
                405                 410                 415

Asn Arg Met Ile Gln Gly Thr Lys Phe Leu Leu Gln Asp Gly Asp Glu
```

420 425 430

Ile Lys Ile Ile Trp Asp Lys Asn Asn Lys Phe Val Ile Gly Phe Lys
435 440 445

Val Glu Ile Asn Asp Thr Thr Gly Leu Phe Asn Glu Gly Leu Gly Met
450 455 460

Leu Gln Glu Gln Arg Val Val Leu Lys Gln Thr Ala Glu Glu Lys Asp
465 470 475 480

Leu Val Lys Lys Leu Gly Ser Gly Gly Ser Gly Gly Ser Gly Gly Thr
485 490 495

Ser Gly Gly Ser Gly Gly Ser Ser Gly Thr Ser Lys Val Tyr Asp Pro
500 505 510

Glu Gln Arg Lys Arg Met Ile Thr Gly Pro Gln Trp Trp Ala Arg Cys
515 520 525

Lys Gln Met Asn Val Leu
530

<210> SEQ ID NO 233
<211> LENGTH: 502
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 233

Met Val Ala Arg Cys Ile Ile Pro Asp Leu Ile Gly Met Gly Lys Ser
1 5 10 15

Gly Lys Ser Gly Asn Gly Ser Tyr Arg Leu Leu Asp His Tyr Lys Tyr
20 25 30

Leu Thr Ala Trp Phe Glu Leu Leu Asn Leu Pro Lys Lys Ile Ile Phe
35 40 45

Val Gly His Asp Trp Gly Ala Cys Leu Ala Phe His Tyr Ser Tyr Glu
50 55 60

His Gln Asp Lys Ile Lys Ala Ile Val His Ala Glu Ser Val Val Asp
65 70 75 80

Val Ile Glu Ser Trp Asp Glu Trp Pro Asp Ile Glu Glu Asp Ile Ala
85 90 95

Leu Ile Lys Ser Glu Glu Gly Glu Lys Met Val Leu Glu Asn Asn Phe
100 105 110

Phe Val Glu Thr Met Leu Pro Ser Lys Ile Met Arg Lys Leu Glu Pro
115 120 125

Glu Glu Phe Ala Ala Tyr Leu Glu Pro Phe Lys Glu Lys Gly Glu Val
130 135 140

Arg Arg Pro Thr Leu Ser Trp Pro Arg Glu Ile Pro Leu Val Lys Gly
145 150 155 160

Gly Lys Pro Asp Val Val Gln Ile Val Arg Asn Tyr Asn Ala Tyr Leu
165 170 175

Arg Ala Ser Asp Asp Leu Pro Lys Met Phe Ile Glu Ser Asp Pro Gly
180 185 190

Phe Phe Ser Asn Ala Ile Val Glu Gly Ala Lys Lys Phe Pro Asn Thr
195 200 205

Glu Phe Val Lys Val Lys Gly Leu His Phe Ser Gln Glu Asp Ala Pro
210 215 220

Asp Glu Met Gly Lys Tyr Ile Lys Ser Phe Val Glu Arg Val Leu Lys
225 230 235 240

Asn Glu Gln Gly Ser Ser Gly Arg Lys Arg Asp Arg Leu Gly Thr Leu
245 250 255

Gly Ile Gly Gly Ser Ser Gly Gly Gly Ser Gly Gly Gly Gly Ser Gly
260 265 270

Gly Gly Asn Gly Arg Phe Leu Thr Leu Lys Pro Leu Pro Asp Ser Ile
275 280 285

Ile Gln Glu Ser Leu Glu Ile Gln Gln Gly Val Asn Pro Phe Phe Ile
290 295 300

Gly Arg Ser Glu Asp Cys Asn Cys Lys Ile Glu Asp Asn Arg Leu Ser
305 310 315 320

Arg Val His Cys Phe Ile Phe Lys Lys Arg His Ala Val Gly Lys Ser
325 330 335

Met Tyr Glu Ser Pro Ala Gln Gly Leu Asp Asp Ile Trp Tyr Cys His
340 345 350

Thr Gly Thr Asn Val Ser Tyr Leu Asn Asn Asn Arg Met Ile Gln Gly
355 360 365

Thr Lys Phe Leu Leu Gln Asp Gly Asp Glu Ile Lys Ile Ile Trp Asp
370 375 380

Lys Asn Asn Lys Phe Val Ile Gly Phe Lys Val Glu Ile Asn Asp Thr
385 390 395 400

Thr Gly Leu Phe Asn Glu Gly Leu Gly Met Leu Gln Glu Gln Arg Val
405 410 415

Val Leu Lys Gln Thr Ala Glu Glu Lys Asp Leu Val Lys Lys Leu Gly
420 425 430

Ser Ser Gly Thr Ser Lys Val Tyr Asp Pro Glu Gln Arg Lys Arg Met
435 440 445

Ile Thr Gly Pro Gln Trp Trp Ala Arg Cys Lys Gln Met Asn Val Leu
450 455 460

Asp Ser Phe Ile Asn Tyr Tyr Asp Ser Glu Lys His Ala Glu Asn Ala
465 470 475 480

Val Ile Phe Leu His Gly Asn Ala Ala Ser Ser Tyr Leu Trp Arg His
485 490 495

Val Val Pro His Ile Glu
500

<210> SEQ ID NO 234
<211> LENGTH: 516
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 234

Met Val Ala Arg Cys Ile Ile Pro Asp Leu Ile Gly Met Gly Lys Ser
1 5 10 15

Gly Lys Ser Gly Asn Gly Ser Tyr Arg Leu Leu Asp His Tyr Lys Tyr
20 25 30

Leu Thr Ala Trp Phe Glu Leu Leu Asn Leu Pro Lys Lys Ile Ile Phe
35 40 45

Val Gly His Asp Trp Gly Ala Cys Leu Ala Phe His Tyr Ser Tyr Glu
50 55 60

His Gln Asp Lys Ile Lys Ala Ile Val His Ala Glu Ser Val Val Asp
65 70 75 80

Val Ile Glu Ser Trp Asp Glu Trp Pro Asp Ile Glu Glu Asp Ile Ala
85 90 95

-continued

```
Leu Ile Lys Ser Glu Glu Gly Glu Lys Met Val Leu Glu Asn Asn Phe
            100                 105                 110

Phe Val Glu Thr Met Leu Pro Ser Lys Ile Met Arg Lys Leu Glu Pro
        115                 120                 125

Glu Glu Phe Ala Ala Tyr Leu Glu Pro Phe Lys Glu Lys Gly Glu Val
    130                 135                 140

Arg Arg Pro Thr Leu Ser Trp Pro Arg Glu Ile Pro Leu Val Lys Gly
145                 150                 155                 160

Gly Lys Pro Asp Val Val Gln Ile Val Arg Asn Tyr Asn Ala Tyr Leu
                165                 170                 175

Arg Ala Ser Asp Asp Leu Pro Lys Met Phe Ile Glu Ser Asp Pro Gly
            180                 185                 190

Phe Phe Ser Asn Ala Ile Val Glu Gly Ala Lys Lys Phe Pro Asn Thr
        195                 200                 205

Glu Phe Val Lys Val Lys Gly Leu His Phe Ser Gln Glu Asp Ala Pro
    210                 215                 220

Asp Glu Met Gly Lys Tyr Ile Lys Ser Phe Val Glu Arg Val Leu Lys
225                 230                 235                 240

Asn Glu Gln Gly Ser Ser Gly Gly Ser Gly Gly Ser Gly Gly Gly Arg
                245                 250                 255

Lys Arg Asp Arg Leu Gly Thr Leu Gly Ile Gly Gly Ser Ser Gly Gly
            260                 265                 270

Gly Ser Gly Gly Gly Gly Ser Gly Gly Gly Asn Gly Arg Phe Leu Thr
        275                 280                 285

Leu Lys Pro Leu Pro Asp Ser Ile Ile Gln Glu Ser Leu Glu Ile Gln
    290                 295                 300

Gln Gly Val Asn Pro Phe Phe Ile Gly Arg Ser Glu Asp Cys Asn Cys
305                 310                 315                 320

Lys Ile Glu Asp Asn Arg Leu Ser Arg Val His Cys Phe Ile Phe Lys
                325                 330                 335

Lys Arg His Ala Val Gly Lys Ser Met Tyr Glu Ser Pro Ala Gln Gly
            340                 345                 350

Leu Asp Asp Ile Trp Tyr Cys His Thr Gly Thr Asn Val Ser Tyr Leu
        355                 360                 365

Asn Asn Asn Arg Met Ile Gln Gly Thr Lys Phe Leu Leu Gln Asp Gly
    370                 375                 380

Asp Glu Ile Lys Ile Ile Trp Asp Lys Asn Asn Lys Phe Val Ile Gly
385                 390                 395                 400

Phe Lys Val Glu Ile Asn Asp Thr Thr Gly Leu Phe Asn Glu Gly Leu
                405                 410                 415

Gly Met Leu Gln Glu Gln Arg Val Val Leu Lys Gln Thr Ala Glu Glu
            420                 425                 430

Lys Asp Leu Val Lys Lys Leu Gly Ser Gly Gly Ser Gly Gly Ser Ser
        435                 440                 445

Gly Thr Ser Lys Val Tyr Asp Pro Glu Gln Arg Lys Arg Met Ile Thr
    450                 455                 460

Gly Pro Gln Trp Trp Ala Arg Cys Lys Gln Met Asn Val Leu Asp Ser
465                 470                 475                 480

Phe Ile Asn Tyr Tyr Asp Ser Glu Lys His Ala Glu Asn Ala Val Ile
                485                 490                 495

Phe Leu His Gly Asn Ala Ala Ser Ser Tyr Leu Trp Arg His Val Val
            500                 505                 510
```

```
Pro His Ile Glu
        515


<210> SEQ ID NO 235
<211> LENGTH: 534
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Met Val Ala Arg Cys Ile Ile Pro Asp Leu Ile Gly Met Gly Lys Ser
1               5                   10                  15

Gly Lys Ser Gly Asn Gly Ser Tyr Arg Leu Leu Asp His Tyr Lys Tyr
            20                  25                  30

Leu Thr Ala Trp Phe Glu Leu Leu Asn Leu Pro Lys Lys Ile Ile Phe
        35                  40                  45

Val Gly His Asp Trp Gly Ala Cys Leu Ala Phe His Tyr Ser Tyr Glu
    50                  55                  60

His Gln Asp Lys Ile Lys Ala Ile Val His Ala Glu Ser Val Val Asp
65                  70                  75                  80

Val Ile Glu Ser Trp Asp Glu Trp Pro Asp Ile Glu Glu Asp Ile Ala
                85                  90                  95

Leu Ile Lys Ser Glu Glu Gly Glu Lys Met Val Leu Glu Asn Asn Phe
            100                 105                 110

Phe Val Glu Thr Met Leu Pro Ser Lys Ile Met Arg Lys Leu Glu Pro
        115                 120                 125

Glu Glu Phe Ala Ala Tyr Leu Glu Pro Phe Lys Glu Lys Gly Glu Val
    130                 135                 140

Arg Arg Pro Thr Leu Ser Trp Pro Arg Glu Ile Pro Leu Val Lys Gly
145                 150                 155                 160

Gly Lys Pro Asp Val Val Gln Ile Val Arg Asn Tyr Asn Ala Tyr Leu
                165                 170                 175

Arg Ala Ser Asp Asp Leu Pro Lys Met Phe Ile Glu Ser Asp Pro Gly
            180                 185                 190

Phe Phe Ser Asn Ala Ile Val Glu Gly Ala Lys Lys Phe Pro Asn Thr
        195                 200                 205

Glu Phe Val Lys Val Lys Gly Leu His Phe Ser Gln Glu Asp Ala Pro
    210                 215                 220

Asp Glu Met Gly Lys Tyr Ile Lys Ser Phe Val Glu Arg Val Leu Lys
225                 230                 235                 240

Asn Glu Gln Gly Ser Ser Gly Gly Ser Gly Gly Ser Gly Gly Gly Ser
                245                 250                 255

Gly Gly Ser Gly Gly Ser Gly Arg Lys Arg Asp Arg Leu Gly Thr Leu
            260                 265                 270

Gly Ile Gly Gly Ser Ser Gly Gly Gly Ser Gly Gly Gly Gly Ser Gly
        275                 280                 285

Gly Gly Asn Gly Arg Phe Leu Thr Leu Lys Pro Leu Pro Asp Ser Ile
    290                 295                 300

Ile Gln Glu Ser Leu Glu Ile Gln Gln Gly Val Asn Pro Phe Phe Ile
305                 310                 315                 320

Gly Arg Ser Glu Asp Cys Asn Cys Lys Ile Glu Asp Asn Arg Leu Ser
                325                 330                 335

Arg Val His Cys Phe Ile Phe Lys Lys Arg His Ala Val Gly Lys Ser
            340                 345                 350
```

```
Met Tyr Glu Ser Pro Ala Gln Gly Leu Asp Asp Ile Trp Tyr Cys His
        355                 360                 365

Thr Gly Thr Asn Val Ser Tyr Leu Asn Asn Asn Arg Met Ile Gln Gly
    370                 375                 380

Thr Lys Phe Leu Leu Gln Asp Gly Asp Glu Ile Lys Ile Ile Trp Asp
385                 390                 395                 400

Lys Asn Asn Lys Phe Val Ile Gly Phe Lys Val Glu Ile Asn Asp Thr
                405                 410                 415

Thr Gly Leu Phe Asn Glu Gly Leu Gly Met Leu Gln Glu Gln Arg Val
            420                 425                 430

Val Leu Lys Gln Thr Ala Glu Glu Lys Asp Leu Val Lys Lys Leu Gly
        435                 440                 445

Ser Gly Gly Ser Gly Gly Ser Gly Gly Thr Ser Gly Gly Ser Gly Gly
    450                 455                 460

Ser Ser Gly Thr Ser Lys Val Tyr Asp Pro Glu Gln Arg Lys Arg Met
465                 470                 475                 480

Ile Thr Gly Pro Gln Trp Trp Ala Arg Cys Lys Gln Met Asn Val Leu
                485                 490                 495

Asp Ser Phe Ile Asn Tyr Tyr Asp Ser Glu Lys His Ala Glu Asn Ala
            500                 505                 510

Val Ile Phe Leu His Gly Asn Ala Ala Ser Ser Tyr Leu Trp Arg His
        515                 520                 525

Val Val Pro His Ile Glu
    530


<210> SEQ ID NO 236
<211> LENGTH: 724
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Met Thr Ala Ile Leu Ser Val Val Pro Phe His His Gly Phe Gly Met
1               5                   10                  15

Phe Thr Thr Leu Gly Tyr Leu Ile Cys Gly Phe Arg Val Val Leu Met
            20                  25                  30

Tyr Arg Phe Glu Glu Glu Leu Phe Leu Arg Ser Leu Gln Asp Tyr Lys
        35                  40                  45

Ile Gln Ser Ala Leu Leu Val Pro Thr Leu Phe Ser Phe Phe Ala Lys
    50                  55                  60

Ser Thr Leu Ile Asp Lys Tyr Asp Leu Ser Asn Leu His Glu Ile Ala
65                  70                  75                  80

Ser Gly Gly Ala Pro Leu Ser Lys Glu Val Gly Glu Ala Val Ala Lys
                85                  90                  95

Arg Phe His Leu Pro Gly Ile Arg Gln Gly Tyr Gly Leu Thr Glu Thr
            100                 105                 110

Thr Ser Ala Ile Leu Ile Thr Pro Glu Gly Asp Asp Lys Pro Gly Ala
        115                 120                 125

Val Gly Lys Val Val Pro Phe Phe Glu Ala Lys Val Val Asp Leu Asp
    130                 135                 140

Thr Gly Lys Thr Leu Gly Val Asn Gln Arg Gly Glu Leu Cys Val Arg
145                 150                 155                 160

Gly Pro Met Ile Met Ser Gly Tyr Val Asn Asn Pro Glu Ala Thr Asn
```

-continued

```
                165                 170                 175

Ala Leu Ile Asp Lys Asp Gly Trp Leu His Ser Gly Asp Ile Ala Tyr
            180                 185                 190

Trp Asp Glu Asp Glu His Phe Phe Ile Val Asp Arg Leu Lys Ser Leu
        195                 200                 205

Ile Lys Tyr Lys Gly Tyr Gln Val Ala Pro Ala Glu Leu Glu Ser Ile
    210                 215                 220

Leu Leu Gln His Pro Asn Ile Phe Asp Ala Gly Val Ala Gly Leu Pro
225                 230                 235                 240

Asp Asp Asp Ala Gly Glu Leu Pro Ala Ala Val Val Val Leu Glu His
                245                 250                 255

Gly Lys Thr Met Thr Glu Lys Glu Ile Val Asp Tyr Val Ala Ser Gln
            260                 265                 270

Val Thr Thr Ala Lys Lys Leu Arg Gly Gly Val Val Phe Val Asp Glu
        275                 280                 285

Val Pro Lys Gly Leu Thr Gly Lys Leu Asp Ala Arg Lys Ile Arg Glu
    290                 295                 300

Ile Leu Ile Lys Ala Lys Lys Gly Ser Gly Gly Gly Asn Gly Arg Phe
305                 310                 315                 320

Leu Thr Leu Lys Pro Leu Pro Asp Ser Ile Ile Gln Glu Ser Leu Glu
                325                 330                 335

Ile Gln Gln Gly Val Asn Pro Phe Phe Ile Gly Arg Ser Glu Asp Cys
            340                 345                 350

Asn Cys Lys Ile Glu Asp Asn Arg Leu Ser Arg Val His Cys Phe Ile
        355                 360                 365

Phe Lys Lys Arg His Ala Val Gly Lys Ser Met Tyr Glu Ser Pro Ala
    370                 375                 380

Gln Gly Leu Asp Asp Ile Trp Tyr Cys His Thr Gly Thr Asn Val Ser
385                 390                 395                 400

Tyr Leu Asn Asn Asn Arg Met Ile Gln Gly Thr Lys Phe Leu Leu Gln
                405                 410                 415

Asp Gly Asp Glu Ile Lys Ile Ile Trp Asp Lys Asn Asn Lys Phe Val
            420                 425                 430

Ile Gly Phe Lys Val Glu Ile Asn Asp Thr Thr Gly Leu Phe Asn Glu
        435                 440                 445

Gly Leu Gly Met Leu Gln Glu Gln Arg Val Val Leu Lys Gln Thr Ala
    450                 455                 460

Glu Glu Lys Asp Leu Val Lys Lys Leu Gly Gly Ser Ser Gly Arg Lys
465                 470                 475                 480

Arg Asp Arg Leu Gly Thr Leu Gly Ile Gly Gly Ser Ser Gly Ala Lys
                485                 490                 495

Asn Ile Lys Lys Gly Pro Ala Pro Phe Tyr Pro Leu Glu Asp Gly Thr
            500                 505                 510

Ala Gly Glu Gln Leu His Lys Ala Met Lys Arg Tyr Ala Leu Val Pro
        515                 520                 525

Gly Thr Ile Ala Phe Thr Asp Ala His Ile Glu Val Asp Ile Thr Tyr
    530                 535                 540

Ala Glu Tyr Phe Glu Met Ser Val Arg Leu Ala Glu Ala Met Lys Arg
545                 550                 555                 560

Tyr Gly Leu Asn Thr Asn His Arg Ile Val Val Cys Ser Glu Asn Ser
                565                 570                 575

Leu Gln Phe Phe Met Pro Val Leu Gly Ala Leu Phe Ile Gly Val Ala
            580                 585                 590
```

Val Ala Pro Ala Asn Asp Ile Tyr Asn Glu Arg Glu Leu Leu Asn Ser
595 600 605

Met Gly Ile Ser Gln Pro Thr Val Val Phe Val Ser Lys Lys Gly Leu
610 615 620

Gln Lys Ile Leu Asn Val Gln Lys Lys Leu Pro Ile Ile Gln Lys Ile
625 630 635 640

Ile Ile Met Asp Ser Lys Thr Asp Tyr Gln Gly Phe Gln Ser Met Tyr
645 650 655

Thr Phe Val Thr Ser His Leu Pro Pro Gly Phe Asn Glu Tyr Asp Phe
660 665 670

Val Pro Glu Ser Phe Asp Arg Asp Lys Thr Ile Ala Leu Ile Met Asn
675 680 685

Ser Ser Gly Ser Thr Gly Leu Pro Lys Gly Val Ala Leu Pro His Arg
690 695 700

Thr Ala Cys Val Arg Phe Ser His Ala Arg Asp Pro Ile Phe Gly Asn
705 710 715 720

Gln Ile Ile Pro

<210> SEQ ID NO 237
<211> LENGTH: 735
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 237

Met Thr Ala Ile Leu Ser Val Val Pro Phe His His Gly Phe Gly Met
1 5 10 15

Phe Thr Thr Leu Gly Tyr Leu Ile Cys Gly Phe Arg Val Val Leu Met
20 25 30

Tyr Arg Phe Glu Glu Glu Leu Phe Leu Arg Ser Leu Gln Asp Tyr Lys
35 40 45

Ile Gln Ser Ala Leu Leu Val Pro Thr Leu Phe Ser Phe Phe Ala Lys
50 55 60

Ser Thr Leu Ile Asp Lys Tyr Asp Leu Ser Asn Leu His Glu Ile Ala
65 70 75 80

Ser Gly Gly Ala Pro Leu Ser Lys Glu Val Gly Glu Ala Val Ala Lys
85 90 95

Arg Phe His Leu Pro Gly Ile Arg Gln Gly Tyr Gly Leu Thr Glu Thr
100 105 110

Thr Ser Ala Ile Leu Ile Thr Pro Glu Gly Asp Asp Lys Pro Gly Ala
115 120 125

Val Gly Lys Val Val Pro Phe Phe Glu Ala Lys Val Val Asp Leu Asp
130 135 140

Thr Gly Lys Thr Leu Gly Val Asn Gln Arg Gly Glu Leu Cys Val Arg
145 150 155 160

Gly Pro Met Ile Met Ser Gly Tyr Val Asn Asn Pro Glu Ala Thr Asn
165 170 175

Ala Leu Ile Asp Lys Asp Gly Trp Leu His Ser Gly Asp Ile Ala Tyr
180 185 190

Trp Asp Glu Asp Glu His Phe Phe Ile Val Asp Arg Leu Lys Ser Leu
195 200 205

Ile Lys Tyr Lys Gly Tyr Gln Val Ala Pro Ala Glu Leu Glu Ser Ile
210 215 220

-continued

```
Leu Leu Gln His Pro Asn Ile Phe Asp Ala Gly Val Ala Gly Leu Pro
225                 230                 235                 240

Asp Asp Asp Ala Gly Glu Leu Pro Ala Ala Val Val Val Leu Glu His
                245                 250                 255

Gly Lys Thr Met Thr Glu Lys Glu Ile Val Asp Tyr Val Ala Ser Gln
            260                 265                 270

Val Thr Thr Ala Lys Lys Leu Arg Gly Gly Val Val Phe Val Asp Glu
        275                 280                 285

Val Pro Lys Gly Leu Thr Gly Lys Leu Asp Ala Arg Lys Ile Arg Glu
    290                 295                 300

Ile Leu Ile Lys Ala Lys Lys Gly Gly Ser Gly Gly Gly Gly Ser Gly
305                 310                 315                 320

Gly Gly Asn Gly Arg Phe Leu Thr Leu Lys Pro Leu Pro Asp Ser Ile
                325                 330                 335

Ile Gln Glu Ser Leu Glu Ile Gln Gln Gly Val Asn Pro Phe Phe Ile
            340                 345                 350

Gly Arg Ser Glu Asp Cys Asn Cys Lys Ile Glu Asp Asn Arg Leu Ser
        355                 360                 365

Arg Val His Cys Phe Ile Phe Lys Lys Arg His Ala Val Gly Lys Ser
    370                 375                 380

Met Tyr Glu Ser Pro Ala Gln Gly Leu Asp Asp Ile Trp Tyr Cys His
385                 390                 395                 400

Thr Gly Thr Asn Val Ser Tyr Leu Asn Asn Asn Arg Met Ile Gln Gly
                405                 410                 415

Thr Lys Phe Leu Leu Gln Asp Gly Asp Glu Ile Lys Ile Ile Trp Asp
            420                 425                 430

Lys Asn Asn Lys Phe Val Ile Gly Phe Lys Val Glu Ile Asn Asp Thr
        435                 440                 445

Thr Gly Leu Phe Asn Glu Gly Leu Gly Met Leu Gln Glu Gln Arg Val
    450                 455                 460

Val Leu Lys Gln Thr Ala Glu Glu Lys Asp Leu Val Lys Lys Leu Gly
465                 470                 475                 480

Gly Ser Ser Gly Arg Lys Arg Asp Arg Leu Gly Thr Leu Gly Ile Gly
                485                 490                 495

Ser Ser Gly Ser Gly Gly Ser Gly Gly Ala Lys Asn Ile Lys Lys Gly
            500                 505                 510

Pro Ala Pro Phe Tyr Pro Leu Glu Asp Gly Thr Ala Gly Glu Gln Leu
        515                 520                 525

His Lys Ala Met Lys Arg Tyr Ala Leu Val Pro Gly Thr Ile Ala Phe
    530                 535                 540

Thr Asp Ala His Ile Glu Val Asp Ile Thr Tyr Ala Glu Tyr Phe Glu
545                 550                 555                 560

Met Ser Val Arg Leu Ala Glu Ala Met Lys Arg Tyr Gly Leu Asn Thr
                565                 570                 575

Asn His Arg Ile Val Val Cys Ser Glu Asn Ser Leu Gln Phe Phe Met
            580                 585                 590

Pro Val Leu Gly Ala Leu Phe Ile Gly Val Ala Val Ala Pro Ala Asn
        595                 600                 605

Asp Ile Tyr Asn Glu Arg Glu Leu Leu Asn Ser Met Gly Ile Ser Gln
    610                 615                 620

Pro Thr Val Val Phe Val Ser Lys Lys Gly Leu Gln Lys Ile Leu Asn
625                 630                 635                 640
```

```
Val Gln Lys Lys Leu Pro Ile Ile Gln Lys Ile Ile Ile Met Asp Ser
                645                 650                 655

Lys Thr Asp Tyr Gln Gly Phe Gln Ser Met Tyr Thr Phe Val Thr Ser
            660                 665                 670

His Leu Pro Pro Gly Phe Asn Glu Tyr Asp Phe Val Pro Glu Ser Phe
        675                 680                 685

Asp Arg Asp Lys Thr Ile Ala Leu Ile Met Asn Ser Ser Gly Ser Thr
    690                 695                 700

Gly Leu Pro Lys Gly Val Ala Leu Pro His Arg Thr Ala Cys Val Arg
705                 710                 715                 720

Phe Ser His Ala Arg Asp Pro Ile Phe Gly Asn Gln Ile Ile Pro
                725                 730                 735


<210> SEQ ID NO 238
<211> LENGTH: 755
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Met Thr Ala Ile Leu Ser Val Val Pro Phe His His Gly Phe Gly Met
1               5                   10                  15

Phe Thr Thr Leu Gly Tyr Leu Ile Cys Gly Phe Arg Val Val Leu Met
            20                  25                  30

Tyr Arg Phe Glu Glu Glu Leu Phe Leu Arg Ser Leu Gln Asp Tyr Lys
        35                  40                  45

Ile Gln Ser Ala Leu Leu Val Pro Thr Leu Phe Ser Phe Phe Ala Lys
    50                  55                  60

Ser Thr Leu Ile Asp Lys Tyr Asp Leu Ser Asn Leu His Glu Ile Ala
65                  70                  75                  80

Ser Gly Gly Ala Pro Leu Ser Lys Glu Val Gly Glu Ala Val Ala Lys
                85                  90                  95

Arg Phe His Leu Pro Gly Ile Arg Gln Gly Tyr Gly Leu Thr Glu Thr
            100                 105                 110

Thr Ser Ala Ile Leu Ile Thr Pro Glu Gly Asp Asp Lys Pro Gly Ala
        115                 120                 125

Val Gly Lys Val Val Pro Phe Phe Glu Ala Lys Val Val Asp Leu Asp
    130                 135                 140

Thr Gly Lys Thr Leu Gly Val Asn Gln Arg Gly Glu Leu Cys Val Arg
145                 150                 155                 160

Gly Pro Met Ile Met Ser Gly Tyr Val Asn Asn Pro Glu Ala Thr Asn
                165                 170                 175

Ala Leu Ile Asp Lys Asp Gly Trp Leu His Ser Gly Asp Ile Ala Tyr
            180                 185                 190

Trp Asp Glu Asp Glu His Phe Phe Ile Val Asp Arg Leu Lys Ser Leu
        195                 200                 205

Ile Lys Tyr Lys Gly Tyr Gln Val Ala Pro Ala Glu Leu Glu Ser Ile
    210                 215                 220

Leu Leu Gln His Pro Asn Ile Phe Asp Ala Gly Val Ala Gly Leu Pro
225                 230                 235                 240

Asp Asp Asp Ala Gly Glu Leu Pro Ala Ala Val Val Val Leu Glu His
                245                 250                 255

Gly Lys Thr Met Thr Glu Lys Glu Ile Val Asp Tyr Val Ala Ser Gln
            260                 265                 270
```

```
Val Thr Thr Ala Lys Lys Leu Arg Gly Gly Val Val Phe Val Asp Glu
        275                 280                 285

Val Pro Lys Gly Leu Thr Gly Lys Leu Asp Ala Arg Lys Ile Arg Glu
    290                 295                 300

Ile Leu Ile Lys Ala Lys Lys Gly Ser Ser Gly Gly Ser Gly Gly Ser
305                 310                 315                 320

Gly Gly Gly Ser Gly Gly Ser Gly Gly Ser Gly Gly Asn Gly Arg Phe
                325                 330                 335

Leu Thr Leu Lys Pro Leu Pro Asp Ser Ile Ile Gln Glu Ser Leu Glu
            340                 345                 350

Ile Gln Gln Gly Val Asn Pro Phe Phe Ile Gly Arg Ser Glu Asp Cys
        355                 360                 365

Asn Cys Lys Ile Glu Asp Asn Arg Leu Ser Arg Val His Cys Phe Ile
    370                 375                 380

Phe Lys Lys Arg His Ala Val Gly Lys Ser Met Tyr Glu Ser Pro Ala
385                 390                 395                 400

Gln Gly Leu Asp Asp Ile Trp Tyr Cys His Thr Gly Thr Asn Val Ser
                405                 410                 415

Tyr Leu Asn Asn Asn Arg Met Ile Gln Gly Thr Lys Phe Leu Leu Gln
            420                 425                 430

Asp Gly Asp Glu Ile Lys Ile Ile Trp Asp Lys Asn Asn Lys Phe Val
        435                 440                 445

Ile Gly Phe Lys Val Glu Ile Asn Asp Thr Thr Gly Leu Phe Asn Glu
    450                 455                 460

Gly Leu Gly Met Leu Gln Glu Gln Arg Val Val Leu Lys Gln Thr Ala
465                 470                 475                 480

Glu Glu Lys Asp Leu Val Lys Lys Leu Gly Gly Ser Ser Gly Arg Lys
                485                 490                 495

Arg Asp Arg Leu Gly Thr Leu Gly Ile Gly Ser Gly Gly Ser Gly Gly
            500                 505                 510

Ser Gly Gly Thr Ser Gly Gly Ser Gly Gly Ser Ser Gly Ala Lys Asn
        515                 520                 525

Ile Lys Lys Gly Pro Ala Pro Phe Tyr Pro Leu Glu Asp Gly Thr Ala
    530                 535                 540

Gly Glu Gln Leu His Lys Ala Met Lys Arg Tyr Ala Leu Val Pro Gly
545                 550                 555                 560

Thr Ile Ala Phe Thr Asp Ala His Ile Glu Val Asp Ile Thr Tyr Ala
                565                 570                 575

Glu Tyr Phe Glu Met Ser Val Arg Leu Ala Glu Ala Met Lys Arg Tyr
            580                 585                 590

Gly Leu Asn Thr Asn His Arg Ile Val Val Cys Ser Glu Asn Ser Leu
        595                 600                 605

Gln Phe Phe Met Pro Val Leu Gly Ala Leu Phe Ile Gly Val Ala Val
    610                 615                 620

Ala Pro Ala Asn Asp Ile Tyr Asn Glu Arg Glu Leu Leu Asn Ser Met
625                 630                 635                 640

Gly Ile Ser Gln Pro Thr Val Val Phe Val Ser Lys Lys Gly Leu Gln
                645                 650                 655

Lys Ile Leu Asn Val Gln Lys Lys Leu Pro Ile Ile Gln Lys Ile Ile
            660                 665                 670

Ile Met Asp Ser Lys Thr Asp Tyr Gln Gly Phe Gln Ser Met Tyr Thr
        675                 680                 685
```

Phe Val Thr Ser His Leu Pro Pro Gly Phe Asn Glu Tyr Asp Phe Val
690 695 700

Pro Glu Ser Phe Asp Arg Asp Lys Thr Ile Ala Leu Ile Met Asn Ser
705 710 715 720

Ser Gly Ser Thr Gly Leu Pro Lys Gly Val Ala Leu Pro His Arg Thr
725 730 735

Ala Cys Val Arg Phe Ser His Ala Arg Asp Pro Ile Phe Gly Asn Gln
740 745 750

Ile Ile Pro
755

<210> SEQ ID NO 239
<211> LENGTH: 750
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 239

Met Pro Gly Ala Val Gly Lys Val Val Pro Phe Phe Glu Ala Lys Val
1 5 10 15

Val Asp Leu Asp Thr Gly Lys Thr Leu Gly Val Asn Gln Arg Gly Glu
20 25 30

Leu Cys Val Arg Gly Pro Met Ile Met Ser Gly Tyr Val Asn Asn Pro
35 40 45

Glu Ala Thr Asn Ala Leu Ile Asp Lys Asp Gly Trp Leu His Ser Gly
50 55 60

Asp Ile Ala Tyr Trp Asp Glu Asp Glu His Phe Phe Ile Val Asp Arg
65 70 75 80

Leu Lys Ser Leu Ile Lys Tyr Lys Gly Tyr Gln Val Ala Pro Ala Glu
85 90 95

Leu Glu Ser Ile Leu Leu Gln His Pro Asn Ile Phe Asp Ala Gly Val
100 105 110

Ala Gly Leu Pro Asp Asp Asp Ala Gly Glu Leu Pro Ala Ala Val Val
115 120 125

Val Leu Glu His Gly Lys Thr Met Thr Glu Lys Glu Ile Val Asp Tyr
130 135 140

Val Ala Ser Gln Val Thr Thr Ala Lys Lys Leu Arg Gly Gly Val Val
145 150 155 160

Phe Val Asp Glu Val Pro Lys Gly Leu Thr Gly Lys Leu Asp Ala Arg
165 170 175

Lys Ile Arg Glu Ile Leu Ile Lys Ala Lys Lys Gly Ser Ser Gly Gly
180 185 190

Ser Gly Gly Ser Gly Gly Gly Ser Gly Gly Ser Gly Gly Asn Gly Arg
195 200 205

Phe Leu Thr Leu Lys Pro Leu Pro Asp Ser Ile Ile Gln Glu Ser Leu
210 215 220

Glu Ile Gln Gln Gly Val Asn Pro Phe Phe Ile Gly Arg Ser Glu Asp
225 230 235 240

Cys Asn Cys Lys Ile Glu Asp Asn Arg Leu Ser Arg Val His Cys Phe
245 250 255

Ile Phe Lys Lys Arg His Ala Val Gly Lys Ser Met Tyr Glu Ser Pro
260 265 270

Ala Gln Gly Leu Asp Asp Ile Trp Tyr Cys His Thr Gly Thr Asn Val
275 280 285

```
Ser Tyr Leu Asn Asn Asn Arg Met Ile Gln Gly Thr Lys Phe Leu Leu
    290                 295                 300

Gln Asp Gly Asp Glu Ile Lys Ile Ile Trp Asp Lys Asn Asn Lys Phe
305                 310                 315                 320

Val Ile Gly Phe Lys Val Glu Ile Asn Asp Thr Thr Gly Leu Phe Asn
                325                 330                 335

Glu Gly Leu Gly Met Leu Gln Glu Gln Arg Val Val Leu Lys Gln Thr
            340                 345                 350

Ala Glu Glu Lys Asp Leu Val Lys Lys Leu Gly Gly Ser Ser Gly Arg
        355                 360                 365

Lys Arg Asp Arg Leu Gly Thr Leu Gly Ile Gly Ser Ser Gly Ser Gly
    370                 375                 380

Gly Ser Gly Gly Thr Ser Gly Gly Ser Gly Gly Ser Ser Gly Ala Lys
385                 390                 395                 400

Asn Ile Lys Lys Gly Pro Ala Pro Phe Tyr Pro Leu Glu Asp Gly Thr
                405                 410                 415

Ala Gly Glu Gln Leu His Lys Ala Met Lys Arg Tyr Ala Leu Val Pro
            420                 425                 430

Gly Thr Ile Ala Phe Thr Asp Ala His Ile Glu Val Asp Ile Thr Tyr
        435                 440                 445

Ala Glu Tyr Phe Glu Met Ser Val Arg Leu Ala Glu Ala Met Lys Arg
    450                 455                 460

Tyr Gly Leu Asn Thr Asn His Arg Ile Val Val Cys Ser Glu Asn Ser
465                 470                 475                 480

Leu Gln Phe Phe Met Pro Val Leu Gly Ala Leu Phe Ile Gly Val Ala
                485                 490                 495

Val Ala Pro Ala Asn Asp Ile Tyr Asn Glu Arg Glu Leu Leu Asn Ser
            500                 505                 510

Met Gly Ile Ser Gln Pro Thr Val Val Phe Val Ser Lys Lys Gly Leu
        515                 520                 525

Gln Lys Ile Leu Asn Val Gln Lys Lys Leu Pro Ile Ile Gln Lys Ile
    530                 535                 540

Ile Ile Met Asp Ser Lys Thr Asp Tyr Gln Gly Phe Gln Ser Met Tyr
545                 550                 555                 560

Thr Phe Val Thr Ser His Leu Pro Pro Gly Phe Asn Glu Tyr Asp Phe
                565                 570                 575

Val Pro Glu Ser Phe Asp Arg Asp Lys Thr Ile Ala Leu Ile Met Asn
            580                 585                 590

Ser Ser Gly Ser Thr Gly Leu Pro Lys Gly Val Ala Leu Pro His Arg
        595                 600                 605

Thr Ala Cys Val Arg Phe Ser His Ala Arg Asp Pro Ile Phe Gly Asn
    610                 615                 620

Gln Ile Ile Pro Asp Thr Ala Ile Leu Ser Val Val Pro Phe His His
625                 630                 635                 640

Gly Phe Gly Met Phe Thr Thr Leu Gly Tyr Leu Ile Cys Gly Phe Arg
                645                 650                 655

Val Val Leu Met Tyr Arg Phe Glu Glu Glu Leu Phe Leu Arg Ser Leu
            660                 665                 670

Gln Asp Tyr Lys Ile Gln Ser Ala Leu Leu Val Pro Thr Leu Phe Ser
        675                 680                 685

Phe Phe Ala Lys Ser Thr Leu Ile Asp Lys Tyr Asp Leu Ser Asn Leu
    690                 695                 700
```

His Glu Ile Ala Ser Gly Gly Ala Pro Leu Ser Lys Glu Val Gly Glu
705 710 715 720

Ala Val Ala Lys Arg Phe His Leu Pro Gly Ile Arg Gln Gly Tyr Gly
725 730 735

Leu Thr Glu Thr Thr Ser Ala Ile Leu Ile Thr Pro Glu Gly
740 745 750

<210> SEQ ID NO 240
<211> LENGTH: 493
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 240

Met Lys Lys Ile Ile Phe Val Gly His Asp Trp Gly Ala Cys Leu Ala
1 5 10 15

Phe His Tyr Ser Tyr Glu His Gln Asp Lys Ile Lys Ala Ile Val His
20 25 30

Ala Glu Ser Val Val Asp Val Ile Glu Ser Trp Asp Glu Trp Pro Asp
35 40 45

Ile Glu Glu Asp Ile Ala Leu Ile Lys Ser Glu Glu Gly Glu Lys Met
50 55 60

Val Leu Glu Asn Asn Phe Phe Val Glu Thr Met Leu Pro Ser Lys Ile
65 70 75 80

Met Arg Lys Leu Glu Pro Glu Glu Phe Ala Ala Tyr Leu Glu Pro Phe
85 90 95

Lys Glu Lys Gly Glu Val Arg Arg Pro Thr Leu Ser Trp Pro Arg Glu
100 105 110

Ile Pro Leu Val Lys Gly Gly Lys Pro Asp Val Val Gln Ile Val Arg
115 120 125

Asn Tyr Asn Ala Tyr Leu Arg Ala Ser Asp Asp Leu Pro Lys Met Phe
130 135 140

Ile Glu Ser Asp Pro Gly Phe Phe Ser Asn Ala Ile Val Glu Gly Ala
145 150 155 160

Lys Lys Phe Pro Asn Thr Glu Phe Val Lys Val Lys Gly Leu His Phe
165 170 175

Ser Gln Glu Asp Ala Pro Asp Glu Met Gly Lys Tyr Ile Lys Ser Phe
180 185 190

Val Glu Arg Val Leu Lys Asn Glu Gln Gly Ser Gly Gly Gly Asn Gly
195 200 205

Arg Phe Leu Thr Leu Lys Pro Leu Pro Asp Ser Ile Ile Gln Glu Ser
210 215 220

Leu Glu Ile Gln Gln Gly Val Asn Pro Phe Phe Ile Gly Arg Ser Glu
225 230 235 240

Asp Cys Asn Cys Lys Ile Glu Asp Asn Arg Leu Ser Arg Val His Cys
245 250 255

Phe Ile Phe Lys Lys Arg His Ala Val Gly Lys Ser Met Tyr Glu Ser
260 265 270

Pro Ala Gln Gly Leu Asp Asp Ile Trp Tyr Cys His Thr Gly Thr Asn
275 280 285

Val Ser Tyr Leu Asn Asn Asn Arg Met Ile Gln Gly Thr Lys Phe Leu
290 295 300

Leu Gln Asp Gly Asp Glu Ile Lys Ile Ile Trp Asp Lys Asn Asn Lys
305 310 315 320

Phe Val Ile Gly Phe Lys Val Glu Ile Asn Asp Thr Thr Gly Leu Phe
325 330 335

Asn Glu Gly Leu Gly Met Leu Gln Glu Gln Arg Val Val Leu Lys Gln
340 345 350

Thr Ala Glu Glu Lys Asp Leu Val Lys Lys Leu Gly Gly Ser Ser Gly
355 360 365

Arg Lys Arg Asp Arg Leu Gly Thr Leu Gly Ile Gly Gly Ser Ser Gly
370 375 380

Thr Ser Lys Val Tyr Asp Pro Glu Gln Arg Lys Arg Met Ile Thr Gly
385 390 395 400

Pro Gln Trp Trp Ala Arg Cys Lys Gln Met Asn Val Leu Asp Ser Phe
405 410 415

Ile Asn Tyr Tyr Asp Ser Glu Lys His Ala Glu Asn Ala Val Ile Phe
420 425 430

Leu His Gly Asn Ala Ala Ser Ser Tyr Leu Trp Arg His Val Val Pro
435 440 445

His Ile Glu Pro Val Ala Arg Cys Ile Ile Pro Asp Leu Ile Gly Met
450 455 460

Gly Lys Ser Gly Lys Ser Gly Asn Gly Ser Tyr Arg Leu Leu Asp His
465 470 475 480

Tyr Lys Tyr Leu Thr Ala Trp Phe Glu Leu Leu Asn Leu
485 490

<210> SEQ ID NO 241
<211> LENGTH: 504
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 241

Met Lys Lys Ile Ile Phe Val Gly His Asp Trp Gly Ala Cys Leu Ala
1 5 10 15

Phe His Tyr Ser Tyr Glu His Gln Asp Lys Ile Lys Ala Ile Val His
20 25 30

Ala Glu Ser Val Val Asp Val Ile Glu Ser Trp Asp Glu Trp Pro Asp
35 40 45

Ile Glu Glu Asp Ile Ala Leu Ile Lys Ser Glu Glu Gly Glu Lys Met
50 55 60

Val Leu Glu Asn Asn Phe Phe Val Glu Thr Met Leu Pro Ser Lys Ile
65 70 75 80

Met Arg Lys Leu Glu Pro Glu Glu Phe Ala Ala Tyr Leu Glu Pro Phe
85 90 95

Lys Glu Lys Gly Glu Val Arg Arg Pro Thr Leu Ser Trp Pro Arg Glu
100 105 110

Ile Pro Leu Val Lys Gly Gly Lys Pro Asp Val Val Gln Ile Val Arg
115 120 125

Asn Tyr Asn Ala Tyr Leu Arg Ala Ser Asp Asp Leu Pro Lys Met Phe
130 135 140

Ile Glu Ser Asp Pro Gly Phe Phe Ser Asn Ala Ile Val Glu Gly Ala
145 150 155 160

Lys Lys Phe Pro Asn Thr Glu Phe Val Lys Val Lys Gly Leu His Phe
165 170 175

Ser Gln Glu Asp Ala Pro Asp Glu Met Gly Lys Tyr Ile Lys Ser Phe

```
            180                 185                 190

Val Glu Arg Val Leu Lys Asn Glu Gln Gly Gly Ser Gly Gly Gly Gly
        195                 200                 205

Ser Gly Gly Gly Asn Gly Arg Phe Leu Thr Leu Lys Pro Leu Pro Asp
    210                 215                 220

Ser Ile Ile Gln Glu Ser Leu Glu Ile Gln Gln Gly Val Asn Pro Phe
225                 230                 235                 240

Phe Ile Gly Arg Ser Glu Asp Cys Asn Cys Lys Ile Glu Asp Asn Arg
                245                 250                 255

Leu Ser Arg Val His Cys Phe Ile Phe Lys Lys Arg His Ala Val Gly
            260                 265                 270

Lys Ser Met Tyr Glu Ser Pro Ala Gln Gly Leu Asp Asp Ile Trp Tyr
        275                 280                 285

Cys His Thr Gly Thr Asn Val Ser Tyr Leu Asn Asn Asn Arg Met Ile
    290                 295                 300

Gln Gly Thr Lys Phe Leu Leu Gln Asp Gly Asp Glu Ile Lys Ile Ile
305                 310                 315                 320

Trp Asp Lys Asn Asn Lys Phe Val Ile Gly Phe Lys Val Glu Ile Asn
                325                 330                 335

Asp Thr Thr Gly Leu Phe Asn Glu Gly Leu Gly Met Leu Gln Glu Gln
            340                 345                 350

Arg Val Val Leu Lys Gln Thr Ala Glu Glu Lys Asp Leu Val Lys Lys
        355                 360                 365

Leu Gly Gly Ser Ser Gly Arg Lys Arg Asp Arg Leu Gly Thr Leu Gly
    370                 375                 380

Ile Gly Ser Ser Gly Ser Gly Gly Ser Gly Gly Thr Ser Lys Val Tyr
385                 390                 395                 400

Asp Pro Glu Gln Arg Lys Arg Met Ile Thr Gly Pro Gln Trp Trp Ala
                405                 410                 415

Arg Cys Lys Gln Met Asn Val Leu Asp Ser Phe Ile Asn Tyr Tyr Asp
            420                 425                 430

Ser Glu Lys His Ala Glu Asn Ala Val Ile Phe Leu His Gly Asn Ala
        435                 440                 445

Ala Ser Ser Tyr Leu Trp Arg His Val Val Pro His Ile Glu Pro Val
    450                 455                 460

Ala Arg Cys Ile Ile Pro Asp Leu Ile Gly Met Gly Lys Ser Gly Lys
465                 470                 475                 480

Ser Gly Asn Gly Ser Tyr Arg Leu Leu Asp His Tyr Lys Tyr Leu Thr
                485                 490                 495

Ala Trp Phe Glu Leu Leu Asn Leu
            500
```

<210> SEQ ID NO 242
<211> LENGTH: 524
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 242

```
Met Lys Lys Ile Ile Phe Val Gly His Asp Trp Gly Ala Cys Leu Ala
1               5                   10                  15

Phe His Tyr Ser Tyr Glu His Gln Asp Lys Ile Lys Ala Ile Val His
            20                  25                  30
```

```
Ala Glu Ser Val Val Asp Val Ile Glu Ser Trp Asp Glu Trp Pro Asp
        35                  40                  45

Ile Glu Glu Asp Ile Ala Leu Ile Lys Ser Glu Glu Gly Glu Lys Met
    50                  55                  60

Val Leu Glu Asn Asn Phe Phe Val Glu Thr Met Leu Pro Ser Lys Ile
65                  70                  75                  80

Met Arg Lys Leu Glu Pro Glu Glu Phe Ala Ala Tyr Leu Glu Pro Phe
                85                  90                  95

Lys Glu Lys Gly Glu Val Arg Arg Pro Thr Leu Ser Trp Pro Arg Glu
            100                 105                 110

Ile Pro Leu Val Lys Gly Gly Lys Pro Asp Val Val Gln Ile Val Arg
        115                 120                 125

Asn Tyr Asn Ala Tyr Leu Arg Ala Ser Asp Asp Leu Pro Lys Met Phe
    130                 135                 140

Ile Glu Ser Asp Pro Gly Phe Phe Ser Asn Ala Ile Val Glu Gly Ala
145                 150                 155                 160

Lys Lys Phe Pro Asn Thr Glu Phe Val Lys Val Lys Gly Leu His Phe
                165                 170                 175

Ser Gln Glu Asp Ala Pro Asp Glu Met Gly Lys Tyr Ile Lys Ser Phe
            180                 185                 190

Val Glu Arg Val Leu Lys Asn Glu Gln Gly Ser Ser Gly Gly Ser Gly
        195                 200                 205

Gly Ser Gly Gly Gly Ser Gly Gly Ser Gly Gly Ser Gly Gly Asn Gly
    210                 215                 220

Arg Phe Leu Thr Leu Lys Pro Leu Pro Asp Ser Ile Ile Gln Glu Ser
225                 230                 235                 240

Leu Glu Ile Gln Gln Gly Val Asn Pro Phe Phe Ile Gly Arg Ser Glu
                245                 250                 255

Asp Cys Asn Cys Lys Ile Glu Asp Asn Arg Leu Ser Arg Val His Cys
            260                 265                 270

Phe Ile Phe Lys Lys Arg His Ala Val Gly Lys Ser Met Tyr Glu Ser
        275                 280                 285

Pro Ala Gln Gly Leu Asp Asp Ile Trp Tyr Cys His Thr Gly Thr Asn
    290                 295                 300

Val Ser Tyr Leu Asn Asn Asn Arg Met Ile Gln Gly Thr Lys Phe Leu
305                 310                 315                 320

Leu Gln Asp Gly Asp Glu Ile Lys Ile Ile Trp Asp Lys Asn Asn Lys
                325                 330                 335

Phe Val Ile Gly Phe Lys Val Glu Ile Asn Asp Thr Thr Gly Leu Phe
            340                 345                 350

Asn Glu Gly Leu Gly Met Leu Gln Glu Gln Arg Val Val Leu Lys Gln
        355                 360                 365

Thr Ala Glu Glu Lys Asp Leu Val Lys Lys Leu Gly Gly Ser Ser Gly
    370                 375                 380

Arg Lys Arg Asp Arg Leu Gly Thr Leu Gly Ile Gly Ser Gly Gly Ser
385                 390                 395                 400

Gly Gly Ser Gly Gly Thr Ser Gly Gly Ser Gly Gly Ser Ser Gly Thr
                405                 410                 415

Ser Lys Val Tyr Asp Pro Glu Gln Arg Lys Arg Met Ile Thr Gly Pro
            420                 425                 430

Gln Trp Trp Ala Arg Cys Lys Gln Met Asn Val Leu Asp Ser Phe Ile
        435                 440                 445

Asn Tyr Tyr Asp Ser Glu Lys His Ala Glu Asn Ala Val Ile Phe Leu
```

```
    450                 455                 460

His Gly Asn Ala Ala Ser Ser Tyr Leu Trp Arg His Val Val Pro His
465                 470                 475                 480

Ile Glu Pro Val Ala Arg Cys Ile Ile Pro Asp Leu Ile Gly Met Gly
                485                 490                 495

Lys Ser Gly Lys Ser Gly Asn Gly Ser Tyr Arg Leu Leu Asp His Tyr
            500                 505                 510

Lys Tyr Leu Thr Ala Trp Phe Glu Leu Leu Asn Leu
        515                 520


<210> SEQ ID NO 243
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Met Ala Glu Asn Ala Val Ile Phe Leu His Gly Asn Ala Ala Ser Ser
1               5                   10                  15

Tyr Leu Trp Arg His Val Val Pro His Ile Glu Pro Val Ala Arg Cys
            20                  25                  30

Ile Ile Pro Asp Leu Ile Gly Met Gly Lys Ser Gly Lys Ser Gly Asn
        35                  40                  45

Gly Ser Tyr Arg Leu Leu Asp His Tyr Lys Tyr Leu Thr Ala Trp Phe
    50                  55                  60

Glu Leu Leu Asn Leu Pro Lys Lys Ile Ile Phe Val Gly His Asp Trp
65                  70                  75                  80

Gly Ala Cys Leu Ala Phe His Tyr Ser Tyr Glu His Gln Asp Lys Ile
                85                  90                  95

Lys Ala Ile Val His Ala Glu Ser Val Val Asp Val Ile Glu Ser Trp
            100                 105                 110

Asp Glu Trp Pro Asp Ile Glu Glu Asp Ile Ala Leu Ile Lys Ser Glu
        115                 120                 125

Glu Gly Glu Lys Met Val Leu Glu Asn Asn Phe Phe Val Glu Thr Met
    130                 135                 140

Leu Pro Ser Lys Ile Met Arg Lys Leu Glu Pro Glu Glu Phe Ala Ala
145                 150                 155                 160

Tyr Leu Glu Pro Phe Lys Glu Lys Gly Glu Val Arg Arg Pro Thr Leu
                165                 170                 175

Ser Trp Pro Arg Glu Ile Pro Leu Val Lys Gly Gly Lys Pro Asp Val
            180                 185                 190

Val Gln Ile Val Arg Asn Tyr Asn Ala Tyr Leu Arg Ala Ser Asp Asp
        195                 200                 205

Leu Pro Lys Met Phe Ile Glu Ser Asp Pro Gly Phe Phe Ser Asn Ala
    210                 215                 220

Ile Val Glu Gly Ala Lys Lys Phe Pro Asn Thr Glu Phe Val Lys Val
225                 230                 235                 240

Lys Gly Leu His Phe Ser Gln Glu Asp Ala Pro Asp Glu Met Gly Lys
                245                 250                 255

Tyr Ile Lys Ser Phe Val Glu Arg Val Leu Lys Asn Glu Gln Gly Ser
            260                 265                 270

Gly Gly Gly Asn Gly Arg Phe Leu Thr Leu Lys Pro Leu Pro Asp Ser
        275                 280                 285
```

```
Ile Ile Gln Glu Ser Leu Glu Ile Gln Gln Gly Val Asn Pro Phe Phe
    290                 295                 300

Ile Gly Arg Ser Glu Asp Cys Asn Cys Lys Ile Glu Asp Asn Arg Leu
305                 310                 315                 320

Ser Arg Val His Cys Phe Ile Phe Lys Lys Arg His Ala Val Gly Lys
                325                 330                 335

Ser Met Tyr Glu Ser Pro Ala Gln Gly Leu Asp Asp Ile Trp Tyr Cys
            340                 345                 350

His Thr Gly Thr Asn Val Ser Tyr Leu Asn Asn Asn Arg Met Ile Gln
        355                 360                 365

Gly Thr Lys Phe Leu Leu Gln Asp Gly Asp Glu Ile Lys Ile Ile Trp
    370                 375                 380

Asp Lys Asn Asn Lys Phe Val Ile Gly Phe Lys Val Glu Ile Asn Asp
385                 390                 395                 400

Thr Thr Gly Leu Phe Asn Glu Gly Leu Gly Met Leu Gln Glu Gln Arg
                405                 410                 415

Val Val Leu Lys Gln Thr Ala Glu Glu Lys Asp Leu Val Lys Lys Leu
            420                 425                 430

Gly Gly Ser Ser Gly Arg Lys Arg Asp Arg Leu Gly Thr Leu Gly Ile
        435                 440                 445

Gly Gly Ser Ser Gly Thr Ser Lys Val Tyr Asp Pro Glu Gln Arg Lys
    450                 455                 460

Arg Met Ile Thr Gly Pro Gln Trp Trp Ala Arg Cys Lys Gln Met Asn
465                 470                 475                 480

Val Leu Asp Ser Phe Ile Asn Tyr Tyr Asp Ser Glu Lys
                485                 490
```

<210> SEQ ID NO 244
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

```
Met Ala Glu Asn Ala Val Ile Phe Leu His Gly Asn Ala Ala Ser Ser
1               5                   10                  15

Tyr Leu Trp Arg His Val Val Pro His Ile Glu Pro Val Ala Arg Cys
            20                  25                  30

Ile Ile Pro Asp Leu Ile Gly Met Gly Lys Ser Gly Lys Ser Gly Asn
        35                  40                  45

Gly Ser Tyr Arg Leu Leu Asp His Tyr Lys Tyr Leu Thr Ala Trp Phe
    50                  55                  60

Glu Leu Leu Asn Leu Pro Lys Lys Ile Ile Phe Val Gly His Asp Trp
65                  70                  75                  80

Gly Ala Cys Leu Ala Phe His Tyr Ser Tyr Glu His Gln Asp Lys Ile
                85                  90                  95

Lys Ala Ile Val His Ala Glu Ser Val Val Asp Val Ile Glu Ser Trp
            100                 105                 110

Asp Glu Trp Pro Asp Ile Glu Glu Asp Ile Ala Leu Ile Lys Ser Glu
        115                 120                 125

Glu Gly Glu Lys Met Val Leu Glu Asn Asn Phe Phe Val Glu Thr Met
    130                 135                 140

Leu Pro Ser Lys Ile Met Arg Lys Leu Glu Pro Glu Glu Phe Ala Ala
145                 150                 155                 160
```

```
Tyr Leu Glu Pro Phe Lys Glu Lys Gly Glu Val Arg Arg Pro Thr Leu
                165                 170                 175

Ser Trp Pro Arg Glu Ile Pro Leu Val Lys Gly Gly Lys Pro Asp Val
            180                 185                 190

Val Gln Ile Val Arg Asn Tyr Asn Ala Tyr Leu Arg Ala Ser Asp Asp
        195                 200                 205

Leu Pro Lys Met Phe Ile Glu Ser Asp Pro Gly Phe Phe Ser Asn Ala
    210                 215                 220

Ile Val Glu Gly Ala Lys Lys Phe Pro Asn Thr Glu Phe Val Lys Val
225                 230                 235                 240

Lys Gly Leu His Phe Ser Gln Glu Asp Ala Pro Asp Glu Met Gly Lys
                245                 250                 255

Tyr Ile Lys Ser Phe Val Glu Arg Val Leu Lys Asn Glu Gln Gly Gly
            260                 265                 270

Ser Gly Gly Gly Gly Ser Gly Gly Gly Asn Gly Arg Phe Leu Thr Leu
        275                 280                 285

Lys Pro Leu Pro Asp Ser Ile Ile Gln Glu Ser Leu Glu Ile Gln Gln
    290                 295                 300

Gly Val Asn Pro Phe Phe Ile Gly Arg Ser Glu Asp Cys Asn Cys Lys
305                 310                 315                 320

Ile Glu Asp Asn Arg Leu Ser Arg Val His Cys Phe Ile Phe Lys Lys
                325                 330                 335

Arg His Ala Val Gly Lys Ser Met Tyr Glu Ser Pro Ala Gln Gly Leu
            340                 345                 350

Asp Asp Ile Trp Tyr Cys His Thr Gly Thr Asn Val Ser Tyr Leu Asn
        355                 360                 365

Asn Asn Arg Met Ile Gln Gly Thr Lys Phe Leu Leu Gln Asp Gly Asp
    370                 375                 380

Glu Ile Lys Ile Ile Trp Asp Lys Asn Asn Lys Phe Val Ile Gly Phe
385                 390                 395                 400

Lys Val Glu Ile Asn Asp Thr Thr Gly Leu Phe Asn Glu Gly Leu Gly
                405                 410                 415

Met Leu Gln Glu Gln Arg Val Val Leu Lys Gln Thr Ala Glu Glu Lys
            420                 425                 430

Asp Leu Val Lys Lys Leu Gly Gly Ser Ser Gly Arg Lys Arg Asp Arg
        435                 440                 445

Leu Gly Thr Leu Gly Ile Gly Ser Ser Gly Ser Gly Gly Ser Gly Gly
    450                 455                 460

Thr Ser Lys Val Tyr Asp Pro Glu Gln Arg Lys Arg Met Ile Thr Gly
465                 470                 475                 480

Pro Gln Trp Trp Ala Arg Cys Lys Gln Met Asn Val Leu Asp Ser Phe
                485                 490                 495

Ile Asn Tyr Tyr Asp Ser Glu Lys
            500
```

<210> SEQ ID NO 245
<211> LENGTH: 521
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

```
Met Ala Glu Asn Ala Val Ile Phe Leu His Gly Asn Ala Ala Ser Ser
```

-continued

```
1               5                   10                  15

Tyr Leu Trp Arg His Val Val Pro His Ile Glu Pro Val Ala Arg Cys
            20                  25                  30

Ile Ile Pro Asp Leu Ile Gly Met Gly Lys Ser Gly Lys Ser Gly Asn
        35                  40                  45

Gly Ser Tyr Arg Leu Leu Asp His Tyr Lys Tyr Leu Thr Ala Trp Phe
    50                  55                  60

Glu Leu Leu Asn Leu Pro Lys Lys Ile Ile Phe Val Gly His Asp Trp
65                  70                  75                  80

Gly Ala Cys Leu Ala Phe His Tyr Ser Tyr Glu His Gln Asp Lys Ile
                85                  90                  95

Lys Ala Ile Val His Ala Glu Ser Val Val Asp Val Ile Glu Ser Trp
            100                 105                 110

Asp Glu Trp Pro Asp Ile Glu Glu Asp Ile Ala Leu Ile Lys Ser Glu
        115                 120                 125

Glu Gly Glu Lys Met Val Leu Glu Asn Asn Phe Phe Val Glu Thr Met
    130                 135                 140

Leu Pro Ser Lys Ile Met Arg Lys Leu Glu Pro Glu Glu Phe Ala Ala
145                 150                 155                 160

Tyr Leu Glu Pro Phe Lys Glu Lys Gly Glu Val Arg Arg Pro Thr Leu
                165                 170                 175

Ser Trp Pro Arg Glu Ile Pro Leu Val Lys Gly Gly Lys Pro Asp Val
            180                 185                 190

Val Gln Ile Val Arg Asn Tyr Asn Ala Tyr Leu Arg Ala Ser Asp Asp
        195                 200                 205

Leu Pro Lys Met Phe Ile Glu Ser Asp Pro Gly Phe Phe Ser Asn Ala
    210                 215                 220

Ile Val Glu Gly Ala Lys Lys Phe Pro Asn Thr Glu Phe Val Lys Val
225                 230                 235                 240

Lys Gly Leu His Phe Ser Gln Glu Asp Ala Pro Asp Glu Met Gly Lys
                245                 250                 255

Tyr Ile Lys Ser Phe Val Glu Arg Val Leu Lys Asn Glu Gln Gly Ser
            260                 265                 270

Ser Gly Gly Ser Gly Gly Ser Gly Gly Gly Ser Gly Gly Ser Gly Gly
        275                 280                 285

Asn Gly Arg Phe Leu Thr Leu Lys Pro Leu Pro Asp Ser Ile Ile Gln
    290                 295                 300

Glu Ser Leu Glu Ile Gln Gln Gly Val Asn Pro Phe Phe Ile Gly Arg
305                 310                 315                 320

Ser Glu Asp Cys Asn Cys Lys Ile Glu Asp Asn Arg Leu Ser Arg Val
                325                 330                 335

His Cys Phe Ile Phe Lys Lys Arg His Ala Val Gly Lys Ser Met Tyr
            340                 345                 350

Glu Ser Pro Ala Gln Gly Leu Asp Asp Ile Trp Tyr Cys His Thr Gly
        355                 360                 365

Thr Asn Val Ser Tyr Leu Asn Asn Asn Arg Met Ile Gln Gly Thr Lys
    370                 375                 380

Phe Leu Leu Gln Asp Gly Asp Glu Ile Lys Ile Ile Trp Asp Lys Asn
385                 390                 395                 400

Asn Lys Phe Val Ile Gly Phe Lys Val Glu Ile Asn Asp Thr Thr Gly
                405                 410                 415

Leu Phe Asn Glu Gly Leu Gly Met Leu Gln Glu Gln Arg Val Val Leu
            420                 425                 430
```

```
Lys Gln Thr Ala Glu Glu Lys Asp Leu Val Lys Lys Leu Gly Gly Ser
        435                 440                 445

Ser Gly Arg Lys Arg Asp Arg Leu Gly Thr Leu Gly Ile Gly Ser Ser
    450                 455                 460

Gly Ser Gly Gly Ser Gly Gly Thr Ser Gly Gly Ser Gly Gly Ser Ser
465                 470                 475                 480

Gly Thr Ser Lys Val Tyr Asp Pro Glu Gln Arg Lys Arg Met Ile Thr
                485                 490                 495

Gly Pro Gln Trp Trp Ala Arg Cys Lys Gln Met Asn Val Leu Asp Ser
            500                 505                 510

Phe Ile Asn Tyr Tyr Asp Ser Glu Lys
        515                 520


<210> SEQ ID NO 246
<211> LENGTH: 676
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Asp Thr Ala Ile Leu Ser Val Val Pro Phe His His Gly Phe Gly Met
1               5                   10                  15

Phe Thr Thr Leu Gly Tyr Leu Ile Cys Gly Phe Arg Val Val Leu Met
            20                  25                  30

Tyr Arg Phe Glu Glu Glu Leu Phe Leu Arg Ser Leu Gln Asp Tyr Lys
        35                  40                  45

Ile Gln Ser Ala Leu Leu Val Pro Thr Leu Phe Ser Phe Phe Ala Lys
    50                  55                  60

Ser Thr Leu Ile Asp Lys Tyr Asp Leu Ser Asn Leu His Glu Ile Ala
65                  70                  75                  80

Ser Gly Gly Ala Pro Leu Ser Lys Glu Val Gly Glu Ala Val Ala Lys
                85                  90                  95

Arg Phe His Leu Pro Gly Ile Arg Gln Gly Tyr Gly Leu Thr Glu Thr
            100                 105                 110

Thr Ser Ala Ile Leu Ile Thr Pro Glu Gly Asp Asp Lys Pro Gly Ala
        115                 120                 125

Val Gly Lys Val Val Pro Phe Phe Glu Ala Lys Val Val Asp Leu Asp
    130                 135                 140

Thr Gly Lys Thr Leu Gly Val Asn Gln Arg Gly Glu Leu Cys Val Arg
145                 150                 155                 160

Gly Pro Met Ile Met Ser Gly Tyr Val Asn Asn Pro Glu Ala Thr Asn
                165                 170                 175

Ala Leu Ile Asp Lys Asp Gly Trp Leu His Ser Gly Asp Ile Ala Tyr
            180                 185                 190

Trp Asp Glu Asp Glu His Phe Phe Ile Val Asp Arg Leu Lys Ser Leu
        195                 200                 205

Ile Lys Tyr Lys Gly Tyr Gln Val Ala Pro Ala Glu Leu Glu Ser Ile
    210                 215                 220

Leu Leu Gln His Pro Asn Ile Phe Asp Ala Gly Val Ala Gly Leu Pro
225                 230                 235                 240

Asp Asp Asp Ala Gly Glu Leu Pro Ala Ala Val Val Val Leu Glu His
                245                 250                 255

Gly Lys Thr Met Thr Glu Lys Glu Ile Val Asp Tyr Val Ala Ser Gln
```

-continued

```
            260                 265                 270

Val Thr Thr Ala Lys Lys Leu Arg Gly Gly Val Val Phe Val Asp Glu
        275                 280                 285

Val Pro Lys Gly Leu Thr Gly Lys Leu Asp Ala Arg Lys Ile Arg Glu
    290                 295                 300

Ile Leu Ile Lys Ala Lys Lys Gly Ser Ser Gly Trp Tyr Phe Gly Lys
305                 310                 315                 320

Ile Thr Arg Arg Glu Ser Glu Arg Leu Leu Leu Asn Ala Glu Asn Pro
                325                 330                 335

Arg Gly Thr Phe Leu Val Arg Glu Ser Glu Thr Thr Lys Gly Ala Tyr
            340                 345                 350

Cys Leu Ser Val Ser Asp Phe Asp Asn Ala Lys Gly Leu Asn Val Lys
        355                 360                 365

His Tyr Lys Ile Arg Lys Leu Asp Ser Gly Gly Phe Tyr Ile Thr Ser
    370                 375                 380

Arg Thr Gln Phe Asn Ser Leu Gln Gln Leu Val Ala Tyr Tyr Ser Lys
385                 390                 395                 400

His Ala Asp Gly Leu Cys His Arg Leu Thr Thr Val Cys Gly Ser Thr
                405                 410                 415

Ser Gly Ser Gly Lys Pro Gly Ser Gly Glu Gly Ser Glu Ile Tyr Gly
            420                 425                 430

Glu Phe Gly Ser Gly Ser Gly Gly Ser Gly Gly Ser Ser Gly Ala Lys
        435                 440                 445

Asn Ile Lys Lys Gly Pro Ala Pro Phe Tyr Pro Leu Glu Asp Gly Thr
    450                 455                 460

Ala Gly Glu Gln Leu His Lys Ala Met Lys Arg Tyr Ala Leu Val Pro
465                 470                 475                 480

Gly Thr Ile Ala Phe Thr Asp Ala His Ile Glu Val Asp Ile Thr Tyr
                485                 490                 495

Ala Glu Tyr Phe Glu Met Ser Val Arg Leu Ala Glu Ala Met Lys Arg
            500                 505                 510

Tyr Gly Leu Asn Thr Asn His Arg Ile Val Val Cys Ser Glu Asn Ser
        515                 520                 525

Leu Gln Phe Phe Met Pro Val Leu Gly Ala Leu Phe Ile Gly Val Ala
    530                 535                 540

Val Ala Pro Ala Asn Asp Ile Tyr Asn Glu Arg Glu Leu Leu Asn Ser
545                 550                 555                 560

Met Gly Ile Ser Gln Pro Thr Val Val Phe Val Ser Lys Lys Gly Leu
                565                 570                 575

Gln Lys Ile Leu Asn Val Gln Lys Lys Leu Pro Ile Ile Gln Lys Ile
            580                 585                 590

Ile Ile Met Asp Ser Lys Thr Asp Tyr Gln Gly Phe Gln Ser Met Tyr
        595                 600                 605

Thr Phe Val Thr Ser His Leu Pro Pro Gly Phe Asn Glu Tyr Asp Phe
    610                 615                 620

Val Pro Glu Ser Phe Asp Arg Asp Lys Thr Ile Ala Leu Ile Met Asn
625                 630                 635                 640

Ser Ser Gly Ser Thr Gly Leu Pro Lys Gly Val Ala Leu Pro His Arg
                645                 650                 655

Thr Ala Cys Val Arg Phe Ser His Ala Arg Asp Pro Ile Phe Gly Asn
            660                 665                 670

Gln Ile Ile Pro
        675
```

<210> SEQ ID NO 247
<211> LENGTH: 684
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

```
Asp Thr Ala Ile Leu Ser Val Val Pro Phe His His Gly Phe Gly Met
1               5                   10                  15

Phe Thr Thr Leu Gly Tyr Leu Ile Cys Gly Phe Arg Val Val Leu Met
            20                  25                  30

Tyr Arg Phe Glu Glu Glu Leu Phe Leu Arg Ser Leu Gln Asp Tyr Lys
        35                  40                  45

Ile Gln Ser Ala Leu Leu Val Pro Thr Leu Phe Ser Phe Phe Ala Lys
    50                  55                  60

Ser Thr Leu Ile Asp Lys Tyr Asp Leu Ser Asn Leu His Glu Ile Ala
65                  70                  75                  80

Ser Gly Gly Ala Pro Leu Ser Lys Glu Val Gly Glu Ala Val Ala Lys
                85                  90                  95

Arg Phe His Leu Pro Gly Ile Arg Gln Gly Tyr Gly Leu Thr Glu Thr
            100                 105                 110

Thr Ser Ala Ile Leu Ile Thr Pro Glu Gly Asp Asp Lys Pro Gly Ala
        115                 120                 125

Val Gly Lys Val Val Pro Phe Phe Glu Ala Lys Val Val Asp Leu Asp
    130                 135                 140

Thr Gly Lys Thr Leu Gly Val Asn Gln Arg Gly Glu Leu Cys Val Arg
145                 150                 155                 160

Gly Pro Met Ile Met Ser Gly Tyr Val Asn Asn Pro Glu Ala Thr Asn
                165                 170                 175

Ala Leu Ile Asp Lys Asp Gly Trp Leu His Ser Gly Asp Ile Ala Tyr
            180                 185                 190

Trp Asp Glu Asp Glu His Phe Phe Ile Val Asp Arg Leu Lys Ser Leu
        195                 200                 205

Ile Lys Tyr Lys Gly Tyr Gln Val Ala Pro Ala Glu Leu Glu Ser Ile
    210                 215                 220

Leu Leu Gln His Pro Asn Ile Phe Asp Ala Gly Val Ala Gly Leu Pro
225                 230                 235                 240

Asp Asp Asp Ala Gly Glu Leu Pro Ala Ala Val Val Val Leu Glu His
                245                 250                 255

Gly Lys Thr Met Thr Glu Lys Glu Ile Val Asp Tyr Val Ala Ser Gln
            260                 265                 270

Val Thr Thr Ala Lys Lys Leu Arg Gly Gly Val Val Phe Val Asp Glu
        275                 280                 285

Val Pro Lys Gly Leu Thr Gly Lys Leu Asp Ala Arg Lys Ile Arg Glu
    290                 295                 300

Ile Leu Ile Lys Ala Lys Lys Gly Ser Ser Gly Trp Tyr Phe Gly Lys
305                 310                 315                 320

Ile Thr Arg Arg Glu Ser Glu Arg Leu Leu Leu Asn Ala Glu Asn Pro
                325                 330                 335

Arg Gly Thr Phe Leu Val Arg Glu Ser Glu Thr Thr Lys Gly Ala Tyr
            340                 345                 350

Cys Leu Ser Val Ser Asp Phe Asp Asn Ala Lys Gly Leu Asn Val Lys
```

```
        355                 360                 365

His Tyr Lys Ile Arg Lys Leu Asp Ser Gly Gly Phe Tyr Ile Thr Ser
    370                 375                 380

Arg Thr Gln Phe Asn Ser Leu Gln Gln Leu Val Ala Tyr Tyr Ser Lys
385                 390                 395                 400

His Ala Asp Gly Leu Cys His Arg Leu Thr Thr Val Cys Gly Ser Thr
                405                 410                 415

Ser Gly Ser Gly Lys Pro Gly Ser Gly Glu Gly Ser Glu Ile Tyr Gly
            420                 425                 430

Glu Phe Gly Ser Gly Gly Ser Gly Gly Ser Gly Gly Gly Ser Gly Gly
        435                 440                 445

Ser Gly Gly Ser Ser Gly Ala Lys Asn Ile Lys Lys Gly Pro Ala Pro
    450                 455                 460

Phe Tyr Pro Leu Glu Asp Gly Thr Ala Gly Glu Gln Leu His Lys Ala
465                 470                 475                 480

Met Lys Arg Tyr Ala Leu Val Pro Gly Thr Ile Ala Phe Thr Asp Ala
                485                 490                 495

His Ile Glu Val Asp Ile Thr Tyr Ala Glu Tyr Phe Glu Met Ser Val
            500                 505                 510

Arg Leu Ala Glu Ala Met Lys Arg Tyr Gly Leu Asn Thr Asn His Arg
        515                 520                 525

Ile Val Val Cys Ser Glu Asn Ser Leu Gln Phe Phe Met Pro Val Leu
    530                 535                 540

Gly Ala Leu Phe Ile Gly Val Ala Val Ala Pro Ala Asn Asp Ile Tyr
545                 550                 555                 560

Asn Glu Arg Glu Leu Leu Asn Ser Met Gly Ile Ser Gln Pro Thr Val
                565                 570                 575

Val Phe Val Ser Lys Lys Gly Leu Gln Lys Ile Leu Asn Val Gln Lys
            580                 585                 590

Lys Leu Pro Ile Ile Gln Lys Ile Ile Ile Met Asp Ser Lys Thr Asp
        595                 600                 605

Tyr Gln Gly Phe Gln Ser Met Tyr Thr Phe Val Thr Ser His Leu Pro
    610                 615                 620

Pro Gly Phe Asn Glu Tyr Asp Phe Val Pro Glu Ser Phe Asp Arg Asp
625                 630                 635                 640

Lys Thr Ile Ala Leu Ile Met Asn Ser Ser Gly Ser Thr Gly Leu Pro
                645                 650                 655

Lys Gly Val Ala Leu Pro His Arg Thr Ala Cys Val Arg Phe Ser His
            660                 665                 670

Ala Arg Asp Pro Ile Phe Gly Asn Gln Ile Ile Pro
        675                 680
```

<210> SEQ ID NO 248
<211> LENGTH: 668
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 248

```
Met Thr Ala Ile Leu Ser Val Val Pro Phe His His Gly Phe Gly Met
1               5                   10                  15

Phe Thr Thr Leu Gly Tyr Leu Ile Cys Gly Phe Arg Val Val Leu Met
            20                  25                  30
```

-continued

```
Tyr Arg Phe Glu Glu Glu Leu Phe Leu Arg Ser Leu Gln Asp Tyr Lys
        35                  40                  45

Ile Gln Ser Ala Leu Leu Val Pro Thr Leu Phe Ser Phe Phe Ala Lys
    50                  55                  60

Ser Thr Leu Ile Asp Lys Tyr Asp Leu Ser Asn Leu His Glu Ile Ala
65                  70                  75                  80

Ser Gly Gly Ala Pro Leu Ser Lys Glu Val Gly Glu Ala Val Ala Lys
                85                  90                  95

Arg Phe His Leu Pro Gly Ile Arg Gln Gly Tyr Gly Leu Thr Glu Thr
            100                 105                 110

Thr Ser Ala Ile Leu Ile Thr Pro Glu Gly Asp Asp Lys Pro Gly Ala
        115                 120                 125

Val Gly Lys Val Val Pro Phe Phe Glu Ala Lys Val Val Asp Leu Asp
    130                 135                 140

Thr Gly Lys Thr Leu Gly Val Asn Gln Arg Gly Glu Leu Cys Val Arg
145                 150                 155                 160

Gly Pro Met Ile Met Ser Gly Tyr Val Asn Asn Pro Glu Ala Thr Asn
                165                 170                 175

Ala Leu Ile Asp Lys Asp Gly Trp Leu His Ser Gly Asp Ile Ala Tyr
            180                 185                 190

Trp Asp Glu Asp Glu His Phe Phe Ile Val Asp Arg Leu Lys Ser Leu
        195                 200                 205

Ile Lys Tyr Lys Gly Tyr Gln Val Ala Pro Ala Glu Leu Glu Ser Ile
    210                 215                 220

Leu Leu Gln His Pro Asn Ile Phe Asp Ala Gly Val Ala Gly Leu Pro
225                 230                 235                 240

Asp Asp Asp Ala Gly Glu Leu Pro Ala Ala Val Val Val Leu Glu His
                245                 250                 255

Gly Lys Thr Met Thr Glu Lys Glu Ile Val Asp Tyr Val Ala Ser Gln
            260                 265                 270

Val Thr Thr Ala Lys Lys Leu Arg Gly Gly Val Val Phe Val Asp Glu
        275                 280                 285

Val Pro Lys Gly Leu Thr Gly Lys Leu Asp Ala Arg Lys Ile Arg Glu
    290                 295                 300

Ile Leu Ile Lys Ala Lys Lys Gly Ser Thr Gly Trp Tyr Phe Gly Lys
305                 310                 315                 320

Ile Thr Arg Arg Glu Ser Glu Arg Leu Leu Leu Asn Ala Glu Asn Pro
                325                 330                 335

Arg Gly Thr Phe Leu Val Arg Glu Ser Glu Thr Thr Lys Gly Ala Tyr
            340                 345                 350

Cys Leu Ser Val Ser Asp Phe Asp Asn Ala Lys Gly Leu Asn Val Lys
        355                 360                 365

His Tyr Lys Ile Arg Lys Leu Asp Ser Gly Gly Phe Tyr Ile Thr Ser
    370                 375                 380

Arg Thr Gln Phe Asn Ser Leu Gln Gln Leu Val Ala Tyr Tyr Ser Lys
385                 390                 395                 400

His Ala Asp Gly Leu Cys His Arg Leu Thr Thr Val Cys Gly Ser Thr
                405                 410                 415

Ser Gly Ser Gly Lys Pro Gly Ser Gly Glu Gly Ser Glu Ile Tyr Gly
            420                 425                 430

Glu Phe Gly Ser Ser Gly Ala Lys Asn Ile Lys Lys Gly Pro Ala Pro
        435                 440                 445

Phe Tyr Pro Leu Glu Asp Gly Thr Ala Gly Glu Gln Leu His Lys Ala
```

```
    450                 455                 460

Met Lys Arg Tyr Ala Leu Val Pro Gly Thr Ile Ala Phe Thr Asp Ala
465                 470                 475                 480

His Ile Glu Val Asp Ile Thr Tyr Ala Glu Tyr Phe Glu Met Ser Val
                485                 490                 495

Arg Leu Ala Glu Ala Met Lys Arg Tyr Gly Leu Asn Thr Asn His Arg
            500                 505                 510

Ile Val Val Cys Ser Glu Asn Ser Leu Gln Phe Phe Met Pro Val Leu
        515                 520                 525

Gly Ala Leu Phe Ile Gly Val Ala Val Ala Pro Ala Asn Asp Ile Tyr
    530                 535                 540

Asn Glu Arg Glu Leu Leu Asn Ser Met Gly Ile Ser Gln Pro Thr Val
545                 550                 555                 560

Val Phe Val Ser Lys Lys Gly Leu Gln Lys Ile Leu Asn Val Gln Lys
                565                 570                 575

Lys Leu Pro Ile Ile Gln Lys Ile Ile Ile Met Asp Ser Lys Thr Asp
            580                 585                 590

Tyr Gln Gly Phe Gln Ser Met Tyr Thr Phe Val Thr Ser His Leu Pro
        595                 600                 605

Pro Gly Phe Asn Glu Tyr Asp Phe Val Pro Glu Ser Phe Asp Arg Asp
    610                 615                 620

Lys Thr Ile Ala Leu Ile Met Asn Ser Ser Gly Ser Thr Gly Leu Pro
625                 630                 635                 640

Lys Gly Val Ala Leu Pro His Arg Thr Ala Cys Val Arg Phe Ser His
                645                 650                 655

Ala Arg Asp Pro Ile Phe Gly Asn Gln Ile Ile Pro
            660                 665


<210> SEQ ID NO 249
<211> LENGTH: 682
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Met Thr Ala Ile Leu Ser Val Val Pro Phe His His Gly Phe Gly Met
1               5                   10                  15

Phe Thr Thr Leu Gly Tyr Leu Ile Cys Gly Phe Arg Val Val Leu Met
            20                  25                  30

Tyr Arg Phe Glu Glu Glu Leu Phe Leu Arg Ser Leu Gln Asp Tyr Lys
        35                  40                  45

Ile Gln Ser Ala Leu Leu Val Pro Thr Leu Phe Ser Phe Phe Ala Lys
    50                  55                  60

Ser Thr Leu Ile Asp Lys Tyr Asp Leu Ser Asn Leu His Glu Ile Ala
65                  70                  75                  80

Ser Gly Gly Ala Pro Leu Ser Lys Glu Val Gly Glu Ala Val Ala Lys
                85                  90                  95

Arg Phe His Leu Pro Gly Ile Arg Gln Gly Tyr Gly Leu Thr Glu Thr
            100                 105                 110

Thr Ser Ala Ile Leu Ile Thr Pro Glu Gly Asp Asp Lys Pro Gly Ala
        115                 120                 125

Val Gly Lys Val Val Pro Phe Phe Glu Ala Lys Val Val Asp Leu Asp
    130                 135                 140
```

-continued

```
Thr Gly Lys Thr Leu Gly Val Asn Gln Arg Gly Glu Leu Cys Val Arg
145                 150                 155                 160

Gly Pro Met Ile Met Ser Gly Tyr Val Asn Asn Pro Glu Ala Thr Asn
                165                 170                 175

Ala Leu Ile Asp Lys Asp Gly Trp Leu His Ser Gly Asp Ile Ala Tyr
            180                 185                 190

Trp Asp Glu Asp Glu His Phe Phe Ile Val Asp Arg Leu Lys Ser Leu
        195                 200                 205

Ile Lys Tyr Lys Gly Tyr Gln Val Ala Pro Ala Glu Leu Glu Ser Ile
    210                 215                 220

Leu Leu Gln His Pro Asn Ile Phe Asp Ala Gly Val Ala Gly Leu Pro
225                 230                 235                 240

Asp Asp Asp Ala Gly Glu Leu Pro Ala Ala Val Val Val Leu Glu His
                245                 250                 255

Gly Lys Thr Met Thr Glu Lys Glu Ile Val Asp Tyr Val Ala Ser Gln
            260                 265                 270

Val Thr Thr Ala Lys Lys Leu Arg Gly Gly Val Val Phe Val Asp Glu
        275                 280                 285

Val Pro Lys Gly Leu Thr Gly Lys Leu Asp Ala Arg Lys Ile Arg Glu
    290                 295                 300

Ile Leu Ile Lys Ala Lys Lys Gly Ser Ser Gly Gly Ser Gly Gly Ser
305                 310                 315                 320

Gly Trp Tyr Phe Gly Lys Ile Thr Arg Arg Glu Ser Glu Arg Leu Leu
                325                 330                 335

Leu Asn Ala Glu Asn Pro Arg Gly Thr Phe Leu Val Arg Glu Ser Glu
            340                 345                 350

Thr Thr Lys Gly Ala Tyr Cys Leu Ser Val Ser Asp Phe Asp Asn Ala
        355                 360                 365

Lys Gly Leu Asn Val Lys His Tyr Lys Ile Arg Lys Leu Asp Ser Gly
    370                 375                 380

Gly Phe Tyr Ile Thr Ser Arg Thr Gln Phe Asn Ser Leu Gln Gln Leu
385                 390                 395                 400

Val Ala Tyr Tyr Ser Lys His Ala Asp Gly Leu Cys His Arg Leu Thr
                405                 410                 415

Thr Val Cys Gly Ser Thr Ser Gly Ser Gly Lys Pro Gly Ser Gly Glu
            420                 425                 430

Gly Ser Glu Ile Tyr Gly Glu Phe Gly Ser Gly Ser Gly Gly Ser Gly
        435                 440                 445

Gly Ser Ser Gly Ala Lys Asn Ile Lys Lys Gly Pro Ala Pro Phe Tyr
    450                 455                 460

Pro Leu Glu Asp Gly Thr Ala Gly Glu Gln Leu His Lys Ala Met Lys
465                 470                 475                 480

Arg Tyr Ala Leu Val Pro Gly Thr Ile Ala Phe Thr Asp Ala His Ile
                485                 490                 495

Glu Val Asp Ile Thr Tyr Ala Glu Tyr Phe Glu Met Ser Val Arg Leu
            500                 505                 510

Ala Glu Ala Met Lys Arg Tyr Gly Leu Asn Thr Asn His Arg Ile Val
        515                 520                 525

Val Cys Ser Glu Asn Ser Leu Gln Phe Phe Met Pro Val Leu Gly Ala
    530                 535                 540

Leu Phe Ile Gly Val Ala Val Ala Pro Ala Asn Asp Ile Tyr Asn Glu
545                 550                 555                 560

Arg Glu Leu Leu Asn Ser Met Gly Ile Ser Gln Pro Thr Val Val Phe
```

```
                565                 570                 575

Val Ser Lys Lys Gly Leu Gln Lys Ile Leu Asn Val Gln Lys Lys Leu
            580                 585                 590

Pro Ile Ile Gln Lys Ile Ile Ile Met Asp Ser Lys Thr Asp Tyr Gln
        595                 600                 605

Gly Phe Gln Ser Met Tyr Thr Phe Val Thr Ser His Leu Pro Pro Gly
    610                 615                 620

Phe Asn Glu Tyr Asp Phe Val Pro Glu Ser Phe Asp Arg Asp Lys Thr
625                 630                 635                 640

Ile Ala Leu Ile Met Asn Ser Ser Gly Ser Thr Gly Leu Pro Lys Gly
                645                 650                 655

Val Ala Leu Pro His Arg Thr Ala Cys Val Arg Phe Ser His Ala Arg
            660                 665                 670

Asp Pro Ile Phe Gly Asn Gln Ile Ile Pro
        675                 680


<210> SEQ ID NO 250
<211> LENGTH: 700
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Met Thr Ala Ile Leu Ser Val Val Pro Phe His His Gly Phe Gly Met
1               5                   10                  15

Phe Thr Thr Leu Gly Tyr Leu Ile Cys Gly Phe Arg Val Val Leu Met
            20                  25                  30

Tyr Arg Phe Glu Glu Glu Leu Phe Leu Arg Ser Leu Gln Asp Tyr Lys
        35                  40                  45

Ile Gln Ser Ala Leu Leu Val Pro Thr Leu Phe Ser Phe Phe Ala Lys
    50                  55                  60

Ser Thr Leu Ile Asp Lys Tyr Asp Leu Ser Asn Leu His Glu Ile Ala
65                  70                  75                  80

Ser Gly Gly Ala Pro Leu Ser Lys Glu Val Gly Glu Ala Val Ala Lys
                85                  90                  95

Arg Phe His Leu Pro Gly Ile Arg Gln Gly Tyr Gly Leu Thr Glu Thr
            100                 105                 110

Thr Ser Ala Ile Leu Ile Thr Pro Glu Gly Asp Asp Lys Pro Gly Ala
        115                 120                 125

Val Gly Lys Val Val Pro Phe Phe Glu Ala Lys Val Val Asp Leu Asp
    130                 135                 140

Thr Gly Lys Thr Leu Gly Val Asn Gln Arg Gly Glu Leu Cys Val Arg
145                 150                 155                 160

Gly Pro Met Ile Met Ser Gly Tyr Val Asn Asn Pro Glu Ala Thr Asn
                165                 170                 175

Ala Leu Ile Asp Lys Asp Gly Trp Leu His Ser Gly Asp Ile Ala Tyr
            180                 185                 190

Trp Asp Glu Asp Glu His Phe Phe Ile Val Asp Arg Leu Lys Ser Leu
        195                 200                 205

Ile Lys Tyr Lys Gly Tyr Gln Val Ala Pro Ala Glu Leu Glu Ser Ile
    210                 215                 220

Leu Leu Gln His Pro Asn Ile Phe Asp Ala Gly Val Ala Gly Leu Pro
225                 230                 235                 240
```

```
Asp Asp Asp Ala Gly Glu Leu Pro Ala Ala Val Val Val Leu Glu His
                245                 250                 255

Gly Lys Thr Met Thr Glu Lys Glu Ile Val Asp Tyr Val Ala Ser Gln
            260                 265                 270

Val Thr Thr Ala Lys Lys Leu Arg Gly Gly Val Val Phe Val Asp Glu
        275                 280                 285

Val Pro Lys Gly Leu Thr Gly Lys Leu Asp Ala Arg Lys Ile Arg Glu
    290                 295                 300

Ile Leu Ile Lys Ala Lys Lys Gly Ser Ser Gly Gly Ser Gly Gly Ser
305                 310                 315                 320

Gly Gly Gly Ser Gly Gly Ser Gly Gly Ser Gly Trp Tyr Phe Gly Lys
                325                 330                 335

Ile Thr Arg Arg Glu Ser Glu Arg Leu Leu Leu Asn Ala Glu Asn Pro
            340                 345                 350

Arg Gly Thr Phe Leu Val Arg Glu Ser Glu Thr Thr Lys Gly Ala Tyr
        355                 360                 365

Cys Leu Ser Val Ser Asp Phe Asp Asn Ala Lys Gly Leu Asn Val Lys
    370                 375                 380

His Tyr Lys Ile Arg Lys Leu Asp Ser Gly Gly Phe Tyr Ile Thr Ser
385                 390                 395                 400

Arg Thr Gln Phe Asn Ser Leu Gln Gln Leu Val Ala Tyr Tyr Ser Lys
                405                 410                 415

His Ala Asp Gly Leu Cys His Arg Leu Thr Thr Val Cys Gly Ser Thr
            420                 425                 430

Ser Gly Ser Gly Lys Pro Gly Ser Gly Glu Gly Ser Glu Ile Tyr Gly
        435                 440                 445

Glu Phe Gly Ser Gly Gly Ser Gly Gly Ser Gly Gly Gly Ser Gly Gly
    450                 455                 460

Ser Gly Gly Ser Ser Gly Ala Lys Asn Ile Lys Lys Gly Pro Ala Pro
465                 470                 475                 480

Phe Tyr Pro Leu Glu Asp Gly Thr Ala Gly Glu Gln Leu His Lys Ala
                485                 490                 495

Met Lys Arg Tyr Ala Leu Val Pro Gly Thr Ile Ala Phe Thr Asp Ala
            500                 505                 510

His Ile Glu Val Asp Ile Thr Tyr Ala Glu Tyr Phe Glu Met Ser Val
        515                 520                 525

Arg Leu Ala Glu Ala Met Lys Arg Tyr Gly Leu Asn Thr Asn His Arg
    530                 535                 540

Ile Val Val Cys Ser Glu Asn Ser Leu Gln Phe Phe Met Pro Val Leu
545                 550                 555                 560

Gly Ala Leu Phe Ile Gly Val Ala Val Ala Pro Ala Asn Asp Ile Tyr
                565                 570                 575

Asn Glu Arg Glu Leu Leu Asn Ser Met Gly Ile Ser Gln Pro Thr Val
            580                 585                 590

Val Phe Val Ser Lys Lys Gly Leu Gln Lys Ile Leu Asn Val Gln Lys
        595                 600                 605

Lys Leu Pro Ile Ile Gln Lys Ile Ile Ile Met Asp Ser Lys Thr Asp
    610                 615                 620

Tyr Gln Gly Phe Gln Ser Met Tyr Thr Phe Val Thr Ser His Leu Pro
625                 630                 635                 640

Pro Gly Phe Asn Glu Tyr Asp Phe Val Pro Glu Ser Phe Asp Arg Asp
                645                 650                 655

Lys Thr Ile Ala Leu Ile Met Asn Ser Ser Gly Ser Thr Gly Leu Pro
```

```
            660                 665                 670

Lys Gly Val Ala Leu Pro His Arg Thr Ala Cys Val Arg Phe Ser His
        675                 680                 685

Ala Arg Asp Pro Ile Phe Gly Asn Gln Ile Ile Pro
    690                 695                 700


<210> SEQ ID NO 251
<211> LENGTH: 666
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Met Pro Gly Ala Val Gly Lys Val Val Pro Phe Phe Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Thr Gly Trp
            180                 185                 190

Tyr Phe Gly Lys Ile Thr Arg Arg Glu Ser Glu Arg Leu Leu Leu Asn
        195                 200                 205

Ala Glu Asn Pro Arg Gly Thr Phe Leu Val Arg Glu Ser Glu Thr Thr
    210                 215                 220

Lys Gly Ala Tyr Cys Leu Ser Val Ser Asp Phe Asp Asn Ala Lys Gly
225                 230                 235                 240

Leu Asn Val Lys His Tyr Lys Ile Arg Lys Leu Asp Ser Gly Gly Phe
                245                 250                 255

Tyr Ile Thr Ser Arg Thr Gln Phe Asn Ser Leu Gln Gln Leu Val Ala
            260                 265                 270

Tyr Tyr Ser Lys His Ala Asp Gly Leu Cys His Arg Leu Thr Thr Val
        275                 280                 285

Cys Gly Ser Thr Ser Gly Ser Gly Lys Pro Gly Ser Gly Glu Gly Ser
    290                 295                 300

Glu Ile Tyr Gly Glu Phe Gly Ser Ser Gly Ala Lys Asn Ile Lys Lys
305                 310                 315                 320
```

```
Gly Pro Ala Pro Phe Tyr Pro Leu Glu Asp Gly Thr Ala Gly Glu Gln
                325                 330                 335

Leu His Lys Ala Met Lys Arg Tyr Ala Leu Val Pro Gly Thr Ile Ala
            340                 345                 350

Phe Thr Asp Ala His Ile Glu Val Asp Ile Thr Tyr Ala Glu Tyr Phe
        355                 360                 365

Glu Met Ser Val Arg Leu Ala Glu Ala Met Lys Arg Tyr Gly Leu Asn
    370                 375                 380

Thr Asn His Arg Ile Val Val Cys Ser Glu Asn Ser Leu Gln Phe Phe
385                 390                 395                 400

Met Pro Val Leu Gly Ala Leu Phe Ile Gly Val Ala Val Ala Pro Ala
                405                 410                 415

Asn Asp Ile Tyr Asn Glu Arg Glu Leu Leu Asn Ser Met Gly Ile Ser
            420                 425                 430

Gln Pro Thr Val Val Phe Val Ser Lys Lys Gly Leu Gln Lys Ile Leu
        435                 440                 445

Asn Val Gln Lys Lys Leu Pro Ile Ile Gln Lys Ile Ile Ile Met Asp
    450                 455                 460

Ser Lys Thr Asp Tyr Gln Gly Phe Gln Ser Met Tyr Thr Phe Val Thr
465                 470                 475                 480

Ser His Leu Pro Pro Gly Phe Asn Glu Tyr Asp Phe Val Pro Glu Ser
                485                 490                 495

Phe Asp Arg Asp Lys Thr Ile Ala Leu Ile Met Asn Ser Ser Gly Ser
            500                 505                 510

Thr Gly Leu Pro Lys Gly Val Ala Leu Pro His Arg Thr Ala Cys Val
        515                 520                 525

Arg Phe Ser His Ala Arg Asp Pro Ile Phe Gly Asn Gln Ile Ile Pro
    530                 535                 540

Asp Thr Ala Ile Leu Ser Val Val Pro Phe His His Gly Phe Gly Met
545                 550                 555                 560

Phe Thr Thr Leu Gly Tyr Leu Ile Cys Gly Phe Arg Val Val Leu Met
                565                 570                 575

Tyr Arg Phe Glu Glu Glu Leu Phe Leu Arg Ser Leu Gln Asp Tyr Lys
            580                 585                 590

Ile Gln Ser Ala Leu Leu Val Pro Thr Leu Phe Ser Phe Phe Ala Lys
        595                 600                 605

Ser Thr Leu Ile Asp Lys Tyr Asp Leu Ser Asn Leu His Glu Ile Ala
    610                 615                 620

Ser Gly Gly Ala Pro Leu Ser Lys Glu Val Gly Glu Ala Val Ala Lys
625                 630                 635                 640

Arg Phe His Leu Pro Gly Ile Arg Gln Gly Tyr Gly Leu Thr Glu Thr
                645                 650                 655

Thr Ser Ala Ile Leu Ile Thr Pro Glu Gly
            660                 665
```

<210> SEQ ID NO 252
<211> LENGTH: 680
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 252

```
Met Pro Gly Ala Val Gly Lys Val Val Pro Phe Phe Glu Ala Lys Val
1               5                   10                  15
```

```
Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Ser Gly Gly
            180                 185                 190

Ser Gly Gly Ser Gly Trp Tyr Phe Gly Lys Ile Thr Arg Arg Glu Ser
        195                 200                 205

Glu Arg Leu Leu Leu Asn Ala Glu Asn Pro Arg Gly Thr Phe Leu Val
    210                 215                 220

Arg Glu Ser Glu Thr Thr Lys Gly Ala Tyr Cys Leu Ser Val Ser Asp
225                 230                 235                 240

Phe Asp Asn Ala Lys Gly Leu Asn Val Lys His Tyr Lys Ile Arg Lys
                245                 250                 255

Leu Asp Ser Gly Gly Phe Tyr Ile Thr Ser Arg Thr Gln Phe Asn Ser
            260                 265                 270

Leu Gln Gln Leu Val Ala Tyr Tyr Ser Lys His Ala Asp Gly Leu Cys
        275                 280                 285

His Arg Leu Thr Thr Val Cys Gly Ser Thr Ser Gly Ser Gly Lys Pro
    290                 295                 300

Gly Ser Gly Glu Gly Ser Glu Ile Tyr Gly Glu Phe Gly Ser Gly Ser
305                 310                 315                 320

Gly Gly Ser Gly Gly Ser Ser Gly Ala Lys Asn Ile Lys Lys Gly Pro
                325                 330                 335

Ala Pro Phe Tyr Pro Leu Glu Asp Gly Thr Ala Gly Glu Gln Leu His
            340                 345                 350

Lys Ala Met Lys Arg Tyr Ala Leu Val Pro Gly Thr Ile Ala Phe Thr
        355                 360                 365

Asp Ala His Ile Glu Val Asp Ile Thr Tyr Ala Glu Tyr Phe Glu Met
    370                 375                 380

Ser Val Arg Leu Ala Glu Ala Met Lys Arg Tyr Gly Leu Asn Thr Asn
385                 390                 395                 400

His Arg Ile Val Val Cys Ser Glu Asn Ser Leu Gln Phe Phe Met Pro
                405                 410                 415

Val Leu Gly Ala Leu Phe Ile Gly Val Ala Val Ala Pro Ala Asn Asp
            420                 425                 430
```

```
Ile Tyr Asn Glu Arg Glu Leu Leu Asn Ser Met Gly Ile Ser Gln Pro
        435                 440                 445

Thr Val Val Phe Val Ser Lys Lys Gly Leu Gln Lys Ile Leu Asn Val
    450                 455                 460

Gln Lys Lys Leu Pro Ile Ile Gln Lys Ile Ile Ile Met Asp Ser Lys
465                 470                 475                 480

Thr Asp Tyr Gln Gly Phe Gln Ser Met Tyr Thr Phe Val Thr Ser His
                485                 490                 495

Leu Pro Pro Gly Phe Asn Glu Tyr Asp Phe Val Pro Glu Ser Phe Asp
            500                 505                 510

Arg Asp Lys Thr Ile Ala Leu Ile Met Asn Ser Ser Gly Ser Thr Gly
        515                 520                 525

Leu Pro Lys Gly Val Ala Leu Pro His Arg Thr Ala Cys Val Arg Phe
    530                 535                 540

Ser His Ala Arg Asp Pro Ile Phe Gly Asn Gln Ile Ile Pro Asp Thr
545                 550                 555                 560

Ala Ile Leu Ser Val Val Pro Phe His His Gly Phe Gly Met Phe Thr
                565                 570                 575

Thr Leu Gly Tyr Leu Ile Cys Gly Phe Arg Val Val Leu Met Tyr Arg
            580                 585                 590

Phe Glu Glu Glu Leu Phe Leu Arg Ser Leu Gln Asp Tyr Lys Ile Gln
        595                 600                 605

Ser Ala Leu Leu Val Pro Thr Leu Phe Ser Phe Phe Ala Lys Ser Thr
    610                 615                 620

Leu Ile Asp Lys Tyr Asp Leu Ser Asn Leu His Glu Ile Ala Ser Gly
625                 630                 635                 640

Gly Ala Pro Leu Ser Lys Glu Val Gly Glu Ala Val Ala Lys Arg Phe
                645                 650                 655

His Leu Pro Gly Ile Arg Gln Gly Tyr Gly Leu Thr Glu Thr Thr Ser
            660                 665                 670

Ala Ile Leu Ile Thr Pro Glu Gly
        675                 680
```

<210> SEQ ID NO 253
<211> LENGTH: 698
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 253

```
Met Pro Gly Ala Val Gly Lys Val Val Pro Phe Phe Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110
```

-continued

```
Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Ser Gly Gly
            180                 185                 190

Ser Gly Gly Ser Gly Gly Gly Ser Gly Gly Ser Gly Gly Ser Gly Trp
        195                 200                 205

Tyr Phe Gly Lys Ile Thr Arg Arg Glu Ser Glu Arg Leu Leu Leu Asn
    210                 215                 220

Ala Glu Asn Pro Arg Gly Thr Phe Leu Val Arg Glu Ser Glu Thr Thr
225                 230                 235                 240

Lys Gly Ala Tyr Cys Leu Ser Val Ser Asp Phe Asp Asn Ala Lys Gly
                245                 250                 255

Leu Asn Val Lys His Tyr Lys Ile Arg Lys Leu Asp Ser Gly Gly Phe
            260                 265                 270

Tyr Ile Thr Ser Arg Thr Gln Phe Asn Ser Leu Gln Gln Leu Val Ala
        275                 280                 285

Tyr Tyr Ser Lys His Ala Asp Gly Leu Cys His Arg Leu Thr Thr Val
    290                 295                 300

Cys Gly Ser Thr Ser Gly Ser Gly Lys Pro Gly Ser Gly Glu Gly Ser
305                 310                 315                 320

Glu Ile Tyr Gly Glu Phe Gly Ser Gly Gly Ser Gly Gly Ser Gly Gly
                325                 330                 335

Gly Ser Gly Gly Ser Gly Gly Ser Ser Gly Ala Lys Asn Ile Lys Lys
            340                 345                 350

Gly Pro Ala Pro Phe Tyr Pro Leu Glu Asp Gly Thr Ala Gly Glu Gln
        355                 360                 365

Leu His Lys Ala Met Lys Arg Tyr Ala Leu Val Pro Gly Thr Ile Ala
    370                 375                 380

Phe Thr Asp Ala His Ile Glu Val Asp Ile Thr Tyr Ala Glu Tyr Phe
385                 390                 395                 400

Glu Met Ser Val Arg Leu Ala Glu Ala Met Lys Arg Tyr Gly Leu Asn
                405                 410                 415

Thr Asn His Arg Ile Val Val Cys Ser Glu Asn Ser Leu Gln Phe Phe
            420                 425                 430

Met Pro Val Leu Gly Ala Leu Phe Ile Gly Val Ala Val Ala Pro Ala
        435                 440                 445

Asn Asp Ile Tyr Asn Glu Arg Glu Leu Leu Asn Ser Met Gly Ile Ser
    450                 455                 460

Gln Pro Thr Val Val Phe Val Ser Lys Lys Gly Leu Gln Lys Ile Leu
465                 470                 475                 480

Asn Val Gln Lys Lys Leu Pro Ile Ile Gln Lys Ile Ile Ile Met Asp
                485                 490                 495

Ser Lys Thr Asp Tyr Gln Gly Phe Gln Ser Met Tyr Thr Phe Val Thr
            500                 505                 510

Ser His Leu Pro Pro Gly Phe Asn Glu Tyr Asp Phe Val Pro Glu Ser
        515                 520                 525
```

```
Phe Asp Arg Asp Lys Thr Ile Ala Leu Ile Met Asn Ser Ser Gly Ser
    530                 535                 540

Thr Gly Leu Pro Lys Gly Val Ala Leu Pro His Arg Thr Ala Cys Val
545                 550                 555                 560

Arg Phe Ser His Ala Arg Asp Pro Ile Phe Gly Asn Gln Ile Ile Pro
                565                 570                 575

Asp Thr Ala Ile Leu Ser Val Val Pro Phe His His Gly Phe Gly Met
            580                 585                 590

Phe Thr Thr Leu Gly Tyr Leu Ile Cys Gly Phe Arg Val Val Leu Met
        595                 600                 605

Tyr Arg Phe Glu Glu Glu Leu Phe Leu Arg Ser Leu Gln Asp Tyr Lys
    610                 615                 620

Ile Gln Ser Ala Leu Leu Val Pro Thr Leu Phe Ser Phe Phe Ala Lys
625                 630                 635                 640

Ser Thr Leu Ile Asp Lys Tyr Asp Leu Ser Asn Leu His Glu Ile Ala
                645                 650                 655

Ser Gly Gly Ala Pro Leu Ser Lys Glu Val Gly Glu Ala Val Ala Lys
            660                 665                 670

Arg Phe His Leu Pro Gly Ile Arg Gln Gly Tyr Gly Leu Thr Glu Thr
        675                 680                 685

Thr Ser Ala Ile Leu Ile Thr Pro Glu Gly
    690                 695


<210> SEQ ID NO 254
<211> LENGTH: 668
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Met Asn Ser Leu Gln Phe Phe Met Pro Val Leu Gly Ala Leu Phe Ile
1               5                   10                  15

Gly Val Ala Val Ala Pro Ala Asn Asp Ile Tyr Asn Glu Arg Glu Leu
            20                  25                  30

Leu Asn Ser Met Gly Ile Ser Gln Pro Thr Val Val Phe Val Ser Lys
        35                  40                  45

Lys Gly Leu Gln Lys Ile Leu Asn Val Gln Lys Lys Leu Pro Ile Ile
    50                  55                  60

Gln Lys Ile Ile Ile Met Asp Ser Lys Thr Asp Tyr Gln Gly Phe Gln
65                  70                  75                  80

Ser Met Tyr Thr Phe Val Thr Ser His Leu Pro Pro Gly Phe Asn Glu
                85                  90                  95

Tyr Asp Phe Val Pro Glu Ser Phe Asp Arg Asp Lys Thr Ile Ala Leu
            100                 105                 110

Ile Met Asn Ser Ser Gly Ser Thr Gly Leu Pro Lys Gly Val Ala Leu
        115                 120                 125

Pro His Arg Thr Ala Cys Val Arg Phe Ser His Ala Arg Asp Pro Ile
    130                 135                 140

Phe Gly Asn Gln Ile Ile Pro Asp Thr Ala Ile Leu Ser Val Val Pro
145                 150                 155                 160

Phe His His Gly Phe Gly Met Phe Thr Thr Leu Gly Tyr Leu Ile Cys
                165                 170                 175

Gly Phe Arg Val Val Leu Met Tyr Arg Phe Glu Glu Glu Leu Phe Leu
            180                 185                 190
```

-continued

```
Arg Ser Leu Gln Asp Tyr Lys Ile Gln Ser Ala Leu Leu Val Pro Thr
        195                 200                 205

Leu Phe Ser Phe Phe Ala Lys Ser Thr Leu Ile Asp Lys Tyr Asp Leu
    210                 215                 220

Ser Asn Leu His Glu Ile Ala Ser Gly Gly Ala Pro Leu Ser Lys Glu
225                 230                 235                 240

Val Gly Glu Ala Val Ala Lys Arg Phe His Leu Pro Gly Ile Arg Gln
                245                 250                 255

Gly Tyr Gly Leu Thr Glu Thr Thr Ser Ala Ile Leu Ile Thr Pro Glu
            260                 265                 270

Gly Asp Asp Lys Pro Gly Ala Val Gly Lys Val Val Pro Phe Phe Glu
        275                 280                 285

Ala Lys Val Val Asp Leu Asp Thr Gly Lys Thr Leu Gly Val Asn Gln
    290                 295                 300

Arg Gly Glu Leu Cys Val Arg Gly Pro Met Ile Met Ser Gly Tyr Val
305                 310                 315                 320

Asn Asn Pro Glu Ala Thr Asn Ala Leu Ile Asp Lys Asp Gly Trp Leu
                325                 330                 335

His Ser Gly Asp Ile Ala Tyr Trp Asp Glu Asp Glu His Phe Phe Ile
            340                 345                 350

Val Asp Arg Leu Lys Ser Leu Ile Lys Tyr Lys Gly Tyr Gln Val Ala
        355                 360                 365

Pro Ala Glu Leu Glu Ser Ile Leu Leu Gln His Pro Asn Ile Phe Asp
    370                 375                 380

Ala Gly Val Ala Gly Leu Pro Asp Asp Asp Ala Gly Glu Leu Pro Ala
385                 390                 395                 400

Ala Val Val Val Leu Glu His Gly Lys Thr Met Thr Glu Lys Glu Ile
                405                 410                 415

Val Asp Tyr Val Ala Ser Gln Val Thr Thr Ala Lys Lys Leu Arg Gly
            420                 425                 430

Gly Val Val Phe Val Asp Glu Val Pro Lys Gly Leu Thr Gly Lys Leu
        435                 440                 445

Asp Ala Arg Lys Ile Arg Glu Ile Leu Ile Lys Ala Lys Lys Gly Ser
    450                 455                 460

Ser Gly Trp Tyr Phe Gly Lys Ile Thr Arg Arg Glu Ser Glu Arg Leu
465                 470                 475                 480

Leu Leu Asn Ala Glu Asn Pro Arg Gly Thr Phe Leu Val Arg Glu Ser
                485                 490                 495

Glu Thr Thr Lys Gly Ala Tyr Cys Leu Ser Val Ser Asp Phe Asp Asn
            500                 505                 510

Ala Lys Gly Leu Asn Val Lys His Tyr Lys Ile Arg Lys Leu Asp Ser
        515                 520                 525

Gly Gly Phe Tyr Ile Thr Ser Arg Thr Gln Phe Asn Ser Leu Gln Gln
    530                 535                 540

Leu Val Ala Tyr Tyr Ser Lys His Ala Asp Gly Leu Cys His Arg Leu
545                 550                 555                 560

Thr Thr Val Cys Gly Ser Thr Ser Gly Ser Gly Lys Pro Gly Ser Gly
                565                 570                 575

Glu Gly Ser Glu Ile Tyr Gly Glu Phe Gly Ser Ser Gly Ala Lys Asn
            580                 585                 590

Ile Lys Lys Gly Pro Ala Pro Phe Tyr Pro Leu Glu Asp Gly Thr Ala
        595                 600                 605
```

Gly Glu Gln Leu His Lys Ala Met Lys Arg Tyr Ala Leu Val Pro Gly
610 615 620

Thr Ile Ala Phe Thr Asp Ala His Ile Glu Val Asp Ile Thr Tyr Ala
625 630 635 640

Glu Tyr Phe Glu Met Ser Val Arg Leu Ala Glu Ala Met Lys Arg Tyr
645 650 655

Gly Leu Asn Thr Asn His Arg Ile Val Val Cys Ser
660 665

<210> SEQ ID NO 255
<211> LENGTH: 680
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 255

Met Asn Ser Leu Gln Phe Phe Met Pro Val Leu Gly Ala Leu Phe Ile
1 5 10 15

Gly Val Ala Val Ala Pro Ala Asn Asp Ile Tyr Asn Glu Arg Glu Leu
20 25 30

Leu Asn Ser Met Gly Ile Ser Gln Pro Thr Val Val Phe Val Ser Lys
35 40 45

Lys Gly Leu Gln Lys Ile Leu Asn Val Gln Lys Lys Leu Pro Ile Ile
50 55 60

Gln Lys Ile Ile Ile Met Asp Ser Lys Thr Asp Tyr Gln Gly Phe Gln
65 70 75 80

Ser Met Tyr Thr Phe Val Thr Ser His Leu Pro Pro Gly Phe Asn Glu
85 90 95

Tyr Asp Phe Val Pro Glu Ser Phe Asp Arg Asp Lys Thr Ile Ala Leu
100 105 110

Ile Met Asn Ser Ser Gly Ser Thr Gly Leu Pro Lys Gly Val Ala Leu
115 120 125

Pro His Arg Thr Ala Cys Val Arg Phe Ser His Ala Arg Asp Pro Ile
130 135 140

Phe Gly Asn Gln Ile Ile Pro Asp Thr Ala Ile Leu Ser Val Val Pro
145 150 155 160

Phe His His Gly Phe Gly Met Phe Thr Thr Leu Gly Tyr Leu Ile Cys
165 170 175

Gly Phe Arg Val Val Leu Met Tyr Arg Phe Glu Glu Glu Leu Phe Leu
180 185 190

Arg Ser Leu Gln Asp Tyr Lys Ile Gln Ser Ala Leu Leu Val Pro Thr
195 200 205

Leu Phe Ser Phe Phe Ala Lys Ser Thr Leu Ile Asp Lys Tyr Asp Leu
210 215 220

Ser Asn Leu His Glu Ile Ala Ser Gly Gly Ala Pro Leu Ser Lys Glu
225 230 235 240

Val Gly Glu Ala Val Ala Lys Arg Phe His Leu Pro Gly Ile Arg Gln
245 250 255

Gly Tyr Gly Leu Thr Glu Thr Thr Ser Ala Ile Leu Ile Thr Pro Glu
260 265 270

Gly Asp Asp Lys Pro Gly Ala Val Gly Lys Val Val Pro Phe Phe Glu
275 280 285

Ala Lys Val Val Asp Leu Asp Thr Gly Lys Thr Leu Gly Val Asn Gln
290 295 300

Arg Gly Glu Leu Cys Val Arg Gly Pro Met Ile Met Ser Gly Tyr Val
305 310 315 320

Asn Asn Pro Glu Ala Thr Asn Ala Leu Ile Asp Lys Asp Gly Trp Leu
325 330 335

His Ser Gly Asp Ile Ala Tyr Trp Asp Glu Asp Glu His Phe Phe Ile
340 345 350

Val Asp Arg Leu Lys Ser Leu Ile Lys Tyr Lys Gly Tyr Gln Val Ala
355 360 365

Pro Ala Glu Leu Glu Ser Ile Leu Leu Gln His Pro Asn Ile Phe Asp
370 375 380

Ala Gly Val Ala Gly Leu Pro Asp Asp Asp Ala Gly Glu Leu Pro Ala
385 390 395 400

Ala Val Val Val Leu Glu His Gly Lys Thr Met Thr Glu Lys Glu Ile
405 410 415

Val Asp Tyr Val Ala Ser Gln Val Thr Thr Ala Lys Lys Leu Arg Gly
420 425 430

Gly Val Val Phe Val Asp Glu Val Pro Lys Gly Leu Thr Gly Lys Leu
435 440 445

Asp Ala Arg Lys Ile Arg Glu Ile Leu Ile Lys Ala Lys Lys Gly Ser
450 455 460

Ser Gly Gly Ser Gly Gly Ser Gly Trp Tyr Phe Gly Lys Ile Thr Arg
465 470 475 480

Arg Glu Ser Glu Arg Leu Leu Leu Asn Ala Glu Asn Pro Arg Gly Thr
485 490 495

Phe Leu Val Arg Glu Ser Glu Thr Thr Lys Gly Ala Tyr Cys Leu Ser
500 505 510

Val Ser Asp Phe Asp Asn Ala Lys Gly Leu Asn Val Lys His Tyr Lys
515 520 525

Ile Arg Lys Leu Asp Ser Gly Gly Phe Tyr Ile Thr Ser Arg Thr Gln
530 535 540

Phe Asn Ser Leu Gln Gln Leu Val Ala Tyr Tyr Ser Lys His Ala Asp
545 550 555 560

Gly Leu Cys His Arg Leu Thr Thr Val Cys Gly Ser Thr Ser Gly Ser
565 570 575

Gly Lys Pro Gly Ser Gly Glu Gly Ser Glu Ile Tyr Gly Glu Phe Gly
580 585 590

Ser Gly Gly Ser Gly Gly Ser Ser Gly Ala Lys Asn Ile Lys Lys Gly
595 600 605

Pro Ala Pro Phe Tyr Pro Leu Glu Asp Gly Thr Ala Gly Glu Gln Leu
610 615 620

His Lys Ala Met Lys Arg Tyr Ala Leu Val Pro Gly Thr Ile Ala Phe
625 630 635 640

Thr Asp Ala His Ile Glu Val Asp Ile Thr Tyr Ala Glu Tyr Phe Glu
645 650 655

Met Ser Val Arg Leu Ala Glu Ala Met Lys Arg Tyr Gly Leu Asn Thr
660 665 670

Asn His Arg Ile Val Val Cys Ser
675 680

<210> SEQ ID NO 256
<211> LENGTH: 668
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 256

```
Met Leu His Glu Ile Ala Ser Gly Gly Ala Pro Leu Ser Lys Glu Val
1               5                   10                  15

Gly Glu Ala Val Ala Lys Arg Phe His Leu Pro Gly Ile Arg Gln Gly
            20                  25                  30

Tyr Gly Leu Thr Glu Thr Thr Ser Ala Ile Leu Ile Thr Pro Glu Gly
        35                  40                  45

Asp Asp Lys Pro Gly Ala Val Gly Lys Val Val Pro Phe Phe Glu Ala
    50                  55                  60

Lys Val Val Asp Leu Asp Thr Gly Lys Thr Leu Gly Val Asn Gln Arg
65                  70                  75                  80

Gly Glu Leu Cys Val Arg Gly Pro Met Ile Met Ser Gly Tyr Val Asn
                85                  90                  95

Asn Pro Glu Ala Thr Asn Ala Leu Ile Asp Lys Asp Gly Trp Leu His
            100                 105                 110

Ser Gly Asp Ile Ala Tyr Trp Asp Glu Asp Glu His Phe Phe Ile Val
        115                 120                 125

Asp Arg Leu Lys Ser Leu Ile Lys Tyr Lys Gly Tyr Gln Val Ala Pro
    130                 135                 140

Ala Glu Leu Glu Ser Ile Leu Leu Gln His Pro Asn Ile Phe Asp Ala
145                 150                 155                 160

Gly Val Ala Gly Leu Pro Asp Asp Asp Ala Gly Glu Leu Pro Ala Ala
                165                 170                 175

Val Val Val Leu Glu His Gly Lys Thr Met Thr Glu Lys Glu Ile Val
            180                 185                 190

Asp Tyr Val Ala Ser Gln Val Thr Thr Ala Lys Lys Leu Arg Gly Gly
        195                 200                 205

Val Val Phe Val Asp Glu Val Pro Lys Gly Leu Thr Gly Lys Leu Asp
    210                 215                 220

Ala Arg Lys Ile Arg Glu Ile Leu Ile Lys Ala Lys Lys Gly Ser Thr
225                 230                 235                 240

Gly Trp Tyr Phe Gly Lys Ile Thr Arg Arg Glu Ser Glu Arg Leu Leu
                245                 250                 255

Leu Asn Ala Glu Asn Pro Arg Gly Thr Phe Leu Val Arg Glu Ser Glu
            260                 265                 270

Thr Thr Lys Gly Ala Tyr Cys Leu Ser Val Ser Asp Phe Asp Asn Ala
        275                 280                 285

Lys Gly Leu Asn Val Lys His Tyr Lys Ile Arg Lys Leu Asp Ser Gly
    290                 295                 300

Gly Phe Tyr Ile Thr Ser Arg Thr Gln Phe Asn Ser Leu Gln Gln Leu
305                 310                 315                 320

Val Ala Tyr Tyr Ser Lys His Ala Asp Gly Leu Cys His Arg Leu Thr
                325                 330                 335

Thr Val Cys Gly Ser Thr Ser Gly Ser Gly Lys Pro Gly Ser Gly Glu
            340                 345                 350

Gly Ser Glu Ile Tyr Gly Glu Phe Gly Ser Ser Gly Ala Lys Asn Ile
        355                 360                 365

Lys Lys Gly Pro Ala Pro Phe Tyr Pro Leu Glu Asp Gly Thr Ala Gly
    370                 375                 380

Glu Gln Leu His Lys Ala Met Lys Arg Tyr Ala Leu Val Pro Gly Thr
385                 390                 395                 400
```

```
Ile Ala Phe Thr Asp Ala His Ile Glu Val Asp Ile Thr Tyr Ala Glu
                405                 410                 415

Tyr Phe Glu Met Ser Val Arg Leu Ala Glu Ala Met Lys Arg Tyr Gly
            420                 425                 430

Leu Asn Thr Asn His Arg Ile Val Val Cys Ser Glu Asn Ser Leu Gln
        435                 440                 445

Phe Phe Met Pro Val Leu Gly Ala Leu Phe Ile Gly Val Ala Val Ala
    450                 455                 460

Pro Ala Asn Asp Ile Tyr Asn Glu Arg Glu Leu Leu Asn Ser Met Gly
465                 470                 475                 480

Ile Ser Gln Pro Thr Val Val Phe Val Ser Lys Lys Gly Leu Gln Lys
                485                 490                 495

Ile Leu Asn Val Gln Lys Lys Leu Pro Ile Ile Gln Lys Ile Ile Ile
            500                 505                 510

Met Asp Ser Lys Thr Asp Tyr Gln Gly Phe Gln Ser Met Tyr Thr Phe
        515                 520                 525

Val Thr Ser His Leu Pro Pro Gly Phe Asn Glu Tyr Asp Phe Val Pro
    530                 535                 540

Glu Ser Phe Asp Arg Asp Lys Thr Ile Ala Leu Ile Met Asn Ser Ser
545                 550                 555                 560

Gly Ser Thr Gly Leu Pro Lys Gly Val Ala Leu Pro His Arg Thr Ala
                565                 570                 575

Cys Val Arg Phe Ser His Ala Arg Asp Pro Ile Phe Gly Asn Gln Ile
            580                 585                 590

Ile Pro Asp Thr Ala Ile Leu Ser Val Val Pro Phe His His Gly Phe
        595                 600                 605

Gly Met Phe Thr Thr Leu Gly Tyr Leu Ile Cys Gly Phe Arg Val Val
    610                 615                 620

Leu Met Tyr Arg Phe Glu Glu Glu Leu Phe Leu Arg Ser Leu Gln Asp
625                 630                 635                 640

Tyr Lys Ile Gln Ser Ala Leu Leu Val Pro Thr Leu Phe Ser Phe Phe
                645                 650                 655

Ala Lys Ser Thr Leu Ile Asp Lys Tyr Asp Leu Ser
            660                 665
```

<210> SEQ ID NO 257
<211> LENGTH: 682
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 257

```
Met Leu His Glu Ile Ala Ser Gly Gly Ala Pro Leu Ser Lys Glu Val
1               5                   10                  15

Gly Glu Ala Val Ala Lys Arg Phe His Leu Pro Gly Ile Arg Gln Gly
            20                  25                  30

Tyr Gly Leu Thr Glu Thr Thr Ser Ala Ile Leu Ile Thr Pro Glu Gly
        35                  40                  45

Asp Asp Lys Pro Gly Ala Val Gly Lys Val Val Pro Phe Phe Glu Ala
    50                  55                  60

Lys Val Val Asp Leu Asp Thr Gly Lys Thr Leu Gly Val Asn Gln Arg
65                  70                  75                  80

Gly Glu Leu Cys Val Arg Gly Pro Met Ile Met Ser Gly Tyr Val Asn
```

-continued

```
                85                  90                  95

Asn Pro Glu Ala Thr Asn Ala Leu Ile Asp Lys Asp Gly Trp Leu His
            100                 105                 110

Ser Gly Asp Ile Ala Tyr Trp Asp Glu Asp Glu His Phe Phe Ile Val
        115                 120                 125

Asp Arg Leu Lys Ser Leu Ile Lys Tyr Lys Gly Tyr Gln Val Ala Pro
    130                 135                 140

Ala Glu Leu Glu Ser Ile Leu Leu Gln His Pro Asn Ile Phe Asp Ala
145                 150                 155                 160

Gly Val Ala Gly Leu Pro Asp Asp Asp Ala Gly Glu Leu Pro Ala Ala
                165                 170                 175

Val Val Val Leu Glu His Gly Lys Thr Met Thr Glu Lys Glu Ile Val
            180                 185                 190

Asp Tyr Val Ala Ser Gln Val Thr Thr Ala Lys Lys Leu Arg Gly Gly
        195                 200                 205

Val Val Phe Val Asp Glu Val Pro Lys Gly Leu Thr Gly Lys Leu Asp
    210                 215                 220

Ala Arg Lys Ile Arg Glu Ile Leu Ile Lys Ala Lys Lys Gly Ser Ser
225                 230                 235                 240

Gly Gly Ser Gly Gly Ser Gly Trp Tyr Phe Gly Lys Ile Thr Arg Arg
                245                 250                 255

Glu Ser Glu Arg Leu Leu Leu Asn Ala Glu Asn Pro Arg Gly Thr Phe
            260                 265                 270

Leu Val Arg Glu Ser Glu Thr Thr Lys Gly Ala Tyr Cys Leu Ser Val
        275                 280                 285

Ser Asp Phe Asp Asn Ala Lys Gly Leu Asn Val Lys His Tyr Lys Ile
    290                 295                 300

Arg Lys Leu Asp Ser Gly Gly Phe Tyr Ile Thr Ser Arg Thr Gln Phe
305                 310                 315                 320

Asn Ser Leu Gln Gln Leu Val Ala Tyr Tyr Ser Lys His Ala Asp Gly
                325                 330                 335

Leu Cys His Arg Leu Thr Thr Val Cys Gly Ser Thr Ser Gly Ser Gly
            340                 345                 350

Lys Pro Gly Ser Gly Glu Gly Ser Glu Ile Tyr Gly Glu Phe Gly Ser
        355                 360                 365

Gly Ser Gly Gly Ser Gly Gly Ser Ser Gly Ala Lys Asn Ile Lys Lys
    370                 375                 380

Gly Pro Ala Pro Phe Tyr Pro Leu Glu Asp Gly Thr Ala Gly Glu Gln
385                 390                 395                 400

Leu His Lys Ala Met Lys Arg Tyr Ala Leu Val Pro Gly Thr Ile Ala
                405                 410                 415

Phe Thr Asp Ala His Ile Glu Val Asp Ile Thr Tyr Ala Glu Tyr Phe
            420                 425                 430

Glu Met Ser Val Arg Leu Ala Glu Ala Met Lys Arg Tyr Gly Leu Asn
        435                 440                 445

Thr Asn His Arg Ile Val Val Cys Ser Glu Asn Ser Leu Gln Phe Phe
    450                 455                 460

Met Pro Val Leu Gly Ala Leu Phe Ile Gly Val Ala Val Ala Pro Ala
465                 470                 475                 480

Asn Asp Ile Tyr Asn Glu Arg Glu Leu Leu Asn Ser Met Gly Ile Ser
                485                 490                 495

Gln Pro Thr Val Val Phe Val Ser Lys Lys Gly Leu Gln Lys Ile Leu
            500                 505                 510
```

```
Asn Val Gln Lys Lys Leu Pro Ile Ile Gln Lys Ile Ile Ile Met Asp
        515                 520                 525

Ser Lys Thr Asp Tyr Gln Gly Phe Gln Ser Met Tyr Thr Phe Val Thr
    530                 535                 540

Ser His Leu Pro Pro Gly Phe Asn Glu Tyr Asp Phe Val Pro Glu Ser
545                 550                 555                 560

Phe Asp Arg Asp Lys Thr Ile Ala Leu Ile Met Asn Ser Ser Gly Ser
                565                 570                 575

Thr Gly Leu Pro Lys Gly Val Ala Leu Pro His Arg Thr Ala Cys Val
            580                 585                 590

Arg Phe Ser His Ala Arg Asp Pro Ile Phe Gly Asn Gln Ile Ile Pro
        595                 600                 605

Asp Thr Ala Ile Leu Ser Val Val Pro Phe His His Gly Phe Gly Met
    610                 615                 620

Phe Thr Thr Leu Gly Tyr Leu Ile Cys Gly Phe Arg Val Val Leu Met
625                 630                 635                 640

Tyr Arg Phe Glu Glu Glu Leu Phe Leu Arg Ser Leu Gln Asp Tyr Lys
                645                 650                 655

Ile Gln Ser Ala Leu Leu Val Pro Thr Leu Phe Ser Phe Phe Ala Lys
            660                 665                 670

Ser Thr Leu Ile Asp Lys Tyr Asp Leu Ser
        675                 680


<210> SEQ ID NO 258
<211> LENGTH: 700
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Met Leu His Glu Ile Ala Ser Gly Gly Ala Pro Leu Ser Lys Glu Val
1               5                   10                  15

Gly Glu Ala Val Ala Lys Arg Phe His Leu Pro Gly Ile Arg Gln Gly
            20                  25                  30

Tyr Gly Leu Thr Glu Thr Thr Ser Ala Ile Leu Ile Thr Pro Glu Gly
        35                  40                  45

Asp Asp Lys Pro Gly Ala Val Gly Lys Val Val Pro Phe Phe Glu Ala
    50                  55                  60

Lys Val Val Asp Leu Asp Thr Gly Lys Thr Leu Gly Val Asn Gln Arg
65                  70                  75                  80

Gly Glu Leu Cys Val Arg Gly Pro Met Ile Met Ser Gly Tyr Val Asn
                85                  90                  95

Asn Pro Glu Ala Thr Asn Ala Leu Ile Asp Lys Asp Gly Trp Leu His
            100                 105                 110

Ser Gly Asp Ile Ala Tyr Trp Asp Glu Asp Glu His Phe Phe Ile Val
        115                 120                 125

Asp Arg Leu Lys Ser Leu Ile Lys Tyr Lys Gly Tyr Gln Val Ala Pro
    130                 135                 140

Ala Glu Leu Glu Ser Ile Leu Leu Gln His Pro Asn Ile Phe Asp Ala
145                 150                 155                 160

Gly Val Ala Gly Leu Pro Asp Asp Asp Ala Gly Glu Leu Pro Ala Ala
                165                 170                 175

Val Val Val Leu Glu His Gly Lys Thr Met Thr Glu Lys Glu Ile Val
```

```
            180                 185                 190

Asp Tyr Val Ala Ser Gln Val Thr Thr Ala Lys Lys Leu Arg Gly Gly
        195                 200                 205

Val Val Phe Val Asp Glu Val Pro Lys Gly Leu Thr Gly Lys Leu Asp
    210                 215                 220

Ala Arg Lys Ile Arg Glu Ile Leu Ile Lys Ala Lys Lys Gly Ser Ser
225                 230                 235                 240

Gly Gly Ser Gly Gly Ser Gly Gly Gly Ser Gly Gly Ser Gly Gly Ser
                245                 250                 255

Gly Trp Tyr Phe Gly Lys Ile Thr Arg Arg Glu Ser Glu Arg Leu Leu
            260                 265                 270

Leu Asn Ala Glu Asn Pro Arg Gly Thr Phe Leu Val Arg Glu Ser Glu
        275                 280                 285

Thr Thr Lys Gly Ala Tyr Cys Leu Ser Val Ser Asp Phe Asp Asn Ala
    290                 295                 300

Lys Gly Leu Asn Val Lys His Tyr Lys Ile Arg Lys Leu Asp Ser Gly
305                 310                 315                 320

Gly Phe Tyr Ile Thr Ser Arg Thr Gln Phe Asn Ser Leu Gln Gln Leu
                325                 330                 335

Val Ala Tyr Tyr Ser Lys His Ala Asp Gly Leu Cys His Arg Leu Thr
            340                 345                 350

Thr Val Cys Gly Ser Thr Ser Gly Ser Gly Lys Pro Gly Ser Gly Glu
        355                 360                 365

Gly Ser Glu Ile Tyr Gly Glu Phe Gly Ser Gly Gly Ser Gly Gly Ser
    370                 375                 380

Gly Gly Gly Ser Gly Gly Ser Gly Gly Ser Ser Gly Ala Lys Asn Ile
385                 390                 395                 400

Lys Lys Gly Pro Ala Pro Phe Tyr Pro Leu Glu Asp Gly Thr Ala Gly
                405                 410                 415

Glu Gln Leu His Lys Ala Met Lys Arg Tyr Ala Leu Val Pro Gly Thr
            420                 425                 430

Ile Ala Phe Thr Asp Ala His Ile Glu Val Asp Ile Thr Tyr Ala Glu
        435                 440                 445

Tyr Phe Glu Met Ser Val Arg Leu Ala Glu Ala Met Lys Arg Tyr Gly
    450                 455                 460

Leu Asn Thr Asn His Arg Ile Val Val Cys Ser Glu Asn Ser Leu Gln
465                 470                 475                 480

Phe Phe Met Pro Val Leu Gly Ala Leu Phe Ile Gly Val Ala Val Ala
                485                 490                 495

Pro Ala Asn Asp Ile Tyr Asn Glu Arg Glu Leu Leu Asn Ser Met Gly
            500                 505                 510

Ile Ser Gln Pro Thr Val Val Phe Val Ser Lys Lys Gly Leu Gln Lys
        515                 520                 525

Ile Leu Asn Val Gln Lys Lys Leu Pro Ile Ile Gln Lys Ile Ile Ile
    530                 535                 540

Met Asp Ser Lys Thr Asp Tyr Gln Gly Phe Gln Ser Met Tyr Thr Phe
545                 550                 555                 560

Val Thr Ser His Leu Pro Pro Gly Phe Asn Glu Tyr Asp Phe Val Pro
                565                 570                 575

Glu Ser Phe Asp Arg Asp Lys Thr Ile Ala Leu Ile Met Asn Ser Ser
            580                 585                 590

Gly Ser Thr Gly Leu Pro Lys Gly Val Ala Leu Pro His Arg Thr Ala
        595                 600                 605
```

Cys Val Arg Phe Ser His Ala Arg Asp Pro Ile Phe Gly Asn Gln Ile
    610                 615                 620

Ile Pro Asp Thr Ala Ile Leu Ser Val Val Pro Phe His His Gly Phe
625                 630                 635                 640

Gly Met Phe Thr Thr Leu Gly Tyr Leu Ile Cys Gly Phe Arg Val Val
                645                 650                 655

Leu Met Tyr Arg Phe Glu Glu Glu Leu Phe Leu Arg Ser Leu Gln Asp
            660                 665                 670

Tyr Lys Ile Gln Ser Ala Leu Leu Val Pro Thr Leu Phe Ser Phe Phe
        675                 680                 685

Ala Lys Ser Thr Leu Ile Asp Lys Tyr Asp Leu Ser
    690                 695                 700

<210> SEQ ID NO 259
<211> LENGTH: 437
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Met Ala Glu Asn Ala Val Ile Phe Leu His Gly Asn Ala Ala Ser Ser
1               5                   10                  15

Tyr Leu Trp Arg His Val Val Pro His Ile Glu Pro Val Ala Arg Cys
            20                  25                  30

Ile Ile Pro Asp Leu Ile Gly Met Gly Lys Ser Gly Lys Ser Gly Asn
        35                  40                  45

Gly Ser Tyr Arg Leu Leu Asp His Tyr Lys Tyr Leu Thr Ala Trp Phe
    50                  55                  60

Glu Leu Leu Asn Leu Pro Lys Lys Ile Ile Phe Val Gly His Asp Trp
65                  70                  75                  80

Gly Ala Cys Leu Ala Phe His Tyr Ser Tyr Glu His Gln Asp Lys Ile
                85                  90                  95

Lys Ala Ile Val His Ala Glu Ser Val Val Asp Val Ile Glu Ser Trp
            100                 105                 110

Asp Glu Trp Pro Asp Ile Glu Glu Asp Ile Ala Leu Ile Lys Ser Glu
        115                 120                 125

Glu Gly Glu Lys Met Val Leu Glu Asn Asn Phe Phe Val Glu Thr Met
    130                 135                 140

Leu Pro Ser Lys Ile Met Arg Lys Leu Glu Pro Glu Glu Phe Ala Ala
145                 150                 155                 160

Tyr Leu Glu Pro Phe Lys Glu Lys Gly Glu Val Arg Arg Pro Thr Leu
                165                 170                 175

Ser Trp Pro Arg Glu Ile Pro Leu Val Lys Gly Gly Lys Pro Asp Val
            180                 185                 190

Val Gln Ile Val Arg Asn Tyr Asn Ala Tyr Leu Arg Ala Ser Asp Asp
        195                 200                 205

Leu Pro Lys Met Phe Ile Glu Ser Asp Pro Gly Phe Phe Ser Asn Ala
    210                 215                 220

Ile Val Glu Gly Ala Lys Lys Phe Pro Asn Thr Glu Phe Val Lys Val
225                 230                 235                 240

Lys Gly Leu His Phe Ser Gln Glu Asp Ala Pro Asp Glu Met Gly Lys
                245                 250                 255

Tyr Ile Lys Ser Phe Val Glu Arg Val Leu Lys Asn Glu Gln Gly Ser

```
            260                 265                 270

Ser Gly Trp Tyr Phe Gly Lys Ile Thr Arg Arg Glu Ser Glu Arg Leu
        275                 280                 285

Leu Leu Asn Ala Glu Asn Pro Arg Gly Thr Phe Leu Val Arg Glu Ser
    290                 295                 300

Glu Thr Thr Lys Gly Ala Tyr Cys Leu Ser Val Ser Asp Phe Asp Asn
305                 310                 315                 320

Ala Lys Gly Leu Asn Val Lys His Tyr Lys Ile Arg Lys Leu Asp Ser
                325                 330                 335

Gly Gly Phe Tyr Ile Thr Ser Arg Thr Gln Phe Asn Ser Leu Gln Gln
            340                 345                 350

Leu Val Ala Tyr Tyr Ser Lys His Ala Asp Gly Leu Cys His Arg Leu
        355                 360                 365

Thr Thr Val Cys Gly Ser Thr Ser Gly Ser Gly Lys Pro Gly Ser Gly
    370                 375                 380

Glu Gly Ser Glu Ile Tyr Gly Glu Phe Gly Ser Ser Gly Thr Ser Lys
385                 390                 395                 400

Val Tyr Asp Pro Glu Gln Arg Lys Arg Met Ile Thr Gly Pro Gln Trp
                405                 410                 415

Trp Ala Arg Cys Lys Gln Met Asn Val Leu Asp Ser Phe Ile Asn Tyr
            420                 425                 430

Tyr Asp Ser Glu Lys
        435


<210> SEQ ID NO 260
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Met Ala Glu Asn Ala Val Ile Phe Leu His Gly Asn Ala Ala Ser Ser
1               5                   10                  15

Tyr Leu Trp Arg His Val Val Pro His Ile Glu Pro Val Ala Arg Cys
            20                  25                  30

Ile Ile Pro Asp Leu Ile Gly Met Gly Lys Ser Gly Lys Ser Gly Asn
        35                  40                  45

Gly Ser Tyr Arg Leu Leu Asp His Tyr Lys Tyr Leu Thr Ala Trp Phe
    50                  55                  60

Glu Leu Leu Asn Leu Pro Lys Lys Ile Ile Phe Val Gly His Asp Trp
65                  70                  75                  80

Gly Ala Cys Leu Ala Phe His Tyr Ser Tyr Glu His Gln Asp Lys Ile
                85                  90                  95

Lys Ala Ile Val His Ala Glu Ser Val Val Asp Val Ile Glu Ser Trp
            100                 105                 110

Asp Glu Trp Pro Asp Ile Glu Glu Asp Ile Ala Leu Ile Lys Ser Glu
        115                 120                 125

Glu Gly Glu Lys Met Val Leu Glu Asn Asn Phe Phe Val Glu Thr Met
    130                 135                 140

Leu Pro Ser Lys Ile Met Arg Lys Leu Glu Pro Glu Glu Phe Ala Ala
145                 150                 155                 160

Tyr Leu Glu Pro Phe Lys Glu Lys Gly Glu Val Arg Arg Pro Thr Leu
                165                 170                 175
```

```
Ser Trp Pro Arg Glu Ile Pro Leu Val Lys Gly Gly Lys Pro Asp Val
            180                 185                 190

Val Gln Ile Val Arg Asn Tyr Asn Ala Tyr Leu Arg Ala Ser Asp Asp
        195                 200                 205

Leu Pro Lys Met Phe Ile Glu Ser Asp Pro Gly Phe Phe Ser Asn Ala
    210                 215                 220

Ile Val Glu Gly Ala Lys Lys Phe Pro Asn Thr Glu Phe Val Lys Val
225                 230                 235                 240

Lys Gly Leu His Phe Ser Gln Glu Asp Ala Pro Asp Glu Met Gly Lys
                245                 250                 255

Tyr Ile Lys Ser Phe Val Glu Arg Val Leu Lys Asn Glu Gln Gly Ser
            260                 265                 270

Ser Gly Gly Ser Gly Gly Ser Gly Trp Tyr Phe Gly Lys Ile Thr Arg
        275                 280                 285

Arg Glu Ser Glu Arg Leu Leu Leu Asn Ala Glu Asn Pro Arg Gly Thr
    290                 295                 300

Phe Leu Val Arg Glu Ser Glu Thr Thr Lys Gly Ala Tyr Cys Leu Ser
305                 310                 315                 320

Val Ser Asp Phe Asp Asn Ala Lys Gly Leu Asn Val Lys His Tyr Lys
                325                 330                 335

Ile Arg Lys Leu Asp Ser Gly Gly Phe Tyr Ile Thr Ser Arg Thr Gln
            340                 345                 350

Phe Asn Ser Leu Gln Gln Leu Val Ala Tyr Tyr Ser Lys His Ala Asp
        355                 360                 365

Gly Leu Cys His Arg Leu Thr Thr Val Cys Gly Ser Thr Ser Gly Ser
    370                 375                 380

Gly Lys Pro Gly Ser Gly Glu Gly Ser Glu Ile Tyr Gly Glu Phe Gly
385                 390                 395                 400

Ser Gly Ser Gly Gly Ser Gly Gly Ser Ser Gly Thr Ser Lys Val Tyr
                405                 410                 415

Asp Pro Glu Gln Arg Lys Arg Met Ile Thr Gly Pro Gln Trp Trp Ala
            420                 425                 430

Arg Cys Lys Gln Met Asn Val Leu Asp Ser Phe Ile Asn Tyr Tyr Asp
        435                 440                 445

Ser Glu Lys
    450


<210> SEQ ID NO 261
<211> LENGTH: 437
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Met Lys Lys Ile Ile Phe Val Gly His Asp Trp Gly Ala Cys Leu Ala
1               5                   10                  15

Phe His Tyr Ser Tyr Glu His Gln Asp Lys Ile Lys Ala Ile Val His
            20                  25                  30

Ala Glu Ser Val Val Asp Val Ile Glu Ser Trp Asp Glu Trp Pro Asp
        35                  40                  45

Ile Glu Glu Asp Ile Ala Leu Ile Lys Ser Glu Glu Gly Glu Lys Met
    50                  55                  60

Val Leu Glu Asn Asn Phe Phe Val Glu Thr Met Leu Pro Ser Lys Ile
65                  70                  75                  80
```

```
Met Arg Lys Leu Glu Pro Glu Glu Phe Ala Ala Tyr Leu Glu Pro Phe
                85                  90                  95

Lys Glu Lys Gly Glu Val Arg Arg Pro Thr Leu Ser Trp Pro Arg Glu
            100                 105                 110

Ile Pro Leu Val Lys Gly Gly Lys Pro Asp Val Val Gln Ile Val Arg
        115                 120                 125

Asn Tyr Asn Ala Tyr Leu Arg Ala Ser Asp Asp Leu Pro Lys Met Phe
    130                 135                 140

Ile Glu Ser Asp Pro Gly Phe Phe Ser Asn Ala Ile Val Glu Gly Ala
145                 150                 155                 160

Lys Lys Phe Pro Asn Thr Glu Phe Val Lys Val Lys Gly Leu His Phe
                165                 170                 175

Ser Gln Glu Asp Ala Pro Asp Glu Met Gly Lys Tyr Ile Lys Ser Phe
            180                 185                 190

Val Glu Arg Val Leu Lys Asn Glu Gln Gly Ser Ser Gly Trp Tyr Phe
        195                 200                 205

Gly Lys Ile Thr Arg Arg Glu Ser Glu Arg Leu Leu Leu Asn Ala Glu
    210                 215                 220

Asn Pro Arg Gly Thr Phe Leu Val Arg Glu Ser Glu Thr Thr Lys Gly
225                 230                 235                 240

Ala Tyr Cys Leu Ser Val Ser Asp Phe Asp Asn Ala Lys Gly Leu Asn
                245                 250                 255

Val Lys His Tyr Lys Ile Arg Lys Leu Asp Ser Gly Gly Phe Tyr Ile
            260                 265                 270

Thr Ser Arg Thr Gln Phe Asn Ser Leu Gln Gln Leu Val Ala Tyr Tyr
        275                 280                 285

Ser Lys His Ala Asp Gly Leu Cys His Arg Leu Thr Thr Val Cys Gly
    290                 295                 300

Ser Thr Ser Gly Ser Gly Lys Pro Gly Ser Gly Glu Gly Ser Glu Ile
305                 310                 315                 320

Tyr Gly Glu Phe Gly Ser Ser Gly Thr Ser Lys Val Tyr Asp Pro Glu
                325                 330                 335

Gln Arg Lys Arg Met Ile Thr Gly Pro Gln Trp Trp Ala Arg Cys Lys
            340                 345                 350

Gln Met Asn Val Leu Asp Ser Phe Ile Asn Tyr Tyr Asp Ser Glu Lys
        355                 360                 365

His Ala Glu Asn Ala Val Ile Phe Leu His Gly Asn Ala Ala Ser Ser
    370                 375                 380

Tyr Leu Trp Arg His Val Val Pro His Ile Glu Pro Val Ala Arg Cys
385                 390                 395                 400

Ile Ile Pro Asp Leu Ile Gly Met Gly Lys Ser Gly Lys Ser Gly Asn
                405                 410                 415

Gly Ser Tyr Arg Leu Leu Asp His Tyr Lys Tyr Leu Thr Ala Trp Phe
            420                 425                 430

Glu Leu Leu Asn Leu
        435
```

<210> SEQ ID NO 262
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 262

Met Lys Lys Ile Ile Phe Val Gly His Asp Trp Gly Ala Cys Leu Ala
1               5                   10                  15

Phe His Tyr Ser Tyr Glu His Gln Asp Lys Ile Lys Ala Ile Val His
            20                  25                  30

Ala Glu Ser Val Val Asp Val Ile Glu Ser Trp Asp Glu Trp Pro Asp
        35                  40                  45

Ile Glu Glu Asp Ile Ala Leu Ile Lys Ser Glu Glu Gly Glu Lys Met
    50                  55                  60

Val Leu Glu Asn Asn Phe Phe Val Glu Thr Met Leu Pro Ser Lys Ile
65                  70                  75                  80

Met Arg Lys Leu Glu Pro Glu Glu Phe Ala Ala Tyr Leu Glu Pro Phe
                85                  90                  95

Lys Glu Lys Gly Glu Val Arg Arg Pro Thr Leu Ser Trp Pro Arg Glu
            100                 105                 110

Ile Pro Leu Val Lys Gly Gly Lys Pro Asp Val Val Gln Ile Val Arg
        115                 120                 125

Asn Tyr Asn Ala Tyr Leu Arg Ala Ser Asp Asp Leu Pro Lys Met Phe
    130                 135                 140

Ile Glu Ser Asp Pro Gly Phe Phe Ser Asn Ala Ile Val Glu Gly Ala
145                 150                 155                 160

Lys Lys Phe Pro Asn Thr Glu Phe Val Lys Val Lys Gly Leu His Phe
                165                 170                 175

Ser Gln Glu Asp Ala Pro Asp Glu Met Gly Lys Tyr Ile Lys Ser Phe
            180                 185                 190

Val Glu Arg Val Leu Lys Asn Glu Gln Gly Ser Ser Gly Gly Ser Gly
        195                 200                 205

Gly Ser Gly Trp Tyr Phe Gly Lys Ile Thr Arg Arg Glu Ser Glu Arg
    210                 215                 220

Leu Leu Leu Asn Ala Glu Asn Pro Arg Gly Thr Phe Leu Val Arg Glu
225                 230                 235                 240

Ser Glu Thr Thr Lys Gly Ala Tyr Cys Leu Ser Val Ser Asp Phe Asp
                245                 250                 255

Asn Ala Lys Gly Leu Asn Val Lys His Tyr Lys Ile Arg Lys Leu Asp
            260                 265                 270

Ser Gly Gly Phe Tyr Ile Thr Ser Arg Thr Gln Phe Asn Ser Leu Gln
        275                 280                 285

Gln Leu Val Ala Tyr Tyr Ser Lys His Ala Asp Gly Leu Cys His Arg
    290                 295                 300

Leu Thr Thr Val Cys Gly Ser Thr Ser Gly Ser Gly Lys Pro Gly Ser
305                 310                 315                 320

Gly Glu Gly Ser Glu Ile Tyr Gly Glu Phe Gly Ser Gly Ser Gly Gly
                325                 330                 335

Ser Gly Gly Ser Ser Gly Thr Ser Lys Val Tyr Asp Pro Glu Gln Arg
            340                 345                 350

Lys Arg Met Ile Thr Gly Pro Gln Trp Trp Ala Arg Cys Lys Gln Met
        355                 360                 365

Asn Val Leu Asp Ser Phe Ile Asn Tyr Tyr Asp Ser Glu Lys His Ala
    370                 375                 380

Glu Asn Ala Val Ile Phe Leu His Gly Asn Ala Ala Ser Ser Tyr Leu
385                 390                 395                 400

Trp Arg His Val Val Pro His Ile Glu Pro Val Ala Arg Cys Ile Ile
                405                 410                 415

```
Pro Asp Leu Ile Gly Met Gly Lys Ser Gly Lys Ser Gly Asn Gly Ser
            420                 425                 430

Tyr Arg Leu Leu Asp His Tyr Lys Tyr Leu Thr Ala Trp Phe Glu Leu
        435                 440                 445

Leu Asn Leu
    450


<210> SEQ ID NO 263
<211> LENGTH: 437
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Met Ser Phe Ile Asn Tyr Tyr Asp Ser Glu Lys His Ala Glu Asn Ala
1               5                   10                  15

Val Ile Phe Leu His Gly Asn Ala Ala Ser Ser Tyr Leu Trp Arg His
            20                  25                  30

Val Val Pro His Ile Glu Pro Val Ala Arg Cys Ile Ile Pro Asp Leu
        35                  40                  45

Ile Gly Met Gly Lys Ser Gly Lys Ser Gly Asn Gly Ser Tyr Arg Leu
    50                  55                  60

Leu Asp His Tyr Lys Tyr Leu Thr Ala Trp Phe Glu Leu Leu Asn Leu
65                  70                  75                  80

Pro Lys Lys Ile Ile Phe Val Gly His Asp Trp Gly Ala Cys Leu Ala
                85                  90                  95

Phe His Tyr Ser Tyr Glu His Gln Asp Lys Ile Lys Ala Ile Val His
            100                 105                 110

Ala Glu Ser Val Val Asp Val Ile Glu Ser Trp Asp Glu Trp Pro Asp
        115                 120                 125

Ile Glu Glu Asp Ile Ala Leu Ile Lys Ser Glu Glu Gly Glu Lys Met
    130                 135                 140

Val Leu Glu Asn Asn Phe Phe Val Glu Thr Met Leu Pro Ser Lys Ile
145                 150                 155                 160

Met Arg Lys Leu Glu Pro Glu Glu Phe Ala Ala Tyr Leu Glu Pro Phe
                165                 170                 175

Lys Glu Lys Gly Glu Val Arg Arg Pro Thr Leu Ser Trp Pro Arg Glu
            180                 185                 190

Ile Pro Leu Val Lys Gly Gly Lys Pro Asp Val Val Gln Ile Val Arg
        195                 200                 205

Asn Tyr Asn Ala Tyr Leu Arg Ala Ser Asp Asp Leu Pro Lys Met Phe
    210                 215                 220

Ile Glu Ser Asp Pro Gly Phe Phe Ser Asn Ala Ile Val Glu Gly Ala
225                 230                 235                 240

Lys Lys Phe Pro Asn Thr Glu Phe Val Lys Val Lys Gly Leu His Phe
                245                 250                 255

Ser Gln Glu Asp Ala Pro Asp Glu Met Gly Lys Tyr Ile Lys Ser Phe
            260                 265                 270

Val Glu Arg Val Leu Lys Asn Glu Gln Gly Ser Ser Gly Trp Tyr Phe
        275                 280                 285

Gly Lys Ile Thr Arg Arg Glu Ser Glu Arg Leu Leu Leu Asn Ala Glu
    290                 295                 300

Asn Pro Arg Gly Thr Phe Leu Val Arg Glu Ser Glu Thr Thr Lys Gly
```

```
305                 310                 315                 320

Ala Tyr Cys Leu Ser Val Ser Asp Phe Asp Asn Ala Lys Gly Leu Asn
                325                 330                 335

Val Lys His Tyr Lys Ile Arg Lys Leu Asp Ser Gly Gly Phe Tyr Ile
            340                 345                 350

Thr Ser Arg Thr Gln Phe Asn Ser Leu Gln Gln Leu Val Ala Tyr Tyr
        355                 360                 365

Ser Lys His Ala Asp Gly Leu Cys His Arg Leu Thr Thr Val Cys Gly
    370                 375                 380

Ser Thr Ser Gly Ser Gly Lys Pro Gly Ser Gly Glu Gly Ser Glu Ile
385                 390                 395                 400

Tyr Gly Glu Phe Gly Ser Ser Gly Thr Ser Lys Val Tyr Asp Pro Glu
                405                 410                 415

Gln Arg Lys Arg Met Ile Thr Gly Pro Gln Trp Trp Ala Arg Cys Lys
            420                 425                 430

Gln Met Asn Val Leu
        435
```

<210> SEQ ID NO 264
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 264

```
Met Ser Phe Ile Asn Tyr Tyr Asp Ser Glu Lys His Ala Glu Asn Ala
1               5                   10                  15

Val Ile Phe Leu His Gly Asn Ala Ala Ser Ser Tyr Leu Trp Arg His
            20                  25                  30

Val Val Pro His Ile Glu Pro Val Ala Arg Cys Ile Ile Pro Asp Leu
        35                  40                  45

Ile Gly Met Gly Lys Ser Gly Lys Ser Gly Asn Gly Ser Tyr Arg Leu
    50                  55                  60

Leu Asp His Tyr Lys Tyr Leu Thr Ala Trp Phe Glu Leu Leu Asn Leu
65                  70                  75                  80

Pro Lys Lys Ile Ile Phe Val Gly His Asp Trp Gly Ala Cys Leu Ala
                85                  90                  95

Phe His Tyr Ser Tyr Glu His Gln Asp Lys Ile Lys Ala Ile Val His
            100                 105                 110

Ala Glu Ser Val Val Asp Val Ile Glu Ser Trp Asp Glu Trp Pro Asp
        115                 120                 125

Ile Glu Glu Asp Ile Ala Leu Ile Lys Ser Glu Glu Gly Glu Lys Met
    130                 135                 140

Val Leu Glu Asn Asn Phe Phe Val Glu Thr Met Leu Pro Ser Lys Ile
145                 150                 155                 160

Met Arg Lys Leu Glu Pro Glu Glu Phe Ala Ala Tyr Leu Glu Pro Phe
                165                 170                 175

Lys Glu Lys Gly Glu Val Arg Arg Pro Thr Leu Ser Trp Pro Arg Glu
            180                 185                 190

Ile Pro Leu Val Lys Gly Gly Lys Pro Asp Val Val Gln Ile Val Arg
        195                 200                 205

Asn Tyr Asn Ala Tyr Leu Arg Ala Ser Asp Asp Leu Pro Lys Met Phe
    210                 215                 220
```

Ile Glu Ser Asp Pro Gly Phe Phe Ser Asn Ala Ile Val Glu Gly Ala
225 230 235 240

Lys Lys Phe Pro Asn Thr Glu Phe Val Lys Val Lys Gly Leu His Phe
245 250 255

Ser Gln Glu Asp Ala Pro Asp Glu Met Gly Lys Tyr Ile Lys Ser Phe
260 265 270

Val Glu Arg Val Leu Lys Asn Glu Gln Gly Ser Ser Gly Gly Ser Gly
275 280 285

Gly Ser Gly Trp Tyr Phe Gly Lys Ile Thr Arg Arg Glu Ser Glu Arg
290 295 300

Leu Leu Leu Asn Ala Glu Asn Pro Arg Gly Thr Phe Leu Val Arg Glu
305 310 315 320

Ser Glu Thr Thr Lys Gly Ala Tyr Cys Leu Ser Val Ser Asp Phe Asp
325 330 335

Asn Ala Lys Gly Leu Asn Val Lys His Tyr Lys Ile Arg Lys Leu Asp
340 345 350

Ser Gly Gly Phe Tyr Ile Thr Ser Arg Thr Gln Phe Asn Ser Leu Gln
355 360 365

Gln Leu Val Ala Tyr Tyr Ser Lys His Ala Asp Gly Leu Cys His Arg
370 375 380

Leu Thr Thr Val Cys Gly Ser Thr Ser Gly Ser Gly Lys Pro Gly Ser
385 390 395 400

Gly Glu Gly Ser Glu Ile Tyr Gly Glu Phe Gly Ser Gly Ser Gly Gly
405 410 415

Ser Gly Gly Ser Ser Gly Thr Ser Lys Val Tyr Asp Pro Glu Gln Arg
420 425 430

Lys Arg Met Ile Thr Gly Pro Gln Trp Trp Ala Arg Cys Lys Gln Met
435 440 445

Asn Val Leu
450

<210> SEQ ID NO 265
<211> LENGTH: 437
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 265

Met Val Ala Arg Cys Ile Ile Pro Asp Leu Ile Gly Met Gly Lys Ser
1 5 10 15

Gly Lys Ser Gly Asn Gly Ser Tyr Arg Leu Leu Asp His Tyr Lys Tyr
20 25 30

Leu Thr Ala Trp Phe Glu Leu Leu Asn Leu Pro Lys Lys Ile Ile Phe
35 40 45

Val Gly His Asp Trp Gly Ala Cys Leu Ala Phe His Tyr Ser Tyr Glu
50 55 60

His Gln Asp Lys Ile Lys Ala Ile Val His Ala Glu Ser Val Val Asp
65 70 75 80

Val Ile Glu Ser Trp Asp Glu Trp Pro Asp Ile Glu Glu Asp Ile Ala
85 90 95

Leu Ile Lys Ser Glu Glu Gly Glu Lys Met Val Leu Glu Asn Asn Phe
100 105 110

Phe Val Glu Thr Met Leu Pro Ser Lys Ile Met Arg Lys Leu Glu Pro
115 120 125

```
Glu Glu Phe Ala Ala Tyr Leu Glu Pro Phe Lys Glu Lys Gly Glu Val
    130                 135                 140

Arg Arg Pro Thr Leu Ser Trp Pro Arg Glu Ile Pro Leu Val Lys Gly
145                 150                 155                 160

Gly Lys Pro Asp Val Val Gln Ile Val Arg Asn Tyr Asn Ala Tyr Leu
                165                 170                 175

Arg Ala Ser Asp Asp Leu Pro Lys Met Phe Ile Glu Ser Asp Pro Gly
            180                 185                 190

Phe Phe Ser Asn Ala Ile Val Glu Gly Ala Lys Lys Phe Pro Asn Thr
        195                 200                 205

Glu Phe Val Lys Val Lys Gly Leu His Phe Ser Gln Glu Asp Ala Pro
    210                 215                 220

Asp Glu Met Gly Lys Tyr Ile Lys Ser Phe Val Glu Arg Val Leu Lys
225                 230                 235                 240

Asn Glu Gln Gly Ser Ser Gly Trp Tyr Phe Gly Lys Ile Thr Arg Arg
                245                 250                 255

Glu Ser Glu Arg Leu Leu Leu Asn Ala Glu Asn Pro Arg Gly Thr Phe
            260                 265                 270

Leu Val Arg Glu Ser Glu Thr Thr Lys Gly Ala Tyr Cys Leu Ser Val
        275                 280                 285

Ser Asp Phe Asp Asn Ala Lys Gly Leu Asn Val Lys His Tyr Lys Ile
    290                 295                 300

Arg Lys Leu Asp Ser Gly Gly Phe Tyr Ile Thr Ser Arg Thr Gln Phe
305                 310                 315                 320

Asn Ser Leu Gln Gln Leu Val Ala Tyr Tyr Ser Lys His Ala Asp Gly
                325                 330                 335

Leu Cys His Arg Leu Thr Thr Val Cys Gly Ser Thr Ser Gly Ser Gly
            340                 345                 350

Lys Pro Gly Ser Gly Glu Gly Ser Glu Ile Tyr Gly Glu Phe Gly Ser
        355                 360                 365

Ser Gly Thr Ser Lys Val Tyr Asp Pro Glu Gln Arg Lys Arg Met Ile
    370                 375                 380

Thr Gly Pro Gln Trp Trp Ala Arg Cys Lys Gln Met Asn Val Leu Asp
385                 390                 395                 400

Ser Phe Ile Asn Tyr Tyr Asp Ser Glu Lys His Ala Glu Asn Ala Val
                405                 410                 415

Ile Phe Leu His Gly Asn Ala Ala Ser Ser Tyr Leu Trp Arg His Val
            420                 425                 430

Val Pro His Ile Glu
        435


<210> SEQ ID NO 266
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Met Val Ala Arg Cys Ile Ile Pro Asp Leu Ile Gly Met Gly Lys Ser
1               5                   10                  15

Gly Lys Ser Gly Asn Gly Ser Tyr Arg Leu Leu Asp His Tyr Lys Tyr
            20                  25                  30

Leu Thr Ala Trp Phe Glu Leu Leu Asn Leu Pro Lys Lys Ile Ile Phe
```

-continued

```
        35                  40                  45

Val Gly His Asp Trp Gly Ala Cys Leu Ala Phe His Tyr Ser Tyr Glu
    50                  55                  60

His Gln Asp Lys Ile Lys Ala Ile Val His Ala Glu Ser Val Val Asp
65                  70                  75                  80

Val Ile Glu Ser Trp Asp Glu Trp Pro Asp Ile Glu Glu Asp Ile Ala
                85                  90                  95

Leu Ile Lys Ser Glu Glu Gly Glu Lys Met Val Leu Glu Asn Asn Phe
            100                 105                 110

Phe Val Glu Thr Met Leu Pro Ser Lys Ile Met Arg Lys Leu Glu Pro
        115                 120                 125

Glu Glu Phe Ala Ala Tyr Leu Glu Pro Phe Lys Glu Lys Gly Glu Val
    130                 135                 140

Arg Arg Pro Thr Leu Ser Trp Pro Arg Glu Ile Pro Leu Val Lys Gly
145                 150                 155                 160

Gly Lys Pro Asp Val Val Gln Ile Val Arg Asn Tyr Asn Ala Tyr Leu
                165                 170                 175

Arg Ala Ser Asp Asp Leu Pro Lys Met Phe Ile Glu Ser Asp Pro Gly
            180                 185                 190

Phe Phe Ser Asn Ala Ile Val Glu Gly Ala Lys Lys Phe Pro Asn Thr
        195                 200                 205

Glu Phe Val Lys Val Lys Gly Leu His Phe Ser Gln Glu Asp Ala Pro
    210                 215                 220

Asp Glu Met Gly Lys Tyr Ile Lys Ser Phe Val Glu Arg Val Leu Lys
225                 230                 235                 240

Asn Glu Gln Gly Ser Ser Gly Gly Ser Gly Gly Ser Gly Trp Tyr Phe
                245                 250                 255

Gly Lys Ile Thr Arg Arg Glu Ser Glu Arg Leu Leu Leu Asn Ala Glu
            260                 265                 270

Asn Pro Arg Gly Thr Phe Leu Val Arg Glu Ser Glu Thr Thr Lys Gly
        275                 280                 285

Ala Tyr Cys Leu Ser Val Ser Asp Phe Asp Asn Ala Lys Gly Leu Asn
    290                 295                 300

Val Lys His Tyr Lys Ile Arg Lys Leu Asp Ser Gly Gly Phe Tyr Ile
305                 310                 315                 320

Thr Ser Arg Thr Gln Phe Asn Ser Leu Gln Gln Leu Val Ala Tyr Tyr
                325                 330                 335

Ser Lys His Ala Asp Gly Leu Cys His Arg Leu Thr Thr Val Cys Gly
            340                 345                 350

Ser Thr Ser Gly Ser Gly Lys Pro Gly Ser Gly Glu Gly Ser Glu Ile
        355                 360                 365

Tyr Gly Glu Phe Gly Ser Gly Ser Gly Gly Ser Gly Gly Ser Ser Gly
    370                 375                 380

Thr Ser Lys Val Tyr Asp Pro Glu Gln Arg Lys Arg Met Ile Thr Gly
385                 390                 395                 400

Pro Gln Trp Trp Ala Arg Cys Lys Gln Met Asn Val Leu Asp Ser Phe
                405                 410                 415

Ile Asn Tyr Tyr Asp Ser Glu Lys His Ala Glu Asn Ala Val Ile Phe
            420                 425                 430

Leu His Gly Asn Ala Ala Ser Ser Tyr Leu Trp Arg His Val Val Pro
        435                 440                 445

His Ile Glu
    450
```

<210> SEQ ID NO 267
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

```
Glu Ile Tyr Gly Glu Phe Gly Ser Ser Gly
1               5                   10
```

<210> SEQ ID NO 268
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

```
Glu Ile Tyr Gly Glu Phe Gly Ser Ser Gly Gly Ser Gly Gly Ser Gly
1               5                   10                  15
```

<210> SEQ ID NO 269
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

```
Glu Ile Tyr Gly Glu Phe Gly Ser Ser Gly Gly Ser Gly Gly Ser Gly
1               5                   10                  15

Gly Gly Ser Gly Gly Ser Gly Gly Ser Gly
            20                  25
```

<210> SEQ ID NO 270
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

```
Gly Ser Ser Gly
1
```

<210> SEQ ID NO 271
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

```
Gly Ser Thr Ser Gly Ser Gly Lys Pro Gly Ser Gly Glu Gly Ser Glu
1               5                   10                  15

Ile Tyr Gly Glu Phe Gly Ser Ser Gly
            20                  25
```

<210> SEQ ID NO 272

<211> LENGTH: 31
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 272

```
Gly Ser Thr Ser Gly Ser Gly Lys Pro Gly Ser Gly Glu Gly Ser Glu
1               5                   10                  15

Ile Tyr Gly Glu Phe Gly Ser Gly Gly Ser Gly Gly Ser Ser Gly
            20                  25                  30
```

<210> SEQ ID NO 273
<211> LENGTH: 41
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 273

```
Gly Ser Thr Ser Gly Ser Gly Lys Pro Gly Ser Gly Glu Gly Ser Glu
1               5                   10                  15

Ile Tyr Gly Glu Phe Gly Ser Gly Gly Ser Gly Gly Ser Gly Gly Gly
            20                  25                  30

Ser Gly Gly Ser Gly Gly Ser Ser Gly
        35                  40
```

<210> SEQ ID NO 274
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 274

```
Gly Ser Thr Ser Gly Ser Gly Lys Pro Gly Ser Gly Glu Gly Ser Glu
1               5                   10                  15

Ile Tyr Gly Glu Phe Gly Ser Gly Ser Gly Gly Ser Gly Gly Ser Ser
            20                  25                  30

Gly
```

<210> SEQ ID NO 275
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 275

```
Gly Ser Thr Gly
1
```

<210> SEQ ID NO 276
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 276

Gly Ser Ser Gly Gly Ser Gly Gly Ser Gly
1 5 10

<210> SEQ ID NO 277
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 277

Gly Ser Ser Gly Gly Ser Gly Gly Ser Gly Gly Gly Ser Gly Gly Ser
1 5 10 15

Gly Gly Ser Gly
20

<210> SEQ ID NO 278
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 278

Gly Ser Gly Gly Ser Gly Gly Ser Gly Gly Thr Ser Gly Gly Ser Gly
1 5 10 15

Gly Ser Ser Gly
20

<210> SEQ ID NO 279
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 279

Gly Ser Ser Gly Arg Lys Arg Asp Arg Leu Gly Thr Leu Gly Ile Gly
1 5 10 15

Gly Ser Ser Gly Gly Gly Ser Gly Gly Gly Gly Ser Gly Gly
20 25 30

<210> SEQ ID NO 280
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 280

Gly Gly Ser Gly Gly Ser Gly Ser Ser Gly Arg Lys Arg Asp Arg Leu
1 5 10 15

Gly Thr Leu Gly Ile Gly Gly Ser Ser Gly Gly Gly Ser Gly Gly Gly
20 25 30

Gly Ser Gly Gly
35

<210> SEQ ID NO 281
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

```
Gly Ser Gly Gly Ser Gly Gly Ser Gly Gly
1               5                   10
```

<210> SEQ ID NO 282
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

```
Gly Ser Ser Gly Gly Ser Gly Gly Ser Gly Gly Gly Ser Gly Gly Ser
1               5                   10                  15

Gly Ser Ser Gly Arg Lys Arg Asp Arg Leu Gly Thr Leu Gly Ile Gly
            20                  25                  30

Gly Ser Ser Gly Gly Gly Ser Gly Gly Gly Gly Ser Gly Gly
        35                  40                  45
```

<210> SEQ ID NO 283
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

```
Arg Lys Arg Asp Arg Leu Gly Thr Leu Gly Ile Gly Gly Ser Ser Gly
1               5                   10                  15

Gly Gly Ser Gly Gly Gly Gly Ser Gly Gly
            20                  25
```

<210> SEQ ID NO 284
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

```
Gly Gly Ser Ser Gly Arg Lys Arg Asp Arg Leu Gly Thr Leu Gly Ile
1               5                   10                  15

Gly Gly Ser Ser Gly
            20
```

<210> SEQ ID NO 285
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

```
Gly Gly Ser Ser Gly Arg Lys Arg Asp Arg Leu Gly Thr Leu Gly Ile
1               5                   10                  15

Gly Ser Ser Gly Ser Gly Gly Ser Gly Gly
            20                  25
```

<210> SEQ ID NO 286
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 286

Gly Ser Gly Gly Ser Gly Gly Ser Gly Gly Gly Ser Gly Gly Ser Gly
1 5 10 15

Gly Ser Ser Gly
20

<210> SEQ ID NO 287
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 287

Gly Gly Ser Ser Gly Arg Lys Arg Asp Arg Leu Gly Thr Leu Gly Ile
1 5 10 15

Gly Ser Gly Gly Ser Gly Gly Ser Gly Gly Thr Ser Gly Gly Ser Gly
20 25 30

Gly Ser Ser Gly
35

<210> SEQ ID NO 288
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 288

Gly Ser Ser Gly Gly Ser Gly Gly Ser Gly Gly Gly Ser Gly Gly Ser
1 5 10 15

Gly

<210> SEQ ID NO 289
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 289

Gly Gly Ser Ser Gly Arg Lys Arg Asp Arg Leu Gly Thr Leu Gly Ile
1 5 10 15

Gly Ser Ser Gly Ser Gly Gly Ser Gly Gly Thr Ser Gly Gly Ser Gly
20 25 30

Gly Ser Ser Gly
35

<210> SEQ ID NO 290
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 290

Gly Ser Ser Gly Gly Ser Gly Gly Ser Gly Gly Gly Arg Lys Arg Asp
1 5 10 15

Arg Leu Gly Thr Leu Gly Ile Gly Gly Ser Ser Gly Gly Gly Ser Gly
20 25 30

Gly Gly Gly Ser Gly Gly
35

<210> SEQ ID NO 291
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 291

Gly Ser Gly Gly Ser Gly Gly Ser Ser Gly
1 5 10

<210> SEQ ID NO 292
<211> LENGTH: 46
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 292

Gly Ser Ser Gly Gly Ser Gly Gly Ser Gly Gly Gly Ser Gly Gly Ser
1 5 10 15

Gly Gly Ser Gly Arg Lys Arg Asp Arg Leu Gly Thr Leu Gly Ile Gly
20 25 30

Gly Ser Ser Gly Gly Gly Ser Gly Gly Gly Gly Ser Gly Gly
35 40 45

<210> SEQ ID NO 293
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 293

Gly Ser Gly Gly
1

<210> SEQ ID NO 294
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 294

Gly Gly Ser Gly Gly Gly Gly Ser Gly Gly
1 5 10

<210> SEQ ID NO 295

<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

```
Gly Ser Thr Ser Gly Ser Gly Lys Pro Gly Ser Gly Glu Gly Ser Glu
1               5                   10                  15

Ile Tyr Gly Glu Phe
            20
```

<210> SEQ ID NO 296
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

```
Glu Ile Tyr Gly Glu Phe
1               5
```

<210> SEQ ID NO 297
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

```
Arg Lys Arg Asp Arg Leu Gly Thr Leu Gly Ile
1               5                   10
```

<210> SEQ ID NO 298
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

```
Gly Ser Gly Gly Ser Thr Ser Gly Ser Gly Lys Pro Gly Ser Gly Glu
1               5                   10                  15

Gly Ser Glu Ile Tyr Gly Glu Phe
            20
```

<210> SEQ ID NO 299
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

```
Gly Ser Gly Ser Gly Gly Ser Gly Gly Ser Ser Gly
1               5                   10
```

<210> SEQ ID NO 300
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 300

Gly Gly Ser Gly Gly Ser Gly Ser Ser Gly
1 5 10

<210> SEQ ID NO 301
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 301

Gly Ser Ser Gly Gly Ser Gly Gly Ser Gly Gly Gly Ser Gly Gly Ser
1 5 10 15

Gly Ser Ser Gly
20

<210> SEQ ID NO 302
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 302

Gly Ser Ser Gly Gly Ser Gly Gly Ser Gly Gly Gly
1 5 10

<210> SEQ ID NO 303
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 303

Gly Gly Ser Ser Gly Arg Lys Arg Asp Arg Leu Gly Thr Leu Gly Ile
1 5 10 15

<210> SEQ ID NO 304
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 304

Gly Gly Ser Ser Gly
1 5

<210> SEQ ID NO 305
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 305

Gly Ser Ser Gly Ser Gly Gly Ser Gly Gly
1 5 10

<210> SEQ ID NO 306
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 306

Leu Glu Gly Ser Gly Gly Gly Gly
1 5

<210> SEQ ID NO 307
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 307

Gly Gly Gly Gly Ser Gly Pro Trp
1 5

<210> SEQ ID NO 308
<211> LENGTH: 311
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 308

Met Thr Ser Lys Val Tyr Asp Pro Glu Gln Arg Lys Arg Met Ile Thr
1 5 10 15

Gly Pro Gln Trp Trp Ala Arg Cys Lys Gln Met Asn Val Leu Asp Ser
20 25 30

Phe Ile Asn Tyr Tyr Asp Ser Glu Lys His Ala Glu Asn Ala Val Ile
35 40 45

Phe Leu His Gly Asn Ala Ala Ser Ser Tyr Leu Trp Arg His Val Val
50 55 60

Pro His Ile Glu Pro Val Ala Arg Cys Ile Ile Pro Asp Leu Ile Gly
65 70 75 80

Met Gly Lys Ser Gly Lys Ser Gly Asn Gly Ser Tyr Arg Leu Leu Asp
85 90 95

His Tyr Lys Tyr Leu Thr Ala Trp Phe Glu Leu Leu Asn Leu Pro Lys
100 105 110

Lys Ile Ile Phe Val Gly His Asp Trp Gly Ala Cys Leu Ala Phe His
115 120 125

Tyr Ser Tyr Glu His Gln Asp Lys Ile Lys Ala Ile Val His Ala Glu
130 135 140

Ser Val Val Asp Val Ile Glu Ser Trp Asp Glu Trp Pro Asp Ile Glu
145 150 155 160

Glu Asp Ile Ala Leu Ile Lys Ser Glu Glu Gly Glu Lys Met Val Leu
165 170 175

Glu Asn Asn Phe Phe Val Glu Thr Met Leu Pro Ser Lys Ile Met Arg
180 185 190

Lys Leu Glu Pro Glu Glu Phe Ala Ala Tyr Leu Glu Pro Phe Lys Glu

```
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310
```

<210> SEQ ID NO 309
<211> LENGTH: 4145
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 309

```
caaacaagtg cggccatttc accagcccag gctggcttct gctgttgact ggctgtggca     60

cctcaagcag cccctttccc ctctagcctc agtttatcac cgcaagagct accattcatc    120

tagcacaacc tgaccatcct cacactggtc agttccaacc ttcccaggaa tcttctgtgg    180

ccatgttcac tccggtttta cagaacagag aacagaagct cagagaagtg aagcaacttg    240

cccagctatg agagacagag ccaggatttg aaaccagatg aggacgctga ggcccagaga    300

gggaaagcca cttgcctagg gacacacagc ggggagaggt ggagcagggc ctctatttcg    360

agacccctga ctccacacct ggtgtttgtg ccaagacccc aggctgcctc ccaggtcctc    420

tgggacagcc cctgccttct accaggacca tgggtagcaa caagagcaag cccaaggatg    480

ccagccagcg gcgccgcagc ctggagcccg ccgagaacgt gcacggcgct ggcgggggcg    540

ctttccccgc ctcgcagacc cccagcaagc cagcctcggc cgacggccac cgcggcccca    600

gcgcggcctt cgcccccgcg gccgccgagc ccaagctgtt cggaggcttc aactcctcgg    660

acaccgtcac ctccccgcag agggcgggcc cgctggccgg tggagtgacc acctttgtgg    720

ccctctatga ctatgagtct aggacggaga cagacctgtc cttcaagaaa ggcgagcggc    780

tccagattgt caacaacaca gagggagact ggtggctggc ccactcgctc agcacaggac    840

agacaggcta catccccagc aactacgtgg cgccctccga ctccatccag gctgaggagt    900

ggtattttgg caagatcacc agacgggagt cagagcggtt actgctcaat gcagagaacc    960

cgagagggac cttcctcgtg cgagaaagtg agaccacgaa aggtgcctac tgcctctcag   1020

tgtctgactt cgacaacgcc aagggcctca acgtgaagca ctacaagatc cgcaagctgg   1080

acagcggcgg cttctacatc acctcccgca cccagttcaa cagcctgcag cagctggtgg   1140

cctactactc caaacacgcc gatggcctgt gccaccgcct caccaccgtg tgccccacgt   1200

ccaagccgca gactcagggc ctggccaagg atgcctggga gatccctcgg gagtcgctgc   1260

ggctggaggt caagctgggc cagggctgct ttggcgaggt gtggatgggg acctggaacg   1320

gtaccaccag ggtggccatc aaaaccctga agcctggcac gatgtctcca gaggccttcc   1380
```

-continued

```
tgcaggaggc ccaggtcatg aagaagctga ggcatgagaa gctggtgcag ttgtatgctg   1440
tggtttcaga ggagcccatt tacatcgtca cggagtacat gagcaagggg agtttgctgg   1500
actttctcaa gggggagaca ggcaagtacc tgcggctgcc tcagctggtg gacatggctg   1560
ctcagatcgc ctcaggcatg gcgtacgtgg agcggatgaa ctacgtccac cgggaccttc   1620
gtgcagccaa catcctggtg ggagagaacc tggtgtgcaa agtggccgac tttgggctgg   1680
ctcggctcat tgaagacaat gagtacacgg cgcggcaagg tgccaaattc cccatcaagt   1740
ggacggctcc agaagctgcc ctctatggcc gcttcaccat caagtcggac gtgtggtcct   1800
tcgggatcct gctgactgag ctcaccacaa agggacgggt gccctaccct gggatggtga   1860
accgcgaggt gctggaccag gtggagcggg gctaccggat gccctgcccg ccggagtgtc   1920
ccgagtccct gcacgacctc atgtgccagt gctggcggaa ggagcctgag gagcggccca   1980
ccttcgagta cctgcaggcc ttcctggagg actacttcac gtccaccgag ccccagtacc   2040
agcccgggga gaacctctag gcacaggcgg gcccagaccg gcttctcggc ttggatcctg   2100
ggctgggtgg cccctgtctc ggggcttgcc ccactctgcc tgcctgctgt tggtcctctc   2160
tctgtggggc tgaattgcca ggggcgaggc ccttcctctt tggtggcatg gaaggggctt   2220
ctggacctag ggtggcctga gagggcggtg ggtatgcgag accagcacgg tgactctgtc   2280
cagctcccgc tgtggccgca cgcctctccc tgcactccct cctggagctc tgtgggtctc   2340
tggaagagga accaggagaa gggctggggc cggggctgag ggtgcccttt tccagcctca   2400
gcctactccg ctcactgaac tccttcccca cttctgtgcc acccccggtc tatgtcgaga   2460
gctggccaaa gagcctttcc aaagaggagc gatgggcccc tggccccgcc tgcctgccac   2520
cctgcccctt gccatccatt ctggaaacac ctgtaggcag aggctgccga gacagaccct   2580
ctgccgctgc ttccaggctg ggcagcacaa ggccttgcct ggcctgatga tggtgggtgg   2640
gtgggatgag tacccccctca aaccctgccc tccttagacc tgagggaccc ttcgagatca   2700
tcacttcctt gcccccattt cacccatggg gagacagttg agagcgggga tgtgacatgc   2760
ccaaggccac ggagcagttc agagtggagg cgggcttgga acccggtgct ccctctgtca   2820
tcctcaggaa ccaacaattc gtcggaggca tcatggaaag actgggacag cccaggaaac   2880
aaggggtctg aggatgcatt cgagatggca gattcccact gccgctgccc gctcagccca   2940
gctgttggga acagcatgga ggcagatgtg gggctgagct ggggaatcag ggtaaaaggt   3000
gcaggtgtgg agagagaggc ttcaatcggc ttgtgggtga tgtttgacct tcagagccag   3060
ccggctatga aagggagcga gcccctcggc tctggaggca atcaagcaga catagaagag   3120
ccaagagtcc aggaggccct ggtcctggcc tccttccccg tactttgtcc cgtggcattt   3180
caattcctgg ccctgttctc ctccccaagt cggcaccctt taactcatga ggagggaaaa   3240
gagtgcctaa gcgggggtga aagaggacgt gttacccact gccatgcacc aggactggct   3300
gtgtaacctt gggtggcccc tgctgtctct ctgggctgca gagtctgccc cacatgtggc   3360
catggcctct gcaactgctc agctctggtc caggccctgt ggcaggacac acatggtgag   3420
cctagccctg ggacatcagg agactgggct ctggctctgt tcggcctttg ggtgtgtggt   3480
ggattctccc tgggcctcag tgtgcccatc tgtaaagggg cagctgacag tttgtggcat   3540
cttgccaagg gtccctgtgt gtgtgtatgt gtgtgcatgt gtgcgtgtct ccatgtgcgt   3600
ccatatttaa catgtaaaaa tgtccccccc gctccgtccc ccaaacatgt tgtacatttc   3660
accatggccc cctcatcata gcaataacat tcccactgcc aggggttctt gagccagcca   3720
```

-continued

```
ggccctgcca gtggggaagg aggccaagca gtgcctgcct atgaaatttc aacttttcct   3780

ttcatacgtc tttattaccc aagtcttctc ccgtccattc cagtcaaatc tgggctcact   3840

caccccagcg agctctcaaa tccctctcca actgcctaag gccctttgtg taaggtgtct   3900

taatactgtc cttttttttt ttttaacagt gttttgtaga tttcagatga ctatgcagag   3960

gcctggggga cccctggctc tgggccgggc ctggggctcc gaaattccaa ggcccagact   4020

tgcggggggt ggggggtat ccagaattgg ttgtaaatac tttgcatatt gtctgattaa   4080

acacaaacag acctcagaaa aaaaaaaaaa aaaaaaaaaa aaaaaaaaaa aaaaaaaaaa   4140

aaaaa                                                               4145
```

<210> SEQ ID NO 310
<211> LENGTH: 821
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

```
Met Glu Asn Ile Thr Gln Pro Thr Gln Gln Ser Thr Gln Ala Thr Gln
1               5                   10                  15

Arg Phe Leu Ile Glu Lys Phe Ser Gln Glu Gln Ile Gly Glu Asn Ile
            20                  25                  30

Val Cys Arg Val Ile Cys Thr Thr Gly Gln Ile Pro Ile Arg Asp Leu
        35                  40                  45

Ser Ala Asp Ile Ser Gln Val Leu Lys Glu Lys Arg Ser Ile Lys Lys
    50                  55                  60

Val Trp Thr Phe Gly Arg Asn Pro Ala Cys Asp Tyr His Leu Gly Asn
65                  70                  75                  80

Ile Ser Arg Leu Ser Asn Lys His Phe Gln Ile Leu Leu Gly Glu Asp
                85                  90                  95

Gly Asn Leu Leu Leu Asn Asp Ile Ser Thr Asn Gly Thr Trp Leu Asn
            100                 105                 110

Gly Gln Lys Val Glu Lys Asn Ser Asn Gln Leu Leu Ser Gln Gly Asp
        115                 120                 125

Glu Ile Thr Val Gly Val Gly Val Glu Ser Asp Ile Leu Ser Leu Val
    130                 135                 140

Ile Phe Ile Asn Asp Lys Phe Lys Gln Cys Leu Glu Gln Asn Lys Val
145                 150                 155                 160

Asp Arg Ile Arg Ser Asn Leu Lys Asn Thr Ser Lys Ile Ala Ser Pro
                165                 170                 175

Gly Leu Thr Ser Ser Thr Ala Ser Ser Met Val Ala Asn Lys Thr Gly
            180                 185                 190

Ile Phe Lys Asp Phe Ser Ile Ile Asp Glu Val Ala Gly Gln Gly Ala
        195                 200                 205

Phe Ala Thr Val Lys Lys Ala Ile Glu Arg Thr Thr Gly Lys Thr Phe
    210                 215                 220

Ala Val Lys Ile Ile Ser Lys Arg Lys Val Ile Gly Asn Met Asp Gly
225                 230                 235                 240

Val Thr Arg Glu Leu Glu Val Leu Gln Lys Leu Asn His Pro Arg Ile
                245                 250                 255

Val Arg Leu Lys Gly Phe Tyr Glu Asp Thr Glu Ser Tyr Tyr Met Val
            260                 265                 270

Met Glu Phe Val Ser Gly Gly Asp Leu Met Asp Phe Val Ala Ala His
```

```
        275                 280                 285

Gly Ala Val Gly Glu Asp Ala Gly Arg Glu Ile Ser Arg Gln Ile Leu
    290                 295                 300

Thr Ala Ile Lys Tyr Ile His Ser Met Gly Ile Ser His Arg Asp Leu
305                 310                 315                 320

Lys Pro Asp Asn Ile Leu Ile Glu Gln Asp Asp Pro Val Leu Val Lys
                325                 330                 335

Ile Thr Asp Phe Gly Leu Ala Lys Val Gln Gly Asn Gly Ser Phe Met
            340                 345                 350

Lys Thr Phe Cys Gly Thr Leu Ala Tyr Val Ala Pro Glu Val Ile Arg
        355                 360                 365

Gly Lys Asp Thr Ser Val Ser Pro Asp Glu Tyr Glu Glu Arg Asn Glu
    370                 375                 380

Tyr Ser Ser Leu Val Asp Met Trp Ser Met Gly Cys Leu Val Tyr Val
385                 390                 395                 400

Ile Leu Thr Gly His Leu Pro Phe Ser Gly Ser Thr Gln Asp Gln Leu
                405                 410                 415

Tyr Lys Gln Ile Gly Arg Gly Ser Tyr His Glu Gly Pro Leu Lys Asp
            420                 425                 430

Phe Arg Ile Ser Glu Glu Ala Arg Asp Phe Ile Asp Ser Leu Leu Gln
        435                 440                 445

Val Asp Pro Asn Asn Arg Ser Thr Ala Ala Lys Ala Leu Asn His Pro
    450                 455                 460

Trp Ile Lys Met Ser Pro Leu Gly Ser Gln Ser Tyr Gly Asp Phe Ser
465                 470                 475                 480

Gln Ile Ser Leu Ser Gln Ser Leu Ser Gln Gln Lys Leu Leu Glu Asn
                485                 490                 495

Met Asp Asp Ala Gln Tyr Glu Phe Val Lys Ala Gln Arg Lys Leu Gln
            500                 505                 510

Met Glu Gln Gln Leu Gln Glu Gln Asp Gln Glu Asp Gln Asp Gly Lys
        515                 520                 525

Ile Gln Gly Phe Lys Ile Pro Ala His Ala Pro Ile Arg Tyr Thr Gln
    530                 535                 540

Pro Lys Ser Ile Glu Ala Glu Thr Arg Glu Gln Lys Leu Leu His Ser
545                 550                 555                 560

Asn Asn Thr Glu Asn Val Lys Ser Ser Lys Lys Lys Gly Asn Gly Arg
                565                 570                 575

Phe Leu Thr Leu Lys Pro Leu Pro Asp Ser Ile Ile Gln Glu Ser Leu
            580                 585                 590

Glu Ile Gln Gln Gly Val Asn Pro Phe Phe Ile Gly Arg Ser Glu Asp
        595                 600                 605

Cys Asn Cys Lys Ile Glu Asp Asn Arg Leu Ser Arg Val His Cys Phe
    610                 615                 620

Ile Phe Lys Lys Arg His Ala Val Gly Lys Ser Met Tyr Glu Ser Pro
625                 630                 635                 640

Ala Gln Gly Leu Asp Asp Ile Trp Tyr Cys His Thr Gly Thr Asn Val
                645                 650                 655

Ser Tyr Leu Asn Asn Asn Arg Met Ile Gln Gly Thr Lys Phe Leu Leu
            660                 665                 670

Gln Asp Gly Asp Glu Ile Lys Ile Ile Trp Asp Lys Asn Asn Lys Phe
        675                 680                 685

Val Ile Gly Phe Lys Val Glu Ile Asn Asp Thr Thr Gly Leu Phe Asn
    690                 695                 700
```

Glu Gly Leu Gly Met Leu Gln Glu Gln Arg Val Val Leu Lys Gln Thr
705 710 715 720

Ala Glu Glu Lys Asp Leu Val Lys Lys Leu Thr Gln Met Met Ala Ala
725 730 735

Gln Arg Ala Asn Gln Pro Ser Ala Ser Ser Ser Ser Met Ser Ala Lys
740 745 750

Lys Pro Pro Val Ser Asp Thr Asn Asn Asn Gly Asn Asn Ser Val Leu
755 760 765

Asn Asp Leu Val Glu Ser Pro Ile Asn Ala Asn Thr Gly Asn Ile Leu
770 775 780

Lys Arg Ile His Ser Val Ser Leu Ser Gln Ser Gln Ile Asp Pro Ser
785 790 795 800

Lys Lys Val Lys Arg Ala Lys Leu Asp Gln Thr Ser Lys Gly Pro Glu
805 810 815

Asn Leu Gln Phe Ser
820

<210> SEQ ID NO 311
<211> LENGTH: 2982
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 311
atggtcgctg cgcacgctgc acactctcag tcctcggccg agtggatcgc ctgcctggat 60
aaaaggccgt tggagcgatc tagtgaagat gtggacataa ttttcacgcg gctgaaagga 120
gttaaagctt ttgagaaatt tcacccaaac ctccttcgtc agatttgttt atgcggttac 180
tatgagaacc tggaaaaagg aatcacactg tttcgccaag ggatattgg aaccaactgg 240 tatgctgtcc tggctgggtc tttggatgtt aaagtgtctg agaccagcag tcaccaggat 300
gcggtgacca tctgcactct gggaattggg acagcctttg gagagtccat tctggataac 360
acccctcgcc atgcaaccat cgttaccagg gagagcagcg aacttctccg cattgagcag 420
gaggacttca aggcactatg ggagaaatac cgacagtata tggccggact tctggctcct 480
ccctatggtg ttatggaaac gggctctaac aatgacagga ttcctgacaa ggagaatgtc 540
ccttcagaga agatcctcag agctggaaaa attttacgaa ttgccattct ctctcgagct 600
ccccacatga taagagacag aaagtaccac ctaaagacat acagacaatg ctgtgttggg 660
actgagctgg tagactggat gatacagcag acatcctgtg ttcactcgcg gactcaagct 720
gttggcatgt ggcaagtctt gctggaagat ggtgtcctca accatgtgga ccaggagcgc 780
catttccaag acaaatattt attttatcga tttctggatg acgagcgtga ggatgcccct 840
ttgcctactg aggaagagaa gaaggagtgt gatgaagaac ttcaggacac catgctgctg 900
ctctcacaga tgggccctga cgcccacatg agaatgatcc tgcgaaaacc acctggccag 960
aggactgtgg atgacctaga gattatctac gacgagctcc ttcatattaa agccttatcc 1020
catctctcta ccacagtgaa acgggagtta gcaggtgttc tcatttttga gtctcacgcc 1080
aaaggaggaa ctgtgttgtt taaccagggg gaagaaggta cctcctggta catcattctg 1140
aaaggatccg tgaatgtagt catttatggc aagggtgtgg tctgcaccct gcacgaagga 1200
gatgactttg gcaagttagc tctagtgaac gatgctccaa gagctgcctc cattgttctt 1260
cgggaagata attgtcactt cctaagagtc gacaaggaag acttcaatcg gattctgagg 1320
gacgttgagg cgaatacagt cagacttaaa gaacatgacc aagatgtctt ggtactggag 1380
aaggtcccag cagggaacag agctgctaat caaggaaact cacagcctca gcaaaagtat 1440
actgtgatgt caggaacacc tgaaaagatt ttagagcatt ttctagaaac aatacgcctt 1500
gagccatcgt tgaatgaagc aacagattcg gttttaaatg actttgttat gatgcactgt 1560
gtttttatgc caaataccca gctttgccct gcccttgtgg cccattacca cgcacagcct 1620
tctcaaggta ccgagcagga gagaatggat tatgccctca acaacaagag gcgggtcatc 1680
cgcttggtcc tgcagtgggc ggccatgtat ggcgatctcc tccaagaaga tgatgtggcc 1740
atggccttcc tggaggagtt ctatgtgtct gtatcagatg acgcacggat gatggctgcc 1800
ttcaaggagc agctgccaga gctggagaag attgtcaagc aaatctcaga agacgcaaaa 1860
gctccacaga agaagcacaa ggtgcttttg caacagttca acacaggtga cgagagggcc 1920
cagaagcgtc agcctattcg tggctctgat gaggttttgt tcaaggtcta ctgcatcgac 1980
cacacctata ctaccattcg tgtgccggta gctgcctcgg tgaaggaagt catcagtgca 2040
gtagctgaca aactgggctc aggggaaggc ctgatcatcg tcaagatgaa ctctggagga 2100
gaaaaggtgg tgctgaaatc taatgatgtt tcagtattta cgacgctcac cattaatgga 2160
cgcctgtttg cctgcccgag agagcaattc gactcactga ctcccttgcc ggaacaggaa 2220
ggcccgacca ctgggacagt gggaacattt gagctgatga gctcgaaaga cctggcgtac 2280
cagatgacaa cctacgattg ggaactcttc aactgtgtgc atgagctgga gctaatctac 2340
cacacatttg gaaggcataa ttttaaaaag accacggcaa acttggattt gttcctgagg 2400
aggtttaatg aaattcagtt ttgggttgtc actgaggtct gcctttgttc ccagctcagc 2460
aaacgtgttc agcttttgaa aaaatttatc aagatagcgg ctcactgcaa ggagtacaaa 2520
aatctaaatt ccttttttcgc catcgtcatg ggactcagca acgtggccgt gagccgcttg 2580
gcactaacgt gggagaaact gccgagcaag tttaagaagt tctatgcgga gtttgagagc 2640
ttgatggatc cttccagaaa ccacagggca tacaggctga cagcagccaa gctggagccc 2700
cctctcatcc ctttcatgcc cttgcttatt aaagatatga catttactca tgaggggaac 2760
aagacgttca ttgacaatct agtaaacttt gaaaaaatgc gcatgattgc aaacactgcc 2820
agaacagtac ggtactacag gagccagccc ttcaatccgg atgccgctca agctaataag 2880
aaccatcagg atgtccggag ttatgtacgg caattaaatg tgattgacaa ccagagaact 2940
ttatcacaga tgtcacacag attagagcct cgaaggccat ag 2982

<210> SEQ ID NO 312
<211> LENGTH: 3745
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 312
ggggccgcgc tcgctcagcc gccgccacca cacggagcag acgcgcgccg ggagccgcgg 60
gccgggccag ccgggccgcc ggggcccagt gcgccgcgct cgcagccggt agcgcgccag 120
cgccgtaggc gctcgctcgg cagccgcggg gctctaggcc gtgccgggga gggggcgagg 180
gcggcgccca ggcgcctgcc gccccggagg caggatgagc atcgagatcc cggcgggact 240
gacggagctg ctgcagggct tcacggtgga ggtgctgagg caccagcccg cggacctgct 300
ggagttcgct ctgcagcact tcacccgcct gcagcaggag aacgagcgca aaggcaccgc 360

```
gcgcttctgc catgagggca ggacctgggg ggacctgggc gccgctgccg ggggcggcac    420
ccccagcaag gggtcaact tcgccgagga gcccatgcag tccgactccg aggacgggga    480
ggaggaggag gcggcgcccg cggacgcagg ggcgttcaat gctccagtaa taaaccgatt    540
cacaaggcgt gcctcagtat gtgcagaagc ttataatcct gatgaagaag aagatgatgc    600
agagtccagg attatacatc caaaaactga tgatcaaaga aataggttgc aagaggcttg    660
caaagacatc ctgctgttta agaatctgga tccggagcag atgtctcaag tattagatgc    720
catgtttgaa aaattggtca aagatgggga gcatgtaatt gatcaaggtg acgatggtga    780
caacttttat gtaattgata gaggcacatt tgatatttat gtgaaatgtg atggtgttgg    840
aagatgtgtt ggtaactatg ataatcgtgg gagtttcggc gaactggcct taatgtacaa    900
tacacccaga gcagctacaa tcactgctac ctctcctggt gctctgtggg gtttggacag    960
ggtaaccttc aggagaataa ttgtgaaaaa caatgccaaa aagagaaaaa tgtatgaaag   1020
ctttattgag tcactgccat tccttaaatc tttggagttt tctgaacgcc tgaaagtagt   1080
agatgtgata ggcaccaaag tatacaacga tggagaacaa atcattgctc agggagattc   1140
ggctgattct tttttcattg tagaatctgg agaagtgaaa attactatga aaagaaaggg   1200
taaatcagaa gtggaagaga atggtgcagt agaaatcgct cgatgctcgc ggggacagta   1260
ctttggagag cttgccctgg taactaacaa acctcgagca gcttctgccc acgccattgg   1320
gactgtcaaa tgtttagcaa tggatgtgca agcatttgaa aggcttctgg gaccttgcat   1380
ggaaattatg aaaaggaaca tcgctaccta tgaagaacag ttagttgccc tgtttggaac   1440
gaacatggat attgttgaac ccactgcatg aagcaaaagt atggagcaag acctgtagtg   1500
acaaaattac acagtagtgg ttagtccact gagaatgtgt ttgtgtagat gccaagcatt   1560
ttctgtgatt tcaggttttt tcctttttt acatttacaa cgtatcaata aacagtagtg   1620
atttaatagt caataggctt taacatcact ttctaaagag tagttcataa aaaaatcaac   1680
atactgataa aatgactttg tactccacaa aattatgact gaaaggttta ttaaaatgat   1740
tgtaatatat agaaagtatc tgtgtttaag aagataatta aaggatgtta tcataggcta   1800
tatgtgtttt acttattcag actgataatc atattagtga ctatccccat gtaagagggc   1860
acttggcaat taaacatgct acacagcatg gcatcacttt tttttataac tcattaaaca   1920
cagtaaaatt ttaatcattt ttgttttaaa gttttctagc ttgataagtt atgtgctggc   1980
cttggcctat tggtgaaatg gtataaaata tcatatgcag ttttaaaact ttttatattt   2040
ttgcaataaa gtacatttg actttgttgg cataatgtca gtaacataca tattccagtg   2100
gttttatgga caggcaattt agtcattatg ataataagga aaacagtgtt ttagatgaga   2160
gatcattaat gcatttttcc ctcatcaagc atatatctgc ttttttttat tttgcaattc   2220
tctgtattct atgtctttaa aaatttgatc ttgacattta atgtcacaaa gttttgtttt   2280
tttaaaaagt gatttaaact taagatccga catttttgt attctttaag attttacacc   2340
taaaaaatct ctcctatccc aaaaataatg tgggatcctt atcagcatgc ccacagttta   2400
tttctttgtt cttcactagg cctgcataat acagtcctat gtagacatct gttcccttgg   2460
gtttccgttc tttcttagga tggttgccaa cccacaatct cattgatcag cagccaatat   2520
gggtttgttt ggttttttta attcttaaaa acatcctcta gaggaataga aacaaatttt   2580
tatgagcata accctatata aagacaaaat gaatttctga ccttaccata tataccatta   2640
ggccttgcca ttgctttaat gtagactcat agttgaaatt agtgcagaaa gaactcagat   2700
```

```
gtactagatt ttcattgttc attgatatgc tcagtatgct gccacataag atgaatttaa   2760

ttatattcaa ccaaagcaat atactcttac atgatttcta ggccccatga cccagtgtct   2820

agagacatta attctaacca gttgtttgct tttaaatgag tgatttcatt ttgggaaaca   2880

ggtttcaaat gaatatatat acatgggtaa aattactctg tgctagtgta gtcttactag   2940

agaatgttta tggtcccact tgtatatgaa aatgtggtta gaatgttaat tggataatgt   3000

atatataaga agttaaagta tgtaaagtat aacttcagcc acatttttag aacactgttt   3060

aacatttttg caaaaccttc ttgtaggaaa agagagctct ctacatgaag atgacttgtt   3120

ttatatttca gattttattt taaaagccat gtctgttaaa caagaaaaaa cacaaaagaa   3180

ctccagattc ctggttcatc attctgtatt cttactcact ttttcaagtt atctattttg   3240

ttgcataaac taattgttaa ctattcatgg aacagcaaac gcctgtttaa taaagaactt   3300

tgaccaaggc tataaatgcc acgtacatta ttttcagtat tgttggttat atttaaattt   3360

tccttacaat aaagcacact tttataataa aatacatgaa ttattgtttt tcatactttt   3420

ttgcttgttt ctttaaagtt ttctgacgtg cataatgcat aattcattga aaagcatgat   3480

agcaatgtgg catgtggaag cgaacccccca gggcataaca tagtaagaaa gtatggttct   3540

gtatggcaat aggtttttaa aattattagc tattcatcat gtgtgggaga aataattgtg   3600

gtgtgttgca gatttatttg gccatttaga ataaccaaat caatctggct aactaggaat   3660

ttatgtgtaa aattatctga ttaaaacagc tcaagtttga aaaaaaaaaa aaaaaaaaaa   3720

aaaaaaaaaa aaaaaaaaaa aaaaa                                         3745
```

```
<210> SEQ ID NO 313
<211> LENGTH: 3600
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 313
```

```
ggtggagctg tcgcctagcc gctatcgcag agtggagcgg ggctgggagc aaagcgctga     60

gggagctcgg tacgccgccg cctcgcaccc gcagcctcgc gcccgccgcc gcccgtcccc    120

agagaaccat ggagtctggc agtaccgccg ccagtgagga ggcacgcagc cttcgagaat    180

gtgagctcta cgtccagaag cataacattc aagcgctgct caaagattct attgtgcagt    240

tgtgcactgc tcgacctgag agacccatgg cattcctcag ggaatacttt gagaggttgg    300

agaaggagga ggcaaaacag attcagaatc tgcagaaagc aggcactcgt acagactcaa    360

gggaggatga gatttctcct cctccaccca acccagtggt taaaggtagg aggcgacgag    420

gtgctatcag cgctgaggtc tacacggagg aagatgcggc atcctatgtt agaaaggtta    480

taccaaaaga ttacaagaca atggccgctt tagccaaagc cattgaaaag aatgtgctgt    540

tttcacatct tgatgataat gagagaagtg atatttttga tgccatgttt tcggtctcct    600

ttatcgcagg agagactgtg attcagcaag gtgatgaagg ggataacttc tatgtgattg    660

atcaaggaga gacggatgtc tatgttaaca atgaatgggc aaccagtgtt ggggaaggag    720

ggagctttgg agaacttgct ttgatttatg gaacaccgag agcagccact gtcaaagcaa    780

agacaaatgt gaaattgtgg ggcatcgacc gagacagcta tagaagaatc ctcatgggaa    840

gcacactgag aaagcggaag atgtatgagg aattccttag taaagtctct attttagagt    900

ctctggacaa gtgggaacgt cttacggtag ctgatgcatt ggaaccagtg cagtttgaag    960
```

-continued

```
atgggcagaa gattgtggtg cagggagaac caggggatga gttcttcatt attttagagg   1020
ggtcagctgc tgtgctacaa cgtcggtcag aaaatgaaga gtttgttgaa gtgggaagat   1080
tggggccttc tgattatttt ggtgaaattg cactactgat gaatcgtcct cgtgctgcca   1140
cagttgttgc tcgtggcccc ttgaagtgcg ttaagctgga ccgacctaga tttgaacgtg   1200
ttcttggccc atgctcagac atcctcaaac gaaacatcca gcagtacaac agttttgtgt   1260
cactgtctgt ctgaaatctg cctcctgtgc ctccctttc tcctctcccc aatccatgct   1320
tcactcatgc aaactgcttt attttcccta cttgcagcgc caagtggcca ctggcatcgc   1380
agcttcctgt ctgtttatat attgaaagtt gcttttattg caccattttc aatttggagc   1440
attaactaaa tgctcataca cagttaaata aatagaaaga gttctatgga gactttgctg   1500
ttactgcttc tctttgtgca gtgttagtat tcaccctggg cagtgagtgc catgcttttt   1560
ggtgagggca gatcccagca cctattgaat taccatagag taatgatgta acagtgcaag   1620
attttttttt taagtgacat aattgtccag ttataagcgt atttagactg tggccatata   1680
tgctgtattt ctttgtagaa taaatggttt ctcattaaac tctaaagatt agggaaaatg   1740
gatatagaaa atcttagtat agtagaaaga catctgcctg taattaaact agtttaaggg   1800
tggaaaaatg cccattttg ctaattatca atgggatatg attggttcag ttttttttt   1860
tccagagttg ttgtttgcca agctaatctg cctggtttta tttatatctt gttattaatg   1920
tttcttctcc aattctgaaa tacttttgag tatggctatc tatacctgcc ttttaagttt   1980
gaaactaact catagattgc aaatattggt tagtatttaa ctacatctgc ctcggctcac   2040
aaattccgat tagaccttta tccagctagt gccaaataat tgatcagatg ctgaattgag   2100
aataagaatt tgaggtctac attcttggtt gttaatttag agcgtttggt taaagtatgt   2160
ccttcagctg actccagtat aatctcctct gctcattaaa ctgattccag gagattggat   2220
ttgctgtgac tagatacaga tggagcaaat gtcctaacag agaaatagag gtgatgctgc   2280
taaagggaga aatgccaggc ggacaaagtt cagtgtcggg aattttcccc gtgacattca   2340
ctggggcatg agattttgga agaagttttt tactttggtt tagtcttttt ttccttcctt   2400
tttattcagc tagaatttct ggtgggttga tggtagggta taatgtgtct gtgttgcttc   2460
aaattggtct gaaaggctat cctgcggaaa gtcctgcttt cctatctagc atttatttct   2520
ctggcaaact tttctttctt ttcttttta aagtaaactt gtgtattgag tcttaactgt   2580
atttcagtat tttccagcct tatgtgttac attattccaa tgatacccaa cagtttattt   2640
ttattatttt tttaaacaaa atttcacagt tctgtaatgt aggcactttt attttcattg   2700
tgatttatat ataaggtaat gtagggttat atttgggagt gactgcaagc atttttccat   2760
ctgtgtgcaa ctaactgact ctgttattga tcccttctcc tgccctttcc caggtaattt   2820
aaattggtca tggtagattt ttttcataga tttgaaaaac ttttaggttg ttaccaagta   2880
tgaagtataa atctggggaa gaggttttat ttacatttta gggtgggtaa gaaagccacc   2940
ttgttacaaa ttttttaatt tccaaaataa tctatattaa atgagggttt ctgatctgta   3000
ctttgtgttt agctaccttt ttatatttaa aaaattaaaa atgaaaatta cgttcttaca   3060
agcttaaagc ttgatttgat ctttgtttaa atgccaaaat gtacttaaat gagttactta   3120
gaatgccata aaattgcagt ttcatgtatg tatataatca tgctcatgta tatttagtta   3180
cgtataatgc tttctgagtg agttttactc ttaaatcatt tggttaaatc atttggcttg   3240
ctgtttactc ccttctgtag tttttaatta aaaactttaa agataagtct acattaaaca   3300
atgatcacat ctaaagcttt atctttgtgt aatctaagta tatgtgagaa atcagaattg   3360
```

gcataatttg tcttagttga tattcaaggc tttaaaagtc attattcctg ggcttggtaa 3420
gtgaatttat gagatttact gctctagaaa gtatagatgg cgaaaggacc gttttgtatt 3480
gcttcctgat taccagtctg attataccat gtgtgctaat atactttttt tgttatagat 3540
tgtcttaatg gtaggtcaag taataaaaag agatgaaata atttaaaaaa aaaaaaaaaa 3600

<210> SEQ ID NO 314
<211> LENGTH: 3740
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 314
aggaagcctc aagacgcgga gcagcggcag gaaggagccc ccggcagccc ggaggagcat 60
gggcaccttg cgggatttac agtacgcgct ccaggagaag atcgaggagc tgaggcagcg 120
ggatgctctc atcgacgagc tggagctgga gttggatcag aaggacgaac tgatccagaa 180
gctgcagaac gagctggaca agtaccgctc ggtgatccga ccagccaccc agcaggcgca 240
gaagcagagc gcgagcacct tgcagggcga gccgcgcacc aagcggcagg cgatctccgc 300
cgagcccacc gccttcgaca tccaggatct cagccatgtg accctgccct tctaccccaa 360
gagcccacag tccaaggatc ttataaagga agctatcctt gacaatgact ttatgaagaa 420
cttggagctg tcgcagatcc aggagattgt ggattgtatg tacccggtgg agtatggcaa 480
ggacagttgc atcatcaaag aaggagacgt ggggtcactg gtgtatgtca tggaagatgg 540
taaggttgaa gttacaaaag aaggtgtgaa gttgtgtacc atgggtccag gaaaagtgtt 600
tggggaattg gctattcttt acaactgtac ccggacagcg accgtcaaga ctcttgtaaa 660
tgtaaaactc tgggccattg atcgacaatg ttttcaaaca ataatgatga ggacaggact 720
catcaagcat accgagtata tggaattttt aaaaagcgtt ccaacattcc agagccttcc 780
tgaagagatc ctcagcaagc ttgctgatgt ccttgaagag acccactatg aaaatggaga 840
atatattatc aggcaaggtg caagagggga caccttcttt atcatcagca aaggaacggt 900
aaatgtcact cgtgaagact caccgagtga agacccagtc tttcttagaa ctttaggaaa 960
aggagactgg tttggagaga aagccttgca gggggaagat gtgagaacag caaacgtaat 1020
tgctgcagaa gctgtaacct gccttgtgat tgacagagac tcttttaaac atttgattgg 1080
agggctggat gatgtttcta ataaagcata tgaagatgca gaagctaaag caaaatatga 1140
agctgaagcg gctttcttcg ccaacctgaa gctgtctgat ttcaacatca ttgataccct 1200
tggagttgga ggtttcggac gagtagaact ggtccagttg aaaagtgaag aatccaaaac 1260
gtttgcaatg aagattctca agaaacgtca cattgtggac acaagacagc aggagcacat 1320
ccgctcagag aagcagatca tgcagggggc tcattccgat ttcatagtga gactgtacag 1380
aacatttaag gacagcaaat atttgtatat gttgatggaa gcttgtctag gtggagagct 1440
ctggaccatt ctcagggata gaggttcgtt tgaagattct acaaccagat tttacacagc 1500
atgtgtggta gaagcttttg cctatctgca ttccaaagga atcatttaca gggacctcaa 1560
gccagaaaat ctcatcctag atcaccgagg ttatgccaaa ctggttgatt ttggctttgc 1620
aaagaaaata ggatttggaa agaaaacatg gacttttttgt gggactccag agtatgtagc 1680
cccagagatc atcctgaaca aaggccatga catttcagcc gactactggt cactgggaat 1740
cctaatgtat gaactcctga ctggcagccc acctttctca ggcccagatc ctatgaaaac 1800
ctataacatc atattgaggg ggattgacat gatagaattt ccaaagaaga ttgccaaaaa 1860
tgctgctaat ttaattaaaa aactatgcag ggacaatcca tcagaaagat tagggaattt 1920
gaaaaatgga gtaaaagaca ttcaaaagca caaatggttt gagggcttta actgggaagg 1980
cttaagaaaa ggtaccttga cacctcctat aataccaagt gttgcatcac ccacagacac 2040
aagtaatttt gacagtttcc ctgaggacaa cgatgaacca ccacctgatg acaactcagg 2100
atgggatata gacttctaat gtatttctct tacctgcttc tgccttgctg aagacagctt 2160
tttctgagac acagctgcca gcaaacctga gggaaagaga gaagattagt gctcggggtc 2220
accatgatgc ctttgatcga tgctgctcca gtaactacag tggcattagg acttatcgct 2280
tagatgacaa tagtgctctt tacatgtttt ctgtttgaac ctaaaatagc agttgacatg 2340
gtggtcctga agcaaagcct ttcaccagta aagagatgtt ttctattgtt gcaatgacct 2400
tgctttgctc tgattataat ttgaaagact gtaggaaaca cttcaatgta gtataagagt 2460
ctgtaccttg ctggaatatt caagaagatg aaagaataat atattgggta caatagatta 2520
ctatggtaca gaaactgggc tattcccttt cttcaagtga aggctgtggg atctattaca 2580
gctgcaggcc ggtgtatata ccatacaaaa gaggaccaca catctgttgg tcacagagtt 2640
catgtcacac cagtgctaga agtttcatga ttttatttcc cagcagtgct gatgacaaga 2700
ctgaatgtta ccttttcttt ctgacagatt ttaaaaattg atatgataaa agcacaactg 2760
ctatagattc tgctgagacc tctcatagta ggtatatatg agttttcaca gaagactgaa 2820
aaataatgca tgatatttgt ttgttttttt tgataaattg gcatgacaga gtggggaaaa 2880
aaagcaattc acaaaaccat ttcatatttt ttaaaatatt gtgcttaaag atggtcctgg 2940
aagtaaatga ctagcagcca attggtttta cttaacatac cctcaaactg aggcttaaag 3000
tattcccttt tataaaaata aatgcttggg gtagggtgga gtggggaggg attaaaaccc 3060
atccaaaaaa taaataaaaa ctatataggt gctatgtata tctttcatct gtaaatgtca 3120
gtgtctgaac agcaacacaa attcaaatca ttatacgtgt agccagaaac tcaagcattt 3180
tcactaaagt tattaaacca aactcctgtc caatttgact tatacaacat agtcagtcta 3240
gagttgagag acaaaggtaa ttataaacct atttgaacta gcttcttgtc ttaggcctga 3300
accaaaaaac aacaaacaaa caaaaaacaa gaatgaaaaa cagaaataaa agaagtagaa 3360
aagacaaaga aagaaagccc aaagtcaaag ttgttaatat ttacaggttt accagatctg 3420
gaacattact tatttgaggt cagagaacaa aacaagaacc tggccaggtg ttgattacct 3480
tttagtgaat aagctgagtc catatacttg tctaactaag aaagcagtac agaggaaaac 3540
aggaacctga ttttttaaa ataaatttta aataaaatag aattactaca attctgcaat 3600
ttcatactac ctaaaaaaga ctagatttga aaatgtcaag ctgatttact ttattcacat 3660
ggagaaaaga atccacaaat taaactgagt ccttcactgg catgccagtt gactattatt 3720
agctgtcata agtaaccccg 3740

<210> SEQ ID NO 315
<211> LENGTH: 4240
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 315
cagcagagct ggattggggt gttgagtcca ggctgagtag ggggcagccc actgctcttg 60

-continued

```
gtccctgtgc ctgctggggg tgccctgccc tgaactccag gcagcgggga cagggcgagg    120
tgccacctta gtctggctgg ggaggcggac gatgaggagt gatggggcag gcatgcggcc    180
actccatcct ctgcaggagc cagcagtacc cggcagcgcg accggctgag ccgcggggcc    240
agcaggtctt cctcaagccg gacgagccgc cgccgccgcc gcagccatgc gccgacagcc    300
tgcaggacgc cttgctgagt ctgggctctg tcatcgacat ttcaggcctg caacgtgctg    360
tcaaggaggc cctgtcagct gtgctccccc gagtggaaac tgtctacacc tacctactgg    420
atggtgagtc ccagctggtg tgtgaggacc ccccacatga gctgccccag gaggggaaag    480
tccgggaggc tatcatctcc cagaagcggc tgggctgcaa tgggctgggc ttctcagacc    540
tgccagggaa gcccttggcc aggctggtgg ctccactggc tcctgatacc caagtgctgg    600
tcatgccgct agcggacaag gaggctgggg ccgtggcagc tgtcatcttg gtgcactgtg    660
gccagctgag tgataatgag gaatggagcc tgcaggcggt ggagaagcat accctggtcg    720
ccctgcggag ggtgcaggtc ctgcagcagc gcgggcccag ggaggctccc cgagccgtcc    780
agaacccccc ggaggggacg gcggaagacc agaagggcgg ggcggcgtac accgaccgcg    840
accgcaagat cctccaactg tgcggggaac tctacgacct ggatgcctct tccctgcagc    900
tcaaagtgct ccaatacctg cagcaggaga cccgggcatc ccgctgctgc ctcctgctgg    960
tgtcggagga caatctccag ctttcttgca aggtcatcgg agacaaagtg ctcggggaag   1020
aggtcagctt tcccttgaca ggatgcctgg gccaggtggt ggaagacaag aagtccatcc   1080
agctgaagga cctcacctcc gaggatgtac aacagctgca gagcatgttg ggctgtgagc   1140
tgcaggccat gctctgtgtc cctgtcatca gccgggccac tgaccaggtg gtggccttgg   1200
cctgcgcctt caacaagcta gaaggagact tgttcaccga cgaggacgag catgtgatcc   1260
agcactgctt ccactacacc agcaccgtgc tcaccagcac cctggccttc cagaaggaac   1320
agaaactcaa gtgtgagtgc caggctcttc tccaagtggc aaagaacctc ttcacccacc   1380
tggatgacgt ctctgtcctg ctccaggaga tcatcacgga ggccagaaac ctcagcaacg   1440
cagagatctg ctctgtgttc ctgctggatc agaatgagct ggtggccaag gtgttcgacg   1500
ggggcgtggt ggatgatgag agctatgaga tccgcatccc ggccgatcag ggcatcgcgg   1560
gacacgtggc gaccacgggc cagatcctga acatccctga cgcatatgcc catccgcttt   1620
tctaccgcgg cgtggacgac agcaccggct tccgcacgcg caacatcctc tgcttcccca   1680
tcaagaacga gaaccaggag gtcatcggtg tggccgagct ggtgaacaag atcaatgggc   1740
catggttcag caagttcgac gaggacctgg cgacggcctt ctccatctac tgcggcatca   1800
gcatcgccca ttctctccta tacaaaaaag tgaatgaggc tcagtatcgc agccacctgg   1860
ccaatgagat gatgatgtac cacatgaagg tctccgacga tgagtatacc aaacttctcc   1920
atgatgggat ccagcctgtg gctgccattg actccaattt tgcaagtttc acctataccc   1980
ctcgttccct gcccgaggat gacacgtcca tggccatcct gagcatgctg caggacatga   2040
atttcatcaa caactacaaa attgactgcc cgaccctggc ccggttctgt ttgatggtga   2100
agaagggcta ccgggatccc ccctaccaca actggatgca cgccttttct gtctcccact   2160
tctgctacct gctctacaag aacctggagc tcaccaacta cctcgaggac atcgagatct   2220
ttgccttgtt tatttcctgc atgtgtcatg acctggacca cagaggcaca aacaactctt   2280
tccaggtggc ctcgaaatct gtgctggctg cgctctacag ctctgagggc tccgtcatgg   2340
agaggcacca ctttgctcag gccatcgcca tcctcaacac ccacggctgc aacatctttg   2400
```

```
atcatttctc ccggaaggac tatcagcgca tgctggatct gatgcgggac atcatcttgg   2460

ccacagacct ggcccaccat ctccgcatct tcaaggacct ccagaagatg gctgaggtgg   2520

gctacgaccg aaacaacaag cagcaccaca gacttctcct ctgcctcctc atgacctcct   2580

gtgacctctc tgaccagacc aagggctgga agactacgag aaagatcgcg gagctgatct   2640

acaaagaatt cttctcccag ggagacctgg agaaggccat gggcaacagg ccgatggaga   2700

tgatggaccg ggagaaggcc tatatccctg agctgcaaat cagcttcatg gagcacattg   2760

caatgcccat ctacaagctg ttgcaggacc tgttccccaa agcggcagag ctgtacgagc   2820

gcgtggcctc caaccgtgag cactggacca aggtgtccca caagttcacc atccgcggcc   2880

tcccaagtaa caactcgctg gacttcctgg atgaggagta cgaggtgcct gatctggatg   2940

gcactagggc ccccatcaat ggctgctgca gccttgatgc tgagtgatcc cctccaggac   3000

acttccctgc ccaggccacc tcccacagcc ctccactggt ctggccagat gcactgggaa   3060

cagagccacg ggtcctgggt cctagaccag gacttcctgt gtgaccctgg acaagtacta   3120

ccttcctggg cctcagcttt ctcgtctgta taatggaagc aagacttcca acctcacgga   3180

gactttgtaa tttgcttctc tgagagcaca ggggtgacca atgagcagtg ggccctactc   3240

tgcacctctg accacacctt ggcaagtctt tcccaagcca ttctttgtct gagcagcttg   3300

atggtttctc cttgccccat ttctgcccca ccagatcttt gctcctttcc ctttgaggac   3360

tcccaccctt tgggtctcca ggatcctcat ggaaggggaa ggtgagacat ctgagtgagc   3420

agagtgtggc atcttggaaa cagtccttag ttctgtggga ggactagaaa cagccgcggc   3480

gaaggccccc tgaggaccac tactatactg atggtgggat tgggacctgg gggatacagg   3540

ggccccagga agaagctggc cagaggggca gctcagtgct ctgcagagag gggccctggg   3600

gagaagcagg atgggattga tgggcaggag ggatccccgc actgggagac aggcccaggt   3660

atgaatgagc cagccatgct tcctcctgcc tgtgtgacgc tgggcgagtc tcttcccctg   3720

tctgggccaa acagggagcg ggtaagacaa tccatgctct aagatccatt ttagatcaat   3780

gtctaaaata gctctatggc tctgcggagt cccagcagag gctatggaat gtttctgcaa   3840

ccctaaggca cagagagcca accctgagtg tctcagaggc cccctgagtg ttccccttgg   3900

cctgagcccc ttacccattc ctgcagccag tgagagacct ggcctcagcc tggcagcgct   3960

ctcttcaagg ccatatccac ctgtgccctg gggcttggga gaccccatag gccgggactc   4020

ttgggtcagc ccgccactgg cttctctctt tttctccgtt tcattctgtg tgcgttgtgg   4080

ggtgggggag gggtccacc  tgccttacct ttctgagttg cctttagaga gatgcgtttt   4140

tctaggactc tgtgcaactg tcgtatatgg tcccgtgggc tgaccgcttt gtacatgaga   4200

ataaatctat ttctttctac caaaaaaaaa aaaaaaaaaa                         4240
```

<210> SEQ ID NO 316
<211> LENGTH: 536
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

```
Met Gly Ser Asn Lys Ser Lys Pro Lys Asp Ala Ser Gln Arg Arg Arg
1               5                   10                  15

Ser Leu Glu Pro Ala Glu Asn Val His Gly Ala Gly Gly Gly Ala Phe
            20                  25                  30
```

```
Pro Ala Ser Gln Thr Pro Ser Lys Pro Ala Ser Ala Asp Gly His Arg
        35                  40                  45

Gly Pro Ser Ala Ala Phe Ala Pro Ala Ala Ala Glu Pro Lys Leu Phe
    50                  55                  60

Gly Gly Phe Asn Ser Ser Asp Thr Val Thr Ser Pro Gln Arg Ala Gly
65                  70                  75                  80

Pro Leu Ala Gly Gly Val Thr Thr Phe Val Ala Leu Tyr Asp Tyr Glu
                85                  90                  95

Ser Arg Thr Glu Thr Asp Leu Ser Phe Lys Lys Gly Glu Arg Leu Gln
            100                 105                 110

Ile Val Asn Asn Thr Glu Gly Asp Trp Trp Leu Ala His Ser Leu Ser
        115                 120                 125

Thr Gly Gln Thr Gly Tyr Ile Pro Ser Asn Tyr Val Ala Pro Ser Asp
    130                 135                 140

Ser Ile Gln Ala Glu Glu Trp Tyr Phe Gly Lys Ile Thr Arg Arg Glu
145                 150                 155                 160

Ser Glu Arg Leu Leu Leu Asn Ala Glu Asn Pro Arg Gly Thr Phe Leu
                165                 170                 175

Val Arg Glu Ser Glu Thr Thr Lys Gly Ala Tyr Cys Leu Ser Val Ser
            180                 185                 190

Asp Phe Asp Asn Ala Lys Gly Leu Asn Val Lys His Tyr Lys Ile Arg
        195                 200                 205

Lys Leu Asp Ser Gly Gly Phe Tyr Ile Thr Ser Arg Thr Gln Phe Asn
    210                 215                 220

Ser Leu Gln Gln Leu Val Ala Tyr Tyr Ser Lys His Ala Asp Gly Leu
225                 230                 235                 240

Cys His Arg Leu Thr Thr Val Cys Pro Thr Ser Lys Pro Gln Thr Gln
                245                 250                 255

Gly Leu Ala Lys Asp Ala Trp Glu Ile Pro Arg Glu Ser Leu Arg Leu
            260                 265                 270

Glu Val Lys Leu Gly Gln Gly Cys Phe Gly Glu Val Trp Met Gly Thr
        275                 280                 285

Trp Asn Gly Thr Thr Arg Val Ala Ile Lys Thr Leu Lys Pro Gly Thr
    290                 295                 300

Met Ser Pro Glu Ala Phe Leu Gln Glu Ala Gln Val Met Lys Lys Leu
305                 310                 315                 320

Arg His Glu Lys Leu Val Gln Leu Tyr Ala Val Val Ser Glu Glu Pro
                325                 330                 335

Ile Tyr Ile Val Thr Glu Tyr Met Ser Lys Gly Ser Leu Leu Asp Phe
            340                 345                 350

Leu Lys Gly Glu Thr Gly Lys Tyr Leu Arg Leu Pro Gln Leu Val Asp
        355                 360                 365

Met Ala Ala Gln Ile Ala Ser Gly Met Ala Tyr Val Glu Arg Met Asn
    370                 375                 380

Tyr Val His Arg Asp Leu Arg Ala Ala Asn Ile Leu Val Gly Glu Asn
385                 390                 395                 400

Leu Val Cys Lys Val Ala Asp Phe Gly Leu Ala Arg Leu Ile Glu Asp
                405                 410                 415

Asn Glu Tyr Thr Ala Arg Gln Gly Ala Lys Phe Pro Ile Lys Trp Thr
            420                 425                 430

Ala Pro Glu Ala Ala Leu Tyr Gly Arg Phe Thr Ile Lys Ser Asp Val
        435                 440                 445

Trp Ser Phe Gly Ile Leu Leu Thr Glu Leu Thr Thr Lys Gly Arg Val
```

-continued

```
    450                 455                 460

Pro Tyr Pro Gly Met Val Asn Arg Glu Val Leu Asp Gln Val Glu Arg
465                 470                 475                 480

Gly Tyr Arg Met Pro Cys Pro Pro Glu Cys Pro Glu Ser Leu His Asp
                485                 490                 495

Leu Met Cys Gln Cys Trp Arg Lys Glu Pro Glu Glu Arg Pro Thr Phe
            500                 505                 510

Glu Tyr Leu Gln Ala Phe Leu Glu Asp Tyr Phe Thr Ser Thr Glu Pro
        515                 520                 525

Gln Tyr Gln Pro Gly Glu Asn Leu
    530                 535


<210> SEQ ID NO 317
<211> LENGTH: 418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Met Ser Ile Glu Ile Pro Ala Gly Leu Thr Glu Leu Leu Gln Gly Phe
1               5                   10                  15

Thr Val Glu Val Leu Arg His Gln Pro Ala Asp Leu Leu Glu Phe Ala
            20                  25                  30

Leu Gln His Phe Thr Arg Leu Gln Gln Glu Asn Glu Arg Lys Gly Thr
        35                  40                  45

Ala Arg Phe Cys His Glu Gly Arg Thr Trp Gly Asp Leu Gly Ala Ala
    50                  55                  60

Ala Gly Gly Gly Thr Pro Ser Lys Gly Val Asn Phe Ala Glu Glu Pro
65                  70                  75                  80

Met Gln Ser Asp Ser Glu Asp Gly Glu Glu Glu Glu Ala Ala Pro Ala
                85                  90                  95

Asp Ala Gly Ala Phe Asn Ala Pro Val Ile Asn Arg Phe Thr Arg Arg
            100                 105                 110

Ala Ser Val Cys Ala Glu Ala Tyr Asn Pro Asp Glu Glu Glu Asp Asp
        115                 120                 125

Ala Glu Ser Arg Ile Ile His Pro Lys Thr Asp Asp Gln Arg Asn Arg
    130                 135                 140

Leu Gln Glu Ala Cys Lys Asp Ile Leu Leu Phe Lys Asn Leu Asp Pro
145                 150                 155                 160

Glu Gln Met Ser Gln Val Leu Asp Ala Met Phe Glu Lys Leu Val Lys
                165                 170                 175

Asp Gly Glu His Val Ile Asp Gln Gly Asp Asp Gly Asp Asn Phe Tyr
            180                 185                 190

Val Ile Asp Arg Gly Thr Phe Asp Ile Tyr Val Lys Cys Asp Gly Val
        195                 200                 205

Gly Arg Cys Val Gly Asn Tyr Asp Asn Arg Gly Ser Phe Gly Glu Leu
    210                 215                 220

Ala Leu Met Tyr Asn Thr Pro Arg Ala Ala Thr Ile Thr Ala Thr Ser
225                 230                 235                 240

Pro Gly Ala Leu Trp Gly Leu Asp Arg Val Thr Phe Arg Arg Ile Ile
                245                 250                 255

Val Lys Asn Asn Ala Lys Lys Arg Lys Met Tyr Glu Ser Phe Ile Glu
            260                 265                 270
```

-continued

```
Ser Leu Pro Phe Leu Lys Ser Leu Glu Phe Ser Glu Arg Leu Lys Val
        275                 280                 285

Val Asp Val Ile Gly Thr Lys Val Tyr Asn Asp Gly Glu Gln Ile Ile
    290                 295                 300

Ala Gln Gly Asp Ser Ala Asp Ser Phe Phe Ile Val Glu Ser Gly Glu
305                 310                 315                 320

Val Lys Ile Thr Met Lys Arg Lys Gly Lys Ser Glu Val Glu Glu Asn
                325                 330                 335

Gly Ala Val Glu Ile Ala Arg Cys Ser Arg Gly Gln Tyr Phe Gly Glu
            340                 345                 350

Leu Ala Leu Val Thr Asn Lys Pro Arg Ala Ala Ser Ala His Ala Ile
        355                 360                 365

Gly Thr Val Lys Cys Leu Ala Met Asp Val Gln Ala Phe Glu Arg Leu
    370                 375                 380

Leu Gly Pro Cys Met Glu Ile Met Lys Arg Asn Ile Ala Thr Tyr Glu
385                 390                 395                 400

Glu Gln Leu Val Ala Leu Phe Gly Thr Asn Met Asp Ile Val Glu Pro
                405                 410                 415

Thr Ala


<210> SEQ ID NO 318
<211> LENGTH: 169
<212> TYPE: PRT
<213> ORGANISM: Artificial Sequence
<220> FEATURE:
<223> OTHER INFORMATION: Synthetic

<400> SEQUENCE: 318

Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Val Val Leu Ser Gly
        35                  40                  45

Glu Asn Gly Leu Lys Ala Asp Ile His Val Ile Ile Pro Tyr Glu Gly
    50                  55                  60

Leu Ser Gly Phe Gln Met Gly Leu Ile Glu Met Ile Phe Lys Val Val
65                  70                  75                  80

Tyr Pro Val Asp Asp His His Phe Lys Ile Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Pro Gly Ile Ala Val Phe Asp Gly Lys Gln Ile Thr Val Thr
        115                 120                 125

Gly Thr Leu Trp Asn Gly Asn Lys Ile Tyr Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165
```